US012440401B2

(12) United States Patent
van der Merwe et al.

(10) Patent No.: US 12,440,401 B2
(45) Date of Patent: Oct. 14, 2025

(54) MOBILITY DEVICE

(71) Applicant: DEKA Products Limited Partnership, Manchester, NH (US)

(72) Inventors: Dirk A. van der Merwe, Canterbury, NH (US); Susan D. Dastous, Litchfield, NH (US); Daniel F. Pawlowski, Mont Vernon, NH (US); David Doherty, Litchfield, NH (US); Matthew A. Norris, Londonderry, NH (US); Alexander D. Streeter, Concord, NH (US); Constance D. Pitenis, Hooksett, NH (US); David E. Collins, Crestview, FL (US); Erik N. Sabin, Manchester, NH (US); David J. Meehan, Londonderry, NH (US); Tania M. F. Zirn, Chester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 18/671,128

(22) Filed: May 22, 2024

(65) Prior Publication Data

US 2024/0398637 A1 Dec. 5, 2024

Related U.S. Application Data

(60) Continuation of application No. 17/878,245, filed on Aug. 1, 2022, now Pat. No. 12,023,285, which is a
(Continued)

(51) Int. Cl.
*A61G 5/04* (2013.01)
*A61G 5/06* (2006.01)
(Continued)

(52) U.S. Cl.
CPC ............ *A61G 5/047* (2013.01); *A61G 5/041* (2013.01); *A61G 5/046* (2013.01); *A61G 5/048* (2016.11);
(Continued)

(58) Field of Classification Search
CPC ...................................................... A61G 5/047
See application file for complete search history.

(56) References Cited

U.S. PATENT DOCUMENTS

| | | | |
|---|---|---|---|
| 584,127 | A | 6/1897 | Draullette et al. |
| 849,270 | A | 4/1907 | Andrew |

(Continued)

FOREIGN PATENT DOCUMENTS

| | | | |
|---|---|---|---|
| AU | 2017250598 | A1 | 11/2018 |
| CA | 2580632 | A1 | 3/2006 |

(Continued)

OTHER PUBLICATIONS

Notice of Allowance mailed Jul. 29, 2020, issued in U.S. Appl. No. 29/690,306, 9 pages.

(Continued)

*Primary Examiner* — Michael A Berns
(74) *Attorney, Agent, or Firm* — William A. Bonk, III

(57) ABSTRACT

Disclosed is a system for controlling a mobility device including a processor configured for a workflow process configured for filtering user commands based on a status of the mobility device and defining filtered commands. A mobility device command process is configured for issuing commands based on the filtered commands. The mobility device responds to the commands that are configured for controlling moving the mobility device.

10 Claims, 489 Drawing Sheets

Related U.S. Application Data division of application No. 16/035,205, filed on Jul. 13, 2018, now Pat. No. 11,399,995, which is a continuation-in-part of application No. 15/982,737, filed on May 17, 2018, now Pat. No. 10,893,028, and a continuation-in-part of application No. 15/787,613, filed on Oct. 18, 2017, now Pat. No. 10,926,756, which is a continuation-in-part of application No. 15/600,703, filed on May 20, 2017, now Pat. No. 10,908,045, and a continuation-in-part of application No. 15/486,980, filed on Apr. 13, 2017, now Pat. No. 10,802,495, said application No. 15/600,703 is a continuation-in-part of application No. 15/441,190, filed on Feb. 23, 2017, now Pat. No. 10,220,843.

(60) Provisional application No. 62/581,670, filed on Nov. 4, 2017, provisional application No. 62/559,263, filed on Sep. 15, 2017, provisional application No. 62/532,993, filed on Jul. 15, 2017, provisional application No. 62/509,061, filed on May 20, 2017, provisional application No. 62/403,030, filed on Sep. 30, 2016, provisional application No. 62/339,723, filed on May 20, 2016, provisional application No. 62/322,522, filed on Apr. 14, 2016, provisional application No. 62/298,721, filed on Feb. 23, 2016.

(51) Int. Cl.

| | |
|---|---|
| ***A61G 5/10*** | (2006.01) |
| ***A61G 5/12*** | (2006.01) |
| ***G16H 20/30*** | (2018.01) |
| ***H04L 9/08*** | (2006.01) |
| ***H04L 9/32*** | (2006.01) |
| ***H04W 12/03*** | (2021.01) |
| ***H04W 12/06*** | (2021.01) |
| ***H04W 12/08*** | (2021.01) |
| ***H04W 12/50*** | (2021.01) |
| *G06F 21/31* | (2013.01) |

(52) U.S. Cl.

CPC ........... *A61G 5/063* (2013.01); *A61G 5/1032* (2013.01); *A61G 5/1089* (2016.11); *A61G 5/122* (2016.11); *A61G 5/125* (2016.11); *A61G 5/128* (2016.11); *G16H 20/30* (2018.01); *H04L 9/0841* (2013.01); *H04L 9/3215* (2013.01); *H04L 9/3226* (2013.01); *H04L 9/3239* (2013.01); *H04L 9/3271* (2013.01); *H04W 12/03* (2021.01); *H04W 12/06* (2013.01); *H04W 12/08* (2013.01); *H04W 12/50* (2021.01); *A61G 5/061* (2013.01); *A61G 5/1078* (2016.11); *A61G 2203/10* (2013.01); *A61G 2203/14* (2013.01); *A61G 2203/20* (2013.01); *A61G 2203/36* (2013.01); *A61G 2203/42* (2013.01); *A61G 2203/70* (2013.01); *A61G 2203/72* (2013.01); *G06F 21/31* (2013.01); *H04L 2209/34* (2013.01); *H04L 2209/80* (2013.01); *H04L 2209/84* (2013.01); *H04L 2209/88* (2013.01)

(56) References Cited

U.S. PATENT DOCUMENTS

| | | | |
|---|---|---|---|
| 880,823 | A | 3/1908 | Redfield |
| 2,224,411 | A | 12/1940 | Smith |
| 2,415,056 | A | 1/1947 | Wheeler |
| 2,618,447 | A | 11/1952 | Lecarme |
| 2,742,973 | A | 4/1956 | Johannesen |
| 2,966,223 | A | 12/1960 | Gleasman et al. |
| 3,017,199 | A | 1/1962 | Sechrist et al. |
| 3,145,797 | A | 8/1964 | Taylor et al. |
| 3,179,355 | A | 4/1965 | Pickering et al. |
| D201,553 | S | 7/1965 | Disman et al. |
| 3,260,324 | A | 7/1966 | Suarez et al. |
| 3,283,398 | A | 11/1966 | Andren et al. |
| 3,288,234 | A | 11/1966 | Feliz et al. |
| 3,306,626 | A | 2/1967 | Tadao et al. |
| 3,313,365 | A | 4/1967 | Jackson et al. |
| 3,338,328 | A | 8/1967 | Cataldo et al. |
| 3,348,518 | A | 10/1967 | Forsyth et al. |
| 3,374,845 | A | 3/1968 | Selwyn et al. |
| 3,399,742 | A | 9/1968 | Malick et al. |
| 3,446,304 | A | 5/1969 | Alimanestiand et al. |
| 3,450,219 | A | 6/1969 | Fleming et al. |
| 3,515,401 | A | 6/1970 | Gross et al. |
| 3,580,344 | A | 5/1971 | Floyd et al. |
| 3,596,298 | A | 8/1971 | Durst, Jr. et al. |
| 3,628,624 | A | 12/1971 | Wesener et al. |
| 3,718,342 | A | 2/1973 | Freed et al. |
| 3,787,066 | A | 1/1974 | Hautier et al. |
| 3,790,150 | A | 2/1974 | Lippert et al. |
| 3,860,264 | A | 1/1975 | Douglas et al. |
| 3,872,945 | A | 3/1975 | Hickman et al. |
| 3,893,689 | A | 7/1975 | Verhoff et al. |
| 3,952,822 | A | 4/1976 | Udden et al. |
| 3,965,402 | A | 6/1976 | Mogle et al. |
| 3,993,154 | A | 11/1976 | Simmons et al. |
| 4,005,907 | A | 2/1977 | Bonomo et al. |
| 4,018,440 | A | 4/1977 | Deutsch et al. |
| 4,030,753 | A | 6/1977 | Meiners et al. |
| 4,054,319 | A | 10/1977 | Fogg, Jr. et al. |
| 4,062,558 | A | 12/1977 | Wasserman et al. |
| 4,065,145 | A | 12/1977 | Chambers et al. |
| 4,065,146 | A | 12/1977 | Denzer et al. |
| 4,076,270 | A | 2/1978 | Winchell et al. |
| 4,078,627 | A | 3/1978 | Brown et al. |
| 4,087,107 | A | 5/1978 | Winchell et al. |
| 4,088,199 | A | 5/1978 | Trautwein et al. |
| 4,094,372 | A | 6/1978 | Notter et al. |
| 4,109,741 | A | 8/1978 | Gabriel et al. |
| 4,111,445 | A | 9/1978 | Haibeck et al. |
| 4,115,445 | A | 9/1978 | Hearsey et al. |
| 4,140,200 | A | 2/1979 | Tucek et al. |
| 4,151,892 | A | 5/1979 | Francken et al. |
| D253,234 | S | 10/1979 | Cooke et al. |
| 4,222,449 | A | 9/1980 | Feliz et al. |
| D258,958 | S | 4/1981 | Fukushima et al. |
| 4,264,082 | A | 4/1981 | Fouchey, Jr. et al. |
| 4,266,627 | A | 5/1981 | Lauber et al. |
| 4,274,503 | A | 6/1981 | Mackintosh et al. |
| 4,281,734 | A | 8/1981 | Johnston et al. |
| 4,293,052 | A | 10/1981 | Daswick et al. |
| 4,307,788 | A | 12/1981 | Shelton et al. |
| 4,325,565 | A | 4/1982 | Winchell et al. |
| 4,354,569 | A | 10/1982 | Eichholz et al. |
| D266,758 | S | 11/1982 | Johannsen et al. |
| 4,363,493 | A | 12/1982 | Veneklasen et al. |
| 4,373,600 | A | 2/1983 | Buschbom et al. |
| 4,375,840 | A | 3/1983 | Campbell et al. |
| 4,413,693 | A | 11/1983 | Derby et al. |
| 4,448,455 | A | 5/1984 | Ellegaard et al. |
| 4,456,086 | A | 6/1984 | Wier et al. |
| 4,484,648 | A | 11/1984 | Jephcott et al. |
| 4,510,956 | A | 4/1985 | King et al. |
| 4,512,588 | A | 4/1985 | Cox et al. |
| 4,556,997 | A | 12/1985 | Takamiya et al. |
| 4,560,022 | A | 12/1985 | Kassai et al. |
| 4,566,707 | A | 1/1986 | Nitzberg et al. |
| 4,570,078 | A | 2/1986 | Yashima et al. |
| 4,571,844 | A | 2/1986 | Komasaku et al. |
| 4,624,469 | A | 11/1986 | Bourne, Jr. et al. |
| 4,648,783 | A | 3/1987 | Tan et al. |
| 4,657,271 | A | 4/1987 | Salmon et al. |
| 4,657,272 | A | 4/1987 | Davenport et al. |
| D290,382 | S | 6/1987 | Sawit et al. |
| 4,674,584 | A | 6/1987 | Watkins et al. |
| 4,685,693 | A | 8/1987 | Vadjunec et al. |
| 4,709,772 | A | 12/1987 | Brunet et al. |

(56) References Cited

U.S. PATENT DOCUMENTS 4,712,806 A 12/1987 Patrin et al.
4,716,980 A 1/1988 Butler et al.
4,722,547 A 2/1988 Kishi et al.
4,732,353 A 3/1988 Studer et al.
4,740,001 A 4/1988 Torleumke et al.
4,746,132 A 5/1988 Eagan et al.
4,750,578 A 6/1988 Brandenfels et al.
4,754,255 A 6/1988 Sanders et al.
4,770,410 A 9/1988 Brown et al.
4,778,133 A 10/1988 Sakurai et al.
4,786,069 A 11/1988 Tang et al.
4,787,679 A 11/1988 Arnold et al.
4,790,400 A 12/1988 Sheeter et al.
4,790,548 A 12/1988 Decelles et al.
4,794,730 A 1/1989 Fischbach et al.
4,794,999 A 1/1989 Hester et al.
4,798,255 A 1/1989 Wu et al.
4,802,542 A 2/1989 Houston et al.
4,809,804 A 3/1989 Houston et al.
4,834,200 A 5/1989 Kajita et al.
4,837,694 A 6/1989 Narita et al.
4,863,182 A 9/1989 Chern et al.
4,867,188 A 9/1989 Reid et al.
4,869,279 A 9/1989 Hedges et al.
4,874,055 A 10/1989 Beer et al.
4,890,853 A 1/1990 Olson et al.
4,897,070 A 1/1990 Wagstaff et al.
4,913,252 A 4/1990 Bartley et al.
4,919,225 A 4/1990 Sturges et al.
D308,364 S 6/1990 Beasley, Jr. et al.
4,941,854 A 7/1990 Takahashi et al.
4,944,360 A 7/1990 Sturges et al.
4,953,851 A 9/1990 Sherlock et al.
4,964,679 A 10/1990 Rath et al.
4,967,862 A 11/1990 Pong et al.
4,973,071 A 11/1990 Ishizaki et al.
4,974,871 A 12/1990 Mao et al.
4,984,754 A 1/1991 Yarrington et al.
4,985,947 A 1/1991 Ethridge et al.
4,998,596 A 3/1991 Miksitz et al.
5,001,636 A 3/1991 Shiraishi et al.
5,002,295 A 3/1991 Lin et al.
5,011,171 A 4/1991 Cook et al.
5,012,176 A 4/1991 Laforge et al.
RE33,675 E 8/1991 Young et al.
5,044,457 A 9/1991 Aikman et al.
5,052,237 A 10/1991 Reimann et al.
5,076,390 A 12/1991 Haskins et al.
5,087,103 A 2/1992 Pompier et al.
5,088,761 A 2/1992 Takehara et al.
5,098,041 A 3/1992 Uetrecht et al.
5,111,899 A 5/1992 Reimann et al.
5,123,972 A 6/1992 Ostrander et al.
5,124,938 A 6/1992 Algrain et al.
5,125,468 A 6/1992 Coker et al.
5,127,709 A 7/1992 Rubinstein et al.
5,136,219 A 8/1992 Takahashi et al.
5,158,493 A 10/1992 Morgrey et al.
5,161,820 A 11/1992 Vollmer et al.
5,165,711 A 11/1992 Tsai et al.
5,168,947 A 12/1992 Rodenborn et al.
5,171,173 A 12/1992 Henderson et al.
5,186,270 A 2/1993 West et al.
5,208,521 A 5/1993 Aoyama et al.
5,217,246 A 6/1993 Williams et al.
5,221,883 A 6/1993 Takenaka et al.
5,229,068 A 7/1993 Johansson et al.
5,241,875 A 9/1993 Kochanneck et al.
5,248,007 A 9/1993 Watkins et al.
5,261,503 A 11/1993 Yasui et al.
5,274,576 A 12/1993 Williams et al.
5,276,588 A 1/1994 Repplinger et al.
5,276,624 A 1/1994 Ito et al.
5,297,646 A 3/1994 Yamamura et al.
5,307,888 A 5/1994 Urvoy et al.
5,307,892 A 5/1994 Phillips et al.
5,314,034 A 5/1994 Chittal et al.
5,350,033 A 9/1994 Kraft et al.
5,364,165 A 11/1994 Okamoto et al.
5,366,036 A 11/1994 Perry et al.
5,369,580 A 11/1994 Monji et al.
5,376,868 A 12/1994 Toyoda et al.
D355,148 S 2/1995 Orsolini et al.
5,388,658 A 2/1995 Ando et al.
5,397,890 A 3/1995 Schueler et al.
5,408,411 A 4/1995 Nakamura et al.
5,408,811 A 4/1995 Satake et al.
5,417,298 A 5/1995 Shibahata et al.
5,419,624 A 5/1995 Adler et al.
5,450,919 A 9/1995 Shitani et al.
5,465,806 A 11/1995 Higasa et al.
5,482,125 A 1/1996 Pagett et al.
D373,121 S 8/1996 DeIuliis et al.
5,551,756 A 9/1996 Gurasich et al.
5,575,348 A 11/1996 Goertzen et al.
5,576,959 A 11/1996 Hrovat et al.
D376,585 S 12/1996 Wathen et al.
5,610,493 A 3/1997 Wieloch et al.
5,615,116 A 3/1997 Gudat et al.
5,639,109 A 6/1997 Liang et al.
D381,325 S 7/1997 McMahan et al.
5,646,845 A 7/1997 Gudat et al.
5,649,605 A 7/1997 Ronne et al.
5,657,828 A 8/1997 Nagamachi et al.
D388,027 S 12/1997 Polak et al.
D388,207 S 12/1997 Houplain et al.
D388,368 S 12/1997 Polak et al.
5,695,021 A 12/1997 Schaffner et al.
5,701,965 A 12/1997 Kamen et al.
5,701,968 A 12/1997 Wright-Ott et al.
5,705,746 A 1/1998 Trost et al.
5,732,379 A 3/1998 Eckert et al.
5,743,347 A 4/1998 Gingerich et al.
5,746,282 A 5/1998 Fujiwara et al.
5,769,441 A 6/1998 Namngani et al.
5,774,819 A 6/1998 Yamamoto et al.
5,775,452 A 7/1998 Patmont et al.
5,791,425 A 8/1998 Kamen et al.
5,794,730 A 8/1998 Kamen et al.
5,799,745 A 9/1998 Fukatani et al.
5,799,914 A 9/1998 Chivallier et al.
5,816,374 A 10/1998 Hsien et al.
5,819,892 A 10/1998 Deliman et al.
5,826,209 A 10/1998 Matsuno et al.
D402,645 S 12/1998 Garguilo et al.
5,848,660 A 12/1998 McGreen et al.
5,850,136 A 12/1998 Kaneko et al.
5,869,943 A 2/1999 Nakashima et al.
5,869,946 A 2/1999 Carobolante et al.
D408,767 S 4/1999 Bar et al.
5,893,896 A 4/1999 Imamura et al.
5,927,414 A 7/1999 Kan et al.
5,928,309 A 7/1999 Korver et al.
5,931,421 A 8/1999 Surauer et al.
5,939,864 A 8/1999 Lenhart et al.
5,965,991 A 10/1999 Koike et al.
5,971,091 A 10/1999 Kamen et al.
5,973,463 A 10/1999 Okuda et al.
5,975,225 A 11/1999 Kamen et al.
5,984,327 A 11/1999 Hsieh et al.
5,986,221 A 11/1999 Stanley et al.
6,002,975 A 12/1999 Schiffmann et al.
6,003,624 A 12/1999 Jorgensen et al.
6,024,182 A 2/2000 Hamada et al.
6,036,619 A 3/2000 Tashiro et al.
6,039,142 A 3/2000 Eckstein et al.
6,047,442 A 4/2000 Workman et al.
6,050,357 A 4/2000 Staelin et al.
6,052,647 A 4/2000 Parkinson et al.
6,053,579 A 4/2000 Nelson et al.
D424,483 S 5/2000 Tripodi et al.
6,059,062 A 5/2000 Staelin et al.
6,062,600 A 5/2000 Kamen et al.
6,062,651 A 5/2000 Schaad et al.

(56) References Cited

U.S. PATENT DOCUMENTS 6,065,558 A 5/2000 Wielenga et al.
6,073,951 A 6/2000 Jindra et al.
6,076,033 A 6/2000 Hamada et al.
6,089,680 A 7/2000 Yoshioka et al.
6,092,249 A 7/2000 Kamen et al.
D428,936 S 8/2000 Serfaty et al.
6,105,704 A 8/2000 Hamada et al.
6,108,592 A 8/2000 Kurtzberg et al.
6,123,398 A 9/2000 Arai et al.
6,125,953 A 10/2000 Arai et al.
6,125,957 A 10/2000 Kauffmann et al.
6,131,057 A 10/2000 Tamaki et al.
6,141,613 A 10/2000 Fan et al.
6,148,939 A 11/2000 Brookhart et al.
6,154,692 A 11/2000 Cielaszyk et al.
D434,762 S 12/2000 Ikenaga et al.
6,169,946 B1 1/2001 Griessbach et al.
6,179,176 B1 1/2001 Saggese et al.
6,189,643 B1 2/2001 Takahashi et al.
6,192,305 B1 2/2001 Schiffmann et al.
6,208,734 B1 3/2001 Ortscheid et al.
6,208,929 B1 3/2001 Matsuno et al.
6,212,276 B1 4/2001 Inoue et al.
6,223,104 B1 4/2001 Kamen et al.
6,223,114 B1 4/2001 Boros et al.
6,225,977 B1 5/2001 Li et al.
D444,184 S 6/2001 Kettler et al.
6,247,548 B1 6/2001 Hayashi et al.
6,260,646 B1 7/2001 Fernandez et al.
6,263,261 B1 7/2001 Brown et al.
6,264,218 B1 7/2001 Slagerman et al.
6,270,105 B1 8/2001 Friedrich et al.
6,273,212 B1 8/2001 Husted et al.
6,276,471 B1 8/2001 Kratzenberg et al.
6,285,778 B1 9/2001 Nakajima et al.
6,288,505 B1 9/2001 Heinzmann et al.
6,292,722 B1 9/2001 Holmes et al.
6,302,230 B1 10/2001 Kamen et al.
6,311,794 B1 11/2001 Morrell et al.
6,320,336 B1 11/2001 Eguchi et al.
6,324,446 B1 11/2001 Brown et al.
6,325,736 B1 12/2001 Hamada et al.
6,328,125 B1 12/2001 Van Den Brink et al.
6,332,103 B1 12/2001 Steenson, Jr. et al.
6,332,104 B1 12/2001 Brown et al.
D452,692 S 1/2002 Fukuda et al.
D453,142 S 1/2002 Watanabe et al.
6,343,664 B2 2/2002 Morrell et al.
6,356,188 B1 3/2002 Meyers et al.
6,357,544 B1 3/2002 Kamen et al.
6,360,996 B1 3/2002 Bockman et al.
6,367,817 B1 4/2002 Kamen et al.
6,371,228 B1 4/2002 Husted et al.
6,375,209 B1 4/2002 Schlangen et al.
6,377,906 B1 4/2002 Rowe et al.
6,386,576 B1 5/2002 Kamen et al.
6,388,580 B1 5/2002 Graham et al.
6,397,046 B1 5/2002 Kfoury et al.
6,405,816 B1 6/2002 Kamen et al.
6,408,240 B1 6/2002 Morrell et al.
6,415,215 B1 7/2002 Nishizaki et al.
6,415,879 B2 7/2002 Kamen et al.
6,416,272 B1 7/2002 Suehiro et al.
6,435,535 B1 8/2002 Field et al.
6,435,538 B2 8/2002 Ellis et al.
D462,329 S 9/2002 Hughes et al.
6,443,250 B1 9/2002 Kamen et al.
6,443,251 B1 9/2002 Morrell et al.
6,446,320 B2 9/2002 Kilgore et al.
6,463,369 B2 10/2002 Sadano et al.
D466,122 S 11/2002 Moody et al.
6,484,829 B1 11/2002 Cox et al.
D466,516 S 12/2002 Peiker et al.
6,502,011 B2 12/2002 Haag et al.
6,508,319 B1 1/2003 Langenfeld et al.
D470,084 S 2/2003 Schlough et al.
6,538,411 B1 3/2003 Field et al.
6,543,564 B1 4/2003 Kamen et al.
6,543,848 B1 4/2003 Yasuo et al.
6,543,858 B1 4/2003 Melton et al.
6,547,026 B2 4/2003 Kamen et al.
6,553,271 B1 4/2003 Morrell et al.
6,554,250 B2 4/2003 Alves et al.
6,556,909 B2 4/2003 Matsumoto et al.
6,561,294 B1 5/2003 Kamen et al.
6,562,511 B2 5/2003 Daroux et al.
6,571,176 B1 5/2003 Shinmura et al.
6,571,892 B2 6/2003 Kamen et al.
6,575,539 B2 6/2003 Reich et al.
6,581,714 B1 6/2003 Kamen et al.
6,582,181 B2 6/2003 Suehiro et al.
6,586,901 B1 7/2003 Singer et al.
6,593,849 B2 7/2003 Chubb et al.
6,598,941 B2 7/2003 Field et al.
6,614,343 B1 9/2003 Fennel et al.
6,615,938 B2 9/2003 Morrell et al.
6,634,451 B2 10/2003 Sakakiyama et al.
6,643,451 B1 11/2003 Tokura et al.
6,647,248 B1 11/2003 Ortscheid et al.
6,651,763 B1 11/2003 Kamen et al.
6,651,766 B2 11/2003 Kamen et al.
6,654,674 B2 11/2003 Lu et al.
6,654,675 B2 11/2003 Pedersen et al.
6,659,211 B2 12/2003 Esposito et al.
6,659,570 B2 12/2003 Nakamura et al.
D485,279 S 1/2004 DeCombe et al.
6,694,225 B2 2/2004 Aga et al.
6,704,622 B2 3/2004 Tinskey et al.
6,713,693 B1 3/2004 Sadowski et al.
D489,027 S 4/2004 Waters et al.
D489,029 S 4/2004 Waters et al.
D489,300 S 5/2004 Chang et al.
6,752,231 B2 6/2004 Hume et al.
D493,127 S 7/2004 Waters et al.
D493,128 S 7/2004 Waters et al.
D493,801 S 8/2004 Byun et al.
D494,099 S 8/2004 Maurer et al.
6,779,621 B2 8/2004 Kamen et al.
6,781,960 B1 8/2004 Charas et al.
6,789,640 B1 9/2004 Arling et al.
6,793,258 B2 9/2004 Gray et al.
6,796,396 B2 9/2004 Kamen et al.
6,799,649 B2 10/2004 Kamen et al.
6,827,163 B2 12/2004 Amsbury et al.
6,856,326 B1 2/2005 Zhai et al.
D503,402 S 3/2005 Su et al.
6,866,107 B2 3/2005 Heinzmann et al.
6,868,931 B2 3/2005 Morrell et al.
D503,928 S 4/2005 Obata et al.
6,874,591 B2 4/2005 Morrell et al.
6,889,784 B2 5/2005 Troll et al.
6,907,949 B1 6/2005 Wang et al.
D507,206 S 7/2005 Wang et al.
6,920,947 B2 7/2005 Kamen et al.
6,938,923 B2 9/2005 Mulhern et al.
6,957,867 B1 10/2005 Su et al.
6,962,383 B2 11/2005 Takenoshita et al.
6,965,206 B2 11/2005 Kamen et al.
6,969,079 B2 11/2005 Kamen et al.
7,000,933 B2 2/2006 Arling et al.
7,004,271 B1 2/2006 Kamen et al.
7,006,901 B2 2/2006 Wang et al.
D517,086 S 3/2006 Siebel et al.
7,017,686 B2 3/2006 Kamen et al.
D521,017 S 5/2006 Jewitt et al.
7,040,713 B2 5/2006 Rudolf et al.
7,052,023 B2 5/2006 Chen et al.
D524,315 S 7/2006 Reusing et al.
7,090,040 B2 8/2006 Kamen et al.
D528,468 S 9/2006 Arling et al.
D529,005 S 9/2006 Hong et al.
7,102,328 B2 9/2006 Long et al.
7,130,702 B2 10/2006 Morrell et al.
7,174,976 B2 2/2007 Kamen et al.

(56) References Cited

U.S. PATENT DOCUMENTS

| | | | |
|---|---|---|---|
| 7,178,611 | B2 | 2/2007 | Zupanick et al. |
| 7,178,614 | B2 | 2/2007 | Ishii et al. |
| 7,182,166 | B2 | 2/2007 | Gray et al. |
| 7,185,910 | B2 | 3/2007 | Beauchesne et al. |
| D539,810 | S | 4/2007 | Cummins et al. |
| 7,198,223 | B2 | 4/2007 | Phelps, III et al. |
| 7,210,544 | B2 | 5/2007 | Kamen et al. |
| 7,219,912 | B2 | 5/2007 | Meyer et al. |
| D544,486 | S | 6/2007 | Hussaini et al. |
| 7,234,779 | B2 | 6/2007 | Bedford et al. |
| D546,782 | S | 7/2007 | Poulet et al. |
| D549,721 | S | 8/2007 | Ito et al. |
| D549,722 | S | 8/2007 | Ito et al. |
| D551,592 | S | 9/2007 | Chang et al. |
| D551,722 | S | 9/2007 | Chang et al. |
| 7,272,681 | B2 | 9/2007 | Davies et al. |
| 7,273,116 | B2 | 9/2007 | Kamen et al. |
| D552,030 | S | 10/2007 | Wright et al. |
| D552,609 | S | 10/2007 | Kornblum et al. |
| 7,275,607 | B2 | 10/2007 | Kamen et al. |
| D556,149 | S | 11/2007 | Kaufhold et al. |
| D557,220 | S | 12/2007 | Ewringmann et al. |
| D557,221 | S | 12/2007 | Ewringmann et al. |
| 7,303,032 | B2 | 12/2007 | Kahlert et al. |
| 7,316,441 | B2 | 1/2008 | Iwatani et al. |
| D563,895 | S | 3/2008 | Stuckmann et al. |
| D564,033 | S | 3/2008 | Itskov et al. |
| 7,363,993 | B2 | 4/2008 | Ishii et al. |
| 7,370,713 | B1 | 5/2008 | Kamen et al. |
| 7,399,035 | B2 | 7/2008 | Kusanagi et al. |
| D576,932 | S | 9/2008 | Strehler et al. |
| D579,417 | S | 10/2008 | Stuckmann et al. |
| D582,848 | S | 12/2008 | Johansson et al. |
| 7,481,291 | B2 | 1/2009 | Nishikawa et al. |
| D585,906 | S | 2/2009 | Berg et al. |
| D587,660 | S | 3/2009 | Lin et al. |
| D591,699 | S | 5/2009 | Correll et al. |
| 7,539,557 | B2 | 5/2009 | Yamauchi et al. |
| 7,546,889 | B2 | 6/2009 | Kamen et al. |
| D598,927 | S | 8/2009 | Hirsch et al. |
| 7,589,643 | B2 | 9/2009 | Dagci et al. |
| 7,592,900 | B2 | 9/2009 | Kamen et al. |
| D601,922 | S | 10/2009 | Imai et al. |
| 7,640,086 | B2 | 12/2009 | Nakashima et al. |
| D610,058 | S | 2/2010 | Wilson et al. |
| 7,688,191 | B2 | 3/2010 | Lu et al. |
| 7,690,447 | B2 | 4/2010 | Kamen et al. |
| 7,690,452 | B2 | 4/2010 | Kamen et al. |
| 7,703,568 | B2 | 4/2010 | Ishii et al. |
| D614,998 | S | 5/2010 | Fujita et al. |
| 7,740,099 | B2 | 6/2010 | Field et al. |
| D619,945 | S | 7/2010 | Sadanowicz et al. |
| 7,757,794 | B2 | 7/2010 | Heinzmann et al. |
| 7,784,816 | B2 | 8/2010 | Jian et al. |
| 7,789,174 | B2 | 9/2010 | Kamen et al. |
| 7,823,676 | B2 | 11/2010 | Yamada et al. |
| 7,856,248 | B1 | 12/2010 | Fujisaki et al. |
| 7,857,088 | B2 | 12/2010 | Field et al. |
| D632,229 | S | 2/2011 | Kruse et al. |
| 7,896,440 | B2 | 3/2011 | Tsai et al. |
| 7,900,725 | B2 | 3/2011 | Heinzmann et al. |
| 7,917,097 | B2 | 3/2011 | Hawkins et al. |
| D636,301 | S | 4/2011 | Dammacco et al. |
| 7,934,727 | B1 | 5/2011 | Parry et al. |
| 7,938,207 | B2 | 5/2011 | Kamen et al. |
| 7,958,956 | B2 | 6/2011 | Kakinuma et al. |
| D644,654 | S | 9/2011 | Maitlen et al. |
| 8,011,459 | B2 | 9/2011 | Serai et al. |
| 8,014,923 | B2 | 9/2011 | Ishii et al. |
| 8,025,325 | B1 | 9/2011 | Carrier et al. |
| 8,028,777 | B2 | 10/2011 | Kakinuma et al. |
| 8,050,820 | B2 | 11/2011 | Yanaka et al. |
| 8,050,837 | B2 | 11/2011 | Yamada et al. |
| 8,074,388 | B2 | 12/2011 | Trainer et al. |
| 8,091,672 | B2 | 1/2012 | Gutsch et al. |
| 8,113,244 | B2 | 2/2012 | Kamen et al. |
| 8,151,912 | B2 | 4/2012 | Koide et al. |
| 8,155,828 | B2 | 4/2012 | Fuwa et al. |
| 8,160,794 | B2 | 4/2012 | Fuwa et al. |
| 8,162,089 | B2 | 4/2012 | Shaw et al. |
| 8,170,780 | B2 | 5/2012 | Field et al. |
| 8,170,781 | B2 | 5/2012 | Fuwa et al. |
| 8,172,016 | B2 | 5/2012 | Goertzen et al. |
| 8,186,462 | B2 | 5/2012 | Kamen et al. |
| 8,224,524 | B2 | 7/2012 | Nakashima et al. |
| 8,225,891 | B2 | 7/2012 | Takenaka et al. |
| 8,239,992 | B2 | 8/2012 | Schnittman et al. |
| 8,248,222 | B2 | 8/2012 | Kamen et al. |
| 8,249,773 | B2 | 8/2012 | Kawada et al. |
| 8,255,105 | B2 | 8/2012 | Weissert et al. |
| 8,265,774 | B2 | 9/2012 | Senba et al. |
| 8,269,130 | B2 | 9/2012 | Mangan et al. |
| 8,285,474 | B2 | 10/2012 | Doi et al. |
| 8,312,017 | B2 | 11/2012 | Martin et al. |
| 8,326,469 | B2 | 12/2012 | Phillips et al. |
| 8,346,441 | B2 | 1/2013 | Miki et al. |
| 8,371,410 | B2 | 2/2013 | Fuwa et al. |
| D678,217 | S | 3/2013 | Helm et al. |
| D678,320 | S | 3/2013 | Kanalakis, Jr. et al. |
| 8,396,611 | B2 | 3/2013 | Phillips et al. |
| 8,417,404 | B2 | 4/2013 | Yen et al. |
| 8,418,705 | B2 | 4/2013 | Ota et al. |
| 8,453,768 | B2 | 6/2013 | Kamen et al. |
| 8,467,941 | B2 | 6/2013 | Field et al. |
| D686,200 | S | 7/2013 | Huang et al. |
| 8,490,723 | B2 | 7/2013 | Heinzmann et al. |
| 8,504,248 | B2 | 8/2013 | Taira et al. |
| 8,564,444 | B2 | 10/2013 | Ota et al. |
| 8,572,822 | B2 | 11/2013 | Hasegawa et al. |
| 8,584,782 | B2 | 11/2013 | Chen et al. |
| 8,587,583 | B2 | 11/2013 | Newcombe et al. |
| 8,608,190 | B2 | 12/2013 | Mountz et al. |
| 8,621,684 | B2 | 1/2014 | Okumatsu et al. |
| 8,636,451 | B2 | 1/2014 | Yamashita et al. |
| 8,639,416 | B2 | 1/2014 | Jones et al. |
| 8,640,807 | B2 | 2/2014 | Takenaka et al. |
| 8,646,150 | B2 | 2/2014 | Okabe et al. |
| 8,672,339 | B2 | 3/2014 | Raike, III et al. |
| 8,672,356 | B2 | 3/2014 | Inaguma et al. |
| 8,681,498 | B2 | 3/2014 | Akiyama et al. |
| 8,684,123 | B2 | 4/2014 | Chen et al. |
| 8,690,265 | B2 | 4/2014 | Noblanc et al. |
| D704,621 | S | 5/2014 | Taylor et al. |
| D705,799 | S | 5/2014 | Funabashi et al. |
| 8,738,238 | B2 | 5/2014 | Rekow et al. |
| 8,738,278 | B2 | 5/2014 | Chen et al. |
| D706,217 | S | 6/2014 | McKune et al. |
| D706,807 | S | 6/2014 | Harre et al. |
| D707,701 | S | 6/2014 | D'Amore et al. |
| 8,744,720 | B1 | 6/2014 | Fujisaki et al. |
| 8,753,208 | B2 | 6/2014 | Jaouen et al. |
| D708,203 | S | 7/2014 | Johnson et al. |
| 8,775,001 | B2 | 7/2014 | Phillips et al. |
| 8,807,250 | B2 | 8/2014 | Chen et al. |
| 8,830,048 | B2 | 9/2014 | Kamen et al. |
| 8,832,875 | B2 | 9/2014 | Odashima et al. |
| 8,843,244 | B2 | 9/2014 | Phillips et al. |
| D716,325 | S | 10/2014 | Brudnicki et al. |
| 8,860,551 | B2 | 10/2014 | Carraher et al. |
| D716,818 | S | 11/2014 | Alegiani et al. |
| D721,315 | S | 1/2015 | Delavy et al. |
| 8,925,563 | B2 | 1/2015 | Ota et al. |
| 8,958,976 | B2 | 2/2015 | Kajima et al. |
| D723,558 | S | 3/2015 | Downs et al. |
| 8,978,791 | B2 | 3/2015 | Ha et al. |
| 9,002,535 | B2 | 4/2015 | Powers et al. |
| 9,016,410 | B2 | 4/2015 | Trowell et al. |
| D729,270 | S | 5/2015 | Clare et al. |
| D729,833 | S | 5/2015 | Clare et al. |
| 9,038,212 | B2 | 5/2015 | Yamaguchi et al. |
| D732,062 | S | 6/2015 | Kwon et al. |
| 9,045,190 | B2 | 6/2015 | Chen et al. |
| 9,056,629 | B2 | 6/2015 | Kamo et al. |
| 9,079,039 | B2 | 7/2015 | Carlson et al. |

(56) References Cited

U.S. PATENT DOCUMENTS 9,096,281 B1 8/2015 Li et al.
D738,907 S 9/2015 Cabrera-Cordon et al.
D738,913 S 9/2015 Cabrera-Cordon et al.
9,126,497 B2 9/2015 Heinzmann et al.
9,156,516 B2 10/2015 Kahlert et al.
D742,300 S 11/2015 Fontaeus et al.
D742,407 S 11/2015 Park et al.
D742,795 S 11/2015 Siao et al.
9,187,071 B2 11/2015 Vinck et al.
9,193,066 B2 11/2015 Ohm et al.
9,218,003 B2 12/2015 Fong et al.
D747,352 S 1/2016 Lee et al.
D750,179 S 2/2016 Foulkes et al.
D752,572 S 3/2016 Kohler et al.
9,278,036 B2 3/2016 Lee et al.
9,309,692 B2 4/2016 Westwinkel et al.
D755,785 S 5/2016 Sirotich et al.
D757,732 S 5/2016 Galanti et al.
9,327,745 B2 5/2016 Tsai et al.
9,338,907 B2 5/2016 Bell et al.
D758,284 S 6/2016 Ringer et al.
D762,179 S 7/2016 Wong et al.
9,400,044 B2 7/2016 Wadhva et al.
D763,359 S 8/2016 Kwong et al.
D764,520 S 8/2016 Lee et al.
9,403,566 B2 8/2016 Jacobsen et al.
9,404,756 B2 8/2016 Fong et al.
D765,718 S 9/2016 Vinna et al.
D766,312 S 9/2016 Hedges et al.
9,455,104 B1 9/2016 Leusenkamp et al.
D769,314 S 10/2016 Piroddi et al.
D770,514 S 11/2016 Bae et al.
D771,574 S 11/2016 Hultquist et al.
D772,255 S 11/2016 Taylor et al.
D772,924 S 11/2016 Begin et al.
D772,930 S 11/2016 Vazquez et al.
D775,148 S 12/2016 Anzures et al.
D775,345 S 12/2016 Aguirre et al.
9,527,213 B2 12/2016 Luo et al.
D778,312 S 2/2017 Goodwin et al.
9,567,021 B2 2/2017 Mailey et al.
D784,296 S 4/2017 Katsuno et al.
D784,405 S 4/2017 Kim et al.
D786,278 S 5/2017 Motamedi et al.
D786,770 S 5/2017 Smallhorn et al.
D787,420 S 5/2017 Smallhorn et al.
D787,996 S 5/2017 Rode et al.
9,636,265 B2 5/2017 Furuta et al.
9,637,149 B1 5/2017 Wang et al.
9,656,704 B2 * 5/2017 Couture .................. B25J 5/005
9,662,438 B2 5/2017 Kamen et al.
D791,174 S 7/2017 Hart et al.
D791,649 S 7/2017 Zhou et al.
D792,444 S 7/2017 Cho et al.
D793,914 S 8/2017 Eriksson et al.
D793,930 S 8/2017 Rode et al.
D794,674 S 8/2017 Brush et al.
9,730,029 B2 8/2017 Choudhury et al.
9,744,879 B2 8/2017 Drako et al.
D797,772 S 9/2017 Mizono et al.
D798,318 S 9/2017 Ferguson et al.
9,750,896 B2 9/2017 Kamen et al.
9,752,652 B2 9/2017 Moore et al.
9,770,825 B2 9/2017 Goldenberg et al.
D801,996 S 11/2017 Yang et al.
D802,002 S 11/2017 Howard et al.
D804,393 S 12/2017 Yoo et al.
D805,972 S 12/2017 Lee et al.
D805,973 S 12/2017 Mullaney et al.
D807,235 S 1/2018 Collins et al.
D807,236 S 1/2018 Collins et al.
D807,277 S 1/2018 Lee et al.
9,894,971 B2 2/2018 Scicluna et al.
D812,533 S 3/2018 Lee et al.
D812,571 S 3/2018 Jackson et al.
D814,370 S 4/2018 Kim et al.
D816,090 S 4/2018 Stonecipher et al.
9,974,467 B2 5/2018 Blahnik et al.
D821,410 S 6/2018 Vinna et al.
9,989,970 B1 6/2018 Morey et al.
9,996,157 B2 6/2018 Chaudhri et al.
10,007,391 B2 6/2018 Sabatelli et al.
10,025,472 B2 7/2018 Sabatelli et al.
D825,437 S 8/2018 Hilton et al.
D825,493 S 8/2018 Chen et al.
D825,497 S 8/2018 Mizushi et al.
D826,244 S 8/2018 Yampolskaya et al.
D826,255 S 8/2018 Andrizzi et al.
10,055,108 B2 8/2018 Bates et al.
10,055,184 B1 8/2018 Ferrell et al.
D827,939 S 9/2018 Jakubowski et al.
D829,612 S 10/2018 Collins et al.
D829,740 S 10/2018 Lepine et al.
D830,304 S 10/2018 Choi et al.
D830,384 S 10/2018 Lepine et al.
D830,385 S 10/2018 Lepine et al.
D830,386 S 10/2018 Lepine et al.
D831,046 S 10/2018 Hashimoto et al.
D832,289 S 10/2018 Chen et al.
10,088,993 B2 10/2018 Hall et al.
10,111,335 B2 10/2018 Furuta et al.
D833,930 S 11/2018 Curtin et al.
10,127,250 B2 11/2018 Dingman et al.
10,130,534 B2 11/2018 Mattes et al.
D835,049 S 12/2018 Wilcox et al.
D835,118 S 12/2018 Lee et al.
D835,139 S 12/2018 Li et al.
D835,141 S 12/2018 Li et al.
D835,632 S 12/2018 Liu et al.
10,149,589 B2 12/2018 Lindhé et al.
D838,731 S 1/2019 Pillalamarri et al.
10,172,752 B2 1/2019 Goffer et al.
D840,413 S 2/2019 Leach et al.
D841,021 S 2/2019 Klar et al.
D841,022 S 2/2019 Klar et al.
D841,676 S 2/2019 Zhang et al.
D841,687 S 2/2019 Müller et al.
D842,897 S 3/2019 Kumar et al.
10,220,843 B2 3/2019 Coulter et al.
10,229,245 B2 3/2019 Laurance et al.
10,230,538 B2 3/2019 Killian et al.
10,235,014 B2 3/2019 Yang et al.
D844,622 S 4/2019 Collins et al.
D845,833 S 4/2019 Asai et al.
D846,452 S 4/2019 Collins et al.
D846,504 S 4/2019 Yang et al.
D847,161 S 4/2019 Chaudhri et al.
10,266,097 B2 4/2019 Takahata et al.
10,272,294 B2 4/2019 Williams et al.
D847,836 S 5/2019 Thoreson et al.
10,296,167 B2 5/2019 Liu et al.
10,296,194 B2 5/2019 McLean et al.
10,318,589 B2 6/2019 Sharp et al.
D854,025 S 7/2019 Rad et al.
10,338,776 B2 7/2019 Andersson et al.
D855,634 S 8/2019 Kim et al.
10,372,304 B2 8/2019 Jaramillo, III et al.
10,379,695 B2 8/2019 Carlos et al.
10,386,942 B2 8/2019 Kim et al.
D860,231 S 9/2019 Hussain et al.
10,423,283 B2 9/2019 Ikeda et al.
D861,558 S 10/2019 Huang et al.
10,474,737 B1 11/2019 Girsova et al.
D874,492 S 2/2020 Henderson et al.
D881,214 S 4/2020 Zimmerman et al.
D881,903 S 4/2020 Lepine et al.
10,613,524 B2 4/2020 Marsolek et al.
D884,010 S 5/2020 Lenz, Jr. et al.
D886,148 S 6/2020 Lepine et al.
D896,255 S 9/2020 Yan et al.
D897,357 S 9/2020 Niijima et al.
10,788,927 B2 9/2020 Anzures et al.
10,799,406 B2 10/2020 Minardo et al.
D903,591 S 12/2020 Norris et al.

(56) References Cited

U.S. PATENT DOCUMENTS 10,893,028 B2 1/2021 Dattolo et al.
D909,407 S 2/2021 Lepine et al.
10,908,045 B2 * 2/2021 Coulter ................ G05D 1/0274
D915,248 S 4/2021 Collins et al.
D926,131 S 7/2021 Norris et al.
2001/0006125 A1 7/2001 Richey et al.
2001/0037163 A1 11/2001 Allard et al.
2002/0007239 A1 1/2002 Matsumoto et al.
2002/0011361 A1 1/2002 Richey et al.
2002/0056582 A1 5/2002 Chubb et al.
2002/0063006 A1 5/2002 Kamen et al.
2002/0074189 A1 6/2002 Hester et al.
2002/0082749 A1 6/2002 Meyers et al.
2002/0121394 A1 9/2002 Kamen et al.
2002/0121572 A1 9/2002 Jacobson et al.
2002/0189870 A1 12/2002 Kamen et al.
2003/0014167 A1 1/2003 Pedersen et al.
2003/0128840 A1 7/2003 Luginbill et al.
2003/0226698 A1 12/2003 Kamen et al.
2004/0005958 A1 1/2004 Kamen et al.
2004/0007121 A1 1/2004 Graves et al.
2004/0007399 A1 1/2004 Heinzmann et al.
2004/0007644 A1 1/2004 Phelps et al.
2004/0055796 A1 3/2004 Kamen et al.
2004/0069543 A1 4/2004 Kamen et al.
2004/0124655 A1 7/2004 Takenoshita et al.
2004/0135434 A1 7/2004 Honda et al.
2004/0201271 A1 10/2004 Kakinuma et al.
2004/0256886 A1 12/2004 Wu et al.
2004/0262871 A1 12/2004 Schreuder et al.
2005/0027396 A1 2/2005 Yang et al.
2005/0029023 A1 2/2005 Takami et al.
2005/0121866 A1 6/2005 Kamen et al.
2005/0134014 A1 6/2005 Xie et al.
2005/0211477 A1 9/2005 Gray et al.
2005/0236208 A1 10/2005 Runkles et al.
2005/0236894 A1 10/2005 Lu et al.
2005/0251292 A1 11/2005 Casey et al.
2005/0285357 A1 12/2005 Lin et al.
2006/0091706 A1 5/2006 Christofferson et al.
2006/0108956 A1 5/2006 Clark et al.
2006/0163437 A1 7/2006 Lin et al.
2006/0187646 A1 8/2006 Belson et al.
2006/0202439 A1 9/2006 Kahlert et al.
2006/0231313 A1 10/2006 Ishii et al.
2006/0259224 A1 11/2006 Auer et al.
2006/0279554 A1 12/2006 Shin et al.
2006/0293850 A1 12/2006 Ahn et al.
2007/0001830 A1 1/2007 Dagci et al.
2007/0055424 A1 3/2007 Peters et al.
2007/0085300 A1 4/2007 Loewenthal et al.
2007/0100511 A1 5/2007 Koerlin et al.
2007/0156286 A1 7/2007 Yamauchi et al.
2007/0208483 A1 9/2007 Rabin et al.
2007/0213900 A1 9/2007 Raab et al.
2007/0216205 A1 9/2007 Davis et al.
2007/0221423 A1 9/2007 Chang et al.
2007/0296170 A1 12/2007 Field et al.
2008/0029985 A1 2/2008 Chen et al.
2008/0042379 A1 2/2008 Amran et al.
2008/0066974 A1 3/2008 Pearlman et al.
2008/0086241 A1 4/2008 Phillips et al.
2008/0106053 A1 5/2008 Tsai et al.
2008/0147281 A1 6/2008 Ishii et al.
2008/0149798 A1 6/2008 Tinoco et al.
2008/0174415 A1 7/2008 Tanida et al.
2008/0197599 A1 8/2008 Comstock et al.
2008/0238005 A1 10/2008 James et al.
2008/0294288 A1 11/2008 Yamauchi et al.
2008/0302938 A1 12/2008 Goodwin et al.
2009/0009984 A1 1/2009 Mangiardi et al.
2009/0032323 A1 2/2009 Kakinuma et al.
2009/0037033 A1 2/2009 Phillips et al.
2009/0045025 A1 2/2009 Bassett et al.
2009/0078485 A1 3/2009 Gutsch et al.
2009/0105908 A1 4/2009 Casey et al.
2009/0115149 A1 5/2009 Wallis et al.
2009/0224524 A1 9/2009 Rathsack et al.
2010/0025139 A1 2/2010 Kosaka et al.
2010/0107076 A1 4/2010 Grohman et al.
2010/0114468 A1 5/2010 Field et al.
2010/0121538 A1 5/2010 Ishii et al.
2010/0126787 A1 5/2010 Kawada et al.
2010/0138128 A1 6/2010 Strothmann et al.
2010/0222994 A1 9/2010 Field et al.
2010/0230919 A1 9/2010 Kawada et al.
2010/0235028 A1 9/2010 Ishii et al.
2010/0237645 A1 9/2010 Trainer et al.
2010/0250040 A1 9/2010 Yamano et al.
2011/0035101 A1 2/2011 Kawada et al.
2011/0054717 A1 3/2011 Yamauchi et al.
2011/0106339 A1 5/2011 Phillips et al.
2011/0123286 A1 5/2011 Van Roosmalen et al.
2011/0175329 A1 7/2011 Gingras et al.
2011/0209929 A1 9/2011 Heinzmann et al.
2011/0215540 A1 9/2011 Hunziker et al.
2011/0220427 A1 9/2011 Chen et al.
2011/0221160 A1 9/2011 Shaw et al.
2011/0225417 A1 9/2011 Maharajh et al.
2011/0238247 A1 9/2011 Yen et al.
2011/0285195 A1 11/2011 Ratgen et al.
2012/0019554 A1 1/2012 Narimatu et al.
2012/0046821 A1 2/2012 Pettersson et al.
2012/0072052 A1 3/2012 Powers et al.
2012/0168240 A1 7/2012 Wilson et al.
2012/0174037 A1 7/2012 Relyea et al.
2012/0185091 A1 7/2012 Field et al.
2012/0185094 A1 7/2012 Rosenstein et al.
2012/0197470 A1 8/2012 Inui et al.
2012/0205176 A1 8/2012 Ha et al.
2012/0215355 A1 8/2012 Bewley et al.
2012/0219395 A1 8/2012 Inaguma et al.
2012/0239284 A1 9/2012 Field et al.
2012/0290162 A1 11/2012 Stevens et al.
2012/0313335 A1 12/2012 Zanderlehn et al.
2013/0032422 A1 2/2013 Chen et al.
2013/0032423 A1 2/2013 Chen et al.
2013/0080015 A1 3/2013 Strothmann et al.
2013/0081885 A1 4/2013 Connor et al.
2013/0105239 A1 5/2013 Fung et al.
2013/0146409 A1 6/2013 Boyle et al.
2013/0188809 A1 7/2013 Jones et al.
2013/0218380 A1 8/2013 Phillips et al.
2013/0228385 A1 9/2013 Chen et al.
2013/0231814 A1 9/2013 Sarokhan et al.
2013/0253769 A1 9/2013 Kamo et al.
2013/0332064 A1 12/2013 Funk et al.
2014/0005933 A1 1/2014 Fong et al.
2014/0018994 A1 1/2014 Panzarella et al.
2014/0034400 A1 2/2014 Underwood et al.
2014/0058600 A1 2/2014 Hoffmann et al.
2014/0083225 A1 3/2014 Downs et al.
2014/0088761 A1 3/2014 Shamlian et al.
2014/0187237 A1 7/2014 Li et al.
2014/0202777 A1 7/2014 Lee et al.
2014/0246257 A1 9/2014 Jacobsen et al.
2014/0246258 A1 9/2014 Wyrobek et al.
2014/0277888 A1 9/2014 Dastoor et al.
2014/0371979 A1 12/2014 Drew et al.
2015/0006005 A1 1/2015 Yu et al.
2015/0012057 A1 1/2015 Carlson et al.
2015/0060162 A1 3/2015 Goffer et al.
2015/0112264 A1 4/2015 Kamen et al.
2015/0119289 A1 4/2015 Chen et al.
2015/0123453 A1 5/2015 Benoit, Jr. et al.
2015/0197247 A1 7/2015 Ichinokawa et al.
2015/0198440 A1 7/2015 Pearlman et al.
2015/0231891 A1 8/2015 Yashiro et al.
2015/0245962 A1 9/2015 Furuta et al.
2015/0246703 A1 9/2015 Oishi et al.
2015/0251713 A1 * 9/2015 Couture ............... B62D 55/075
901/1
2015/0289653 A1 10/2015 Hector et al.
2015/0342517 A1 12/2015 Rabischong et al.

(56) References Cited

U.S. PATENT DOCUMENTS

| | | | |
|---|---|---|---|
| 2016/0014252 A1 | 1/2016 | Biderman et al. | |
| 2016/0031497 A1 | 2/2016 | Luo et al. | |
| 2016/0035161 A1 | 2/2016 | Friedli et al. | |
| 2016/0036949 A1 | 2/2016 | Holden et al. | |
| 2016/0069691 A1 | 3/2016 | Fong et al. | |
| 2016/0075535 A1 | 3/2016 | Ooms et al. | |
| 2016/0101685 A1 | 4/2016 | Darpino et al. | |
| 2016/0144505 A1 | 5/2016 | Fong et al. | |
| 2016/0170411 A1 | 6/2016 | Wei et al. | |
| 2016/0264019 A1 | 9/2016 | Drako et al. | |
| 2016/0291848 A1 | 10/2016 | Hall et al. | |
| 2016/0362147 A1 | 12/2016 | Mailey et al. | |
| 2017/0052033 A1 | 2/2017 | Fong et al. | |
| 2017/0080967 A1 | 3/2017 | Atkins et al. | |
| 2017/0101685 A1 | 4/2017 | Lo et al. | |
| 2017/0176188 A1 | 6/2017 | Georgy et al. | |
| 2017/0225321 A1 | 8/2017 | Deyle et al. | |
| 2017/0240169 A1 | 8/2017 | Coulter et al. | |
| 2017/0243365 A1 | 8/2017 | Nuijten et al. | |
| 2017/0259811 A1* | 9/2017 | Coulter ............... | B60W 30/143 |
| 2017/0300058 A1 | 10/2017 | Peret et al. | |
| 2017/0362147 A1 | 12/2017 | Jun et al. | |
| 2018/0024553 A1 | 1/2018 | Kong et al. | |
| 2018/0056985 A1 | 3/2018 | Coulter et al. | |
| 2018/0102227 A1 | 4/2018 | Poon et al. | |
| 2018/0143801 A1 | 5/2018 | Stucker et al. | |
| 2018/0146757 A1 | 5/2018 | Singh Johar et al. | |
| 2018/0164829 A1 | 6/2018 | Oshima et al. | |
| 2018/0185212 A1 | 7/2018 | Lucas et al. | |
| 2018/0203522 A1 | 7/2018 | Stucki et al. | |
| 2018/0253220 A1 | 9/2018 | Tuhami et al. | |
| 2019/0025853 A1 | 1/2019 | Julian et al. | |
| 2019/0038487 A1 | 2/2019 | Cherny et al. | |
| 2019/0046373 A1 | 2/2019 | Coulter et al. | |
| 2019/0224057 A1 | 7/2019 | Jordan et al. | |
| 2019/0231617 A1 | 8/2019 | Cazali et al. | |
| 2019/0269567 A1 | 9/2019 | Kao et al. | |
| 2020/0008990 A1 | 1/2020 | Harrison et al. | |
| 2024/0398637 A1* | 12/2024 | van der Merwe ... | A61G 5/1089 |

FOREIGN PATENT DOCUMENTS

| | | | |
|---|---|---|---|
| CA | 2822729 | A1 | 3/2006 |
| CA | 2897221 | A1 | 3/2006 |
| CA | 2897542 | A1 | 1/2016 |
| CN | 101056680 | A | 10/2007 |
| CN | 104071275 | A | 10/2014 |
| DE | 2048593 | A1 | 5/1971 |
| DE | 3103961 | A1 | 9/1982 |
| DE | 3128112 | A1 | 2/1983 |
| DE | 3242880 | A1 | 6/1983 |
| DE | 3411489 | A1 | 10/1984 |
| DE | 4110905 | A1 | 10/1991 |
| DE | 4404594 | A1 | 8/1995 |
| DE | 19625498 | C1 | 11/1997 |
| DE | 29808091 | U1 | 8/1998 |
| DE | 29808096 | U1 | 8/1998 |
| DE | 10209093 | A1 | 9/2003 |
| EP | 0109927 | A2 | 5/1984 |
| EP | 0193473 | A1 | 9/1986 |
| EP | 0537698 | A1 | 4/1993 |
| EP | 0551986 | A1 | 7/1993 |
| EP | 0663313 | A1 | 7/1995 |
| EP | 0746089 | A1 | 12/1996 |
| EP | 0958978 | A2 | 11/1999 |
| EP | 1063530 | A1 | 12/2000 |
| EP | 1759973 | A1 | 3/2007 |
| EP | 1791609 | A1 | 6/2007 |
| EP | 1805071 | A1 | 7/2007 |
| FR | 980237 | A | 3/1908 |
| FR | 2502090 | A1 | 9/1982 |
| GB | 152664 | A | 1/1922 |
| GB | 1213930 | A | 11/1970 |
| GB | 2139576 | A | 11/1984 |
| GB | 2388579 | A | 11/2003 |
| JP | S5244933 | A | 4/1977 |
| JP | S5243795 | B2 | 11/1977 |
| JP | S5787766 | A | 6/1982 |
| JP | S57110569 | A | 7/1982 |
| JP | S5973372 | A | 4/1984 |
| JP | S60255580 | A | 12/1985 |
| JP | S615415 | A | 1/1986 |
| JP | S6212810 | A | 1/1987 |
| JP | S63305082 | A | 12/1988 |
| JP | H01316810 | A | 12/1989 |
| JP | H02190277 | A | 7/1990 |
| JP | H04201793 | A | 7/1992 |
| JP | H05213240 | A | 8/1993 |
| JP | H06171562 | A | 6/1994 |
| JP | H07255780 | A | 10/1995 |
| JP | H0910375 | A | 1/1997 |
| JP | H09248320 | A | 9/1997 |
| JP | H1023613 | A | 1/1998 |
| JP | 2000070308 | A | 3/2000 |
| JP | 2000288032 | A | 10/2000 |
| JP | 2004/135747 | A | 5/2004 |
| JP | 2005/022631 | A | 1/2005 |
| JP | 2007069688 | A | 3/2007 |
| JP | D1314974 | S | 11/2007 |
| JP | D1323922 | S | 3/2008 |
| JP | 2010240011 | A | 10/2010 |
| JP | 4572594 | B2 | 11/2010 |
| JP | 2010274759 | A | 12/2010 |
| JP | 4687784 | B2 | 5/2011 |
| JP | 2011246124 | A | 12/2011 |
| JP | 5243795 | B2 | 7/2013 |
| JP | 2014019212 | A | 2/2014 |
| JP | 2014174275 | A | 9/2014 |
| JP | 2014195403 | A | 10/2014 |
| JP | 2014204544 | A | 10/2014 |
| JP | 2014218247 | A | 11/2014 |
| JP | 2015/070897 | A | 4/2015 |
| JP | 2015171895 | A | 10/2015 |
| JP | 2015186321 | A | 10/2015 |
| JP | 2016012918 | A | 1/2016 |
| JP | 2016084135 | A | 5/2016 |
| JP | 2018062344 | A | 4/2018 |
| TW | D124942 | B2 | 9/2008 |
| TW | D124942 | S | 9/2008 |
| TW | D124943 | S | 9/2008 |
| WO | 8605752 | A1 | 10/1986 |
| WO | 8906117 | A1 | 7/1989 |
| WO | 9623478 | A1 | 8/1996 |
| WO | WO1997045038 | A1 | 12/1997 |
| WO | WO1998002122 | A1 | 1/1998 |
| WO | 9846474 | A2 | 10/1998 |
| WO | 9911488 | A1 | 3/1999 |
| WO | WO1999018907 | A1 | 4/1999 |
| WO | WO1999048459 | A1 | 9/1999 |
| WO | 0023315 | A2 | 4/2000 |
| WO | 0054719 | A1 | 9/2000 |
| WO | 0054721 | A2 | 9/2000 |
| WO | WO2000054720 | A1 | 9/2000 |
| WO | 0075001 | A1 | 12/2000 |
| WO | WO2000073101 | A1 | 12/2000 |
| WO | 0102920 | A1 | 1/2001 |
| WO | WO2001015962 | A1 | 3/2001 |
| WO | WO2001042077 | A2 | 6/2001 |
| WO | 0230730 | A2 | 4/2002 |
| WO | WO2002030730 | A2 | 4/2002 |
| WO | 02072383 | A1 | 9/2002 |
| WO | 03068342 | A1 | 8/2003 |
| WO | 03103559 | A2 | 12/2003 |
| WO | 03106250 | A2 | 12/2003 |
| WO | WO2003106250 | A2 | 12/2003 |
| WO | 2004007264 | A1 | 1/2004 |
| WO | WO2004007233 | A2 | 1/2004 |
| WO | WO 2004/078603 | A2 | 9/2004 |
| WO | WO2005032797 | A1 | 4/2005 |
| WO | WO2005036797 | A2 | 4/2005 |
| WO | WO2005036798 | A2 | 4/2005 |
| WO | 2006031917 | A1 | 3/2006 |
| WO | 2006042302 | A1 | 4/2006 |
| WO | 2009052471 | A2 | 4/2009 |

(56) References Cited

FOREIGN PATENT DOCUMENTS

| | | | |
|---|---|---|---|
| WO | 2010084421 | A1 | 7/2010 |
| WO | 2011132491 | A1 | 10/2011 |
| WO | 2012090248 | A1 | 7/2012 |
| WO | 2013096789 | A1 | 6/2013 |
| WO | 2015167411 | A1 | 11/2015 |
| WO | 2017147347 | A1 | 8/2017 |
| WO | 2017156586 | A1 | 9/2017 |
| WO | 2017180868 | A2 | 10/2017 |
| WO | 2017201513 | A1 | 11/2017 |

OTHER PUBLICATIONS

Notice of Allowance mailed Mar. 24, 2021, issued in U.S. Appl. No. 29/757,855, 8 pages.
Notice of Allowance mailed Nov. 18, 2021, issued in U.S. Appl. No. 29/800,990, 8 pages.
Notice of Allowance mailed Oct. 27, 2021, issued in U.S. Appl. No. 15/931,048, 5 pages.
Notice of Allowance mailed Oct. 9, 2020 issued in U.S. Appl. No. 29/733,462, 8 pages.
Notice of Allowance mailed Sep. 30, 2020, issued in U.S. Appl. No. 15/982,737, 13 pages.
Office Action mailed Feb. 4, 2020, issued in U.S. Appl. No. 15/982,737, 19 pages.
Office Action mailed Jun. 9, 2021, issued in U.S. Appl. No. 15/931,048, 9 pages.
Office Action mailed Oct. 21, 2021, issued in U.S. Appl. No. 17/108,575, 10 pages.
Oishi et al., "Building A Smart Wheelchair On A Flexible Software Platform", RESNA International Conference on Technology and Aging, 2011.
Osaka et al., "Stabilization of unicycle", Systems and Control, vol. 25, No. 3, Japan Mar. 1981, pp. 159-166.
Pavroo. "LightScribe technology on Sparky host." Sparky Linux, published Mar. 11, 2015 (Retrieved from the Internet Jan. 15, 2020).
Rasmussen et al."Proximity-based Access Control for Implantable Medical Devices", in Proceedings of the 16th ACM Conference on Computer and Communications Security CCS'09, Nov. 9-13, 2009, Year 2009).
Roy et al., "Five-Wheel Unicycle System", Medical & Biological Engineering & Computing, vol. 23, No. 6, United Kingdom Nov. 1985, pp. 593-596. Entire document can be purchased via: https://link.springer.com/article/10.1007%2FBF02455316.
Sabatini, A, "Quaternion-based Extended Kalman Filter for Determining Orientation by Inertial and Magnetic Sensing", IEEE Transactions on Biomedical Engineering, vol. 53:7, Jul. 2006, pp. 1346-1356.
Schoonwinkel, A., "Design and Test of a Computer-Stabilized Unicycle", Stanford University (1988), UMI Dissertation Services, Dissertation Abstracts International, vol. 49/03-B, Stanford University 1987, pp. 890-1294.
Sheng et al., "Postural Stability of a Human Riding a Unicycle and Its Emulation by a Robot," IEEE Transactions on Robotics and Automation, vol. 13:5, Oct. 1997.
Sheng, Zaiquan; Yamafuji, Kazuo: "Realization of a Human Riding a Unicycle by a Robot". Proceedings of the 1995 IEEE International Conference on Robotics and Automation, vol. 2, 1995, pp. 1319-1326.
Stew's Hovercraft Page, http://www.stewcam.com/hover-craft.html.
Takahashi et al., "Back and Forward Moving Scheme of Front Wheel Raising for Inverse Pendulum Control Wheel Chair Robot", Proceedings of the 2001 IEEE International Conference of Robotics & Automation, Seoul, Korea, May 21-26, 2001, pp. 3189-3194.
Takahashi et al., "Front Wheel Raising and Inverse Pendulum Control of Power Assist Wheel Chair Robot", IEEE, 1999, pp. 668-673.
Tanaka et al., "A Mobile Robot for Service Use: Behaviour Simulation System and Intelligent Control," Proceedings of the 1997 IEEE/RSJ International Conference on Intelligent Robots and Systems, 1997.
TECKNICO'S Home Page, "Those Amazing Flying Machines", http://www.swiftsite.com/technico, May 24, 1999.
Ulyanov et al., "Fuzzy Intelligent Emotion and Instinct Control of a Robotic Unicycle," Proceedings of the 1996 4th International Workshop on Advanced Motion Control, Mar. 18-21, 1996.
Ulyanov et al., "Soft computing for the intelligent robust control of a robotic unicycle with a new physical measure for mechanical controllability". Soft Computing vol. 2:2, Jun. 1998, pp. 73-88.
Umpad, Leomar. "How Do I Use My Samsung Galaxy Device as a TV Remote Control?" Tech Recipes, published Nov. 27, 2014 (Retrieved from the Internet Sep. 27, 2019). Internet URL: <https://www. Tech-recipes.com/rx/51556/ how-do-i-use-my-samsung-galaxy-device-as-a-tv-remote-control/> (Year: 2014).
Viswanathan et al., "Navigation Assistance for Intelligent Wheelchairs", 3rd International Conference on Technology and Aging/RESNA, Toronto, 2011.
Vos et al., "Dynamics and Nonlinear Adaptive Control of an Autonomous Unicycle—Theory and Experiment", American Institute of Aeronautics and Astronautics, A90-26772 10-39, Washington, D.C. 1990, Abstract only.
Vos, D., "Nonlinear Control of an Autonomous Unicycle Robot: Practical Issues", Massachusetts Institute of Technology, Jun. 5, 1992.
Vos, D., Dynamics and Nonlinear Adaptive Control of an Autonomous Unicycle, Massachusetts Institute of Technology, Jun. 7, 1989.
Wang et al., "Real-time Model-based Electrical Powered Wheelchair Control", Med Eng Phys. Dec. 2009: 31(10): 1244-1254.
Watson Industries, Inc., "Single Axis Vertical Reference System Owner's Manual ADS-C132-1A", Apr. 20, 2015, pp. 3-4.
Welch et al., "An Introduction to the Kalman Filter," SIGGRAPH 2001, Department of Computer Science University of North Carolina at Chapel Hill, http://www.cs.unc.edu/~{welch,gb}, 2001.
WO 2000/073101, IPER of the International Search Authority, filing date Mar. 14, 2000.
WO 2000/075001, IPER of the International Search Authority, filing date Jun. 1, 2000.
WO 2000054719, ISR of the International Searching Authority, Int. App. #PCT/US2000/006581 Intl. filing date Apr. 13, 2017.
WO 2001/02920, Written Opinion of the International Searching Authority, Int. App. #PCT/US1999/029183, Intl. filing date Dec. 9, 1999.
WO 2017/147347 Written Opinion of the International Search Authority, Int. App. #PCT/US2017/019214, priority date Feb. 23, 2016.
WO 2017/201513, Invitation to pay additional fees and partial search report, Int. App. #PCT/US2017/033705, Intl. filing date May 20, 2017.
WO 2017/201513, Written Opinion of the International Searching Authority, Int. App. #PCT/US2017/033705, Intl. filing date May 20, 2017.
WO 2019/018235, Written Opinion of the International Searching Authority, Int. App. #PCT/US2019/042114, Intl. filing date Jul. 13, 2018.
WO2002/030730, Iper of the International Search Authority, filing date Oct. 11, 2001.
WO2004/007264, Initial Publication with ISR, International Publication Date Jan. 22, 2004.
Wolstenholme, Kevin. "Updating Glide—The Full Breakdown." RisingHigh Academy, published Aug. 26, 2017 (Retrieved from the Internet Sep. 26, 2019). Internet URL: https://risinghighacademy.com/category/games/(Year:2017).
Written Opinion of the International Search Authority, PCT/US2017/019214, mailed Aug. 31, 2017.
Written Opinion of the International Search Authority, PCT/US2017/027410, mailed Dec. 4, 2017.
Yamafuji & Kawamura, "Study on the Postural and Driving Control of Coaxial Bicycle", Paper Read at Meeting of Japan Society of

(56) References Cited

OTHER PUBLICATIONS

Mechanical Engineering (Series C), vol. 54, No. 501, (May 1988), pp. 1114-1121, Abstract in English.
Yamafuji et al., “Synchronization and Steering Control of Parallel Bicycle”, Paper Read at Meeting of Japan Society of Mechanical Engineering (Series C), vol. 55, No. 513, (May 1989), pp. 1229-1234.
Yamafuji, “A Proposal for Modular-Structured Mobile Robots for Work that Principally Involve a Vehicle with Two Parallel Wheels”, Automation Technology, vol. 20, pp. 113-118 (1988).
Yun et al., “Design, Implementation and Experimental Results of a Quarternion-Based Kalman Filter for Human Body Motion Tracking”, IEEE Transactions on Robotics, vol. 22, No. 6, Dec. 2006, pp. 1216-1227.
Yun et al., “Implementation and Experimental Results of a Quarternion-Based Kalman Filter for Human Body Motion Tracking”, Proceedings of the 2005 IEEE International Conference on Robotics and Automation, Barcelona, Spain, Apr. 2005, pp. 317-322.
Zenkov, DV, AM Bloch, and JE Marsden [2001] “The Lyapunov-Malkin Theorem and Stabilization of the Unicycle with Rider”. Systems and Control Letters, vol. 45, No. 4, Apr. 5, 2002, pp. 293-302(10).
I-Real, Personal Mobility Device, https://www.youtube.com/watch?v=WAGpxIUpdWw, Published on Jan. 15, 2013, appeared first in Apr. 2012, D1 Grand Prix event, Odaiba, JP.
PCT/US2017/033705, Written Opinion of the International Search Authority, mailed Nov. 23, 2017.
Zenkov, DV, AM Bloch, NE Leonard and JE Marsden, “Matching and Stabilization of Low-Dimensional Nonholonomic Systems”. Proc. CDC, 39, (2000), 1289-1295.
“BTCR9 Fansyn Bluetooth . . . ” Fanimation, published Feb. 4, 2017 (Retrieved from the Internet Sep. 27, 2019). Internet URL: https://web.archive.org/web/20170204193258/https://www.fanimation.com/products/index.php/controls-remotes/fansync-bluetooth-receiver-transmitter-downlight.html(Year : 2017).
Adhikari, B., A Single Subject Participatory Action Design Method for Powered Wheelchairs Providing Automated Back-in Parking Assistance to Cognitively Impaired Older Adults: A pilot study, Master’s Thesis, Department of Comptuer Science, The University of British Columbia, Vancouver, Canada, Dec. 2014.
Bloomua. “Media Player Vector Interface.” CanStockPhoto, published Jul. 5, 2013 (Retrieved from the Internet Sep. 30, 2020). Internet URL: <https://www .canstockphoto.com/media-player-vector-interface-14725014.html> (Year: 2013).
Bluetooth Specification, “Core System Package, Specification of the Bluetooth System”, Version 5.0, vol. 6, Dec. 6, 2016, pp. 2600-2648, Year 2016).
Bob_Schor. “Re: Cannot get latch mechanical action on Boolean button . . . ” NI Community, published Jun. 2, 2018 (Retrieved from the Internet Sep. 26, 2019). Internet URL: https://forums.ni.com/t5/LabVIEW/Cannot-get-latch-mechanical-action-on-boolean-button-inside-a/td-p/3799821?profile.language=en (Year: 2018).
Brown, Jr. et al., “A Single-Wheel, Gyroscopically Stabilized Robot,” IEEE Robotics & Automation Magazine, Sep. 1997.
Chang-Seop Park, “Security Mechanism Based on Hospital Authentication Server for Secure Application of Implantable Medical Devices”, Jul. 24, 2014, BioMed Research International, vol. 2014, Article ID 543051, Year 2014).
Cho et al, Sloped Terrain Segmentation for Autonomous Drive Using Sparse 3D Point Cloud, The Scientific World Journal, 2014, https://www.hindawi.com/journals/tswj/2014/582753/.
Controllers. (Design-©Questel) orbit.com. [online PDF] 9 pgs. Print Dates range Oct. 16, 2013 to Mar. 25, 2015. [Retrieved on Aug. 15, 2018] https://sobjprd.questel.fr/export/QPTUJ214/pdf2/ded442a0-b76c-4173-9dae-7cbb93247074-235637. pdf.
Cooper, Rory A., “Intelligent Control of Power Wheelchairs”, IEEE Engineering in Medicine and Biology Magazine, IEEE Service Center, Piscataway, NJ, US, vol. 14, No. 4, Jul. 1, 1995, pp. 423-431, XP11084628.
Corrected Notice of Allowability mailed Nov. 20, 2020, issued in U.S. Appl. No. 15/982,737, 10 pages.
Dejun Yin and Yoichi Hori, “A Novel Traction Control for Electric Vehicle without Chassis Velocity, Motion Control”, Federico Casolo (Ed.), InTech, DOI: 10.5772/6962. Available from: https://mts.intechopen.com/books/motion-control/a-novel-traction-control-for-electric-vehicle-without-chassis-velocity, 2010.
Derry et al., Automated Doorway Detection for Assistive Shared-Control Wheelchairs, 2013 IEEE International Conference on Robotics and Automation, May 6-10, 2013, https://cpb-e1.wpmucdn.com/sites.northwestern.edu/dist/5/1812/files/2016/05/13icra_derry.pdf.
Dos Santos, William G. “Metronome Idea.” Dribbble, published Oct. 10, 2013 (Retrieved from the Internet Sep. 30, 2020). Internet URL: <https://dribbble.com/shots/12677 41-Metronome-Idea> (Year: 2013).
Elnagar, A., “Prediction of Moving Objects in Dynamic Environments Using Kalman Filters,” Proceedings of 2001 IEEE International Symposium on Computational Intelligence in Robotics and Automation, Jul. 29-Aug. 1, 2001.
Examination Report mailed Jun. 3, 2021, issued in Australian Patent Application No. 2017223823, 6 pages.
Examination Report mailed May 19, 2021, issued in Australian Patent Application No. 2017250598, 4 pages.
Examination Report mailed May 20, 2021, issued in European Patent Application No. 17713499.6, 11 pages.
Final Office Action mailed Jun. 5, 2020, issued in U.S. Appl. No. 15/982,737, 24 pages.
Fresk, et al., “Full Quaternion Based Attitude Control for a Quadrator”, 2013 European Control Conference (EDD), Jul. 17-19, 2013, Zurich, Switzerland, pp. 3864-3869.
Grasser, F. et al., “JOE: A Mobile, Inverted Pendulum,” IEEE Transactions on Industrial Electronics, vol. 49, No. 1, Feb. 2002.
Ha, et al. “Trajectory Tracking Control for Navigation of Self-Contained Mobile Inverse Pendulum” Intelligent Robots and Systems ’94. ‘Advanced Robotic Systems and the Real World’, IROS ’94. Proceedings of the IEEE/RSJ/GI International Conference on, vol. 3, No., pp. 1875-1882, Sep. 12-16, 1994.
Ha, et al., “Trajectory Tracking Control for Navigation of the Inverse Pendulum Type Self-Contained Mobile Robot” Robotics and Autonomous Systems 17, 65-80 (1996).
Helgesson, L., “Pitch and roll estimating Kalman filter for stabilizing quadrocopters”, http://lhelge.se/2012/04/pitch-and-roll-estimating-kalman-filter-for-stabilizing-quadrocopters/, Oct. 15, 2012.
Hooper, Craig. “Material Design Android TV Remote App.” Uplabs, published Feb. 14, 2016 (Retrieved from the Internet Sep. 30, 2020). Internet URL: <https://www.uplabs.com/posts/material-design-android-tv-remote-app-application> (Year: 2016).
How et al., “Clinical Evaluation of the Intelligent Wheelchair System”, Proceedings of Festival of international Conference on Caregiving, Disability, Aging and Technology, Toronto, Canada, 2011.
International Search Report and Written Opinion, PCT/US2018/042114, Filing date Jul. 13, 2018.
Internet URL: <https://sparkylinux.org/lightscribe-technology-on-sparky-host/> (Year: 2015).
Introducing electric wheelchair without stairs Scewo. Blog.naver.com. [online] 2 pgs. Posted Mar. 19, 2017. [Retrieved on Aug. 15, 2018] http://blog.naver.com/PostView.nhn?blogld=hwh7588&logNo=220987227590&categoryNo=0&parentCategoryNo=0&viewDate=&currentPage=1&postListTopCurrentPage=1&from=postView.
Ishida and Miyamoto, “Collision-Detecting Device for Omnidirectional Electric Wheelchair”, Research Article, ISRN Robotics, vol. 2013, Article ID 672826, Nov. 1, 2012.
I-swing, Single Person Vehicle, https://www.youtube.com/watch?feature=player_embedded&v=IQSybf7sLtg, Published on Sep. 14, 2006, Featured on Hacked Gadgets, http://hackedgadgets.com.
I-Unit, Wheelchair, https://www.youtube.com/watch?v=RbrrIrh3GBE, Published on Jun. 6, 2006, Filmed at Megaweb Center at Tokyo.
Jae Dong Lee et al., Service-Oriented Security Framework for Remote Medical Services in the Internet of Things Environment, The Korean Society of Medical Informatics, Healthcare Informatics Research, Oct. 2015, vol. 21, No. 4, 12 pages.

(56) References Cited

OTHER PUBLICATIONS

Johnson, R.C., "Unicycles and Bifurcations", American J. of Physics, vol. 66, No. 7, 589-92 (Oct. 22, 2002).
Kanoh, "Applied Control of Inverted Pendulum", Computrol, vol. 2, (1983), pp. 69-75.
Kawaji, S., "Stabilization of Unicycle Using Spinning Motion", Denki Gakkai Ronbushi, D, vol. 107, Issue 1, Japan (1987), pp. 21-28.
Koyanagi et al., "A Wheeled Inverse Pendulum Type Self-Contained Mobile Robot and its Posture Control and Vehicle Control", The Society of Instrument and Control Engineers, Special issue of the 31st SICE Annual Conference, Japan, 1992, pp. 13-16.
Koyanagi et al., "A Wheeled Inverse Pendulum Type Self-Contained Mobile Robot and its Two Dimensional Trajectory Control", Proceeding of the Second International Symposium on Measurement and Control in Robotics, Japan 1992, pp. 891-897.
Koyanagi et al., "A Wheeled Inverse Pendulum Type Self-Contained Mobile Robot", The Society of Instrument and Control Engineers, Special issue of the 31st SICE Annual Conference, Japan 1992, pp. 51-56.
Kwiatkowski, Piotr Adam. "Clock App Concept." Dribbble, published Dec. 18, 2012 (Retrieved from the Internet Jan. 15, 2020).
Lam, H. K. et al., "Fuzzy Model Reference Control of Wheeled Mobile Robots," The 27th Annual Conference of the IEEE Industrial Electronics Society (2001).
Liu, H.S. et al., "Accelerometer for Mobile Robot Positioning," IEEE Transactions on Industry Applications, vol. No. 3, Oct. 1999.
Maybeck, "Stochastic Models, Estimation, and Control", vol. 1, Academic Press, 1979—Chapter 1.
Meeussen et al., Autonomous Door Opening and Plugging In with a Personal Robot, Willow Garage, USA, IEEE International Conference on Robotics and Automation, May 3-7, 2010, http://www.willowgarage.com/sites/default/files/m2.pdf.
Momoi & Yamafuji, "Motion Control of the Parallel Bicycle-Type Mobile Robot Composed of a Triple Inverted Pendulum", Paper Read at Meeting of Japan Society of Mechanical Engineering (Series C), vol. 57, No. 541, (Sep. 1991), pp. 154-159.
Montella, C., et al., "To the Bookstore! Autonomous Wheelchair Navigation in an Urban Environment", Lehigh University, published in FSR, 2012, Part of the Springer Tracts in Advanced Robotics book series (STAR, vol. 92), first online Dec. 31, 2013.
News article, "Amazing Wheelchair Goes Up and Down Stairs".
U.S. Appl. No. 17/878,245, filed Dec. 1, 2022.
U.S. Appl. No. 16/035,205, filed Jul. 13, 2018.
U.S. Appl. No. 15/787,613, filed Oct. 18, 2017.
U.S. Appl. No. 15/600,703, filed May 20, 2017.

* cited by examiner

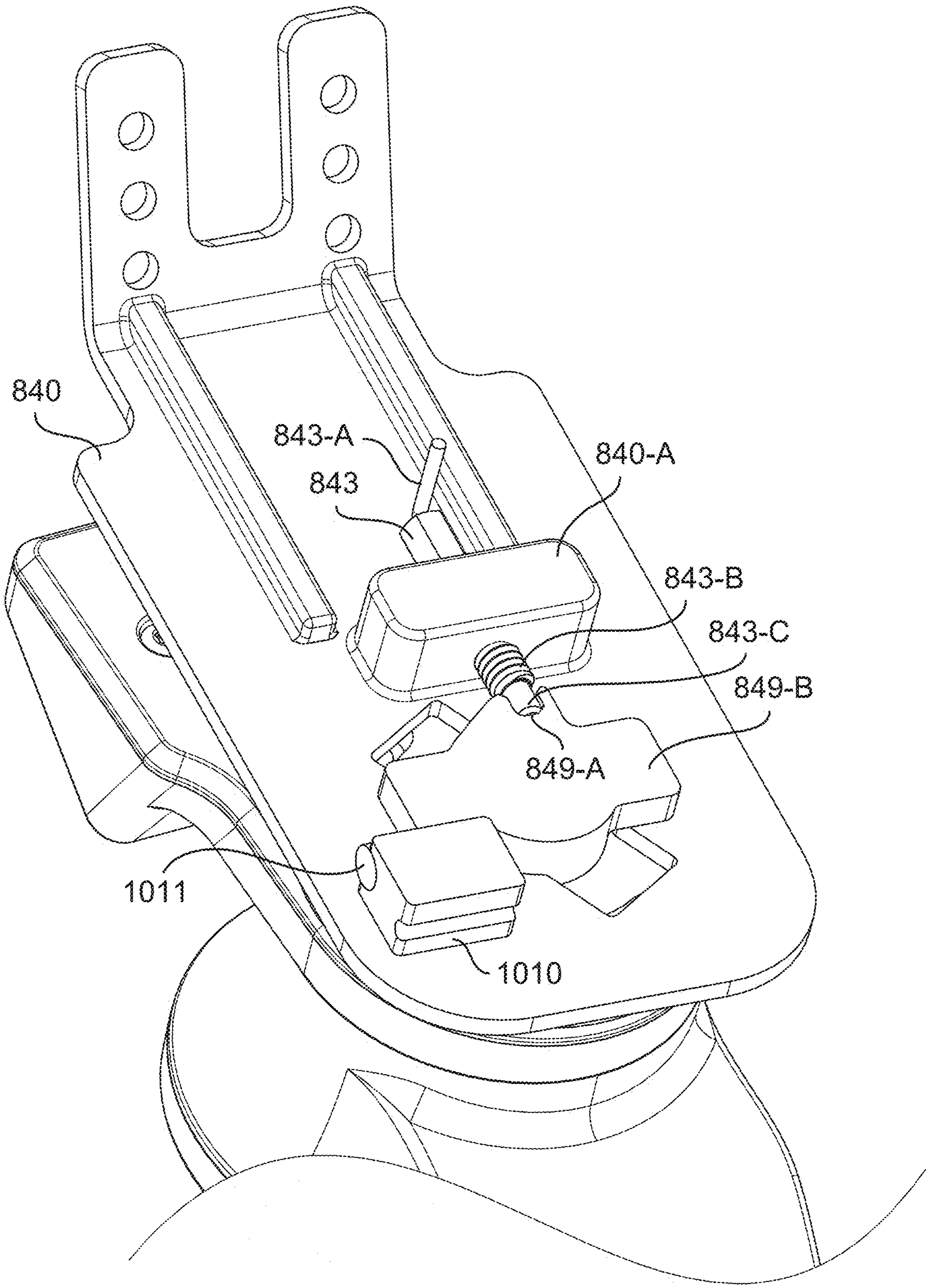
FIG. 12AAA

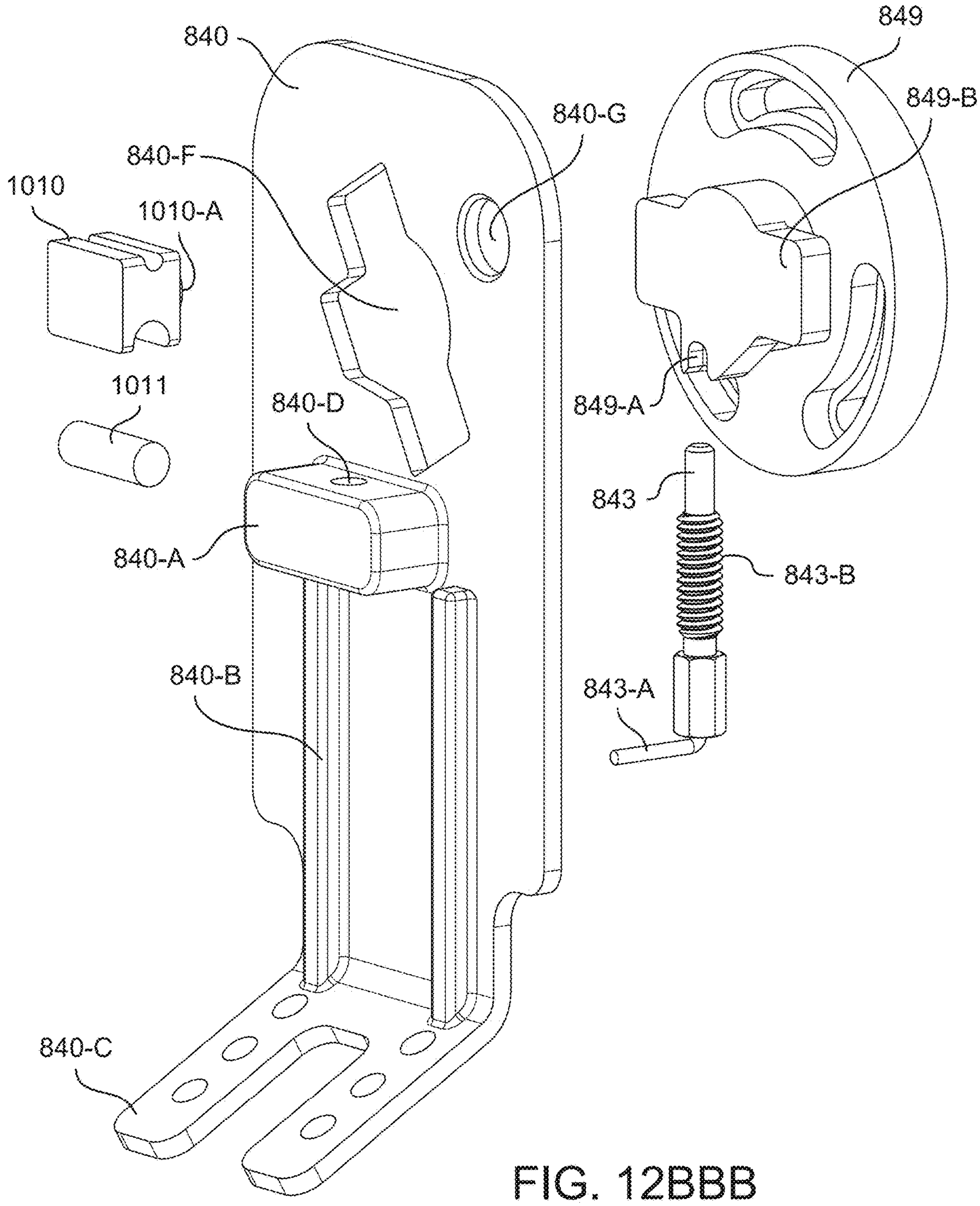
FIG. 12BBB

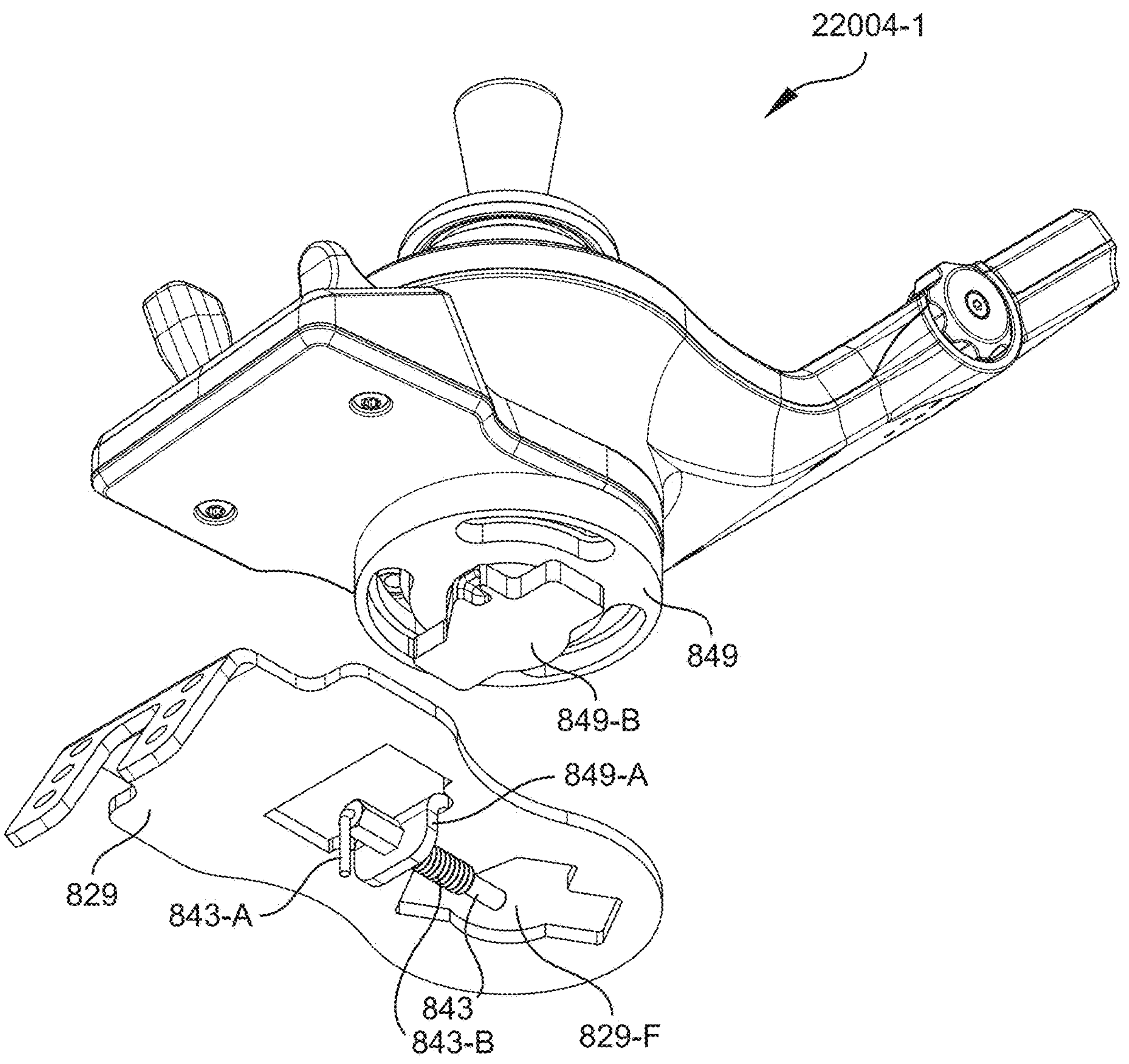
FIG. 12CCC

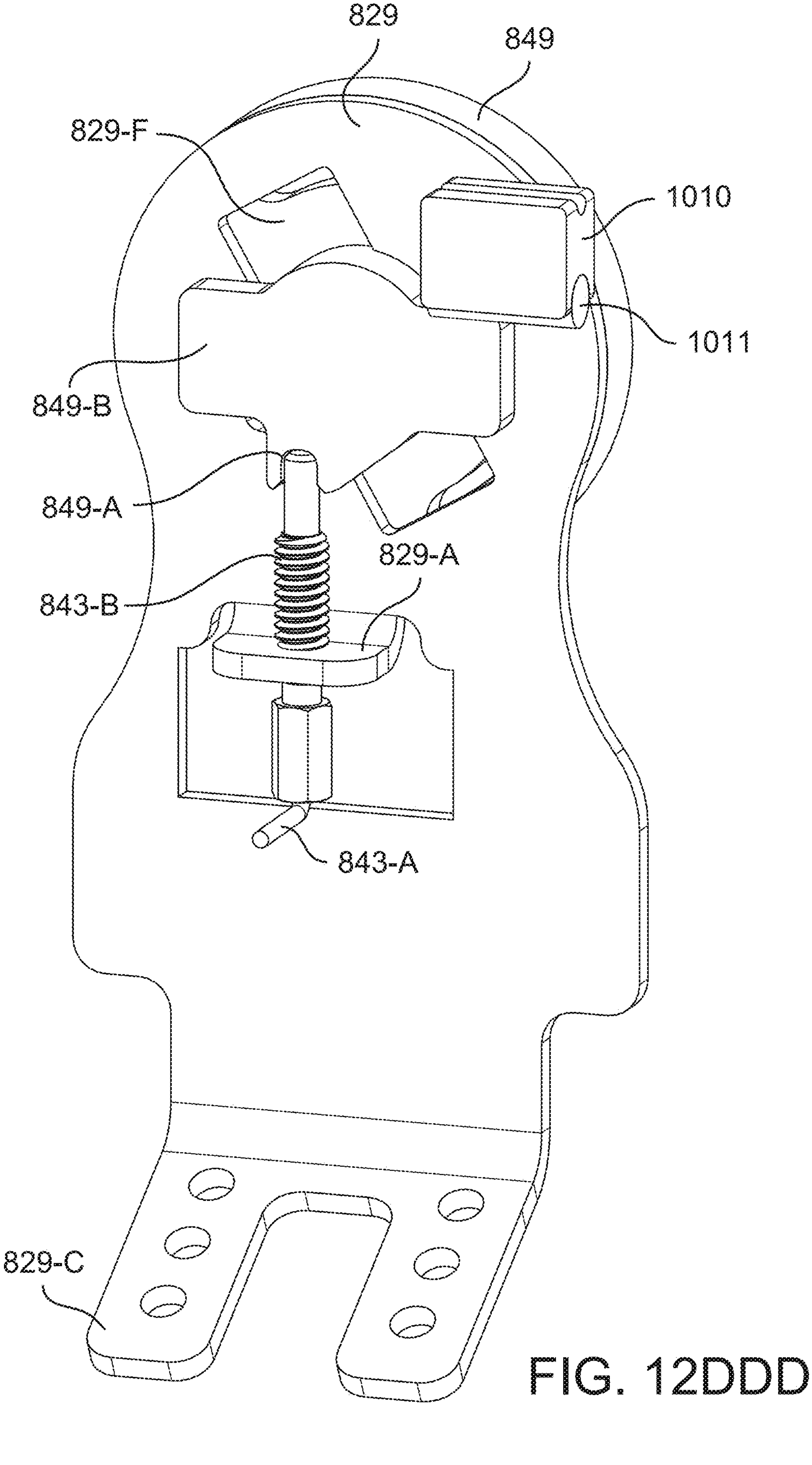
FIG. 12DDD

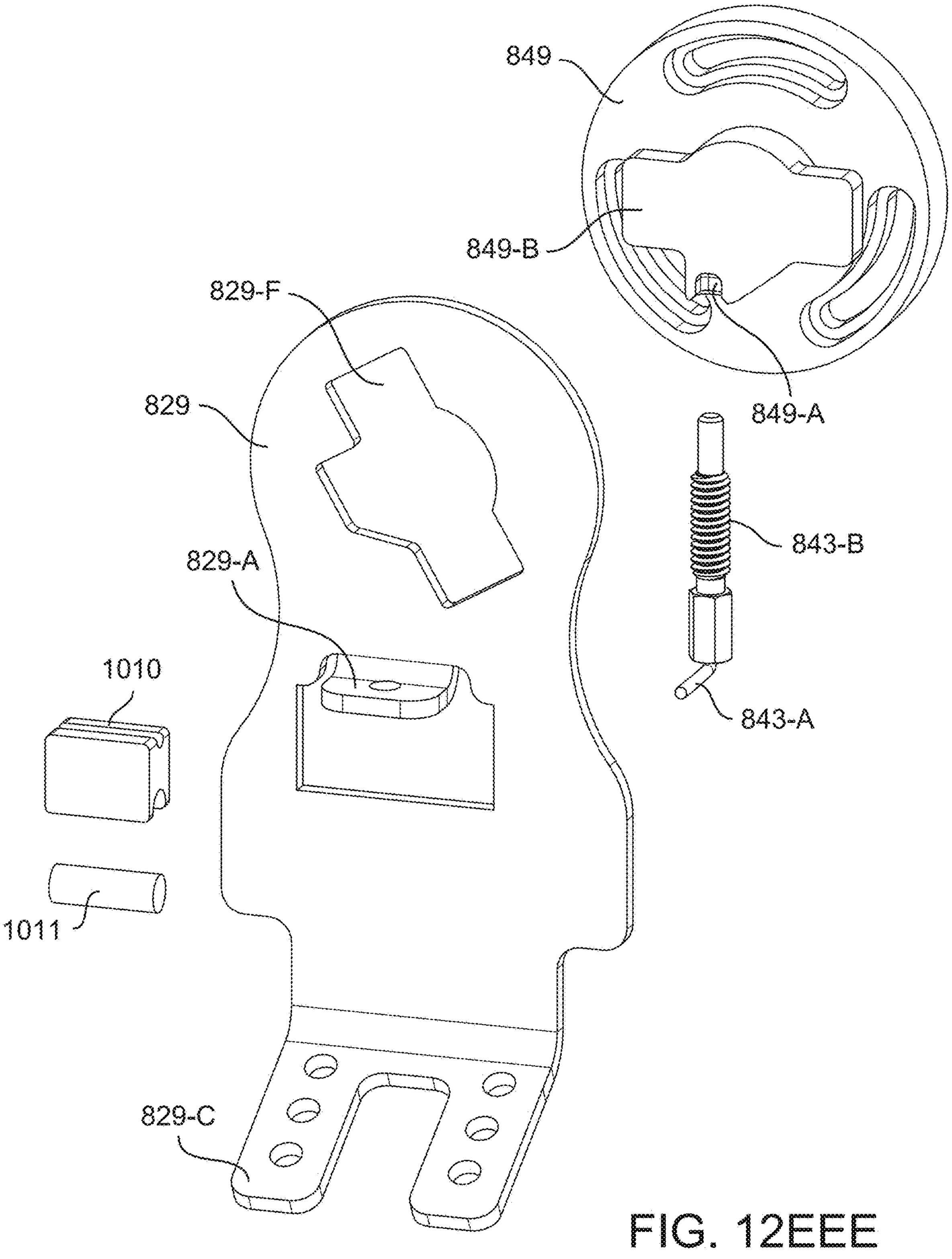
FIG. 12EEE

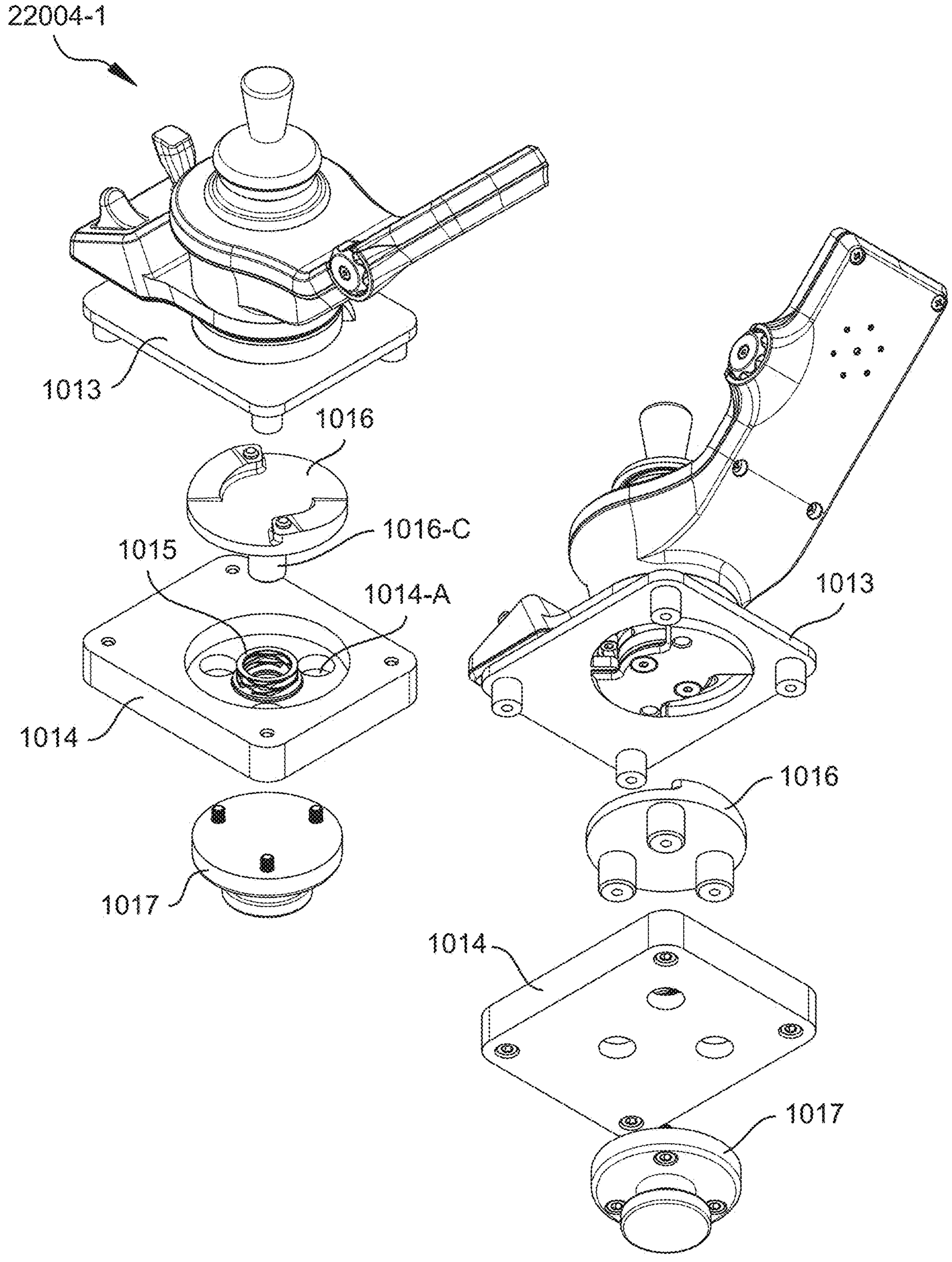
FIG. 12FFF

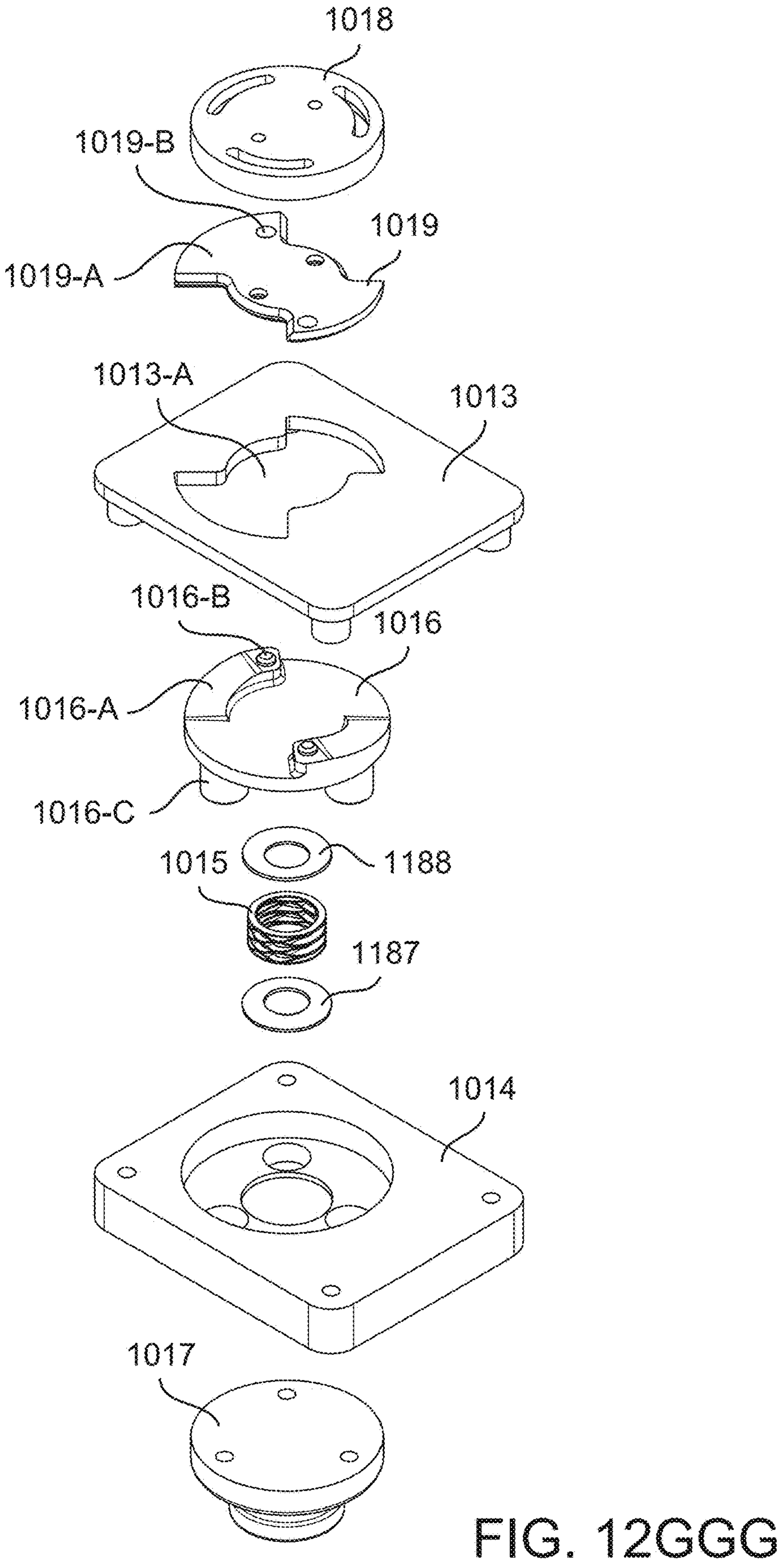
FIG. 12GGG

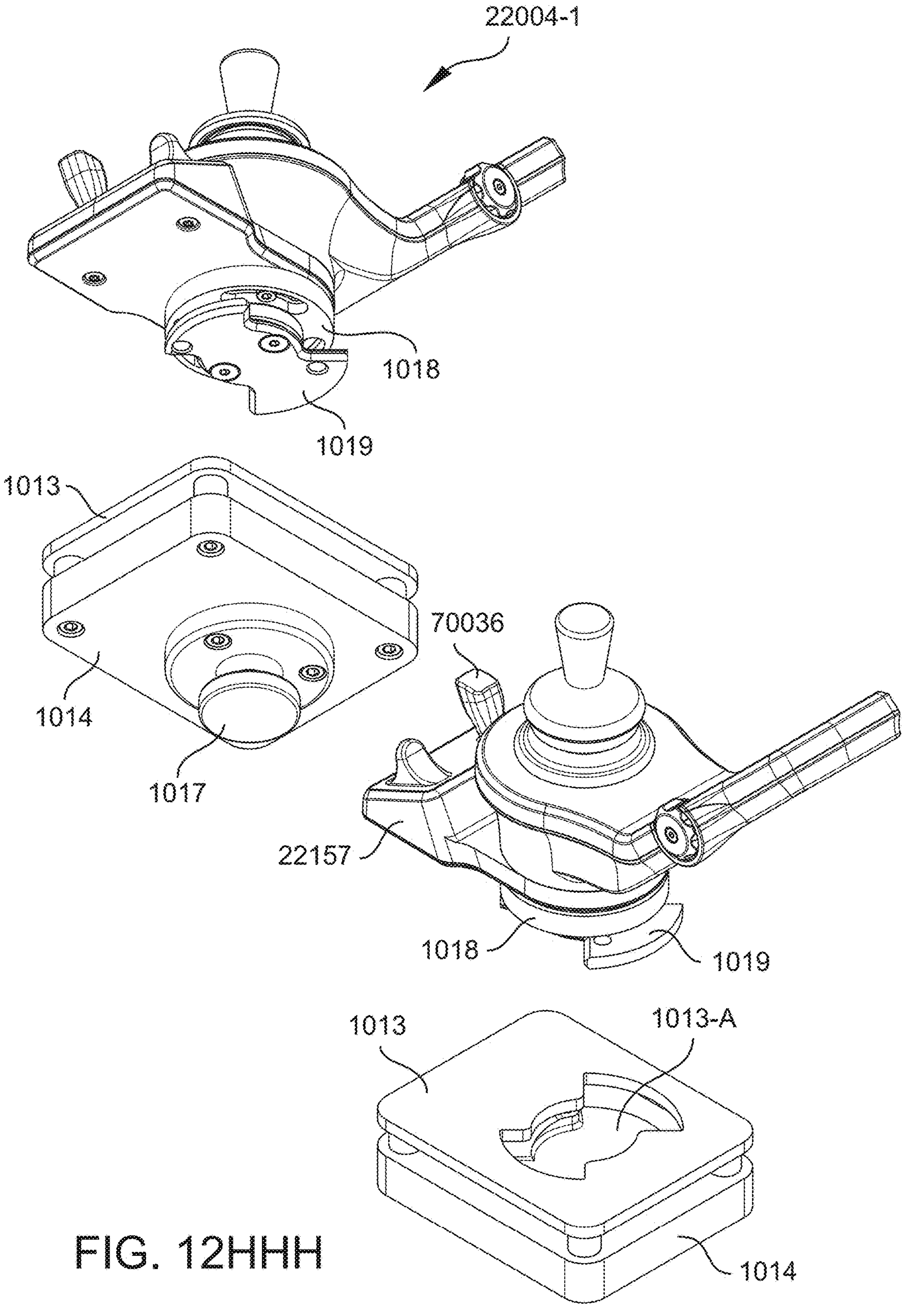
FIG. 12HHH

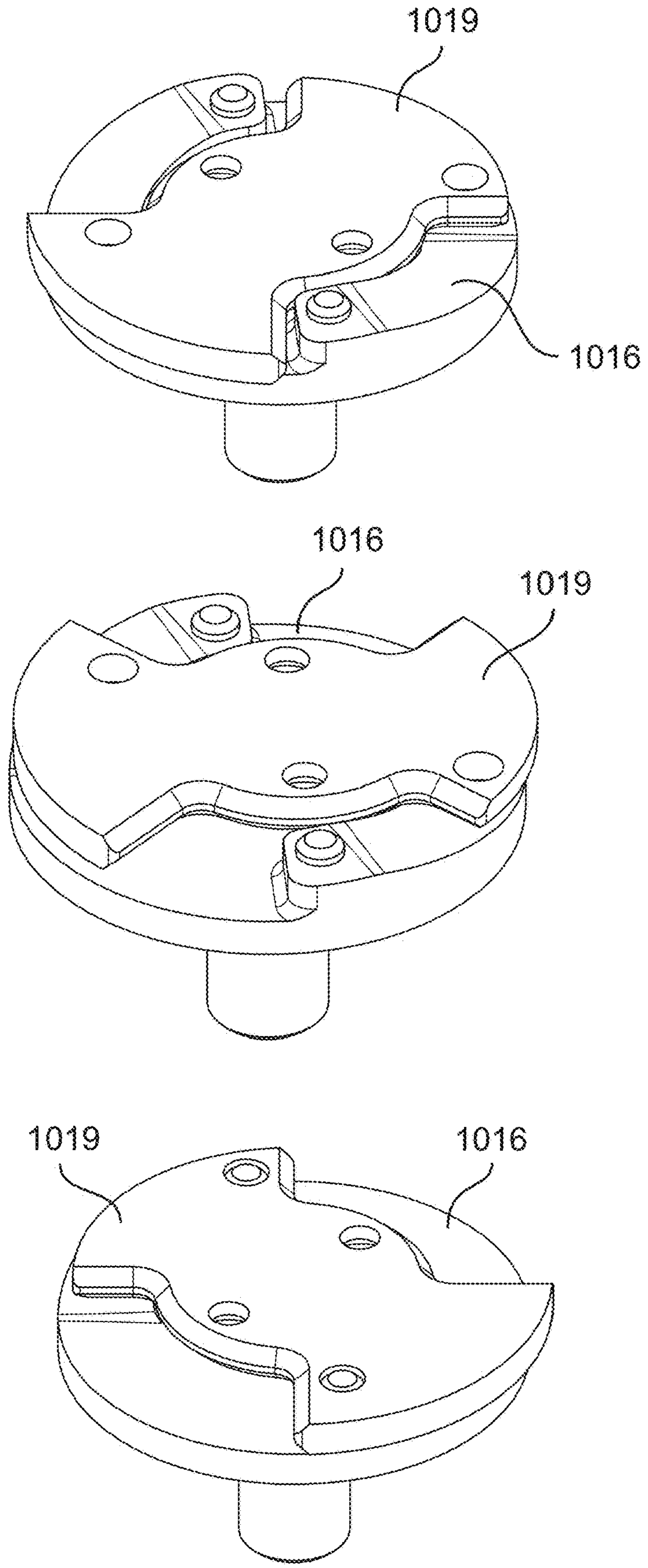
FIG. 12III

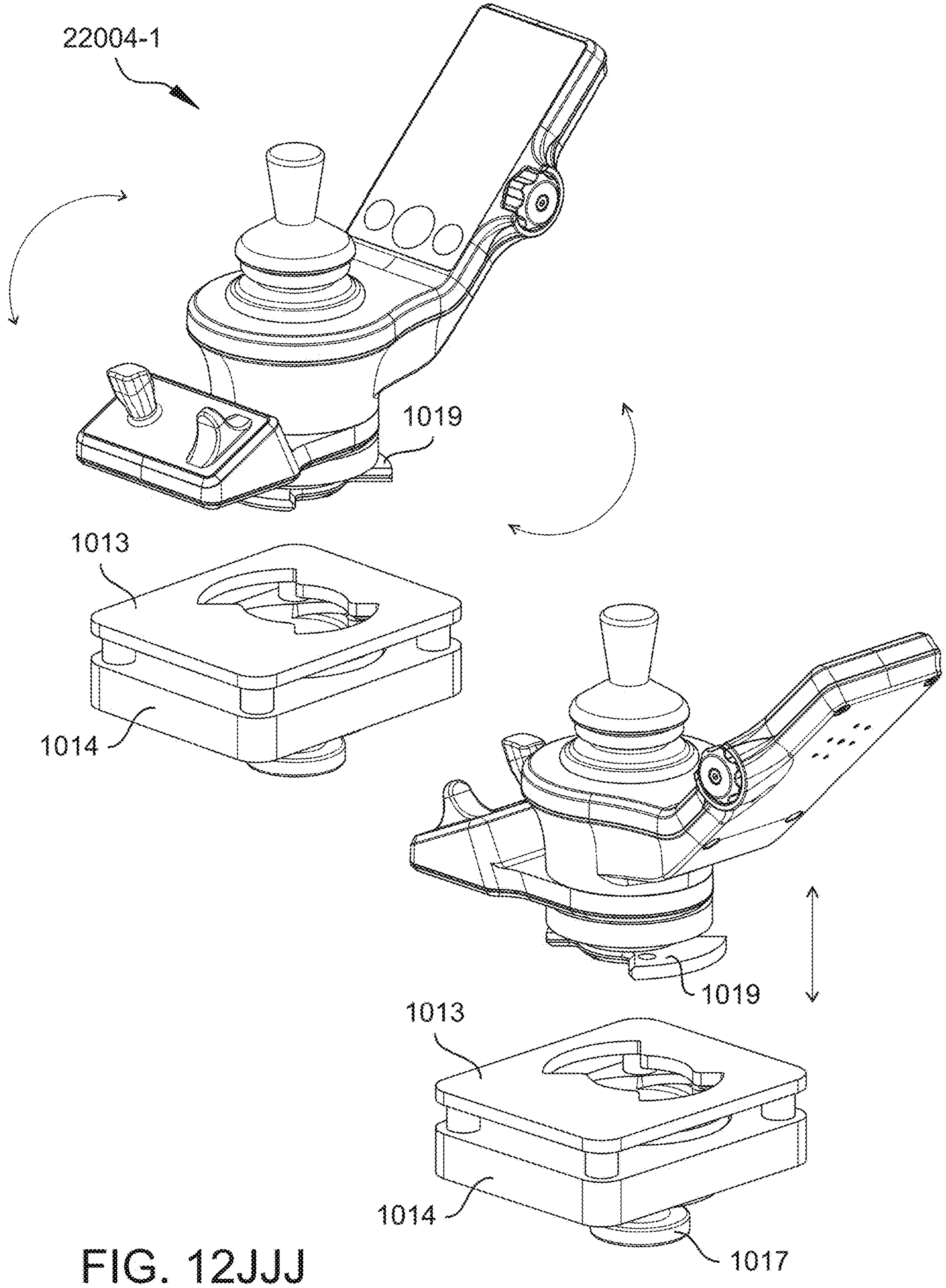
FIG. 12JJJ

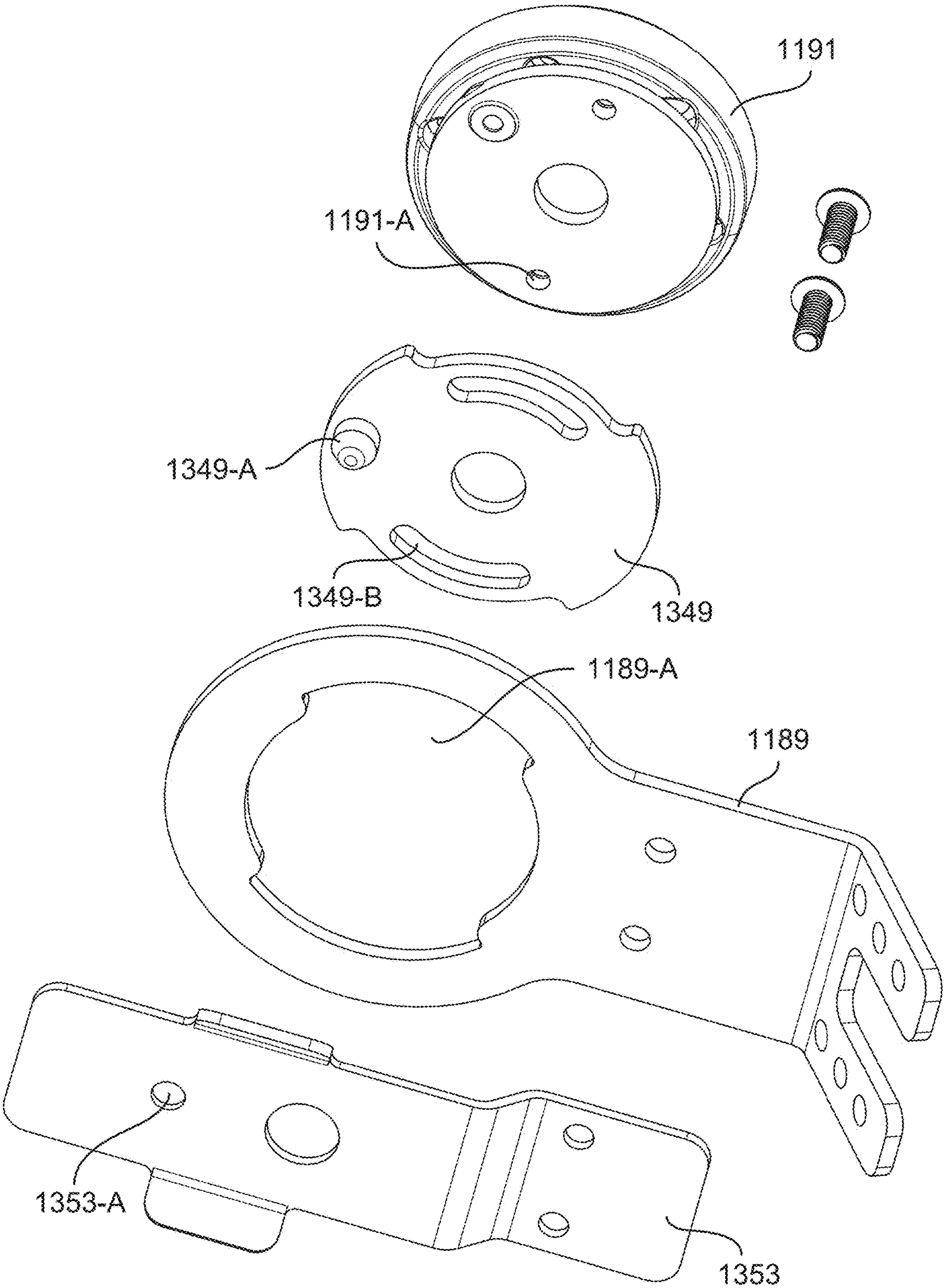
FIG. 12KKK

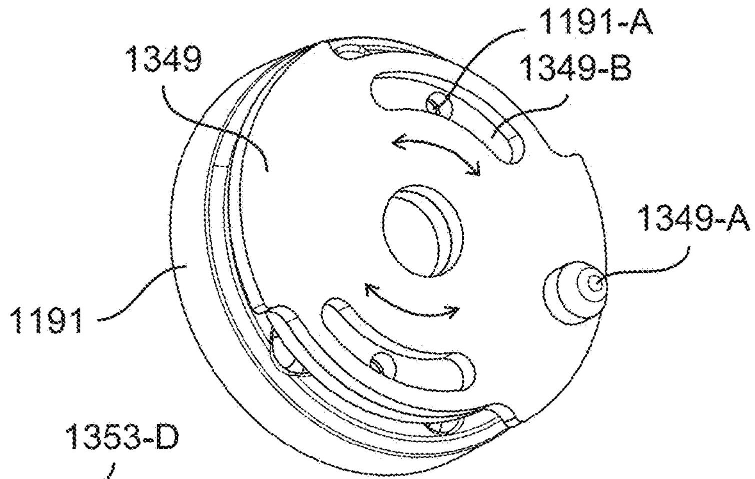
FIG. 12LLL
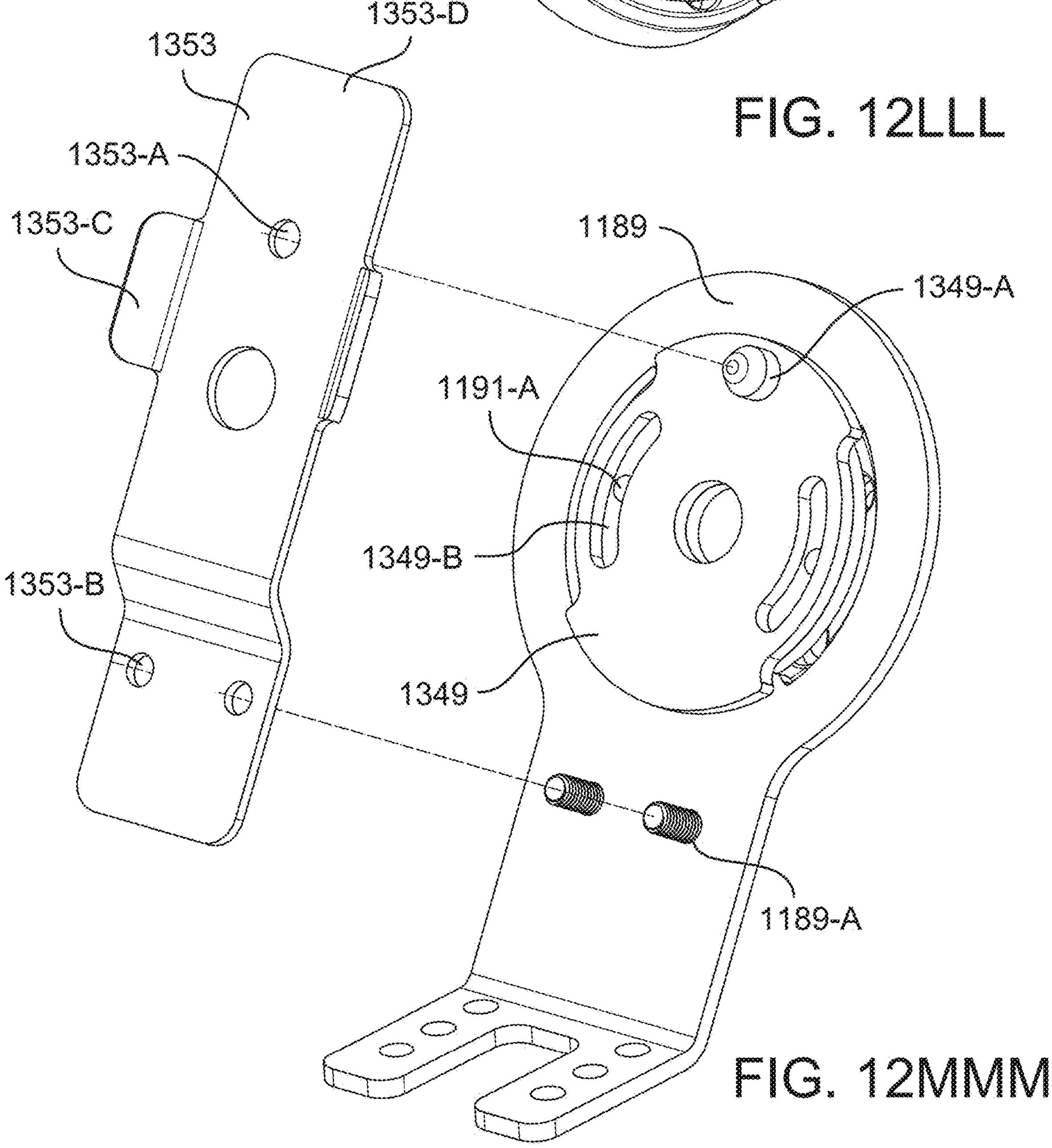
FIG. 12MMM

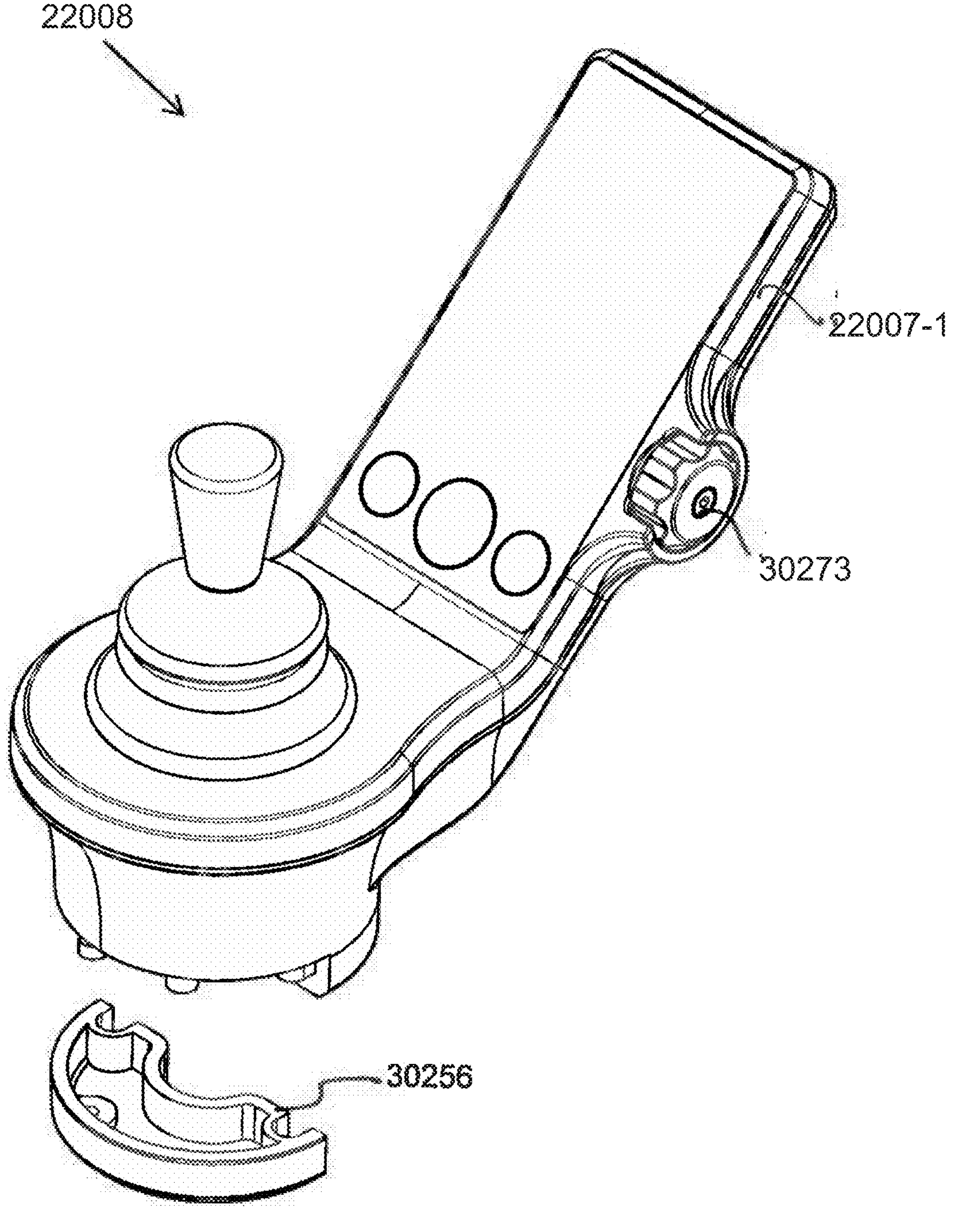
FIG. 12NNN

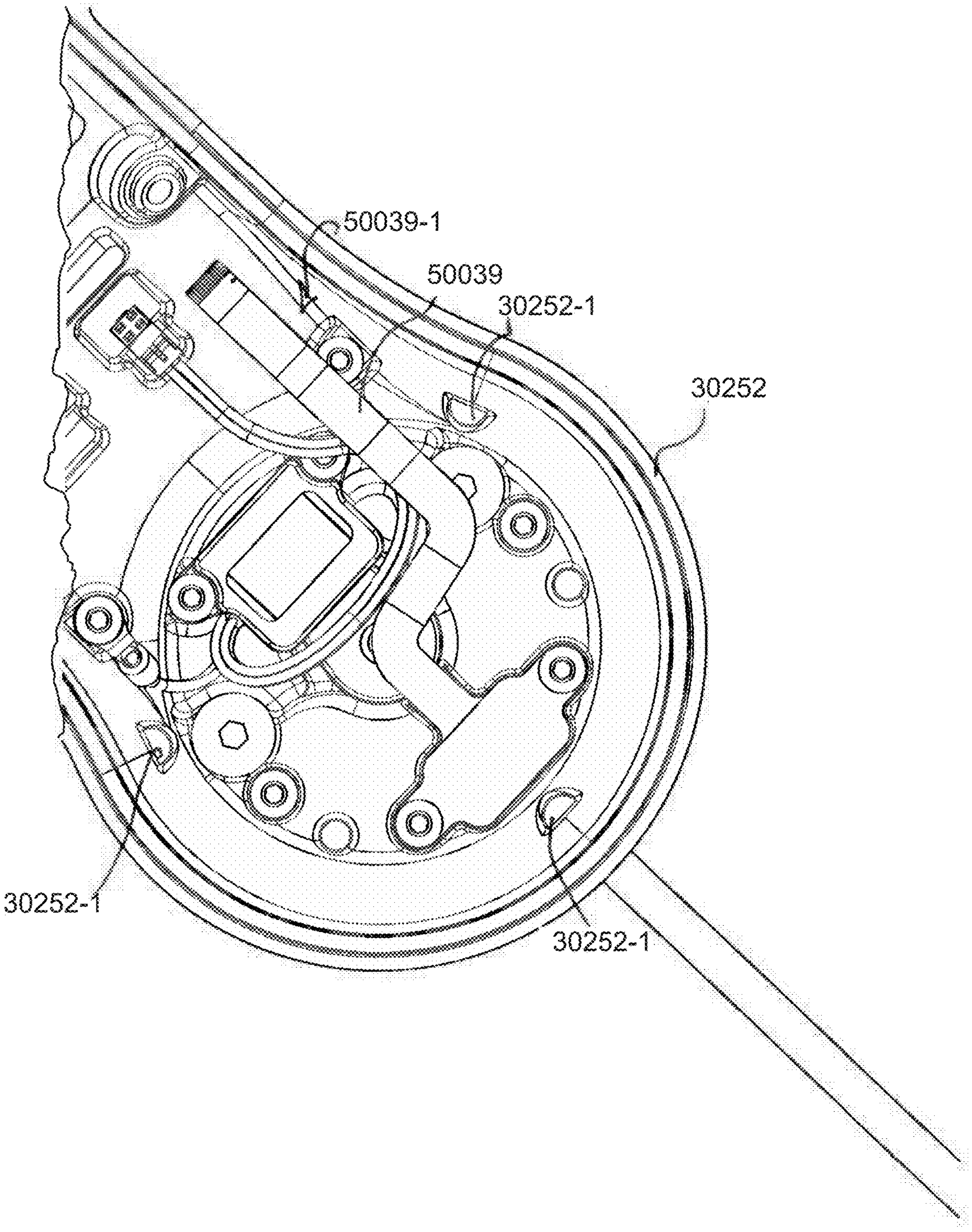
FIG. 12OOO

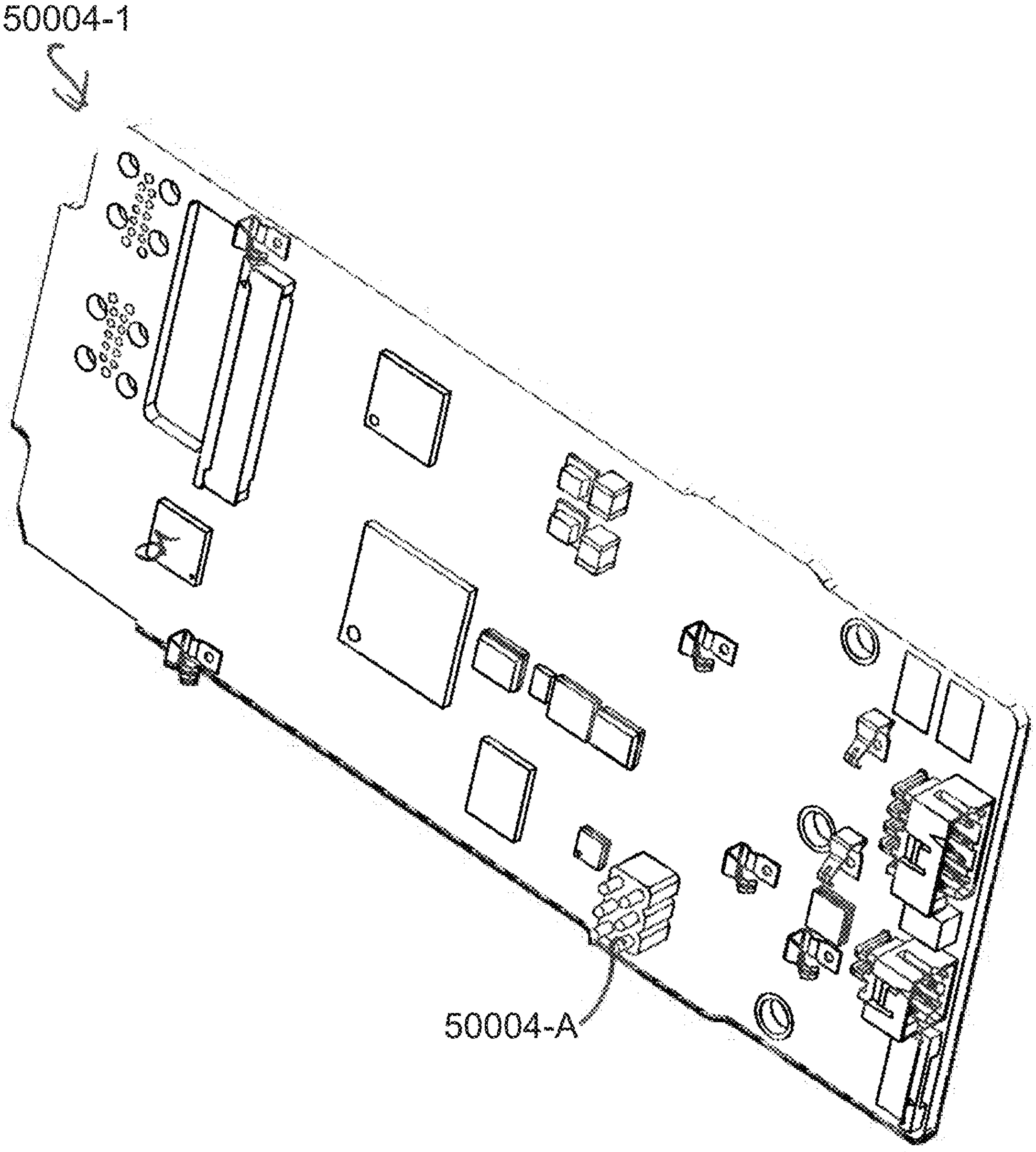
FIG. 12PPP

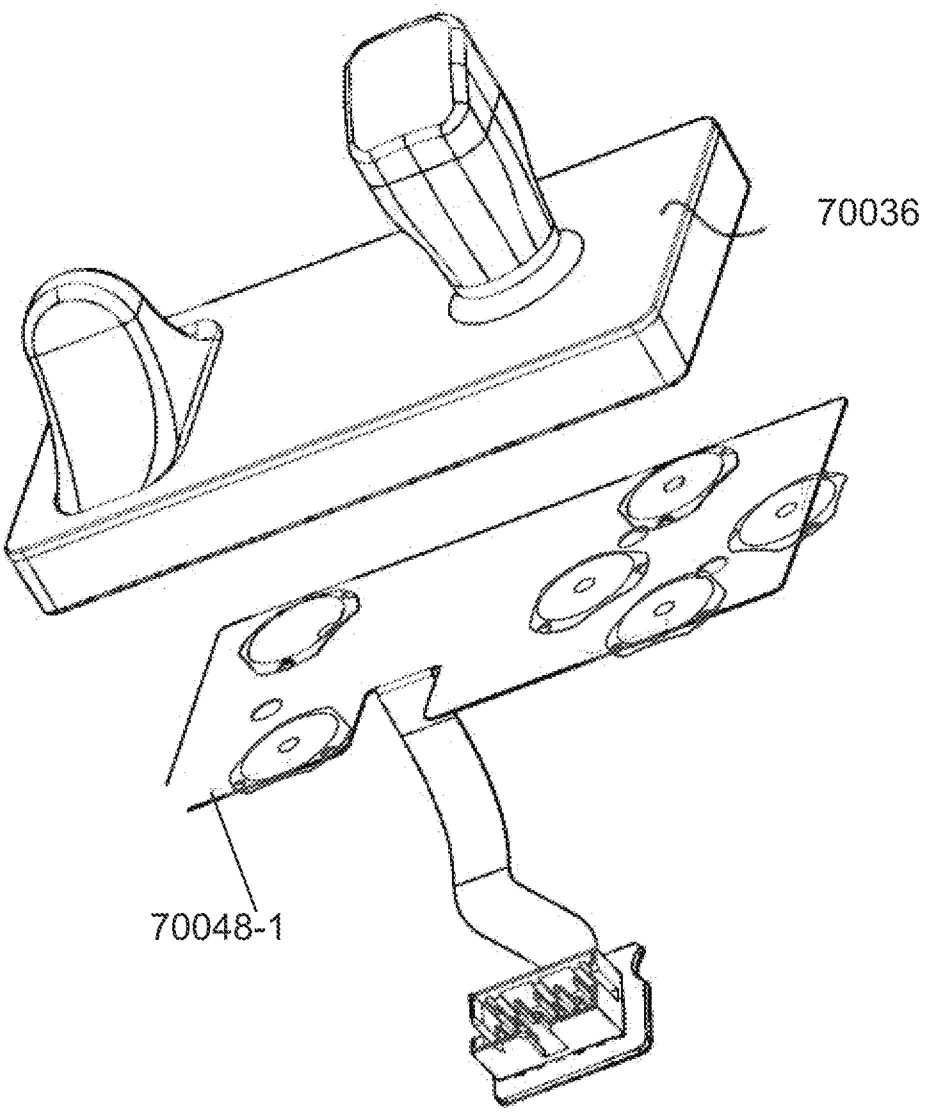
FIG. 12QQQ

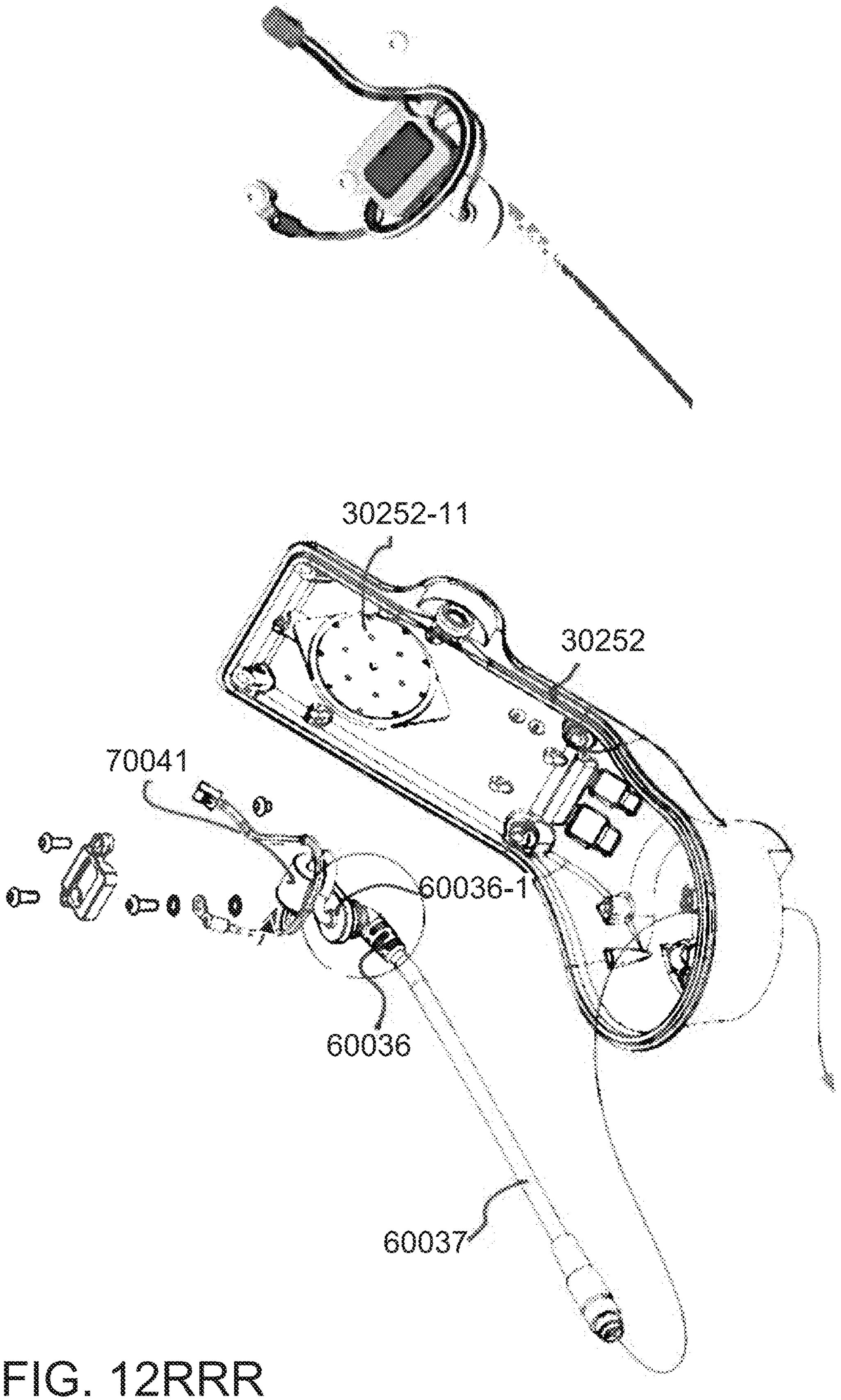
FIG. 12RRR

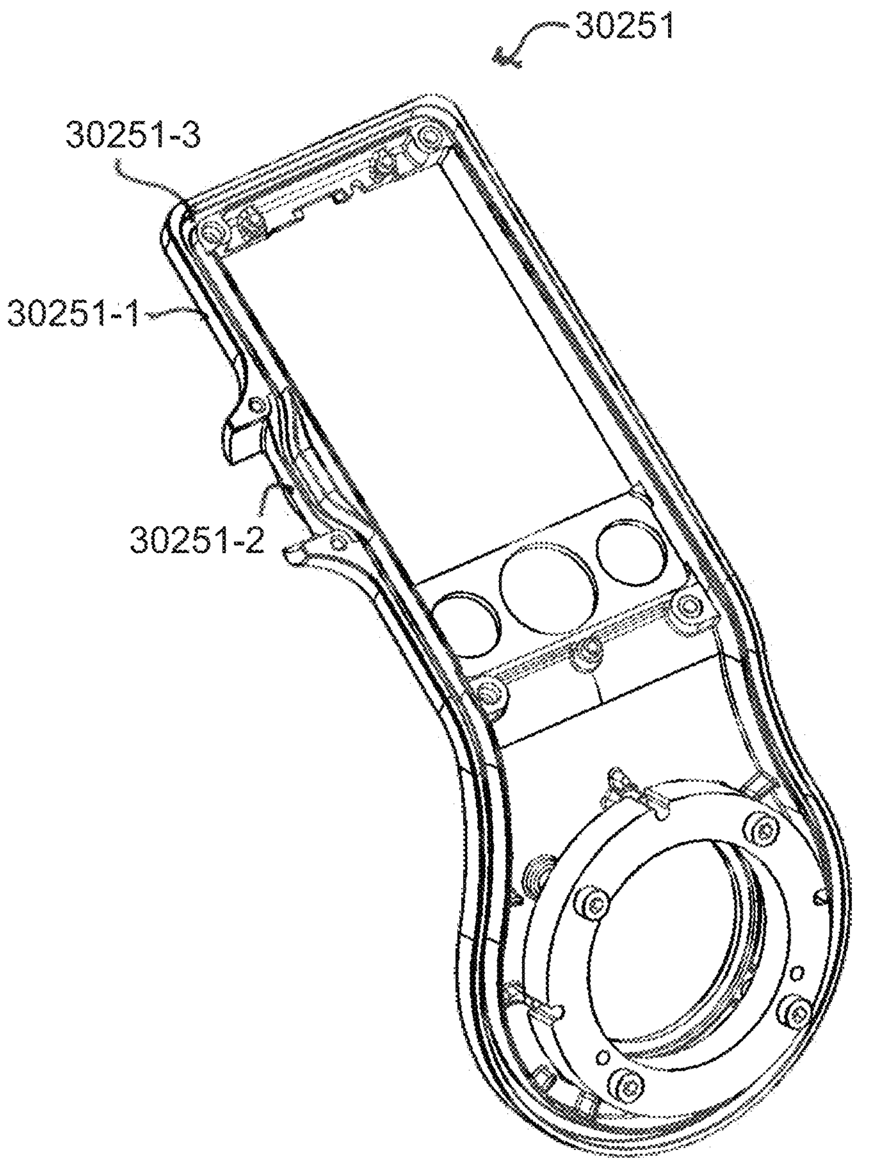
FIG. 12SSS

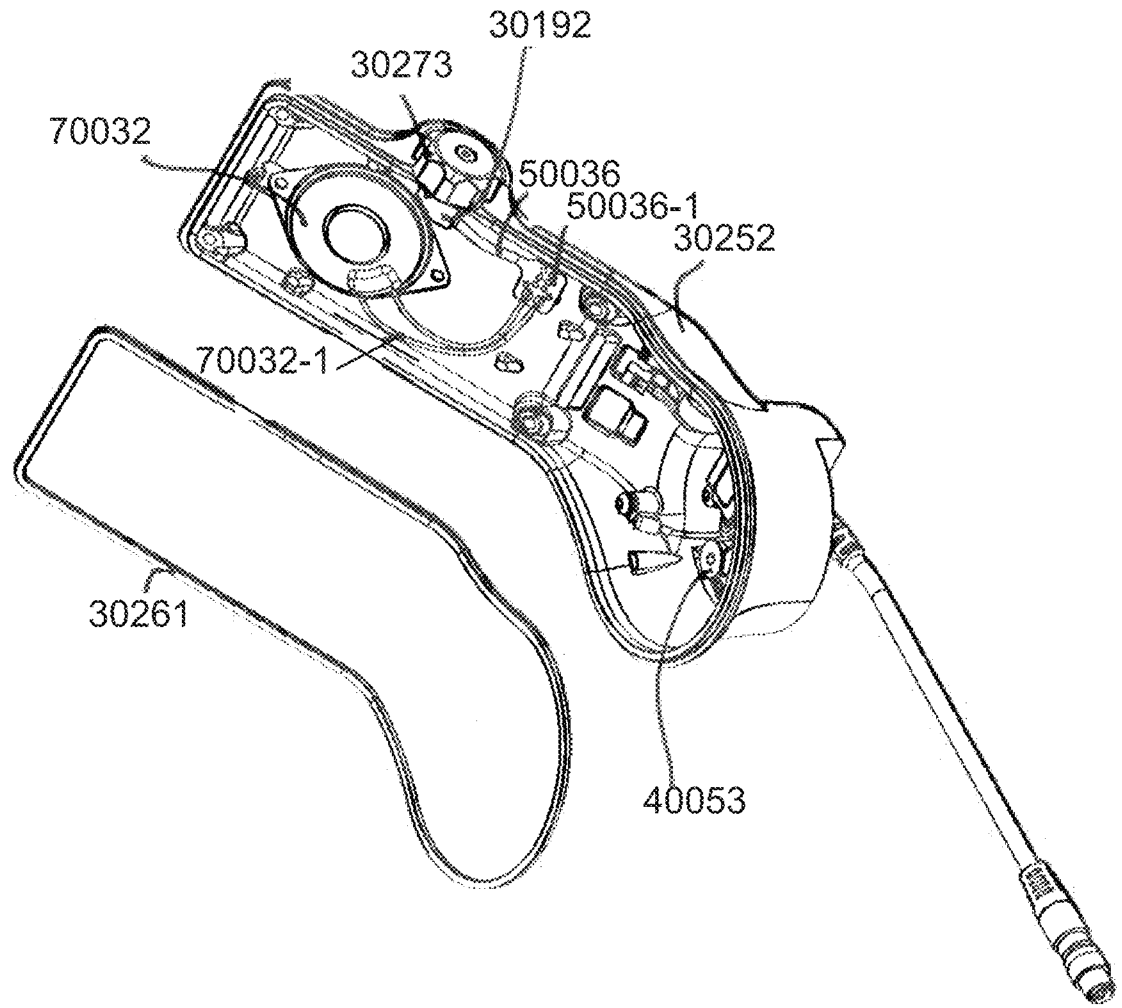
FIG. 12TTT 22008-1
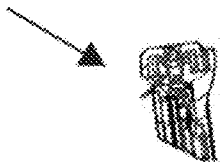
SECTION A-A
SCALE 1/2
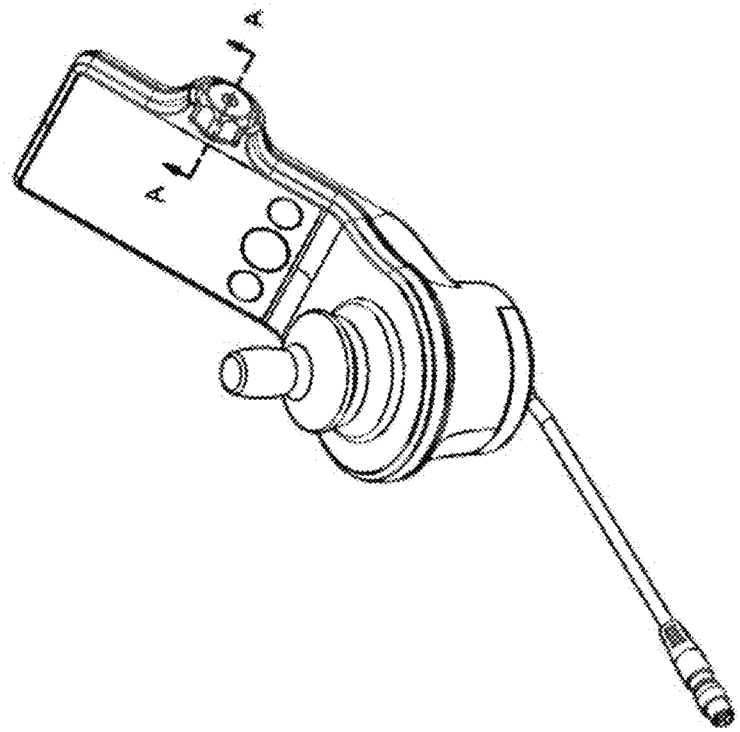
FIG. 12UUU

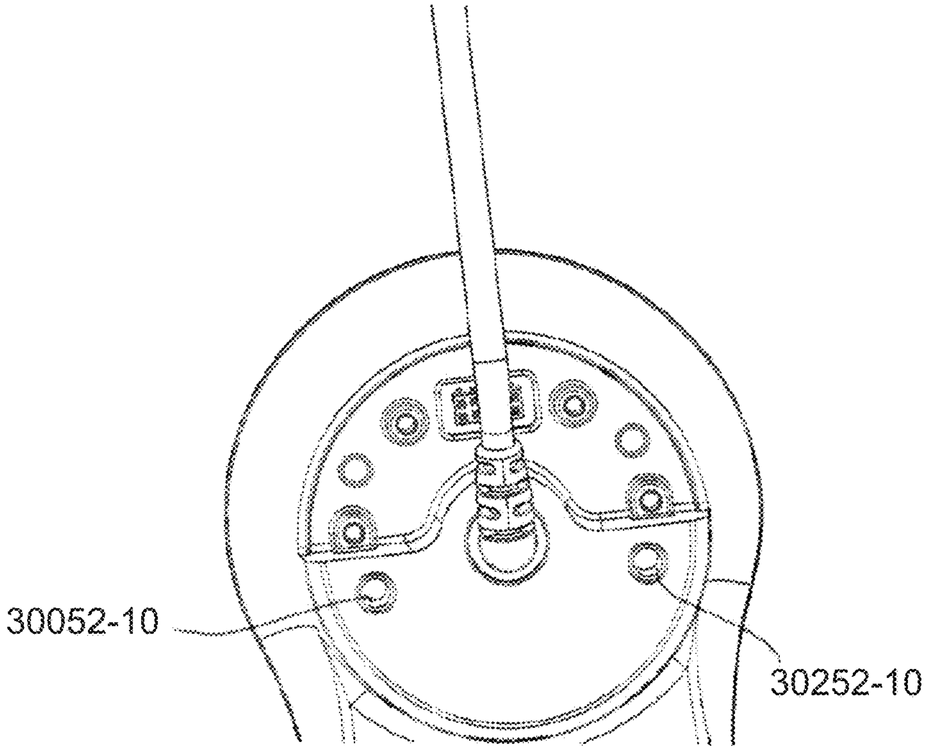
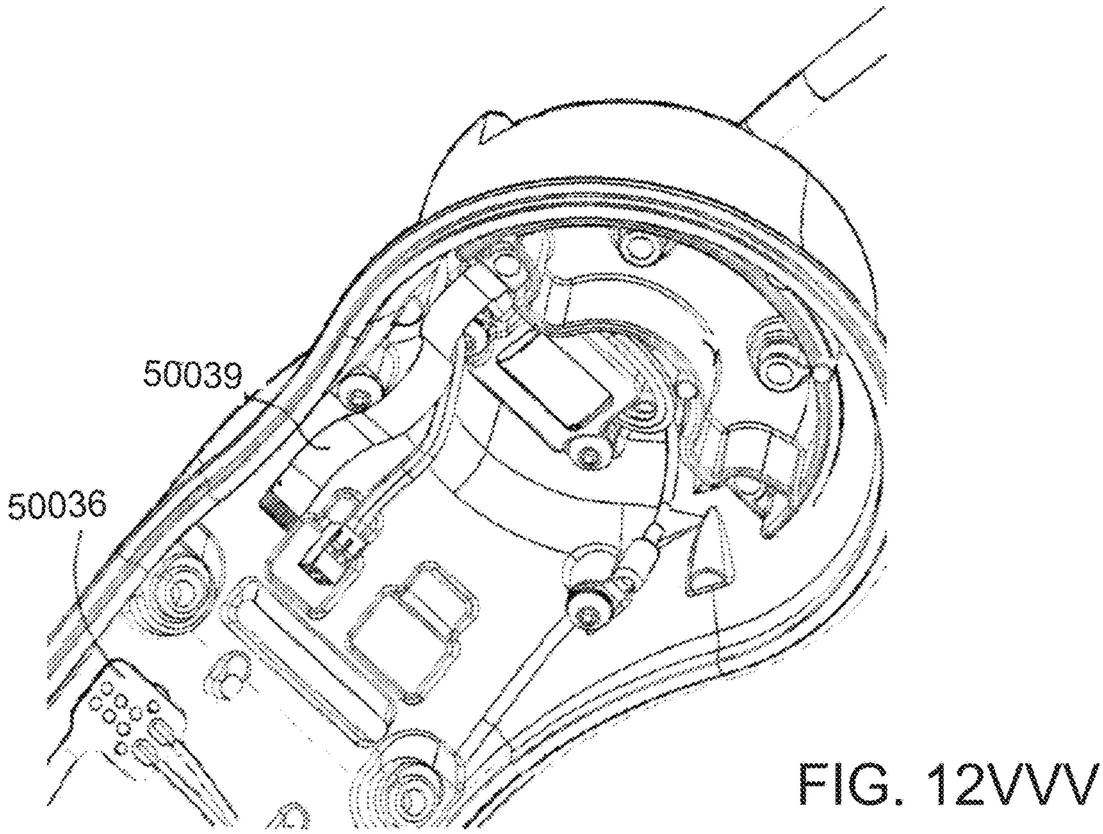
FIG. 12VVV

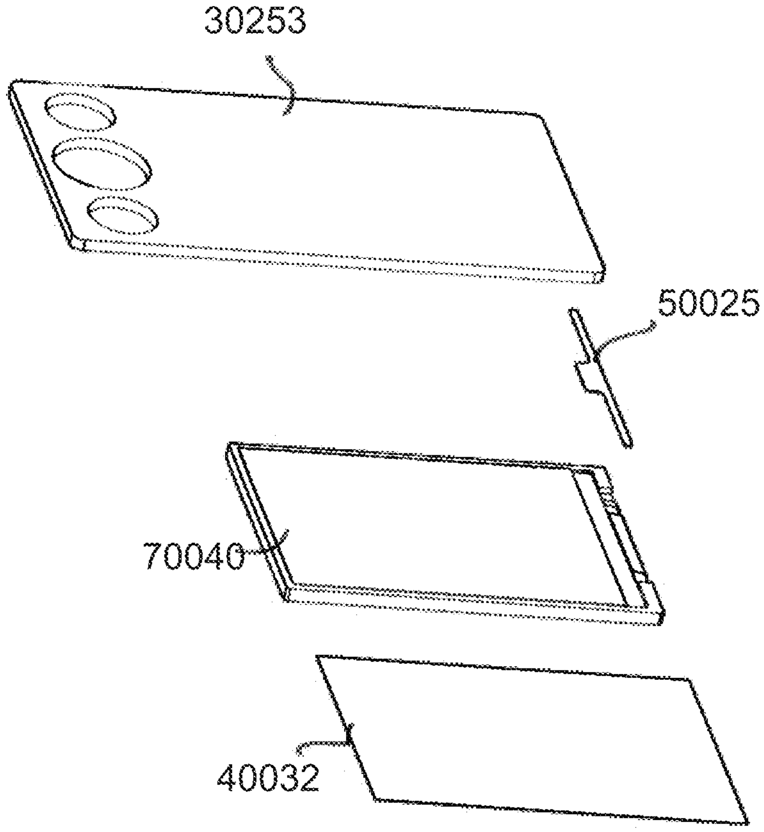
FIG. 12WWW

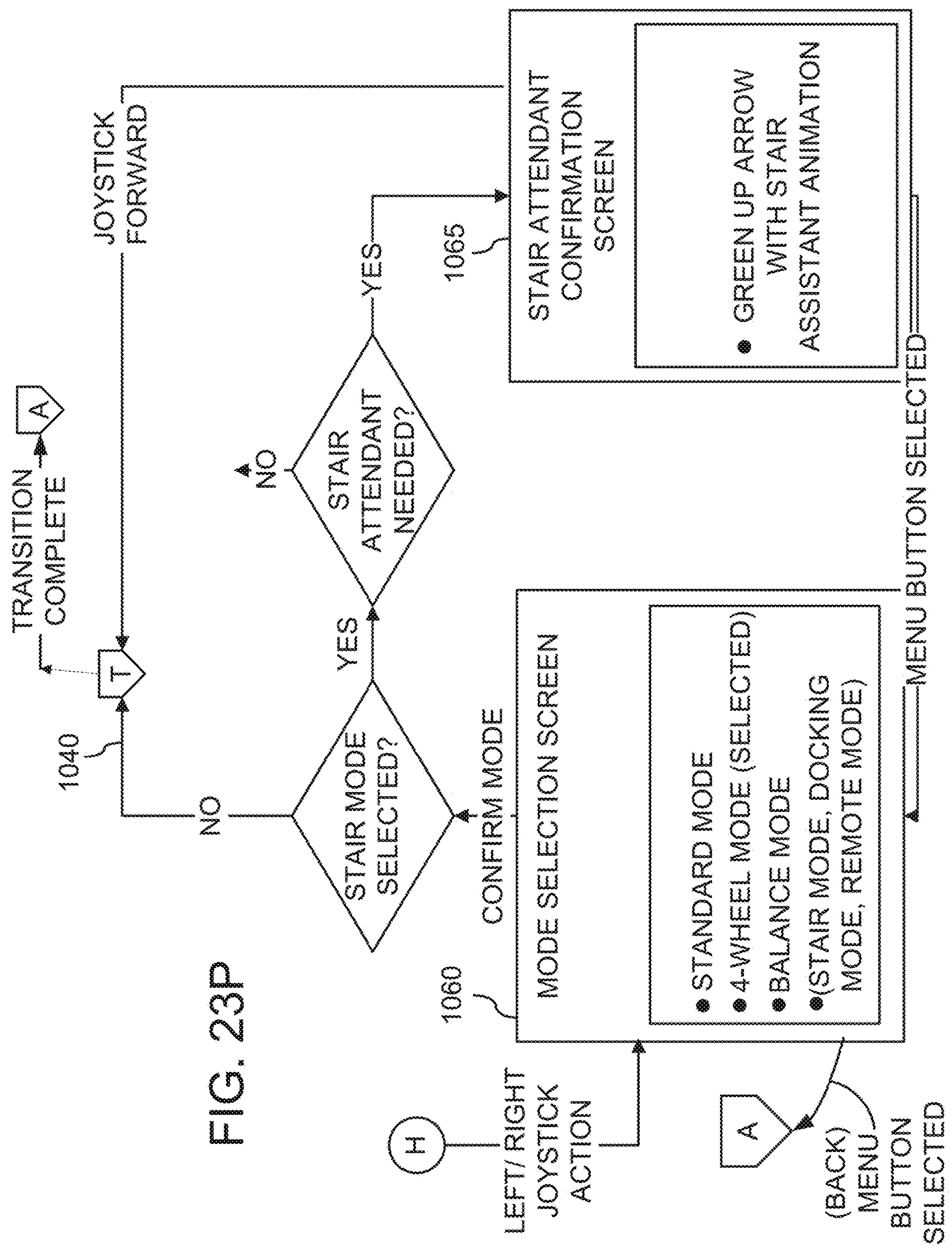

FIG. 23P
H
LEFT/ RIGHT JOYSTICK ACTION
1060
MODE SELECTION SCREEN
STANDARD MODE
4-WHEEL MODE (SELECTED)
BALANCE MODE
(STAIR MODE, DOCKING MODE, REMOTE MODE)
A
(BACK) MENU BUTTON SELECTED
CONFIRM MODE
STAIR MODE SELECTED?
NO
YES
1040
T
TRANSITION COMPLETE
A
STAIR ATTENDANT NEEDED?
NO
YES
JOYSTICK FORWARD
1065
STAIR ATTENDANT CONFIRMATION SCREEN
GREEN UP ARROW WITH STAIR ASSISTANT ANIMATION
MENU BUTTON SELECTED

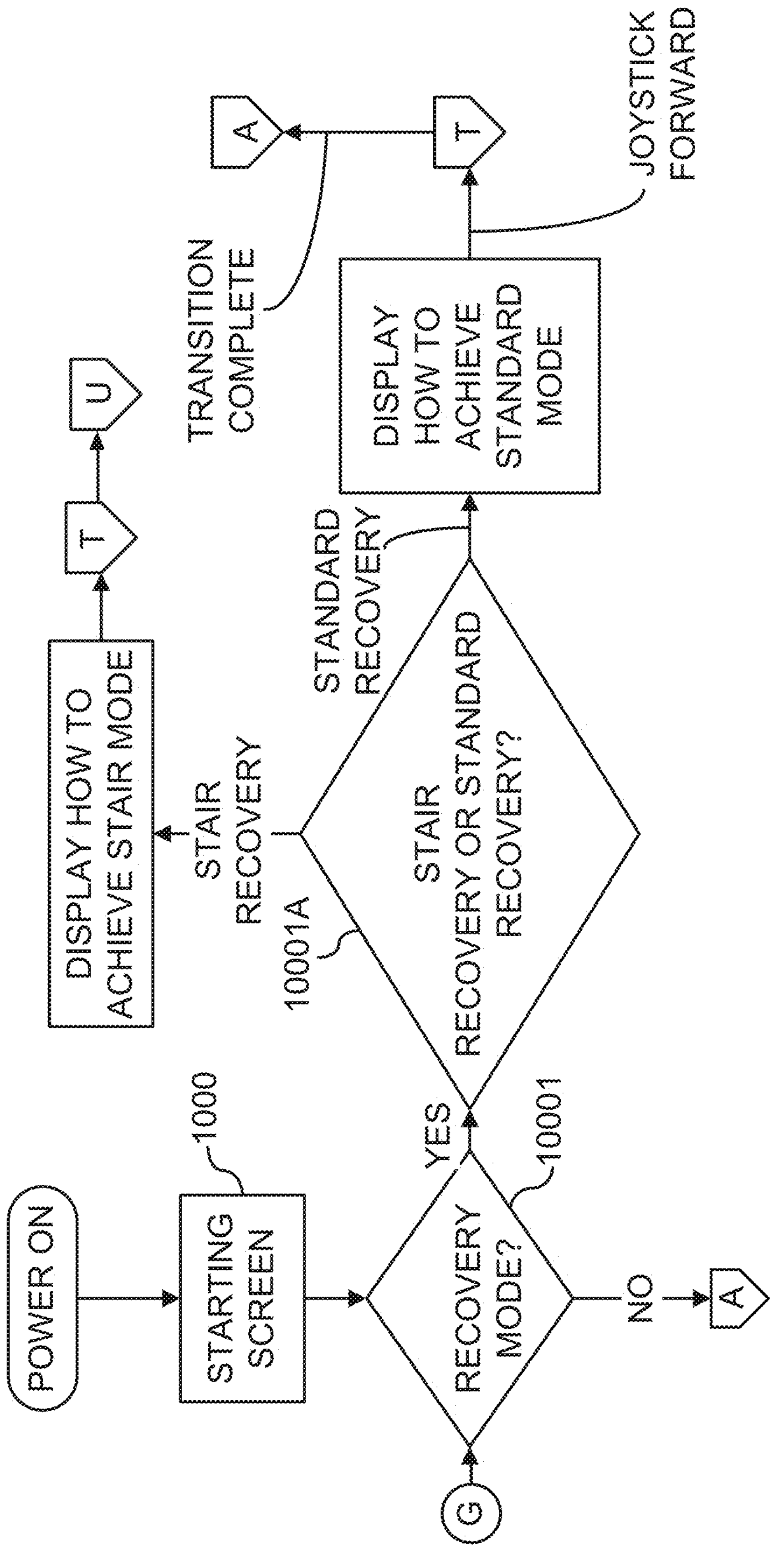
FIG. 23III

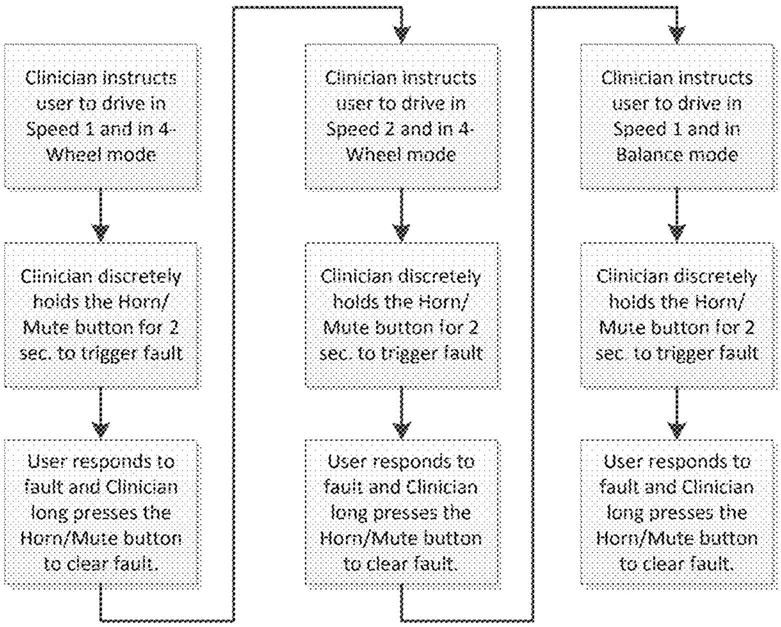
FIG. 23AAA

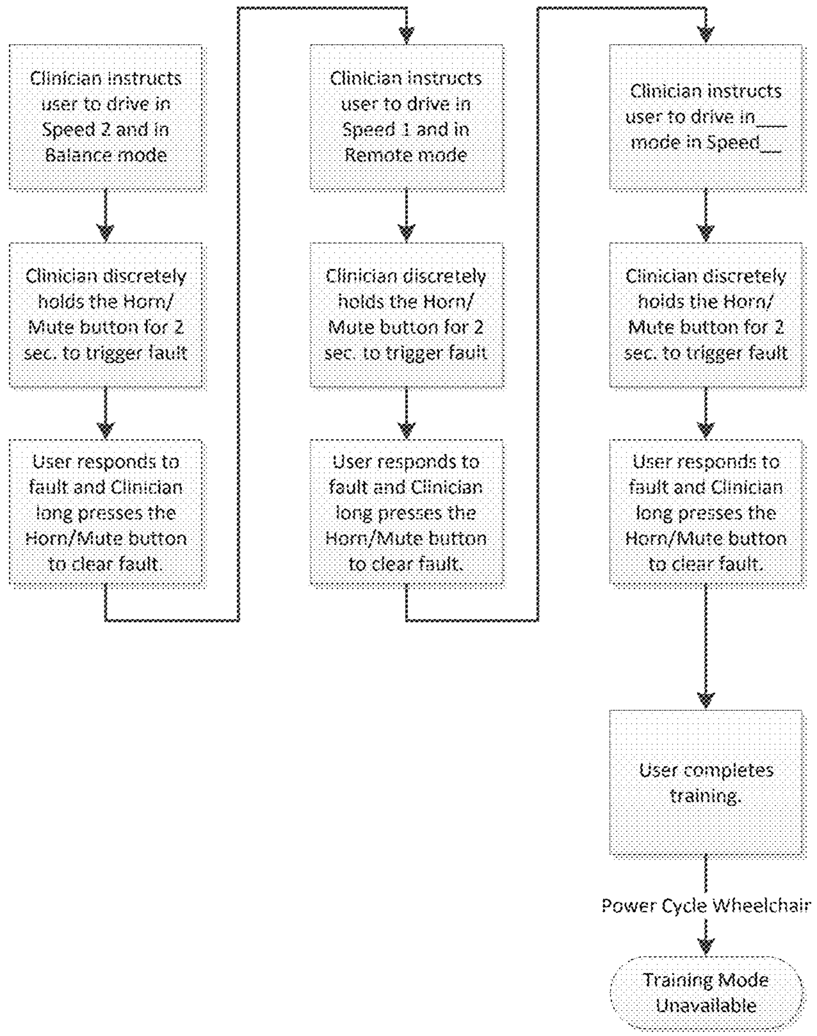
FIG. 23BBB

| | PACKET | TRANSMITTING DEVICE |
|---|---|---|
| 901 | MASTER SYNC PACKET | BUS MASTER |
| 903 | USER CONTROL PACKETS | UC |
| 905 | POWER SOURCE CONTROLLER PACKETS | PSC A, PSC B |
| 907 | POWER BASE PROCESSOR PACKETS | PBP A1, PBP A2, PBP B1, PBP B2 |

FIG. 30A

701

| Ref. | Byte # | Data | Destination |
|---|---|---|---|
| 701A | 0 | Status | All |
| 701B | 1 | Error Device ID | Power base processors (PBP) |
| 701C | 2 | Mode Requested | PBP |
| 701D | 3 | Control Out | PBP |
| 701E | 4 | Commanded Velocity | PBP |
| 701F | 5 | Commanded Turn Rate | PBP |
| 701G | 6 | Seat Control | PBP |
| 701H | 7 | System Data | All |

FIG. 30B

| Data | Bit | Meaning |
|---|---|---|
| Request Type | 7 | 0 = Normal Request<br>Mode being requested should be processed by the PBP as a maintenance of current mode or a normal mode change request.<br>1 = Special Request<br>This bit indicates a special mode request that requires situation-dependant consideration. |
| Requested Mode | 6:0 | Mode byte codes set in association with possible modes |

FIG. 30C

| Data | Bit | Meaning |
|---|---|---|
| 801A OK to Power Down | 7 | 0= Not OK |
| 801B Drive Selection | 6 | 0= Drive 1<br>1= Drive 2 |
| 801C Emergency Power Off Request | 5 | 0= Normal<br>1= EPO request sequence is in process (clears when aborted/completed) |
| 801D Calibration State | 4 | 1= Request for User Calibration state |
| 801E Mode Restriction | 3 | 0 = No restriction<br>1 = Balance critical functions should be restricted |
| 801F User Training | 2 | 0= Disabled<br>1= Enabled |
| 801G Joystick centered | 1:0 | 00= Invalid<br>10= Centered<br>01= Not Centered<br>11= Invalid |

FIG. 30D

| Data | Bit | Meaning |
|---|---|---|
| Frame Lean Command | 7:6 | 00 = Invalid<br>10 = Lean Forward<br>01 = Lean Rearward<br>11 = Idle |
| Reserved | 5:2 | - |
| Seat Height Command | 1:0 | 00 = Invalid<br>10 = Lower Seat Down<br>01 = Raise Seat Up<br>11 = Idle |

921

923

FIG. 30E

MOBILITY DEVICE

CROSS REFERENCE TO RELATED APPLICATIONS

This application is a continuation of U.S. patent application Ser. No. 17/878,245, filed Dec. 1, 2022, division of U.S. patent application Ser. No. 16/035,205, filed Jul. 13, 2018, now U.S. Pat. No. 11,399,995. issued Aug. 2, 2022, which is a continuation-in-part of U.S. patent application Ser. No. 15/982,737, filed May 17, 2018, now U.S. Pat. No. 10,893,028, issued Jan. 12, 2021 and a continuation-in-part of U.S. patent application Ser. No. 15/787,613, filed on Oct. 18, 2017, now U.S. Pat. No. 10,926,756, issued Feb. 23, 2021, which are incorporated herein by reference in their entirety. U.S. patent application Ser. No. 16/035,205, also claims the benefit of U.S. Provisional Application Ser. No. 62/532,993, filed Jul. 15, 2017, U.S. Provisional Application Ser. No. 62/559,263, filed Sep. 15, 2017, and U.S. Provisional Application Ser. No. 62/581,670, filed Nov. 4, 2017, which are incorporated herein by reference in their entirety.

U.S. patent application Ser. No. 15/982,737 claims the benefit of U.S. Provisional Application Ser. No. 62/509,061, filed May 20, 2017.

U.S. patent application Ser. No. 15/787,613 is a continuation-in-part of U.S. patent application Ser. No. 15/600,703, filed May 20, 2017, now U.S. Pat. No. 10,908,045, issued Feb. 2, 2021, which is a continuation-in-part of U.S. patent application Ser. No. 15/441,190, filed Feb. 23, 2017, now U.S. Pat. No. 10,220,843, issued Mar. 5, 2019, and claims the benefit of U.S. Provisional Application Ser. No. 62/298,721, filed Feb. 23, 2016.

U.S. patent application Ser. No. 15/787,613 is also a continuation-in-part of U.S. patent application Ser. No. 15/486,980, filed Apr. 13, 2017, now U.S. Pat. No. 10,802,495, issued Oct. 13, 2020, which claims the benefit of U.S. Provisional Application Ser. No. 62/322,522, filed Apr. 14, 2016.

U.S. patent application Ser. No. 15/787,613 also claims the benefit of U.S. Provisional Application Ser. No. 62/339,723, filed May 20, 2016 and U.S. Provisional Application Ser. No. 62/403,030, filed Sep. 30, 2016.

BACKGROUND

The present teachings relate generally to mobility devices, and more specifically to vehicles that have heightened requirements for safety and reliability.

A wide range of devices and methods are known for transporting human subjects experiencing physical incapacitation. The design of these devices has generally required certain compromises to accommodate the physical limitations of the users. When stability is deemed essential, relative ease of locomotion can be compromised. When transporting a physically disabled or other person up and down stairs is deemed essential, convenient locomotion along regions that do not include stairs can be compromised. Devices that achieve features that could be useful to a disabled user can be complex, heavy, and difficult for ordinary locomotion. Some systems provide for travel in upright positions, while others provide for ascending or descending stairs. Some systems can provide fault detection and operation after a fault has been detected, while others provide for transporting a user over irregular terrain.

The control system for an actively stable personal vehicle or mobility device can maintain the stability of the mobility device by continuously sensing the orientation of the mobility device, determining the corrective action to maintain stability, and commanding the wheel motors to make the corrective action. Currently, if the mobility device loses the ability to maintain stability, such as through the failure of a component, the user may experience, among other things, discomfort at the sudden loss of balance. Further, the user may desire enhanced safety features and further control over the reaction of the mobility device to unstable situations.

Mobility devices such as, for example, wheelchairs, typically include a seat that is integrated with a chassis and wheels. Seats can include a variety of features, and some seats may be structured to help a user accommodate for certain challenges. Likewise, the mobility device chassis and wheels can come in a variety of configurations, for example some are motorized and some are not. When the seat is integrated with the chassis, the user may have to weigh the features of the integrated seat against the features of the chassis and wheels to decide which features are most important to the user. Combining the most important features in a seat with the most important features in a chassis and wheels can be useful when selecting a mobility device. Conveniently engaging a user-preferred seat with the mobility device can provide additional user options. Quickly releasing the engaged seat can provide for readily interchanging various seating options.

Wheelchair seats are further required to provide a user control device engaged therewith to maneuver the wheelchair as per user preference. Positioning of the user control (UC) can be challenging. The UC must be placed to align with comfort of the user or the wheelchair operator. Additionally, the positioning of the UC should be qualified to avoid obstructing any other movements or activities of the user. A rigidly positioned UC can cause such constraints to the user. Adjustable positioning of the UC can enable the user to perform required or routine activities without the UC's being a hindrance.

Electromagnetic holding brakes with and without manual brakes, can be coupled to each motor in a mobility device. In each brake, a friction disk that is keyed to the motor shaft can be trapped between two plates. One plate can be fixed, and the other can move axially under pressure. A magnet can be energized when the motor supply is switched on, releasing the pressure on the plates, allowing the motor shaft to rotate. A motor interface can include a prismatic profile that can mate with a like prismatic motor shaft. Mobility devices can exhibit noise under low motor speed operation. The noise can originate from the interface between the brake disk and motor coupling. This interface can function as a clearance fit between a shaft which passes through a hole in the brake disk. Because there can be a clearance in this interface, the brake disk can have rotational freedom with respect to the brake coupling. During low motor speed operation, this clearance can allow the brake disk to vibrate which can cause a sound due to motor speed fluctuations. A brake disk/motor coupling interface can reduce the vibrations while maintaining a relatively low sensitivity to brake position, the ability to transfer torque, the ability to restrain the brake disk rotational freedom under the no brake load condition, or cushion the rotational impacts that occur between the two parts.

On occasion, motors in a mobility device such as a powered wheelchair need to run faster to accommodate the needs of a user, in particular safety needs. A reliable, lightweight, and stable mobility device can include an automatic response capability to situations that are commonly encountered by a disabled user such as, for example, but not limited to positional obstacles, slippery surfaces, tipping conditions, and component failure. A mobility device can include long-lived redundant batteries, ergonomically positioned and shock buffered caster wheel assemblies, and ride management bumpers. A mobility device can include automatic mode transitions, improved performance over other mobility vehicles, remote control, and a vehicle locking mechanism. A mobility device can include foreign substance sealing and slope management, a cabled charging port, and accommodations for an increased payload over the prior art. A mobility device can include mode control based on battery charge, thumbwheel speed control, and accommodations for a loss of communications among processors.

SUMMARY

The powered balancing mobility device of the present teachings can include, but is not limited to including a powerbase assembly processing movement commands for the mobility device, and at least one cluster assembly operably coupled to the powerbase assembly, the at least one cluster assembly being operably coupled to a plurality of wheels, the plurality of wheels supporting the powerbase assembly, the plurality of wheels and the at least one cluster assembly moving the mobility device based at least on the processed movement commands. The mobility device can include an active stabilization processor estimating the center of gravity of the mobility device, the active stabilization processor estimating at least one value associated with the mobility device required to maintain balance of the mobility device based on the estimated center of gravity. The powerbase processor can actively balance the mobility device on at least two of the plurality of wheels based at least on the at least one value. The powerbase assembly can optionally include redundant motors moving the at least one cluster assembly and the plurality of wheels, redundant sensors sensing sensor data from the redundant motors and the at least one cluster assembly, redundant processors executing within the powerbase assembly, the redundant processors selecting information from the sensor data, the selecting being based on agreement of the sensor data among the redundant processors, the redundant processors processing the movement commands based at least on the selected information.

The powered balancing mobility device can optionally include an anti-tipping controller stabilizing the mobility device based on stabilization factors, the anti-tipping controller executing commands including computing a stabilization metric, computing a stabilization factor, determining movement commands information required to process the movement commands, and processing the movement commands based on the movement command information and the stabilization factor if the stabilization metric indicates that stabilization is required. The powered balancing mobility device can optionally include a stair-climbing failsafe means forcing the mobility device to fall safely if stability is lost during stair climbing. The powered balancing mobility device can optionally include a caster wheel assembly operably coupled with the powerbase assembly, a linear acceleration processor computing mobility device acceleration of the mobility device based at least on the speed of the wheels, the linear acceleration processor computing the inertial sensor acceleration of an inertial sensor mounted upon the mobility device based at least on sensor data from the inertial sensor, a traction control processor computing the difference between the mobility device acceleration and the inertial sensor acceleration, the traction control processor comparing the difference to a pre-selected threshold, and a wheel/cluster command processor commanding the at least one cluster assembly to drop at least one of the plurality of wheels and the caster assembly to the ground based at least on the comparison.

The powerbase processor can optionally use field weakening to provide bursts of speed to motors associated with the at least one cluster assembly and the plurality of wheels. The powerbase processor can optionally estimate the center of gravity of the mobility device by (1) measuring data including a pitch angle required to maintain balance of the mobility device at a pre-selected position of the at least one wheel cluster and a pre-selected position of the seat, (2) moving the mobility device/user pair to a plurality of points, repeats step (1) at each of the plurality of points, (3) verifying that the measured data fall within pre-selected limits, and (4) generating a set of calibration coefficients to establish the center of gravity during operation of the mobility device, the calibration coefficients based at least on the verified measured data. The powerbase processor can optionally include a closed loop controller maintaining stability of the mobility device, the closed loop controller automatically decelerating forward motion and accelerating backward motion under pre-selected circumstances, the pre-selected circumstances being based on the pitch angle of the mobility device and the center of gravity of the mobility device.

The powered balancing mobility device can optionally include an all-terrain wheel pair including an inner wheel having at least one locking means accessible by an operator of the mobility device while the mobility device is operating, the inner wheel having at least one retaining means, the all-terrain wheel pair including an outer wheel having an attachment base, the attachment base accommodating the at least one locking means and the at least one retaining means, the at least one retaining means operable by the operator while the mobility device is in operation to connect the inner wheel to the outer wheel.

The powered balancing mobility device can optionally include a powerbase processor board including at least one inertial sensor, the at least one inertial sensor being mounted on an inertial sensor board, the at least one inertial sensor board being flexibly coupled with the powerbase processor board, the at least one inertial sensor board being separate from the powerbase processor board, the at least one inertial sensor being calibrated in isolation from the powerbase processor board. The powered balancing mobility device can optionally include at least one inertial sensor including a gyro and an accelerometer.

The powerbase processor can optionally include a mobility device wireless processor enabling communications with an external application electronically remote from the mobility device, the mobility device wireless processor receiving and decoding incoming messages from a wireless radio, the powerbase processor controlling the mobility device based at least one the decoded incoming messages. The powerbase processor can optionally include a secure wireless communications system including data obfuscation and challenge-response authentication.

The powered balancing mobility device can optionally include an indirect heat dissipation path between the powerbase processor board and the chassis of the mobility device. The powered balancing mobility device can optionally include a seat support assembly enabling connection of a plurality of seat types to the powerbase assembly, the powerbase assembly having seat position sensors, the seat position sensors providing seat position data to the powerbase processor. The seat support assembly can optionally include seat lift arms lifting the seat, a shaft operably coupled with the seat lift arms, the shaft rotation being measured by the seat position sensors, the shaft rotating through <90°, the shaft being couple to the seat position sensor by a one-stage gear train causing the seat position sensor to rotate >180°, the combination doubling the sensitivity of the seat position data.

The powerbase assembly can optionally include a plurality of sensors fully enclosed within the powerbase assembly, the plurality of sensors including co-located sensor groups sensing substantially similar characteristics of the mobility device. The powerbase assembly can optionally include a manual brake including internal components, the internal components including a hard stop and a damper, the manual brake including a brake release lever replaceable separately from the internal components.

The powerbase processor can optionally include user-configurable drive options limiting speed and acceleration of the mobility device based on pre-selected circumstances. The powered balancing mobility device can optionally include a user control device including a thumbwheel, the thumbwheel modifying at least one speed range for the mobility device.

The powered balancing mobility device can optionally include a drive lock element enabling operable coupling between the powerbase assembly and a docking station, and a skid plate having a pop-out cavity accommodating the drive lock element, the skid plate enabling retention of oil escaping from the powerbase assembly.

The powered balancing mobility device can optionally include a seat, wherein the powerbase processor receiving an indication that the mobility device is encountering a ramp between the ground and a vehicle, the powerbase processor directing the clusters of wheels to maintain contact with the ground, the powerbase processor changing the orientation of the at least one cluster assembly according to the indication to maintain the center of gravity of the mobility device based on the position of the plurality of wheels, the powerbase processor dynamically adjusting the distance between the seat and the at least one cluster assembly to prevent contact between the seat and the plurality of wheels while maintaining the seat as close to the ground as possible.

The powerbase processor can optionally include an obstacle system including receiving obstacle data, automatically identifying the at least one obstacle within the obstacle data, automatically determining at least one situation identifier, automatically maintaining a distance between the mobility device and the at least one obstacle based on the at least one situation identifier, automatically accessing at least one allowed command related to the distance, the at least one obstacle, and the at least one situation identifier, automatically accessing at least one automatic response to at least one movement command, receiving at least one movement command, automatically mapping the at least one movement command with one of the at least one allowed commands, and automatically moving the mobility device based on the at least one movement command and the at least one automatic response associated with the mapped allowed command.

The powerbase processor can optionally include a stair processor including receiving at least one stair command, receiving sensor data from sensors mounted on the mobility device, automatically locating, based on the sensor data, at least one staircase within the sensor data, receiving a selection of a selected staircase of the at least one staircase, automatically measuring at least one characteristic of the selected staircase, automatically locating, based on the sensor data, obstacles, if any, on the selected staircase, automatically locating, based on the sensor data, a last stair of the selected staircase, and automatically navigating the mobility device on the selected staircase based on the measured at least one characteristic, the last stair, and the obstacles, if any.

The powerbase processor can optionally include a rest room processor including automatically locating a rest room stall door, automatically moving the mobility device through the rest room stall door into the rest room stall, automatically positioning the mobility device relative to rest room fixtures, automatically locating the rest room stall door, and automatically moving the mobility device through the rest room stall door exiting the rest room stall.

The powerbase processor can optionally include a door processor including receiving sensor data from sensors mounted on the mobility device, automatically identifying the door within the sensor data, automatically measuring the door, automatically determining the door swing, automatically moving the mobility device forward through the doorway, the mobility device opening the door and maintaining the door in an open position, if the door swing is away from the mobility device, and automatically positioning the mobility device for access to a handle of the door, moving the mobility device away from the door, as the door opens, by a distance based on the width of the door, and moving the mobility device forward though the doorway, the mobility device maintaining the door in an open position, if the door swing is towards the mobility device.

The powerbase processor can optionally include a door processor including receiving sensor data from sensors mounted on the mobility device, automatically identifying the door within the sensor data, automatically measuring the door, including the width of the door, automatically generating an alert if the door is smaller than the a pre-selected size related to the size of the mobility device, automatically positioning the mobility device for access to the door, the positioning being based on the width of the door, automatically generating a signal for opening the door, and automatically moving the mobility device though the doorway.

The powerbase processor can optionally include a docking processor including automatically locating a transfer point at which a patient transfers out of the mobility device, automatically positioning the mobility device in the vicinity of the transfer point, automatically determining when the patients transfers out of the mobility device, automatically locating a docking station, automatically positioning the mobility device at the docking station, and operably connecting the mobility device to the docking station.

The method of the present teachings for controlling the speed of a mobility device, where the mobility device can include a plurality of wheels and a plurality of sensors, the method can include, but is not limited to including receiving terrain and obstacle detection data from the plurality of sensors, mapping terrain and obstacles, if any, in real time based at least on the terrain and obstacle detection data, computing collision possible areas, if any, based at least on the mapped data, computing slow-down areas if any based at least on the mapped data and the speed of the mobility device, receiving user preferences, if any, with respect to the slow-down areas and desired direction and speed of motion, computing wheel commands to command the plurality of wheels based at least on the collision possible areas, the slow-down areas, and the user preferences, and providing the wheel commands to the plurality of wheels.

The method of the present teachings for moving a balancing mobility device on relatively steep terrain, where the mobility device including clusters of wheels and a seat, and the clusters of wheels and the seat are separated by a distance, and the distance varies based on pre-selected characteristics, the method can include, but is not limited to including, receiving an indication that the mobility device will encounter the steep terrain, directing the clusters of wheels to maintain contact with the ground, and dynamically adjusting the distance between the seat and the clusters of wheels based on maintaining the balance of the mobility device and the indication.

The mobility device of the present teachings includes a reliable, lightweight, stable mobility device that includes a powerbase operably coupled with a user controller. The powerbase can include a powerbase controller, a power source controller, wheel cluster assemblies, all-terrain wheels, caster arms, and casters. The powerbase can include long-lived redundant batteries having, for example, on-board battery management systems, ergonomically positioned and shock buffered caster wheel assemblies, a docking capability, generic seat attachment hardware, and ride management bumpers. The powerbase and the user controller can communicate with an external device that can, for example, monitor and control the mobility device. The mobility device can be protected from foreign substance entry and tipping hazards, and can accommodate an increased payload over the prior art.

The powerbase controller can include, but is not limited to including, at least two redundant processors controlling the mobility device. The at least one user controller can receive desired actions for the mobility device and can, along with the powerbase controller, process the desired actions. The at least two processors can each include at least one controller processing task. The at least one controller processing task can receive sensor data and motor data associated with sensors and motors that can be operably coupled with the mobility device. The mobility device can include at least one inertial measurement unit (IMU) board that can be operably coupled with the powerbase controller. The at least one IMU can be mounted on a daughter board, and can be calibrated remotely from the mobility device. The coupling of the daughter board with the powerbase controller can enable shock-resistance in the IMU.

In addition to redundant processors, the mobility device of the present teachings can include reliability features such as, for example, redundant motors and sensors, such as, for example. IMU sensors. Eliminating data that could be incorrect from the redundant components can improve the safety and reliability of the mobility device. The method of the present teachings, referred to herein as "voting", for resolving which value to use from redundant of the at least one processor of the present teachings can include, but is not limited to including, initializing a counter, averaging values, for example, but not limited to, sensor or command values, from each processor (referred to herein as processor values), computing the absolute value difference between each processor value and the average, and discarding the highest difference. The method can further include computing differences between the remaining processor values and each other. If there are any differences greater than a preselected threshold, the method can include comparing the values that have the highest difference between them to the remaining value, voting out the value with the highest difference from the remaining value, comparing the voted out values to the remaining values, and voting out any difference above the pre-selected threshold and selecting one of the remaining processor values or an average of the processor values. If there are no differences greater than the pre-selected threshold, the method can compare the voted out value to the remaining values. If there are any differences greater than the pre-selected threshold, the method can include voting out the value voted out in the compare step, and selecting one of the remaining processor values or an average of the remaining processor values. If there are no differences greater than the pre-selected threshold, the method can include selecting one of the remaining processor values or an average of the remaining processor values. If a processor value is voted out a pre-selected number of times, the method can include raising an alarm. If the voting scheme fails to find a processor value that satisfies the selection criteria, the method can include incrementing the counter. If the counter has not exceeded a pre-selected number, the method can include discarding the frame having no remaining processor values and selecting a previous frame having at least one processor value that meets the selection criteria. If the frame counter is greater than the pre-selected number, the method can include moving the mobility device to a failsafe mode. The mobility device of the present teachings can include a filter to fuse gyro and accelerometer data to produce an accurate estimate of a gravity vector, and the gravity vector can be used to define the orientation and inertial rotation rates of the mobility device. The orientation and inertial rotation rates of the mobility device can be shared and combined across redundant processors of the present teachings.

To facilitate a beneficial user experience, the mobility device can operate in several functional modes including, but not limited to, standard, 4-Wheel, stair, balance, remote, utility, calibration, and, optionally, docking modes, all described herein. When first powered, the mobility device can include a pre-determined start-up process. The mobility device can perform self-diagnostics to check the integrity of features of the mobility device that are not readily testable during normal operation. Power off requests can be detected and qualified by the mobility device to determine whether to grant the request or not. Prior to powering off, the mobility device position can be secured and all state information and logged information can be stored.

In some configurations, the mobility device of the present teachings can accommodate users of varying levels of physical ability and device acumen. In particular, users can adjust the response of the mobility device to joystick commands. In some configurations, the mobility device of the present teachings can allow user configurable drive options in the form of joystick command shaping and thumbwheel control that can allow individual users to configure the mobility device, including the user controller of the present teachings, for driving preferences. The mobility device of the present teachings can accommodate speed sensitive steering that can adjust the turn behavior of the mobility device as a function of the speed of the mobility device, making the mobility device responsive at high speeds and less jerky at low speeds.

In some configurations, the mobility device of the present teachings can still further accommodate adaptive speed control to assist users in avoiding potentially dangerous conditions while driving. Adaptive speed control can reduce required driver concentration by using sensors to detect obstacles, and can help users negotiate difficult terrain or situations. The method of the present teachings for adaptive speed control of the mobility device can include, but is not limited to including, receiving terrain and obstacle detection data, and mapping terrain and obstacles, if any, in real time based at least on the terrain and obstacle detection data. The method can optionally include computing virtual valleys, if any, based at least on the mapped data. The method can still further include computing collision possible areas, if any, based at least on the mapped data, and computing slow-down areas if any based at least on the mapped data and the speed of the mobility device. The method can also include receiving user preferences, if any, with respect to the slow-down areas and desired direction and speed of motion. The method can still further include computing at least one wheel command based at least on the collision possible areas, the slow-down areas, and the user preferences and optionally the virtual valleys, and providing the at least one wheel command to the wheel motor drives.

The method for obstacle processing of the present teachings can include, but is not limited to including, receiving and segmenting PCL data, identifying at least one plane within the segmented PCL data, and identifying at least one obstacle within the at least one plane. The method for obstacle processing can further include determining at least one situation identifier based at least on the obstacles, user information, and movement commands, and determining the distance between the mobility device and the obstacles based at least on the situation identifier. The method for obstacle processing can also include accessing at least one allowed command related to the distance, the obstacle, and the situation identifier. The method for obstacle processing can still further include accessing an automatic response to the allowed command, receiving a movement command, mapping the movement command with one of the allowed commands, and providing the movement command and the automatic response associated with the mapped allowed command to the mode-dependent processors.

The obstacles can be stationary or moving. The distance can include a fixed amount and/or can be a dynamically varying amount. The movement command can include a follow command, a pass-the-obstacle command, a travel-beside-the-obstacle command, and a do-not-follow-the-obstacle command. The obstacle data can be stored and retrieved locally and/or in a cloud-based storage area, for example. The method for obstacle processing can include collecting sensor data from a time-of-flight camera mounted on the mobility device, analyzing the sensor data using a point cloud library (PCL), tracking the moving object using SLAM based on the location of the mobility device, identifying a plane within the obstacle data using, and providing the automatic response associated with the mapped allowed command to the mode-dependent processors. The method for obstacle processing can receive a resume command, and provide, following the resume command, a movement command and the automatic response associated with the mapped allowed command to the mode-dependent processors. The automatic response can include a speed control command.

The obstacle processor of the present teachings can include, but is not limited to including, a nav/PCL data processor. The nav/PCL processor can receive and segment PCL data from a PCL processor, identify a plane within the segmented PCL data, and identify obstacles within the plane. The obstacle processor can include a distance processor. The distance processor can determine a situation identifier based user information, the movement command, and the obstacles. The distance processor can determine the distance between the mobility device and the obstacles based at least on the situation identifier. The moving object processor and/or the stationary object processor can access the allowed command related to the distance, the obstacles, and the situation identifier. The moving object processor and/or the stationary object processor can access an automatic response from an automatic response list associated with the allowed command. The moving object processor and/or the stationary object processor can access the movement command and map the movement command with one of the allowed commands. The moving object processor and/or stationary object processor can provide movement commands and the automatic response associated with the mapped allowed command to the mode-dependent processors. The movement command can include a follow command, a pass command, a travel-beside command, a move-to-position command, and a do-not-follow command. The nav/PCL processor can store obstacles in local storage and/or on storage cloud, and can allow access to the stored obstacles by systems external to the mobility device.

In some configurations, the mobility device of the present teachings can include weight sensitive controllers that can accommodate the needs of a variety of users. Further, the weight sensitive controllers can detect an abrupt change in weight, for example, but not limited to, when the user exits the mobility device. The weight and center of gravity location of the user can be significant contributors to the system dynamics. By sensing the user weight and adjusting the controllers, improved active response and stability of the mobility device can be achieved.

The method of the present teachings for stabilizing the mobility device can include, but is not limited to including, estimating the weight and/or change in weight of a load on the mobility device, choosing a default value or values for the center of gravity of the mobility device and load combination, computing controller gains based at least on the weight and/or change in weight and the center of gravity values, and applying the controller gains to control the mobility device. The method of the present teachings for computing the weight of a load on the mobility device can include, but is not limited to including, receiving the position of the load on the mobility device, receiving the setting of the mobility device to standard mode, measuring the motor current required to move the mobility device to enhanced mode at least once, computing a torque based at least on the motor current, computing a weight of the load based at least on the torque, and adjusting controller gains based at least on the computed weight to stabilize the mobility device.

In some configurations, the mobility device of the present teachings can include traction control that can adjust the torque applied to the wheels to affect directional and acceleration control. In some configurations, traction control can be assisted by rotating the cluster so that four wheels contact the ground when braking above a certain threshold is requested. The method of the present teachings for controlling traction of the mobility device can include, but is not limited to including, computing the linear acceleration of the mobility device, and receiving the IMU measured acceleration of the mobility device. If the difference between an expected linear acceleration and a measured linear acceleration of the mobility device is greater than or equal to a preselected threshold, adjusting the torque to the cluster/wheel motor drives. If the difference between an expected linear acceleration and a measured linear acceleration of the mobility device is less than a preselected threshold, the method can continue testing for loss of traction.

The mobility device of the present teachings can include a user controller (UC) assist that can assist a user in avoiding obstacles, traversing doors, traversing stairs, traveling on elevators, and parking/transporting the mobility device. The UC assist can receive user input and/or input from components of the mobility device, and can enable the invocation of a processing mode that has been automatically or manually selected. A command processor can enable the invoked mode by generating movement commands based at least on previous movement commands, data from the user, and data from sensors. The command processor can receive user data that can include signals from a joystick that can provide an indication of a desired movement direction and speed of the mobility device. User data can also include mode selections into which the mobility device could be transitioned. Modes such as door mode, rest room mode, enhanced stair mode, elevator mode, mobile storage mode, and static storage/charging mode can be selected. Any of these modes can include a move-to-position mode, or the user can direct the mobility device to move to a certain position. UC assist can generate commands such as movement commands that can include, but are not limited to including, speed and direction, and the movement commands can be provided to wheel motor drives and cluster motor drives.

Sensor data can be collected by sensor-handling processors that can include, but are not limited to including, a geometry processor, a point cloud library (PCL) processor, a simultaneous location and mapping (SLAM) processor, and an obstacle processor. The movement commands can also be provided to the sensor handling processors. The sensors can provide environmental information that can include, for example, but not limited to, obstacles and geometric information about the mobility device. The sensors can include at least one time-of-flight sensor that can be mounted anywhere on the mobility device. There can be multiple sensors mounted on the mobility device. The PCL processor can gather and process environmental information, and can produce PCL data that can be processed by a PCL library.

The geometry processor of the present teachings can receive geometry information from the sensors, can perform any processing necessary to prepare the geometry information for use by the mode-dependent processors, and can provide the processed of geometry information to mode-dependent processors. The geometry of the mobility device can be used for automatically determining whether or not the mobility device can fit in and/or through a space such as, for example, a stairway and a door. The SLAM processor can determine navigation information based on, for example, but not limited to, user information, environmental information, and movement commands. The mobility device can travel in a path at least in part set out by navigation information. An obstacle processor can locate obstacles and distances to the obstacles. Obstacles can include, but are not limited to including, doors, stairs, automobiles, and miscellaneous features in the vicinity of the path of the mobility device.

The method of the present teachings for navigating stairs can include, but is not limited to including, receiving a stair command, and receiving environmental information from the obstacle processor. The method for navigating stairs can include locating, based on the environmental information, staircases within environmental information, and receiving a selection of one of the staircases located by the obstacle processor. The method for navigating stairs can also include measuring the characteristics of the selected staircase, and locating, based on the environmental information, obstacles, if any, on the selected staircase. The method for navigating stairs can also include locating, based on the environmental information, a last stair of the selected staircase, and providing movement commands to move the mobility device on the selected staircase based on the measured characteristics, the last stair, and the obstacles, if any. The method for navigating stairs can continue providing movement commands until the last stair is reached. The characteristics can include, but are not limited to including, the height of the stair riser of the selected staircase, the surface texture of the riser, and the surface temperature of the riser. Alerts can be generated if the surface temperature falls outside of a threshold range and the surface texture falls outside of a traction set.

The navigating stair processor of the present teachings can include, but is not limited to including, a staircase processor receiving at least one stair command included in user information, and a staircase locator receiving, through, for example, the obstacle processor, environmental information from sensors mounted on the mobility device. The staircase locator can locate, based on environmental information, the staircases within the environmental information, and can receive the choice of a selected staircase. The stair characteristics processor can measure the characteristics of the selected staircase, and can locate, based on environmental information, obstacles, if any, on the selected staircase. The stair movement processor can locate, based on environmental information, a last stair of the selected staircase, and can provide to movement processor movement commands to instruct the mobility device to move on the selected staircase based on the characteristics, the last stair, and the obstacles, if any. The staircase locator can locate staircases based on GPS data, and can build and save a map of the selected staircase. The map can be saved for use locally and/or by other devices unrelated to the mobility device. The staircase processor can access the geometry of the mobility device, compare the geometry to the characteristics of the selected staircase, and modify the navigation of the mobility device based on the comparison. The staircase processor can optionally generate an alert if the surface temperature of the risers of the selected staircase falls outside of a threshold range and the surface texture of selected staircase falls outside of a traction set. The stair movement processor can determine, based on the environmental information, the topography of an area surrounding the selected staircase, and can generate an alert if the topography is not flat. The stair movement processor can access a set of extreme circumstances that can be used to modify the movement commands generated by the stair movement processor.

When the mobility device traverses the threshold of a door, where the door can include a door swing, a hinge location, and a doorway, the method of the present teachings for navigating a door can include receiving and segmenting environmental information from sensors mounted on the mobility device. The environmental information can include the geometry of the mobility device. The method can include identifying a plane within the segmented sensor data, and identifying the door within the plane. The method for navigating a door can include measuring the door, and providing movement commands that can move the mobility device away from the door if the door measurements are smaller than the mobility device. The method for navigating a door can include determining the door swing and providing movement commands to move the mobility device for access to a handle of the door. The method for navigating a door can include providing movement commands to move the mobility device away from the door as the door opens by a distance based on the door measurements. The method for navigating a door can include providing movement commands to move the mobility device forward though the doorway. The mobility device can maintain the door in an open position if the door swing is towards the mobility device.

The method of the present teachings for processing sensor data can determine, through information from the sensors, the hinge side of the door, the direction and angle of the door, and the distance to the door. The movement processor of the present teachings can generate commands to the MD such as start/stop turning left, start/stop turning right, start/stop moving forward, start/stop moving backwards, and can facilitate door mode by stopping the mobility device, cancelling the goal that the mobility device can be aiming to complete, and centering the joystick. The door processor of the present teachings can determine whether the door is, for example, a push to open, a pull to open, or a slider. The door processor can determine the width of the door based on the current position and orientation of the mobility device, and can determine the x/y/z location of the door pivot point. If the door processor determines that the number of valid points in the image of the door derived from the set of obstacles and/or PCL data is greater than a threshold, the door processor can determine the distance from the mobility device to the door. The door processor can determine if the door is moving based on successive samples of PCL data from the sensor processor. In some configurations, the door processor can assume that a side of the mobility device is even with the handle side of the door, and can use that assumption, along with the position of the door pivot point, to determine the width of the door. The door processor can generate commands to move the mobility device through the door based on the swing and the width of the door. The mobility device itself can maintain the door in an open state while the mobility device traverses the threshold of the door.

In some configurations, the mobility device can automatically negotiate the use of rest room facilities. The doors to the rest room and to the rest room stall can be located as discussed herein, and the mobility device can be moved to locations with respect to the doors as discussed herein. Fixtures in the rest room can be located as obstacles as discussed herein, and the mobility device can be automatically positioned in the vicinity of the fixtures to provide the user with access to, for example, the toilet, the sink, and the changing table. The mobility device can be automatically navigated to exit the rest room stall and the rest room through door and obstacle processing discussed herein. The mobility device can automatically traverse the threshold of the door based on the geometry of the mobility device.

The method of the present teachings for automatically storing the mobility device in a vehicle, such as, for example, but not limited to, an accessible van, can assist a user in independent use of the vehicle. When the user exits the mobility device and enters the vehicle, possibly as the vehicle's driver, the mobility device can remain parked outside of the vehicle. If the mobility device is to accompany the user in the vehicle for later use, the mobile park mode of the present teachings can provide movement commands to the mobility device to cause the mobility device to store itself either automatically or upon command, and to be recalled to the door of the vehicle as well. The mobility device can be commanded to store itself through commands received from external applications, for example. In some configurations, a computer-driven device such as a cell phone, laptop, and/or tablet can be used to execute one or more external applications and generate information that could ultimately control the mobility device. In some configurations, the mobility device can automatically proceed to mobile park mode after the user exits the mobility device. Movement commands can include commands to locate the door of the vehicle at which the mobility device will enter to be stored, and commands to direct the mobility device to the vehicle door. Mobile park mode can determine error conditions such as, for example, but not limited to, if the vehicle door is too small for the mobility device to enter, and mobile park mode can alert the user of the error condition through, for example, but not limited to, an audio alert through audio interface and/or a message to one or more external applications. If the vehicle door is wide enough for the mobility device to enter, mobile park mode can provide vehicle control commands to command the vehicle to open the vehicle door. Mobile park mode can determine when the vehicle door is open and whether or not there is space for the mobility device to be stored. Mobile park mode can invoke the method for obstacle processing to assist in determining the status of the vehicle door and if there is room in the vehicle to store the mobility device. If there is enough room for the mobility device, mobile park mode can provide movement commands to move the mobility device into the storage space in the vehicle. Vehicle control commands can be provided to command the vehicle to lock the mobility device into place, and to close the vehicle door. When the mobility device is again needed, one or more external applications, for example, can be used to bring the mobility device back to the user. The status of the mobility device can be recalled, and vehicle control commands can command the vehicle to unlock the mobility device and open the door of the vehicle. The vehicle door can be located and the mobility device can be moved through the vehicle door and to the passenger door to which it had been summoned by, for example, one or more external applications. In some configurations, the vehicle can be tagged in places such as, for example, the vehicle entry door where the mobility device can be stored.

The method of the present teachings for storing/recharging the mobility device can assist the user in storing and possibly recharging the mobility device, possibly when the user is sleeping. After the user exits the mobility device, commands can be initiated by one or more external applications, to move the perhaps riderless mobility device to a storage/docking area. In some configurations, a mode selection by the user while the user occupies the mobility device can initiate automatic storage/docking functions after the user has exited the mobility device. When the mobility device is again needed, commands can be initiated by one or more external applications to recall the mobility device to the user. The method for storing/recharging the mobility device can include, but is not limited to including, locating at least one storage/charging area, and providing at least one movement command to move the mobility device from a first location to the storage/charging area. The method for storing/recharging the mobility device can include locating a charging dock in the storage/charging area and providing at least one movement command to couple the mobility device with the charging dock. The method for storing/recharging the mobility device can optionally include providing at least one movement command to move the mobility device to the first location when the mobility device receives an invocation command. If there is no storage/charging area, or if there is no charging dock, or if the mobility device cannot couple with the charging dock, the method for storing/recharging the mobility device can optionally include providing at least one alert to the user, and providing at least one movement command to move the mobility device to the first location.

The method of the present teachings for negotiating an elevator while maneuvering the mobility device can enable a user to get on and off the elevator while seated in the mobility device. When the elevator is, for example, automatically located, and when the user selects the desired elevator direction, and when the elevator arrives and the door opens, movement commands can be provided to move the mobility device into the elevator. The geometry of the elevator can be determined and movement commands can be provided to move the mobility device into a location that makes it possible for the user to select a desired activity from the elevator selection panel. The location of the mobility device can also be appropriate for exiting the elevator. When the elevator door opens, movement commands can be provided to move the mobility device to fully exit the elevator.

The powered balancing mobility device of the present teachings can include, but is not limited to including, a powerbase assembly including a powerbase controller and a power source controller. The power source controller can supply power to the powerbase controller, and the powerbase assembly can process movement commands for the mobility device. The powered balancing mobility device can include cluster assemblies operably coupled to the powerbase assembly. The cluster assemblies can include operable coupling with a plurality of wheels. The wheels can support the powerbase assembly and can move based on the processed movement commands. The powerbase assembly and the cluster assembly can enable balance of the mobility device on two of the plurality of wheels.

The powered balancing mobility device can optionally include caster arms that can be operably coupled to the powerbase assembly. The caster arms can include operable coupling to the caster wheels, and the caster wheels can support the powerbase assembly. The powered balancing mobility device can optionally include a seat support assembly that can enable connection of a seat to the powerbase assembly. The powerbase assembly can include seat position sensors, and the seat position sensors can provide seat position data to the powerbase assembly. The powered balancing mobility device can optionally include terrain wheels that can include a means for user-detachability. The powered balancing mobility device can optionally include a powerbase controller board including the powerbase controller and at least one inertial measurement unit (IMU). The at least one IMU can be mounted upon an IMU board, and the IMU can include flexibly coupling with the powerbase controller board. The IMU board can be separate from the powerbase controller board, and the at least one IMU can be calibrated in isolation from the powerbase controller board.

The powered balancing mobility device can optionally include at least one field-effect transistor (FET) positioned on the powerbase controller board, and at least one heat spreader plate receiving heat from the FET. The at least one heat spreader plate can transfer the heat to the chassis of the mobility device. The powered balancing mobility device can optionally include at least one motor being thermally pressed into at least one housing of the mobility device, and at least one thermistor associated with the at least one motor, the at least one thermistor enabling reduced power usage when the associated at least one motor exceeds a heat threshold. The powered balancing mobility device can optionally include a plurality of batteries that can power the mobility device. The plurality of batteries can be mounted with mounting gaps between each pair of the batteries. The batteries can be connected to the powerbase assembly through environmentally isolated seals. The powered balancing mobility device can optionally include a powerbase controller board that can include redundant processors. The redundant processors can be physically separated from each other, and can enable fault tolerance based on a voting process.

The powered balancing mobility device can optionally include a drive lock element that can enable operable coupling between the powerbase assembly and a docking station. The powered balancing mobility device can optionally include a skid plate having a pop-out cavity that can accommodate the drive lock element. The skid plate can enable retention of oil escaping from the powerbase assembly. The powered balancing mobility device can optionally include an anti-tipping process that can reduce the likelihood of the mobility device tipping over. The powered balancing mobility device can optionally include a field weakening process that can enable management of abnormal circumstances by the mobility device by supplying relatively short bursts of relatively high motor speed. The powered balancing mobility device can optionally include a stair-climbing failsafe means that can force the mobility device to fall backwards if stability is lost during stair climbing. The powered balancing mobility device can optionally include at least one magnet mounted within the cluster assembly. The at least one magnet can attract particles within the cluster assembly. The powered balancing mobility device can optionally include at least one seal between sections of the cluster assembly. The powered balancing mobility device can optionally include electrical connectors that can include printed circuit boards (PCBs) having electromagnetic (EM) energy shielding. The PCBs can disable transmission of EM energy along cables associated with the electrical connectors.

The mobility device of the present teachings can include, but is not limited to including, a seat and a cluster. The mobility device can include a fully internal and redundant sensor system, and the sensor system can include a plurality of sensors. The plurality of sensors can include a plurality of absolute position sensors that can enable new location reports if the seat and/or cluster move during a power off of the mobility device. The plurality of sensors can include a plurality of seat sensors and a plurality of cluster sensors operating during power on. The sensor system can enable fail-over from a failing one of the plurality of sensors to another of the plurality of the sensors. The plurality of sensors can include co-located sensor groups that can sense substantially similar characteristics of the mobility device. The mobility device can include an environmentally isolated gearbox. The contents of the gearbox being can be shielded from physical contaminants and electromagnetic transmissions. The gearbox can be oiled by an oil port in a housing of the mobility device. The mobility device can include a manual brake that can include a hard stop and a damper. The manual brake can include a brake release lever isolated from the contents of the gearbox. The manual brake can include a mechanically isolated sensor reporting when the manual brake is engaged, and the isolated sensor can include a flux shield.

The method of the present teachings for establishing the center of gravity for a mobility device/user pair, where the mobility device can include a balancing mode that can include a balance of the mobility device/user pair, and where the mobility device can include at least one wheel cluster and a seat, can include, but is not limited to including, (1) entering the balancing mode, (2) measuring data including a pitch angle required to maintain the balance at a pre-selected position of the at least one wheel cluster and a pre-selected position of the seat, (3) moving the mobility device/user pair to a plurality of pre-selected points, (4) repeating step (2) at each of the plurality of pre-selected points, (5) verifying that the measured data fall within pre-selected limits, and (6) generating a set of calibration coefficients to establish the center of gravity during operation of the mobility device. The calibration coefficients can be based at least on the verified measured data. The method can optionally include storing the verified measured data in non-volatile memory.

The method of the present teachings for filtering parameters associated with the movement of a mobility device having an IMU, where the IMU includes a gyro, and the gyro includes a gyro bias and gyro data, can include, but is not limited to including, (1) subtracting the gyro bias from gyro data to correct the gyro data, (2) integrating a filtered gravity rate over time to produce a filtered gravity vector, (3) computing a gravity rate vector and a projected gravity rate estimate based at least on filtered body rates and the filtered gravity vector, (4) subtracting the product of a first gain K1 and a gravity vector error from the gravity rate vector, the gravity vector error being based at least on the filtered gravity vector and a measured gravity vector, (5) computing a pitch rate, a roll rate, a yaw rate, a pitch, and a roll of the mobility device based on a filtered gravity rate vector and the filtered body rates, (6) subtracting a differential wheel speed between wheels of the mobility device from the projected gravity rate estimate to produce a projected rate error and the gyro bias, (7) computing the cross product of gravity vector error and the filtered gravity vector, and adding the cross product to the dot product of the filtered gravity vector and a projected gravity rate estimate error to produce a body rate error, (8) applying a second gain to an integration over time of the body rate error to produce the gyro bias, and (9) looping through steps (1)-(8) to continually modify the gyro data.

The method of the present teachings for making an all-terrain wheel pair can include, but is not limited to including, constructing an inner wheel having at least one locking pin receiver, the inner wheel having a retaining lip accommodating twist-lock attachment, and constructing an outer wheel having an attachment base. The attachment base can include a locking pin cavity, and the locking pin cavity can accommodate a locking pin. The locking pin cavity can include at least one retaining tang that can accommodate twist-lock attachment. The method can include attaching the outer wheel to the inner wheel by mating the locking pin with one of the at least one locking pin receivers and mating the retaining lip with the at least one retaining tang.

The method of the present teachings for traveling over rough terrain in a mobility device can include, but is not limited to including, attaching an inner wheel having at least one locking pin receiver. The inner wheel can include a retaining lip accommodating twist-lock attachment. The method can include attaching an outer wheel having at least one retaining tang and an attachment base having a locking pin cavity to the inner wheel by threading a locking pin into the locking pin cavity and mating the locking pin with one of the at least one locking pin receivers, and mating the retaining lip with the at least one retaining tang.

The all-terrain wheel pair of the present teachings can include, but is not limited to including, an inner wheel having at least one locking pin receiver. The inner wheel can include a retaining lip accommodating twist-lock attachment. The wheel pair can include an outer wheel having an attachment base. The attachment base can include a locking pin cavity, and the locking pin cavity can accommodate a locking pin. The locking pin cavity can include at least one retaining tang that can accommodate twist-lock attachment. The outer wheel can be attached to the inner wheel by mating the locking pin with one of the at least one locking pin receivers and mating the retaining lip with the at least one retaining tang.

The user controller for a mobility device of the present teachings can include, but is not limited to including, a thumbwheel that can modify at least one speed range for the mobility device. The thumbwheel can generate signals during movement of the thumbwheel, and the signals can be provided to the user controller. The user controller can maintain environmental isolation from the thumbwheel while receiving the signals. The user controller can optionally include a casing first part including mounting features for at least one speaker, at least one circuit board, and at least one control device. The control device can enable selection of at least one option for the mobility device. The user controller can optionally include at least one first environmental isolation device, and a casing second part that can include mounting features for at least one display, at least one selection device, and at least one antenna. The casing second part and the casing first part can be operably coupled around the at least one first environmental isolation device. The at least one display can enable monitoring of the status of the mobility device, and the at least one display can present the at least one option. The at least one selection device can enable selection of the at least one option. The user controller can optionally include a power/data cable enabling power to flow from the mobility device to the user controller. The power/data cable can enable data exchange between the user controller and the mobility device. The user controller can optionally include a toggle platform first part including toggles, and the toggles can be field replaceable. The toggles can enable selection of the at least one option. The user controller can optionally include at least one second environmental isolation device, and a toggle platform second part that can include mobility device mounting features. The toggle platform second part and the toggle platform first part can be operably coupled around the at least one second environmental isolation device. The mobility device mounting features can enable mounting of the user controller on the mobility device. The user controller can optionally include 2-way shortcut toggles, 4-way shortcut toggles, and at least one integration device integrating the 2-way shortcut toggles with the 4-way shortcut toggles.

The at least one option can include desired speed, desired direction, speed mode, mobility device mode, seat height, seat tilt, and maximum speed. The control device can include at least one joystick and at least one thumbwheel. The at least one joystick can enable receiving the desired speed and the desired direction, and the at least one thumbwheel can enable receiving the maximum speed. The at least one toggle can include at least one toggle switch and at least one toggle lever. The at least one display can include at least one battery status indicator, a power switch, at least one audible alert and mute capability, and at least one antenna receiving wireless signals.

The thumbwheel for a user controller of the present teachings can include, but is not limited to including, a full rotation selector that can enable movement of the thumbwheel to produce movement data throughout a full rotation of the thumbwheel. The movement data can be dynamically associated with at least one user controller characteristic. The thumbwheel can include a thumbwheel position, at least one sensor receiving the movement data, and memory that can retain the thumbwheel position and the at least one user controller characteristic across a power down state. The at least one user controller characteristic can include maximum speed. The at least one sensor can be environmentally isolated from the user controller. The at least one sensor can include a Hall-effect sensor.

The method of the present teachings for controlling the speed of a mobility device that includes a non-stop thumbwheel and a joystick, where the thumbwheel includes a persistently stored position, can include, but is not limited to including, (a) accessing a relationship between a change in the rotational position of the thumbwheel and a multiplier for a maximum speed of the personal transport device, (b) receiving a change in the persistently stored position of the non-stop thumbwheel, (c) determining the multiplier based on the change and the relationship, (d) persistently storing the changed position, (e) receiving a speed signal from the joystick, (f) adjusting the speed signal based on the multiplier, and (g) repeating steps (a) through (f) while the mobility device is active. The method can optionally include receiving an indication of the sensitivity of the thumbwheel, and adjusting the relationship based on the indication. The multiplier can be <1.

The mobility device of the present teachings can overcome the limitations of the prior art by including redundancy, a lightweight housing, an inertial measurement system, advanced heat management strategy, wheel and cluster gear trains specifically designed with the wheelchair user in mind, lightweight, long-lived redundant batteries, ergonomically positioned and shock buffered caster wheel assemblies, and ride management bumpers. Other improvements can include, but are not limited to including, automatic mode transitions, anti-tipping, improved performance, remote control, a generic mounting for a vehicle locking mechanism and the locking mechanism itself, foreign substance sealing, slope management, and a cabled charging port. Because of the reduction in weight of the mobility device, the mobility device can accommodate increased payload over the prior art.

The powered balancing mobility device of the present teachings can include, but is not limited to including, a plurality of redundant processors processing movement commands for the mobility device, each of the plurality of redundant processors receiving sensor data, and a voting processor executing on each of the plurality of redundant processors. The voting processor can receive the sensor data from each of the plurality of redundant processors, and can determine valid data of the sensor data based at least on whether the sensor data are within a pre-selected range. The voting processor can determine whether the voting processor has received invalid of the sensor data from an associated one of the plurality of sensors, and whether there are communications among the plurality of redundant processors. The plurality of redundant processors can compute the movement commands based at least on the valid data. The voting processor can optionally execute commands that can create a list of candidate processors from the plurality of redundant processors associated with the valid data, determine the average value of the valid data for the candidate processors, order the list of the candidate processors based at least on the comparison between the valid data for each of the candidate processors and the average values, perform a three-way vote of the valid data if there are at least three of the candidate processors, and indicate which of the candidate processors is associated with voted out sensor data. The voting processor can optionally execute commands that can perform a two-way vote of the valid data if there are two of the candidate processors, indicate that the two candidate processors are associated with voted out sensor data if the valid data from each of the two candidate processors do not agree, indicate that one of the candidate processors is associated with voted out sensor data if there is only a single candidate processor associated with valid data, and average any of the valid data that is not voted out. The powered balancing mobility can optionally include at least four processors.

The powered balancing mobility device of the present teachings can include, but is not limited to including, a plurality of redundant processors processing movement commands for the mobility device, at least four batteries, and a power source controller including connections for the at least four batteries. The power source controller can receive power from the at least four batteries, and can manage power to the plurality of redundant processors. The power source controller can include at least one sensor collecting current data and voltage data for the at least four batteries. The mobility device can include a plurality of modes governing the movement commands. The plurality of redundant processors can determine which of the plurality of modes the mobility device can enter based at least in part on the current data and voltage data. The powered balancing mobility device can optionally include six batteries. The connections can include, but are not limited to including, up to four of the connections for operably coupling up to four batteries with the power source controller. The power source controller can include at least one battery recharge circuit. At least one of the connections can operably couple at least one shunt circuit with the power source controller. The at least one shunt circuit can prevent overcharge of the at least four batteries. The power source controller can optionally include a plurality of states including an on state, a charging state, a sleep state, and an off state.

The powered balancing mobility device of the present teachings can include, but is not limited to including, a plurality of redundant processors processing movement commands for the mobility device. Each of the plurality of redundant processors can receive sensor data. The mobility device can include a user controller including a thumbwheel. The thumbwheel can be associated with a virtual thumbwheel position. The user controller can receive signals based on movement of the thumbwheel. The sensitivity of the thumbwheel can be adjustable according to the virtual thumbwheel position. The signals can be processed to produce a value, and the movement commands can be based at least in part on the value. The mobility device can optionally include at least one drive speed setting. The at least one drive speed setting can limit the speed of the mobility device. The value can be based at least in part on the at least one drive speed setting. The powered balancing mobility device can optionally include a thumbwheel position processor. The thumbwheel position processor can include a sampler that can sample the signals and save the virtual thumbwheel position for the drive speed setting. The sampler can recover a previous of the virtual thumbwheel position for the drive speed setting. The position processor can include a recorder that can record the sampled signals, and a filter that can filter the signals to determine a set of filtered signals. The filter can determine a change in the signals. The position processor can include an absolute position processor that can integrate the change in signals into the virtual thumbwheel position, and a speed percent processor that can calculate a speed percent based at least on the virtual thumbwheel position. The position processor can include a transmitter that can make the speed percent available for further processing. The thumbwheel position processor can optionally include storing the virtual thumbwheel position for the drive speed setting. The filter can optionally include a change in signals processorthat can compute the change in signals, a threshold processor that can set the change in signals to zero if the change in signals exceeds a wrap threshold, and a weighted average processor that can compute a weighted average on the computed change in signals between a first sample of the signals and a second sample of the signals. The weighted average processor can calculate a weighted average of data stored in an historic buffer and can set the change in signals equal to the weighted average. The filter can include a deadband processor that can set the change in signals to zero, flag the change in signals as noise, and integrate the change in signals into the virtual thumbwheel position if the change in signals does not exceed, or is equal to, a deadband. The deadband processor can set the change in signals to zero and integrate the change in signals into the virtual thumbwheel position if the change in signals exceeds the deadband and if the previous one of the samples was noise. The deadband processor can integrate the change in signals into the virtual thumbwheel position if the change in signals exceeds the deadband, and if the previous one of the samples was not noise. The filter can include an historical buffer processor that can add the change in signals to the historic buffer. The historical buffer processor can set the change in signals equal to a maximum of the previous samples and can add the change in signals to the historical buffer if the change in signals does not exceed the wrap threshold, and if the change in signals exceeds the maximum of the previous samples. The deadband optionally includes a threshold filtering noise signals. The filtered noise signals can be unlikely to constitute actual movement of the thumbwheel. The change in signals can optionally include the difference between a first sample of the signal and a second sample of the signal.

A powered balancing mobility device of the present teachings can include, but is not limited to including, a control device and a controlled device. The controlled device can include a plurality of redundant processors processing movement commands for the mobility device, each of the plurality of redundant processors receiving data from the control device, a second protocol relaying commands specific to the controlled device from the control device, and a first protocol supporting communications between the control device and the controlled device. The controlled device can be physically remote from the control device. The first protocol can transparently tunnel messages formatted in the second protocol and encapsulated within messages formatted according to the first protocol for transmission and reception. The mobility device can include a communication message manager that can identify first protocol messages and extract tunneled second protocol messages. The first protocol can optionally include a RIS protocol. The control device can optionally include a portable computer processor. The controlled device can optionally include a medical device. The control device can optionally include a virtual joystick. The second protocol can optionally include a SCA protocol.

The quick-release system of the present teachings can enable a user to combine the most important features in a seat with the most important features in a chassis and wheels when selecting a mobility device. The seat can be engaged with base of the mobility device, and seats can be readily interchanged. The quick-release feature can include a pairing assembly comprising the pairing bracket in combination with the first and second mounts, pins related to the mounts. The two mounts can jointly function to provide quick-release. The quick-release assembly can include a rotating handle that can lock in a pocket of first mount can partially and subsequently completely release the seat. The quick-release assembly can include a first mount providing supplemental features that can engage the pairing bracket, for example, but not limited to, a catch that can capture a part of the pairing bracket when the mount pins perform complete engagement. The quick-release feature can include a pairing assembly that can allow rapid engaging and disengaging of a seat to a mobility device.

At least two seat support brackets can mount to powerbase 21514 (FIG. 1) by bolting to their corresponding lifting arm pivot in the front and stabilizer link pivot in the back. A seat mounting pin is bolted on to each seat support bracket in the rear, facing outwards. The seat support brackets and rear mounting pins stay attached to the powerbase and interface with the seat assembly as it is attached to and removed from the powerbase. Each of the 2 rear mounting pins interface with a seat mounted rear bracket. The rear brackets are each mounted to the seat by bolting to an outer component to clamp across the seat tubes and hold the bracket in place with friction. The seat mounted rear brackets both have a groove that accepts its corresponding pin when the seat is being placed on. Once the seat mounted rear bracket grooves are guided over the pins, the seat assembly is constrained to one degree of rotation. The seat assembly is then rotated forwards until the alignment features of the seat support brackets accept the corresponding alignment features of two seat mounted forward brackets. The front brackets are each mounted to the seat by bolting to an outer component to clamp across the seat tubes and hold the bracket in place with friction. With these features aligned and the seat assembly held in place by gravity, the retractable pins can be engaged. This is accomplished by pulling both retractable pin handles out of their locked position in resting grooves, and rotating them each approximately 180 degrees. Each retractable pin handle can sit at a different position, causing each pin to be inserted into its corresponding hole in the seat support bracket. The seat assembly can be reversed by reversing the mounting procedure.

The mobility device of the present teachings can include, but is not limited to including, a brake disk/motor coupling interface that can reduce chattering while maintaining a low sensitivity to brake position. The brake disk/motor coupling can maintain a low sensitivity to brake position. The tight clearance of the interface of the present teachings can allow the brake disk to use the motor coupling to define a rotation axis, which can allow the brake to be assembled without tight control of its radial position, because the brake disk and the brake assembly do not require perfect radial alignment. The shape of the motor coupling can allow the brake disk to be positioned anywhere along its length, which can remove the sensitivity of the brake disk/motor coupling to axial position. The brake disk/motor coupling assembly can transmit all of the available brake torque, and can restrain the brake disk rotational freedom under the no brake load condition, and can cushion the rotational impacts that occur between the two parts.

The method of the present teachings for reducing motor brake noise, where the motor brake includes a brake disk and a motor coupling, can include, but is not limited to including, manufacturing a compliant insert, providing a brake disk having cavity including a geometry compatible with the compliant insert, mounting the compliant insert in the cavity, and assembling the motor brake by sliding the motor coupling into the compliant insert. The compliant insert can optionally include an enclosed shape including a first surface and a second surface. The first surface can optionally include at least one protrusion. The first surface can optionally enable flush mounting of the motor coupling against the at least one protrusion. The second surface can optionally rest within the cavity. The second surface can optionally include a geometry compatible with the cavity. At least one retention clip can optionally be operably coupled with the enclosed shape. The at least one retention clip can supply pressure to the motor coupling. The second surface can optionally include a hexagonal shape. The first surface can optionally include at least one face including the at least one protrusion, and at least one face including the at least one retention clip.

The compliant insert of the present teachings for reducing motor brake noise, where the motor brake includes a brake disk and a motor coupling, can include, but is not limited to including, an enclosed shape including a first surface and a second surface. The first surface can include at least one protrusion, and the first surface can enable flush mounting of the motor coupling against the at least one protrusion. The second surface can rest within the cavity, and the second surface can include a geometry that can be compatible with the cavity. The compliant insert can include at least one retention clip that can be operably coupled with the enclosed shape. The at least one retention clip can supply pressure to the motor coupling. The second surface can optionally include a hexagonal shape. The first surface can optionally include at least one face including the at least one protrusion, and at least one face including the at least one retention clip.

The method for reducing motor brake noise, where the motor brake includes a brake disk and a motor coupling, can include, but is not limited to including, manufacturing a motor coupling. The motor coupling can include a first surface and a second surface. The motor coupling can include at least one groove machined circumferentially into the first surface. The method can include fitting a gasket into the at least one grooved, and providing a brake disk having a cavity. The cavity can include a geometry compatible with the first surface. The method can include assembling the motor brake by sliding the motor coupling into the cavity adjacent to the gasket. The gasket can optionally include an o-ring. The first surface can optionally include a hexagonal shape.

The method of the present teachings for controlling a motor using field weakening can include, but is not limited to including, measuring system parameters, converting phase current and voltage to a stationary frame, converting the stationary phase current and voltage to a synchronous rotary frame, calculating the minimum and maximum quadrature and direction current commands from the measured motor parameters, calculating the desire direct current, closing the loop on commanded motor voltage, commanded direct current, and command quadrature current, adjusting the measured motor angle, converting the direct and quadrature command voltage to the stationary frame, and converting the stationary command voltage to phase voltage commands.

The seat of the present teachings can include a combination of features. A first feature relates to the connection of the seat to a wheelchair base. The connection can consequently allow the user to remove and replace the seat from the wheelchair base. A second feature relates to a removable attendant handle that can allow the wheelchair to operate with or without an attendant handle. A third feature relates to adjustability and changeability of the seat backrest. In some configurations, the angle of the seat backrest can be adjusted, and the seat backrest cushion, and the entire seat backrest, can be removed and replaced. The backrest can be selected based on a desired curvature. A fourth feature relates to the adjustability of the armrest positions. The armrests, mounted between coupling brackets, can be raised and lowered independently from one another along a slide between the coupling brackets, by the user, with a simple button depression. A fifth feature relates to the removability of the seat cushion structure and the seat cushion itself. The seat cushion structure can be selected based on a desired shape and comfort level. A sixth feature relates to the height and tilt angle adjustments of the footrest. A seventh feature relates to the transportability of the seat. The backrest can be hinged and can be folded upon the seat cushion, and the footrest can be hinged and can be folded towards the footrest post. When the backrest is folded towards the seat cushion, the armrests can fold flush with the backrest. A single footrest can accommodate both feet.

The method of the present teachings for assembling a seat for a mobility device, where the seat includes a footrest, a bracket, at least one arm, a seat shell, and a backrest, the method can include, but is not limited to including, pivotally connecting the footrest to a rod. The rod can include a rod first end and a rod second end. The footrest can include a first pivot means at the connection between the footrest and the rod first end. The method can include sliding, to adjust the footrest to a desired height, the rod second end into a receiving port of a hollow tube. The hollow tube can include a connection port, and the connection port can include shock absorbing features. The method can include pivotally connecting the connection port to the bracket. The bracket can include seat shell connection features, and at least one mobility device motor connection feature. The method can include operably connecting the seat shell to the seat shell connection features and bracket, and pivotally connecting the backrest to the bracket. The backrest can include a third pivot means, that can be enabled by a spring-loaded latch. The method can include operably connecting at least one armrest mount to the bracket. The at least one armrest mount can include a height adjustment means. The method can include pivotally connecting the at least one arm to the at least one armrest mount. The bracket can optionally include an aluminum alloy. The method can optionally include operably connecting a seat cushion to the seat shell. The height adjustment means can optionally include a push button actuation mounted on the at least one armrest mount. The footrest can optionally include an accommodation for two feet. The first pivot means can optionally include a thumbscrew. The second pivot means can optionally include a multipositional clamping means. The at least one mobility device connection feature can optionally include at least one bracket extension. The backrest can optionally include a backrest angle adjustment means, and the backrest angle adjustment means can optionally include a tension knob. The connection port can optionally include the second pivot means.

The method of the present teachings for transporting a seat of a mobility device, where the seat can include a footrest operably coupled with to a seat bracket, and the seat bracket can be operably coupled with a tube holder bracket. The tube holder bracket can be operably coupled with at least one armrest and a frame bracket, and the frame bracket can be operably coupled with a backrest. The method can include, but is not limited to including, pivoting the footrest towards a rod connected to the footrest until the footrest is approximately flush with the rod. The rod can include a rod first end and a rod second end, and the footrest can include a first pivot means at the connection between the footrest and the rod first end. The method can include sliding the rod second end into a receiving port of a hollow tube. The hollow tube can include a connection port, and the connection port can be operably coupled with the seat bracket. The method can include pivoting the backrest towards the seat bracket at a second pivot means. The second pivot means can be enabled by a spring-loaded latch. The method can include pivoting the at least one armrest towards the backrest. The method can include reducing the height of the at least one arm rest mount by adjusting a height adjustment means, and pivoting the at least one arm towards the at least one arm rest mount until the at least one arm is flush with the at least one arm rest mount.

The seat for a mobility device of the present teachings can include, but is not limited to including, a footrest pivotally connected to a footrest rod. The footrest rod can include a rod first end and a rod second end, and a first pivot means at the connection between the footrest and the rod first end. The rod second end can be operably coupled with a receiving port of a hollow tube, and the hollow tube can include a connection port. The connection port can be pivotally connected a seat bracket. The seat bracket can include seat shell connection features, and at least one mobility device motor connection feature. The seat shell can be operably connected to the seat shell connection features and bracket, and can pivotally connect a backrest to the bracket. The backrest can include a second pivot means that can be enabled by a spring-loaded latch. At least one armrest mount can be pivotally connected to the bracket. The at least one armrest mount can include a height adjustment means. The at least one arm can be pivotally connected to the at least one armrest mount. The bracket can optionally include aluminum alloy. A seat cushion can optionally be operably connected to the seat shell. The height adjustment means can optionally include a push button actuation mounted on the at least one armrest mount. The footrest can optionally include an accommodation for two feet. The first pivot means can optionally include a thumbscrew. The second pivot means can optionally include a multipositional clamping means. The at least one mobility device connection feature can optionally include at least one bracket extension. The backrest can optionally include a backrest angle adjustment means, and the backrest angle adjustment means can optionally include a tension knob. The connection port can optionally include the second pivot means.

The locking mechanism of the present teachings for adjusting a length of a handle projecting from a portable device, where the handle includes a user-operable portion and a rail portion exposed to the locking mechanism, and the rail portion travels along rail slots occupying a portion of the portable device, where the locking mechanism can include, but is not limited to including, a user-operable segment. The user-operable segment can be disposed externally to the portable device and can advance a user operation to a plurality of inter-operable components of the locking mechanism. The user-operable segment can include, but is not limited to including, a latch with a flange portion. The latch can be switched from a locked position to an unlocked position and can cause a motion of the flange. The flange can serve as an intermediate component between the latch and the inter-operable components of the locking mechanism. The inter-operable components can include, but are not limited to including, a first stopper operably engaged with one of the rails of the rail portion. The first stopper can operate on at least one of the rails occupying the corresponding rail slot. The inter-operable components can include a second stopper that can engage with a second of the rails in the rail portion when the second of the rails is occupying a second corresponding rail slot. The inter-operable components can include a central beam in contact with the flange in receiving the user-operation and controlling the first and second stopper. The central beam can include, but is not limited to including, a focal point on one end and a flexible joint on the other end. At least one first side beam can include, but is not limited to including, a first end and a second end. The at least one first side beam can engage with the central beam on the focal point and can engage with the first stopper on the second end. The at least one second side beam can include, but is not limited to including, a first end and a second end. The at least one second side beam can engage with the central beam on the focal point and with the second stopper on the second end. When the latch is in the locked position, the first and second stopper can restrain movement of the rail portion along the rail slots. When the latch is in the unlocked position the first and second stopper can decouple from the rails, and allow the rails to travel in the rail slots.

An adjustable mount of the present teachings for supporting a user control assembly, where the user control assembly can control a mobility device, the mount can include, but is not limited to including, a platform supporting the user control assembly, and a bar including a proximal end, a distal end and a central region there between. The bar can be operably coupled with the platform at the distal end. The mount can include a pivoting assembly operably coupled with the proximal end. The pivoting assembly can include, but is not limited to including, at least one bracket that can engage the user control mount with an armrest of the mobility device. The bracket can include, but is not limited to including, a roller facing away from the bar. The mount can include a housing fastened to the at least one bracket. The housing can include, but is not limited to including, a receptacle. The mount can include a rotary structure that can include, but is not limited to including, a protrusion segment and an elongated segment. The rotary structure can operably couple with the bracket and the housing. The receptacle can movably receive the protrusion segment. The elongated segment can operably couple with the proximal end of the bar. The roller can receive the rotary structure, and a pre-determined radial fit can be achieved there between. The mount can include a locking assembly occupying the central region of the bar. The locking assembly can include, but is not limited to including, a lever portion and a barb portion. The lever portion and the barb portion can jointly engaged the bar of the user control assembly mount. When the bar is displaced, the platform is displaced.

The pivotable mount assembly for a mobility device of the present teachings can include, but is not limited to including, a platform to engage a user-operable component, and a shaft having a distal end and a proximal end. The distal end can operably couple with the platform, and the platform can operably couple with an armrest of the mobility device through the proximal end. The assembly can include a rotary structure that can operably couple with the proximal end. The rotary structure can enable the shaft to pivot with respect to the armrest. The rotary structure can include, but is not limited to including, a brace that can operably couple with the armrest. The brace can include, but is not limited to including, an axle facing away from the shaft. The assembly can include a receiver that can operably couple with the brace. The receiver can include, but is not limited to including, a pocket. The assembly can include a roller that can include, but is not limited to including, a projection and an elongation. The roller can operably couple with the brace by receiving the axle into a roller space. The roller can pivot around the axle, and the pivoting can be constrained by the projection in the pocket. The roller can operably couple with the shaft through the elongation. The assembly can include a lock assembly that can include, but is not limited to including, a clasp that can include, but is not limited to including, a handle portion and a spike portion. The operation of the handle portion can cause the spike portion to trap into or release the shaft from the clasp.

The method of the present teachings for adjustably mounting a user-operable device to a mobility device can include, but is not limited to including, engaging a brace piece with an armrest of the mobility device. The brace piece can include, but is not limited to including, at least one roller projecting away from the brace piece. The method can include providing a bar having a proximal end, a distal end, and a central region. The central region can operably couple the proximal end and the distal end. The proximal end, the distal end, and the central region can cooperate to telescopically adjust a length of the bar. The method can include coupling a support platform with the distal end. The support platform can retain the user-operable device therewith. The method can include coupling a pivoting assembly with the proximal end. The pivoting assembly can operably couple the bar with the armrest by coupling the bar with the brace piece. The method can include providing a locking mechanism that can operably couple with the central region of the bar. The locking mechanism can be operated by a user to engage the bar with and disengage the bar from the armrest. The method can optionally include receiving a housing on the brace piece. The housing can at least partially occupy the brace piece.

The method of the present teachings for assembling a mount for engaging a user-operable device therewith, where the mount can operably couple with a seating device providing an armrest, the method can include, but is not limited to including, providing a shaft with a first end and a second end. The first end and the second end can define a central region there between. The method can include operably coupling a support platform to the first end. The support platform can engage the user-operable device. The method can include providing a pivoting assembly on the second end. The pivoting assembly can include, but is not limited to including, a rotary structure having a projection and an elongation. The projection can oppose the elongation, and the rotary structure can include, but is not limited to including, a roller space. The roller space can receive a complementing component from the armrest. The roller space can pivotally engage the shaft with the armrest.

The seat assembly of the present teachings for a mobility device, where the seat can include, but is not limited to including, a backrest, a seat pan, and an armrest, and the seat assembly can include, but is not limited to including, a back frame bracket enabling coupling with the backrest, a tube holder bracket enabling coupling with the seatpan, an armrest bracket enabling coupling with the armrest, and a cane. The cane can be surrounded by the armrest bracket, and can enable adjustment of the armrest bracket. The cane can enable coupling between the back frame bracket and the tube holder bracket. The armrest bracket can optionally include a cane cavity receiving the cane. The cane can include a plurality of set cavities. The armrest bracket can optionally include at least one fastener cavity, and an armrest geometry that can accommodate bracket geometry in the armrest. The armrest geometry and the bracket geometry can enable movement of the armrest. The cane can optionally include at least one channel surrounding the plurality of set cavities, and the armrest bracket can optionally include cane geometry complementing the at least one channel. The cane geometry can enable alignment between at least one of the plurality of set cavities and the at least one fastener cavity. The seat assembly can optionally include an armrest height adjustment button, a button slide including a straight edge interrupted by a divot, and a button transition rod achieving aligned coupling with the button slide. The button transition rod can operably couple the height adjustment button with the button slide. The seat assembly can optionally include a lock pin having a first end and a second end. The first end can be in contact with the straight edge of the button slide when there is no pressure on the height adjustment button, and the first end being in contact with the divot when there is pressure on the height adjustment button. The second end can be captured in one of the plurality of set cavities when the first end is in contact with the straight edge of the button slide, and the second end being in contact with one of the at least one cane channels when the first end is in contact with the divot.

The seat assembly of the present teachings for a mobility device, where the seat can include, but is not limited to including, a backrest assembly, a seat pan, an armrest, and an attendant handle, and the seat assembly can include, but is not limited to including, a back frame bracket enabling coupling with the backrest. The back frame bracket can include an attendant handle operating mechanism that can enable movement of the attendant handle. The seat assembly can include a tube holder bracket enabling coupling with the seatpan, an armrest bracket enabling coupling with the armrest, and a cane. The cane can be surrounded by the armrest bracket, and can enable adjustment of the armrest bracket. The cane can enable coupling between the back frame bracket and the tube holder bracket. The attendant handle operating mechanism can optionally include at least one attendant handle stopper in contact with the attendant handle, and a first beam that can have a first beam first end and a first beam second end. The first beam second end can be movably coupled with one of the at least one attendant handle stoppers. The attendant handle operating mechanism can optionally include a second beam that can have a second beam first end and a second beam second end. The second beam second end can be movably coupled with one of the at least one attendant handle stoppers. The attendant handle operating mechanism can optionally include a central beam that can have a central beam first end and a central beam second end. The central beam first end can movably couple the first beam first end and the second beam first end. The movement of the attendant handle can be based at least on movement of the central beam. The seat assembly can optionally include a latch that can be operably coupled with the central beam second end. The latch can be disengaged from the central beam second end which can enable movement of the attendant handle. The latch being engaged with the central beam second end which can disable movement of the attendant handle. The backrest further can optionally include a frame housing the attendant handle operating mechanism. The backrest can optionally include a plate between the attendant handle operating mechanism and a backrest cushion.

BRIEF DESCRIPTION OF THE DRAWINGS

The present teachings will be more readily understood by reference to the following description, taken with the accompanying drawings, in which:

FIG. 3AA is a perspective diagram of the grooved motor coupling and o-rings of the present teachings;

FIG. 3BB is a perspective detailed diagram of grooves and o-rings of the present teachings;

FIG. 3CC is a perspective detailed diagram of the o-ring protrusion of the present teachings;

FIG. 3DD is a perspective diagram of a disk having a disk cavity edge and a groove 2007 of the present teachings;

FIG. 3K-1 is a perspective diagram of a second configuration of the seat position sensor gear teeth clamp with mating notch of the present teachings;

FIG. 51 is a bottom right-side perspective view depicting seat raiVs captured by an exemplary pairing assembly;

FIG. 9K is a perspective diagram of the manual brake lever hard travel of the present teachings;

FIG. 9L is an exploded perspective diagram of the manual brake lever travel stop of the present teachings;

FIG. 9M is an exploded perspective diagram of the manual brake lever travel stop of the present teachings;

FIG. 9N is an exploded plan view of the manual brake lever travel stop of the present teachings;

FIG. 10A is a perspective diagram of the cable ports of the present teachings;

FIG. 10B is an exploded perspective diagram of the harnesses of the present teachings;

FIG. 10C is a perspective diagram of the UC port harness of the present teachings;

FIG. 10D is a perspective diagram of the charge input port harness of the present teachings;

FIG. 10E is a perspective diagram of the accessory port harness of the present teachings;

FIGS. 11A-11D are schematic block diagrams of various wiring configurations of the present teachings;

FIG. 11E is a perspective diagram of the power off request switch of the present teachings;

FIGS. 12A and 12B are perspective diagrams of the first configuration of the UC of the present teachings;

Figure 12A:
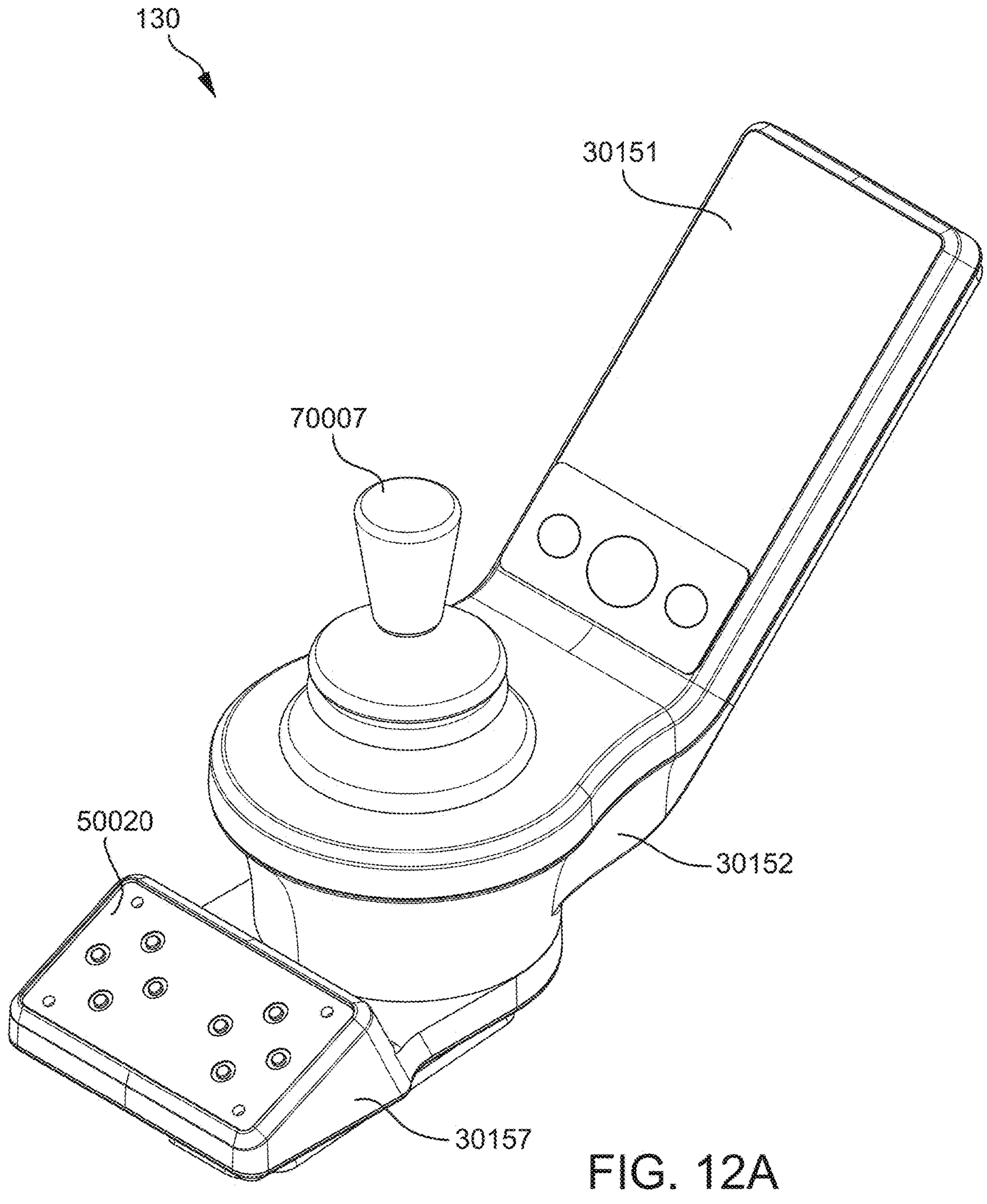
Figure 12B:
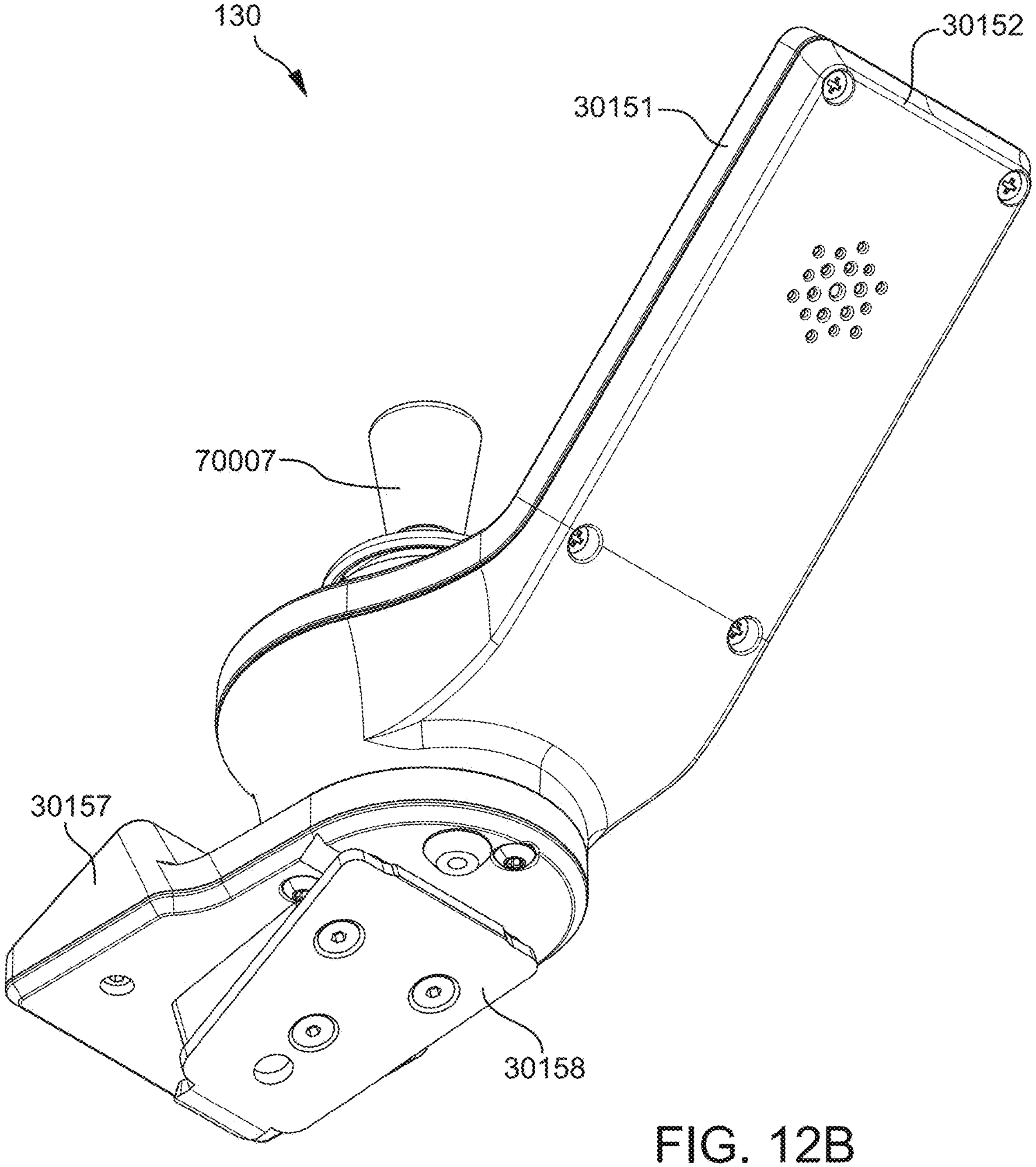
Figure 12C:
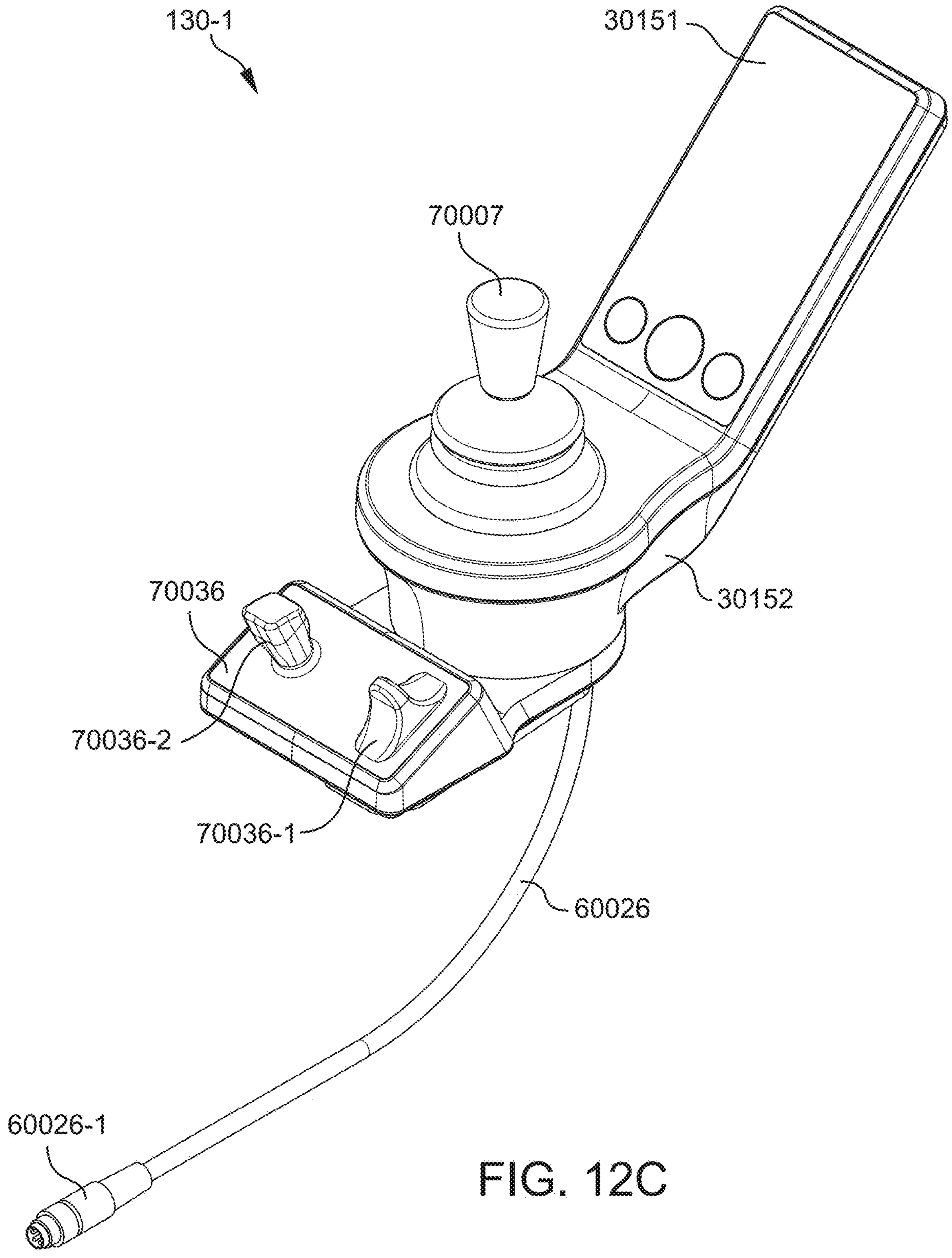
Figure 12D:
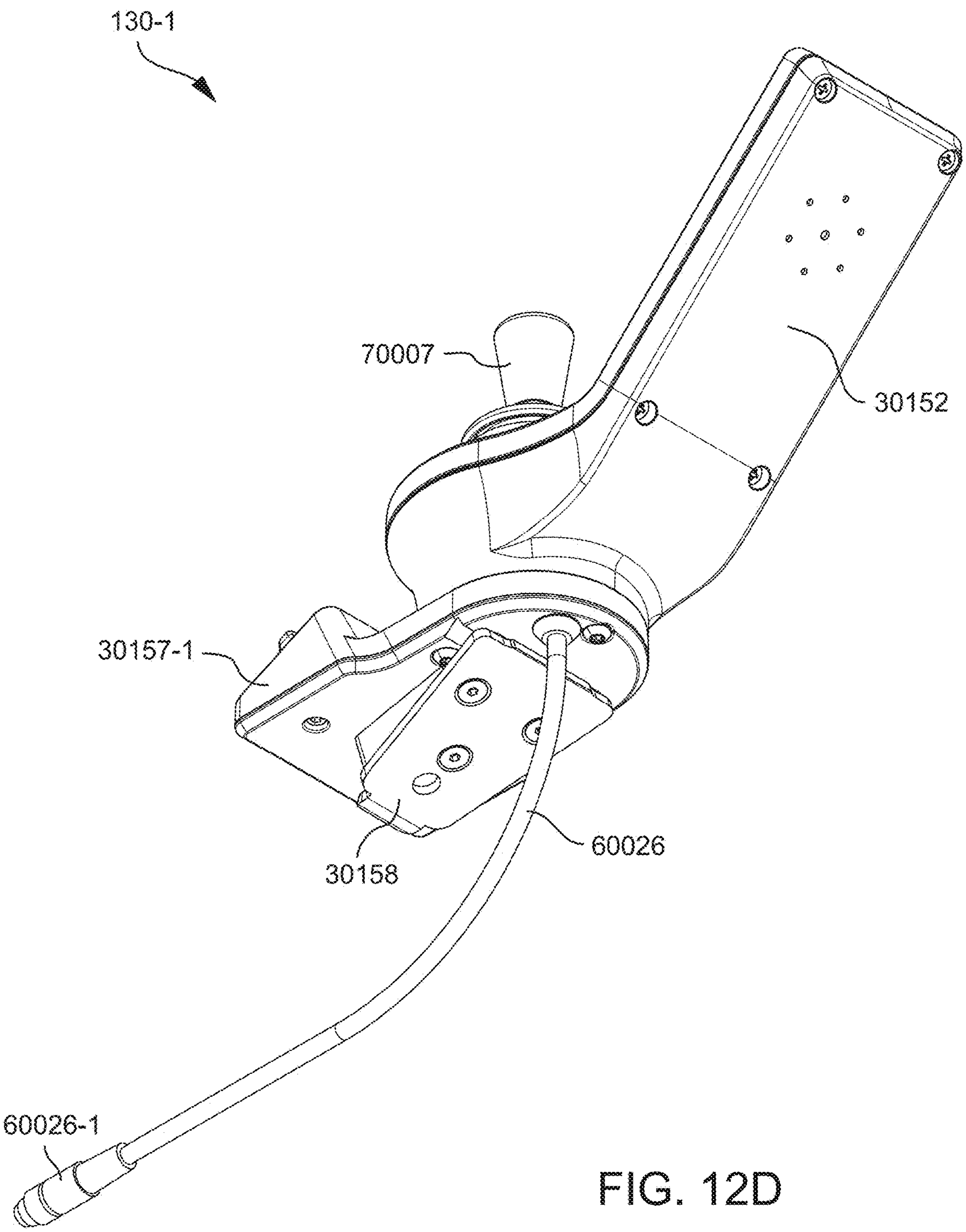
Figure 12E:
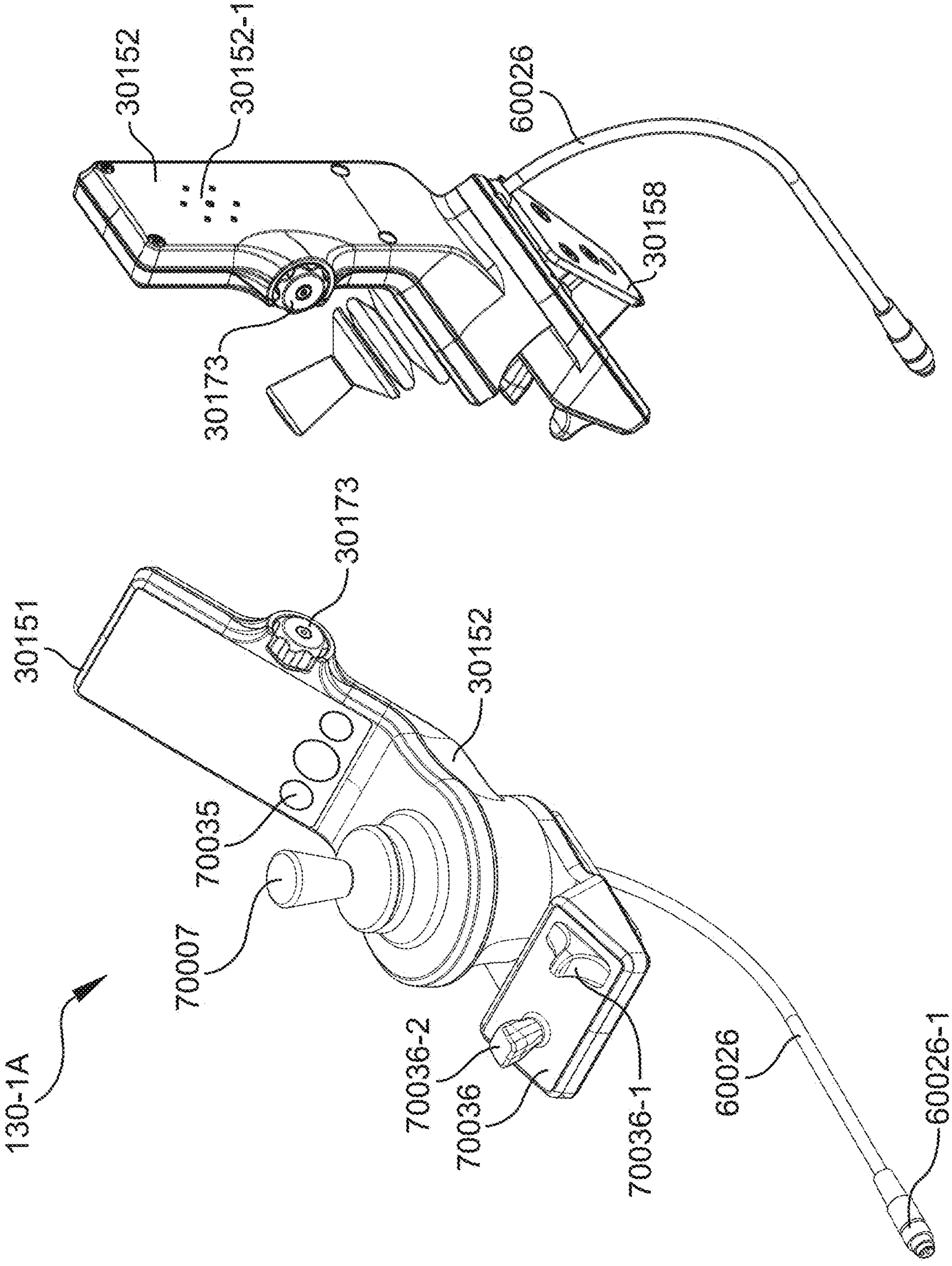
Figure 12F:
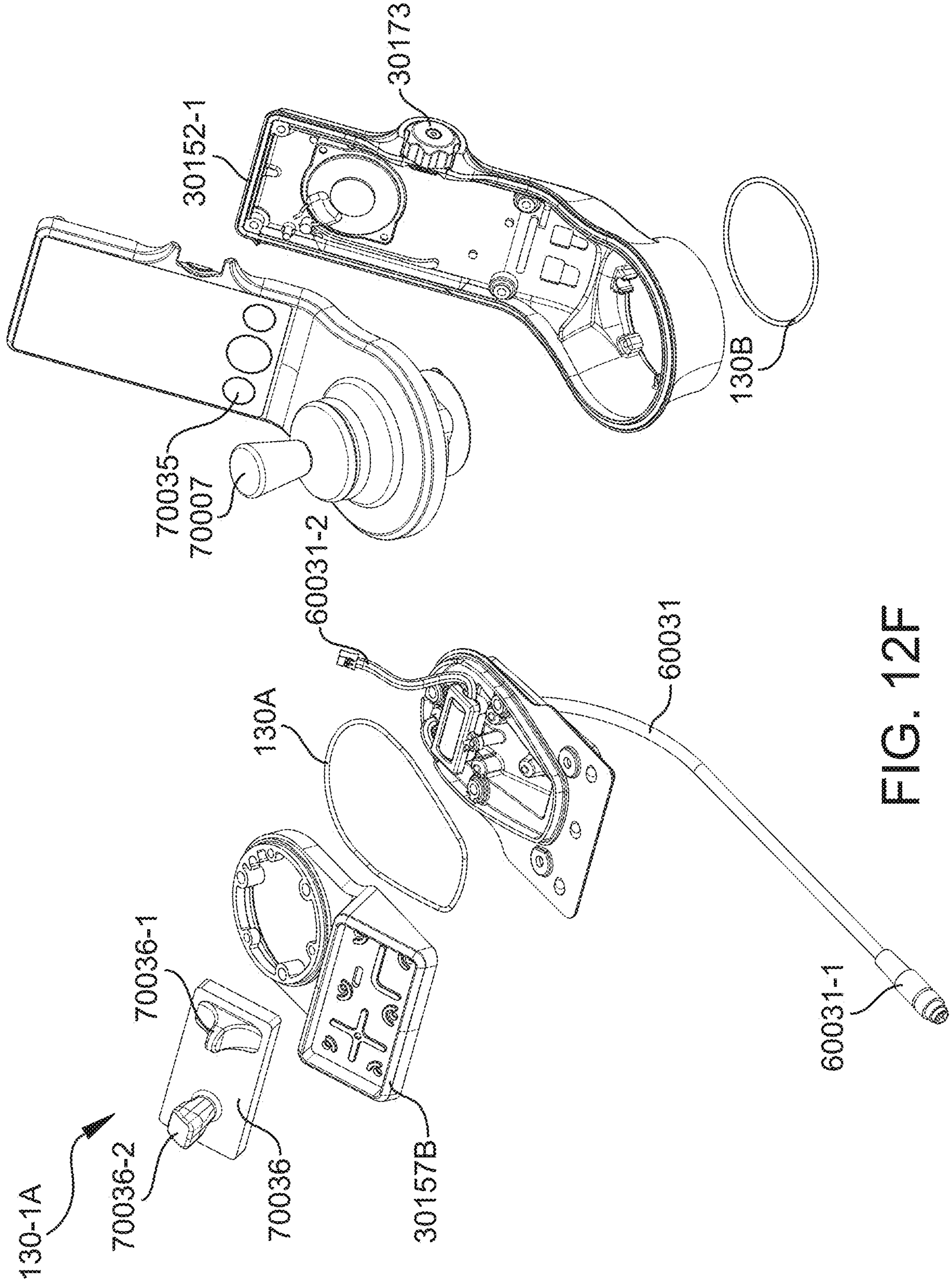
Figure 12G:
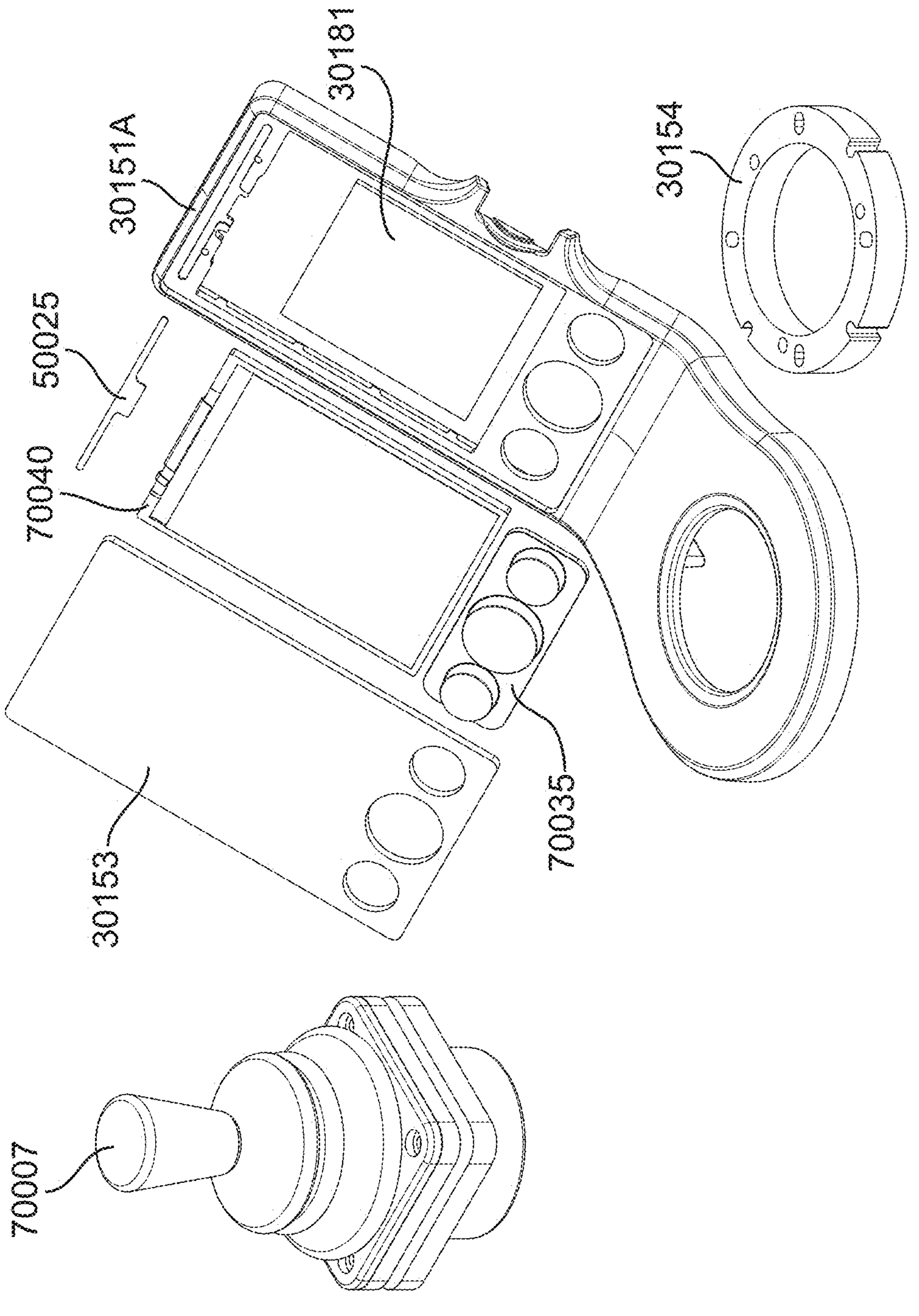
Figure 12H:
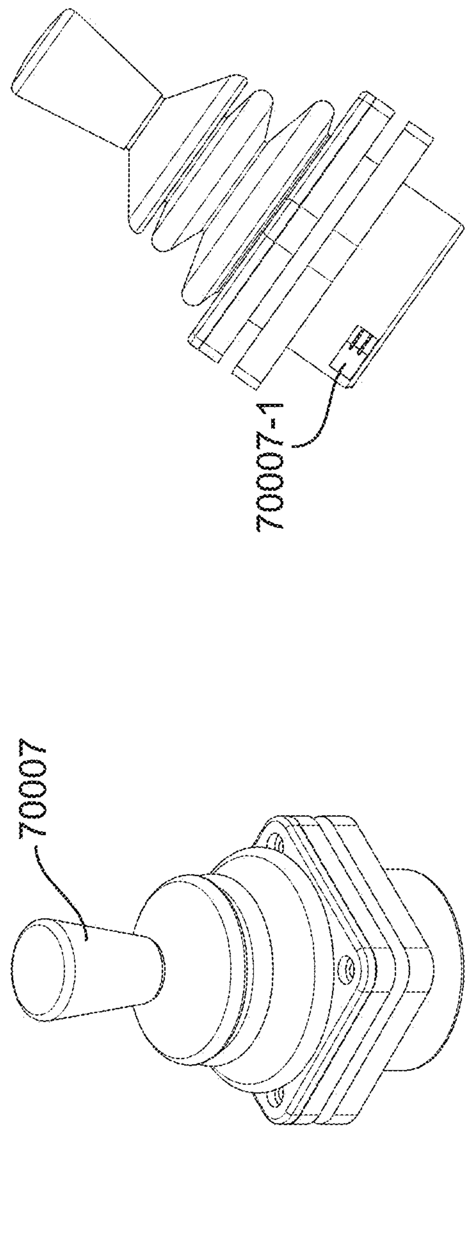
Figure 12I:
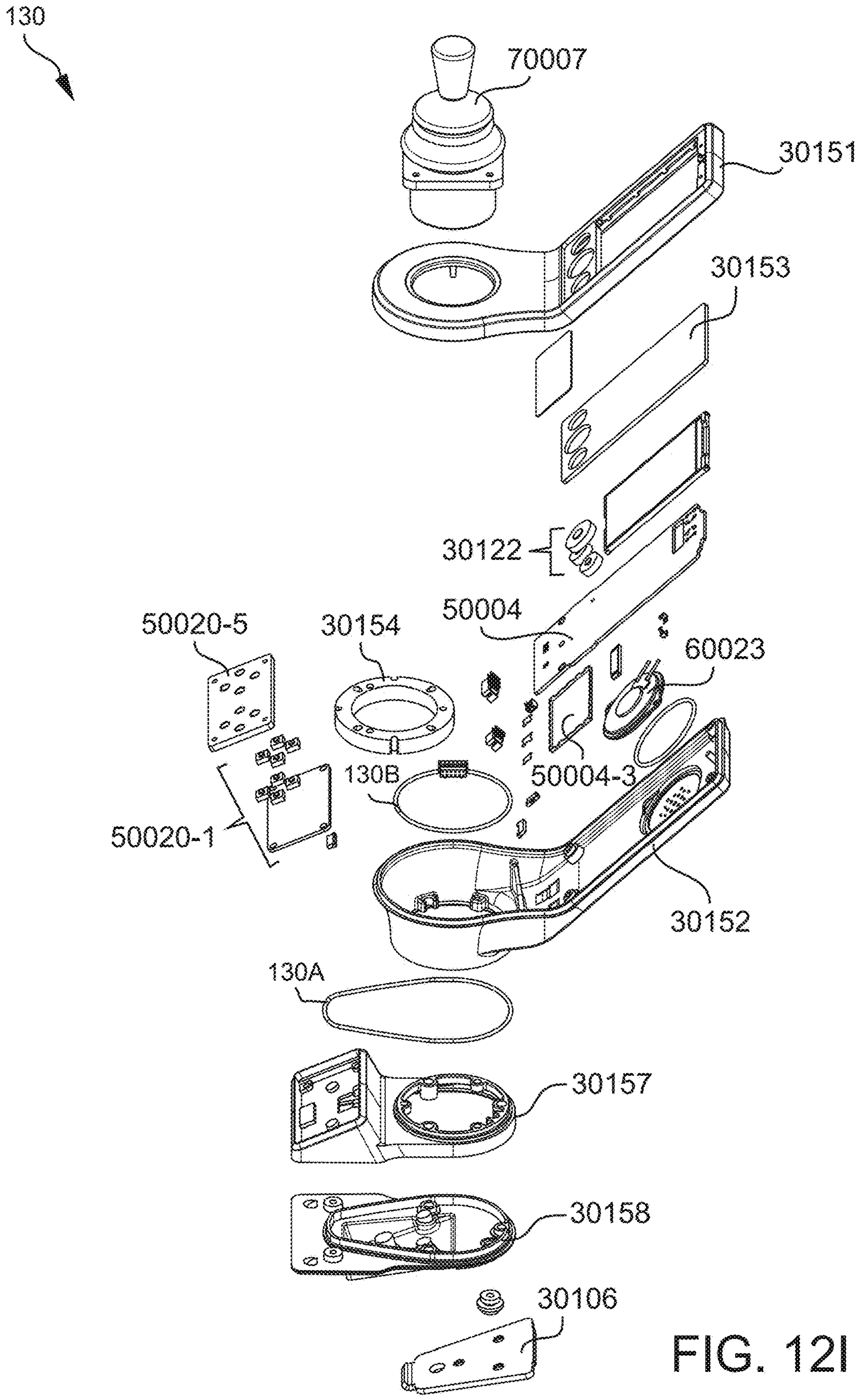
Figure 12J:
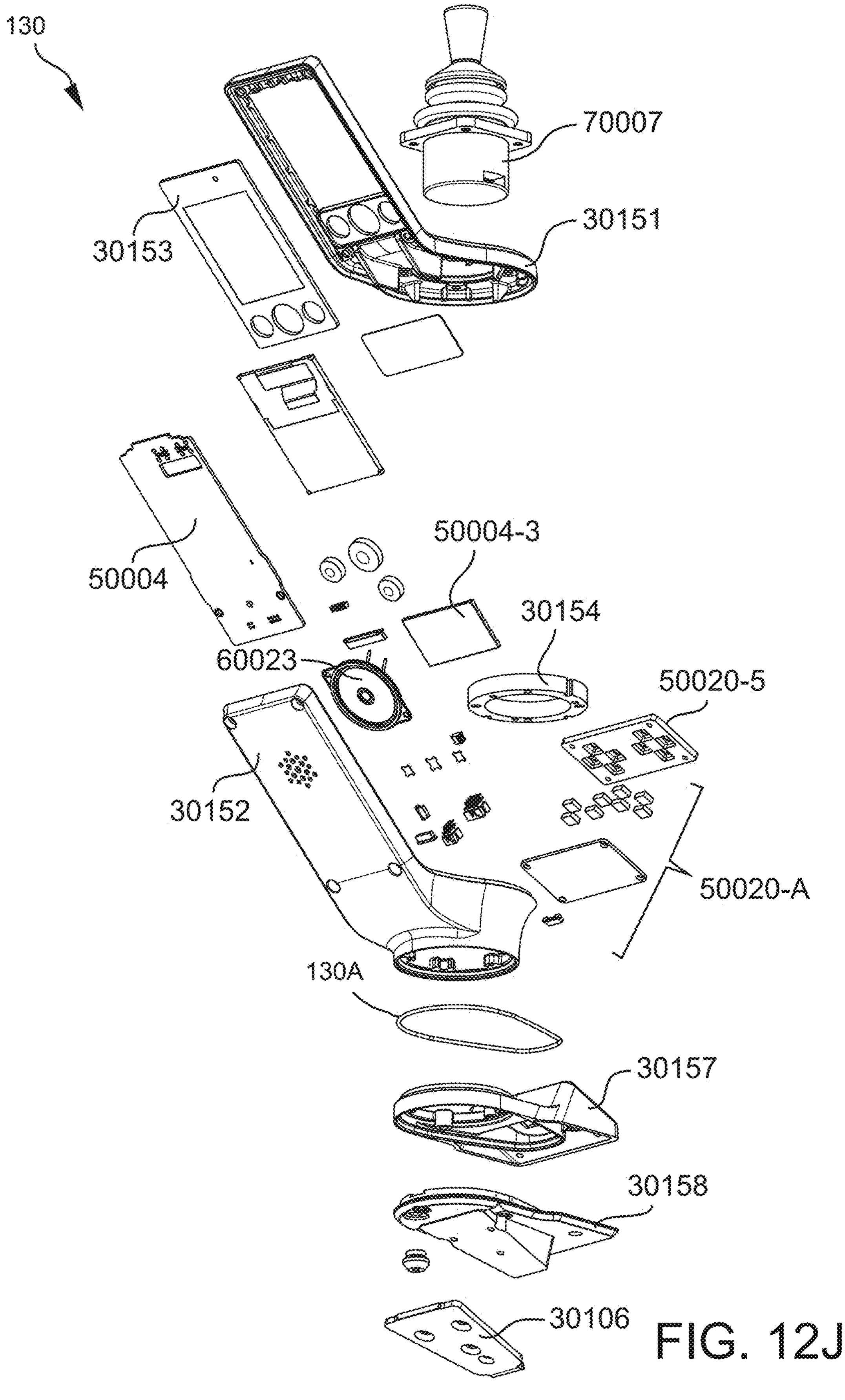
Figure 12K:
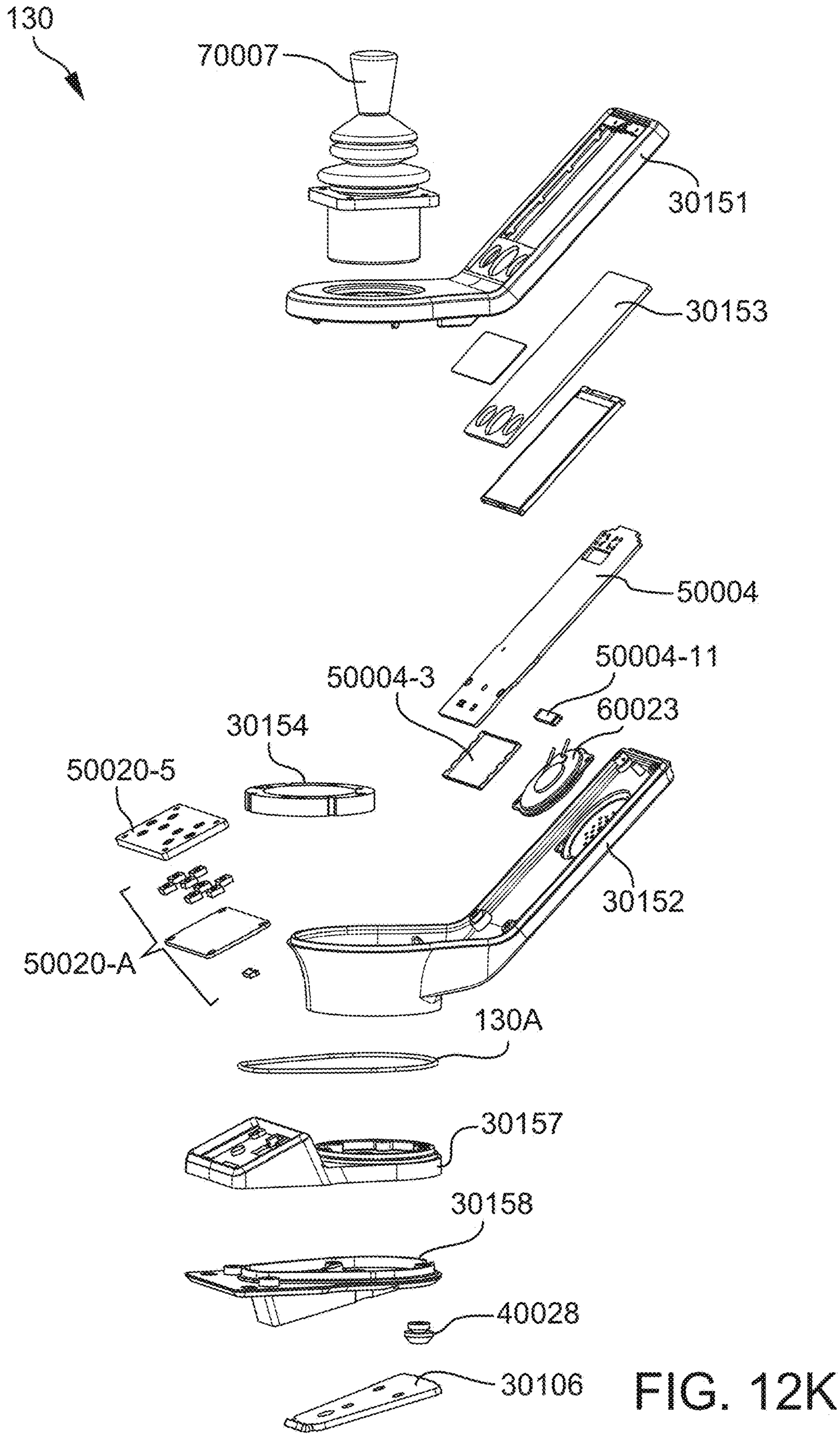
Figure 12L:
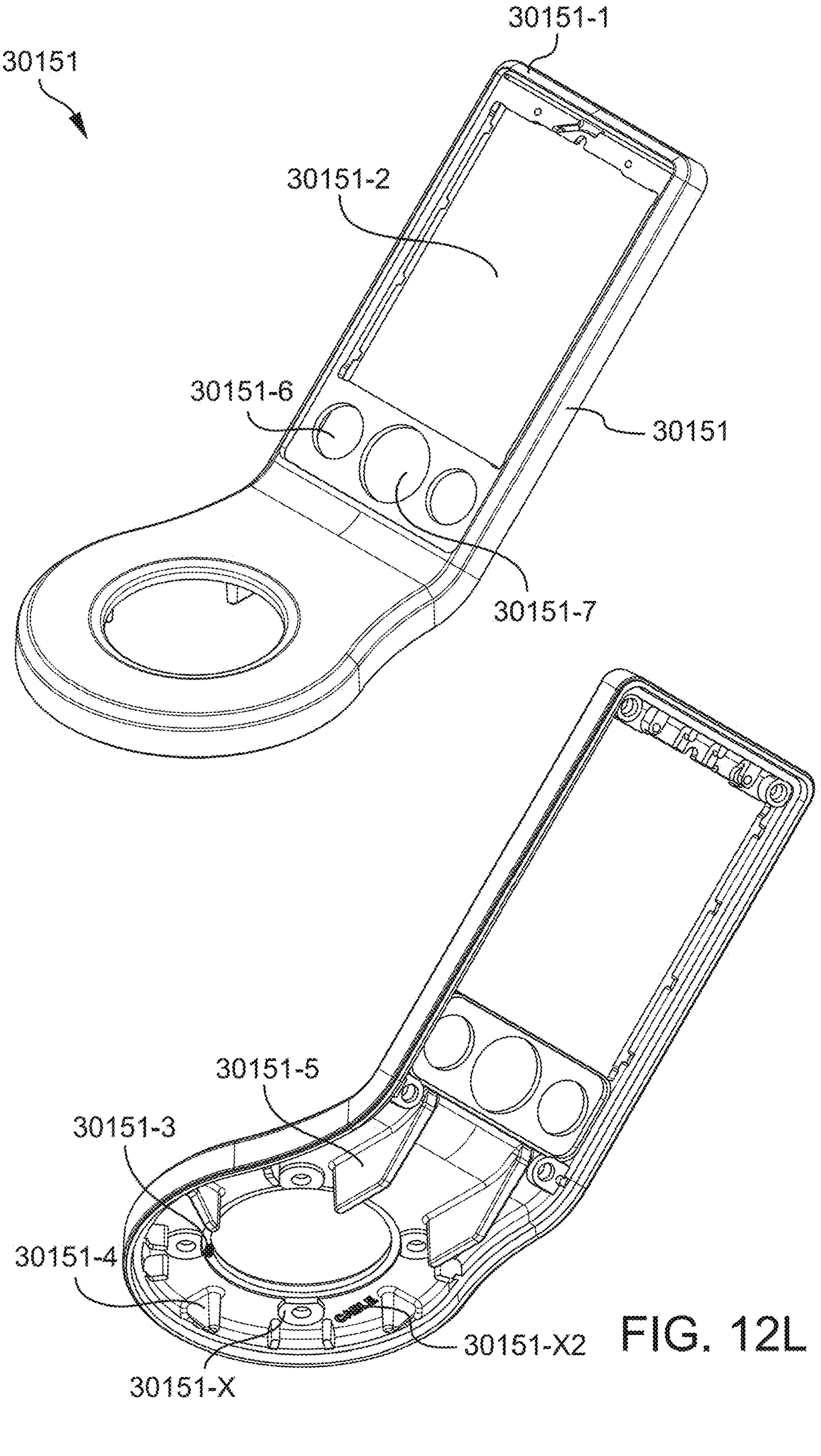
Figure 12M:
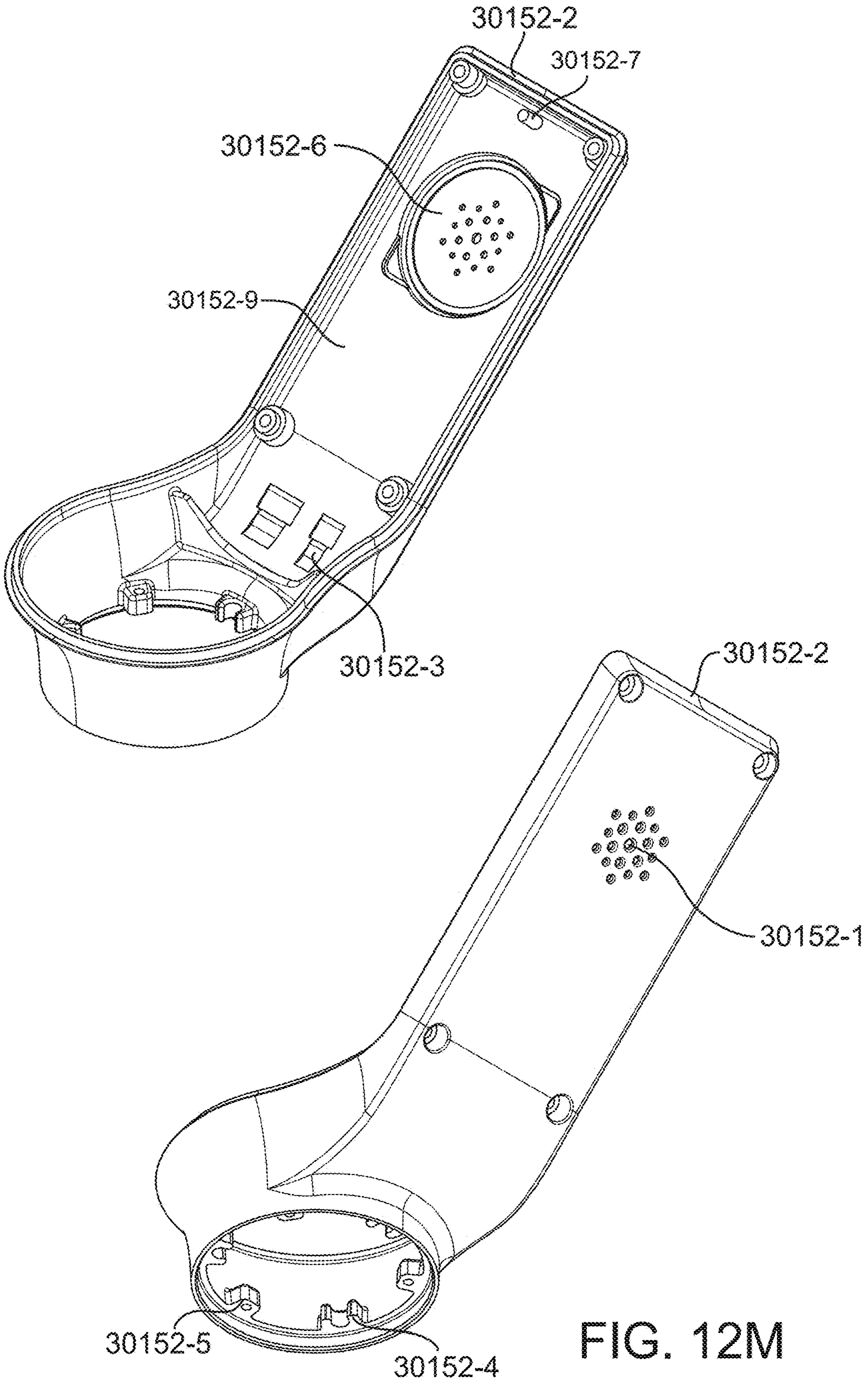
Figure 12N:
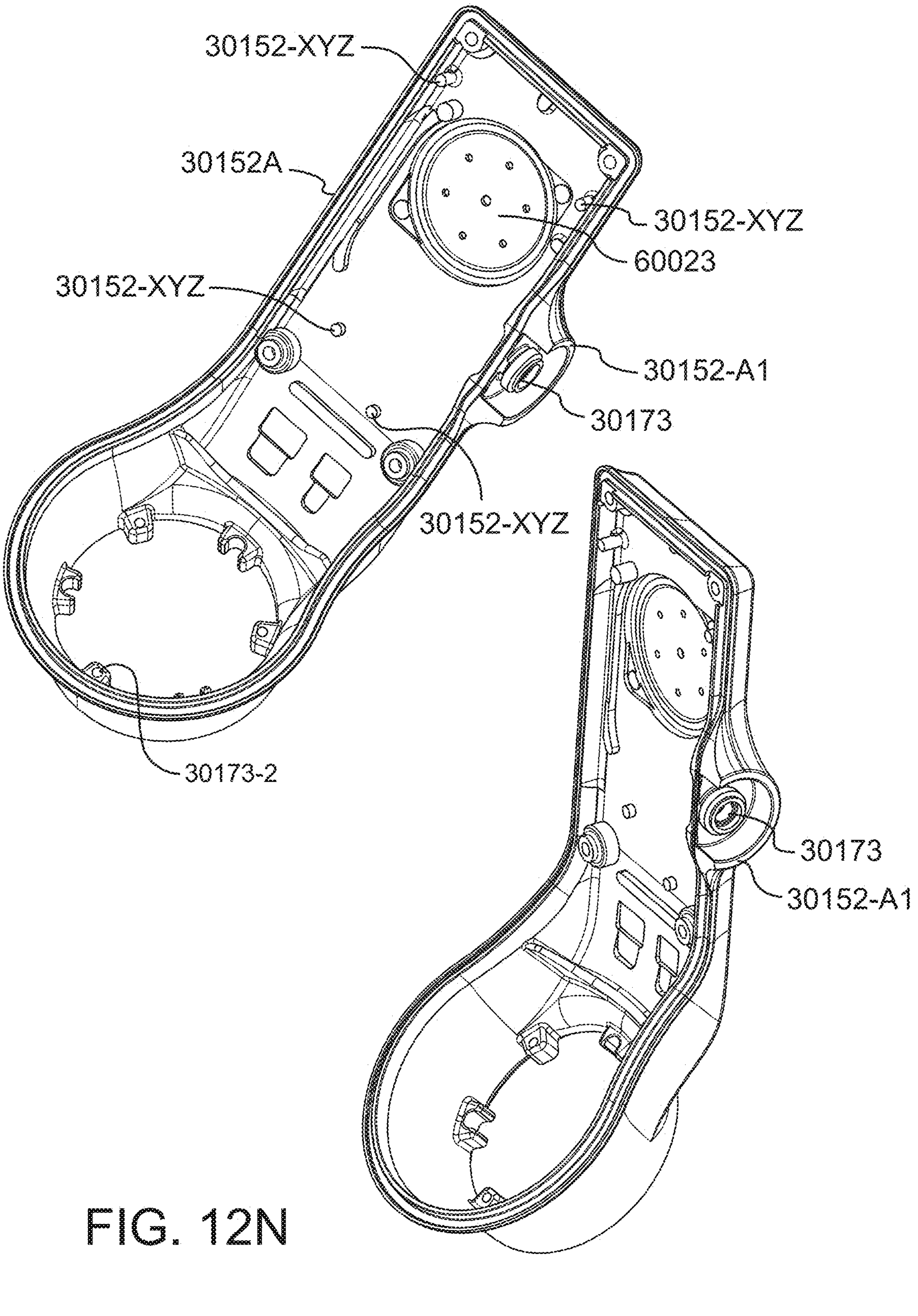
Figure 12O:
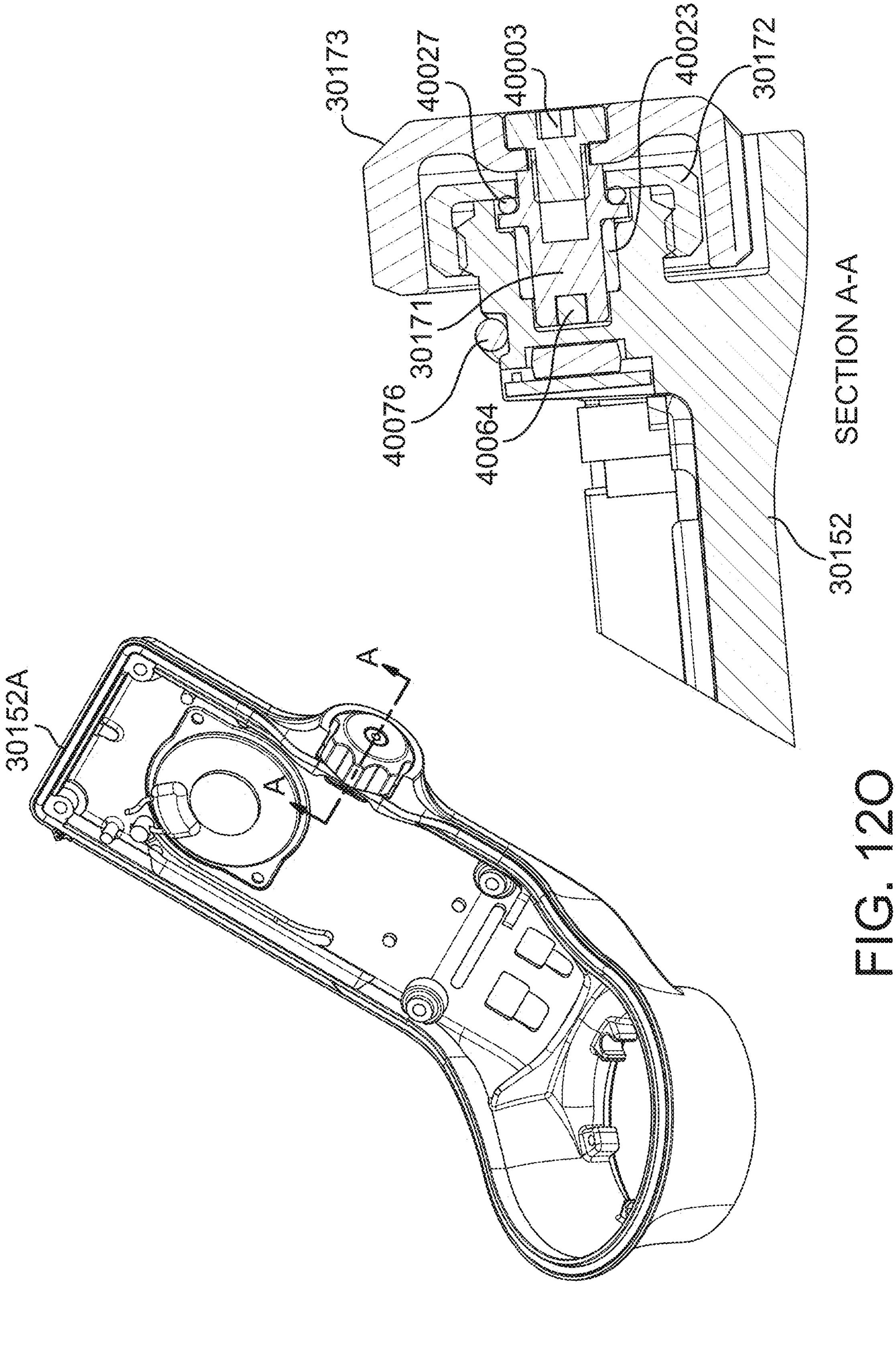
Figure 12P:
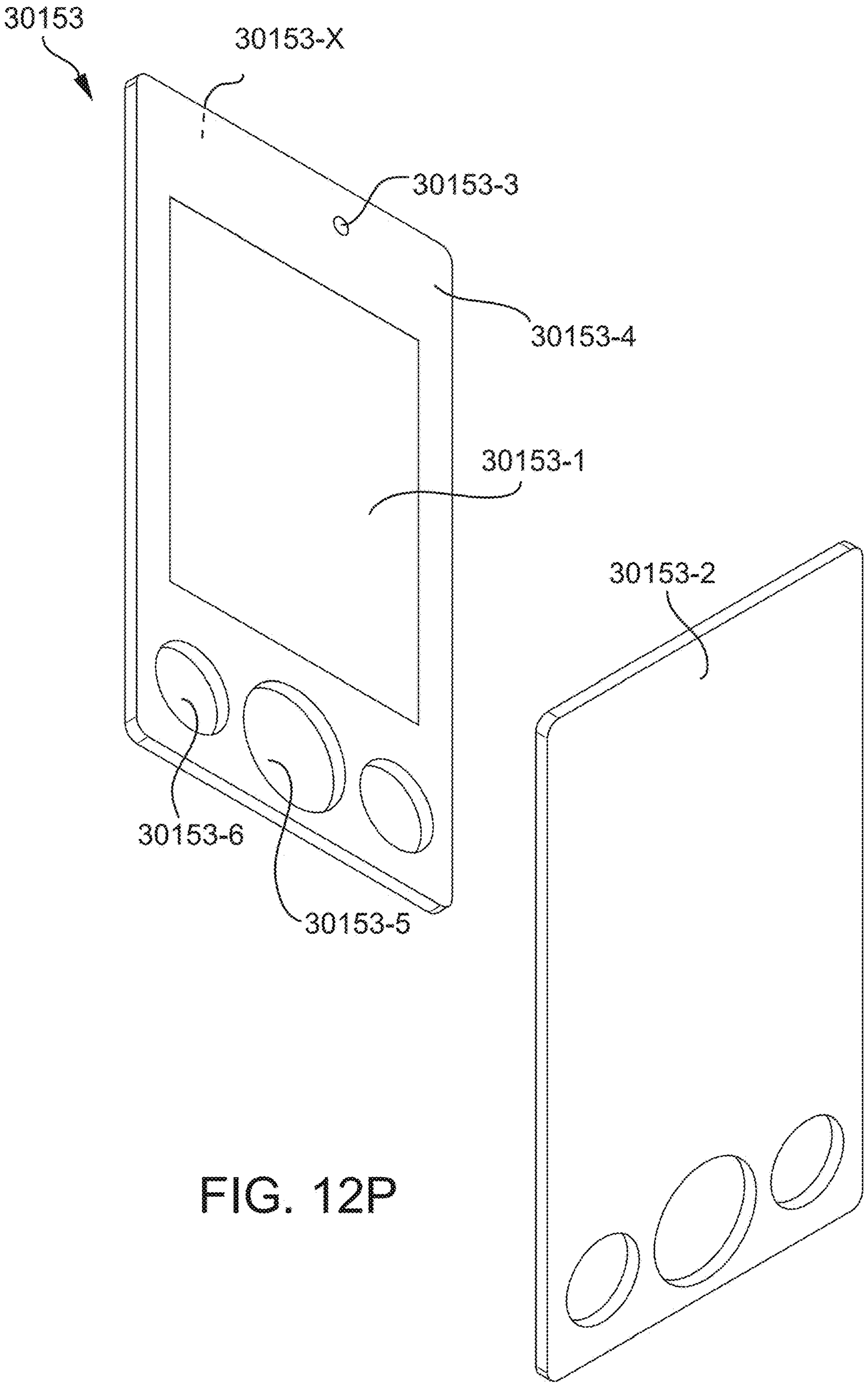
Figure 12Q:
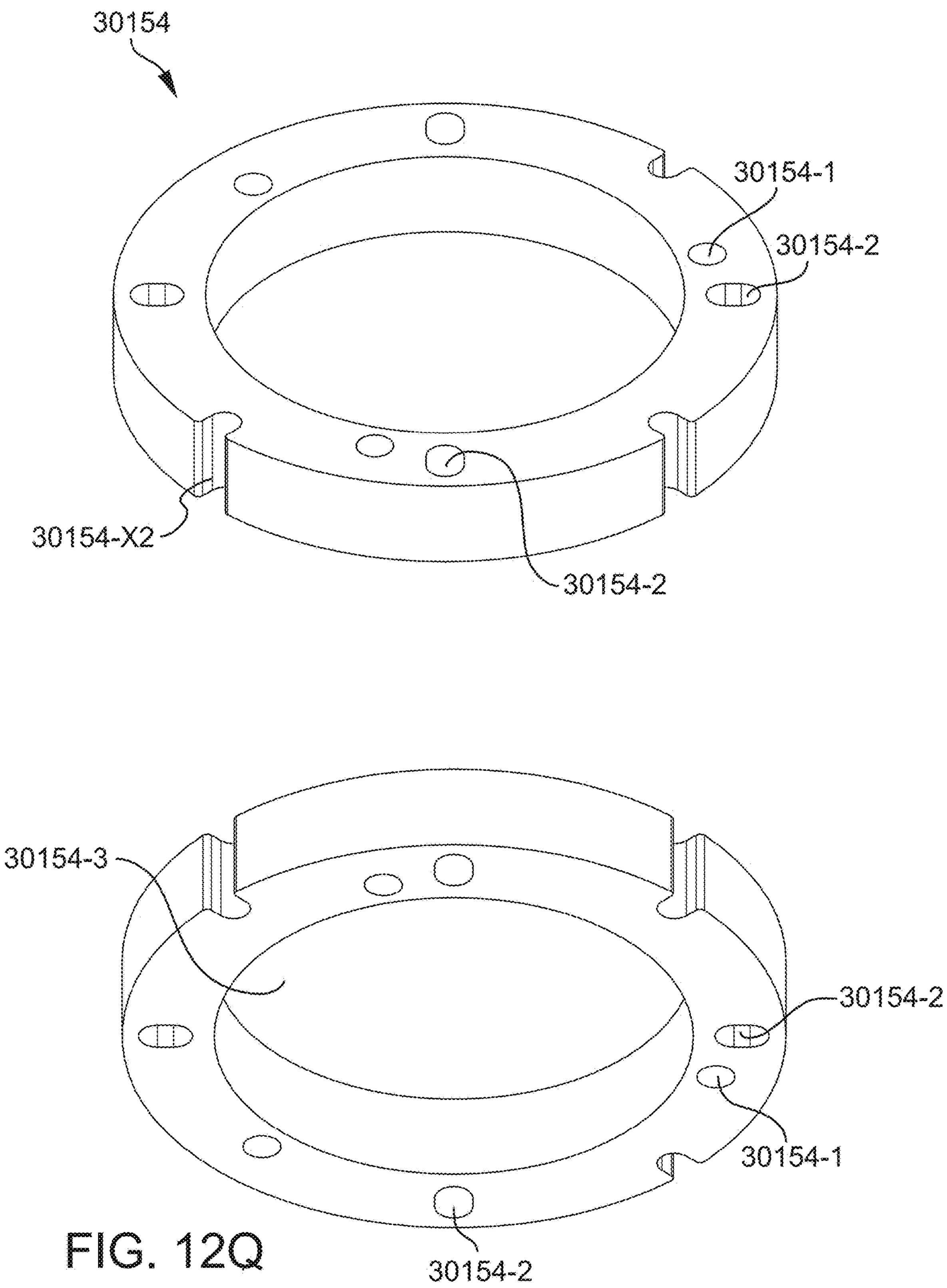
Figure 12R:
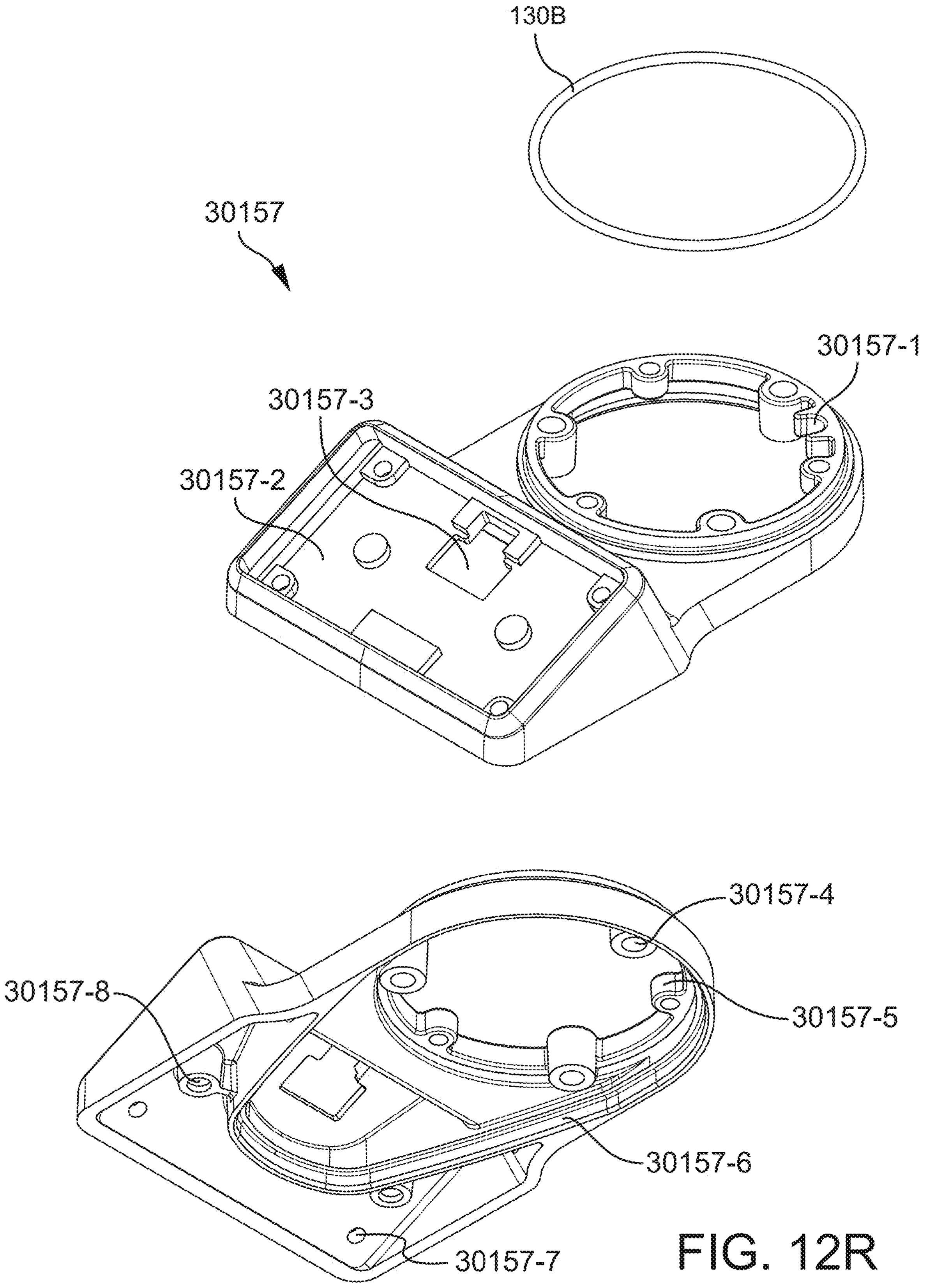
Figure 12S:
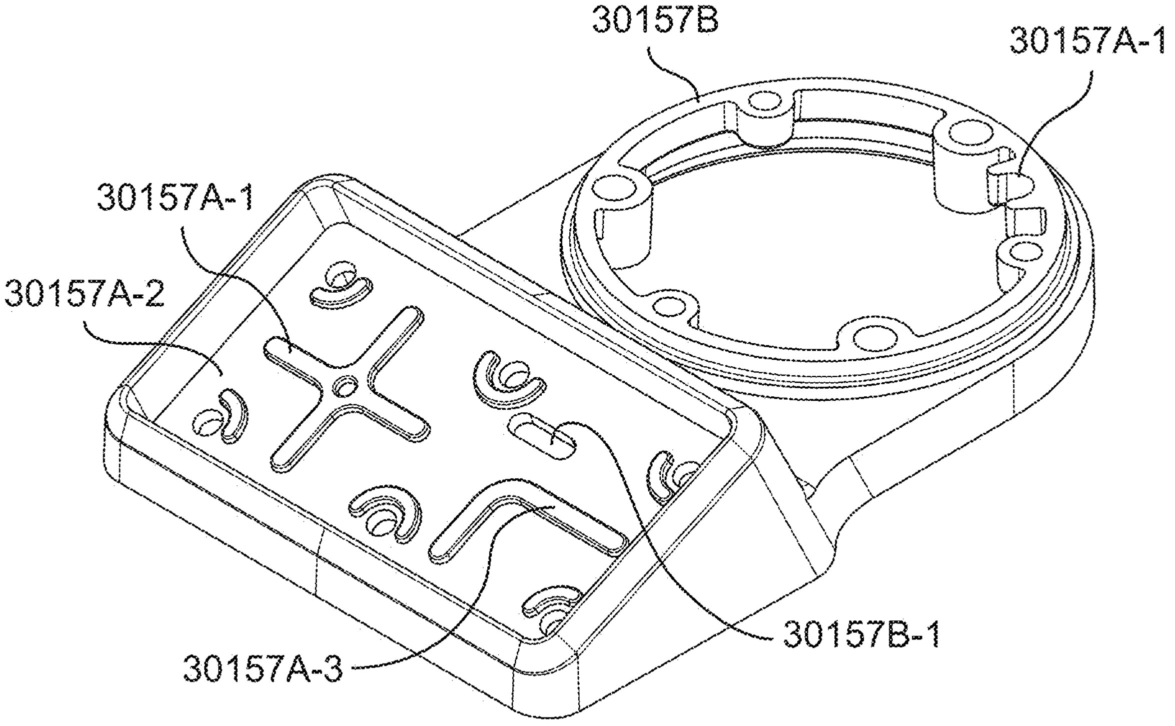
Figure 12S:
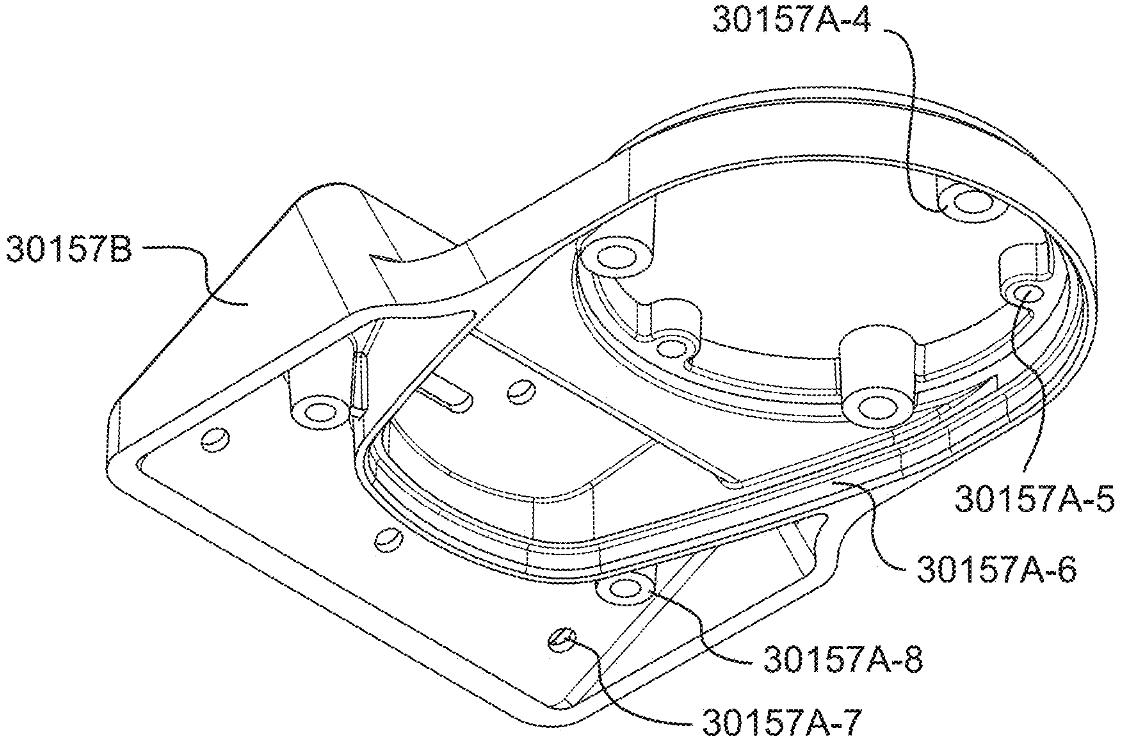
Figure 12T:
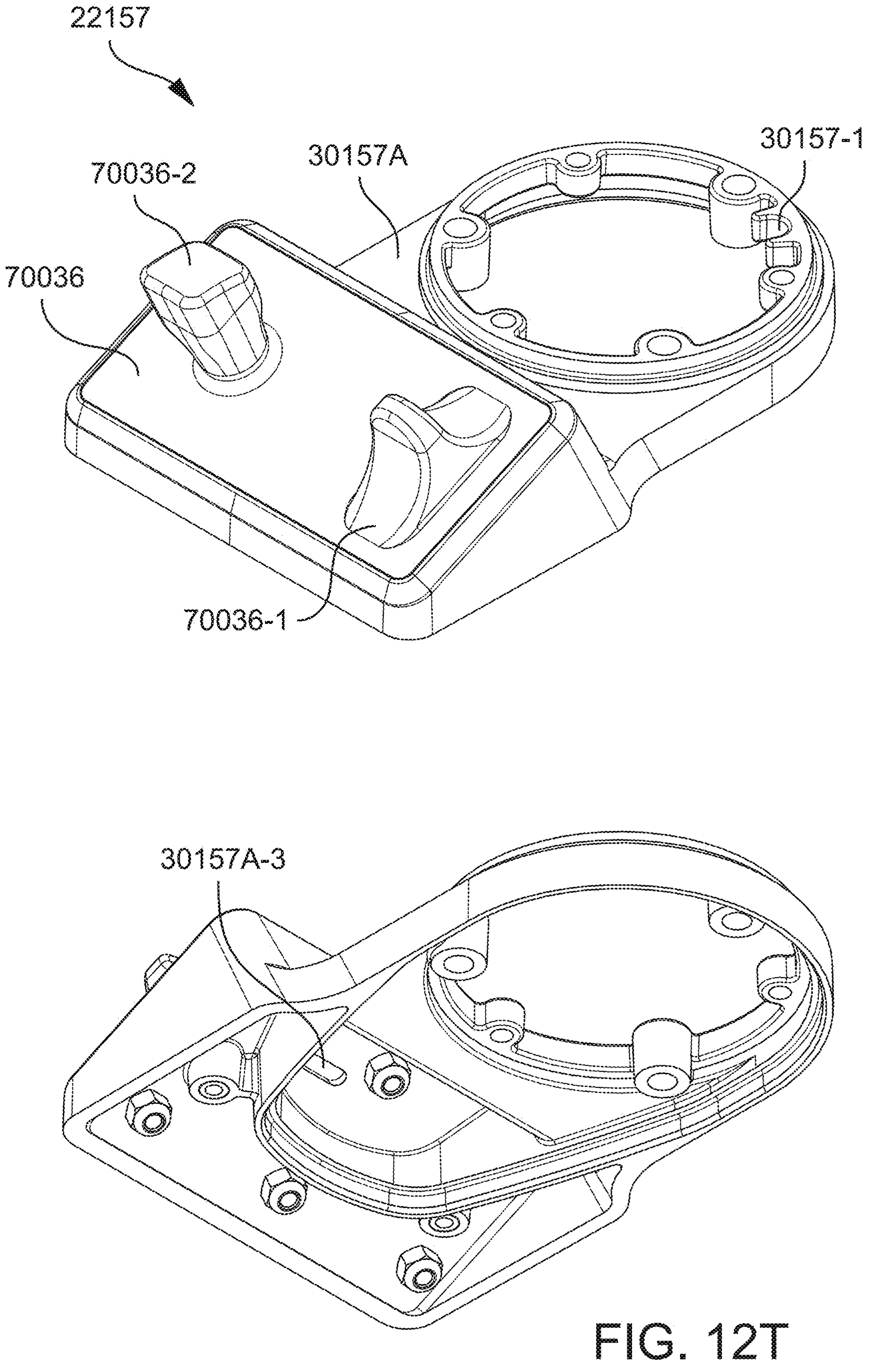
Figure 12U:
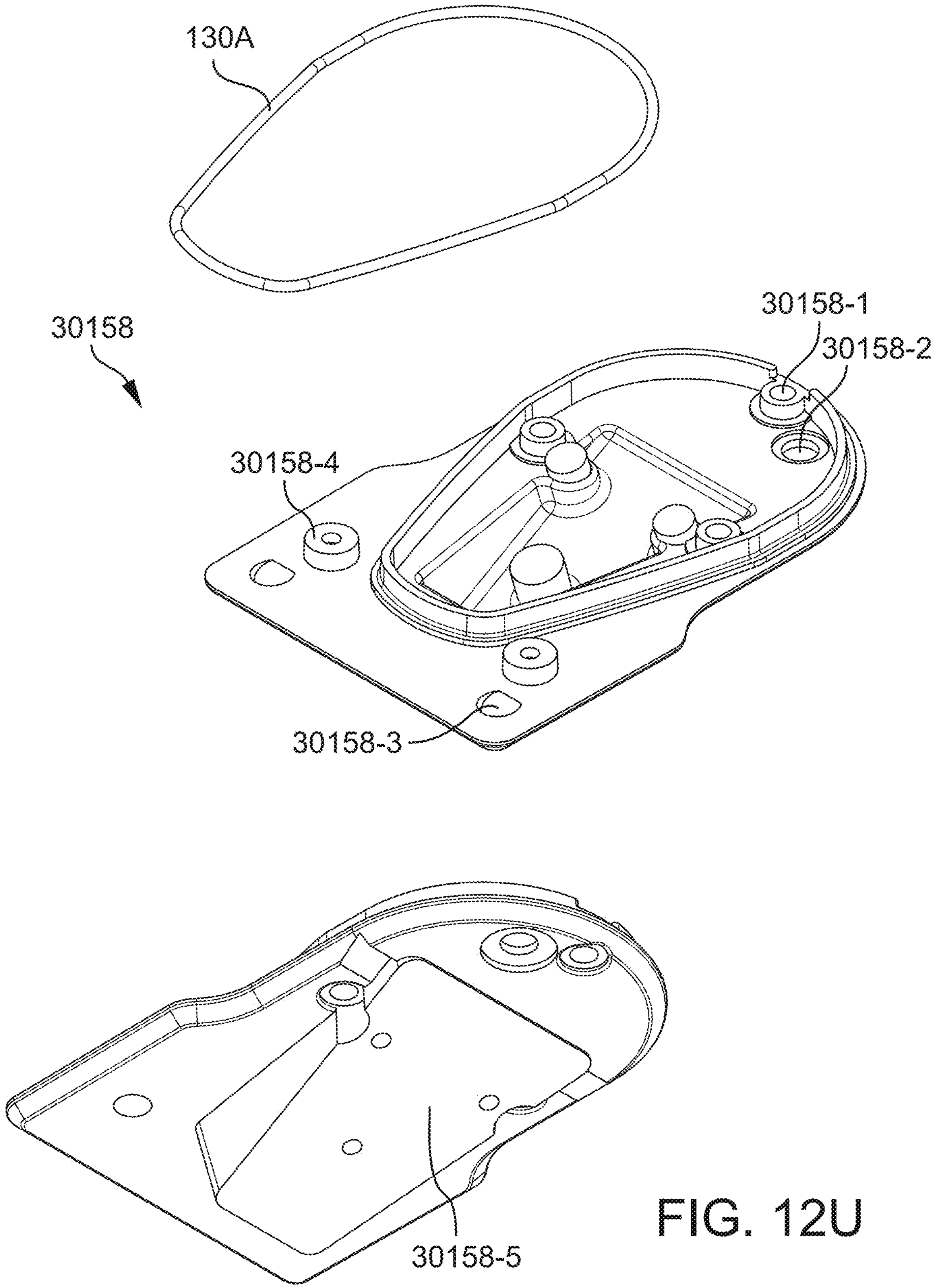
Figure 12V:
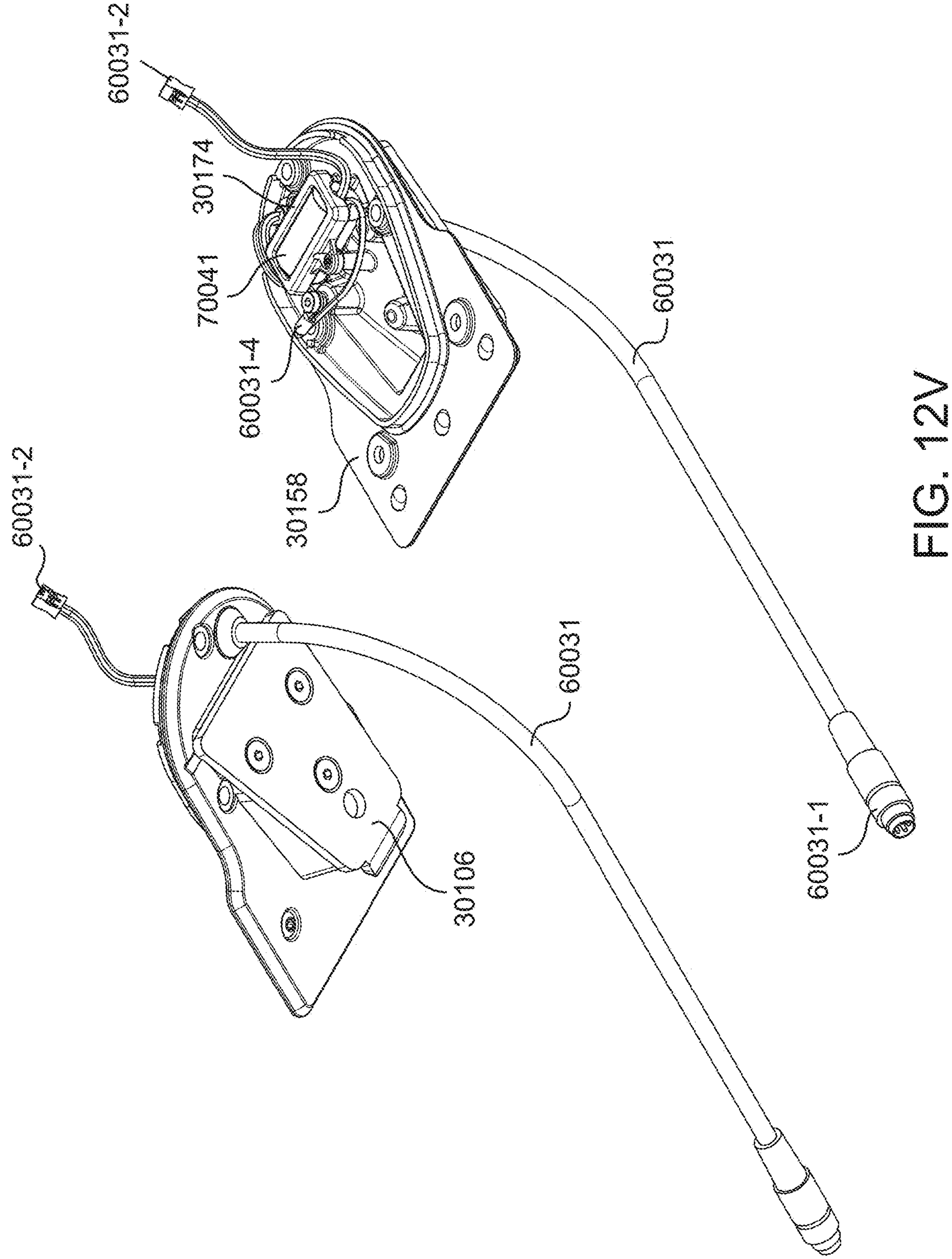
Figure 12W:
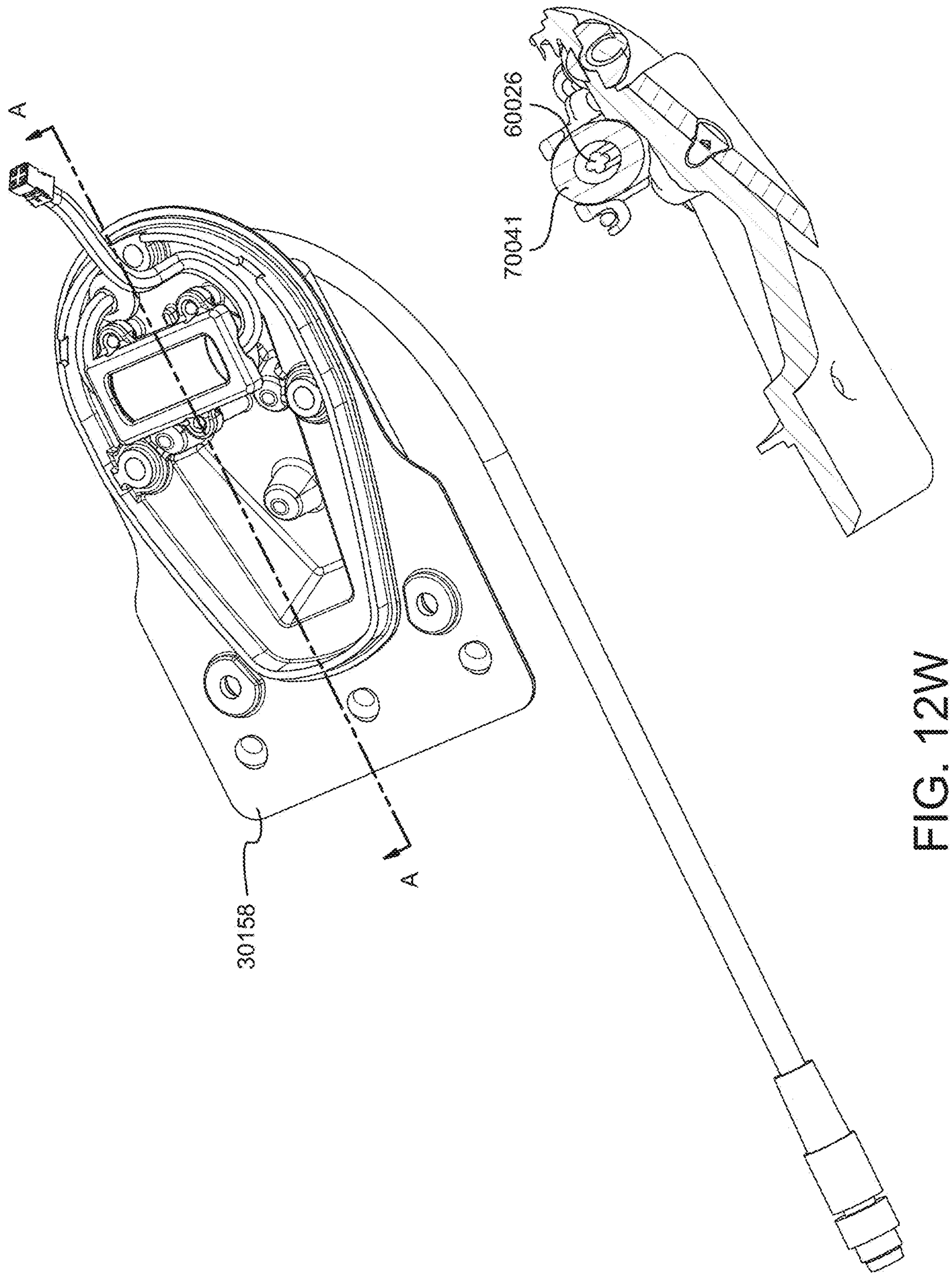
Figure 12X:
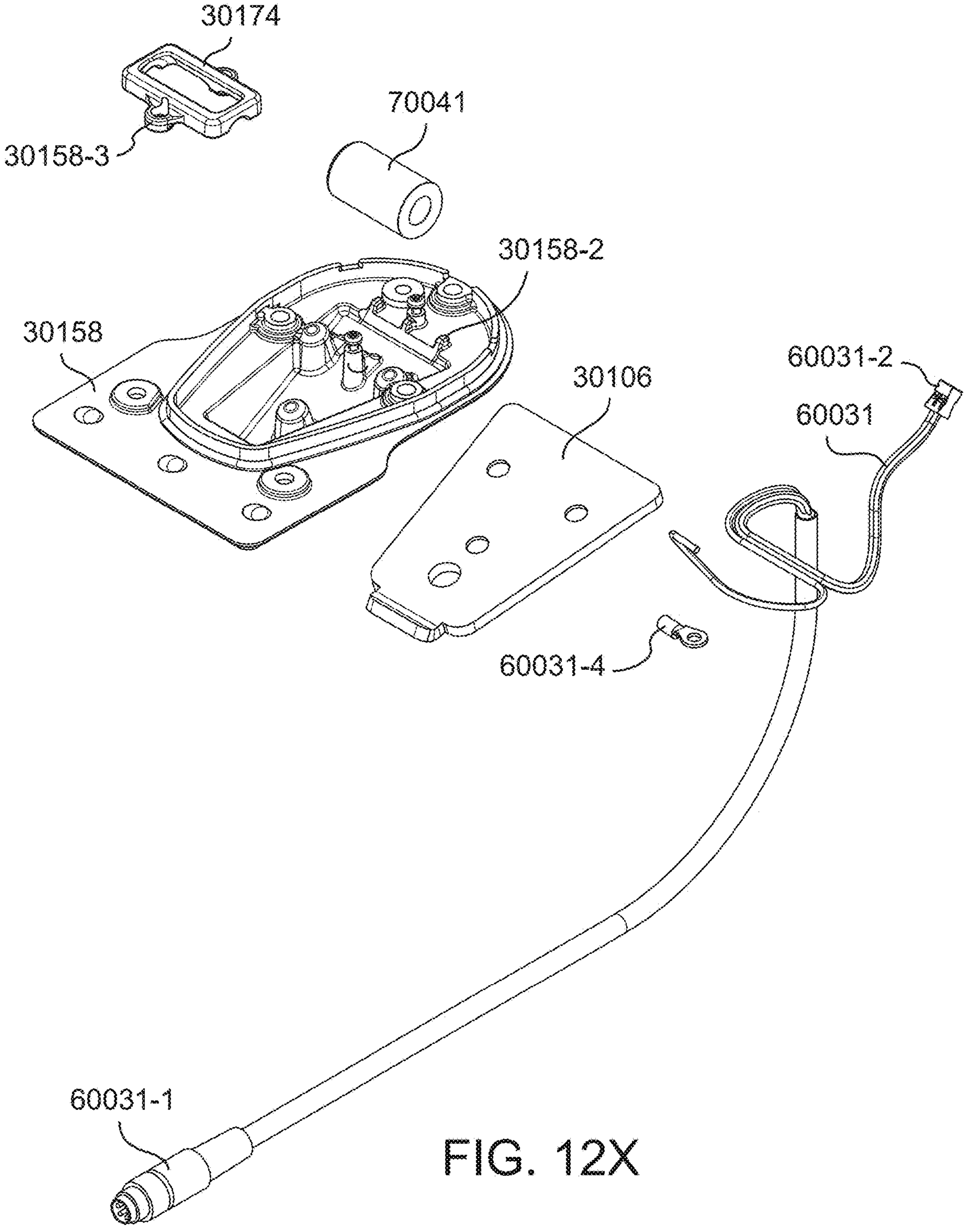
Figure 12Y:
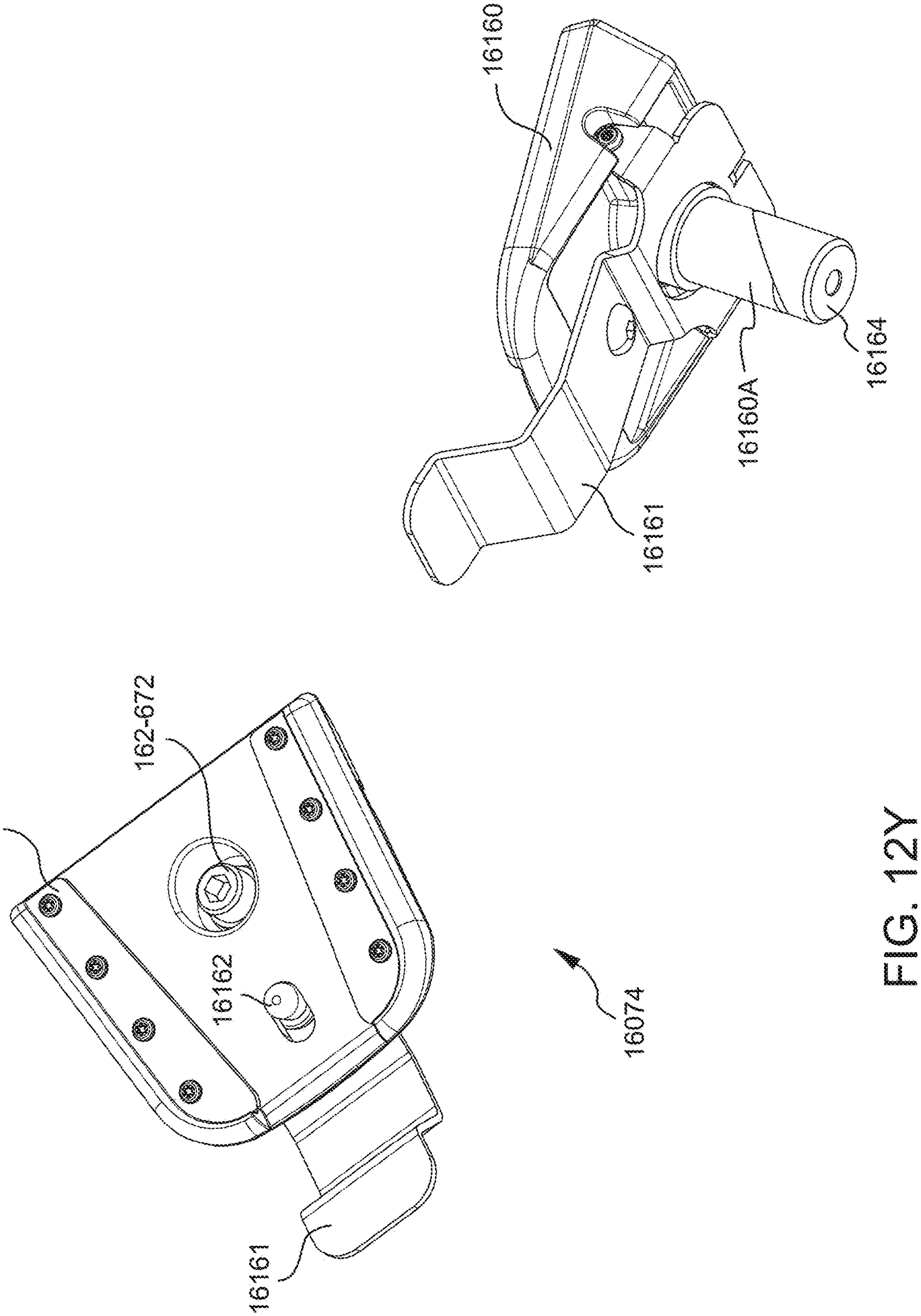
Figure 12Z:
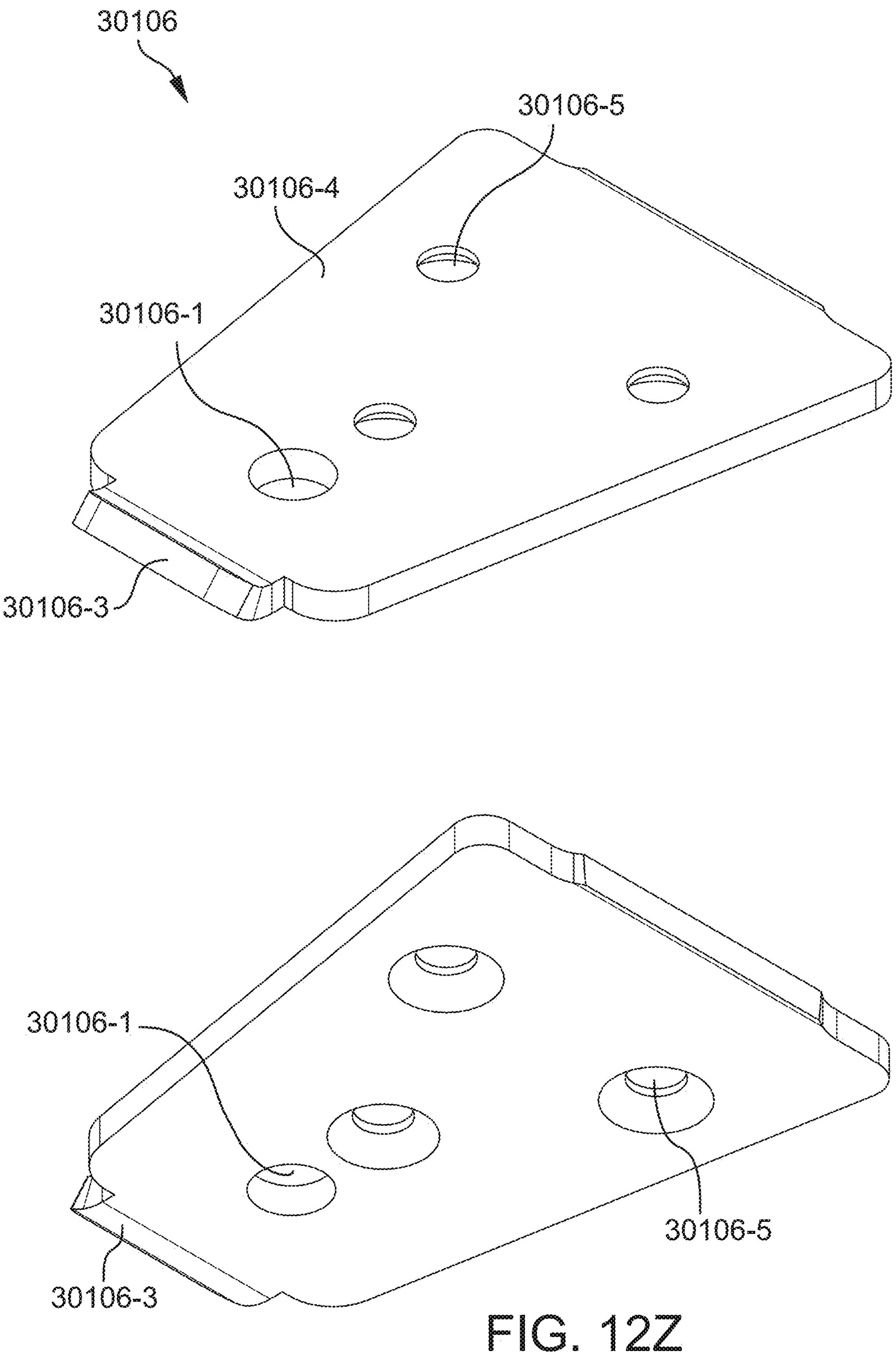
Figure 12A:
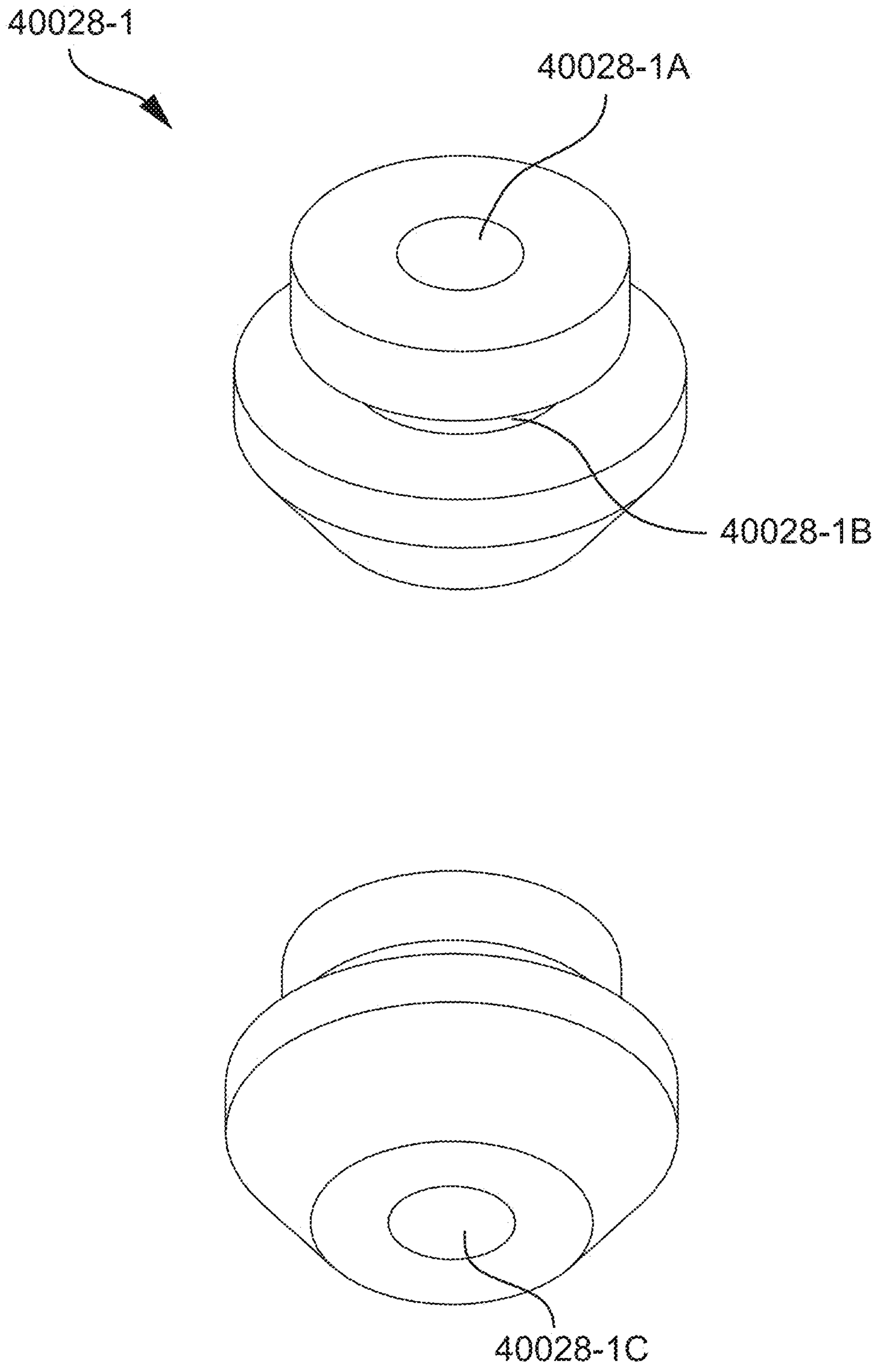
Figure 12B:
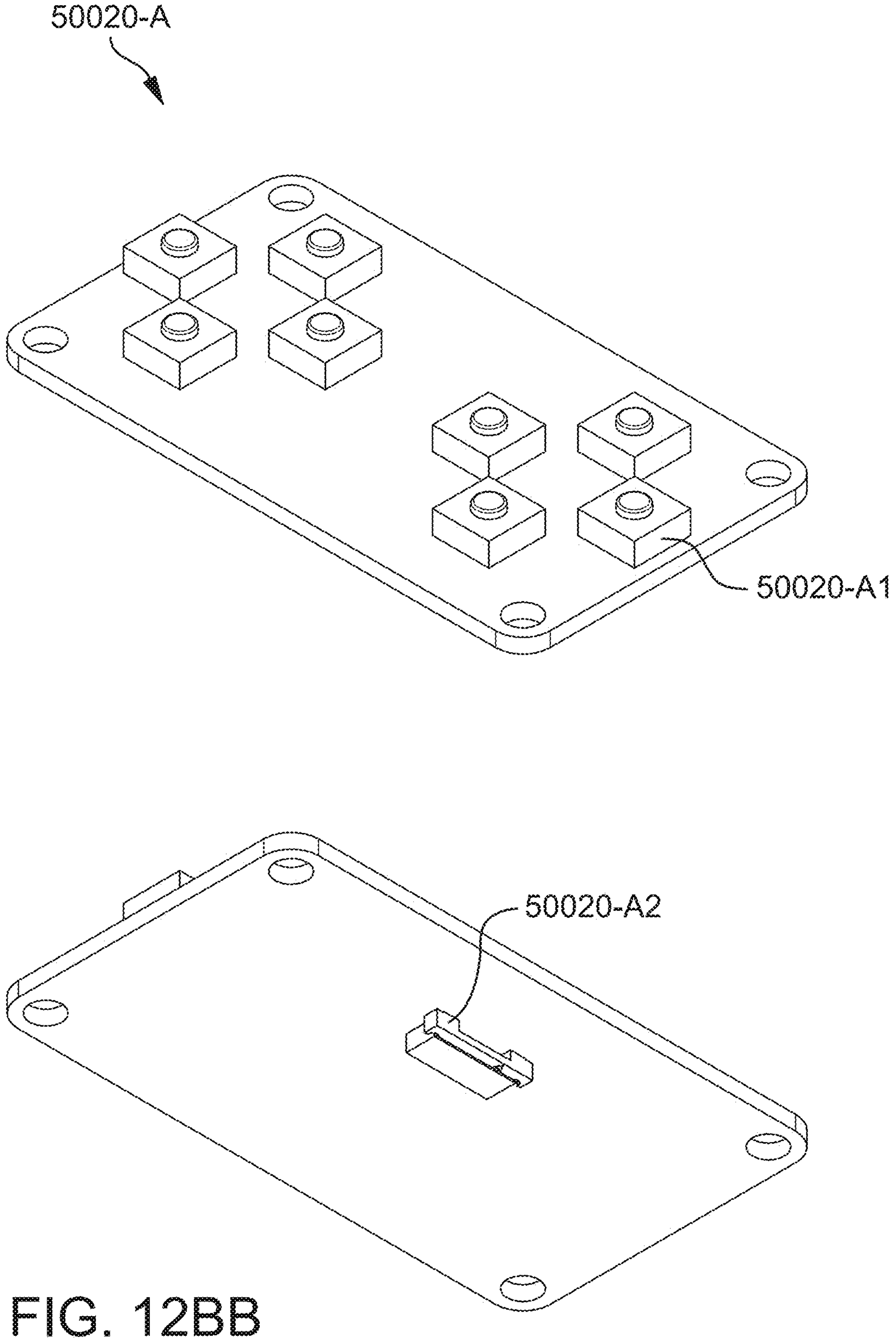
Figure 12C:
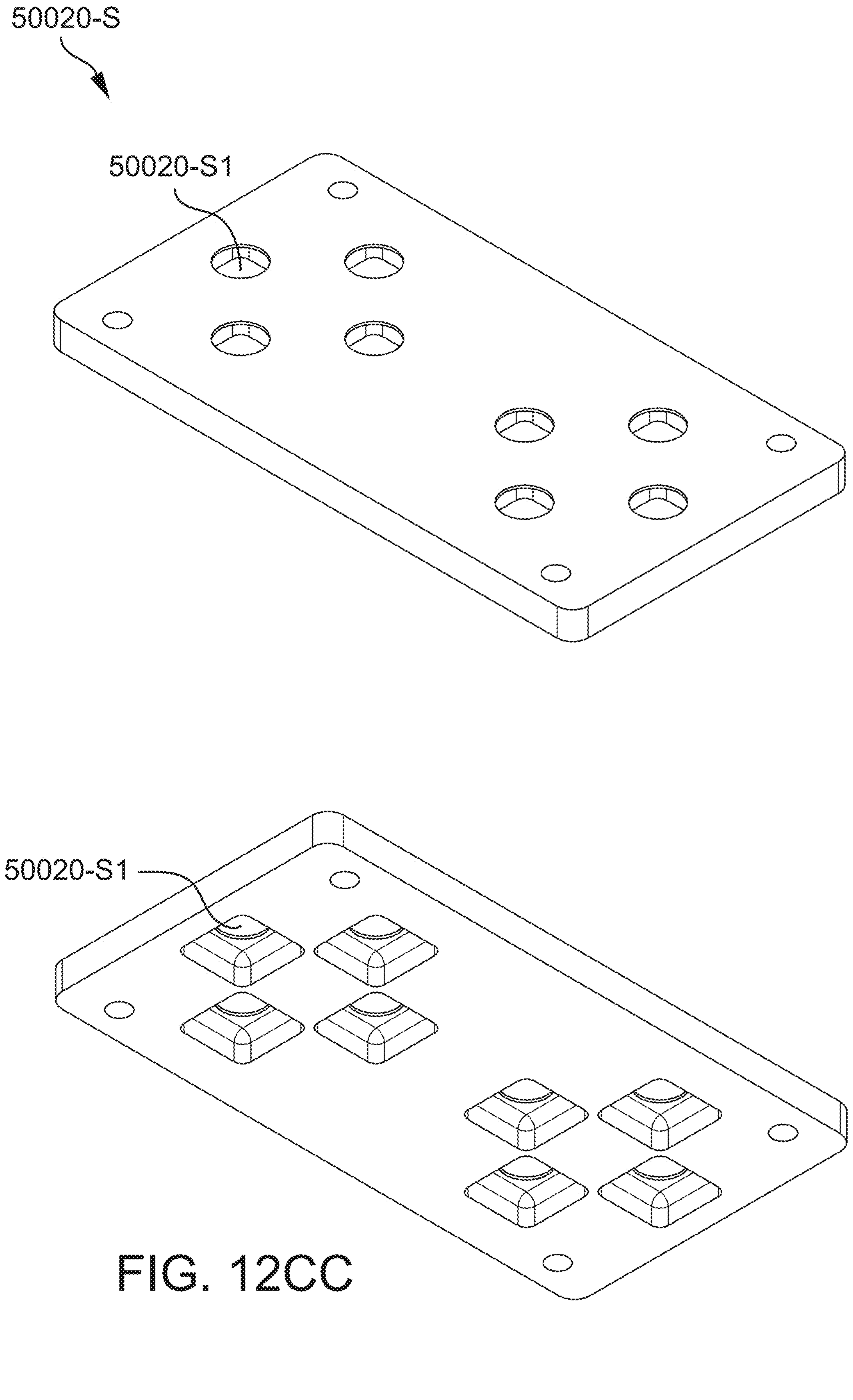
Figure 12D:
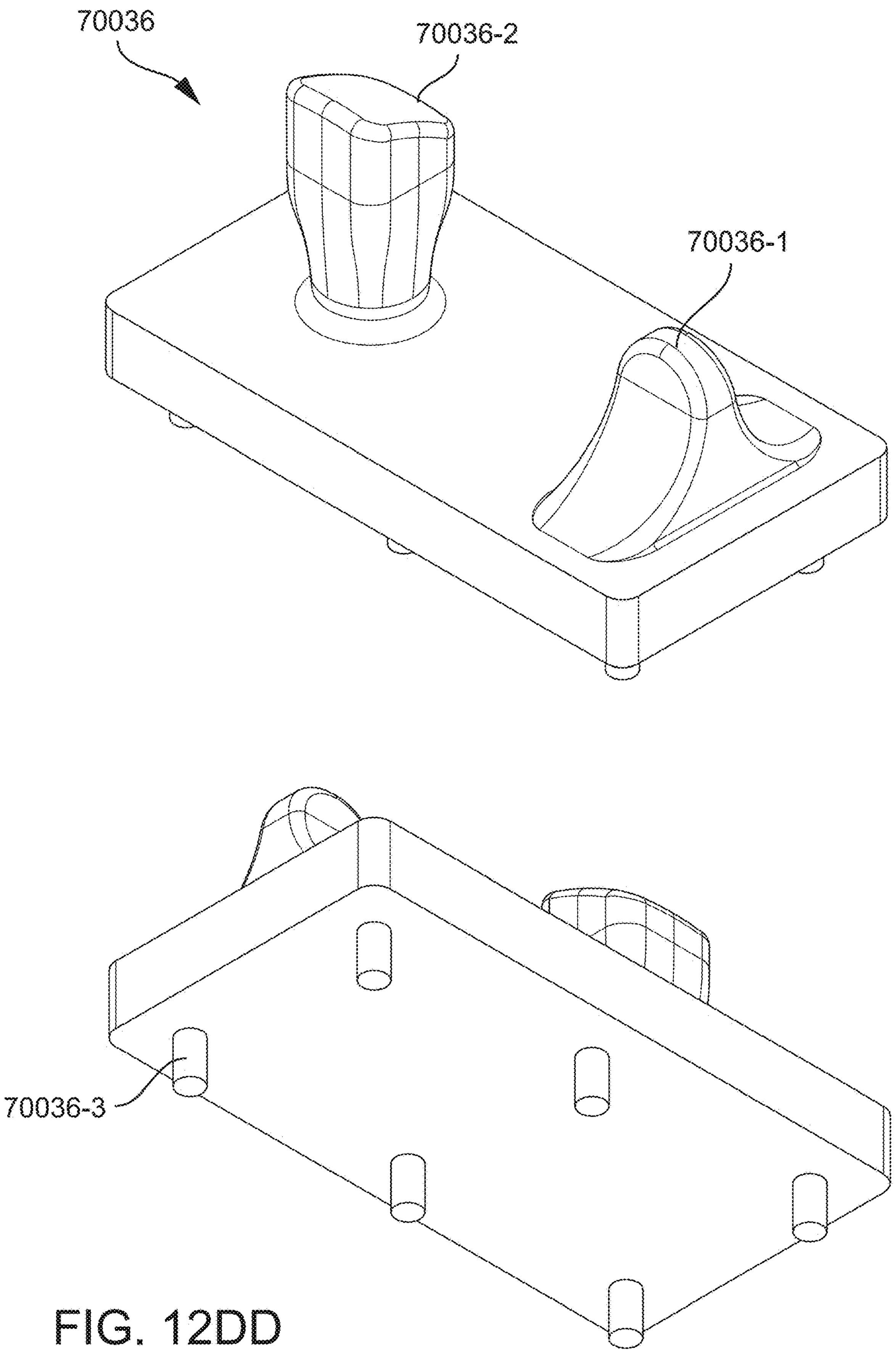
Figure 12E:
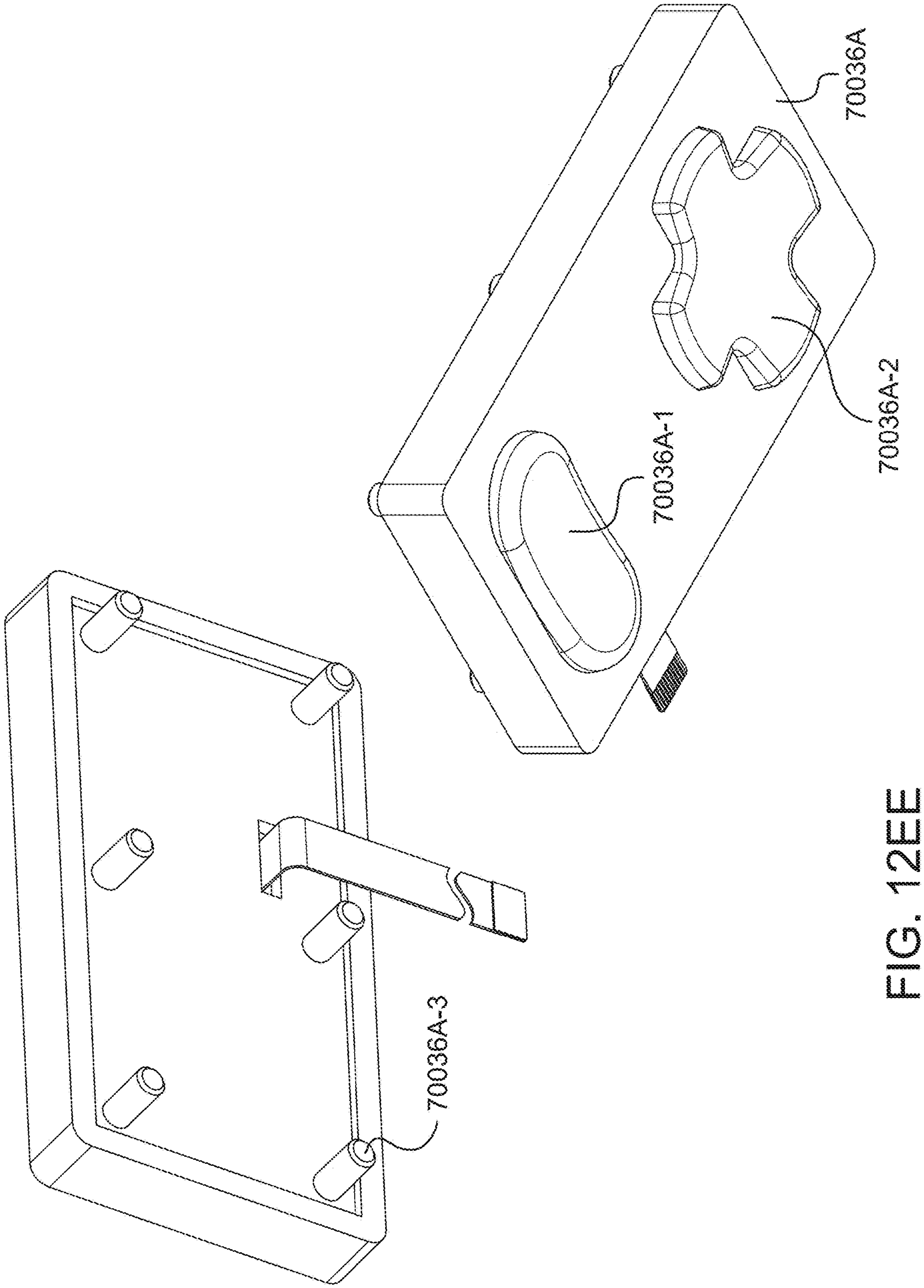
Figure 12F:
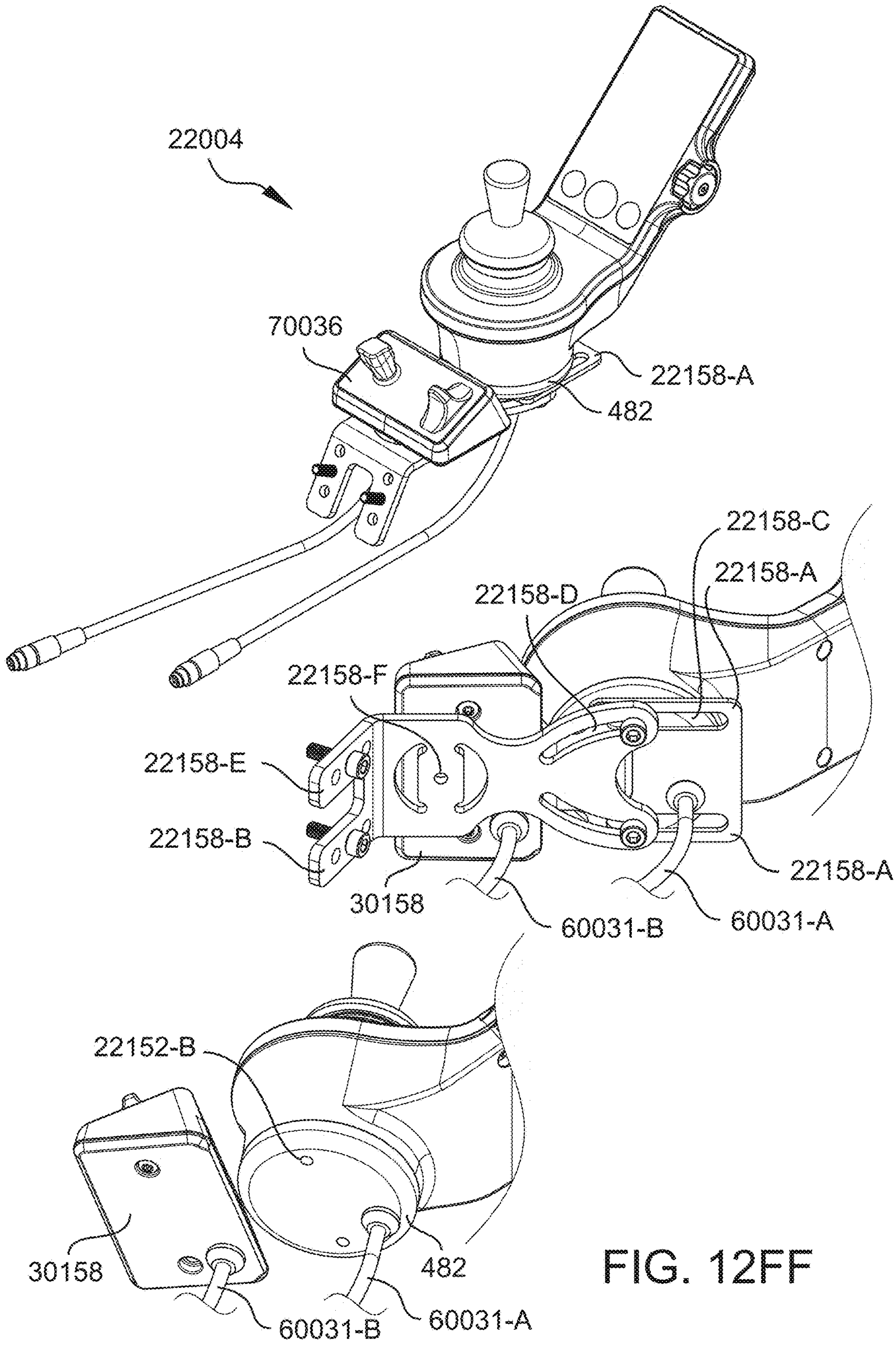
Figure 12G:
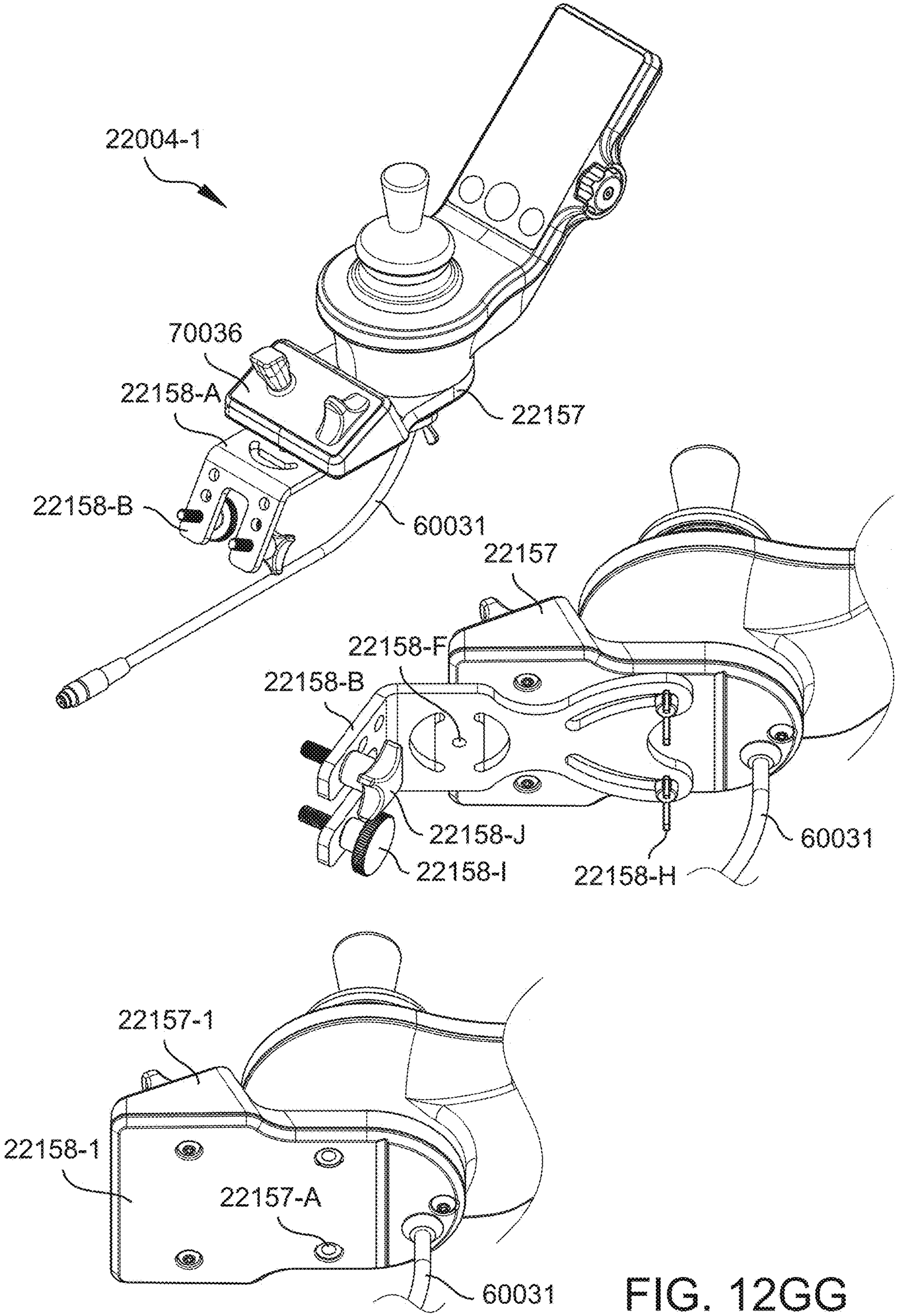
Figure 12H:
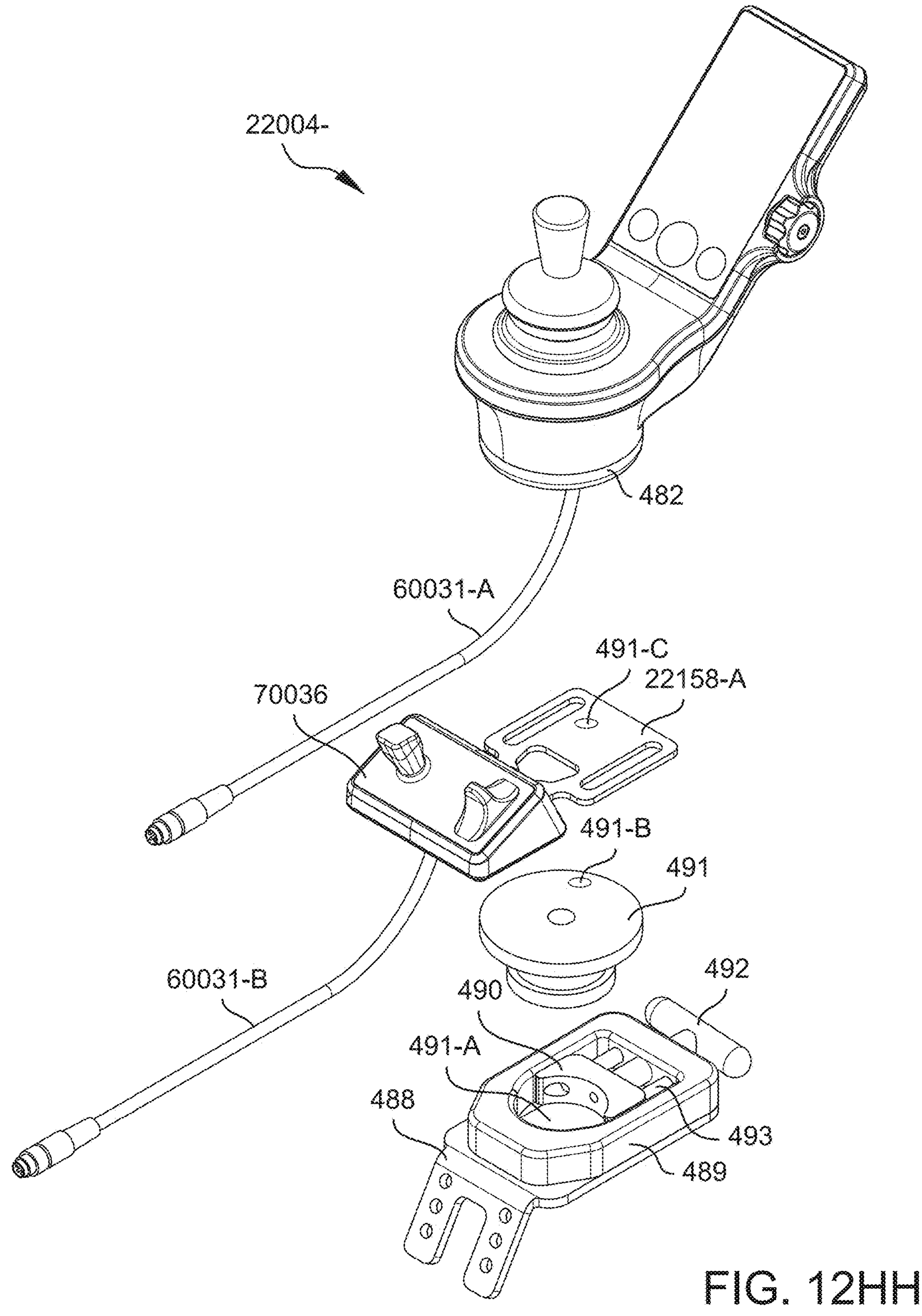
Figure 12I:
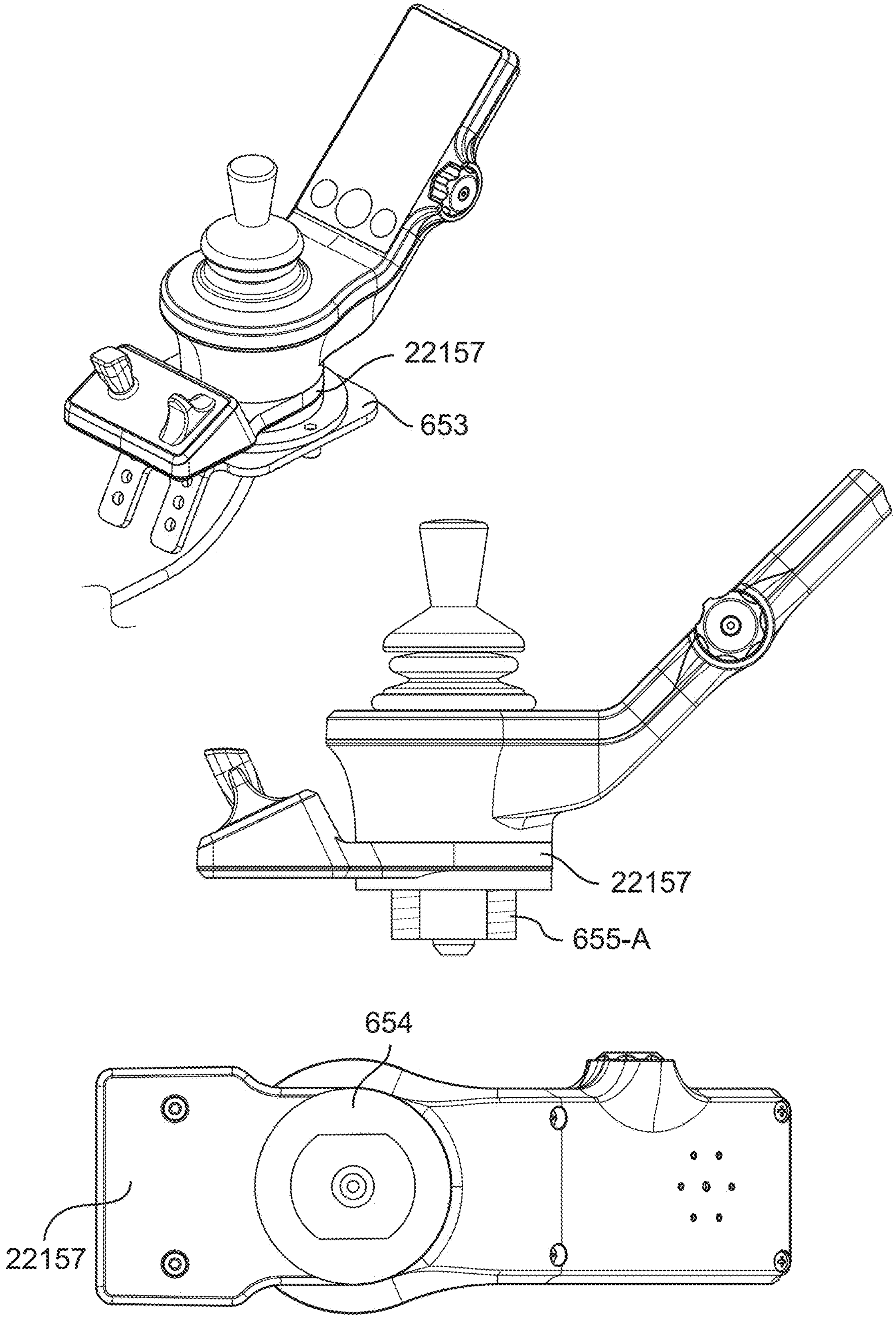
Figure 12J:
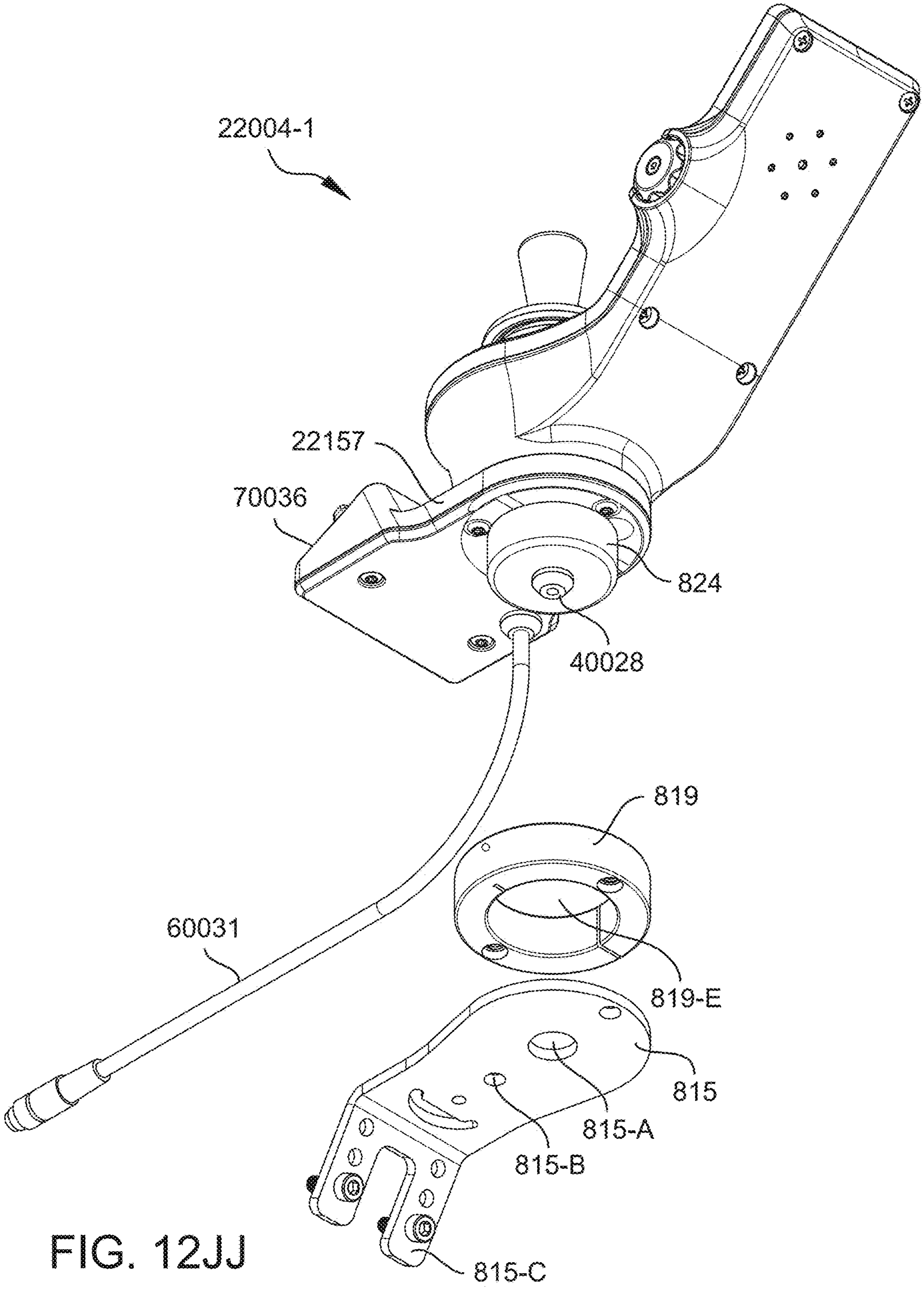
Figure 12K:
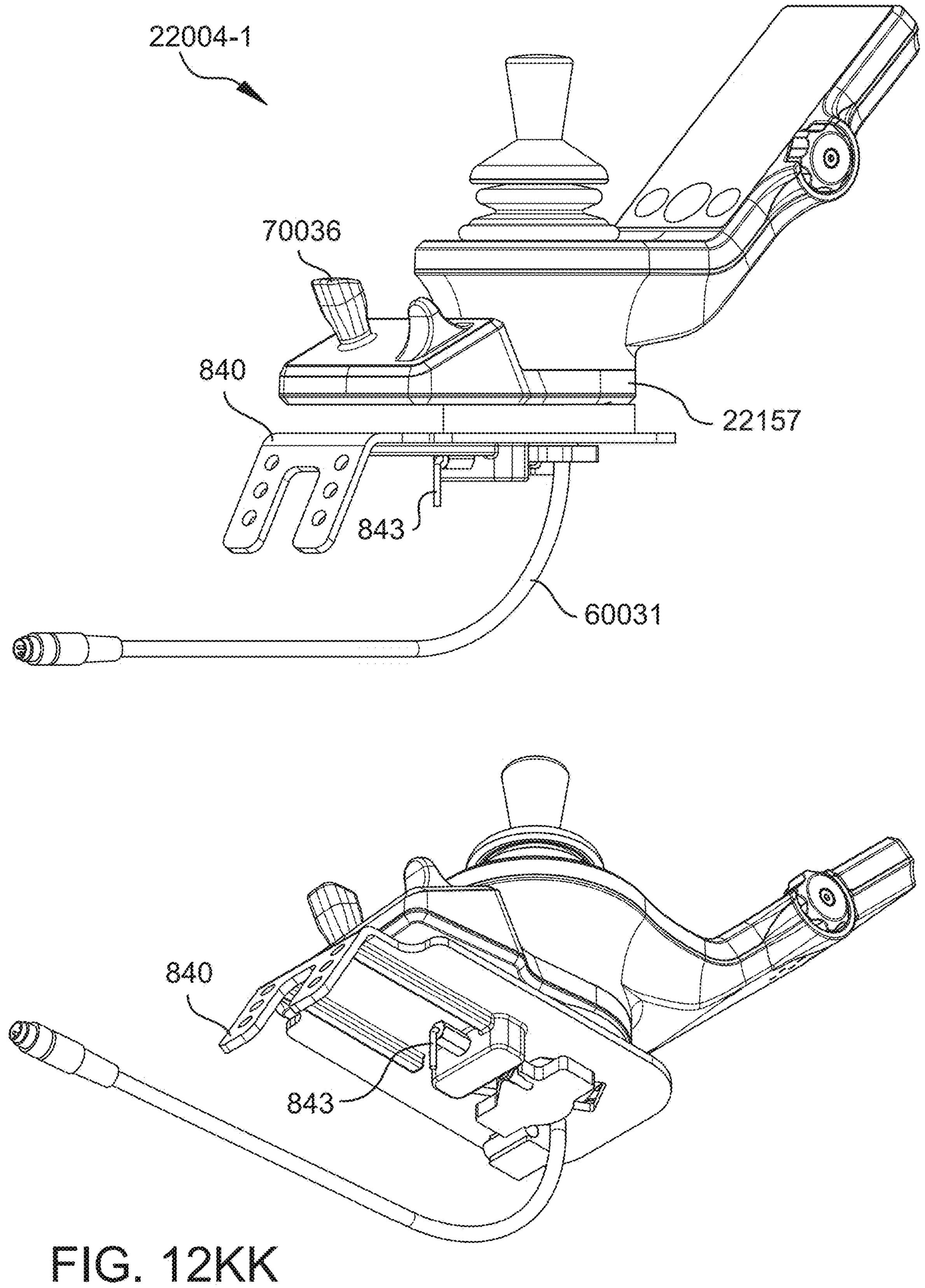
Figure 12L:
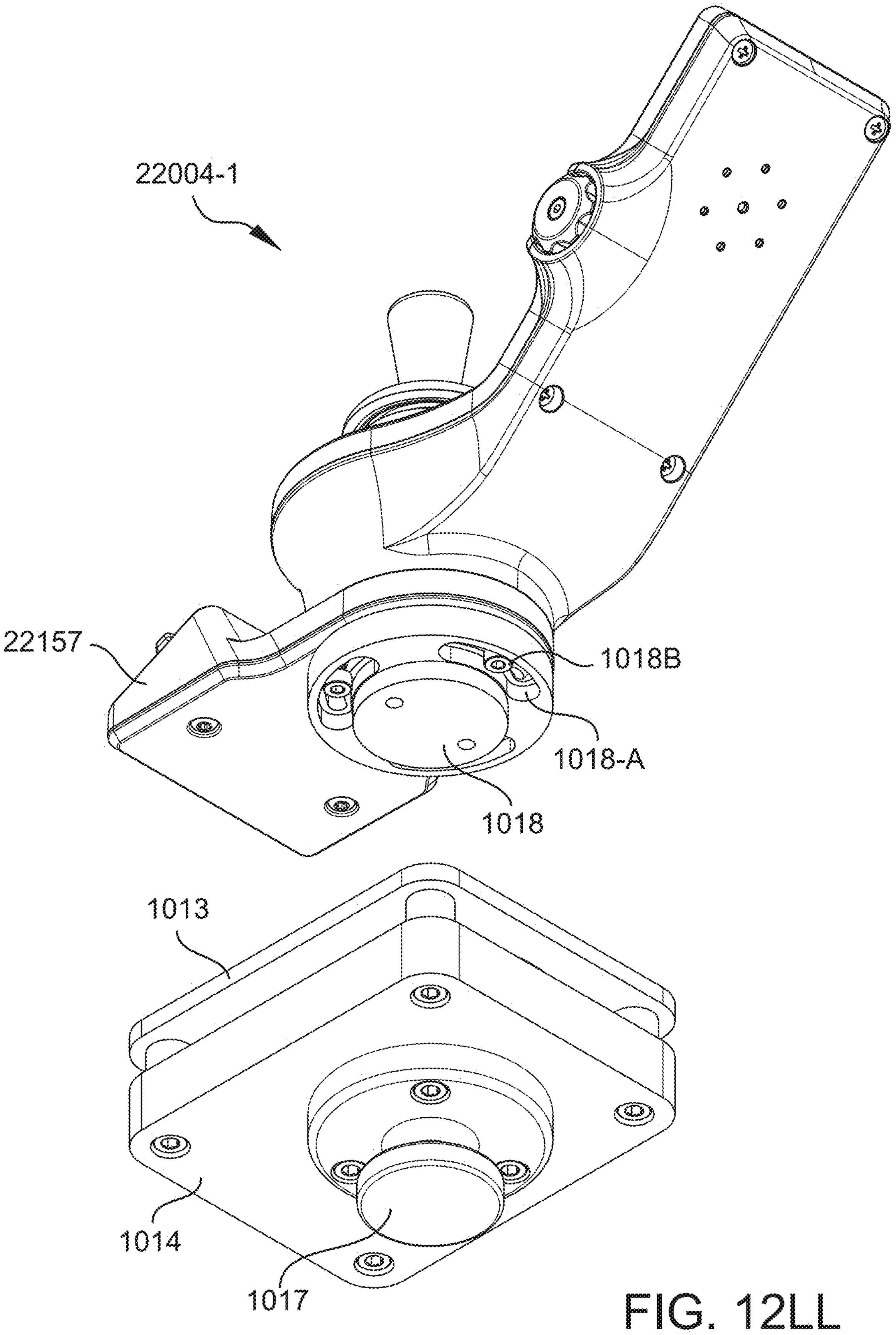
Figure 12M:
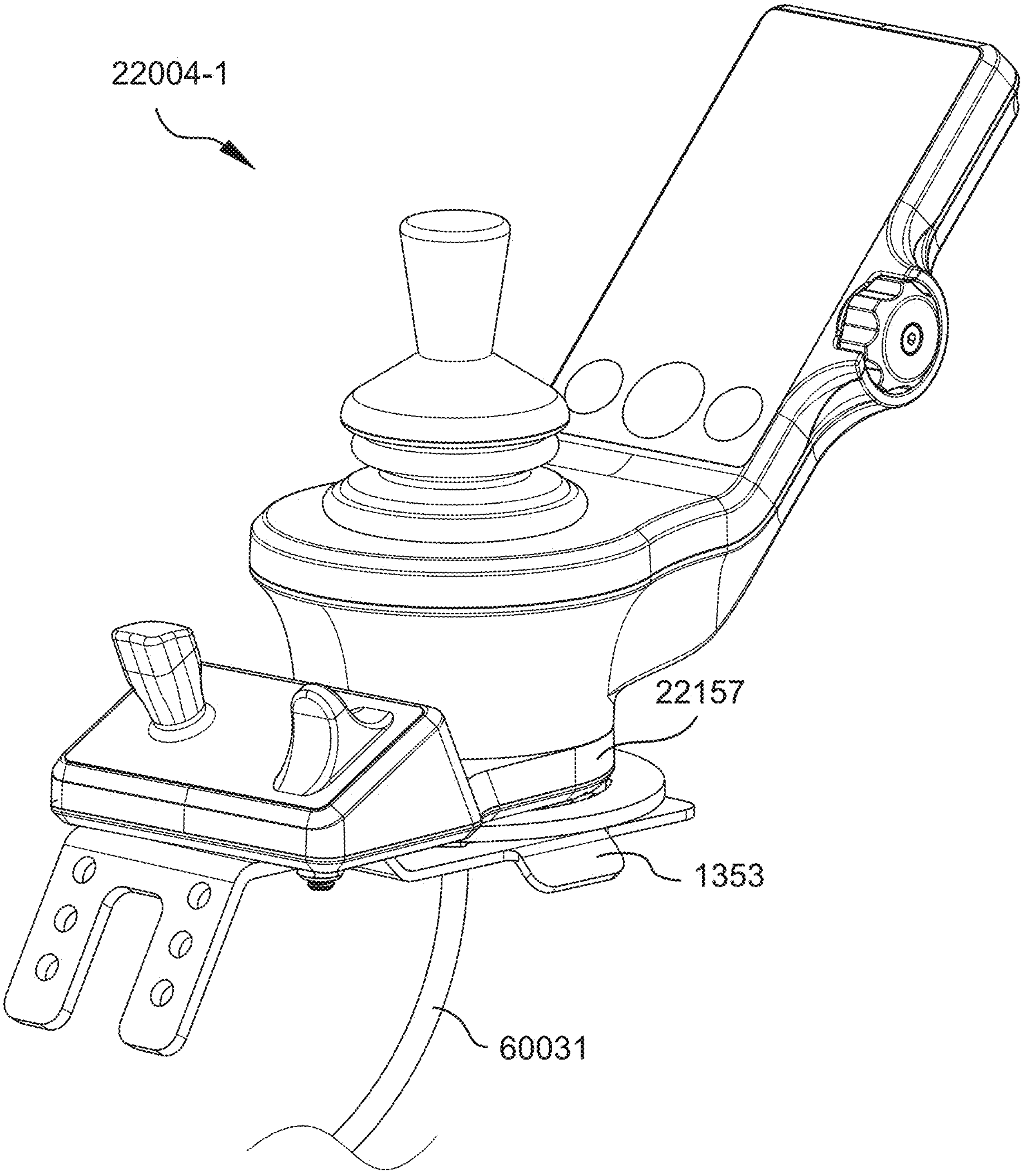
Figure 12N:
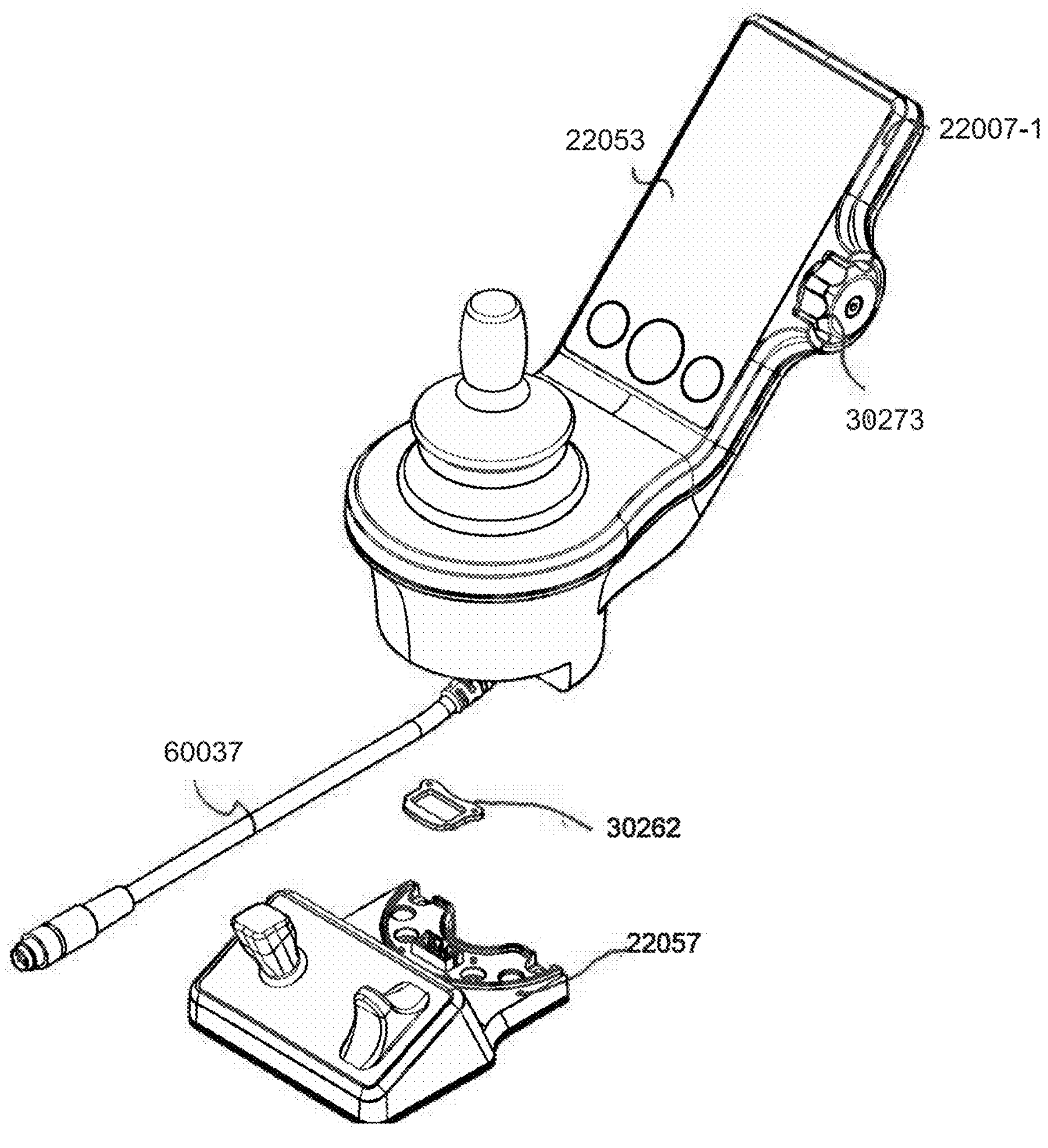
Figure 12P:
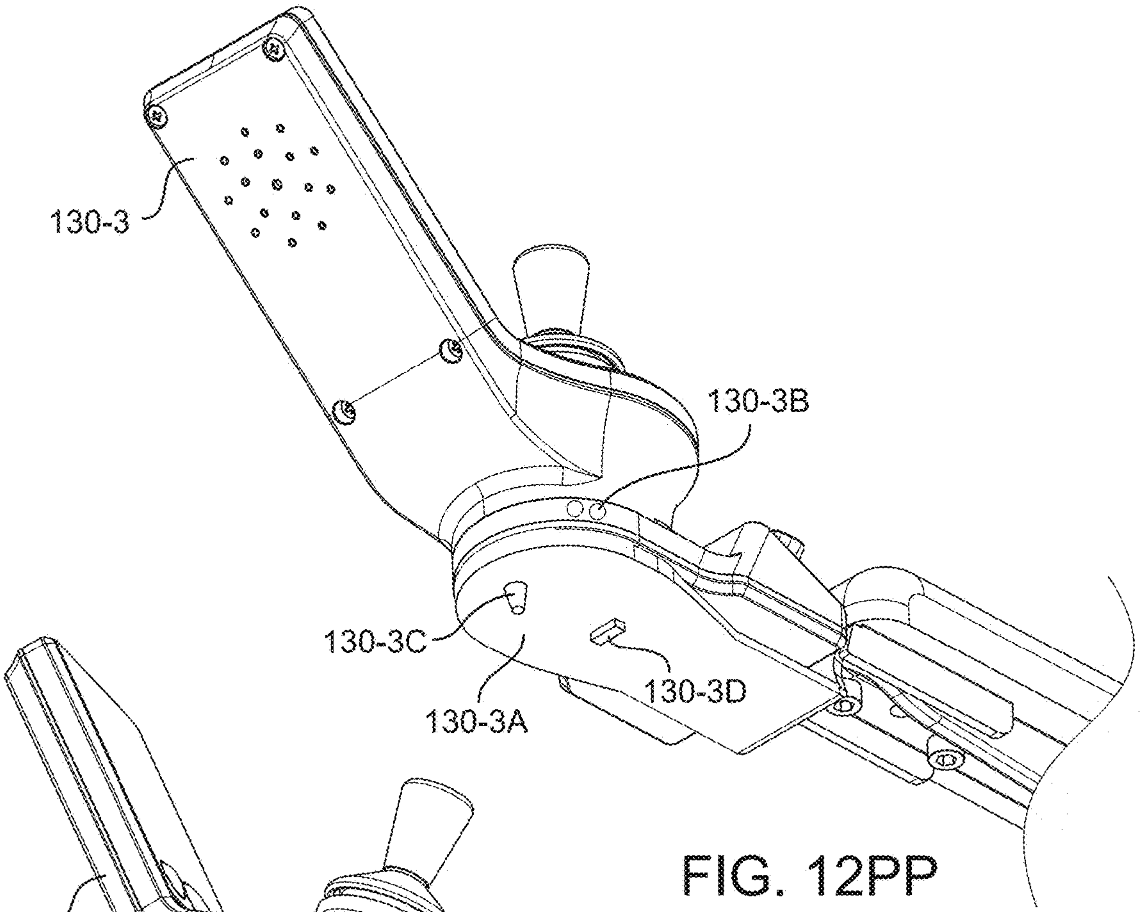
Figure 12O:
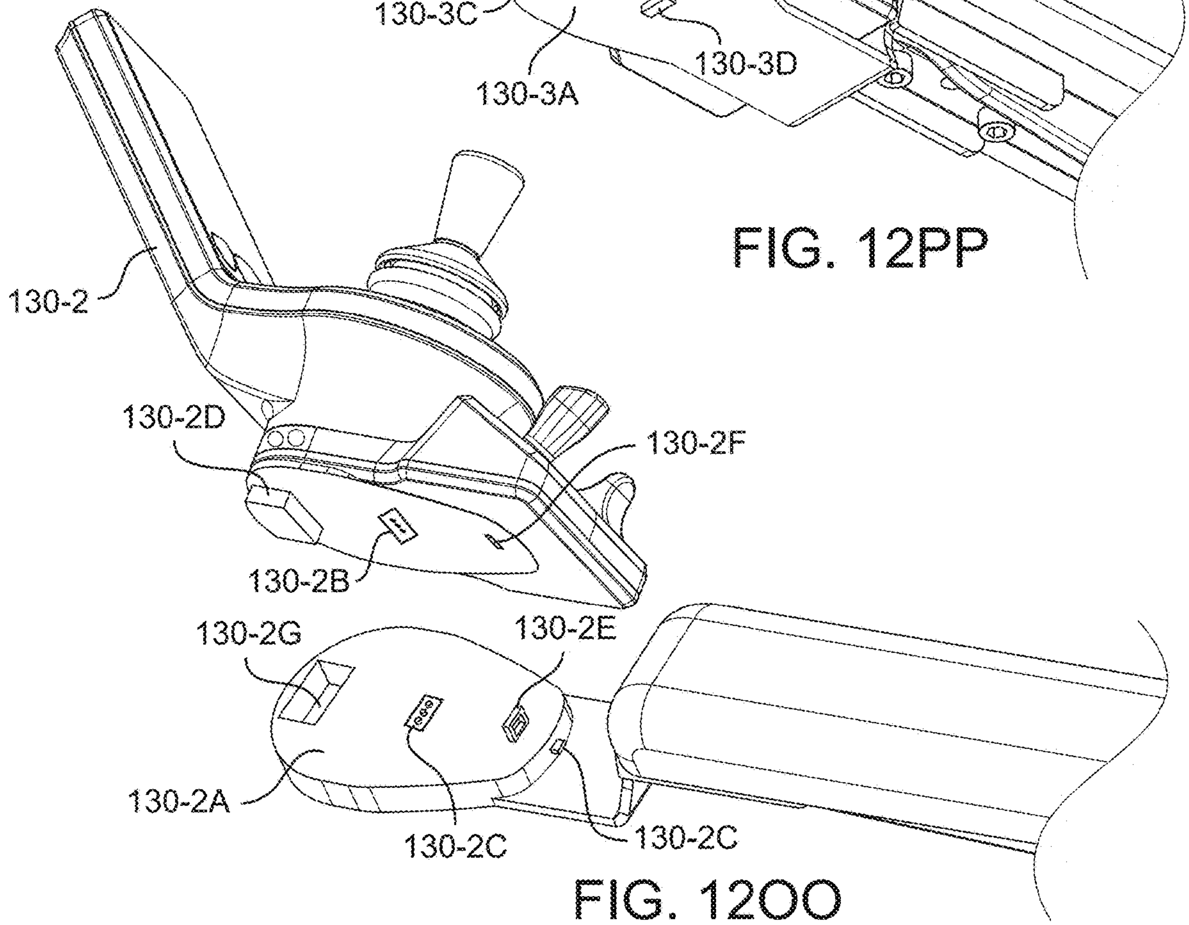
Figure 12R:
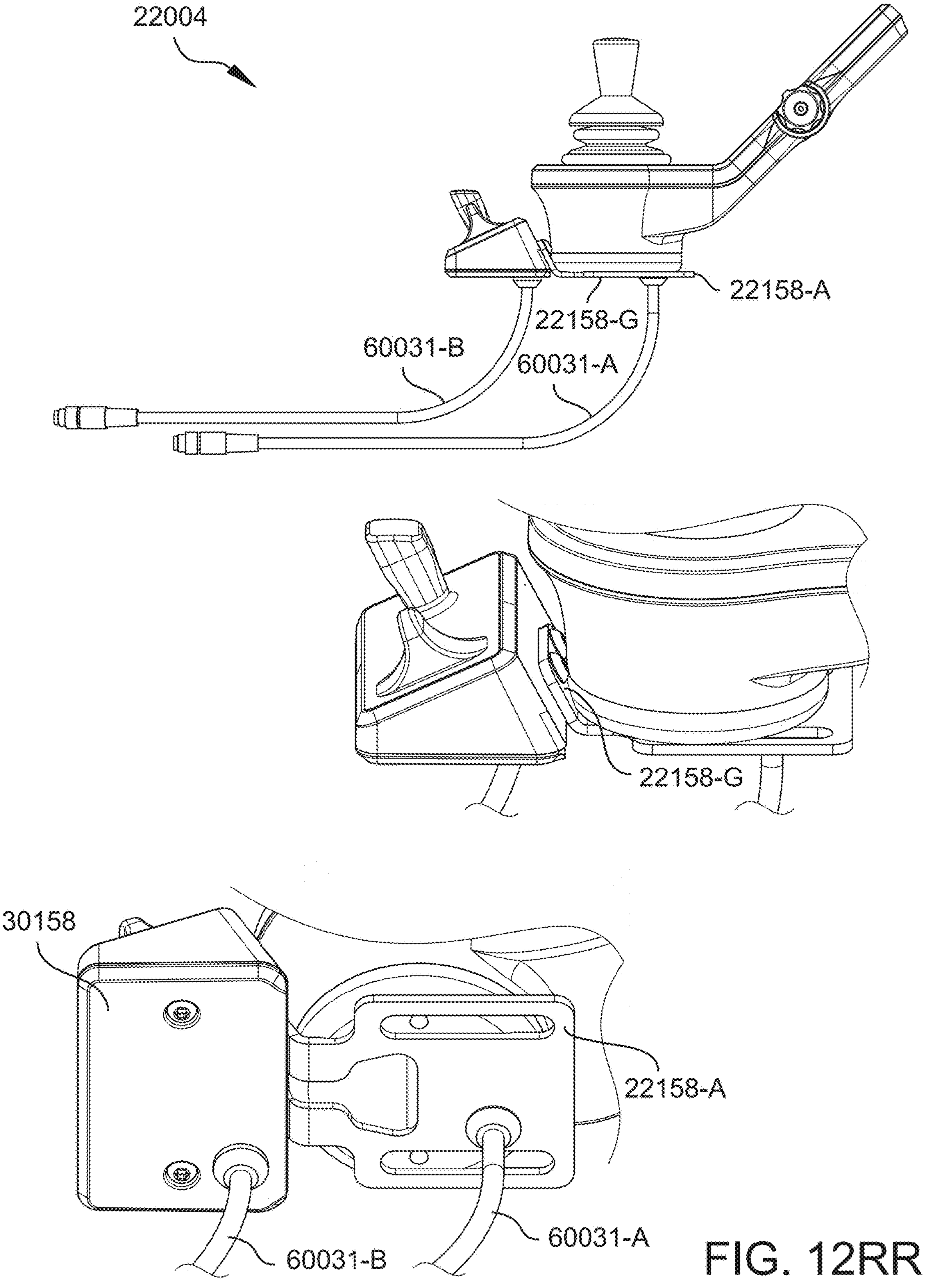
Figure 12S:
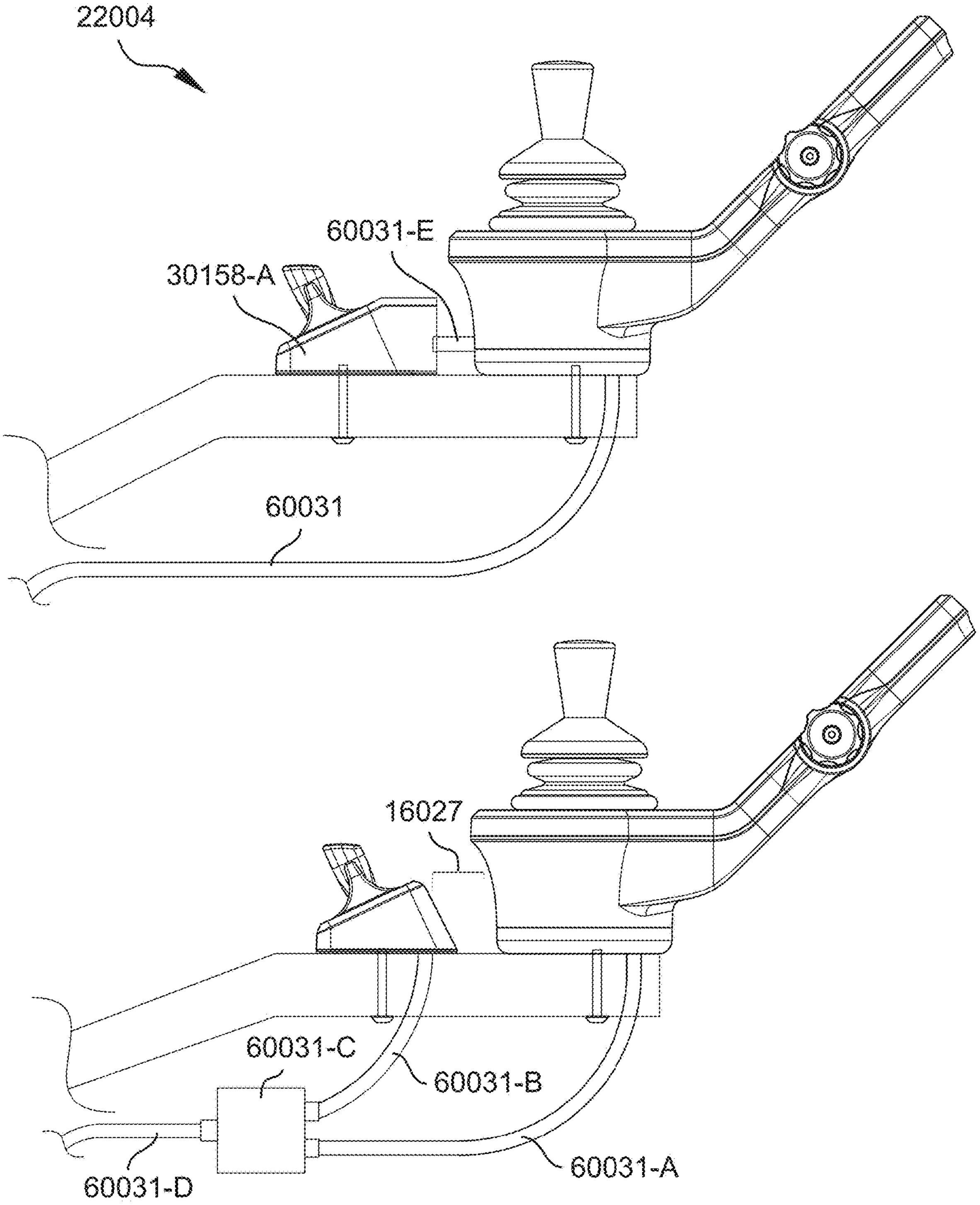
Figure 12Q:
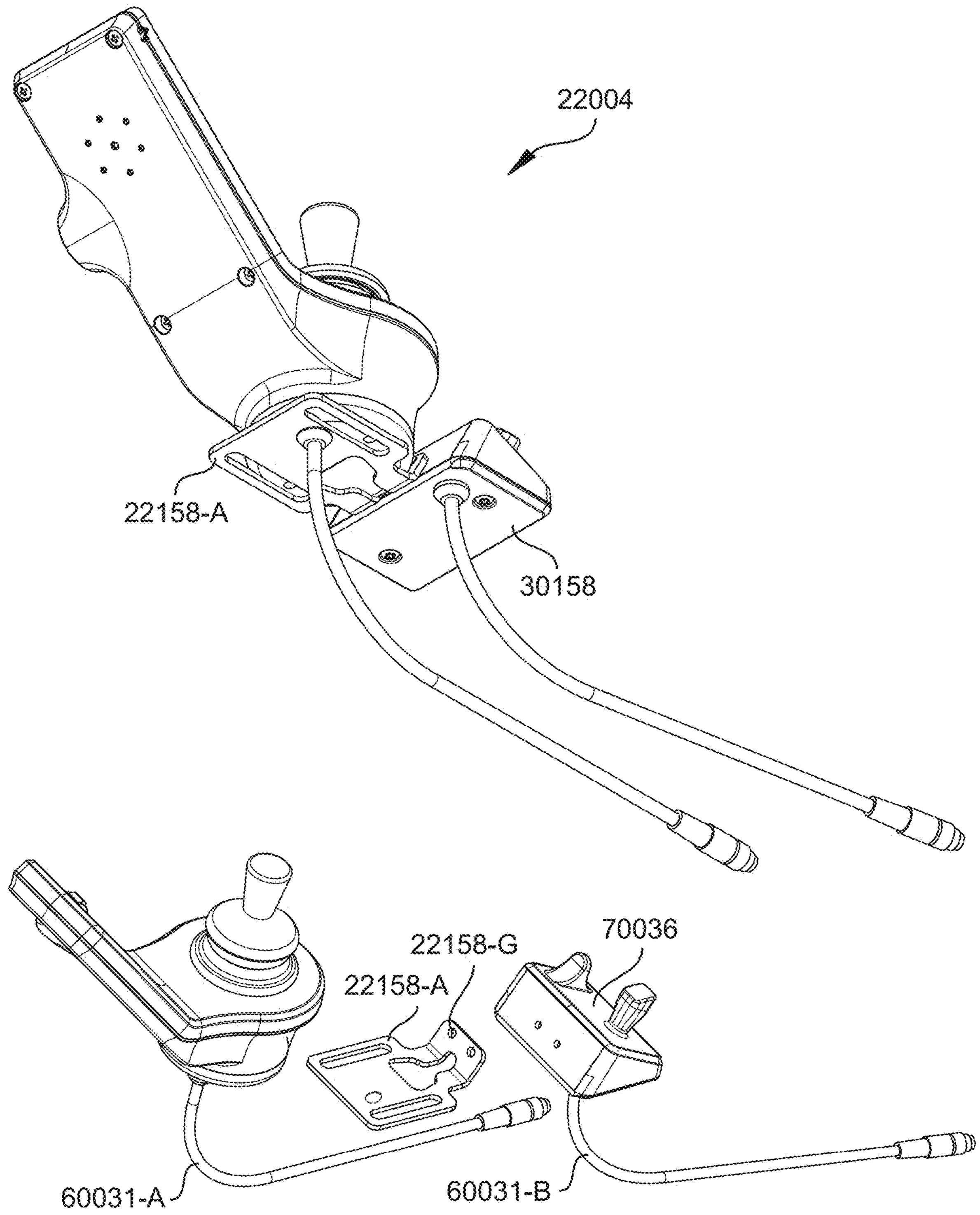
Figure 12U:
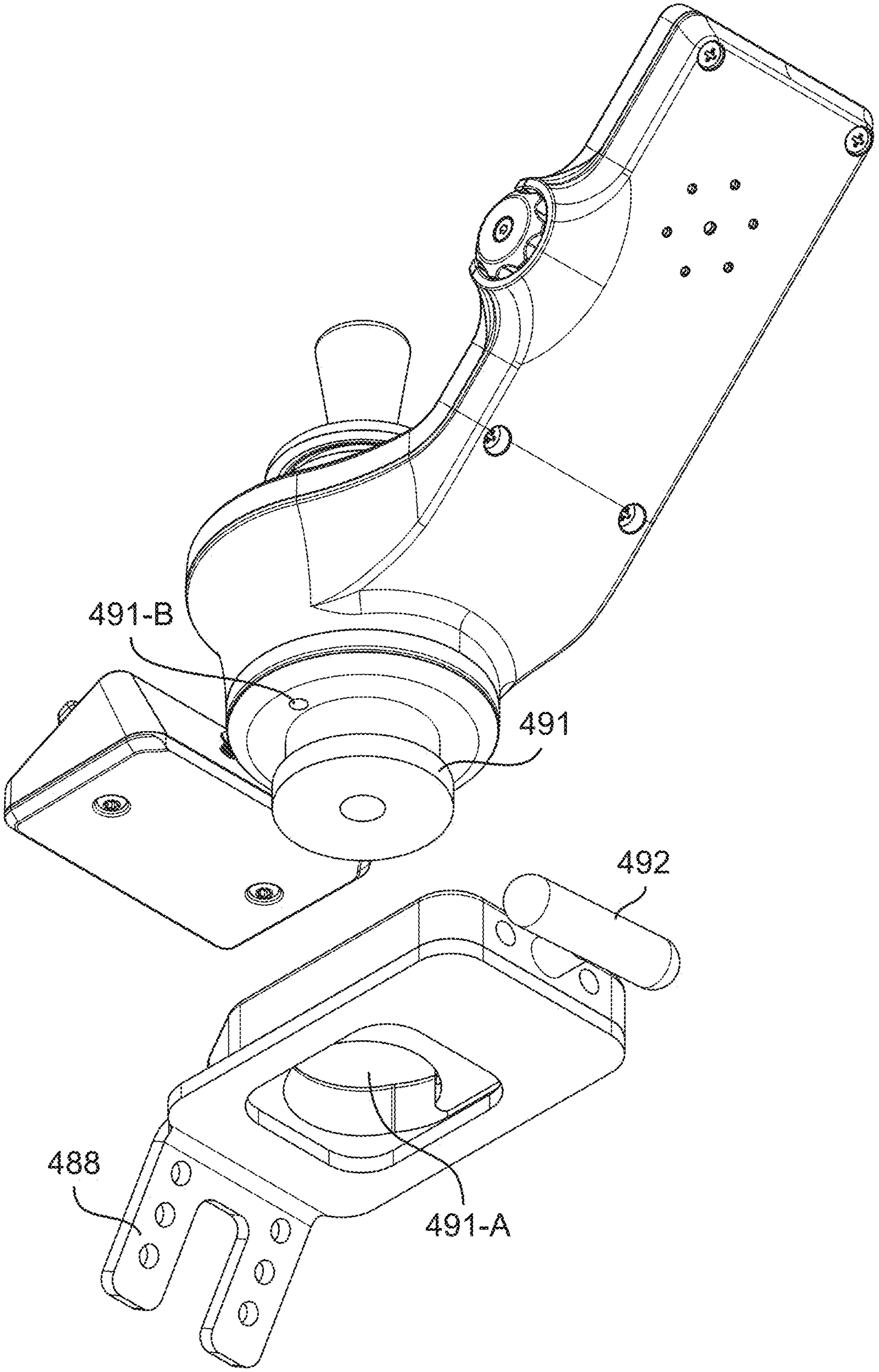
Figure 12V:
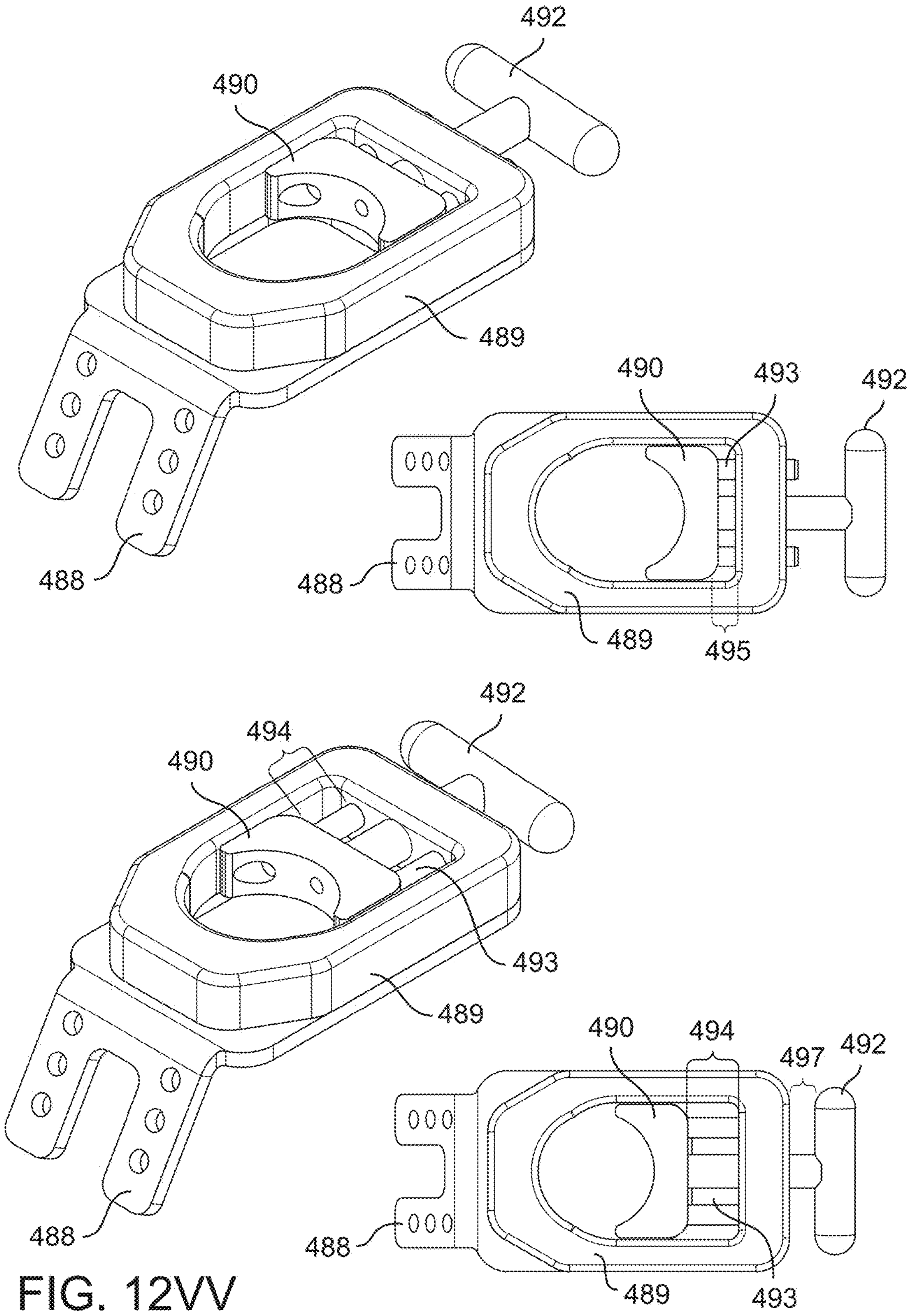
Figure 12T:
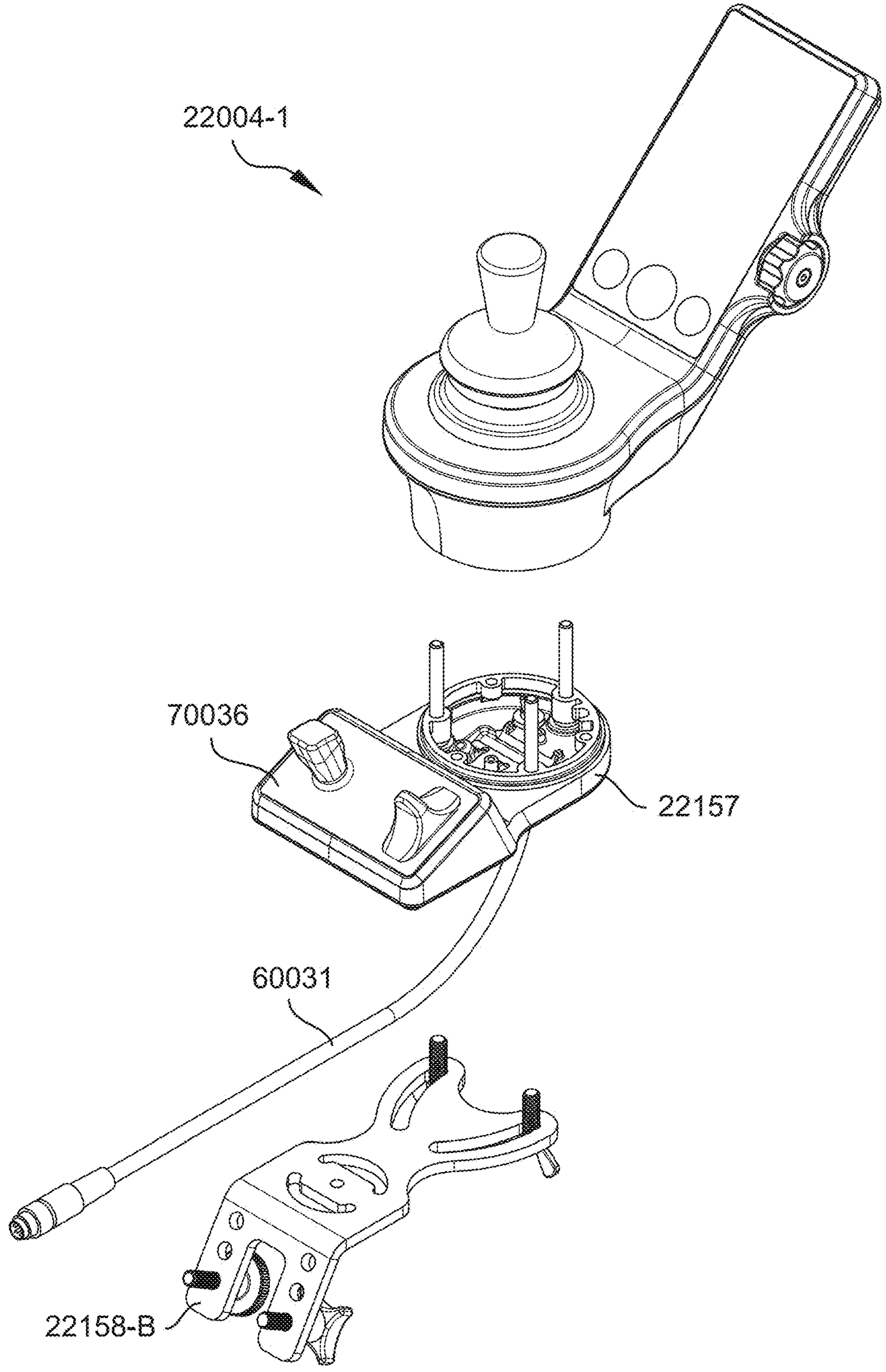
Figure 12W:
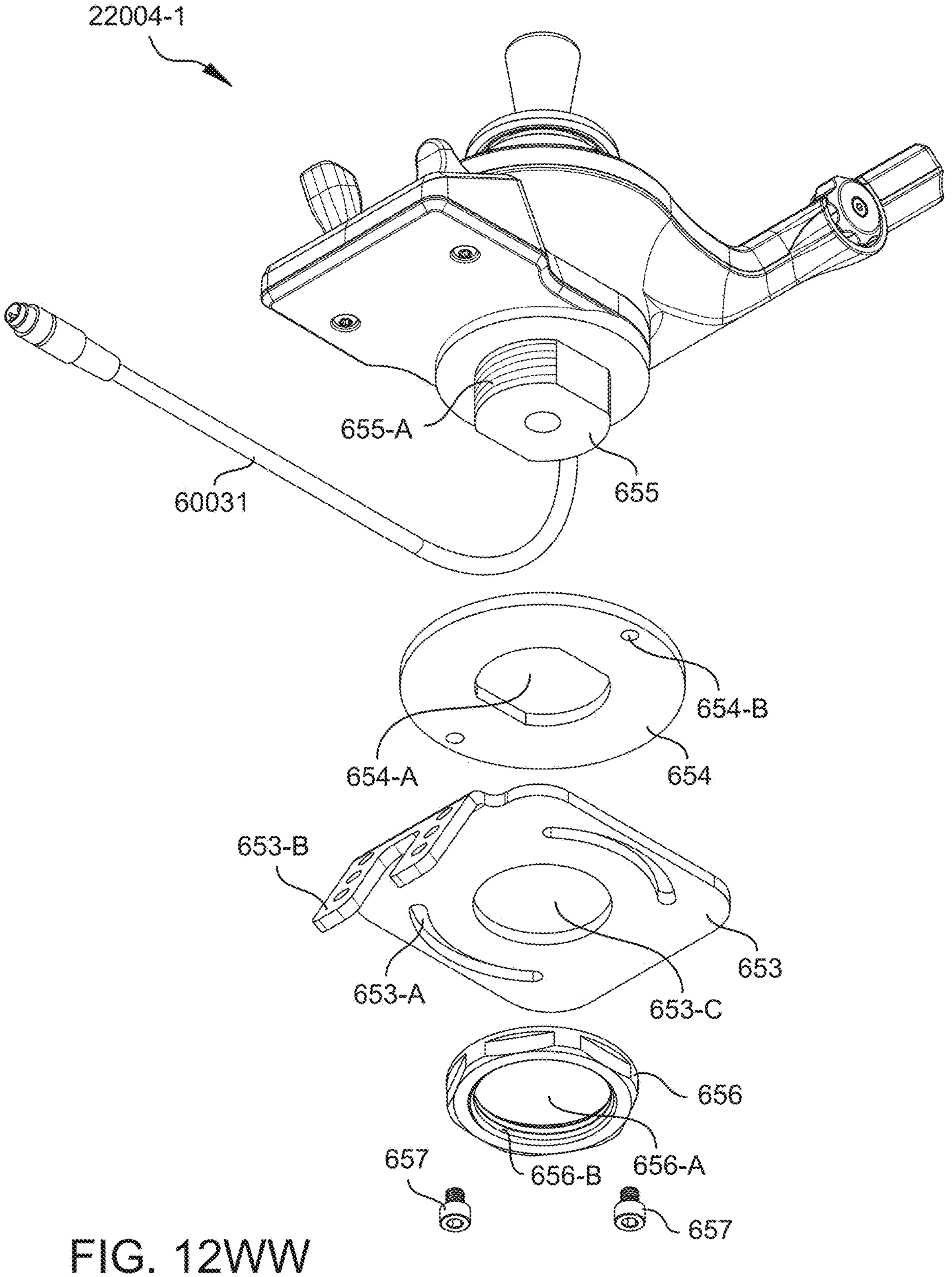
Figure 12X:
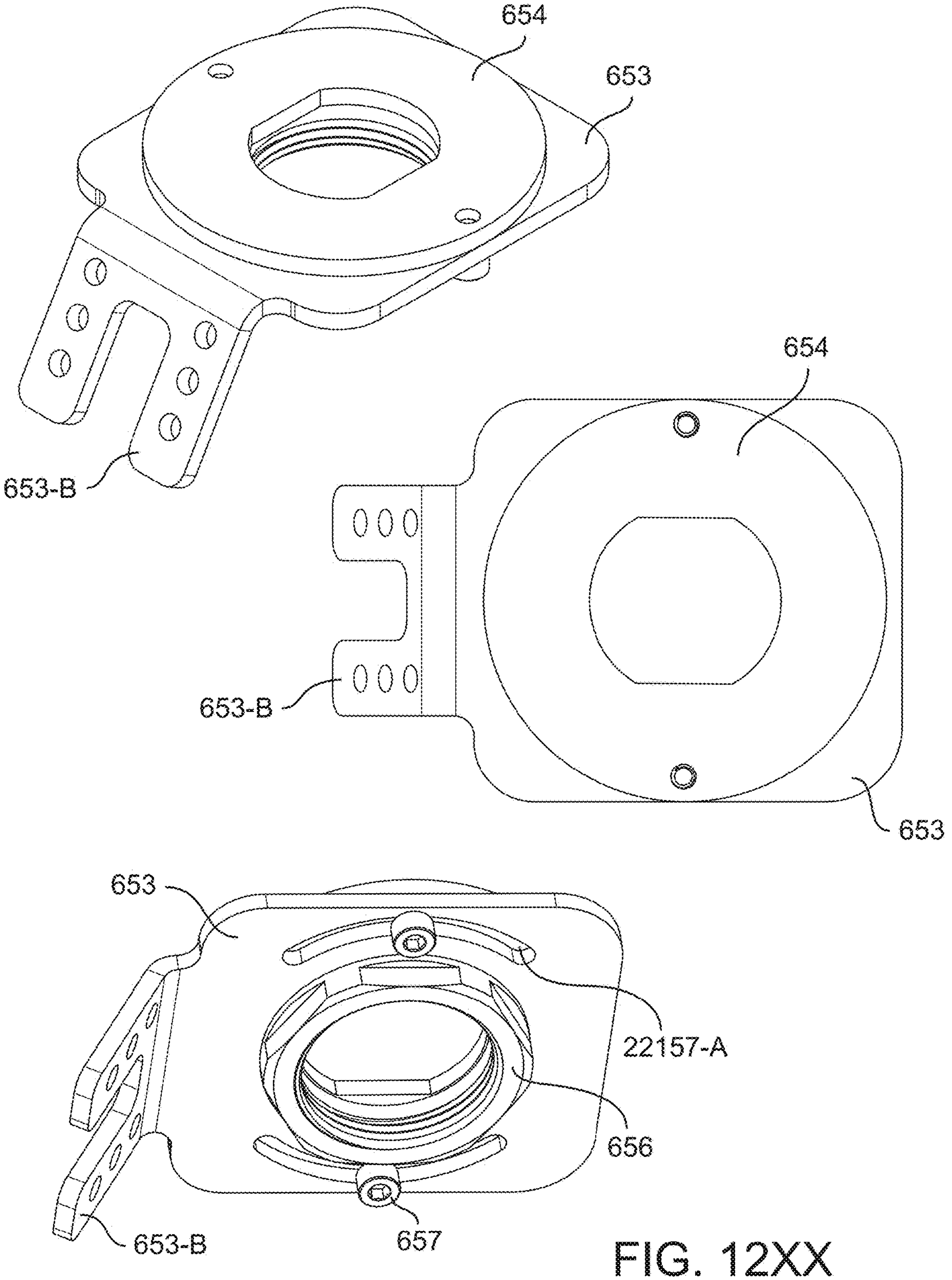
Figure 12Y:
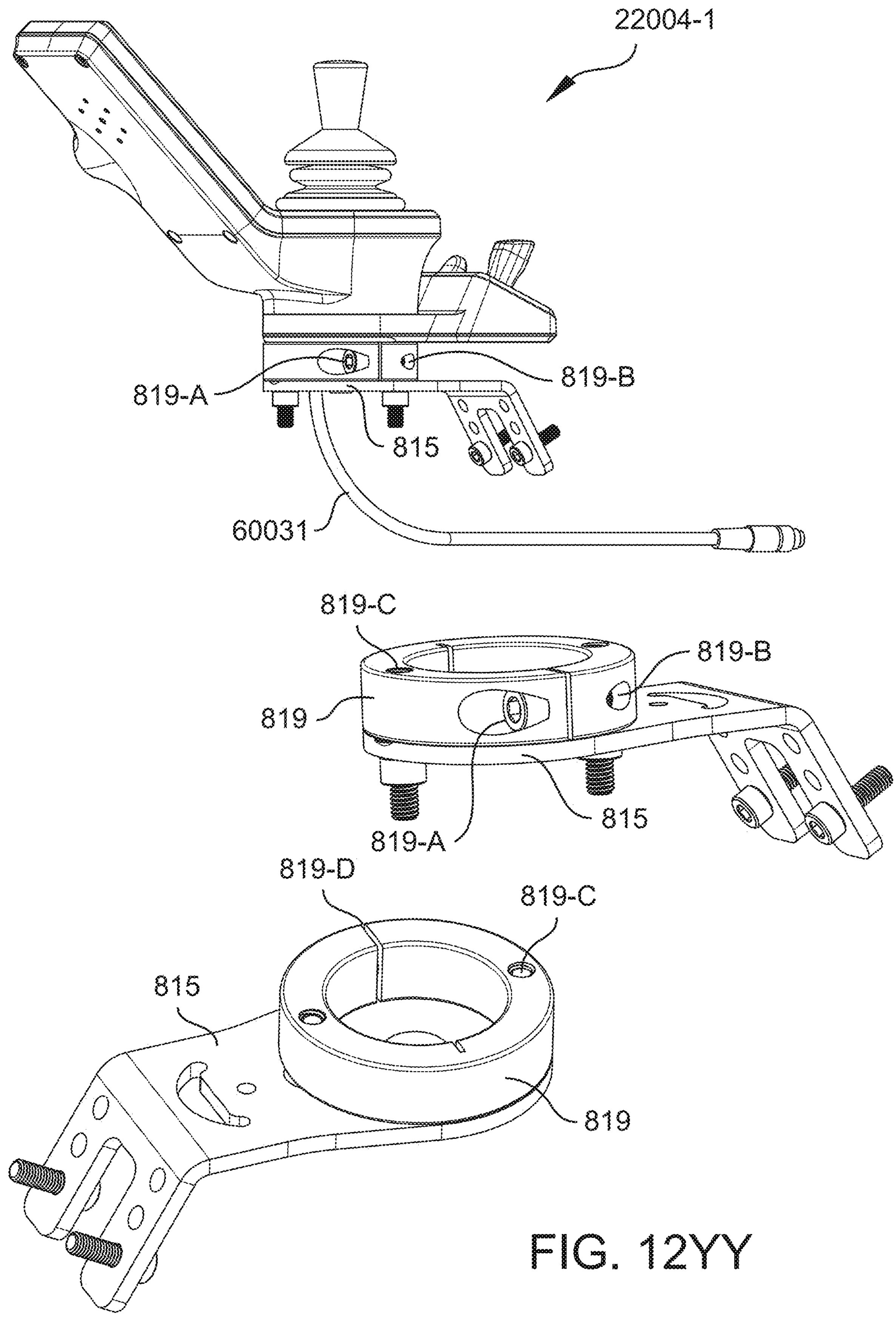
Figure 12Z:
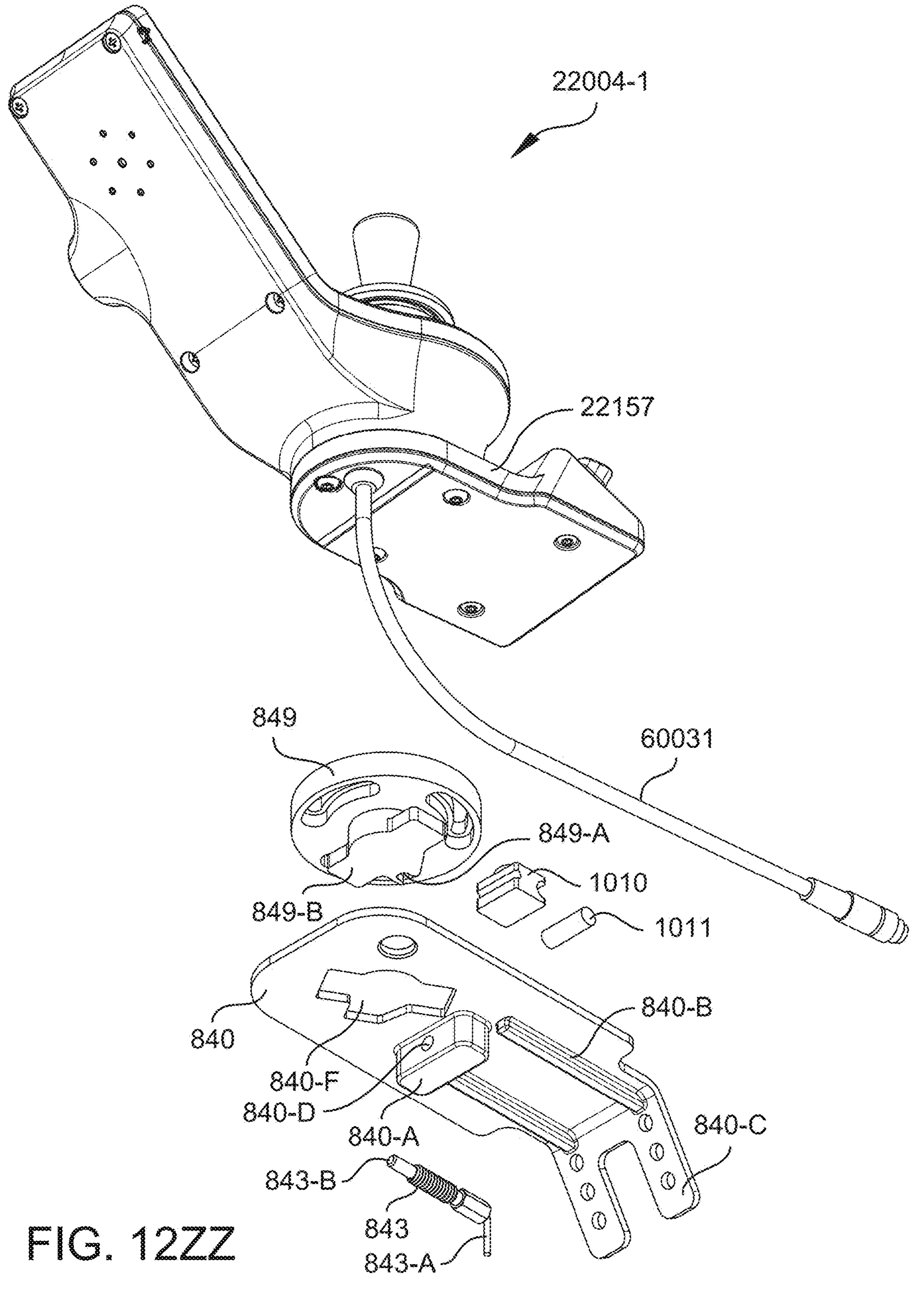
Figure 13A:
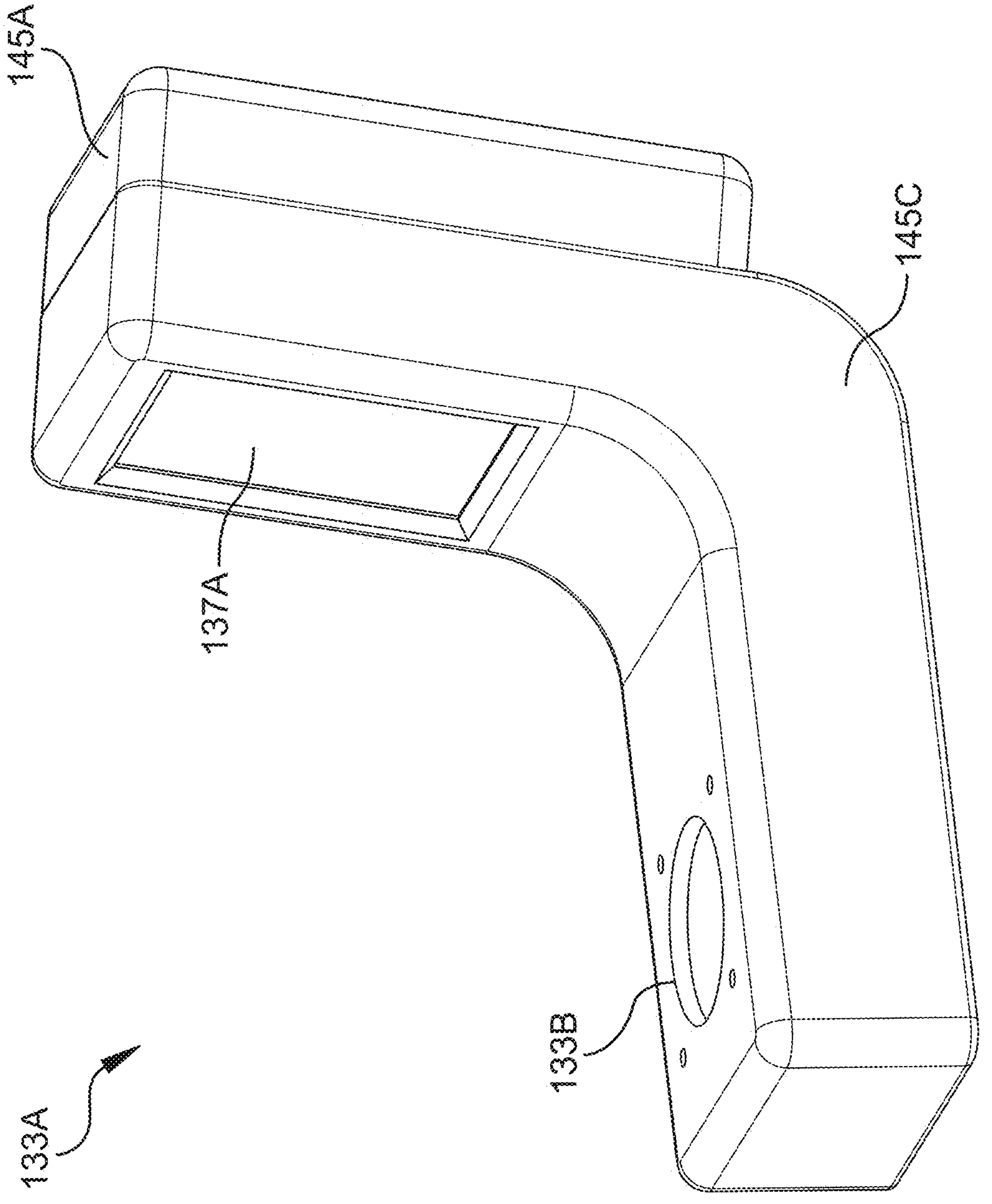
Figure 13B:
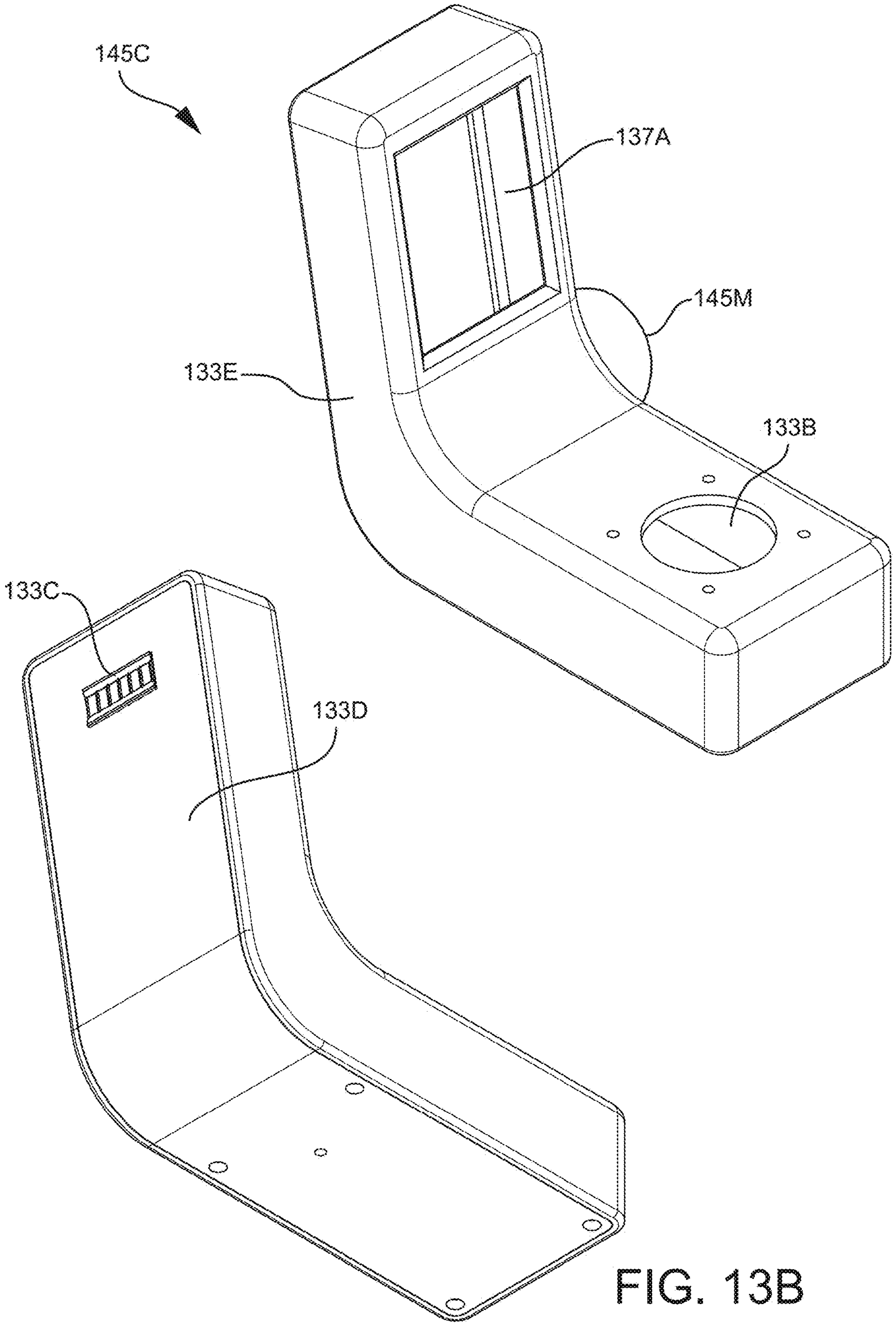
Figure 13C:
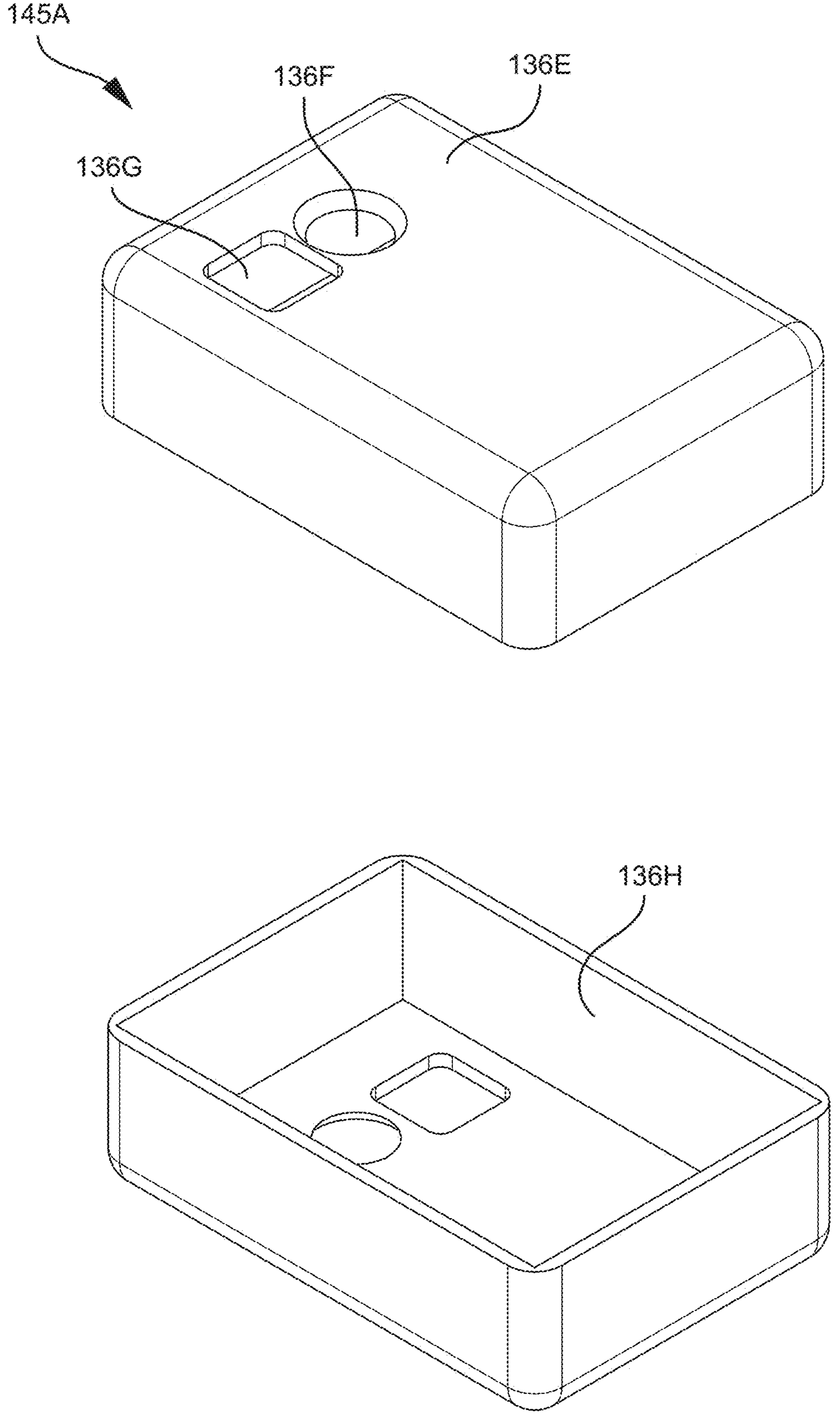
Figure 13D:
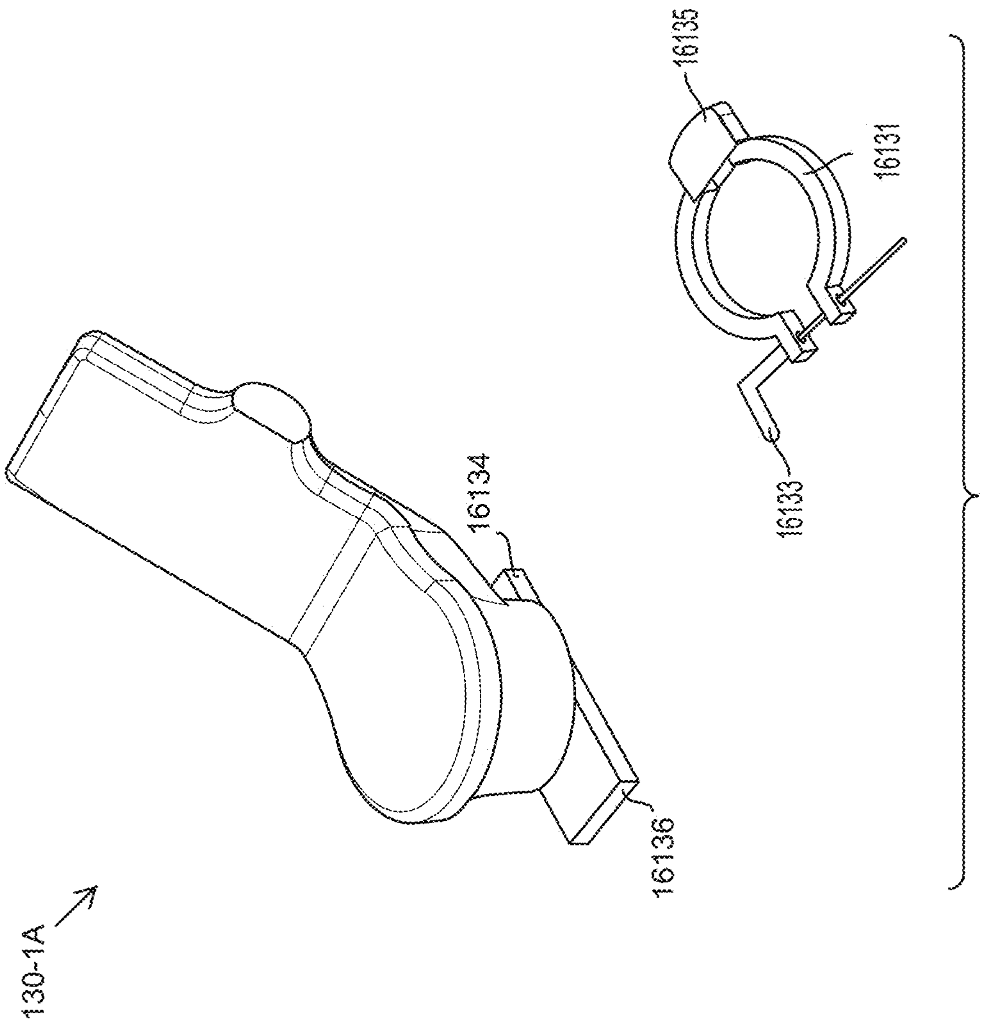
Figure 13E:
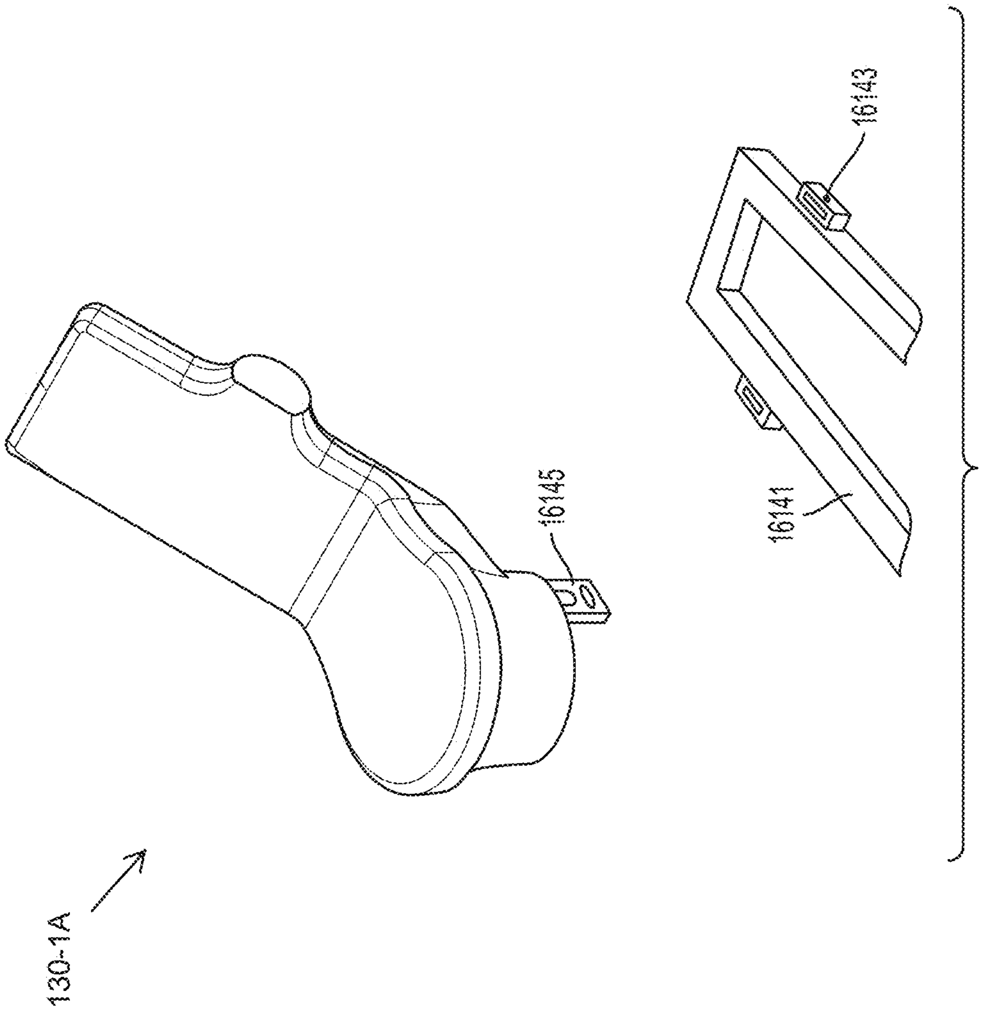
Figure 13F:
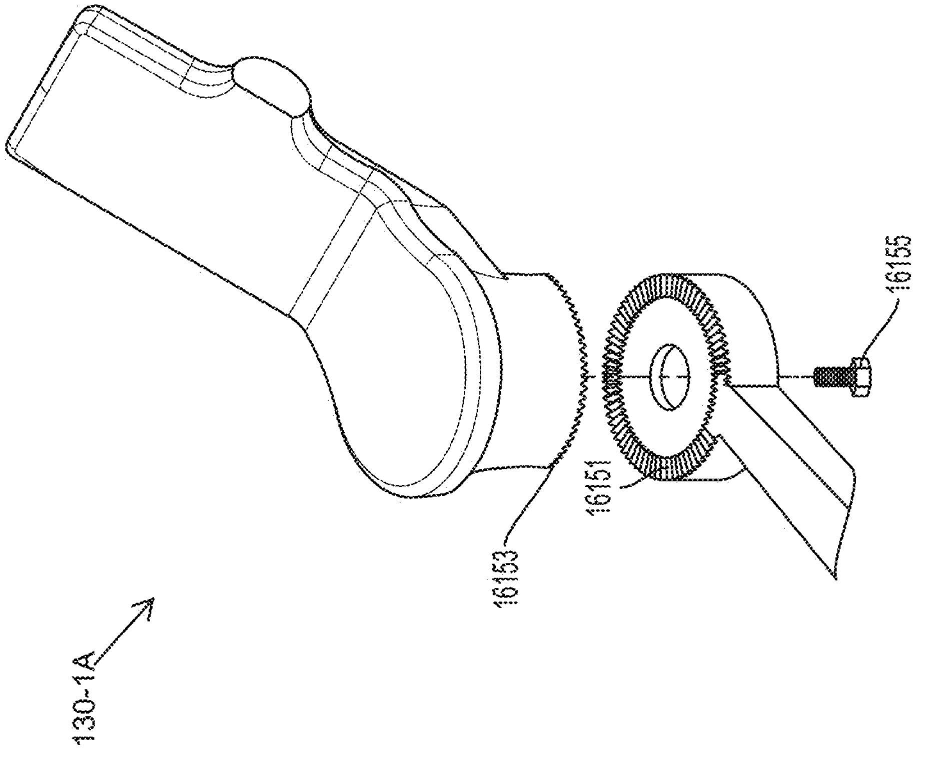
Figure 13G:
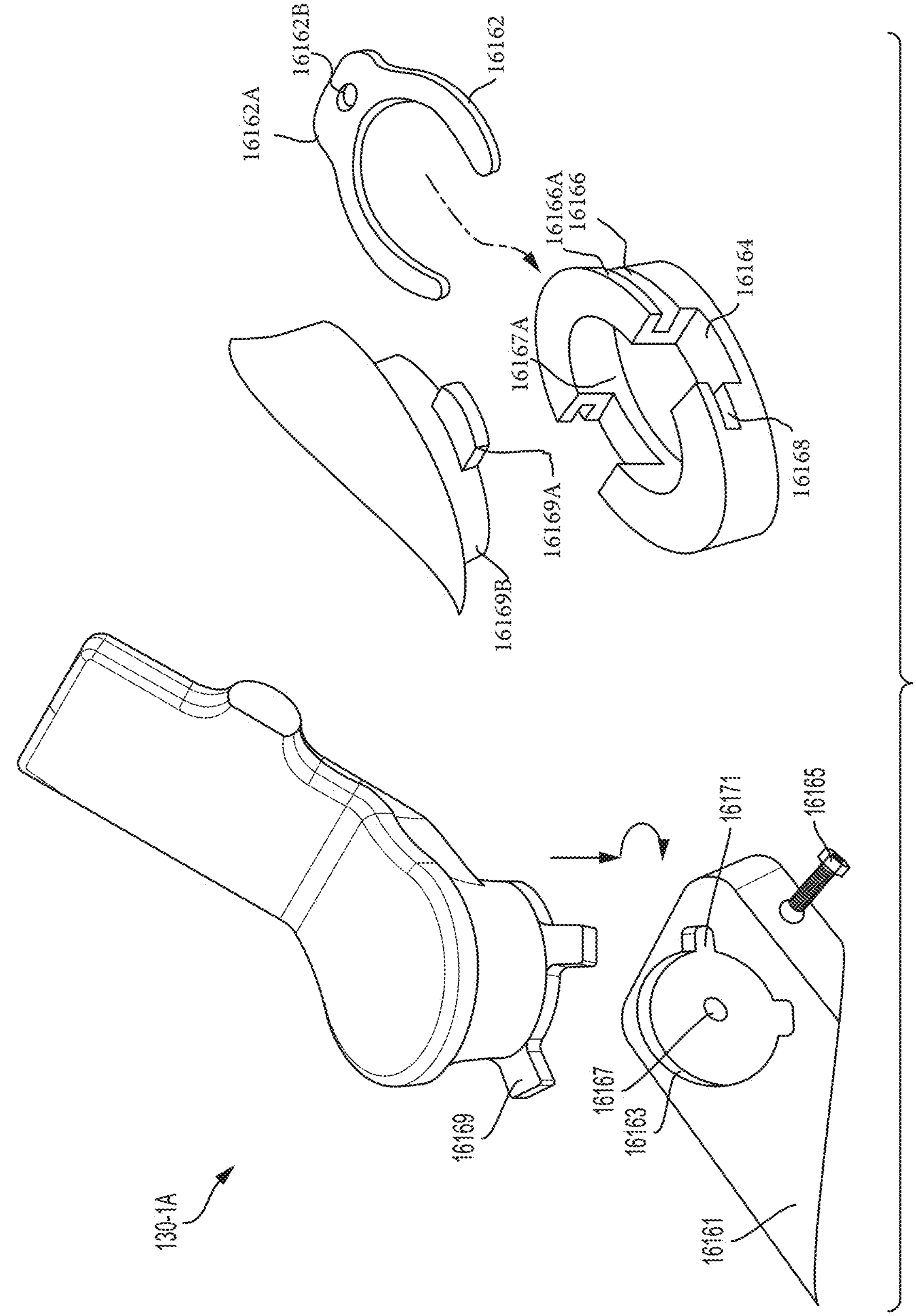
Figure 13H:
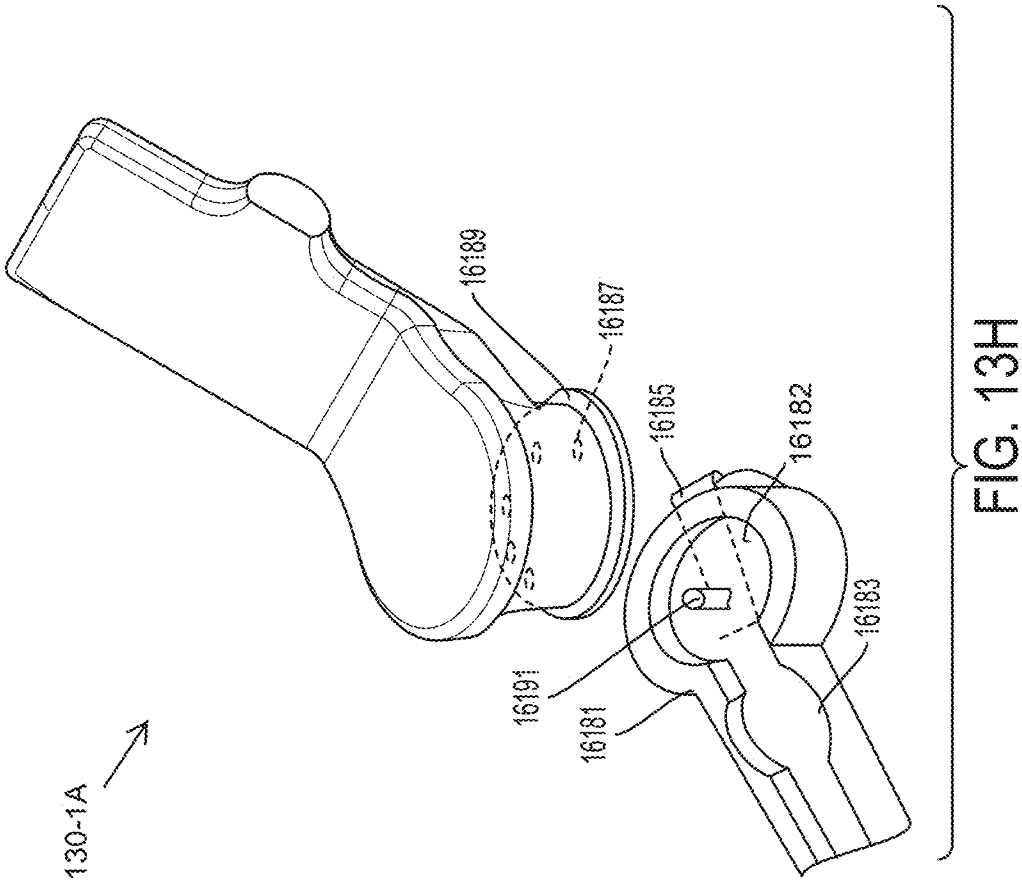
Figure 13I:
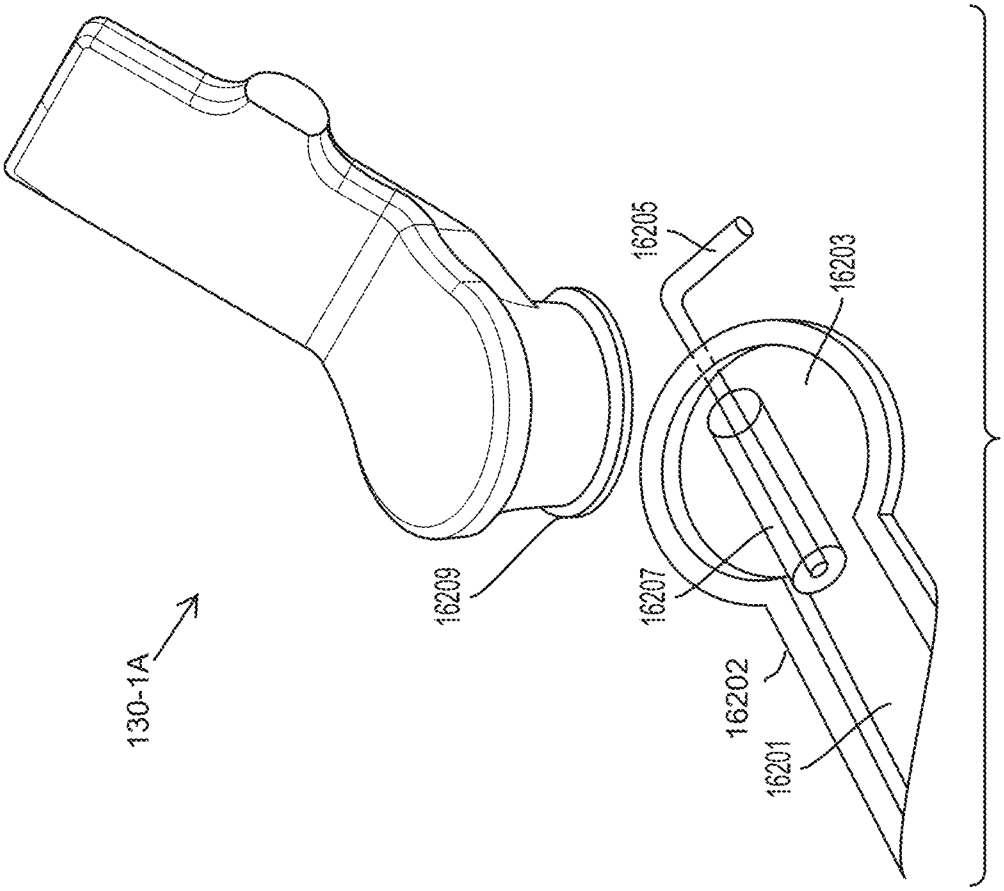
Figure 13J:
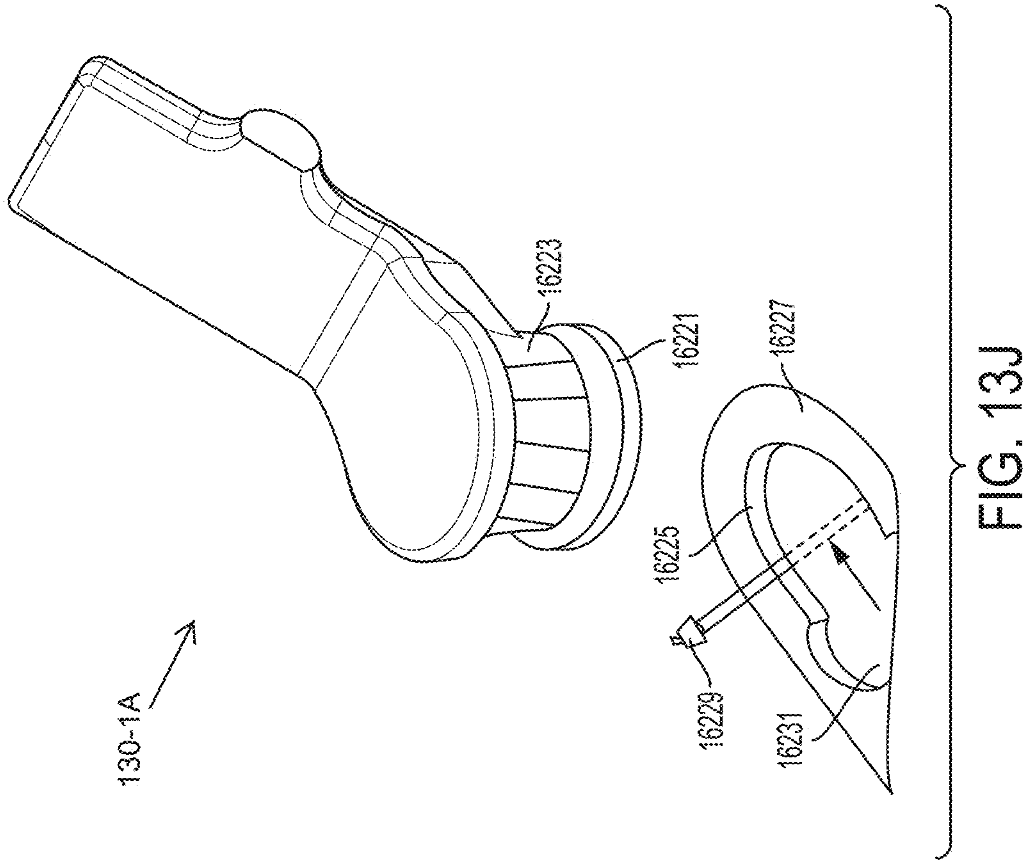
Figure 13K:
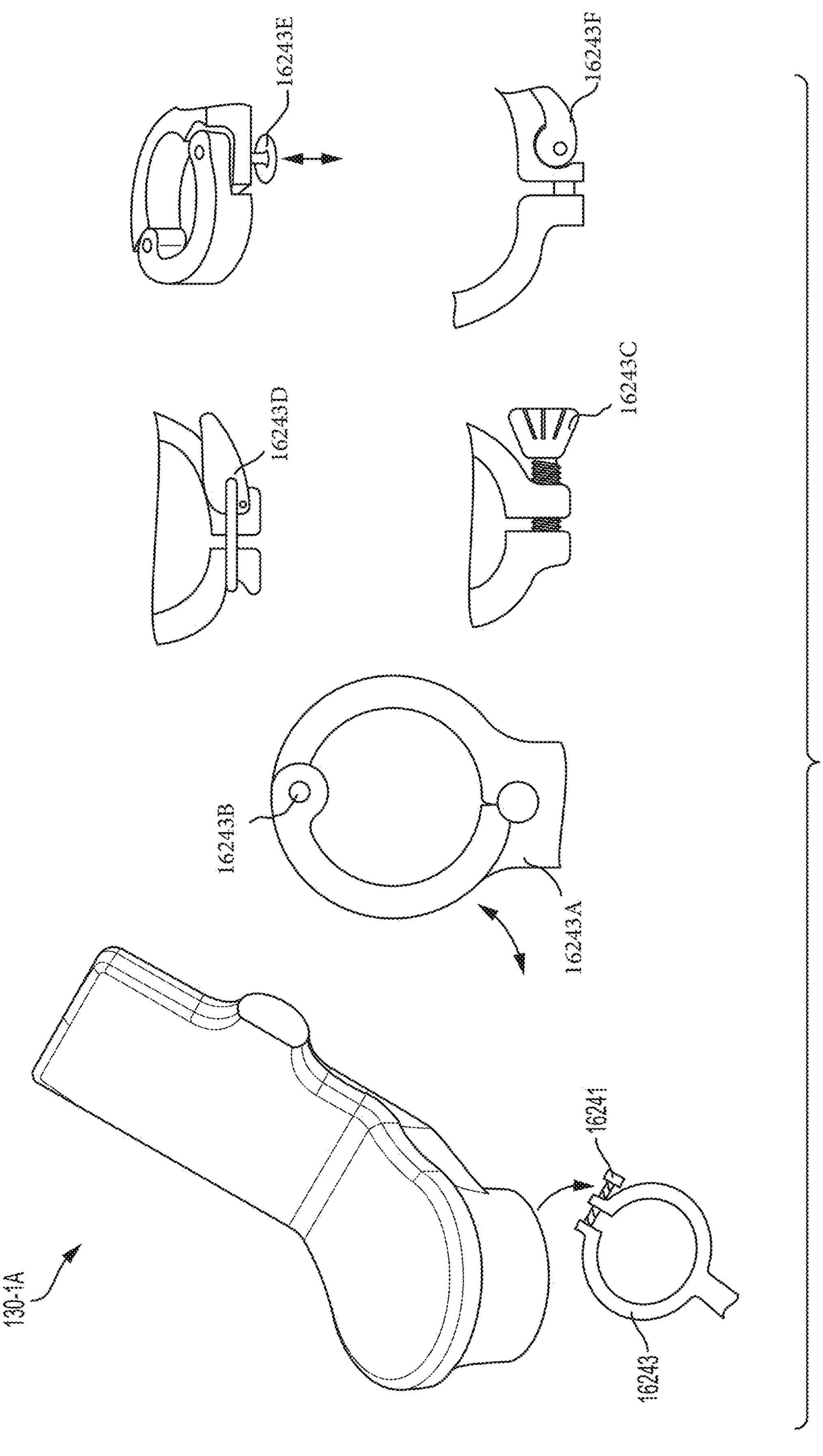
Figure 13L:
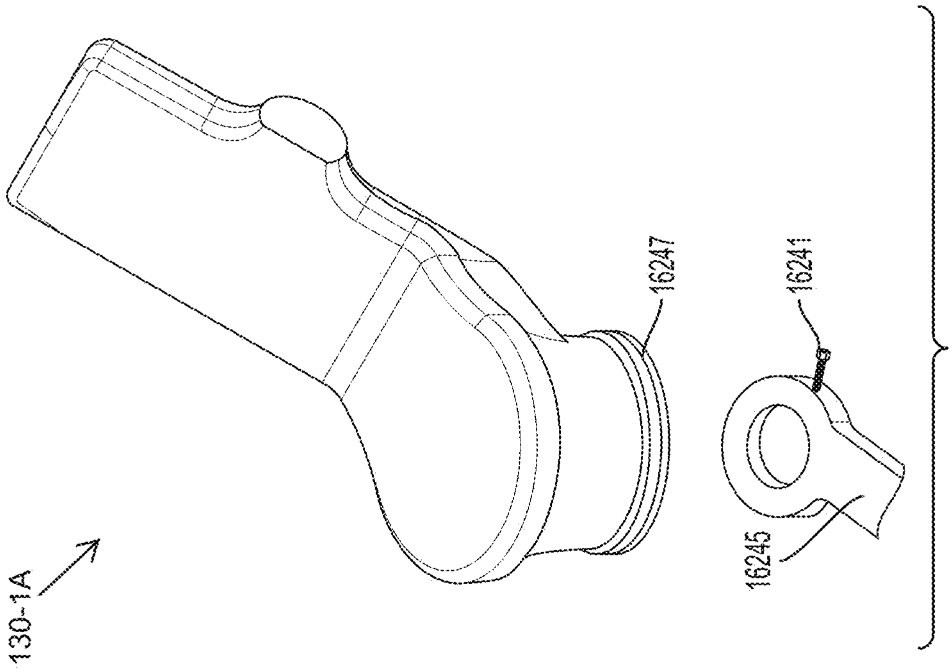
Figure 13M:
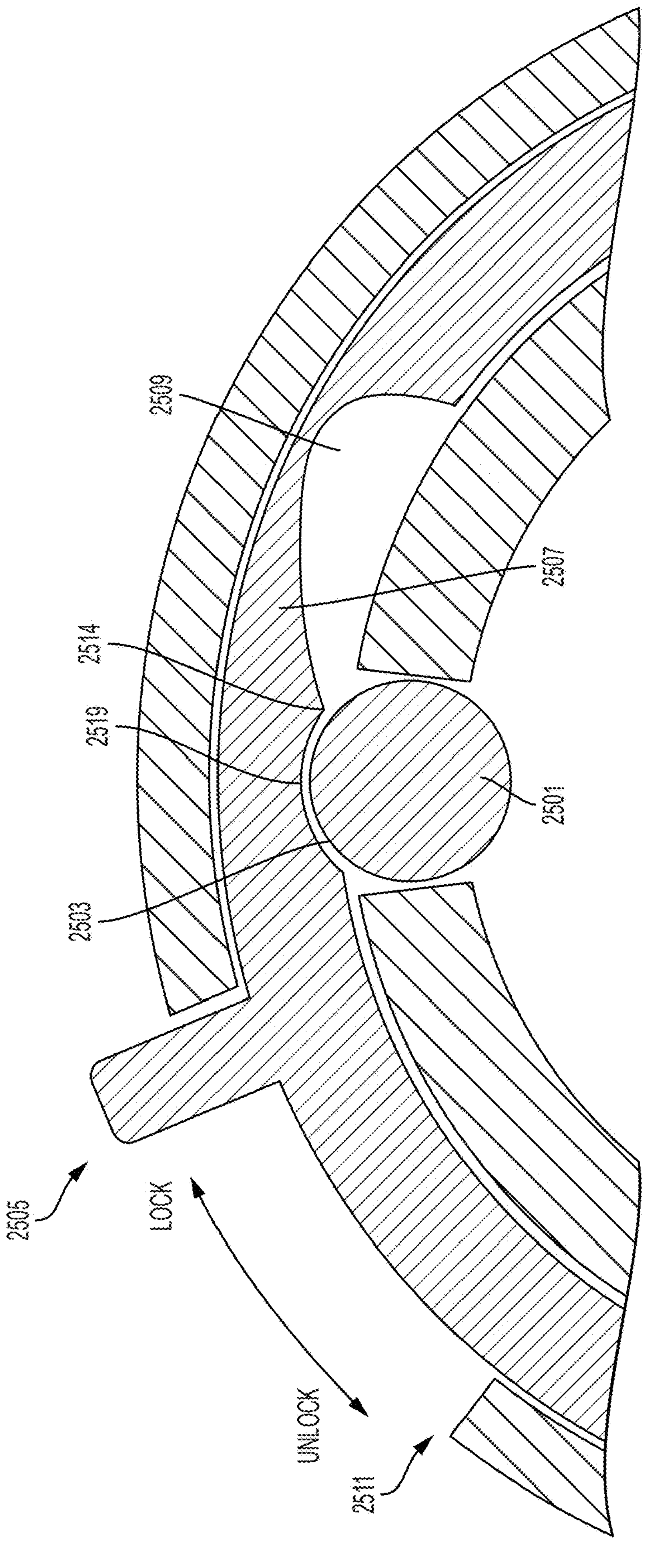
Figure 13N:
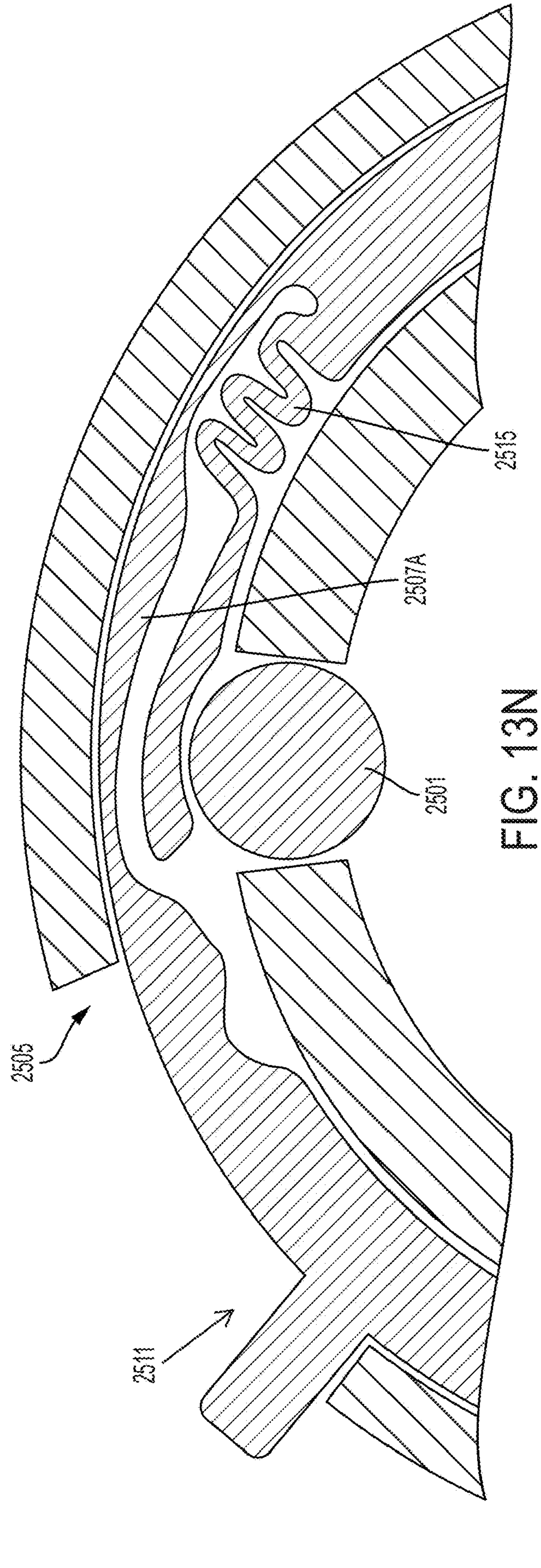
Figure 14A:
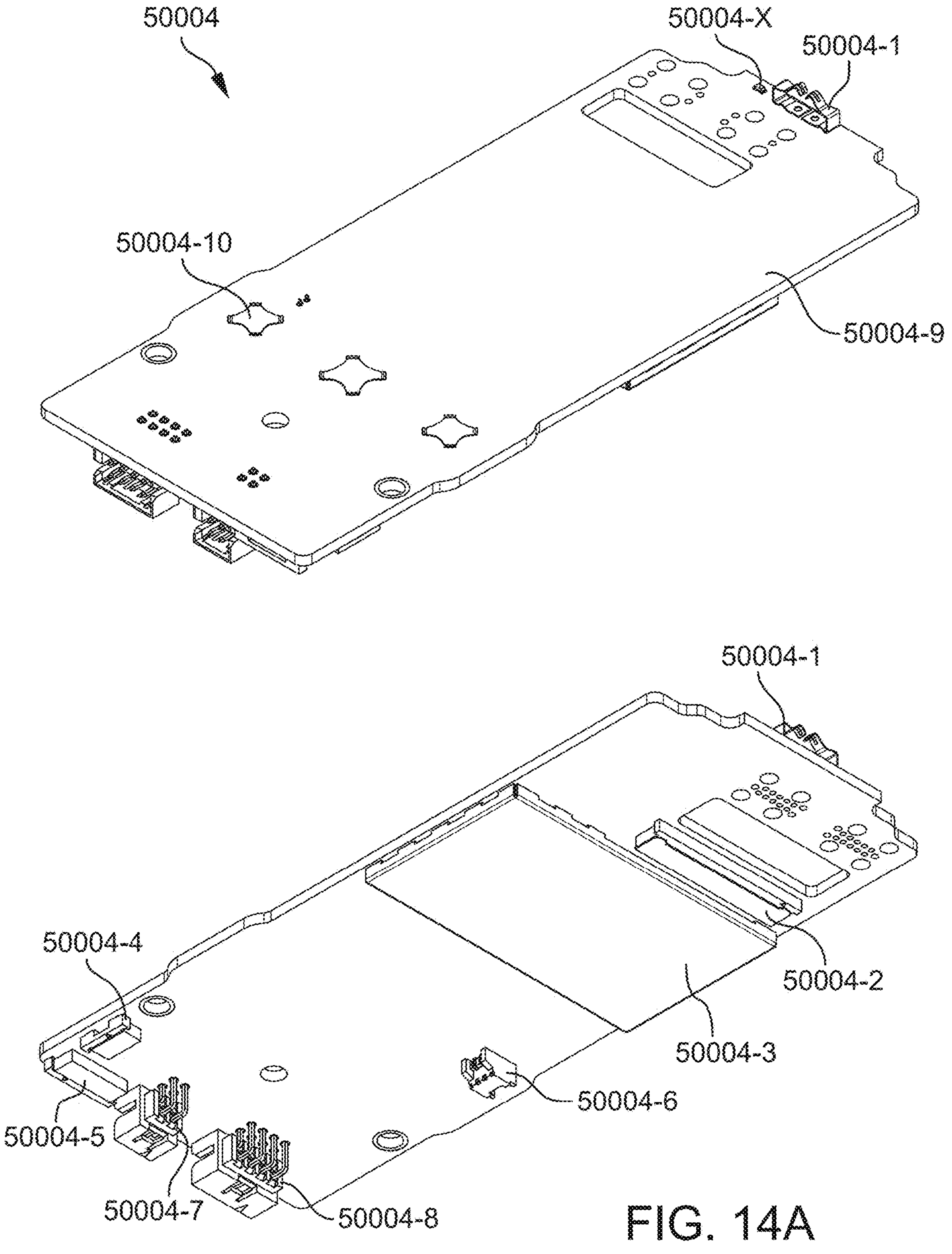
Figure 14B:
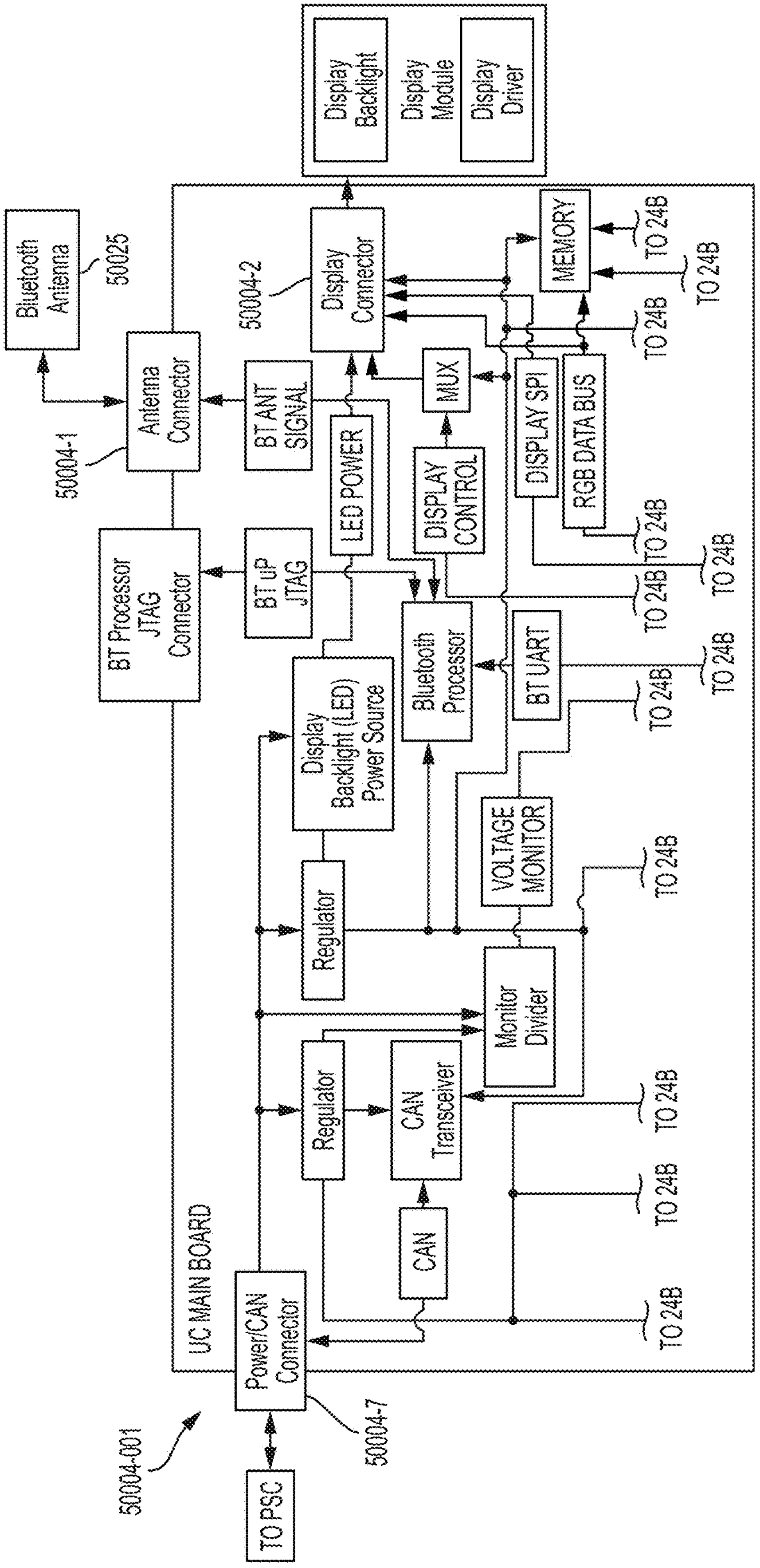
Figure 14C:
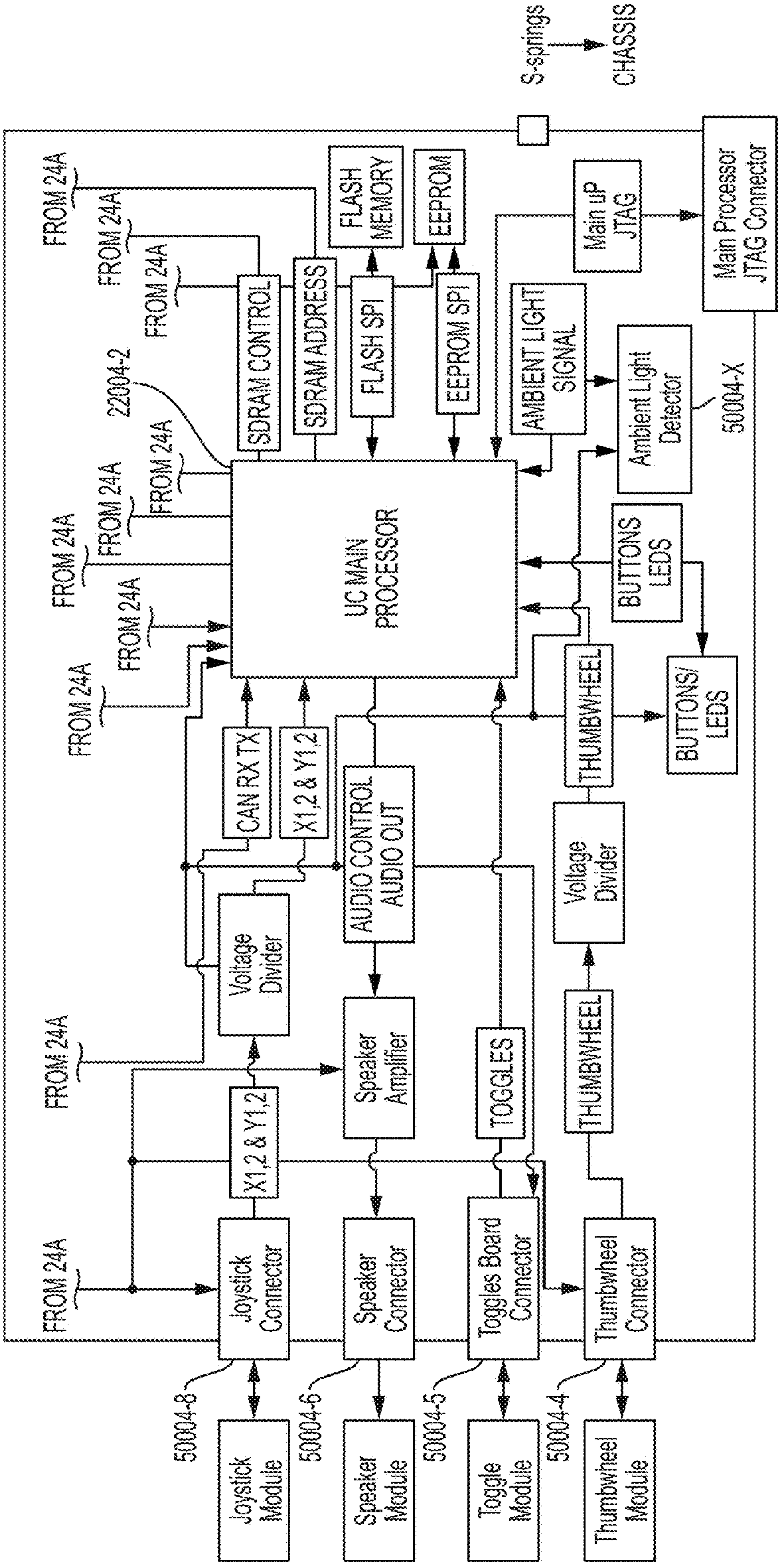
Figure 14D:
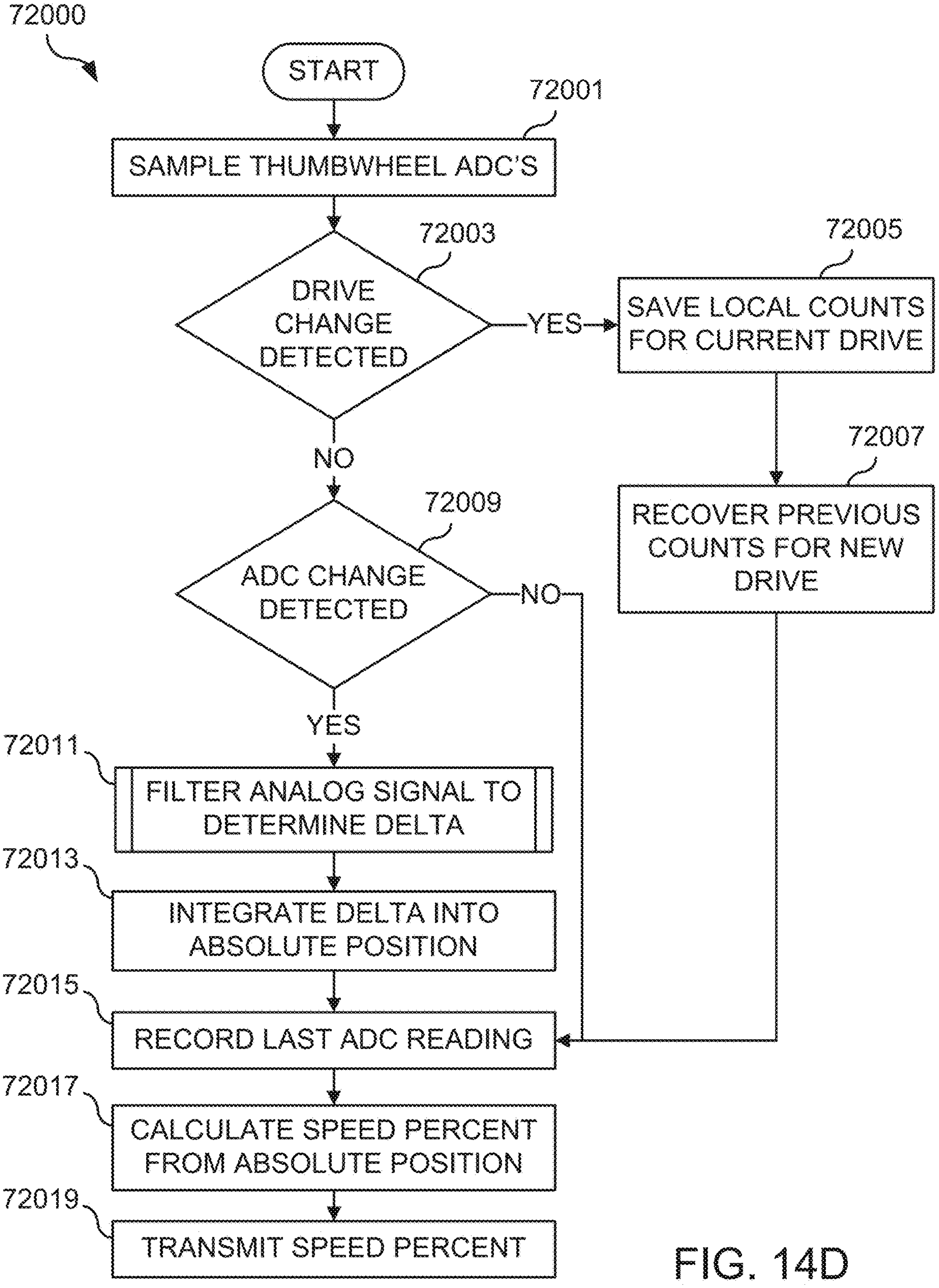
Figure 14E:
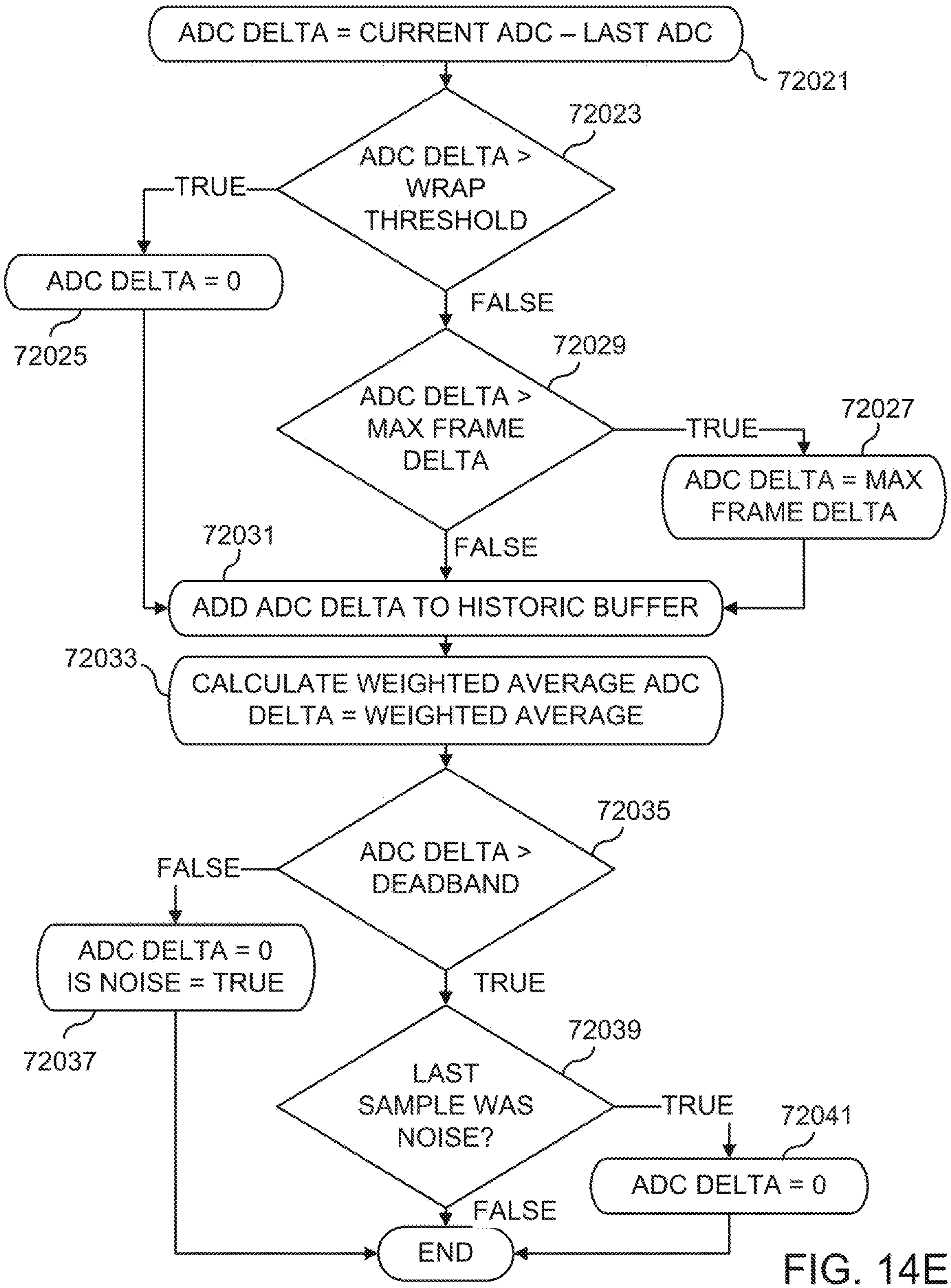
Figure 14F:
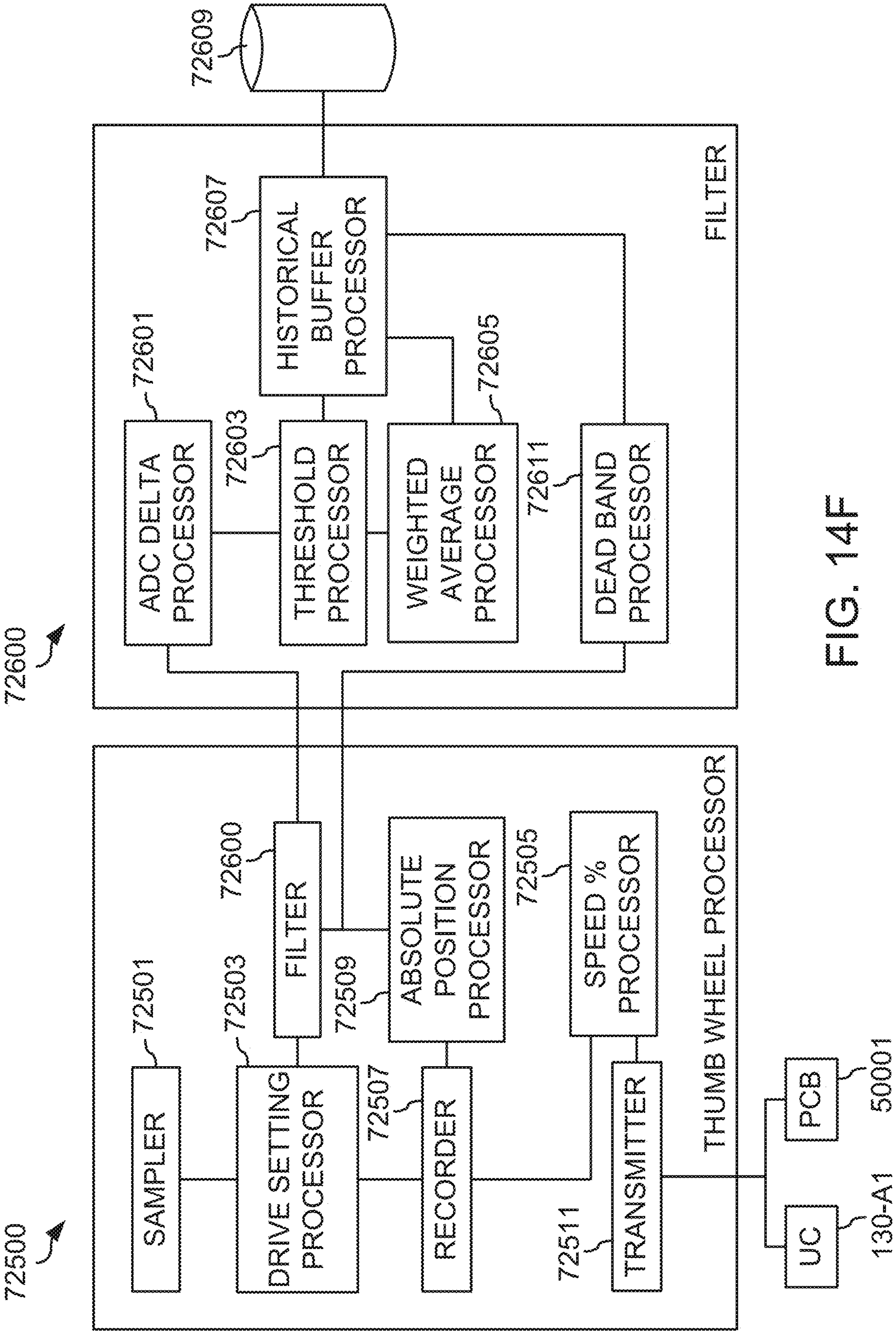
Figure 15A:
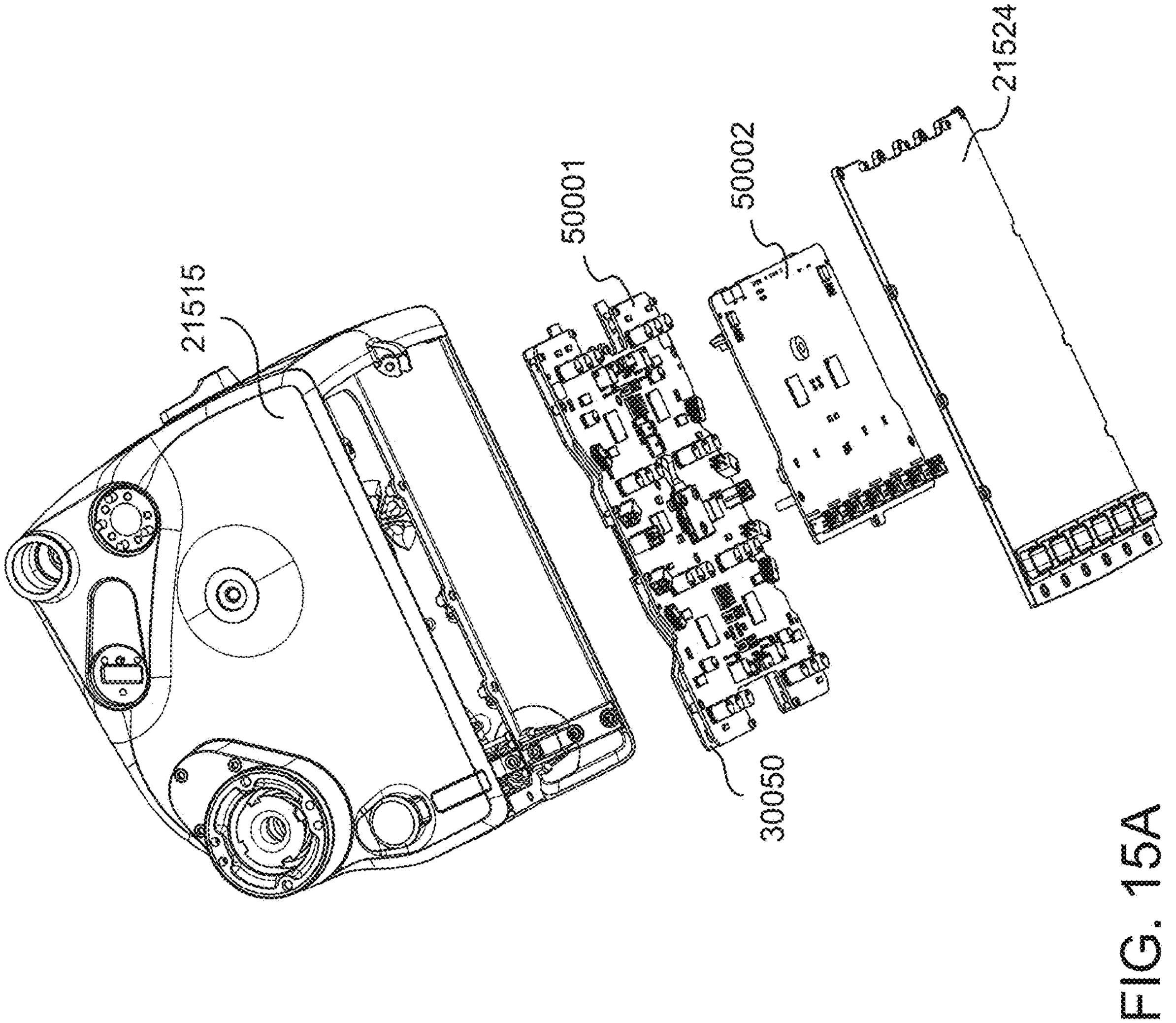
Figure 15B:
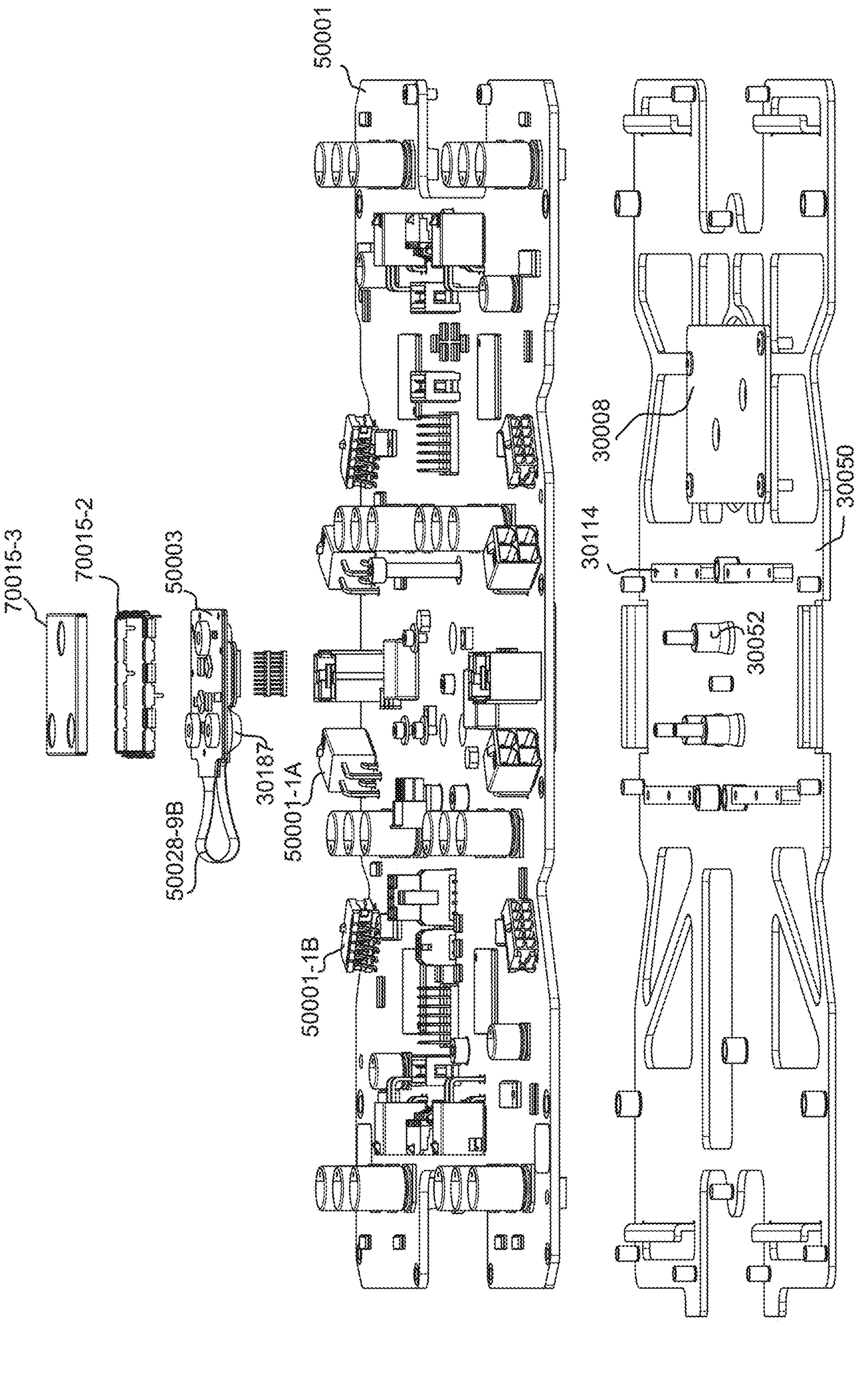
Figure 15C:
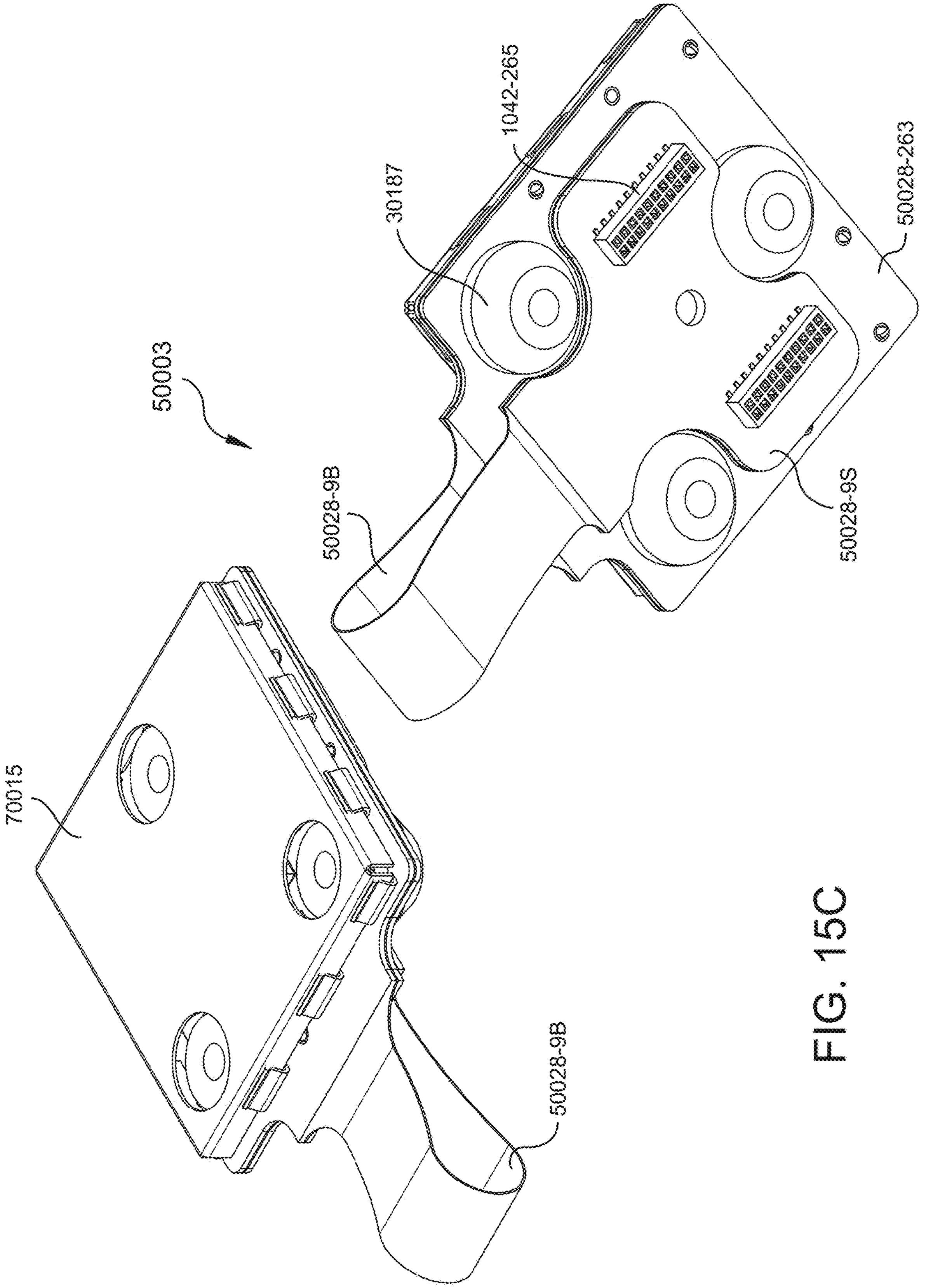
Figure 15D:
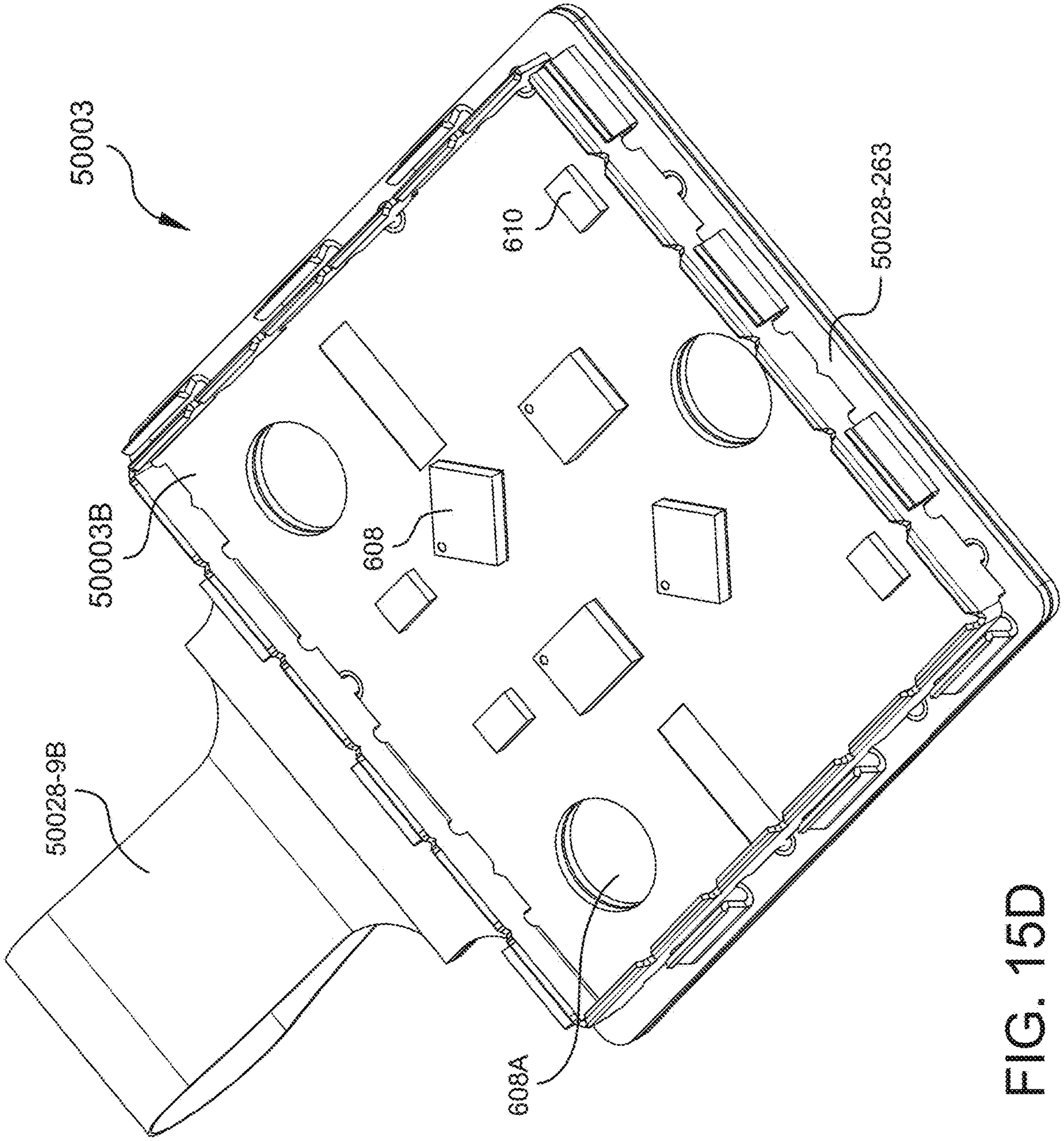
Figure 15E:
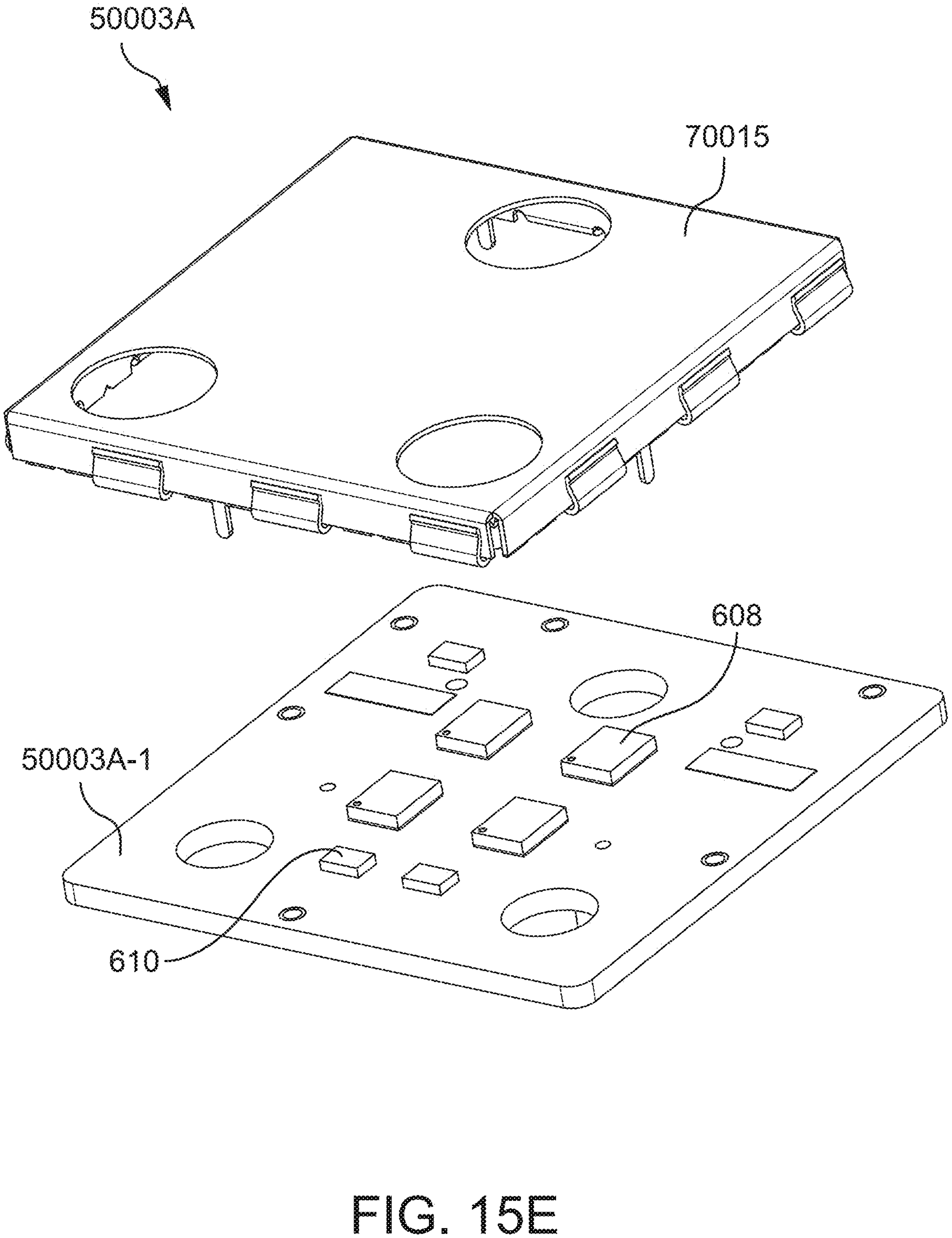
Figure 15F:
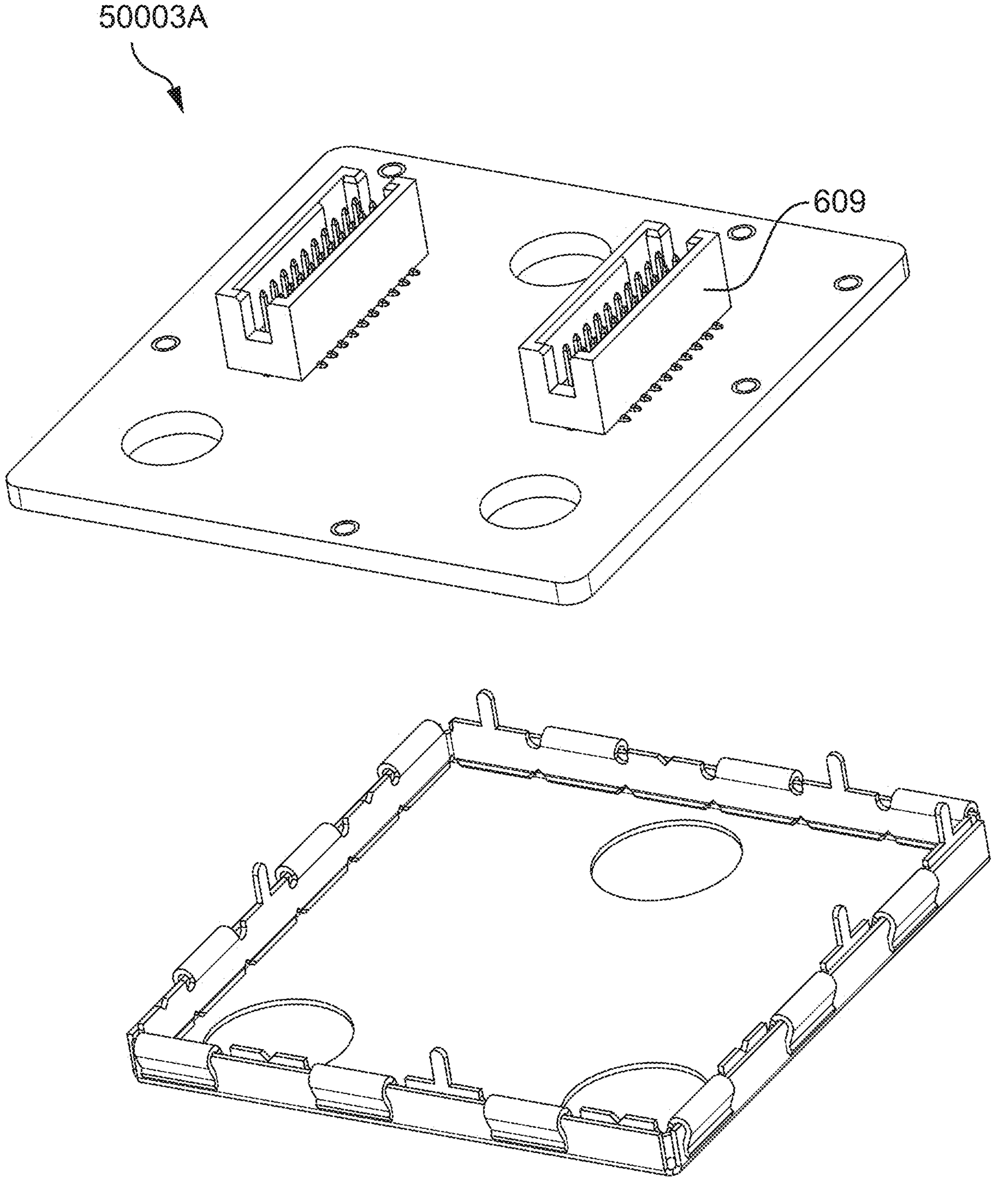
Figure 15G:
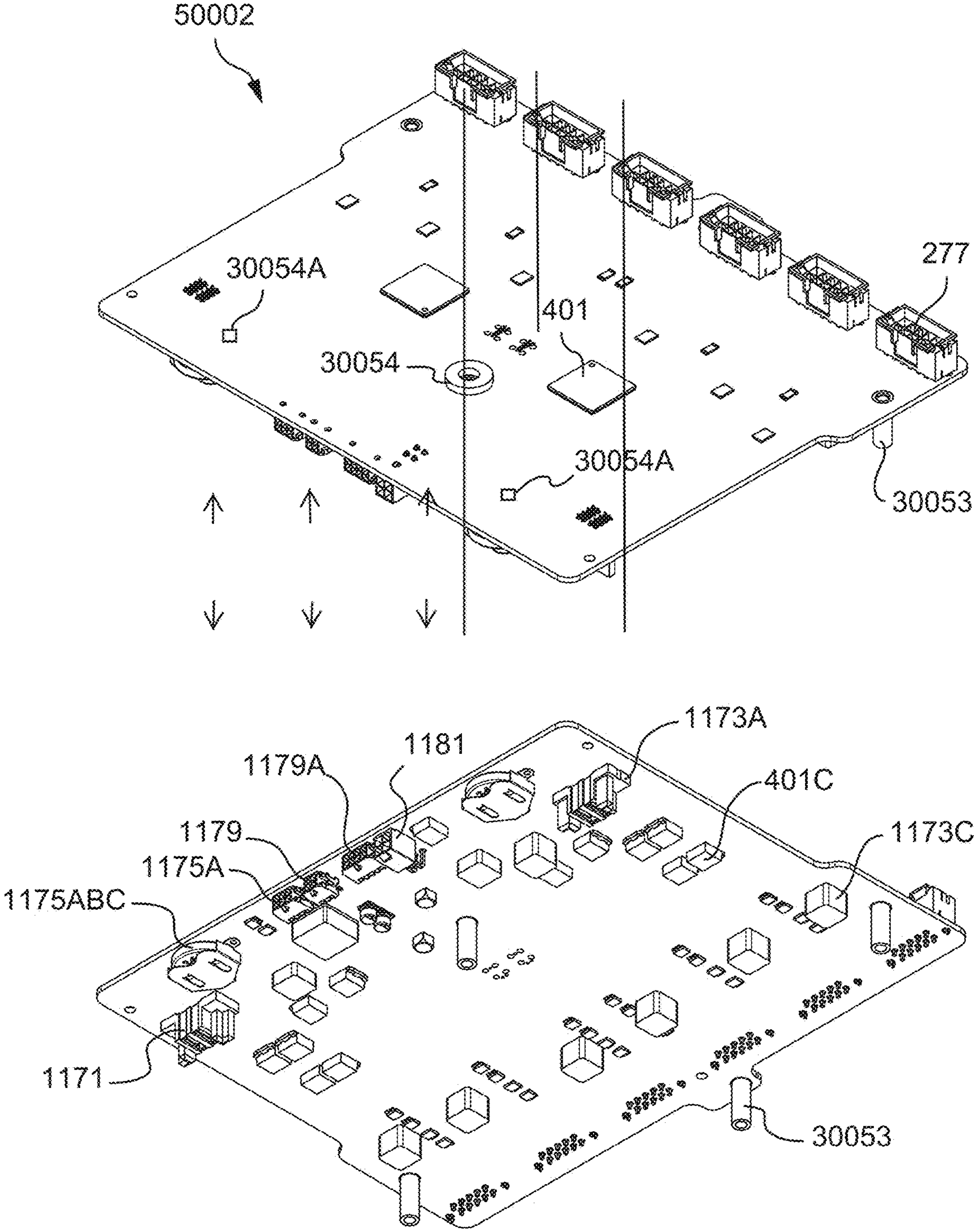
Figure 15H:
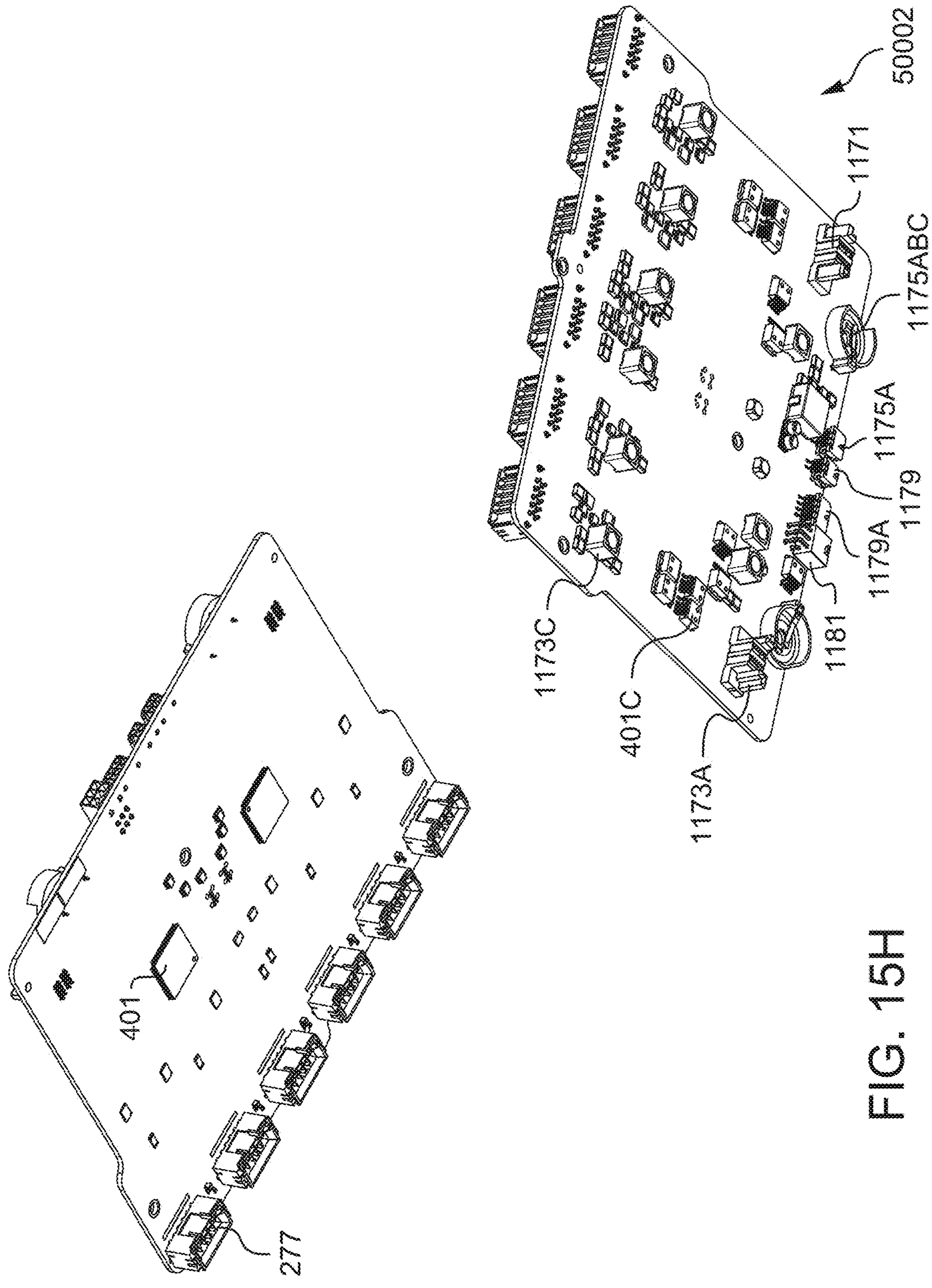
Figure 15I:
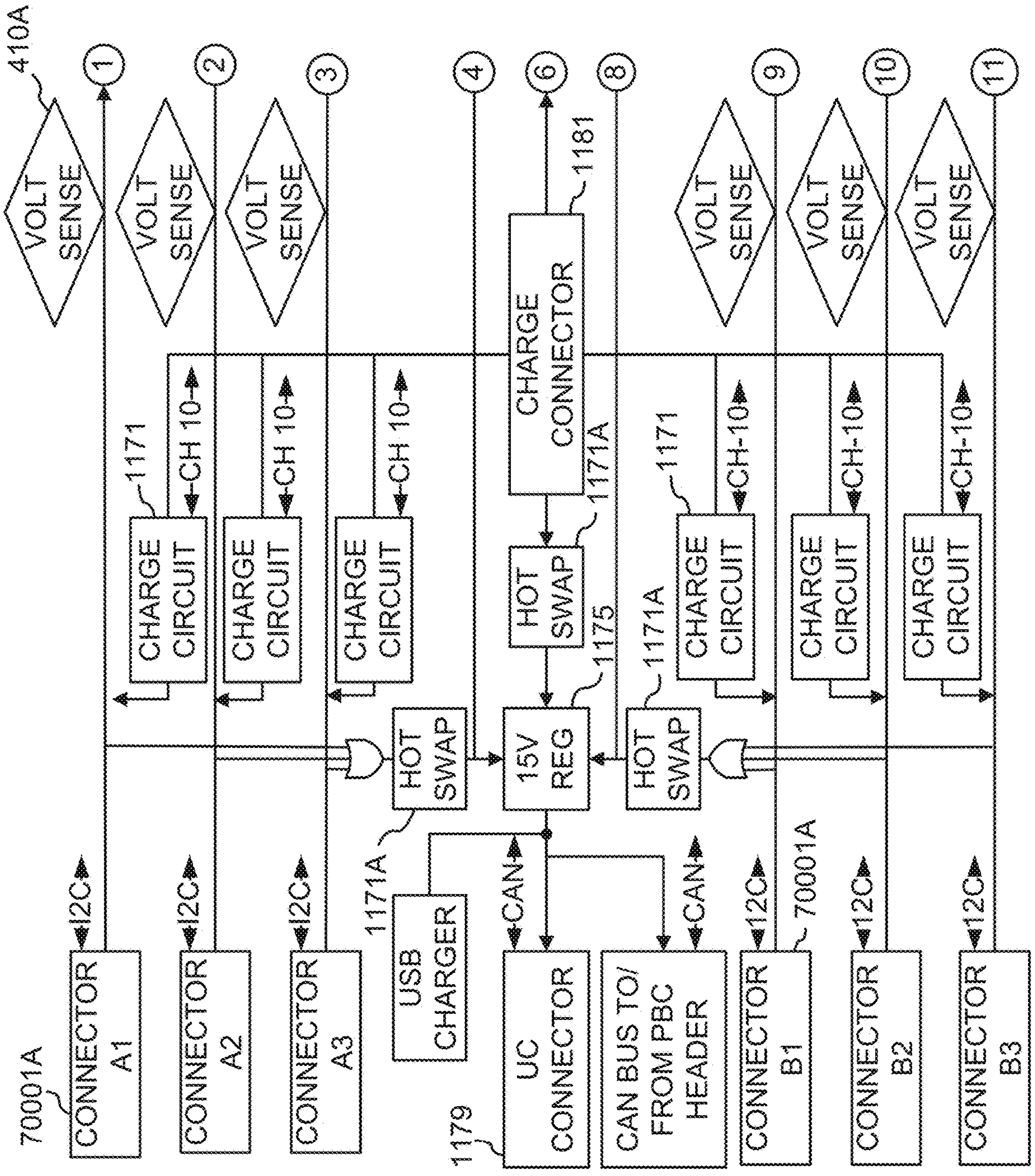
Figure 15J:
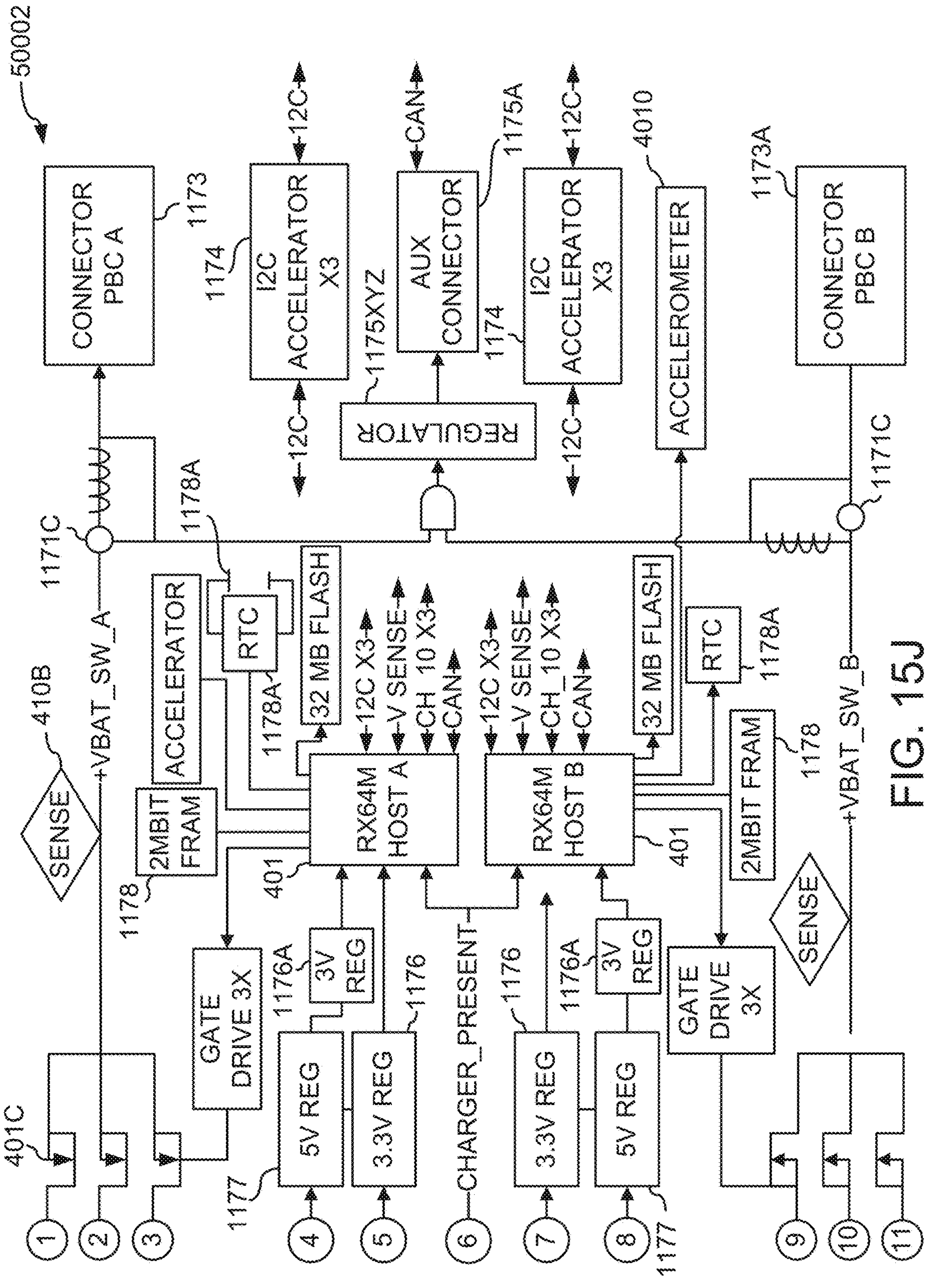
Figure 15K:
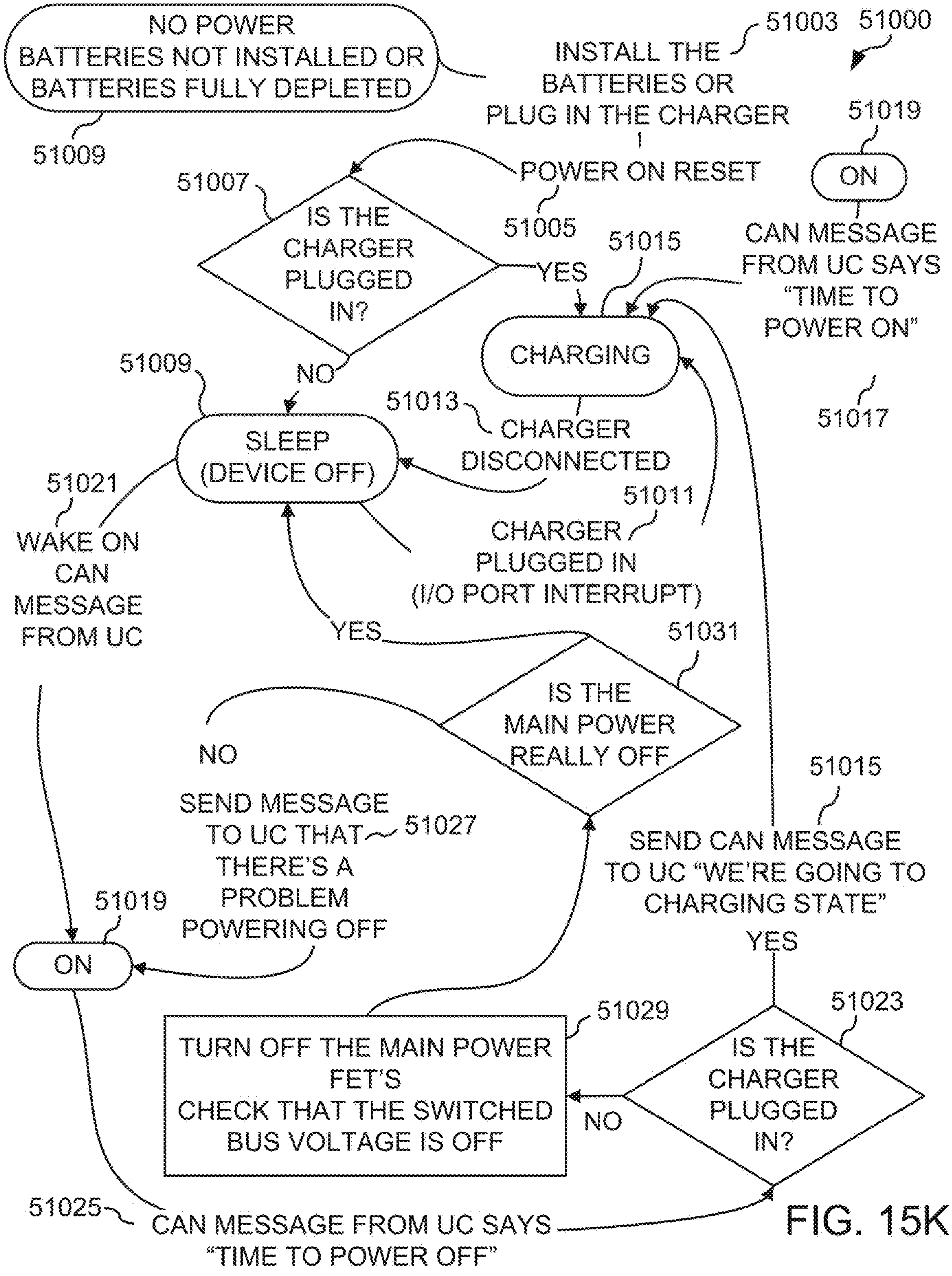
Figure 16A:
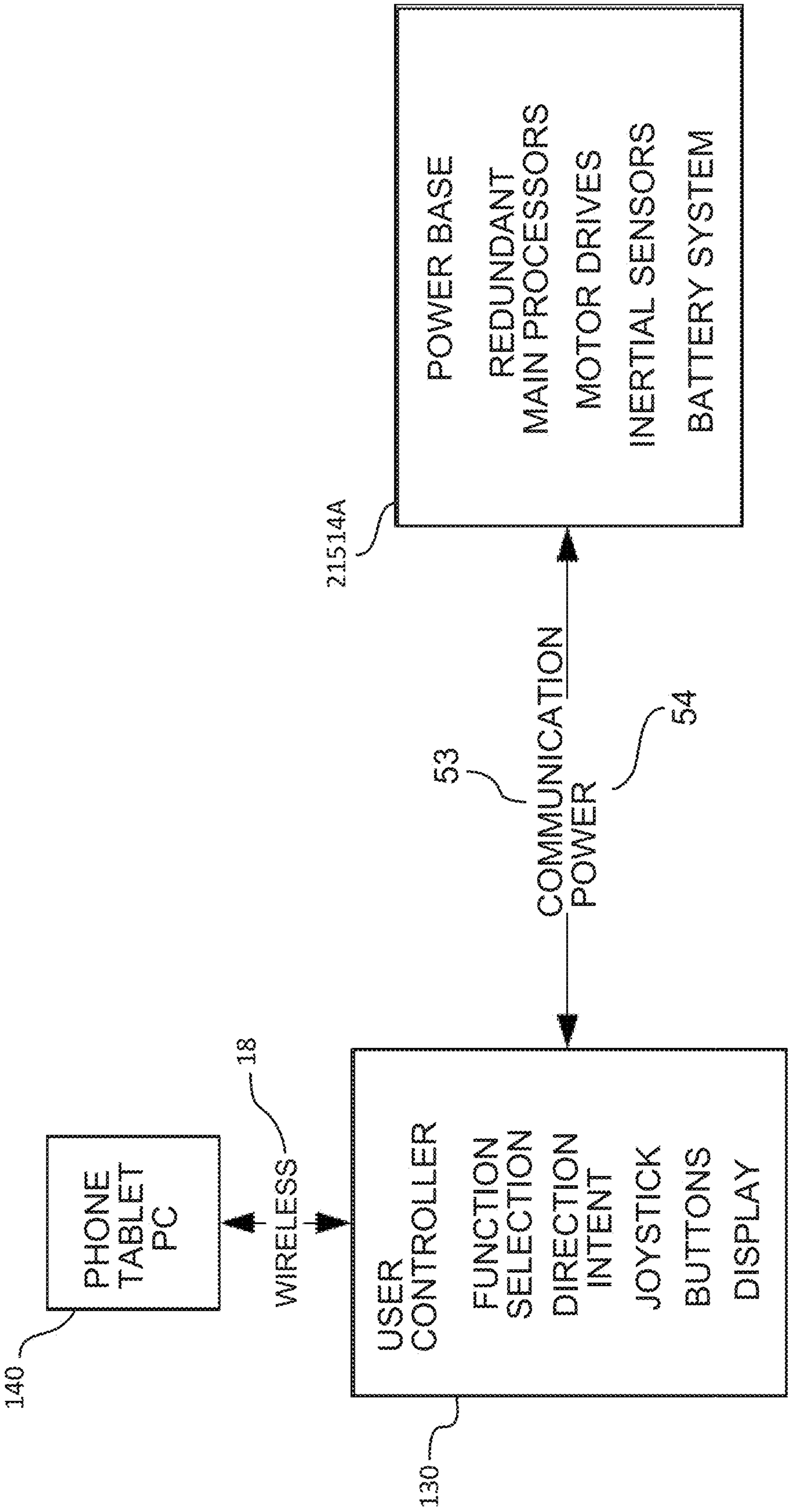
Figure 16B:
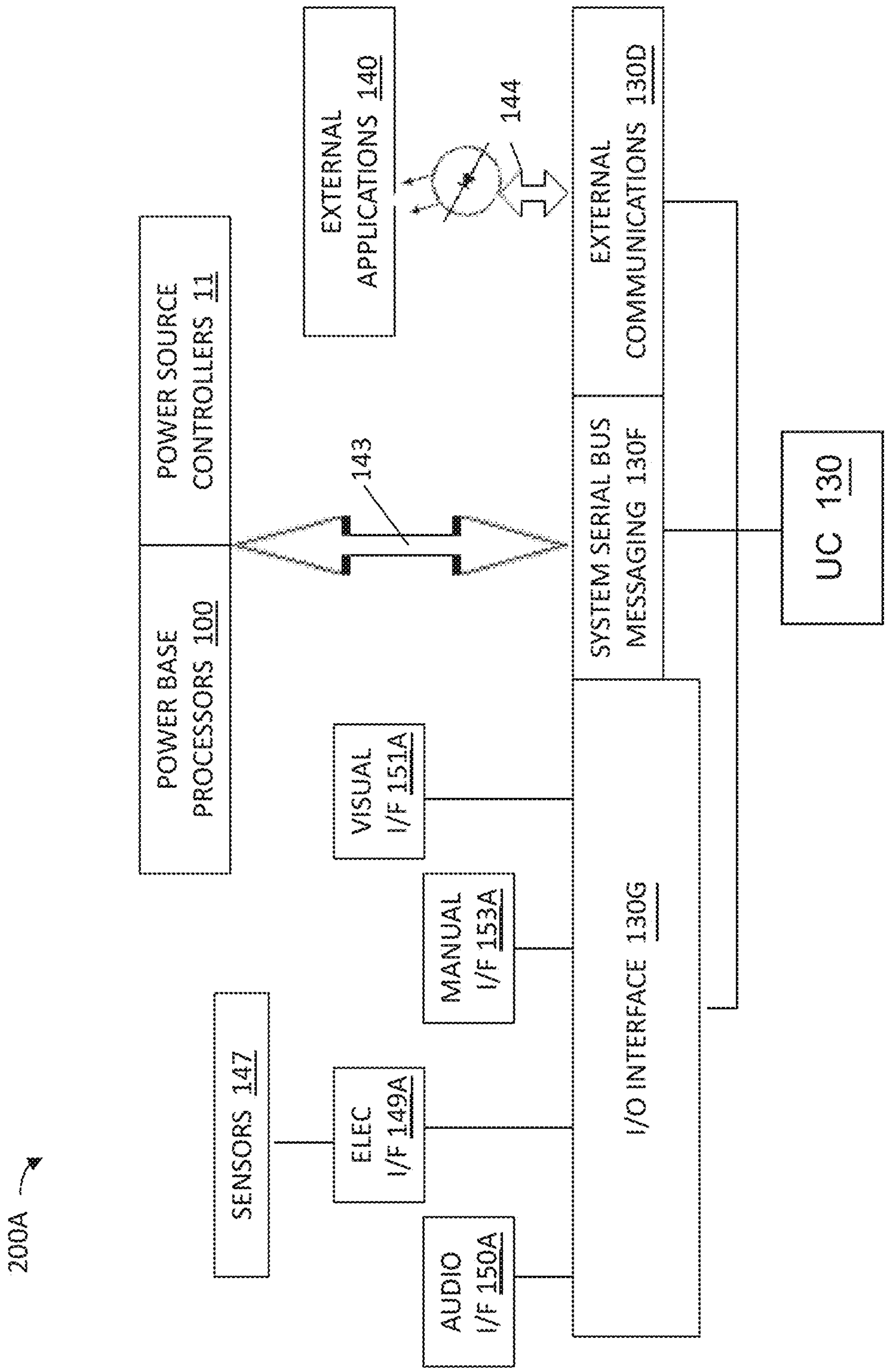
Figure 17A:
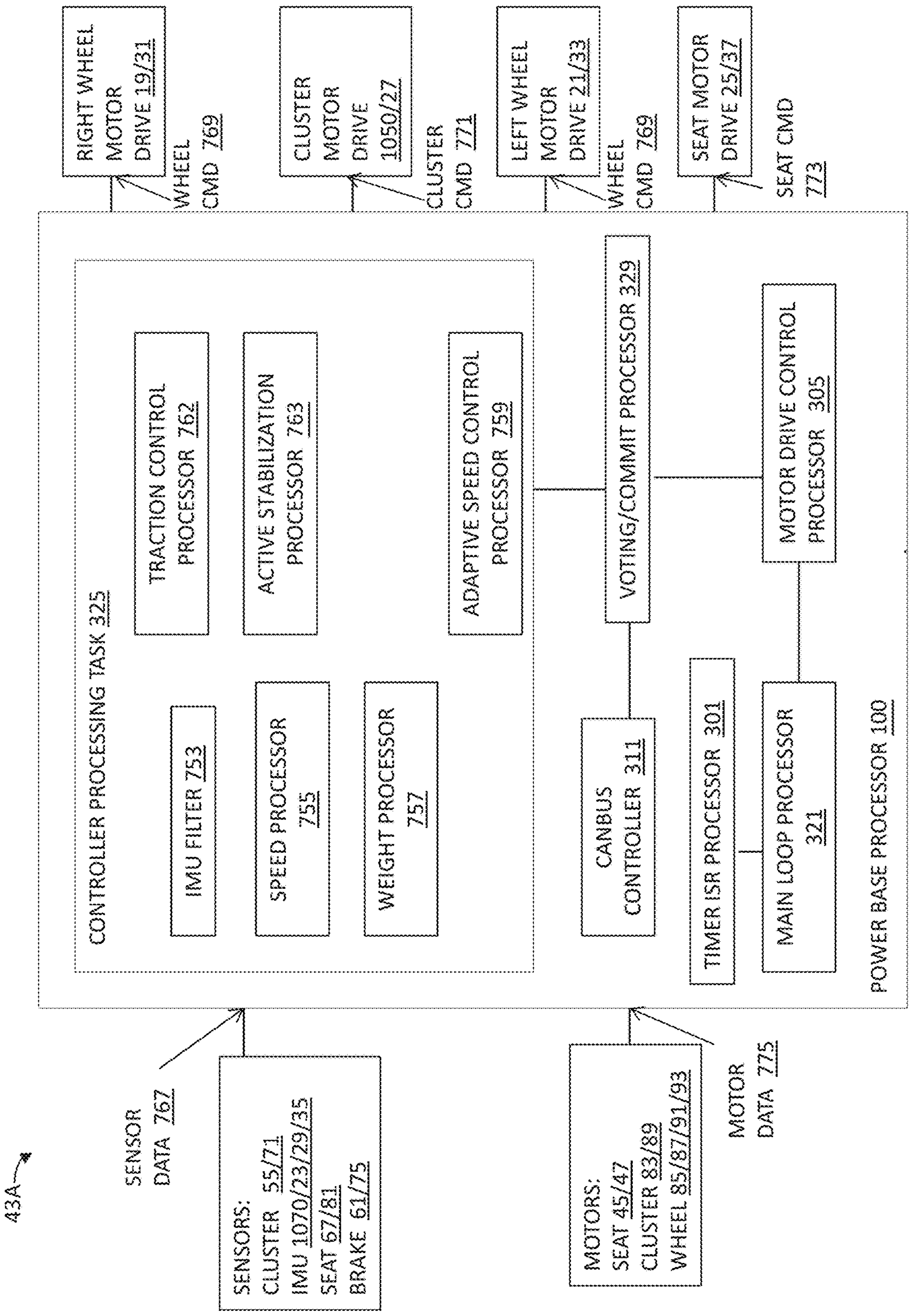
Figure 17B:
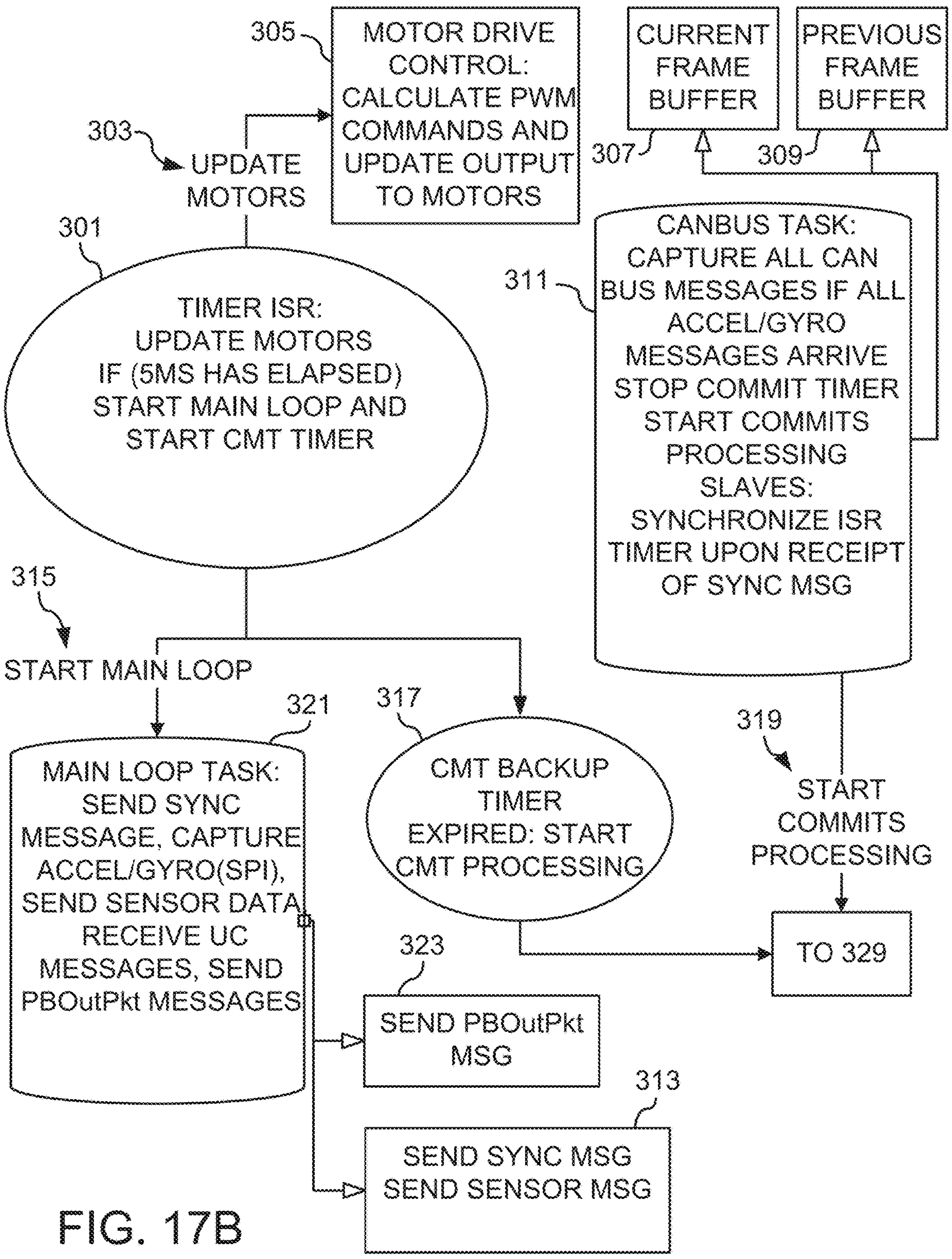
Figure 17C:
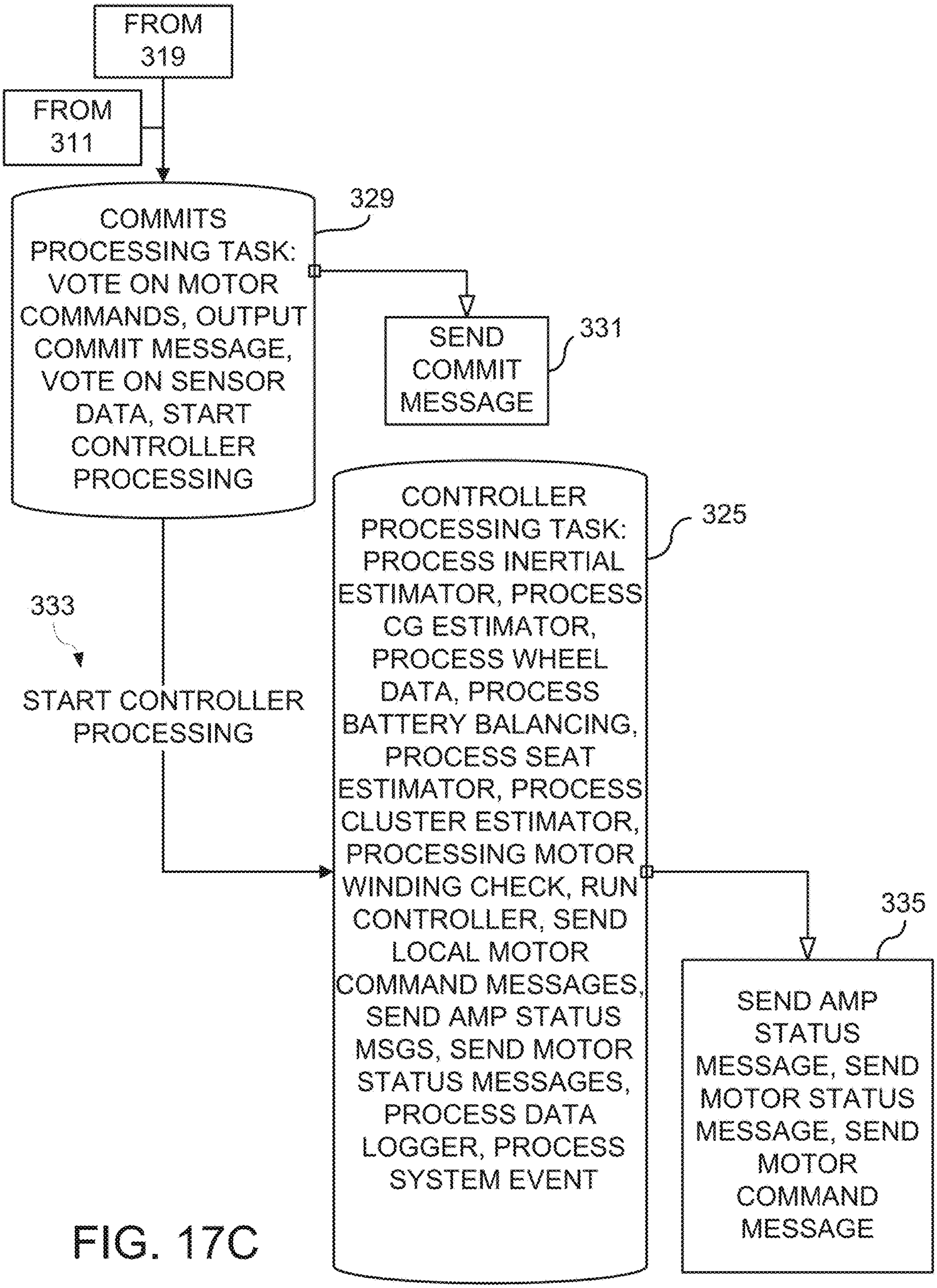
Figure 19A:
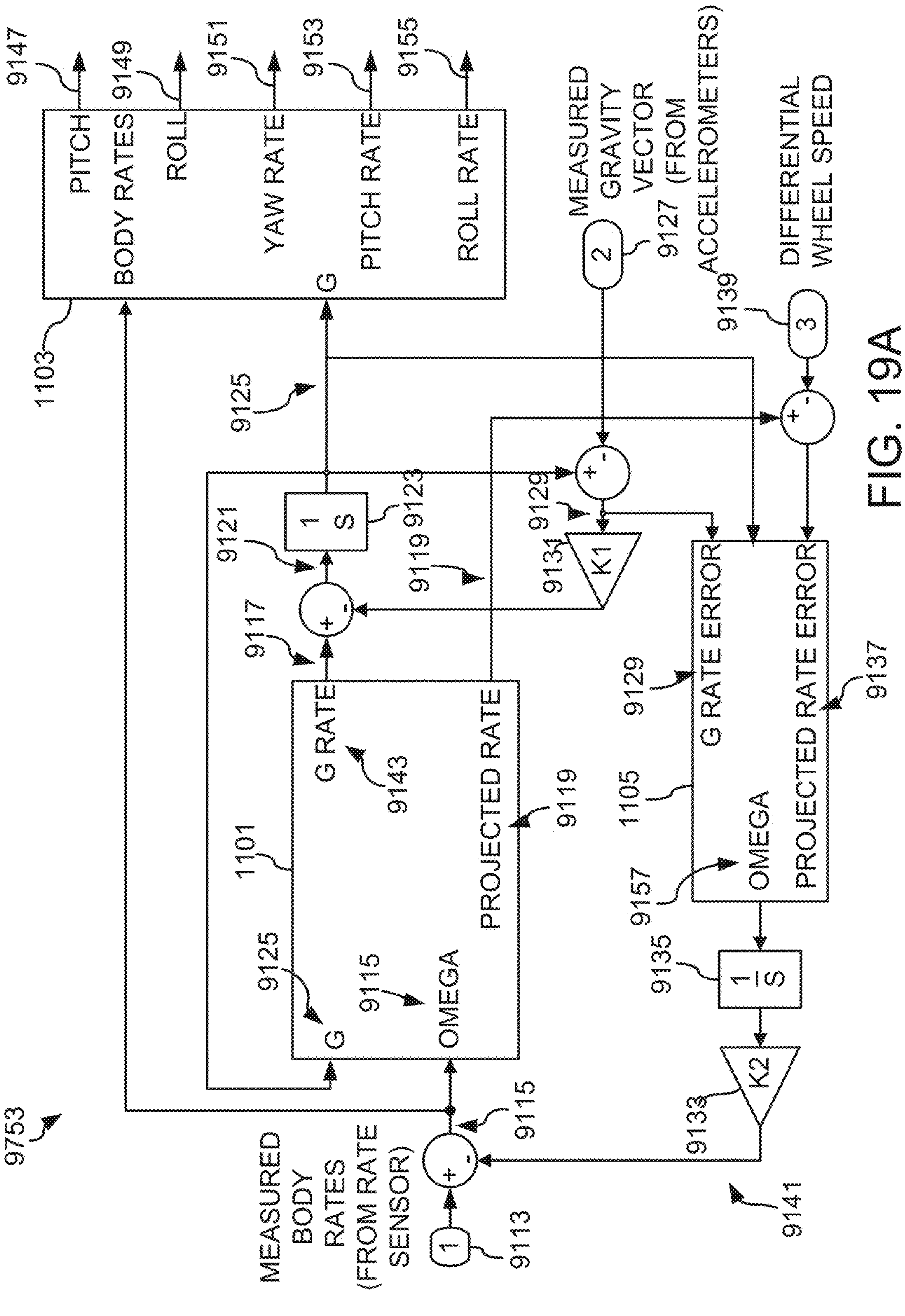
Figure 19B:
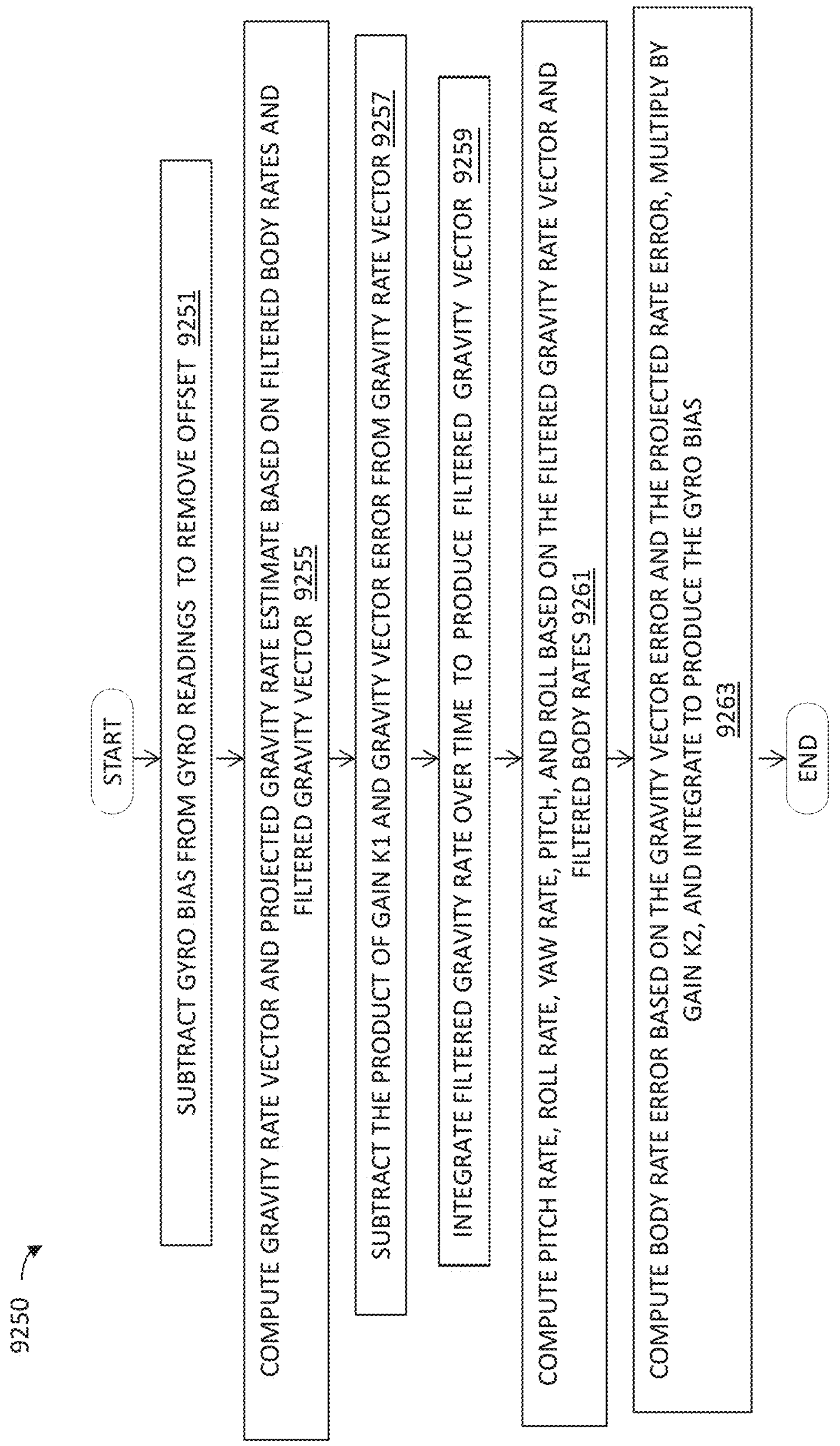
Figure 20:
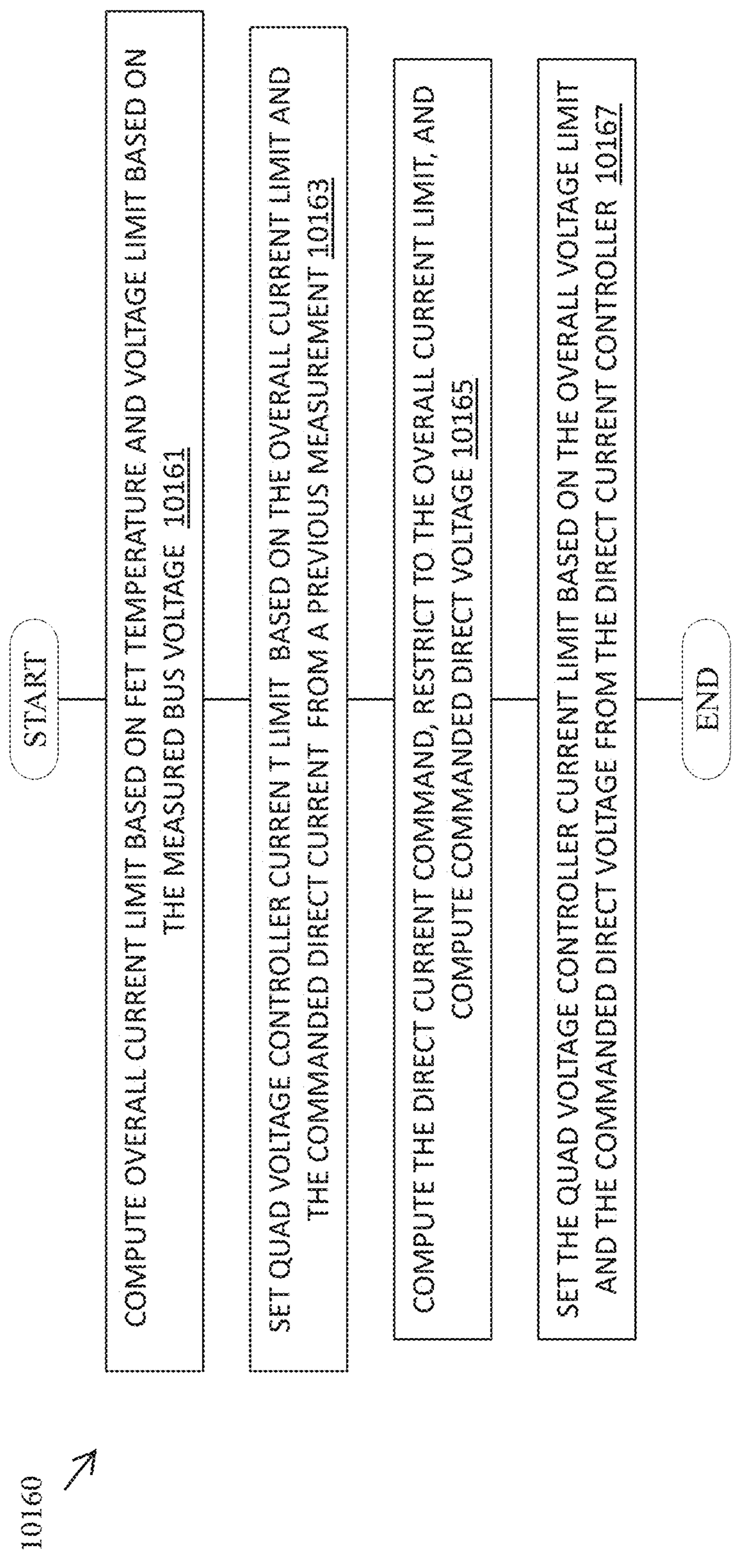
Figure 20A:
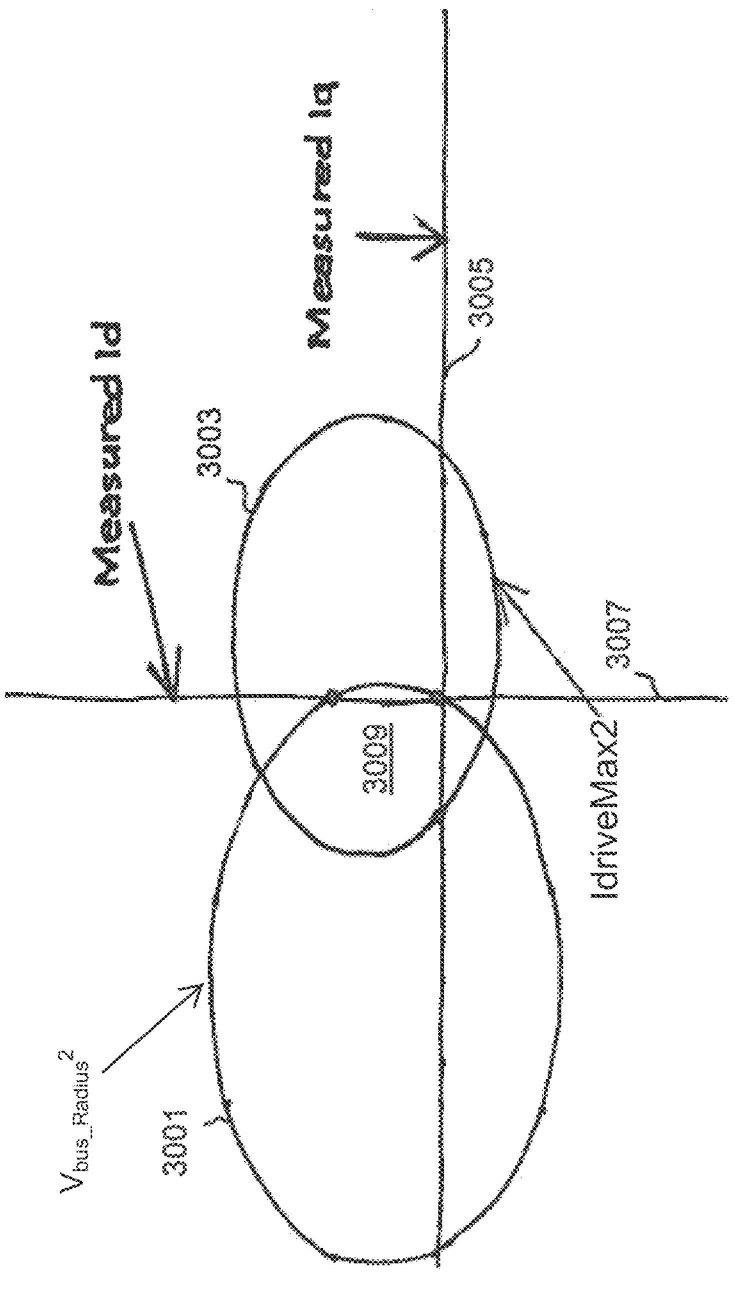

FIGS. 12C and 12D are perspective diagrams of the second configuration of the UC of the present teachings;

FIGS. 12E and 12F are perspective diagrams of the third configuration of the UC of the present teachings;

FIG. 12G is a perspective diagram of the forward-facing components of the second configuration of the UC of the present teachings;

FIG. 12H is a perspective diagram of the joystick of the UC of the present teachings;

FIGS. 121, 12J, and 12K are exploded perspective diagrams of the first configuration of the UC of the present teachings;

FIGS. 12L and 12M are perspective diagrams of the upper and lower housings of the first configuration of the UC of the present teachings;

FIG. 12N is an exploded perspective diagram of the thumbwheel components of the lower housing of the third configuration of the UC of the present teachings;

FIG. 12O is a cross section diagram of the thumbwheel sensor environmental isolation of the lower housing of the third configuration of the UC of the present teachings;

FIG. 12P is a perspective diagram of the display coverglass of the UC of the present teachings;

FIG. 12Q is a perspective diagram of the joystick backer ring of the UC of the present teachings;

FIG. 12R is a perspective diagram of the toggle housing of the UC of the present teachings;

FIGS. 12S and 12T are perspective diagrams of the toggle housing of the UC of the present teachings;

FIGS. 12U and 12V are perspective diagrams of the undercap of the UC of the present teachings;

FIGS. 12W and 12X are cross section and exploded perspective diagrams of the EMI suppression ferrite of the UC of the present teachings;

FIG. 12Y is a perspective diagram of the UC mounting device of the present teachings;

FIG. 12OO is a perspective diagram of the cleated mounting mechanism of the present teachings;

FIG. 12 PP is a perspective diagram of the power charging receiver bracket mounting mechanism of the present teachings;

FIG. 12Z is a perspective diagram of the mounting cleat of the UC of the present teachings;

FIG. 12AA is a perspective diagram of the grommet of the UC of the present teachings;

FIGS. 12BB and 12CC are perspective diagrams of the button assembly of the UC of the present teachings;

FIGS. 12DD and 12EE are perspective diagrams of the toggle module of the UC of the present teachings;

FIGS. 12FF through 12SS are perspective diagrams of the toggles optional configuration of the present teachings;

FIGS. 12GG and 12TT are perspective diagrams of the toggles with an integral UC connection of the present teachings;

FIGS. 12HH through 12VV are perspective diagrams of the cap back clamp configuration of the present teachings;

FIGS. 12II through 12XX are perspective diagrams of the toolless screw mounting configuration of the present teachings;

FIGS. 12JJ and 12YY are perspective diagrams of the UC/clamp post configuration of the present teachings;

FIGS. 12KK through 12EEE are perspective diagrams of the cap latch configuration of the present teachings;

FIGS. 12LL through 12JJJ are perspective diagrams of the UC top plate configuration of the present teachings;

FIGS. 12MM through 12MMM are perspective diagrams of the undercapconfiguration of the present teachings;

FIGS. 12NN through 12WWW are perspective diagrams of a second toggles optional configuration of the present teachings;

FIGS. 13A and 13B are perspective diagrams of the fourth configuration the UC of the present teachings;

FIG. 13C is a perspective diagram of the UC assist holder of the UC of the present teachings;

FIG. 13D is a perspective diagram of the tabbed binding mechanism of the UC of the present teachings;

FIG. 13E is a perspective diagram of the tab lock mounting mechanism of the UC of the present teachings;

FIG. 13F is a perspective diagram of the shaped mounting base of the UC of the present teachings;

FIG. 13G is a perspective diagram of the second configuration of the tabbed mounting mechanism of the UC of the present teachings;

FIG. 13H is a perspective diagram of the flanged mounting mechanism of the UC of the present teachings;

FIG. 131 is a perspective diagram of the retention cam mounting mechanism of the UC of the present teachings;

FIG. 13J is a perspective diagram of the flange/faceted mounting mechanism of the UC of the present teachings;

FIG. 13K is a perspective diagram of the receiving bracket/tubing clamp mounting mechanism of the UC of the present teachings;

FIGS. 13M and 13N are cross-section diagrams of the ring/lock mounting mechanism of the UC of the present teachings;

FIG. 13L is a perspective diagram of the grooved flange mounting mechanism of the UC of the present teachings;

FIG. 14A is a perspective diagram of the UC circuit board of the UC of the present teachings;

FIGS. 14B and 14C are schematic block diagrams of the layout of the UC circuit board of the UC of the present teachings;

FIGS. 14D-14E are flowcharts of the method for thumbwheel processing of the present teachings;

FIG. 14F is a schematic block diagram of the system for thumbwheel processing of the present teachings;

FIG. 15A s a perspective diagram of the electronics component boards of the present teachings;

FIG. 15B is an exploded perspective diagram of the circuit boards of the present teachings;

FIGS. 15C-15D are perspective diagrams of the IMU assembly of the present teachings;

FIG. 15E is a perspective diagram of a first view of the IMU board and the EMF shield of the present teachings;

FIG. 15F is a perspective diagram of a second view of the IMU board and the EMF shield of the present teachings;

FIG. 15G is a perspective diagram of the first configuration of the power source controller board of the present teachings;

FIG. 15H is a perspective diagram of the second configuration of the power source controller board of the present teachings;

FIGS. 151-15J are schematic block diagrams of the power source controller board of the present teachings;

FIG. 15K is a state diagram of the states of the user controller of the present teachings;

FIG. 16A is a schematic block diagram of an overview of the system of the present teachings;

FIG. 16B is a schematic block diagram of the electronic components of the mobility device of the present teachings;

FIG. 17A is a schematic block diagram of a powerbase controller of the present teachings;

FIG. 17B and 17C are message flow diagrams of the powerbase controller of the present teachings;

FIGS. 18A-18D are schematic block diagrams of the processors of the present teachings;

FIG. 19A is a schematic block diagram of the inertial measurement unit filter of the present teachings;

FIG. 19B is a flowchart of the method of the present teachings for filtering gyro and acceleration data;

FIG. 20 is a flowchart of the method of the present teachings for field weakening;

FIG. 20A is a graphical representation of the locus of allowed limits referenced during the field weakening calculation of the present teachings.

Figure 21A:
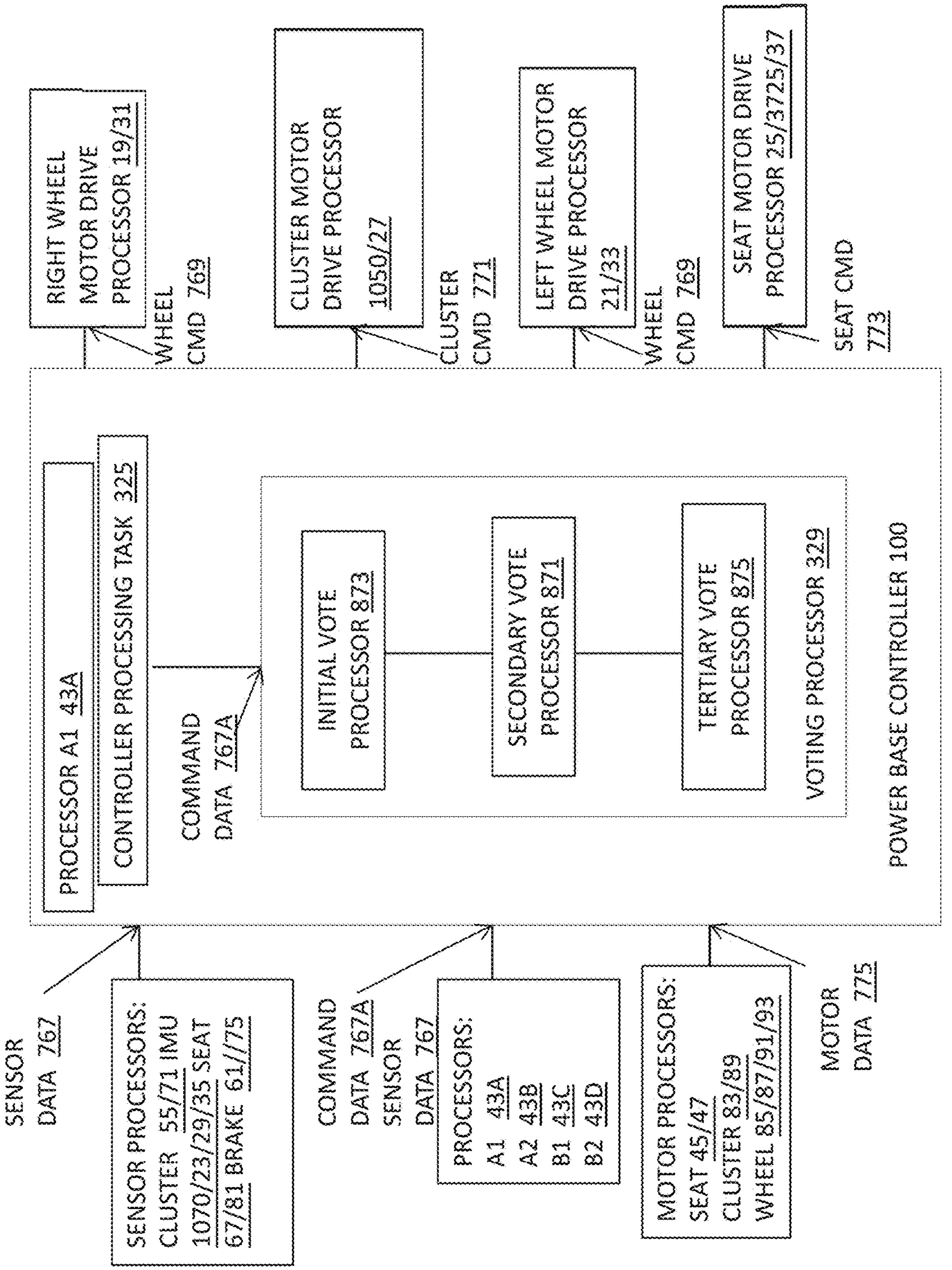
Figure 21B:
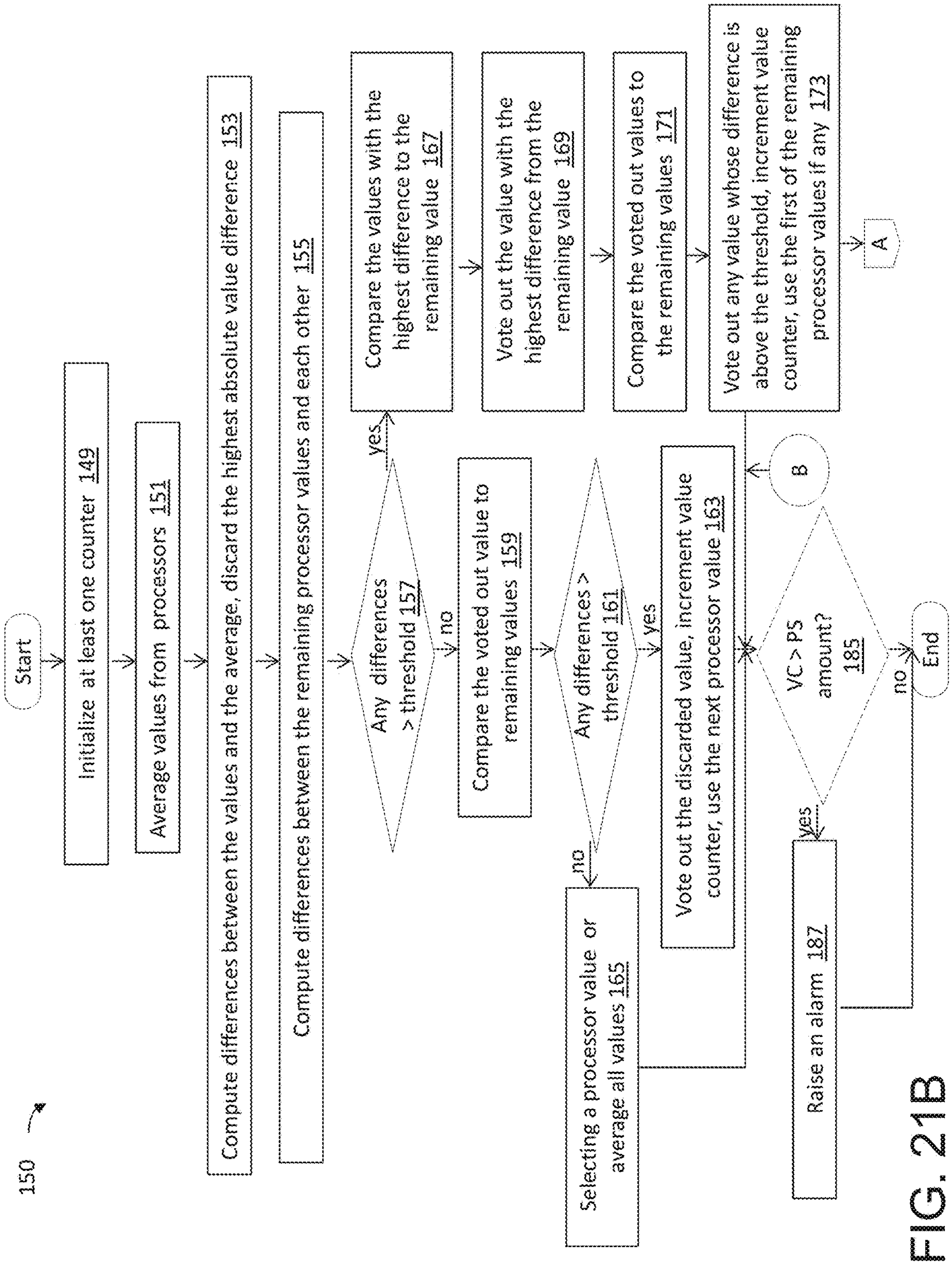
Figure 21C:
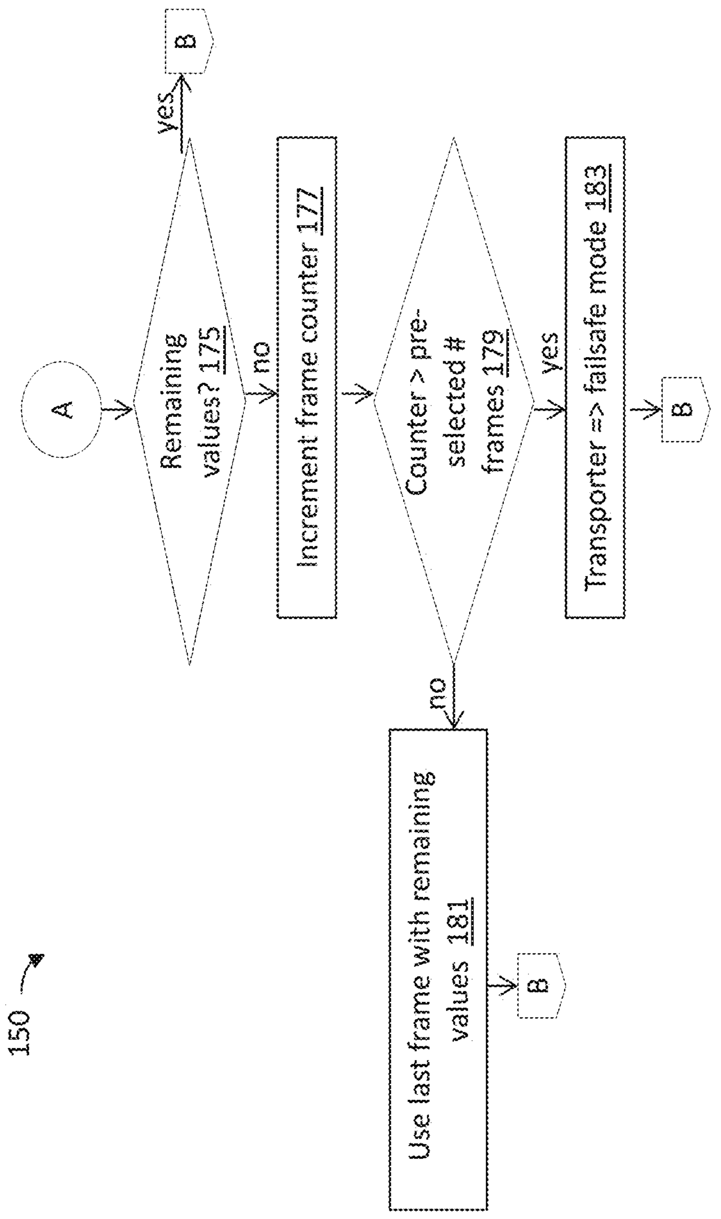
Figure 21D:
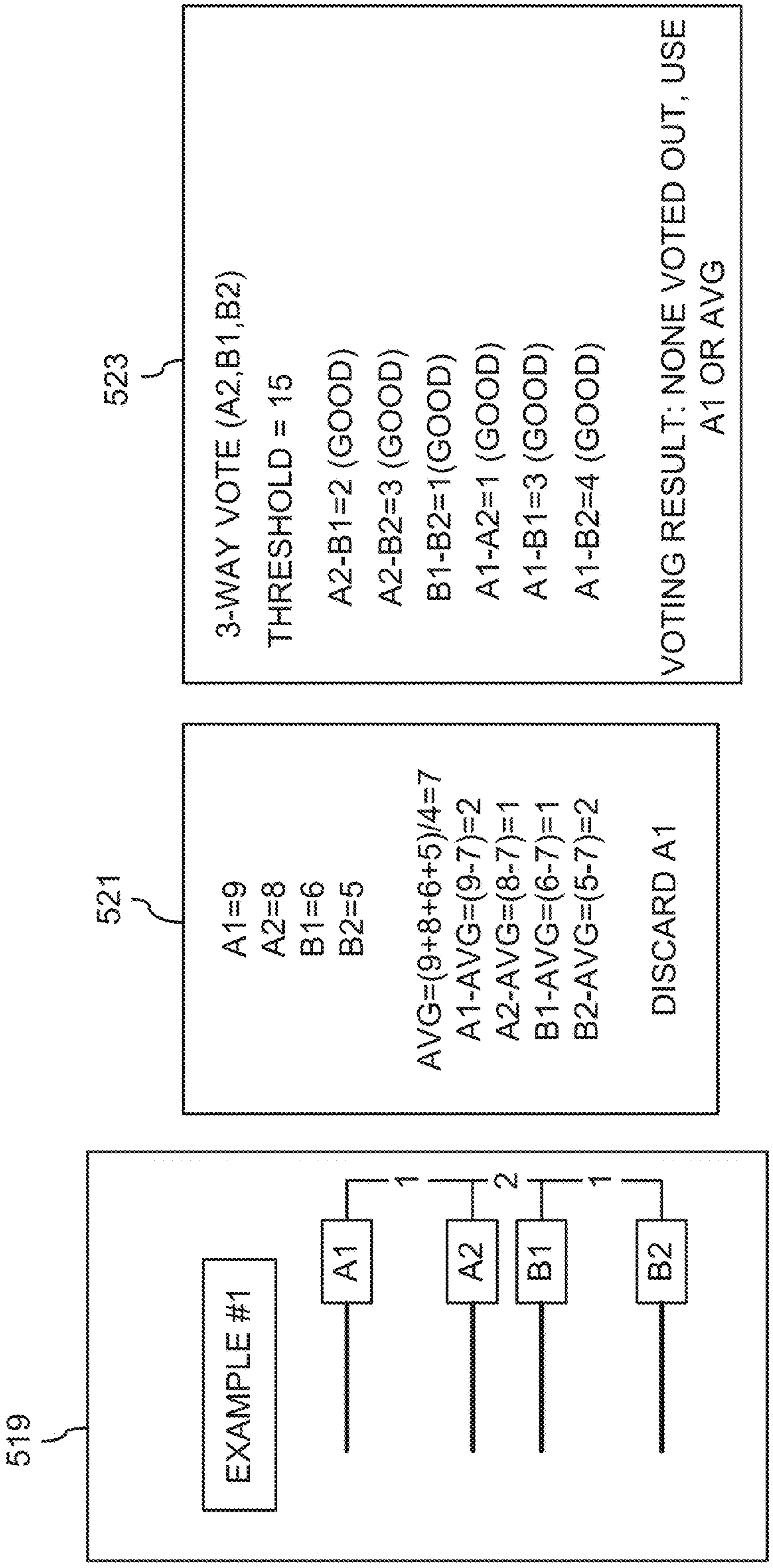
Figure 21E:
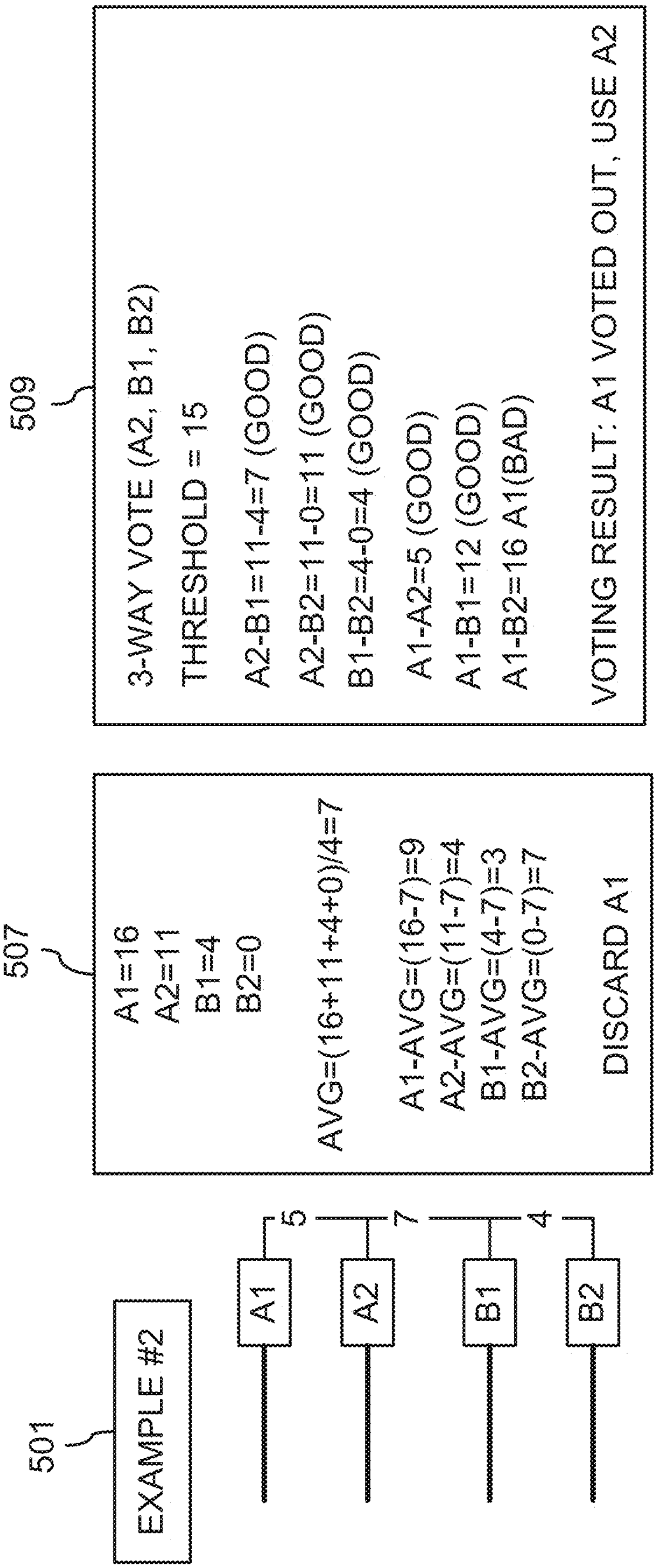
Figure 21F:
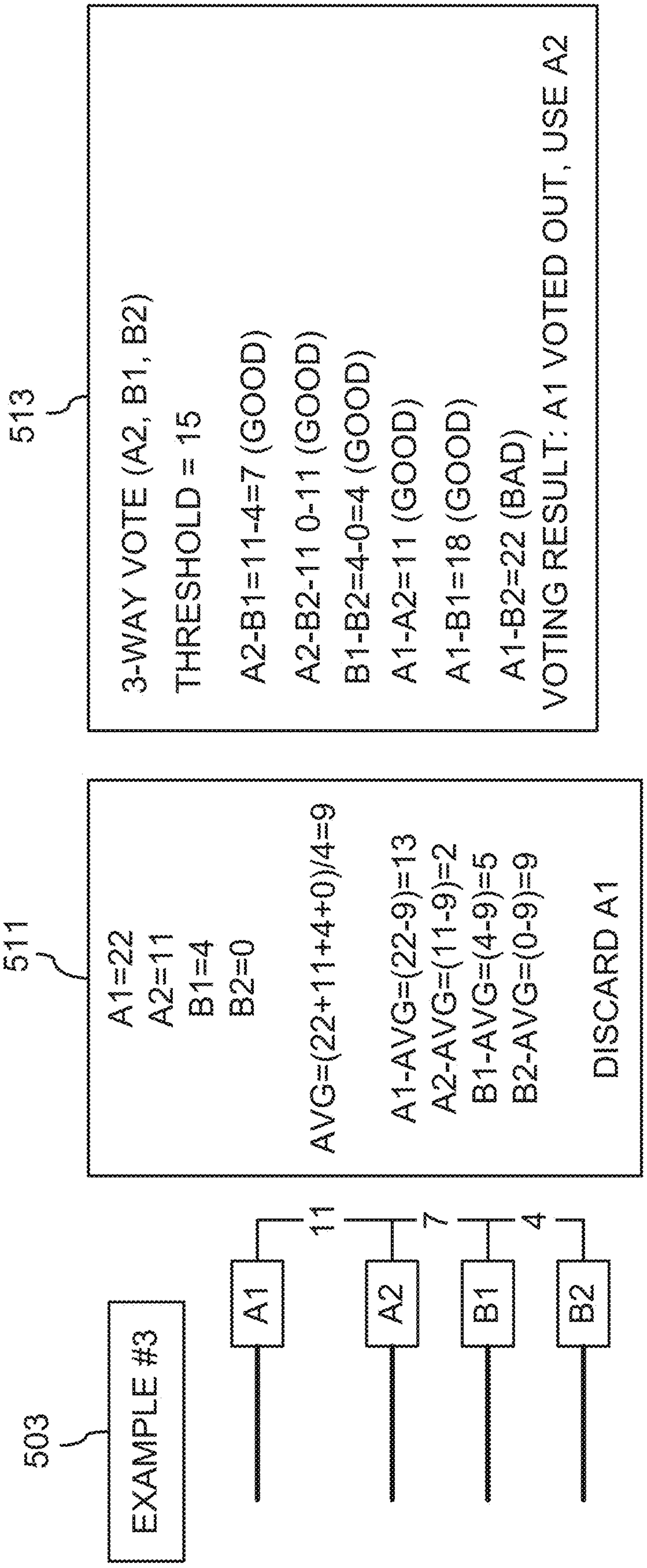
Figure 21G:
Figure 21I:
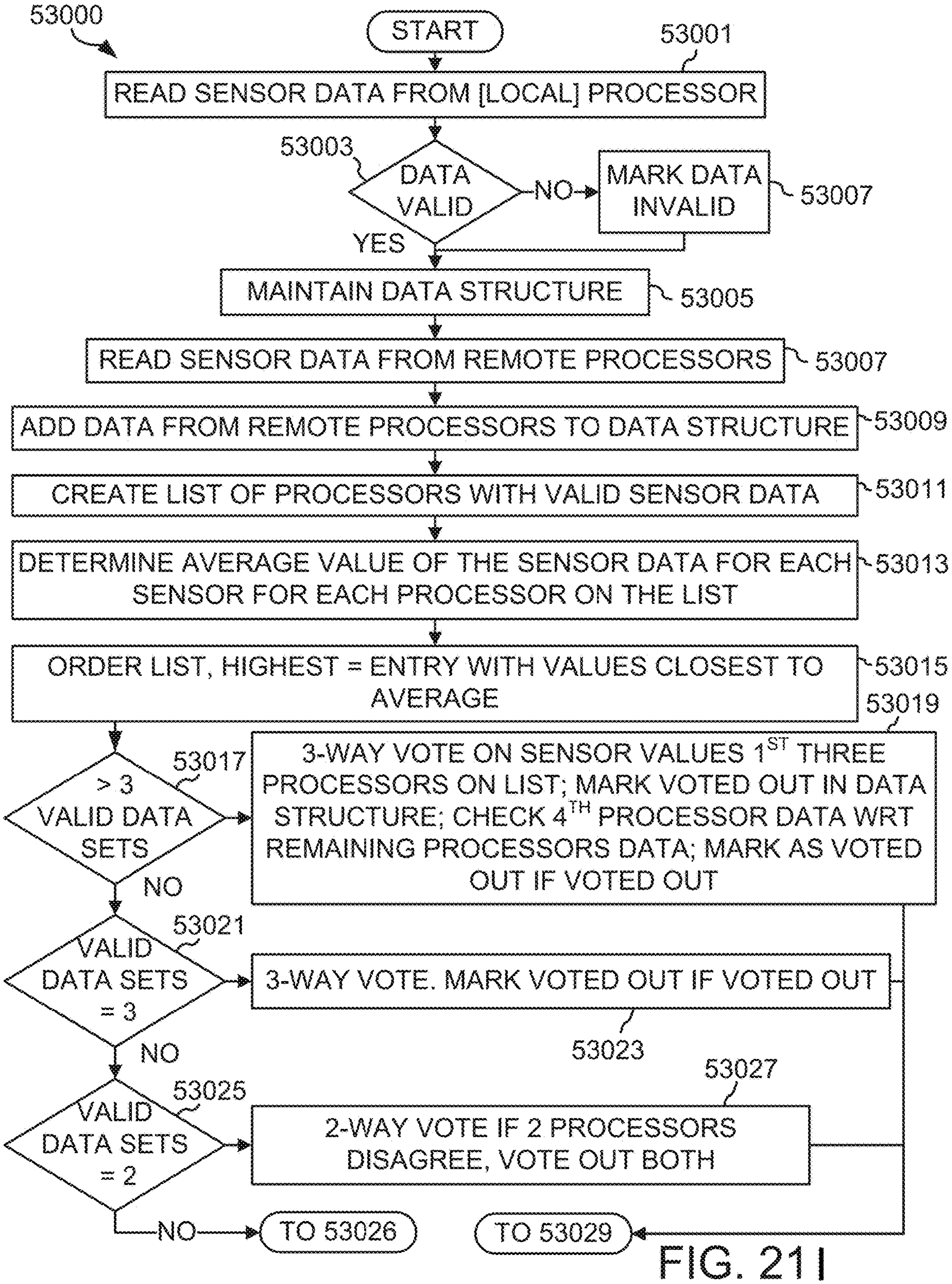
Figure 21J:
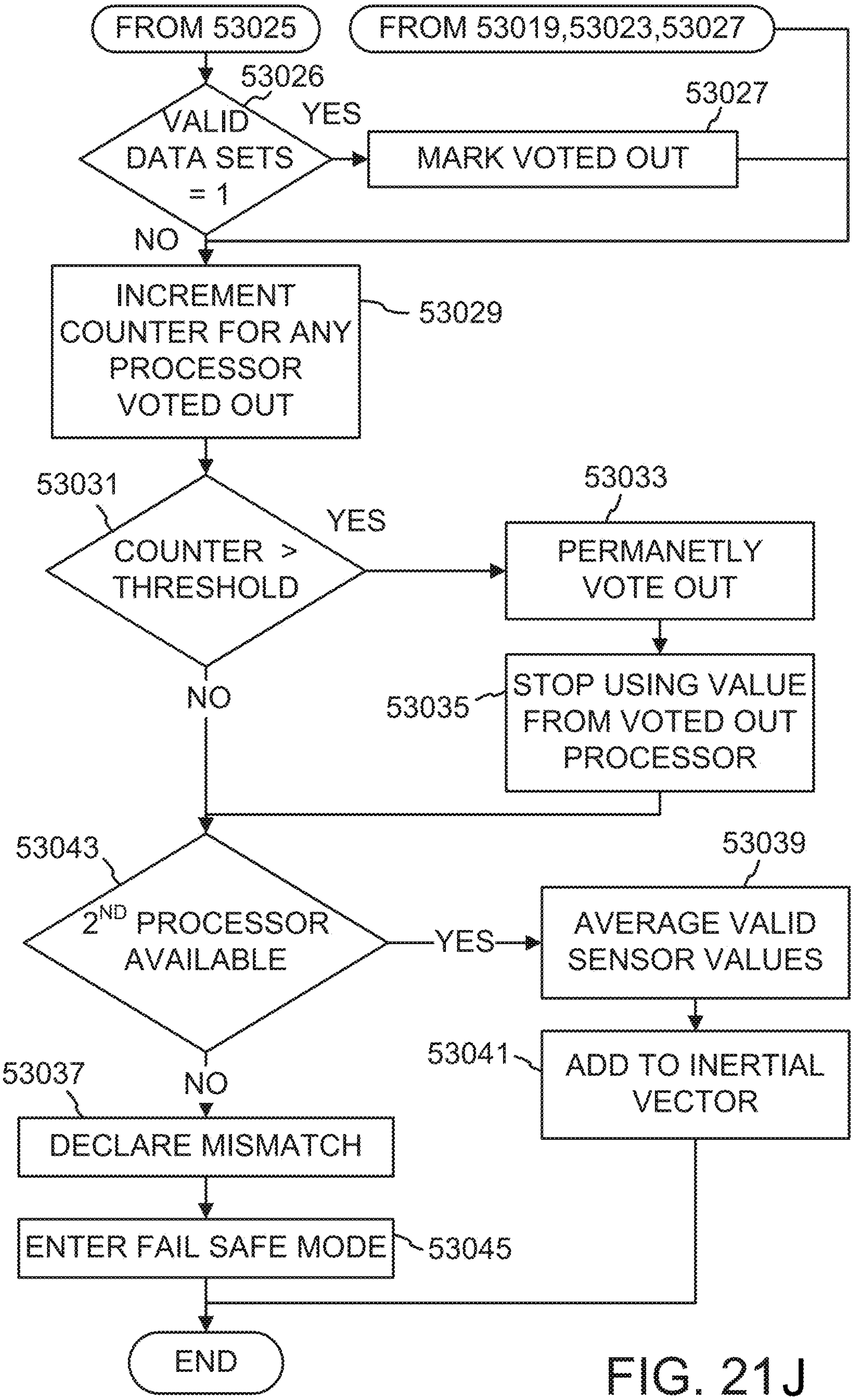
Figure 22A:
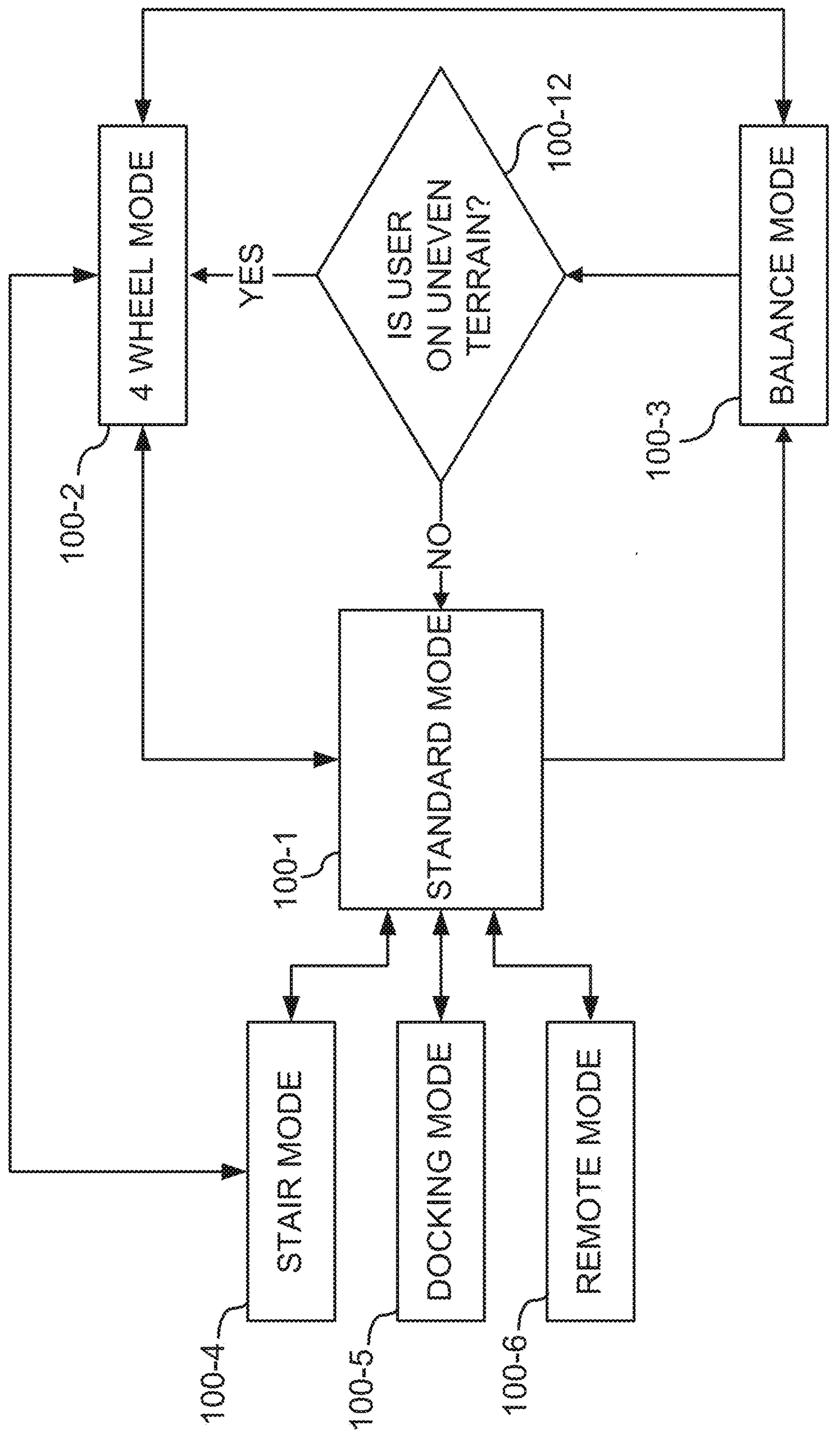
Figure 22E:
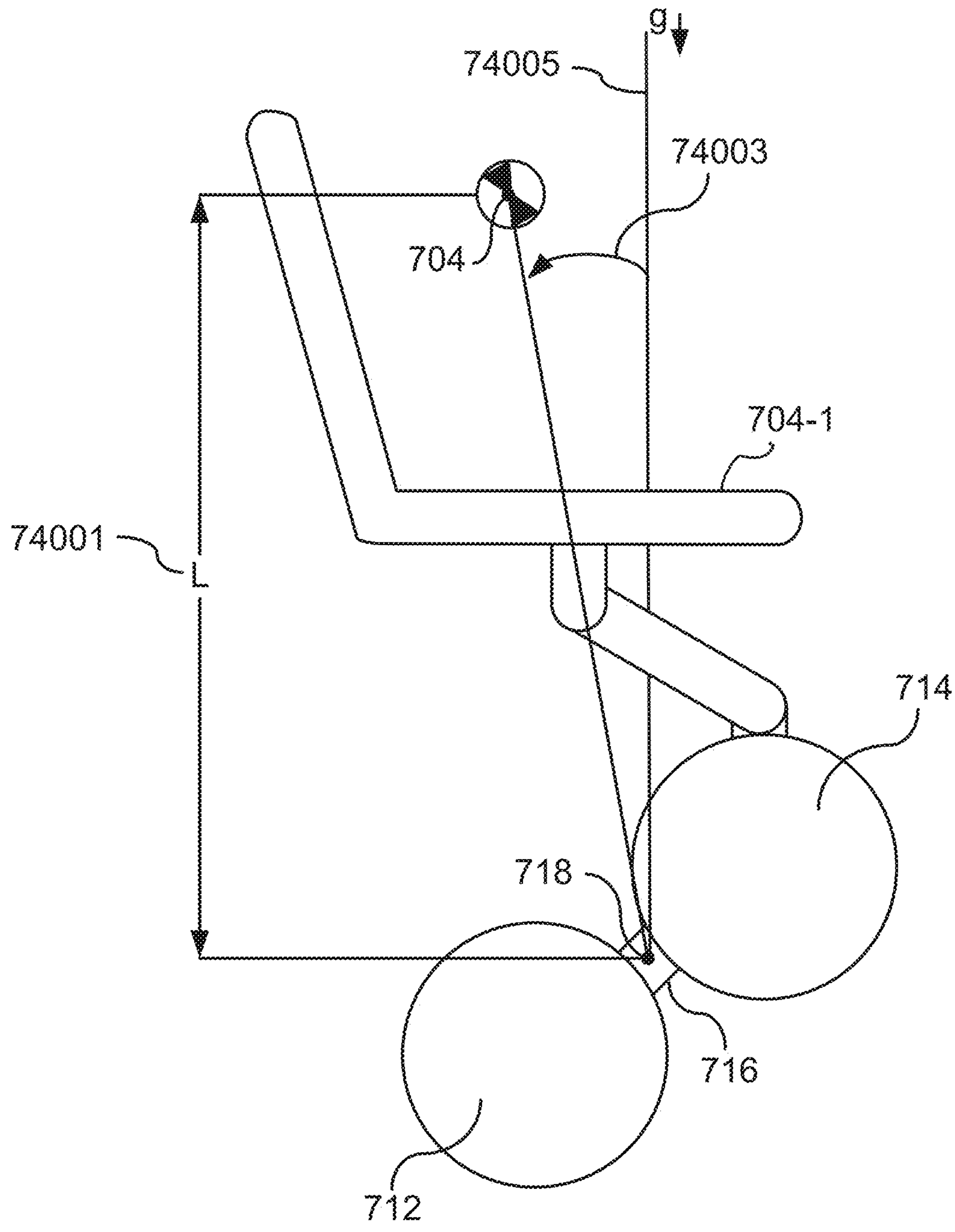
Figure 22B:
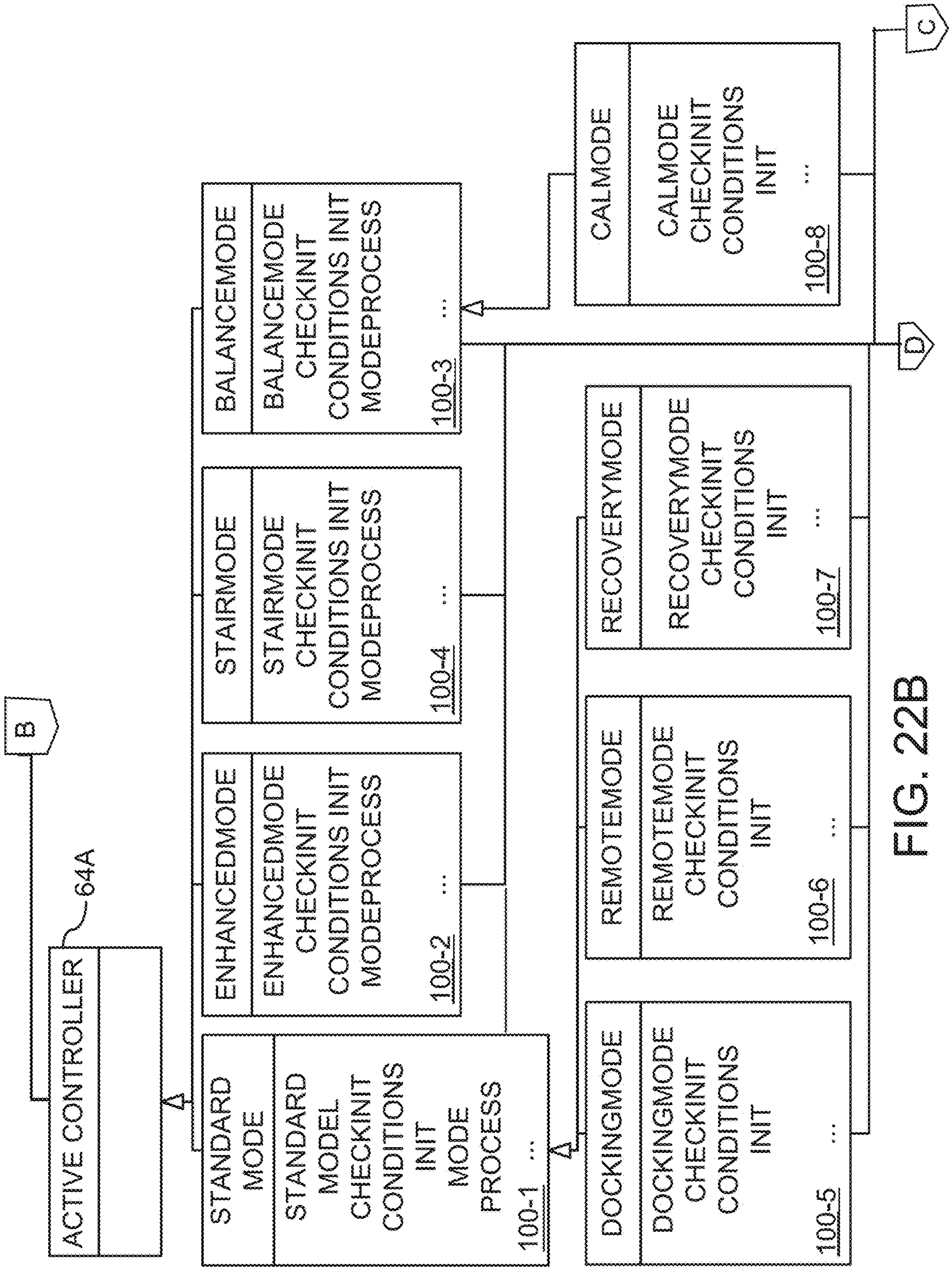
Figure 22C:
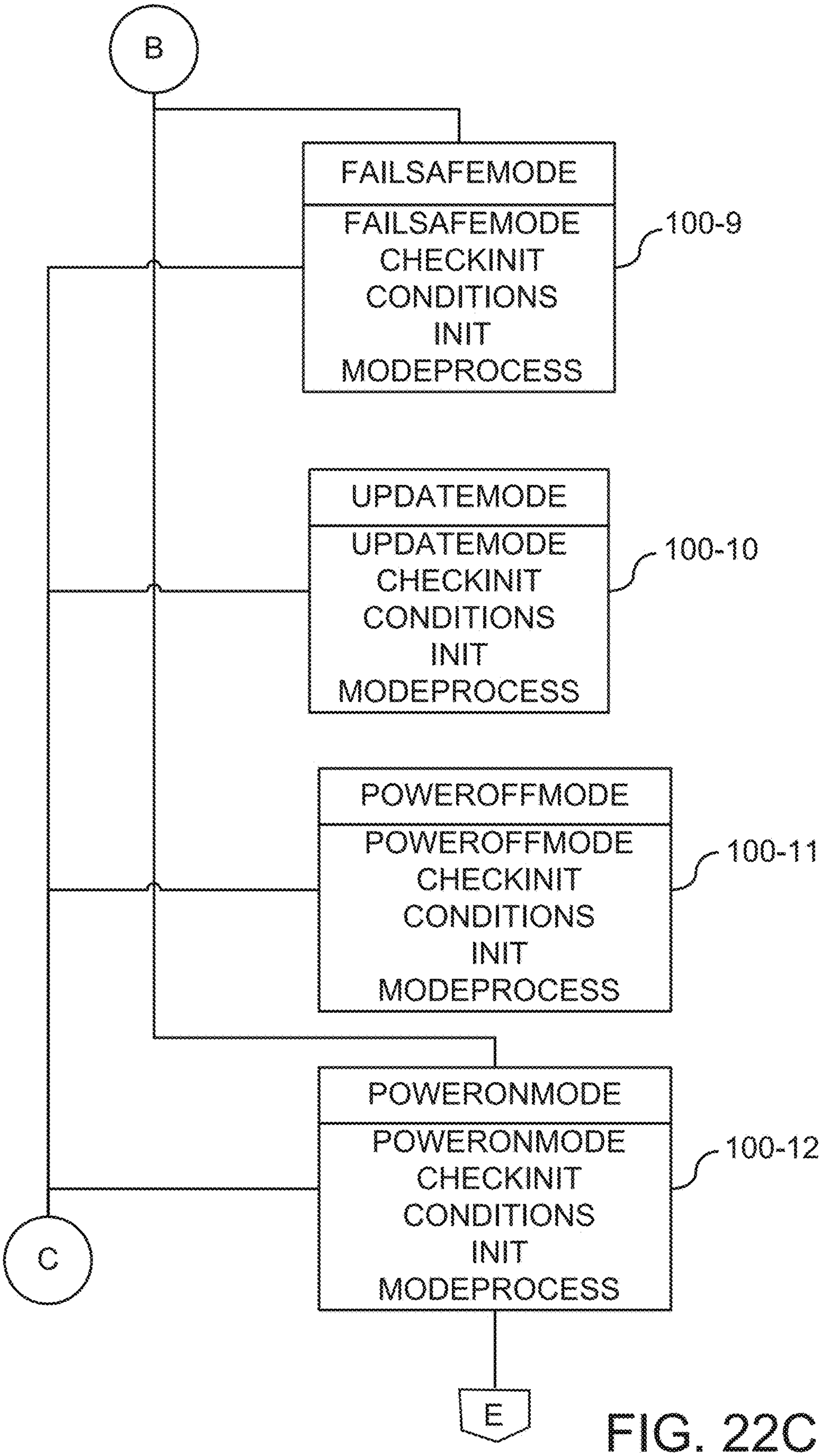
Figure 22D:
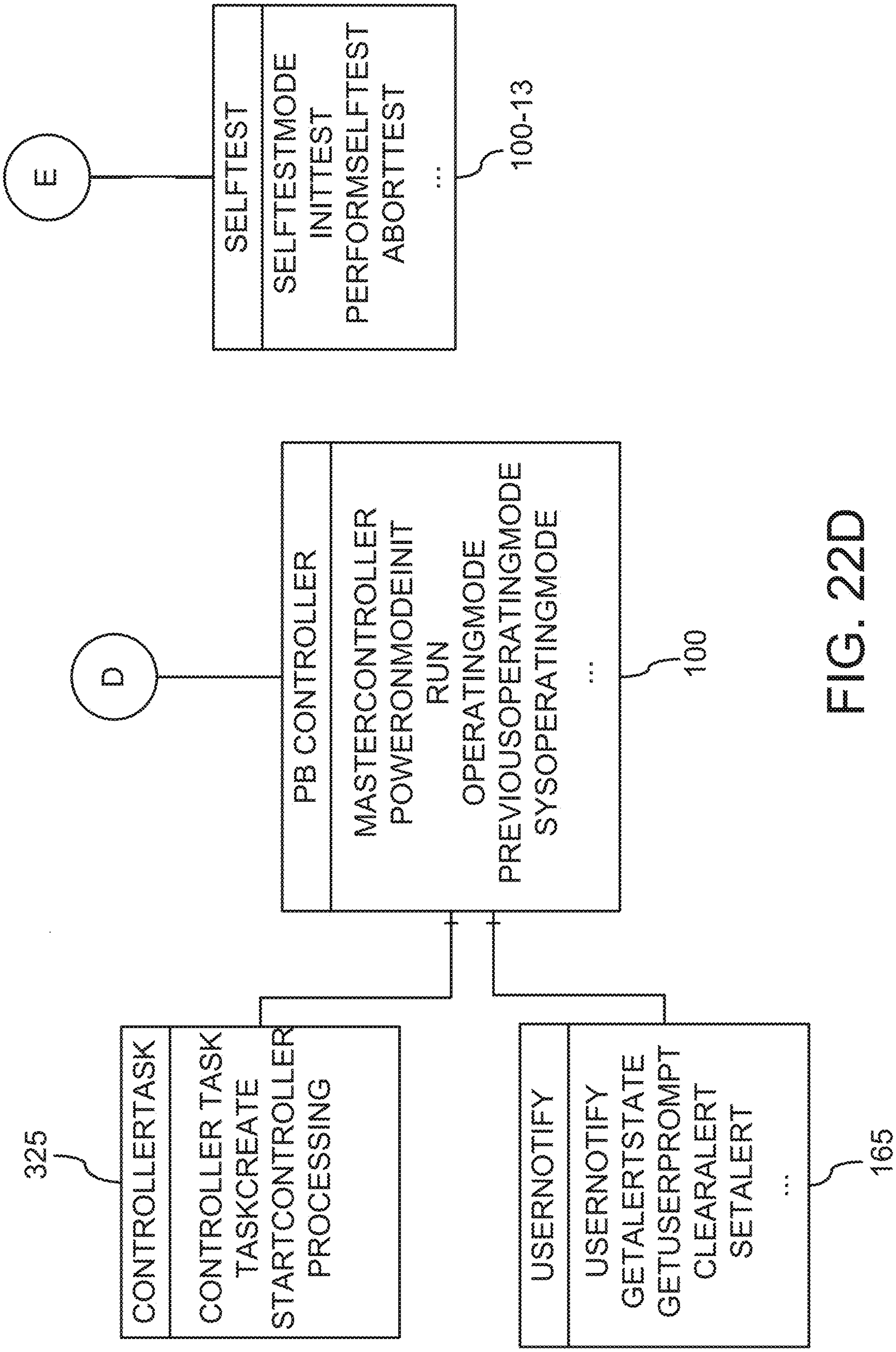
Figure 23A:
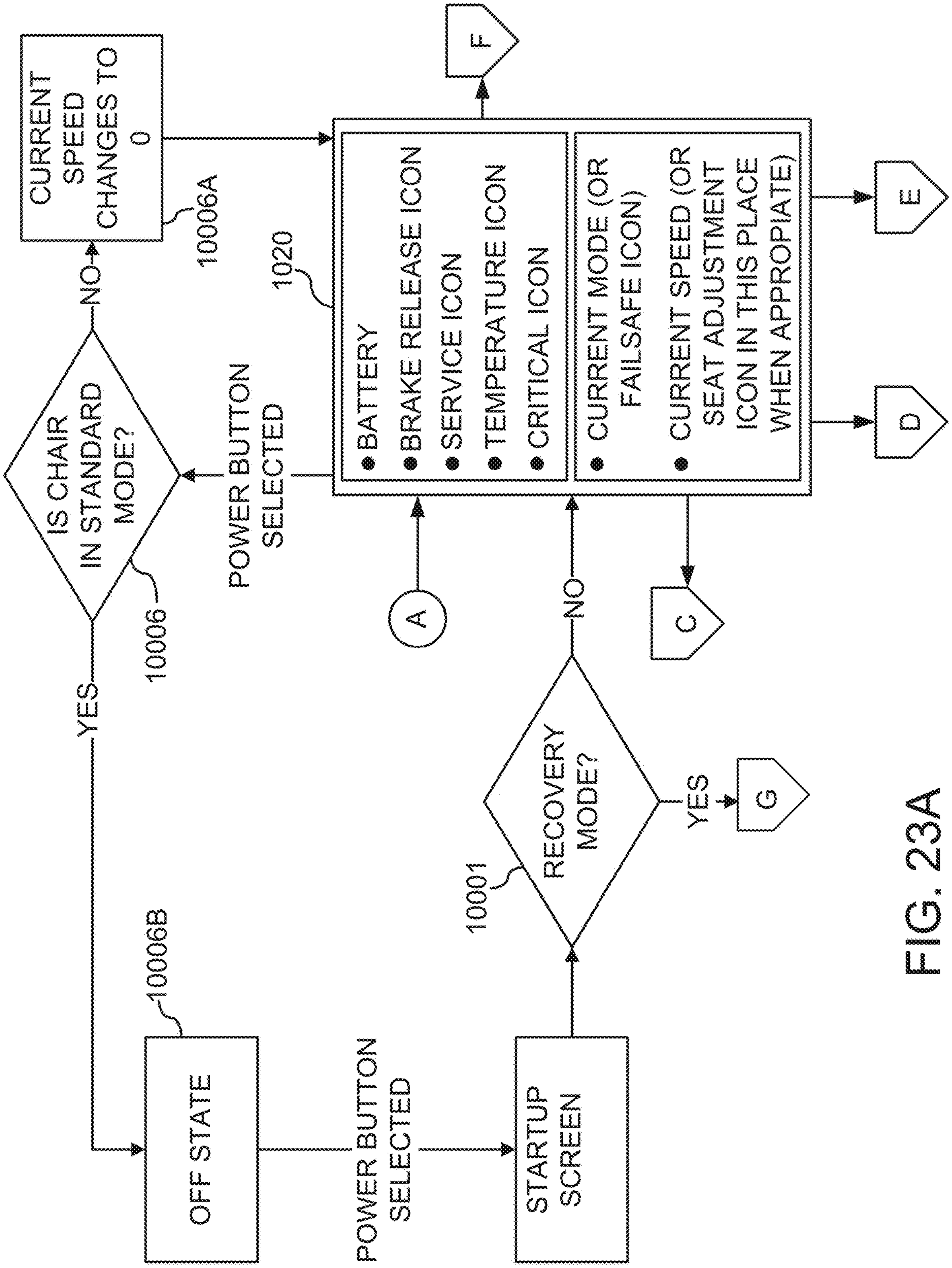
Figure 23B:
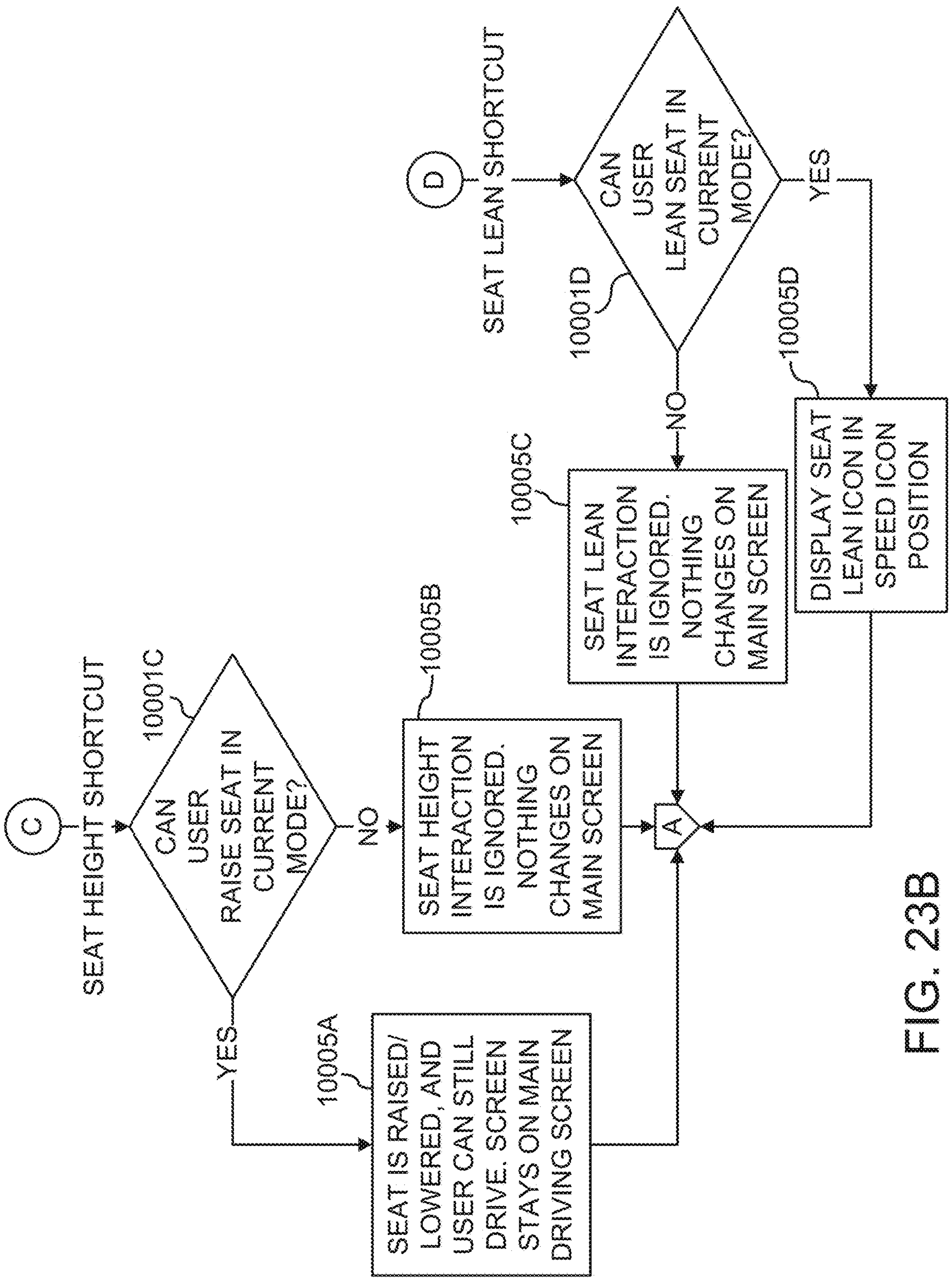
Figure 23C:
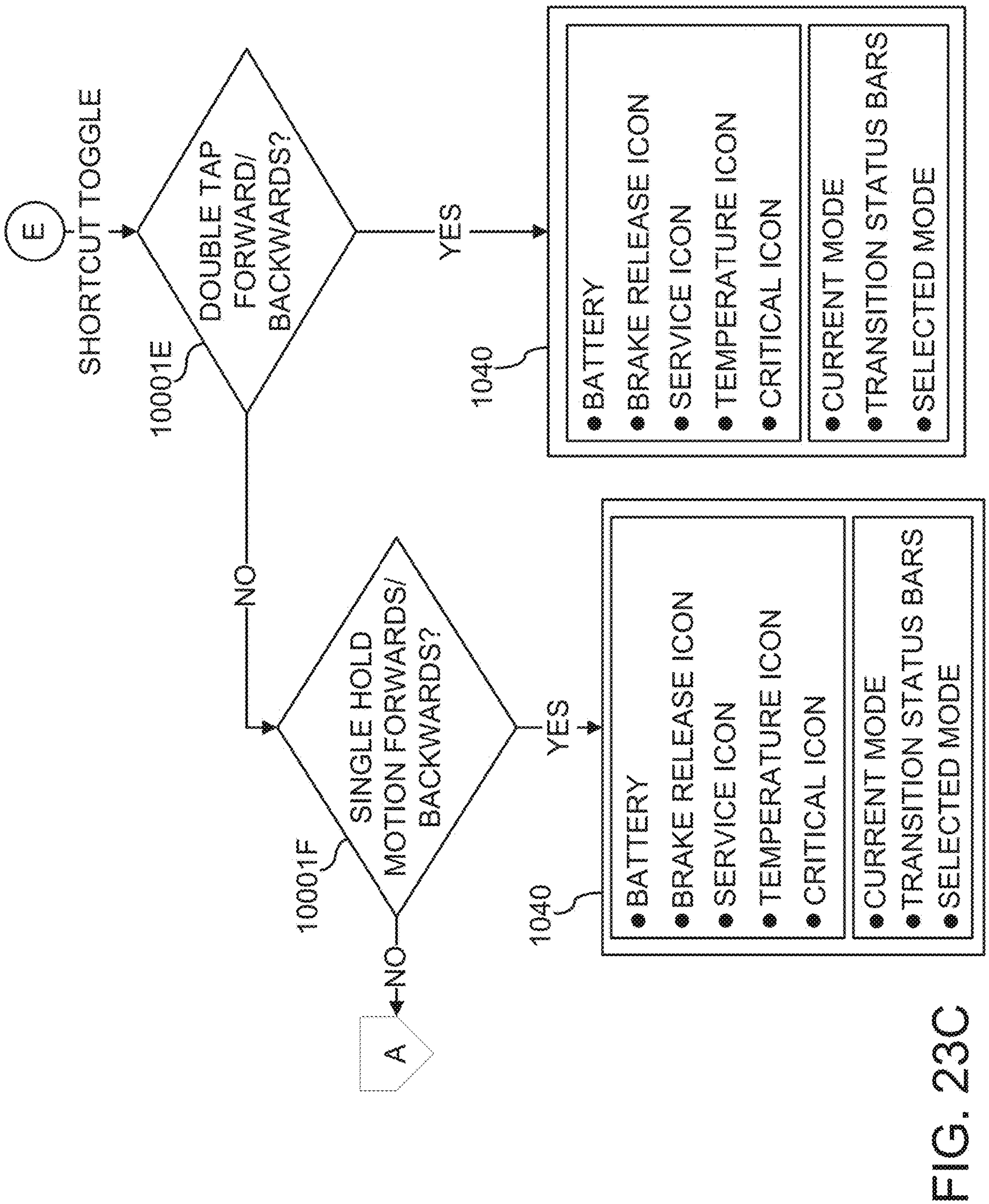
Figure 23D:
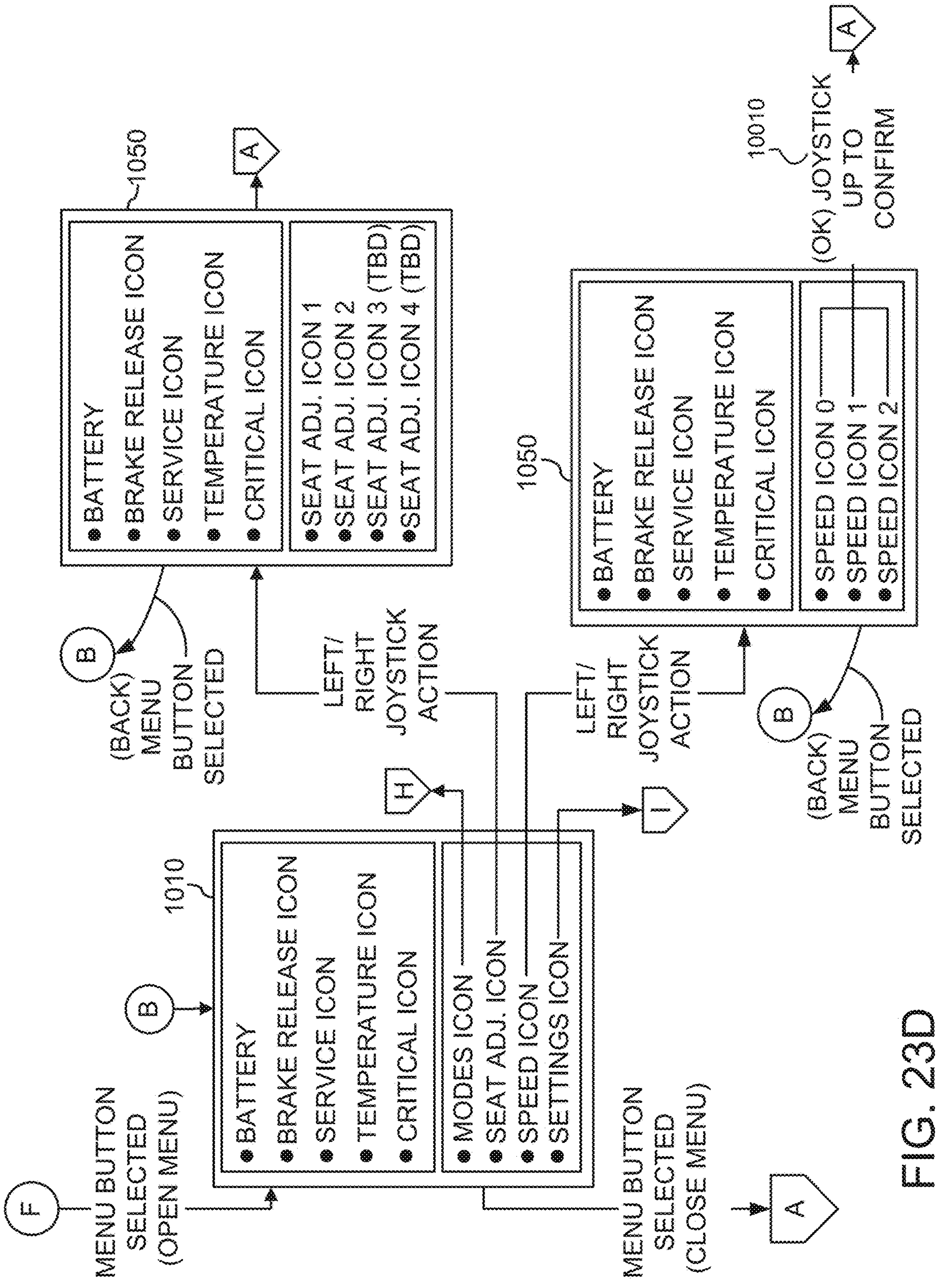
Figure 23E:
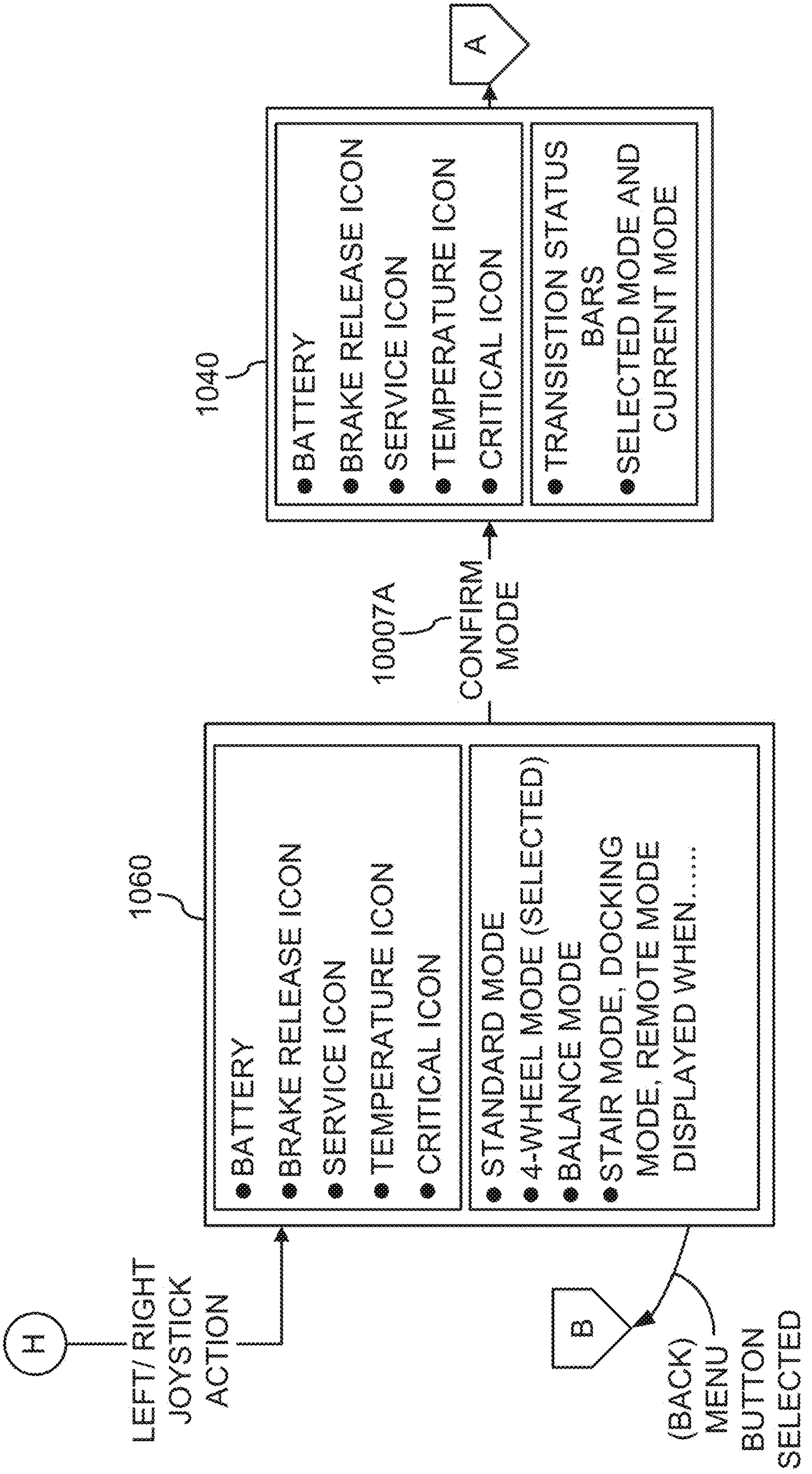
Figure 23F:
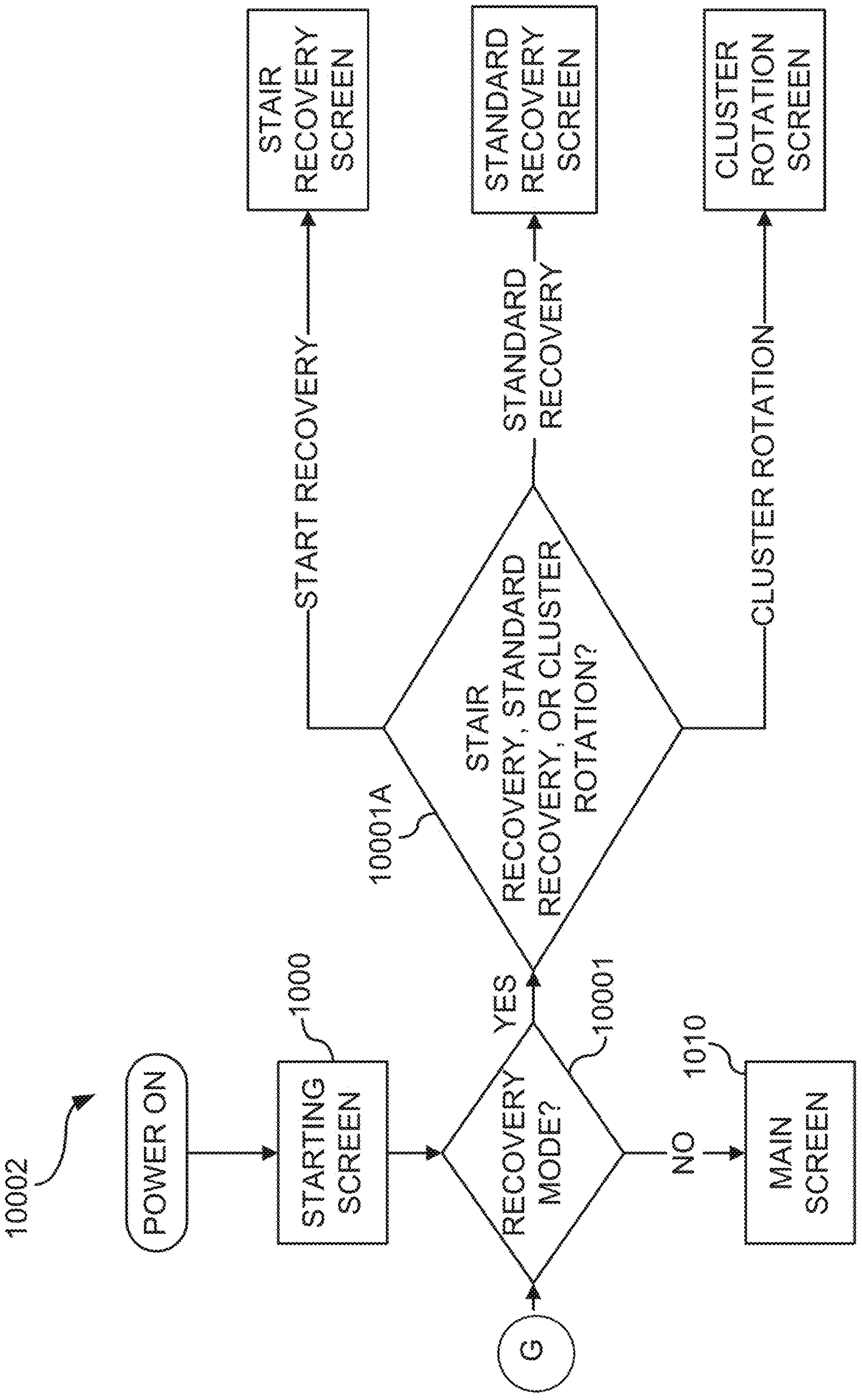
Figure 23G:
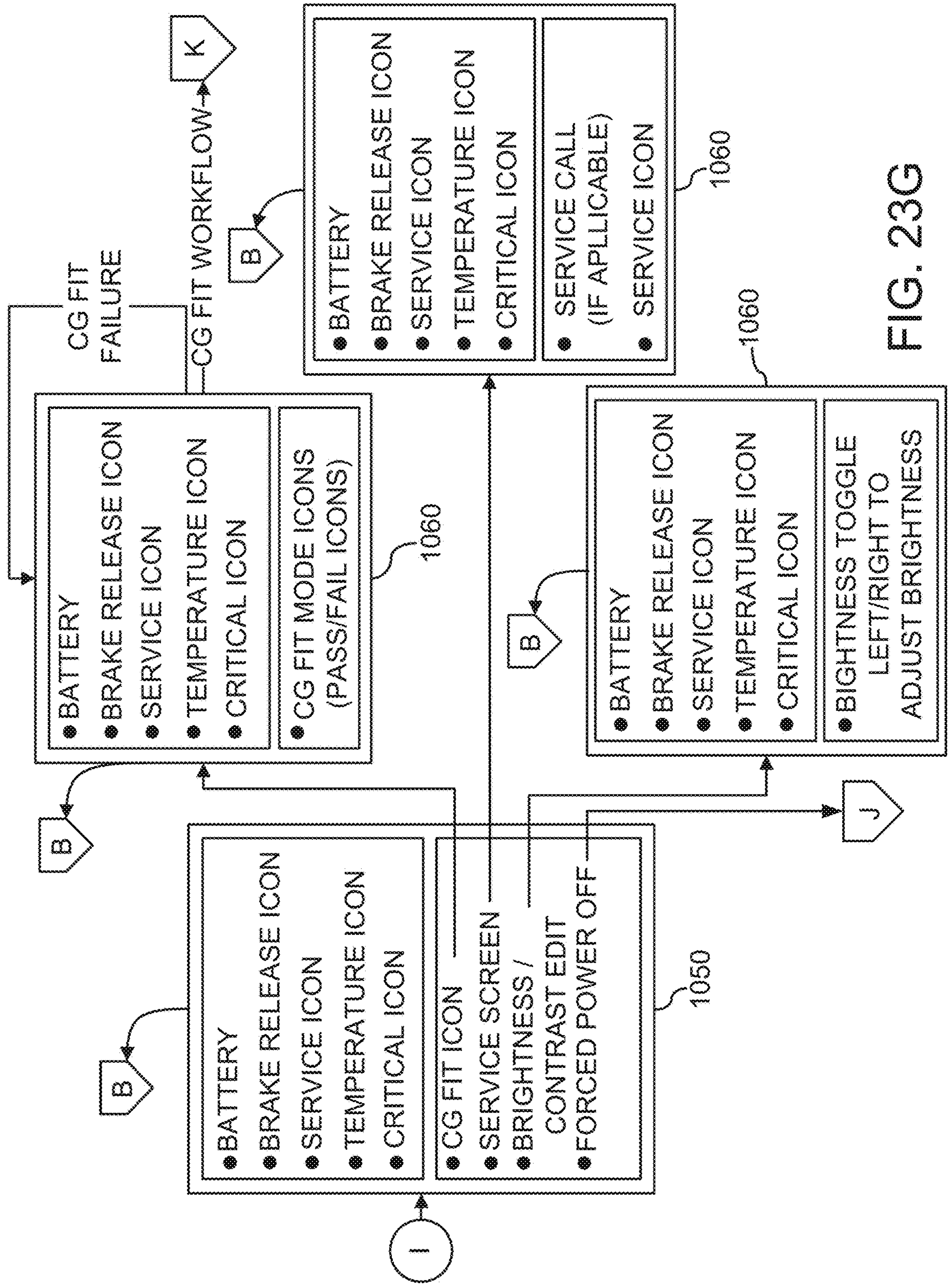
Figure 23H:
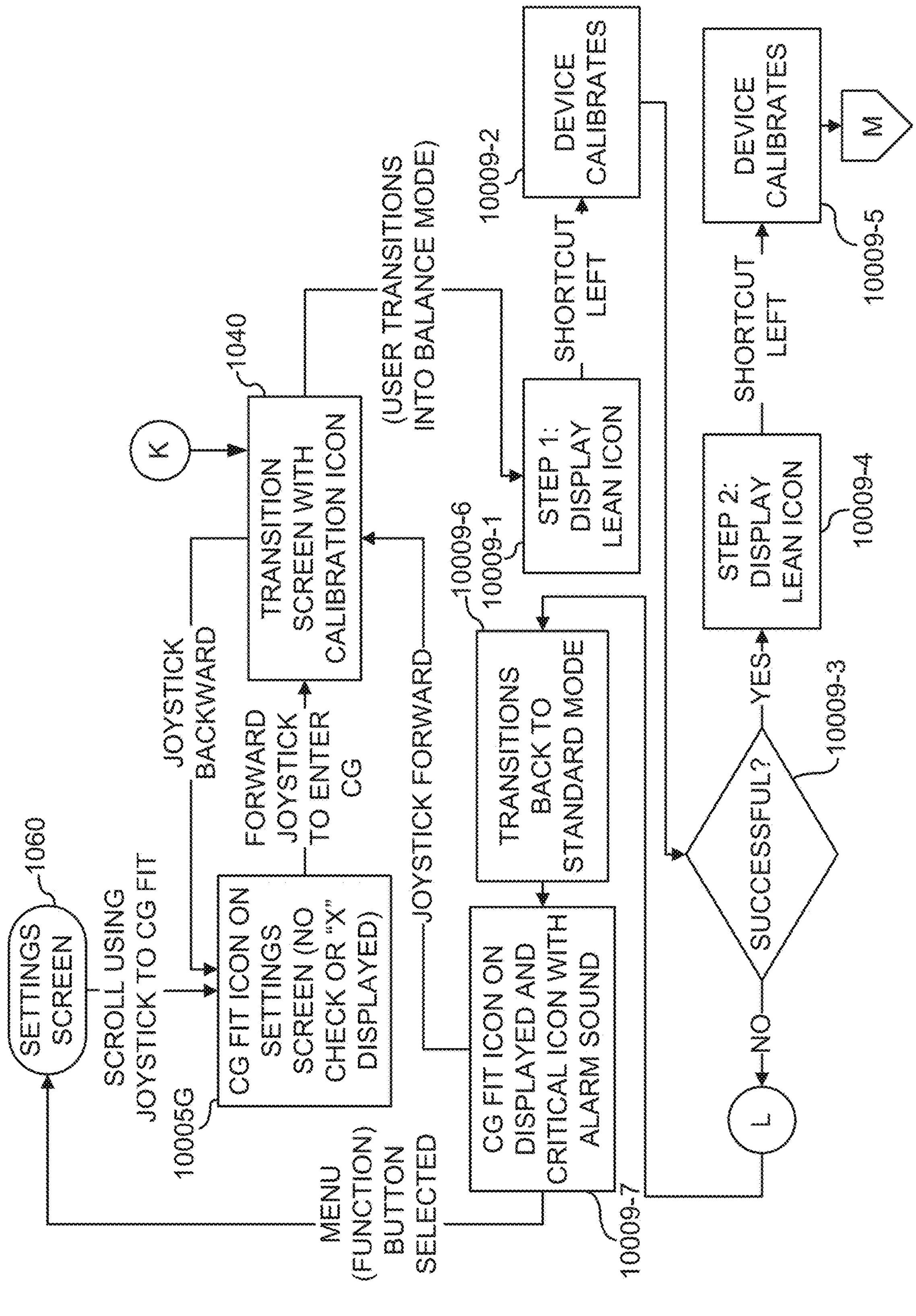
Figure 23I:
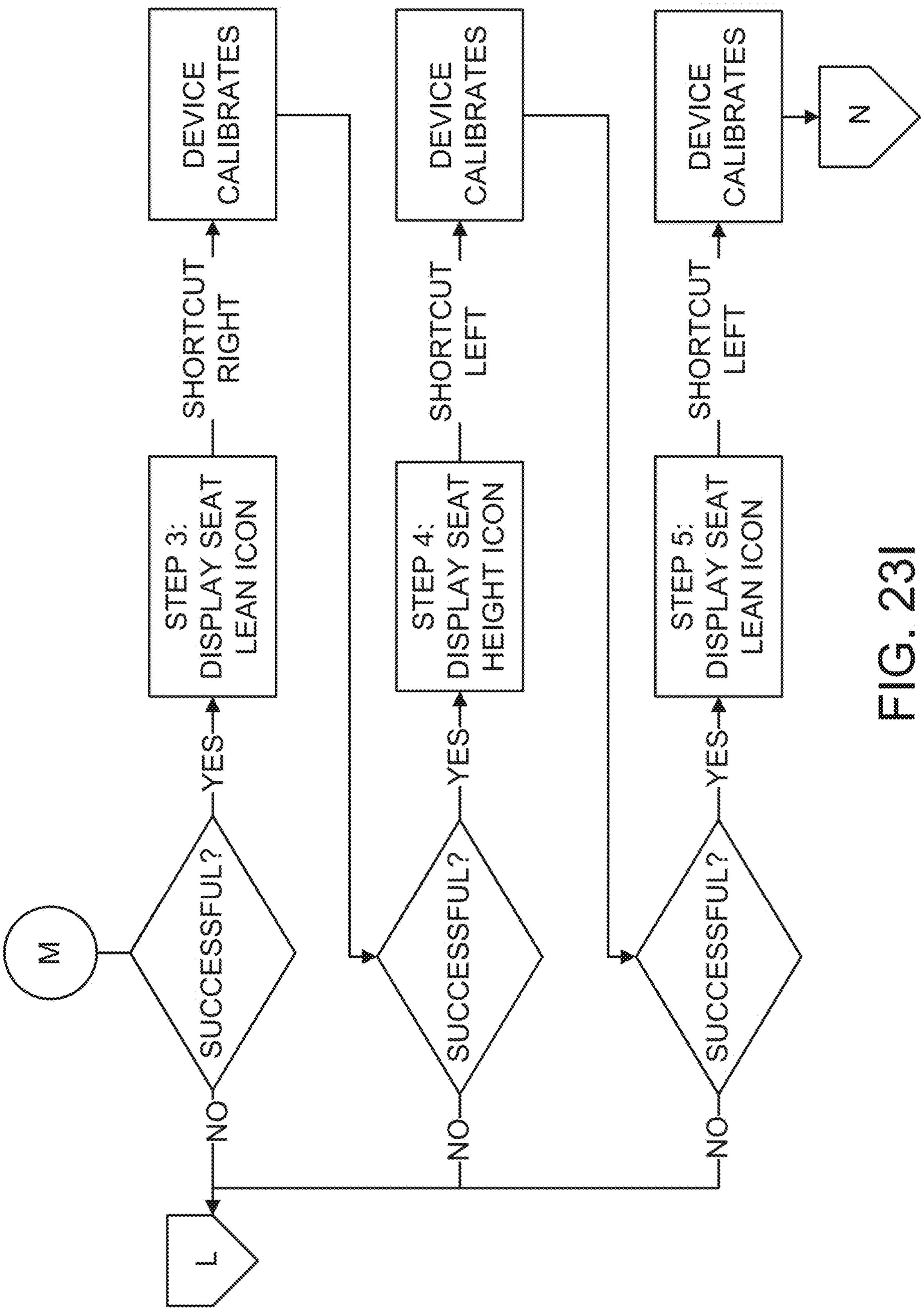
Figure 23J:
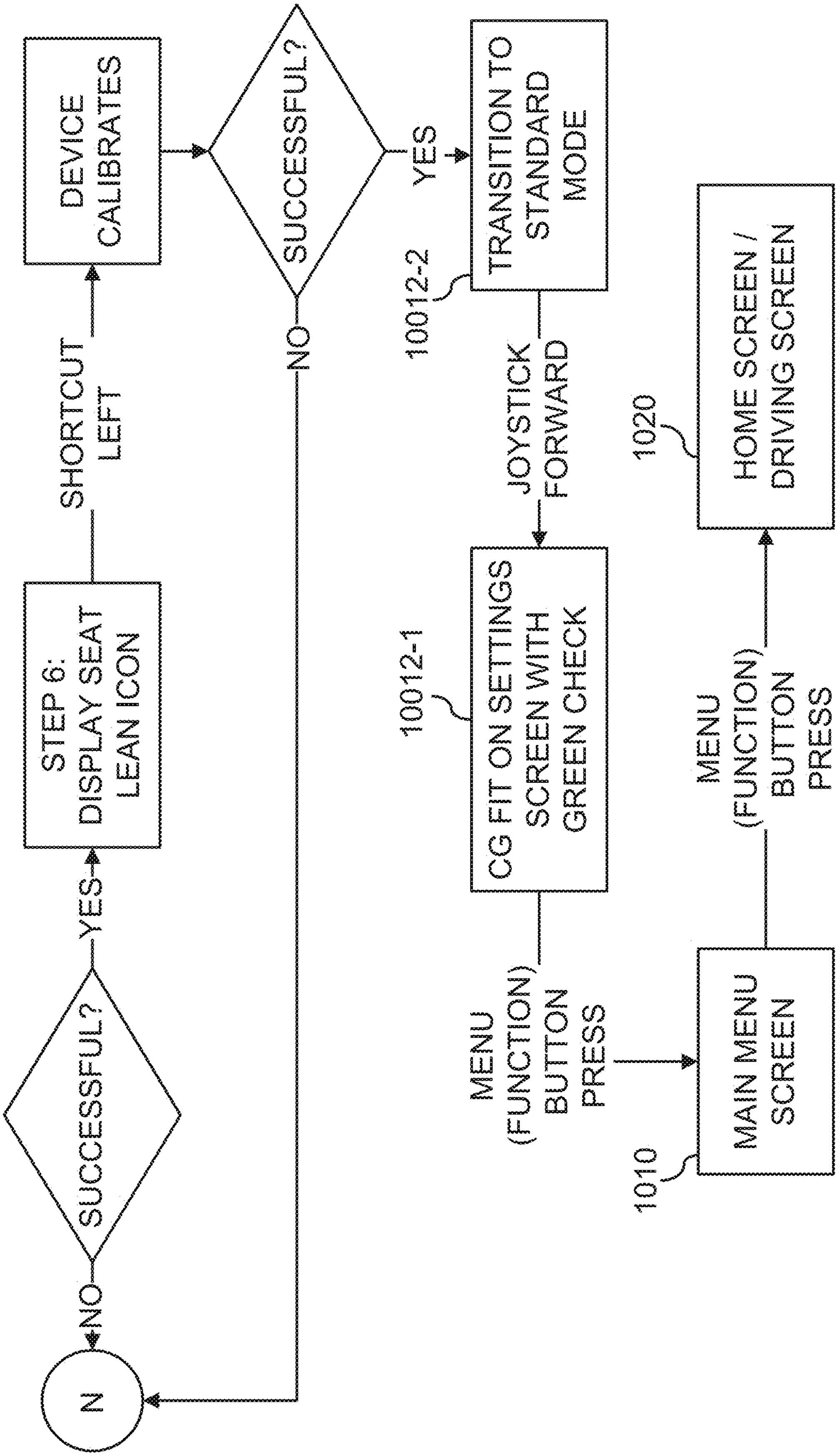
Figure 23K:
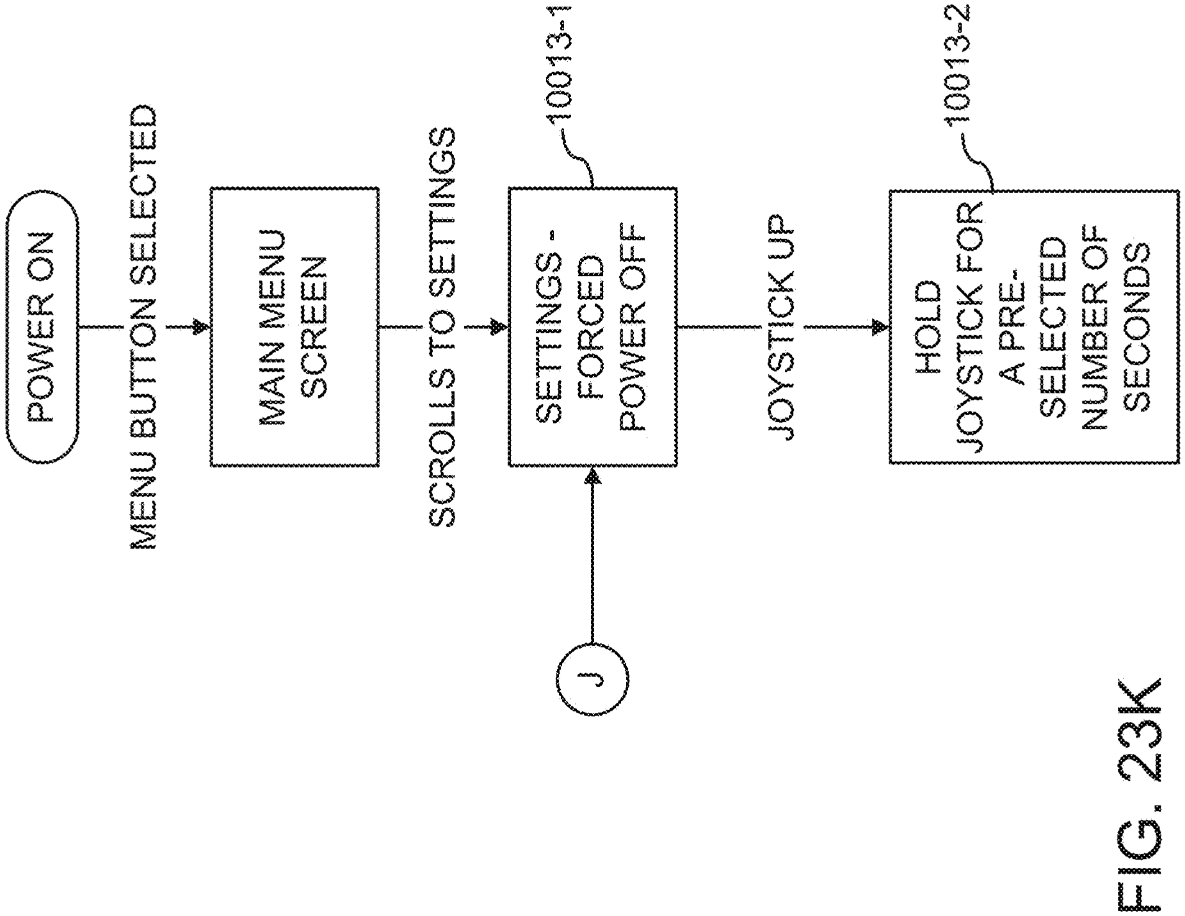
Figure 23L:
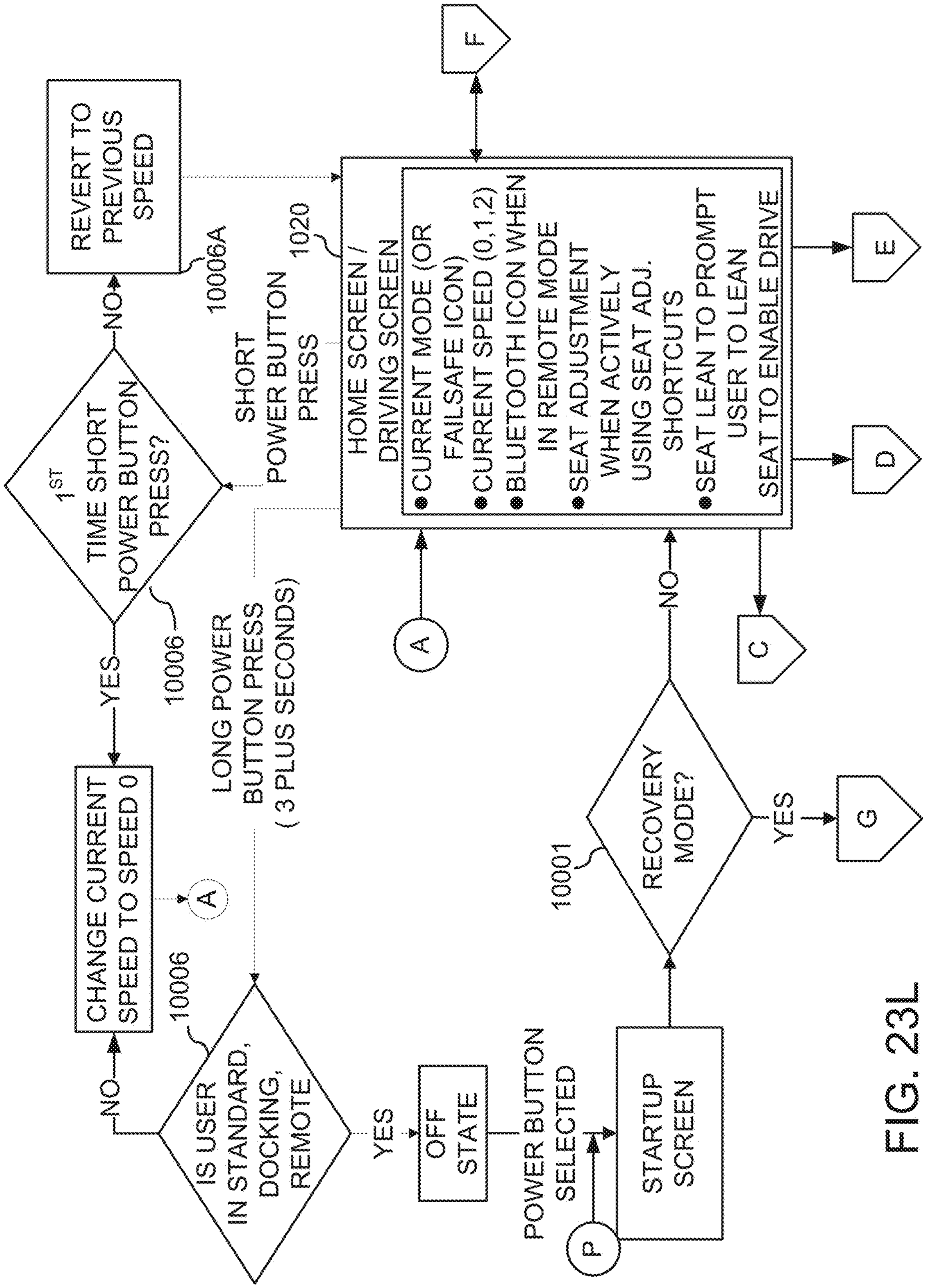
Figure 23M:
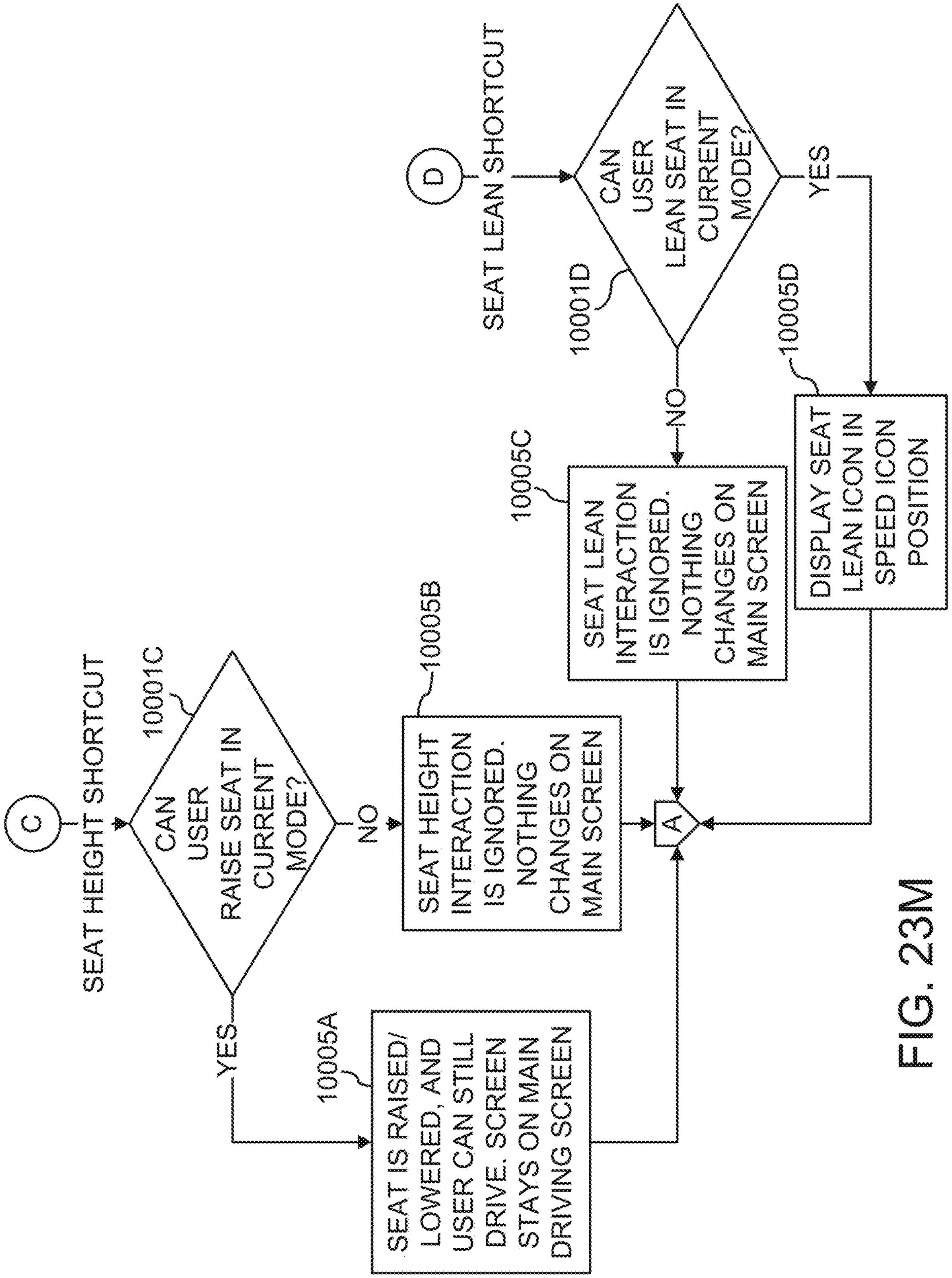
Figure 23N:
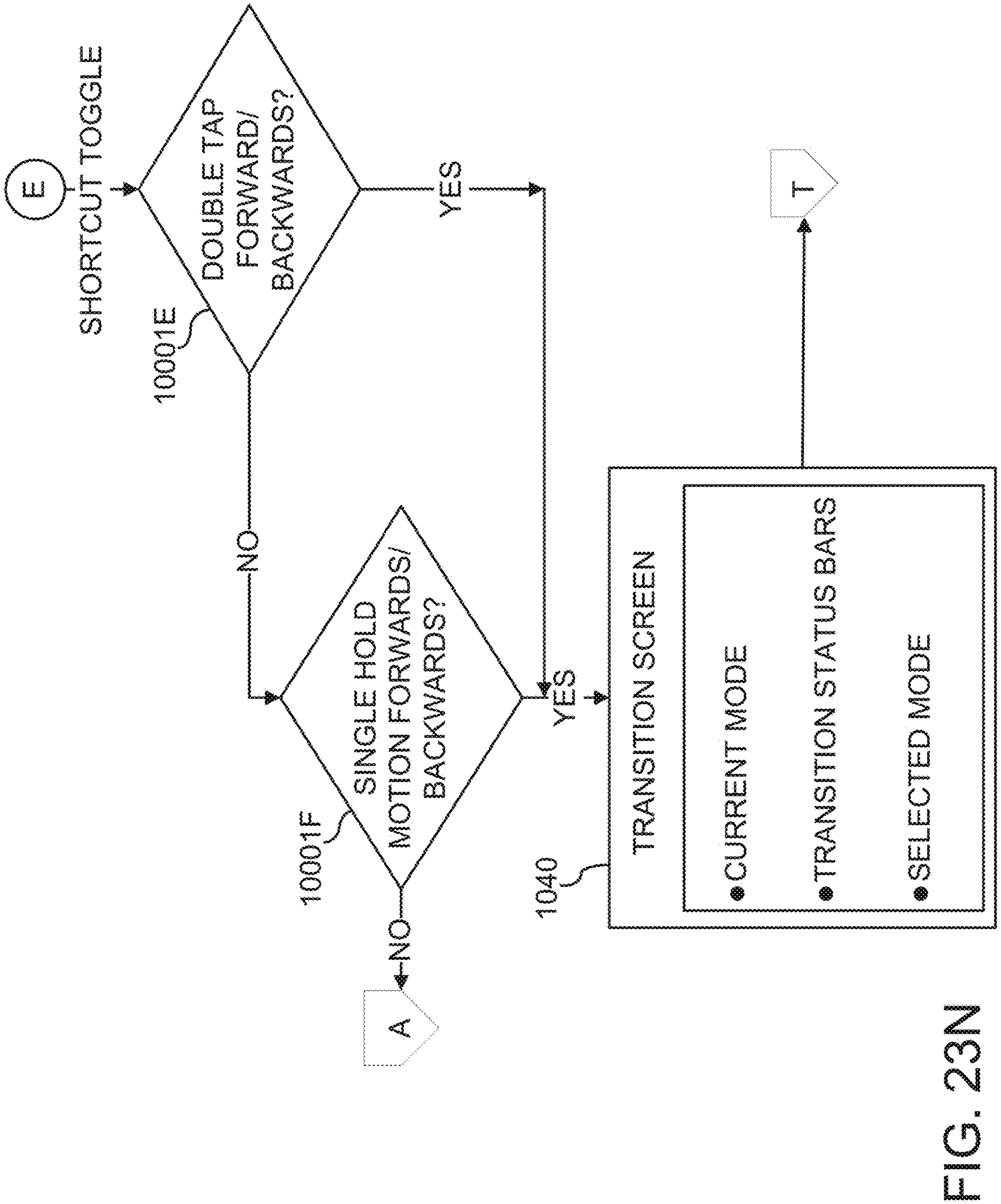
Figure 23O:
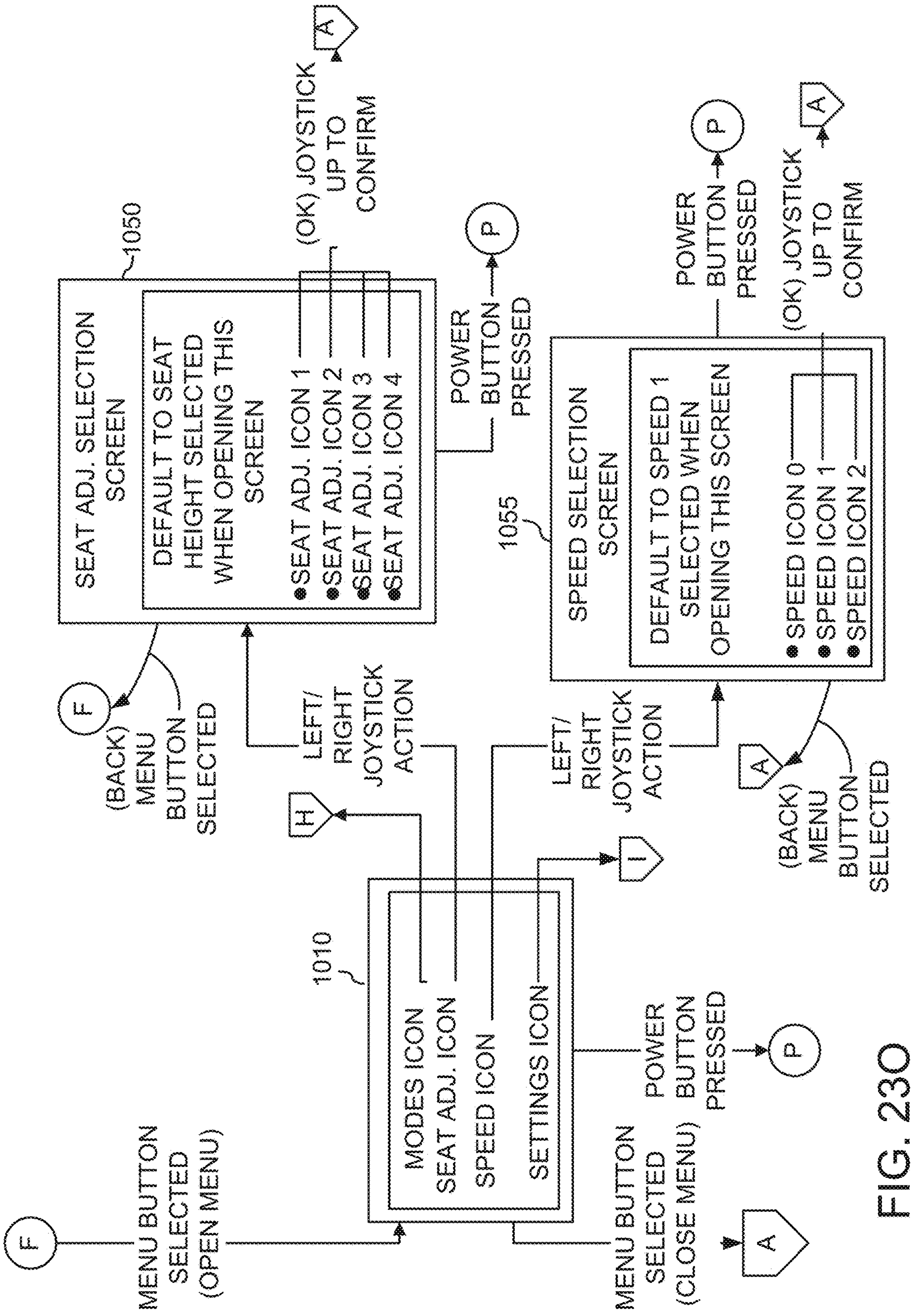
Figure 23Q:
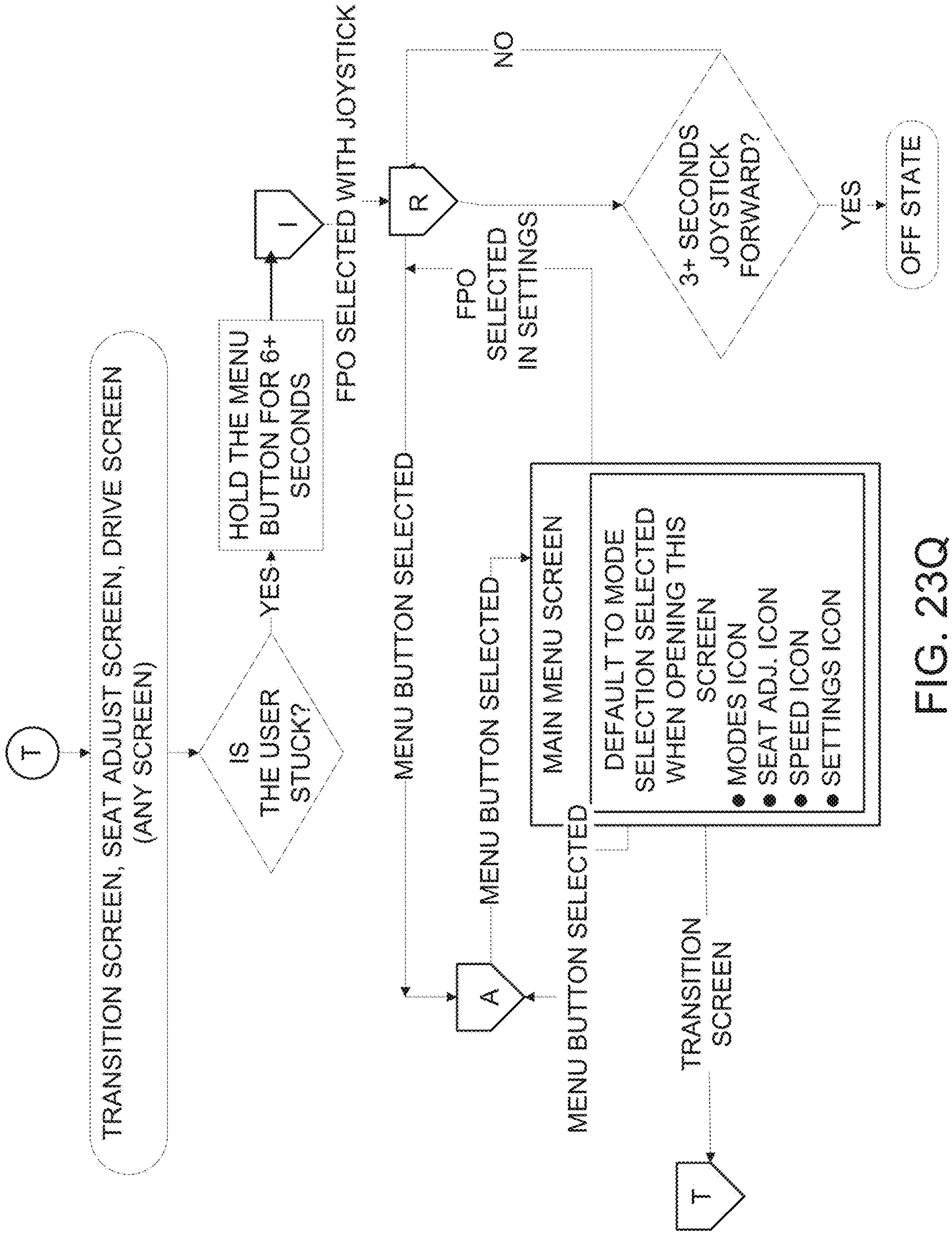
Figure 23R:
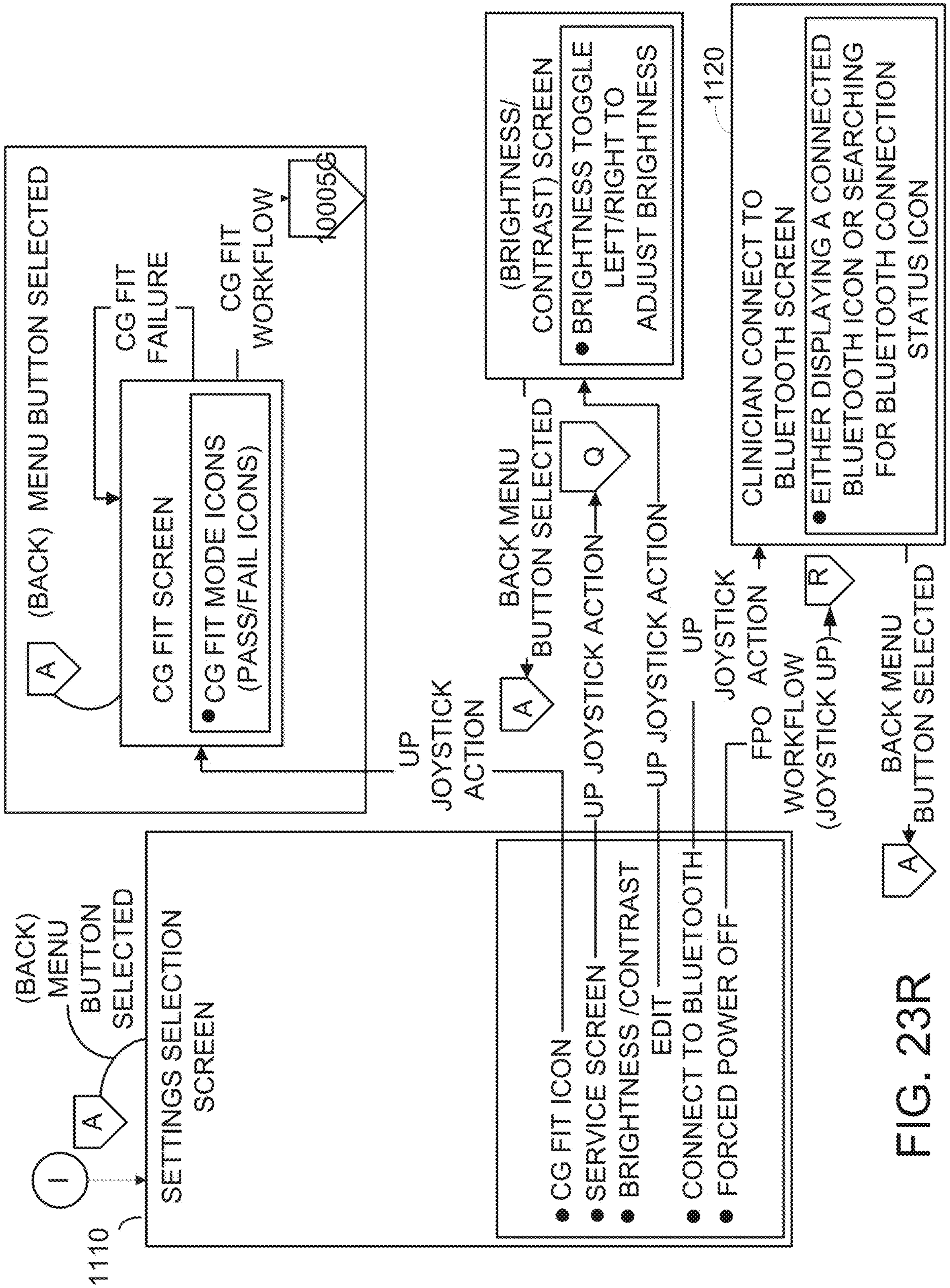
Figure 23S:
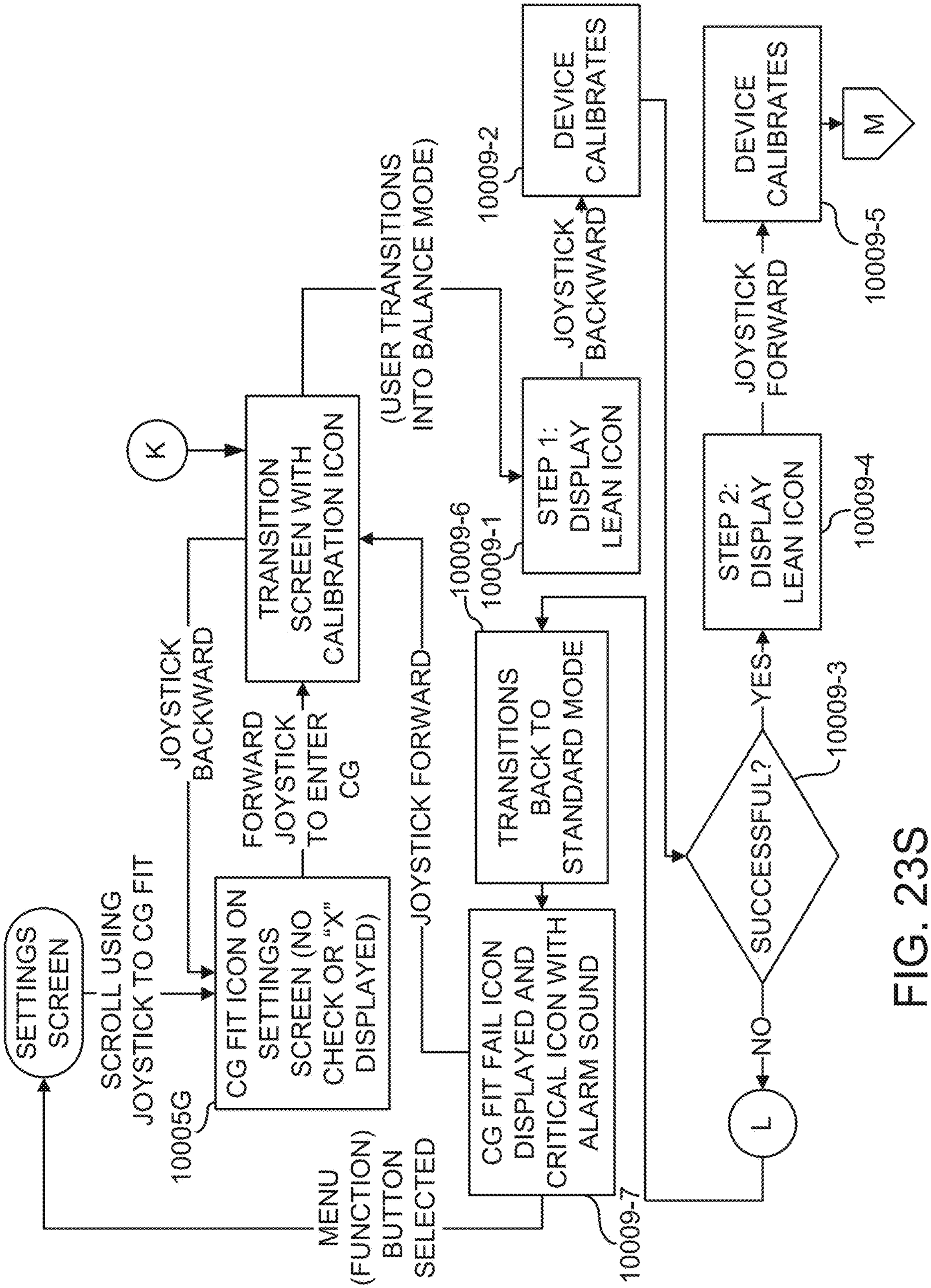
Figure 23T:
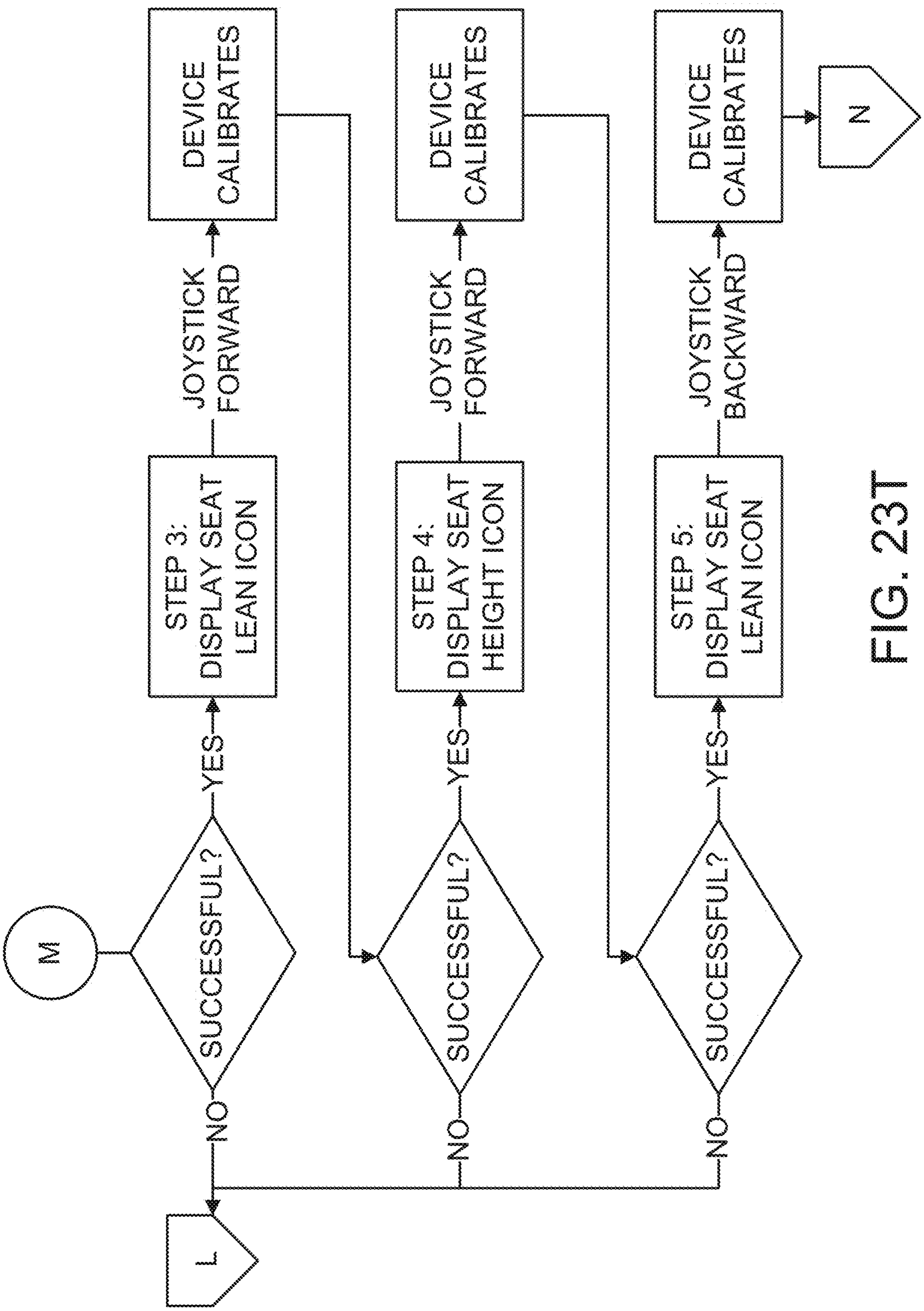
Figure 23U:
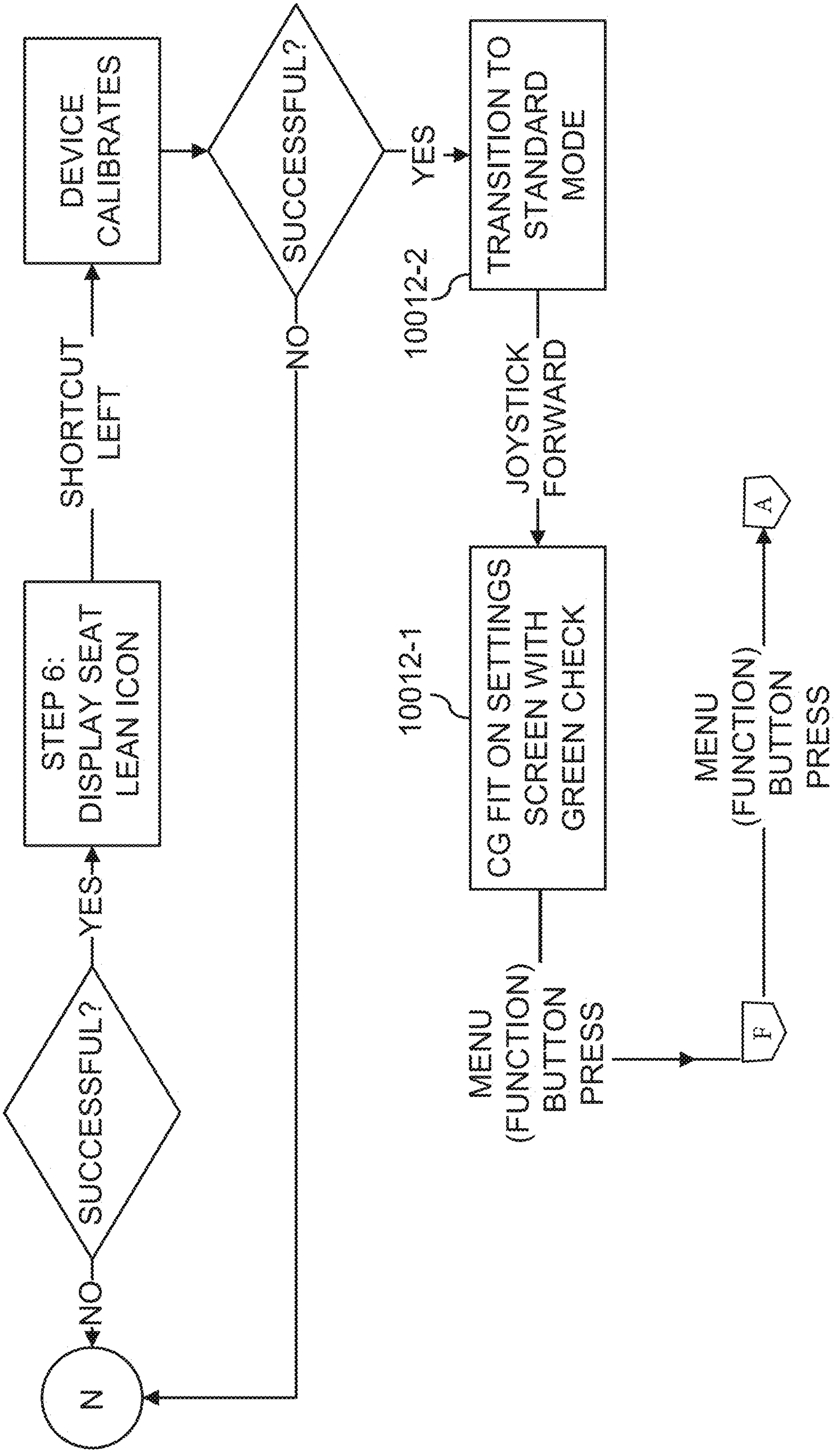
Figure 23V:
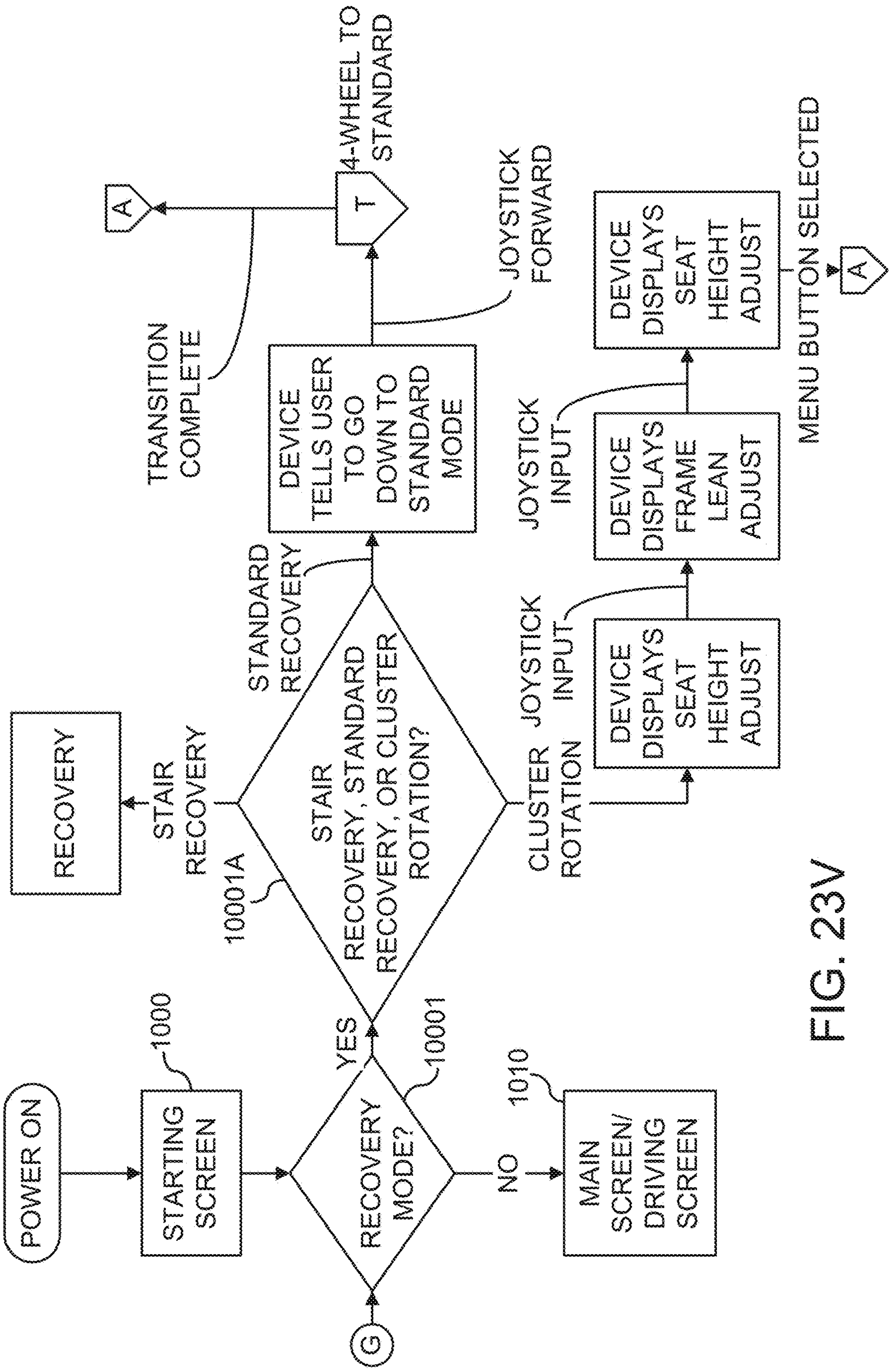
Figure 23W:
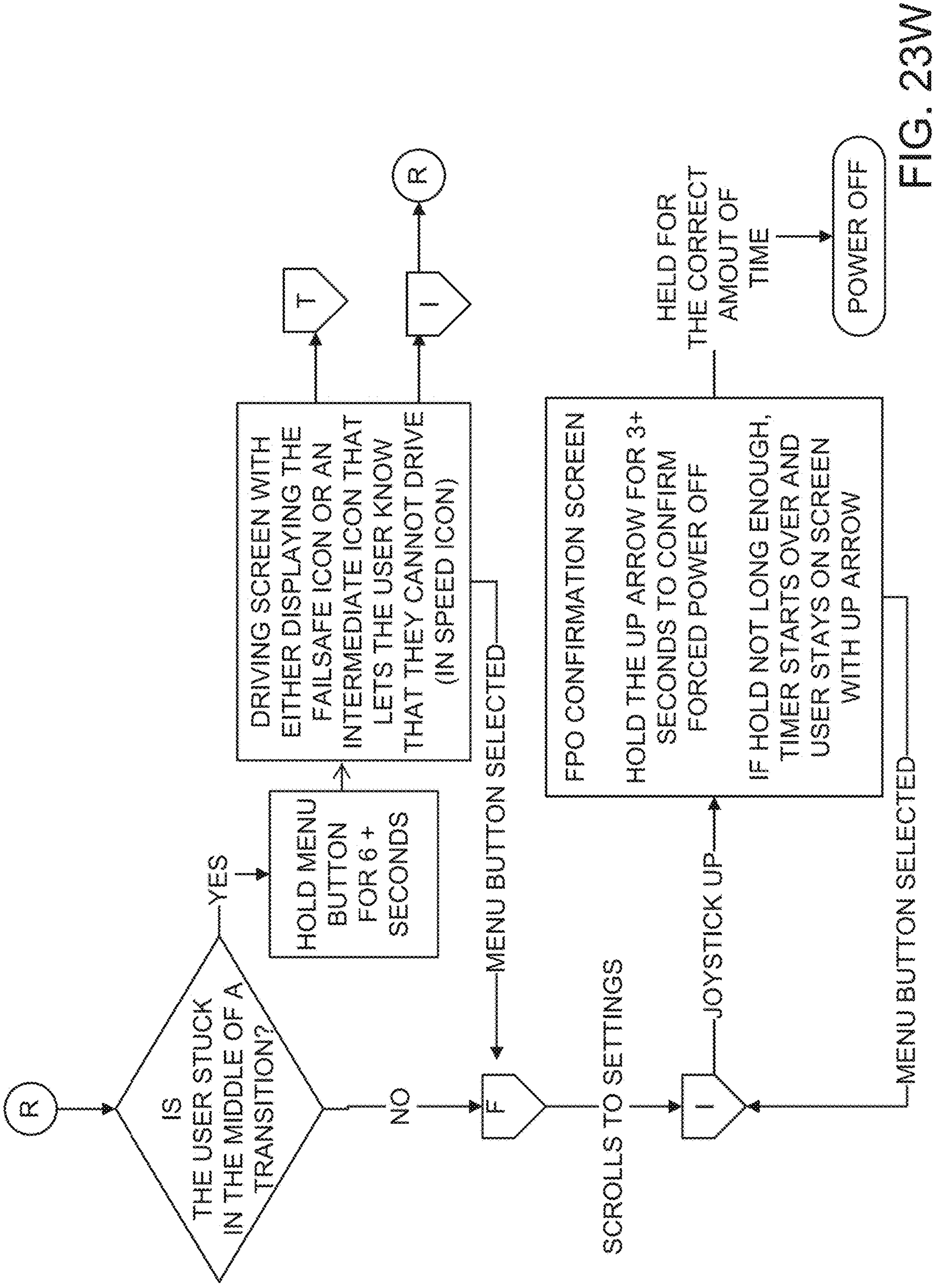
Figure 23X:
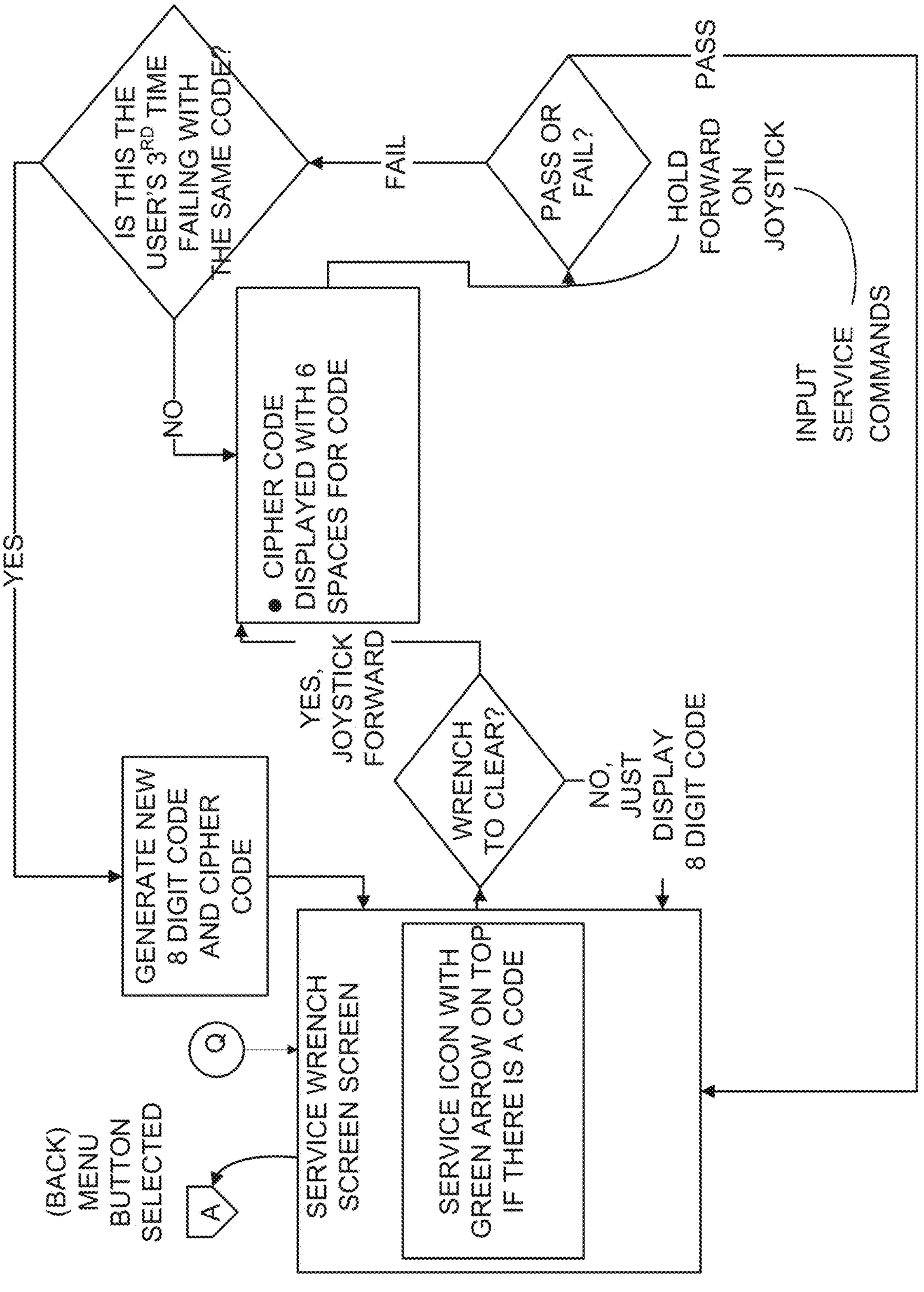
Figure 23Y:
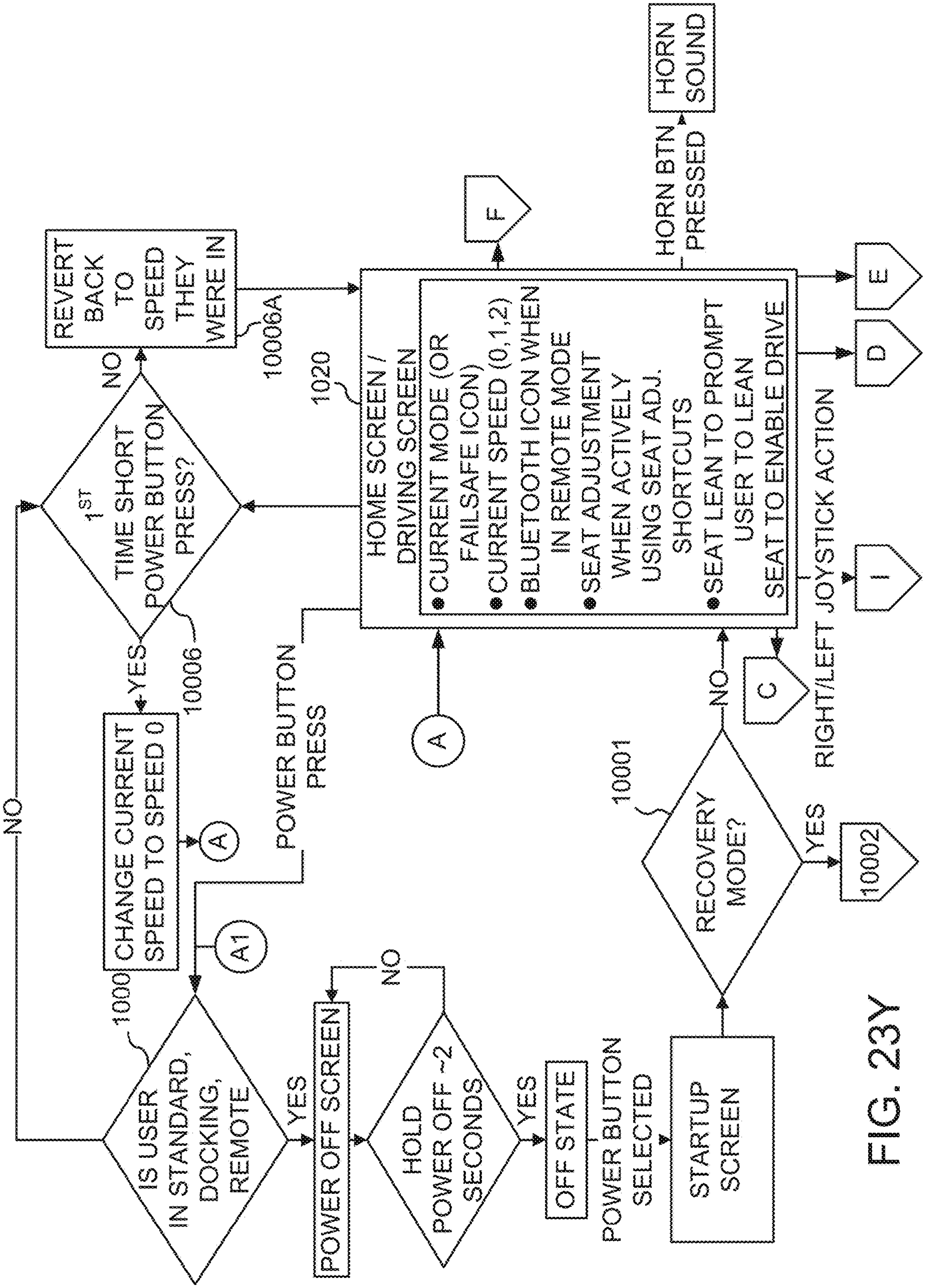
Figure 24A:
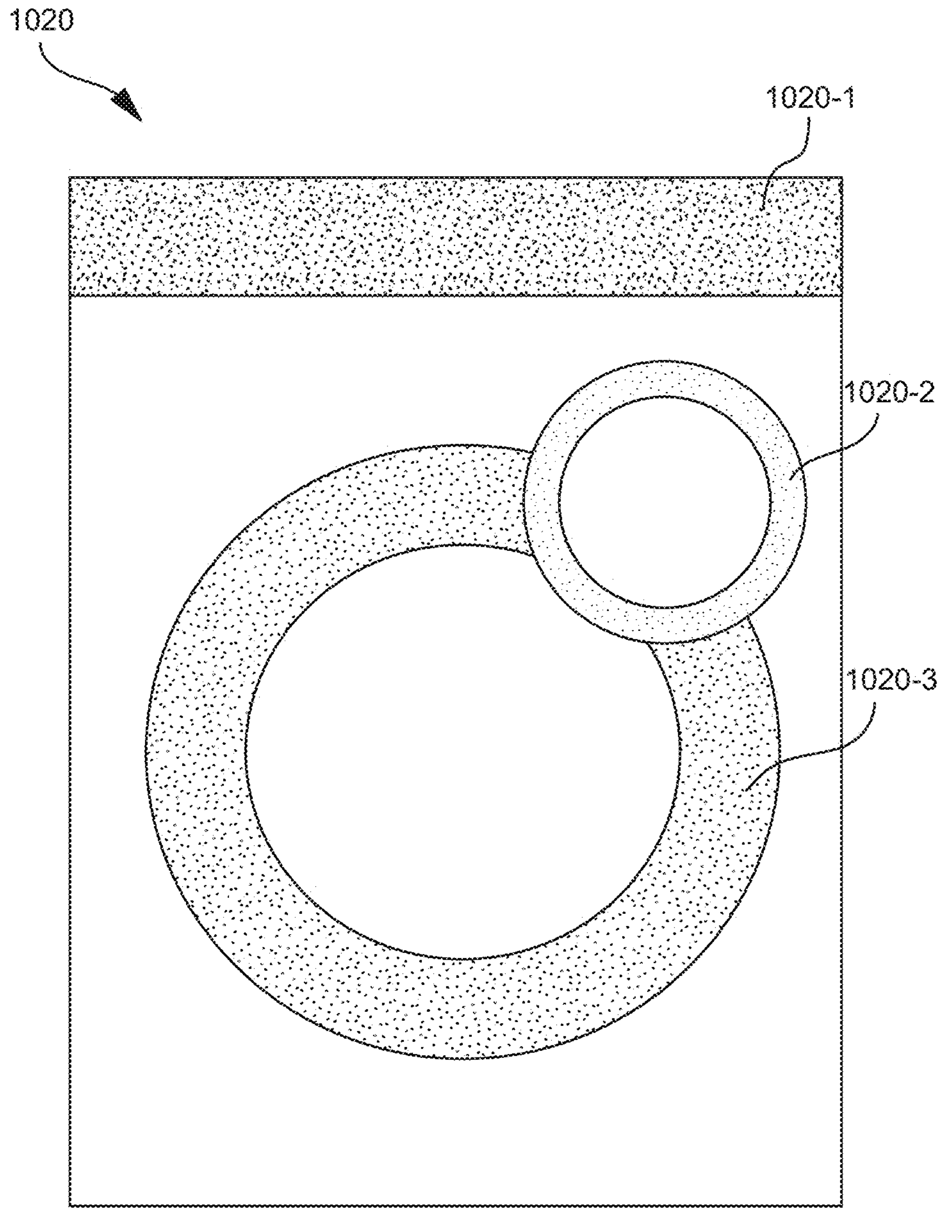
Figure 24B:
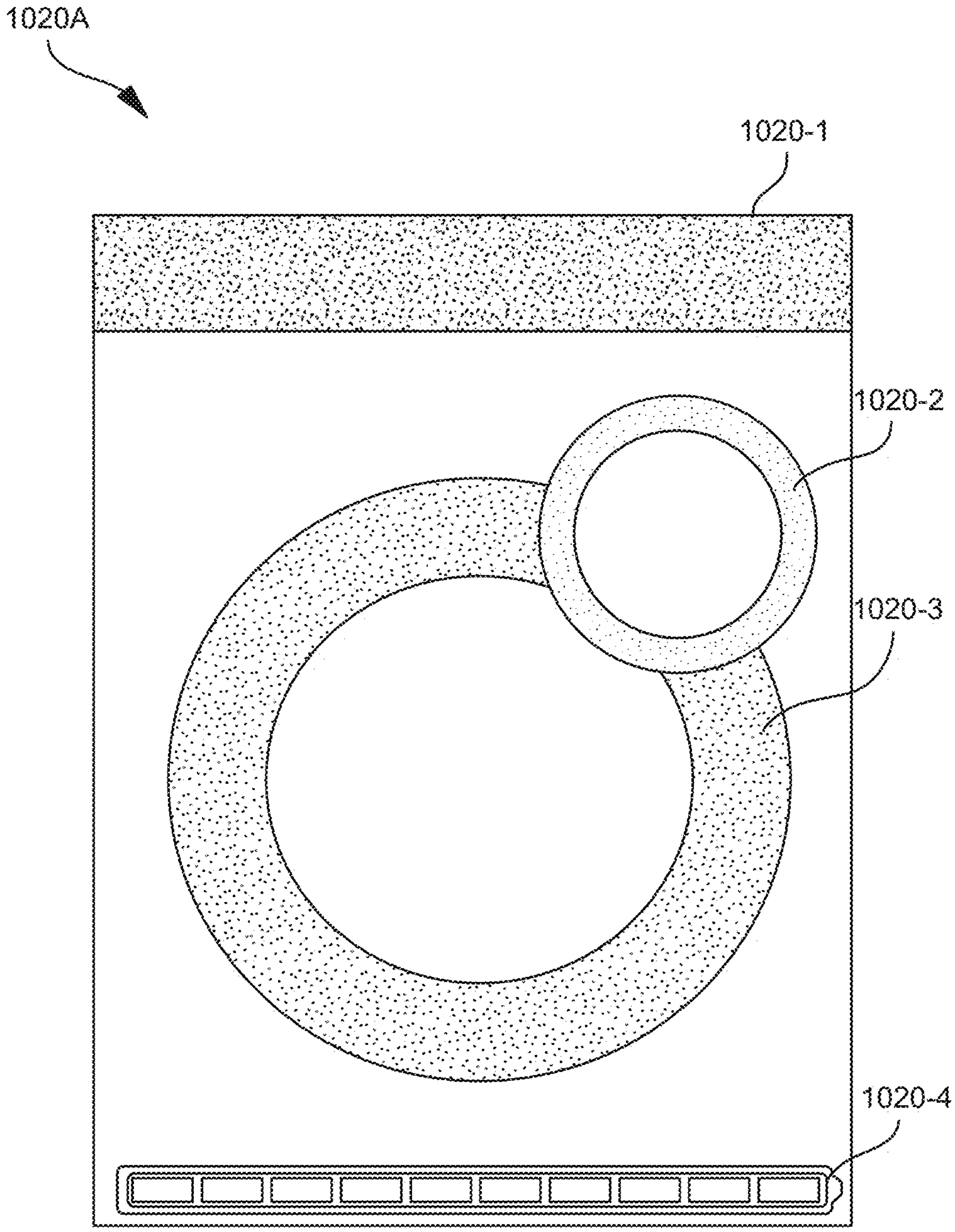
Figure 24C:
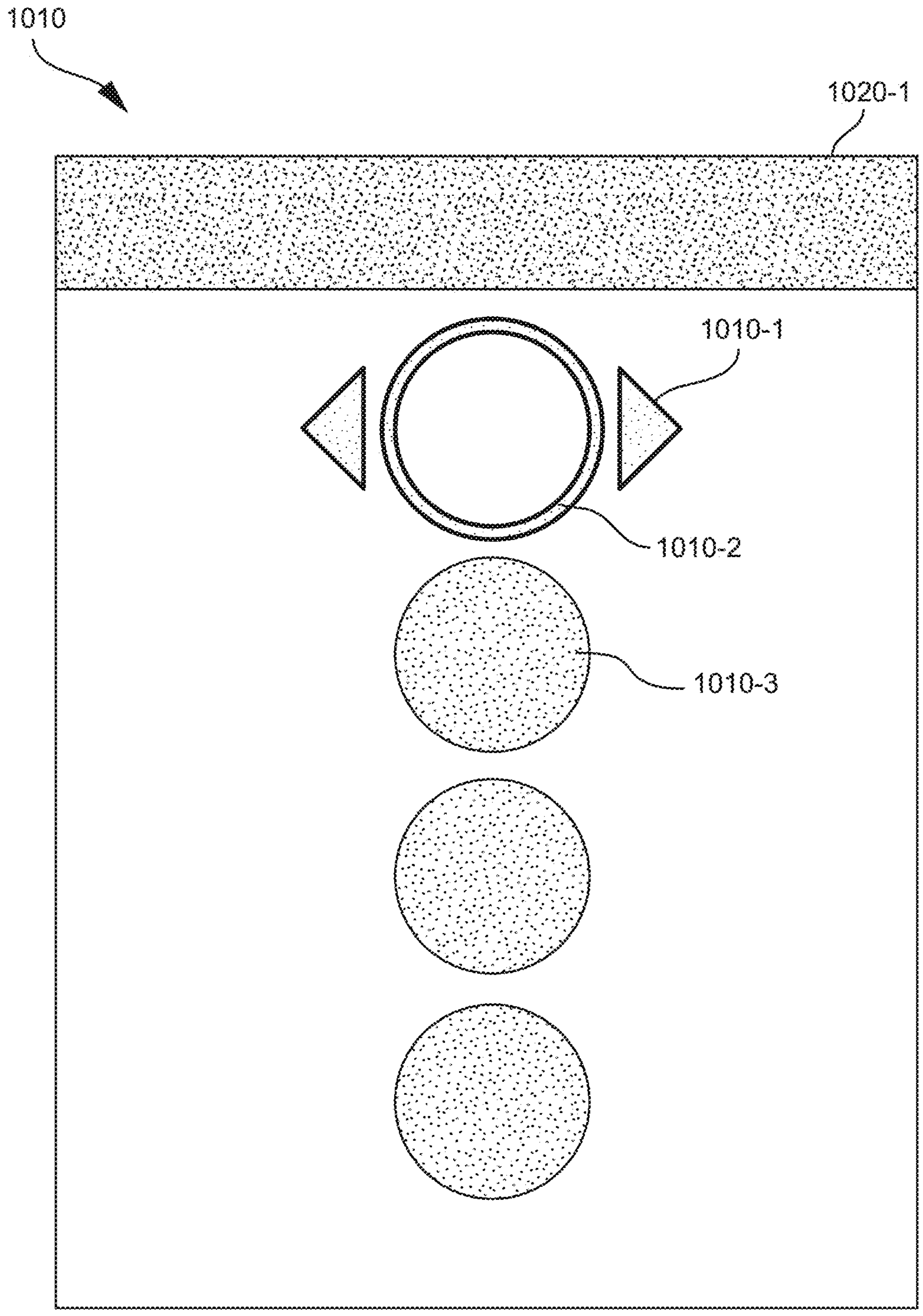
Figure 24D:
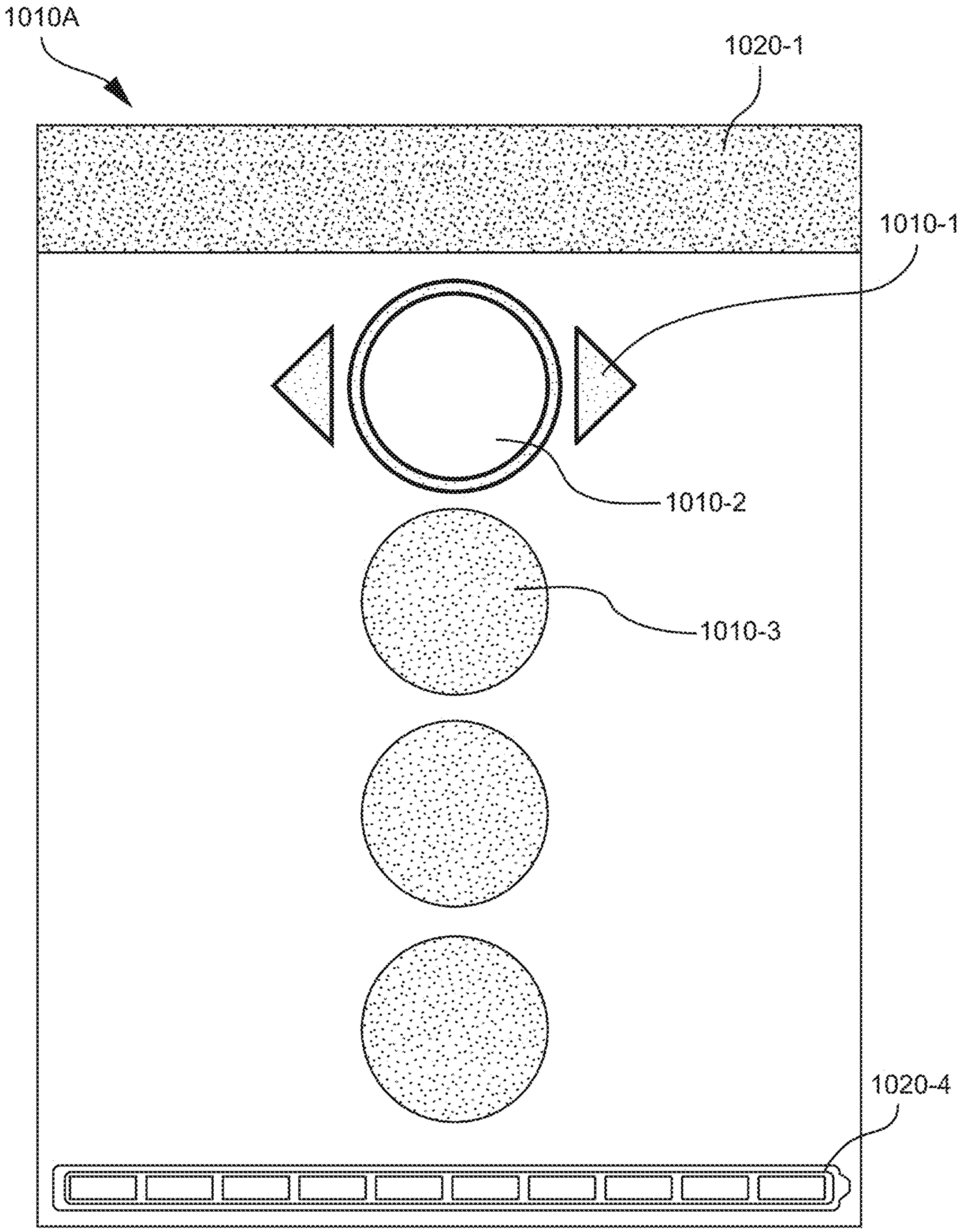
Figure 24E:
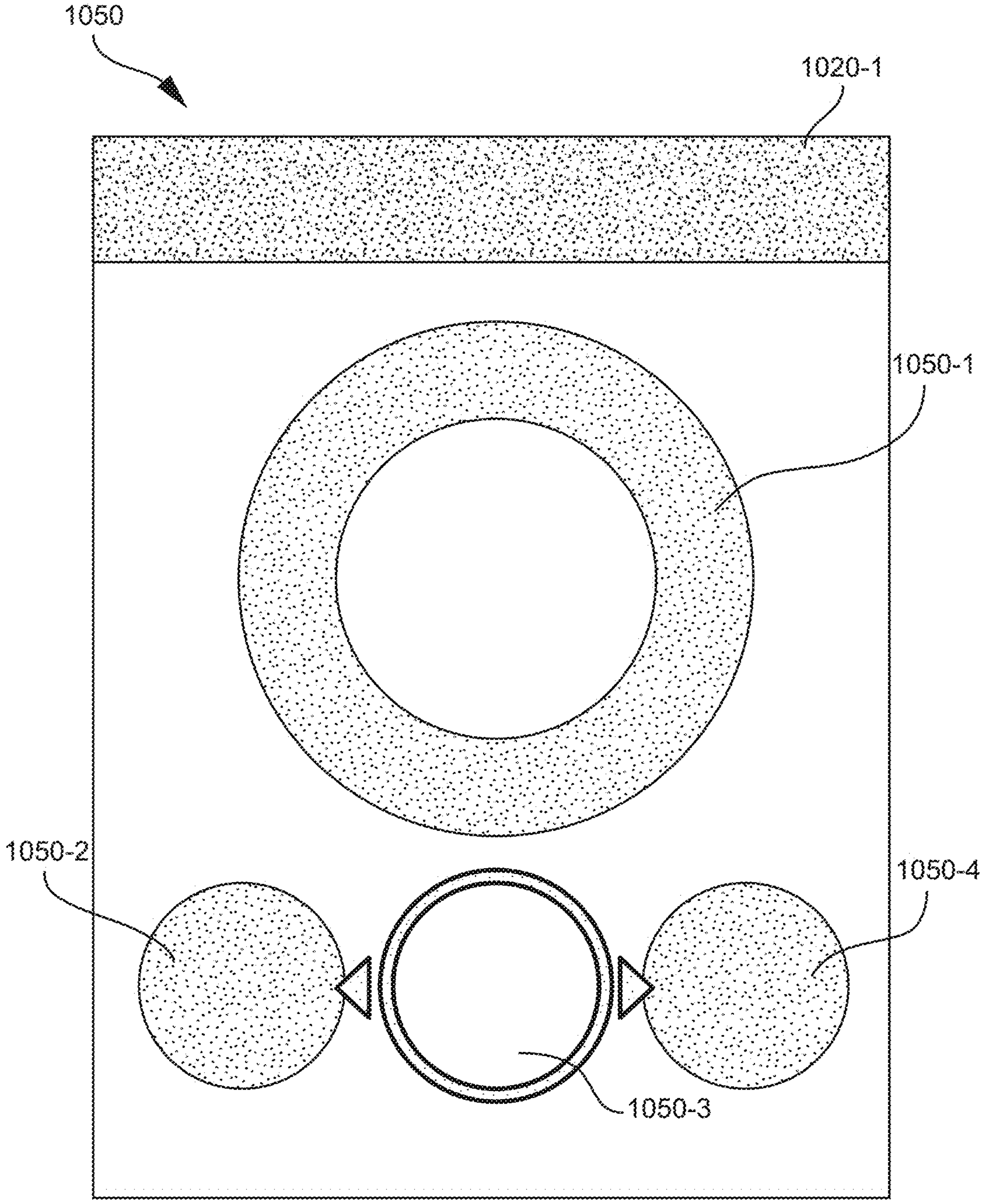
Figure 24F:
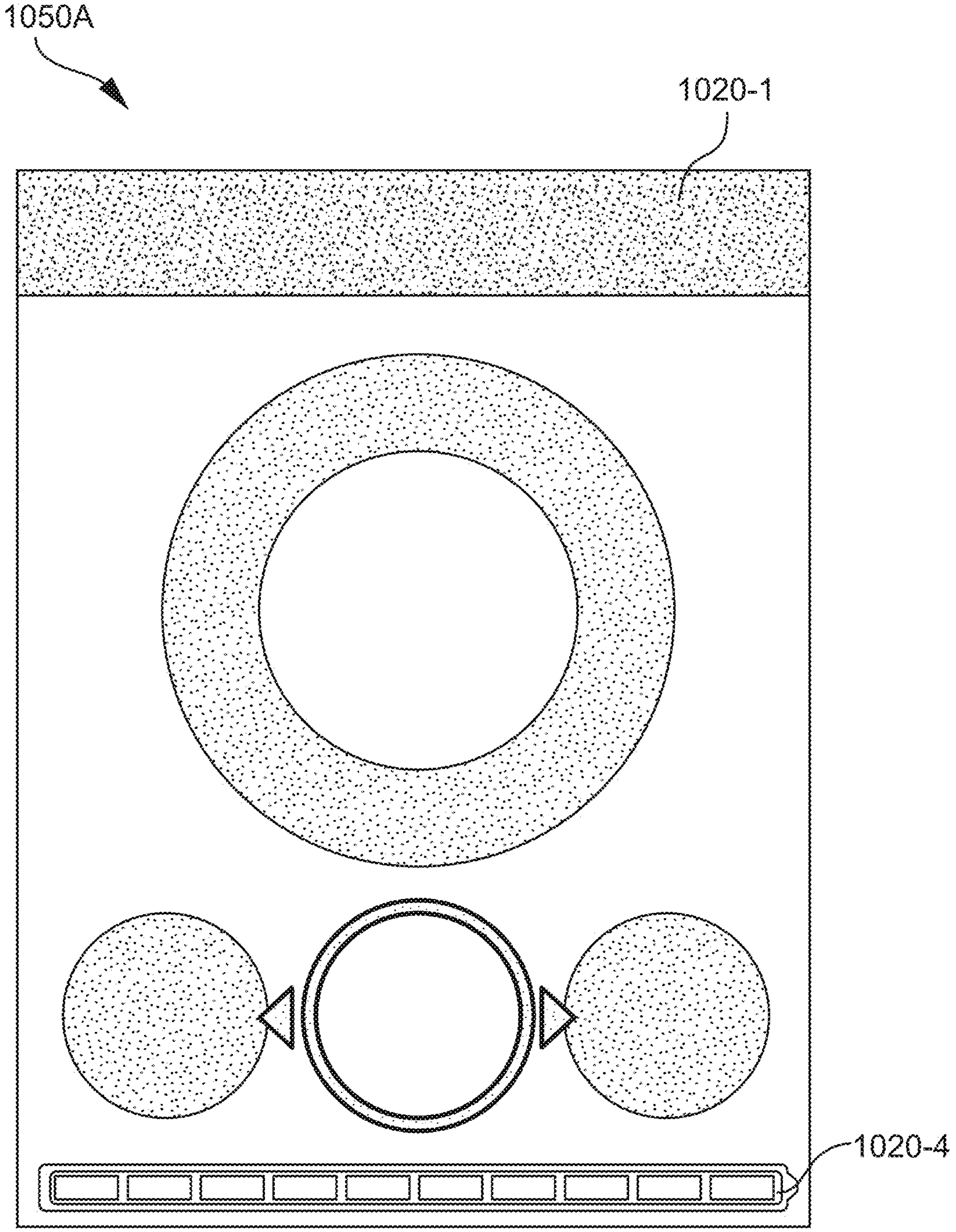
Figure 24G:
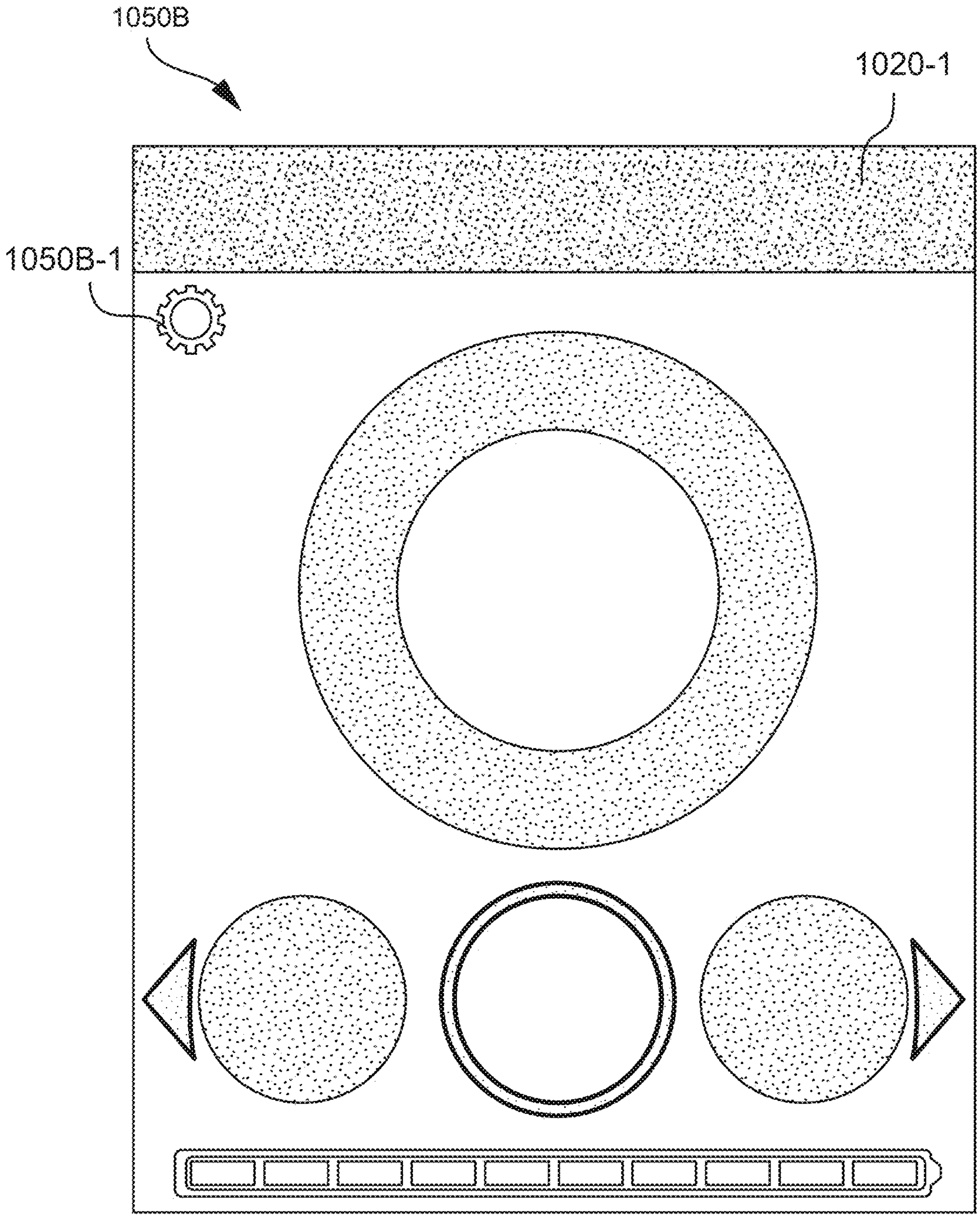
Figure 24H:
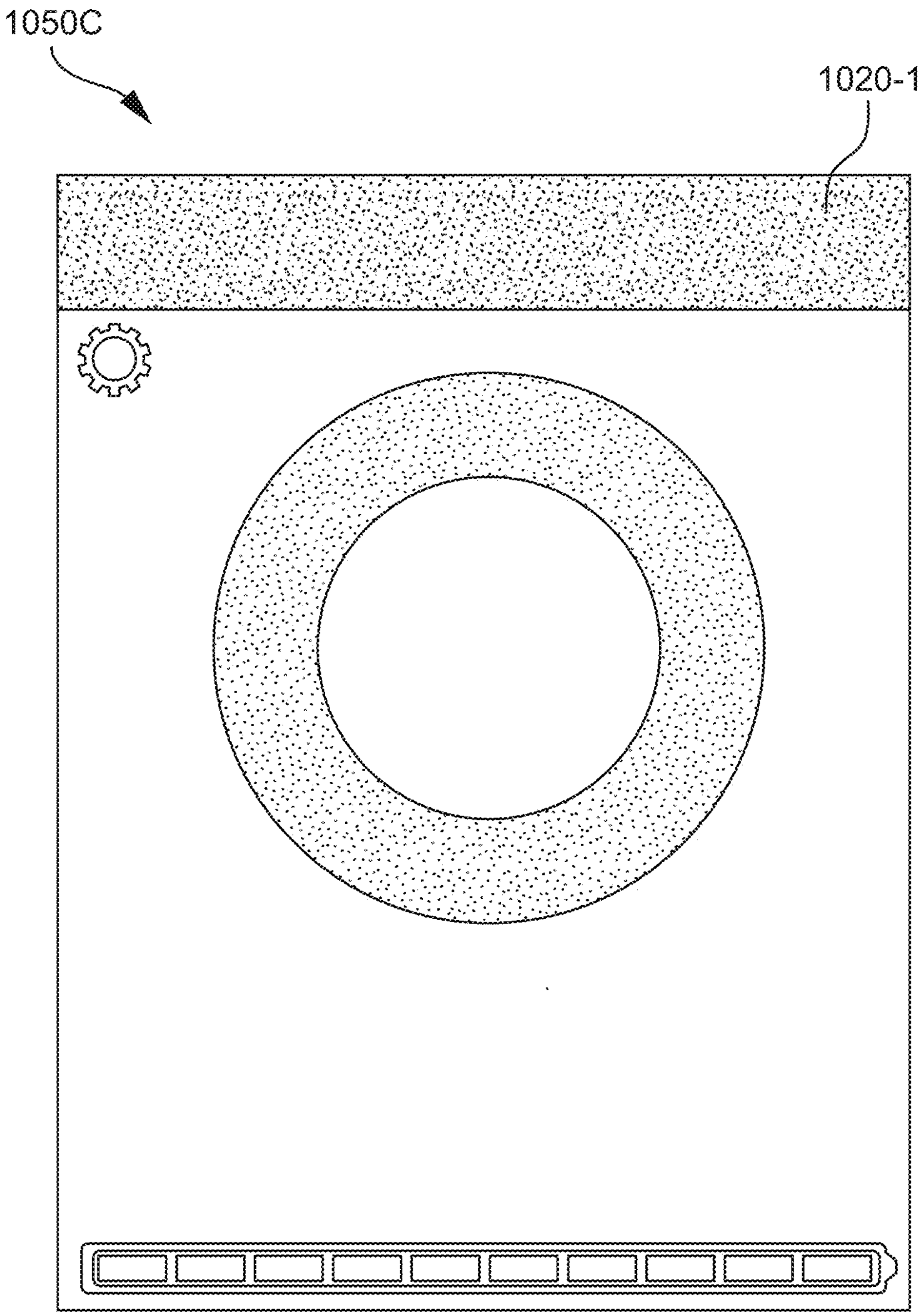
Figure 24I:
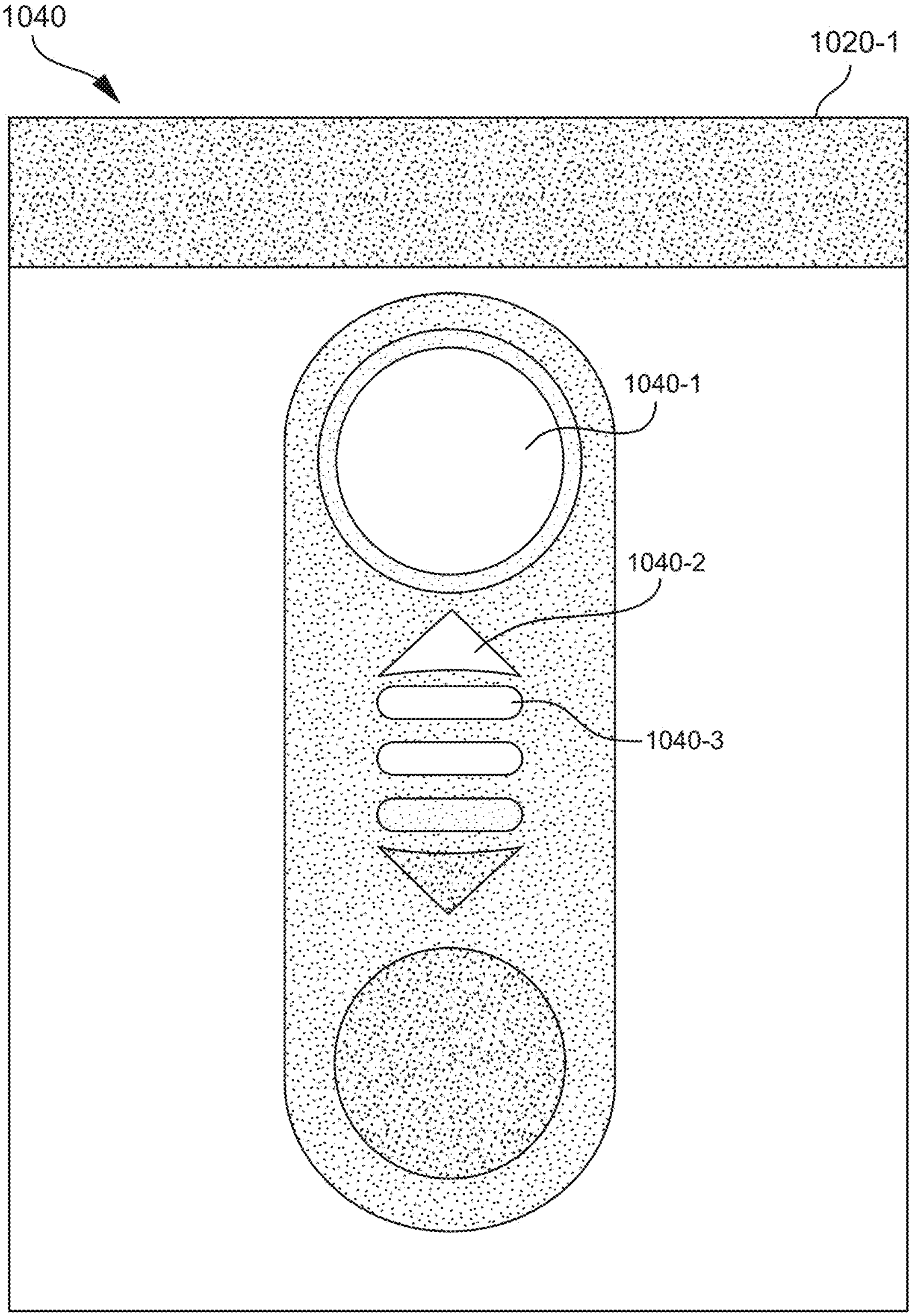
Figure 24J:
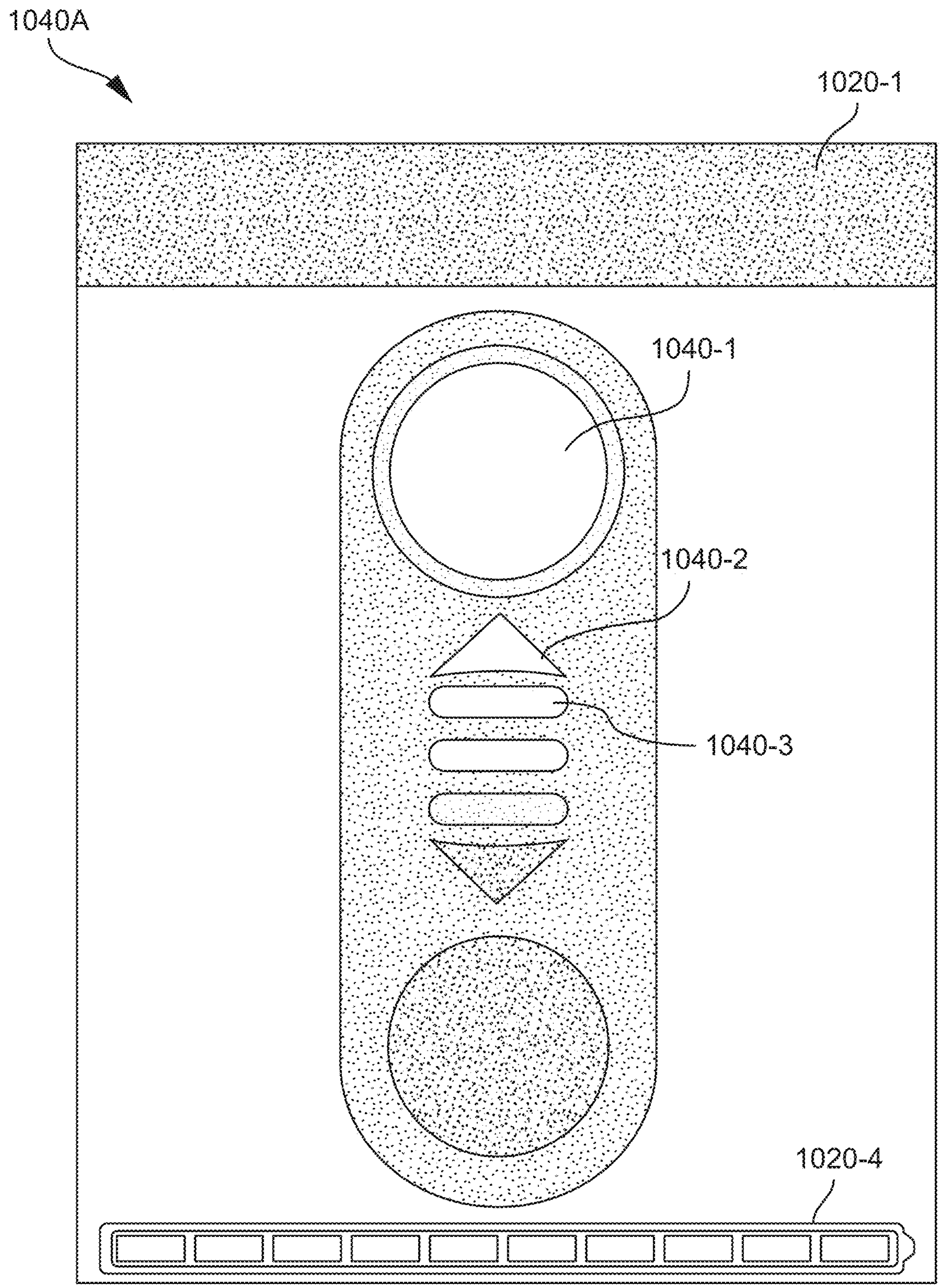
Figure 24K:
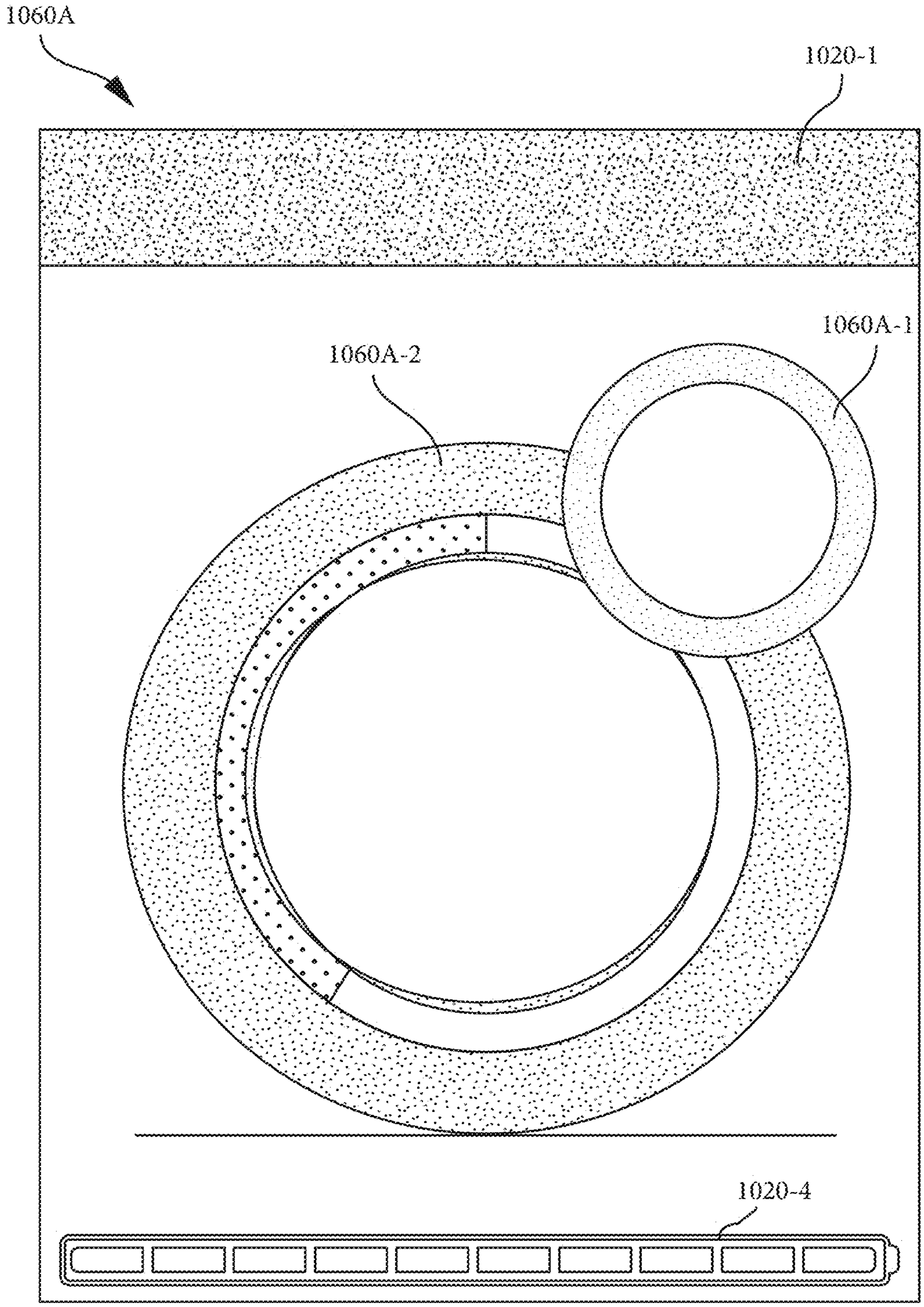
Figure 24L:
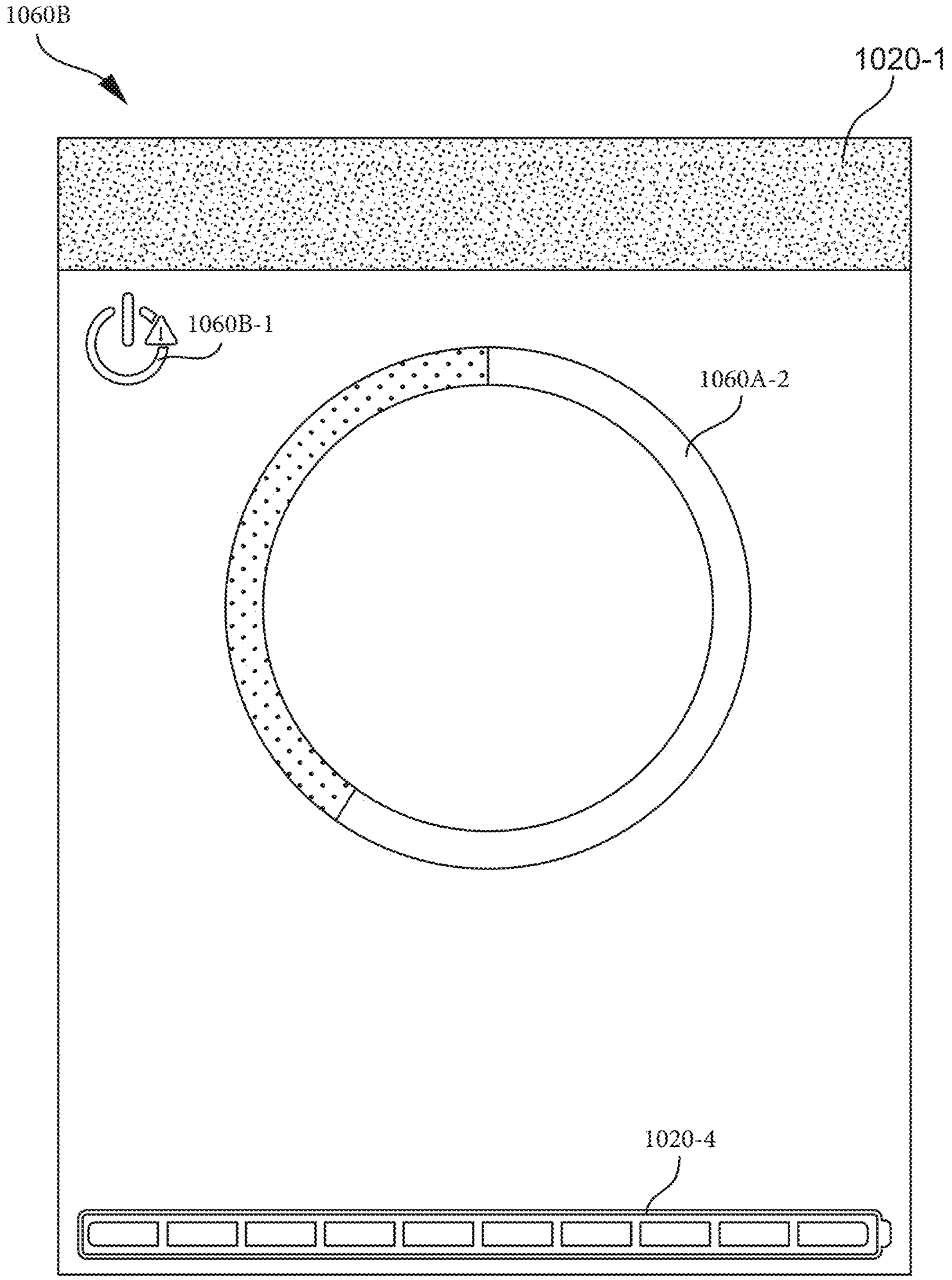
Figure 24M:
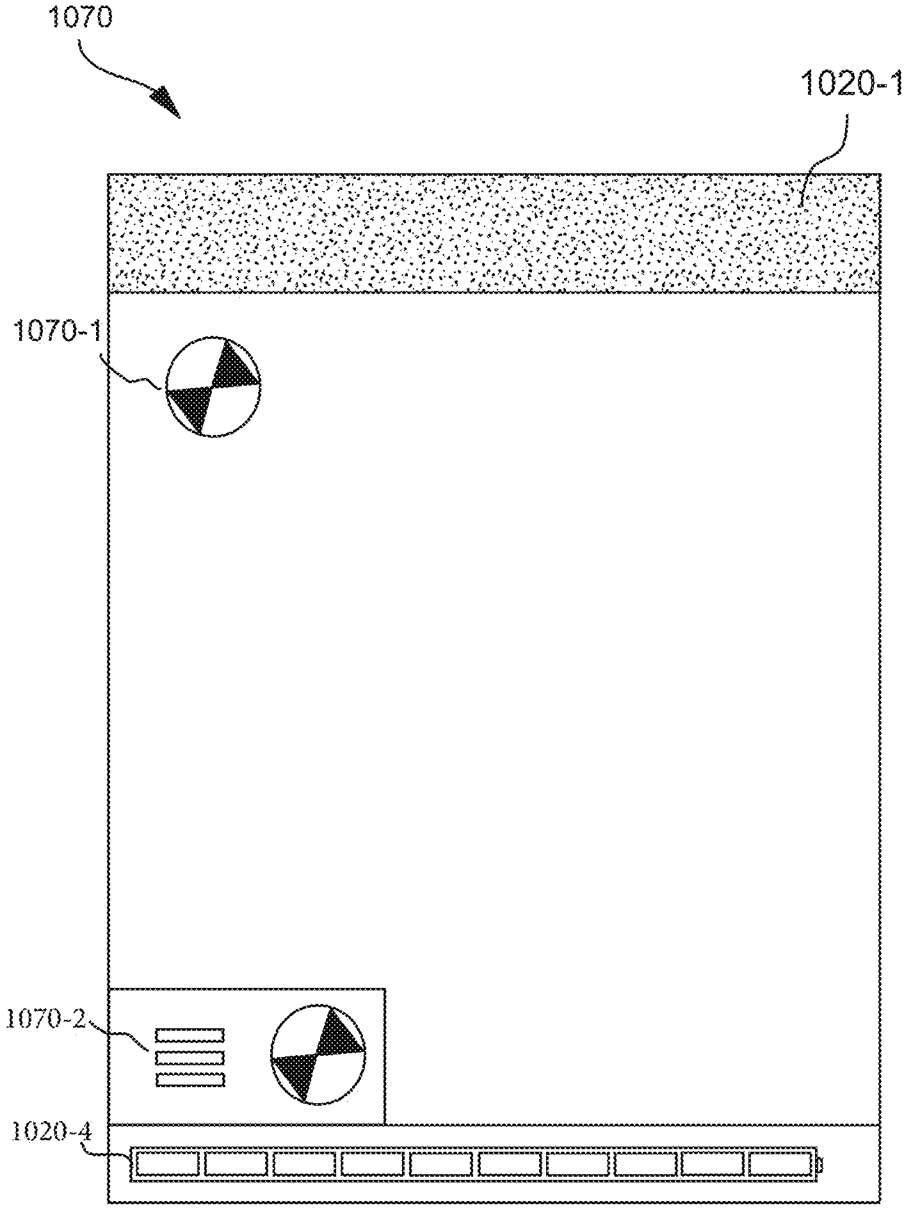
Figure 24N:
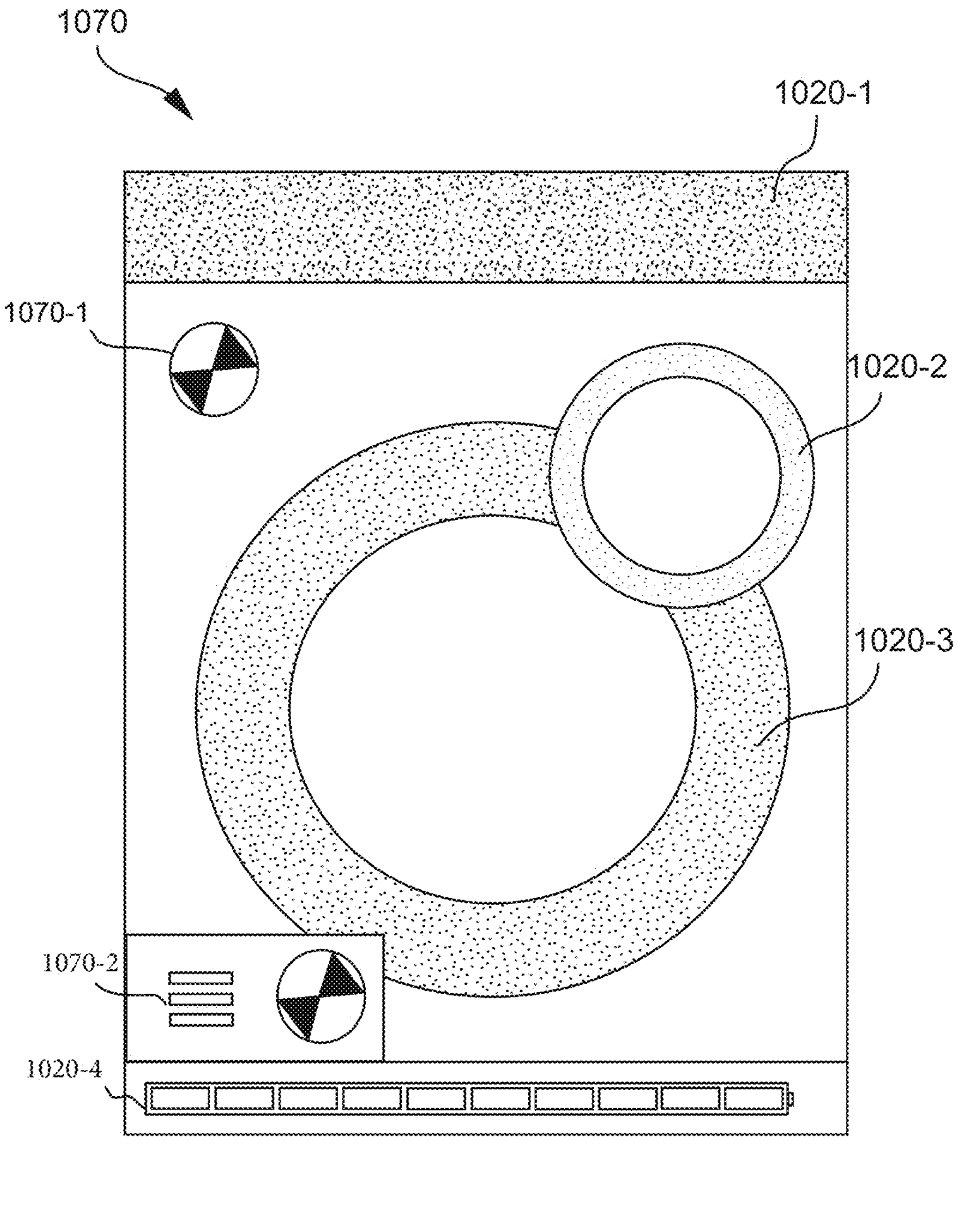
Figure 25A:
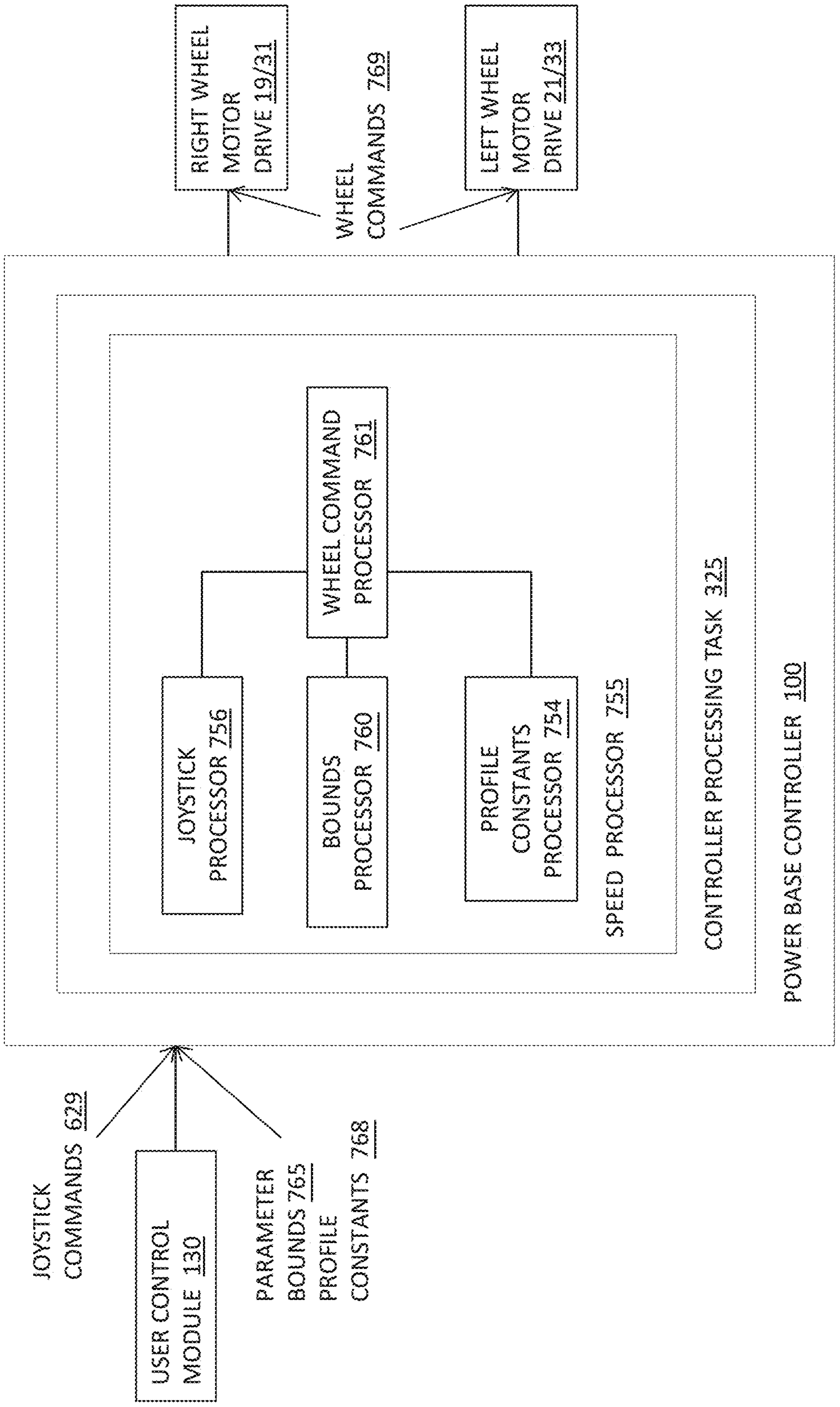
Figure 25B:
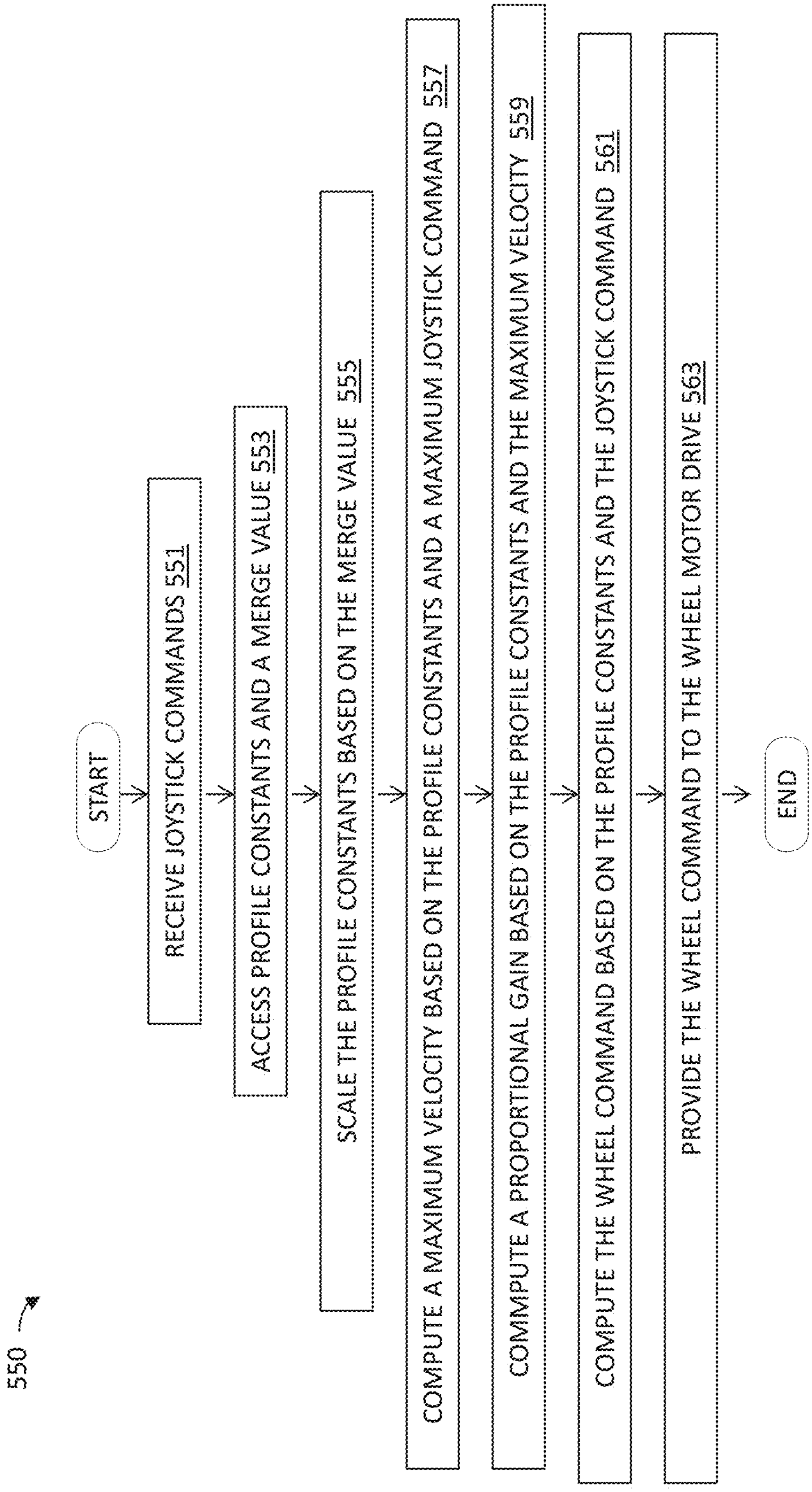
Figure 25C:
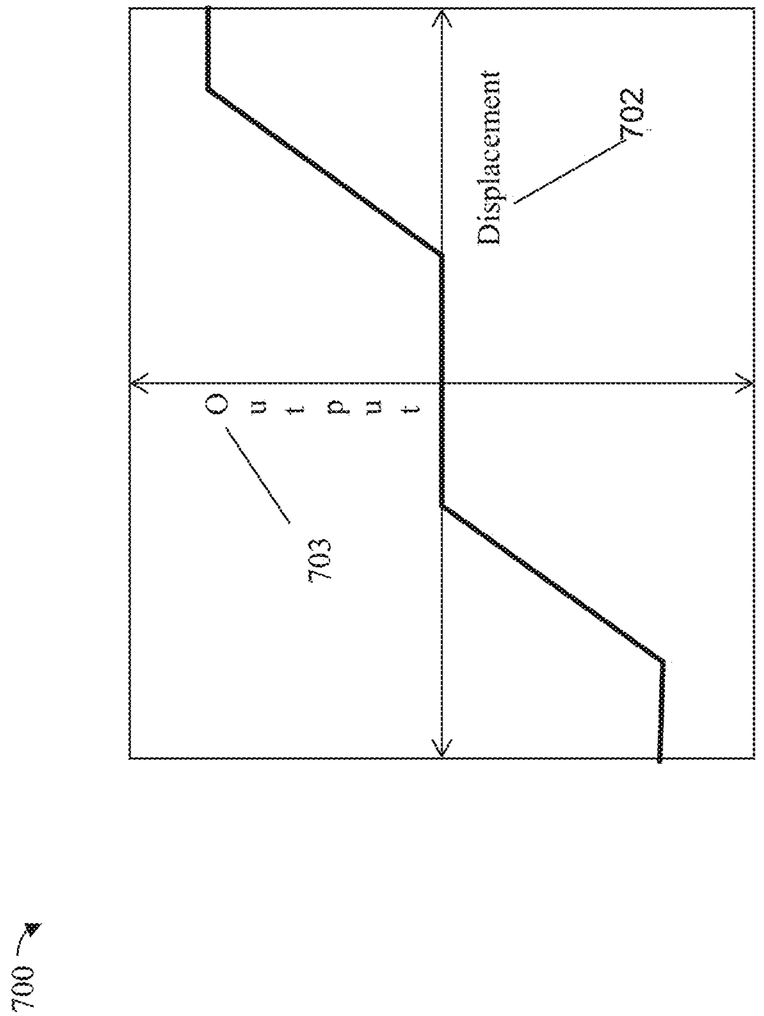
Figure 25D:
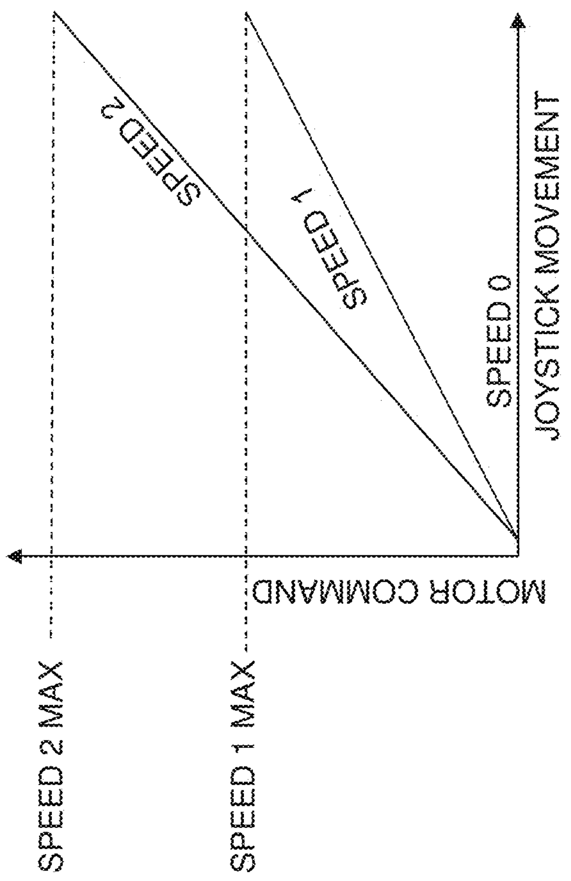
Figure 25L:
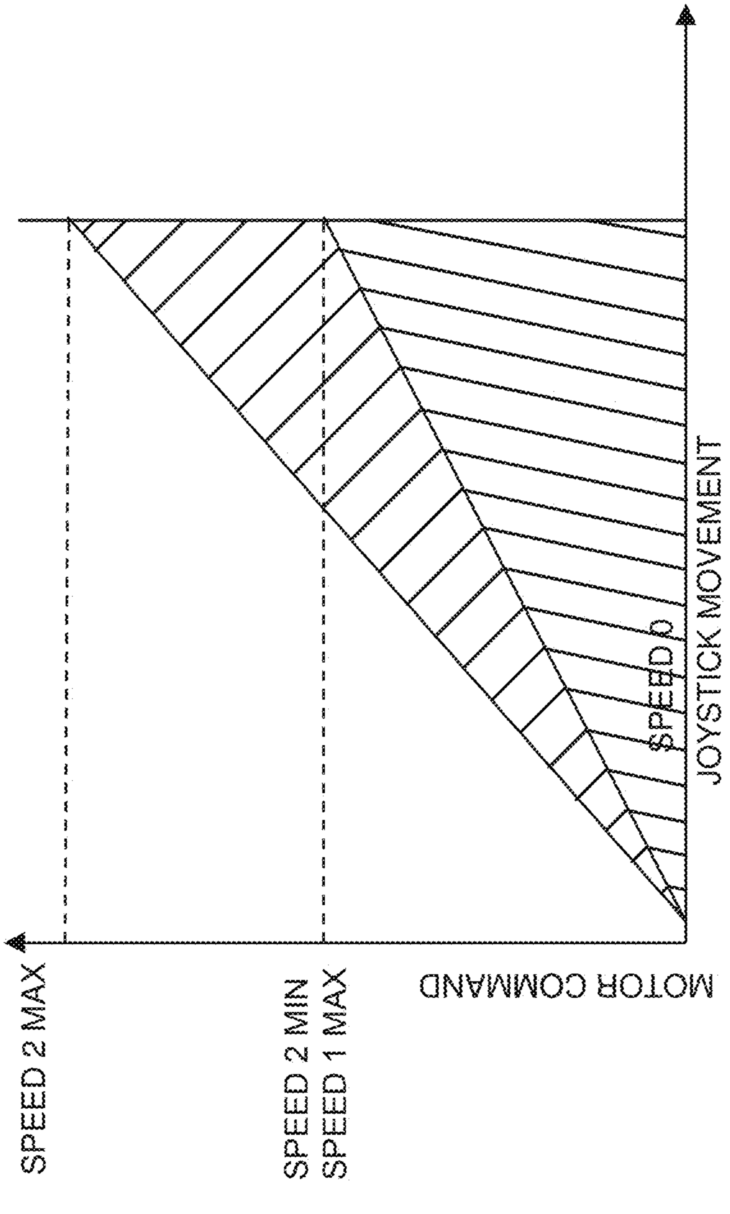
Figure 25M:
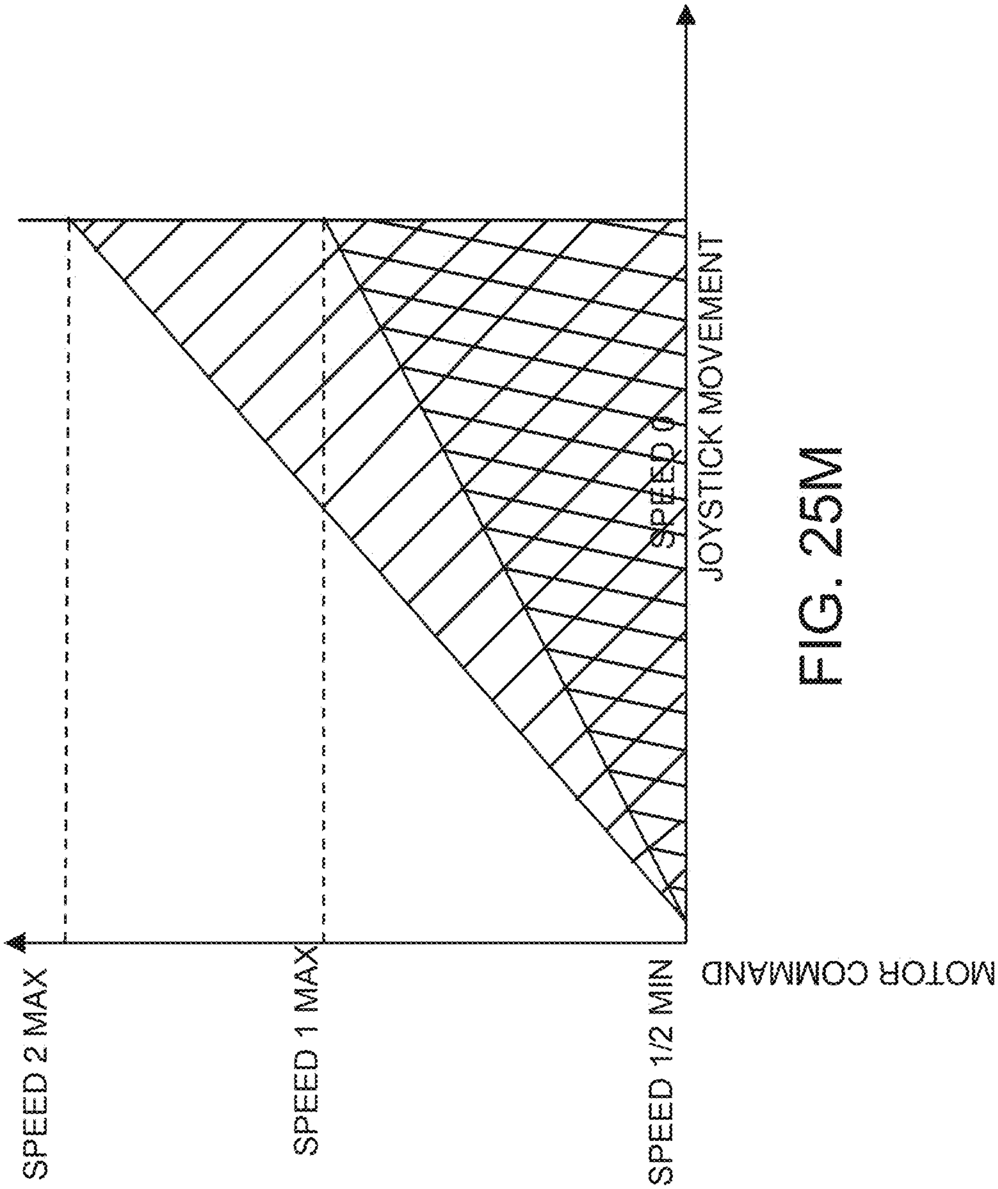
Figure 25N:
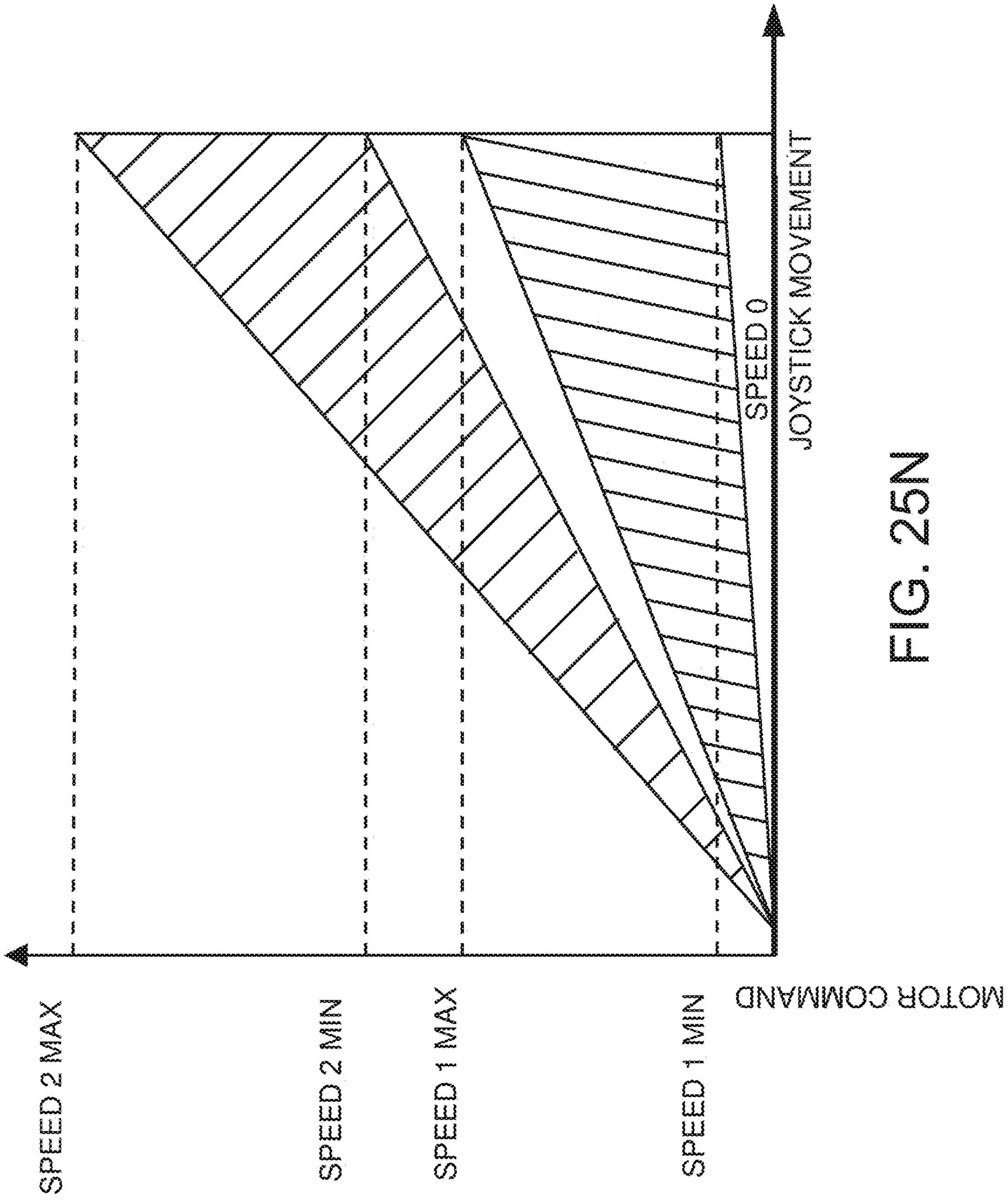
Figure 25E:
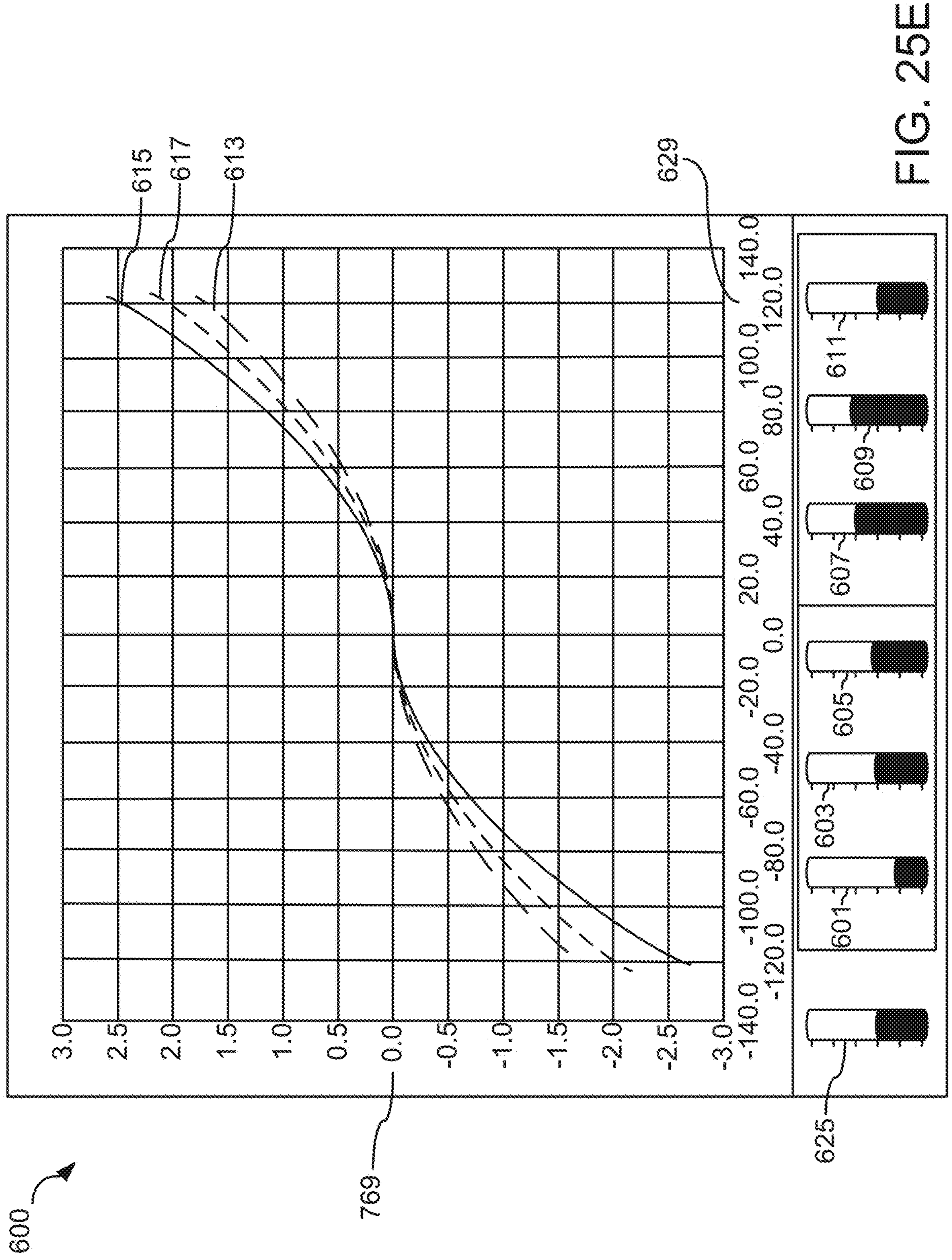
Figure 25F:
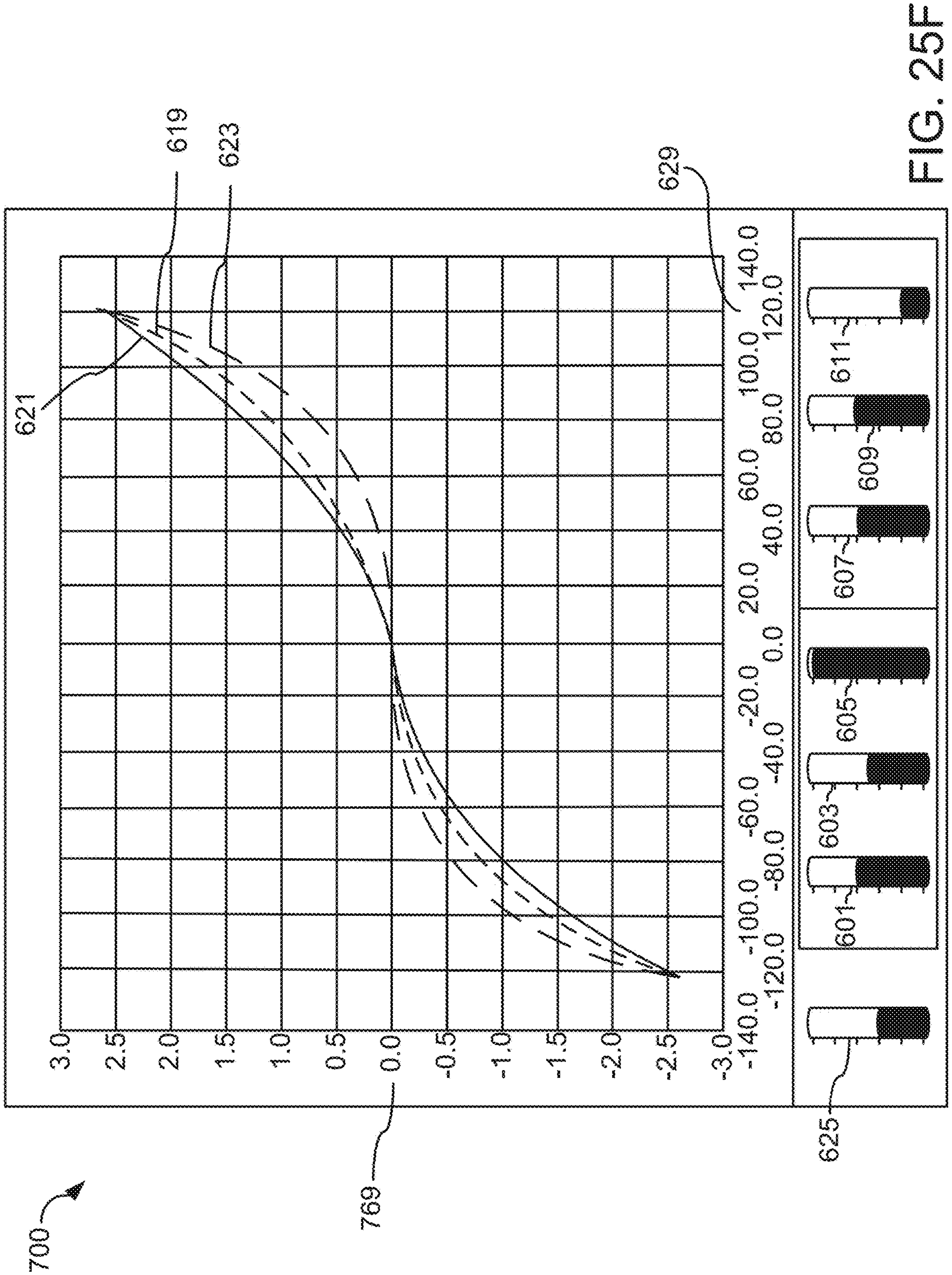
Figure 25G:
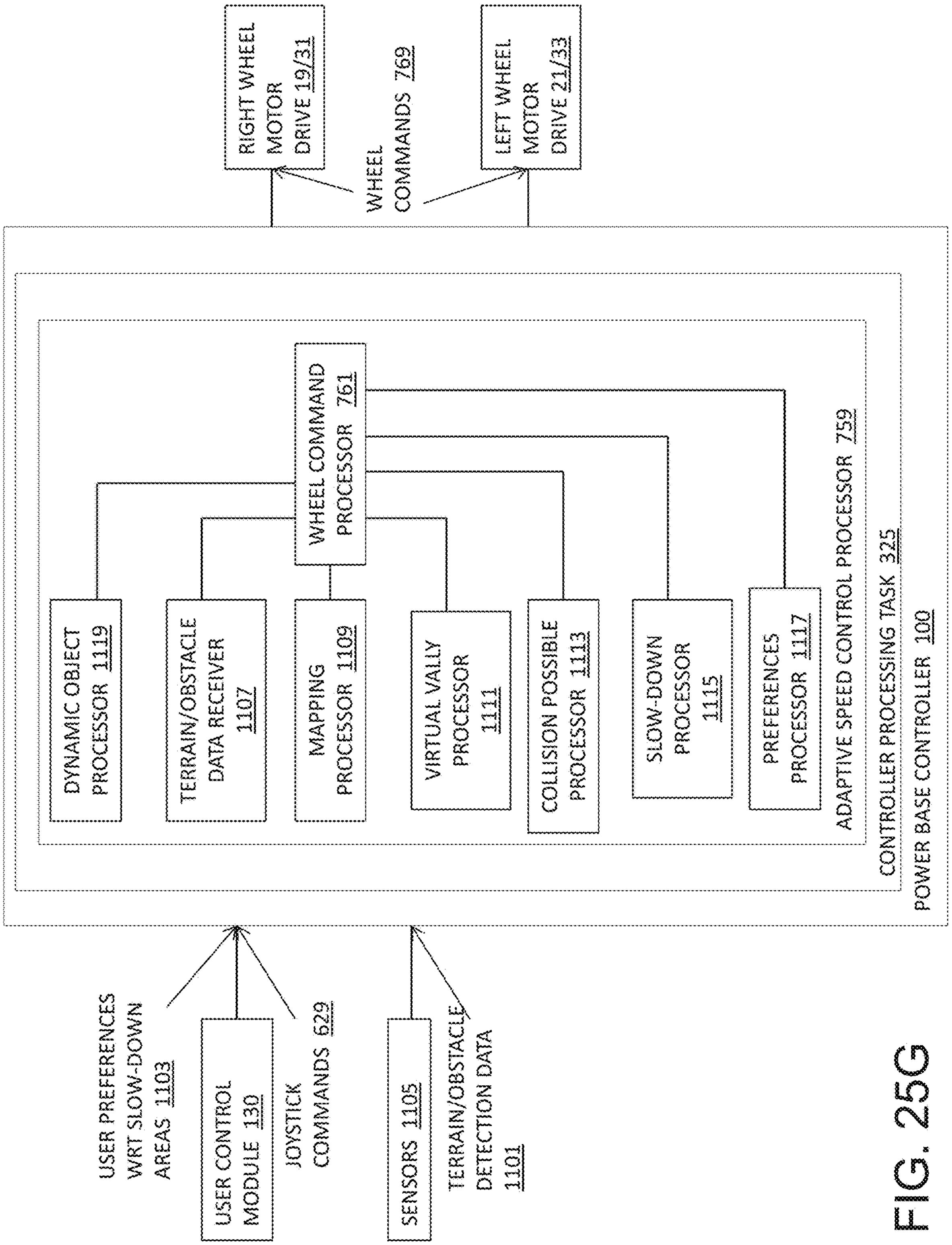
Figure 25H:
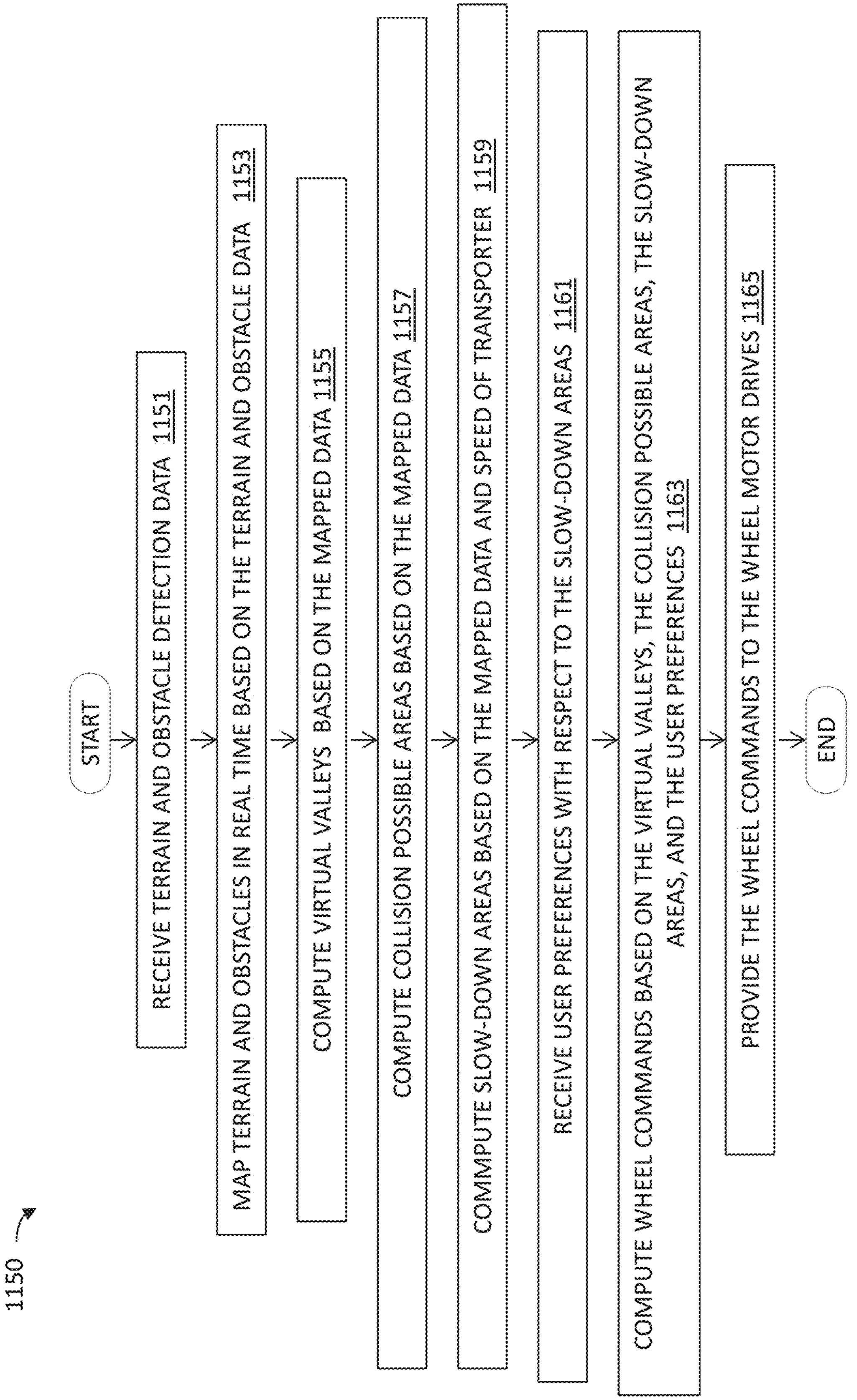
Figure 25I:
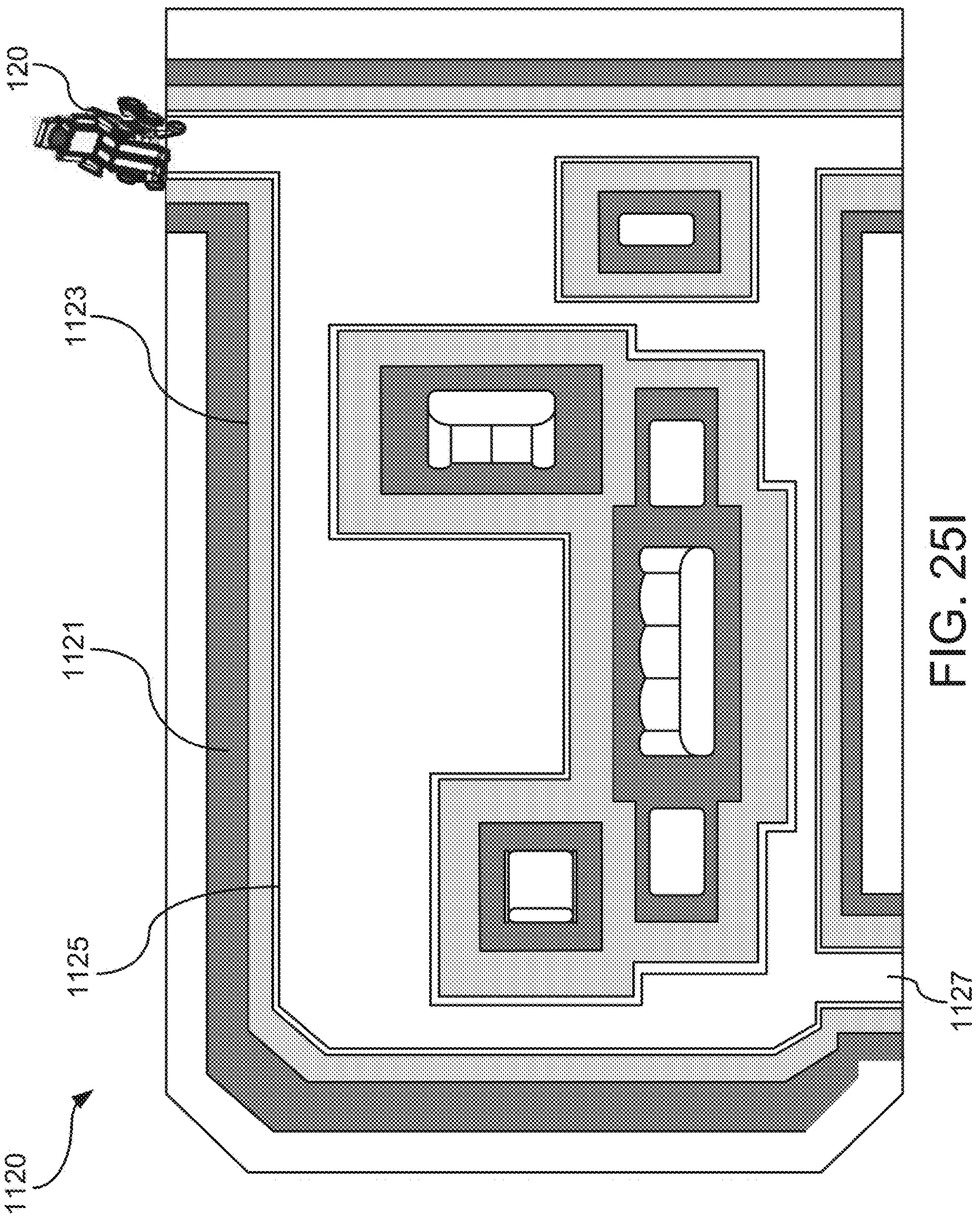
Figure 25J:
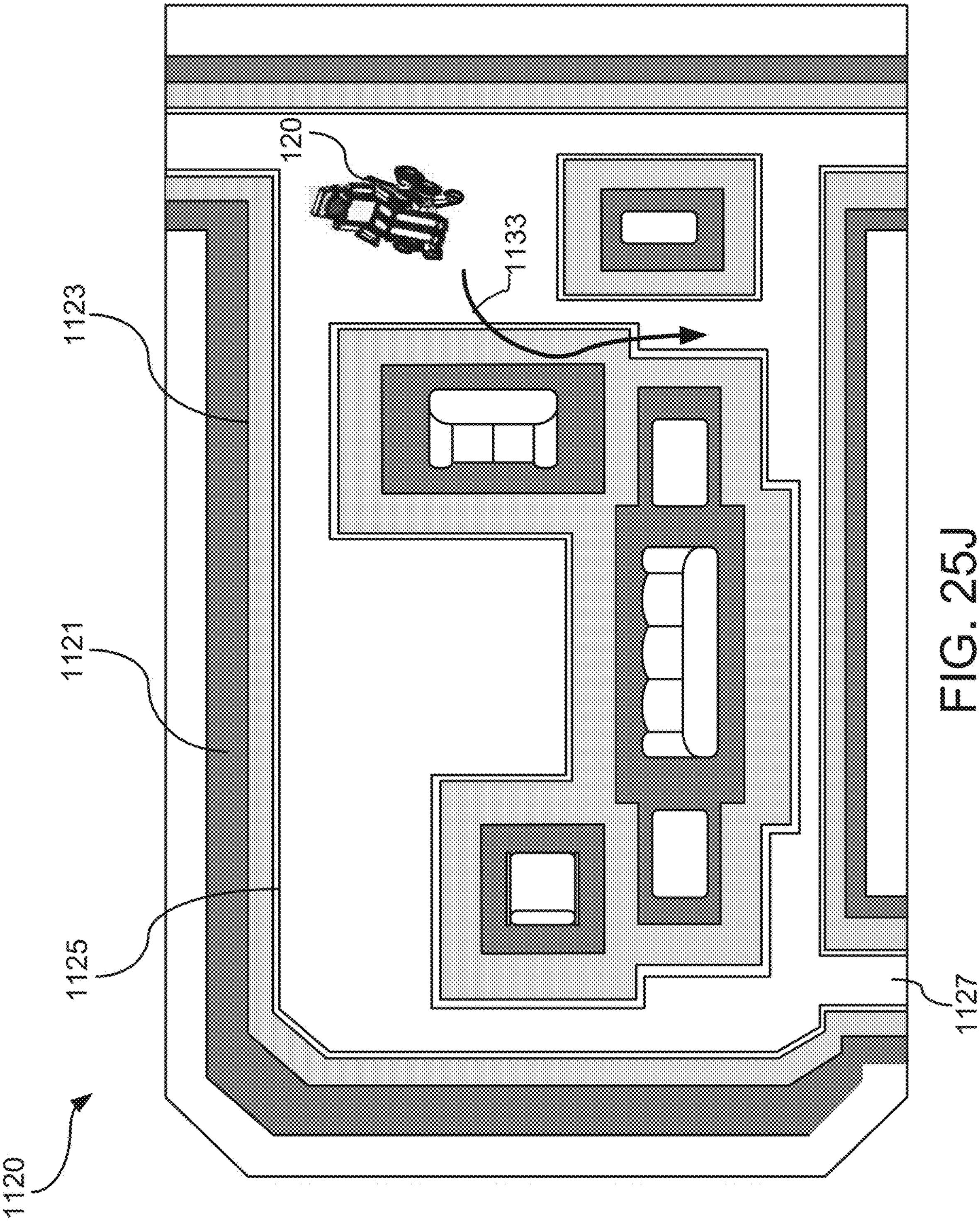
Figure 25K:
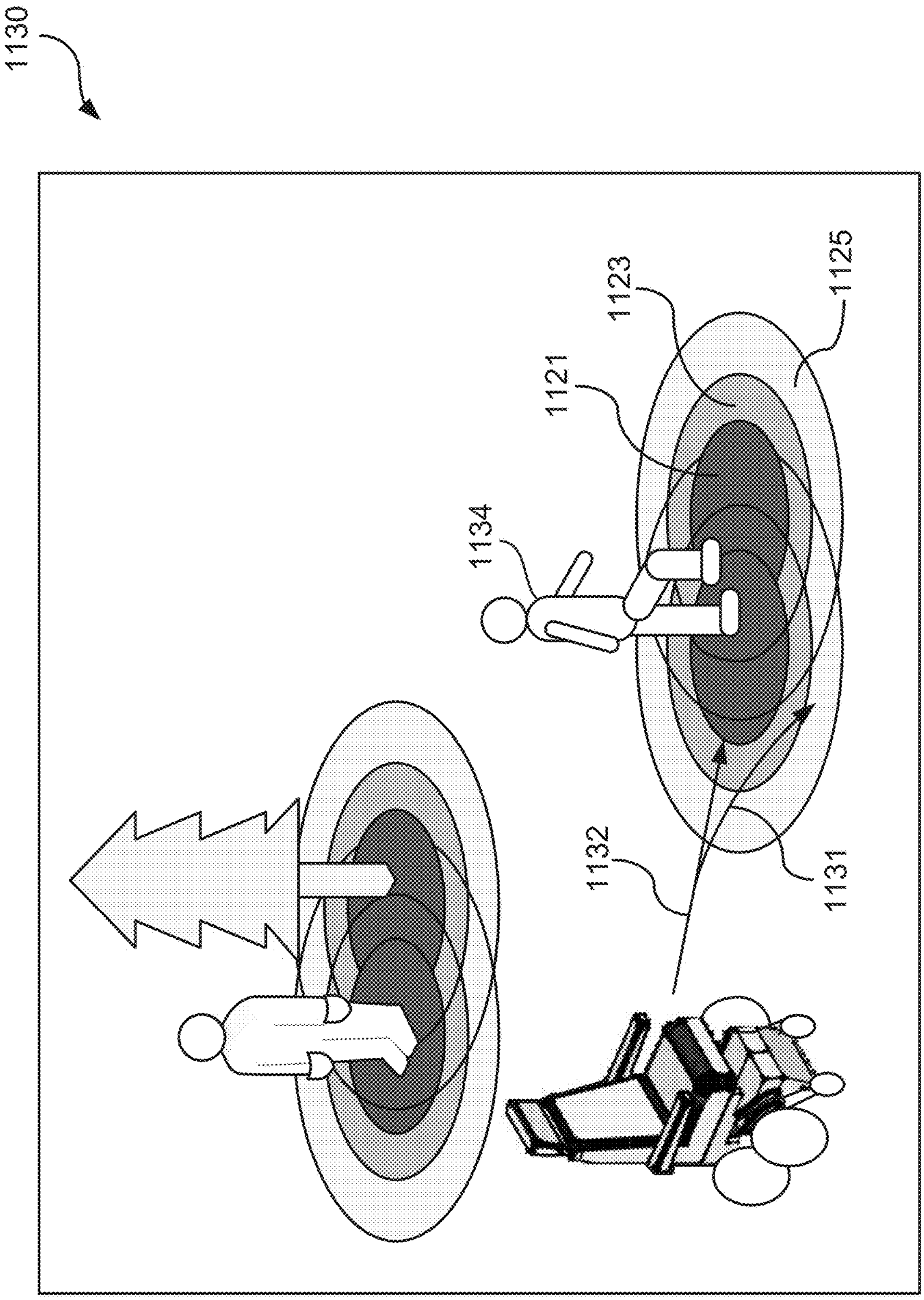
Figure 26A:
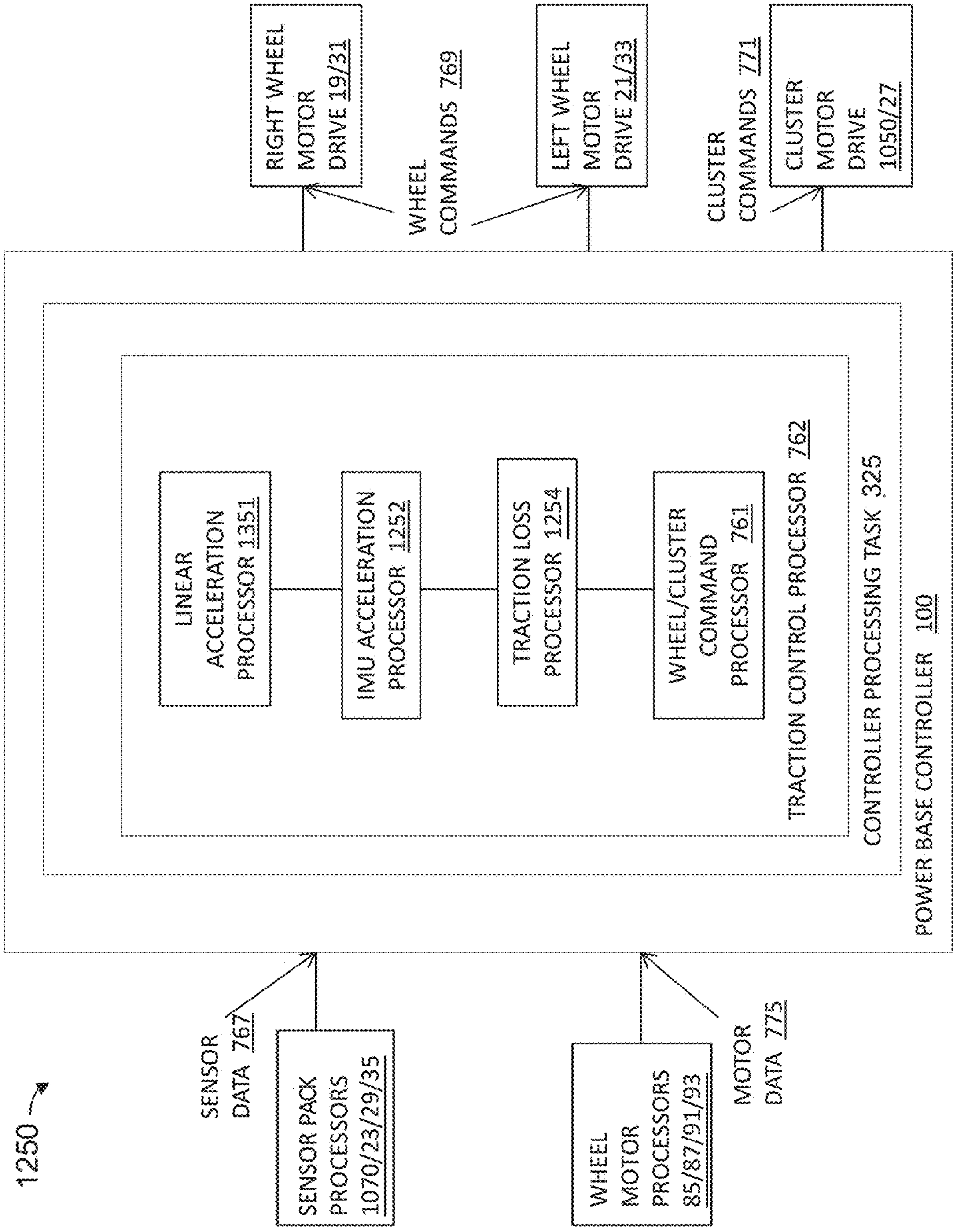
Figure 26B:
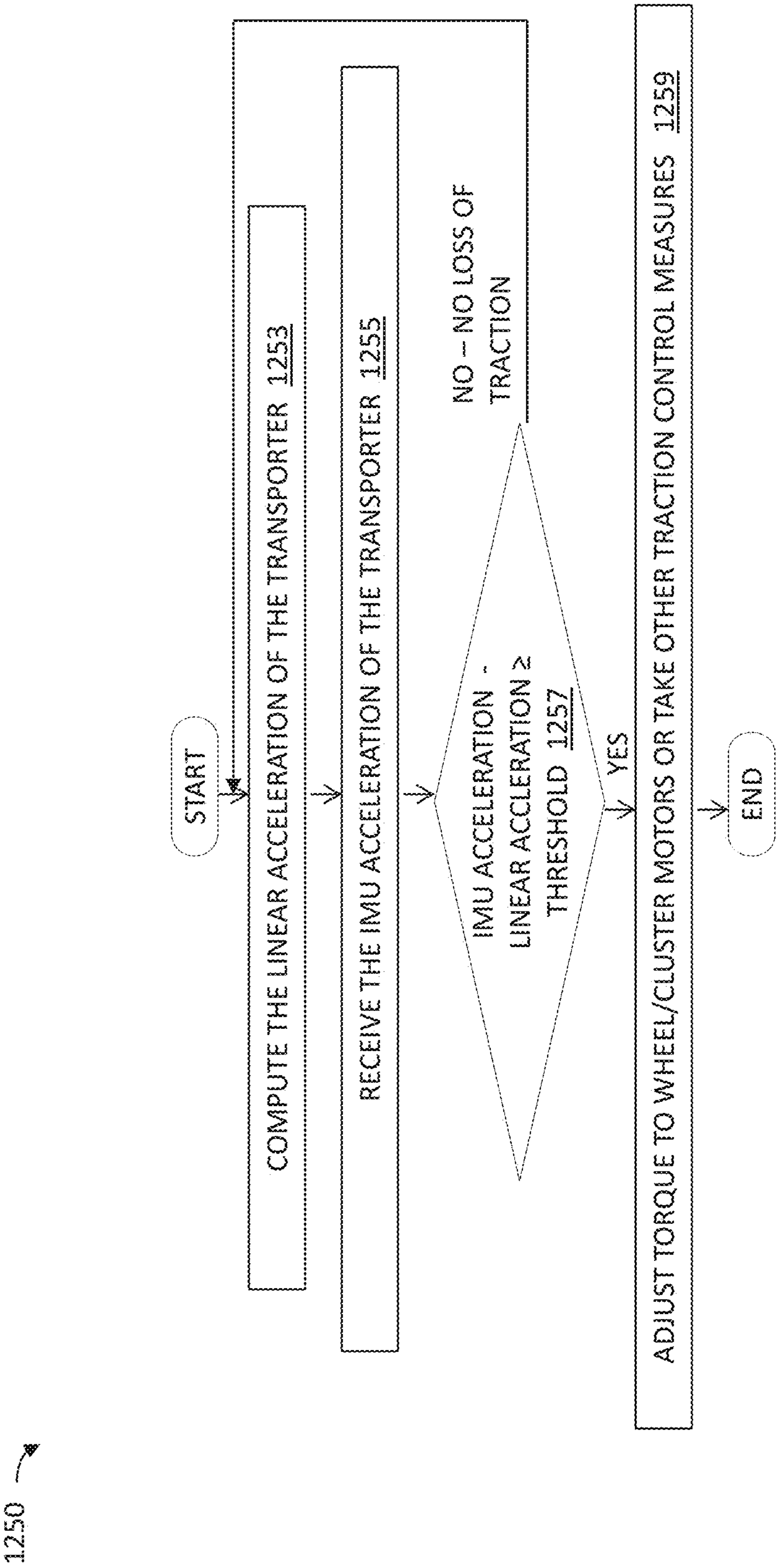
Figure 27A:
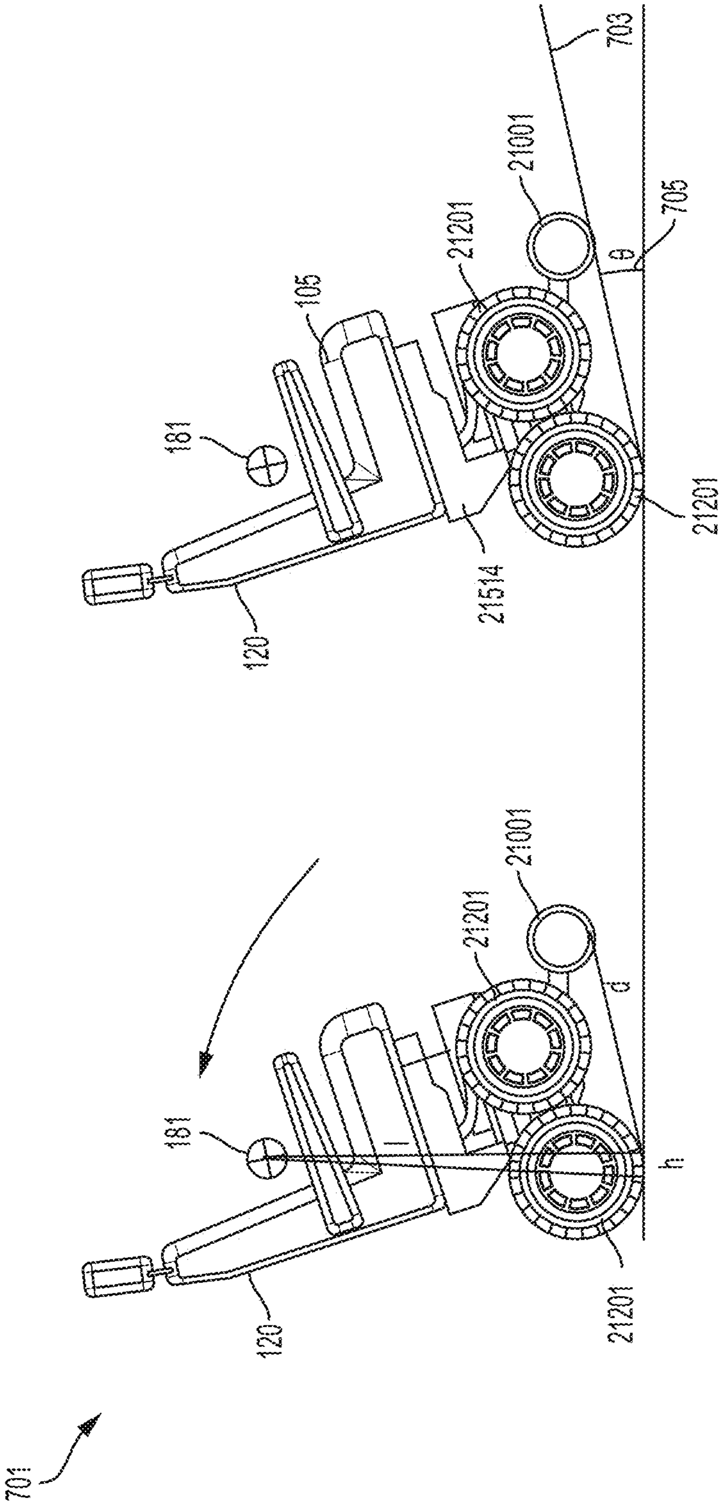
Figure 27B:
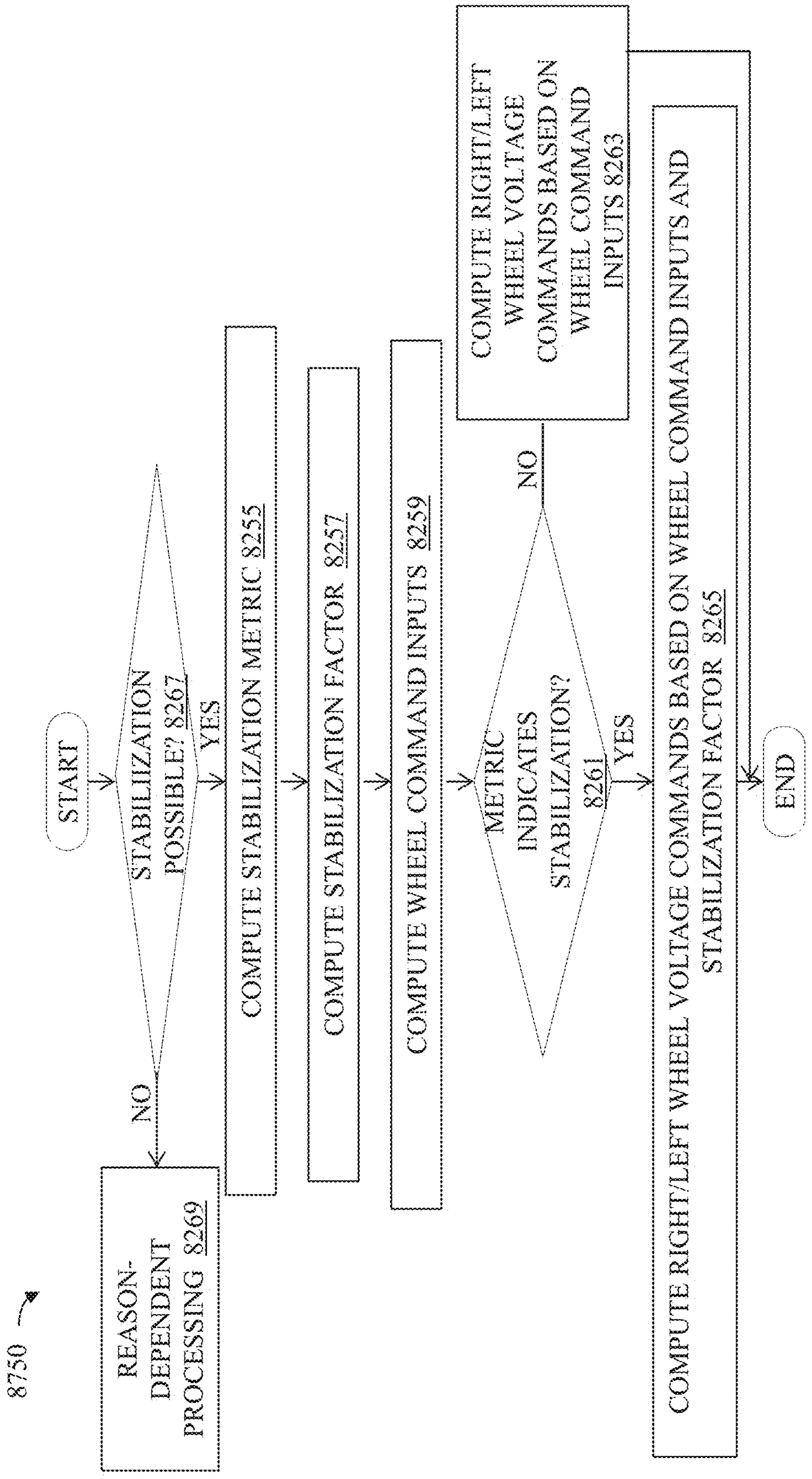
Figure 27C:
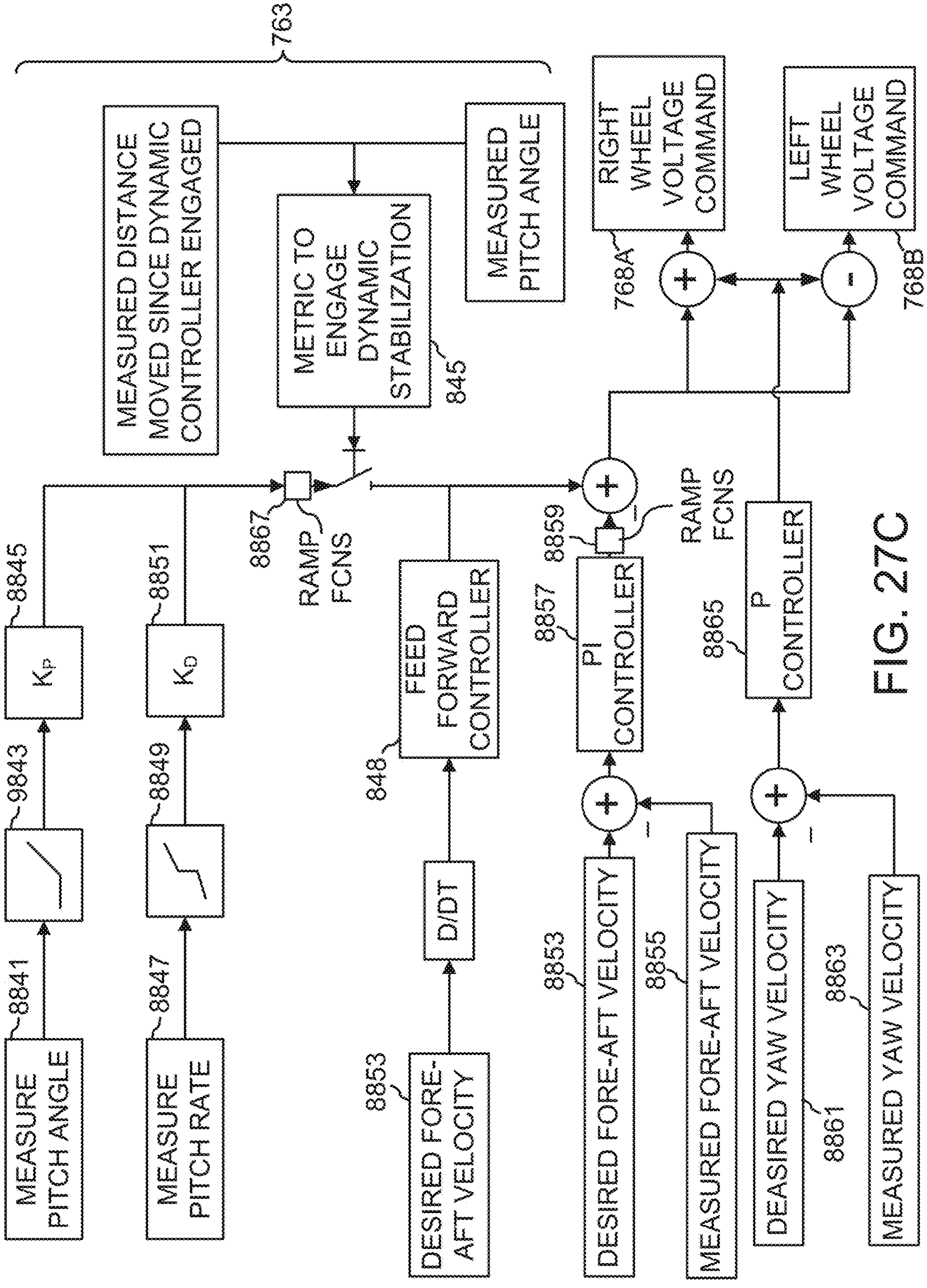
Figure 27D:
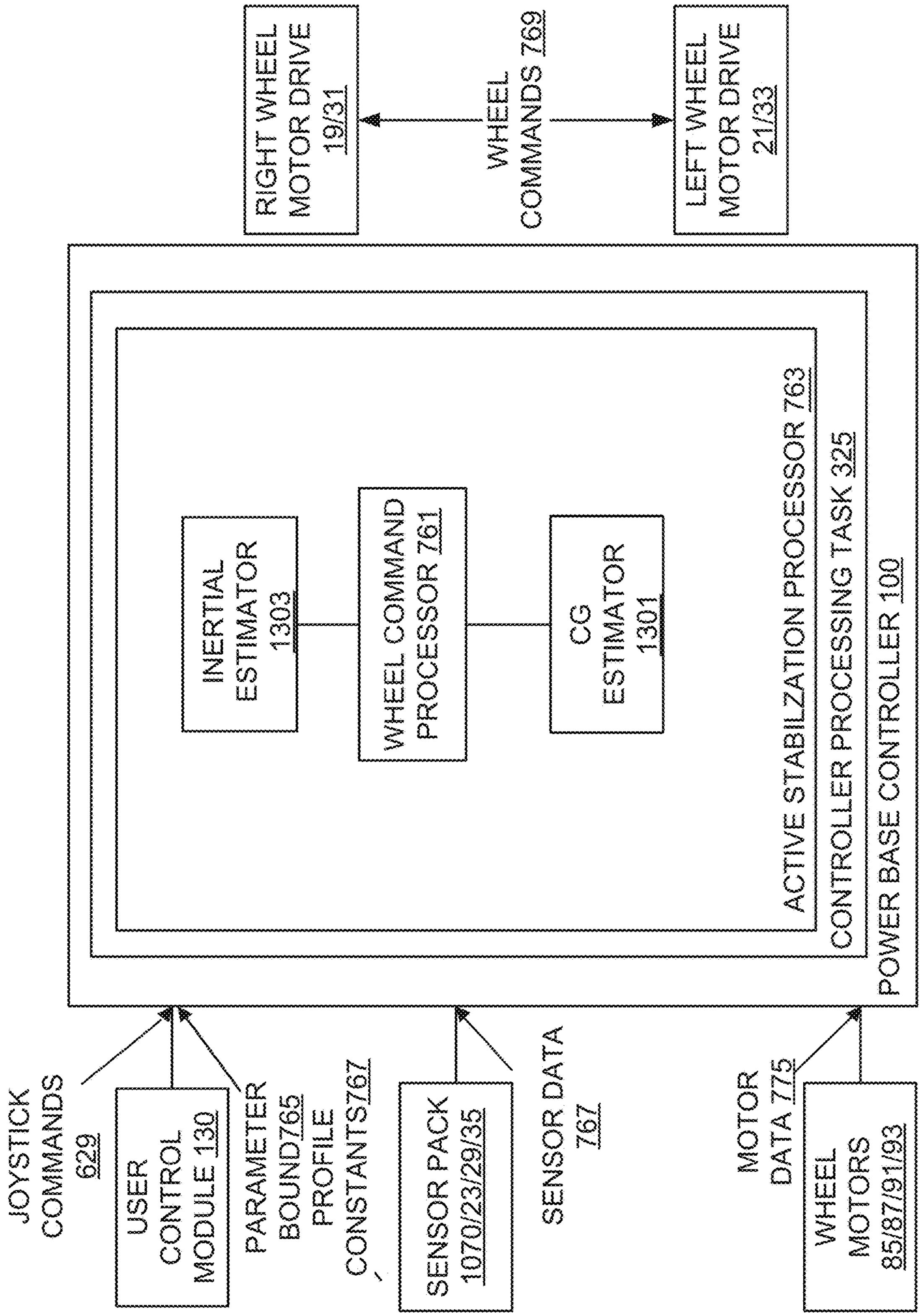
Figure 27E:
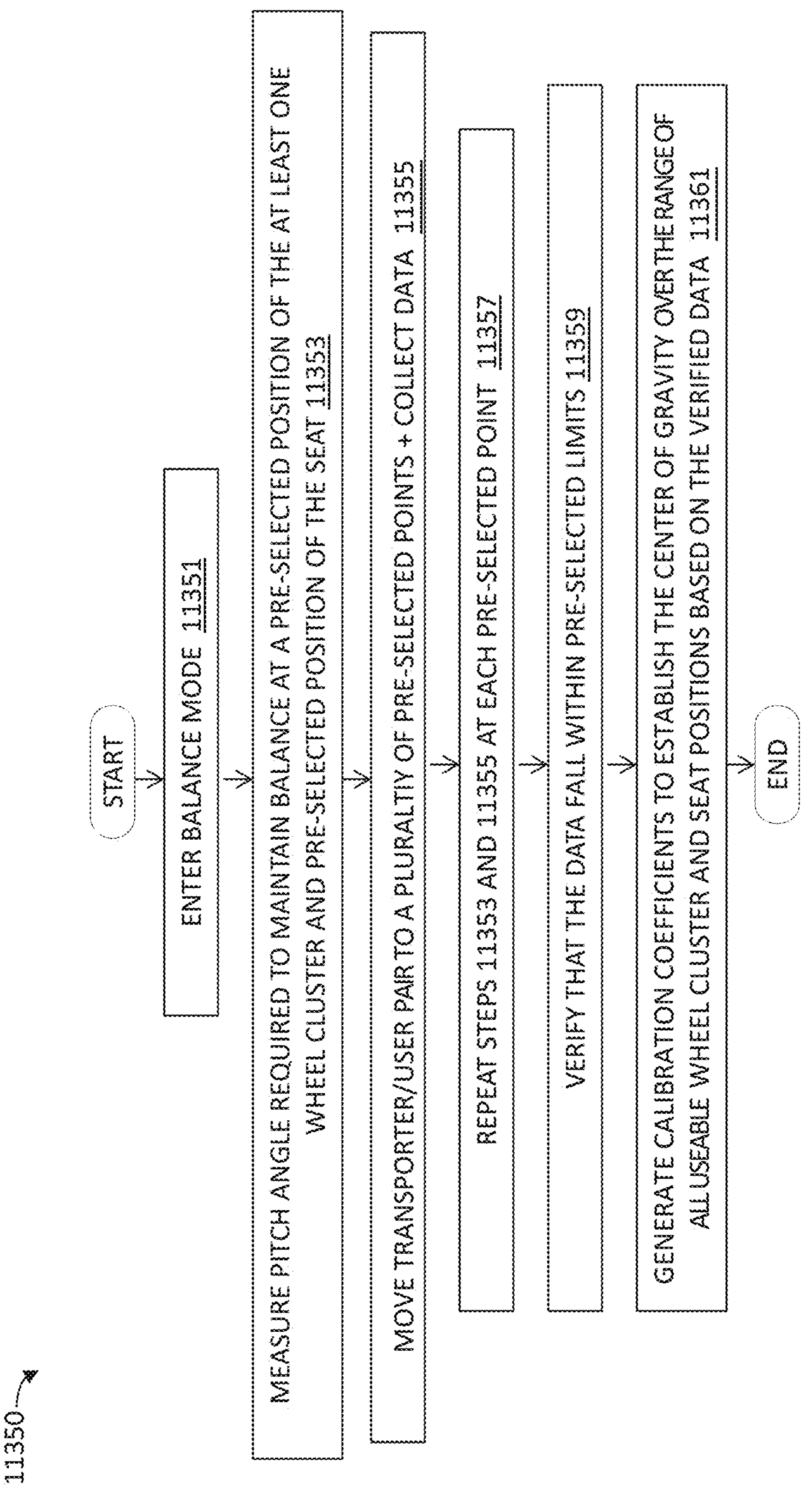
Figure 28A:
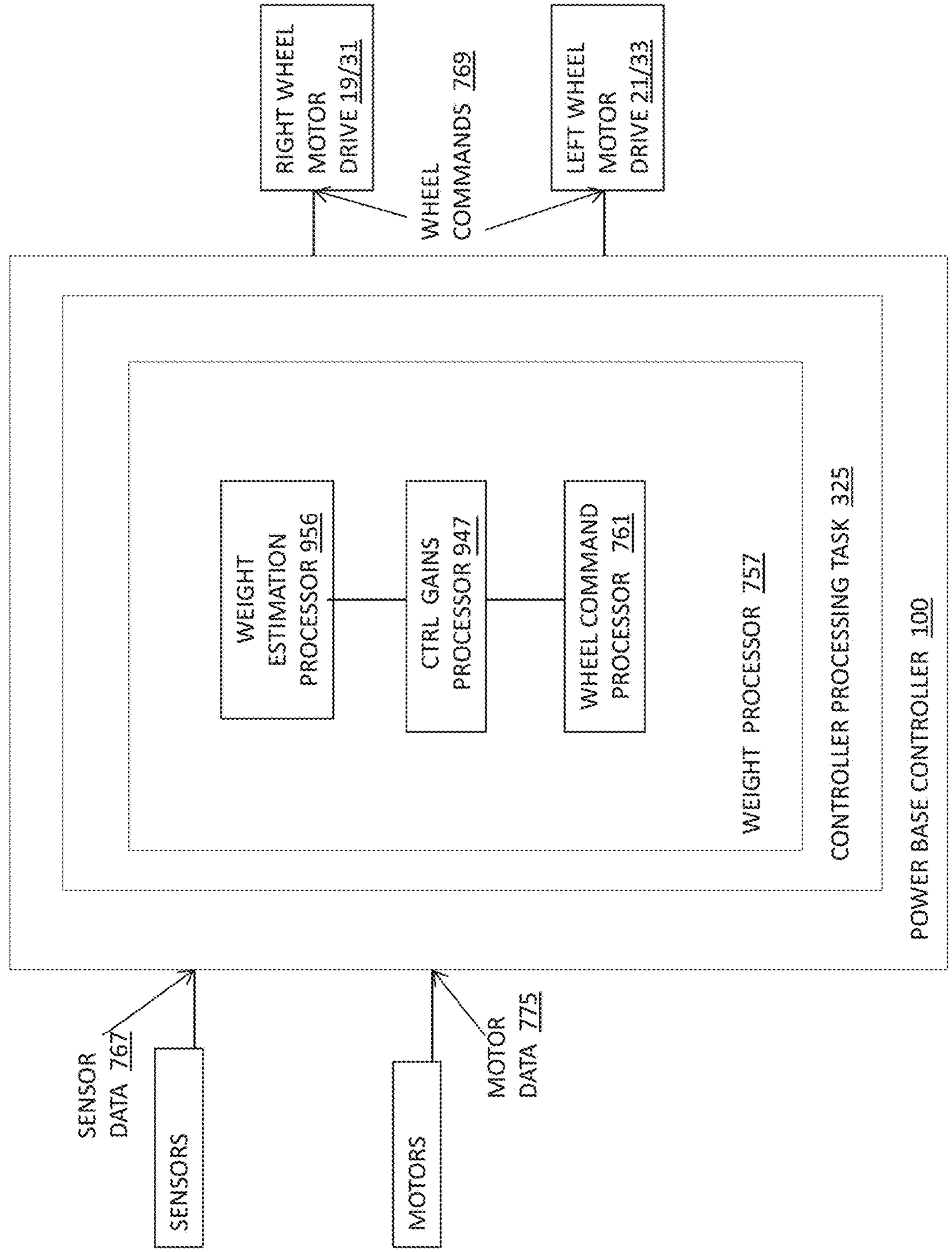
Figure 28B:
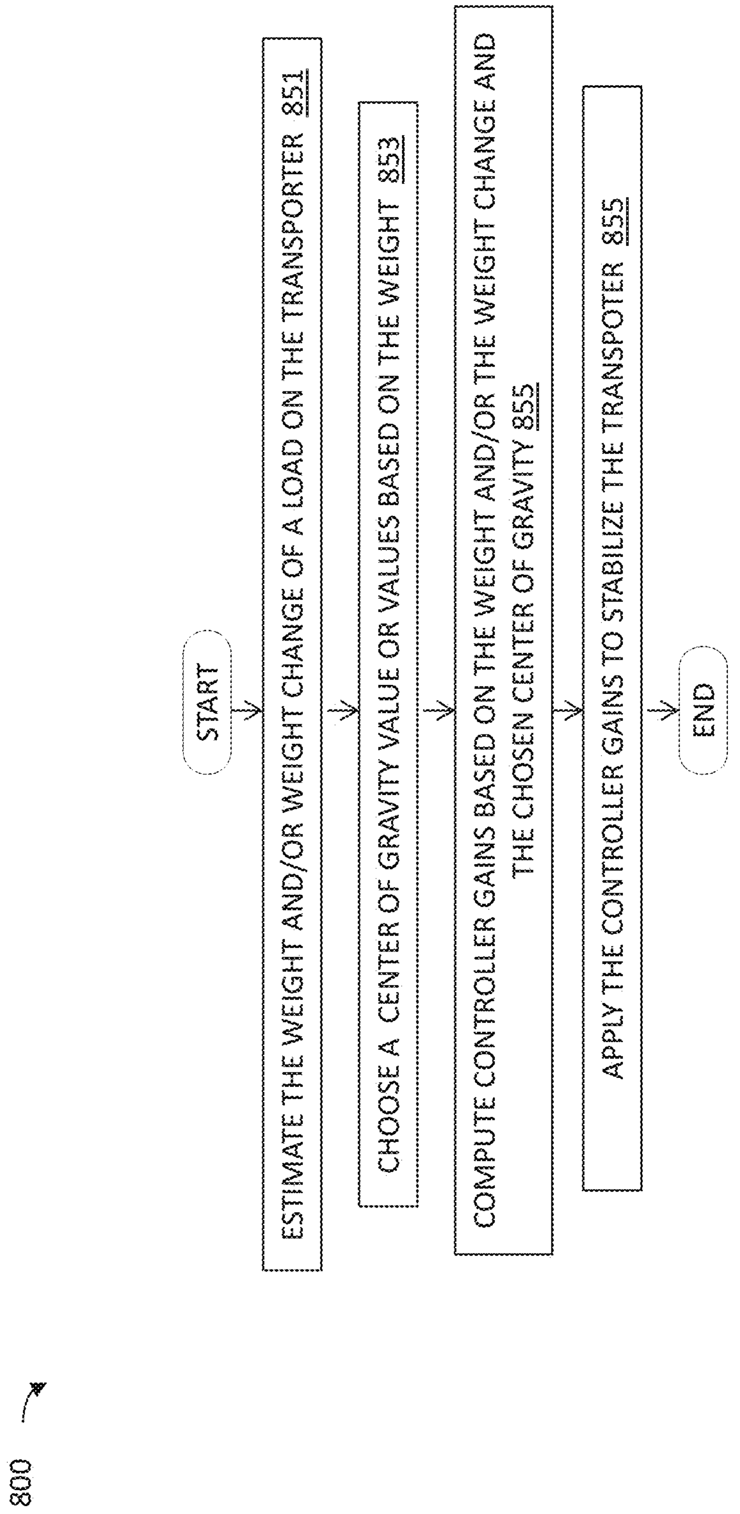
Figure 28C:
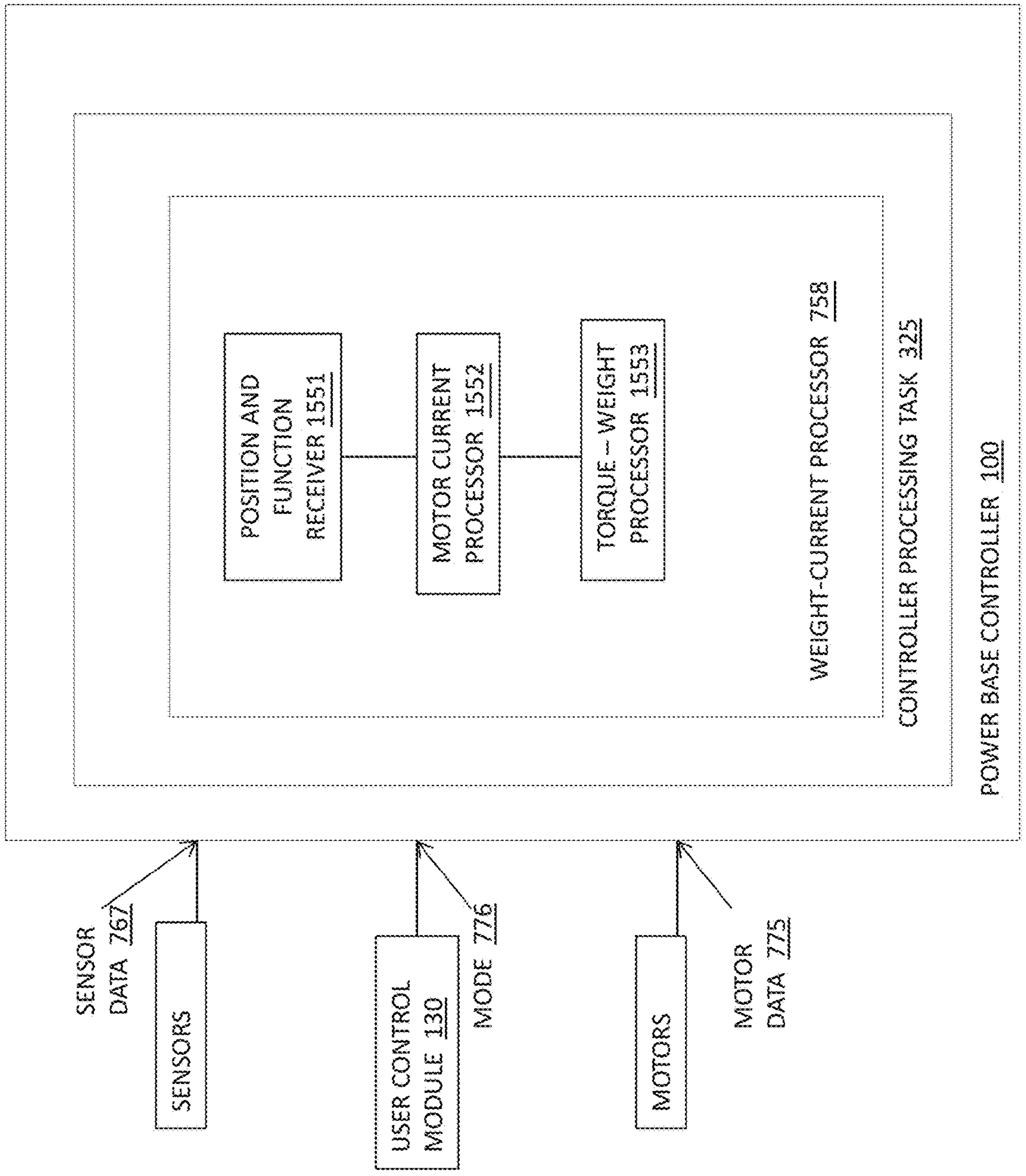
Figure 28D:
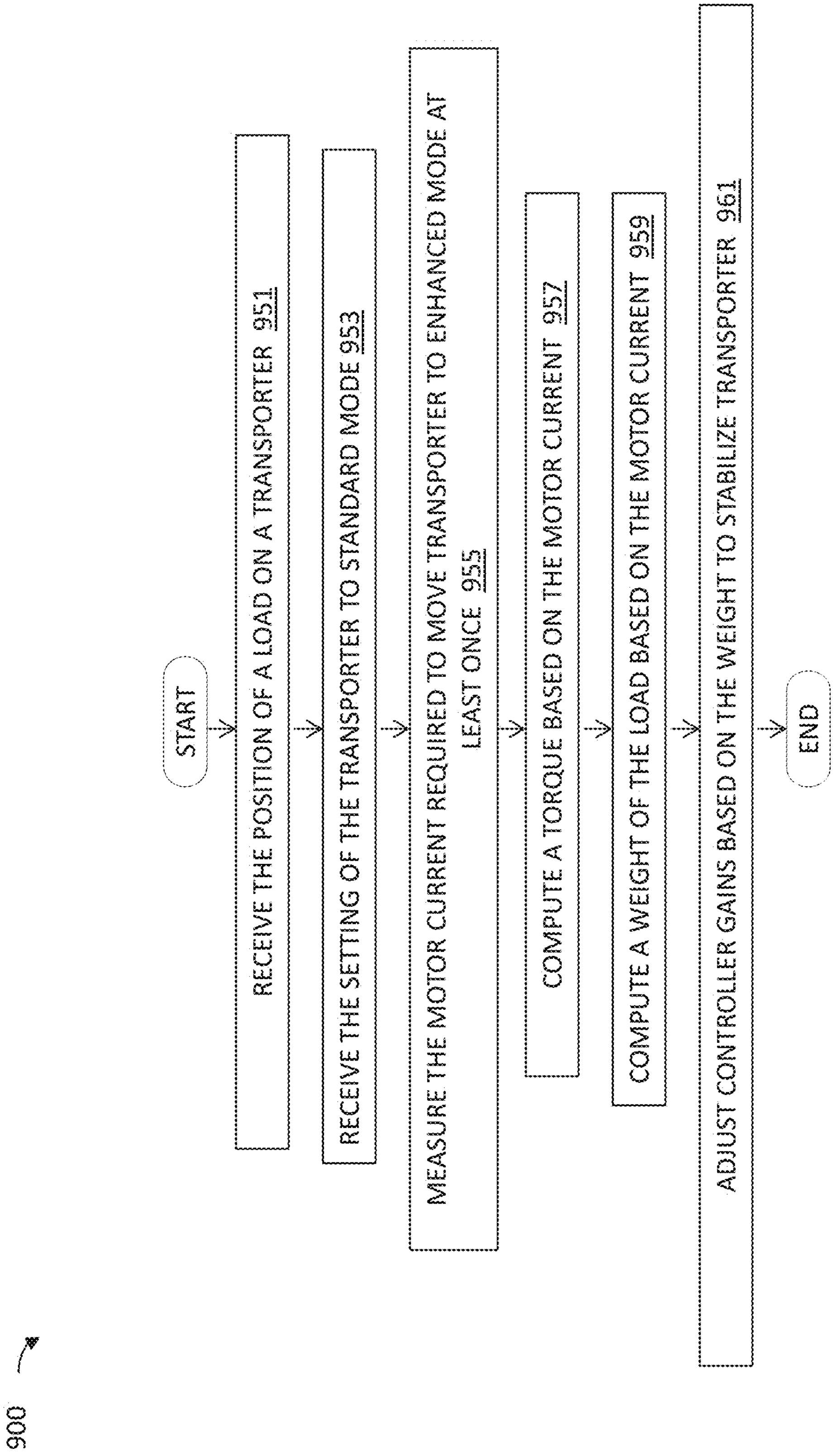
Figure 29A:
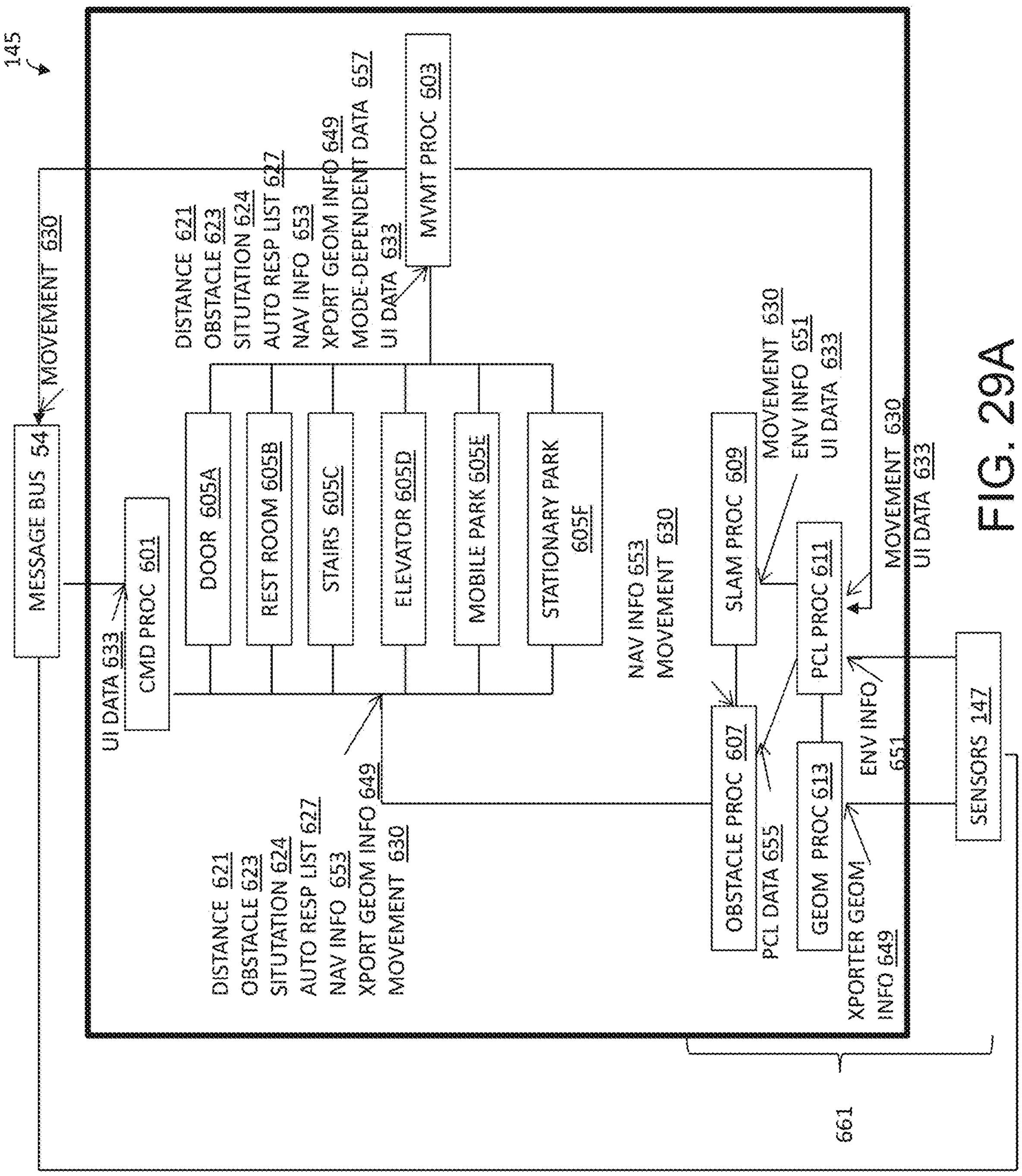
Figure 29B:
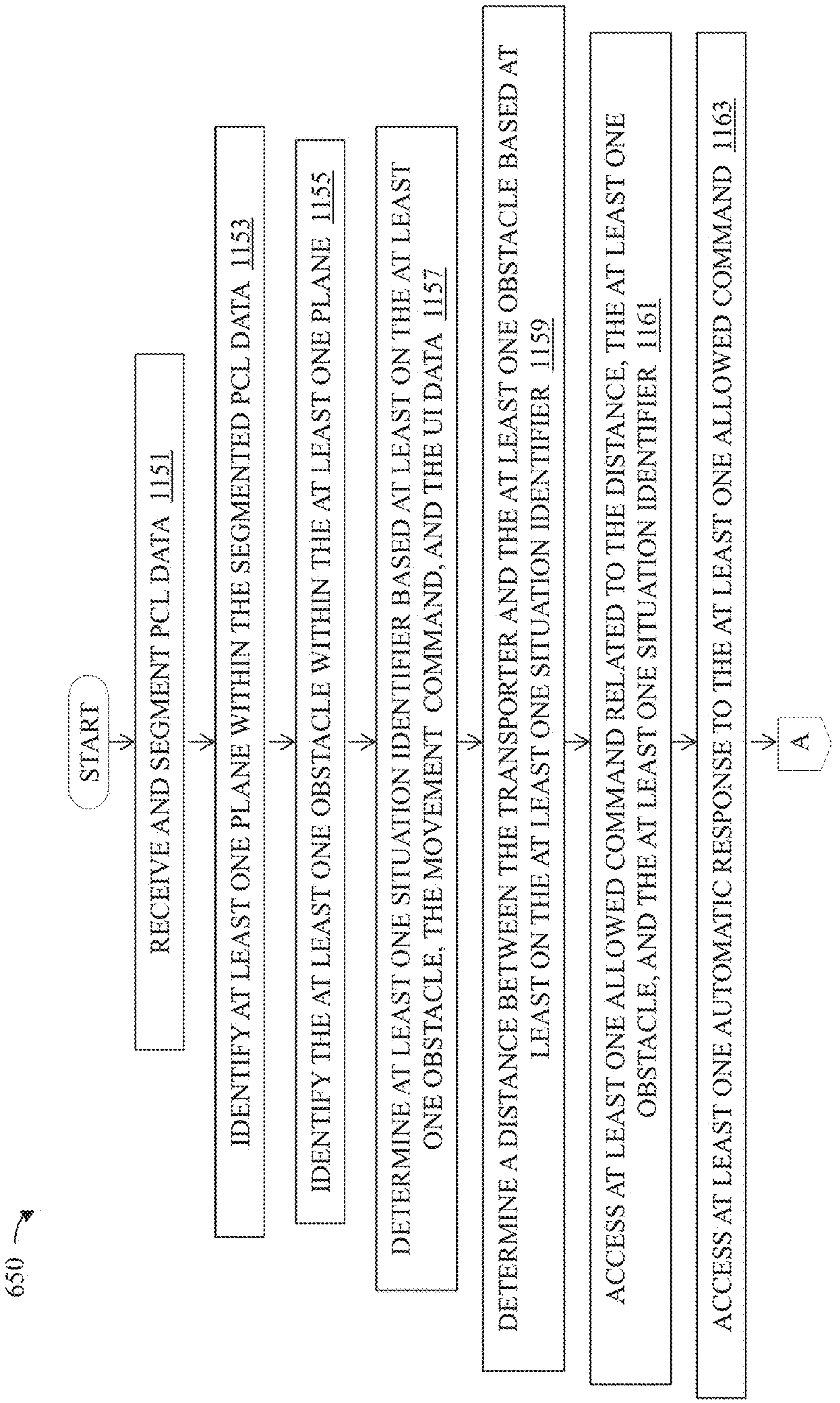
Figure 29C:
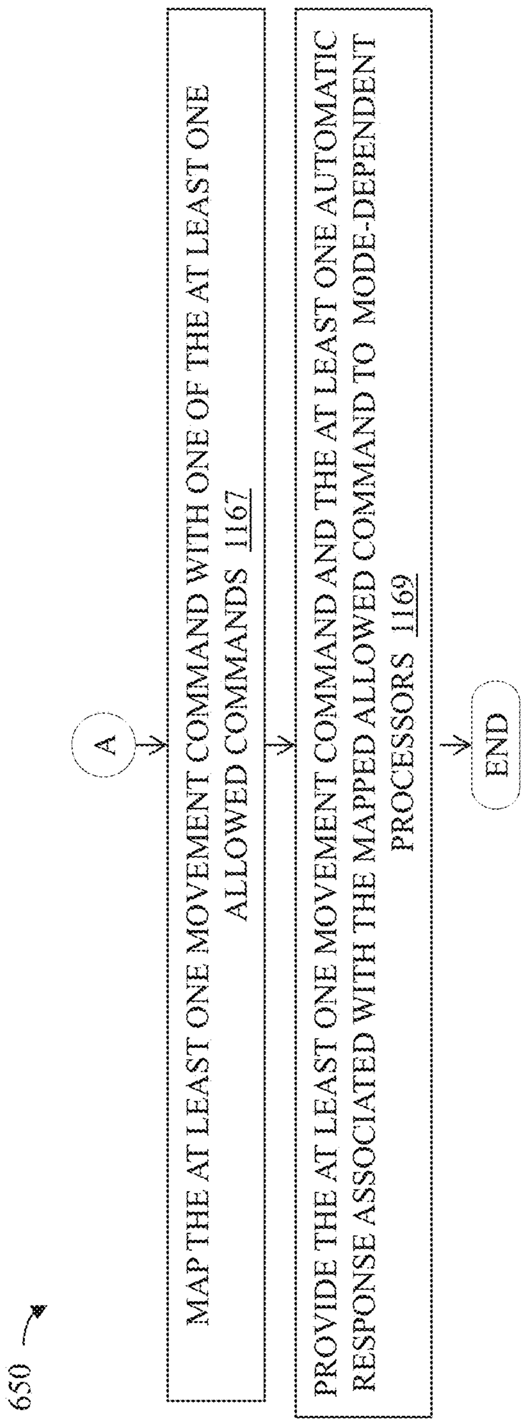
Figure 29D:
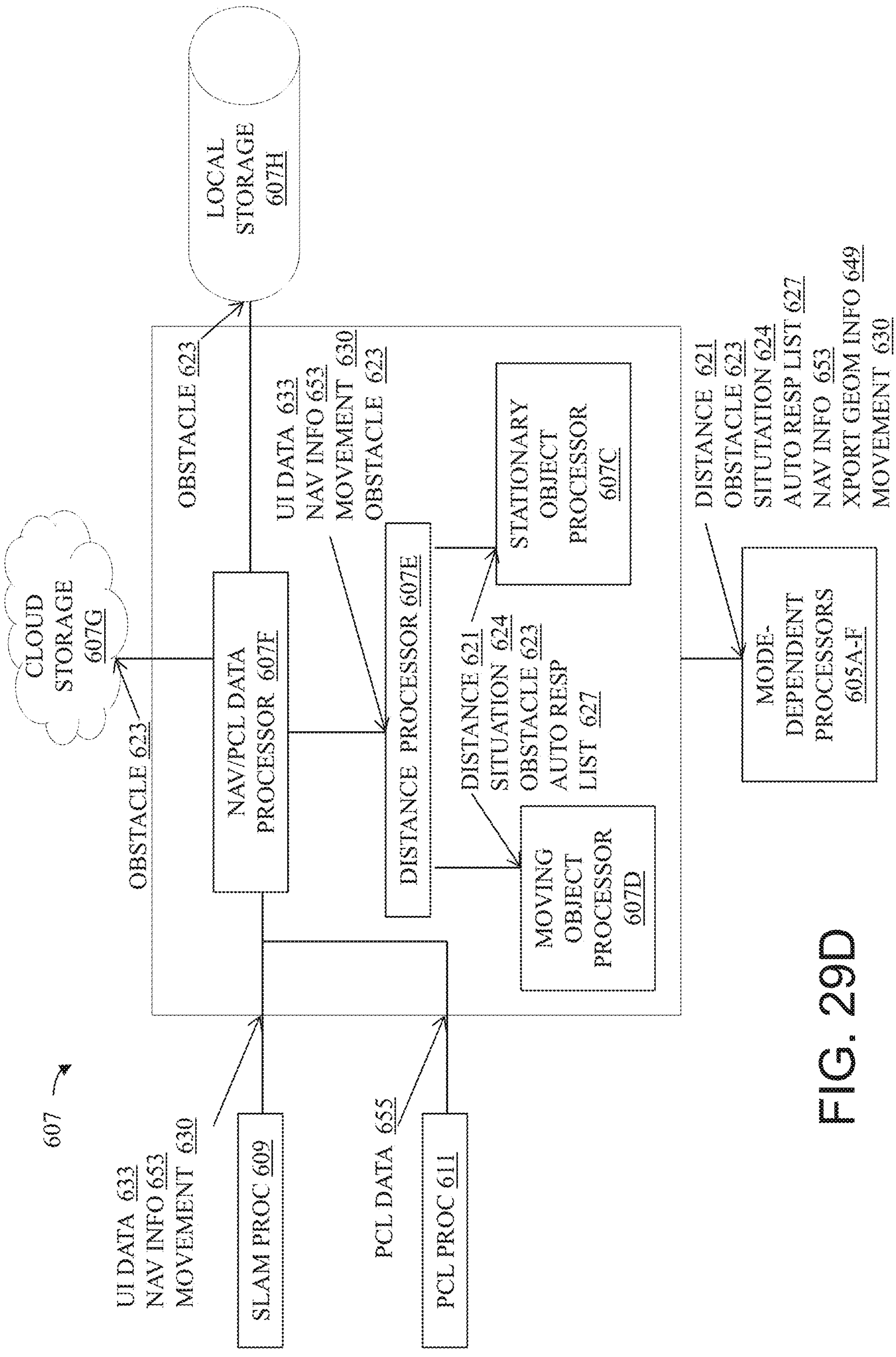
Figure 29E:
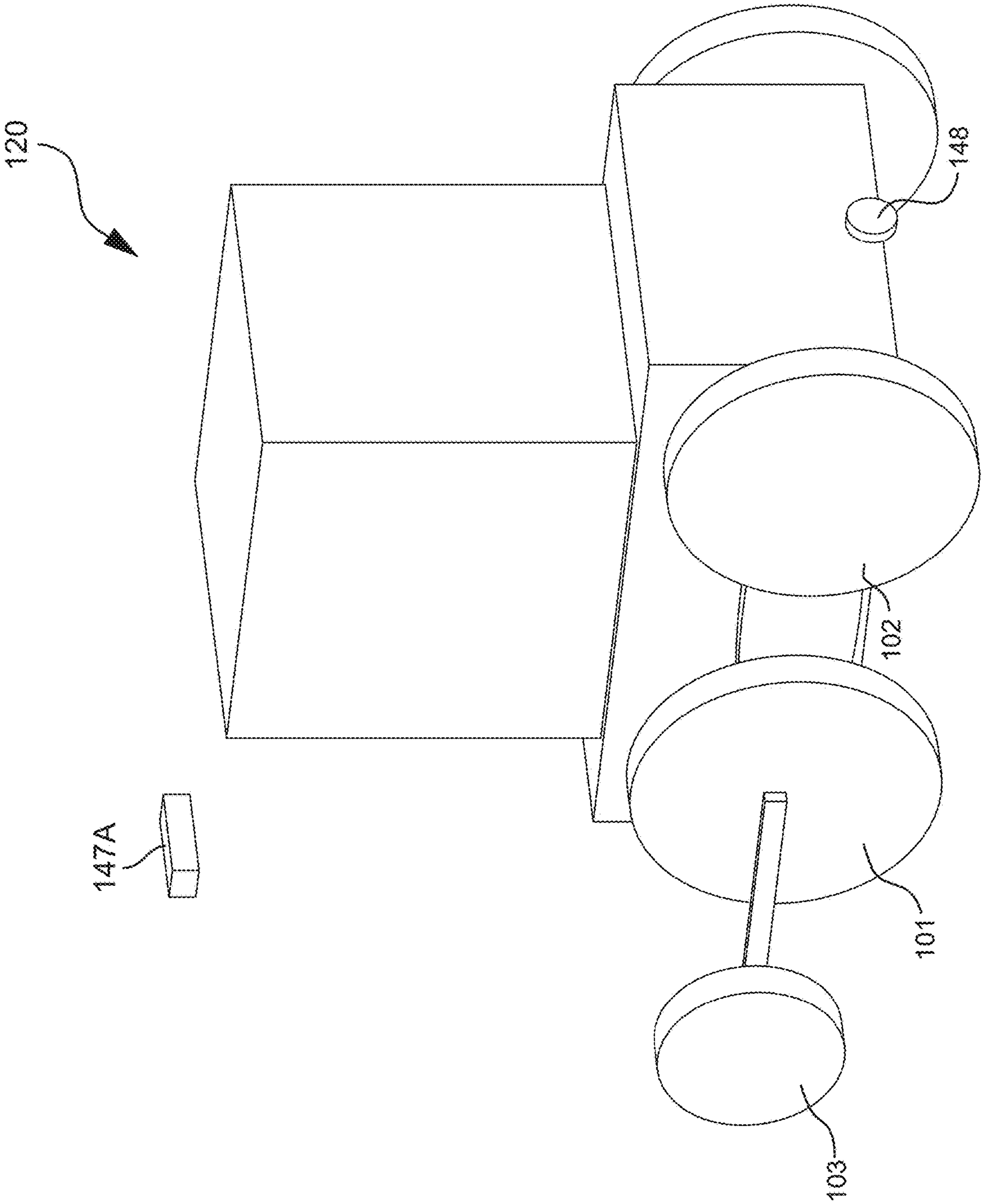
Figure 29F:
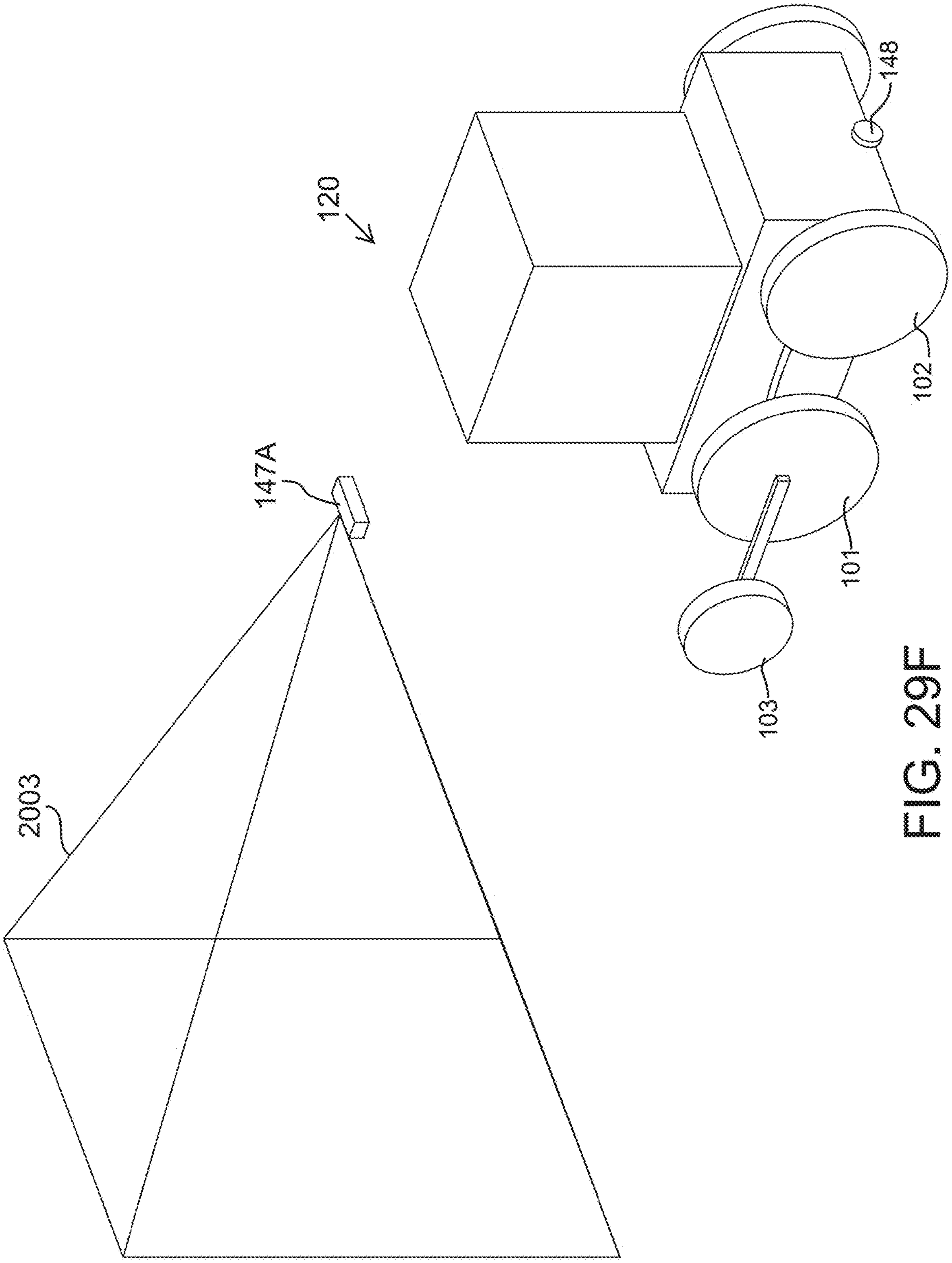
Figure 29G:
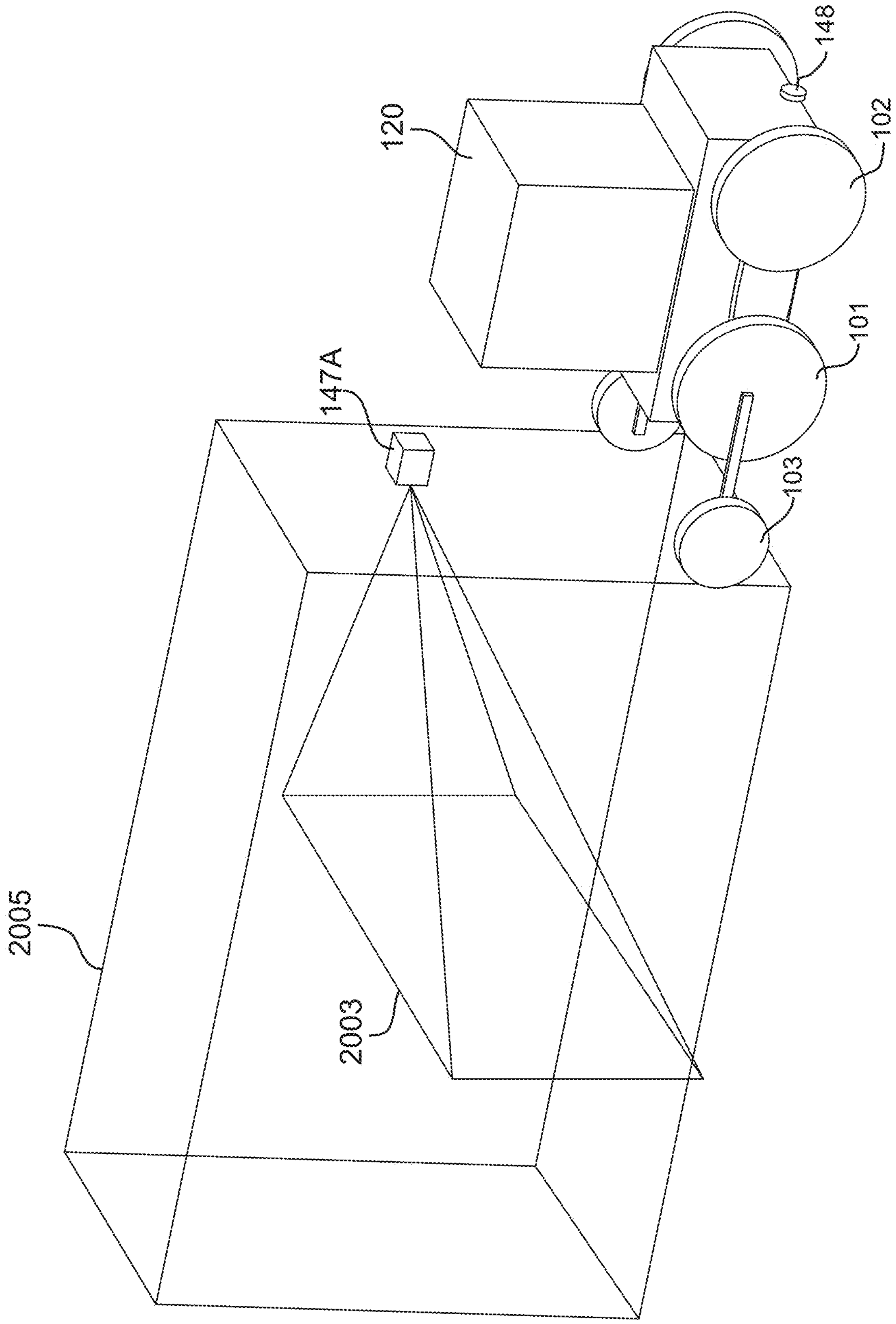
Figure 29H:
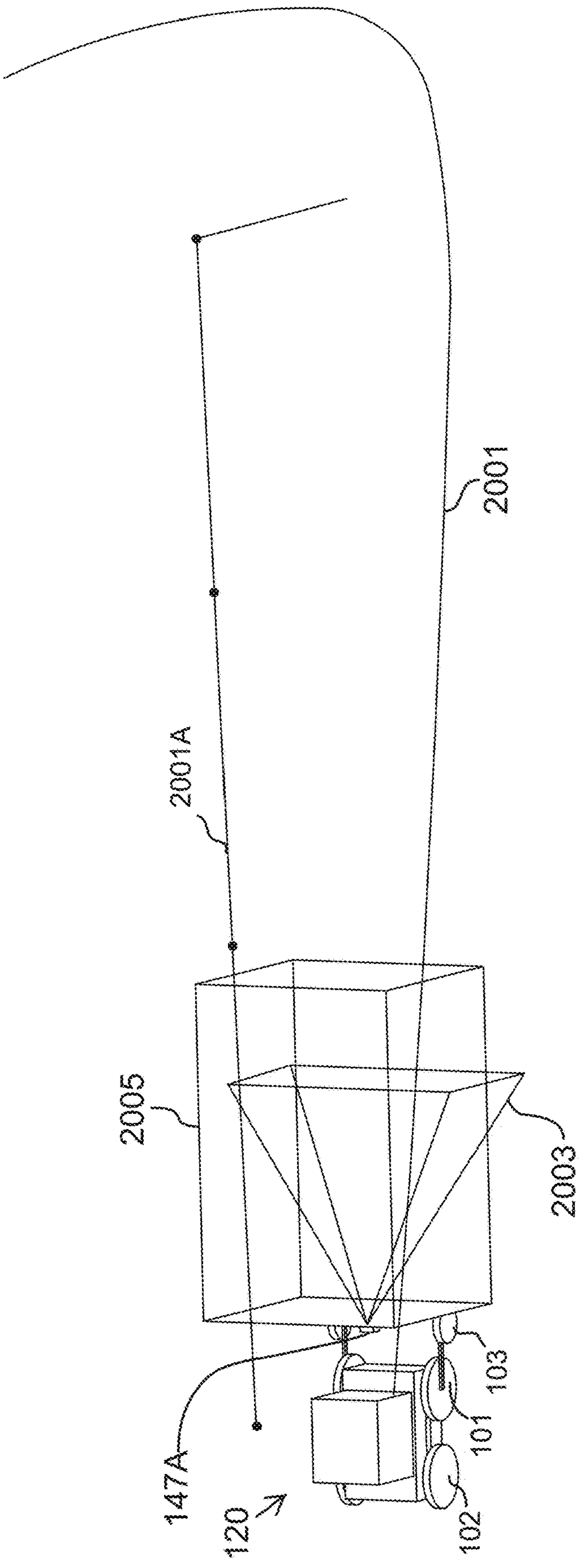
Figure 29I:
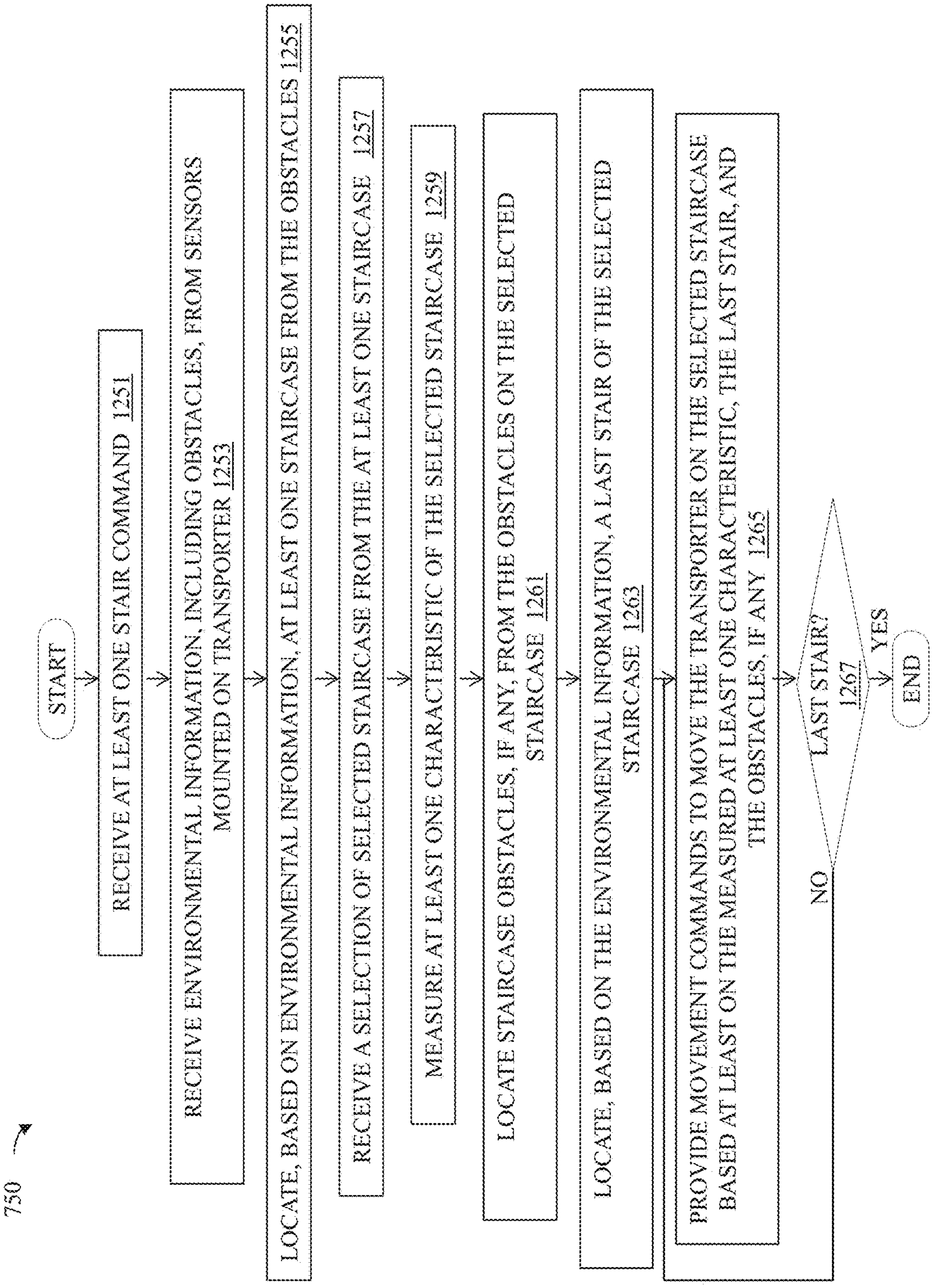
Figure 29J:
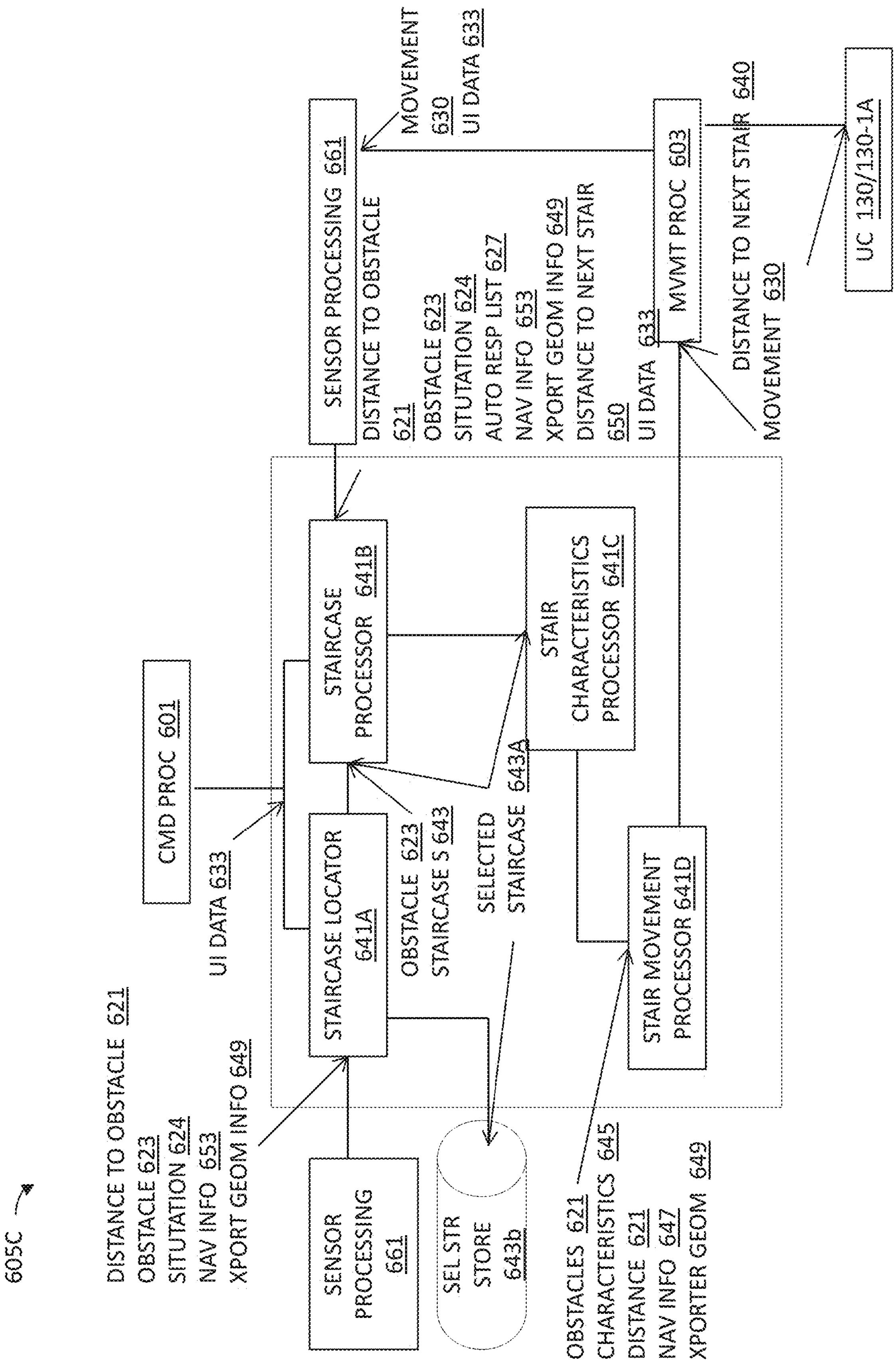
Figure 29K:
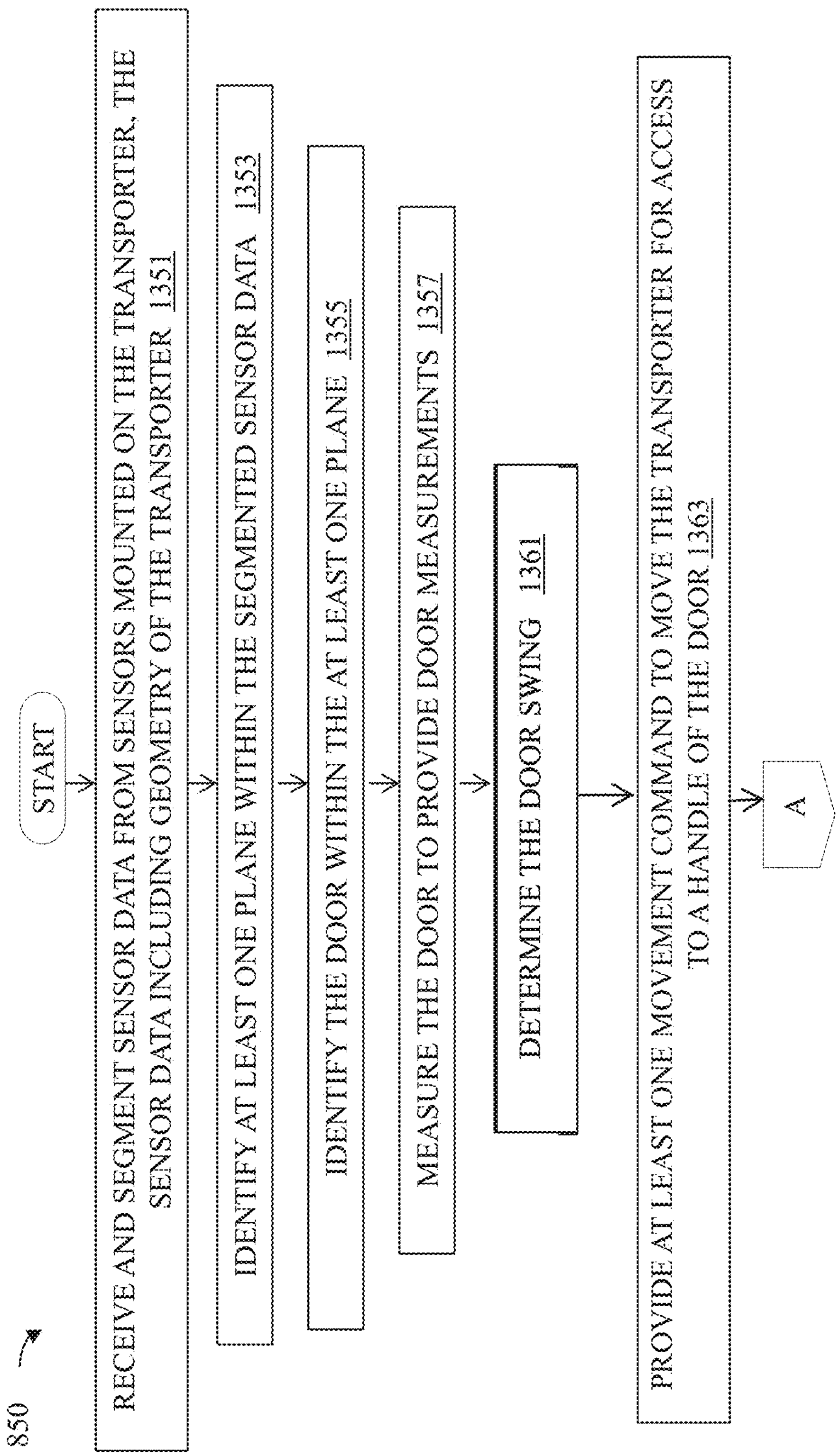
Figure 29L:
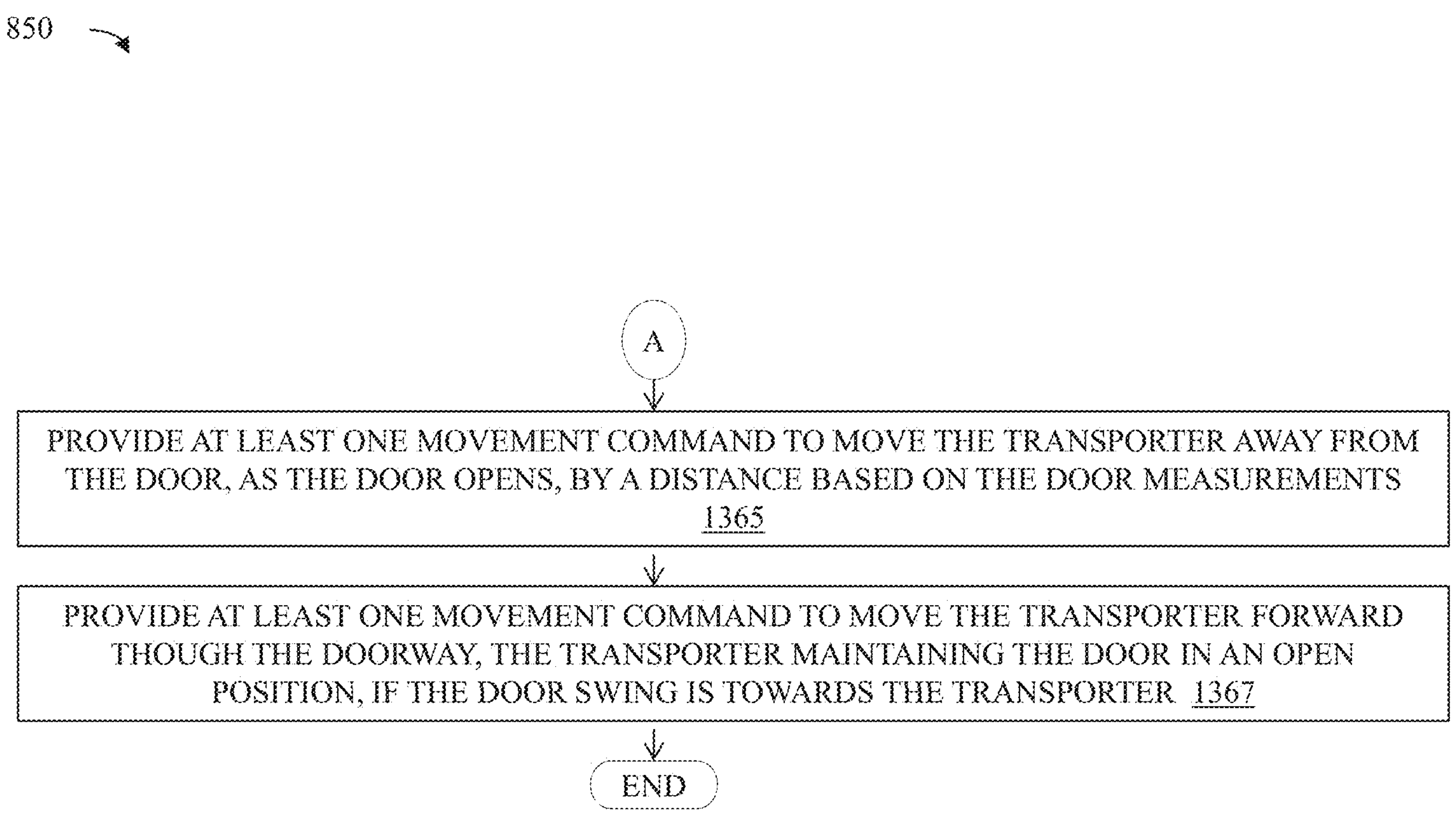
Figure 29M:
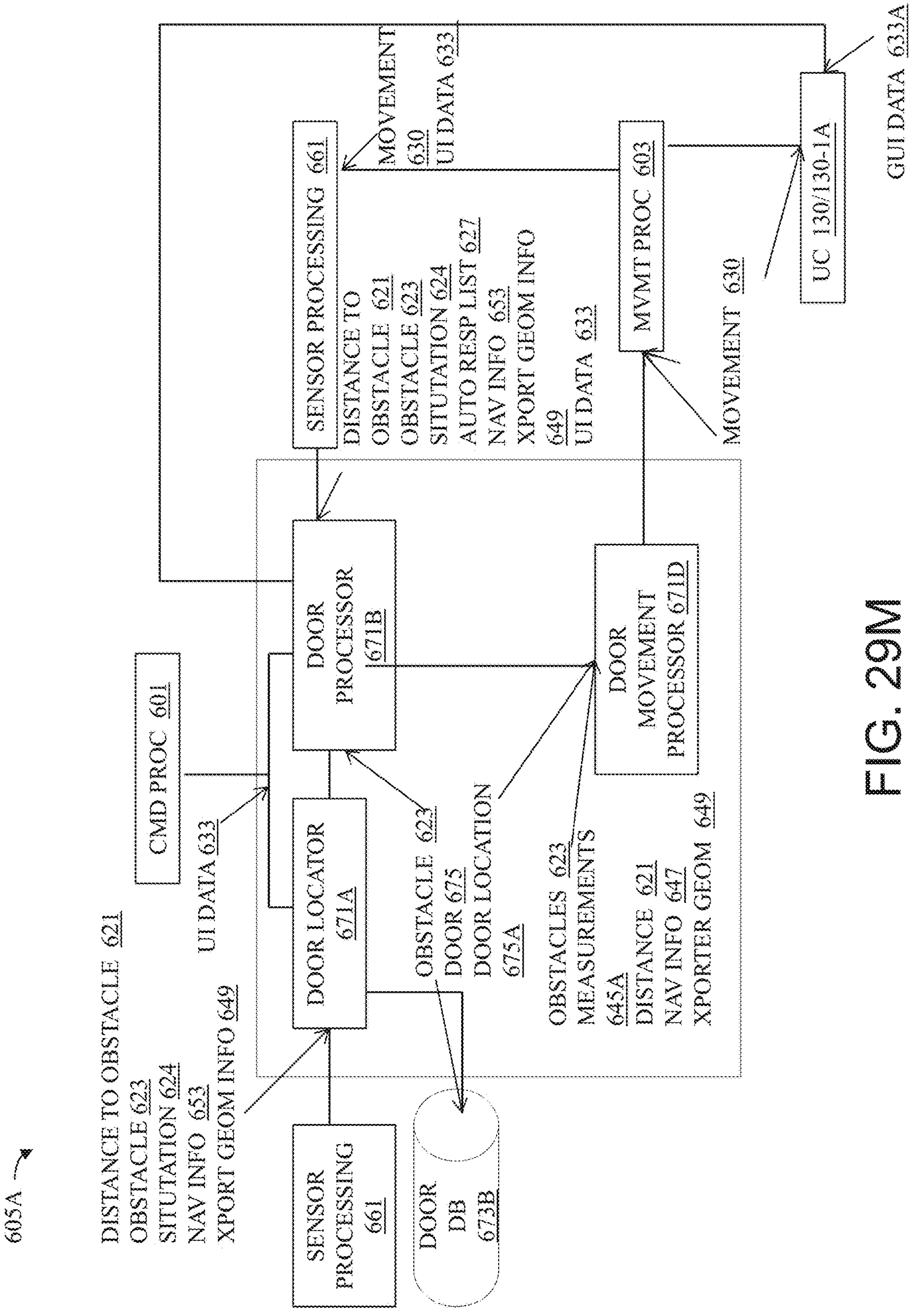
Figure 29N:
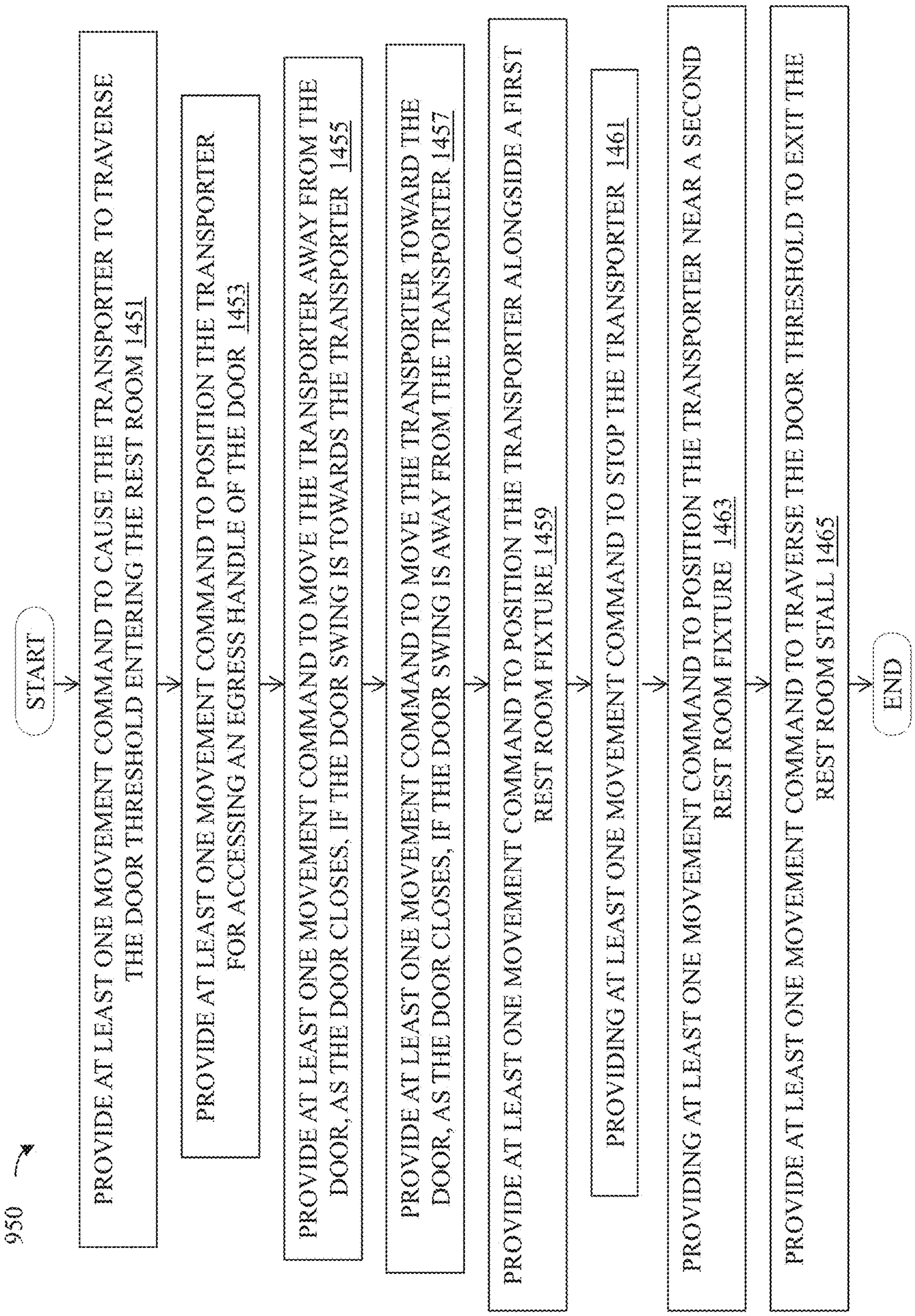
Figure 29O:
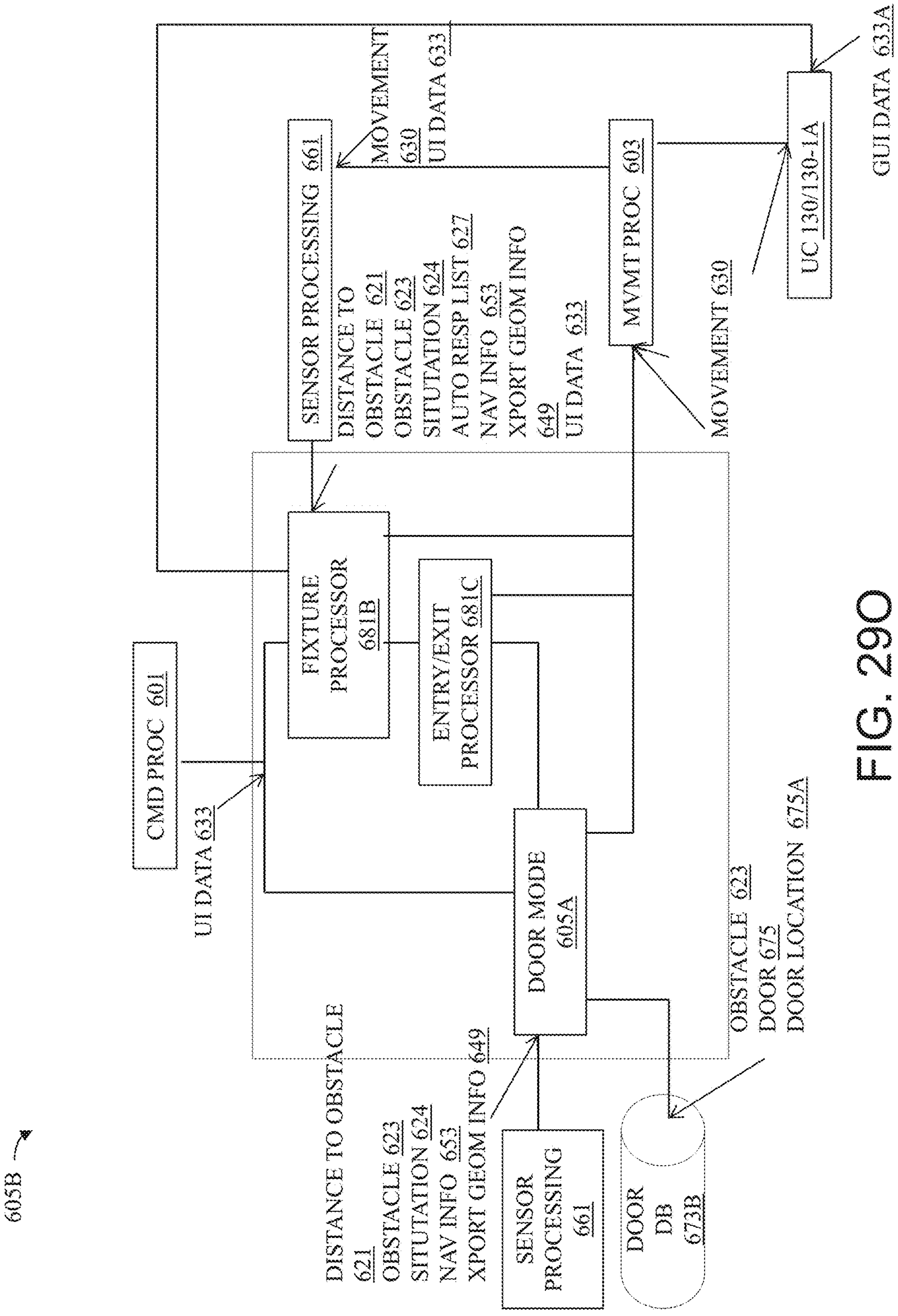
Figure 29P:
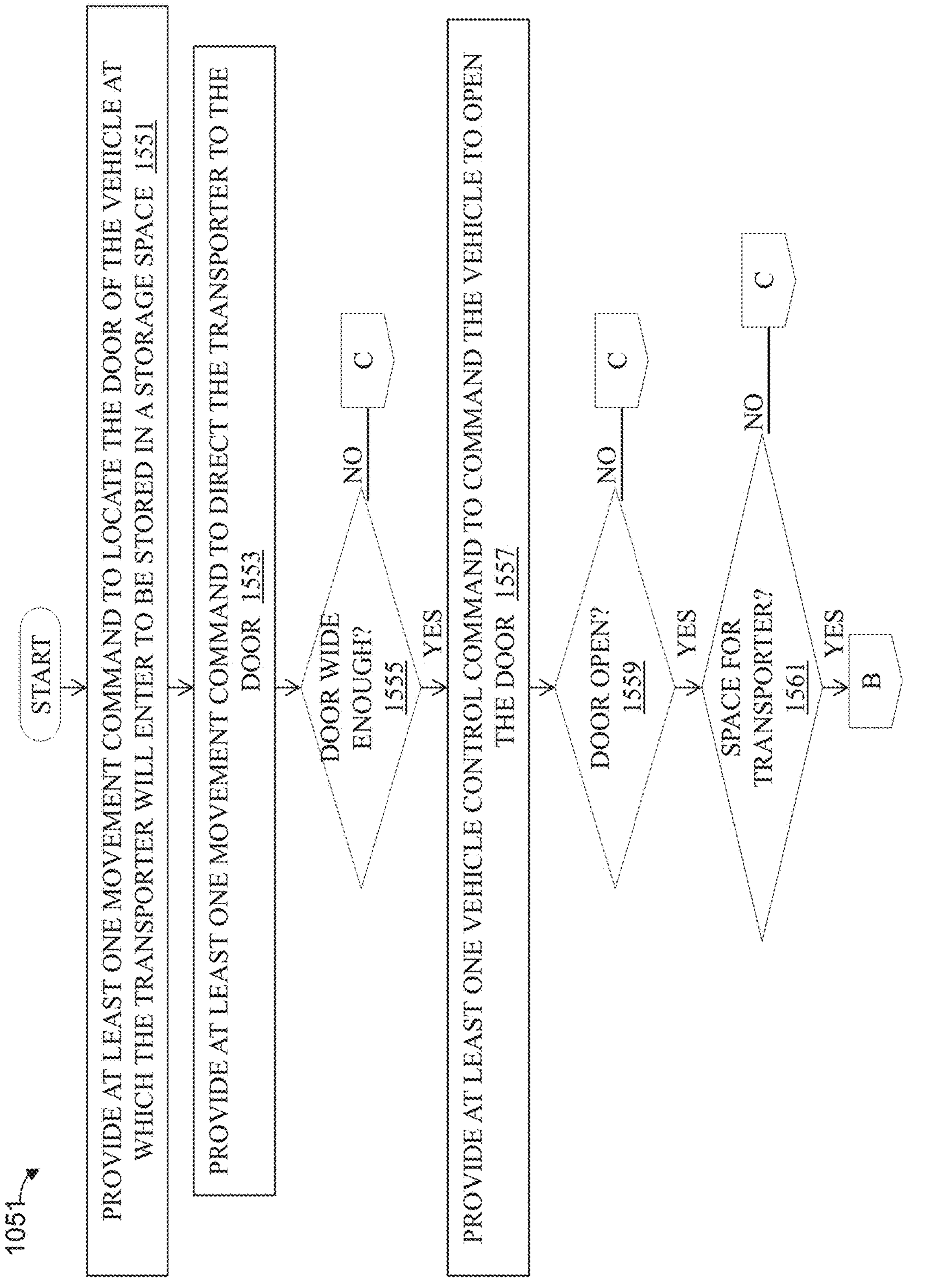
Figure 29Q:
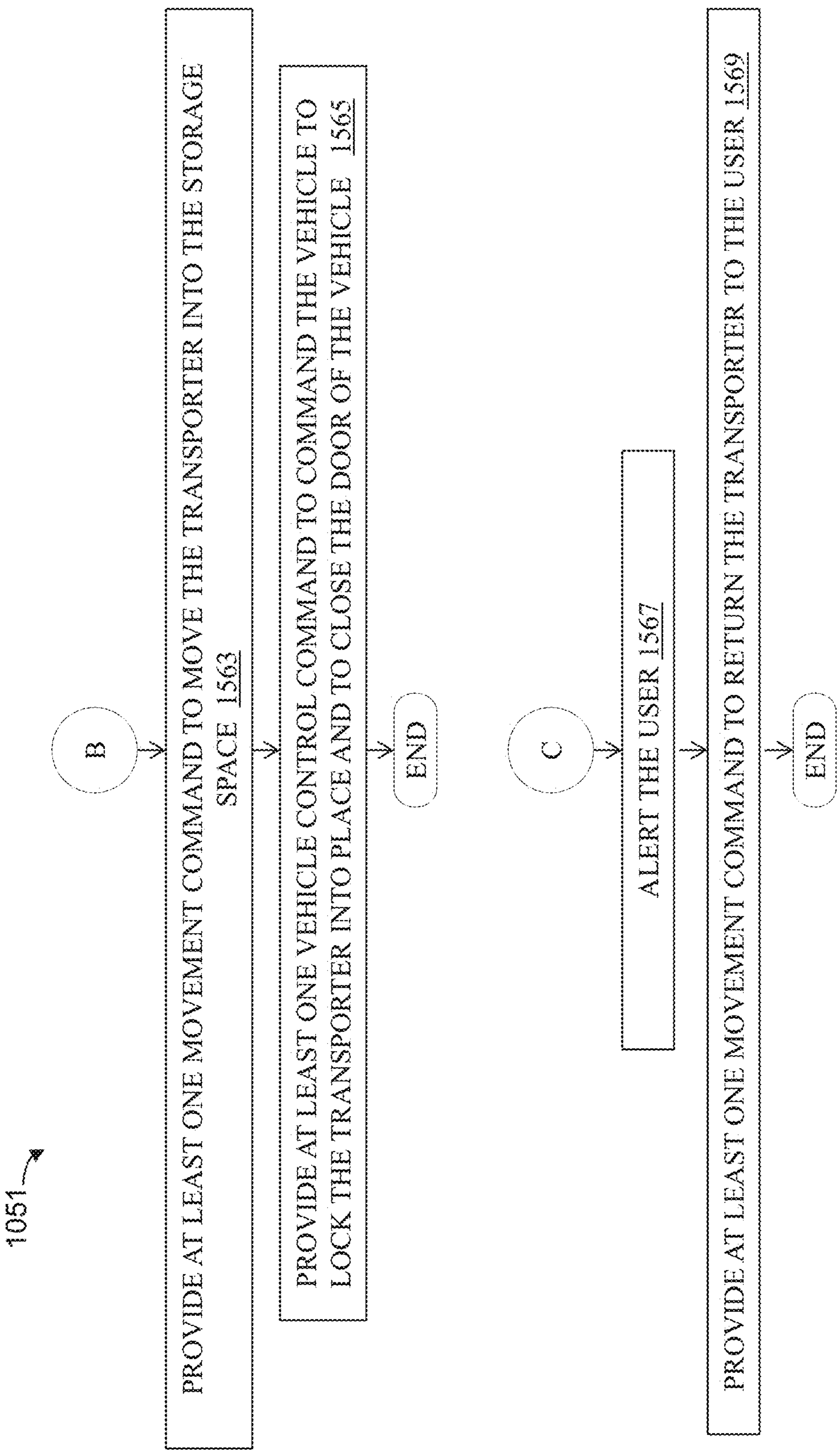
Figure 29R:
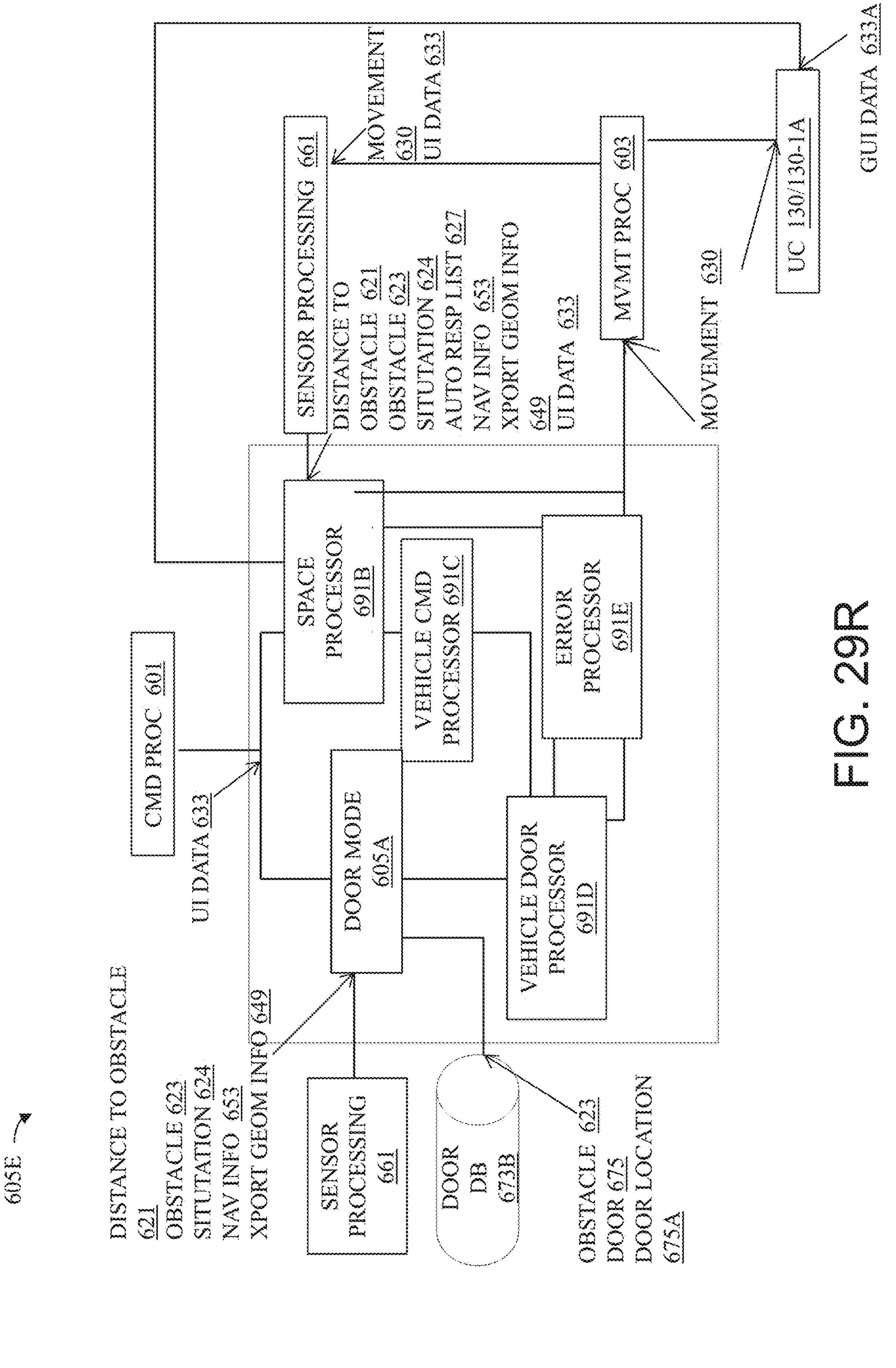
Figure 29S:
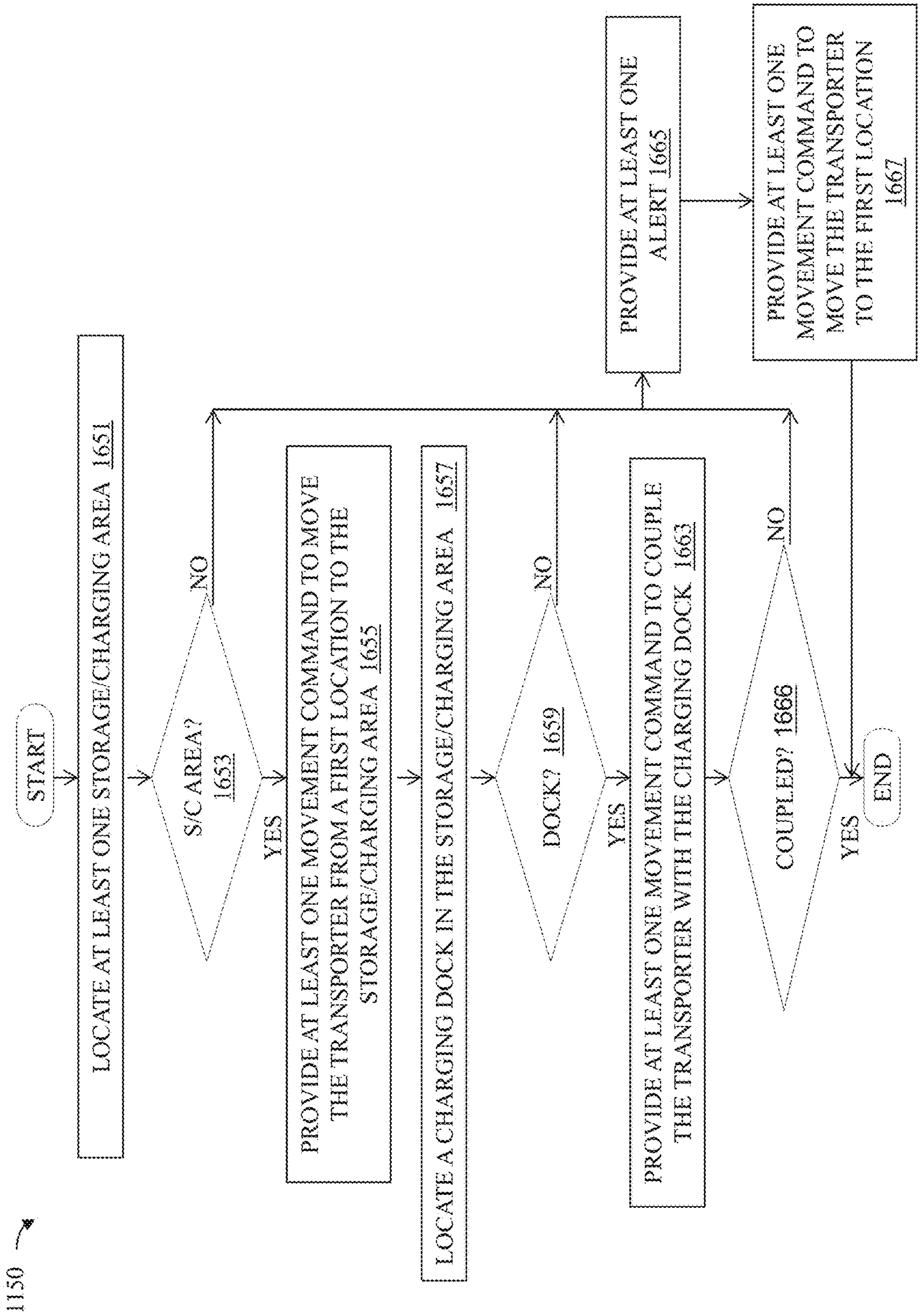
Figure 29T:
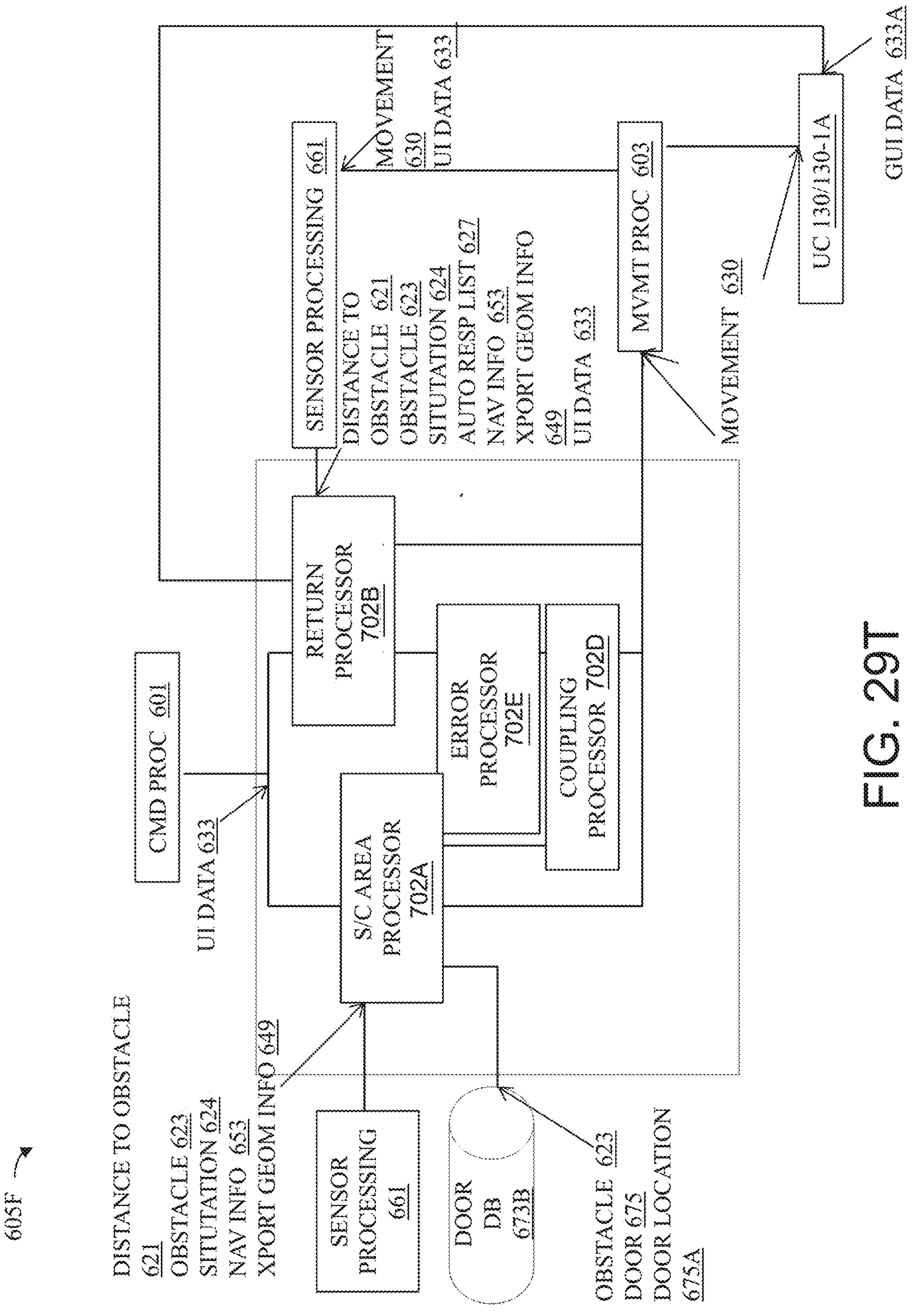
Figure 29U:
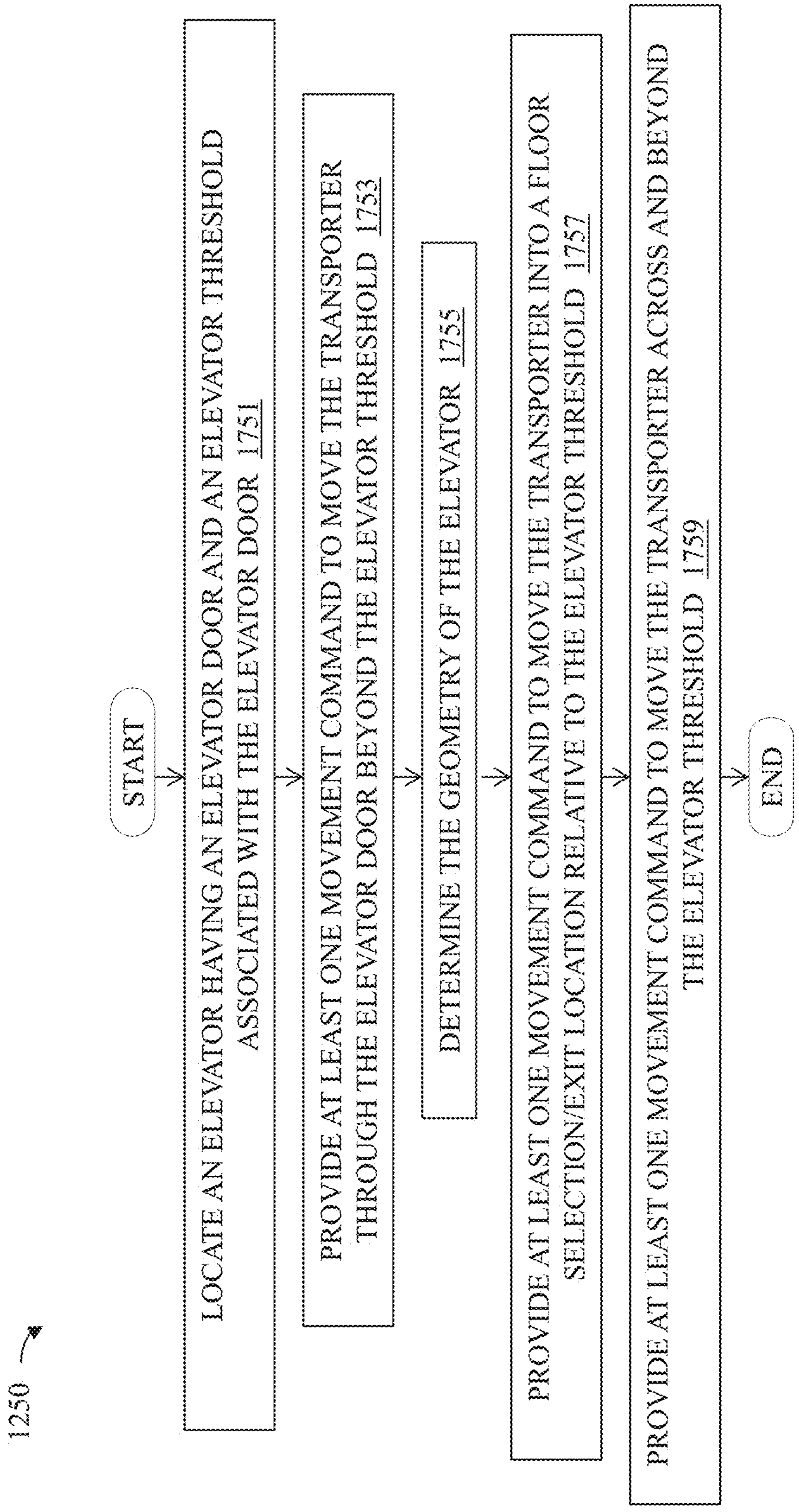
Figure 29V:
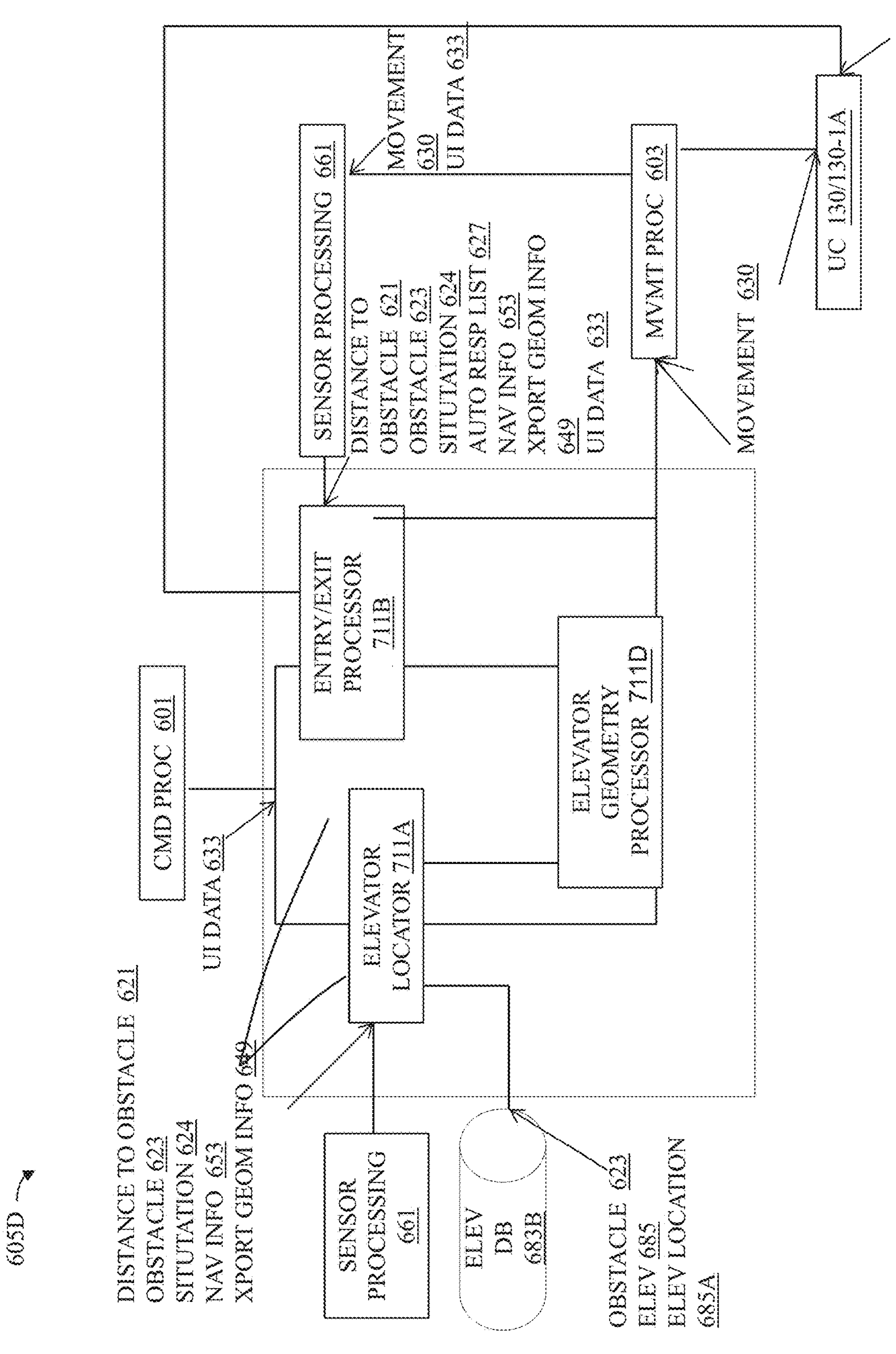

FIG. 21A is a schematic block diagram of the voting processor of the present teachings;

FIGS. 21B and 21C are flowcharts of the method of the present teachings for 4-way voting;

FIGS. 21D through 21G are tabular representations of voting examples of the present teachings;

FIGS. 21I and 21J are flowcharts of the second configuration of the voting process of the present teachings:

FIG. 22A is a schematic block diagram of allowed mode transitions in one configuration of the present teachings;

FIG. 22E is a pictorial representation of the center of gravity with respect to the wheelchair of the present teachings:

FIGS. 22B-22D are schematic block diagrams of the control structure with respect to modes of the system of the present teachings;

FIGS. 23A-23K are flow diagrams of the operational use of the mobility device of the present teachings;

FIGS. 23L-23X are flow diagrams of a second configuration of the operational use of the mobility device of the present teachings:

FIGS. 23Y-23KK are flow diagrams of a third configuration of the operational use of the mobility device of the present teachings;

FIGS. 23 LL-23 BBB are flow diagrams of a fourth configuration of the operational use of the mobility device of the present teachings;

FIGS. 24A and 24B are representations of the graphical user interface of the home screen display of the present teachings;

FIGS. 24C and 24D are representations of the graphical user interface of the main menu display of the present teachings;

FIGS. 24E-24H are representations of the graphical user interface of the selection screen display of the present teachings;

FIGS. 241 and 24J are representations of the graphical user interface of the transition screen display of the present teachings;

FIGS. 24K and 24L are representations of the graphical user interface of the forced power off display of the present teachings;

FIGS. 24M and 24N are representations of the CG fit screen of the present teachings;

FIG. 25A is a schematic block diagram of the components of the speed processor of the present teachings;

FIG. 25B is a flowchart of the method of speed processing of the present teachings;

FIG. 25C is a graph of the manual interface response template of the present teachings;

FIGS. 25D, 25L, 25M, and 25N are graphs of interface responses of the present teachings based on speed categories;

FIGS. 25E and 25F are graphical representations of joystick control profiles of the present teachings;

FIG. 25G is a schematic block diagram of the components of the adaptive speed control processor of the present teachings;

FIG. 25H is a flowchart of the method of adaptive speed processing of the present teachings;

FIGS. 251-25K are pictorial descriptions of exemplary uses of the adaptive speed control of the present teachings;

FIG. 26A is a schematic block diagram of the components of the traction control processor of the present teachings;

FIG. 26B is a flowchart of the method of traction control processing of the present teachings;

FIG. 27A is a pictorial representation of a comparison of a mobility device of the present teachings tipping versus a mobility device of the present teachings traversing an incline;

FIG. 27B is a flowchart of the method of anti-tipping processing of the present teachings;

FIG. 27C is a schematic block diagram of an anti-tipping controller of the present teachings;

FIG. 27D is a schematic block diagram of the CG fit processor of the present teachings;

FIG. 27E is a flowchart of the method of CG fit processing of the present teachings;

FIG. 28A is a schematic block diagram of the weight processor of the present teachings;

FIG. 28B is a flowchart of the method of weight processing of the present teachings;

FIG. 28C is a schematic block diagram of the weight-current processor of the present teachings;

FIG. 28D is a flowchart of the method of weight-current processing of the present teachings;

FIG. 29A is a schematic block diagram of the components of the UC assist of the present teachings;

FIGS. 29B-29C are flowcharts of the method of obstacle detection of the present teachings;

FIG. 29D is a schematic block diagram of the components of the obstacle detection of the present teachings;

FIGS. 29E-29H are computer-generated representations of the mobility device configured with a sensor;

FIG. 29I is a flowchart of the method of enhanced stair climbing of the present teachings;

FIG. 29J is a schematic block diagram of the components of the enhanced stair climbing of the present teachings;

FIGS. 29K-29L are flowcharts of the method of door traversal of the present teachings;

FIG. 29M is a schematic block diagram of the components of the door traversal of the present teachings;

FIG. 29N is a flowchart of the method of rest room navigation of the present teachings;

FIG. 29O is a schematic block diagram of the components of the rest room navigation of the present teachings;

FIGS. 29P-29O are flowcharts of the method of mobile storage of the present teachings;

FIG. 29R is a schematic block diagram of the components of the mobile storage of the present teachings;

FIG. 29S is a flowchart of the method of storage/charging of the present teachings;

FIG. 29T is a schematic block diagram of the components of the storage/charging of the present teachings;

FIG. 29U is a flowchart of the method of elevator navigation of the present teachings;

FIG. 29V is a schematic block diagram of the components of the elevator navigation of the present teachings.

Figure 31A:
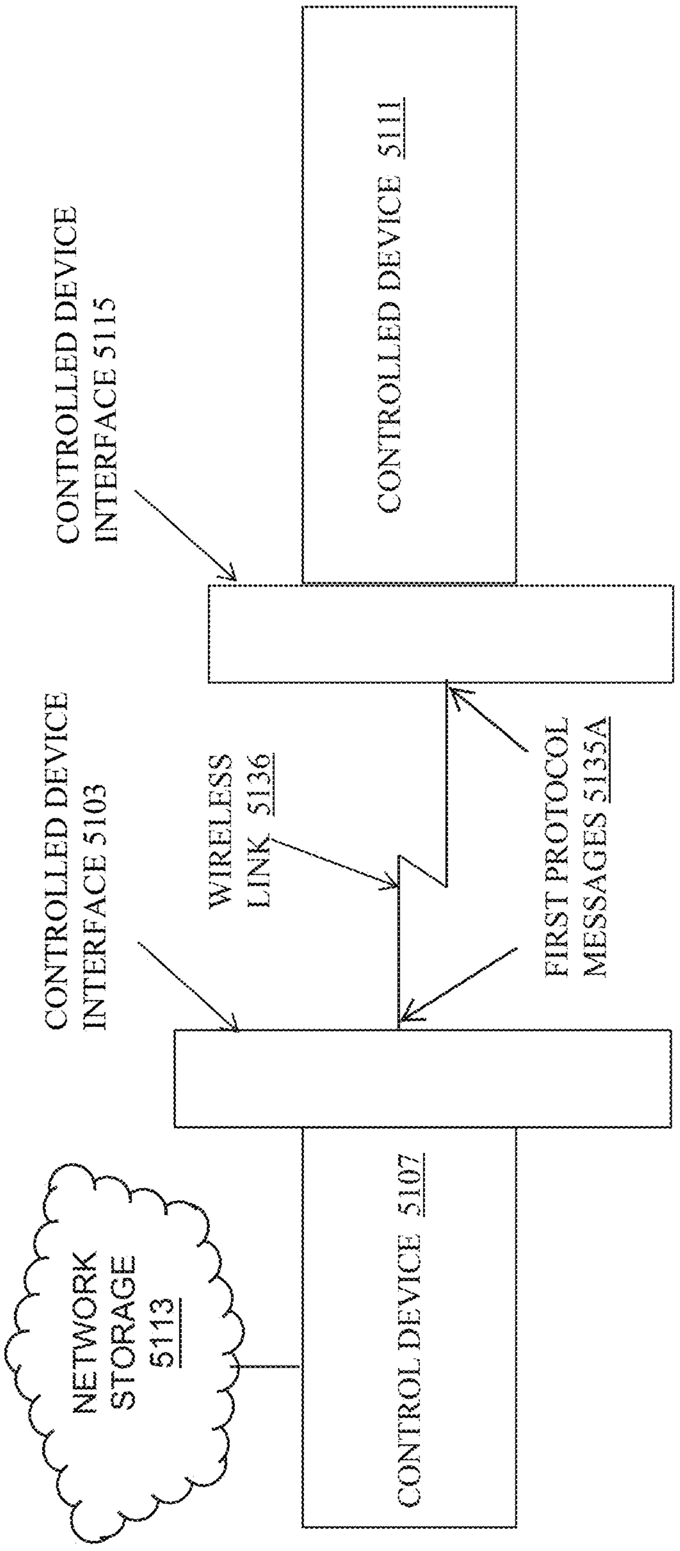
Figure 31B:
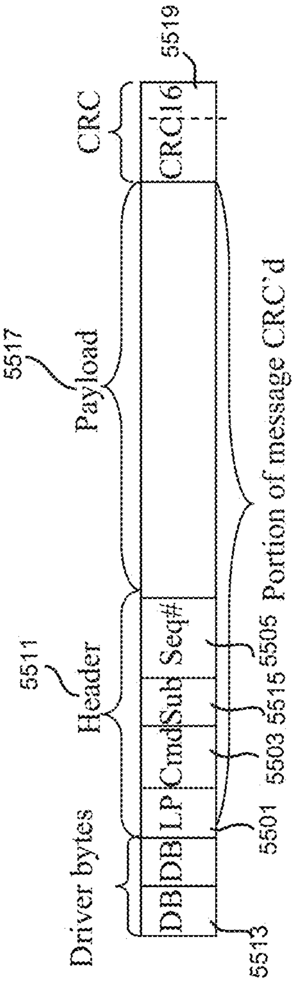
Figure 31C:
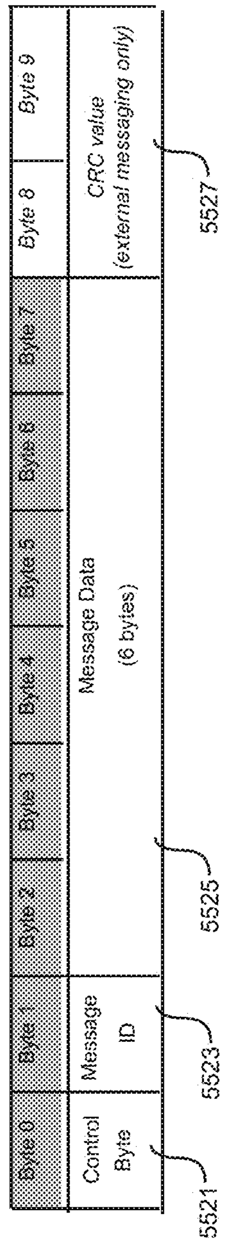
Figure 31D:
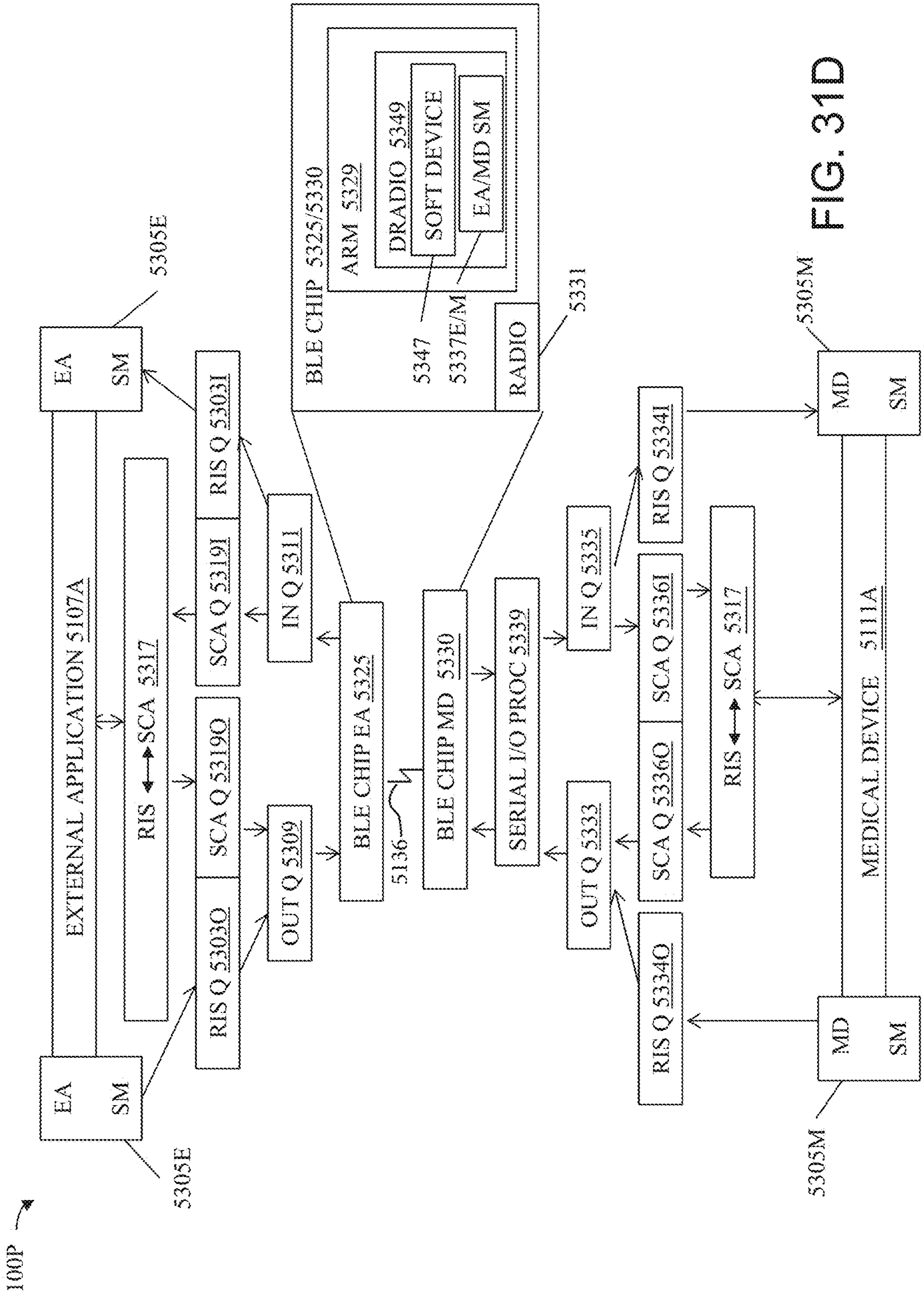
Figure 31E:
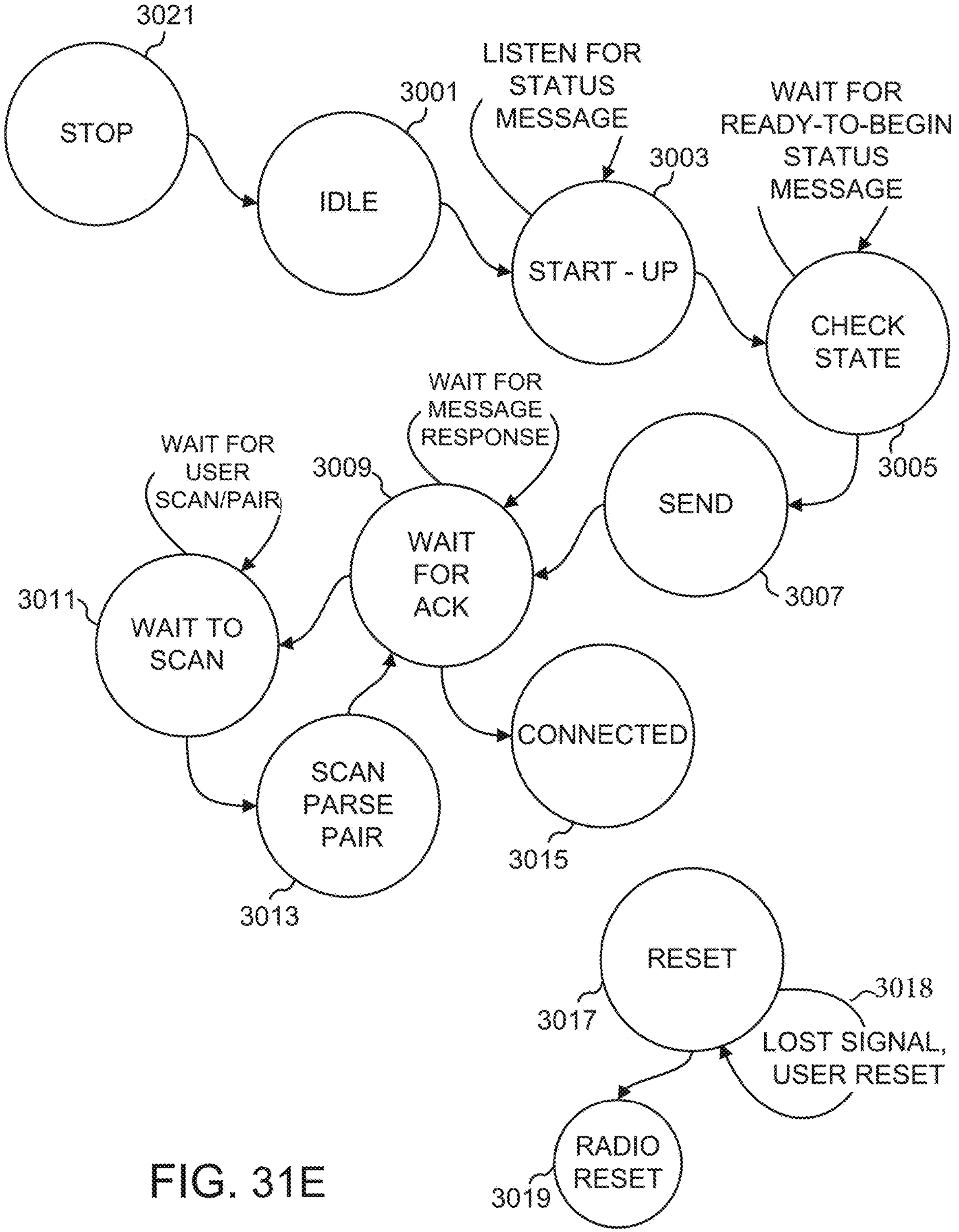
Figure 31F:
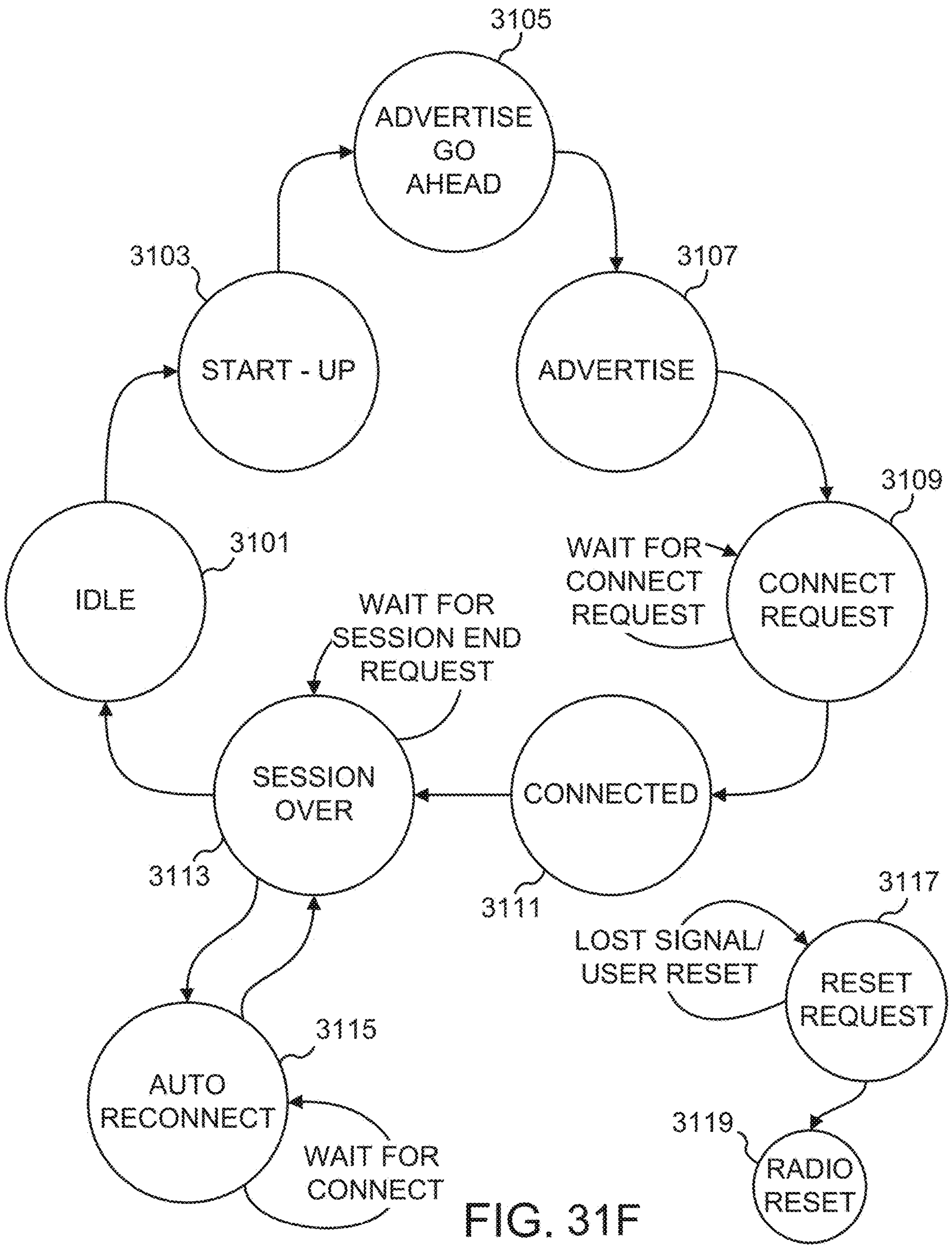
Figure 31G:
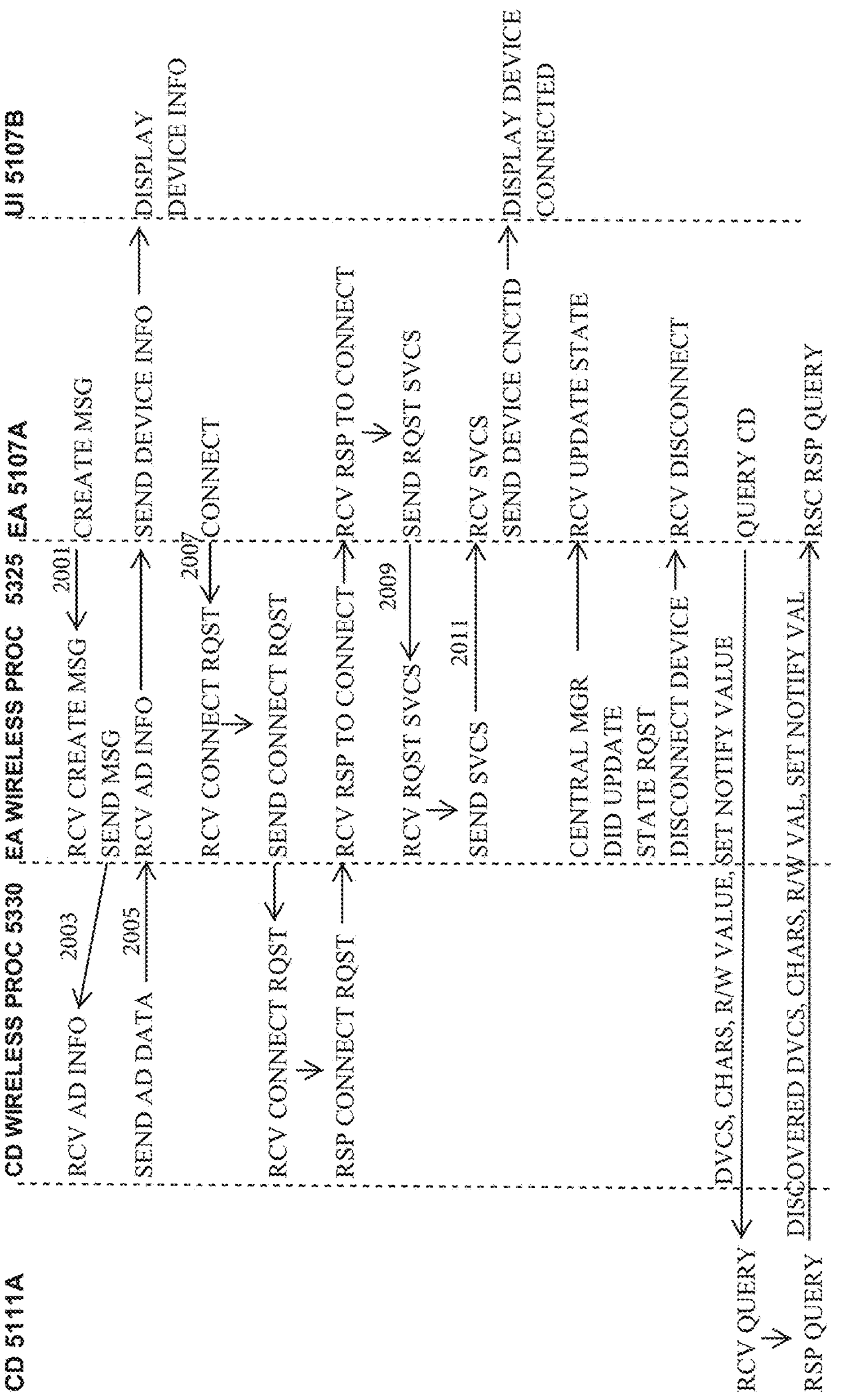
Figure 31H:
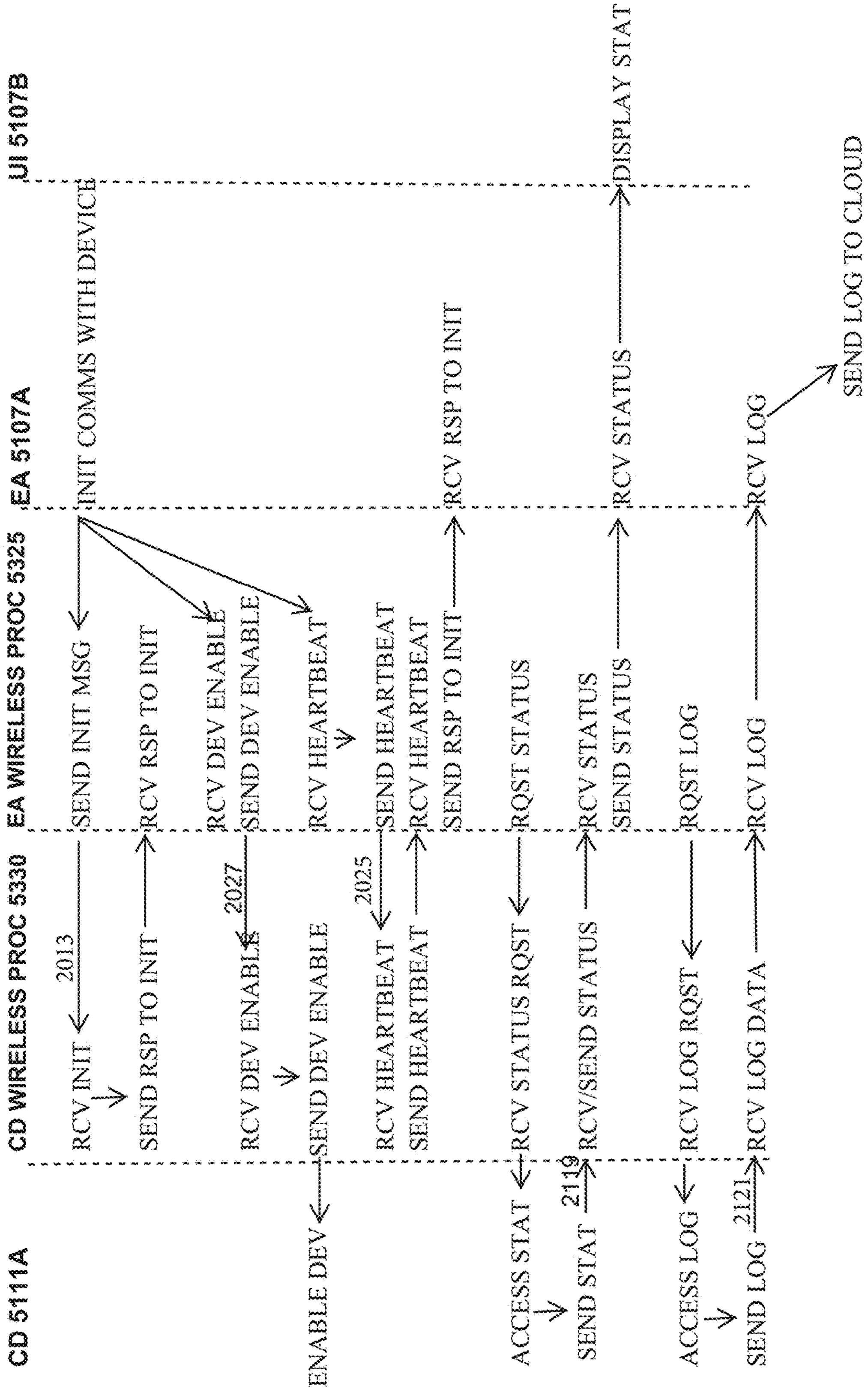
Figure 32A:
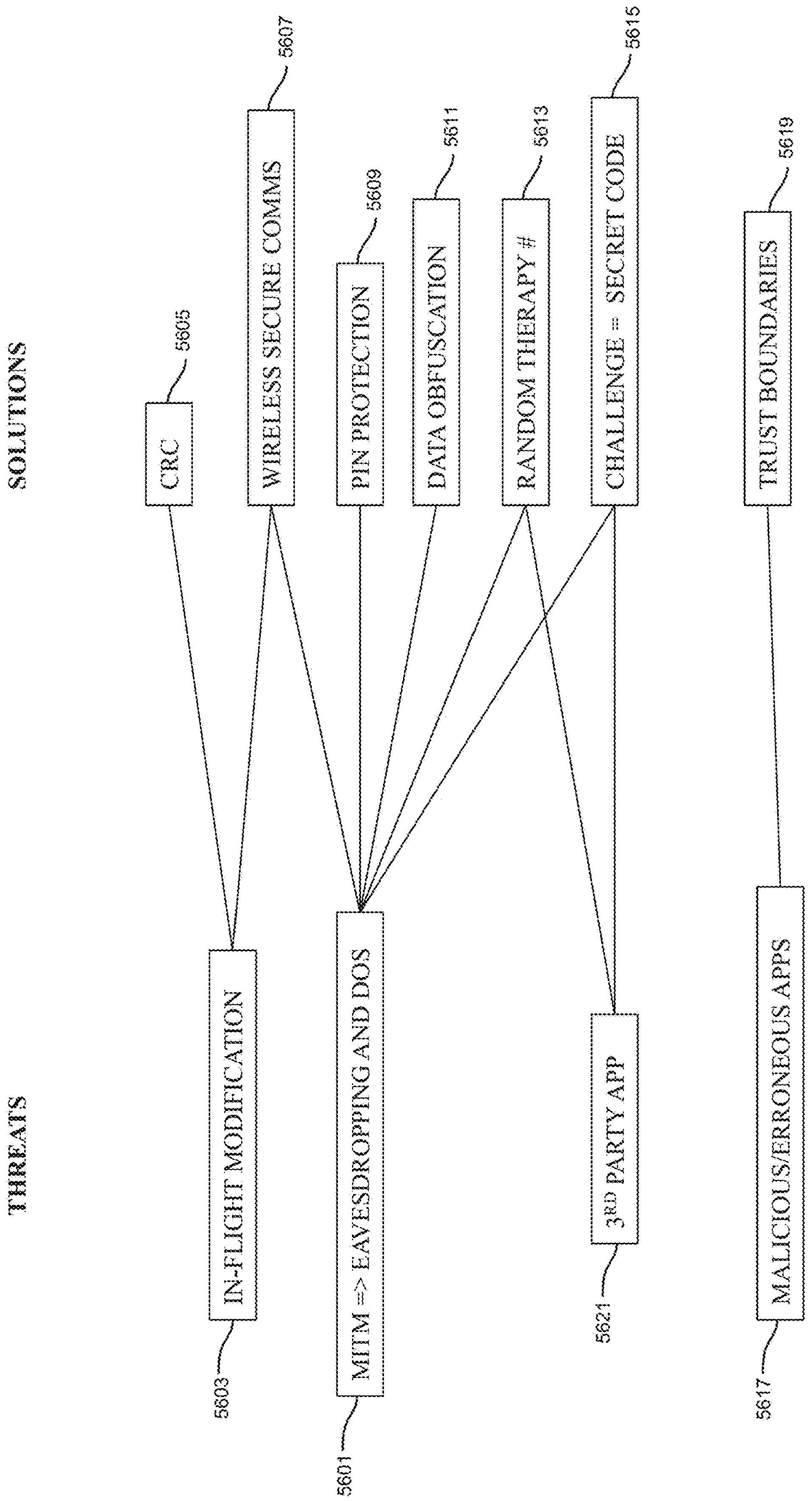
Figure 32B:
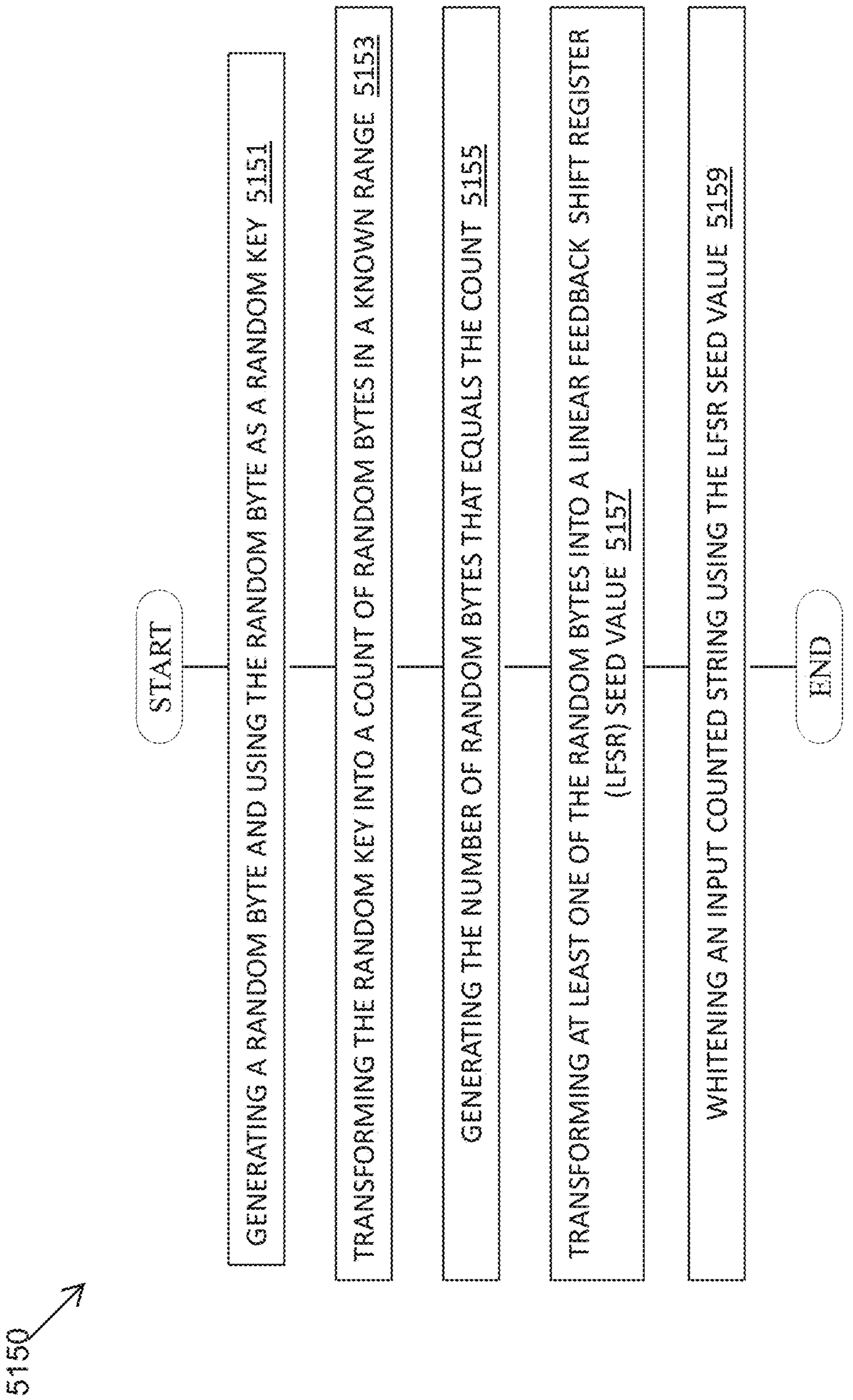
Figure 32C:
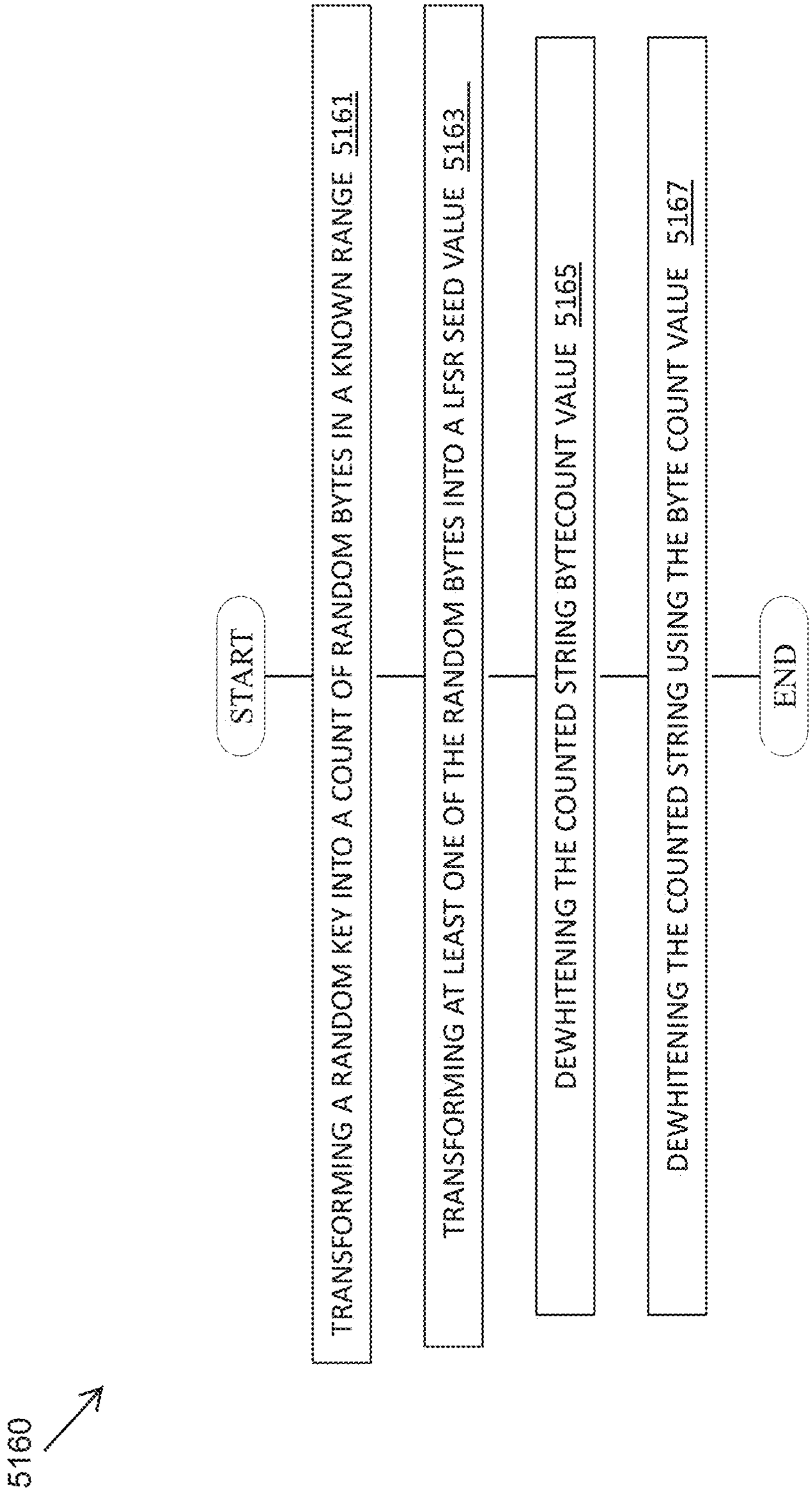
Figure 32D:
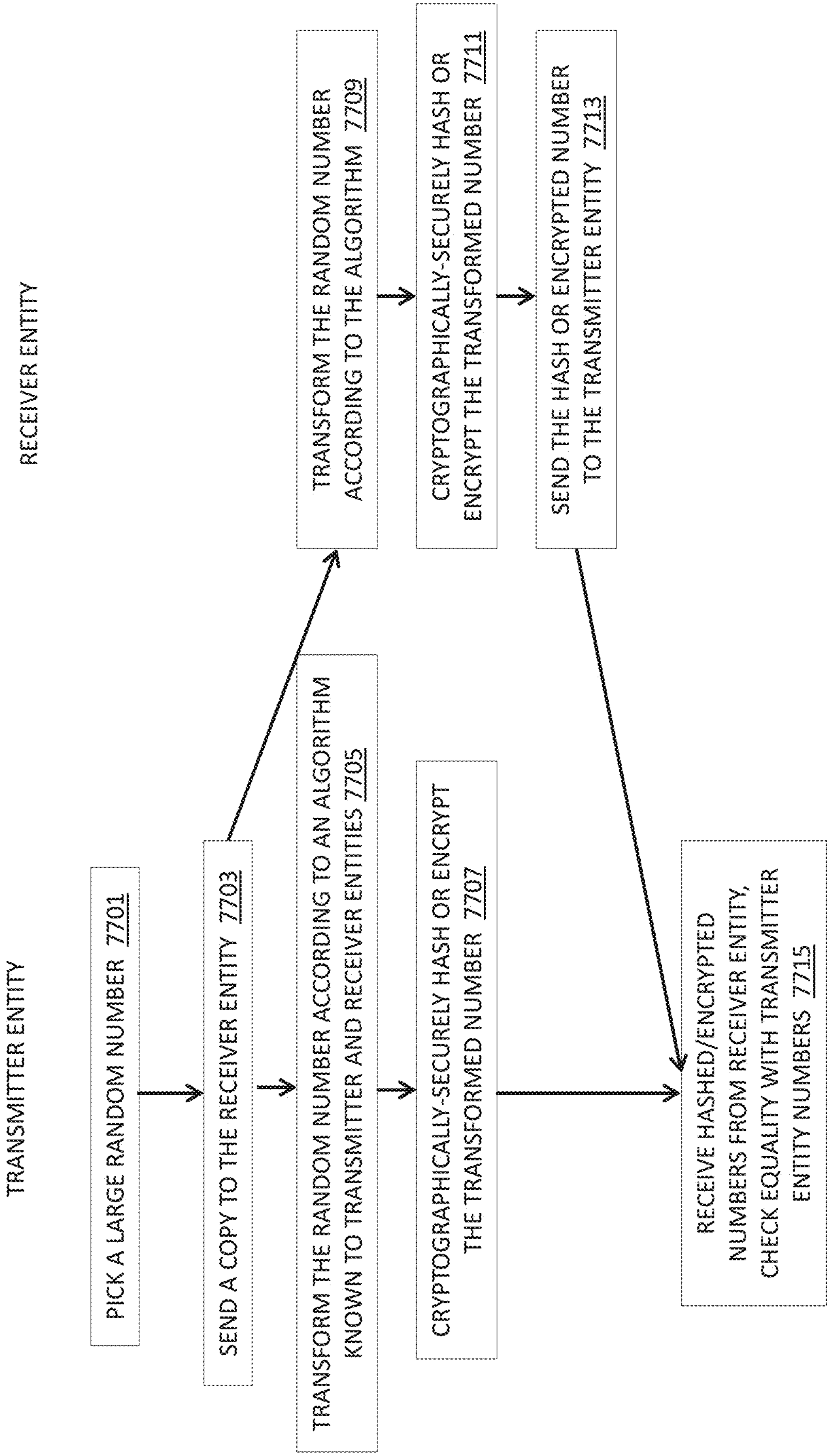
Figure 33:
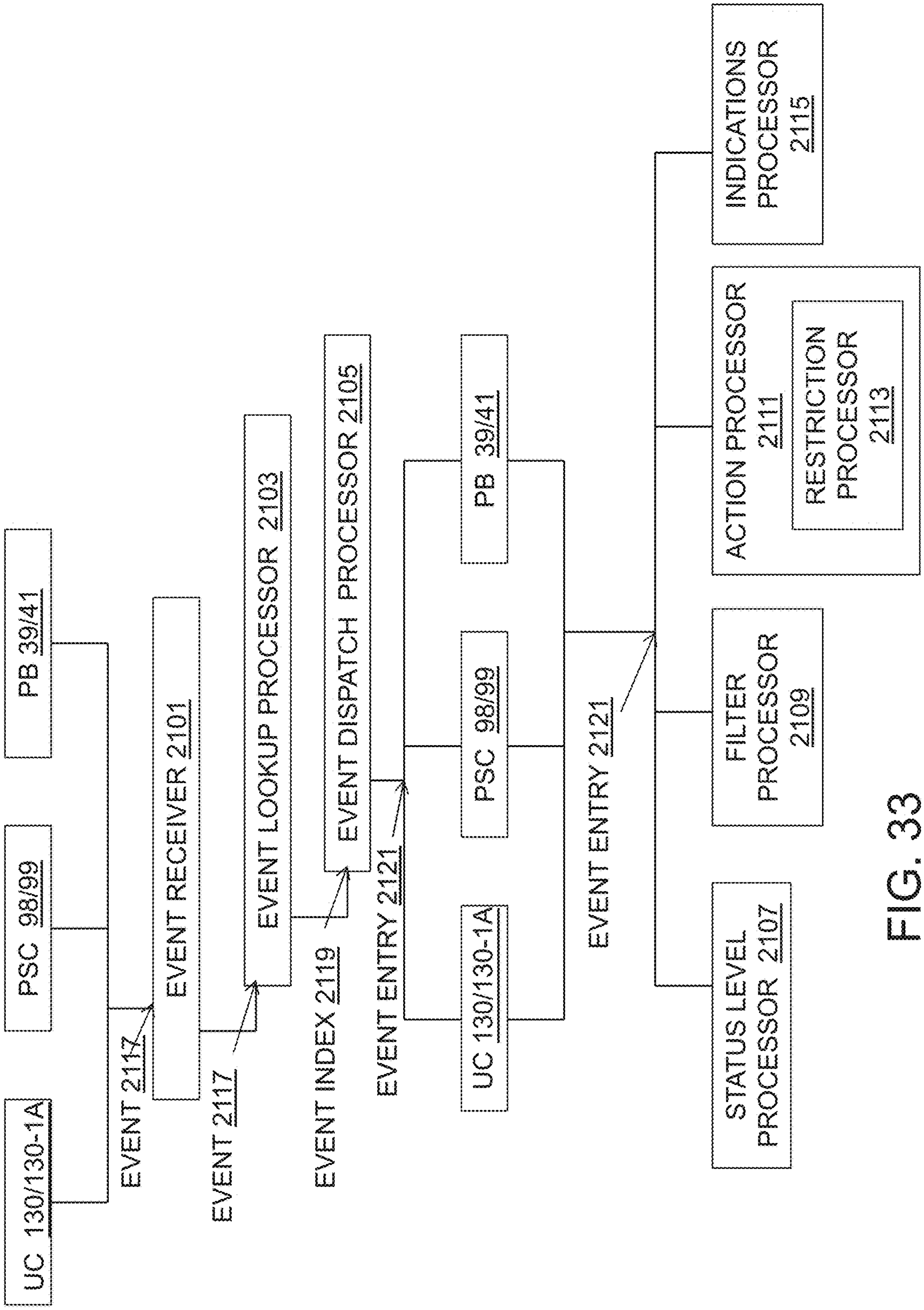

FIG. 30A is a table of communications packets exchanged in the MD of the present teachings;

FIGS. 30B-30E are tables of communication packet contents of the present teachings;

FIG. 31A is a schematic block diagram of remote communications interfaces of the present teachings;

FIGS. 31B and 31C are packet formats for exemplary protocols of the present teachings;

FIG. 31D is a schematic block diagram of the wireless communications system of the present teachings;

FIGS. 31E and 31F are bubble format diagrams for wireless communications state transitions of the present teachings;

FIGS. 31G and 31H are message communications diagrams for wireless communications of the present teachings;

FIG. 32A is a threat/solution block diagram of possible threats to the MD of the present teachings;

FIG. 32B is a flowchart of the method for obfuscating plain text of the present teachings;

FIG. 32C is a flowchart of the method for de-obfuscating plain text of the present teachings;

FIG. 32D is a transmitter/receiver communications block diagram of the method for challenge/response of the present teachings; and FIG. 33 is a schematic block diagram of event processing of the present teachings.

Figure 34A:
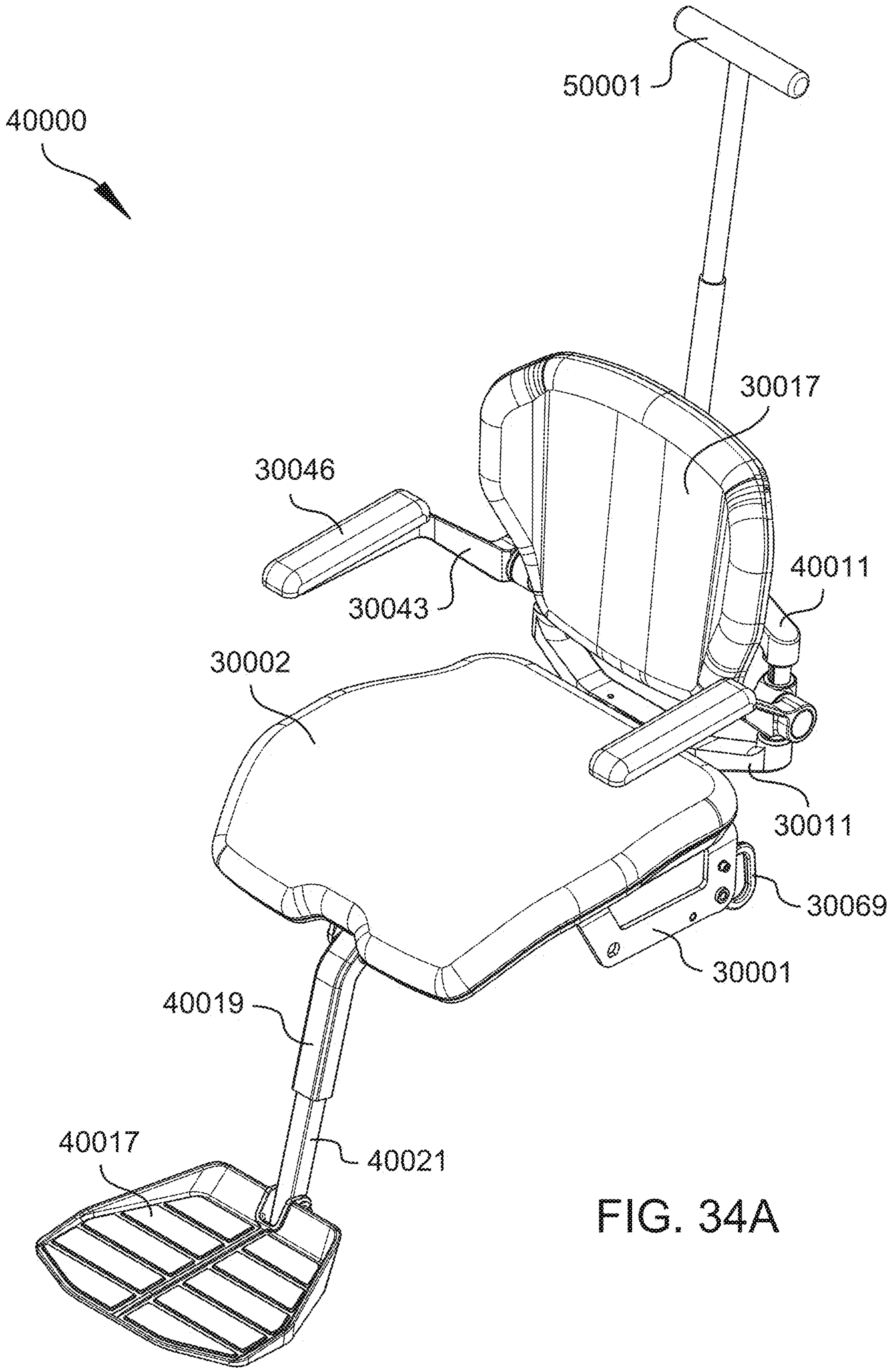
Figure 34B:
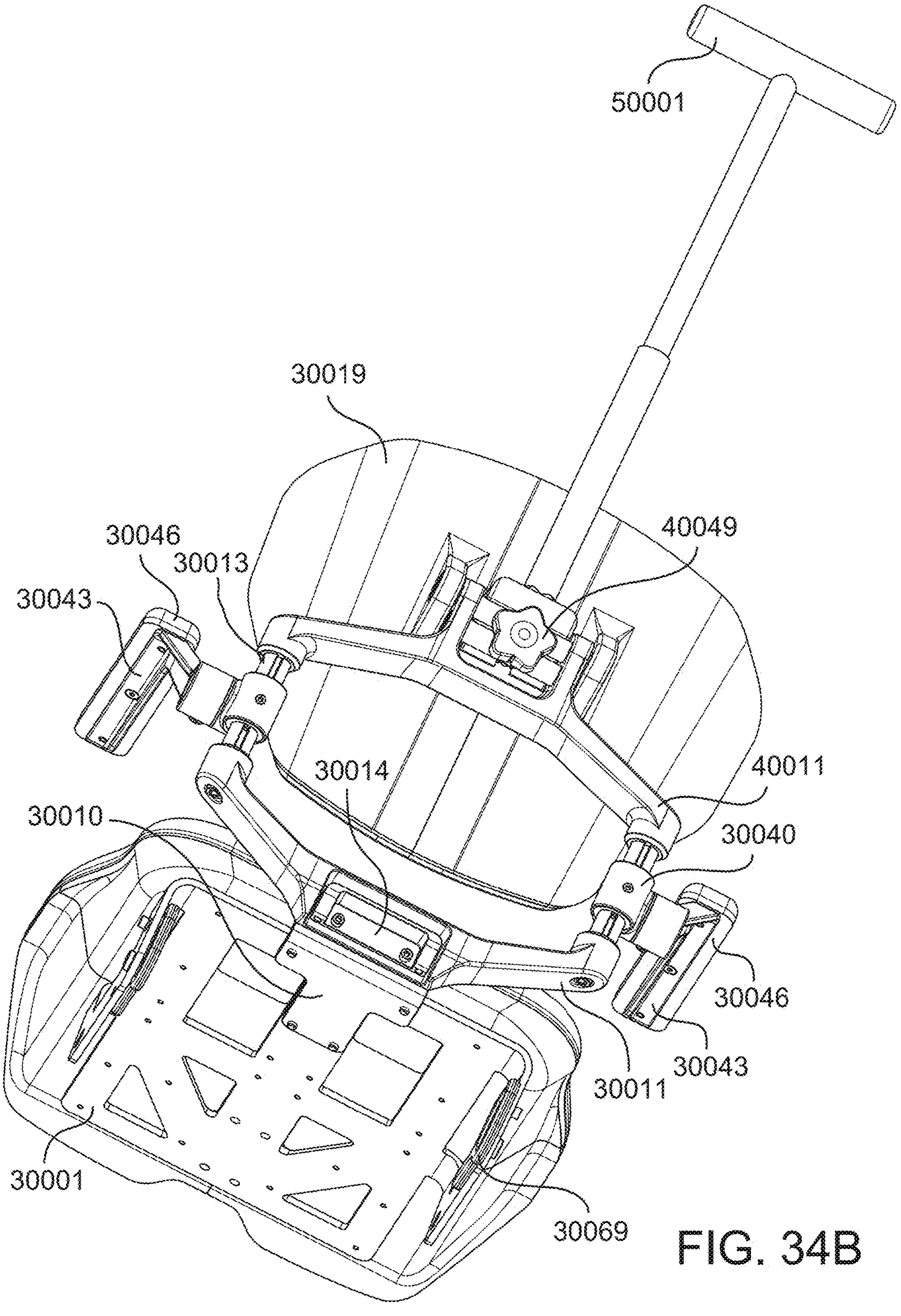
Figure 34C:
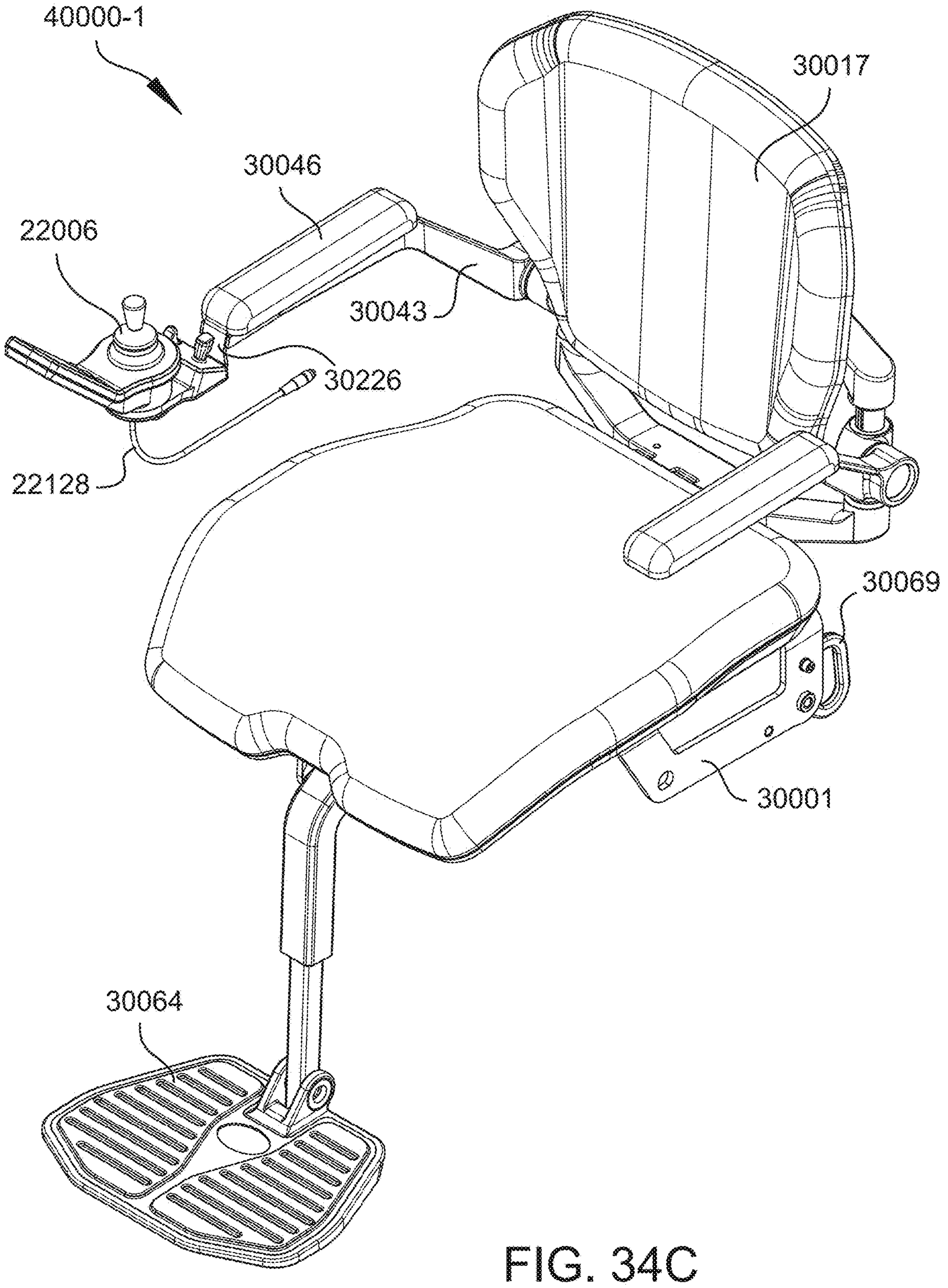
Figure 34D:
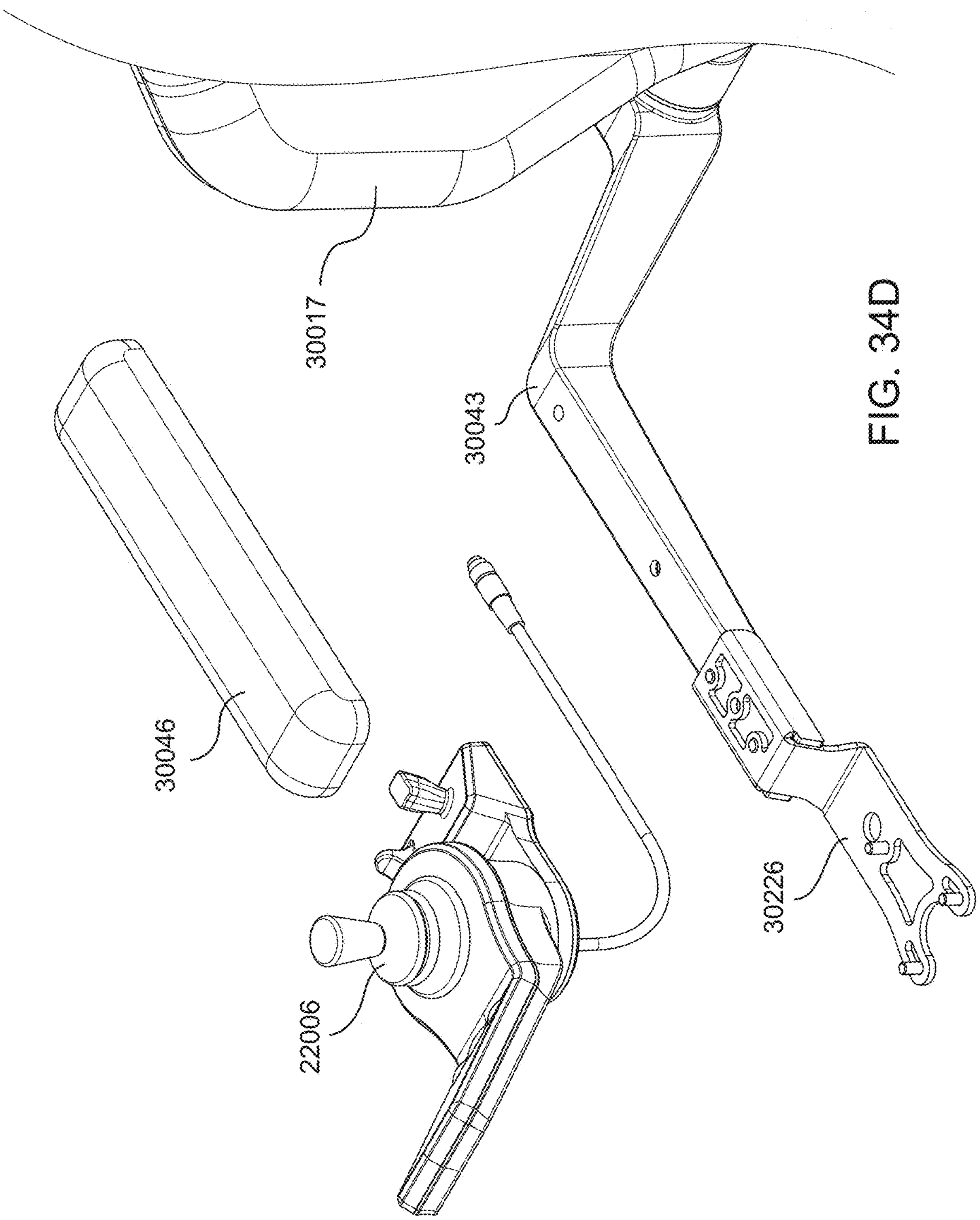
Figure 34E:
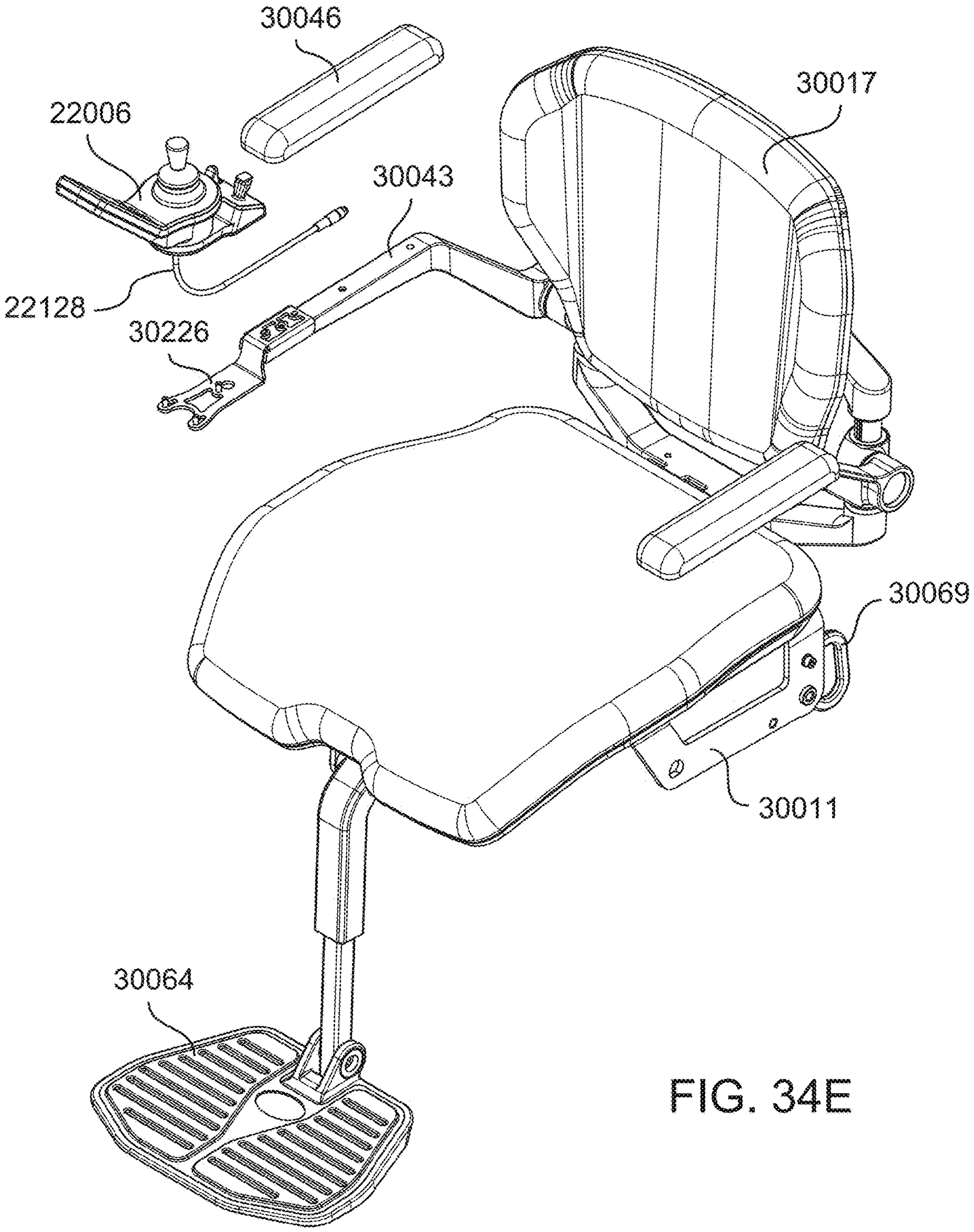
Figure 34F:
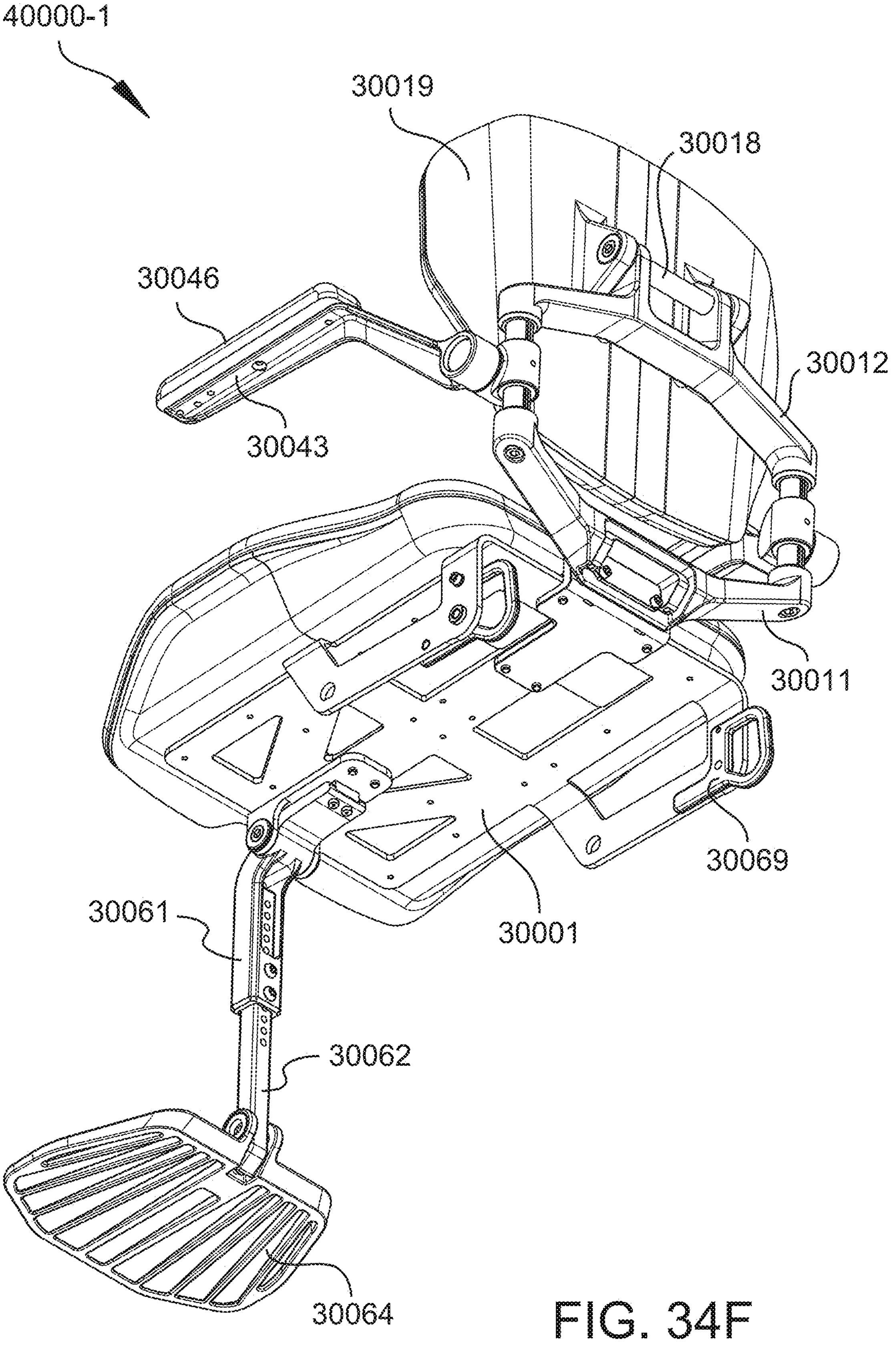
Figure 34G:
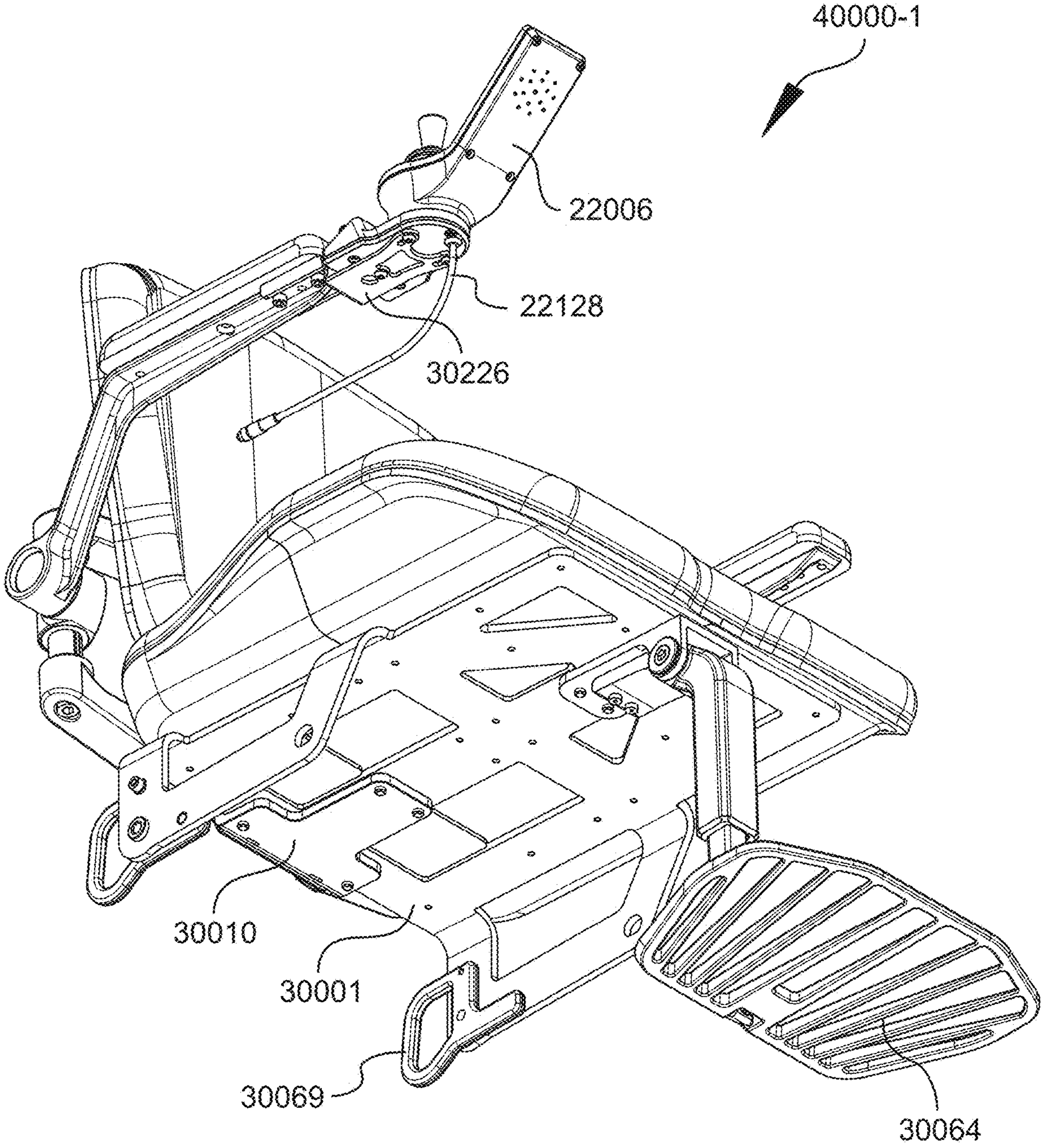
Figure 34H:
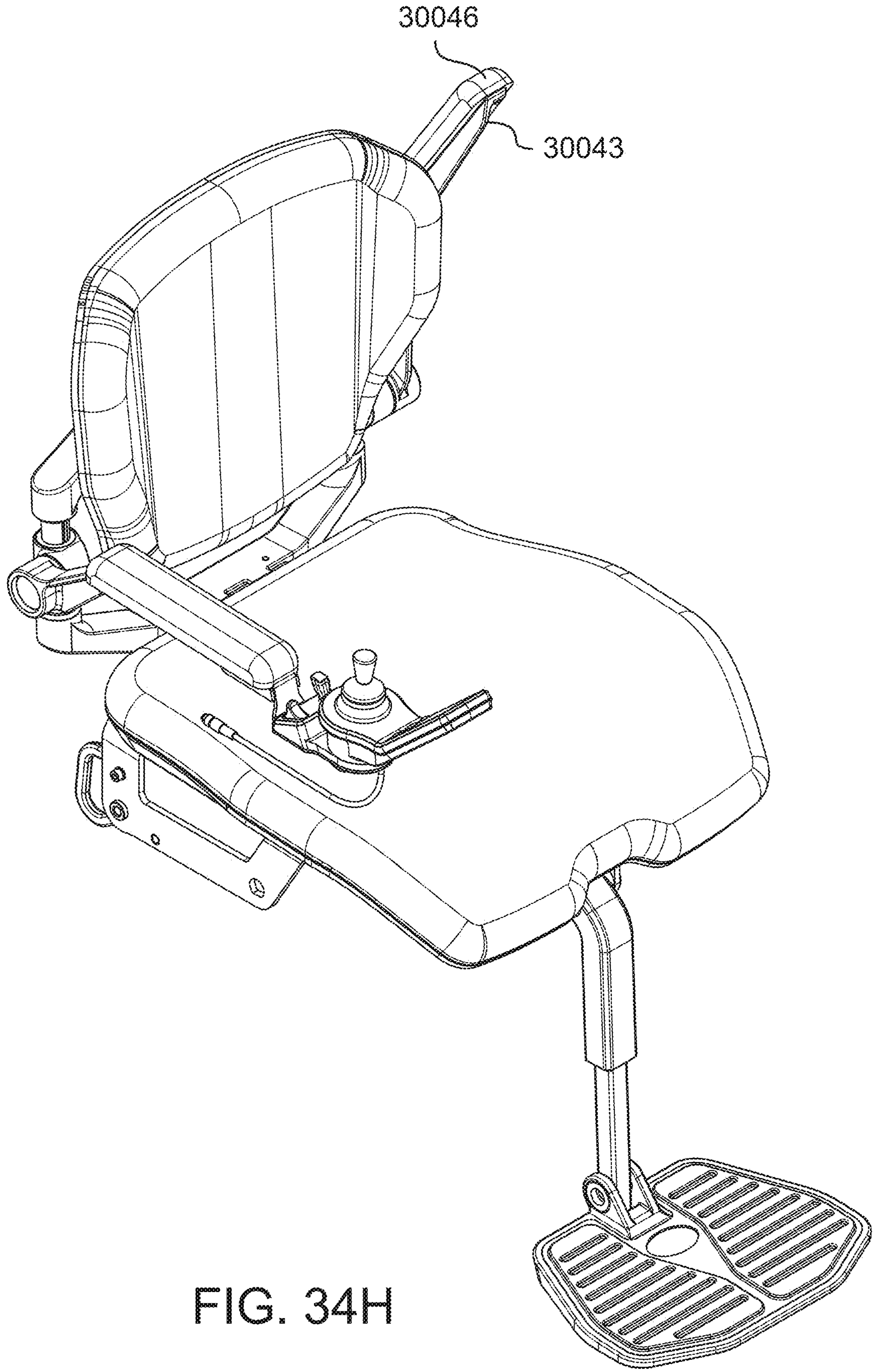
Figure 34I:
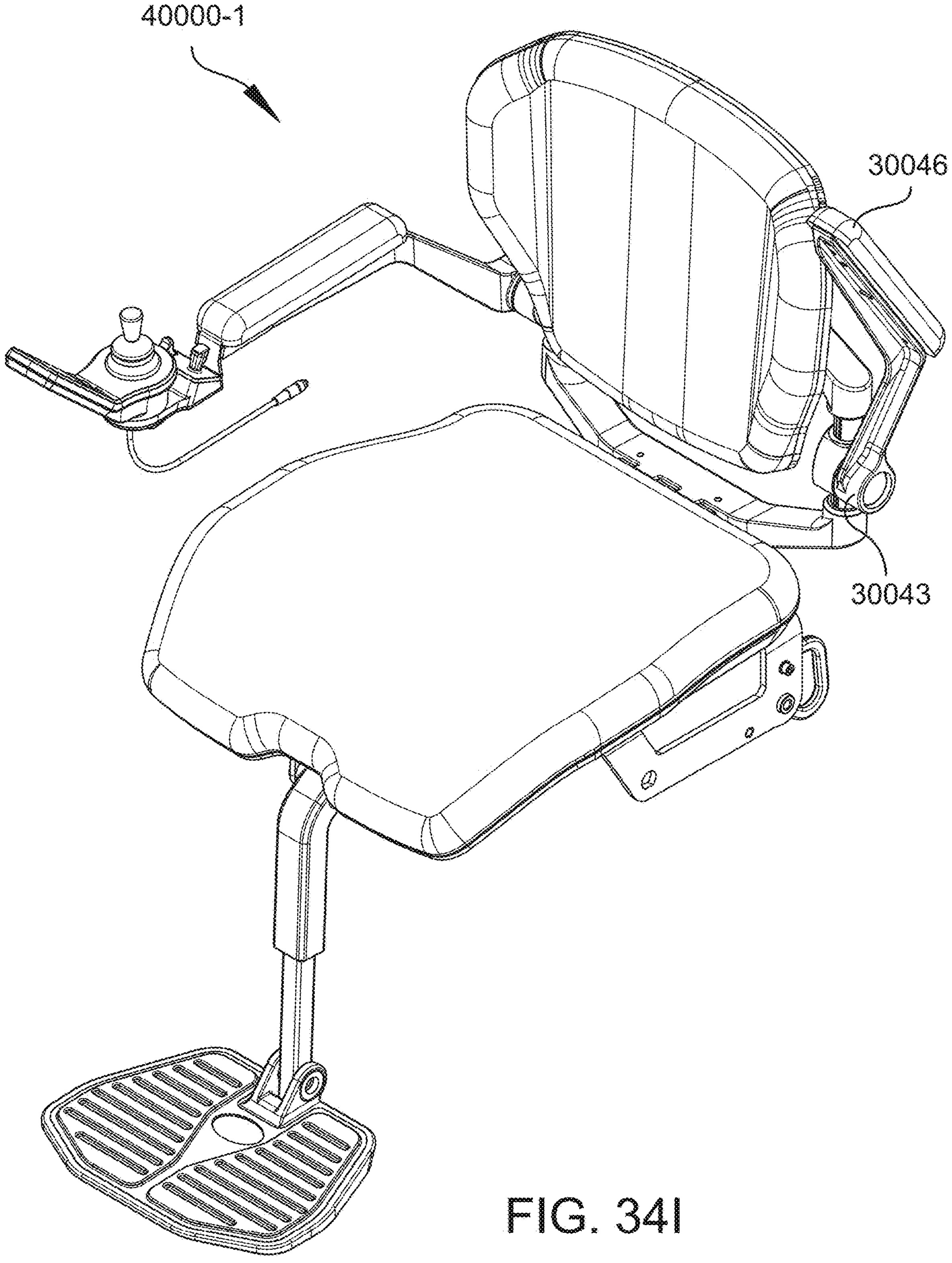
Figure 35A:
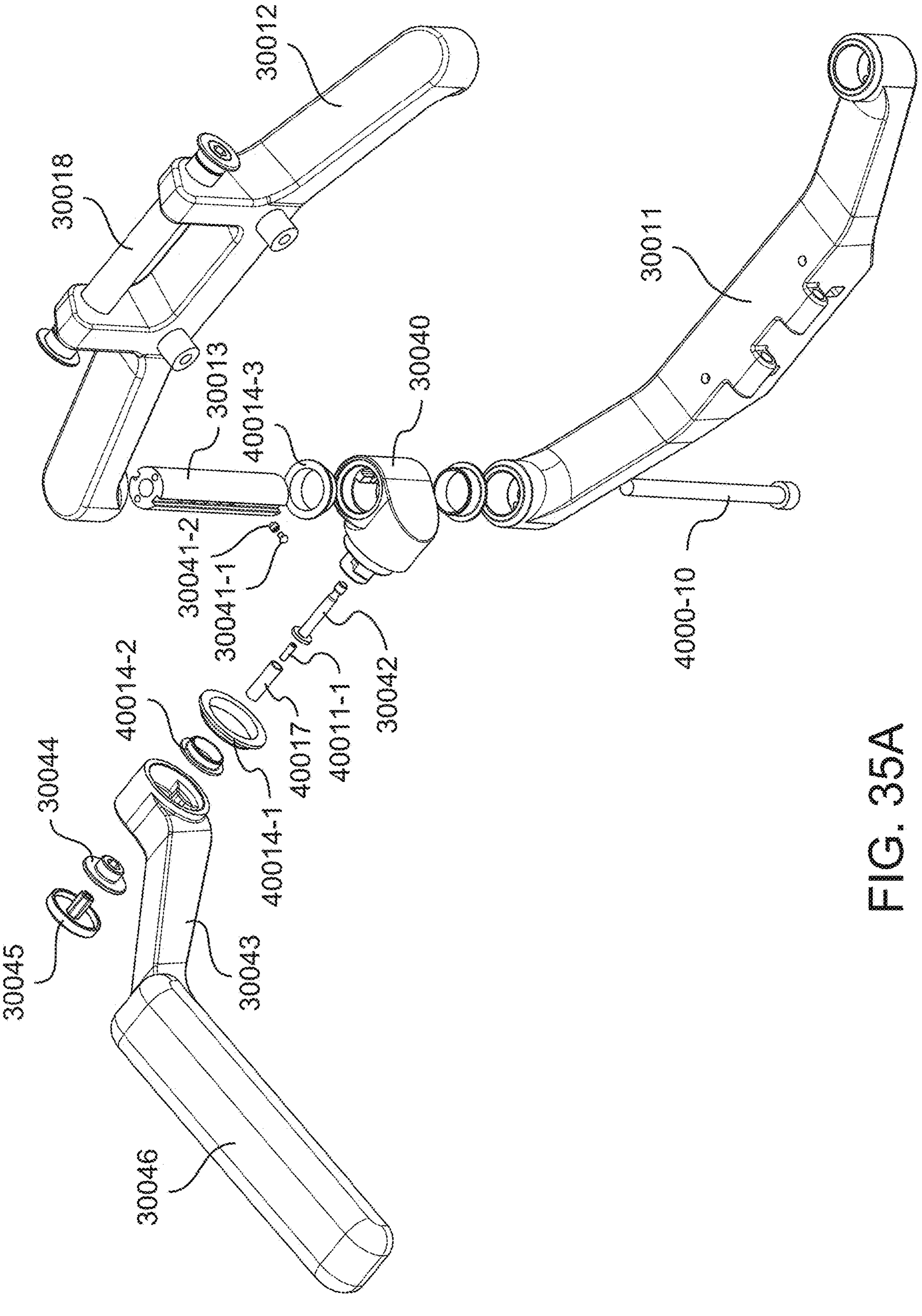
Figure 35B:
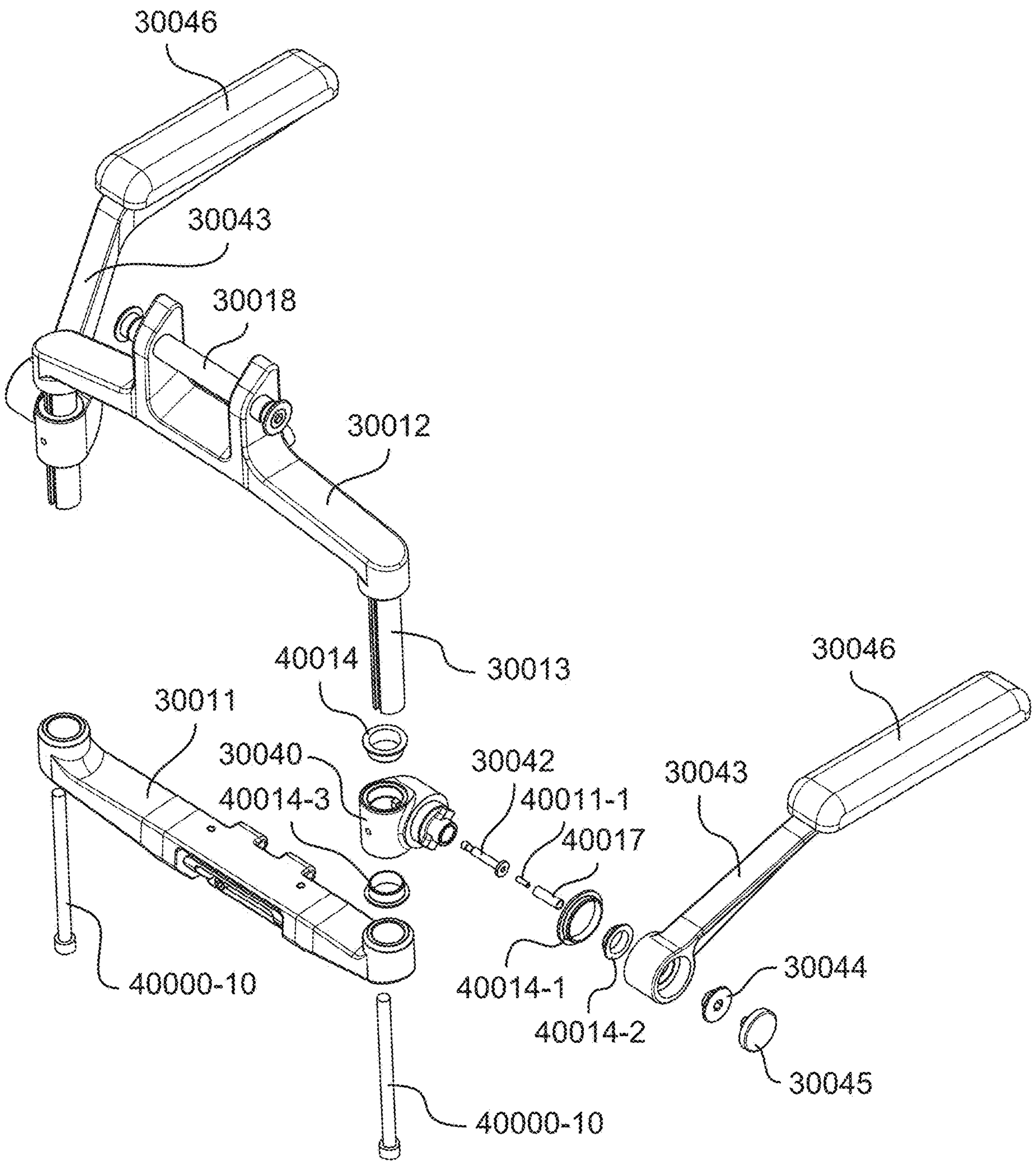
Figure 35C:
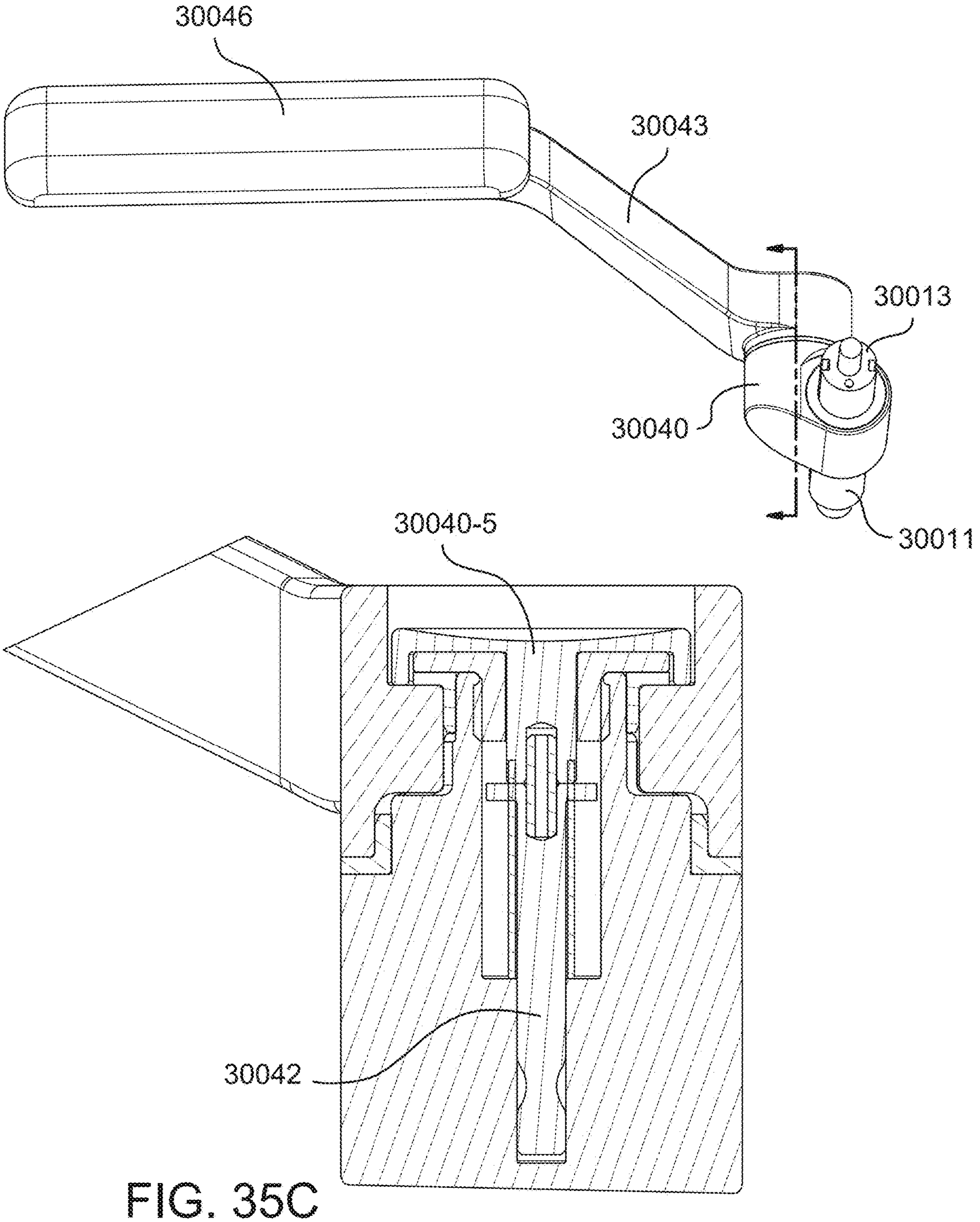
Figure 35D:
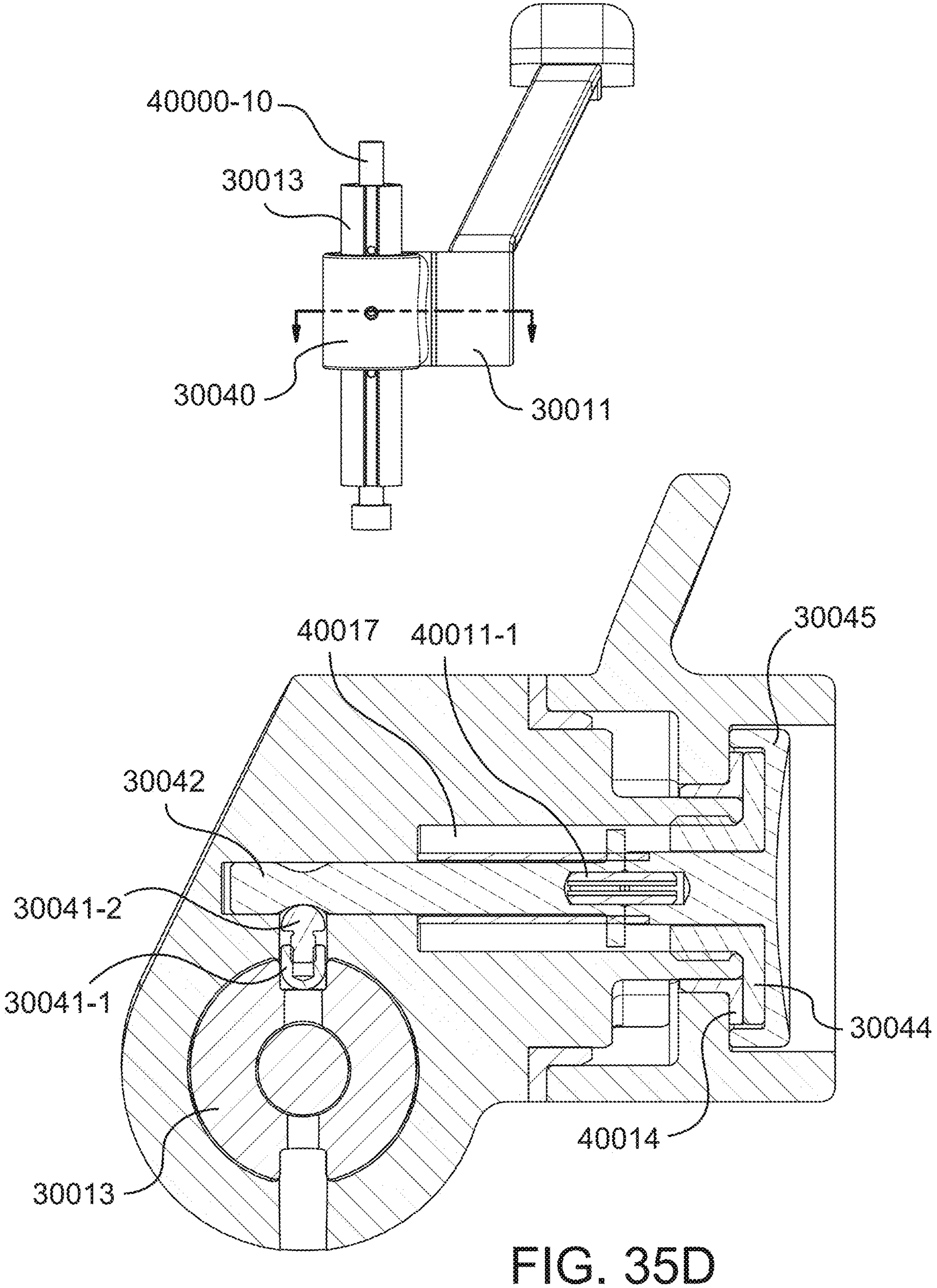
Figure 35E:
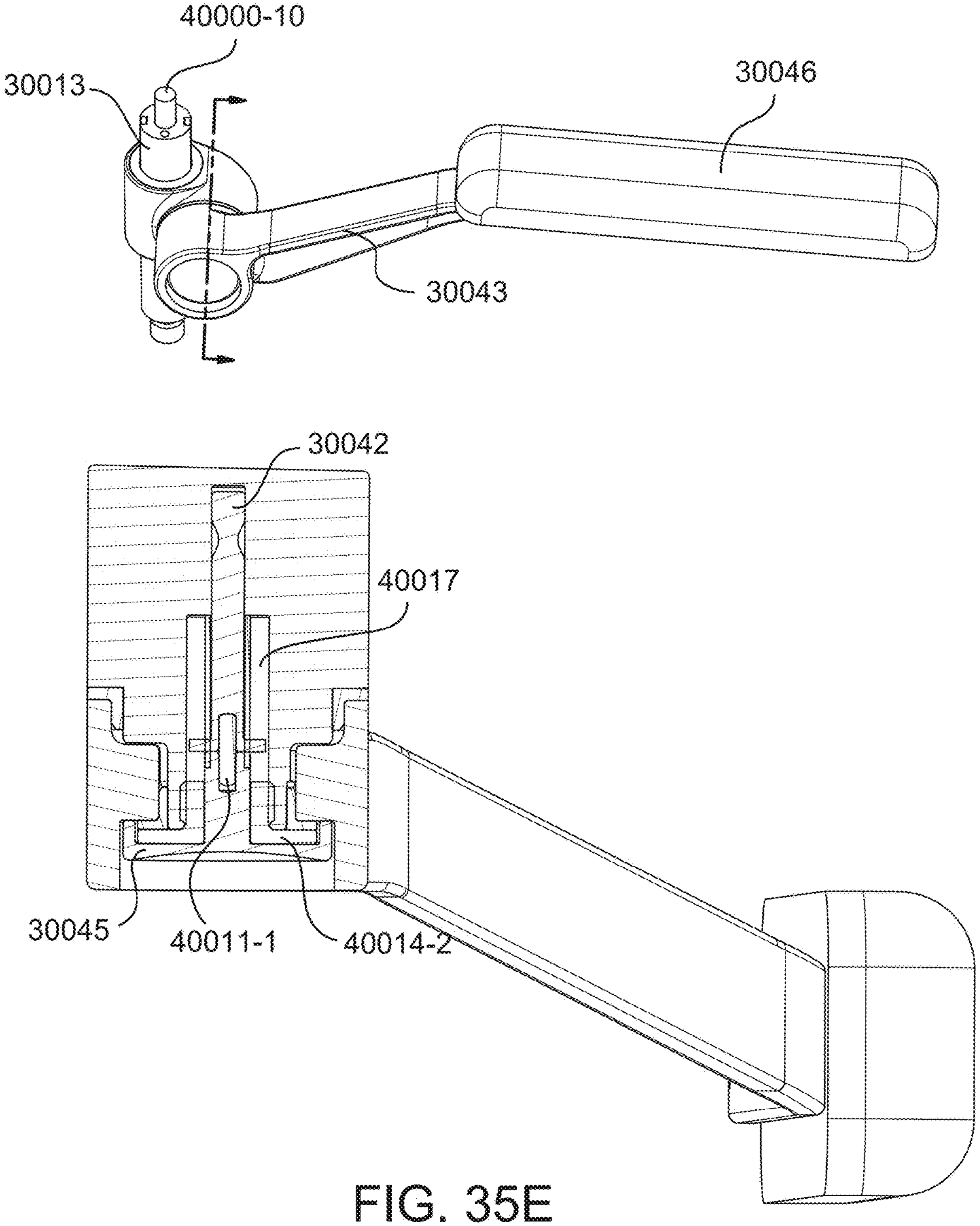
Figure 35F:
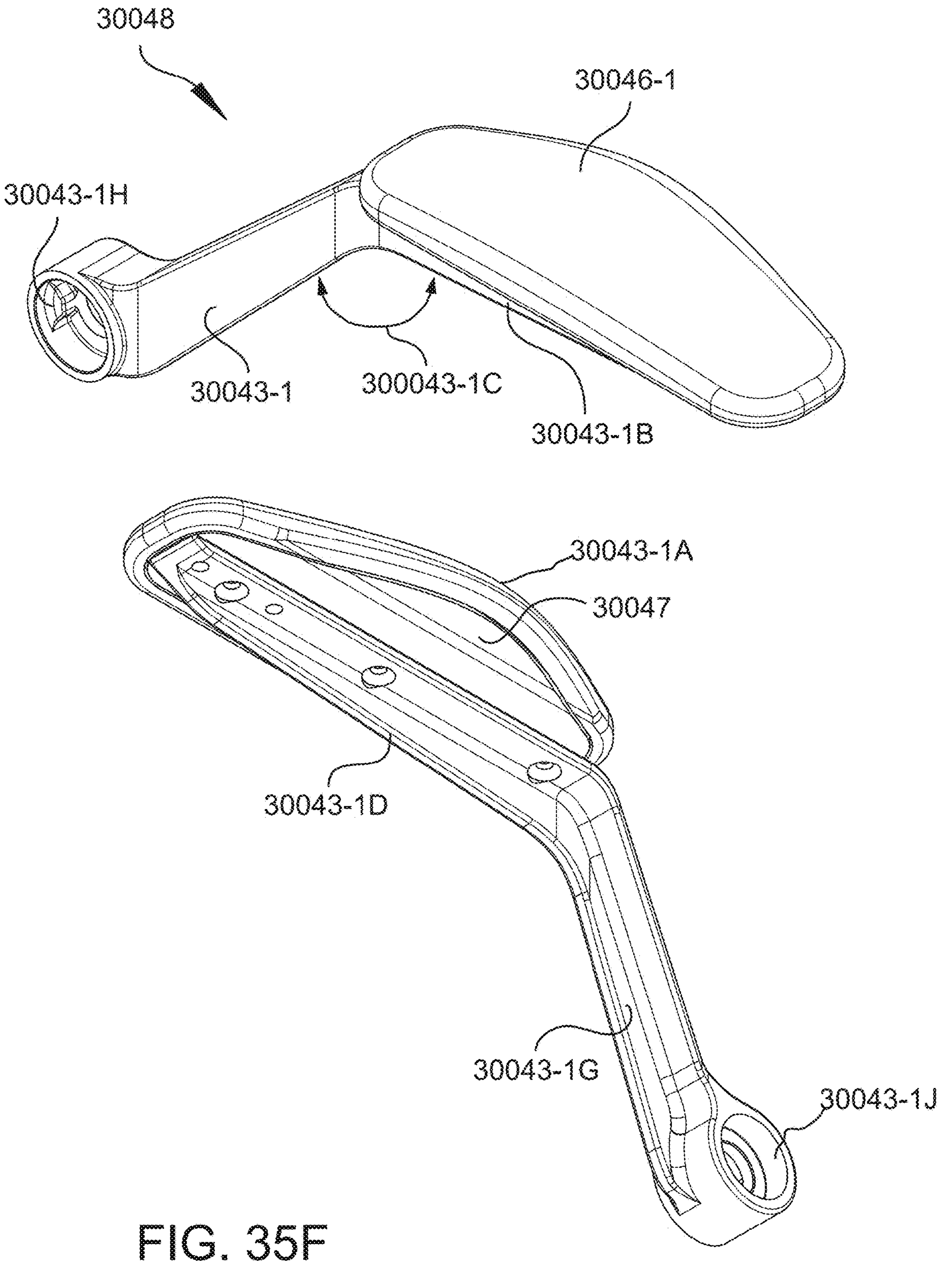
Figure 35G:
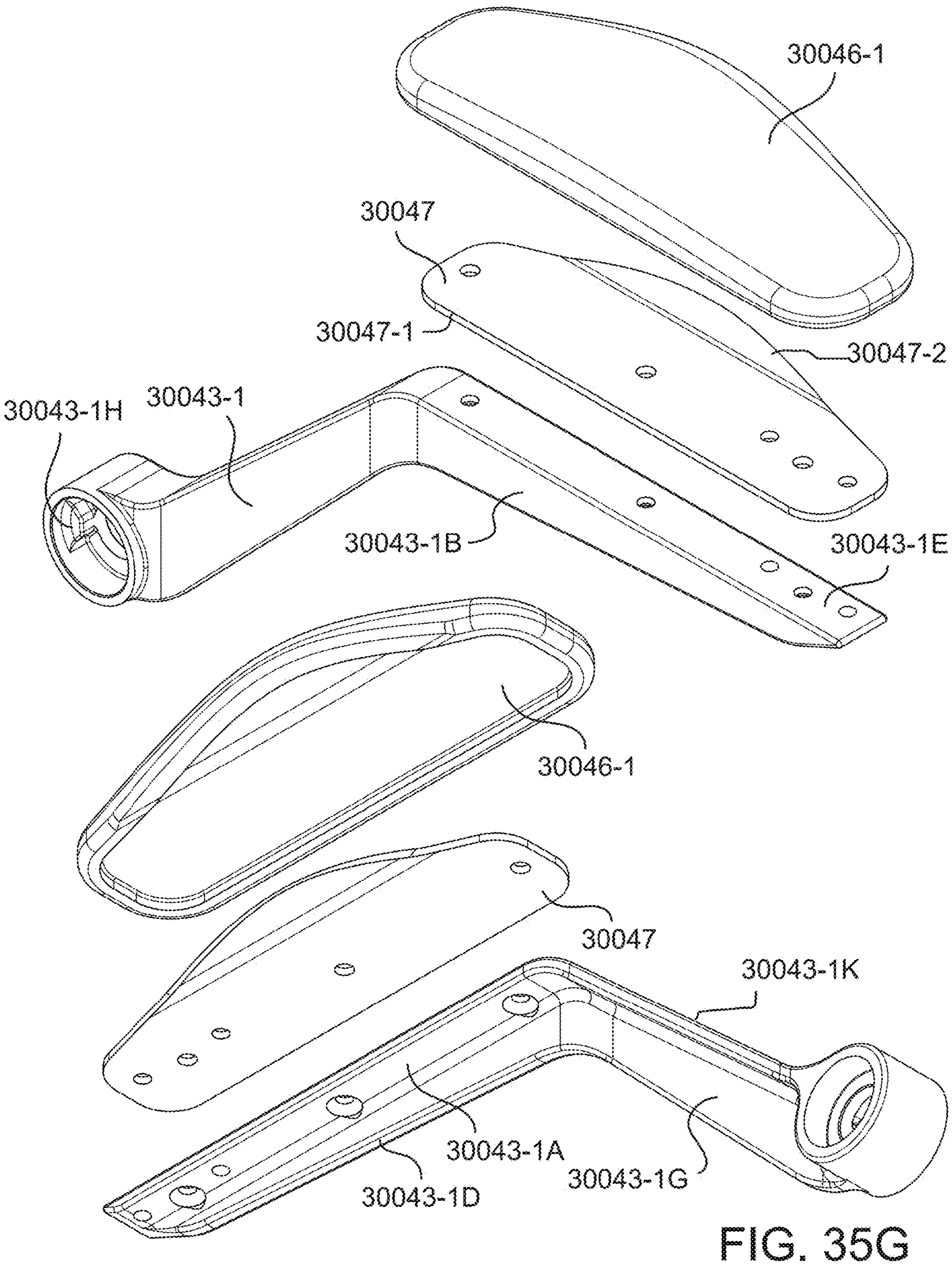
Figure 36A:
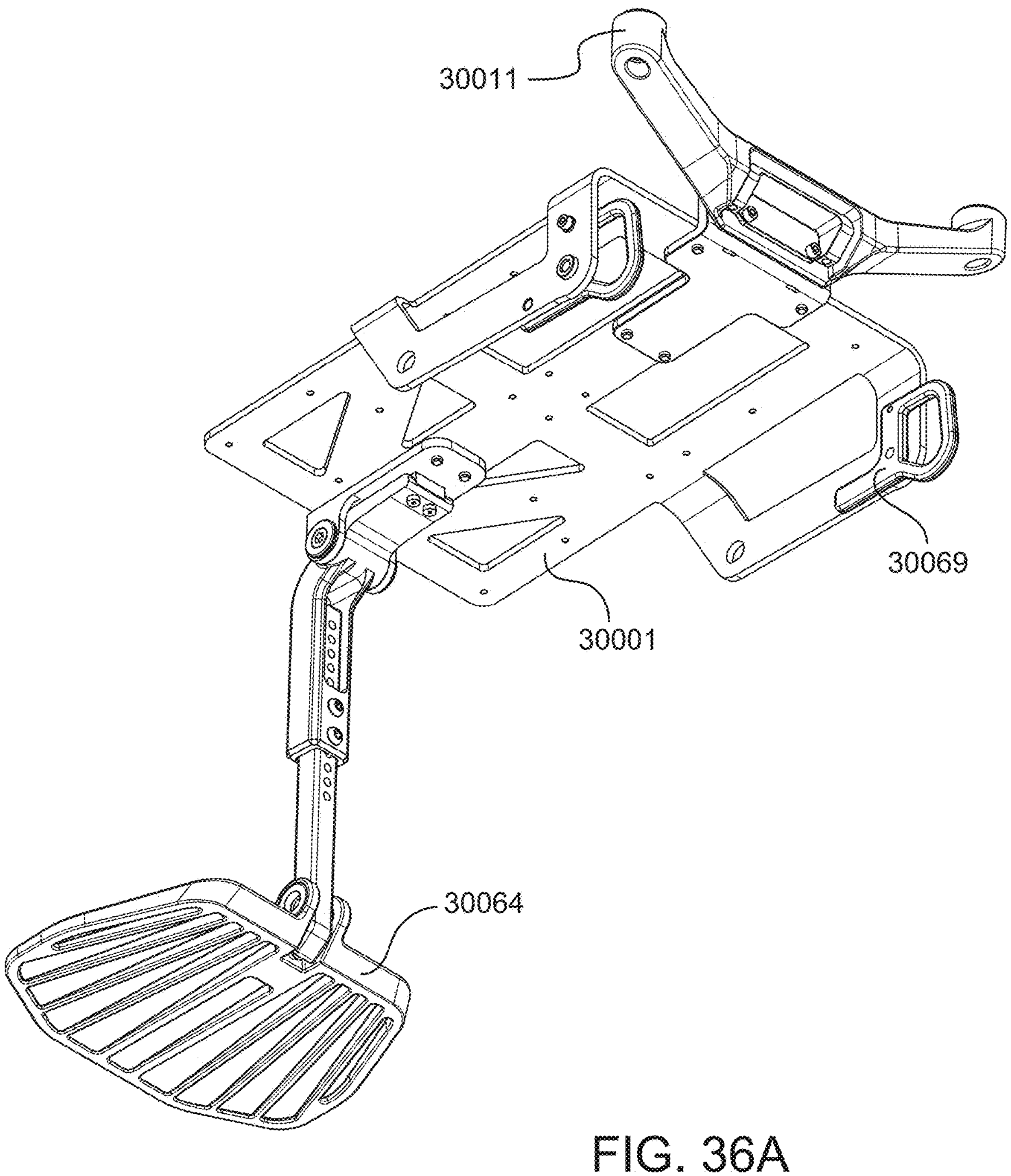
Figure 36B:
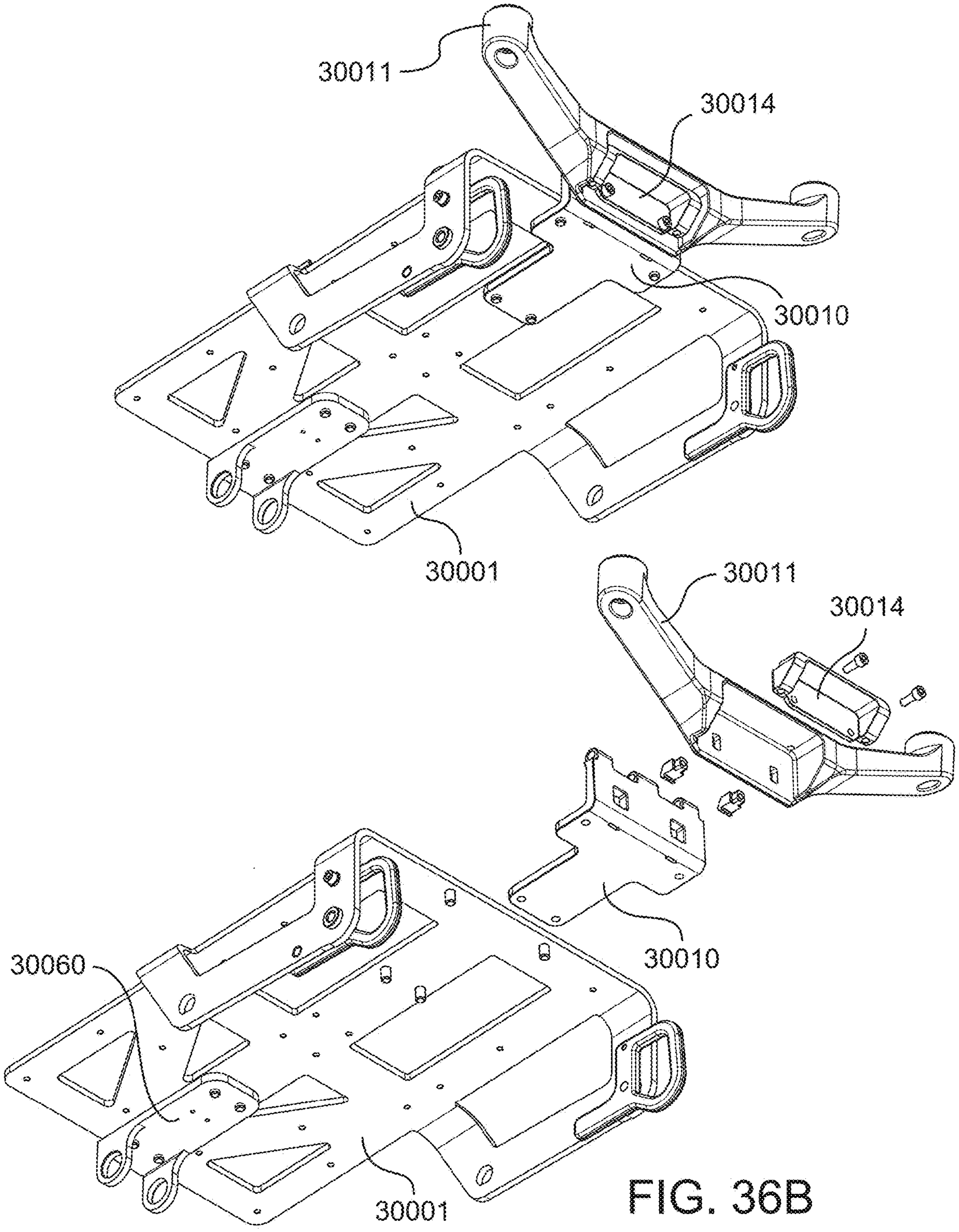
Figure 37A:
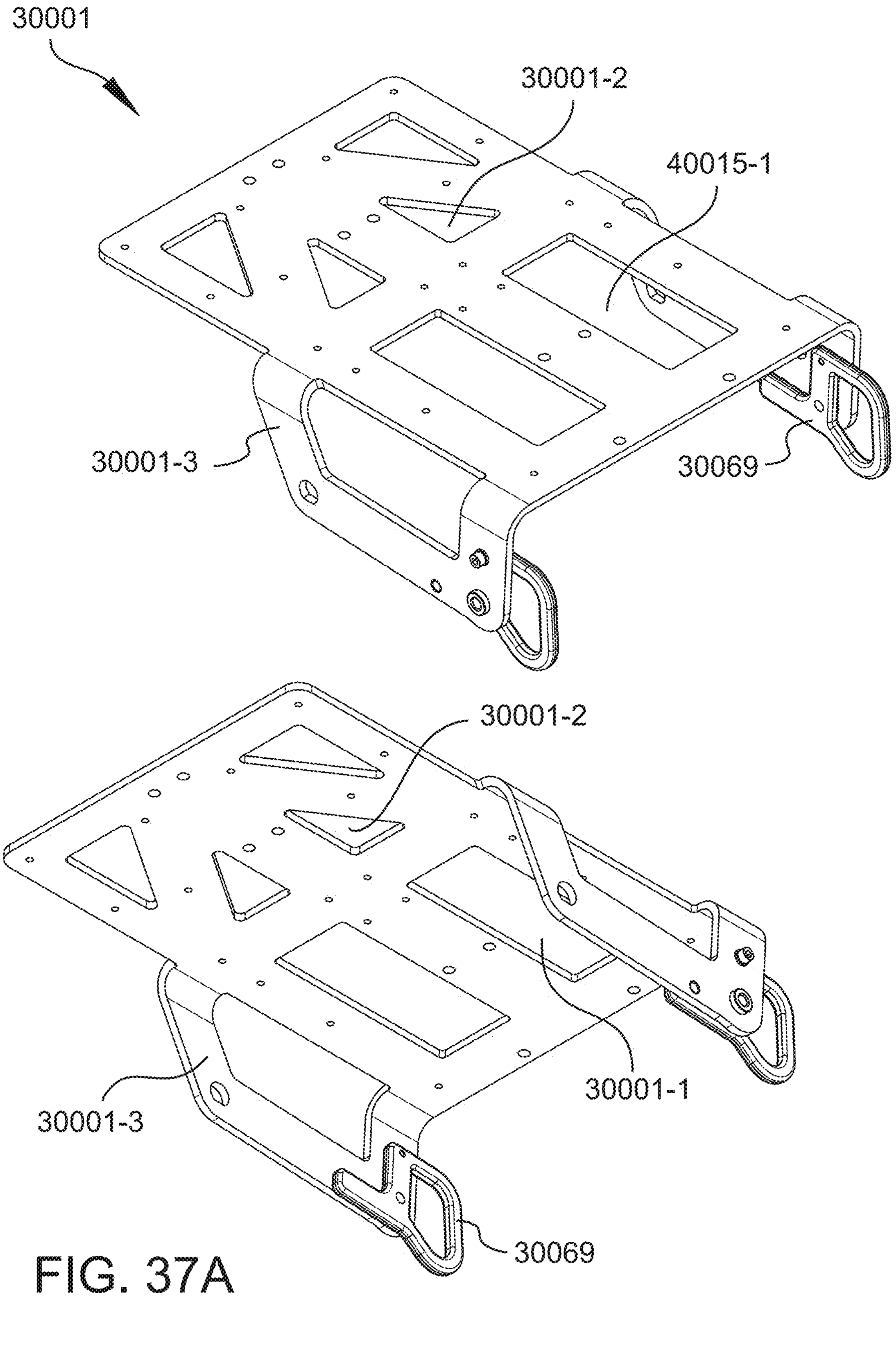
Figure 37B:
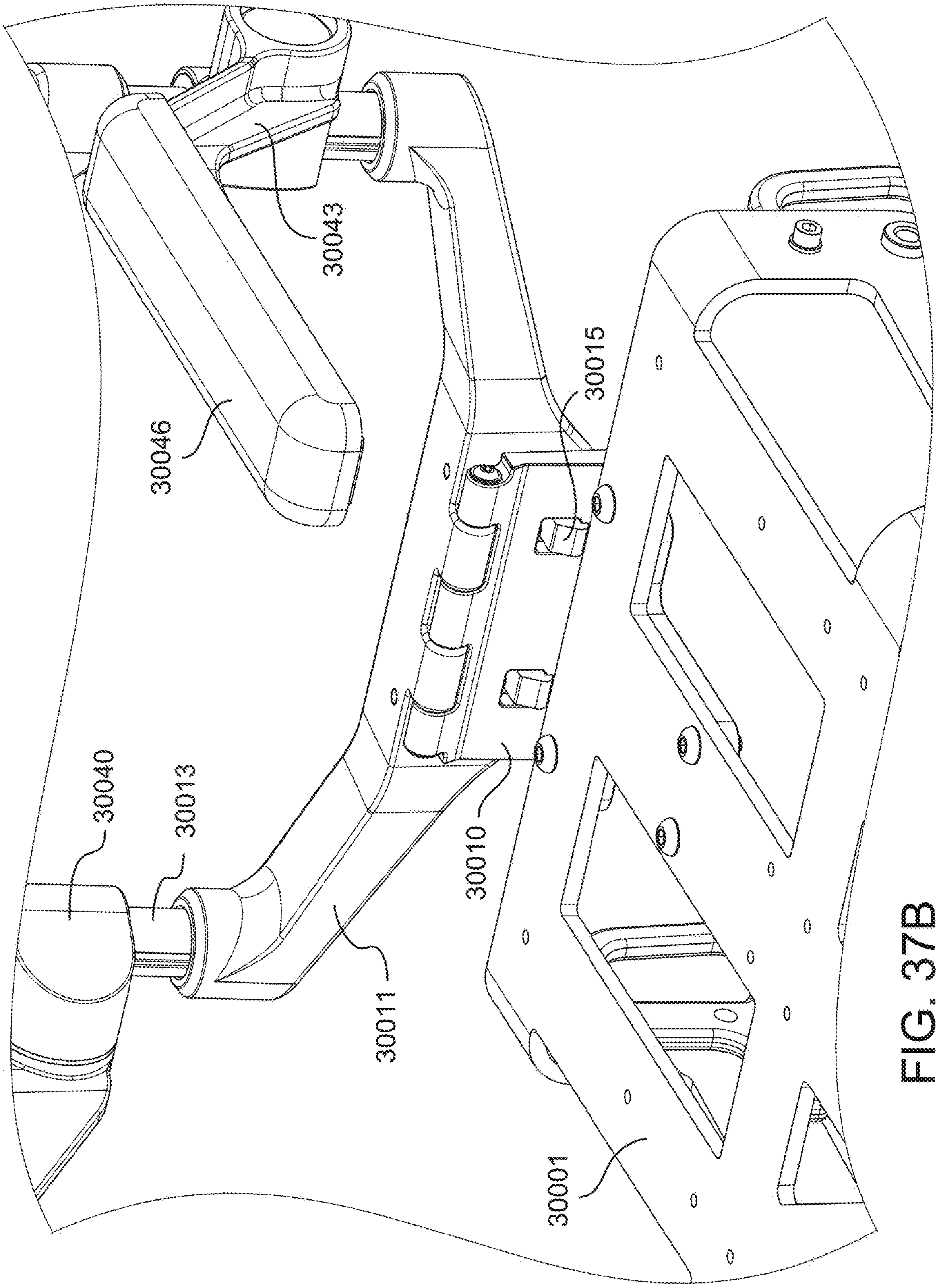
Figure 37C:
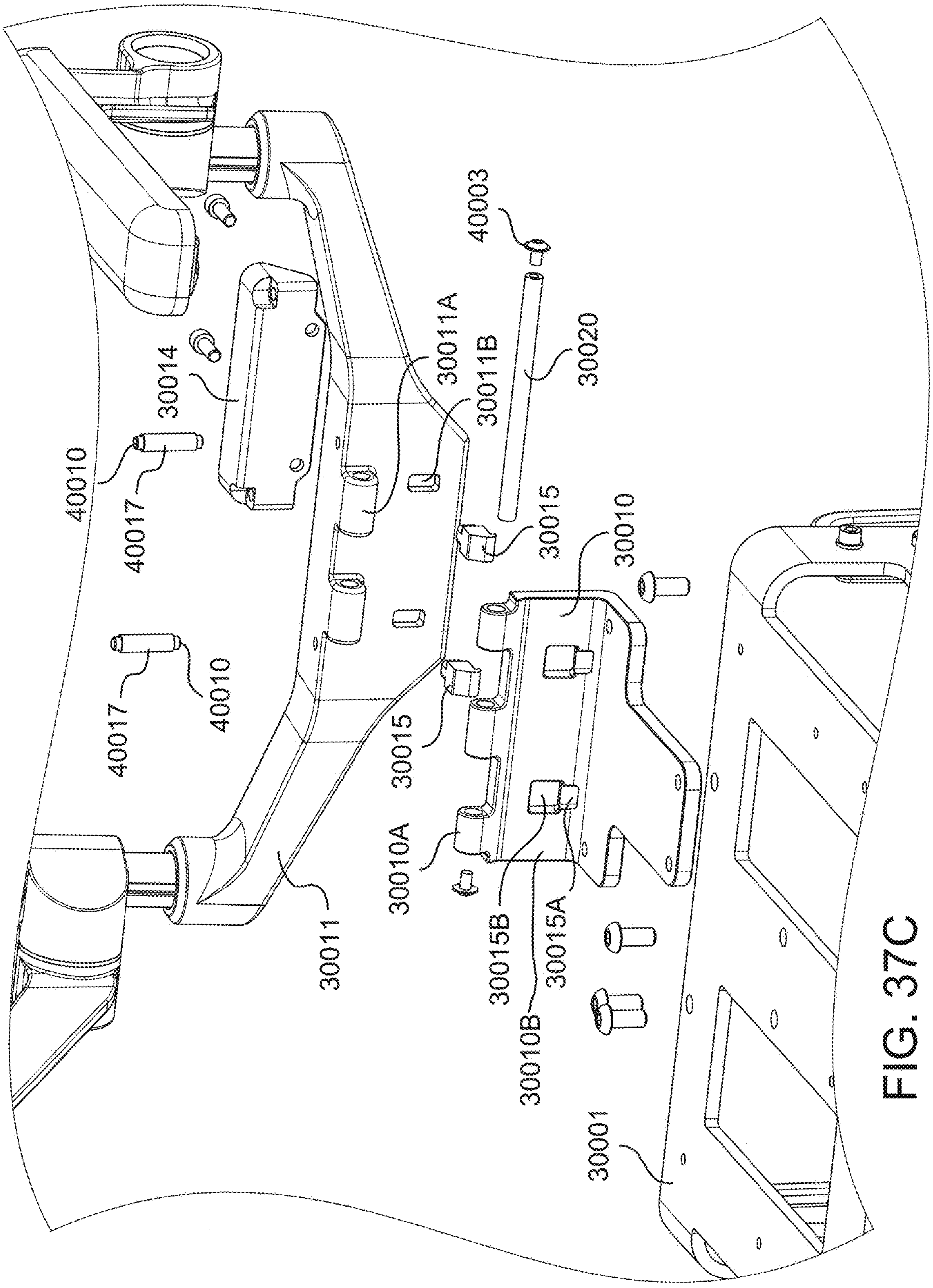
Figure 37D:
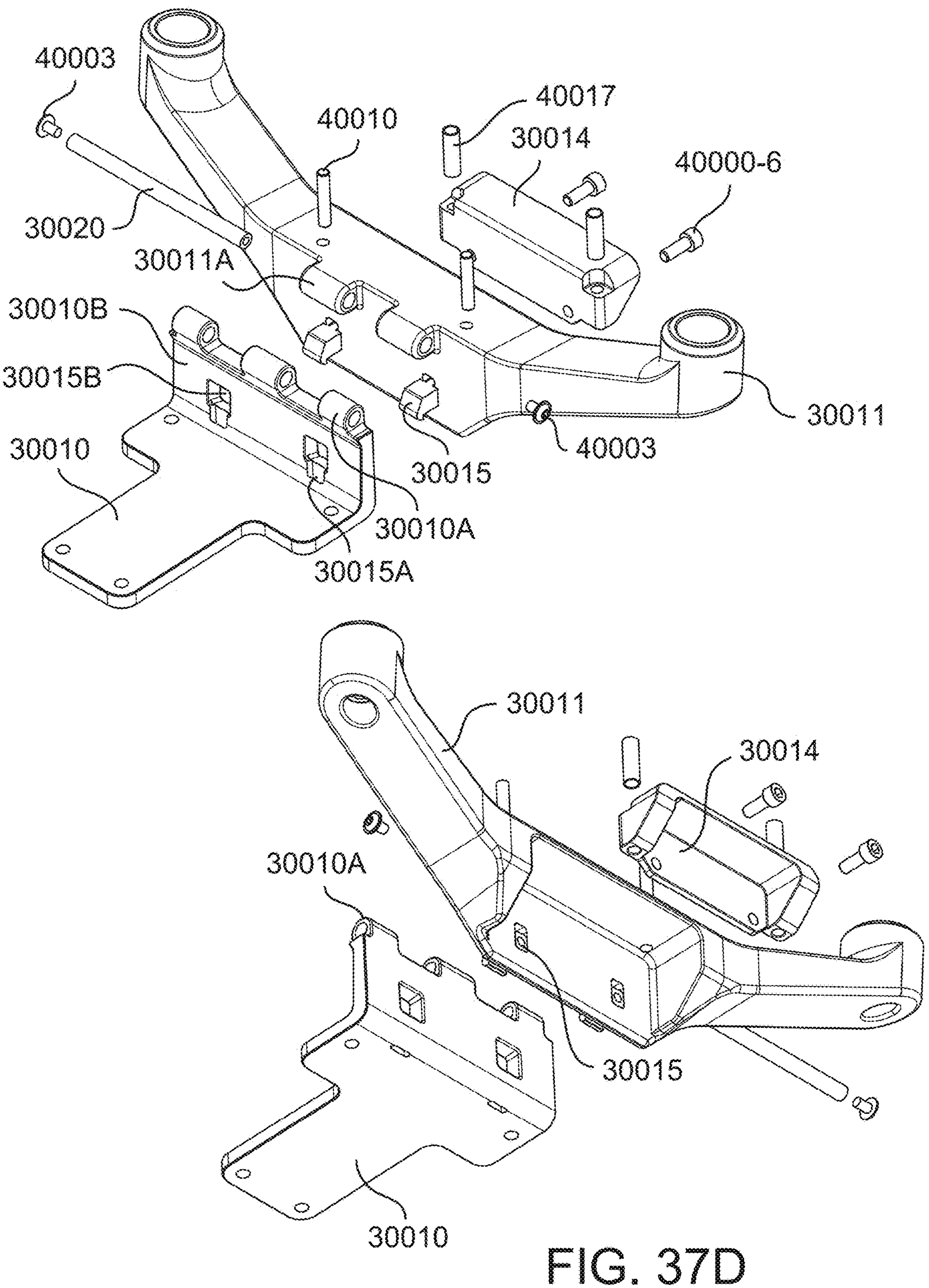
Figure 37E:
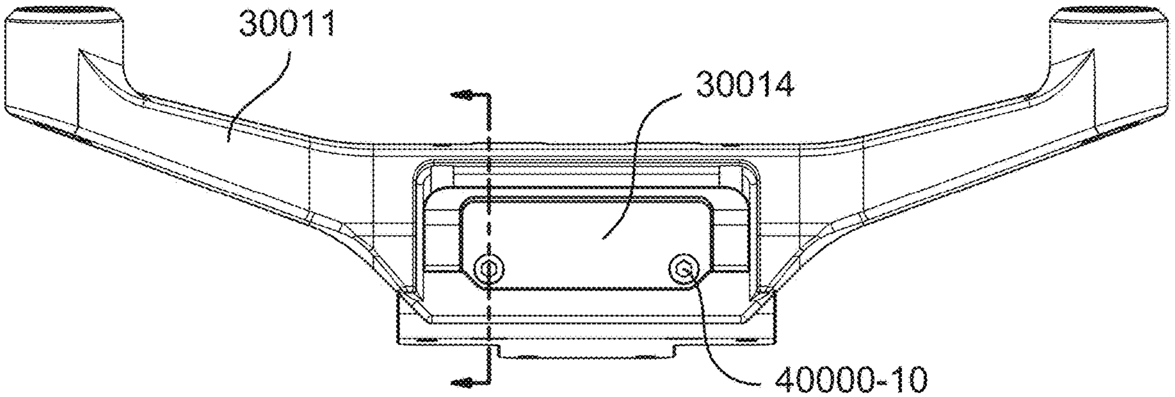
Figure 37E:
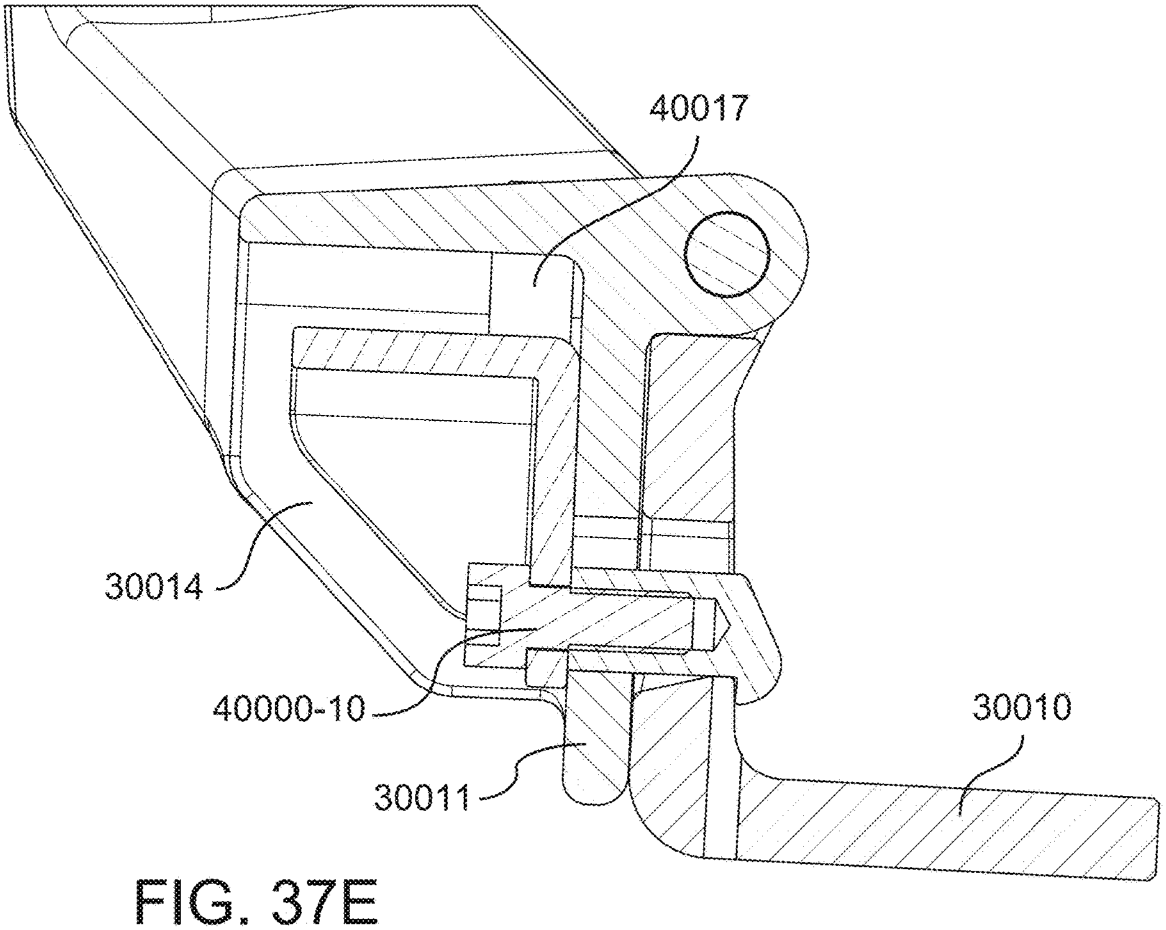
Figure 37F:
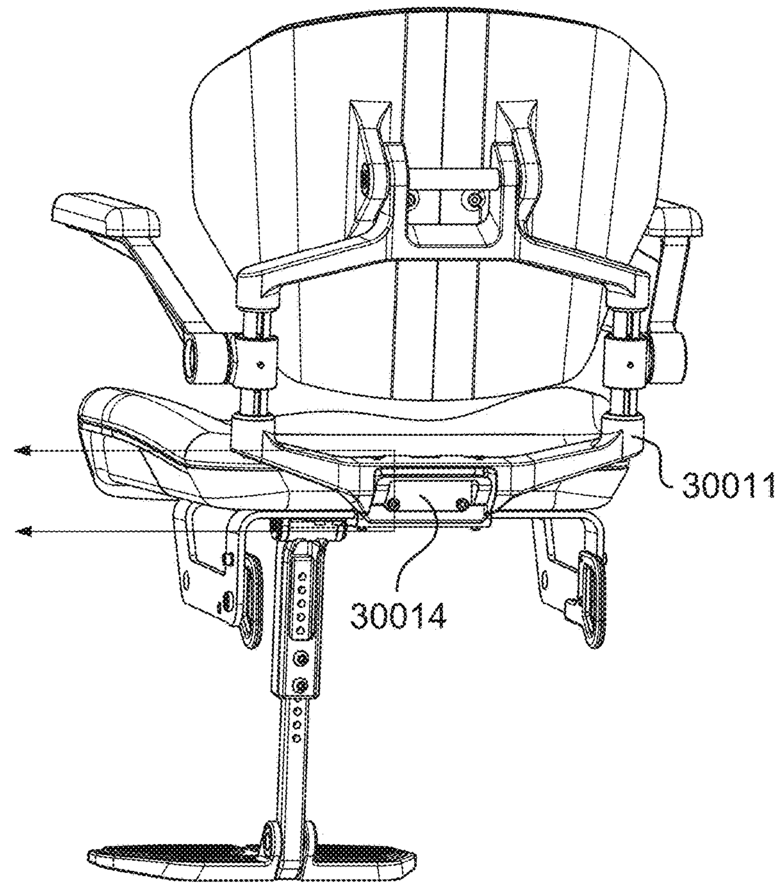
Figure 37F:
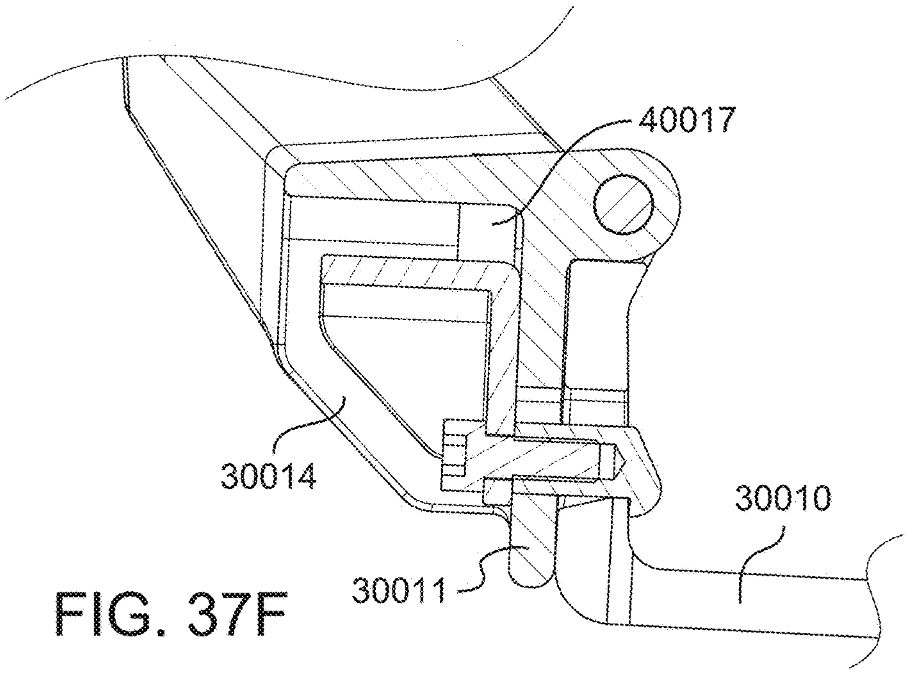
Figure 37G:
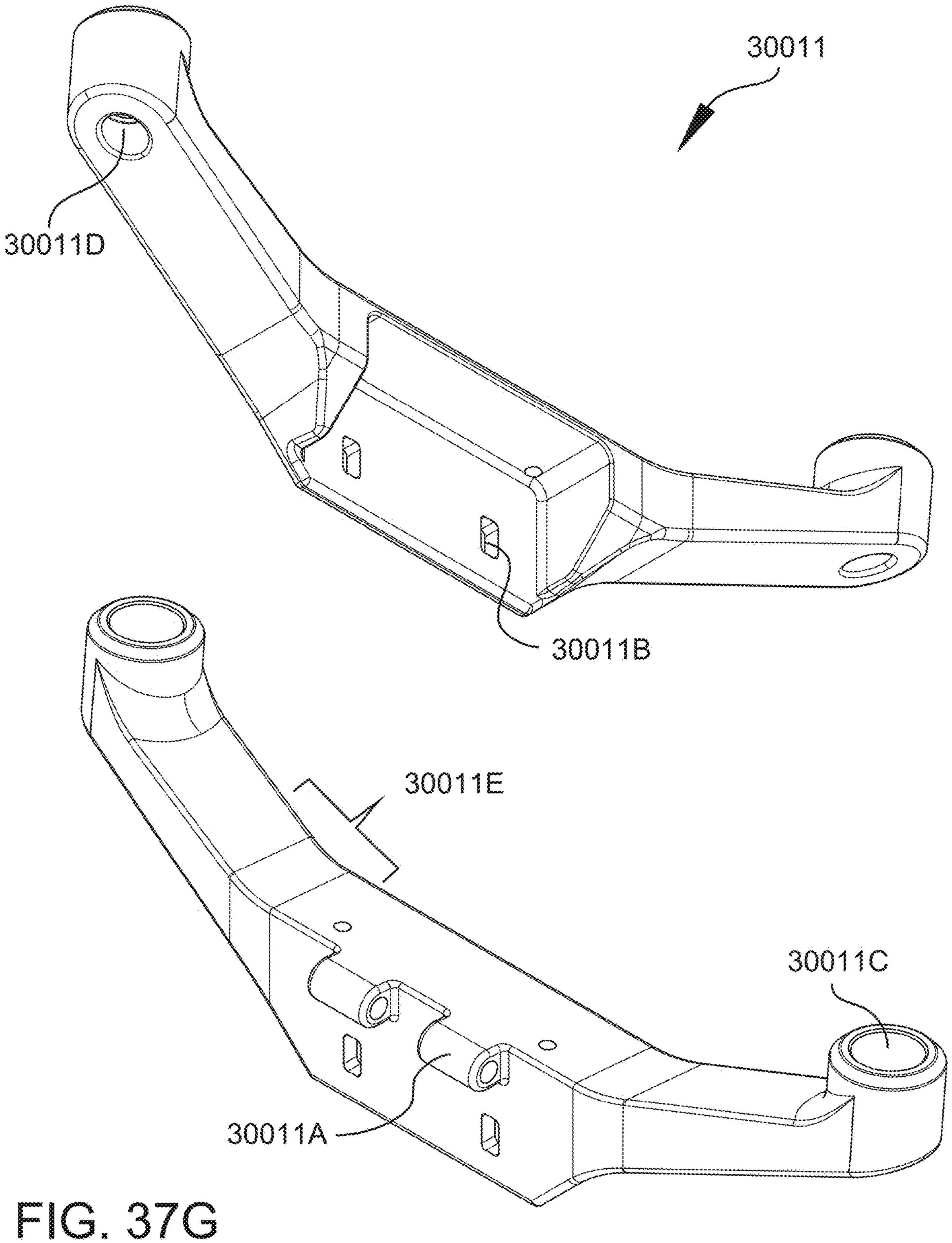
Figure 37H:
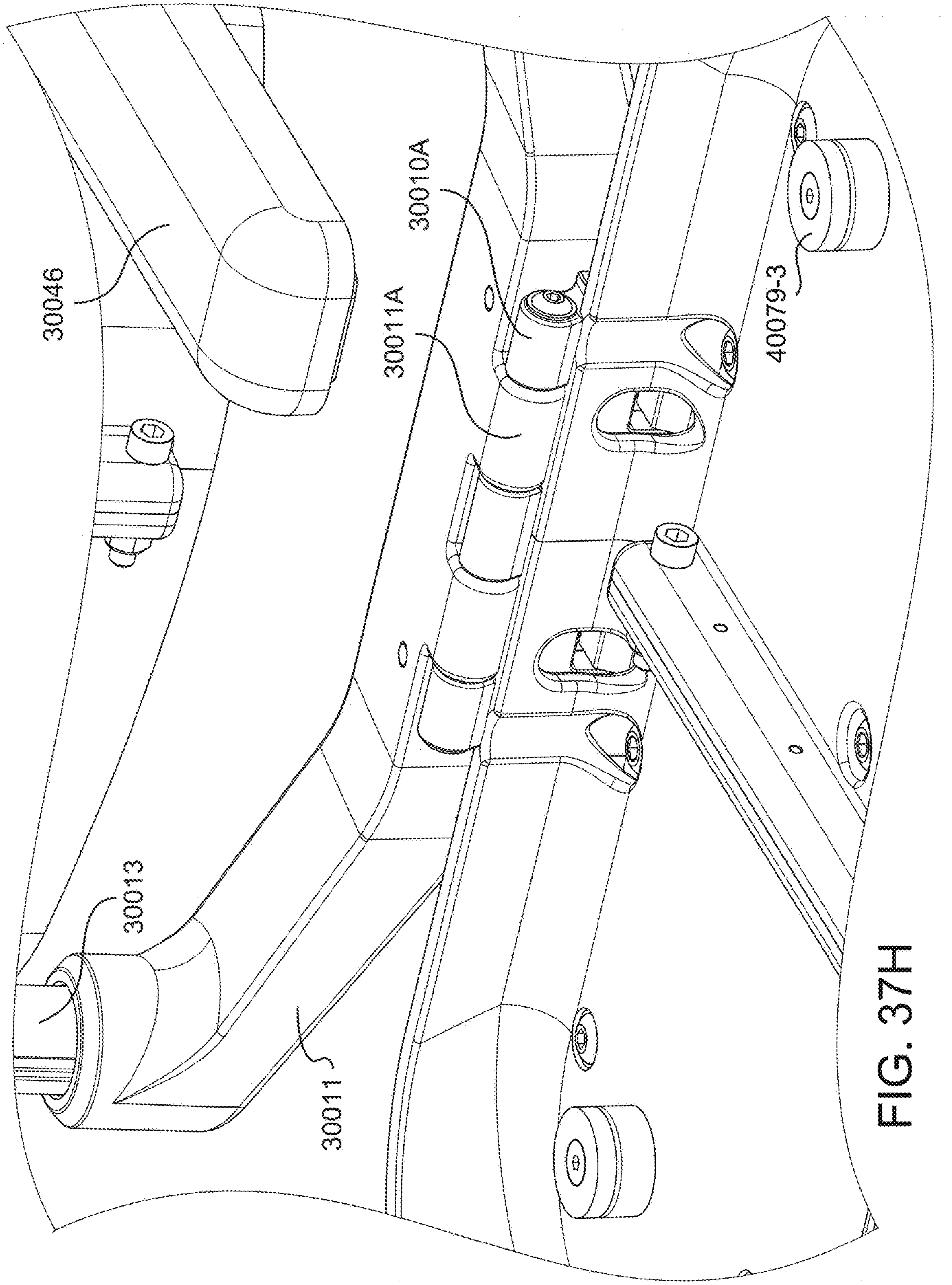
Figure 37I:
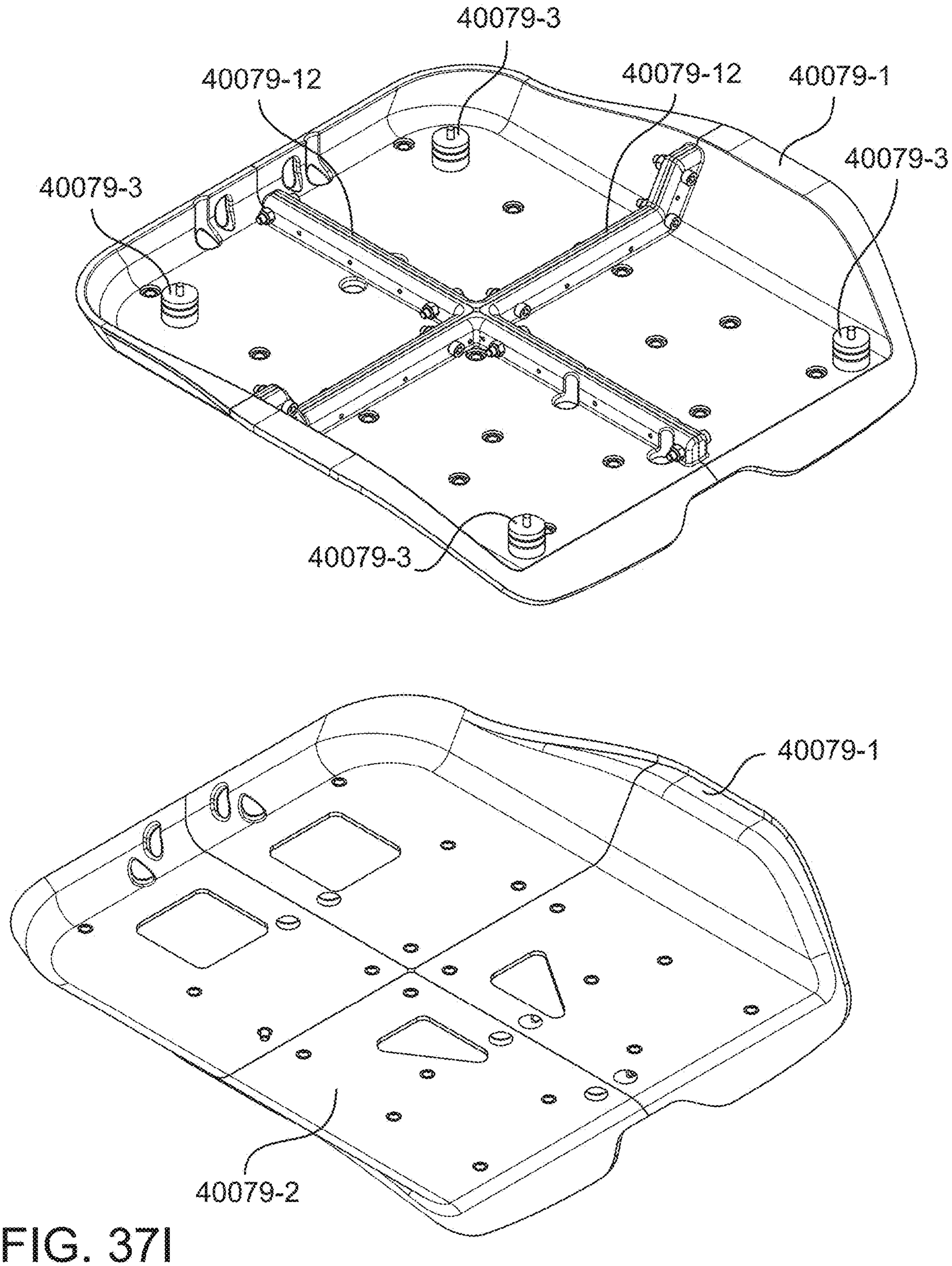
Figure 37J:
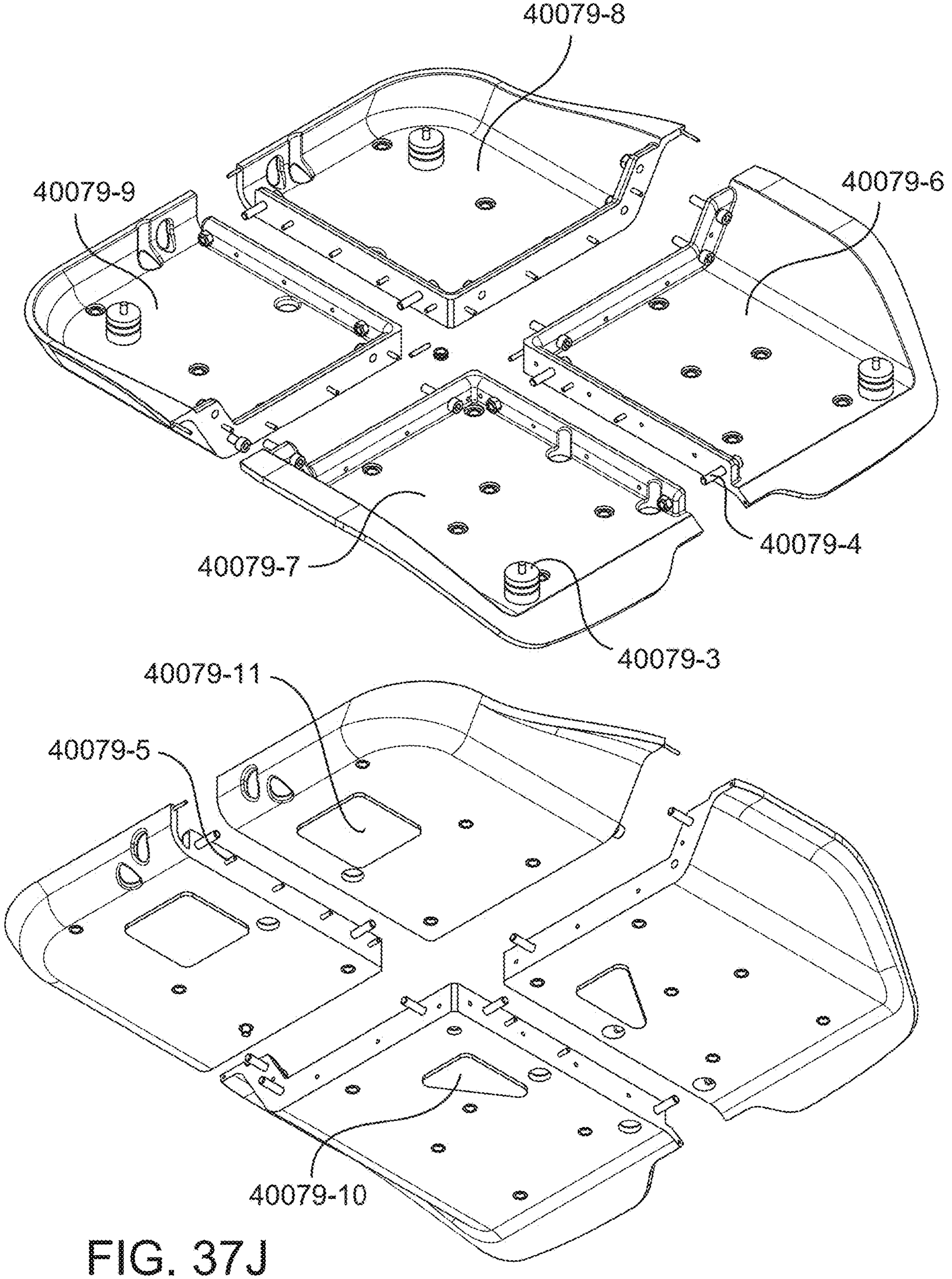
Figure 37K:
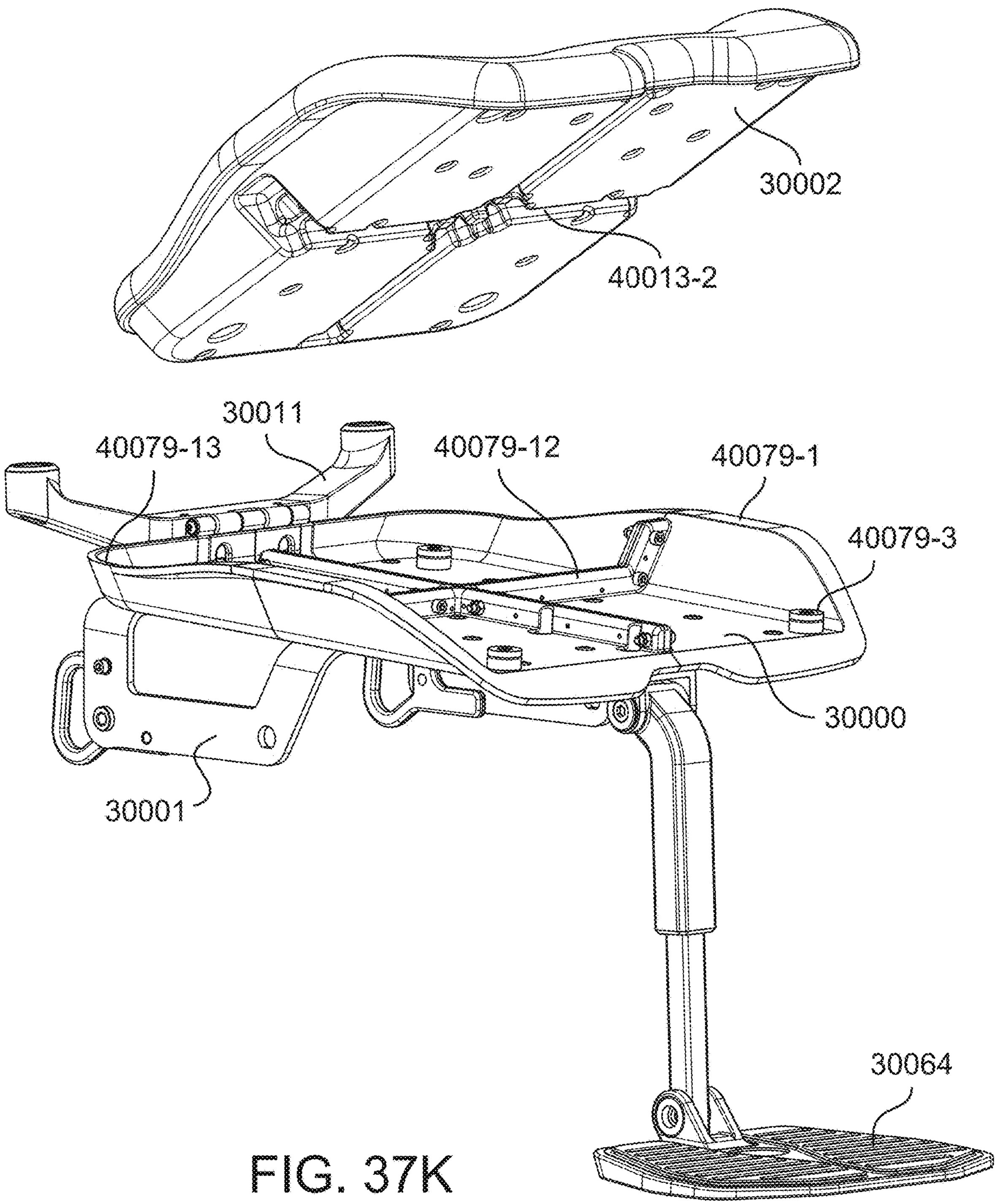
Figure 37L:
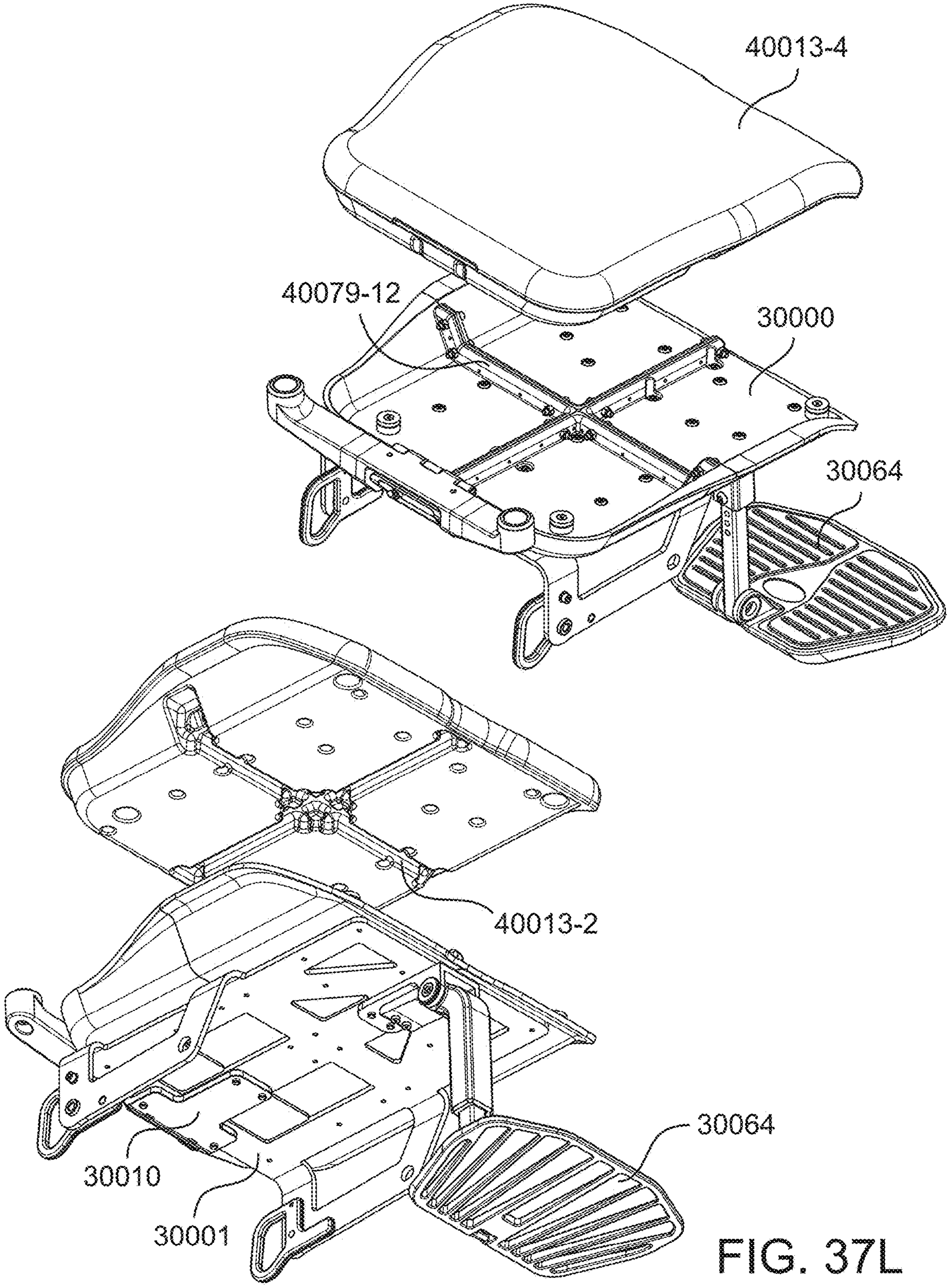
Figure 37M:
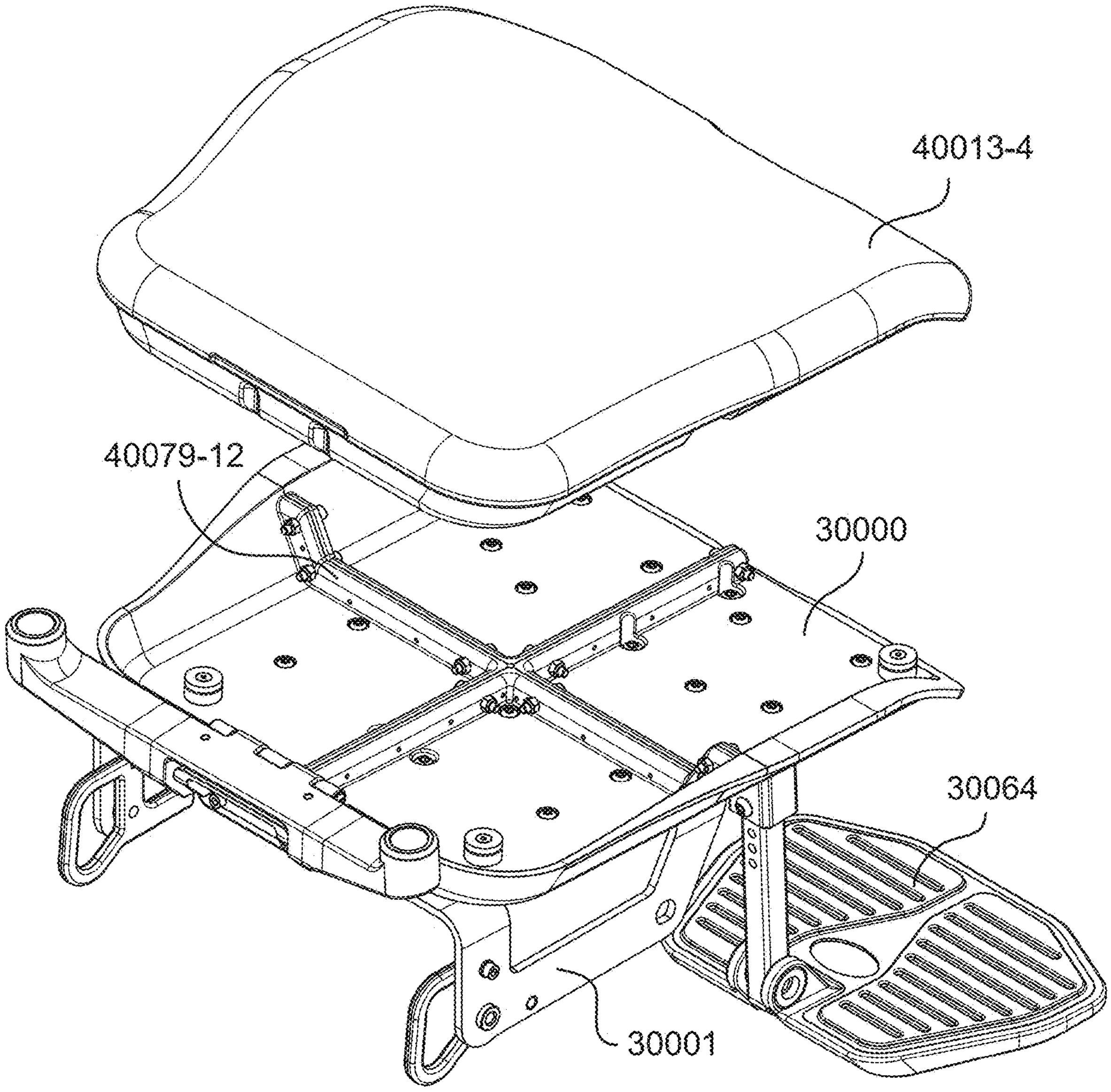
Figure 37N:
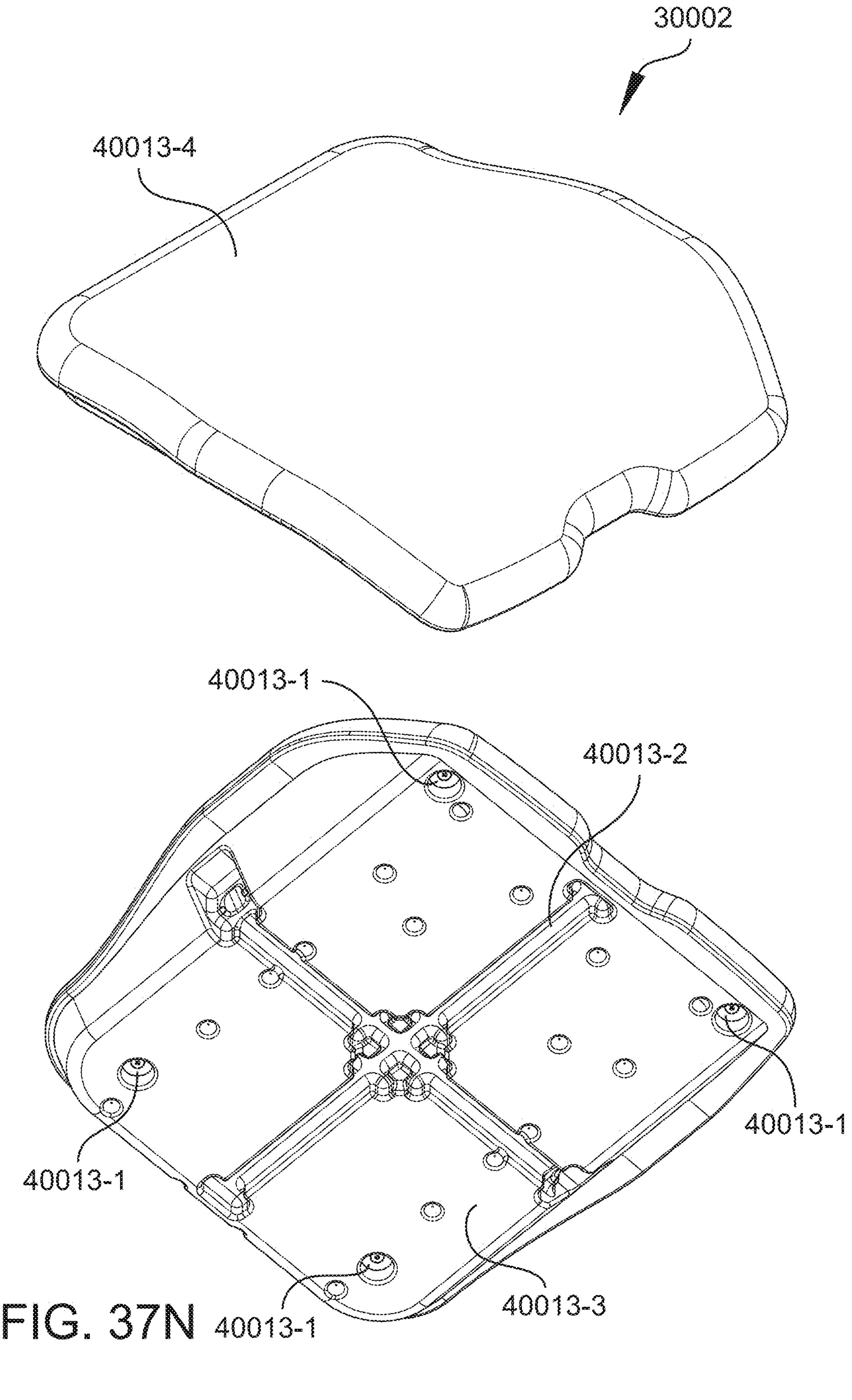
Figure 38:
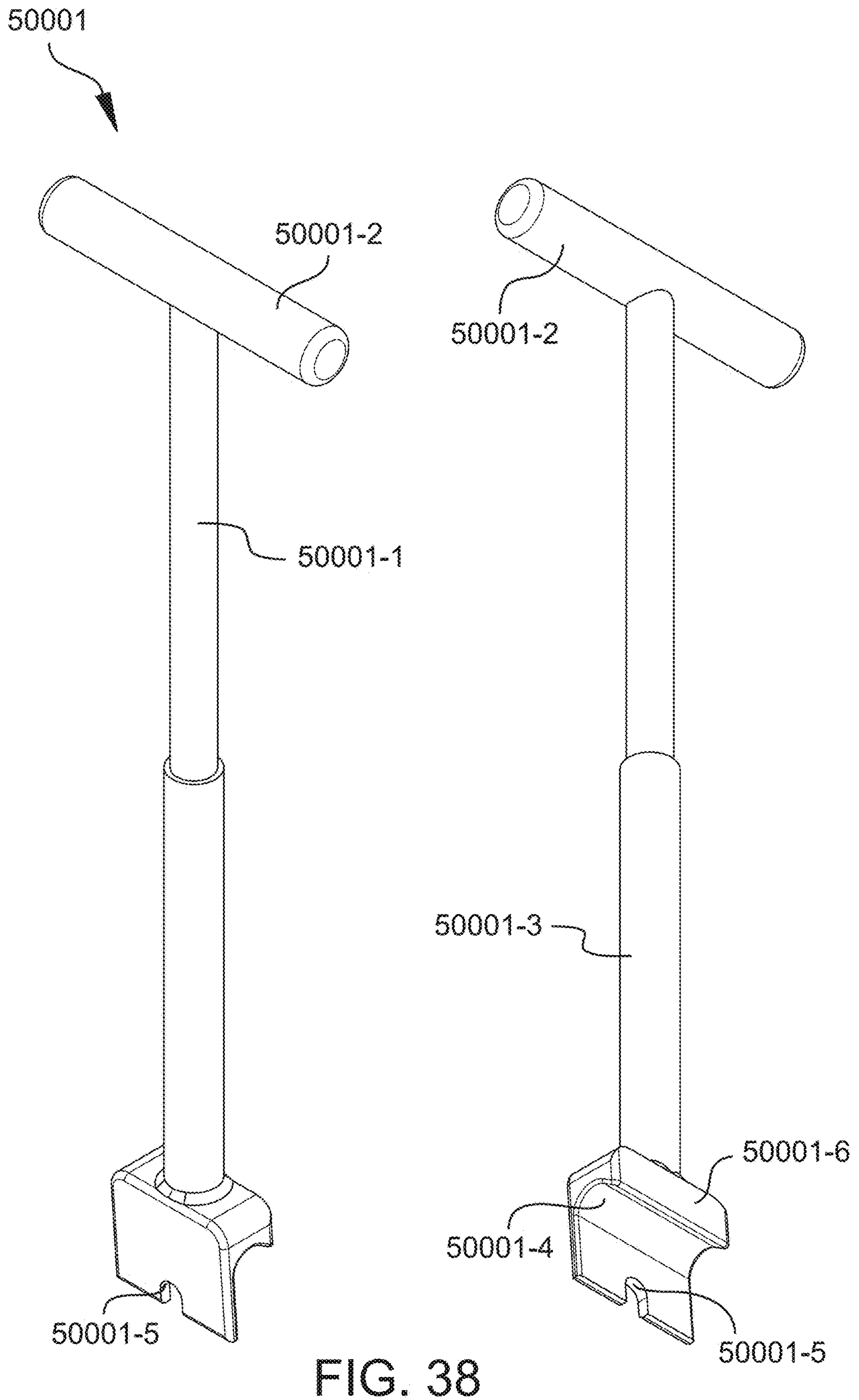
Figure 39A:
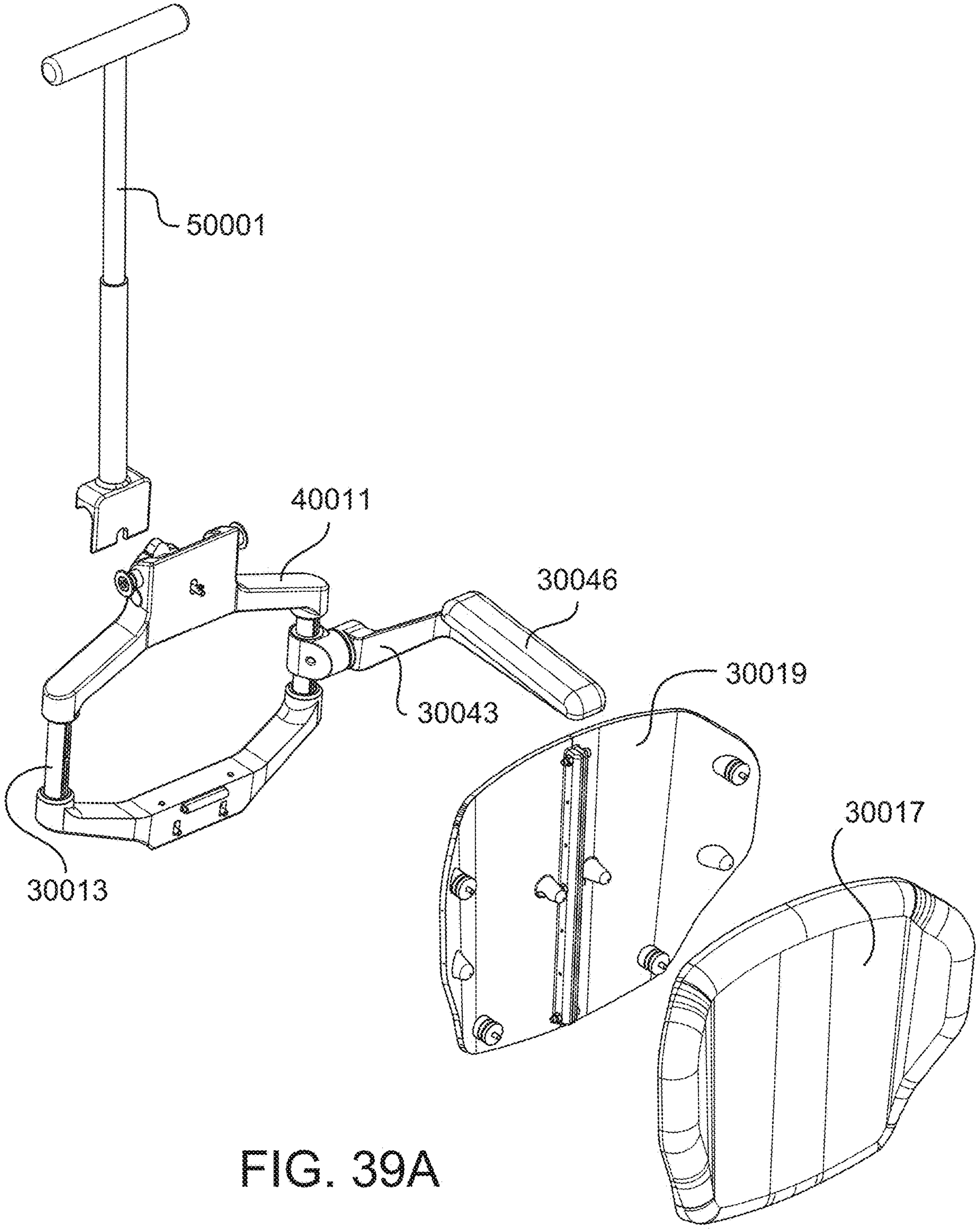
Figure 39B:
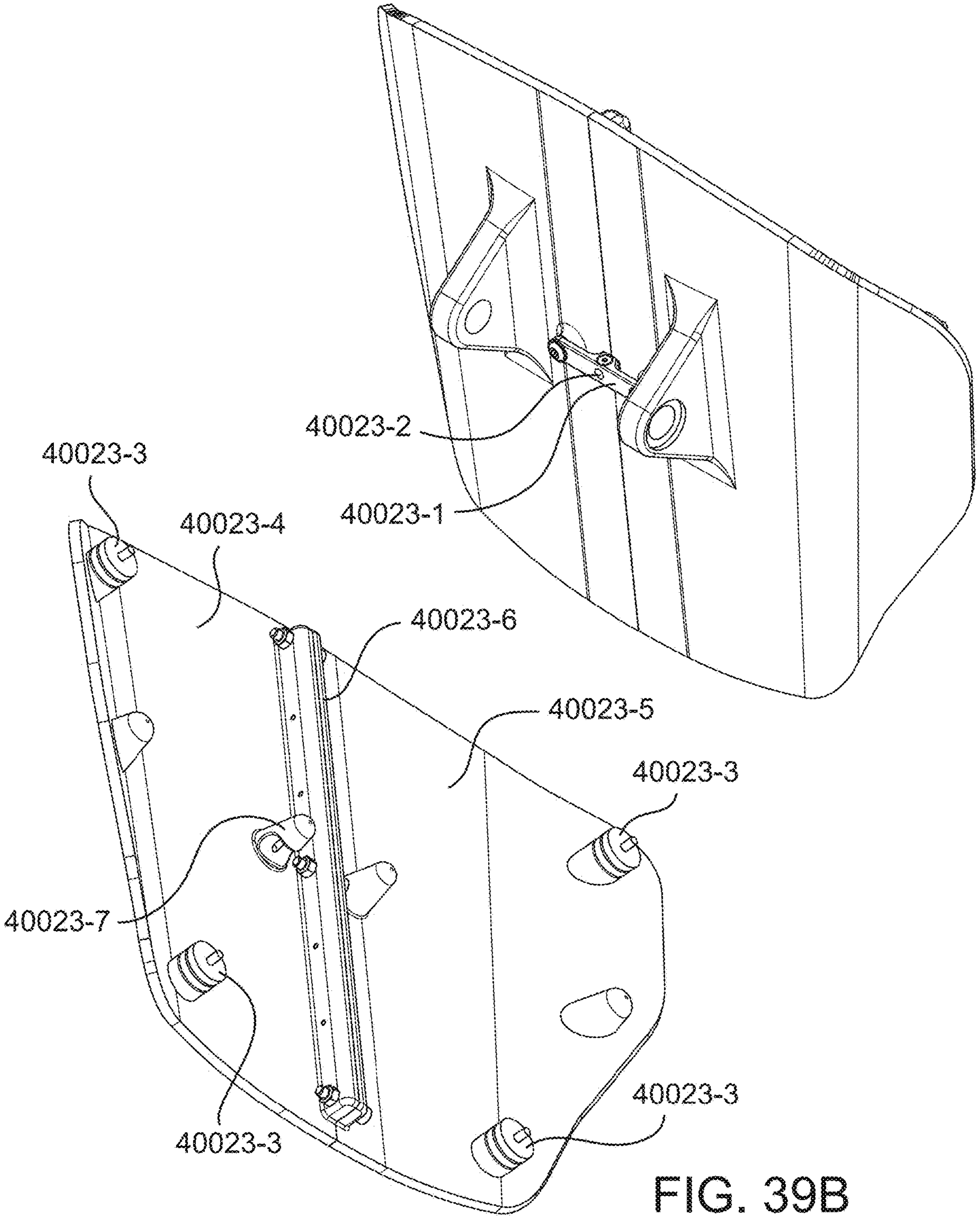
Figure 39C:
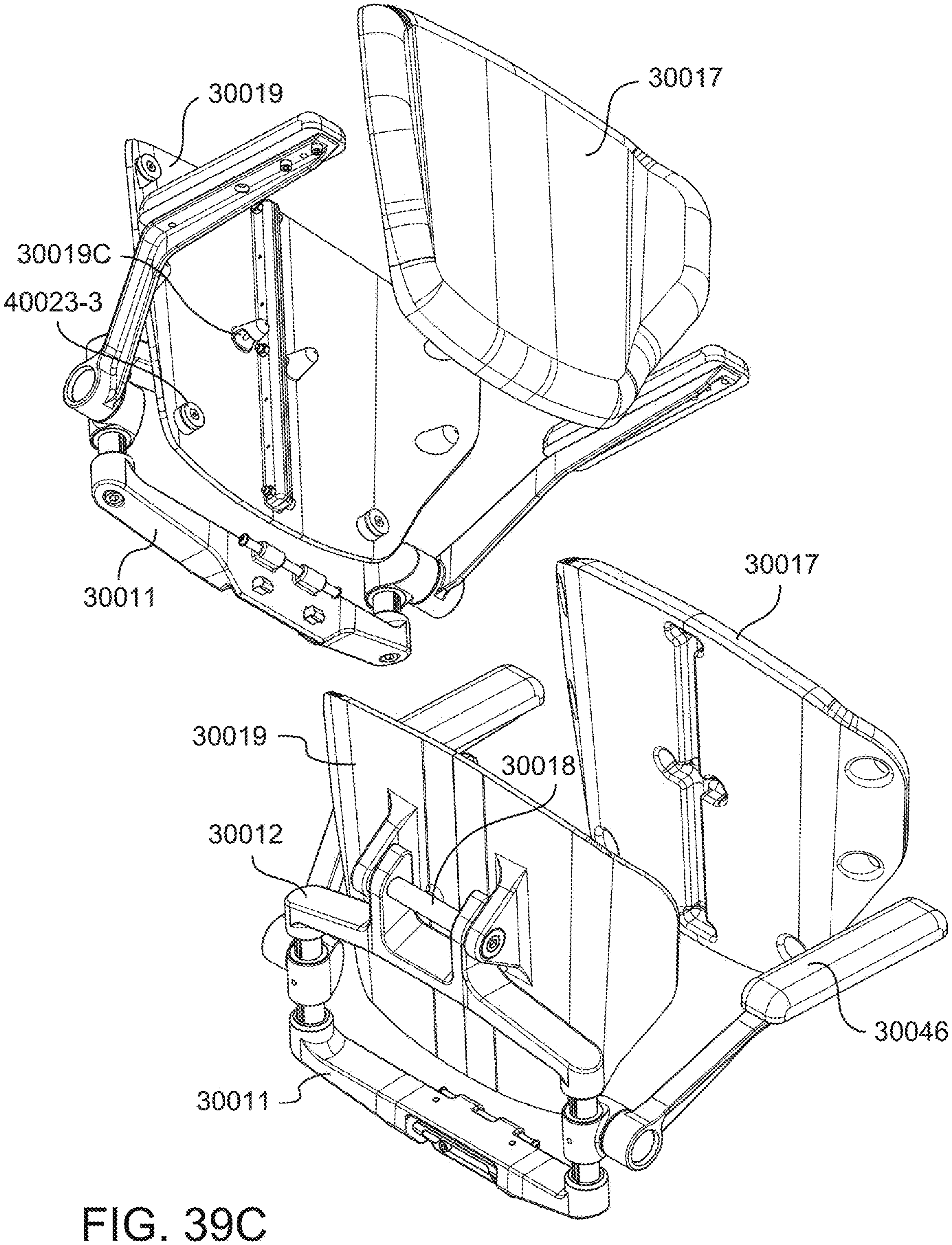
Figure 39D:
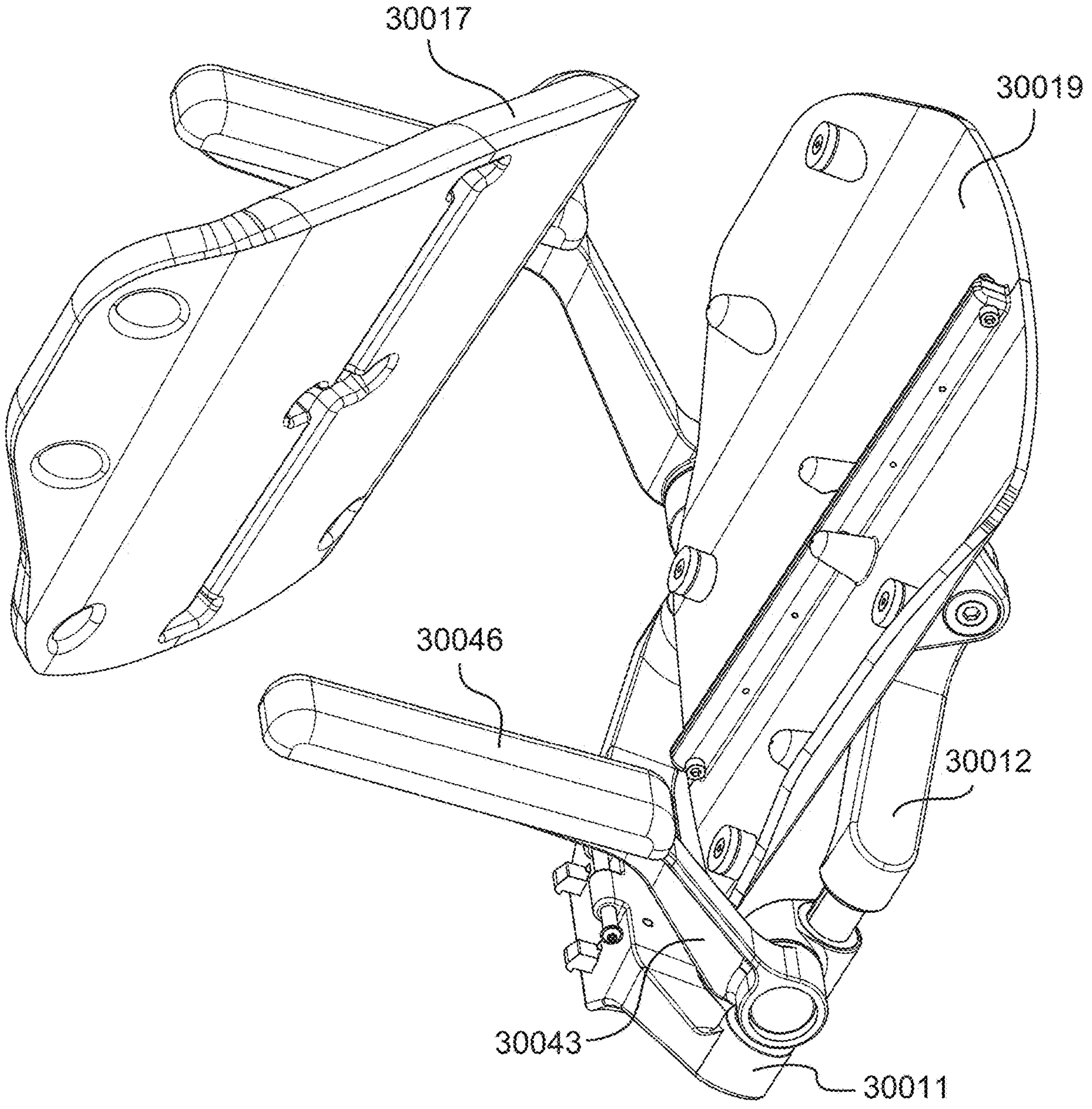
Figure 39E:
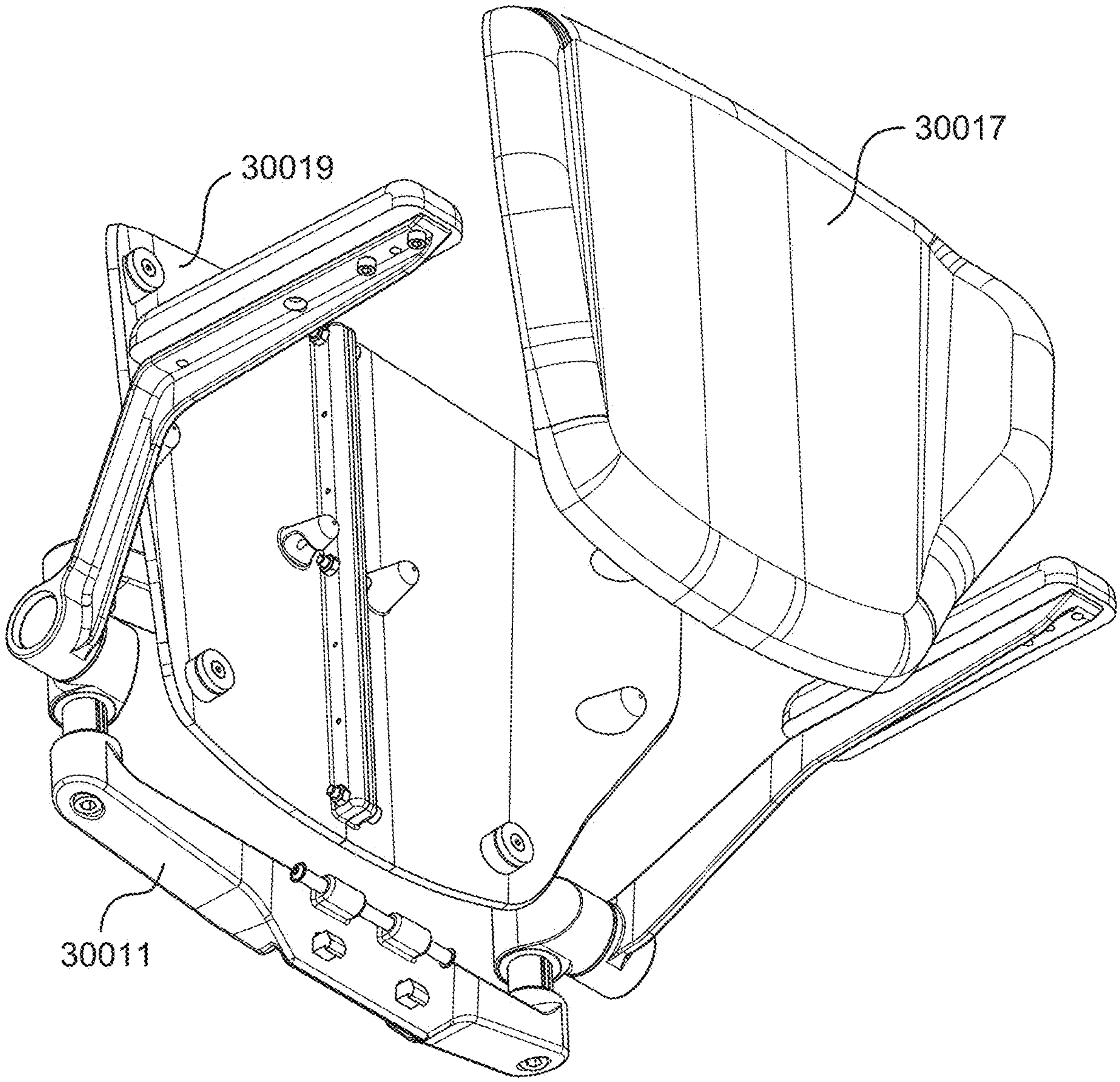
Figure 39F:
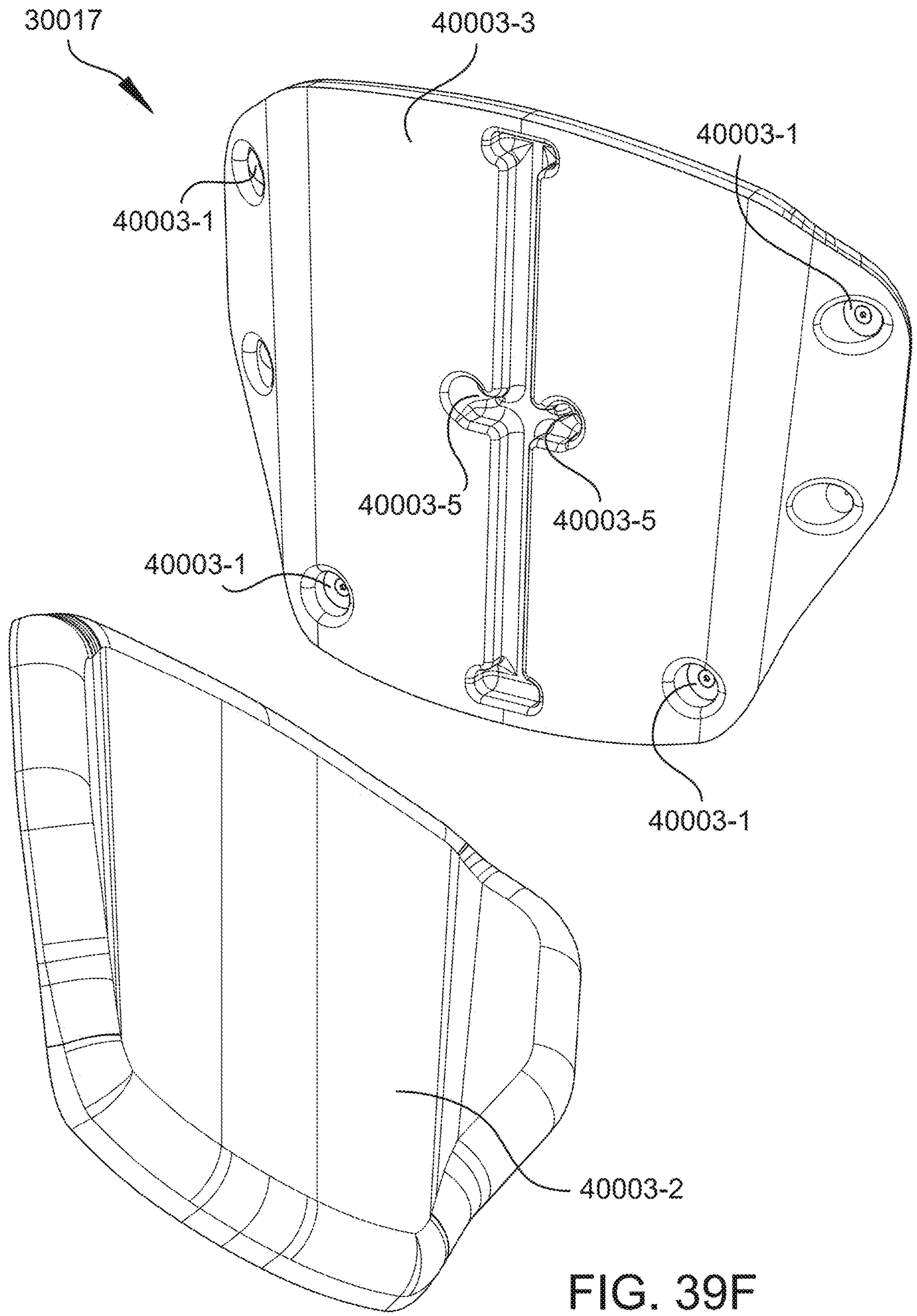
Figure 39G:
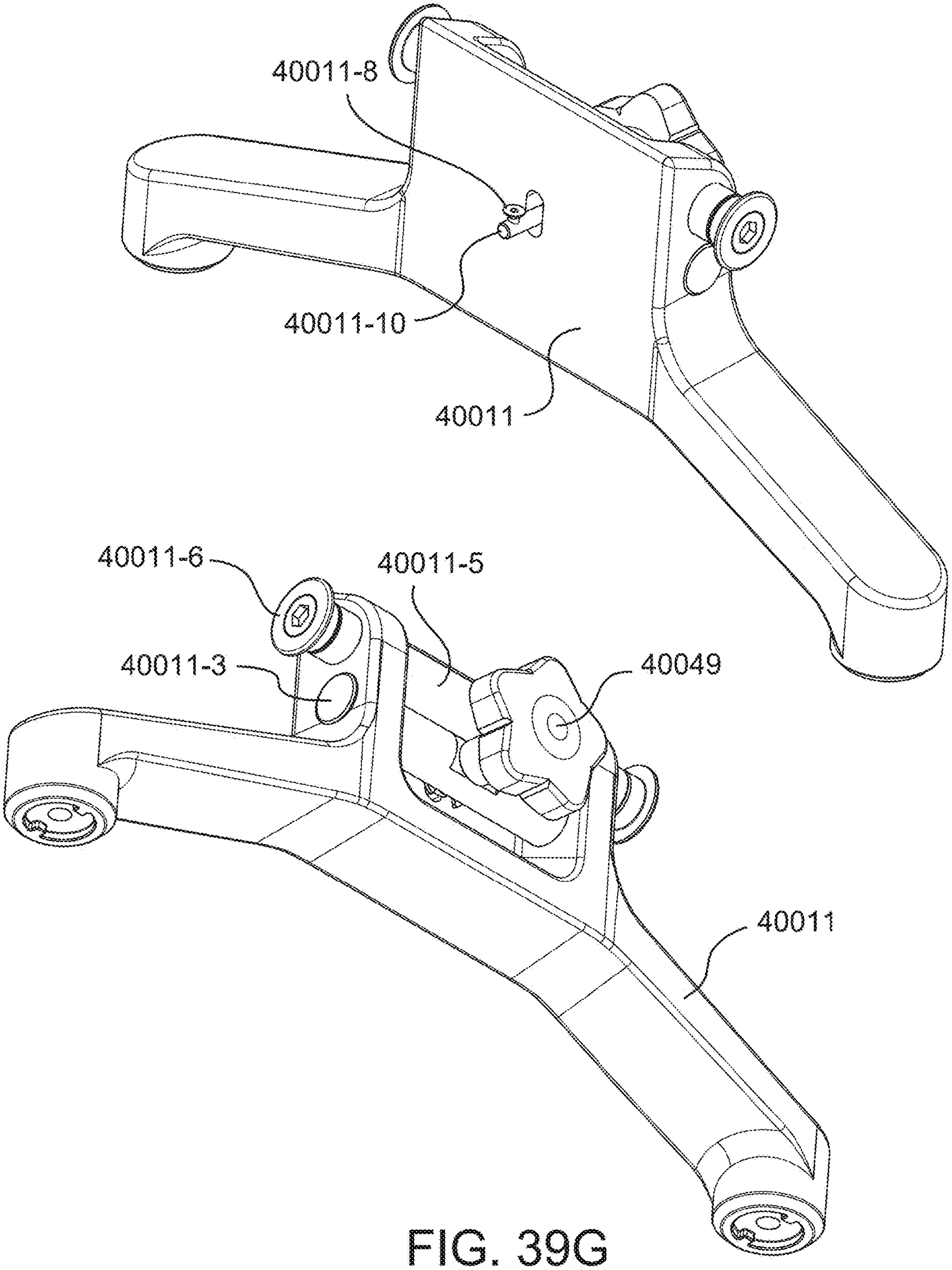
Figure 39H:
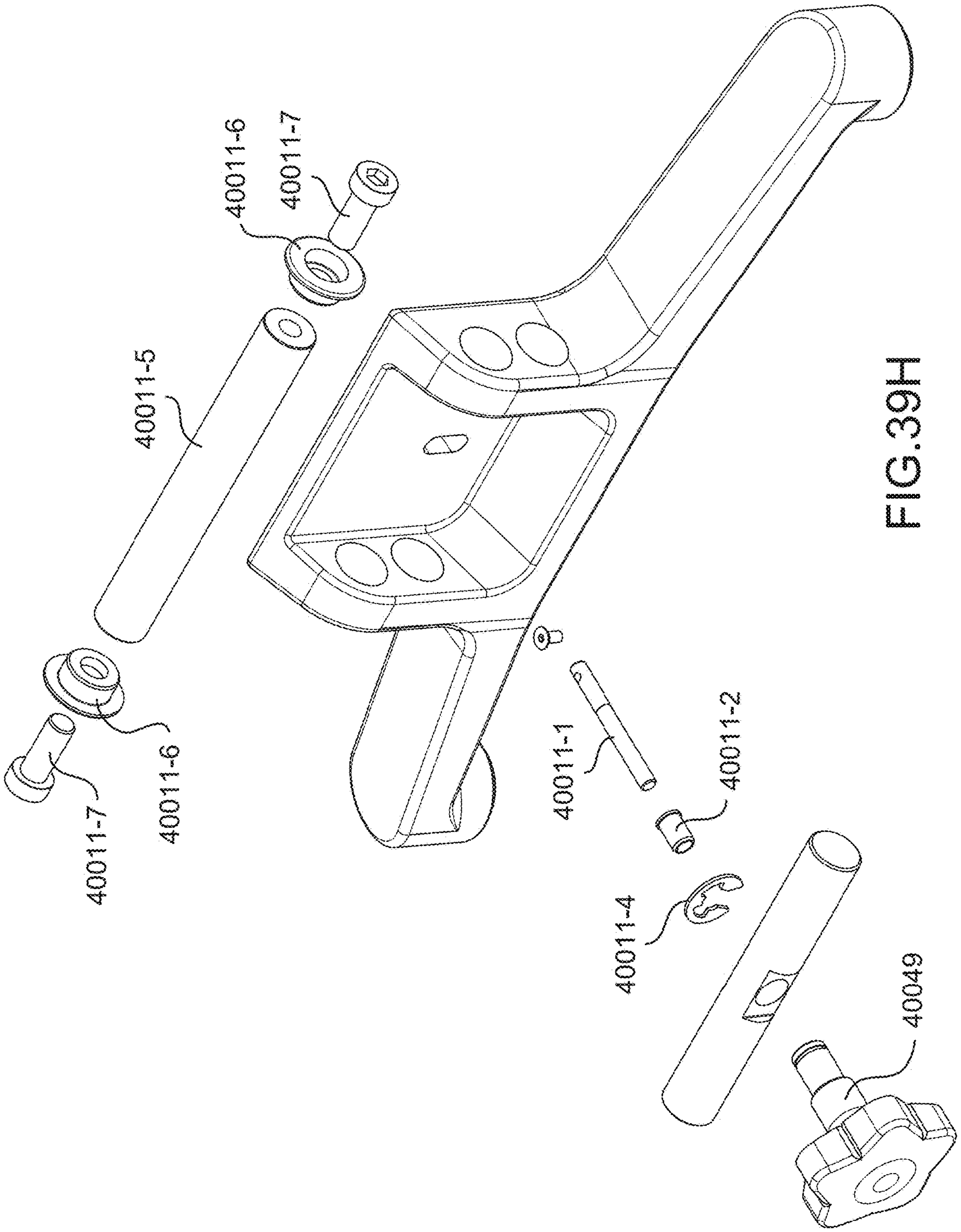
Figure 39I:
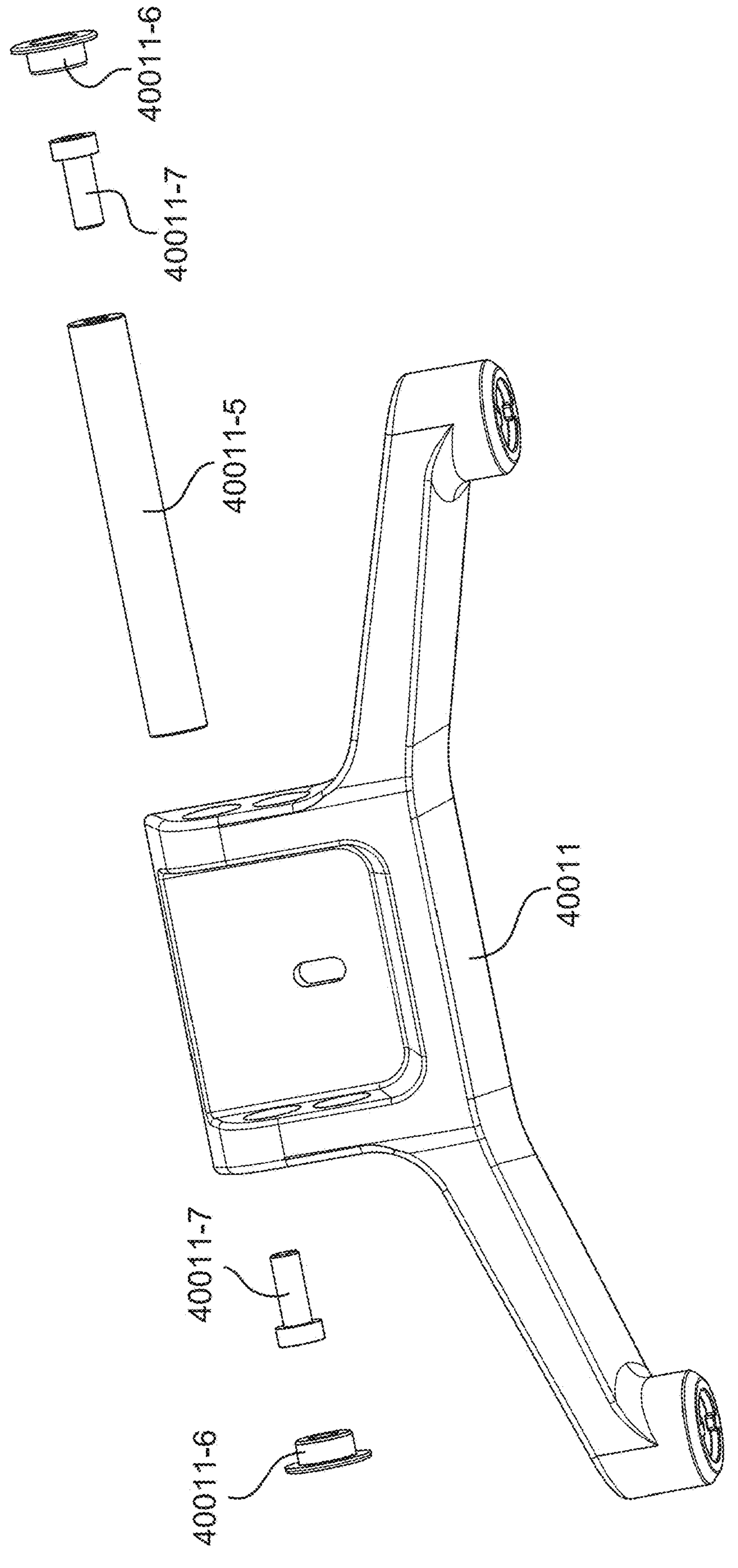
Figure 39J:
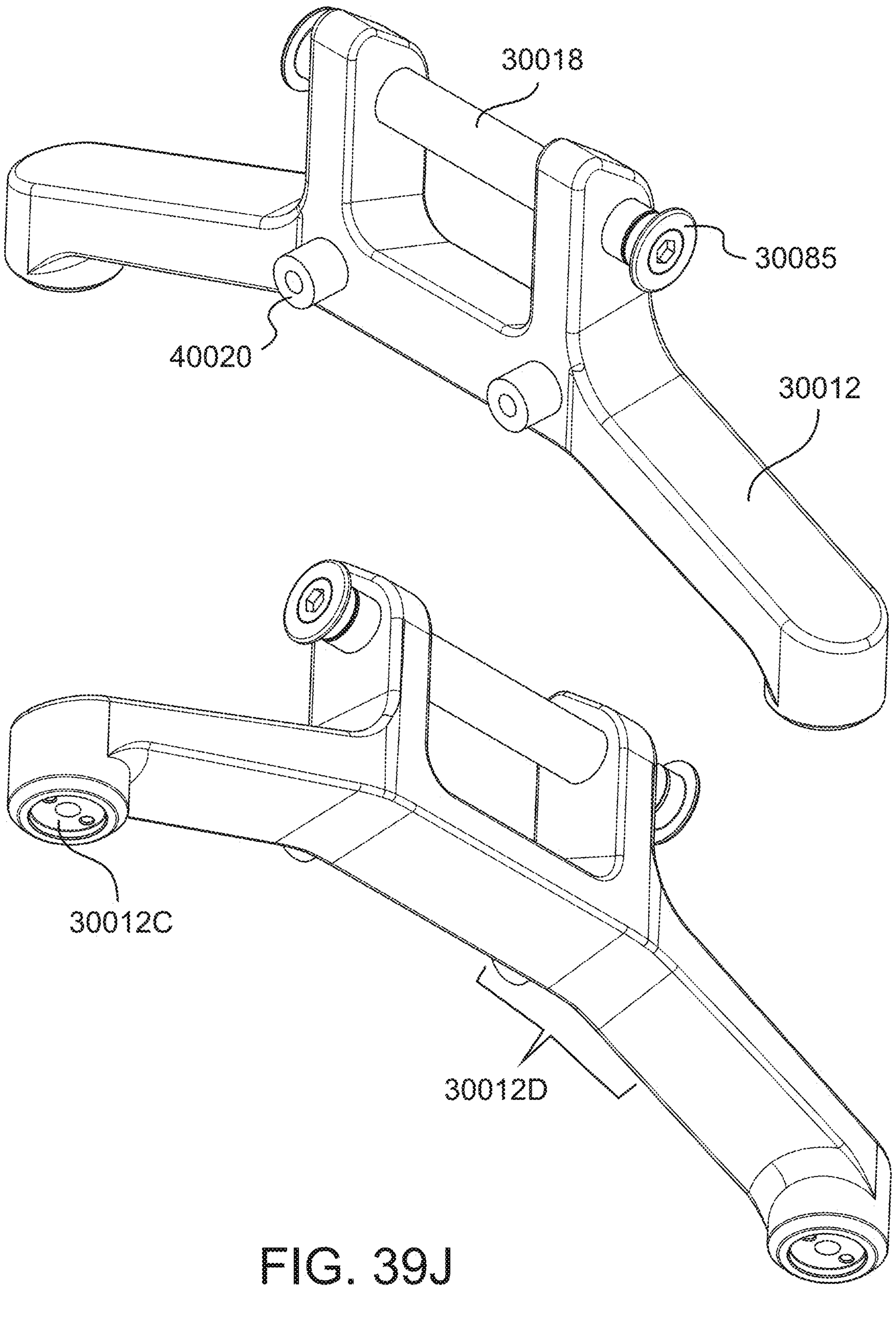
Figure 39K:
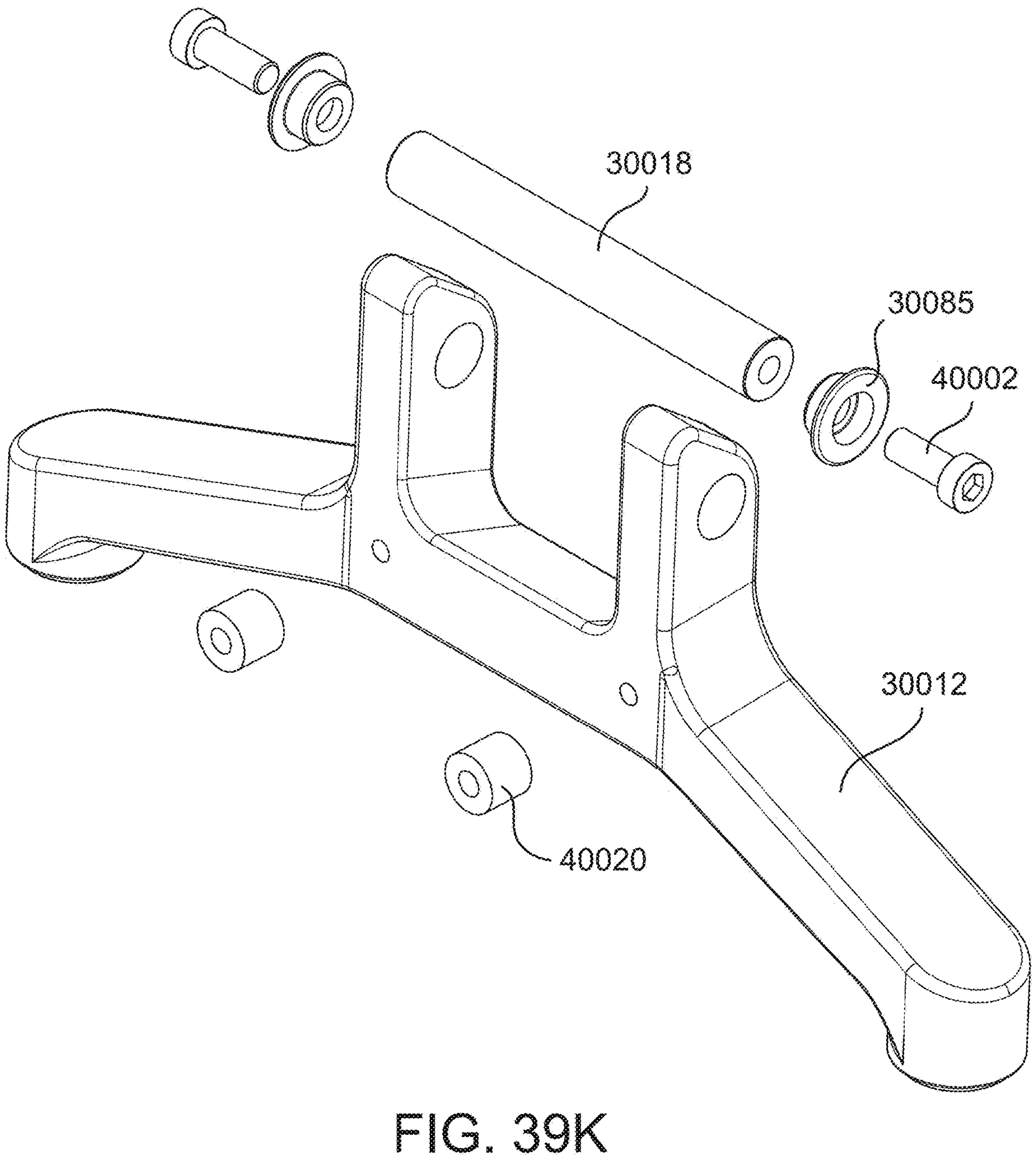
Figure 39L:
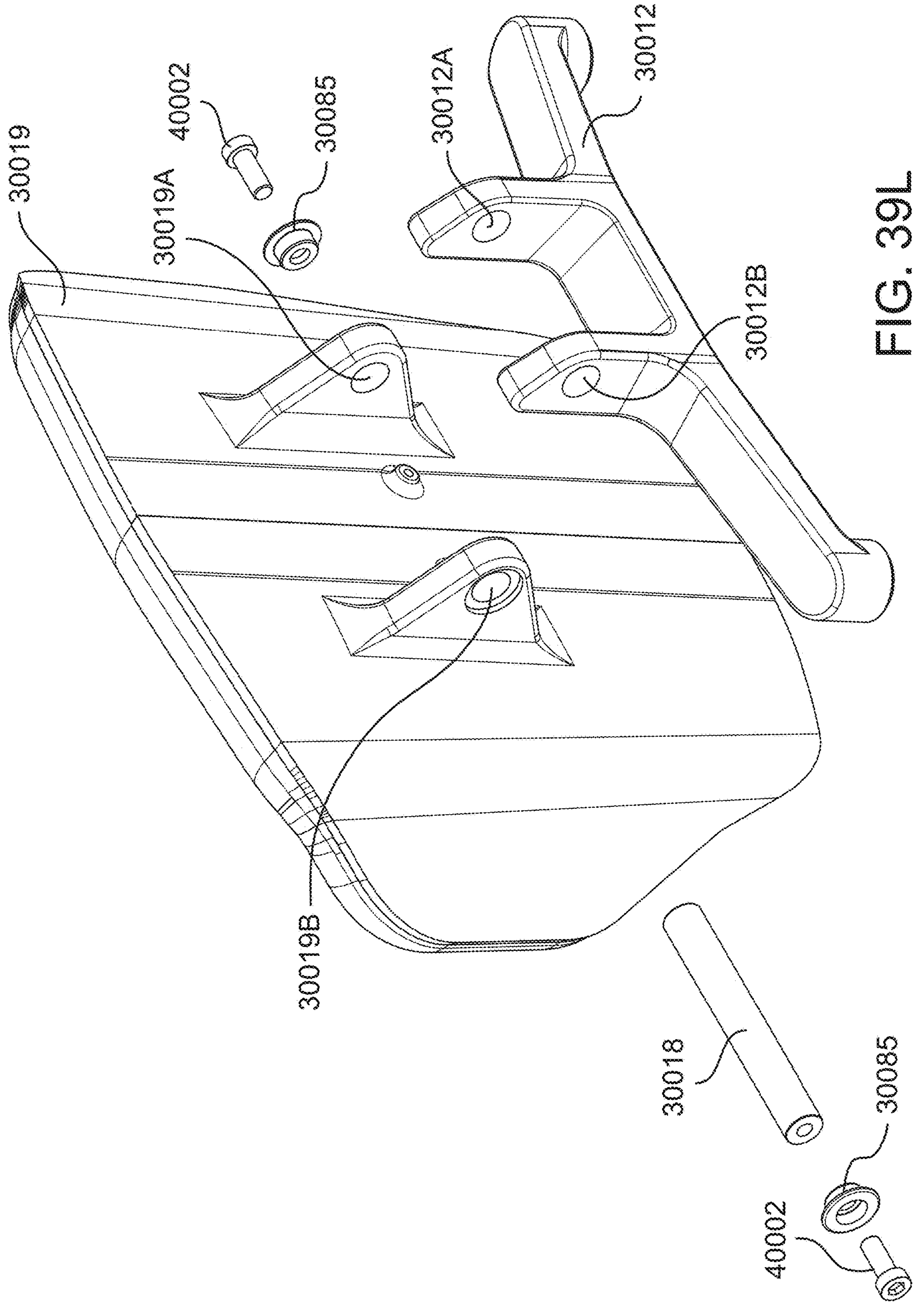
Figure 40A:
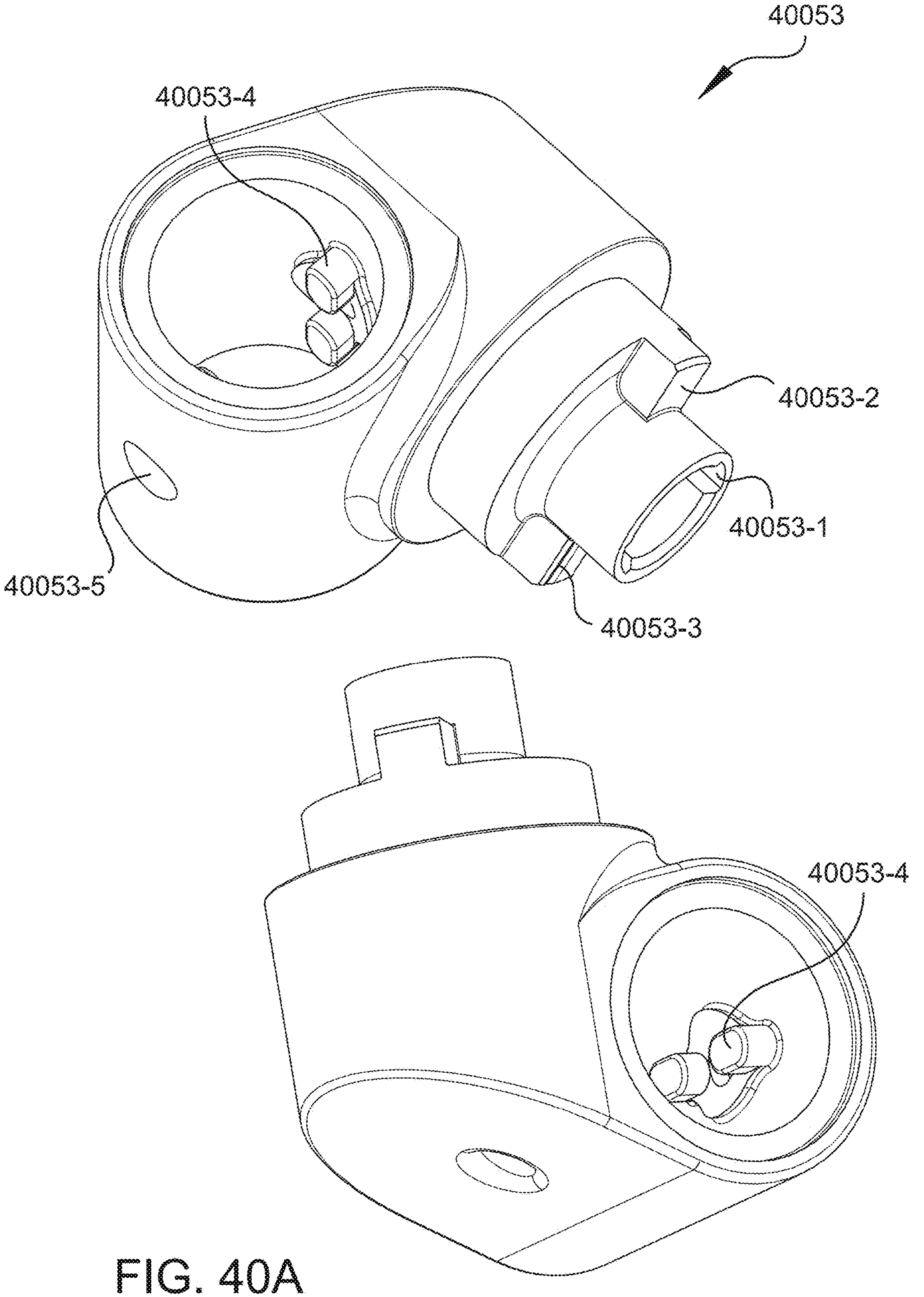
Figure 40B:
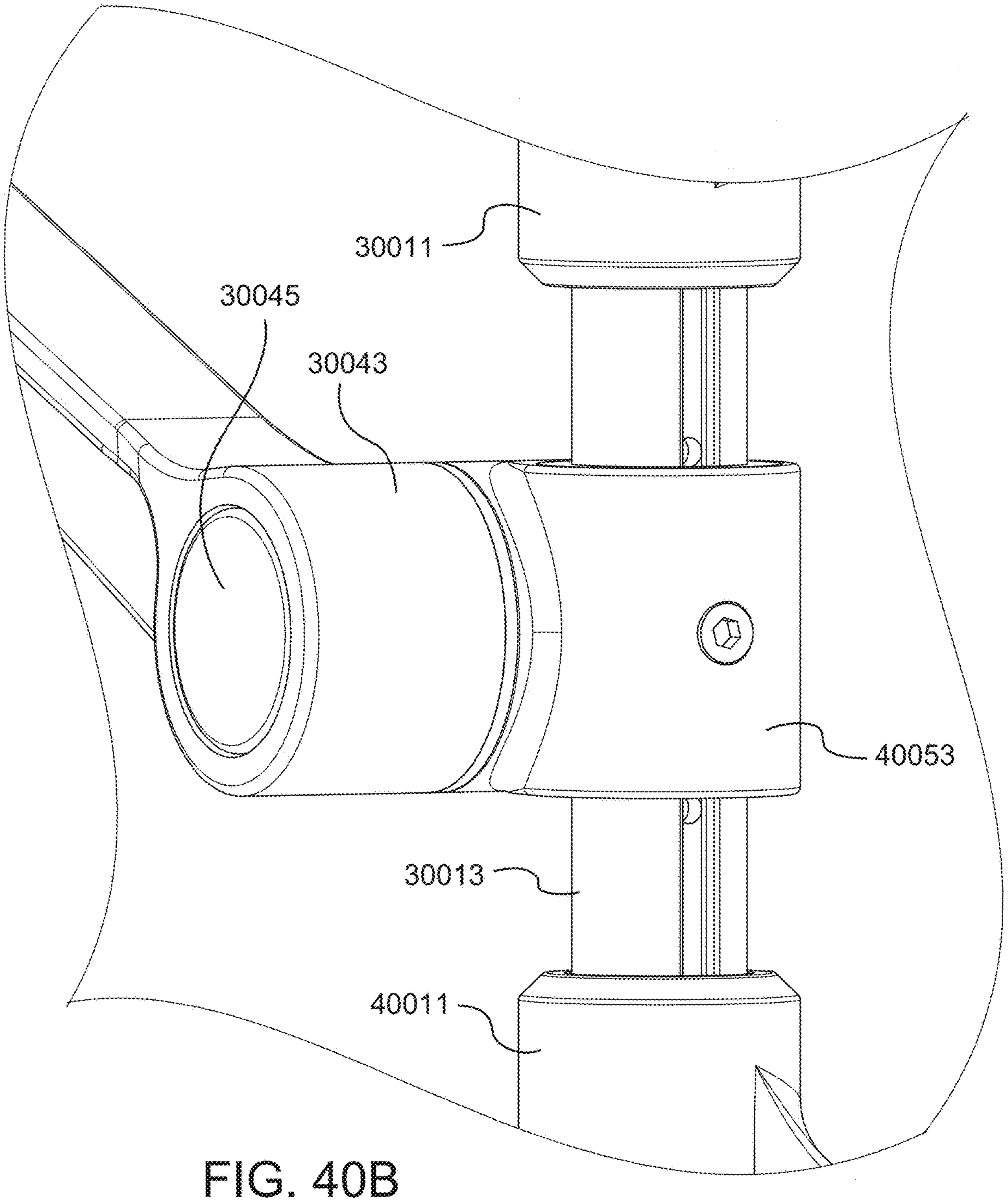
Figure 40C:
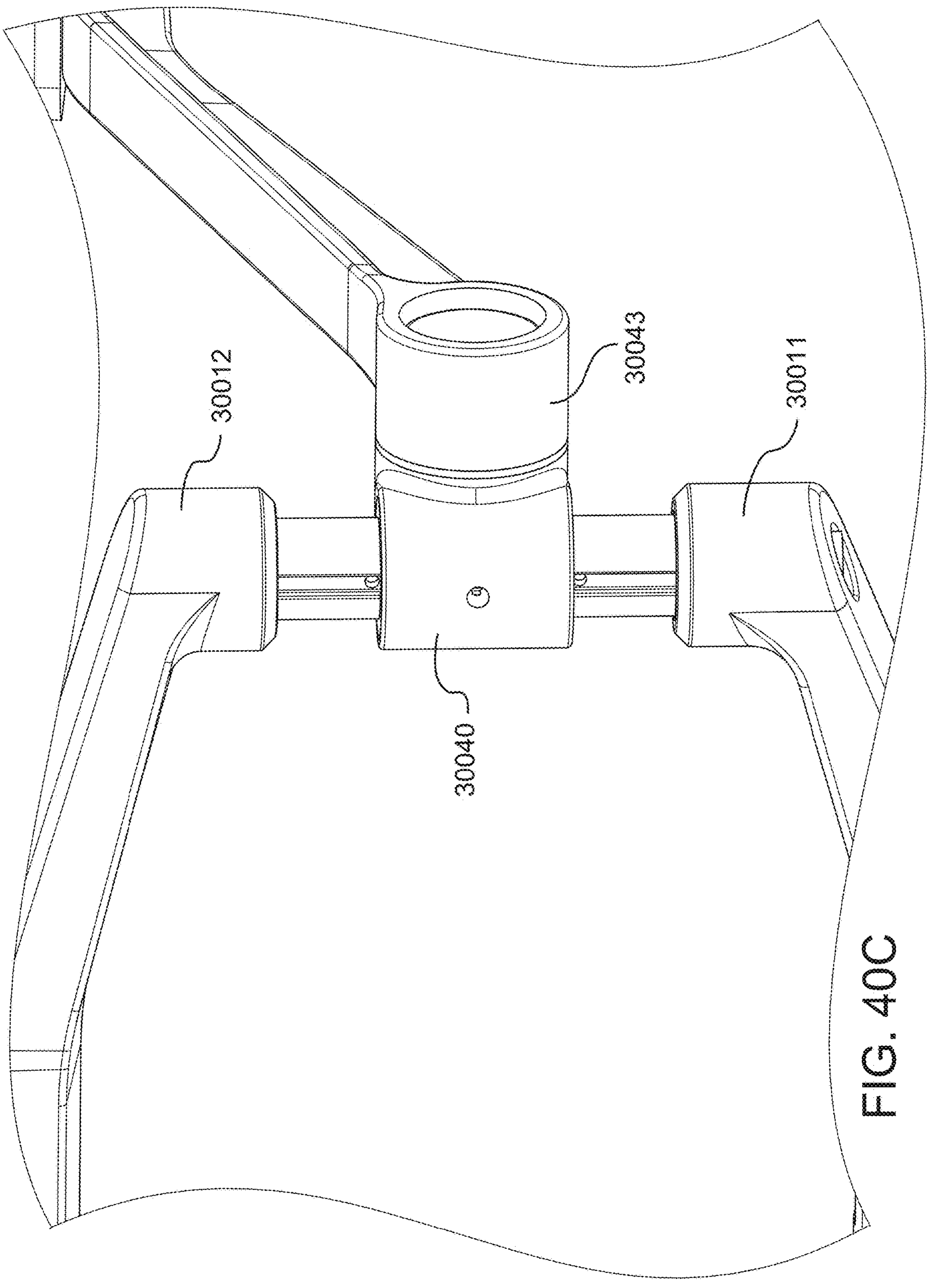
Figure 40D:
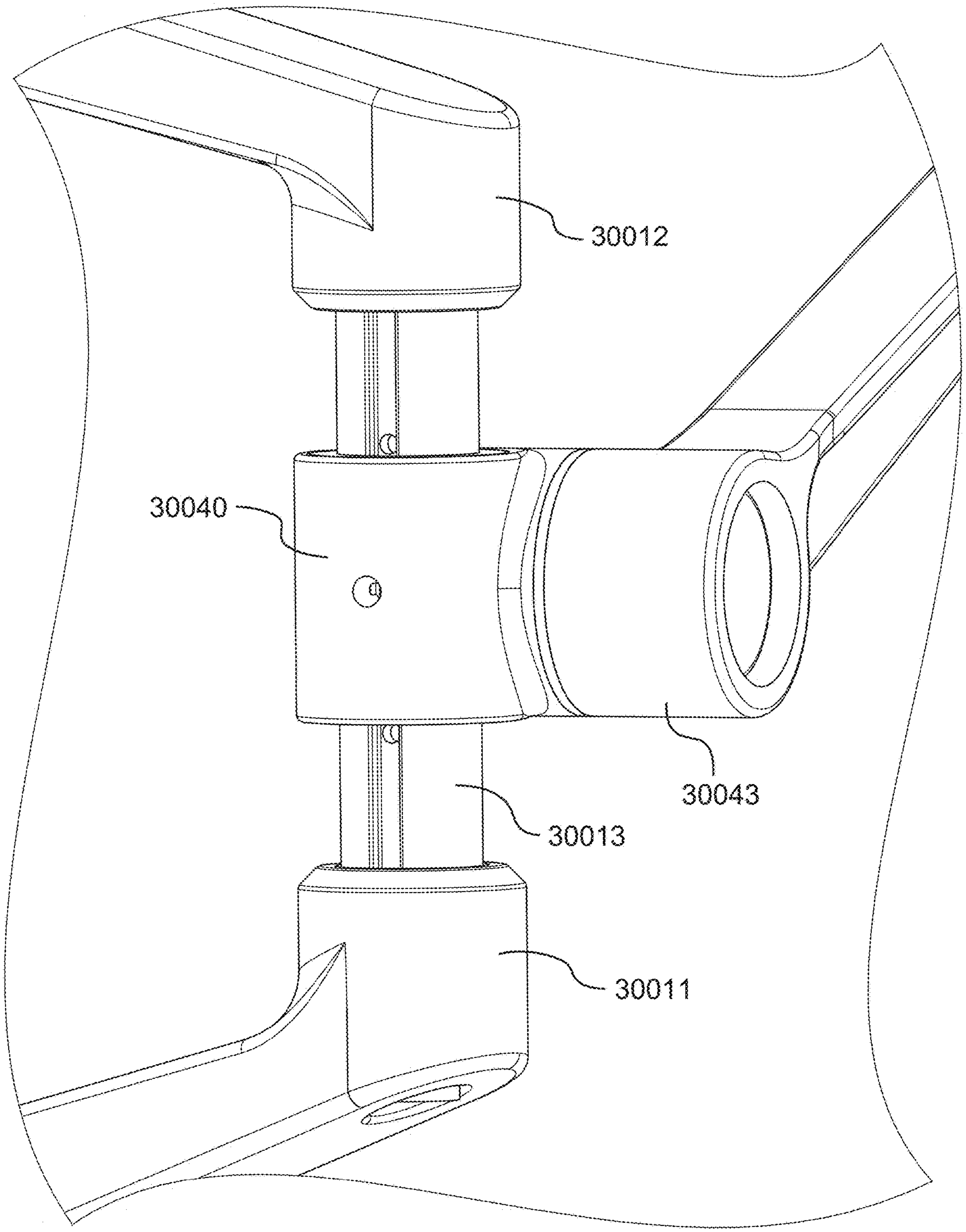
Figure 40E:
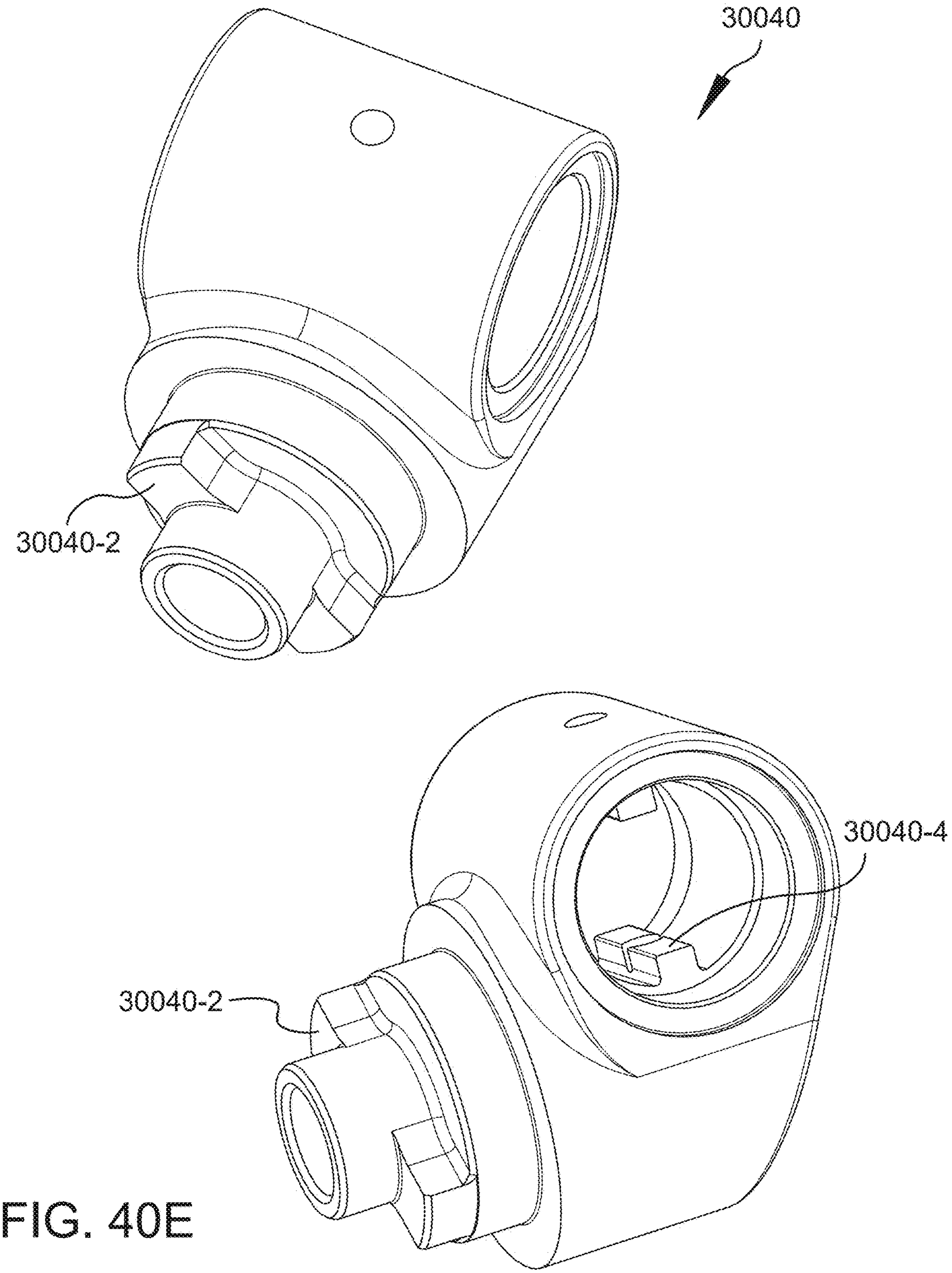
Figure 40F:
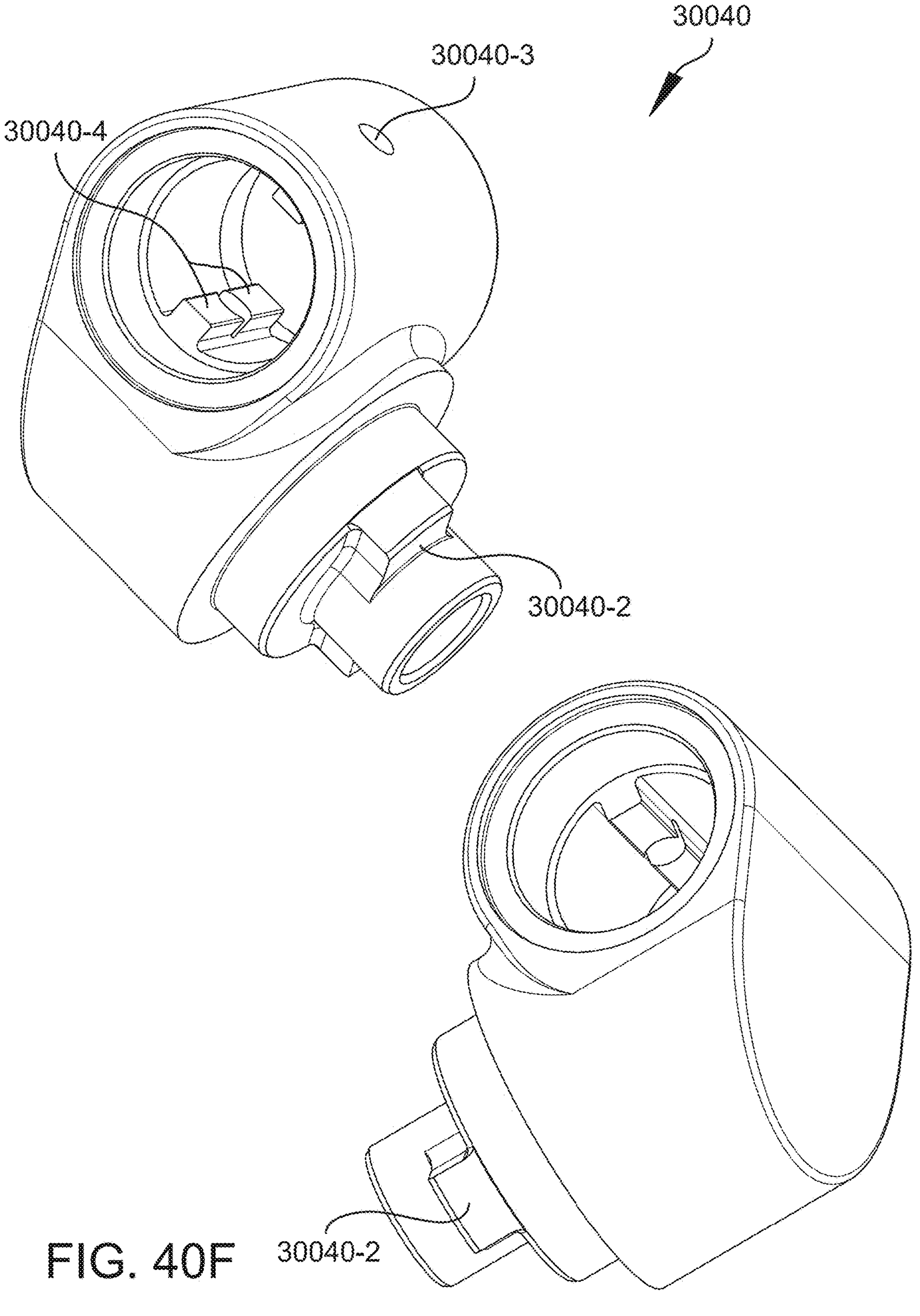
Figure 40G:
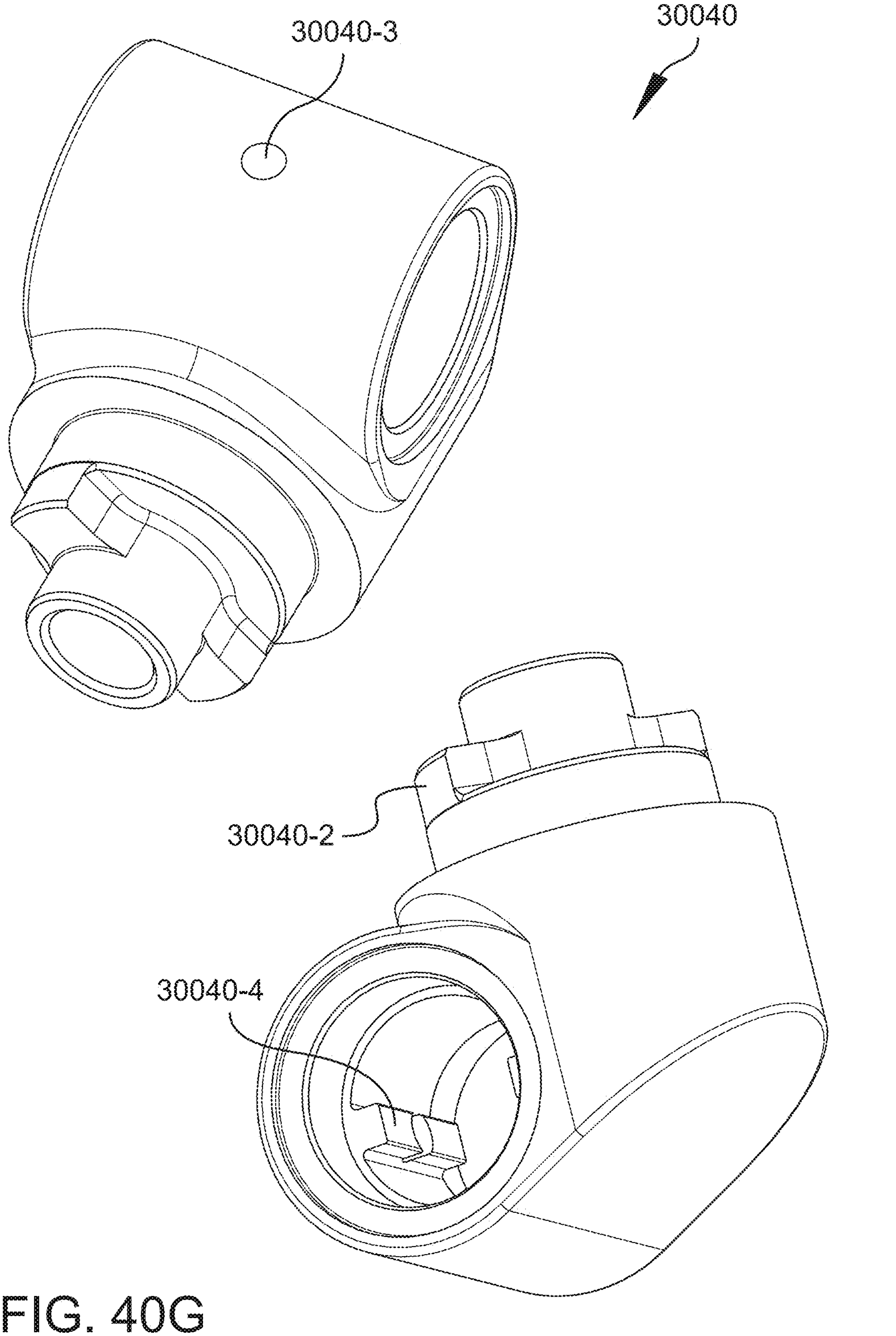
Figure 40H:
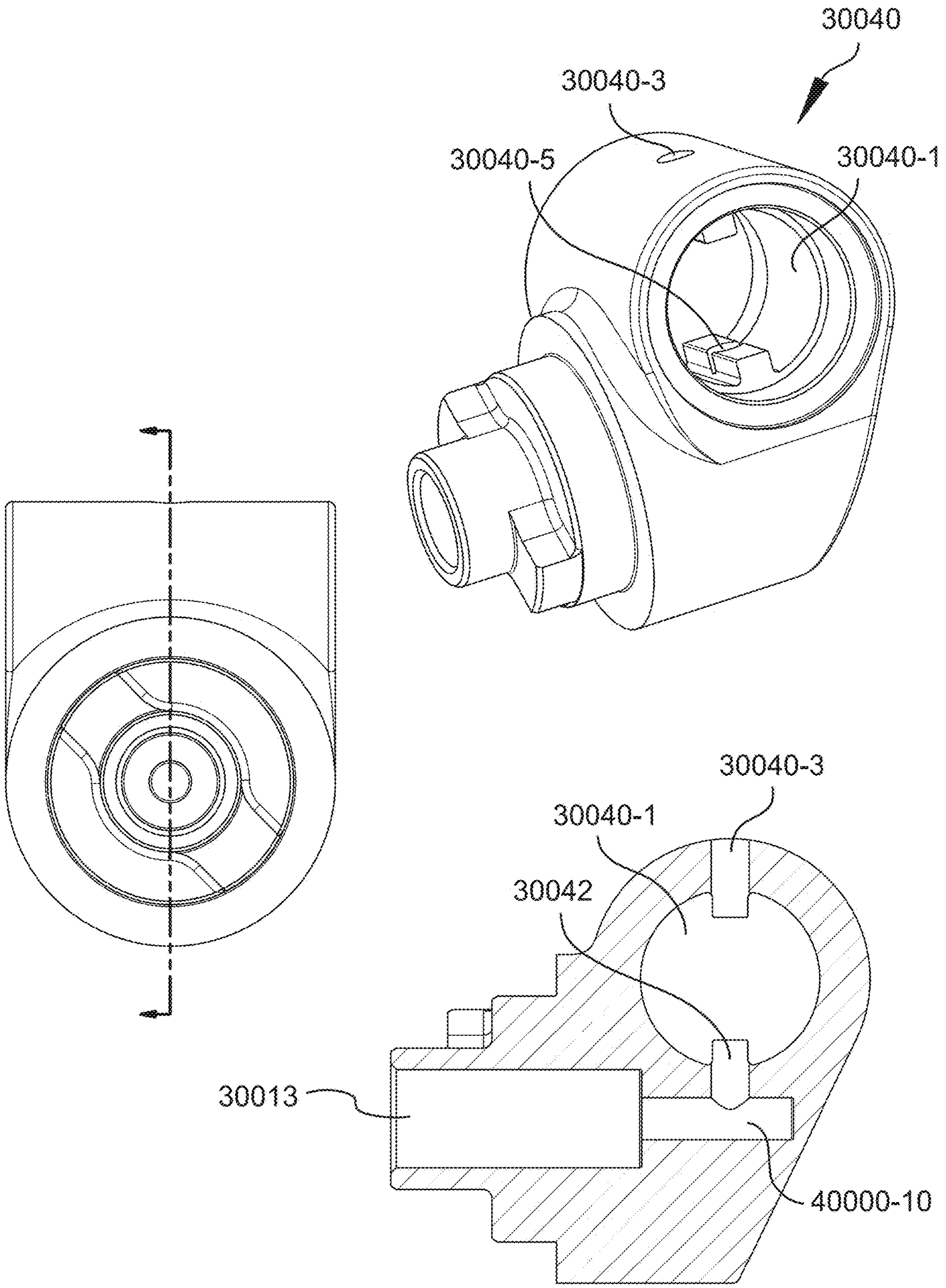
Figure 40I:
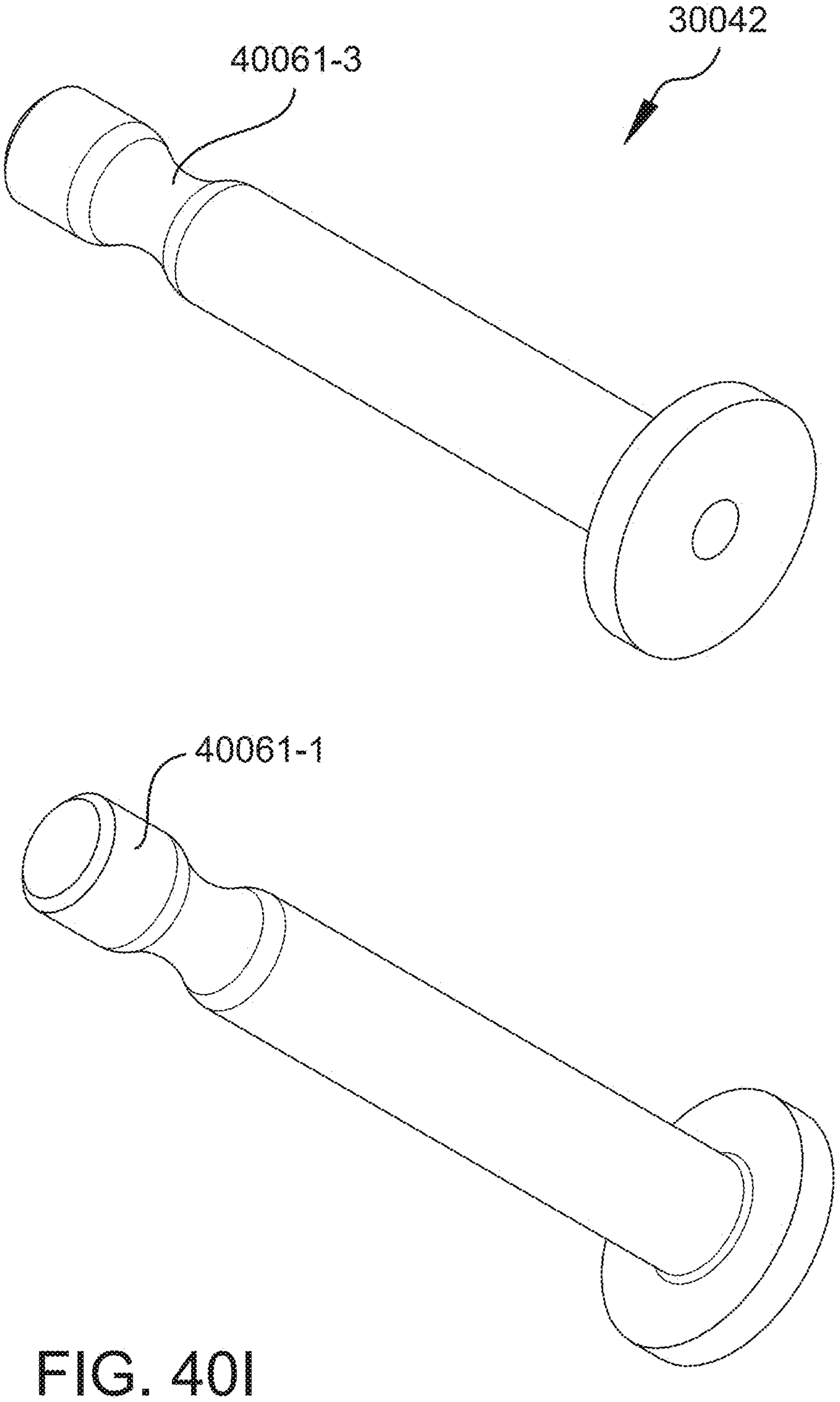
Figure 40J:
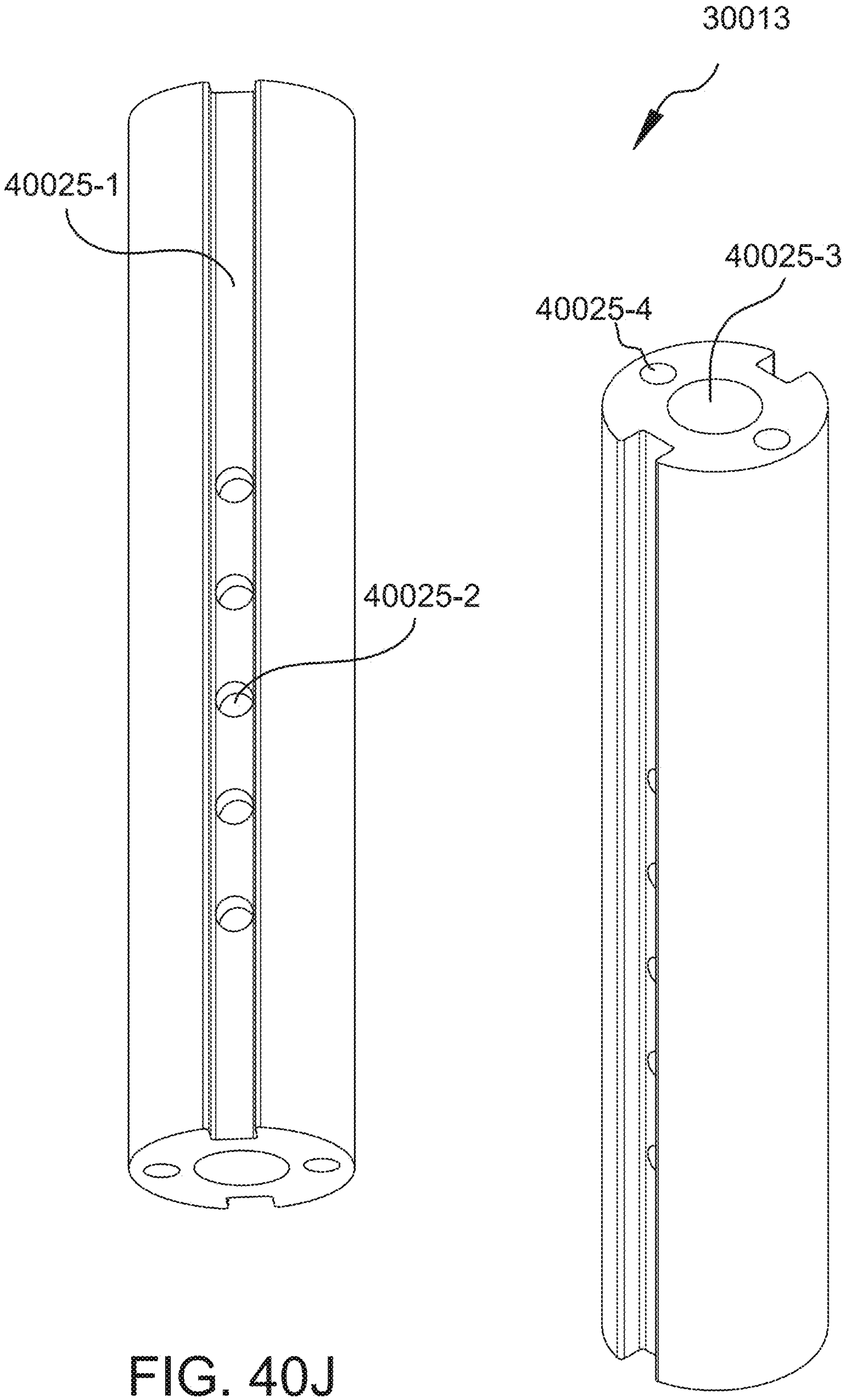
Figure 40K:
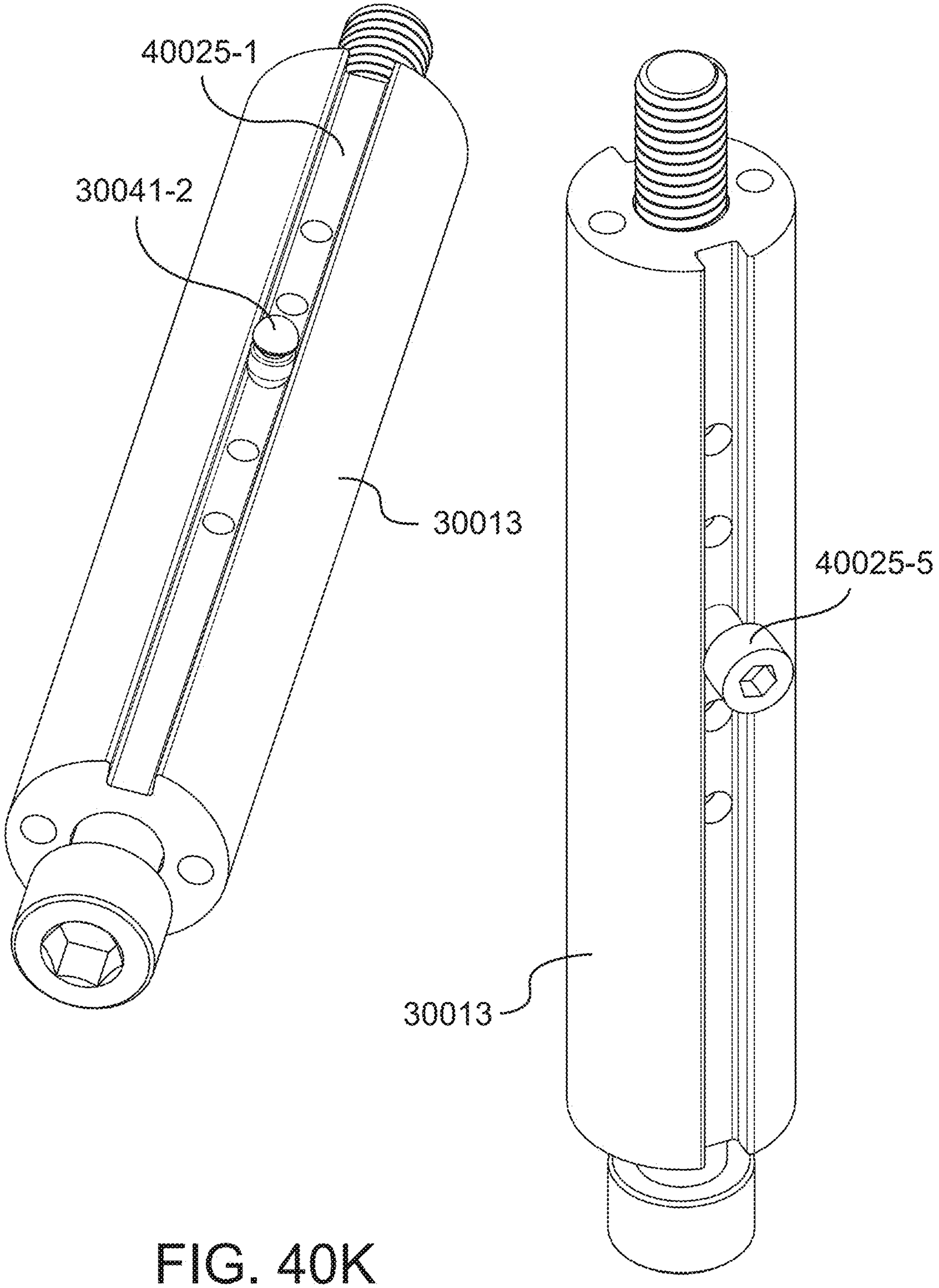
Figure 40L:
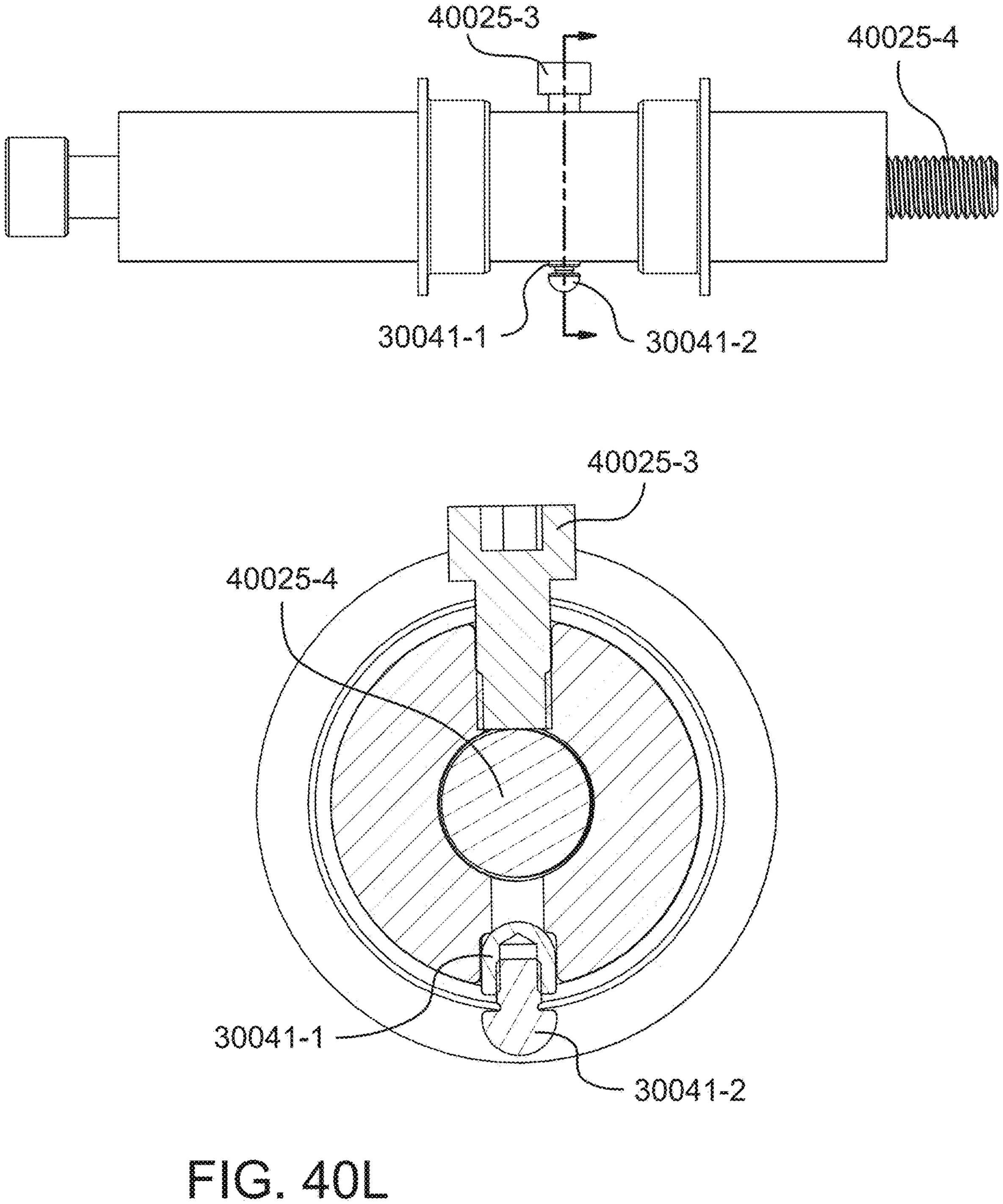
Figure 41A:
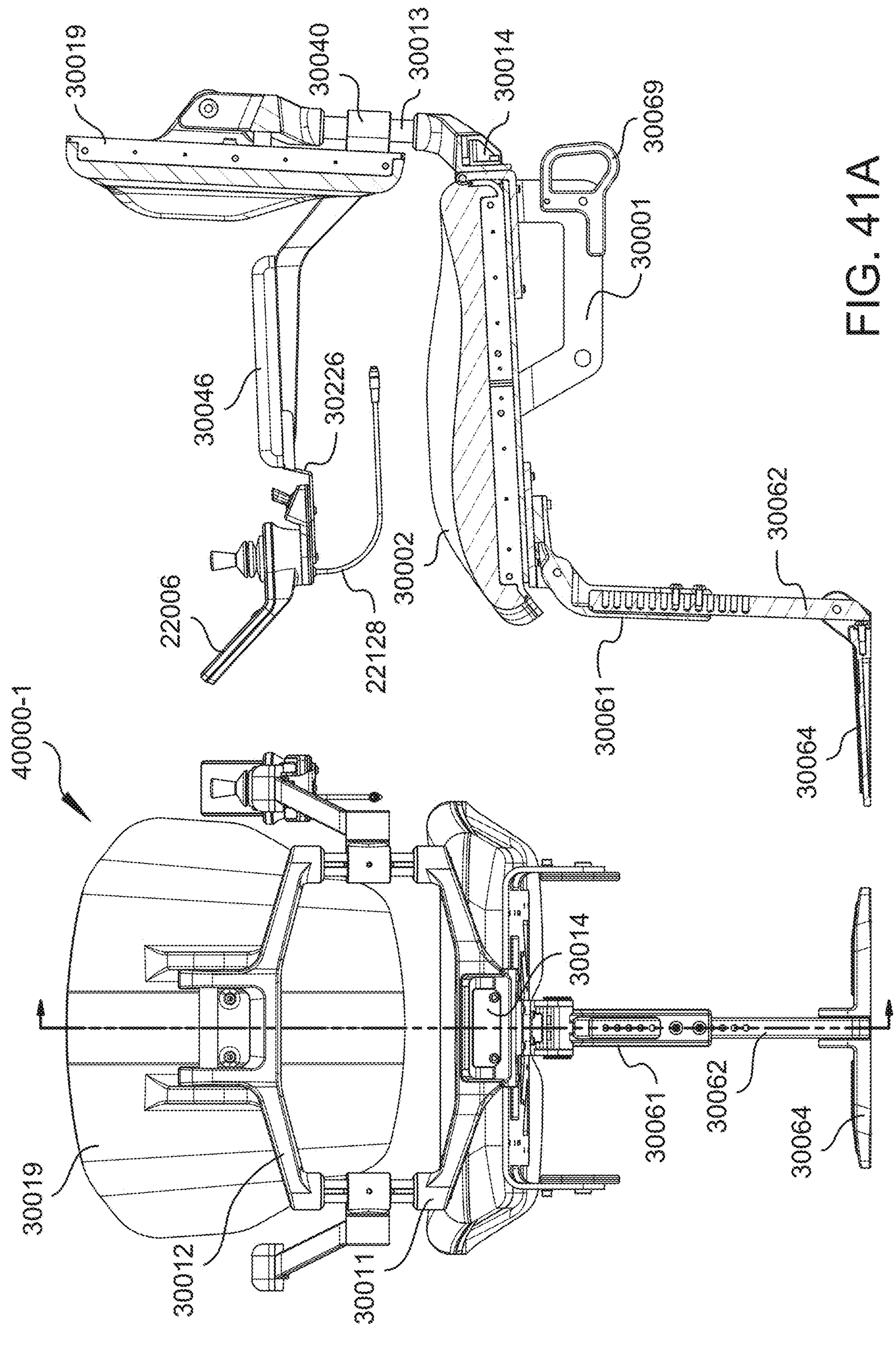
Figure 41B:
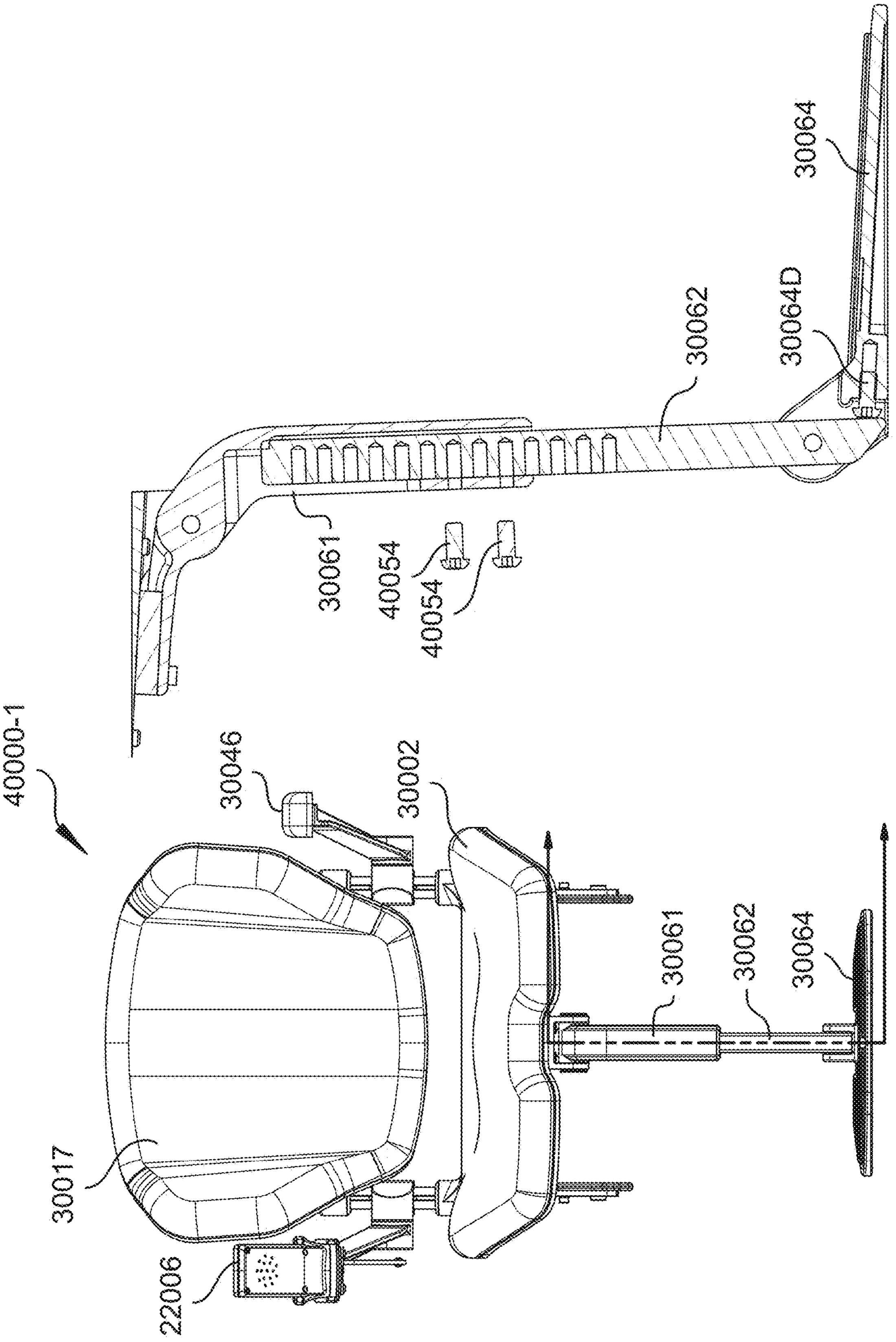
Figure 41C:
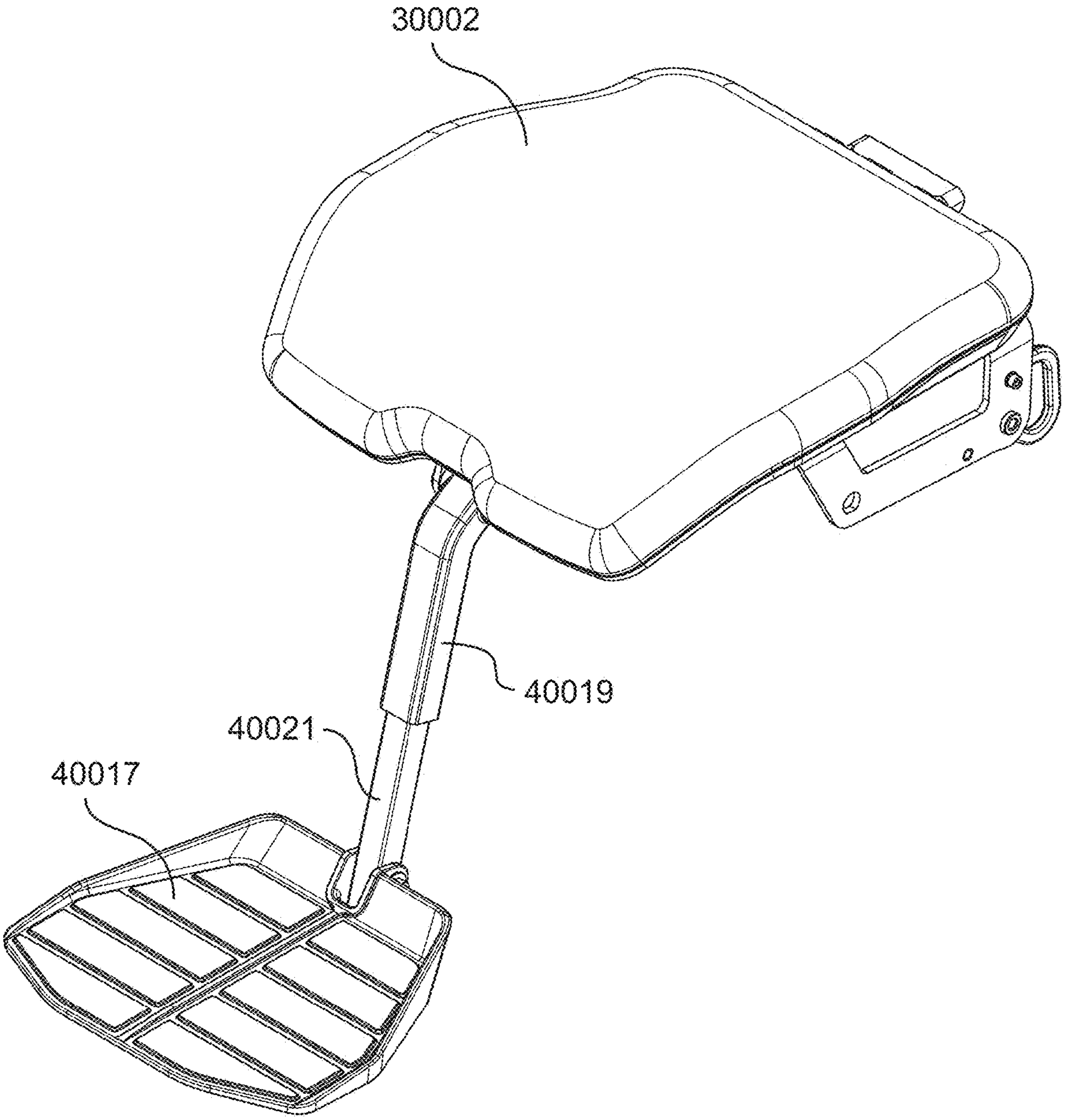
Figure 41D:
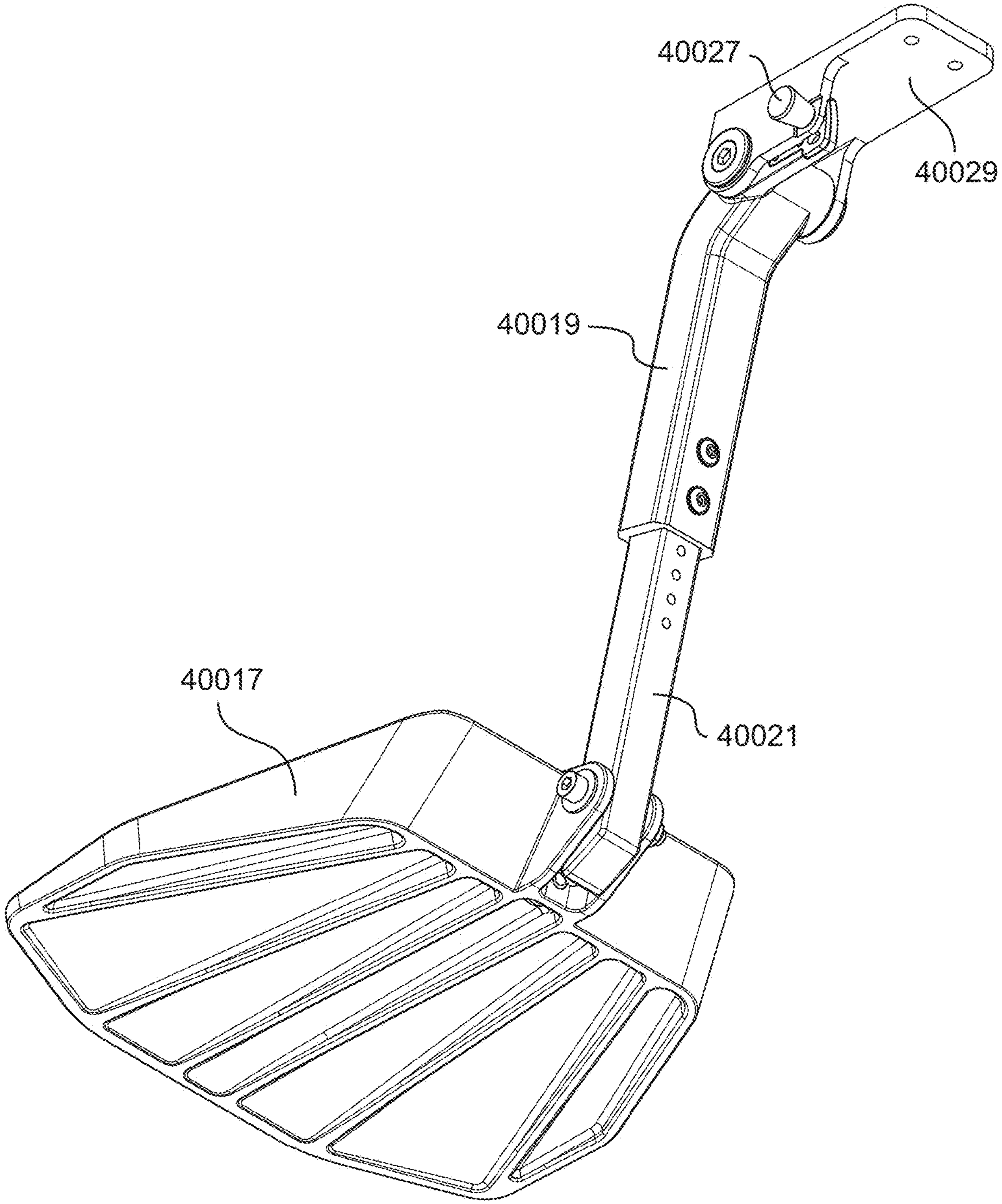
Figure 41E:
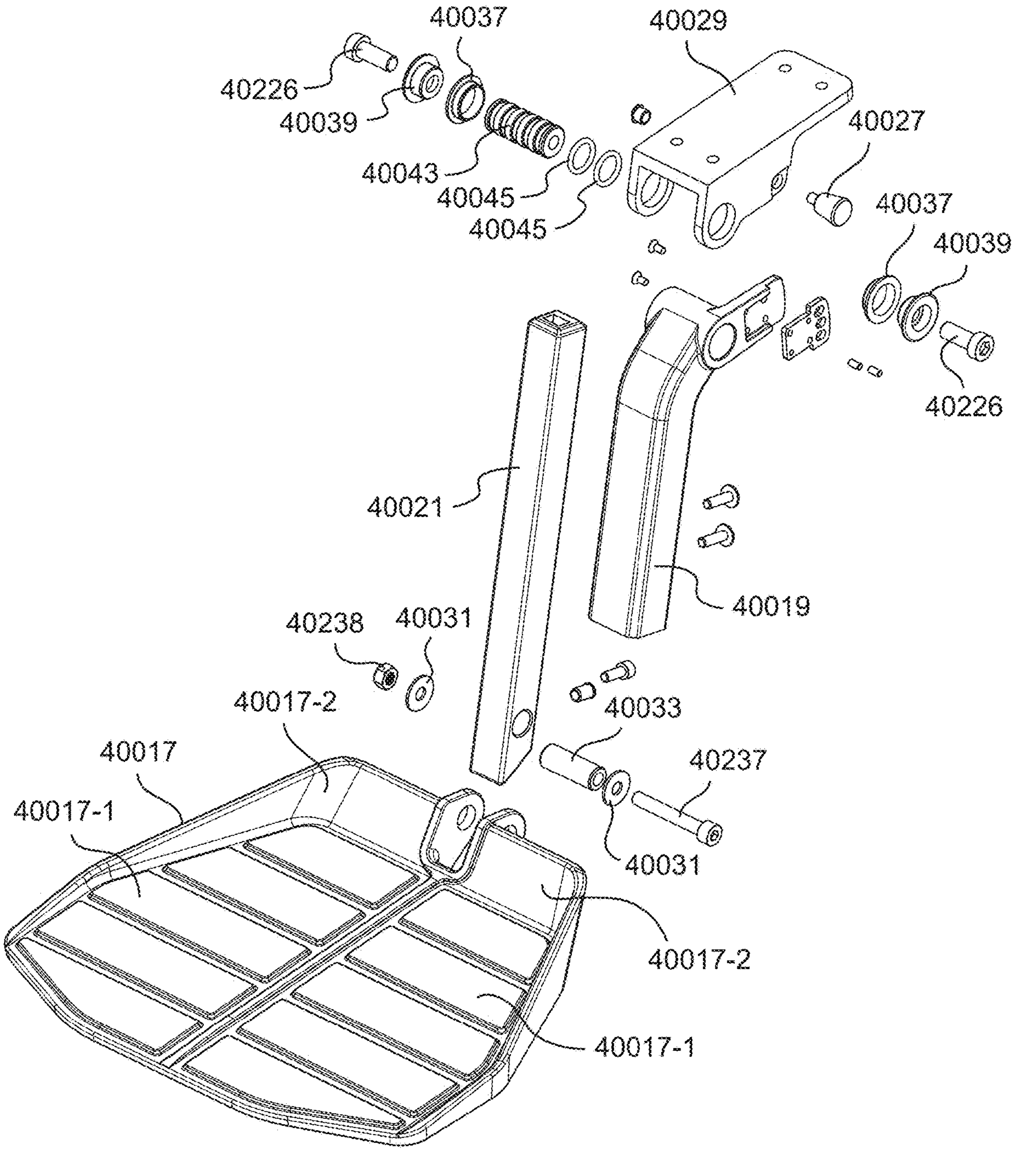
Figure 41F:
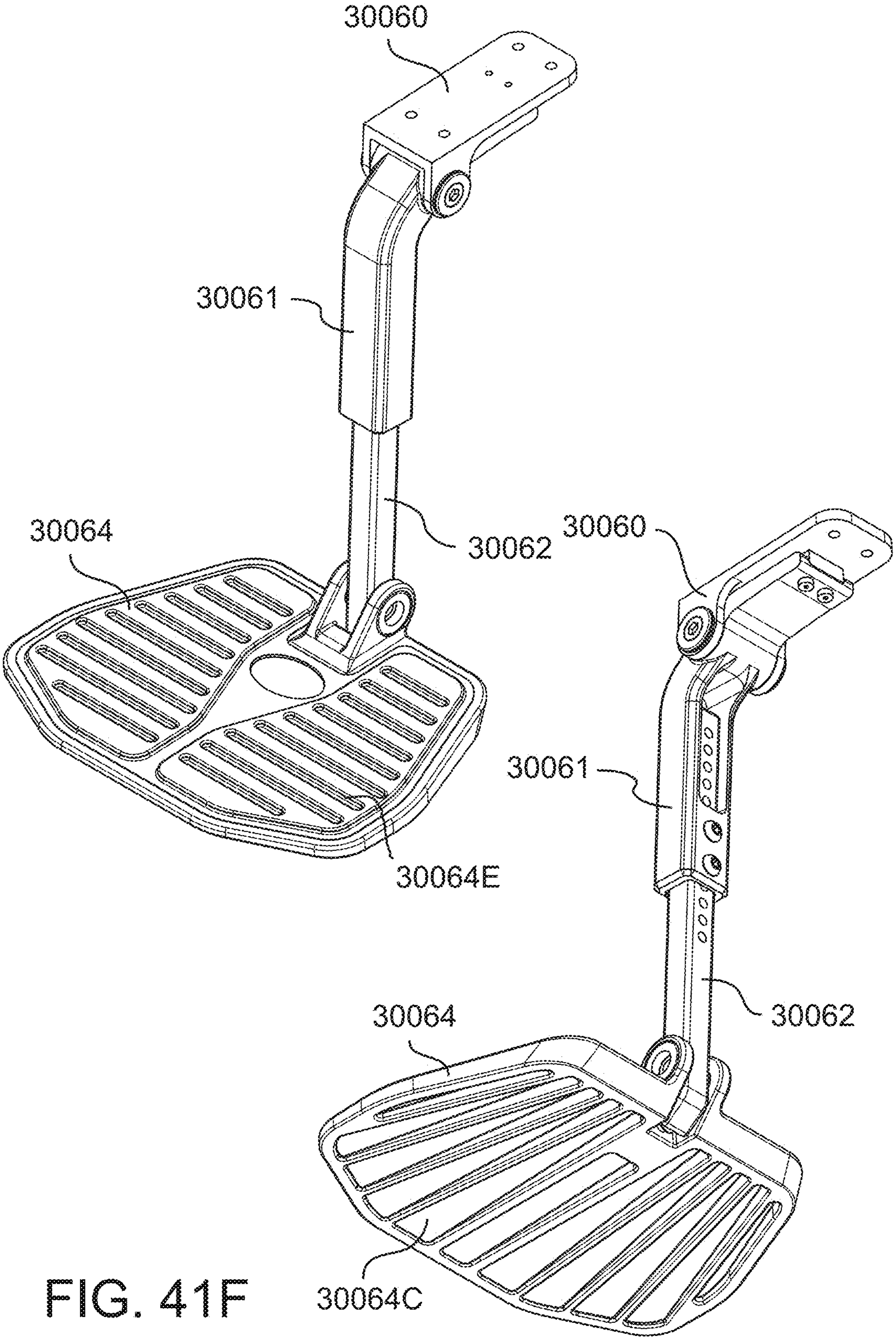
Figure 41G:
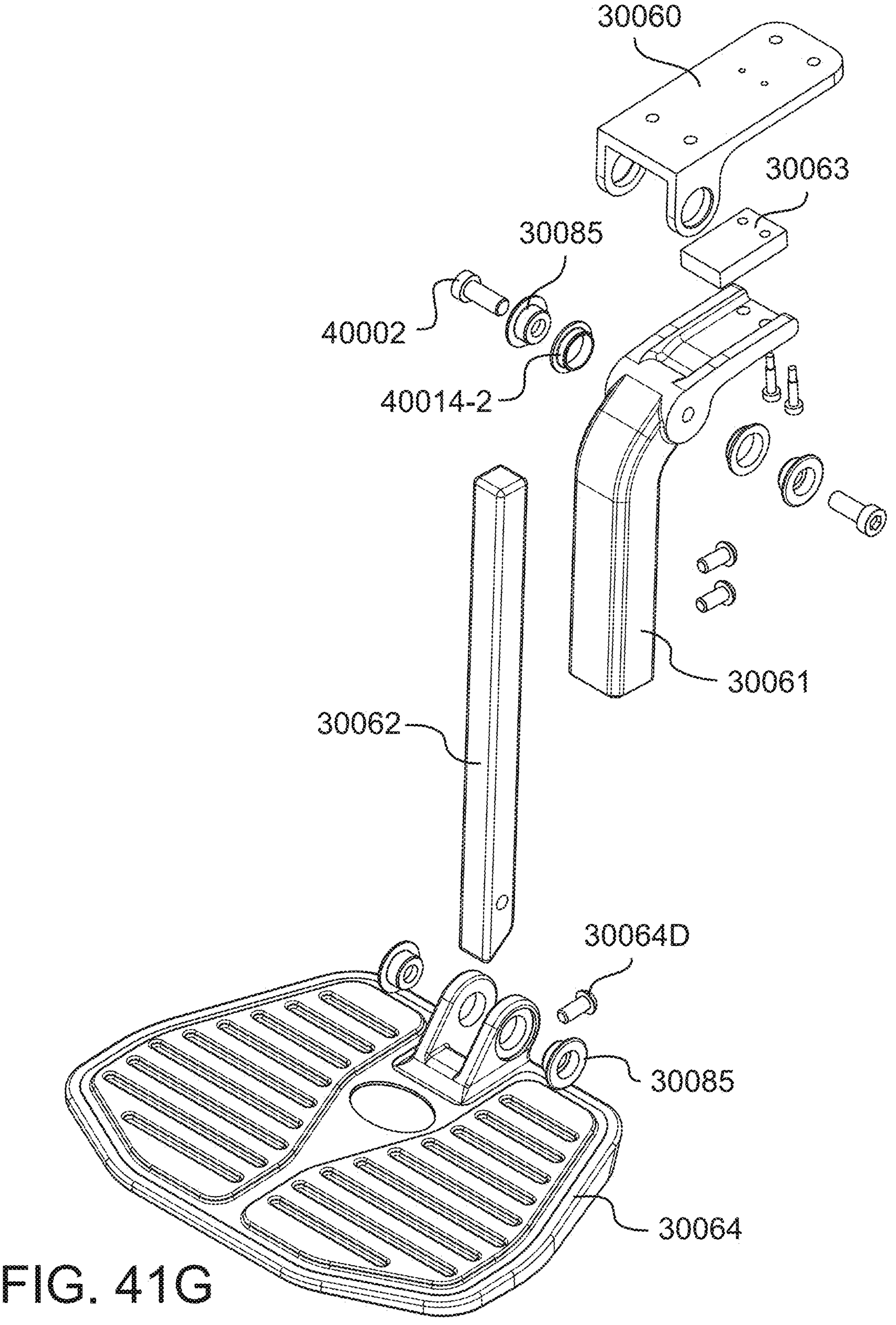
Figure 41H:
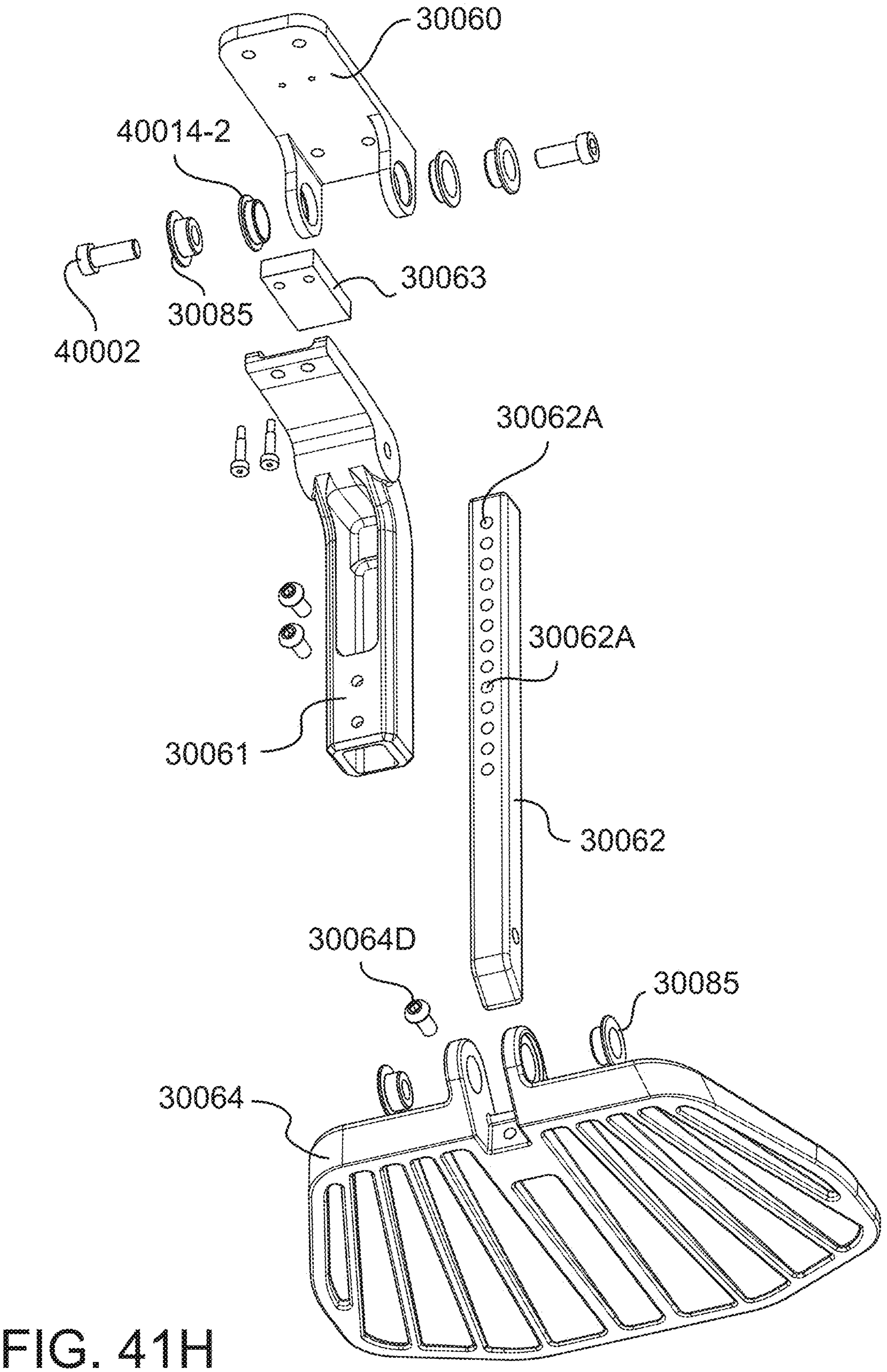
Figure 41I:
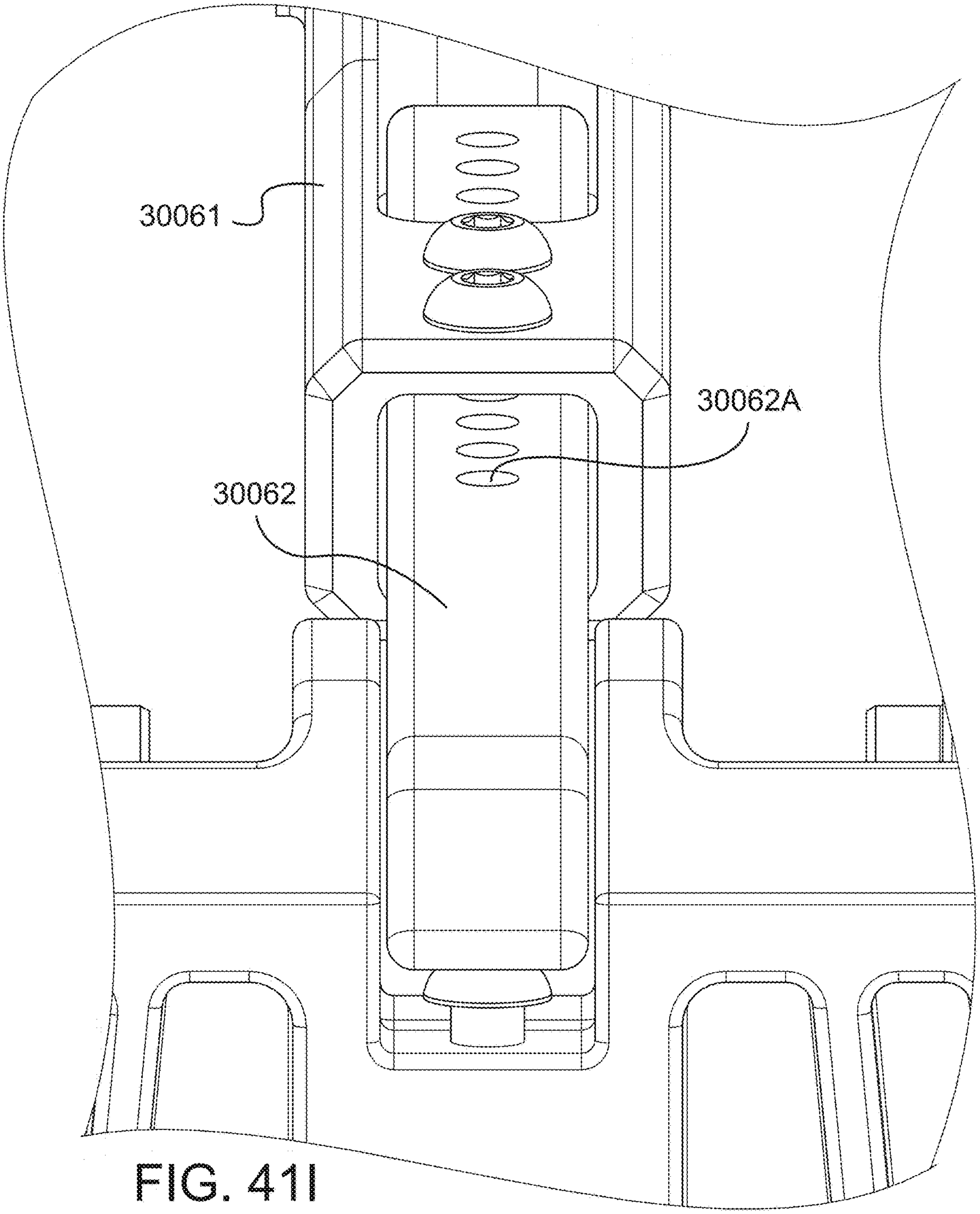
Figure 42A:
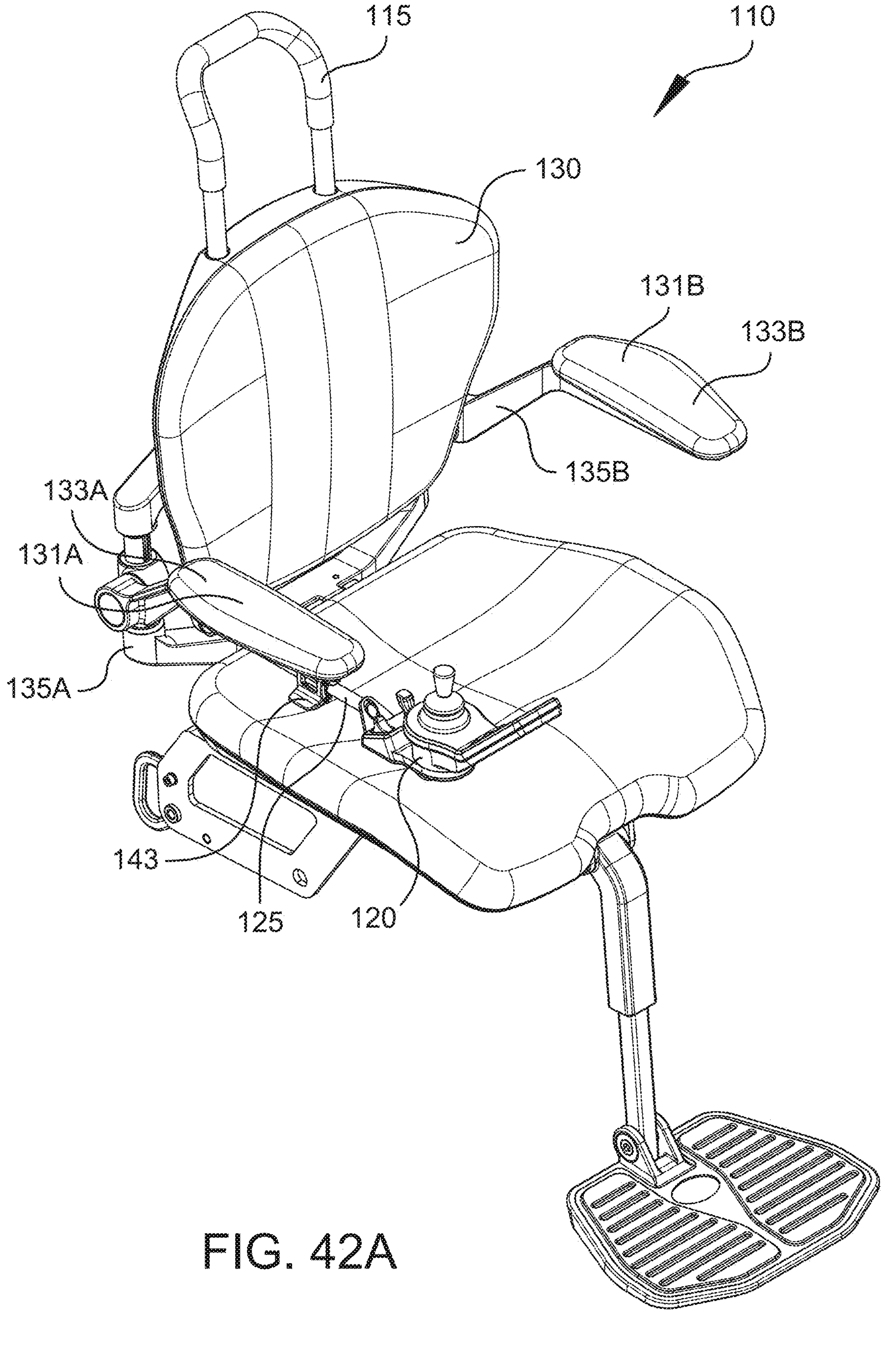
Figure 42B:
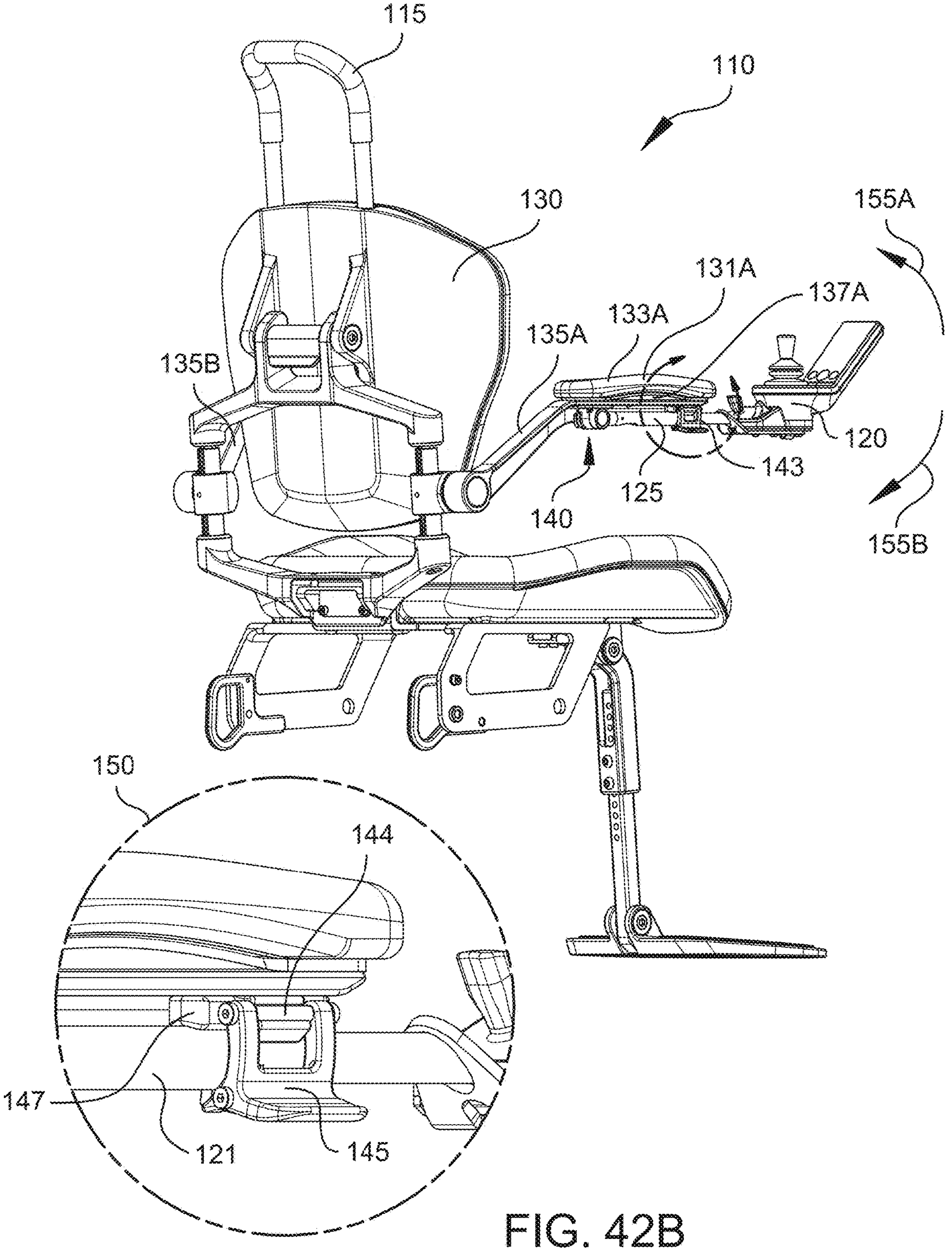
Figure 42C:
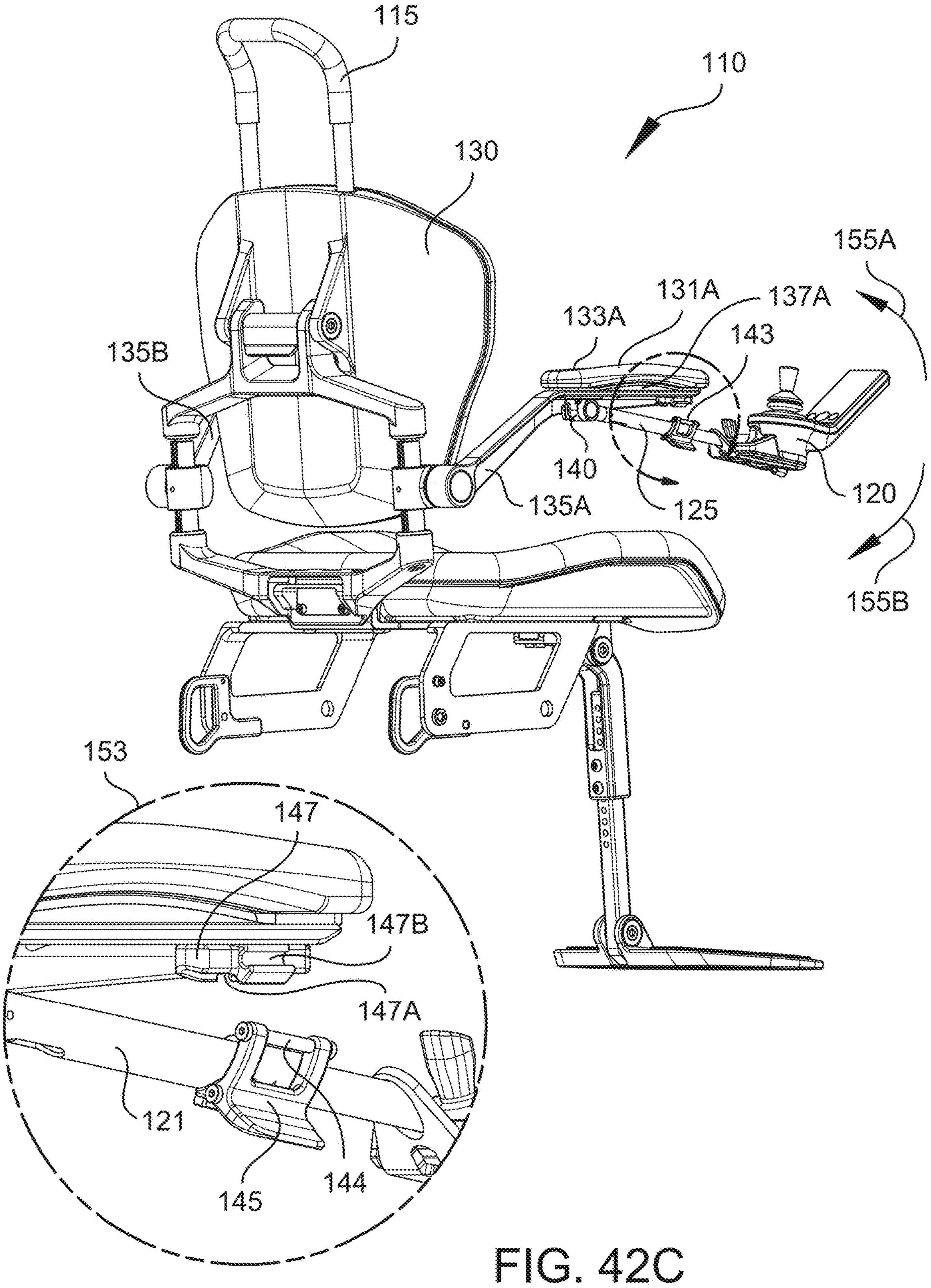
Figure 43A:
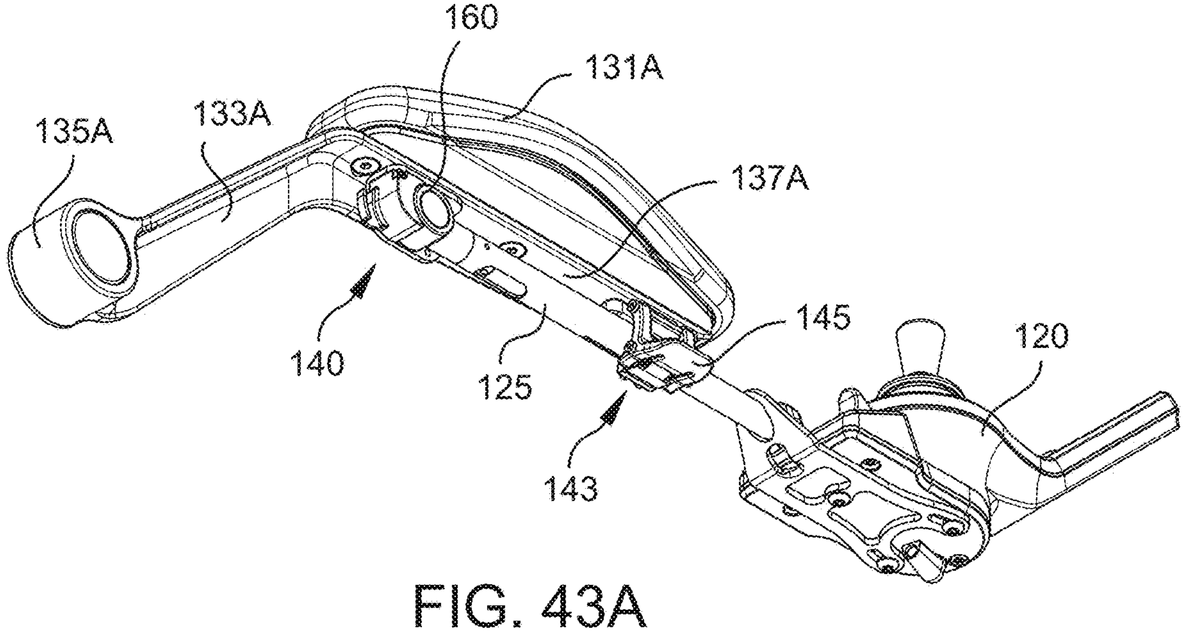
Figure 43B:
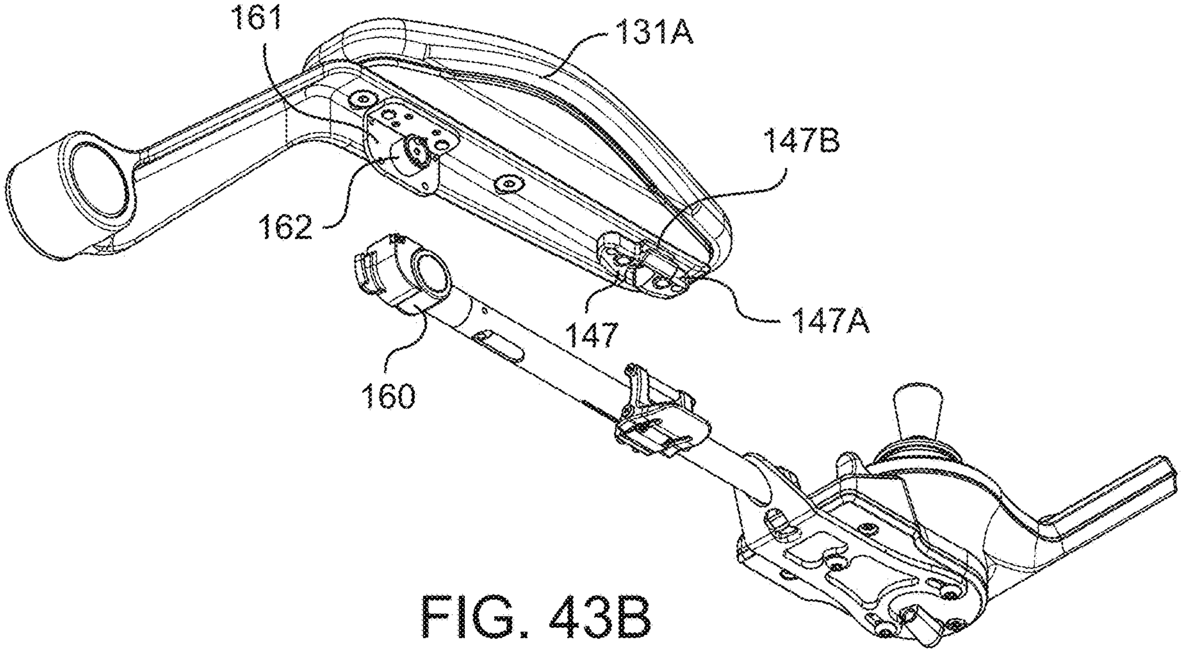
Figure 45A:
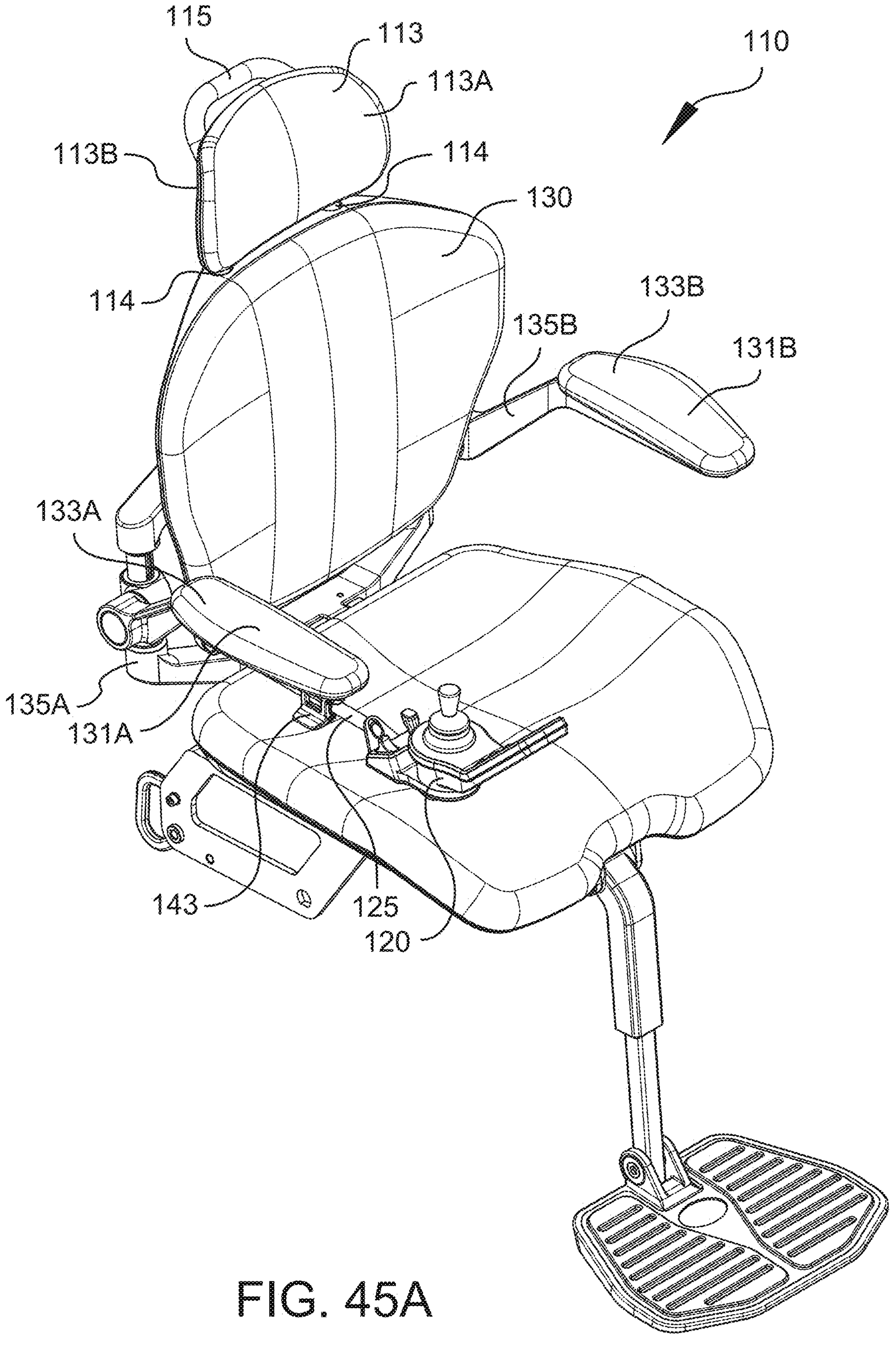
Figure 45B:
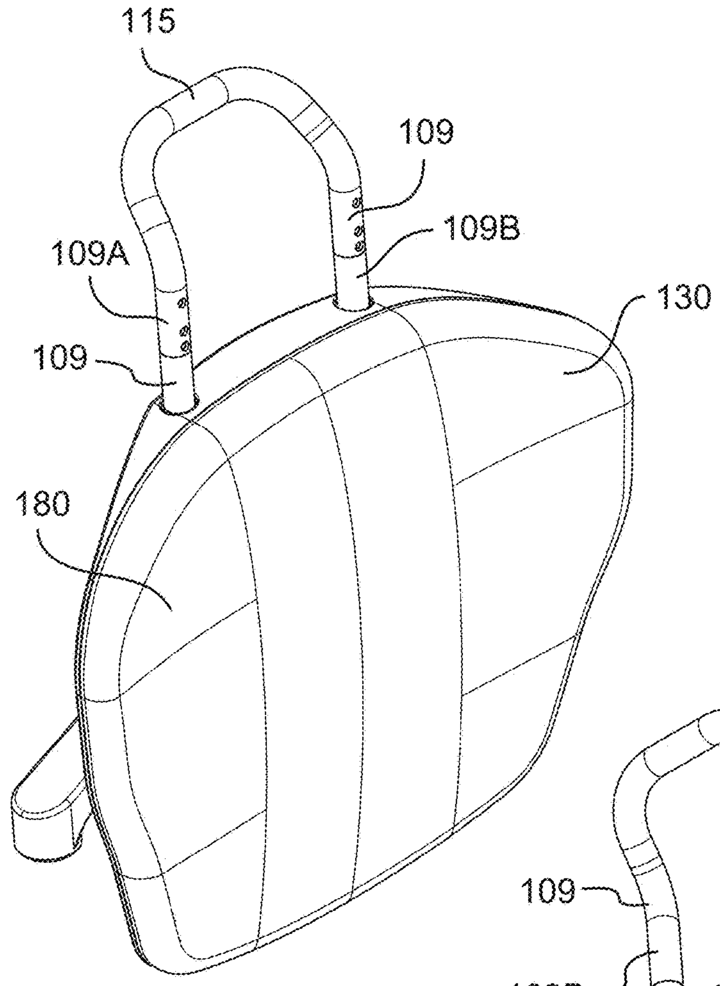
Figure 45C:
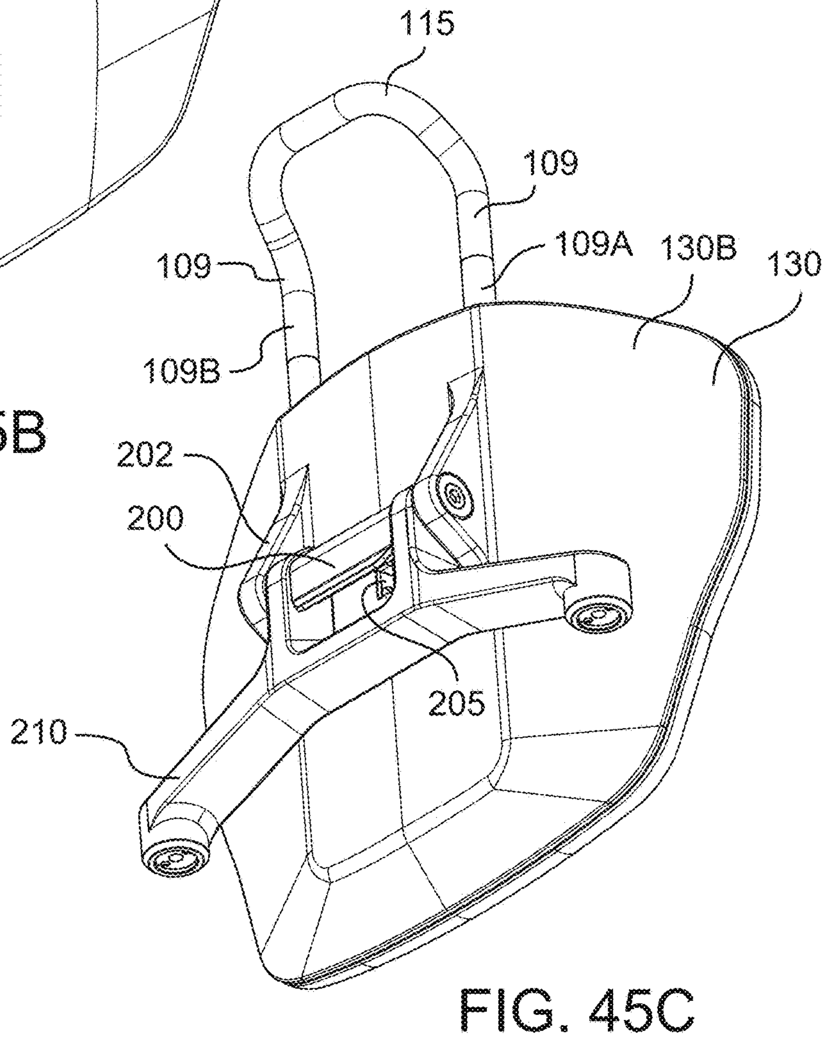

FIG. 34A is a schematic perspective diagram of the first configuration of the seat assembly of the present teachings;

FIG. 34B is a schematic perspective diagram of the attachment bracket, seat back, and attendant handle of the first configuration of the seat assembly of the present teachings;

FIG. 34C is a schematic perspective front view diagram of the second configuration of the seat assembly of the present teachings;

FIG. 34D is a schematic perspective exploded diagram of the second configuration of the armrest and user controller of the present teachings;

FIG. 34E is a schematic perspective exploded diagram of the second configuration of the seat assembly and user controller of the present teachings;

FIG. 34F is a schematic perspective rear view diagram of the second configuration of the seat assembly of the present teachings;

FIG. 34G is a schematic perspective undercarriage view diagram of the second configuration of the seat assembly of the present teachings;

FIGS. 34H-34I are schematic perspective diagrams of the second configuration of the seat assembly of the present teachings with a rotated armrest;

FIG. 35A is a schematic perspective exploded first view diagram of the connection features of the second configuration of the seat assembly of the present teachings;

FIG. 35B is a schematic perspective exploded second view diagram of the connection features of the second configuration of the seat assembly of the present teachings;

FIGS. 35C-35E are cross section diagrams of the second configuration of the armrest mount bracket operably coupled with the armrest and vertical back frame cane of the present teachings;

FIG. 35F is a schematic perspective diagram of the second configuration armrest of the present teachings;

FIG. 35G is a schematic perspective exploded diagram of the second configuration armrest of the present teachings;

FIG. 36A is a schematic perspective undercarriage diagram of the seat bracket, footrest, and rear bracket of the second configuration of the seat assembly of the present teachings;

FIG. 36B is a schematic perspective exploded diagram of the seat bracket, bracket fold hinge, and rear bracket of the second configuration of the seat assembly of the present teachings;

FIG. 37A is a schematic perspective diagram of the seatpan mounting bracket of the present teachings;

FIG. 37B is a schematic perspective detailed diagram of the seat bracket, bracket fold hinge, and rear bracket of the second configuration of the seat assembly of the present teachings;

FIG. 37C is a schematic perspective detailed exploded diagram of the seat bracket, bracket fold hinge, and rear bracket of the second configuration of the seat assembly of the present teachings;

FIG. 37D is a schematic perspective exploded diagram of the connecting bracket, rear bracket, and release handle of the second configuration of the seat assembly of the present teachings;

FIG. 37E is a cross section diagram of a first view of the release handle of the present teachings;

FIG. 37F is a cross section diagram of a second view of the release handle of the present teachings;

FIG. 37G is a schematic perspective diagram of the rear bracket of the second configuration of the seat assembly of the present teachings;

FIG. 37H is a schematic perspective detailed diagram of the seat shell, bracket fold hinge, and rear bracket of the second configuration of the seat assembly of the present teachings;

FIG. 37I is a schematic perspective diagram of the seat shell of the present teachings;

FIG. 37J is a schematic perspective exploded diagram of the seat shell of the present teachings;

FIG. 37K is a schematic perspective exploded first view diagram of the seat shell, seat cushion, rear bracket, and footrest of the second configuration of the seat assembly of the present teachings;

FIG. 37L is a schematic perspective exploded second view diagram of the seat shell, seat cushion, rear bracket, and footrest of the second configuration of the seat assembly of the present teachings;

FIG. 37M is a schematic perspective exploded third view diagram of the seat shell, seat cushion, rear bracket, and footrest of the second configuration of the seat assembly of the present teachings;

FIG. 37N is a schematic perspective diagram of the seat cushion of the present teachings;

FIG. 38 is a schematic perspective diagram of the attendant handle of the first configuration of the seat assembly of the present teachings;

FIG. 39A is a schematic perspective exploded diagram of the attendant handle, backrest shell, backrest cushion, brackets, and armrest of the first configuration of the seat assembly of the present teachings;

FIG. 39B is a schematic perspective diagram of the backrest shell of the present teachings;

FIG. 39C is a schematic perspective exploded diagram of the second configuration of the top back frame bracket, backrest shell, and backrest cushion of the seat assembly of the present teachings;

FIG. 39D is a schematic perspective exploded diagram of the second configuration of the backrest shell, backrest cushion, and armrests of the seat assembly of the present teachings;

FIG. 39E is a schematic perspective exploded diagram of the rear tube holder bracket, backrest cushion, armrests, and backrest shell of the seat assembly of the present teachings;

FIG. 39F is a schematic perspective exploded diagram of the cushion and backrest shell of the seat assembly of the present teachings;

FIG. 39G is a schematic perspective diagram of the first configuration of the top back frame bracket of the seat assembly of the present teachings;

FIG. 39H is a schematic perspective exploded first view diagram of the first configuration of the top back frame bracket of the seat assembly of the present teachings;

FIG. 391 is a schematic perspective exploded second view diagram of the first configuration of the top back frame bracket of the seat assembly of the present teachings;

FIG. 39J is a schematic perspective exploded first view diagram of the second configuration of the top back frame bracket of the seat assembly of the present teachings;

FIG. 39K is a schematic perspective exploded second view diagram of the second configuration of the top back frame bracket of the seat assembly of the present teachings;

FIG. 39L is a schematic perspective exploded diagram of the second configuration of the top back frame bracket and backrest shell of the seat assembly of the present teachings;

FIG. 40A is a schematic perspective diagram of the first configuration of the armrest mount bracket of the present teachings;

FIG. 40B is a schematic perspective detailed diagram of the first configuration of the armrest mount bracket, armrest, and vertical back frame cane of the present teachings;

FIG. 40C is a schematic perspective detailed first view diagram of the second configuration of the armrest mount bracket, armrest, and vertical back frame cane of the present teachings;

FIG. 40D is a schematic perspective detailed second view diagram of the second configuration of the armrest mount bracket, armrest, and vertical back frame cane of the present teachings;

FIGS. 40E-40G are various views of schematic perspective diagrams of the second configuration of the armrest mount bracket of the present teachings;

FIG. 40H is a cross section diagram of the second configuration of the armrest mount bracket of the present teachings;

FIG. 40I is a perspective diagram of the button slide of the present teachings;

FIG. 40J is a perspective diagram of the vertical back frame cane of the present teachings;

FIG. 40K is a perspective diagram of the vertical back frame cane operably coupled with the top back frame bracket and the rear tube holder bracket of the present teachings;

FIG. 40L is a cross section diagram of the female and male lock pins engaged with the vertical back frame cane of the present teachings;

FIGS. 41A-41B are cross section diagrams of the footrest assembly operably coupled with the seat bracket of the present teachings;

FIG. 41C is a perspective diagram of the first configuration of the footrest assembly and seat cushion of the present teachings;

FIG. 41D is a perspective diagram of the first configuration of the footrest assembly of the present teachings;

FIG. 41E is a perspective exploded diagram of the first configuration of the footrest assembly of the present teachings;

FIG. 41F is a perspective diagram of the second configuration of the footrest assembly of the present teachings;

FIGS. 41G-41H are perspective exploded diagrams of the second configuration of the footrest assembly of the present teachings;

FIG. 41I is a detailed diagram of the footrest mounting rods of the present teachings;

FIGS. 42A-42C are perspective diagrams of another configuration of the seat assembly of the present teachings including a user control mounting means;

FIGS. 43A-43B are perspective diagrams of the coupling assembly for the user control mounting means of FIGS. 42A-42C;

FIGS. 44A-44D are perspective diagrams of details of the user control mounting means of the present teachings;

FIGS. 45A-45C are perspective diagrams of the attendant handle and headrest of another configuration of the seat assembly of the present teachings;

FIGS. 46A-46D are perspective diagrams of the backrest of another configuration of the seat assembly of the present teachings; and FIGS. 47A-47D are perspective diagrams of the attendant handle attachment of another configuration of the seat assembly of the present teachings.

DETAILED DESCRIPTION

The mobility device (MD) of the present teachings can include a small, lightweight, powered vehicle which can provide the user the ability to navigate environments of daily living including the ability to maneuver in confined spaces and to climb curbs, stairs, and other obstacles. The MD can improve the quality of life for individuals who have mobility impairments by allowing for traversing aggressive and difficult terrain and by operating at elevated seat heights. The elevated seat heights can offer benefits in activities of daily living (e.g., accessing higher shelves) and interaction with other people at "eye level"—while either stationary or moving.

Figure 1A:
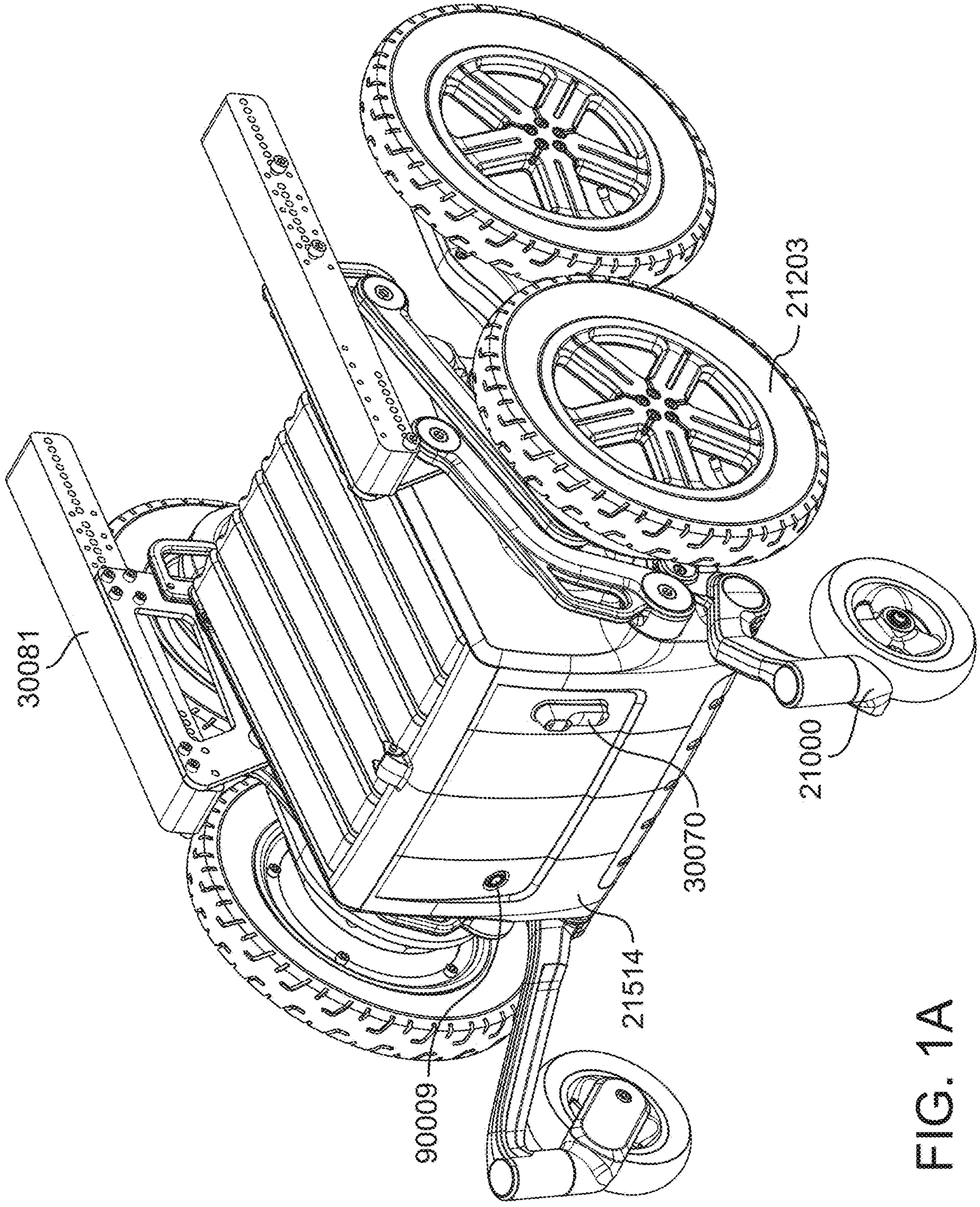
FIG. 1A is a perspective schematic diagram of a front views the mobility device base of the present teachings.
Figure 1B:
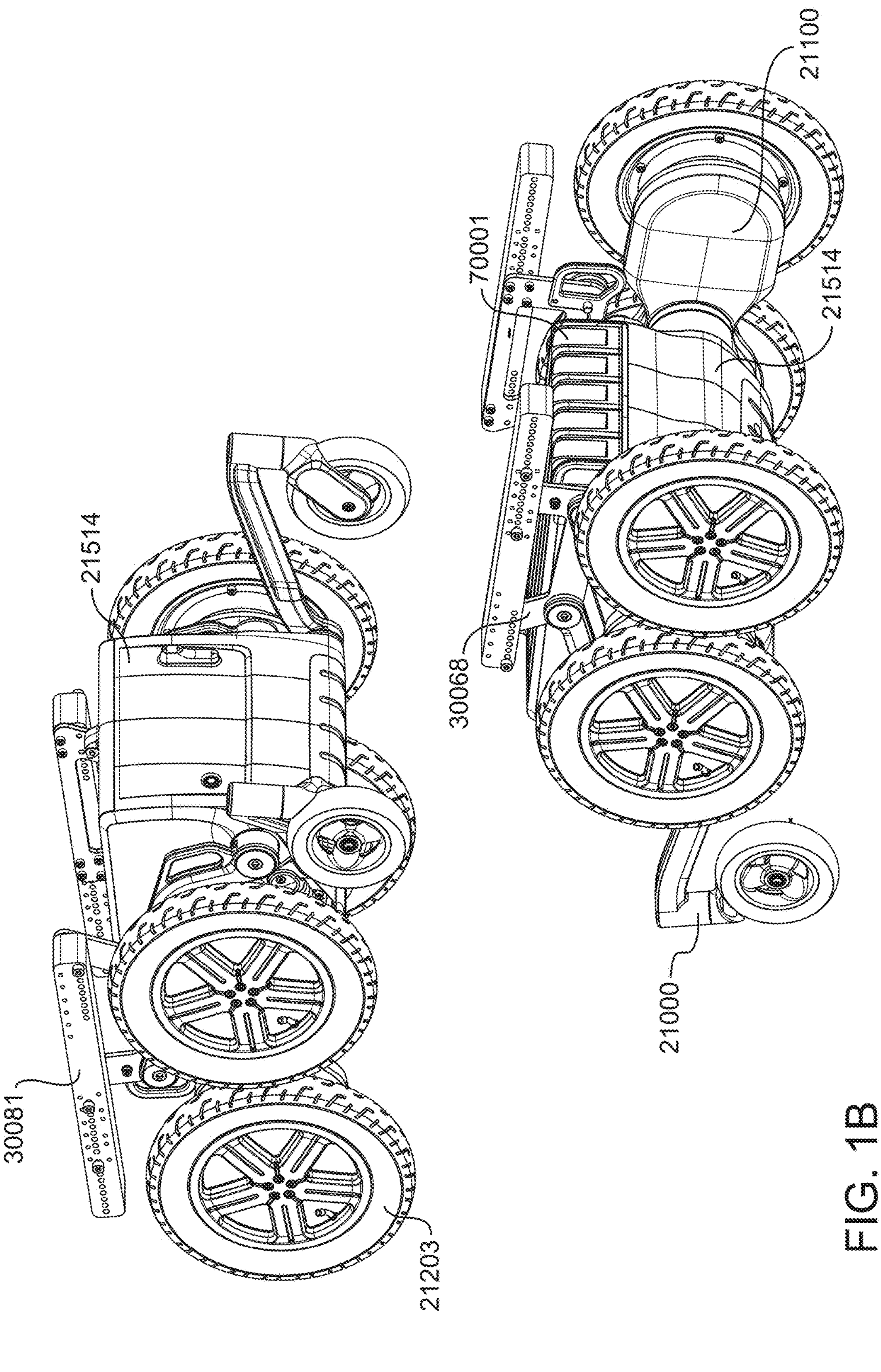
FIG. 1B is a perspective schematic diagram of side views the wheelchair base of the present teachings.
Figure 6A:
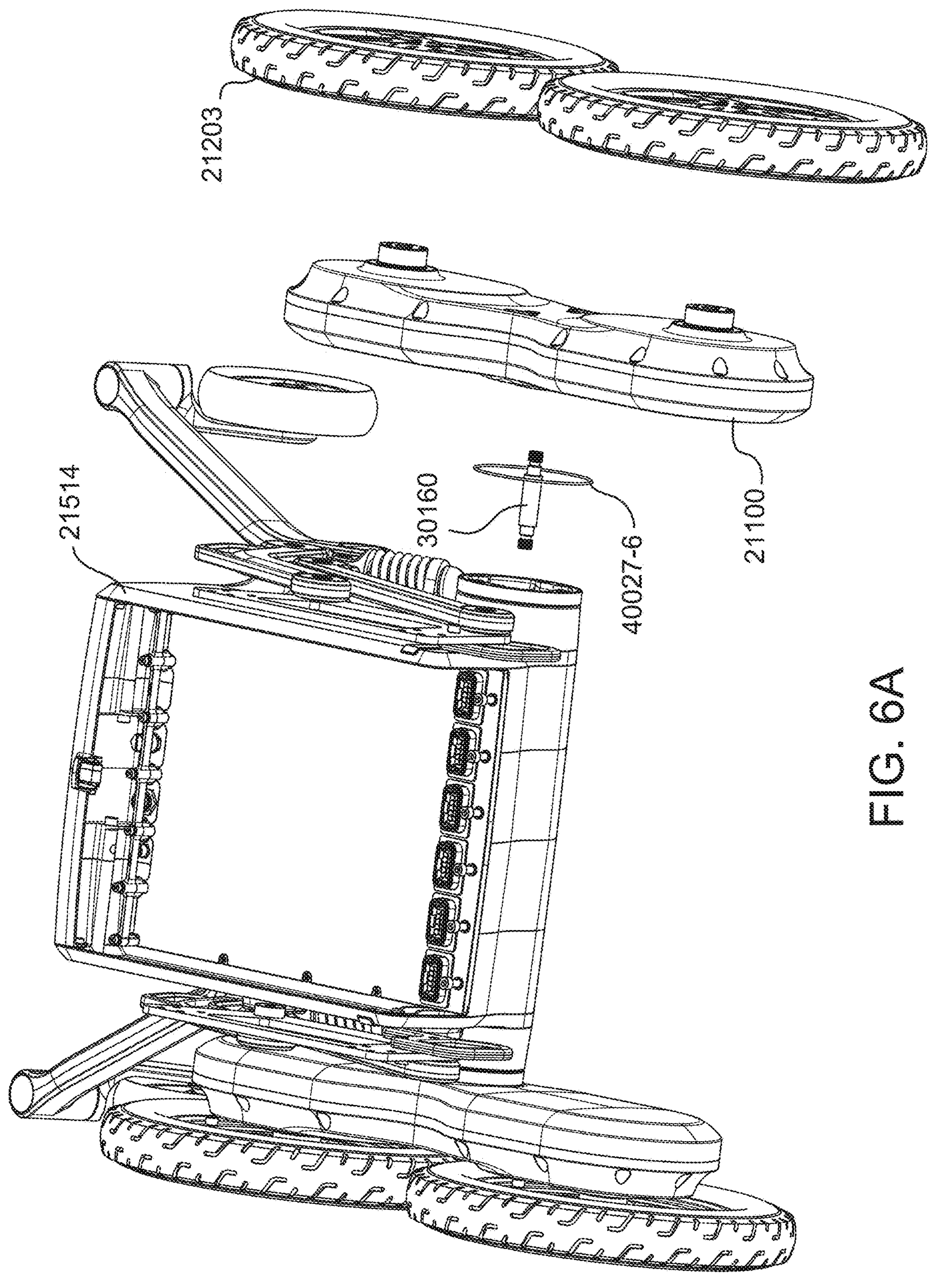
FIG. 6A is a perspective diagram of the cluster assembly of the present teachings.

Referring now primarily to FIGS. 1A and 1B, the mobility device (MD) of the present teachings can include a powerbase assembly that can include central gearbox 21514, power mechanisms, and wheel cluster assembly 21100/21201 (FIG. 6A). Central gearbox 21514 can control the rotation of assembly 21100/21201 (FIG. 6A), can limit backlash, and can provide structural integrity to the MD. In some configurations, central gearbox 21514 can be constructed of highly durable materials that can be lightweight, thereby increasing the possible payload that the MD can accommodate, and improving the operational range of the MD. Central gearbox 21514 can include the drive transmissions for the cluster drive and seat height transmissions, and can provide structural mounting interfaces for the electronics, two caster assemblies, two wheel cluster assemblies, two sets of seat height arms, and motors and brakes for two wheel drives. Other components and the seat can be attached to the powerbase assembly, for example, by use of rail 30081. Moving transmission parts can be contained internal to the powerbase assembly and sealed to protect from contamination. Central gearbox 21514 can include gear trains that can provide power to rotate the wheel clusters and drive the seat height actuator. The powerbase assembly can provide the structure and mounting points for the elements of the four-bar linkage, two drive arms (one on each side of central gearbox 21514), two stabilizer arms (one on each side of central gearbox 21514), and seat brackets 24001. The powerbase assembly can provide the electrical and mechanical power to the drive the wheels and clusters, and provide seat height actuation. Central gearbox 21514 can house the cluster transmission, the seat height actuator transmissions, and the electronics. Two wheel cluster assemblies 21100 (FIG. 6A) can be attached to central gearbox 21514. The seat support structure, casters, batteries, and optional docking bracket can also attach to central gearbox 21514. Central gearbox 21514 can be constructed to provide EM shielding to the parts housed within central gearbox 21514. Central gearbox 21514 can be constructed to block electromagnetic energy transmission, and can be sealed at its joints by a material that can provide EM shielding, such as, for example, but not limited to, NUSIL room temperature vulcanizing (RTV) silicone.

Continuing to refer to FIGS. 1A and 1B, the MD can accommodate seating through connection of a seating option to lifting and stabilizing arms. The MD can provide power, communication and structural interface for optional features, such as lights and seating control options such as, for example, but not limited to, power seating. Materials that can be used to construct the MD can include, but are not limited to including, aluminum, polyoxymethylene, magnesium, plywood, medium carbon steel, and stainless steel. Active stabilization of the MD can be accomplished by incorporating, into the MD, sensors that can detect the orientation and rate of change in orientation of the MD, motors that can produce high power and high-speed servo operation, and controllers that can assimilate information from the sensors and motors, and can compute appropriate motor commands to achieve active stability and implement the user's commands. The left and right wheel motors can drive the main wheels on the either side of the device. The front and back wheels can be coupled to drive together, so the two left wheels can drive together and the two right wheels can drive together. Turning can be accomplished by driving the left and right motors at different rates. The cluster motor can rotate the wheel base in the fore/aft direction. This can allow the MD to remain level while the front wheels become higher or lower than the rear wheels. The cluster motor can be used to keep the device level when climbing up and down curbs, and it can be used to rotate the wheel base repeatedly to climb up and down stairs. The seat can be automatically raised and lowered.

Figure 1C:
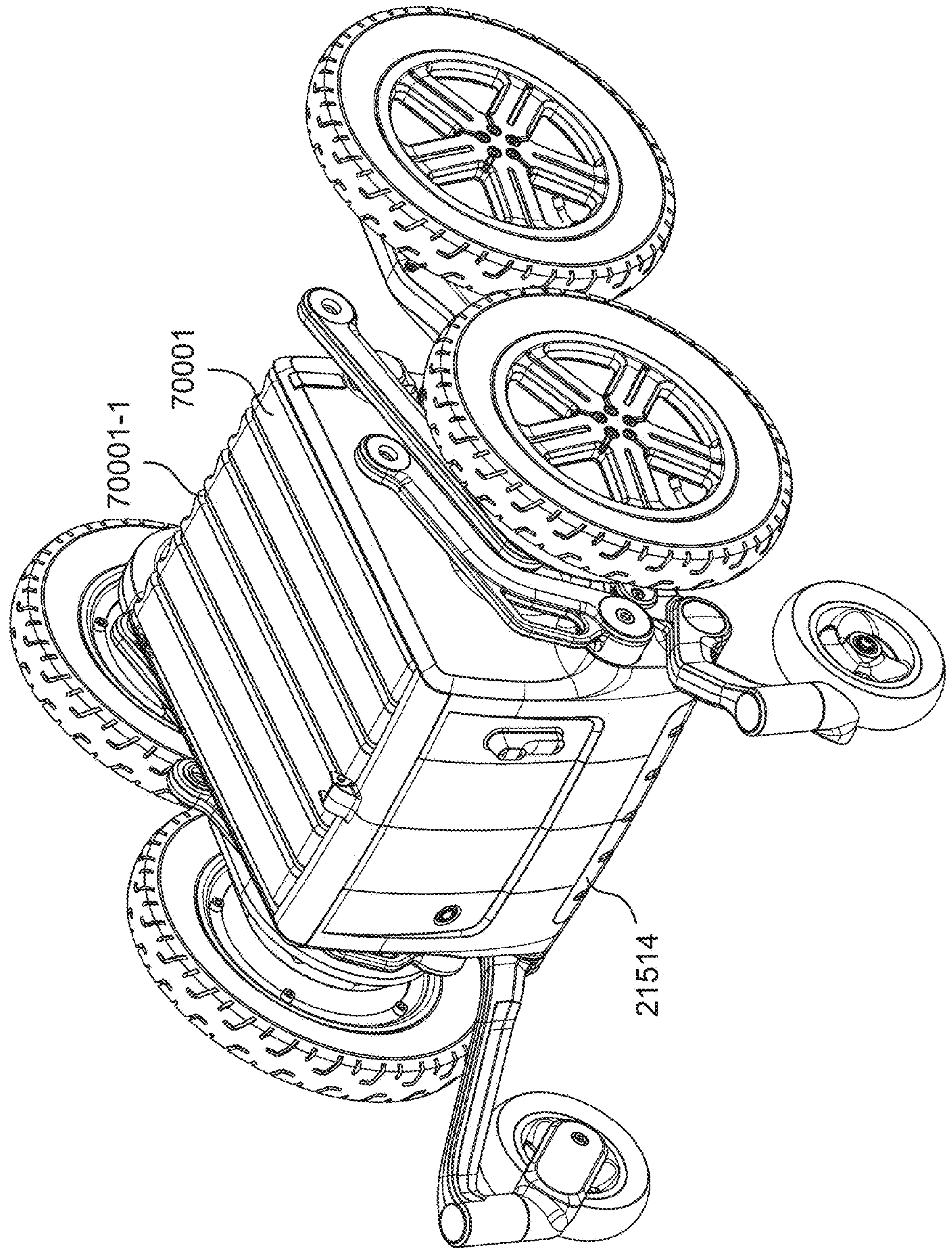
FIG. 1C is a perspective schematic diagram of the wheelchair base of the present teachings including batteries.
Figure 1D:
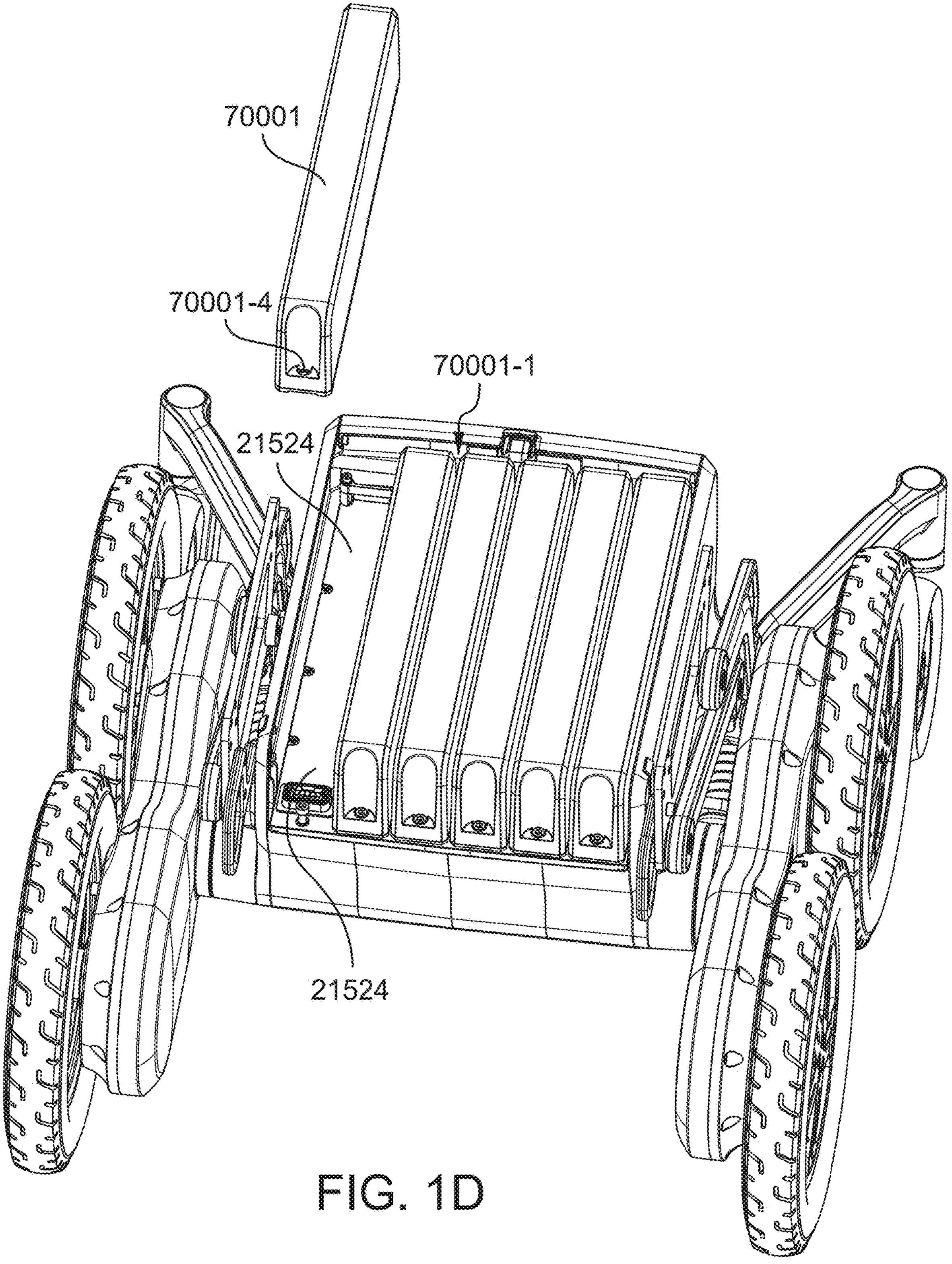
FIG. 1D is a perspective schematic diagram of the wheelchair base of the present teachings illustrating removable batteries.

Referring now to FIGS. 1C and 1D, battery packs 70001 can generate heat when charging and discharging. Positioning battery packs 70001 atop the central housing 21514, and including air gaps 70001-1 between battery packs 70001 can allow air flow that can assist with heat dissipation. Battery packs 70001 can operably couple with gearbox lid 21524 at fastener port 70001-4. The MD can include multiple slots for batteries 70001 (FIG. 1E) to operably couple with connectors 21524-1 (FIG. 1F). When four of batteries 70001 (FIG. 1E) are used, there can be two of connectors 21524-1 (FIG. 1F) that are free. In cold weather, during recharging of batteries 70001 (FIG. 1E), either while the MD is operating or while the MD is idle and being recharged, to protect against overcharge of batteries 70001 (FIG. 1E) below a certain pre-selected temperature or range of temperatures, the charge can be diverted to at least one shunt circuit that can be operably coupled with at least one connector 21524-1 (FIG. 1F). The shunt circuit can include at least one resistor, and optionally at least one fuse.

Figure 1E:
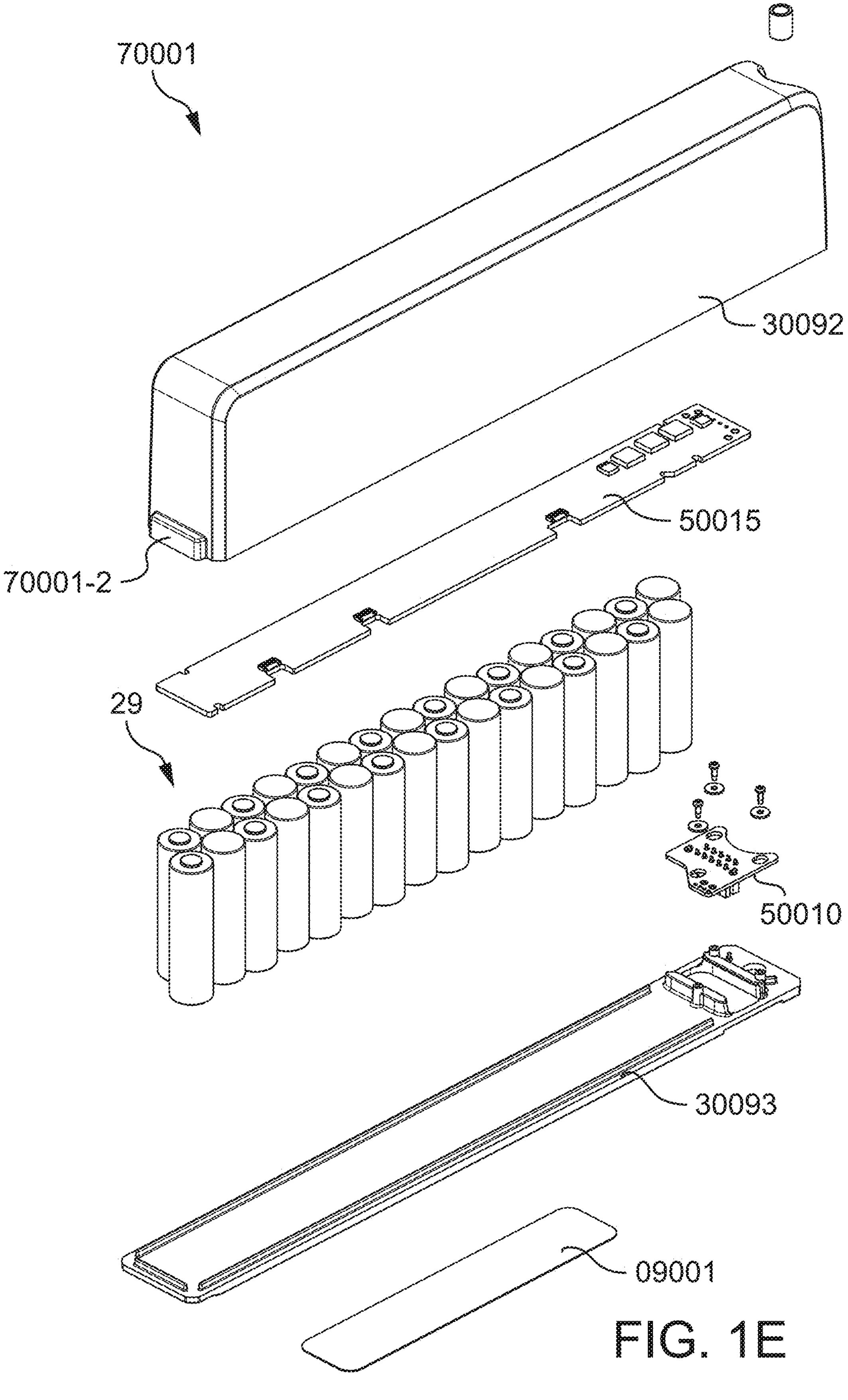
FIG. 1E is a perspective schematic diagram of an exploded side view of the battery pack of the present teachings.
Figure 1F:
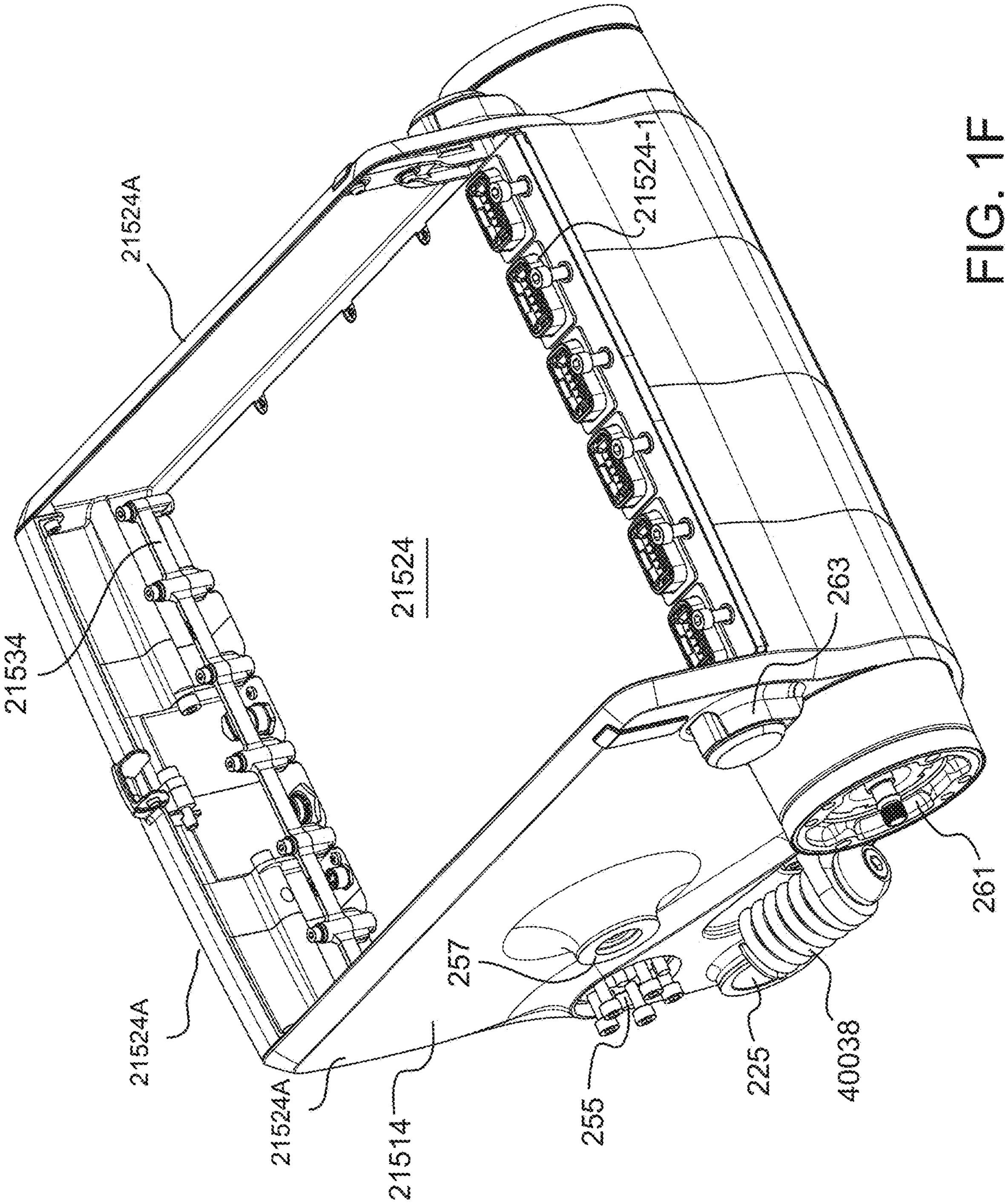
FIG. 1F is a perspective schematic diagram of the gearbox of the present teachings.

Referring now to FIG. 1E, batteries 70001 can serve as the main energy source for the MD. Multiple separate, identical batteries 70001 can provide a redundant energy supply to the device. Each battery 70001 can supply a separate power bus, from which other components can draw power. Each battery 70001 can provide power to sensors, controllers, and motors, through switching power converters. Batteries 70001 can also accept regeneration power from the motors. Batteries 70001 can be changeable and can be removable with or without tools. Each battery 70001 can connect to the MD via, for example, but not limited to, a blind-mate connector. During battery installation, the power terminals of the connector can mate before the battery signal terminals to prevent damage to the battery circuit. The connector can enable correct connection, and can discourage and/or prevent incorrect connection. Each battery 70001 can include relatively high energy density and relatively low weight cells 29, such as, for example, but not limited to, rechargeable lithium ion (Li-ION) cells, for example, but not limited to, cylindrical 18650 cells in a 16s2p arrangement, providing a nominal voltage of about 58 V and about 5 Ah capacity. Each battery can operate within the range about 50-100 V.

Continuing to refer to FIG. 1E, in some configurations, at least two batteries 70001 must be combined in parallel. These combined packs can form a battery bank. In some fail-operative configurations, there can be two independent battery banks ("Bank A' and'Bank B"). In some configurations, there can be an optional third battery in each battery bank. In some configurations, the load can be shared equally across all packs. In some configurations, up to six battery packs can be used on the system at one time. In some configurations, a minimum of four battery packs is needed for operation. An additional two batteries can be added for extended range. In some configurations, the energy storage level for these battery packs can be the same as standard computer batteries, enabling transport by commercial aircraft possible. Placement of empty of battery packs 70001 can protect the unused battery connection port on the MD and can provide a uniform and complete appearance for the MD. In some configurations, empty battery packs slots can be replaced with a storage compartment (not shown) that can store, for example, a battery charger or other items. The storage container can seal off the empty battery openings to the electronics to prevent environmental contamination of the central housing. The battery packs can be protected from damage by walls 21524A.

Figure 18A:
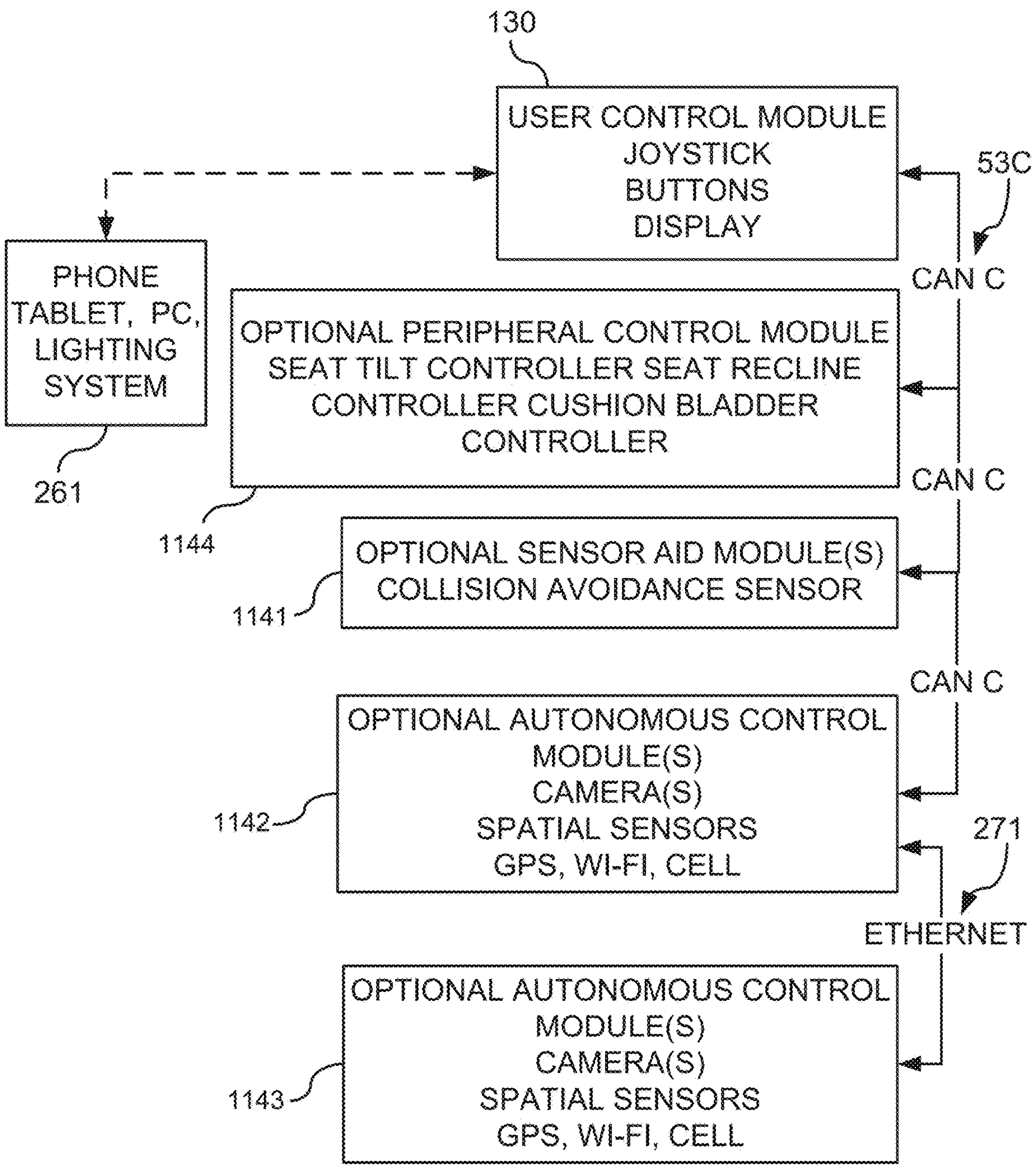

Continuing to refer to FIG. 1E, information from a fuel gauge such as, for example, but not limited to, TI bq34 z100-G1 wide range fuel gauge, can be provided to PSC board 50002 (FIG. 15G) over an 12C bus connection. Battery pack 70001 can communicate with PSC board 50002 (FIG. 15G) and therefore with power base (PB) controller (PBC) board 50001 (FIG. 15G). Battery packs 70001 can be mounted in pairs to maintain redundancy. One battery pack 70001 of the pair can be connected to processors A1/A2 43A/43B (FIG. 18C) and one can be connected to processors B1/B2 43C/43D (FIG. 18D). Therefore, if one of the pair of battery packs 70001 fails to function, the other of the pair can remain operational. Further, if both of battery packs 70001 in a pair fail to function, one or more other pairs of battery packs 70001 can remain operational.

Continuing to refer to FIG. 1E, a battery controller that can execute on processor 401 (FIG. 15J) can include, but is not limited to including, commands to initialize each battery, run each battery task if the battery is connected, average the results of the tasks from each battery, obtain the bus battery voltage that will be seen by processors A/B 39/41 (FIGS. 18C/18D), obtain the voltage from an ADC channel for the battery that is currently in use, obtain the battery voltage from fuel gauge data, compare the voltage from the fuel gauge data to the voltage from the ADC channel, obtain the number of connected batteries, connect batteries 70001 to a bus to power the MD, monitor the batteries, and check the battery temperature. The temperature thresholds that can be reported can include, but are not limited to including, cold, warm, and hot battery states. The battery controller can check the charge of batteries 70001, compare the charge to thresholds, and issue warning levels under low charge conditions. In some configurations, there can be four thresholds—low charge, low charge alert, low charge with restrictions, and minimum charge. The battery controller can check to make sure that batteries 70001 can be charged. In some configurations, batteries 70001 must be a least a certain voltage, for example, but not limited to, about 30 V, and must be communicating with PSC 50002 (FIG. 15G) in order to be charged. The battery controller can recover batteries 70001 by, for example, pre-charging batteries 70001 if, for example, batteries 70001 have been discharged to the point at which a battery protection circuit has been enabled. DC power for charging batteries 70001 can be supplied by an external AC/DC power supply. A user can be isolated from potential shock hazards by isolating the user from batteries 70001.

Figure 11A:
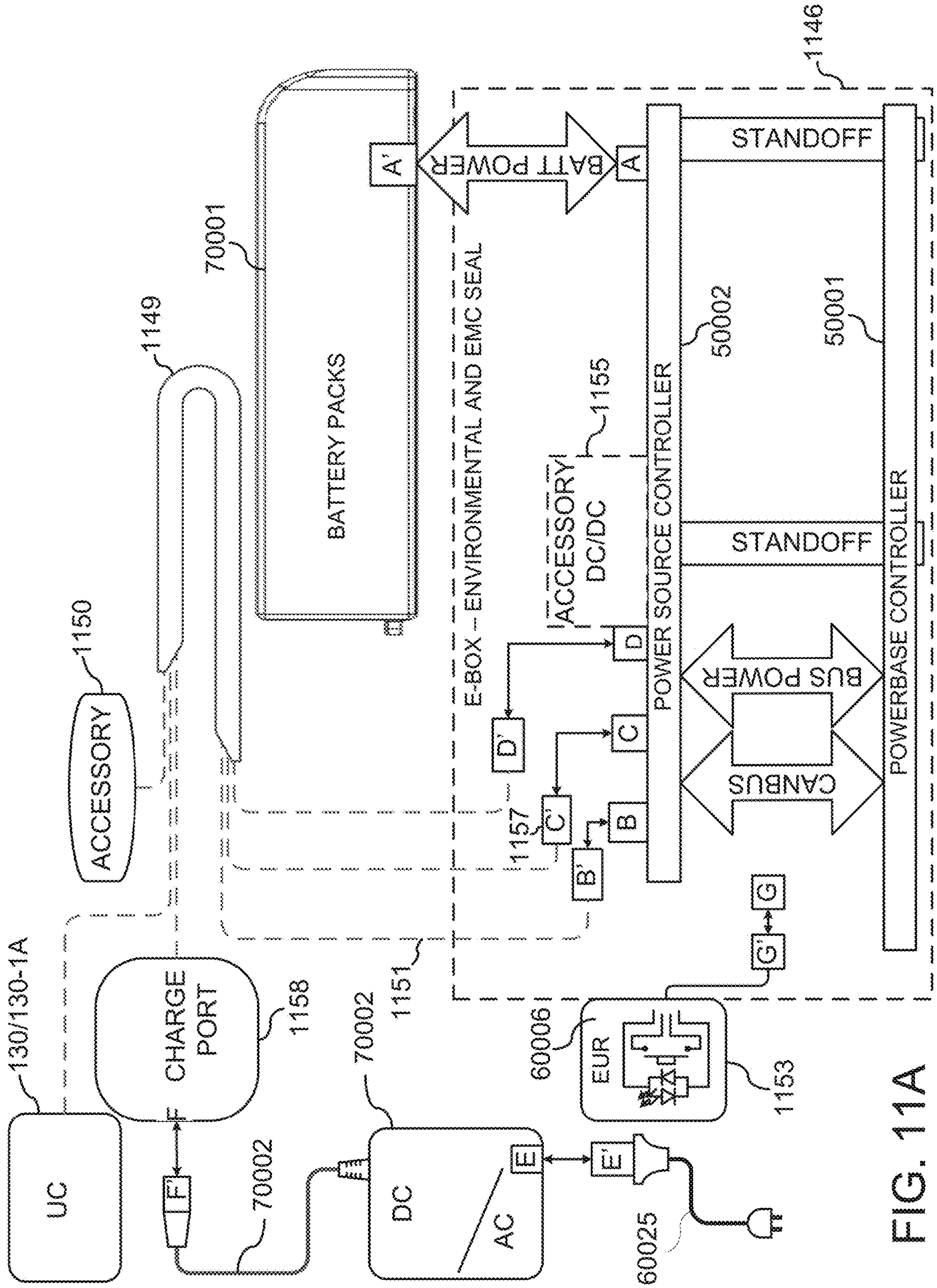

Referring now primarily to FIG. 1F, central gearbox 21514 can include e-box lid 21524 (FIG. 1G), brake lever 30070 (FIG. 1A), power off request switch 60006 (FIG. 1A), fastening port 257, lift arm control port 255, caster arm port 225, cluster port 261, and bumper housing 263. Power off request switch 60006 (FIG. 11E) can be mounted on the front of gearbox 21514 (FIG. 1A) and can be wired to PBC board 50001 (FIG. 11A). At least one battery pack 70001 (FIG. 1C) can be mounted upon e-box lid 21524. Cleats 21534 can enable positioning and securing of battery packs 70001 (FIG. 1C) at battery pack lip 70001-2 (FIG. 1E). Connector cavities 21524-1 can include a snout that can protrude from lid 21524. Connector cavities 21524-1 can include a gasket (not shown), for example, but not limited to, an elastomeric gasket, around the base of the snout. Battery connectors 50010 (FIG. 1E) can operably couple batteries 70001 (FIG. 1C) to the electronics of the MD though connector cavities 21524-1, and the pressure of batteries 70001 (FIG. 1C) enabled by fasteners mounted in fastening cavity 70001-4 (FIG. 1D) can seal against the gaskets in connector cavities 21524-1, protecting the gears and electronics of the MD from environmental contamination.

Figure 1G:
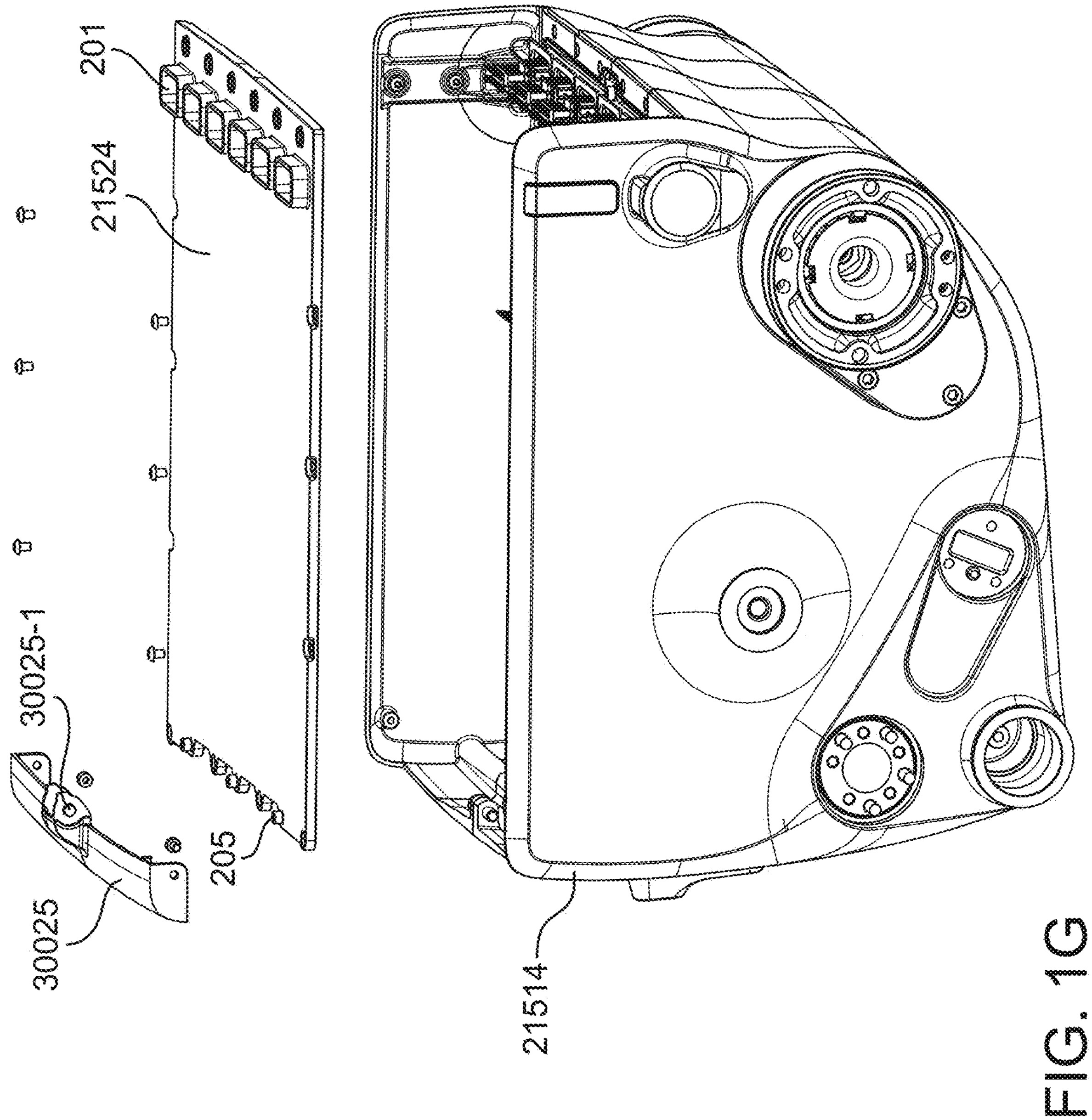
FIG. 1G is a perspective diagram of the e-box lid of the present teachings.
Figure 10A:
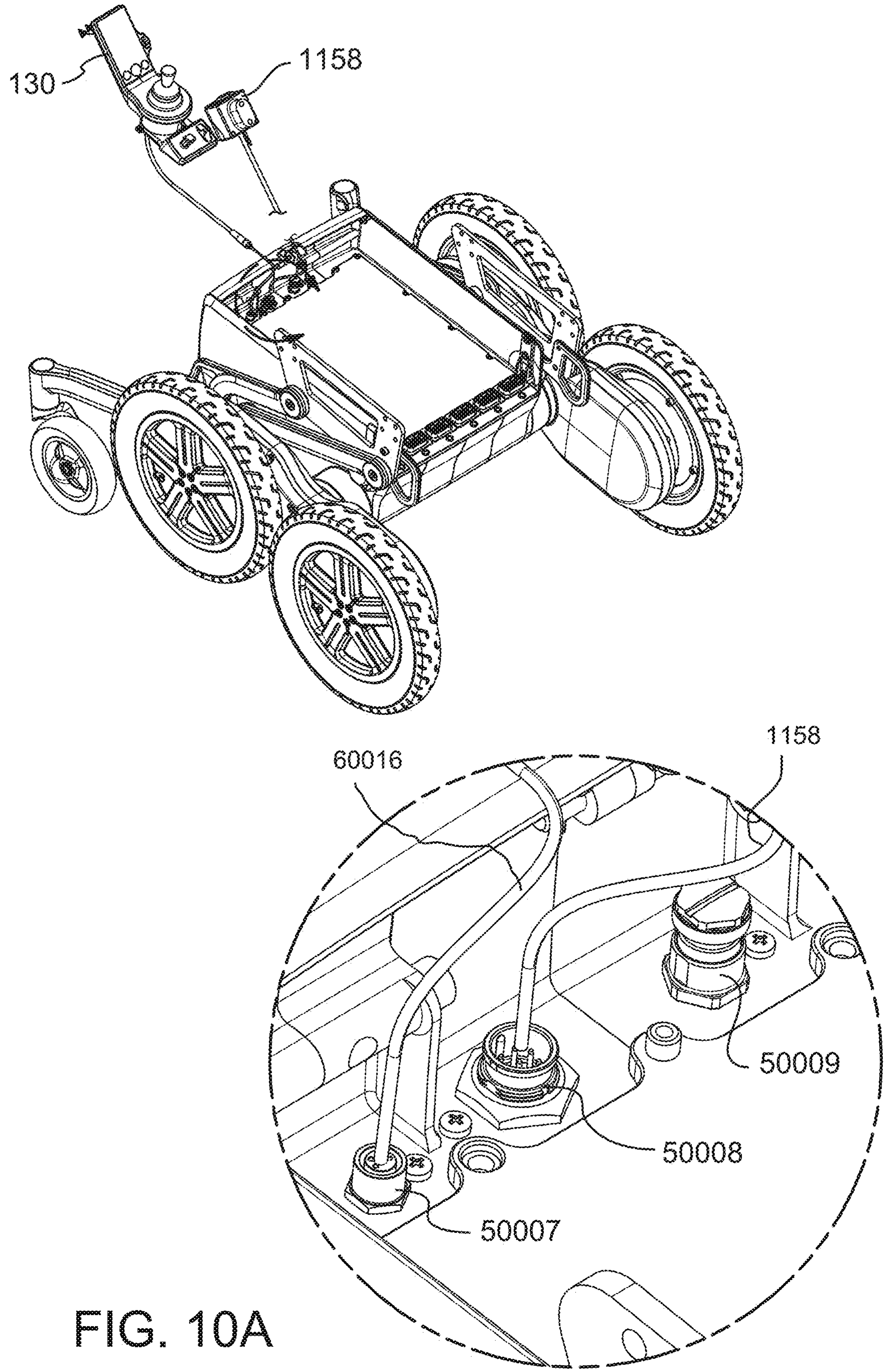
Figure 10B:
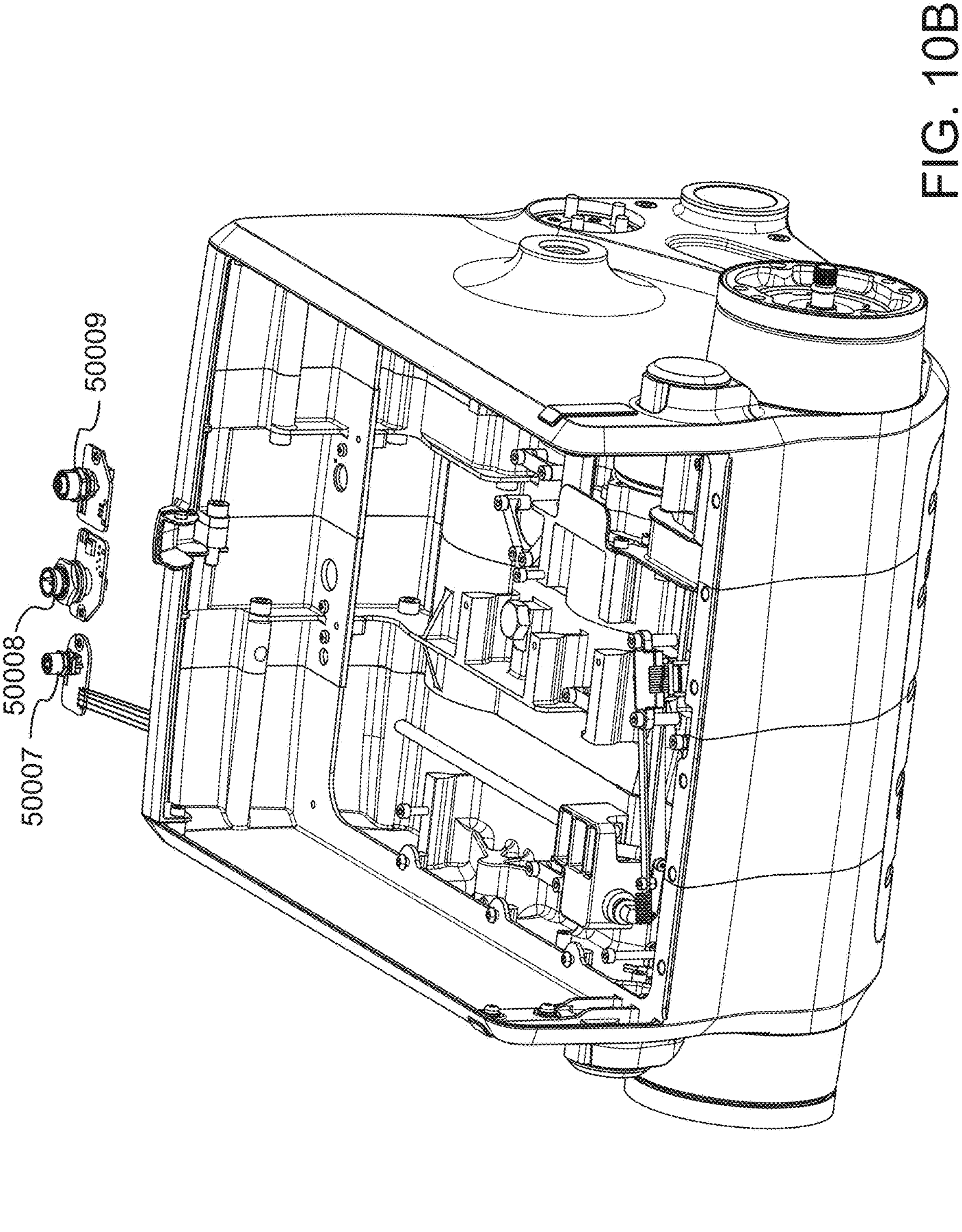
Figure 10C:
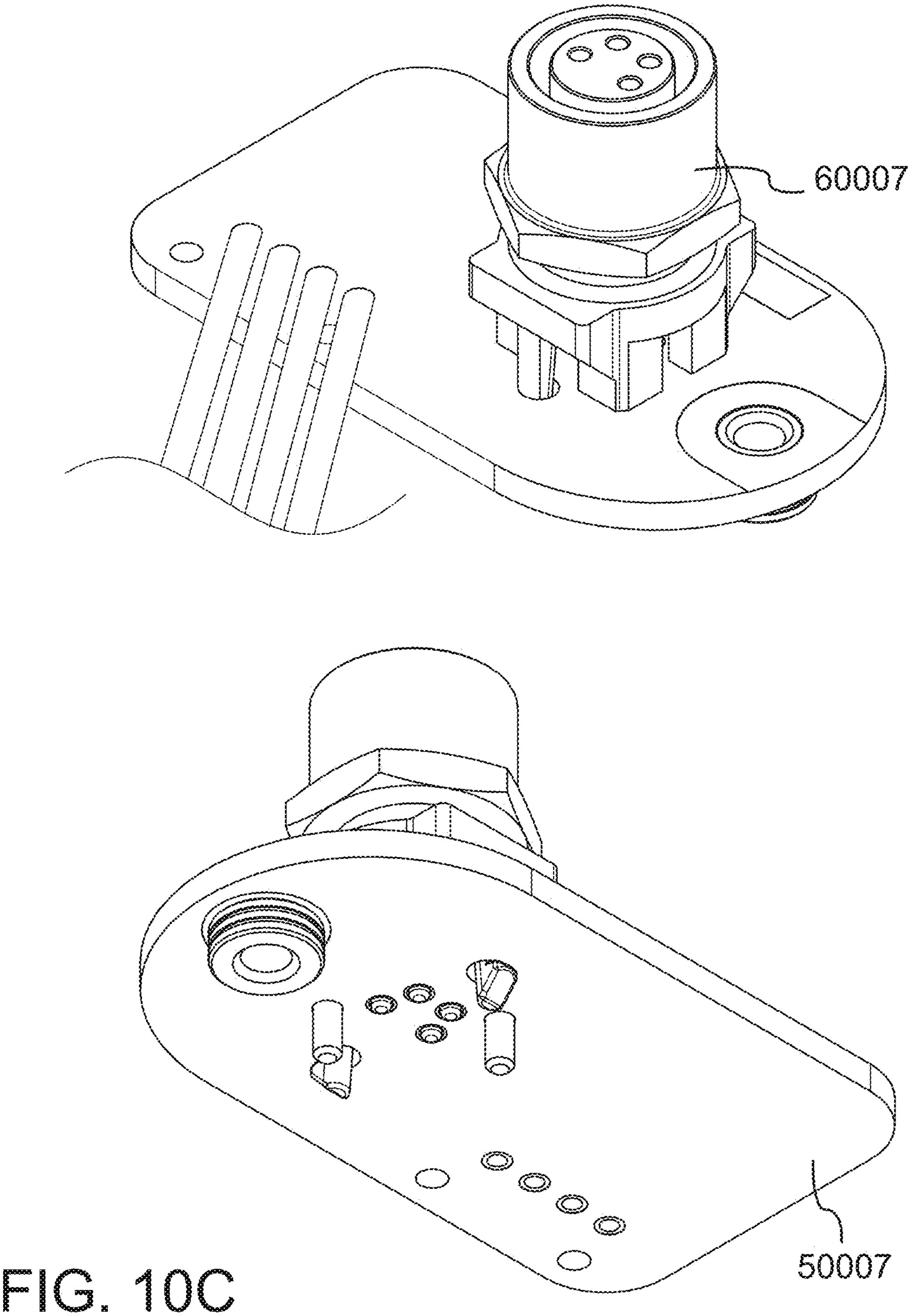
Figure 10D:
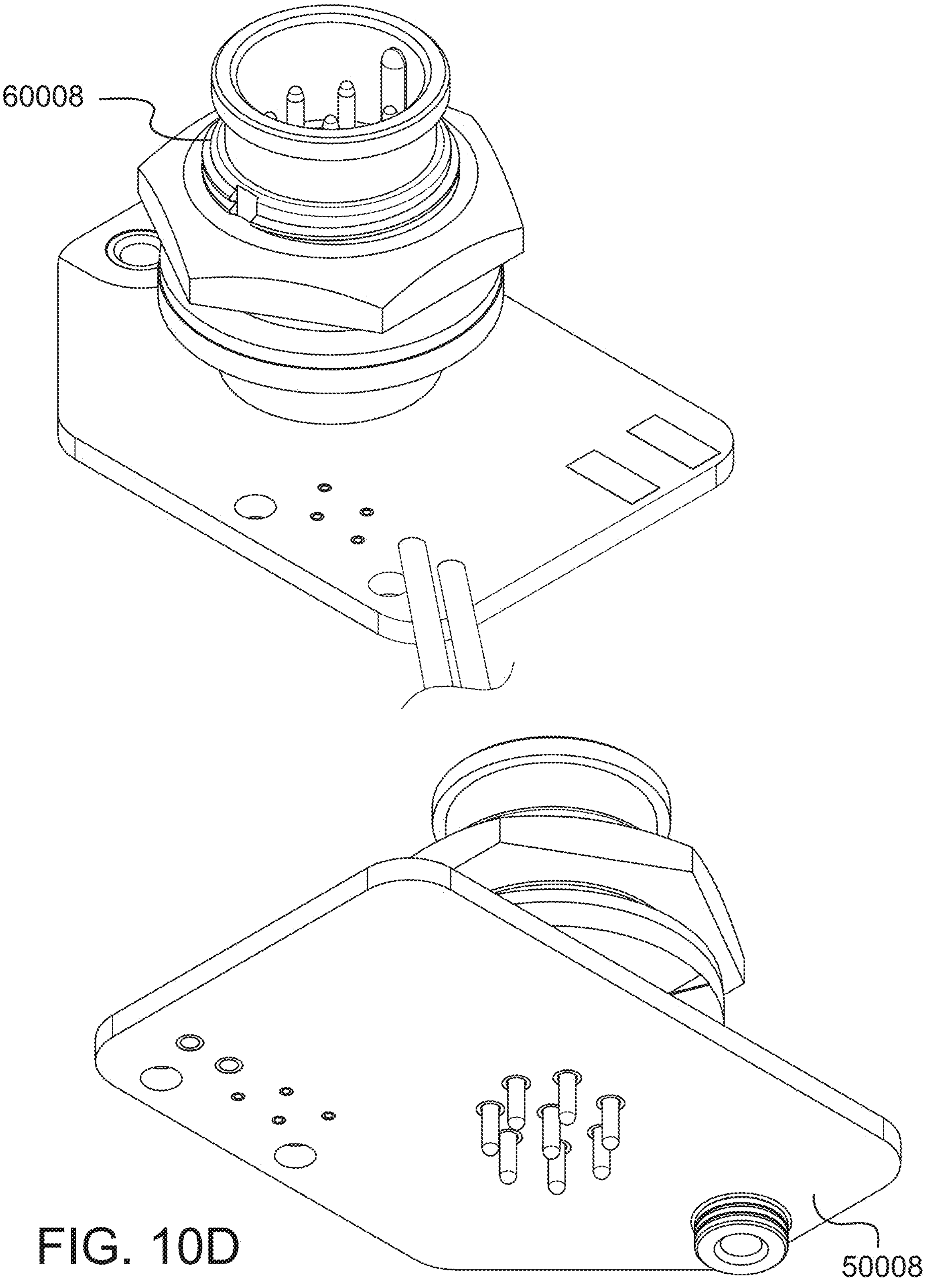
Figure 10E:
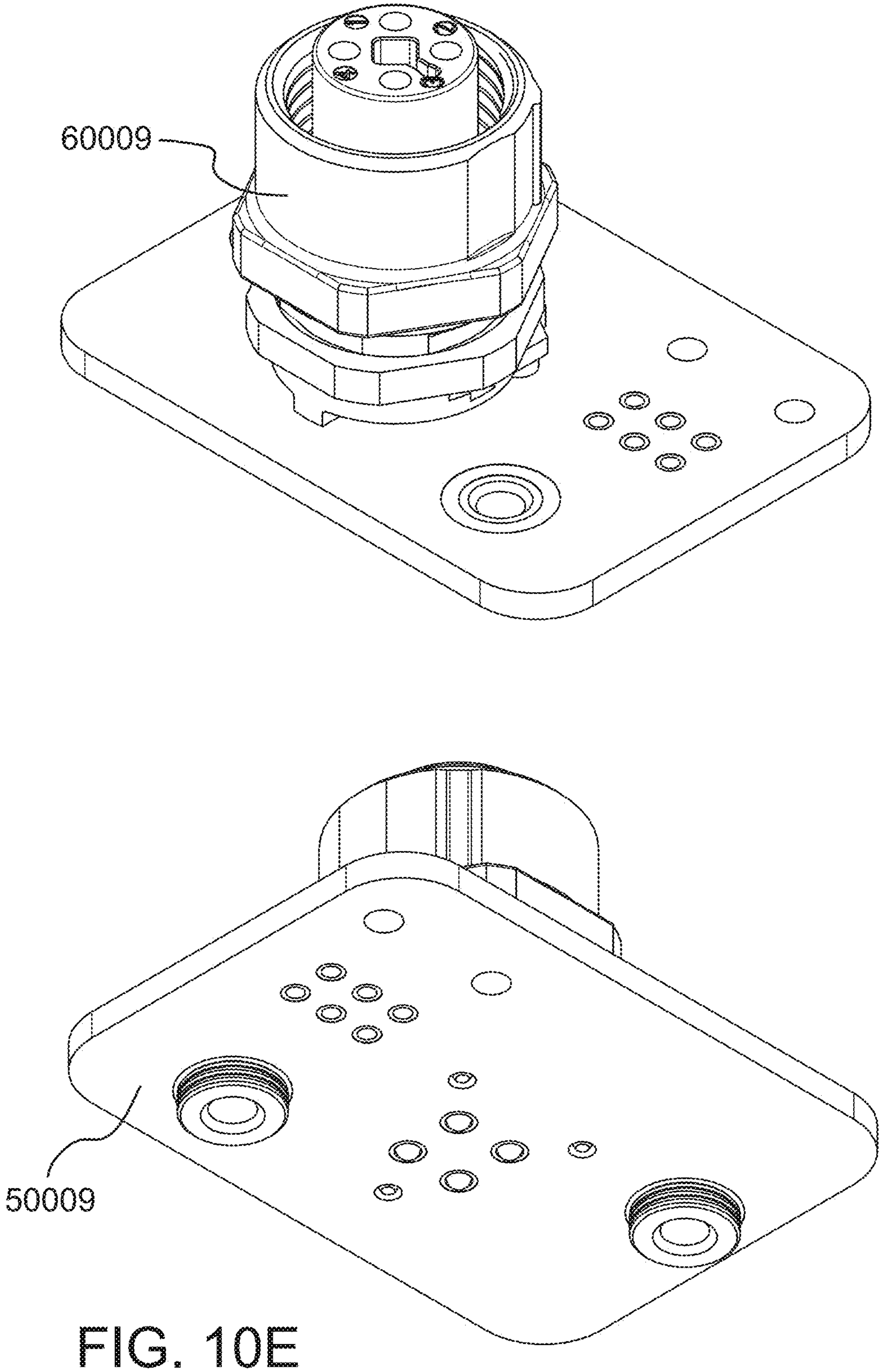

Referring now to FIG. 1G, an electronics enclosure can house the primary stabilization sensors and decision-making systems for the MD. The electronics enclosure can protect the contents from electro-magnetic interference while containing emissions. The electronics enclosure can inhibit foreign matter ingress while dissipating the excess heat generated within the enclosure. The enclosure can be sealed with a cover and environmental gaskets. Components within the enclosure that can generate significant amounts of heat can be physically connected to the enclosure frame via heat conductive materials. E-box lid 21524 can include battery connector openings 201, a form-in-place gasket (not shown), and mounting cleat attachment points 205 to accommodate mounting of battery packs 70001 (FIG. 1E) on e-box lid 21524. Battery connector openings 201 can include slim rectangles that can include planar gaskets. Batteries can compress against the planar gaskets during assembly, and these gaskets can form an environmental seal between the batteries and chassis of the MD. A form-in-place gasket (not shown) can seal the part of central gearbox 21514 that can include gears, motors, and electronics from intrusion of foreign substances including fluids. In some configurations, harnesses 60007 (FIG. 10C), 60008 (FIG. 10D), and 60009 (FIG. 10E) can connect to sealed, panel-mounted connectors to maintain environmental and EMC protection. Harnesses 60007 (FIG. 10C), 60008 (FIG. 10D), and 60009 (FIG. 10E) can be surrounded by glands and/or panel-mounted connectors that incorporate planar gaskets or o-rings that can be impervious to foreign substances.

Figure 1H:
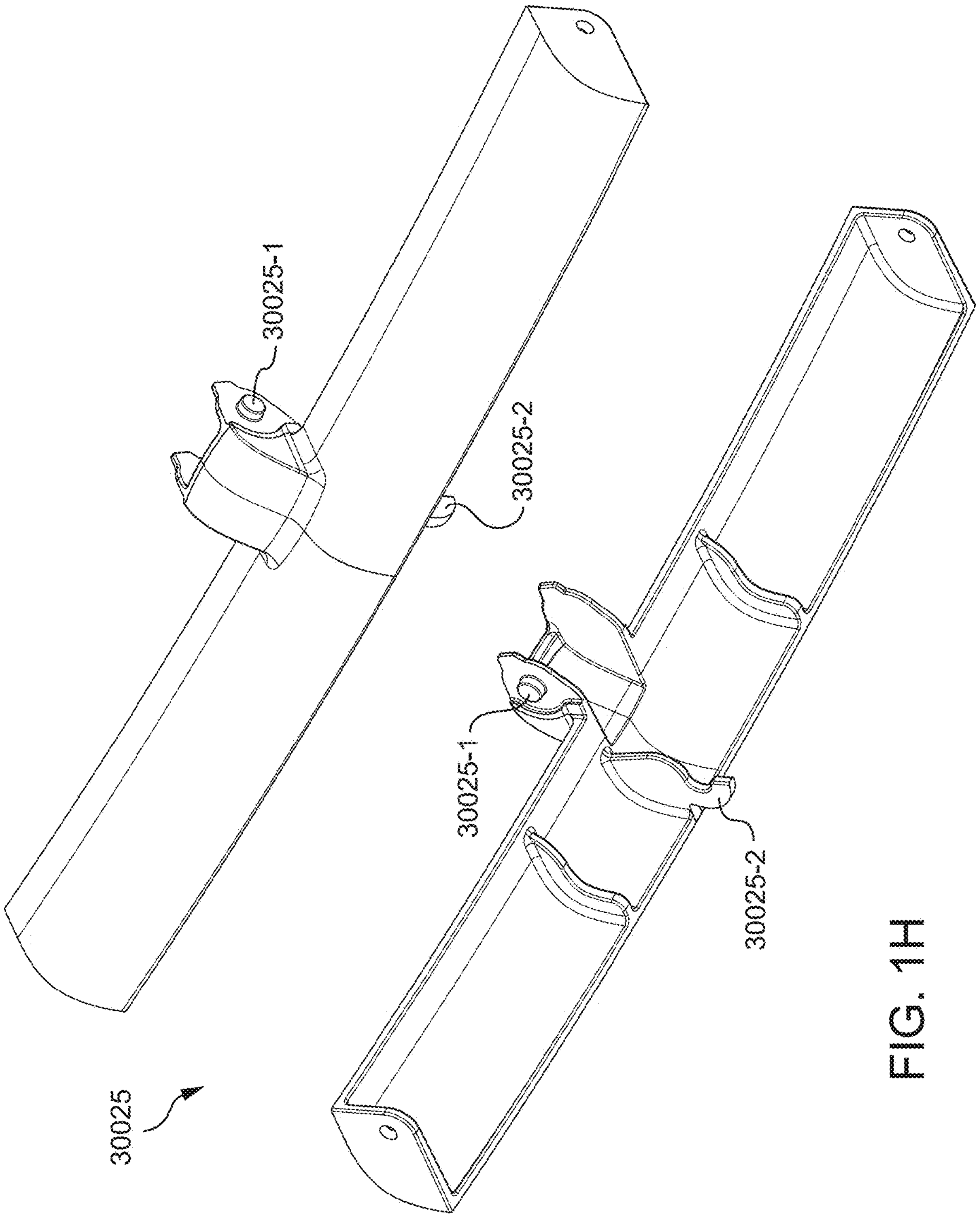
FIG. 1H is a perspective diagram of the top cap of the present teachings.
Figure 1I:
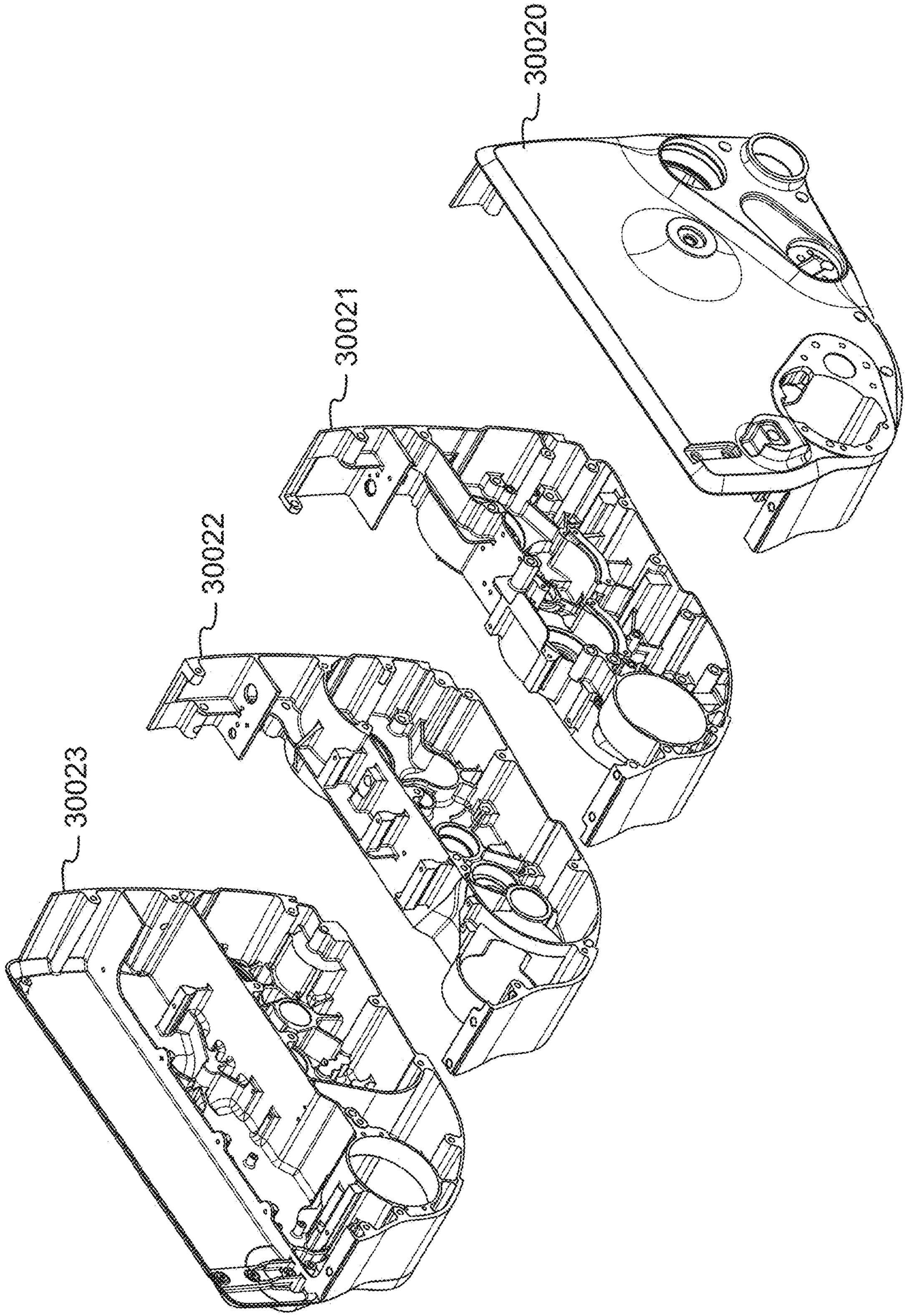
FIGS. 1I and 1J are perspective schematic diagrams of the sections of the gearbox of the present teachings.
Figure 1J:
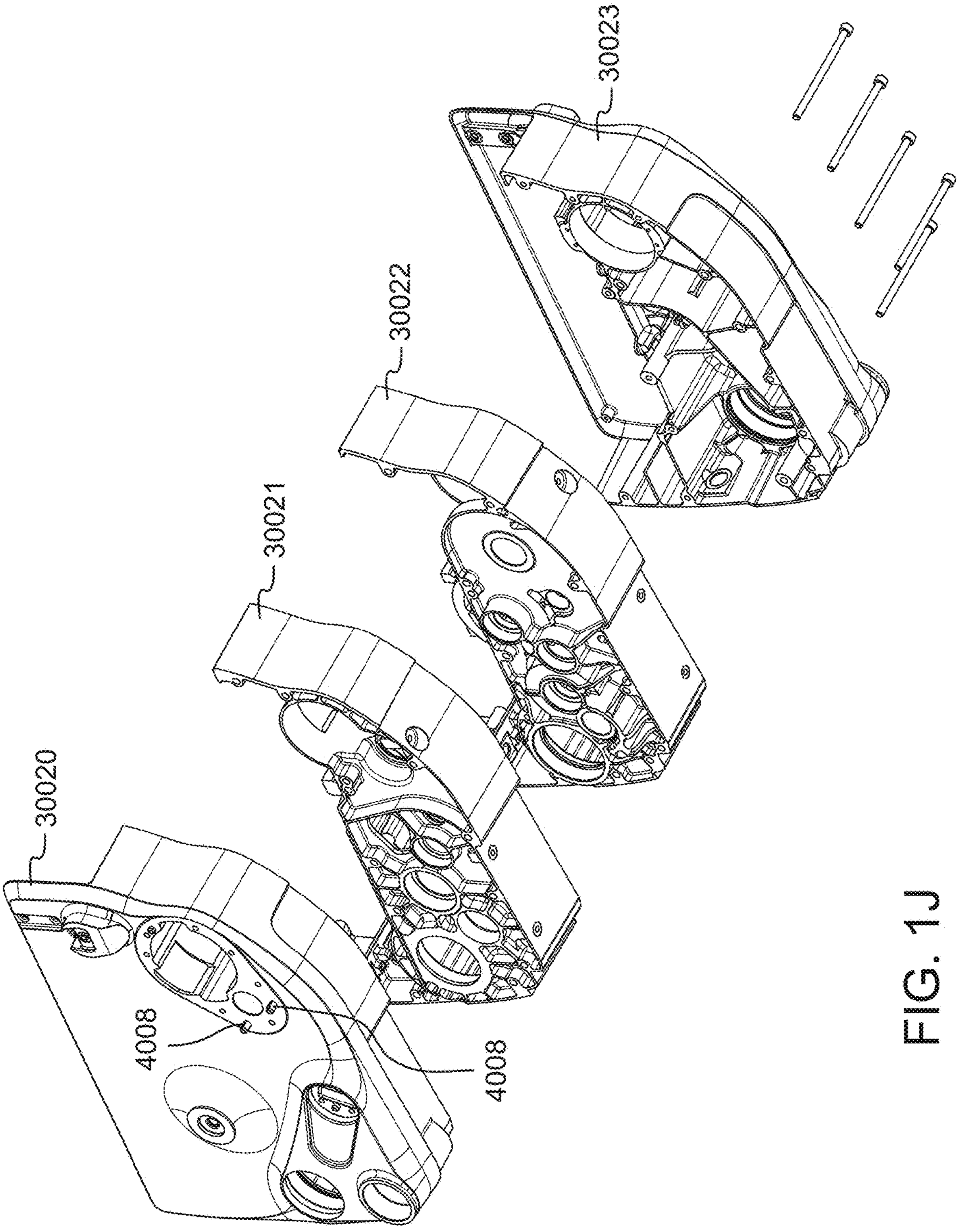
Figure 1K:
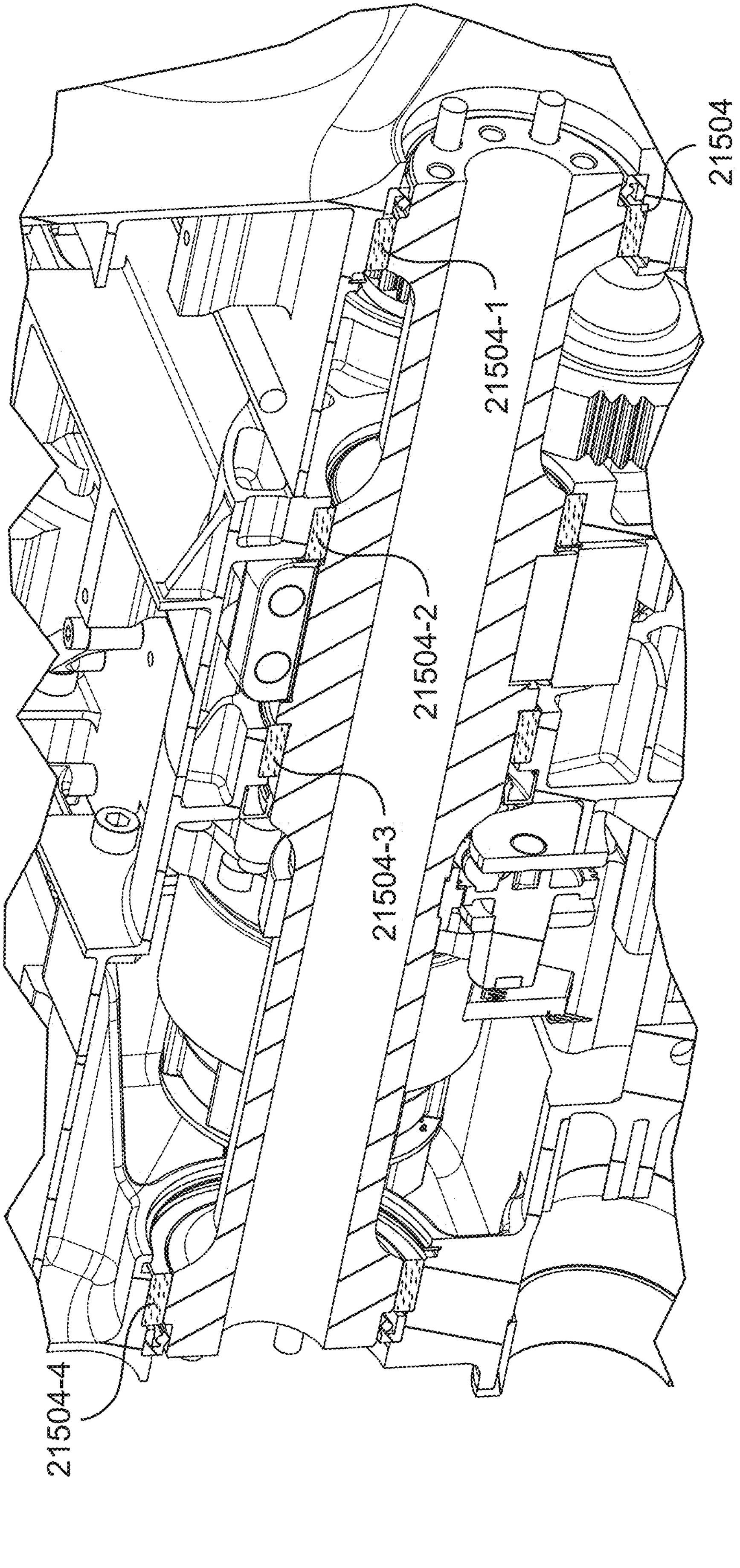
FIG. 1K is a cross section diagram of the sector gear cross shaft of the present teachings.
Figure 1L:
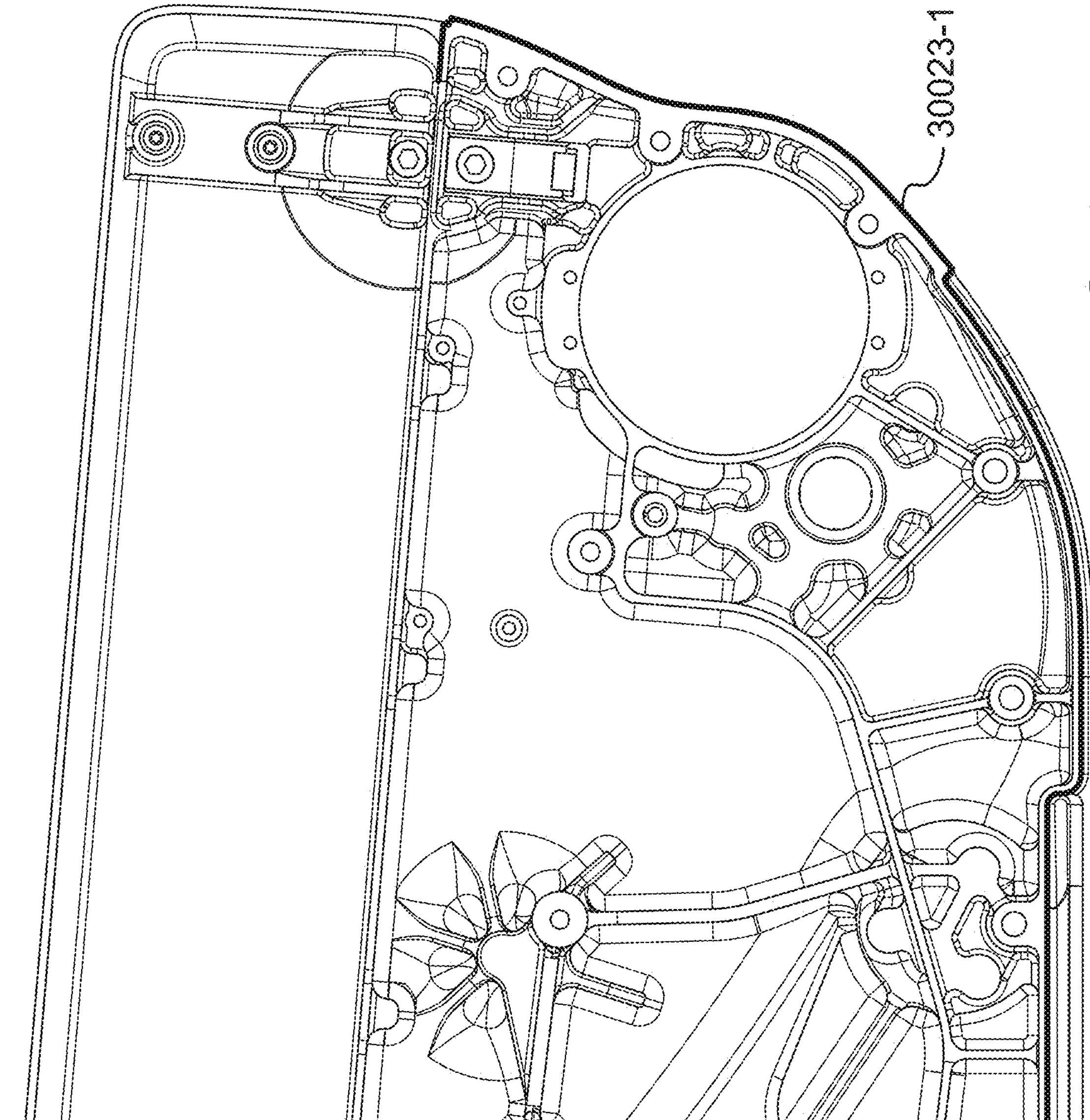
FIG. 1L is a plan diagram of the sealing bead location of the present teachings.
Figure 1M:
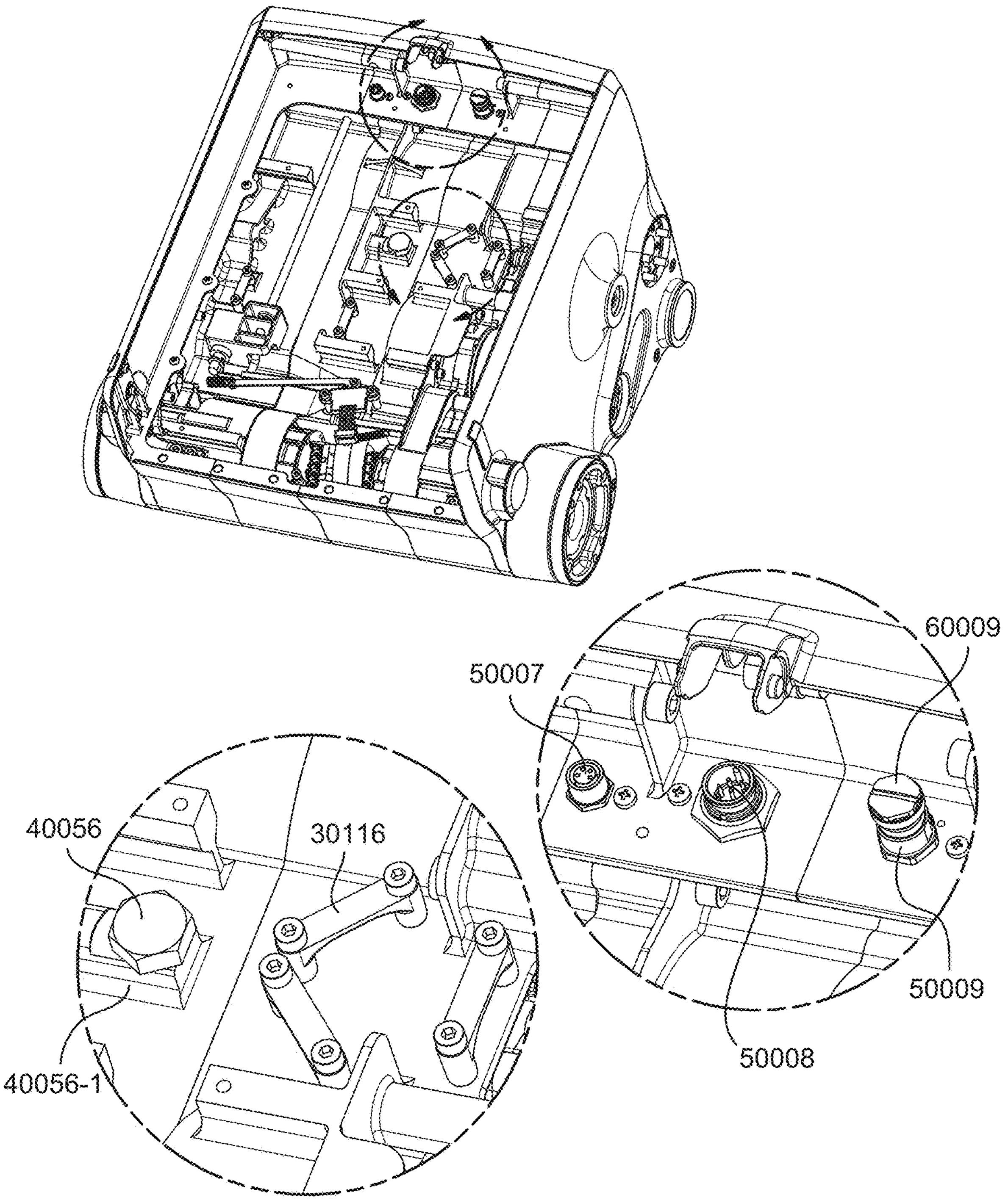
FIG. 1M is a perspective schematic diagram of the oil port of the gearbox of the present teachings.
Figure 1N:
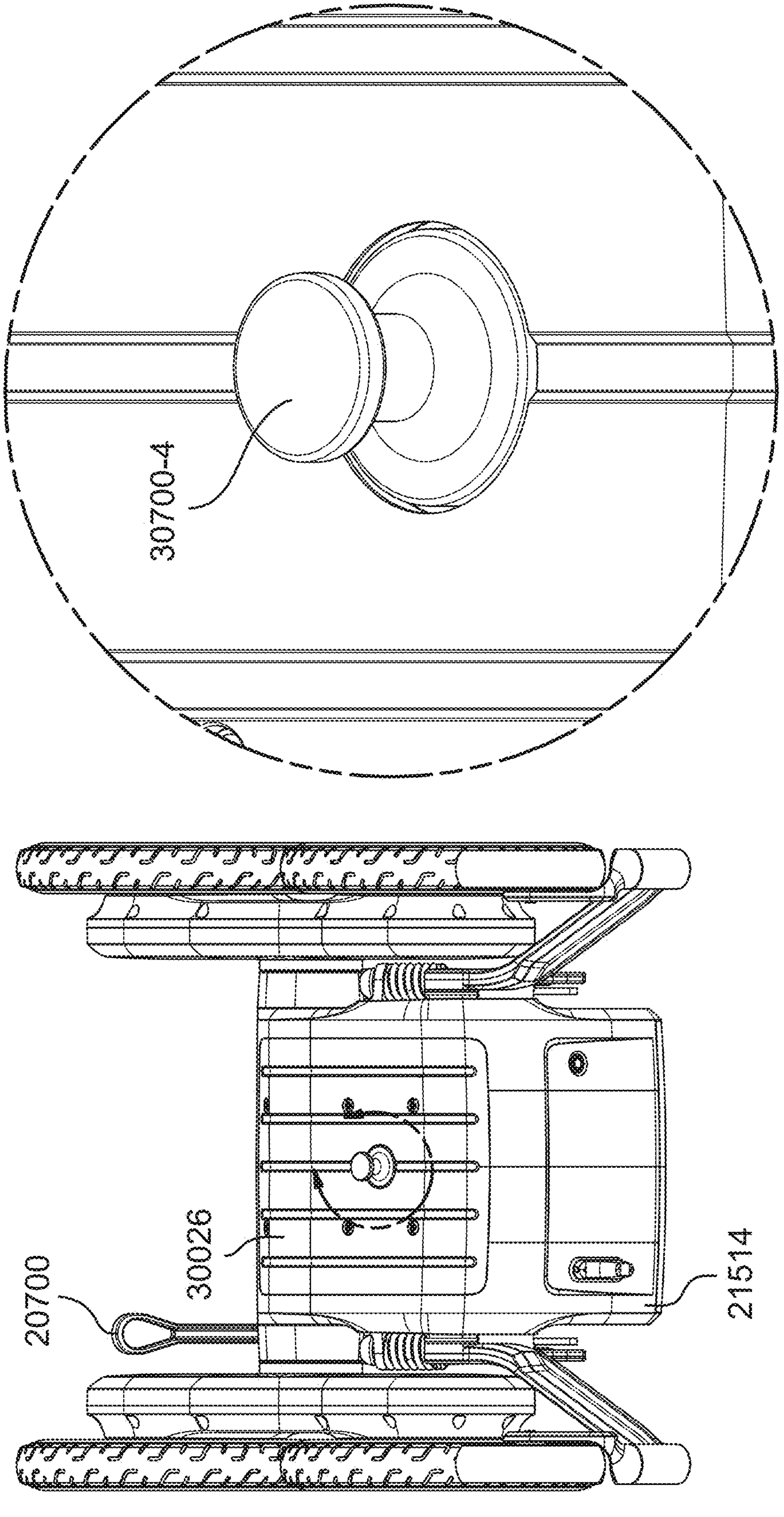
FIG. 1N is a perspective schematic diagram of the drive lock kingpin of the present teachings.
Figure 1O:
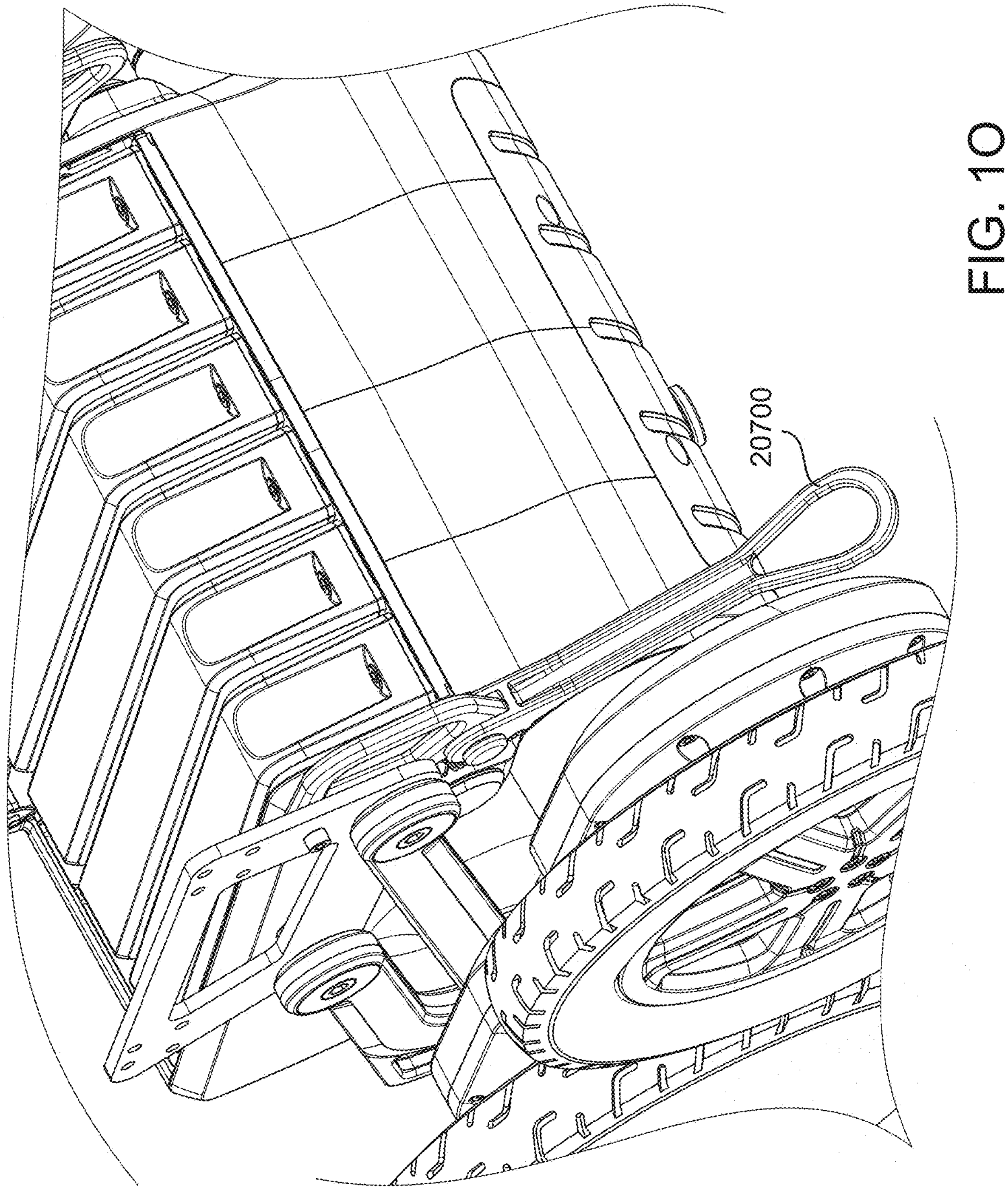
FIG. 1O is a perspective schematic diagram of the rear securement loop of the present teachings.
Figure 1P:
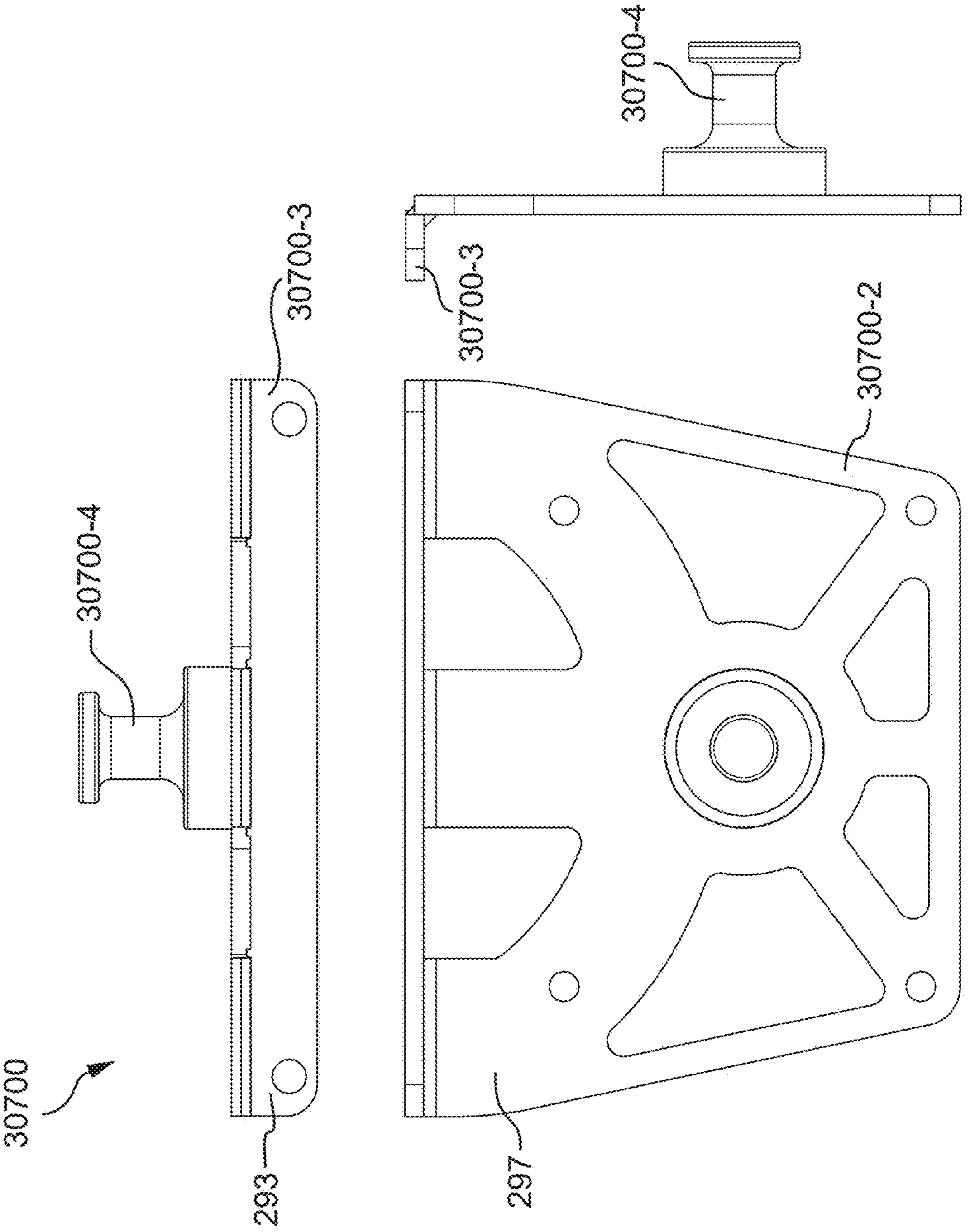
FIGS. 1P, 1Q, and 1R are perspective schematic diagrams of the skid plate and drive lock kingpin of the present teachings.
Figure 1Q:
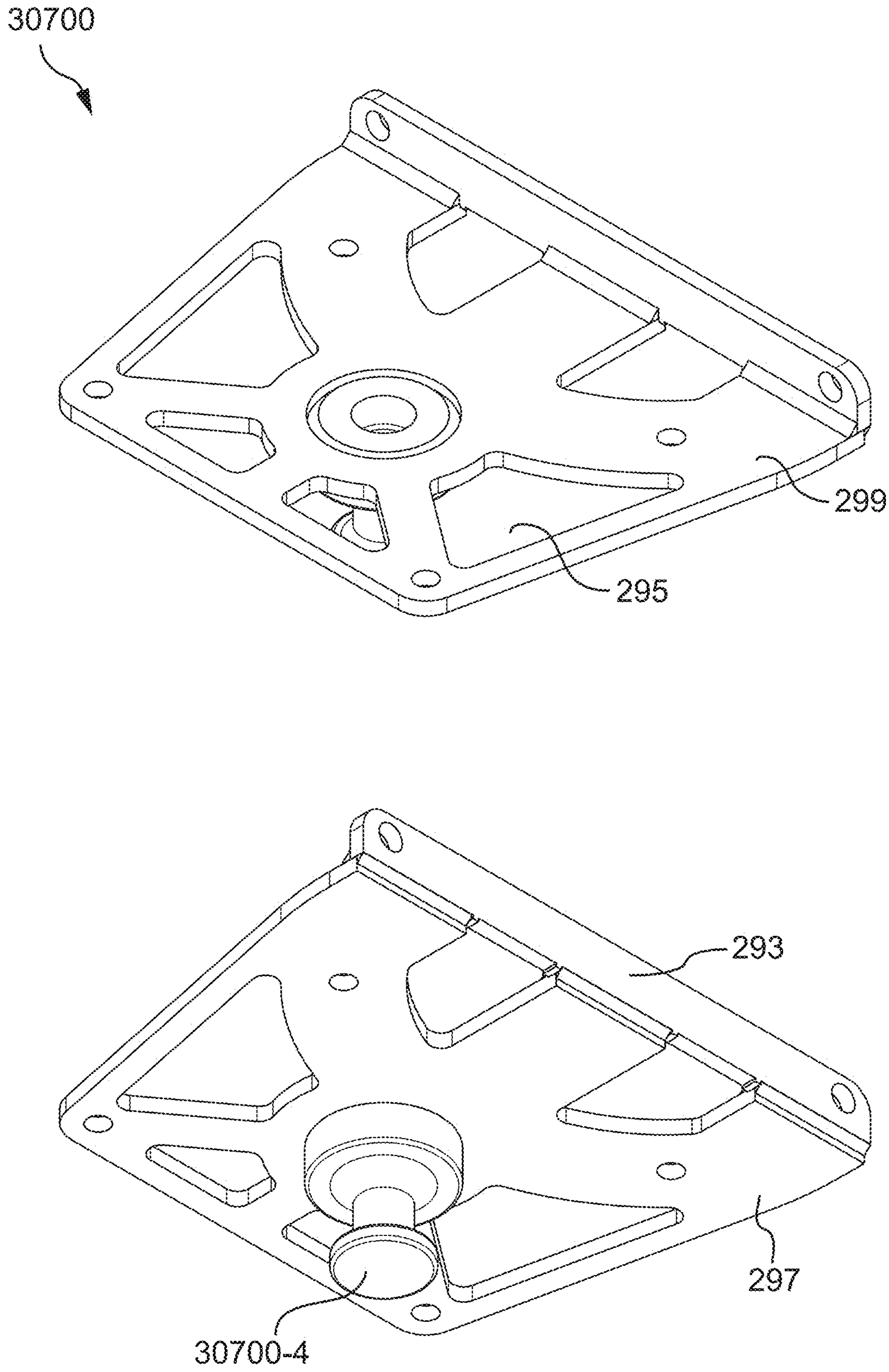
Figure 1R:
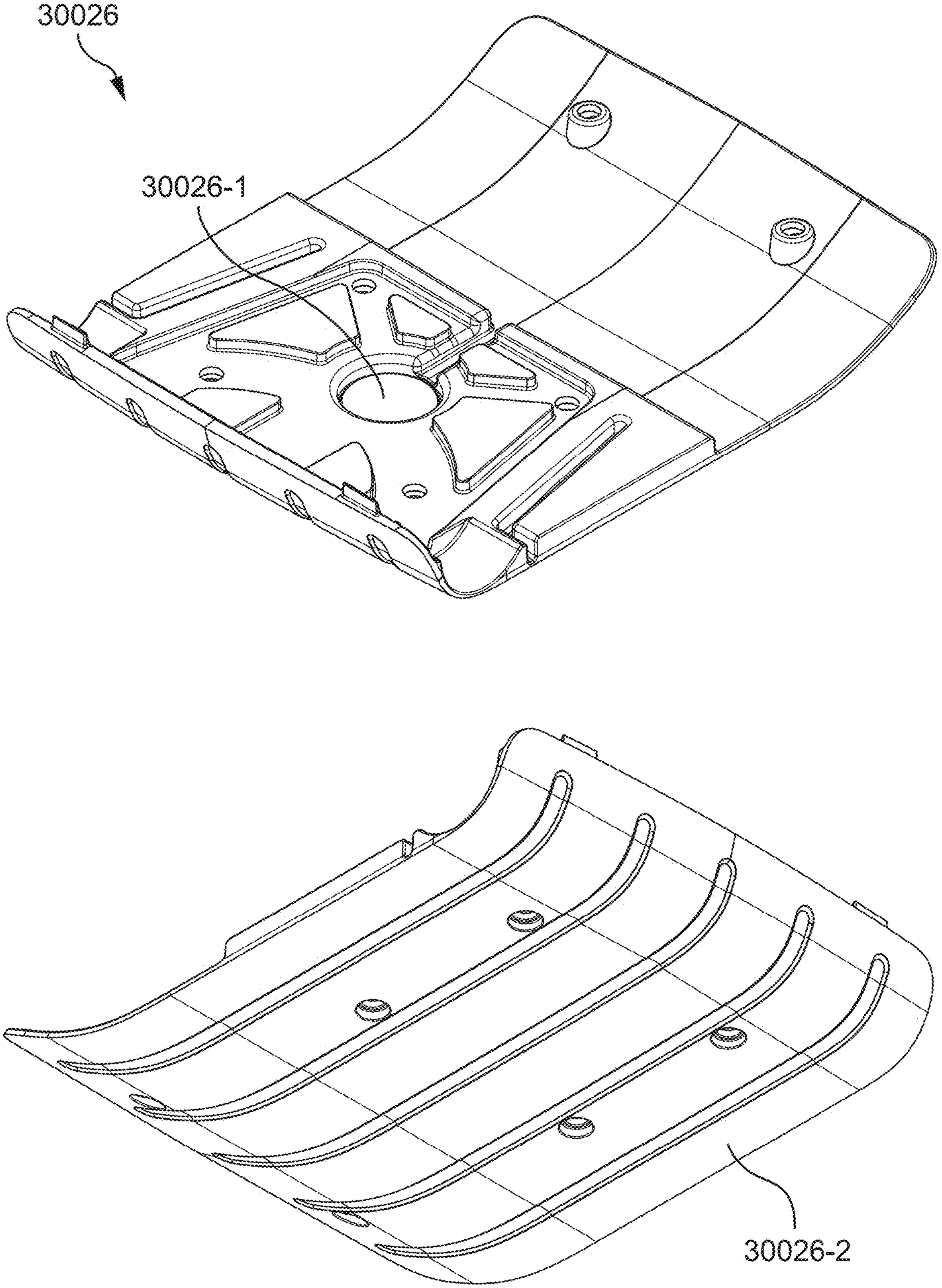
Figure 1S:
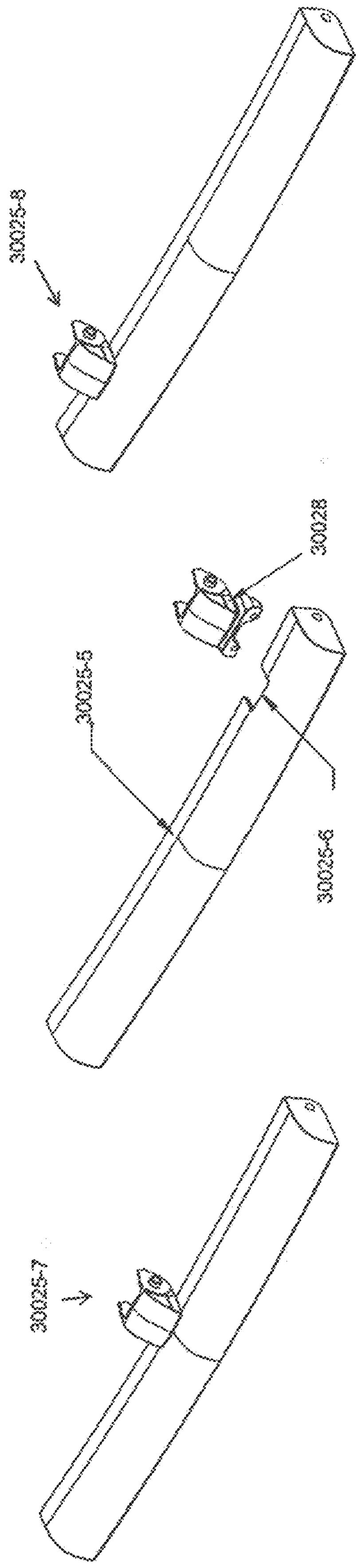
FIG. 1S is a perspective diagram of the top cap of the present teachings having variable cable restraint locations.

Referring now to FIGS. 1H and 1S, surfaces within central gearbox 21514 can be sloped such that environmental contamination, if present, can be channeled away from sensitive parts of the MD. Between the powerbase and the underside of the seat is flexible cable carrier 1149 (FIGS. 11A-11D) that can contain and protect the cables. Central gearbox top cap housing 30025 (FIG. 1H) can include hinge 30025-1 (FIG. 1H) and cable routing guide 30025-2 (FIG. 1H). Cables can be routed between UC 130 (FIG. 12A) and central gearbox 21514 through routing guide 30025-2, for example, that can avoid entanglement of the cables with a seat, especially as the seat moves up and down. The lower end of cable carrier 1149 (FIGS. 11A-11D) can be removably coupled with hinged feature 30028 (FIG. 1S) along the top edge of the powerbase on top cap 30025. A hinged cable housing (not shown) can be operably attached to hinge 30025-1 (FIG. 1H). The hinged cable housing (not shown) can further restrain cables to avoid entanglement. In some configurations, top cap 30025-5 (FIG. 1S) can include notches 30025-6 (FIG. 1S) that can accept hinged feature 30028 (FIG. 1S) at various locations across top cap 30025-8 (FIG. 1S). In some configurations, hinged feature 30028 (FIG. 1S) can be mounted near a first edge of top cap 30025-5 (FIG. 1S) at notch 30025-6 (FIG. 1S), or at an approximate mid-location 30025-7 (FIG. 1S), or near a second edge 30025-8 (FIG. 1S) of top cap 30025-5 (FIG. 1S). In some configurations, multiple hinged features 30028 (FIG. 1S) can be mounted in multiple notches 30025-6 (FIG. 1S) in top cap 30025-5 (FIG. 1S), thus accommodating multiple cable carriers 1149 (FIGS. 11A-11D).

Referring now to FIGS. 1I and 1J, central gearbox 21514 can include of first section enclosure 30020, second section enclosure 30021, third section enclosure 30022, and fourth section enclosure 30023 that can be bonded together to form an enclosure for the seat and cluster gear trains and an enclosure for the electronics of the MD. The sections can be bound together by, for example, but not limited to, an elastomeric bonding material. The bonding material can be applied to the edge of each of the sections, and the sections can be fastened together with edges meeting to form the enclosures.

Referring now to FIG. 1K, sector gear cross shaft 21504 can be supported on glass filled plastic bushings 21504-1, 21504-2, 21504-3, and 21504-4. Each bushing can be supported by one of first section enclosure 30020, second section enclosure 30021, third section enclosure 30022, and fourth section enclosure 30023. Redundant shaft support can efficiently share the load among first section enclosure 30020, second section enclosure 30021, third section enclosure 30022, and fourth section enclosure 30023, and can reduce the load on any single of first section enclosure 30020, second section enclosure 30021, third section enclosure 30022, and fourth section enclosure 30023, enabling the housing structures to be lighter.

Referring now to FIG. 1L, prior to mating one of sections 30020-30023 with each other, a sealant bead having such characteristics as high temperature resistance, acid and alkali resistance, and aging resistance, such as, for example, but not limited to, a room temperature vulcanization silicon bead, can be applied to perimeter 30023-1, for example.

Figure 1T:
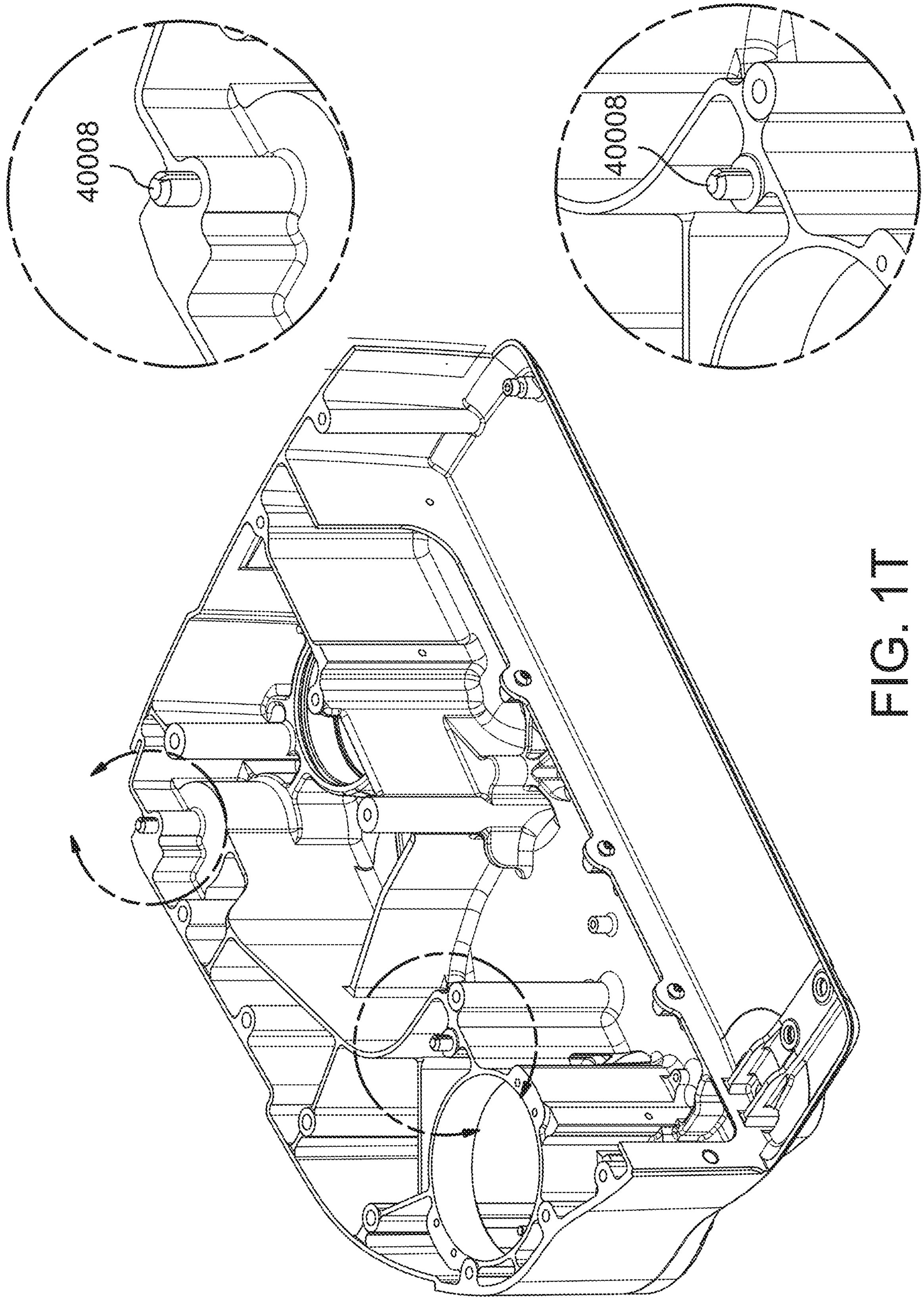
FIG. 1T is a detailed perspective view of the spring pins of the present teachings.

Referring now to FIG. 1M, oil port 40056-1, stopped by bolt 40056, can be used to add oil to the gear train enclosure. Each shaft that penetrates the housings can be surrounded by an elastomeric lip and/or o-ring seals. Electrical cable harness housings that exit the central housing do so through leak proof connectors that can seal to the housings with o-rings. The electronics enclosure is closed off by lid 21524 (FIG. 1F) that can include a seal around the perimeter that is clamped to the central housings. The electronics enclosure can provide shielding from the transmission of electromagnetic energy into or out of the enclosure. In some configurations, the sealing material that can bond the housings together and the gaskets coupling e-box lid 21524 (FIG. 1G) and the central housing can be manufactured from electrically conductive materials, improving the ability of the enclosure to shield against electromagnetic energy transmission. Electrical connectors that exit the central housing can include printed circuit boards having electromagnetic energy shielding circuits, stopping the transmission of electromagnetic energy along the cables that can be held in place by cable clamps 30116. Each of central housings 30020/30021/30022/30023 (FIGS. 1I and 1J) can be aligned to adjacent housings by spring pins 40008 (FIG. 1T) pressed into the adjacent housing.

Referring now to FIGS. 1N-1R, skid plate 30026 (FIG. 1R) can protect the underside of the housings from impacts and scrapes. Skid plate 30026 (FIG. 1R) can accommodate optional drive lock kingpin 30070-4 (FIGS. 1N and 1P) when installed. In some configurations, skid plate 30026 (FIG. 1R) can be manufactured of a fracture resistant plastic that can be tinted to limit the visibility of scrapes and scratches. Skid plate 30026 (FIG. 1R) can provide a barrier to oil if the oil drips from central gearbox 21514. When equipped with optional docking attachments, the MD can be secured for transport in conjunction with a vehicle-mounted user-actuated restraint system that can, for example, be commercially available. The docking attachments can include, but are not limited to including, docking weldment 30700 (FIG. 1P) and rear stabilizer loop 20700 (FIG. 1O). Docking weldment 30700 (FIG. 1P) can be mounted to the main chassis of the MD. Docking weldment 30700 (FIG. 1P) can engage with a vehicle mounted restraint system, can provide anchorage for the MD, and can limit its movement in the event of an accident. The restraint system of the MD can enable a user to remain seated in the MD for transport in a vehicle. Docking weldment 30700 (FIG. 1P) can include, but is not limited to including, drive lock kingpin 30700-4 (FIGS. 1N and 1P), drive lock plate base 30700-2 (FIG. 1P), and drive lock plate front 30700-3 (FIG. 1P). Docking weldment 30700 (FIG. 1P) can be optionally included with the MD and can be attached to central gearbox 21514 (FIG. 1N) at drive lock plate front 30700-3 (FIG. 1P). Drive lock base 30700-2 (FIG. 1P) can include drive lock base first side 297 (FIG. 1P) that can include drive lock kingpin 30700-4 (FIG. 1P), and drive lock base second side 299 (FIG. 1Q) that can oppose drive lock base first side 297 (FIG. 1Q) and can be mounted flush with central gearbox 21514 (FIG. 1N). Drive lock plate base 30700-2 (FIG. 1P) can optionally include at least one cavity 295 (FIG. 1Q) that can, for example, enable weight management of the MD, and reduce weight and materials costs. Drive lock kingpin 30700-4 can protrude from drive lock base first side 297, and can interlock with a female connector (not shown) in, for example, a vehicle. Drive lock kingpin 30700-4 can protrude from the underside of the MD to provide enough clearance to interlock with the female connector (not shown), and also to provide enough clearance from the ground to avoid any operational interruptions. In some configurations, drive lock kingpin 30700-4 can clear the ground by, for example, 1.5 inches. In some configurations, the rear securement loop 20700 (FIG. 1O) can engage a hook (not shown) in, for example, a vehicle, at the same time or before or after drive lock kingpin 30700-4 (FIG. 1R) interlocks with a female connector. The hook that engages with rear securement loop 20700 (FIG. 1O) can include a sensor that can report, for example, to the vehicle if rear securement loop 20700 (FIG. 1O) is engaged. If rear securement loop 20700 (FIG. 1O) is not engaged, the vehicle can provide a warning to the user, or may not allow the vehicle to move until engagement is reported. In some configurations, drive lock base plate 30700-2 (FIG. 1P) can include a removable punch-out 30026-1 (FIG. 1R) that can be used to insert and remove drive lock kingpin 30700-4 at any time. For example, the MD could be equipped with drive lock base plate 30700-2 (FIG. 1P) with the removable punch-out 30026-1 (FIG. 1R). Various types of drive lock kingpins 30700-4 can be accommodated to enable mounting flexibility.

Figure 2A:
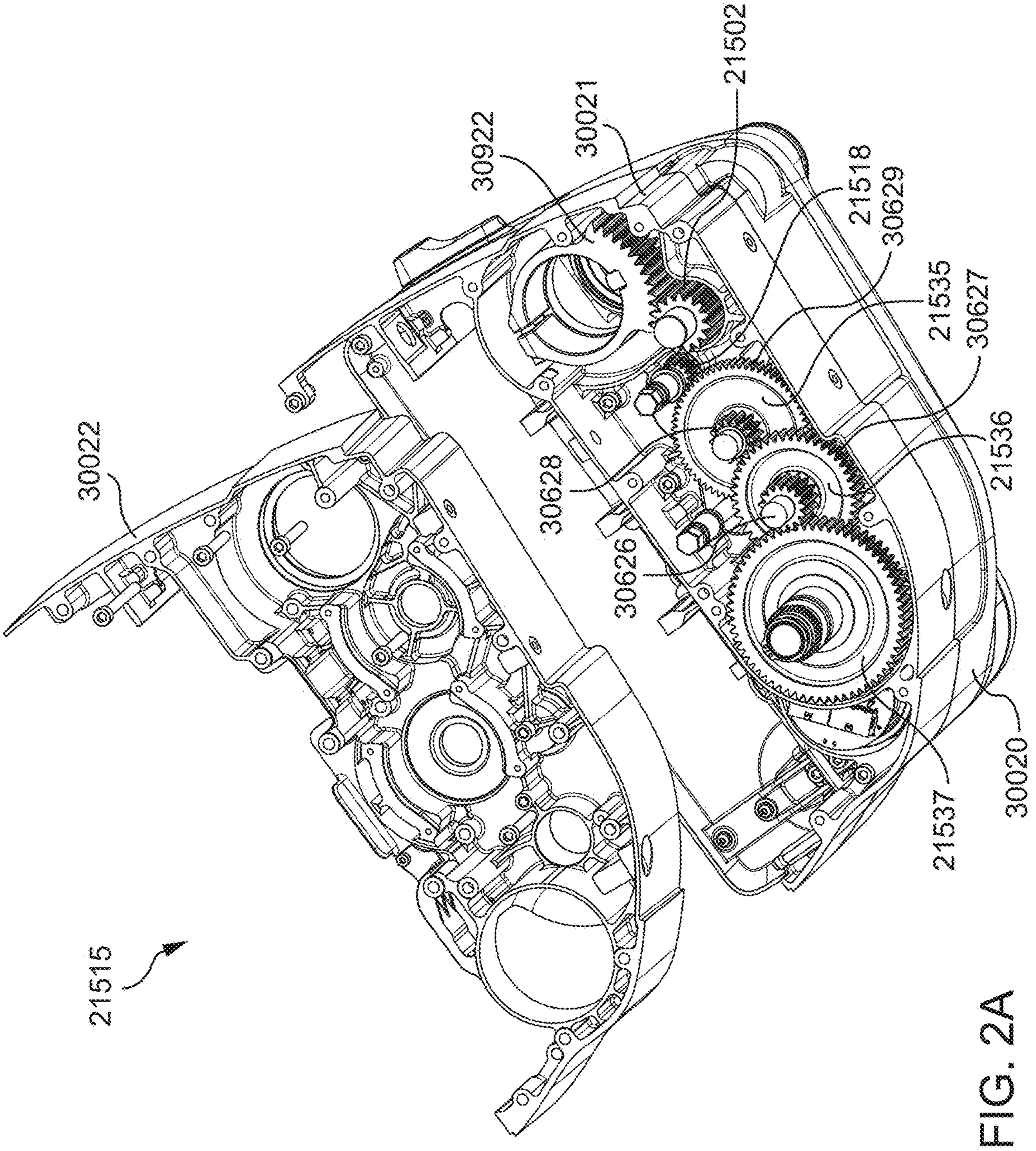
FIG. 2A is a perspective diagram of the gears within the gearbox of the present teachings.
Figure 2B:
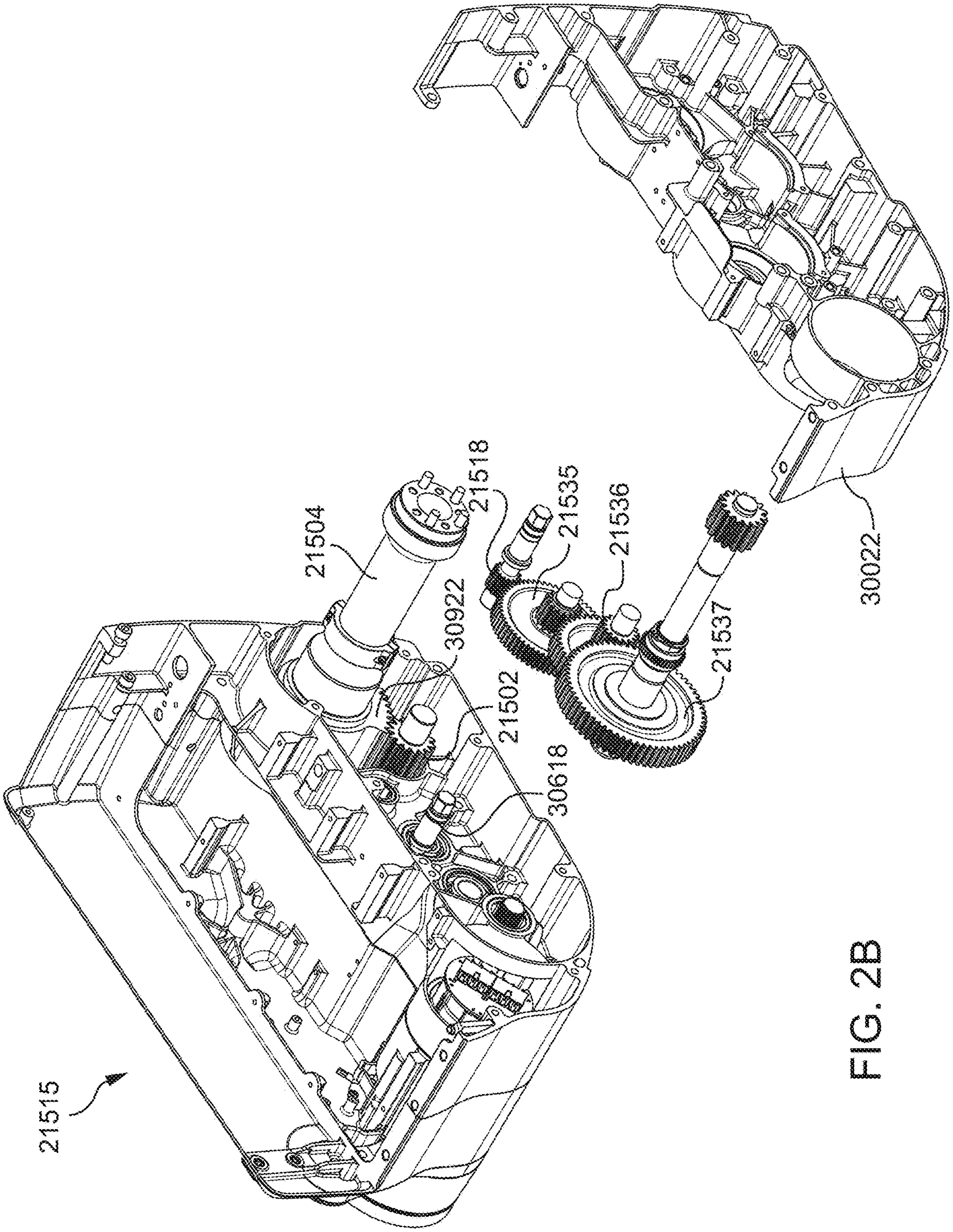
FIGS. 2B-2E are perspective diagrams and plan views of the detail of the gears and cluster cross shaft of the present teachings.

Referring now to FIG. 2A, central gearbox wet section can include, but is not limited to including, central gearbox housing left outer 30020 (FIG. 2A), central gearbox housing left inner 30021 (FIG. 2A), and right inner housing 30022 (FIG. 2A) that can include seat and cluster gears and shafts, and position sensors.

Figure 2C:
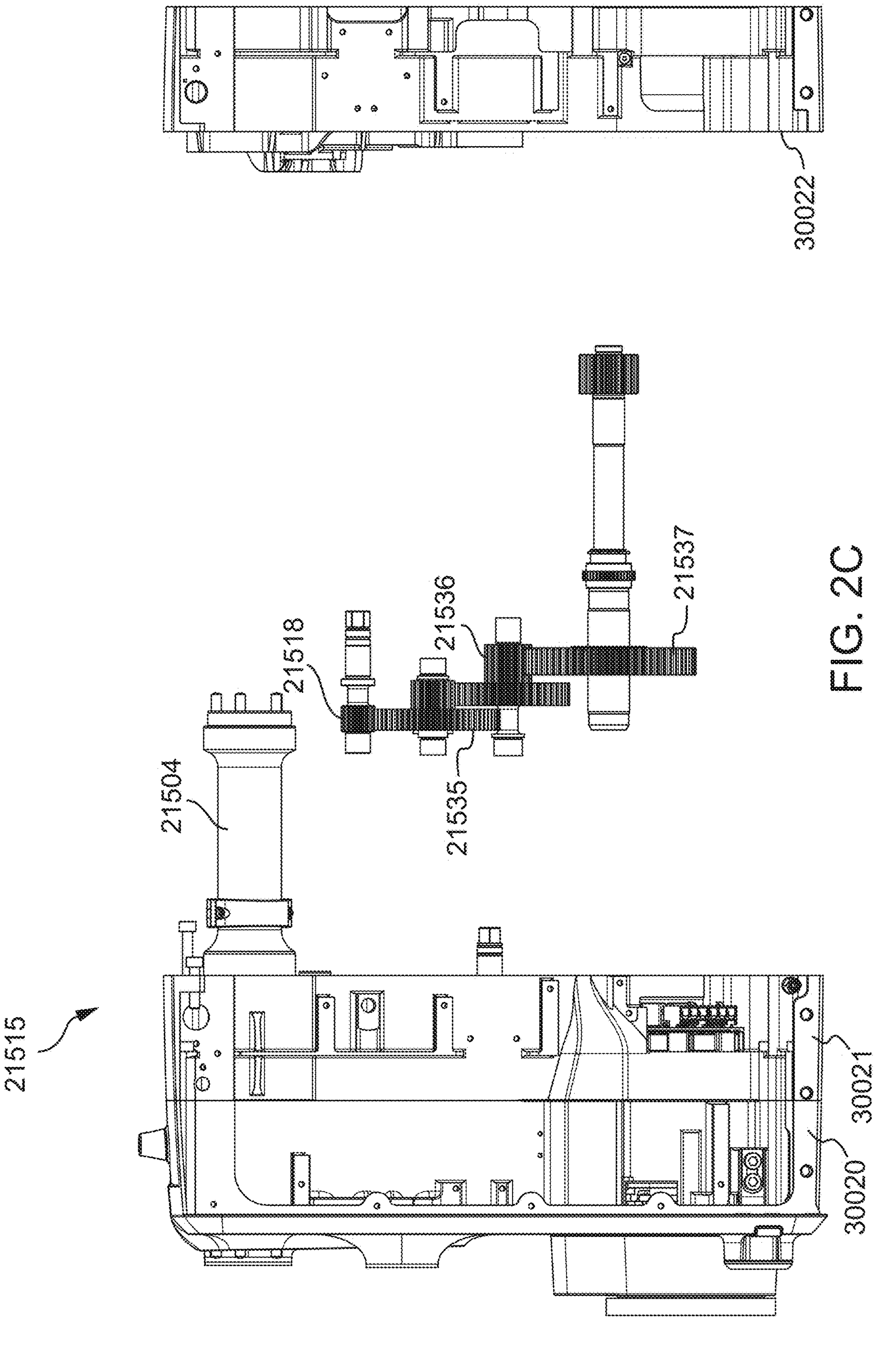
Figure 2D:
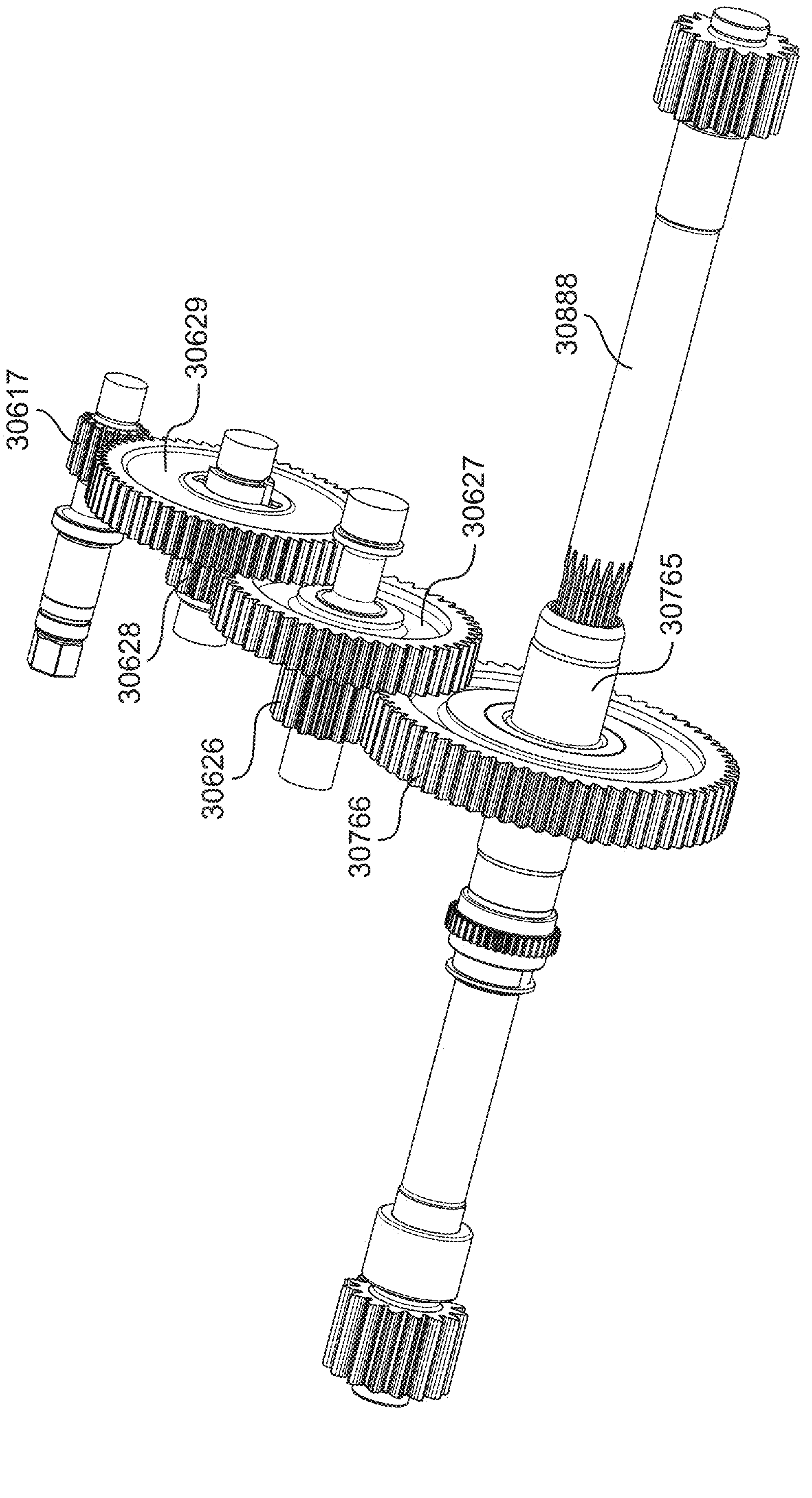
Figure 2E:
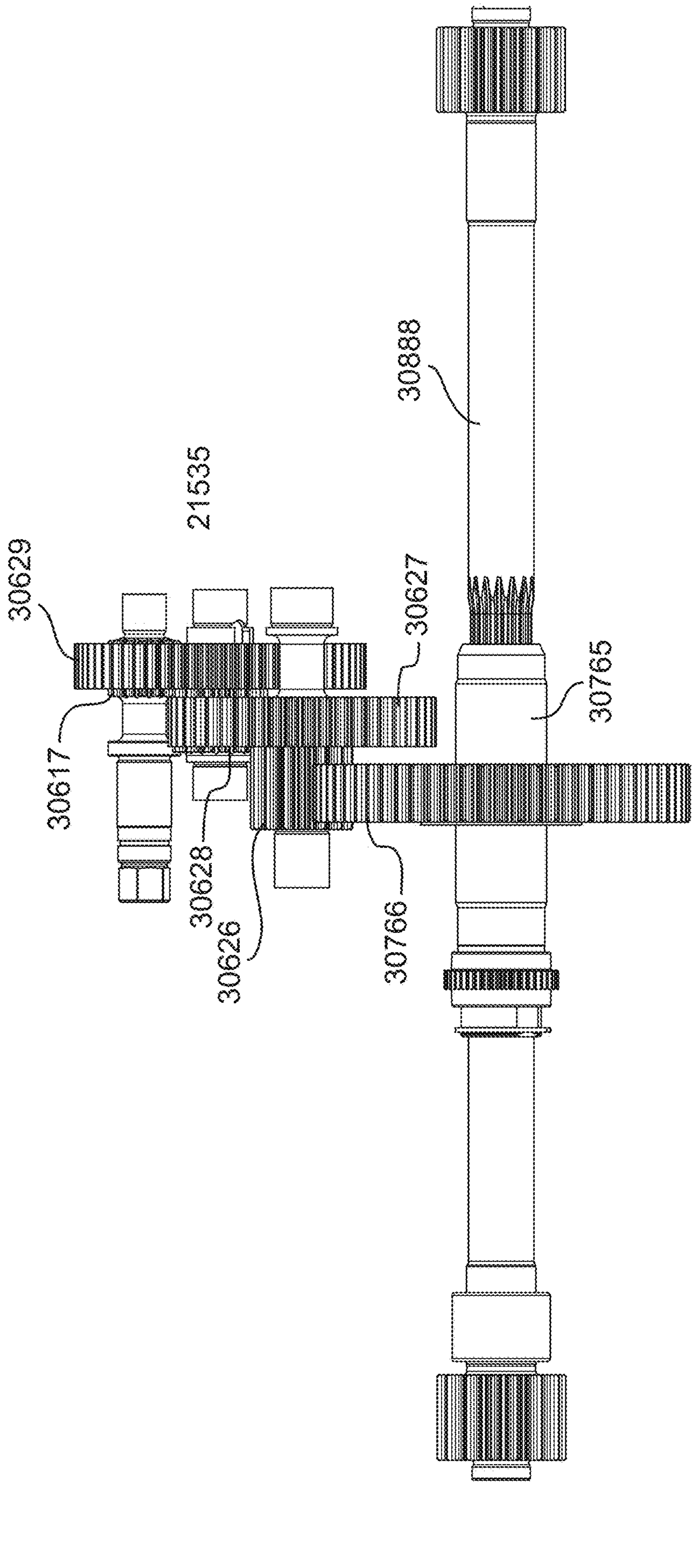

Referring now to FIGS. 2B-2E, gear trains for cluster and seat are shown. The cluster drive gear train can include four stages with two outputs. The shaft on the third stage gear can span the powerbase. The final stage gear on each side can provide the mounting surface for the wheel cluster assembly. Central gearbox wet section can include the cluster drive gear set that can include shaft pinion stage one cluster rotate 21518 (FIG. 2M), that itself can drive pinion-gear cluster rotate stage 2 pinion 21535 (FIGS. 2O, 2P, 2B), that can drive cluster rotate pinion-gear stage 3 pinion 21536 (FIGS. 2Q, 2B), that itself can drive cluster rotate gear-pinion cross-shaft stage 3 21537 (FIG. 2R, 2B) that is connected to the left and right cluster cross shafts 30888 and 30888-1 (FIGS. 6D, 2D, and 2E), that can drive the cluster rotate stage 4 ring gears 30891 (FIG. 6D). The left and right cluster ring gears 30891 (FIG. 6D) can be operably coupled with wheel cluster housings 21100 (FIG. 6A). The cluster drive gear train can include pinion shaft stage 1 30617 (FIG. 2D), that can drive gear cluster stage 1 30629 (FIG. 2D) and pinion shaft stage 2 30628 (FIG. 2D), that can in turn drive gear cluster stage 2 30627 (FIG. 2D) and pinion shaft 30626 (FIG. 2D), that can drive gear cluster rotate stage 3 30766 (FIG. 2D) and cross shaft cluster rotate 30765 (FIG. 2D). The input shaft of the wheel cluster assembly can engage two gear trains, placed symmetrically with respect to the input shaft. There are two stages of gear reduction to transmit power from the input shaft to the output shafts, on which wheel assemblies 21203 (FIG. 1A) can be mounted. The two wheel cluster assemblies can be identical.

Figure 2F:
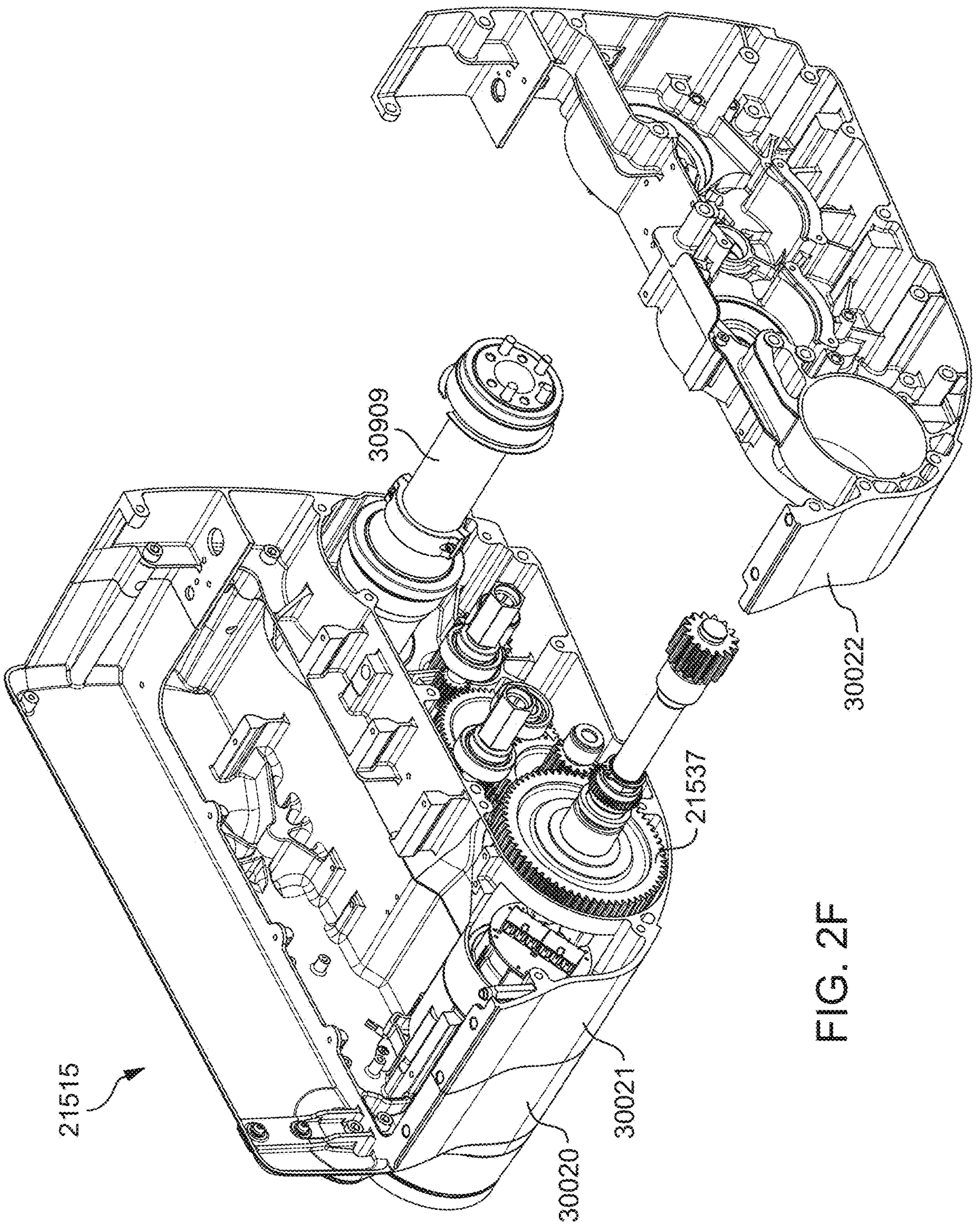
FIG. 2F is a perspective diagram of the cluster cross shaft and the sector gear cross shaft of the present teachings.
Figure 2G:
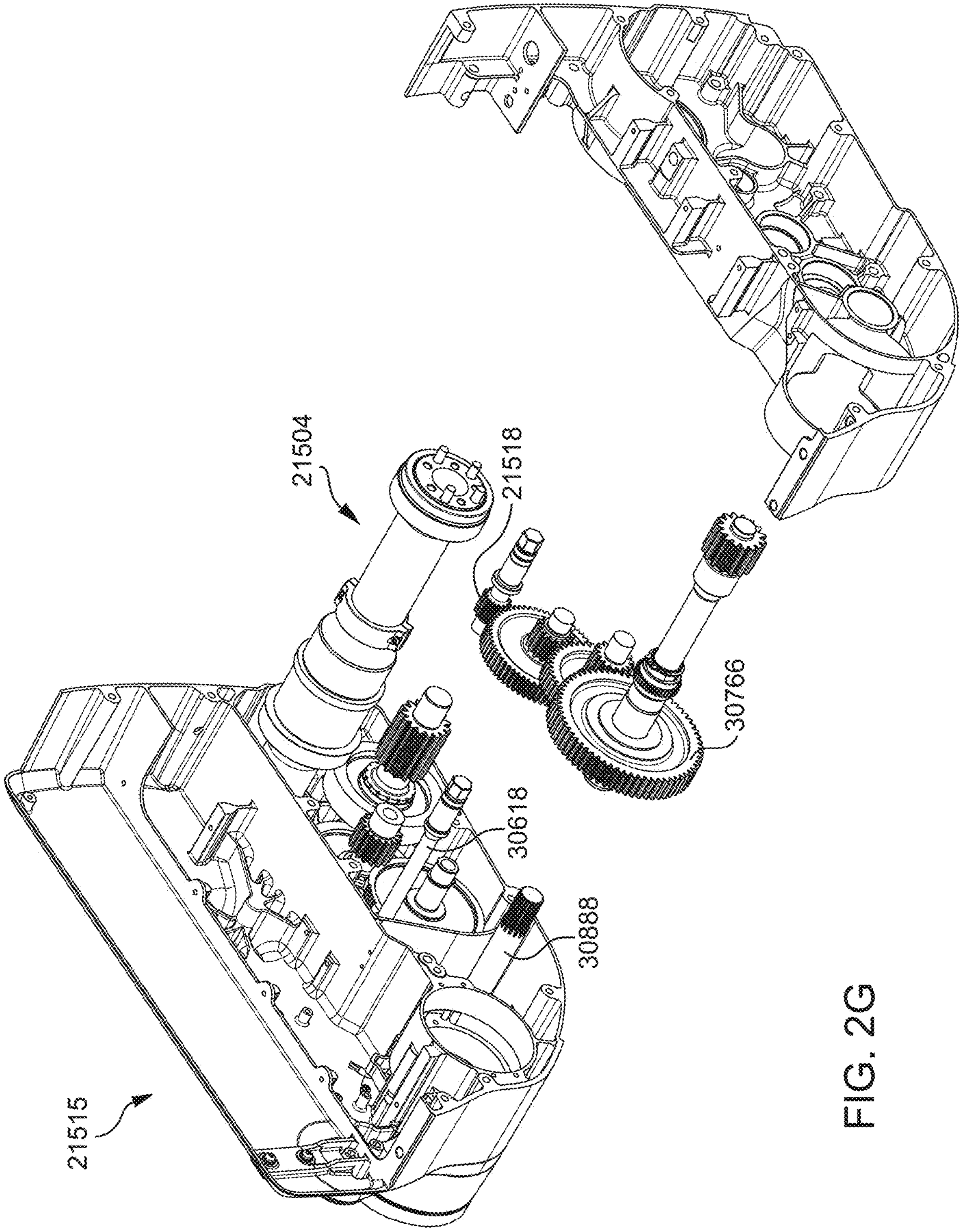
FIG. 2G is a perspective diagram of detail of the gears and the sector gear cross shaft of the present teachings.
Figure 2H:
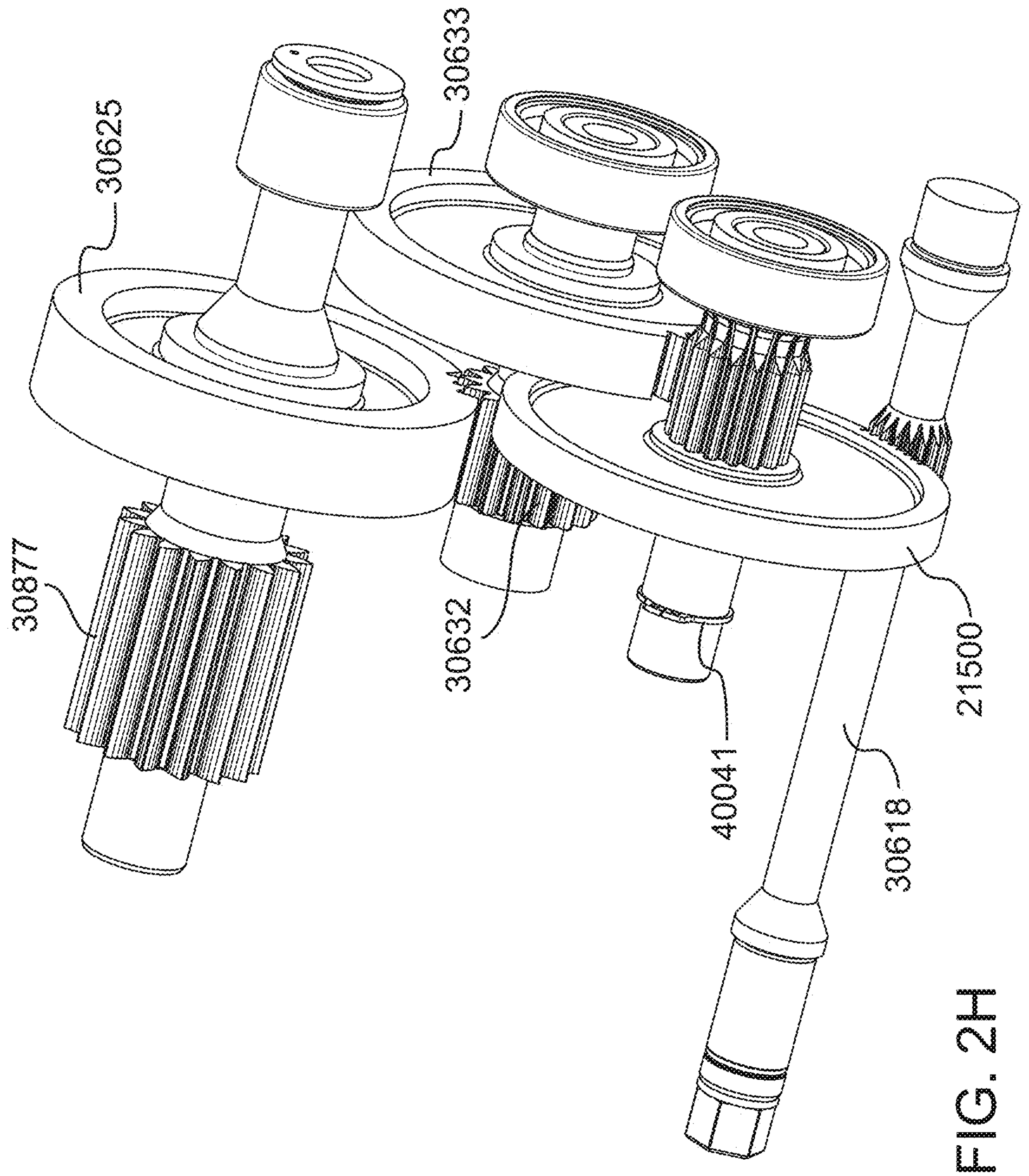
FIG. 2H is a perspective diagram of detail of the gears and pinion height actuator stage 1 of the present teachings.
Figure 2I:
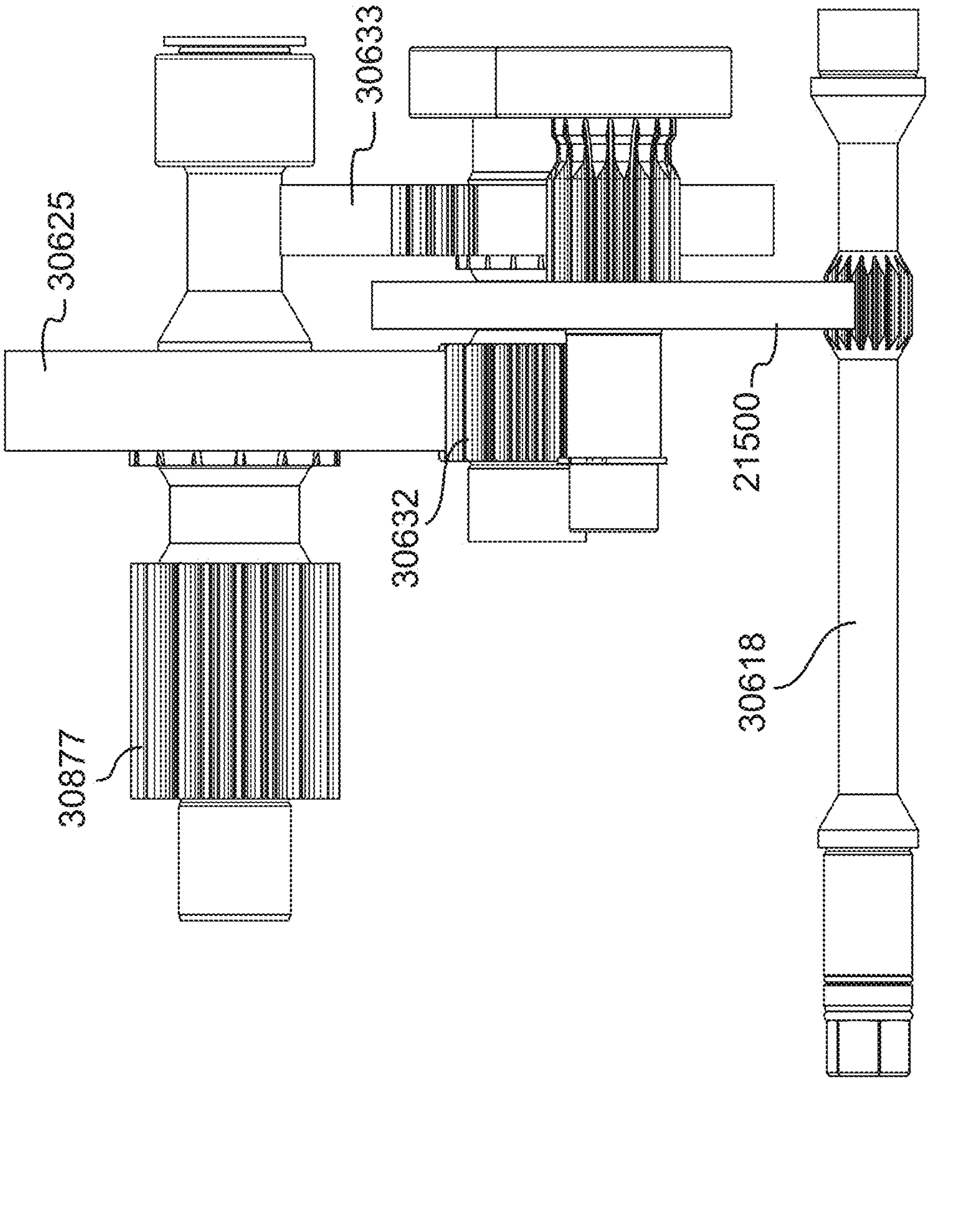
FIGS. 2I and 2J are plan views of detail of the gears and pinion height actuator stage 1 of the present teachings.
Figure 2J:
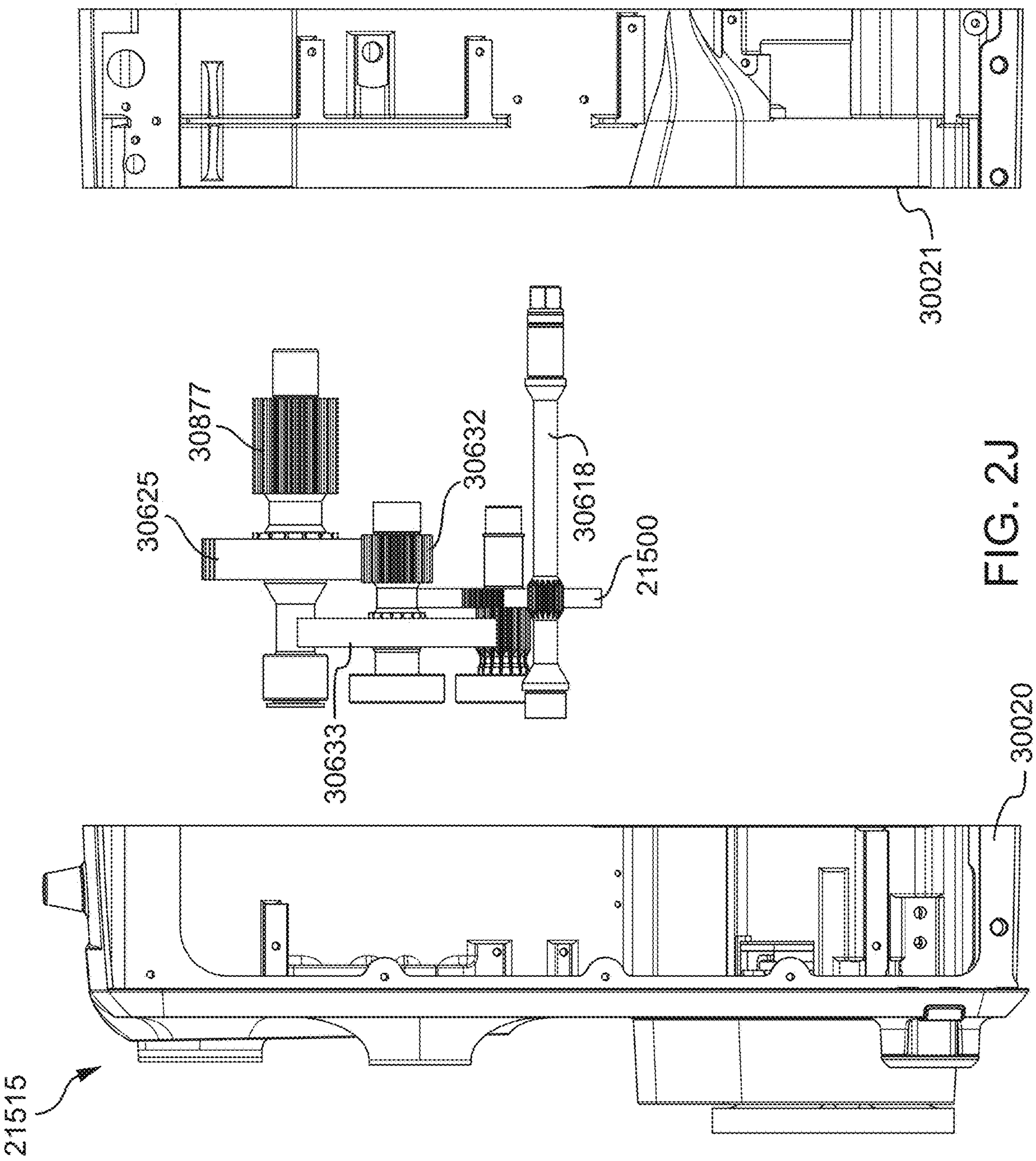
Figure 2K:
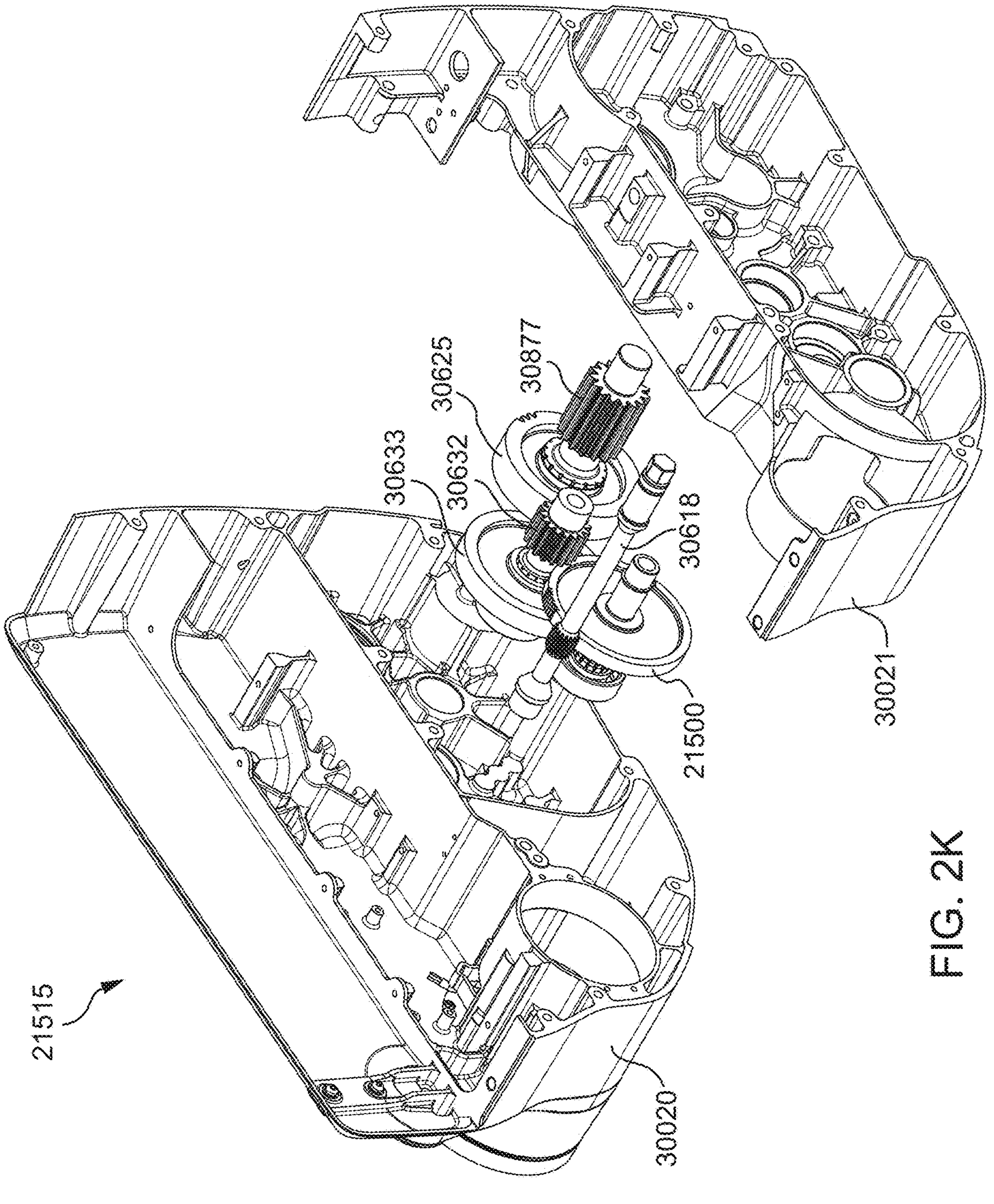
FIG. 2K is a perspective diagram of the gears and cluster cross shaft of the present teachings.
Figure 2L:
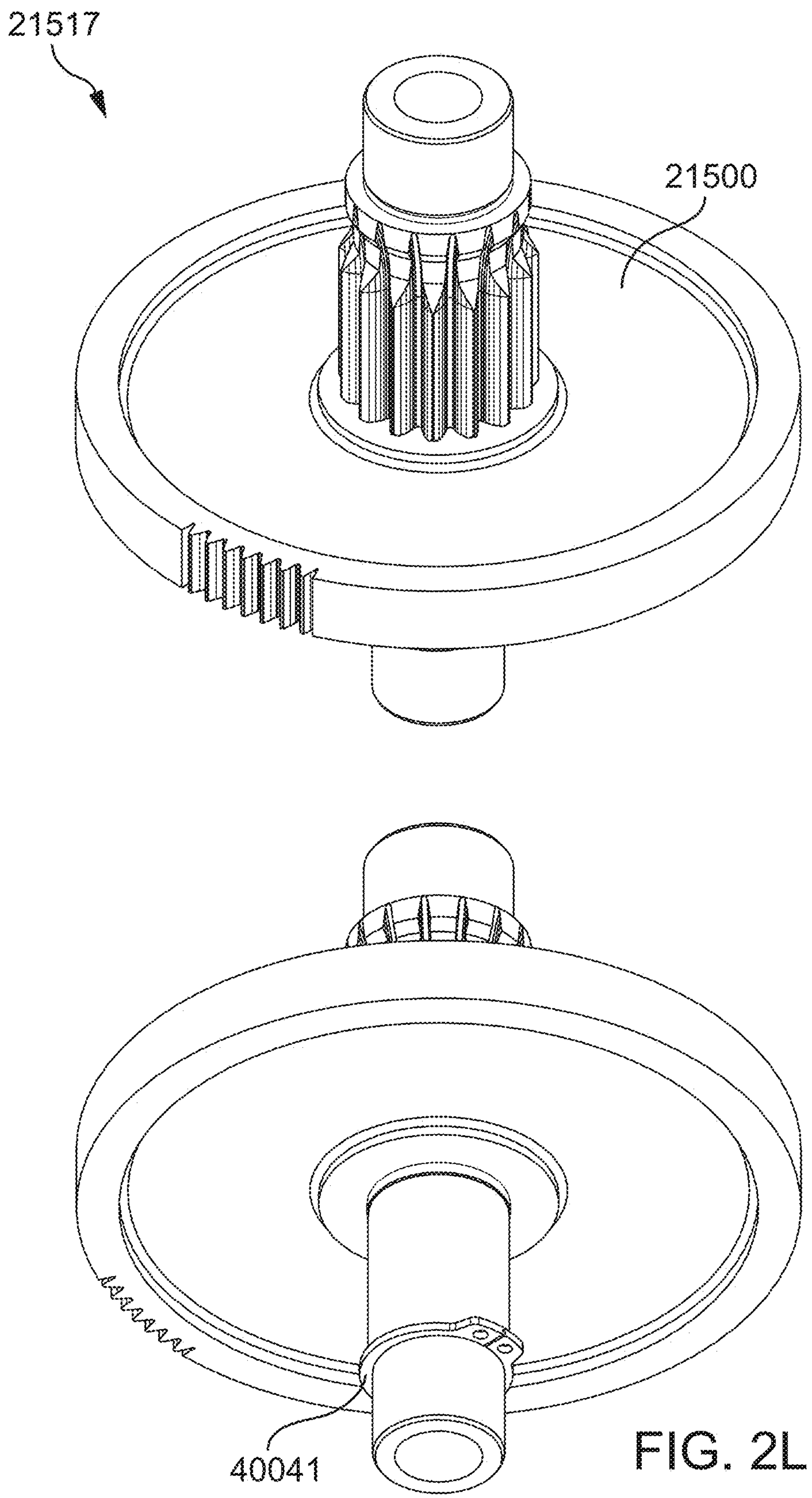
FIG. 2L is a perspective diagram of the pinion-gear height actuator stage 2 pinion with retaining ring of the present teachings.
Figure 2M:
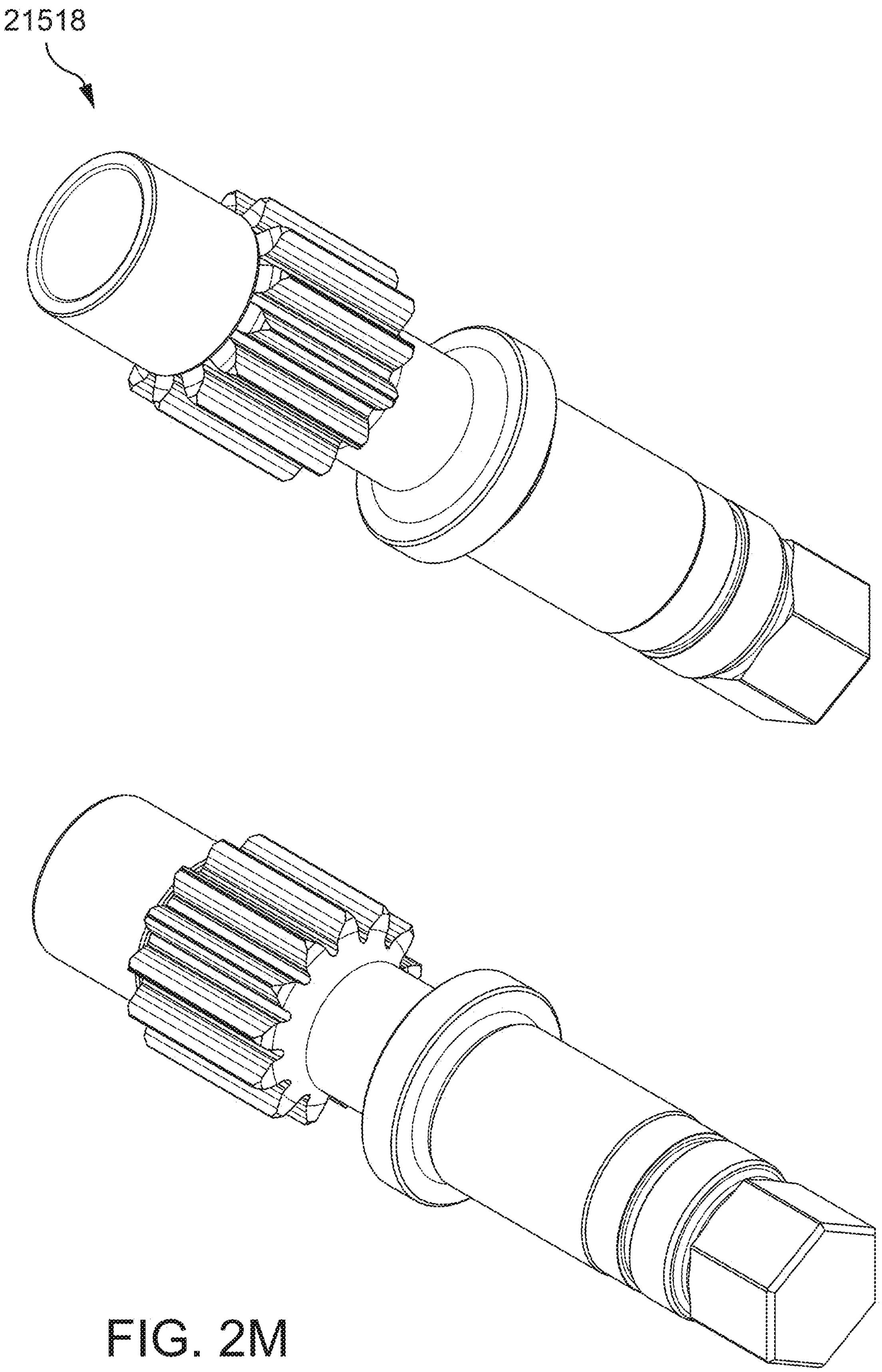
FIG. 2M is a perspective diagram of the shaft pinion cluster rotation stage 1 with inner ring of the present teachings.
Figure 2N:
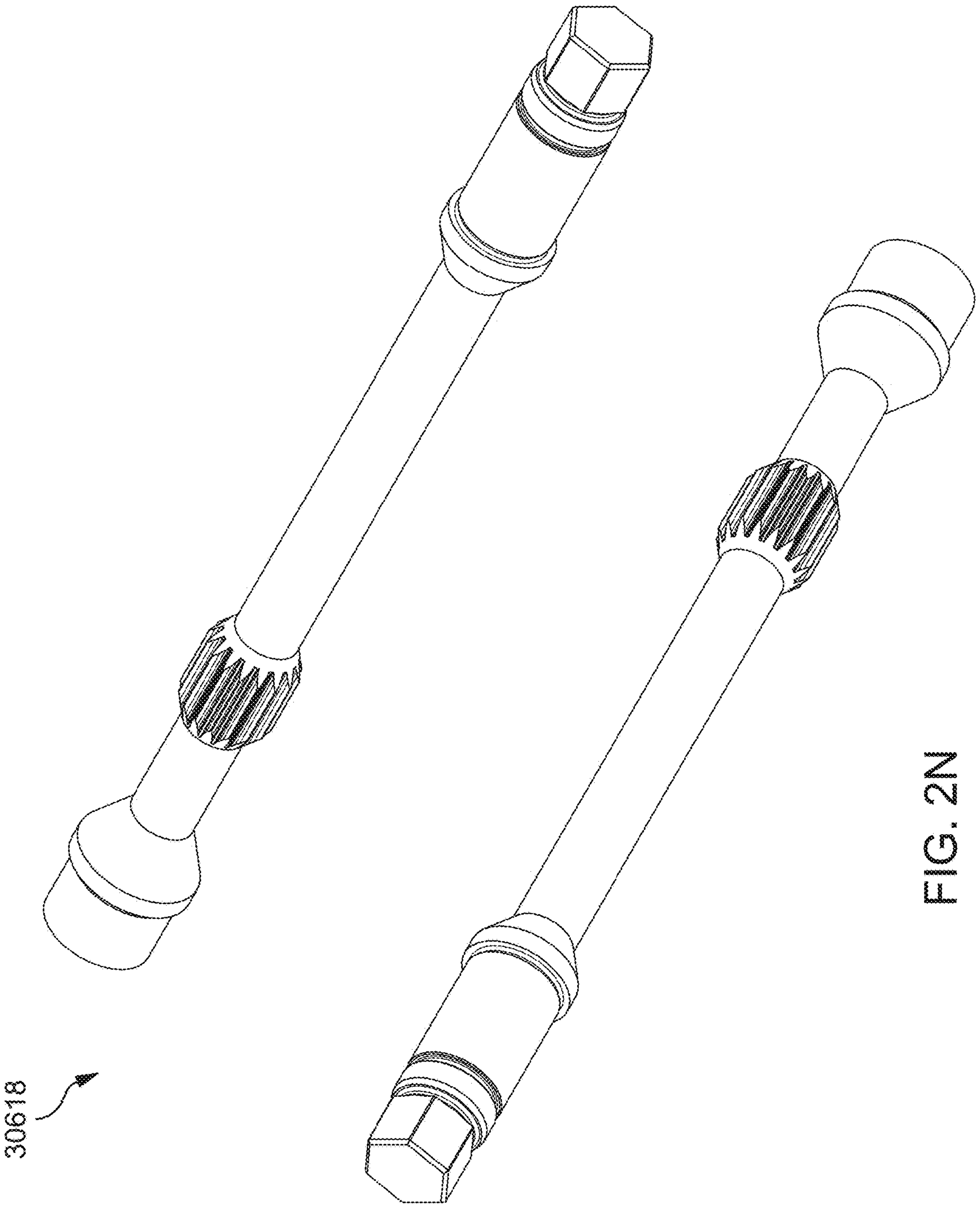
FIG. 2N is a perspective diagram of the pinion height actuator shaft stage 1 of the present teachings.
Figure 2O:
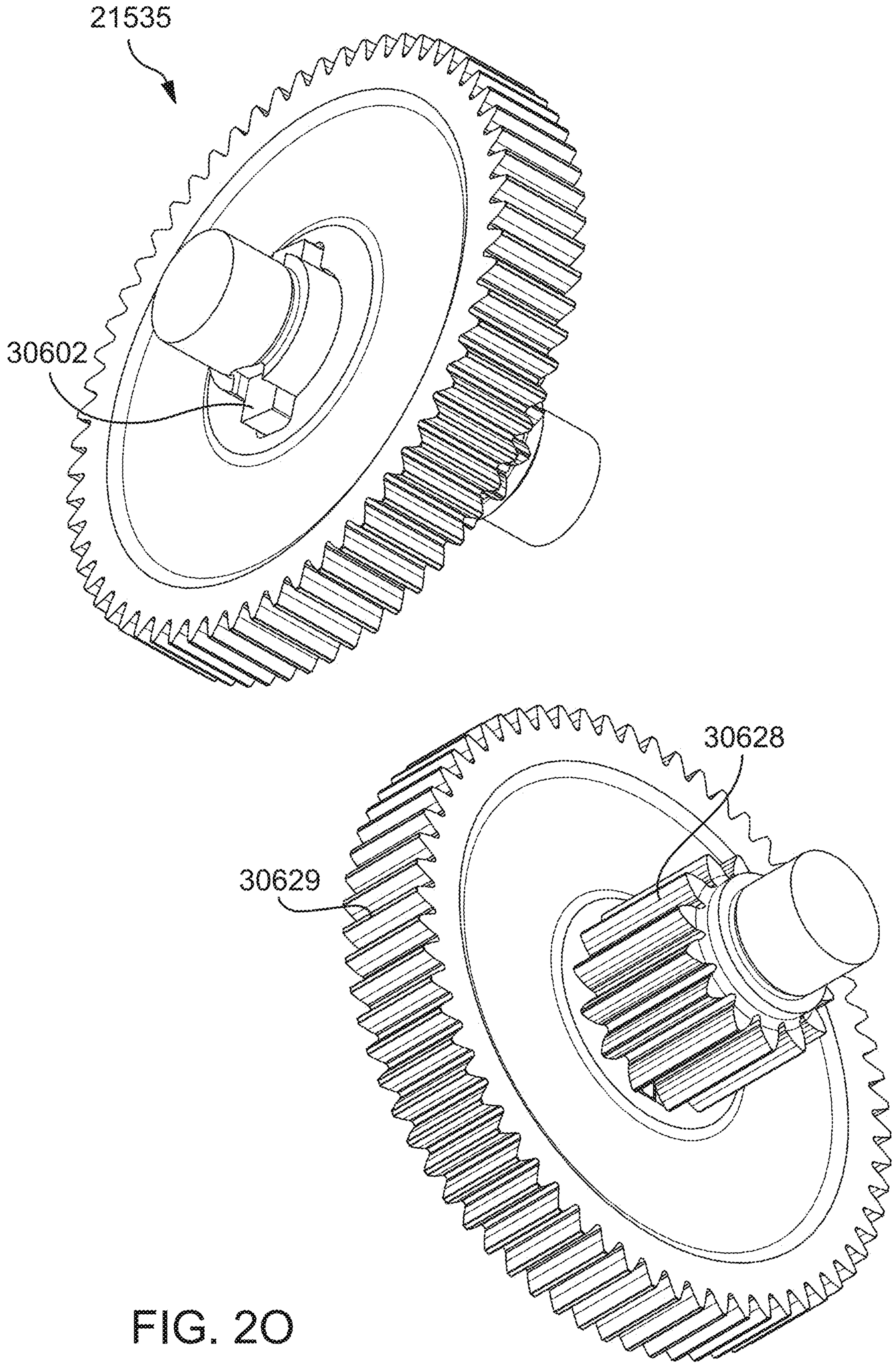
FIGS. 2O and 2P are perspective diagrams of the cluster rotate pinion-gear stage 2 pinion of the present teachings.
Figure 2P:
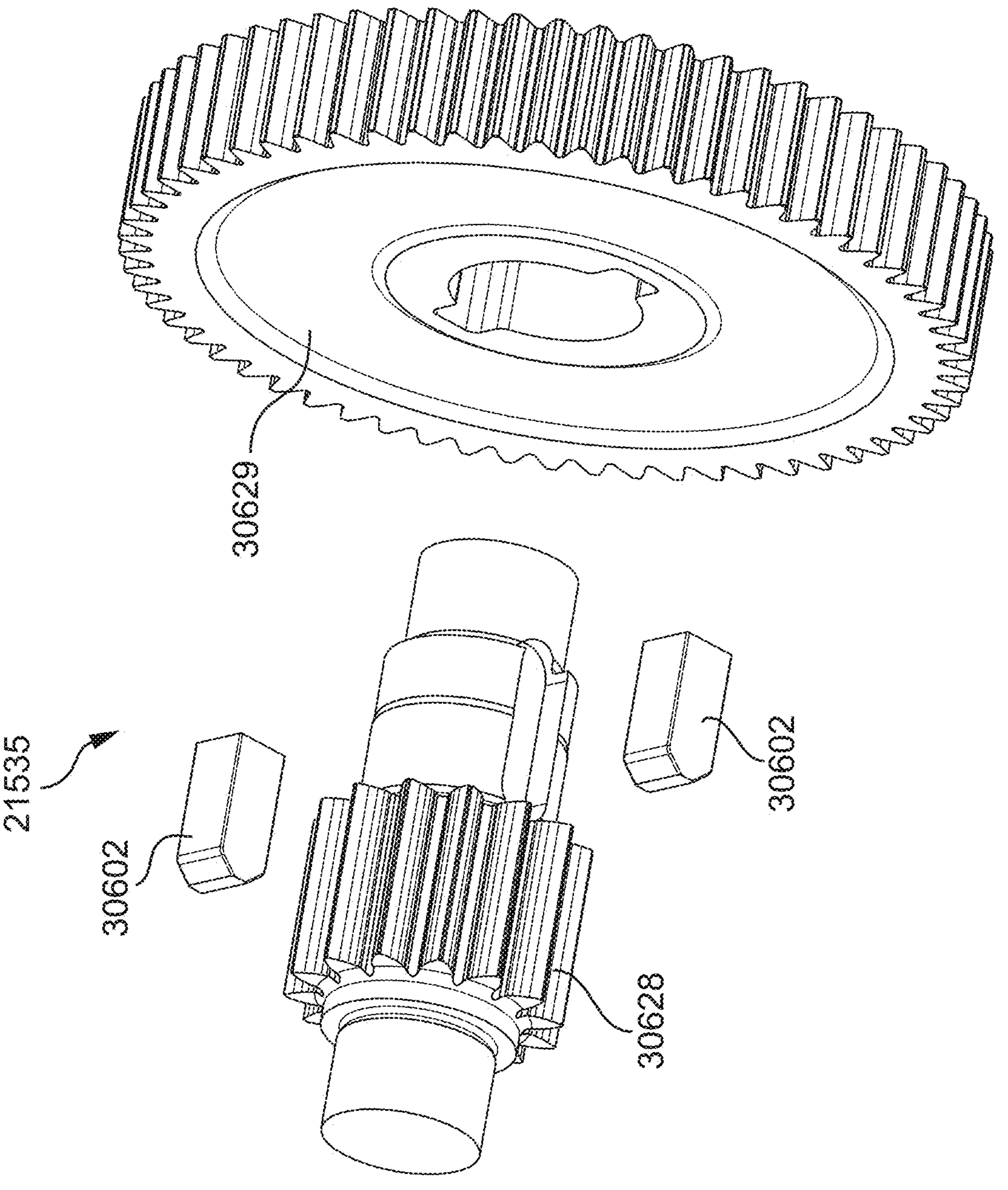
Figure 2Q:
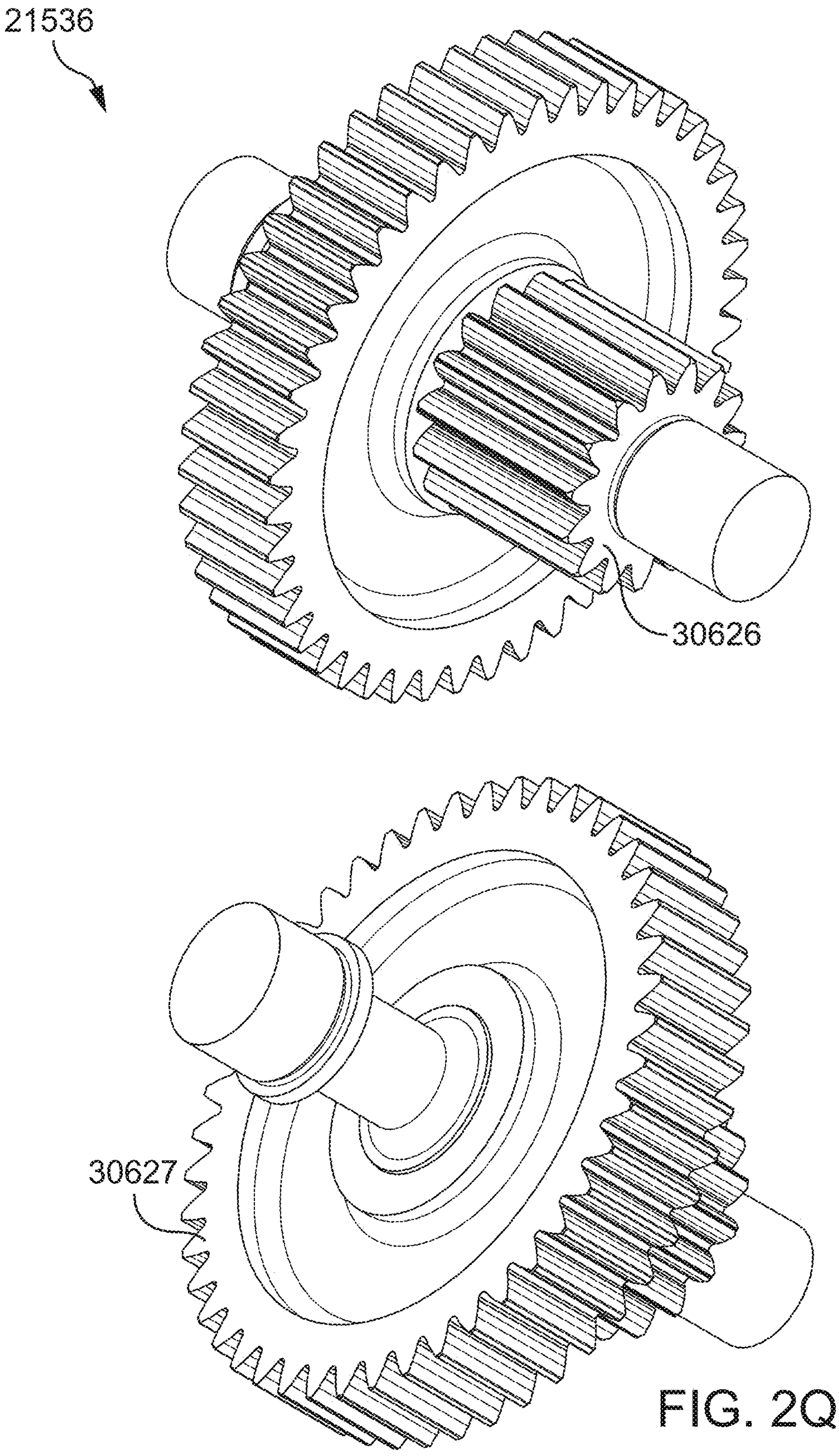
FIG. 2Q is a perspective diagram of the cluster rotate pinion-gear stage 3 pinion of the present teachings.
Figure 2R:
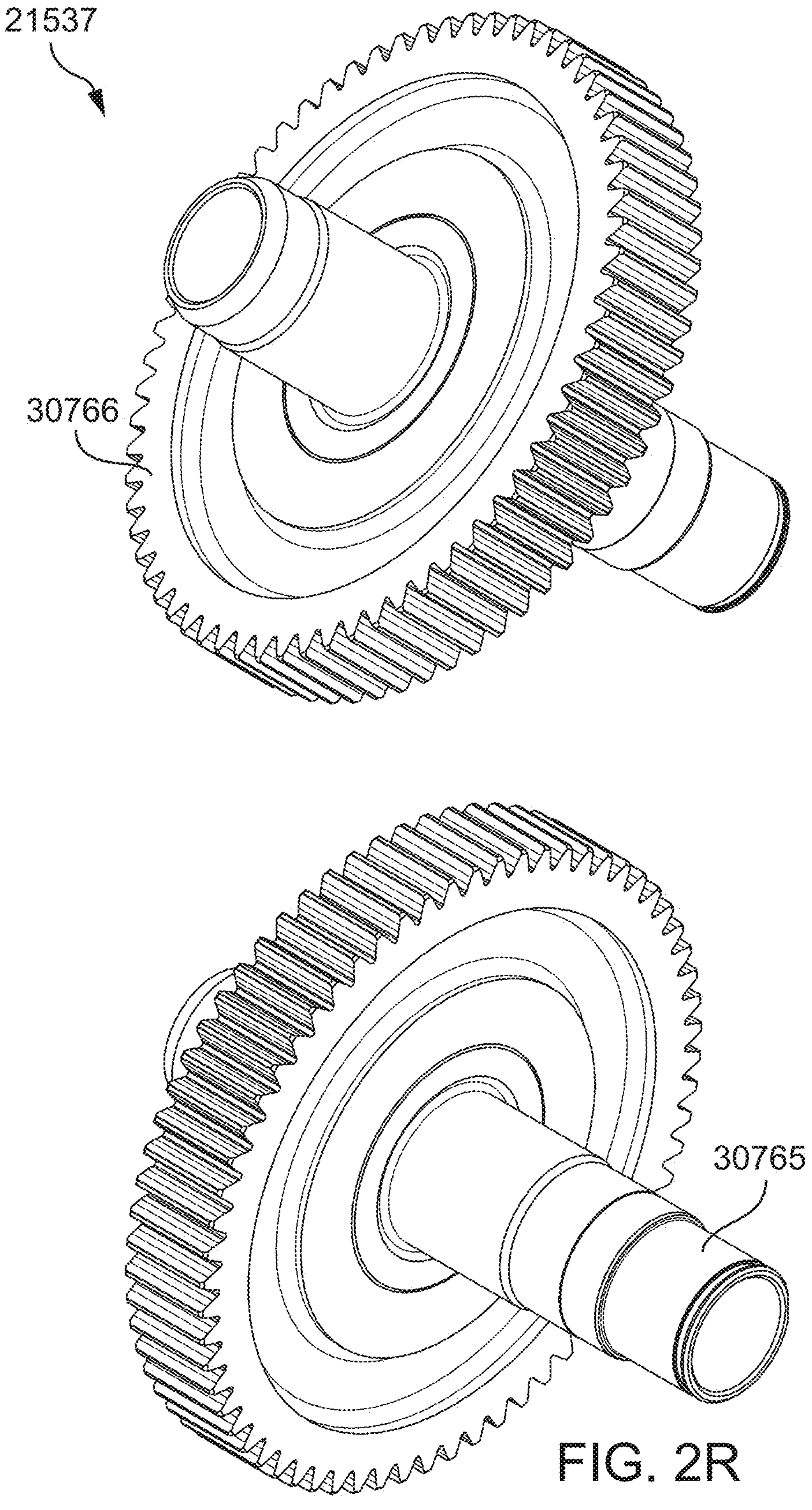
FIG. 2R is a perspective diagram of the cluster rotate gear-pinion cross-shaft stage 3 of the present teachings.
Figure 2S:
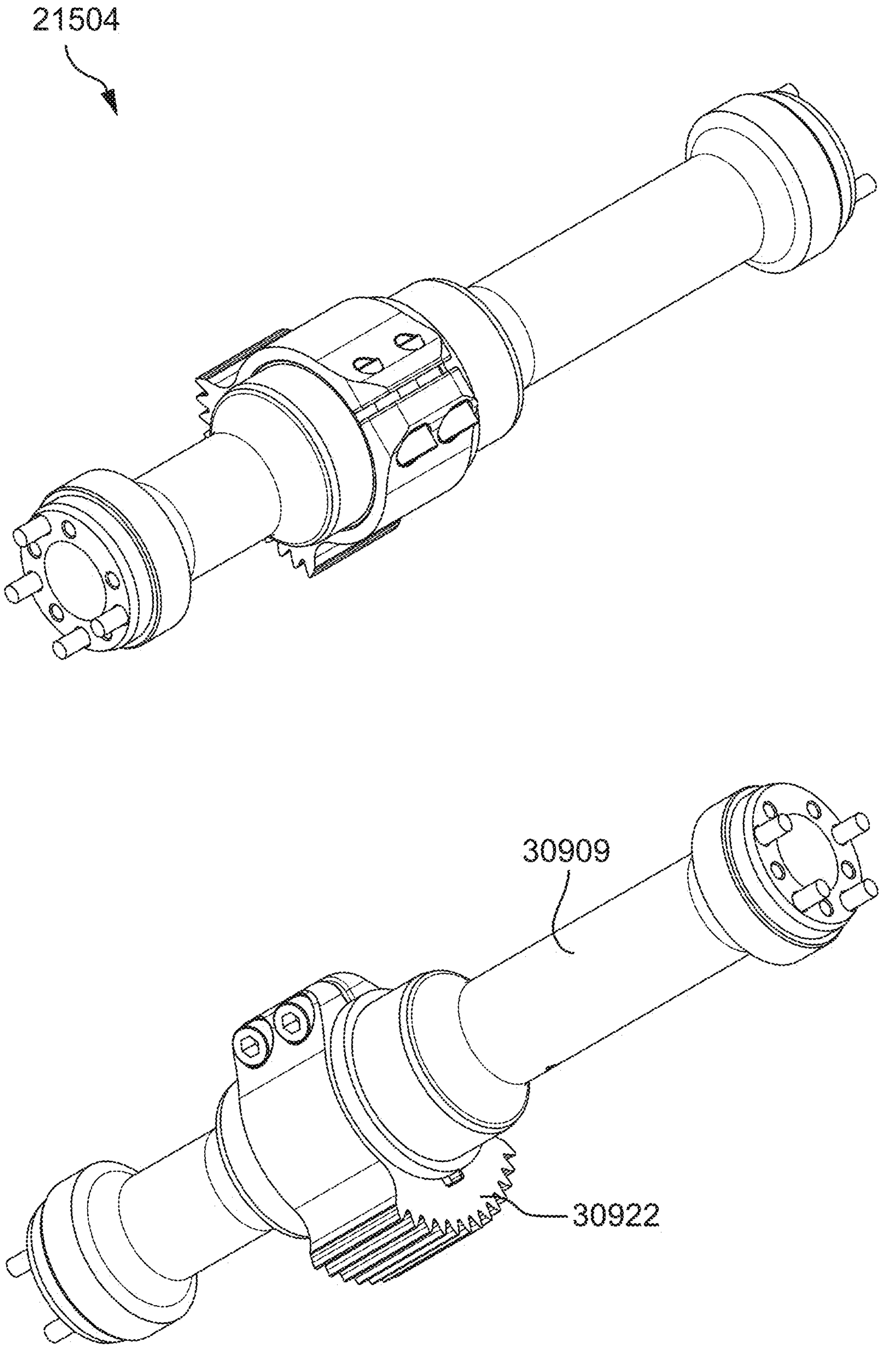
FIG. 2S is a perspective diagram of the sector gear cross shaft of the present teachings.
Figure 2T:
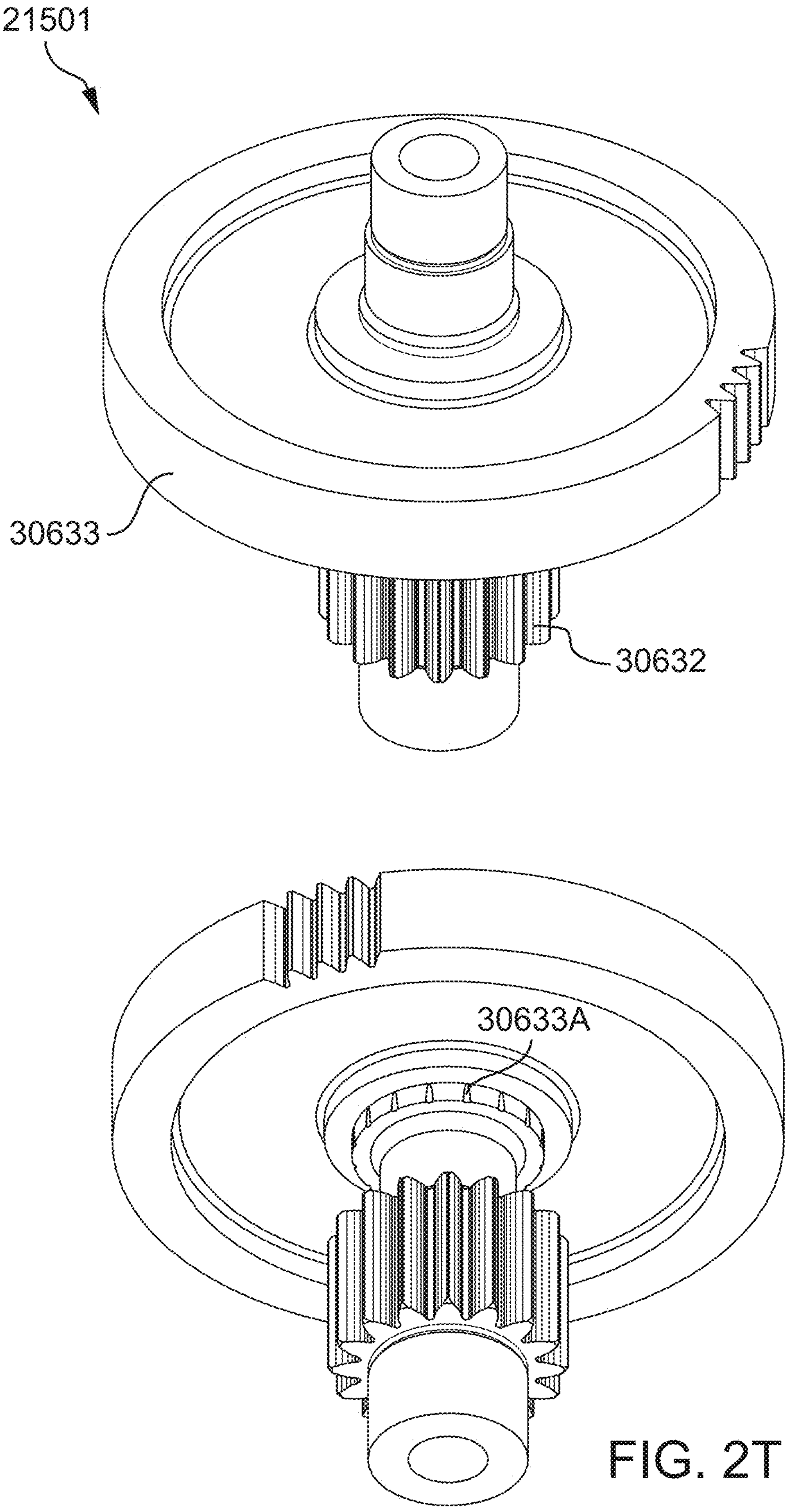
FIG. 2T is a perspective diagram of the pinion-gear height actuator stage 3 pinion of the present teachings.
Figure 2U:
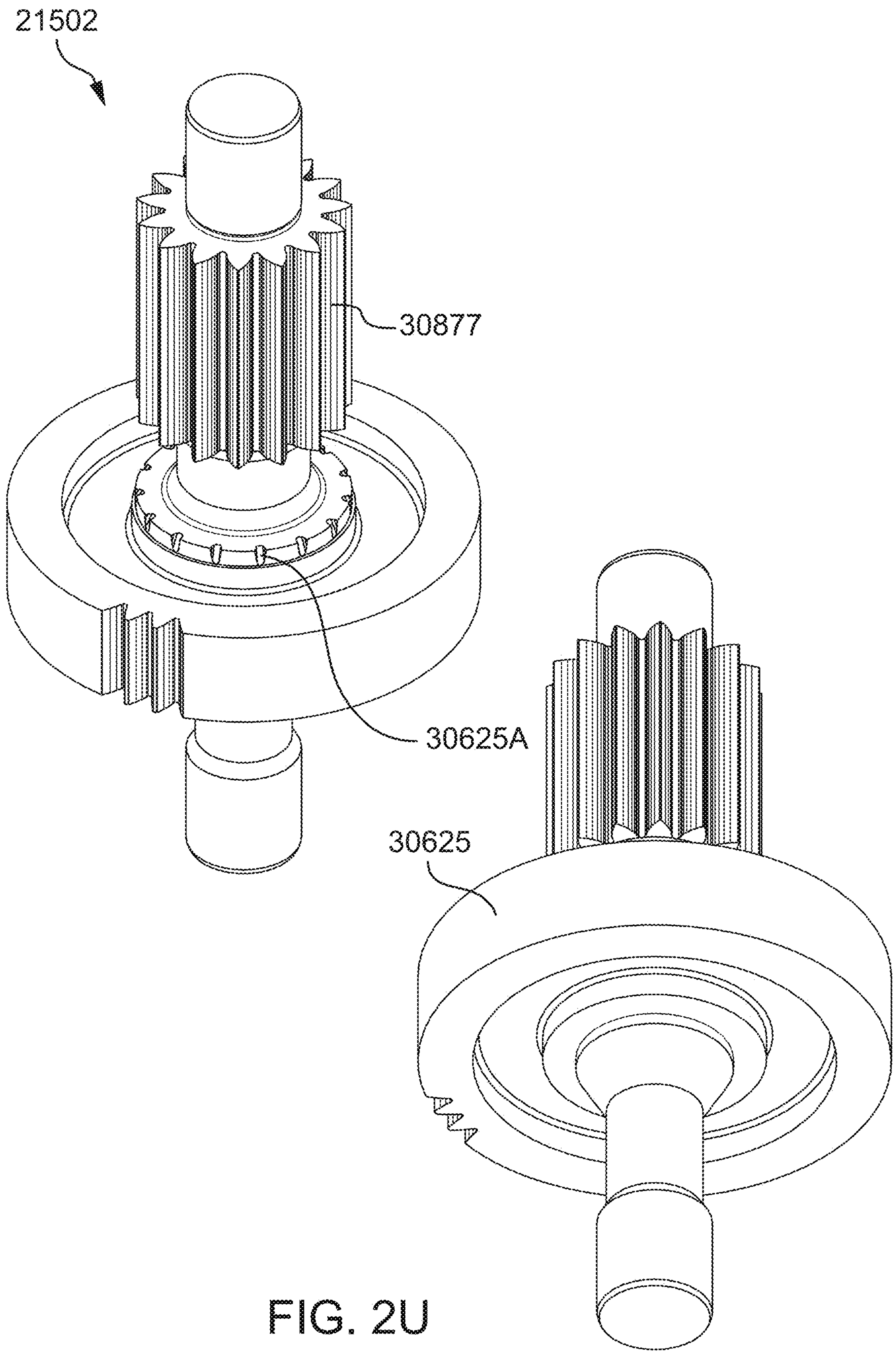
FIG. 2U is a perspective diagram of the pinion-gear height actuator stage 4 of the present teachings.
Figure 2V:
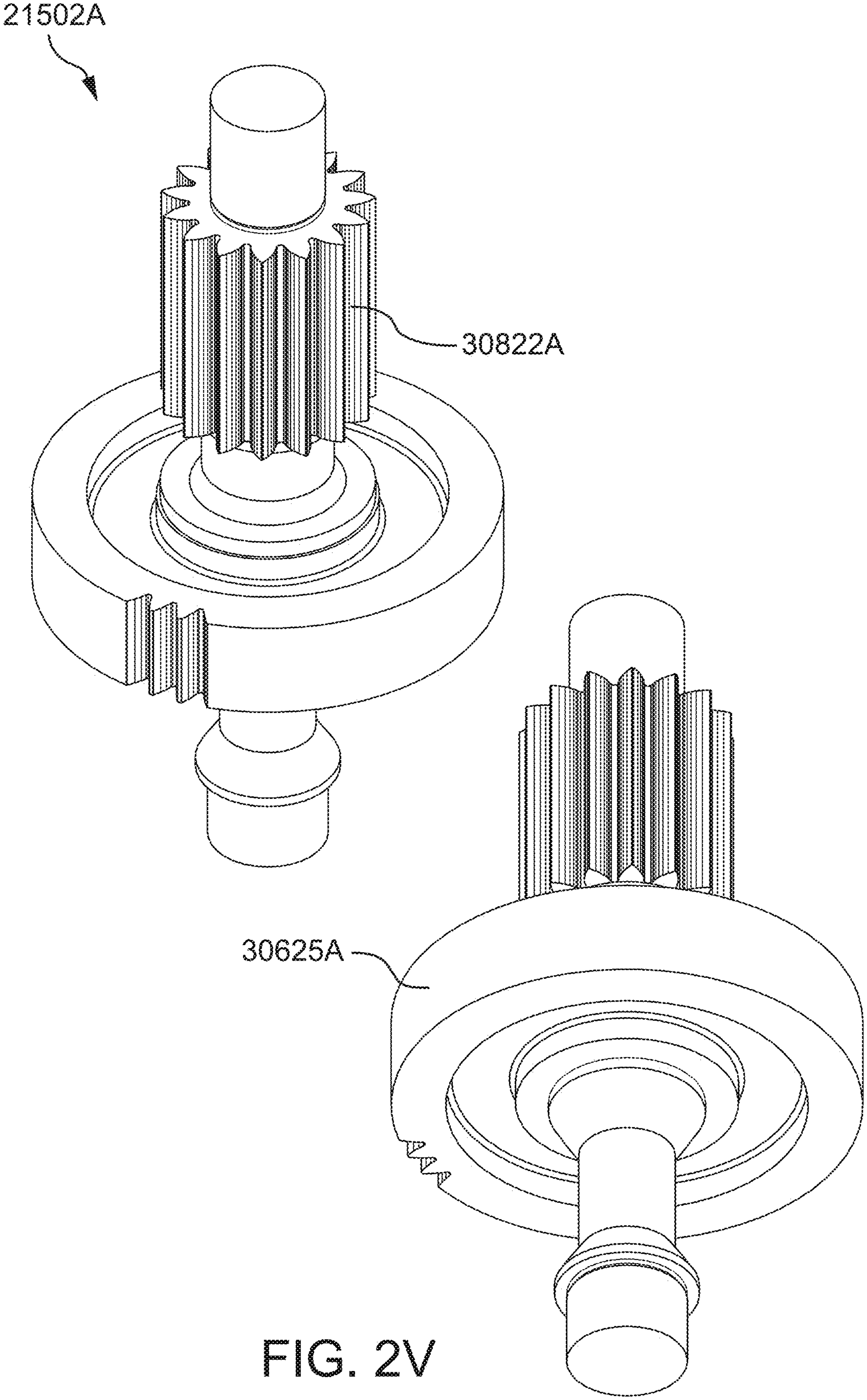
FIG. 2V is a perspective diagram of the second configuration of the pinion-gear height actuator stage 4 of the present teachings.
Figure 5A:
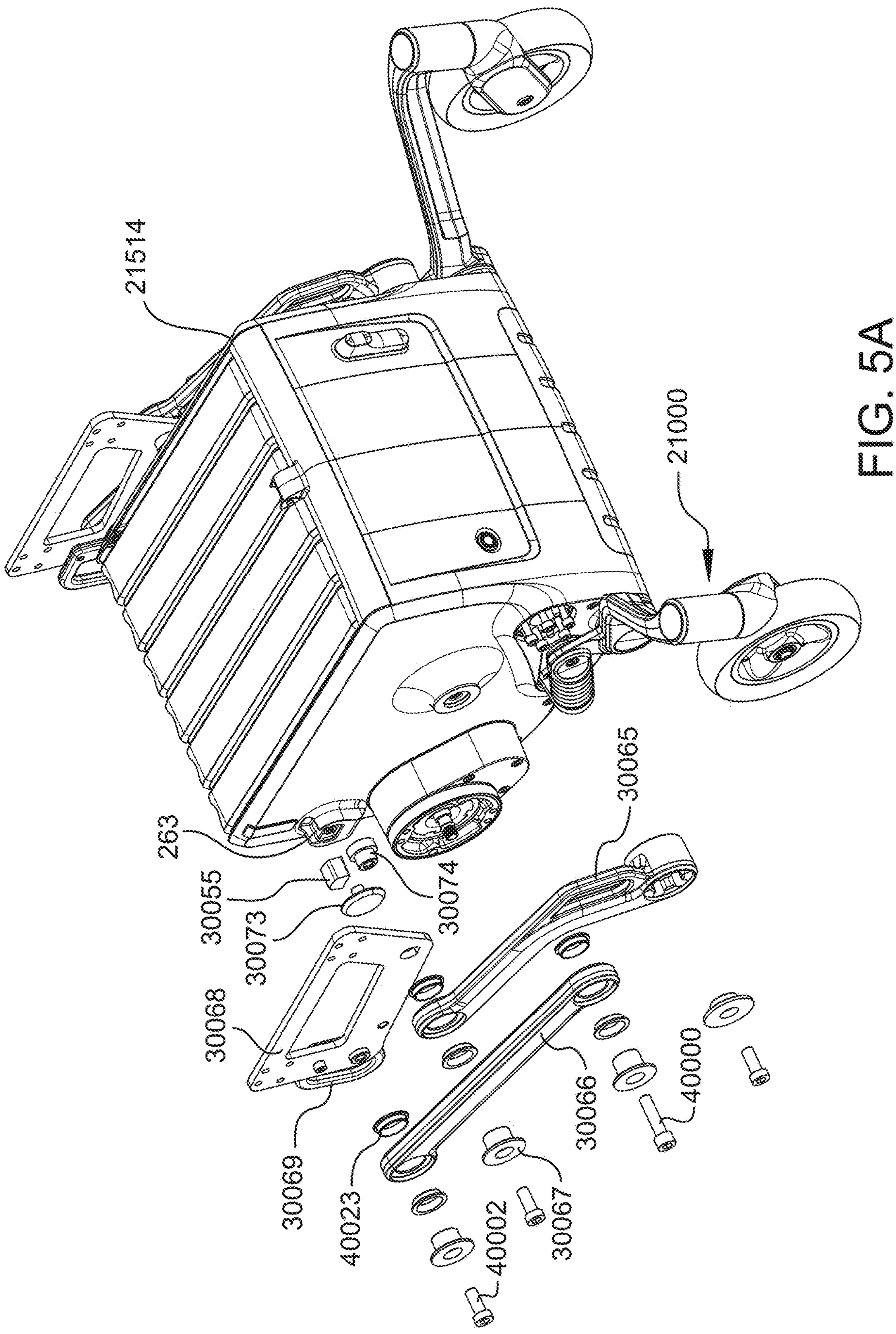
FIG. 5A is a perspective diagram of the linkage arms and seat support structure of the gearbox of the present teachings.

Referring now to FIGS. 2F-2V, the seat drive transmission gear train can include four stages with two outputs. The shaft on the final stage gear can span the powerbase and can provide interfaces to the drive arms. Central gearbox wet section can also include the seat drive gear train that can include the pinion height actuator shaft stage 1 30618 (FIG. 2G, 2N) that can drive pinion-gear height actuator stage 2 21500 (FIG. 2H), that can drive gear height actuator stage 2 30633 (FIG. 2T), that can drive gear height actuator stage 3 30625 (FIG. 2U) and pinion height actuator shaft stage 4 30877 (FIG. 2U). Gear height actuator stage 3 30625 (FIG. 2U) can drive pinion height actuator shaft stage 3 30632 (FIG. 2T). Stage four pinion-gear height actuator 21502 (FIG. 2U) can drive the cross shaft sector gear stage four height actuator 30922 (FIG. 2S) that is mounted upon cross shaft sector gear height actuator stage 4 30909 (FIG. 2S), that is operably coupled at 255 to the left and right lifting arms 30065 (FIG. 5A). Seat absolute position sensor 21578 (FIG. 3L) can be associated with cross shaft sector gear height actuator 30909 (FIG. 2S).

Figure 3A:
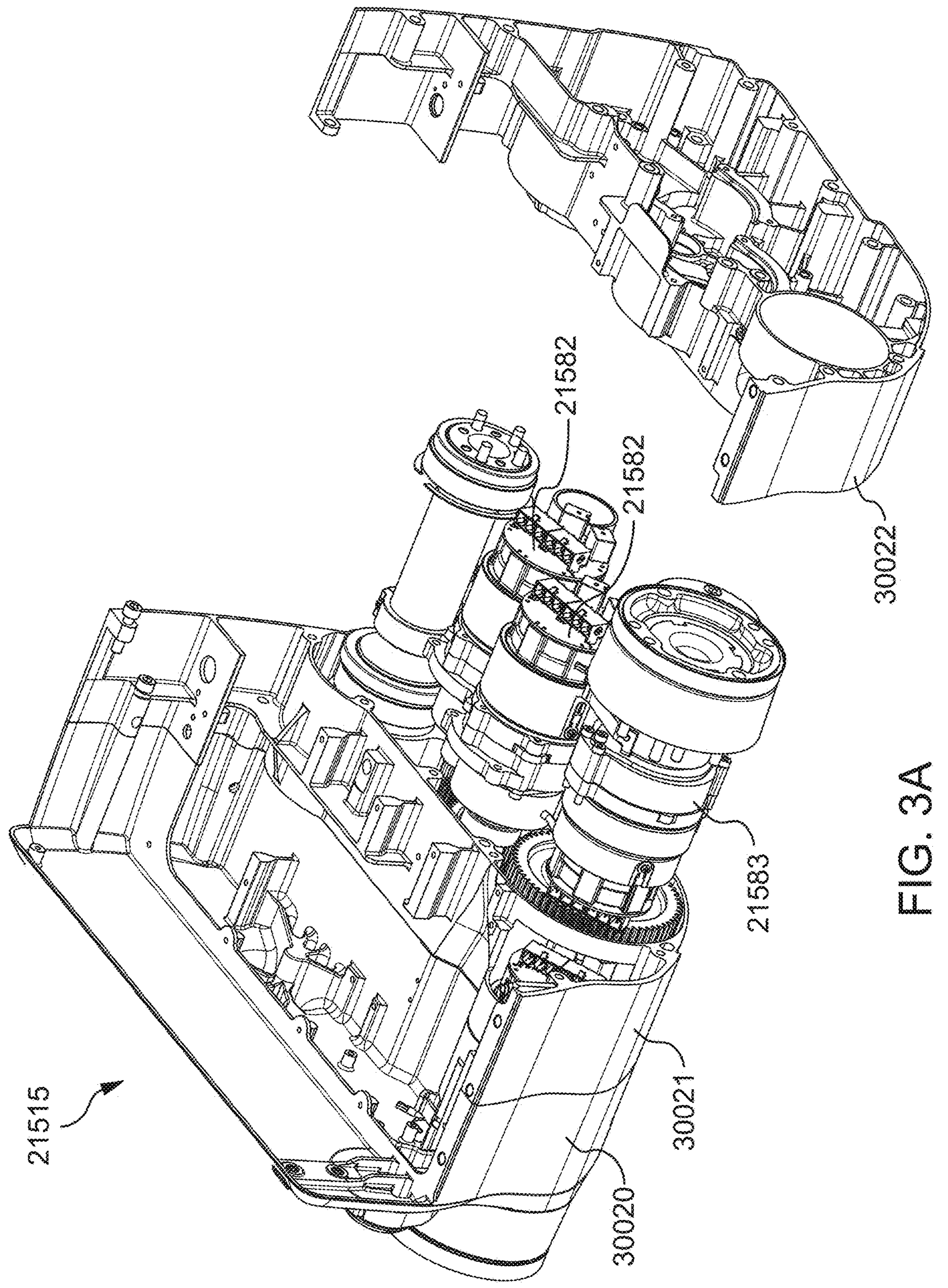
FIG. 3A is a perspective diagram of the motors and sector gear cross shaft of the present teachings.
Figure 3B:
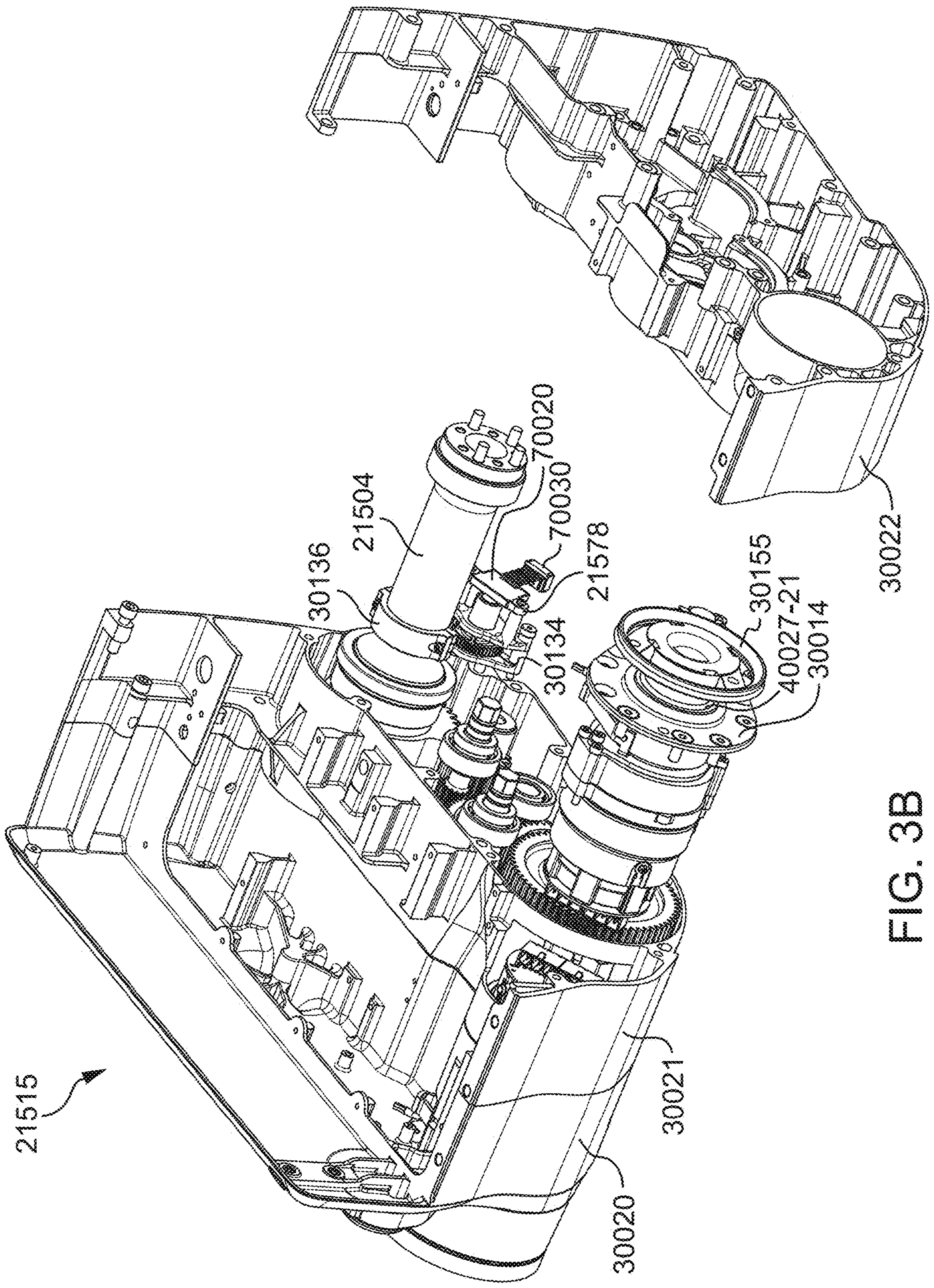
FIG. 3B is a perspective diagram of the cluster and seat position sensor of the present teachings.

Referring now to FIGS. 3A and 3B, seat motors assemblies 21582 (FIG. 3A) and cluster motor assemblies 21583 can be securely positioned within housings 30020, 30021, and 30022. Seat height absolute position sensor 21578 (FIG. 3B) can be operably coupled with gear teeth rear clamp 30135 (FIG. 3J) operably coupled with rear half gear clamp 30135 (FIG. 3J) and mounted upon sector gear cross shaft 30909 (FIG. 3B).

Figure 3C:
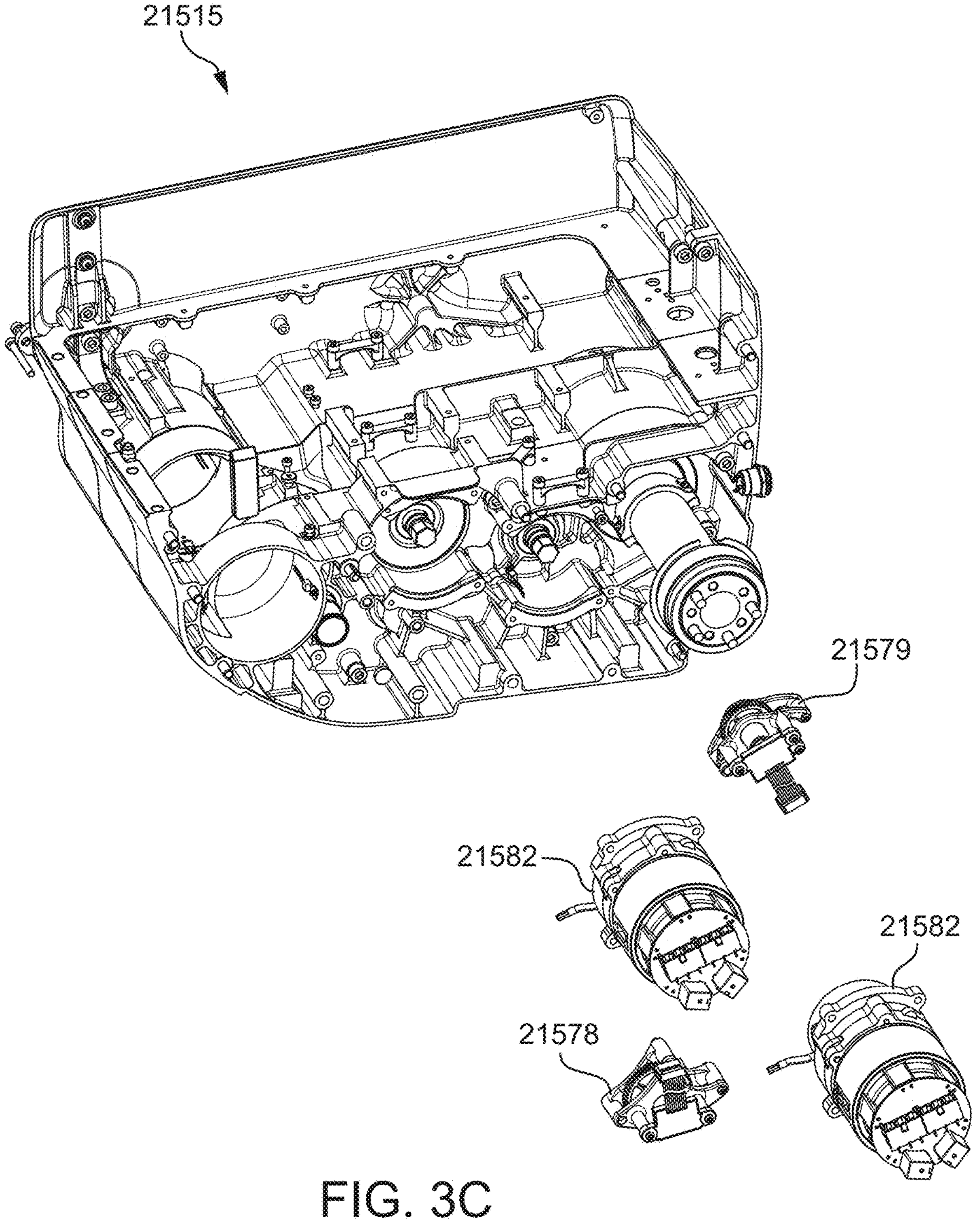
FIG. 3C is a perspective diagram of the motors and sensors of the present teachings.
Figure 3D:
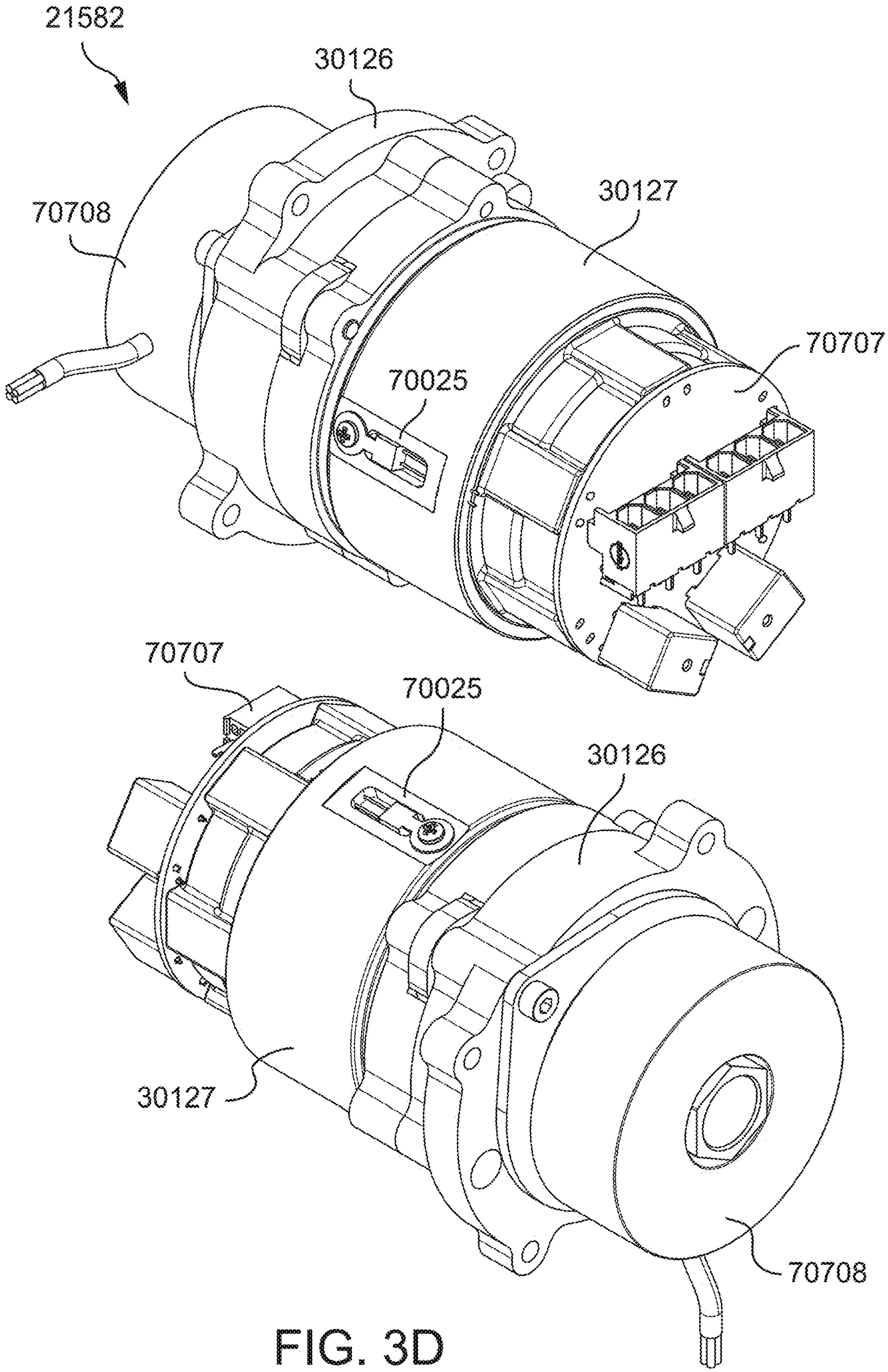
FIG. 3D is a perspective diagram of the seat/cluster motor of the present teachings.
Figure 3E:
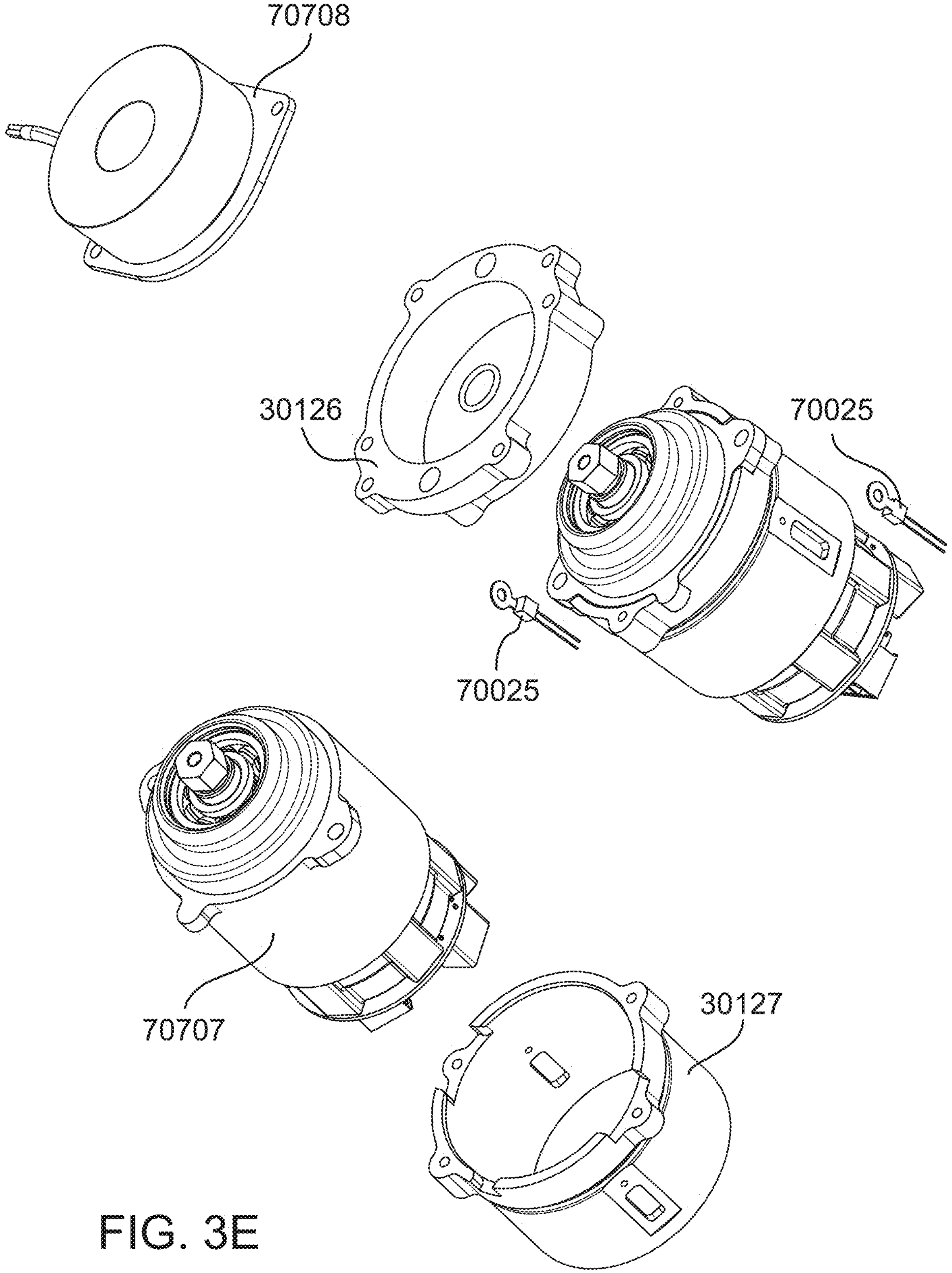
FIG. 3E is an exploded perspective diagram of the seat/cluster motor of the present teachings.
Figure 3F:
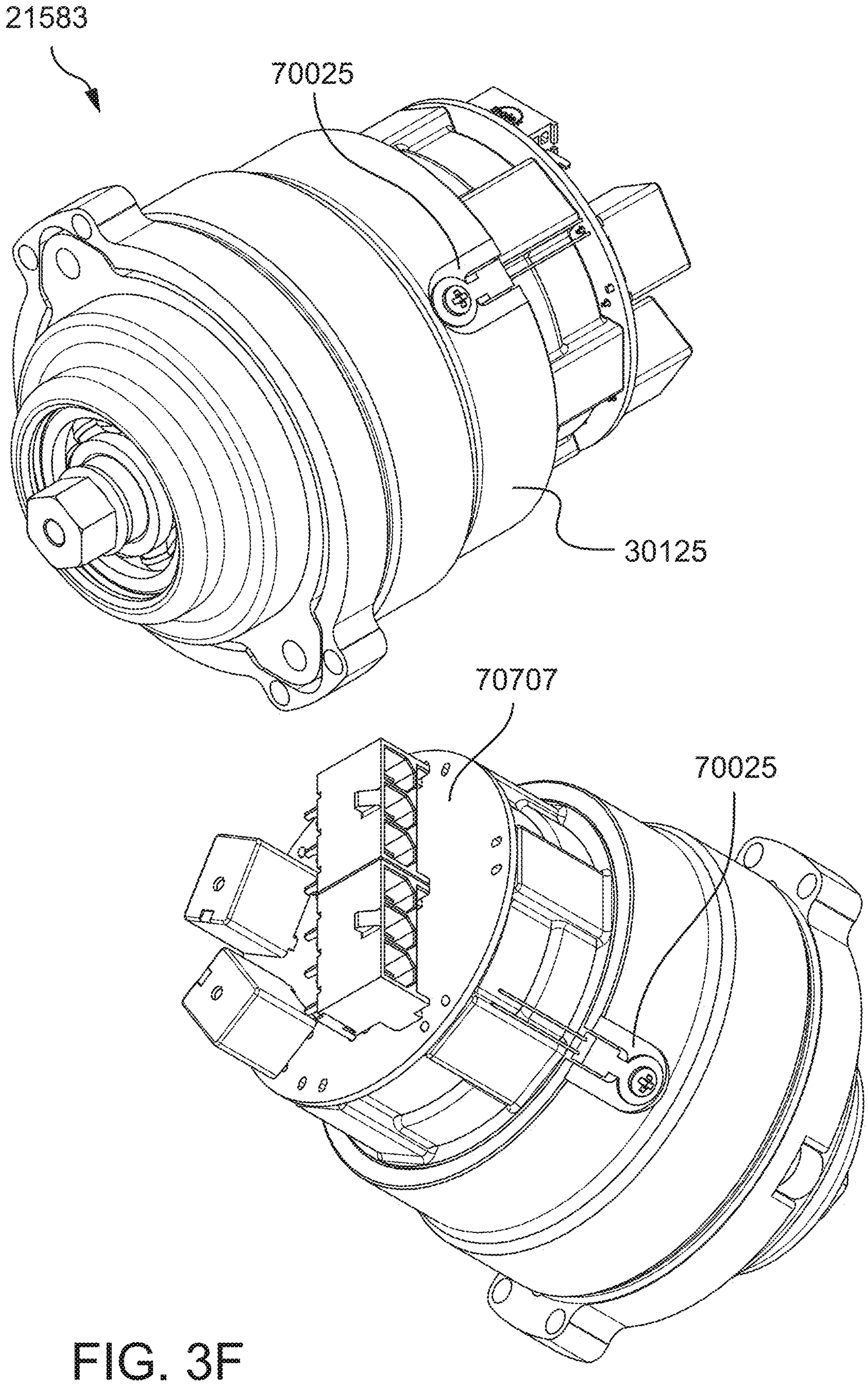
FIG. 3F is a perspective diagram of the wheel motor of the present teachings.
Figure 3G:
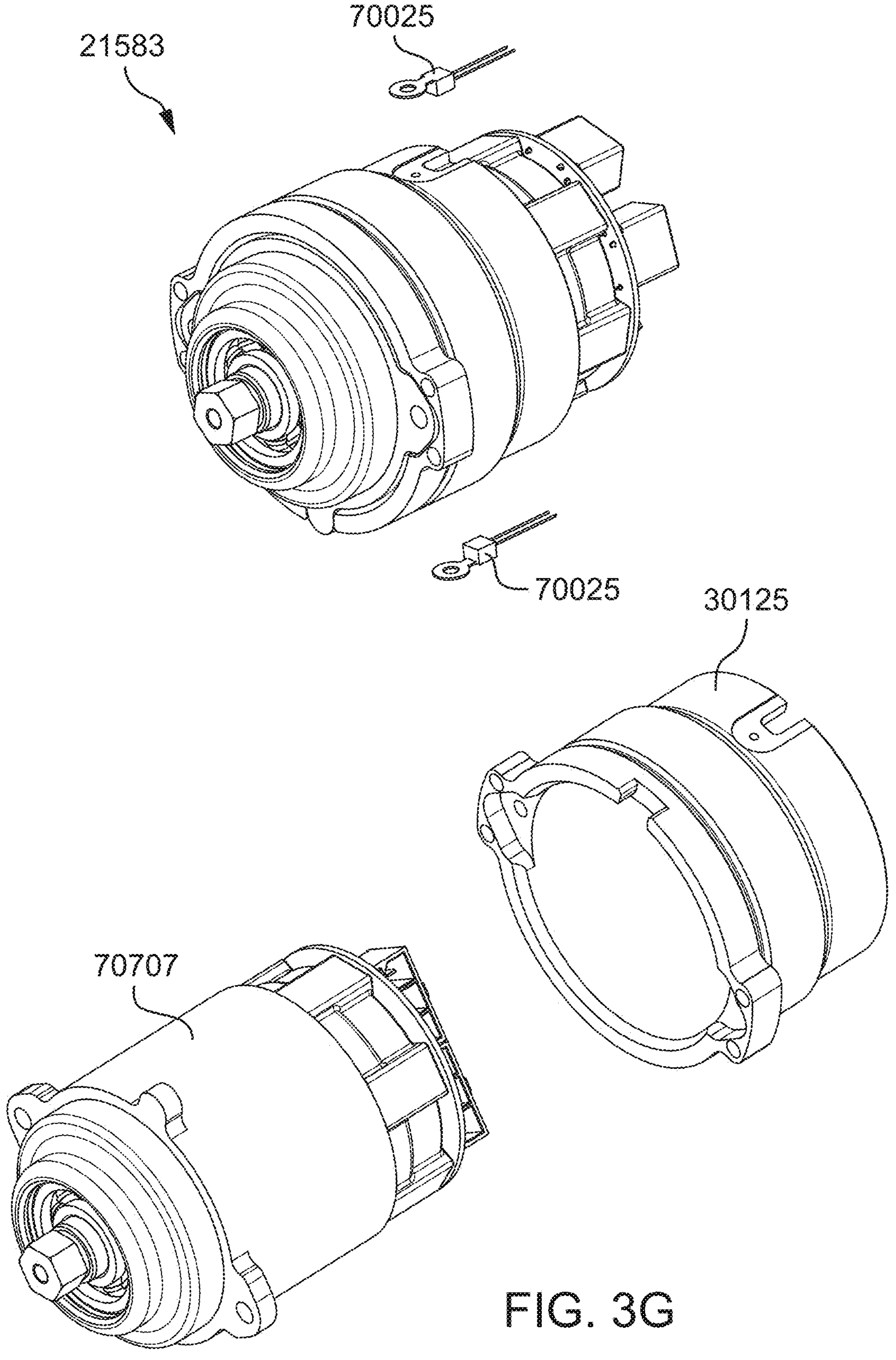
FIG. 3G is an exploded perspective diagram of the wheel motor of the present teachings.
Figure 3H:
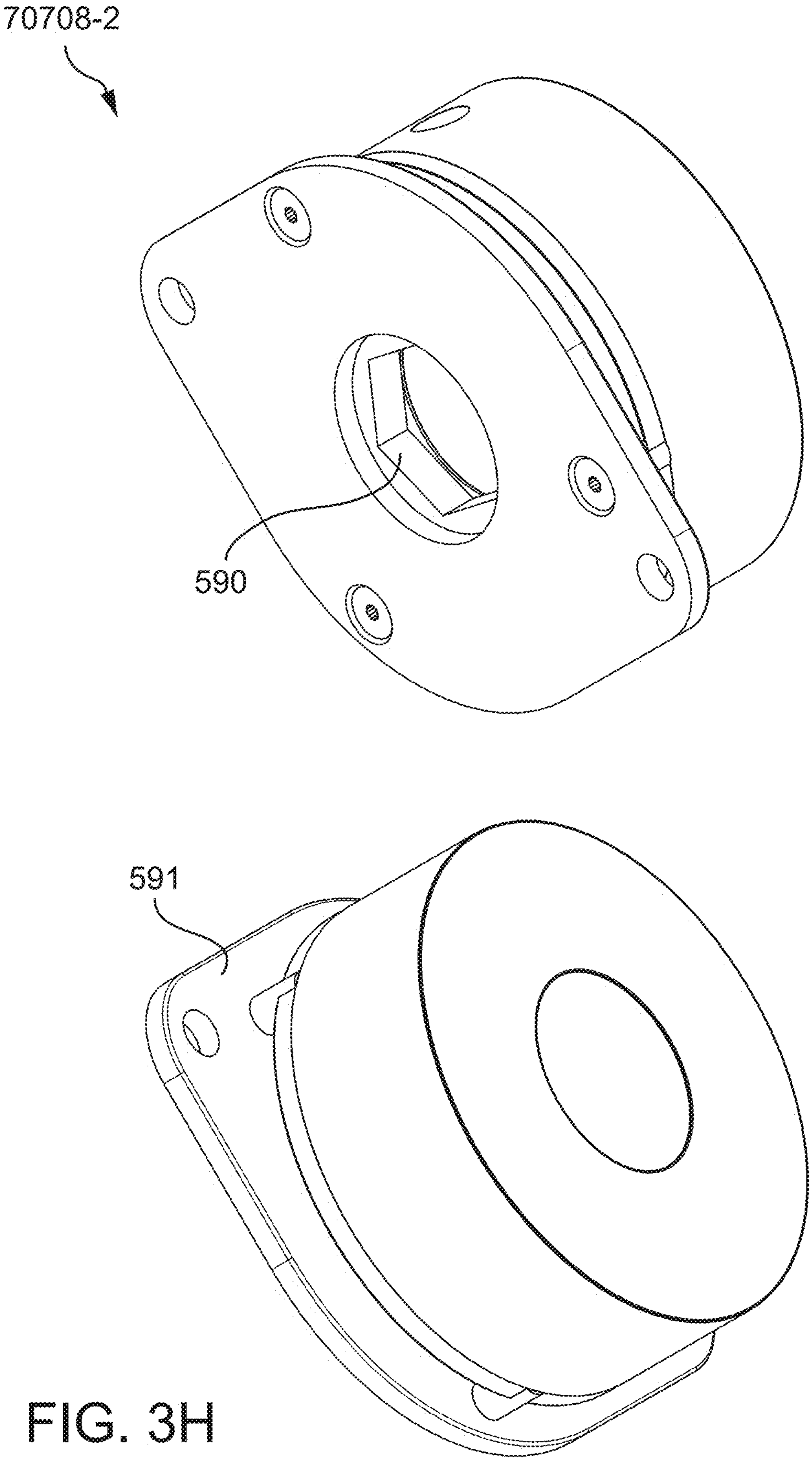
FIG. 3H is a perspective diagram of the brake without brake lever of the present teachings.

Referring now primarily to FIG. 3C, central gearbox housings 21515 can include mounting areas for seat/cluster brakes, motors, and sensors. Each drive transmission can include a motor, brake, and gear transmission. The brake can be disengaged when electrical power is applied, and can be engaged when electrical power is removed. A seat/cluster motor mounting area can house motor mount bottom 30126 (FIGS. 3D and 3E) and motor mount top 30127 (FIGS. 3D and 3E), seat/cluster motor assembly 21582 (FIGS. 3D and 3E), DC motor 70707 (FIG. 3D) and brake without manual release 70708-2 (FIG. 3H). A wheel motor mounting area can house wheel motor assembly 21583 (FIGS. 3F and 3G), motor mount top 30125, and brake without manual release 70708-2 (FIG. 3H). In some configurations, seat and cluster cross shafts, motors, brakes, and motor couplings can include the same or similar parts. Motors can provide the primary types of motion on the MD: wheel, cluster and seat. Wheel motors 21583 (FIG. 3F) can drive each wheel transmission. Cluster motor 21582 (FIG. 3D) can drive the cluster transmission. Device safety and reliability requirements can suggest a dual redundant, load sharing motor configuration. Each motor can have two sets of stator windings, mounted in a common housing. Two separate motor drives can be used to power the two sets of stator windings. The power supply for each drive can be a separate battery. This configuration can minimize the effects of any single point failure in the path from battery 70001 (FIG. 1E) to motor output. Each set of stator windings, together with its corresponding segment of the rotor (referred to as a motor half) can contribute approximately equal torque during normal operation. One motor half can be capable of providing the required torque for device operation. Each motor half can include a set of rotor position feedback sensors for commutation. Seat/cluster motors 21582 (FIG. 3D) and wheel motors 21583 (FIG. 3F) can include, but are not limited to including, a single shaft and a dual (redundant) stator brushless DC electric (BLDC) motor operating at up to 66 VDC with a sine drive (voltage range 50-66 VDC). The motors can include two 12-V relays mounted on an interface board. One relay can govern the activity of the motor. In some configurations, there can be three sensor outputs per motor half, each sensor being 60° offset from the next. Sensors can include, for example, but not limited to, Hall sensors. The sensors can be used for commutation and can provide position information for further feedback. The motors can include a dual motor winding, drive, and brake coil configuration. That is, two separate sets of motor windings and two separate motor drives can be utilized in driving one shaft. Similarly, the brake drives can be used to drive two coils to disengage the brake for one shaft. This configuration can allow the system to respond to a single point failure of the electronics by continuing to operate its motors and brakes until a safe state can be achieved. The seat and cluster motor shafts are aligned with the seat and cluster drive train input shafts by the motor couplings as the motors are installed. The motor shafts are secured in this correct alignment by motor mount fasteners.

Continuing to refer to FIG. 3C, the mechanical package of each seat sensor 21578 (FIG. 3M) and cluster sensor 21579 (FIG. 3O) can house two independent electronic sensors that can relay information to PBC board 50001 (FIG. 15B). Seat position sensor processor A (FIG. 18C) and cluster position sensor processor A (FIG. 18C) can receive position information into A-side electronics, and seat position sensor processor B (FIG. 18D) and cluster position sensor processor B (FIG. 18D) receive position information into the B-side electronics, providing redundant electronics that can enable full system operation even if one side of the electronics has issues. Seat sensors and cluster sensors that feed A- and B-side electronics can be co-located to enable measurement of similar mechanical movement. Co-location can enable results comparison and fault detection. The absolute seat and cluster position sensors can report the position of the seat and cluster, and can be referenced each time the MD is powered up, and as a backup position reference when the MD is powered. While the MD is powered, position sensors built into seat and cluster motors can be used to determine seat and cluster position. Seat position sensor upper/lower housings 30138/30137 (FIG. 3M) can house the electronic sensors, shaft, and gear of the single stage gear train that connects the sensors to sector gear cross shaft assembly 21504 (FIG. 3J) and the cluster cross shaft 30765 (FIG. 6D) respectively. The shaft and gear can be molded as a single part, for example, from a plastic such as, for example, a lubricous plastic that can enable molding with no additional bearing material or lubricant.

Referring now to FIGS. 3D-3G, seat/cluster motor 21583 (FIG. 3F) and wheel motors 21582 (FIG. 3D) can each include at least one thermistor 70025 that can be thermally connected to the motors. At least one thermistor 70025 can report temperature data to the A-side and B-side electronics. The temperature data can be used, for example, but not limited to, for reducing power usage when the motors reach a pre-selected threshold temperature to avoid damage to the motors. In some configurations, each motor can include two thermistors 70025—one for each redundant half of the motor. Thermistor 70025 can be affixed to a sleeve that can be operably coupled with the laminations that make up the motor body. Thermistor 70025 can enable an indirect estimate of the motor winding temperature. The temperature data for a particular motor can be routed to the processor associated with the motor. In some configurations, the temperature data can be quantized by the analog/digital converter on the processor, if necessary, and the quantized values can be fed into a temperature estimator algorithm. The algorithm can include a model of the heat transfer path, empirically derived for each motor, that can account for the electrical power delivered to the windings, the heat flux through the windings and housing (where thermistor 70025 makes its measurement), and from the housing to the chassis the motor is mounted to. A thermal estimator algorithm can use the electrical current going to the motor as well as the motor housing (thermistor) temperature to provide an estimate of motor winding temperature and other variables such as, but not limited to, motor speed. If the motor is spinning quickly, there can be greater heating due to, for example, eddy current losses. If the motor is stalled, the current can be concentrated in one phase and can increase the rate of heating in that winding. The thermistor signal can be transmitted along the cable between the motor and PBC 50001 (FIG. 15B). At PBC 50001 (FIG. 15B), each motor cable can break into two connectors: (1) first connector 50001-1A (FIG. 15B) including pins for three motor phase wires, and second connector 50001-1B (FIG. 15B) for Hall sensors, phase relay, brake, and thermistors 70025. In some configurations, first connector 50001-1A (FIG. 15B) can include, but is not limited to including, a 4-pin Molex Mega-Fit connector. In some configurations, second connector 50001-1B (FIG. 15B) can include, but is not limited to including, a 10-pin Molex Micro-Fit connector. The motors of the MD can be thermally pressed into the housings of the MD that are fastened to the central housing. The thermal pressing can provide a thermal conduction path from the motors to the central housing.

Figure 3I:
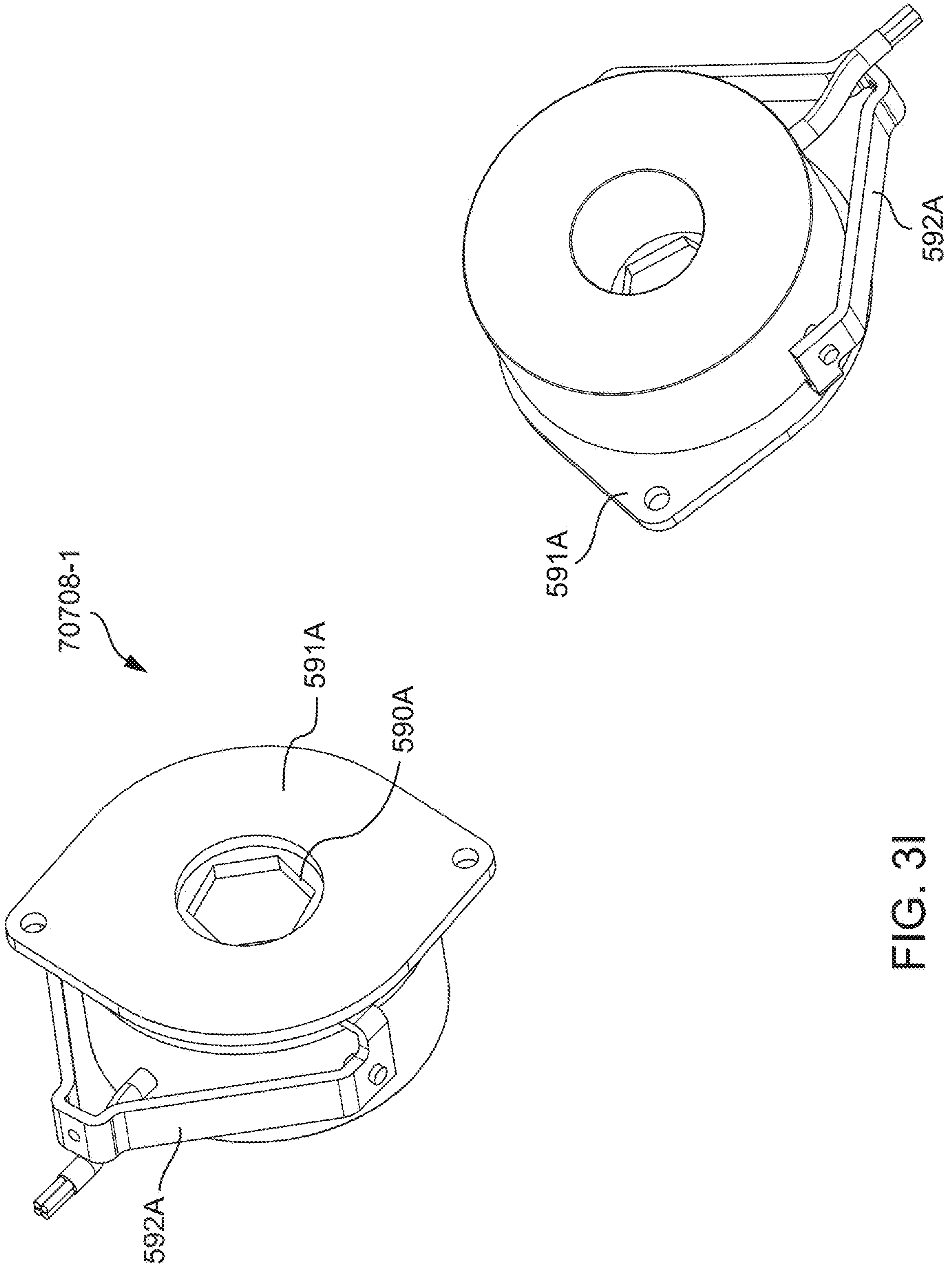
FIG. 3I is a perspective diagram of the brake with brake lever of the present teachings.

Referring now to FIGS. 3H and 3I, separate electromagnetic holding brakes can be coupled to each motor. The electromagnetic holding brakes can include two electrically isolated coils, and each can be energized by a brake drive in each of the motor drives. The brake can disengage when both of its coils are energized, and can be disengaged when only one of its coils is energized. The brakes can be designed to automatically engage when the unit is off or in the case of a total power loss, therefore holding position and/or failing safe. The electromagnetic brakes can be used to hold the MD in place when the wheels are not in motion and similar brakes can hold the cluster and seat in place when not in motion. The brakes can be controlled by commands from the powerbase processors. When the MD is powered down, the brakes can automatically engage to prevent the MD from rolling. If the automatic brakes are manually disengaged at power on, the motor drives can activate to hold the MD in position and the system can report to the user that the wheel brakes have been disengaged. If a brake lever is disengaged after power is on, power off requests can be blocked, under some circumstances, to avoid unintentional rolling of the MD after it has powered down. Disengaging the automatic brakes can be used to manually push the MD when it is powered off. Each of the four motors that drive the right wheels, left wheels, cluster and seat can be coupled to a holding brake. Each brake can be a spring-applied, electromagnetically released brake, with dual redundant coils. In some configurations, the motor brakes can include a manual release lever. Brake without brake lever 70708-2 (FIG. 3H) can include, but is not limited to including, motor interface 590 and mounting interface 591. In some configurations, motor interface 590 can include a hexagonal profile that can mate with a hexagonal motor shaft. Brake with brake lever 70708-1 (FIG. 3I) can include mounting interface 591A that can include hexagonal profile 590A. Brake with brake lever 70708-1 can include manual brake release lever 592A that can operably couple with brake release spring arms 30000 (FIG. 9G) that can operably couple with spring 40037 (FIG. 9J).

Referring to FIGS. 3 CCQ and 3R, noise encountered during operation of the MD can be reduced. In some configurations, a coating of, for example, but not limited to, a rubber-like substance can be applied to either the exterior of motor coupling 70808-1 (FIG. 3 CCQ) or 70808-2 (FIG. 3-R), or the interior of disk 590A (FIG. 3R) to cushion low speed impacts and reduce sound.

Figure 3J:
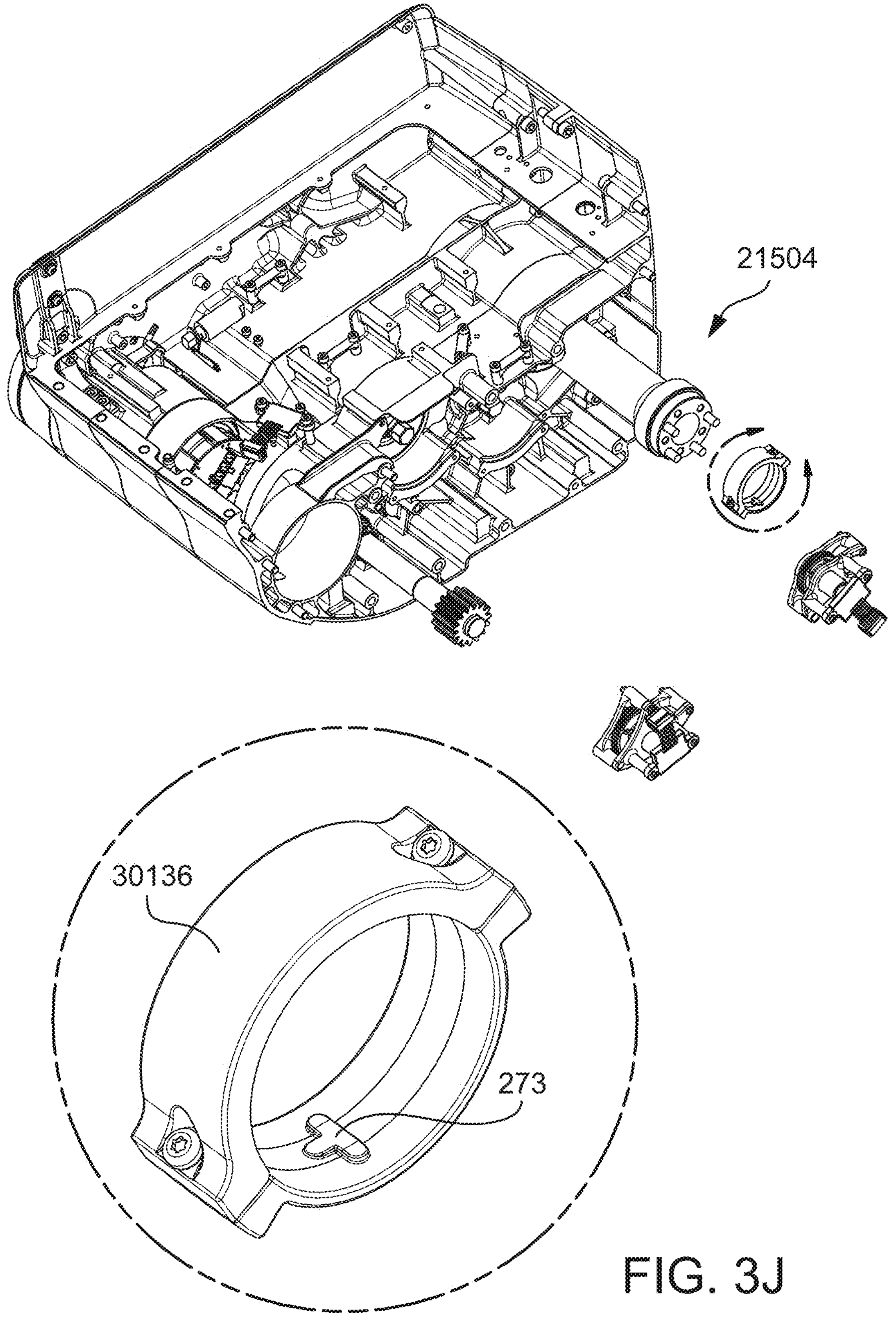
FIG. 3J is a perspective diagram of the mating notch on the gear clamp of the present teachings.
Figure 3K:
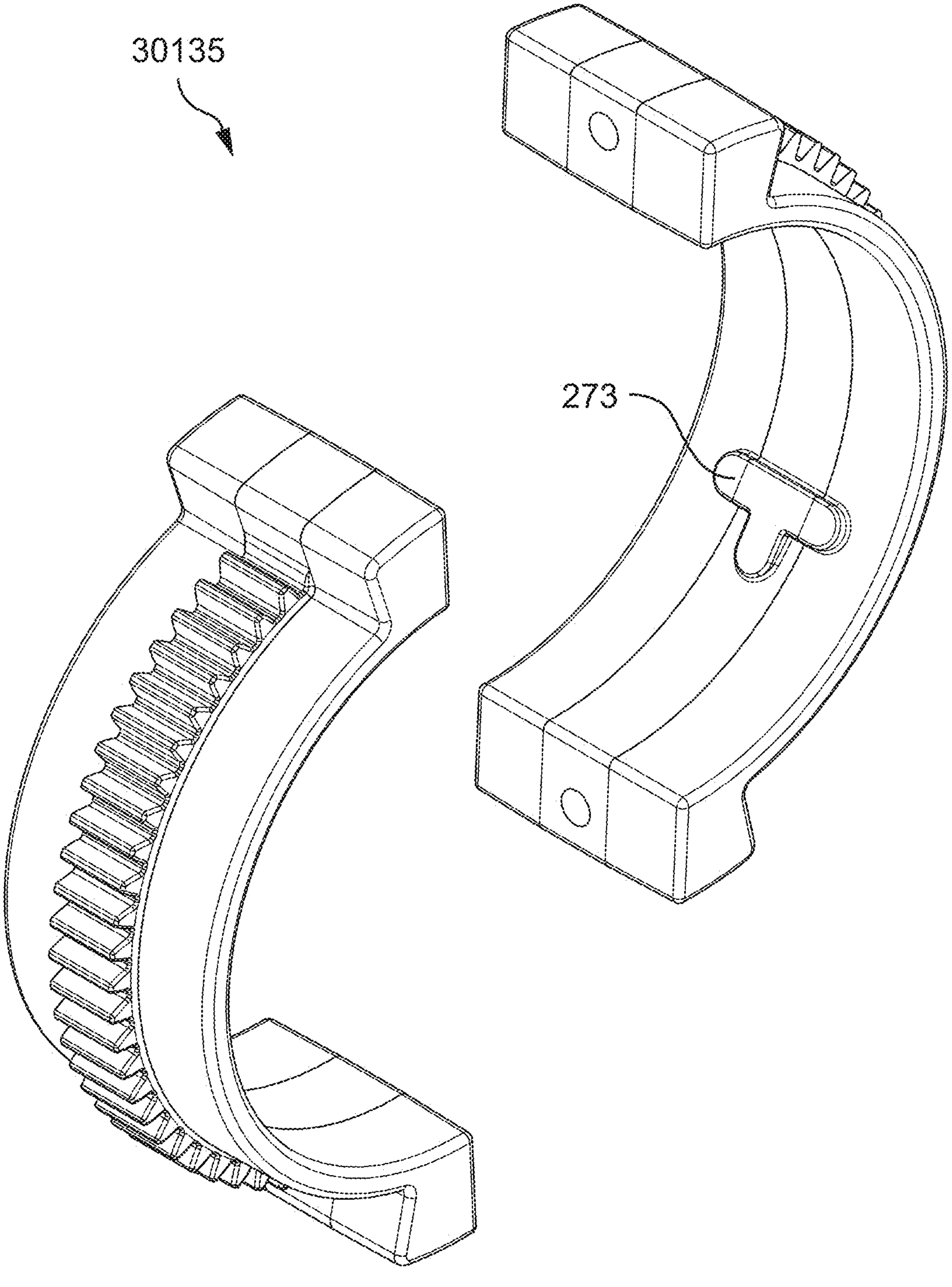
FIG. 3K is a perspective diagram of the seat position sensor gear teeth clamp with mating notch of the present teachings.
Figures 1, 3K:
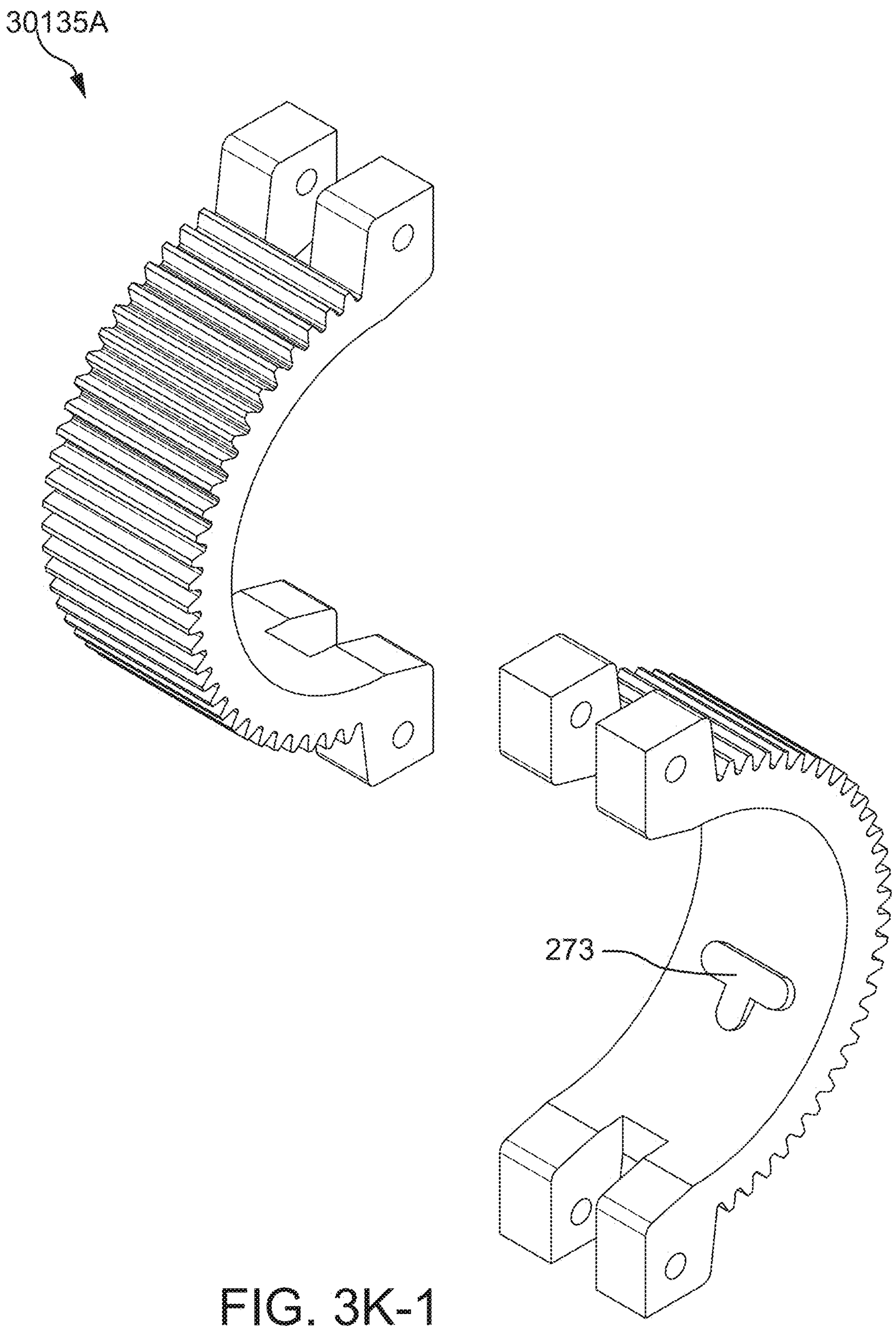
Figure 3L:
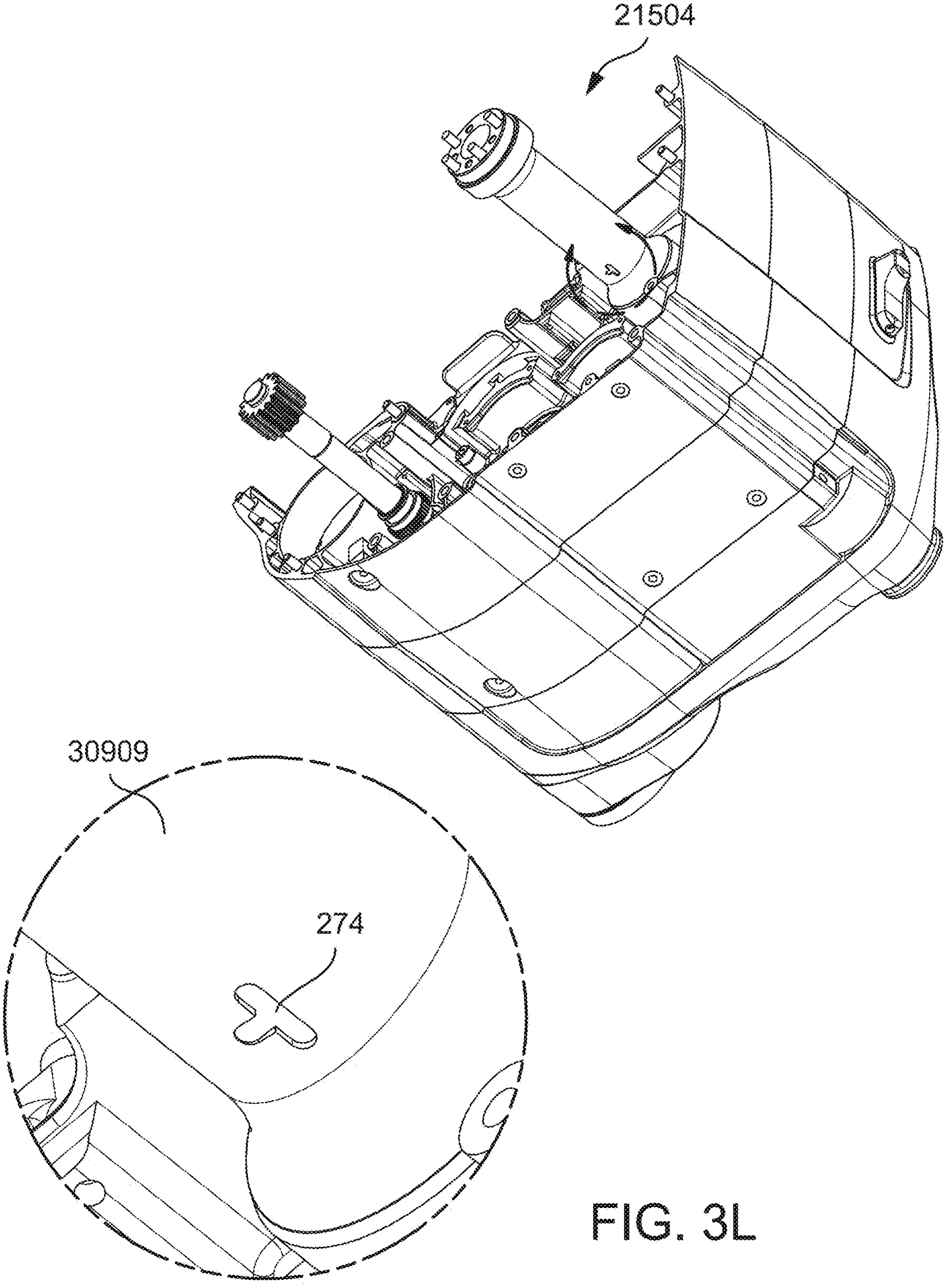
FIG. 3L is a perspective diagram of the mating notch of the seat position sensor of the present teachings.
Figure 3M:
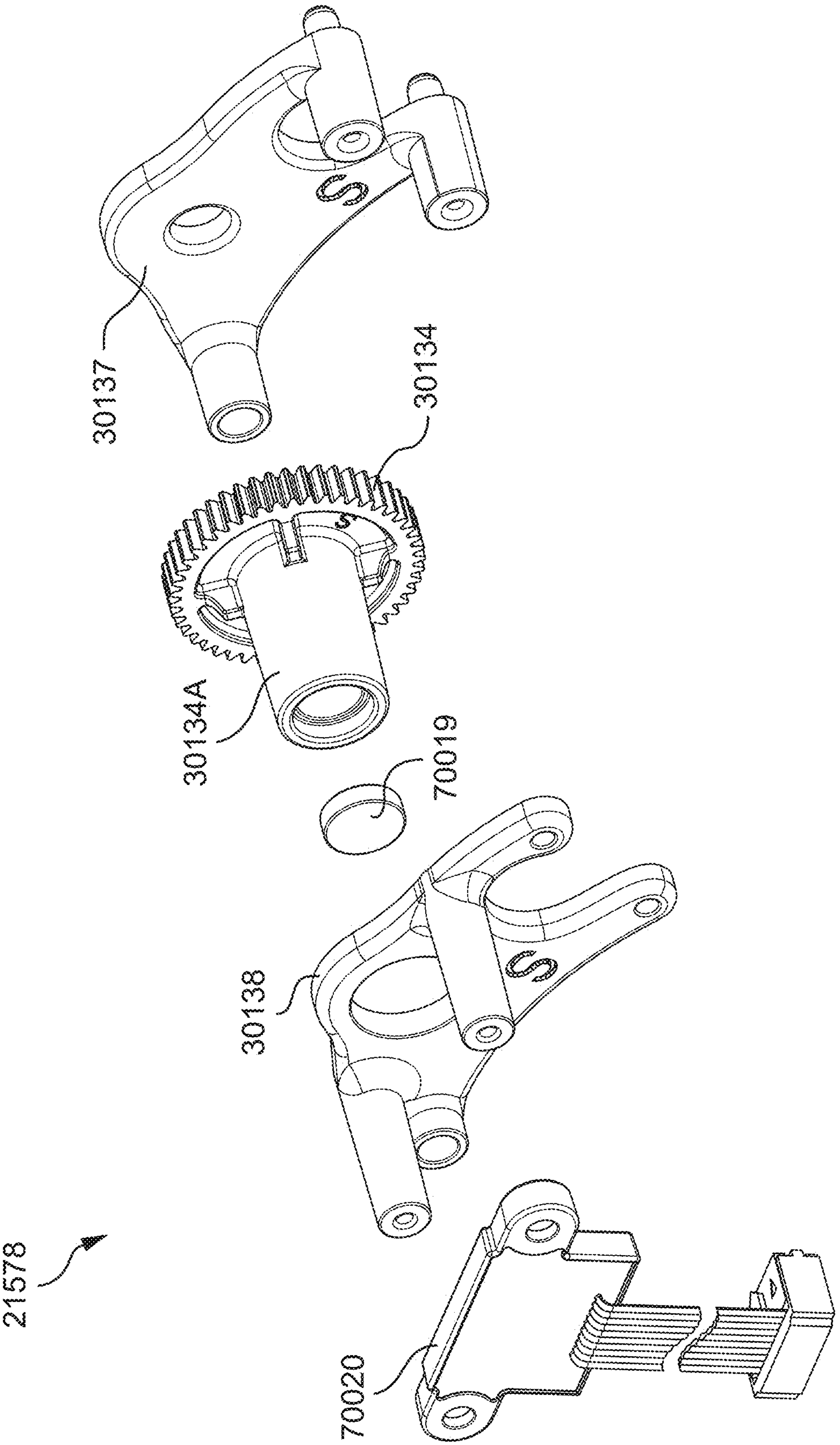
FIG. 3M is an exploded perspective diagram of the seat position sensor of the present teachings.
Figure 3N:
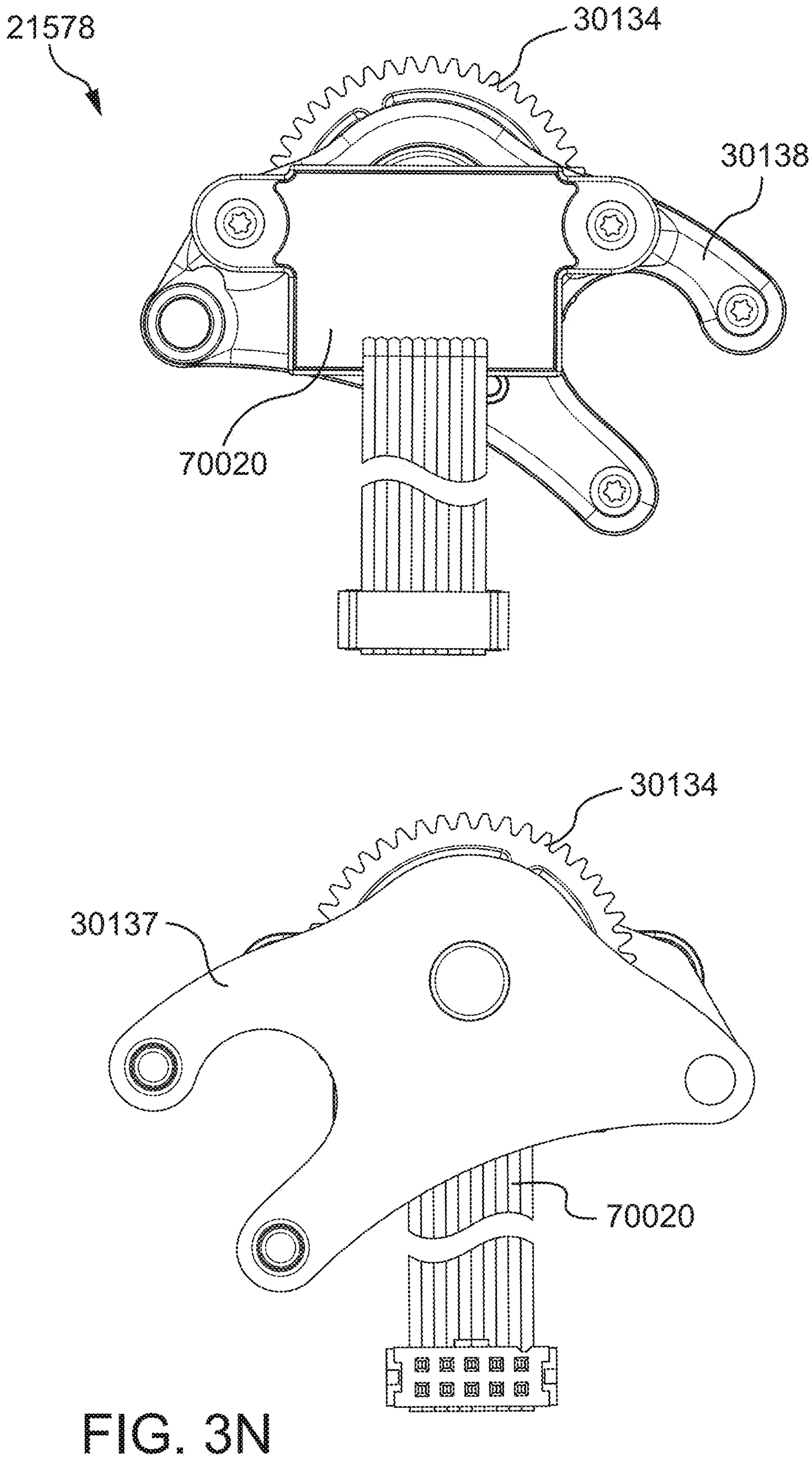
FIG. 3N is a plan view of the seat position sensor of the present teachings.
Figure 3O:
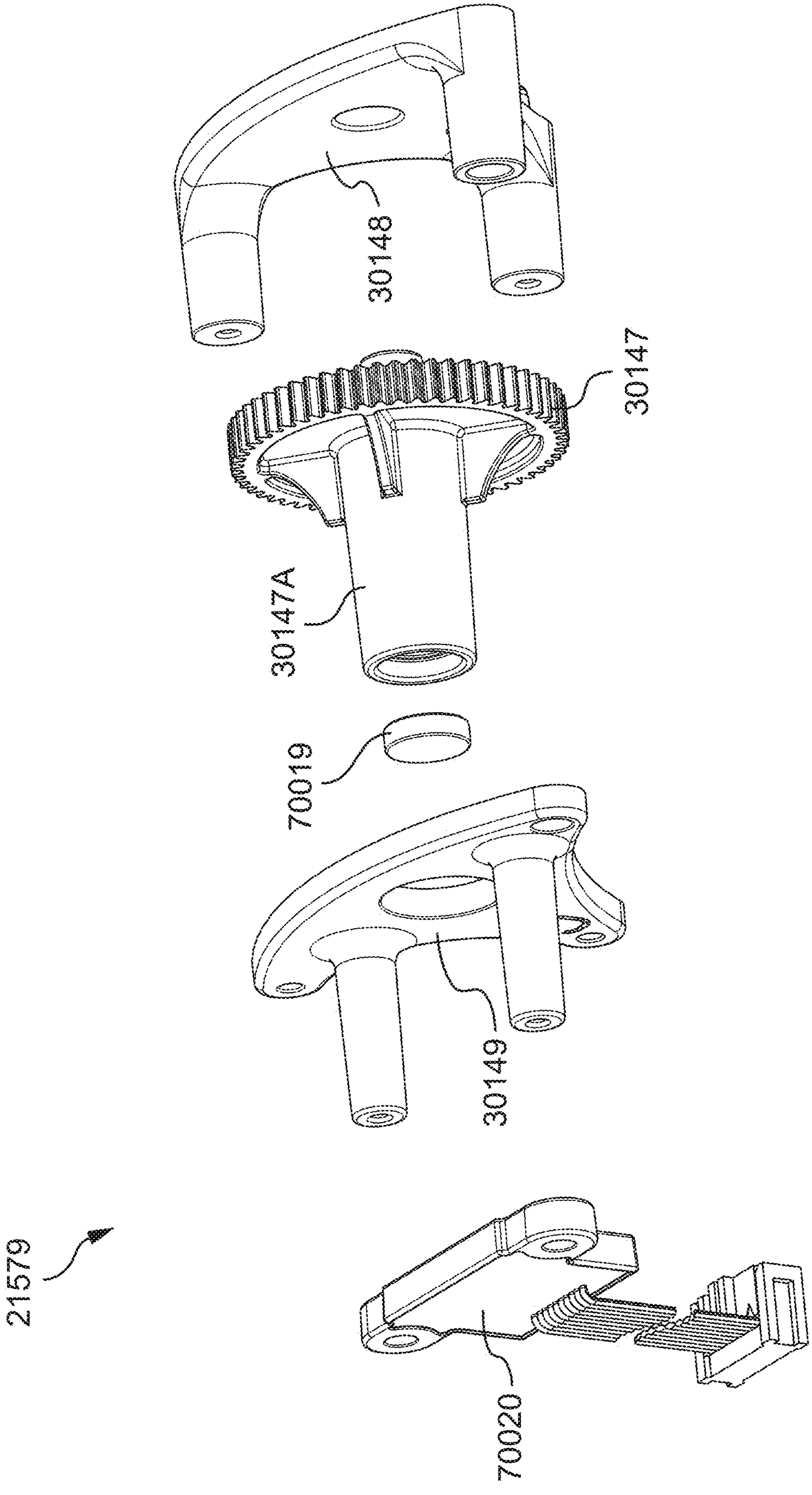
FIG. 3O is an exploded perspective diagram of the cluster position sensor of the present teachings.
Figure 3P:
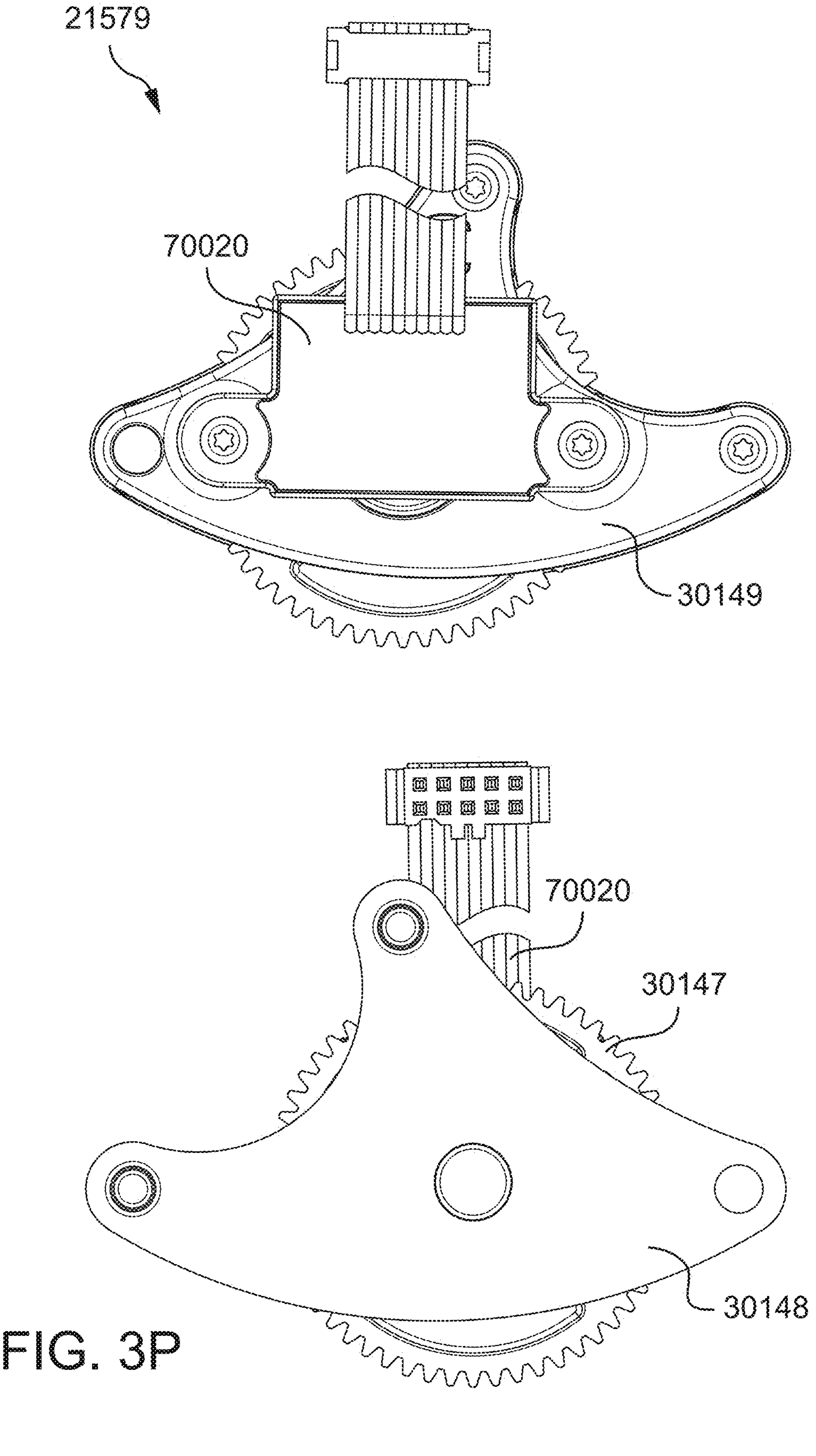
FIG. 3P is a plan view of the cluster position sensor of the present teachings.
Figure 3Q:
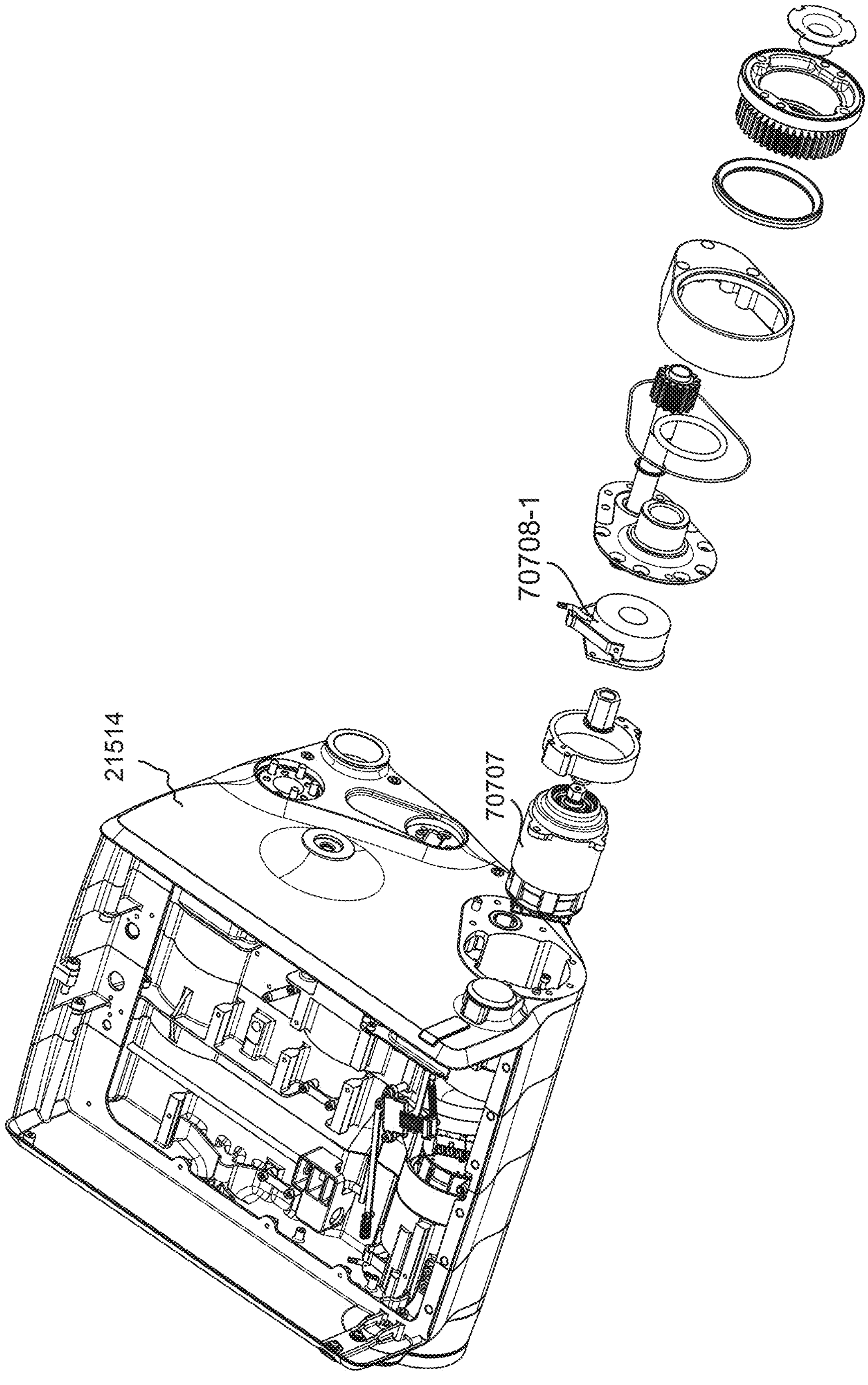
FIG. 3Q is an exploded perspective diagram of an exemplary mobility device base including motor and brake examples.
Figure 3R:
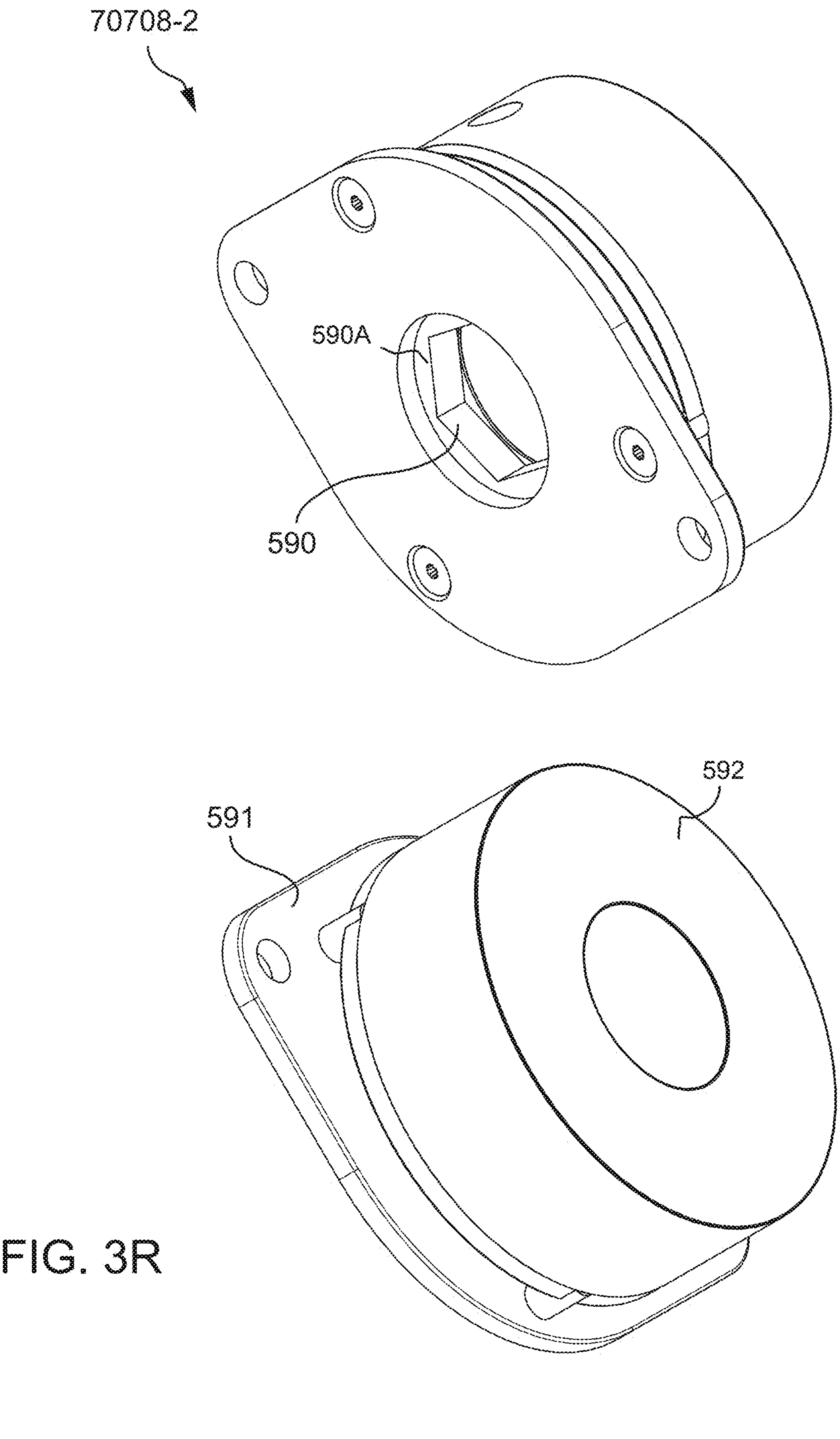
FIG. 3R is a perspective diagram of an exemplary motor brake.
Figure 3S:
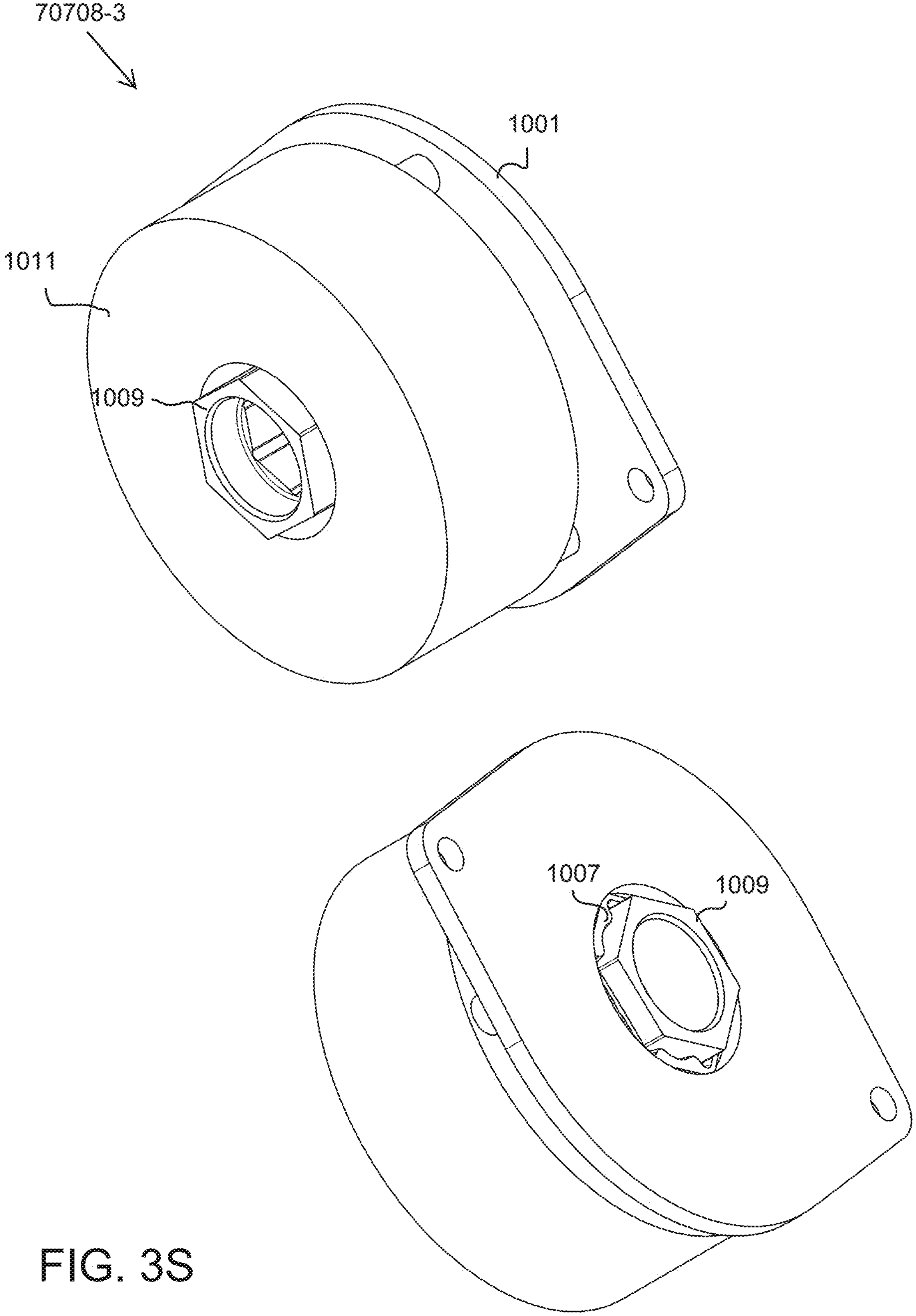
FIG. 3S is a perspective diagram of a motor brake with the insert of the present teachings.
Figure 3T:
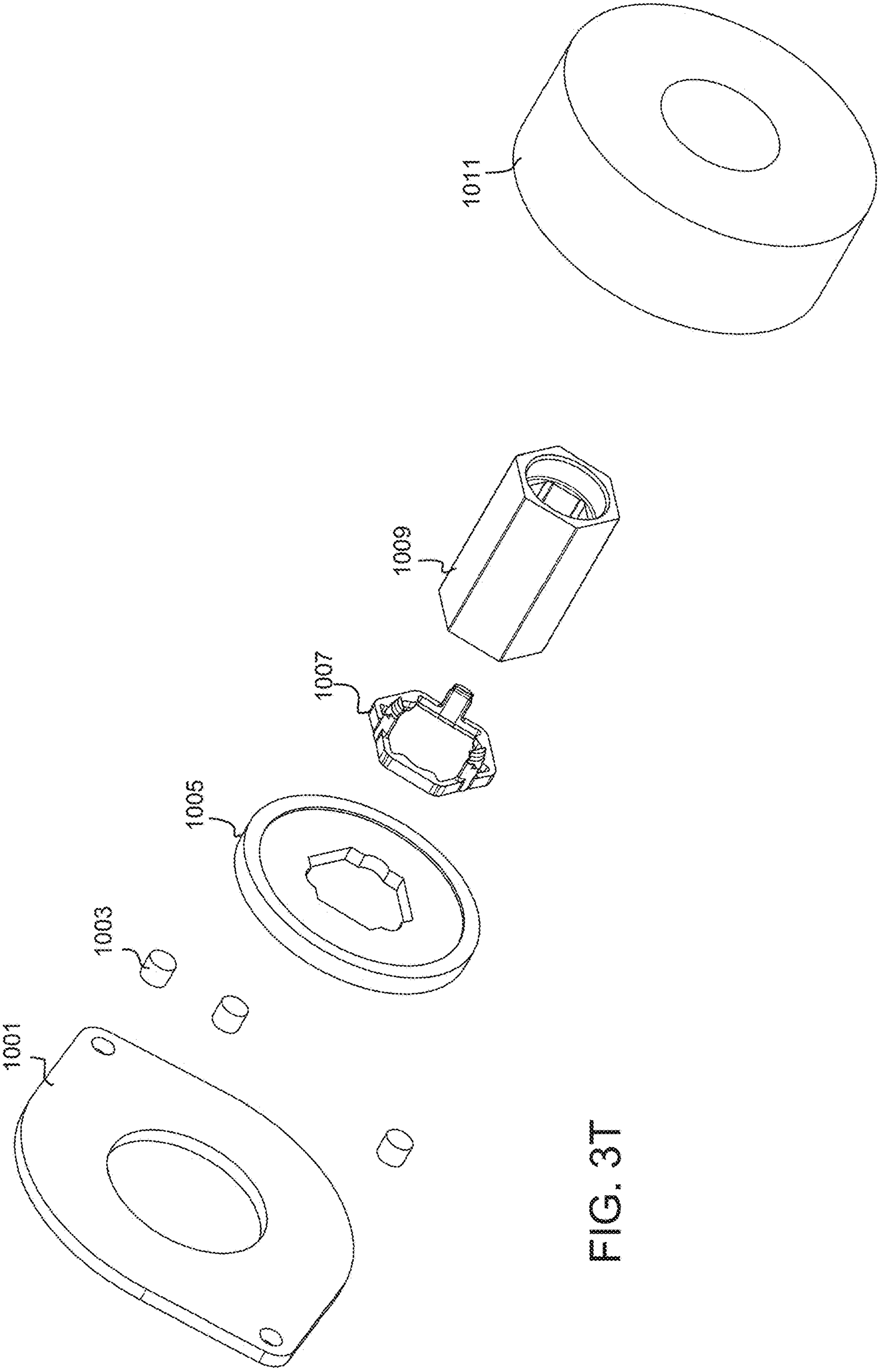
FIG. 3T is an exploded perspective diagram of a motor brake with the insert of the present teachings.
Figure 3U:
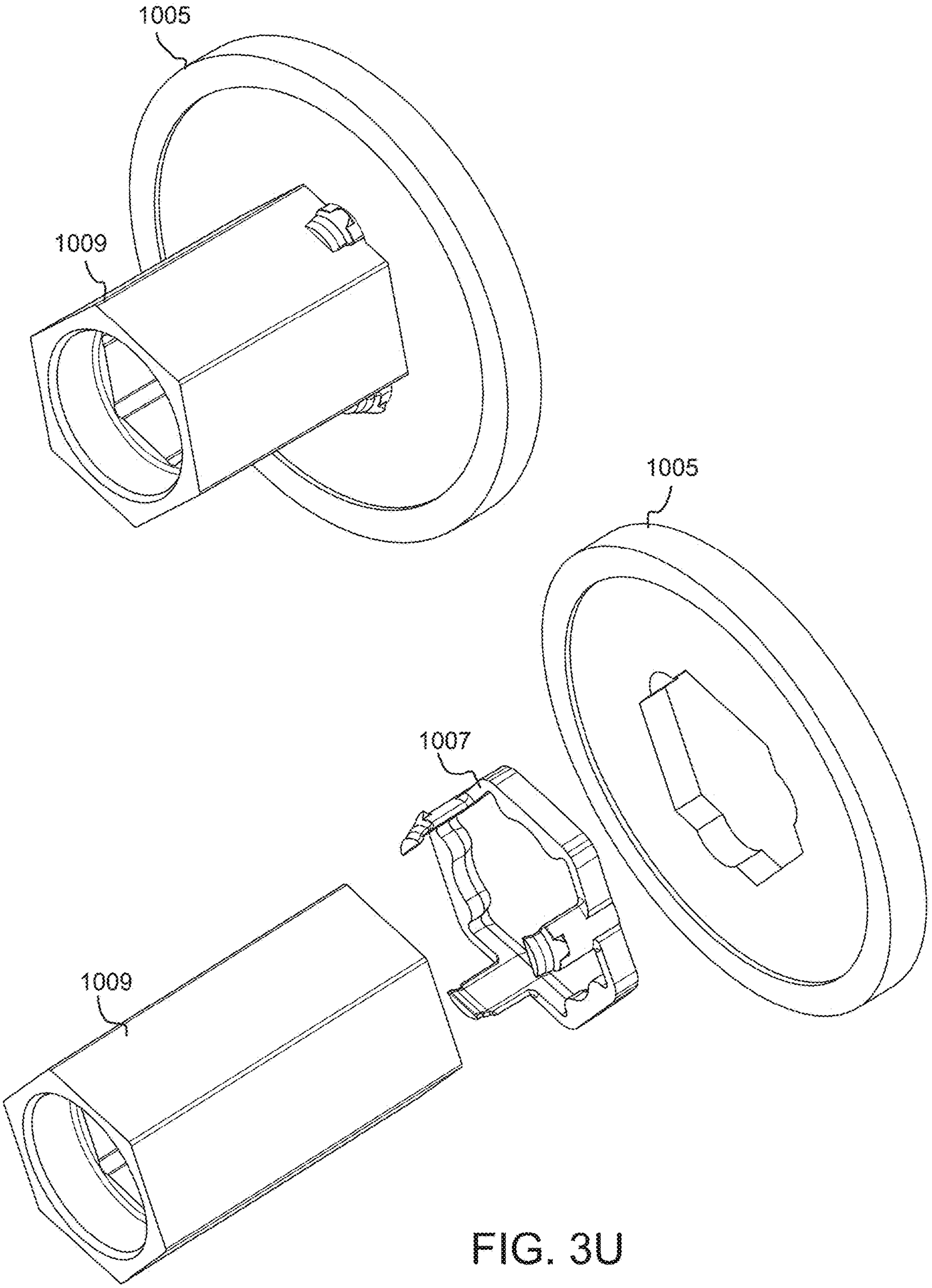
FIG. 3U is a perspective diagram of a motor coupling, disk, and insert of the present teachings.
Figure 3V:
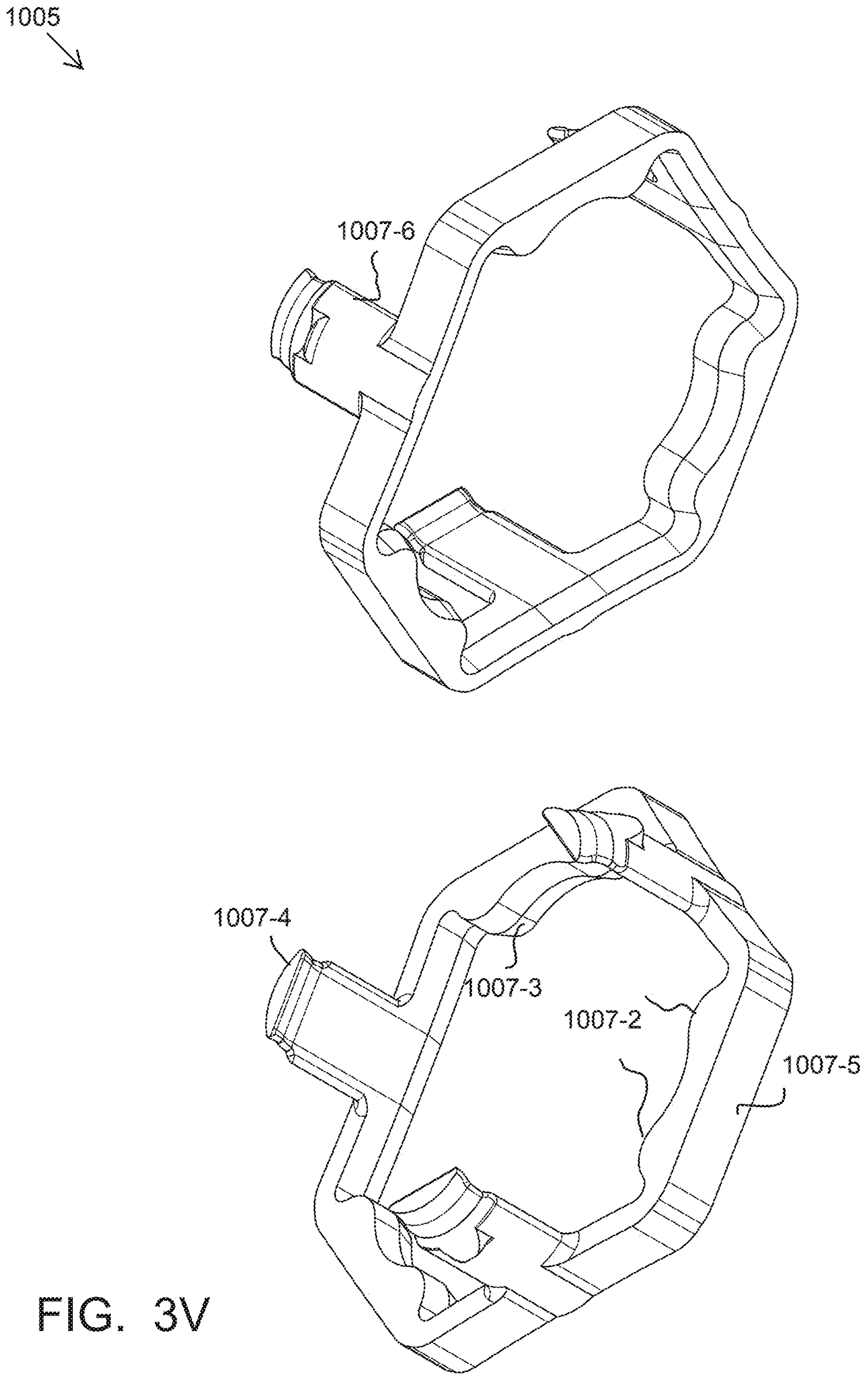
FIG. 3V is a perspective diagram of the insert of the present teachings.
Figure 3W:
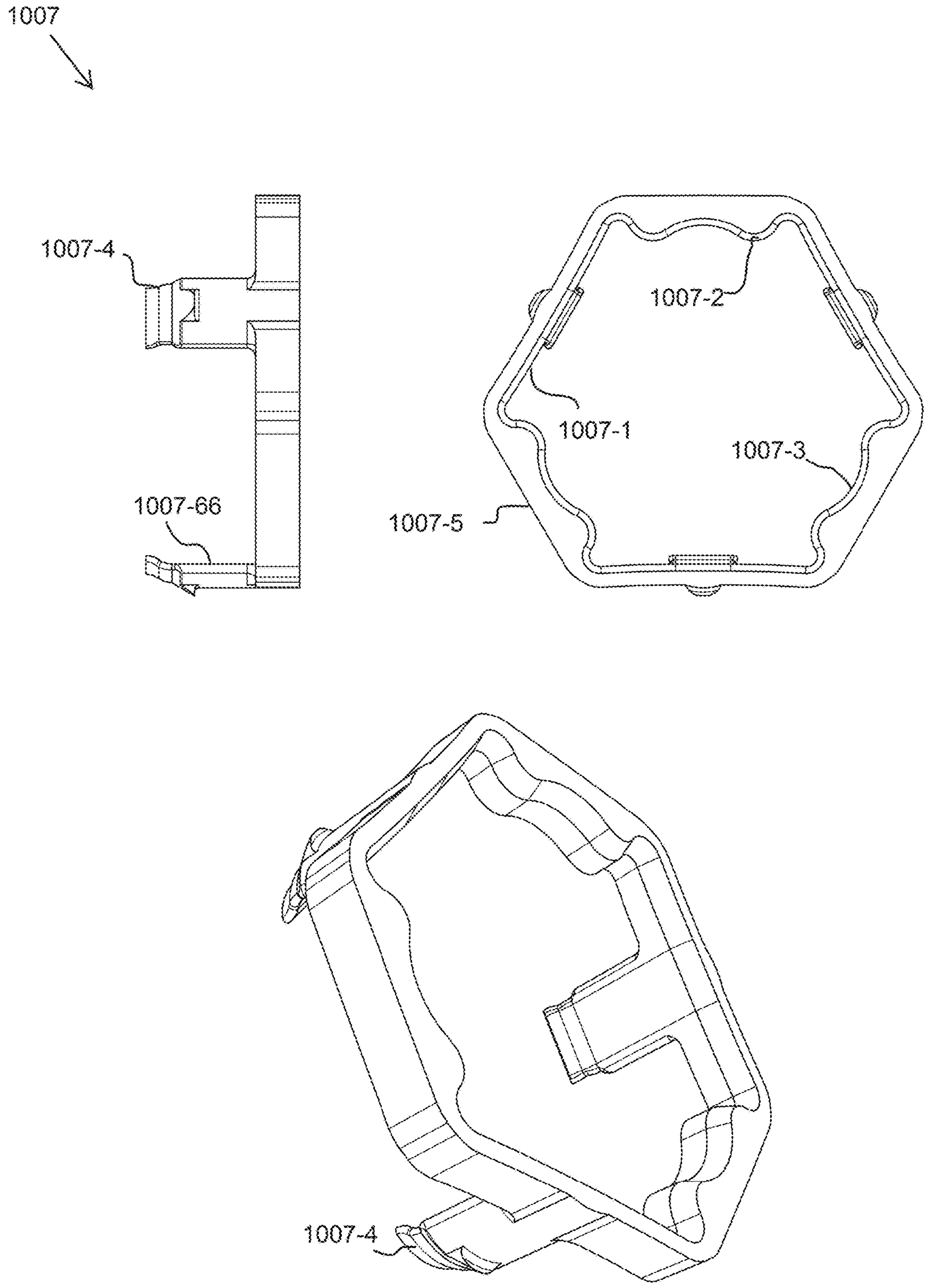
FIG. 3W shows front, side, and perspective schematic diagrams of the insert of the present teachings.

Referring now to FIGS. 3S through 3U, brake assembly 70808-3 of the present teachings, that can reduce vibration, and therefore reduce noise during operation of the MD can include, but is not limited to including, plates 1001/1011, spacers 1003 (FIG. 3T), disk 1005 (FIG. 3T), motor coupling 1009, and insert 1007. Motor coupling 1009 can be encompassed by insert 1007. Motor coupling 1009 can include any shape, for example, but not limited to, hexagonal, and insert 1007 can be constructed to accommodate any shape. Insert 1007 can remove rotational freedom between motor coupling 1009 and disk 1005. Disk 1005 and insert 1007 can together be positioned anywhere along the length motor coupling 1009. Insert 1007 can effectively expand motor coupling 1009 towards disk 1005. Under low load, insert 1007 can prevent relative motion between motor coupling 1009 and disk 1005. Under higher loads, motor coupling 1009 and disk 1005 can come into contact to transmit the operating torque.

Referring now to FIGS. 3 V and 3W, insert 1007 can include, but is not limited to including, at least one protrusion 1007-2 that can enable flush mounting between motor coupling 1009 and insert 1007. Insert 1007 can include any number and size of protrusions 1007-2 along the interface surface between insert 1007 and motor coupling 1009. The number of protrusions 1007-2 can affect the size of the gap between motor coupling 1009 and insert 1007, and can affect the ability of insert 1007 to slide along motor coupling 1009. Insert 1007 can include chamfered edges 1007-3 that can enable smooth assembling of motor coupling 1009 with insert 1007. In some configurations, the interface surface between motor coupling 1009 and insert 1007 can include any number of interior faces 1007-1. In some configurations, protrusions 1007-2 can be positioned on some or all of interior faces 1007-1. In some configurations, protrusions 1007-2 can be placed on alternate of interior faces 1007-1. Insert 1007 can include any number of exterior faces 1007-5 along the interface surface between insert 1007 and disk 1005. The number of interior faces 1007-1 and the number of exterior faces 1007-5 can be the same or different. Insert 1007 can include clips 1007-6 that can accommodate assembly with disk 1005. Clips 1007-6 can include grip 1007-4 that can flexibly retain motor coupling 1009 while enabling axial movement along motor coupling 1009. Grip 1007-4 can be positioned to allow for ease of part moldability. The flexibility of insert 1007 can enable the metal parts of brake assembly 70808-3 to accommodate torque under a relatively high load.

Figure 3X:
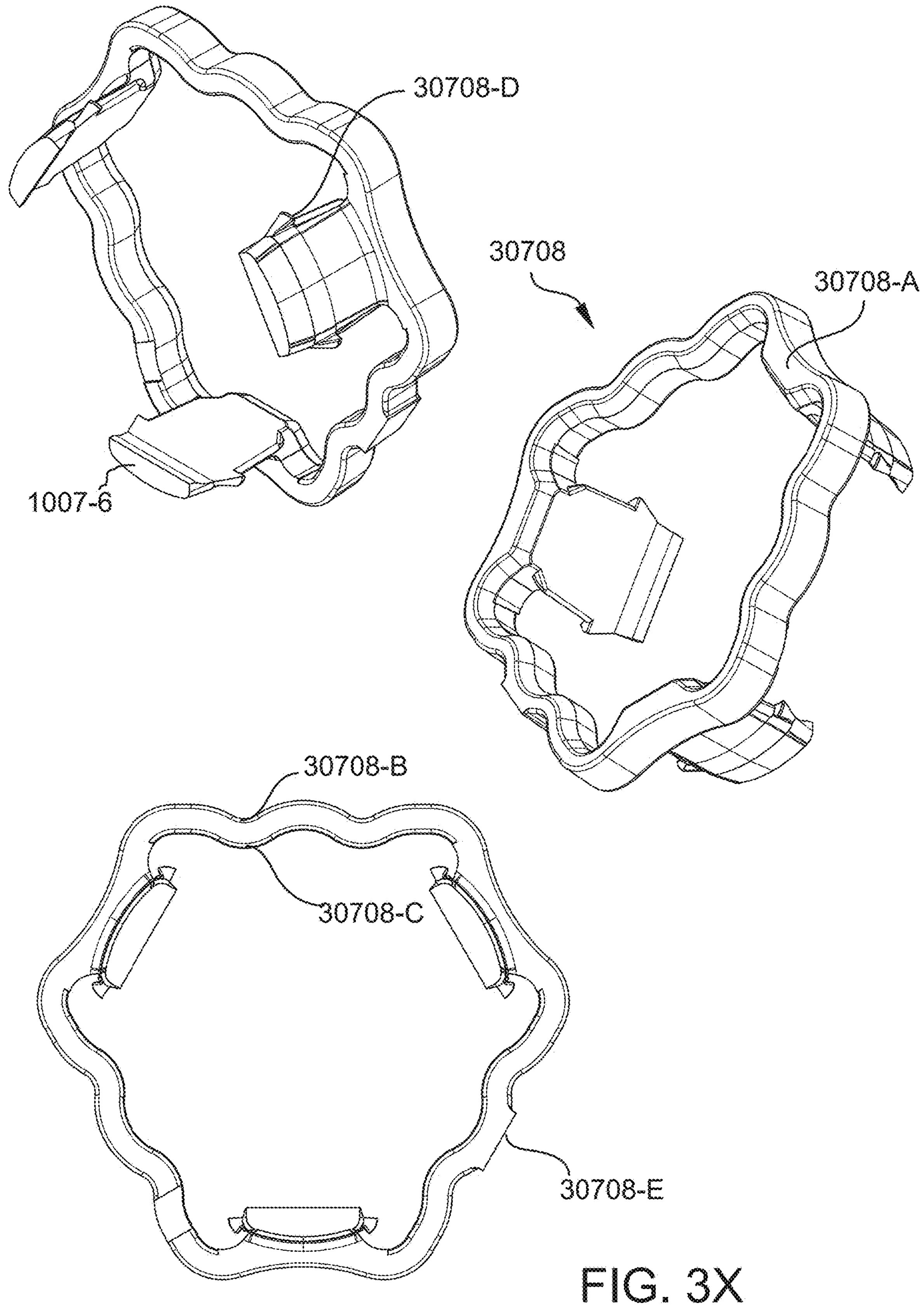
FIG. 3X shows front, side, and perspective schematic diagrams of the second configuration of the insert of the present teachings.

Referring now to FIG. 3X, second configuration brake insert 30708 can include, but is not limited to including, geometrically similar interior edge 30708-C and exterior edge 30708-B. Reinforcement material 30708-A can strengthen the intersection between clips 1007-6 and interior edge 30708-C. Clips 1007-6 can include retention geometry 30708-D.

Figure 3Y:
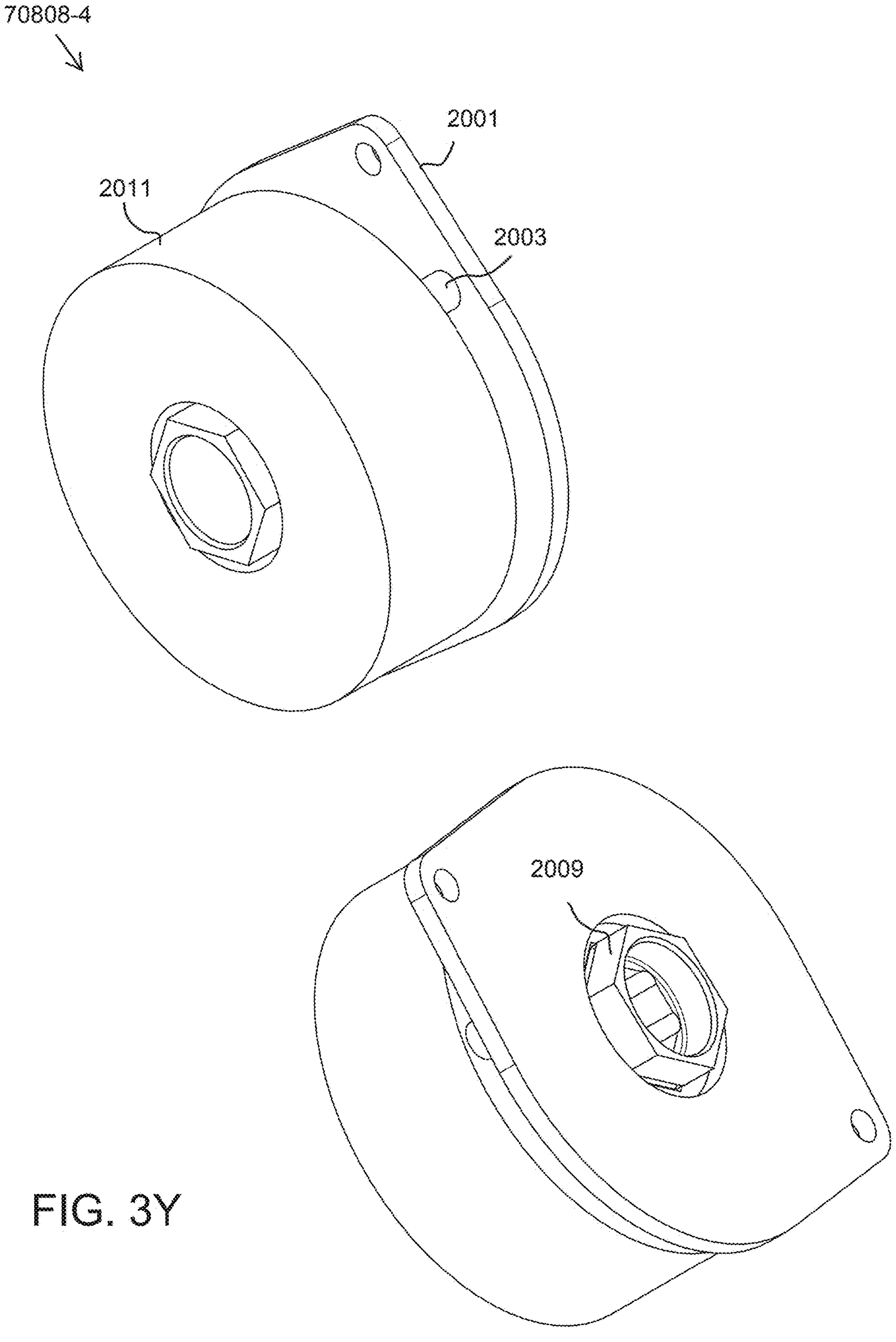
FIG. 3Y is a perspective diagram of a motor brake with grooved motor coupling of the present teachings.
Figure 3Z:
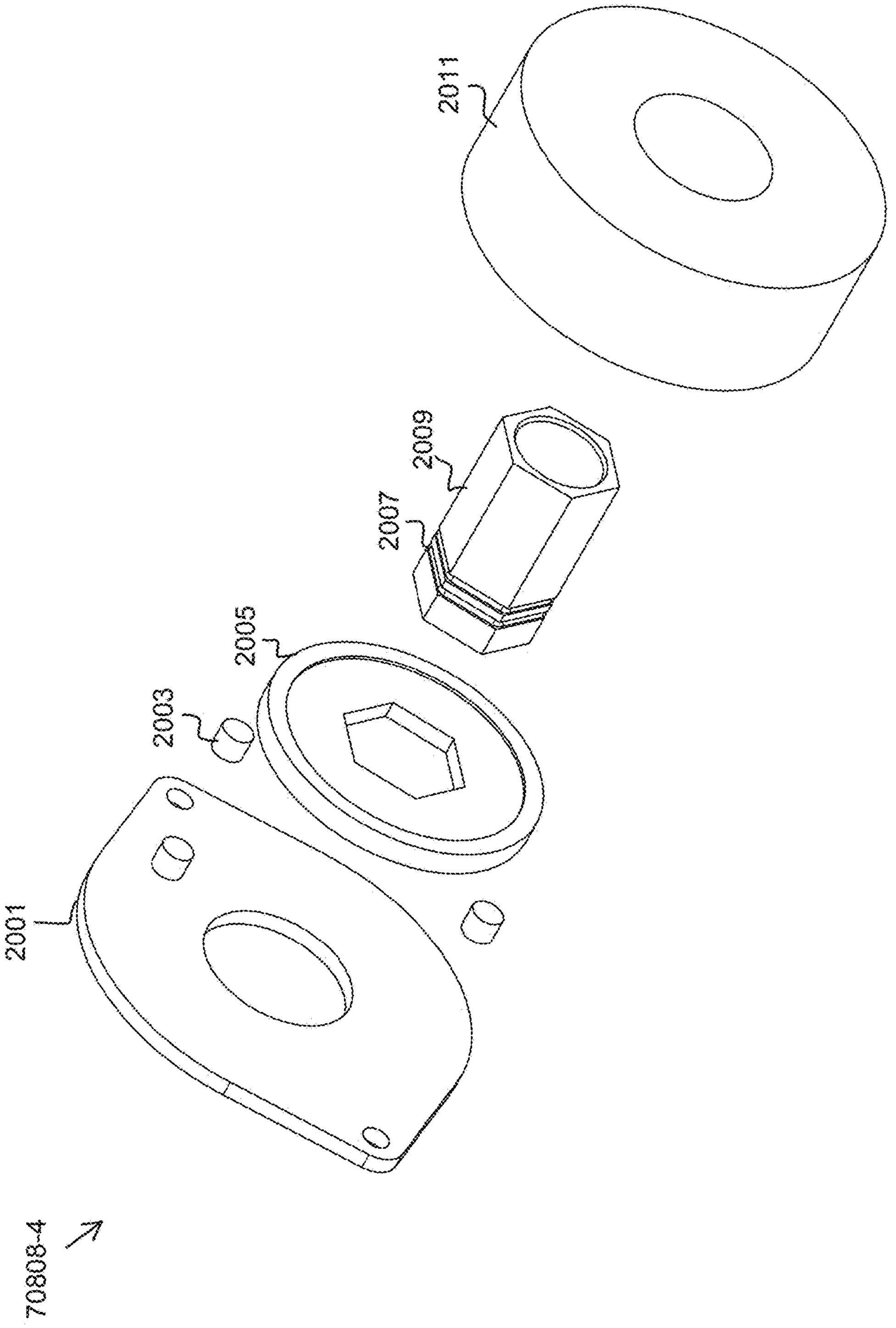
FIG. 3Z is an exploded perspective diagram of a motor brake with grooved motor coupling of the present teachings.
Figure 3A:
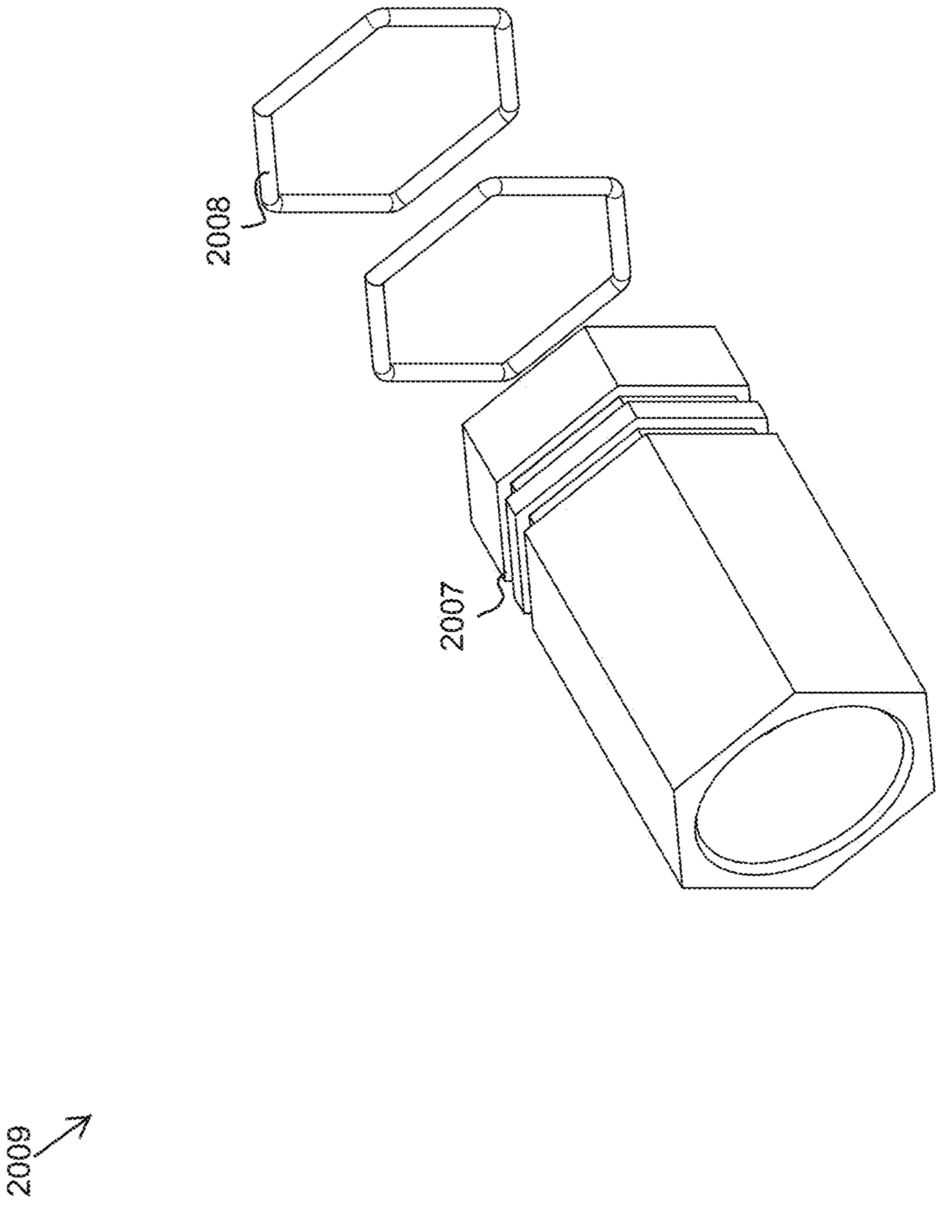
Figure 3B:
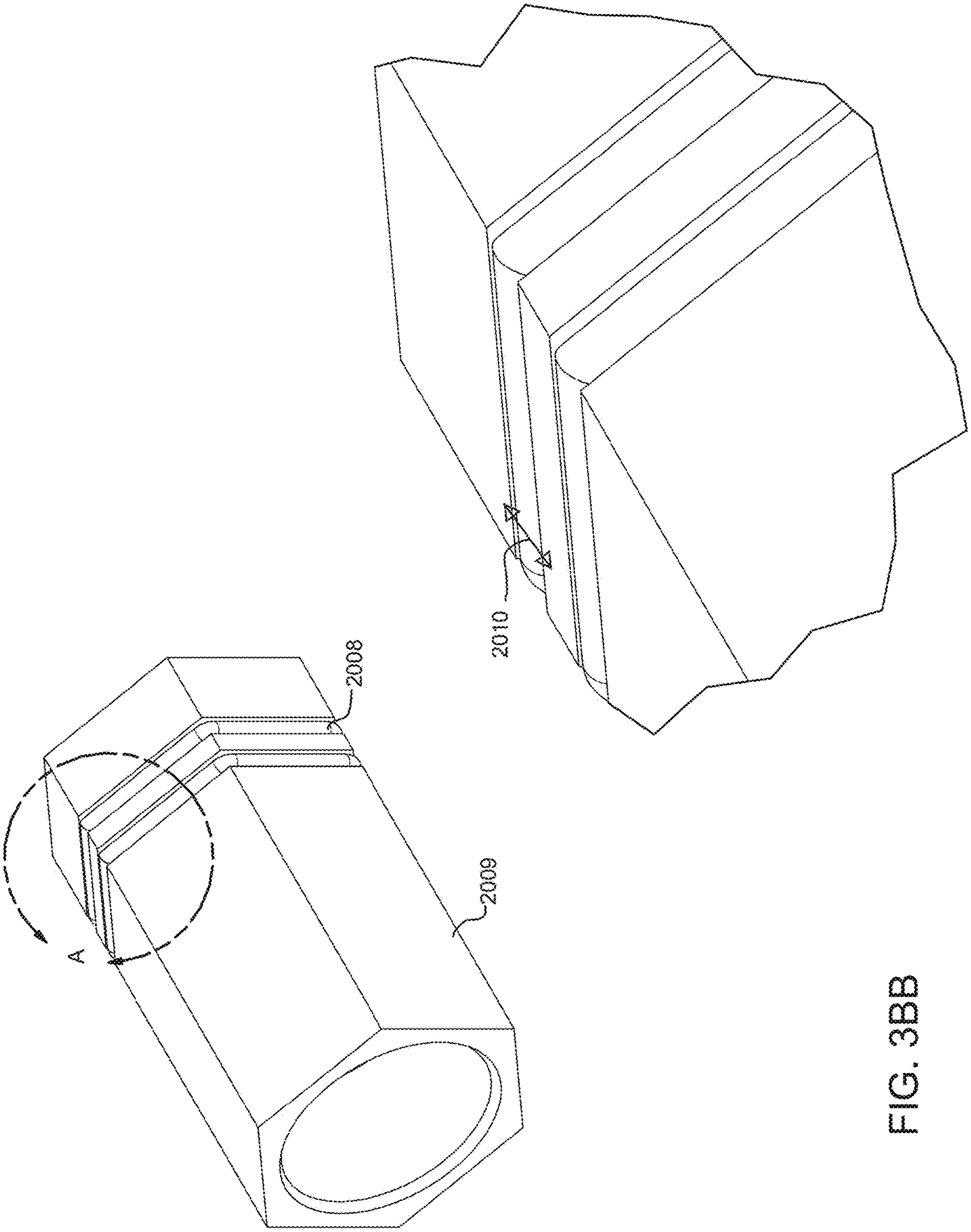
Figure 3D:
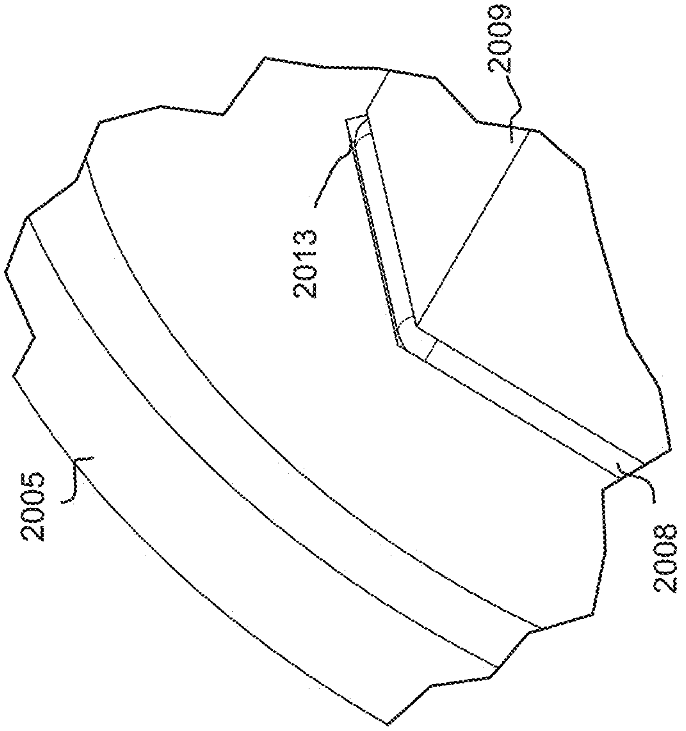
Figure 3C:
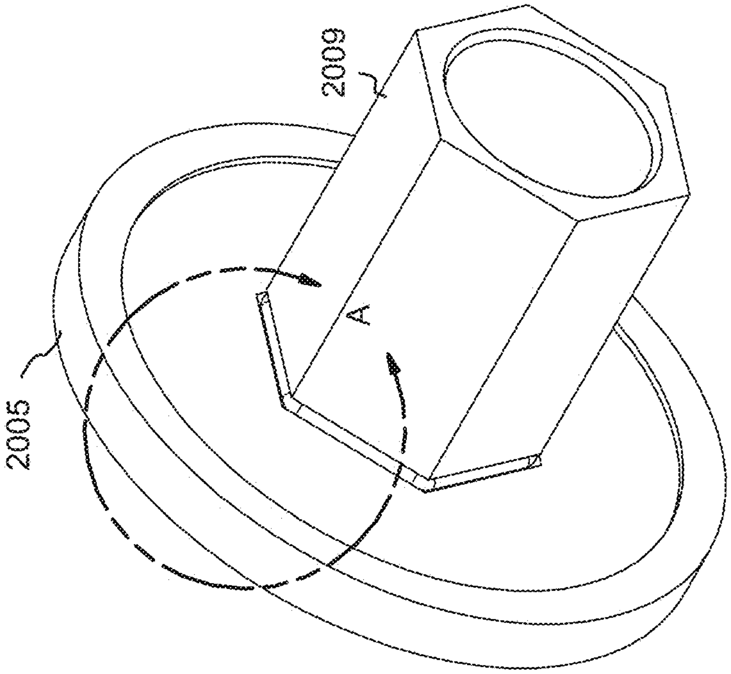

Referring now to FIGS. 3Y through 3 CCQ2, brake assembly 70808-4 of the present teachings can allow for some relative motion between motor coupling 2009 and disk 2005, and can cushion the interface to reduce impact sounds. Motor coupling 2009 can include at least one groove machined into motor coupling 2009 to fit a recessed O-ring 2008 (FIG. 3 CCQ1). O-ring 2008 (FIG. 3 CCQ1) can prevent metal-to-metal contact during low loads. Under high brake loads, O-ring 2008 (FIG. 3 CCQ1) can be compressed into groove 2007, and the metal can contact each other to transmit the necessary torque. Brake assembly 70808-4 can allow brake disk 2005 to function properly while tolerating error in axial position. Brake assembly 70808-4, that can reduce vibration, and therefore reduce noise during operation of the MD can include, but is not limited to including, plates 2001/2011, spacers 2003, disk 2005 (FIG. 3 CCQ0), motor coupling 2009, and at least one o-ring 2008 (FIG. 3 CCQ1). Motor coupling 1009 can be encircled by at least one groove 2007. Motor coupling 2009 can include any shape, for example, but not limited to, hexagonal, and at least one groove 2007 can include any depth that can accommodate the placement and protrusion of at least one o-ring 2008. To determine a desired depth of at least one groove 2007 and the desired size of at least one o-ring 2008, a target amount of o-ring protrusion 2010 (FIG. 3 CCQ2) can be selected, for example, but not limited to, 0.4 mm to 0.5 mm. Selecting o-ring protrusion 2010 (FIG. 3 CCQ2) can be based on balancing the amount of clearance desired between disk 2005 and motor coupling 2009, and the amount of vibration damping desired. For example, if o-ring protrusion 2010 (FIG. 3 CCQ2) is too high, there can be too much clearance between disk 2005 and motor coupling 2009. If o-ring protrusion 2010 (FIG. 3 CCQ2) is too low, there can be a deficit of vibration damping and allowance for tolerancing. In some configurations, the diameter of o-ring 2008 can be selected to achieve a maximum compression of ~30% before metal-to-metal contact occurs between motor coupling 2009 and disk 2005. The depth of groove 2007 can be chosen to accommodate o-ring 2008 (FIG. 3 CCQ1), and achieve the desired height of protrusions 2010 to property position o-ring 2008 (FIG. 3 CCQ1). Brake assembly 70808-4 (FIG. 3Y) can tolerate a relatively large range of axial positions, possibly reducing assembly constraints.

Referring now to FIG. 3 CCQ3, motor coupling 2009 along with at least one property-selected o-ring 2008 can remove rotational freedom between motor coupling 2009 and disk 2005. Motor coupling 2009 can include any number of grooves 2007 and accompanying o-rings 2008, the number being based at least on how much axial movement of disk 2005 along motor coupling 2009 is desired. Disk 2005 can be positioned against o-ring 2008 at disk cavity edge 2013. Disk 2005 and o-ring 2008/groove 2007 can together be positioned anywhere along the length motor coupling 2009. Under low load, o-ring 2008/groove 2007 can prevent relative motion between motor coupling 2009 and disk 2005. Under higher loads, motor coupling 2009 and disk 2005 can come into contact to transmit the operating torque.

Referring now to FIGS. 3J-3L, central gearbox housings 21515 can include at least one absolute seat position sensor 21578 (FIG. 3M) that can be operably coupled with seat position sensor gear teeth clamp 30135 (FIG. 3K). Seat position sensor gear teeth clamp 30135 (FIG. 3K) can include embossing 273 (FIG. 3K) to assist in aligning and orientation of seat position sensor gear teeth clamp 30135 (FIG. 3K) around cross shaft stage 4 sector gear 21504, and fastened to rear half gear clamp 30136. Seat position sensor tooth gear 30134 (FIG. 3M) of absolute seat position sensor 21578 (FIG. 3M) can interlock seat position sensor tooth gears 30134 (FIG. 3M) with position sensor gear teeth clamp 30135 (FIG. 3K) as cross shaft sector gear height actuator 30909 (FIG. 21A-3) moves. Sector cross shaft 30909 (FIG. 3L) can include a hollow shaft that can operably couple the seat drive train to the seat lifting arms on the left and right side of the central housing. The fourth stage seat height sector gear is clamped onto the shaft and restrained from rotating about the shaft by a key connection between the shaft and gear. The left and right lifting arms are needed to be aligned with each other to assure the seat will be lifted symmetrically. The left and right lifting arms are connected by pins and bolts in an asymmetric pattern that can only be assembled in the correct orientation. This forces the lifting arms to always be aligned. Seat absolute position sensor 21578 (FIG. 3M) can measure the rotation of sector gear cross shaft 30909 (FIG. 3L) that connects to and lifts the seat lifting drive arms 21301 (FIG. 5D) on the left and right side of central gearbox 21514 (FIG. 1A). Sector gear cross shaft 30909 (FIG. 3J) can rotate through less than 90° of rotation, and can be coupled to seat position sensor 21578 (FIG. 3M) through a one-stage gear train that can cause seat position sensor 21578 (FIG. 3M) to rotate more than 180°, thereby doubling the sensitivity of the position measurement of the seat. Seat position sensor gear clamp 30136 (FIG. 3J) can matingly interlock with seat position sensor gear teeth clamp 30135 (FIG. 3K) around sector gear cross shaft 30909 (FIG. 3J). The interlocked combination can provide geared interaction with seat absolute position sensor 21578 (FIG. 3M). Seat absolute position sensor 21578 (FIG. 3M) can include, but is not limited to including, seat position sensor tooth gear 30134 (FIG. 3M). Hall sensor 70020 (FIG. 3M), magnet 70019 (FIG. 3M), seat position sensor upper plate 30138 (FIG. 3M), and seat position sensor lower plate 30137 (FIG. 3M). Magnet 70019 (FIG. 3M) can be mounted on upper plate 30138 (FIG. 3M). Upper plate 30138 (FIG. 3M) can be securely mounted upon lower plate 30137 (FIG. 3M).

Referring now to FIG. 30, at least one absolute cluster position sensor 21579 (FIG. 30) can include Hall sensor 70020 (FIG. 30), cluster position sensor cluster cross-shaft gear 30145 (FIG. 6E) and cluster position tooth gear 30147 (FIG. 30). Cluster rotate stage three cross shaft 21537 (FIG. 2R) can be geared to interface with absolute cluster position sensor 21579 (FIG. 30) through cluster position sensor tooth gear 30147 (FIG. 30). Seat absolute position sensor 21578 (FIG. 3M) can determine the location of the seat support bracket 24001 (FIG. 8B) relative to central gearbox 21514 (FIG. 9). Cluster position sensor 21579 (FIG. 30) can determine the position of wheel cluster housing 21100 (FIG. 6A) relative to central gearbox 21514 (FIG. 9). Seat absolute position sensor 21578 (FIG. 3M) and cluster position sensor 21579 (FIG. 30) can together determine the position of the seat with respect to the wheel cluster assembly 21100 (FIG. 6A). Seat position sensor 21578 (FIG. 3M) and cluster position sensor 21579 (FIG. 30) can sense absolute position. Absolute seat position sensor 21578 (FIG. 3M) can sense that the seat has moved since a previous power off/on. If the MD is powered off and the seat or cluster drive train move, the seat and cluster sensors can sense the new location of the seat and cluster relative to central gearbox 21514 (FIG. 9) when the MD is powered back on. The fully internal sensor system of the MD can provide protection to the sensors with respect to mechanical impact, debris, and water damage.

Figure 4:
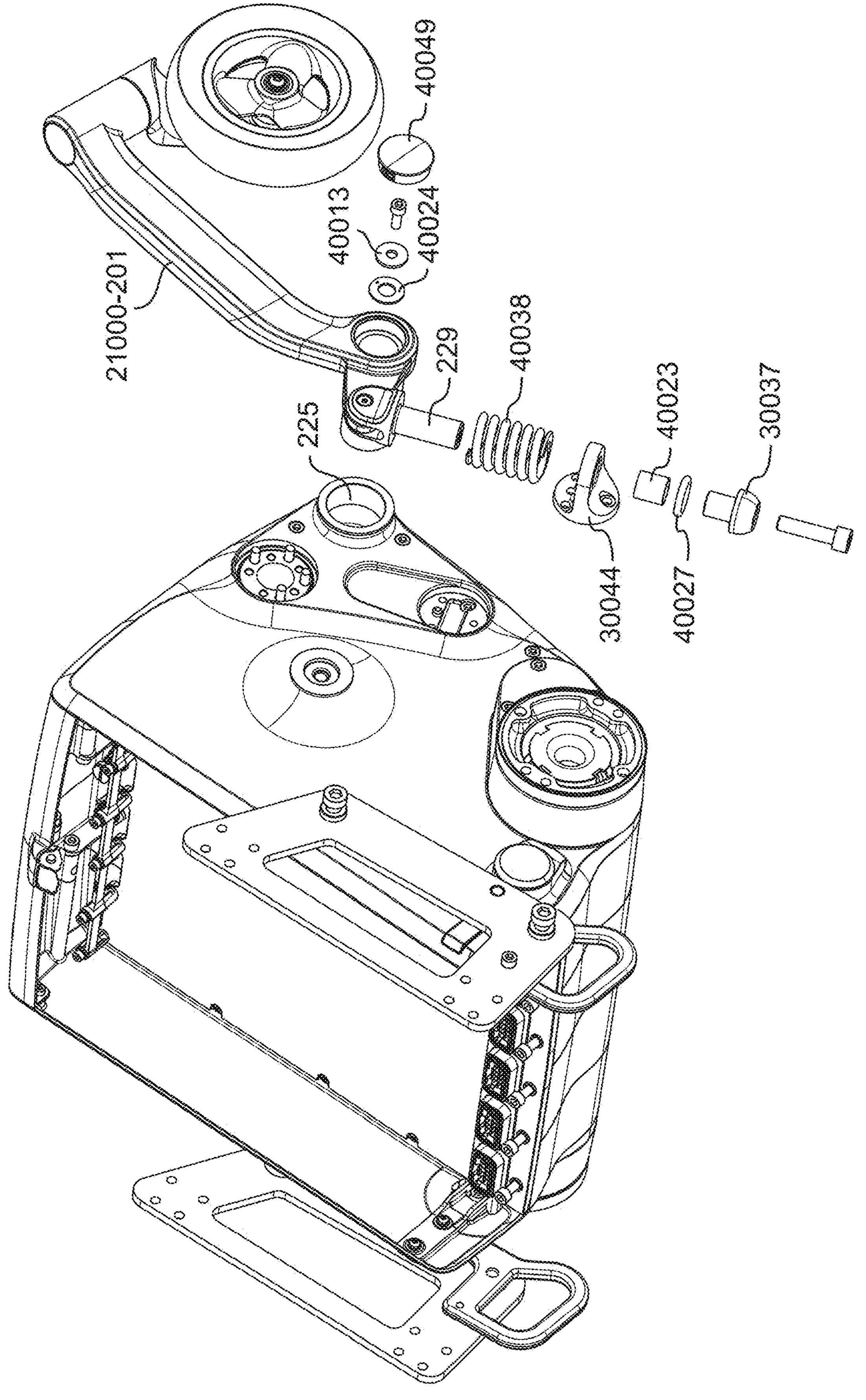
FIG. 4 is a perspective diagram of the caster arm of the caster of the present teachings.

Referring now primarily to FIG. 4, caster wheels 21001 can be attached to central gearbox 21514 for use when the seat height is at its lowest position, supporting a portion of the MD when the MD is in standard mode 100-1 (FIG. 22A). Caster wheels 21001 can swivel about a vertical axis allowing changes in direction. Caster wheels 21001 can allow maneuverability and obstacle traversal. Caster assembly 21000 can include caster arm 21000-201 that can be operably connected, at a first end, to caster wheel 21001 (FIG. 27A). Caster arm 21000-201 can include caster arm shaft 229 that can enable operable connection between caster arm 21000-201 and central gearbox 21514 at caster arm port 225. Caster arms 21000-201 can be secured in pockets 225 to prevent sliding out while enabling rotation. Pockets 225 can be lined with plastic bushings to enable caster arms 21000-201 to rotate. Caster spring plate 30044 can be operably connected to central gearbox 21514. Compression spring 40038 can enable shock absorption, stability, and continued operation when caster assembly 21000 encounters obstacles. Compression spring 40038 can provide suspension to the system when caster wheels 21001 (FIG. 27A) are in operation. Caster assembly 21000 can rest upon compression spring 40038 that can itself rest upon caster spring plate 30044. Compression spring 40038 can be attached to caster spring plate 30044 by spring cap 30037, sleeve bushing 40023, and o-ring 40027. In some configurations, o-ring 40027-3 can be used as a rebound bumper. Compression spring 40038 can restrict the range of rotation of caster arms 21000-201 to maintain caster wheel 21001 (FIG. 27A) in an acceptable location.

Referring now primarily to FIG. 5A, the vertical position of the user can be changed through the seat drive mechanism, consisting of a transmission and a four-bar linkage attaching the seat assembly to central gearbox 21514. The elements of the four-bar linkage can include, but are not limited to including, central gearbox 21514, two drive arms 30065 (one on each side of the central gearbox), two stabilizer arms 30066 (one on each side), and seat brackets 30068. The seat drive transmission can include a significant reduction to provide torque to both drive arm links for lifting the user and seat assembly relative to central gearbox 21514. Because central gearbox 21514 acts as an element of the four-bar linkage driving the seat, central gearbox 21514 can rotate relative to the ground to maintain the seat angle during a seat transition. Thus, the cluster drive and seat drive can act in concert during a seat transition. The rotation of central gearbox 21514 can move caster assemblies 21000, the movement of which can avoid obstacles such as, for example, but not limited to, curbs. A seat of any kind can be used with the MD by attaching the seat to seat brackets 30068. Lift arm 21301 (FIGS. SD/SE) can operably couple with seat brackets 30068 at a lift arm first end. Lift arm 21301 (FIGS. 5D/5E) can be operably coupled with central gearbox 21514 at a lift arm second end. The movement of lift arm 21301 (FIGS. 5D/5E) can be controlled with signals transmitted from electronics housed in central gearbox 21514 through control port 255 (FIG. 1F) to lift arm 21301 (FIGS. 5D/5E). Lift arm 21301 (FIGS. 5D/5E) can include a tie-down that can enable a secure placement of the MD in, for example, but not limited to, a vehicle. Stabilizer arm 21302 (FIG. 5C) can operably couple with seat brackets 30068 at a link first end. Stabilizer arm 21302 (FIG. 5C) can be operably coupled with central gearbox 21514 at a link second end. The movement of stabilizer arm 21302 (FIG. 5C) can be controlled by the movement of lift arm 21301 (FIGS. 5D/5E). Stabilizer link rest bumper 30055 can smooth the ride for the user of the MD, and can reduce wear on gears within central gearbox with electronics 21514. In some configurations, bumper 30055 can rest in bumper housing 263, and can be secured in place by stabilizer link rest end cap 30073. The linkage assembly that is formed by lift arm 21301 and stabilizer arm 21302 (FIG. 5C) can rest on bumper 30055 when the MD is in standard mode. The absolute position of the motor, determined by an absolute position sensor associated with the motor, can determine when the linkage assembly should be resting on bumper 30055. The motor current required to move the linkage can be monitored to determine when the linkage assembly is resting on the bumper 30055. When the linkage assembly is resting on bumper 30055, the gear train may not be exposed to impacts that can result from, for example, obstacles encountered by the MD and/or obstacles and vehicle motion encountered by a vehicle transporting the MD.

Figure 5B:
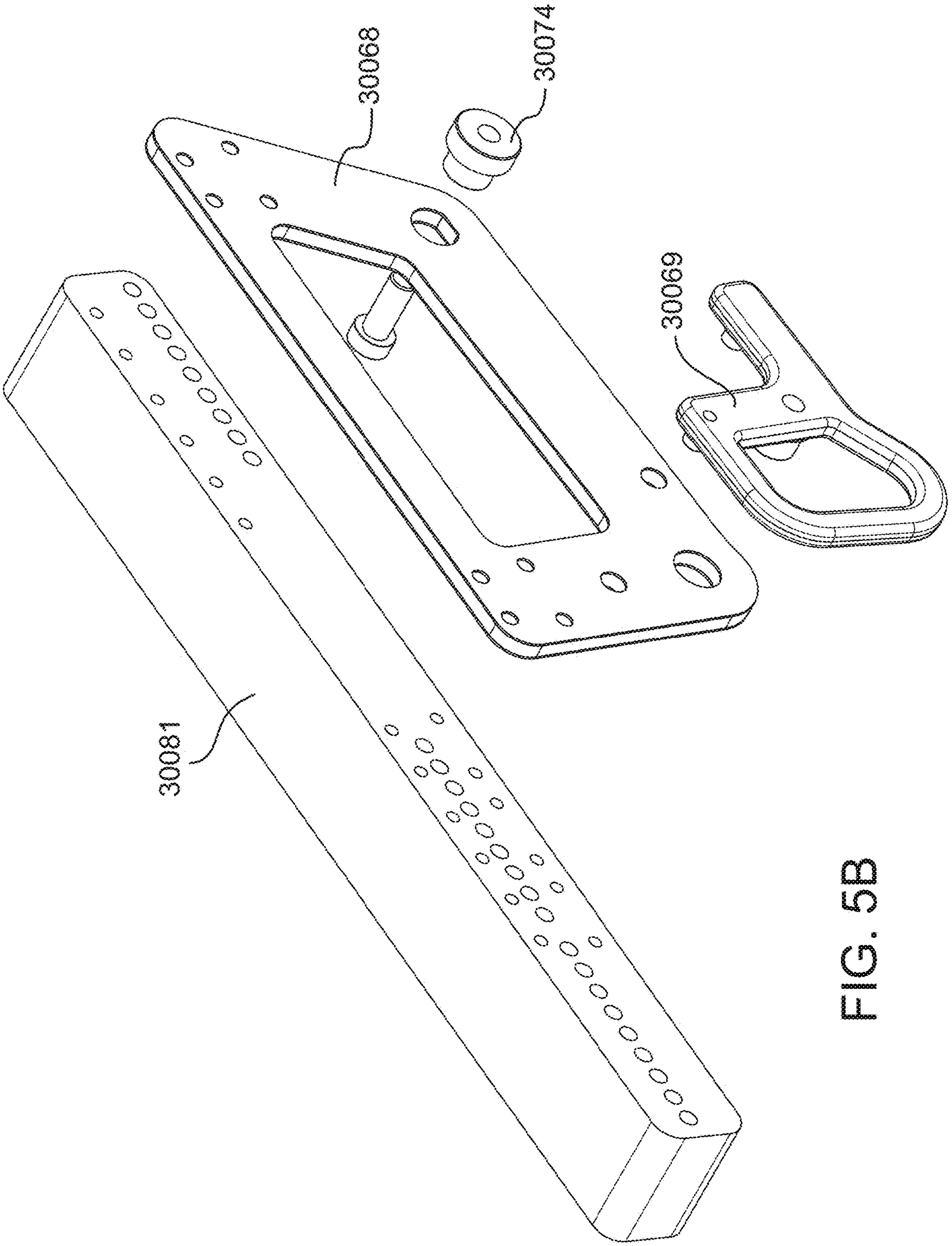
FIG. 5B is a perspective diagram of the connective features of the seat support structure of the present teachings.
Figure 5C:
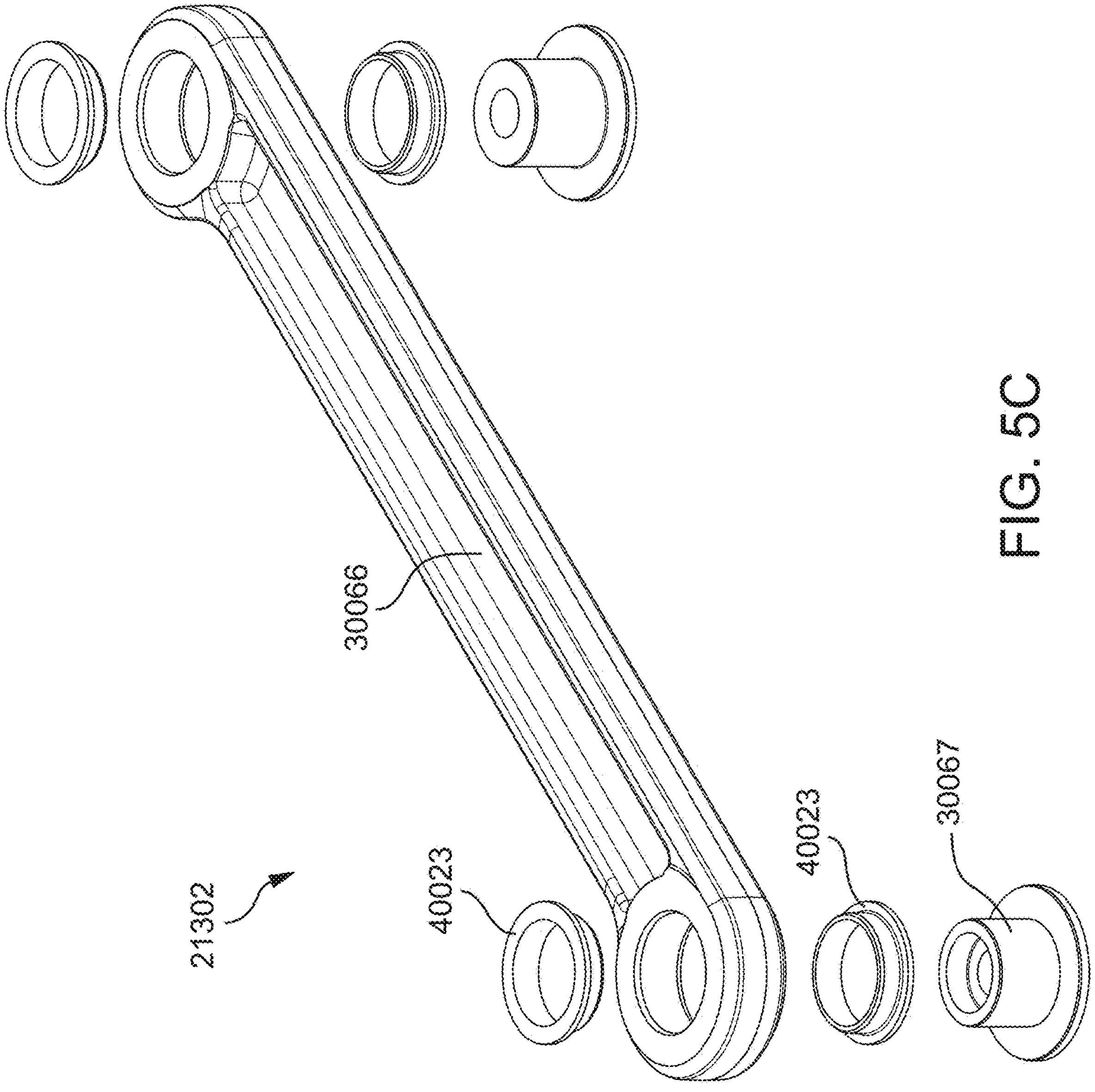
FIG. 5C is a perspective diagram of the seat height linkage stabilizer link of the present teachings.
Figure 5D:
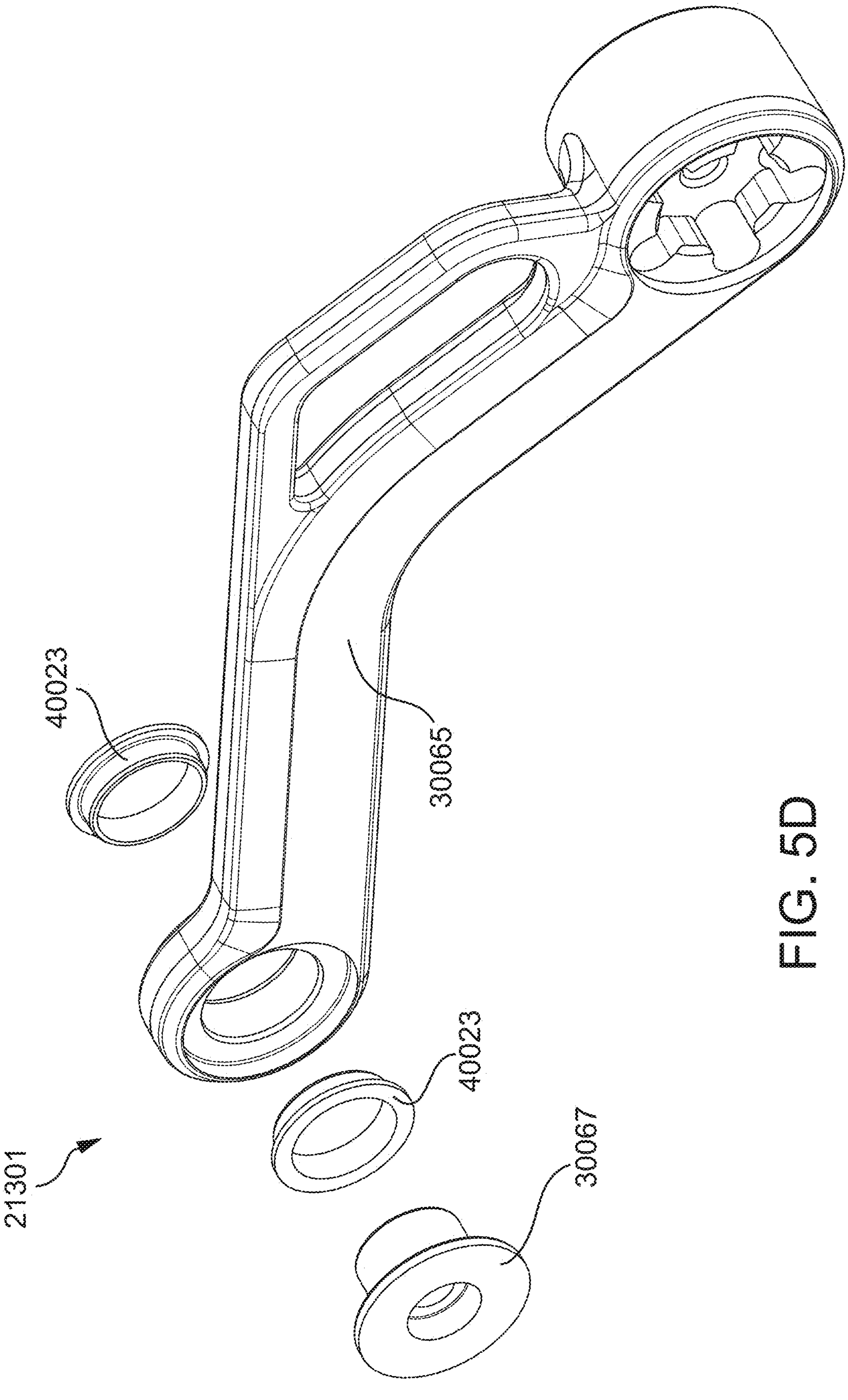
FIG. 5D is a perspective diagram of a first view of the seat height linkage lift arm of the present teachings.
Figure 5E:
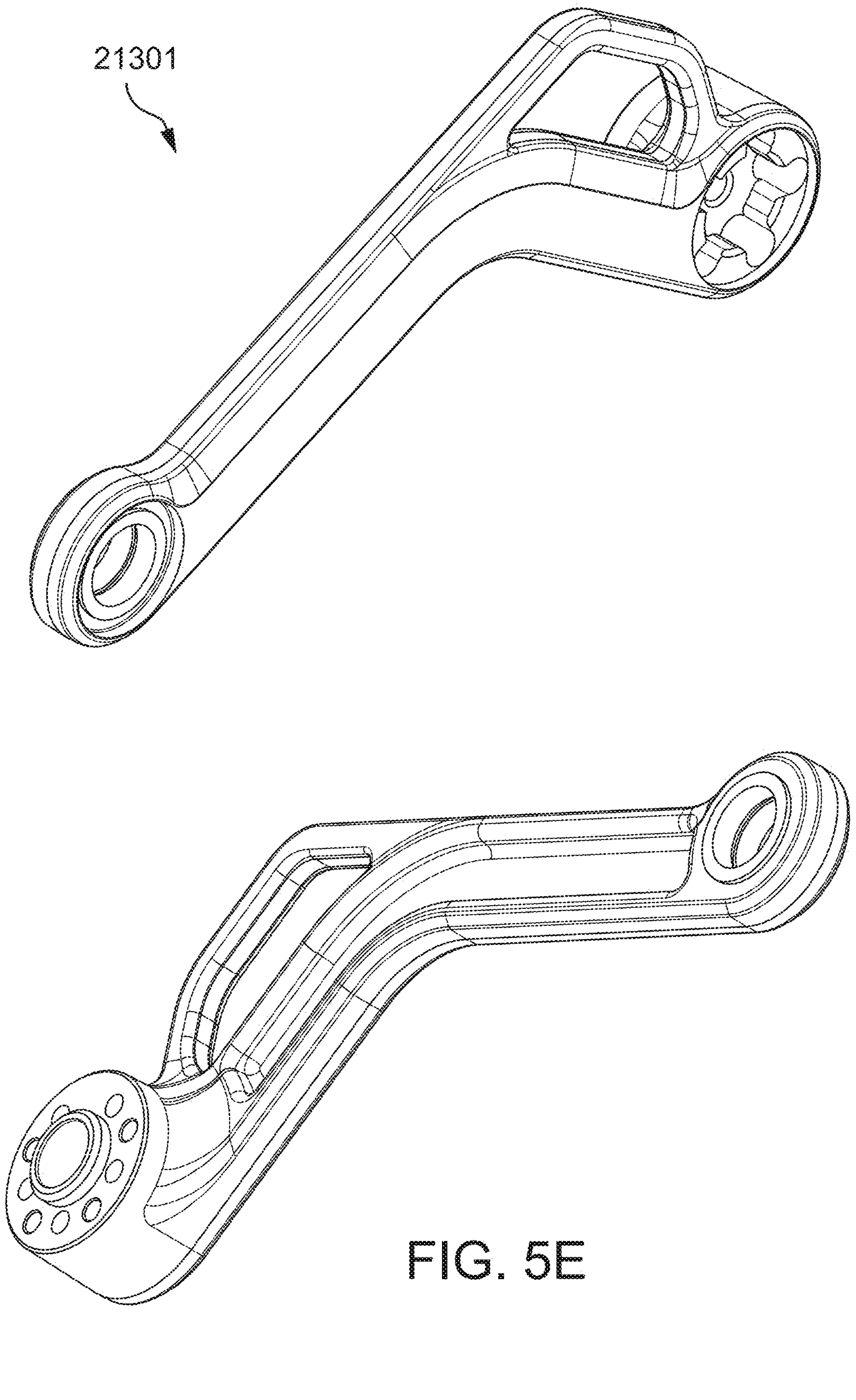
FIG. 5E is a perspective diagram of a second view of the seat height linkage lift arm of the present teachings.

Referring now to FIG. 5B, vehicle tie-downs 30069 can be operably coupled with seat brackets 30068 to allow the MD to be secured in a motor vehicle. The restraint system of the MD can be designed to allow a user to remain seated in the MD for transport in a vehicle. Seat brackets 30068 can include, but are not limited to including, a seat support bracket plate that can provide an interface between seat support bracket 30068 and central gearbox 21514 (FIG. 5A). Seat attachment rail 30081 can be sized according to the seat chosen for use. Seat brackets 30068 can be customized to attach each type of seat to lifting arms 21301 (FIG. SD) and stabilizer arms 21302 (FIG. 5C). Seat brackets 30068 can enable the seat to quickly and easily be removed for changing the seat and for enabling transport and storage, for example.

Figure 5F:
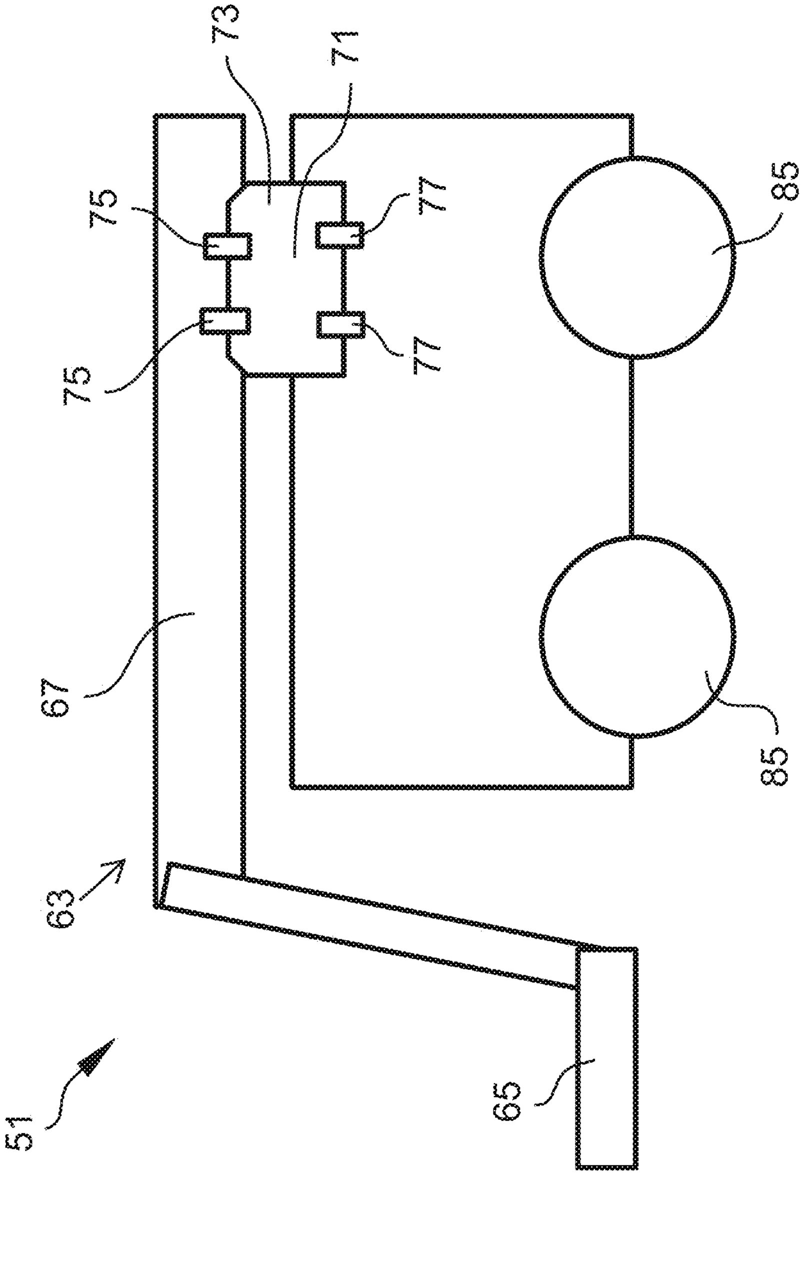
FIGS. 5F-5H are pictorial representations of a release mechanism between seat rails and base of a mobility device.
Figure 5G:
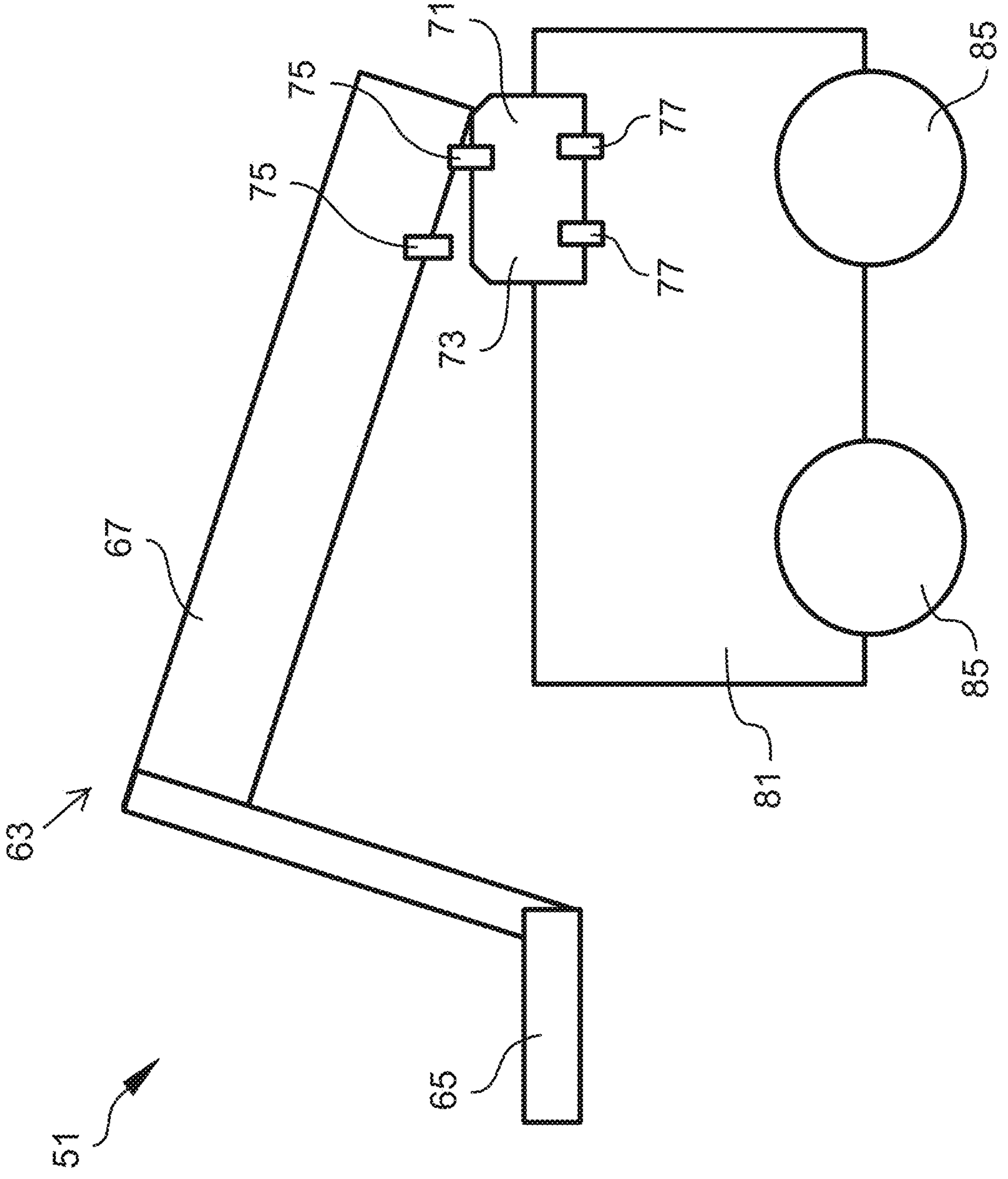
Figure 5H:
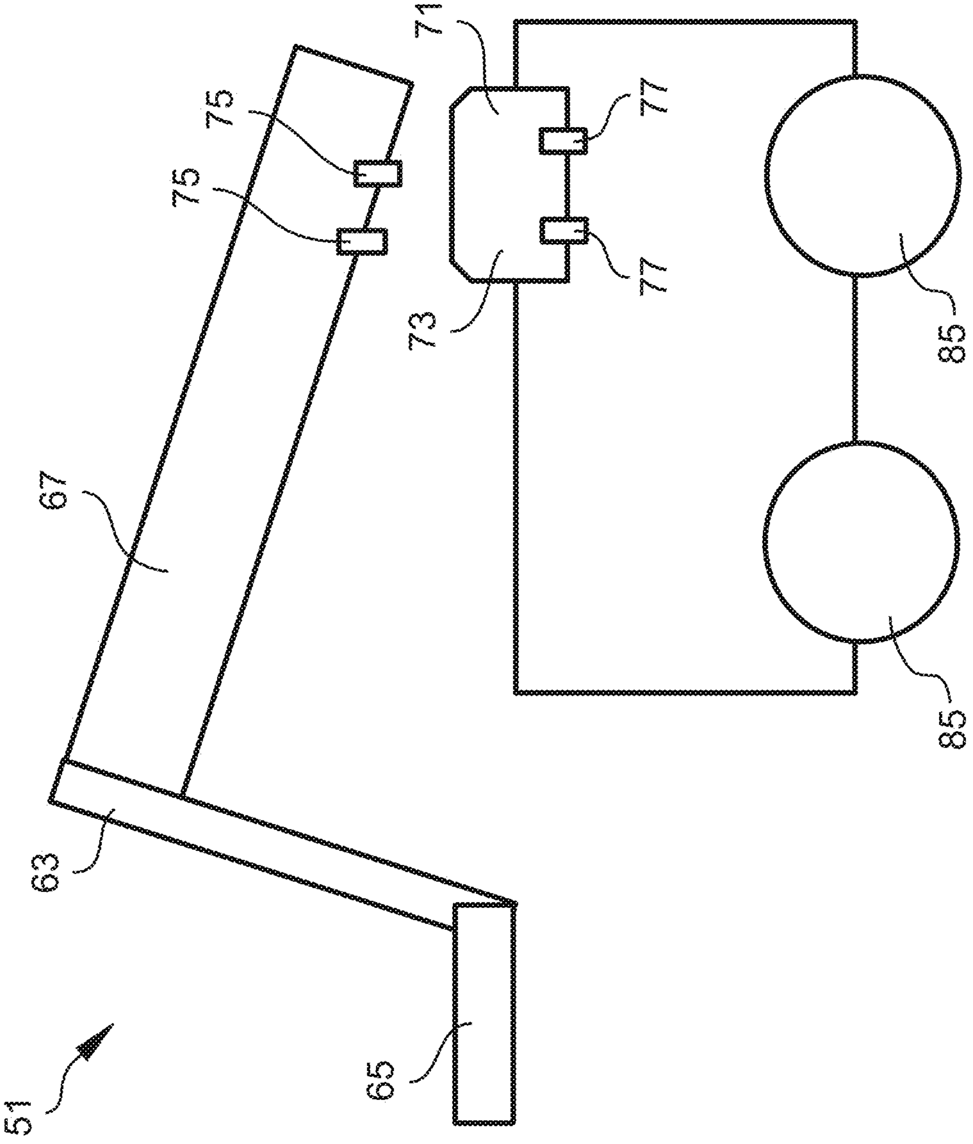

Referring now to FIGS. 5F-5H, assembly 51 depicts seat 67 that can be removably paired with a base 81 of the MD. Seat 63 can comprise seat rail 67 that can be optionally combined with leg-supports (not shown) and footrest 65. Seat rail/s 67 can accept cushioning or sitting surface for the user of the MD to rest upon. In some configurations, base 81 can include wheels 85. Pairing assembly 73 can be configured to engage with seat rail/s 67 on one end and optionally engage with base 81 on another end. Pairing bracket 71 of pairing assembly 73 can conjointly function with first coupling features 75 oriented to engage seat rail/s 67 and second coupling features 77 configured to engage assembly 73 with base 81 of the MD. In some configurations, first coupling features 75 can be rigidly clamped with or molded to seat rail/s 67. In some configurations, first coupling features 75 can be removably clamped with pairing bracket 71 in assembly 73.

Continuing to refer to FIGS. 5F-5H, in some configurations, one of first coupling features 75 can be engaged with pairing bracket 71 using a first release mechanism, and another of first coupling features 75 can be engaged with pairing bracket 71 through a second release mechanism. The first and second release mechanisms can jointly operate to engage and/or release seat rail/s 67 with base 81 of the MD.

Figure 5I:
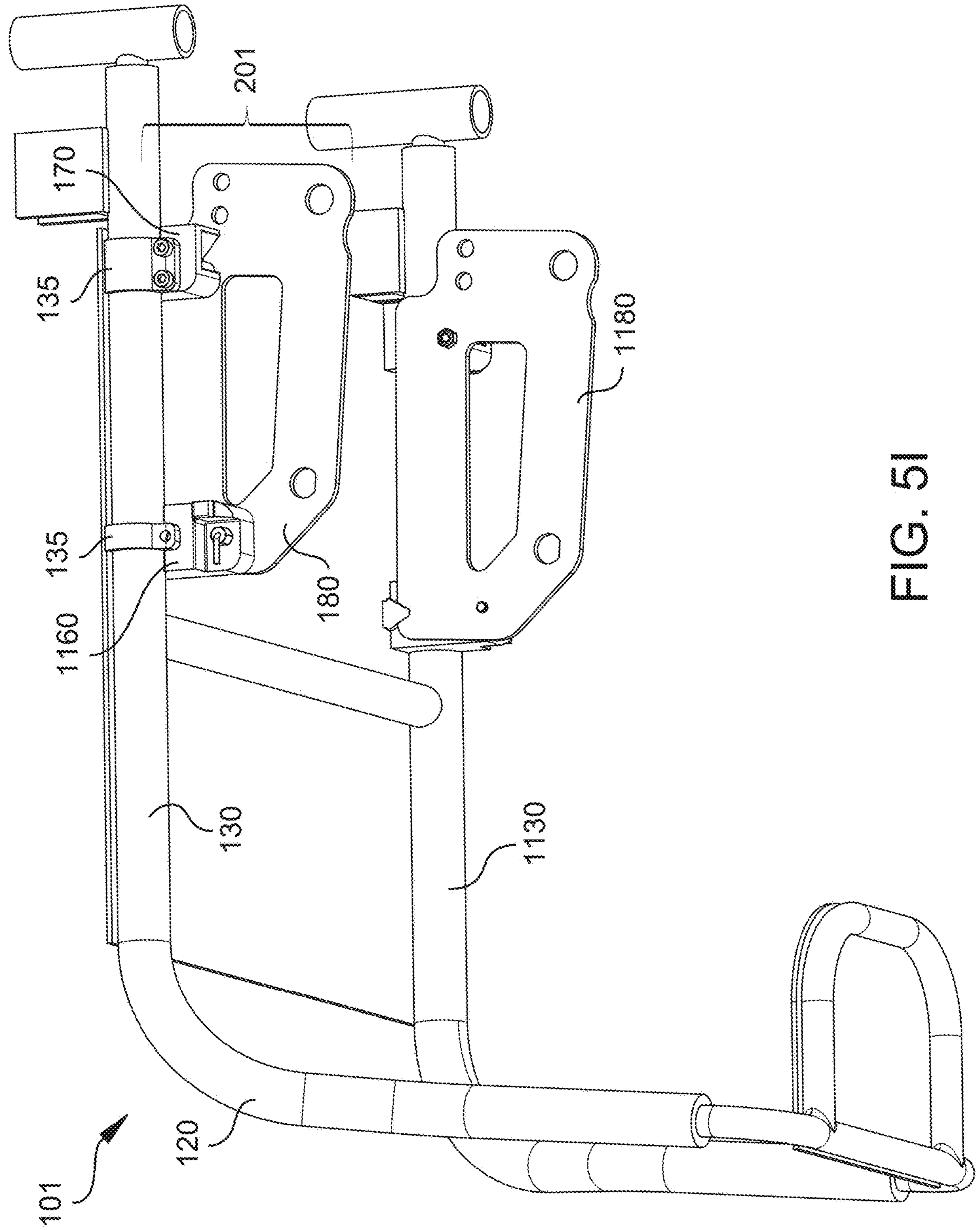
FIGS. 5J-5M are right-side perspective views depicting engagement and disengagement of seat rail with exemplary pairing assembly.
FIGS. 5N and 5O are right side detailed perspective views depicting alignment before engagement of first and second mounts with exemplary pairing bracket.
FIGS. 5P and 5Q are right side detailed views depicting engagement of first and second mounts with exemplary pairing bracket.
FIGS. 5R and 5S are perspective views of the attachment mechanism between the seat bracket of the present teachings and a seat.
Figure 5J:
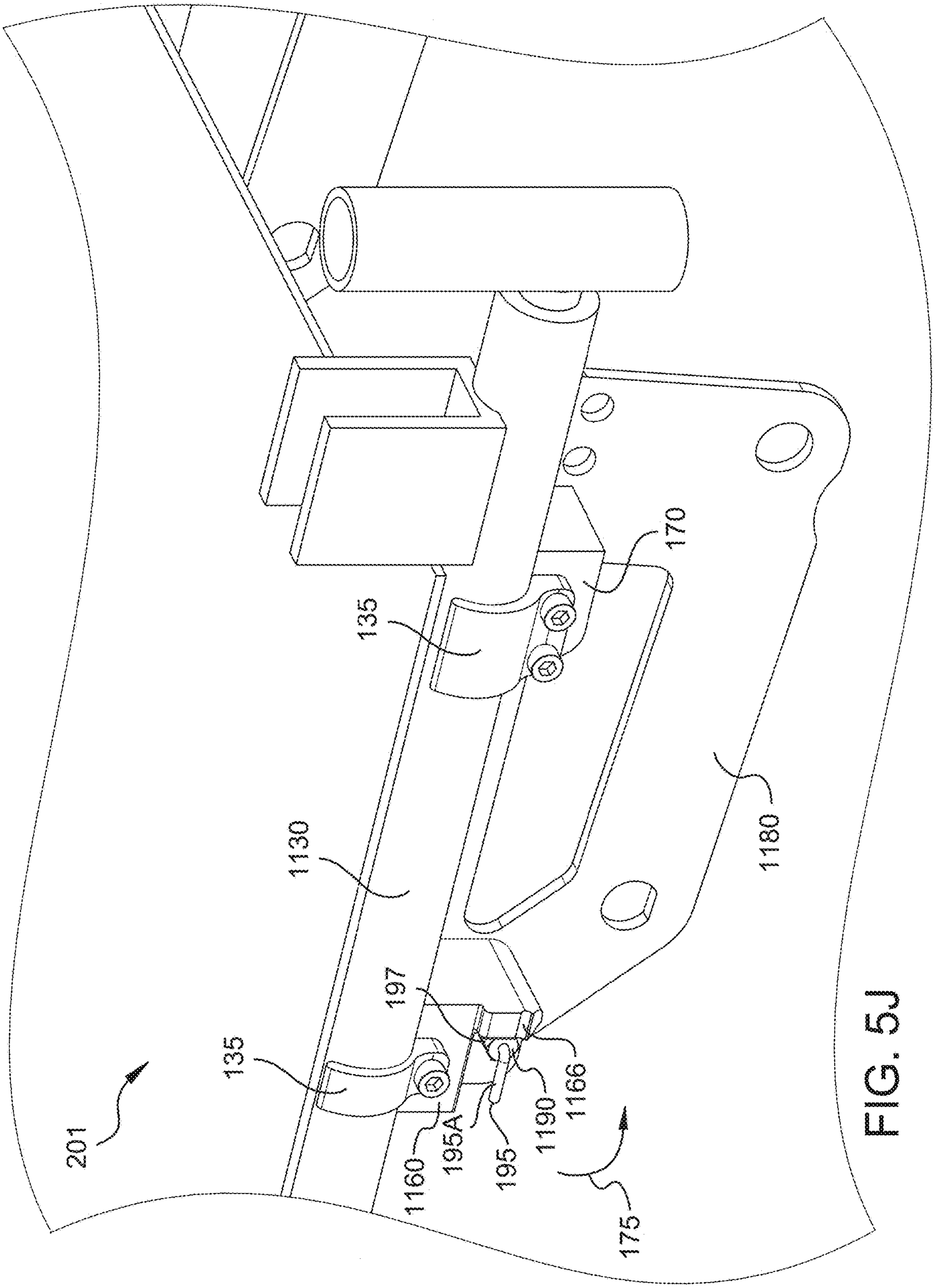
Figure 5K:
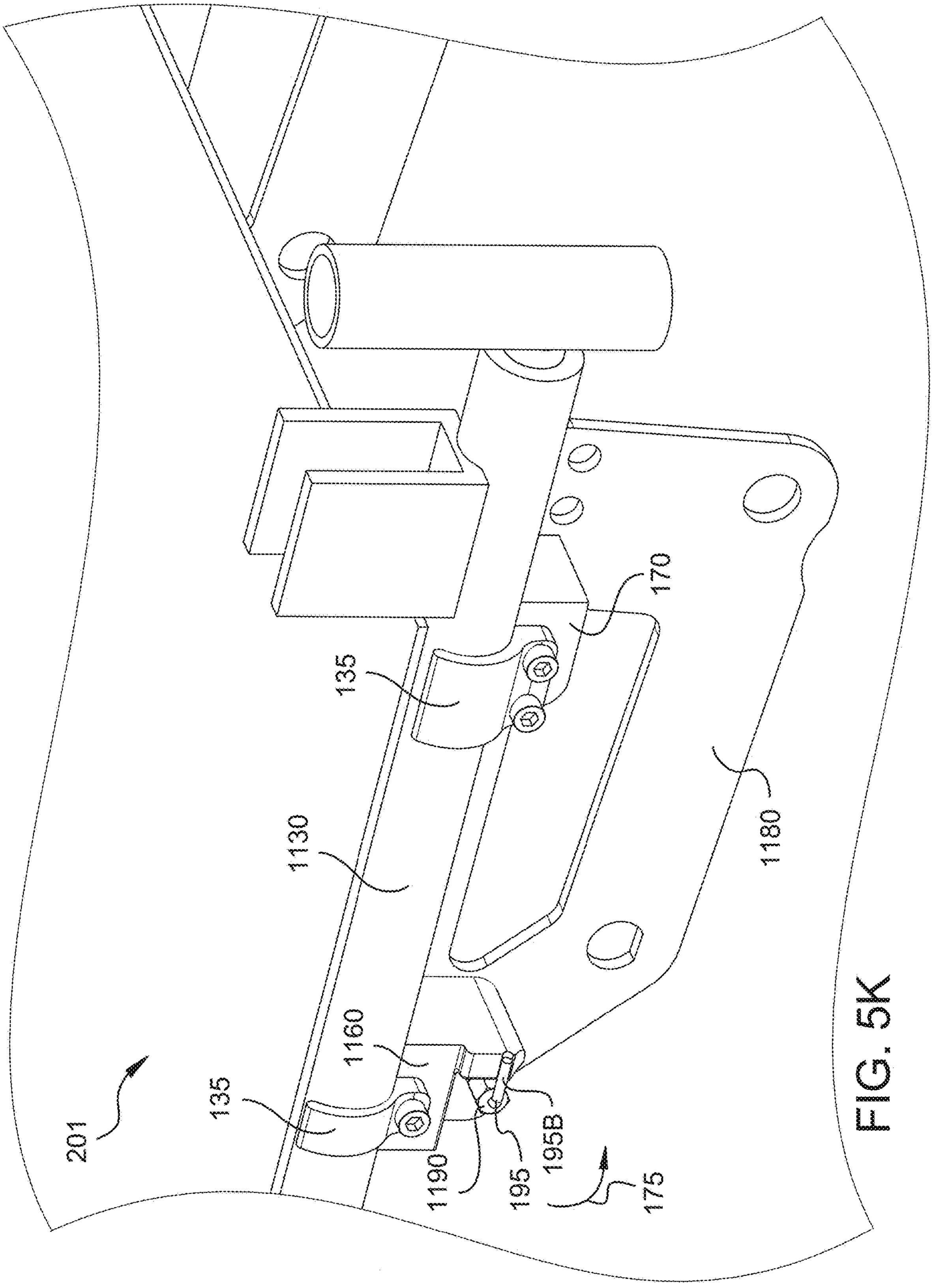

Referring now primarily to FIG. 5I, assembly 101 can include user seat 120 engaged to a device such as, for example, but not limited to, the MD through pairing assembly 201. The device can be mobile or stationary. User seat 120 can comprise at least one rail 1130 co-jointly positioned with partnering rails to support a platform or cushioning on which the user can rest. Seat rails 1130 can be of any geometry configured to engage one or more clamping features 135 that can be engaged therewith. Configuration of the present teachings depicts a tube-like geometry of seat rails 1130. In some configurations, the geometry of clamping features 135 can vary with the geometry of seat rails 1130. Clamping features 135 can be fastened with one or more mounts. Mounts, for example, but not limited to, first mount 1160 and second mount 170 can serve as intermediates to engage seat rail/s 1130 with pairing brackets 1180. A plurality of pairing brackets 1180 can commit to single seat rail 1130. In some configurations, pairing bracket 1180 can be paired with seat rail 1130. Pairing bracket 1180 can partly engage with seat rails 1130 on one end and can further engage with, for example, the MD or a sitting structure, on another end.

Figure 5L:
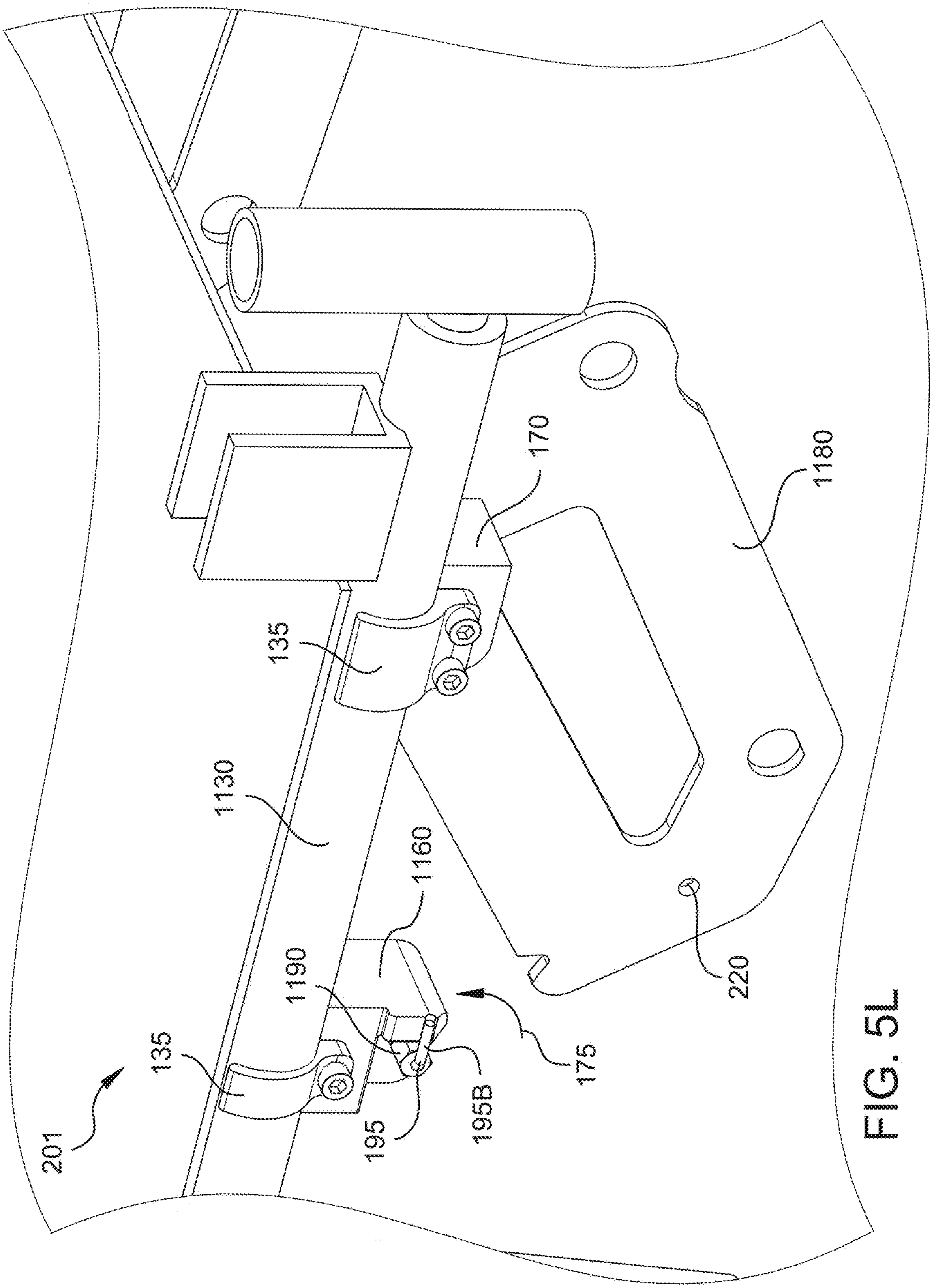

Continuing to refer to FIG. 5I, pairing brackets 1180 can provide (1) first receptacles 220 (FIG. 5L) that can align to engage with first and second mounts 1160, 170 and (2) second receptacles (not shown) that can align with components (not shown) to engage the base of the MD therewith. An individual receptacle of first receptacles 220 and an individual receptacle of the second receptacles (not shown) can be of varying dimensions to engage fastening features such as, but not limited to, mounting pins 1190, 177 respective to first and second mounts. Quick release engagement of pairing bracket 1180, first and second mounts 1160, 170 along with their respective pins 1190, 177 is discussed herein.

Figure 5M:
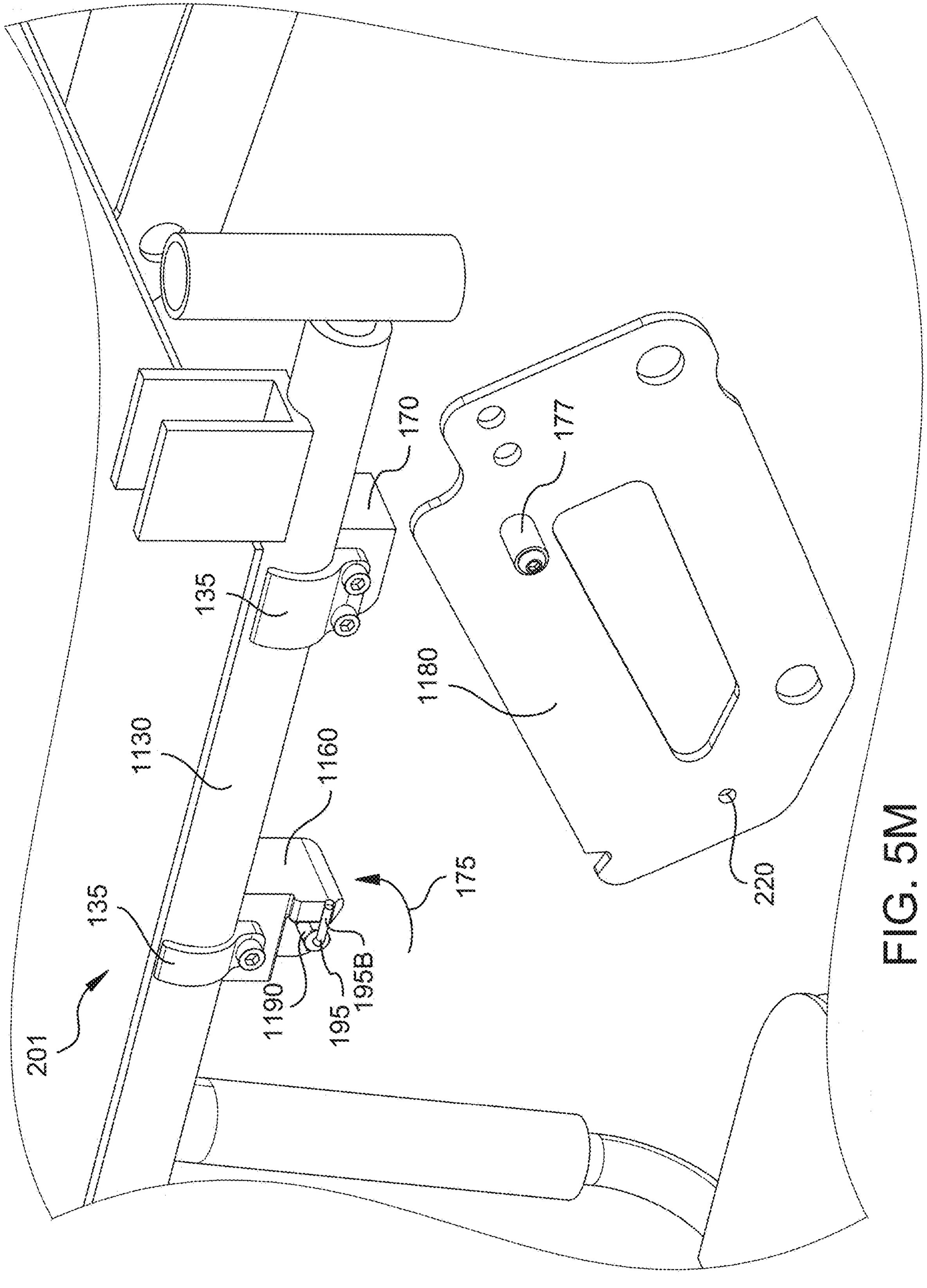

Referring now to FIGS. 5J-5M, pairing assembly 201 can include, but is not limited to including, pairing bracket 1180 engaged with seat rail 1130 through first mount/s 1160 and second mount/s170. First and second mounts 1160, 170 can operably couple with seat rail 1130 through clamping features 135. The number of clamping features 135 used and the dimensions of clamping features 135 can be altered to suit the geometry of seat rail 1130 and the dimensions of first and second mounts 1160, 170. At least one first mounting pin 1190 can allow a releasable engagement of first mount 1160 with pairing bracket 1180. Second mount 170 can engage with pairing bracket 1180 through at least one rear pin 177 (FIG. 5M). First and second mounts 1160, 170 can further provide corresponding pockets (not shown) therewith that can operatively accommodate the at least one front pin 1190 and the at least one second pin 177 (FIG. 5M), respectively.

Continuing to refer to FIGS. 5J-5M, second mount 170 can further optionally operate in conjunction with first mount 1160 such that disengagement between second mount 170 and pairing bracket 1180 cannot be achieved without disengaging first mount 1160 and pairing bracket 1180. This releasable engagement can be operated by user of the MD and/or any operator requiring to detach or replace seat of the MD through operation of first mounting pin 1190. First mounting pin 1190 can further comprise body 197 and handle 195. Body 1190 can be operated upon by handle 195. First mount 1160 can provide a pocket (not shown) to operatively accommodate first mounting pin 1190 such that body 197 of mounting pin 1190 can rest in the pocket thereof. Handle 195 can serve as an operating feature to transition first mounting pin 1190 from a first position to a second position and vice-versa. First position of first mount pin 1190 can be confirmed by first handle position 195A and second position of first mount pin 1190 can be confirmed by second handle position 195B. In first handle position 195A, first mounting pin 1190 can occupy corresponding pocket (not shown) provided by first mount 1160 and further extend into a receptacle (not shown) on paring bracket 1180. The first position of the at least first mounting pin 1190 can engage first mount 1160 with pairing bracket 1180. Handle 195 can be rotated in direction 175 to cause handle 195 to be in a second handle position 195B and thereby can cause first mounting pin 1190 to be in its second position or release position.

Continuing to refer to FIGS. 5J-5M, during second handle position 195B, handle 195 can be rested into groove 166 that can be provided on first mount 1160. Rotating handle 195 to second handle position 195B can cause first mounting pin 1190 to be in a second position wherein, first mounting pin 1190 can withdraw from corresponding receptacle (not shown) provided by paring bracket 1180. First mount 1160 can disengage with pairing bracket 1180, and can cause seat rail 1130 to be partially disengaged from pairing bracket 1180. Second mount 170, that can be configured to jointly function with first mount 1160, and can include slot 176 (FIGS. 5N and 5O) therein. Second mount pin 177 can occupy slot 176 without descending out of slot 176 during engagement of seat rail 1130 with pairing bracket 1180. Disengagement between pairing bracket 1180 and seat rail 1130 can allow second mount pin 177 to descend out of slot 176, thereby causing seat rail/s 1130 to disengage from pairing bracket 1180. As a result, user seat can be expediently released from base of the MD.

Figure 5N:
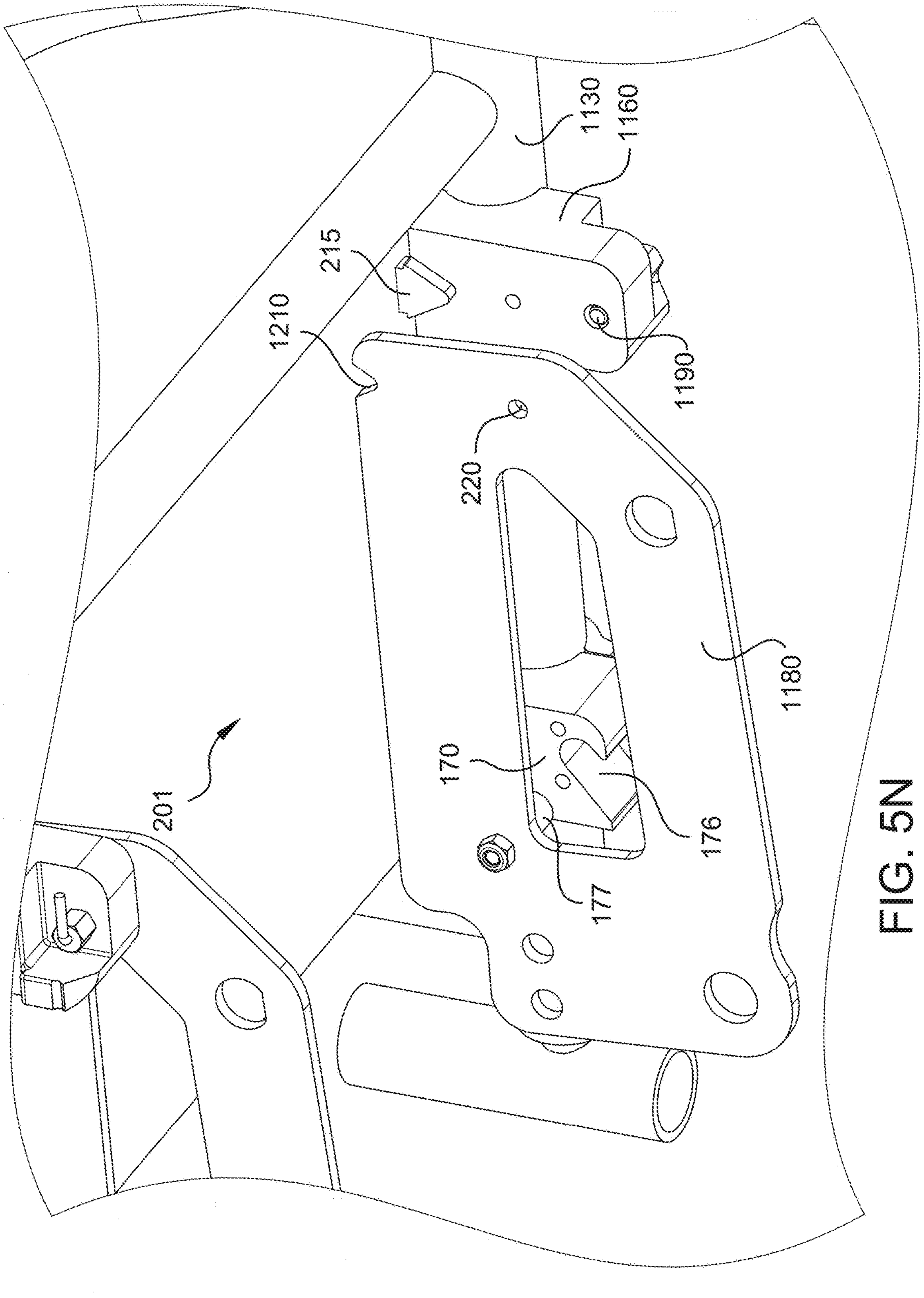
Figure 5O:
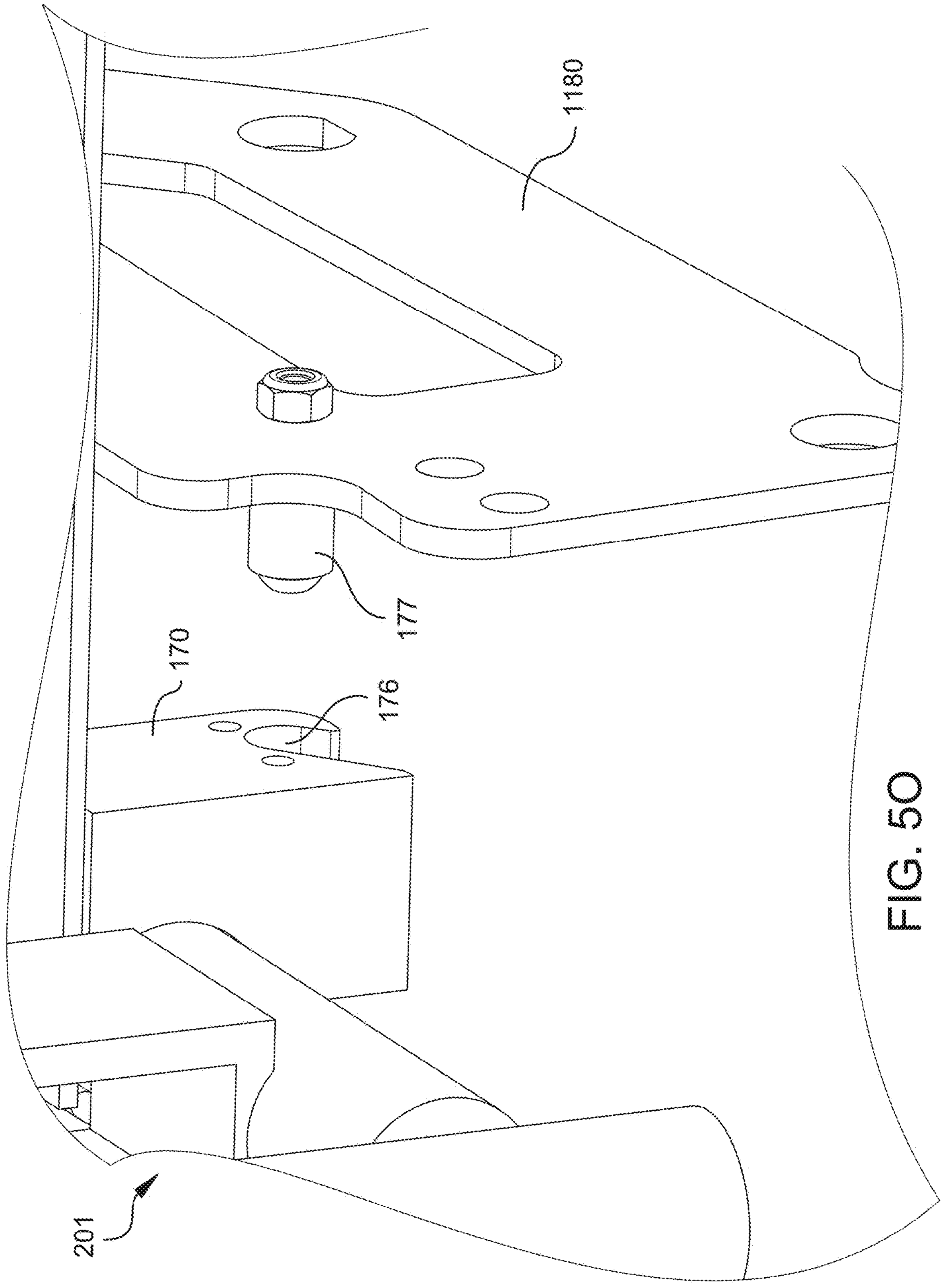
Figure 5P:
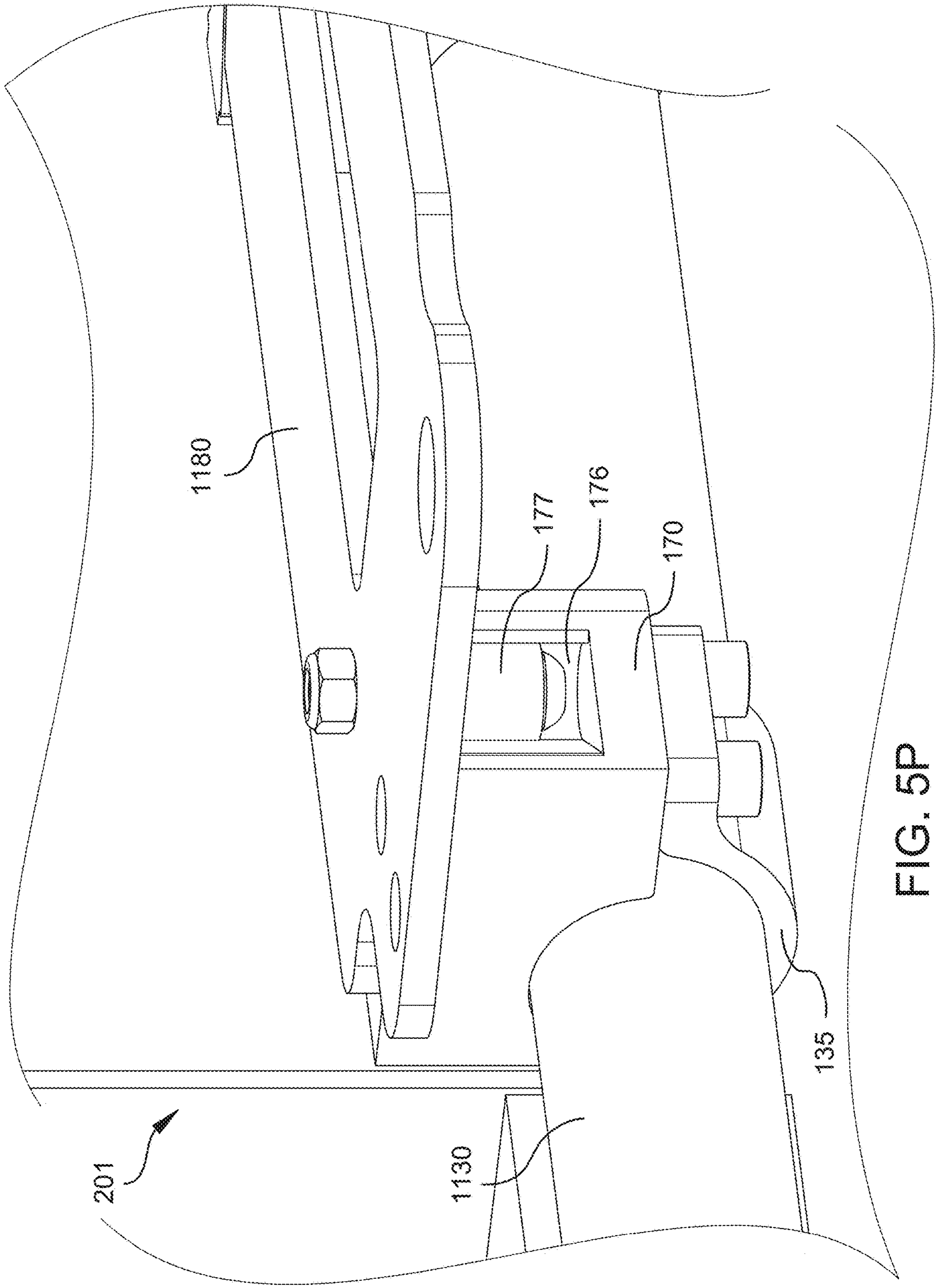
Figure 5Q:
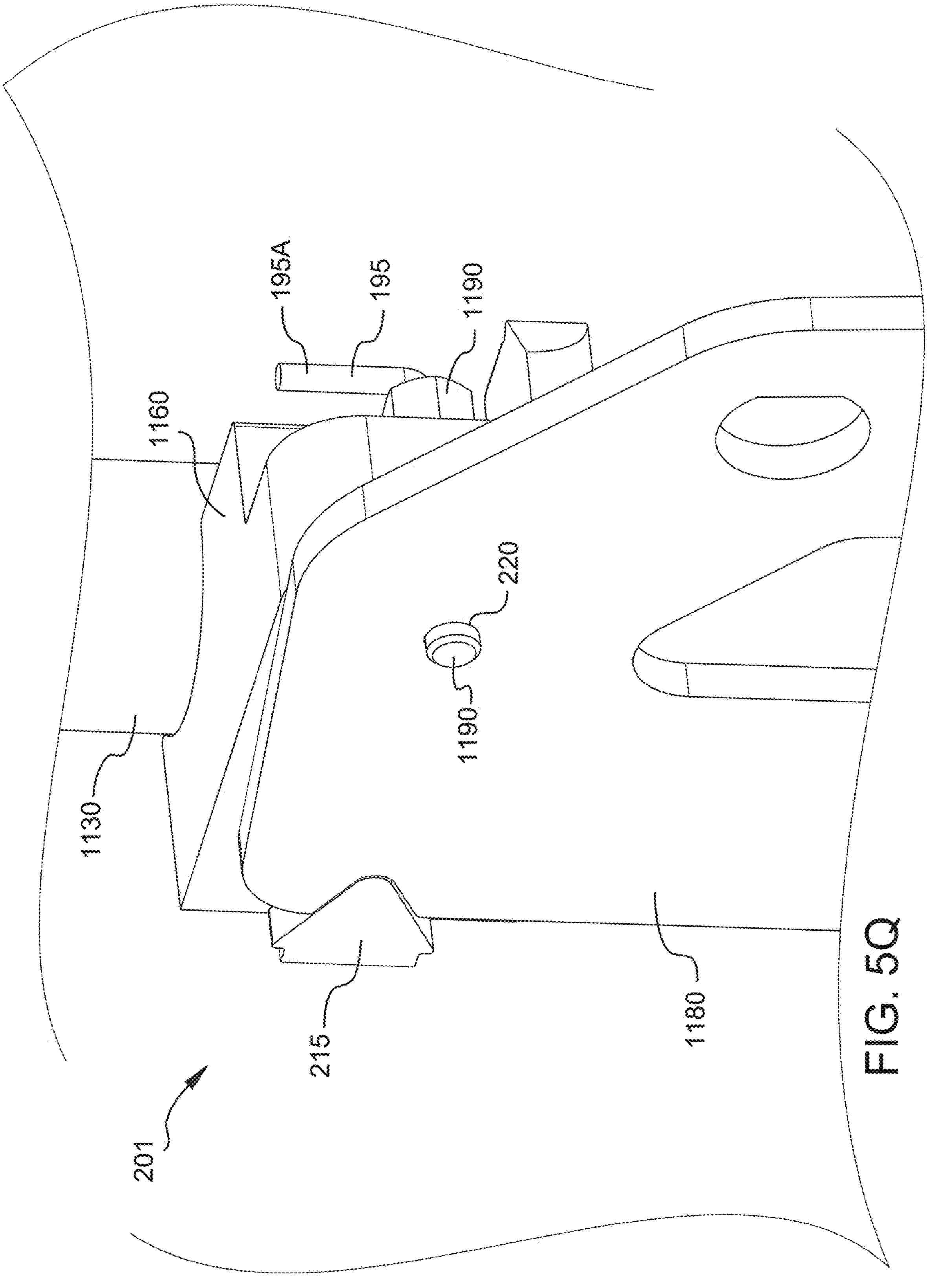
Figure 5R:
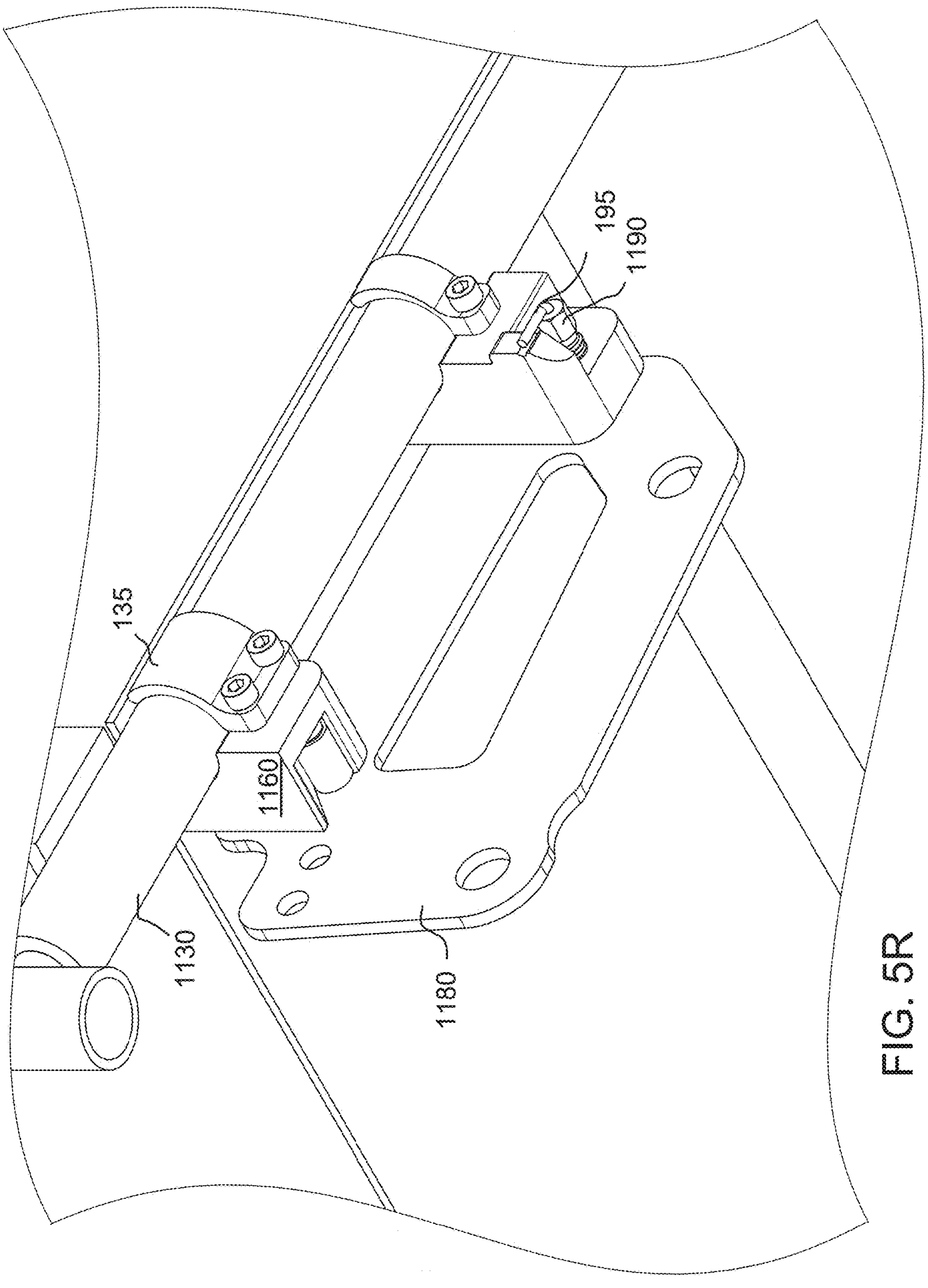
Figure 5S:
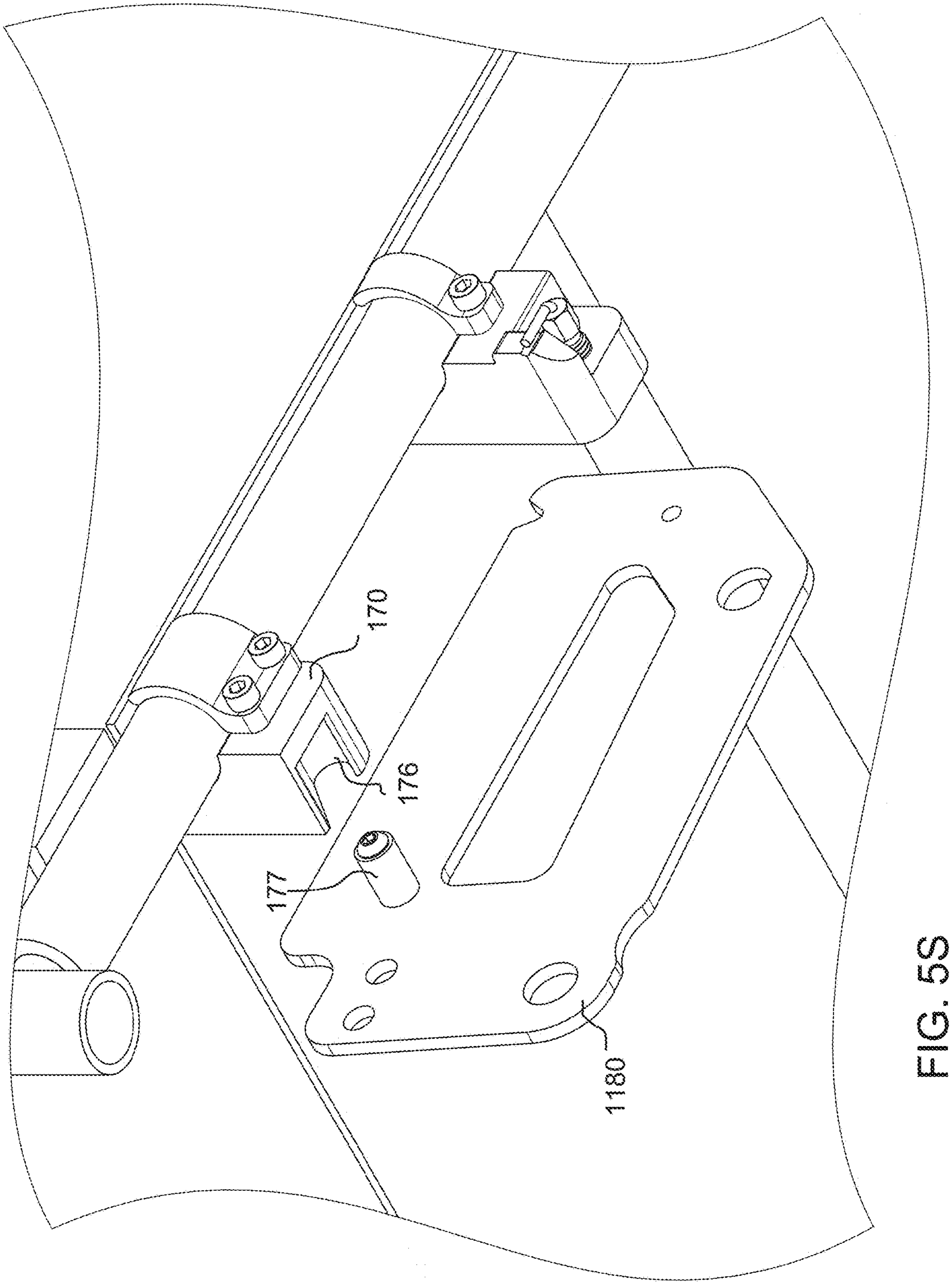

Referring now to FIGS. 5N and 5O, first mount 1160 can further provide a supplementing catch feature 215 configured to capture pairing bracket 1180. Pocket 210 on pairing bracket 1180 can receive catch feature 215 therein to secure first mount 1160 with pairing bracket 1180. Above discussed engagement can work in conjunction with engagement between first mount 1160 and pairing bracket 1180 through first mount pin 1190 that can be received in receptacle 220 of pairing bracket. This dual engaging mechanism can securely fasten at least a part of seat rail 1130 with pairing bracket 1160. Second mount pin 177 can be securely fastened with pairing bracket 1180 and on appropriate alignment can slide into slot 176 of second mount 170.

Referring now to FIGS. 5P-5S, comprehensive engagement of seat rail 1130 with pairing bracket 1180 can be achieved by sliding in second mount pin 177 into slot 176 of second mount and securing pin 177 therein. This step can be followed by aligning pairing bracket 1180 with first mount 1160 such that first mount pin 1190 can be received into receptacle 220 of pairing bracket 1180 and catch features 215 can capture a part of pairing bracket 1180 by resting in pocket 210. During this arrangement pin handle 195 can be in a first position 195A. As a result, switching position of pin handle 195 from position 195A to second position 195B can allow disengaging seat rail 1130 and paring bracket 1180. Discussed mechanism can allow a variety of user-preferred seat/s with complementing seat rails to engage and disengage with the MD through pairing assembly 201.

Figure 6B:
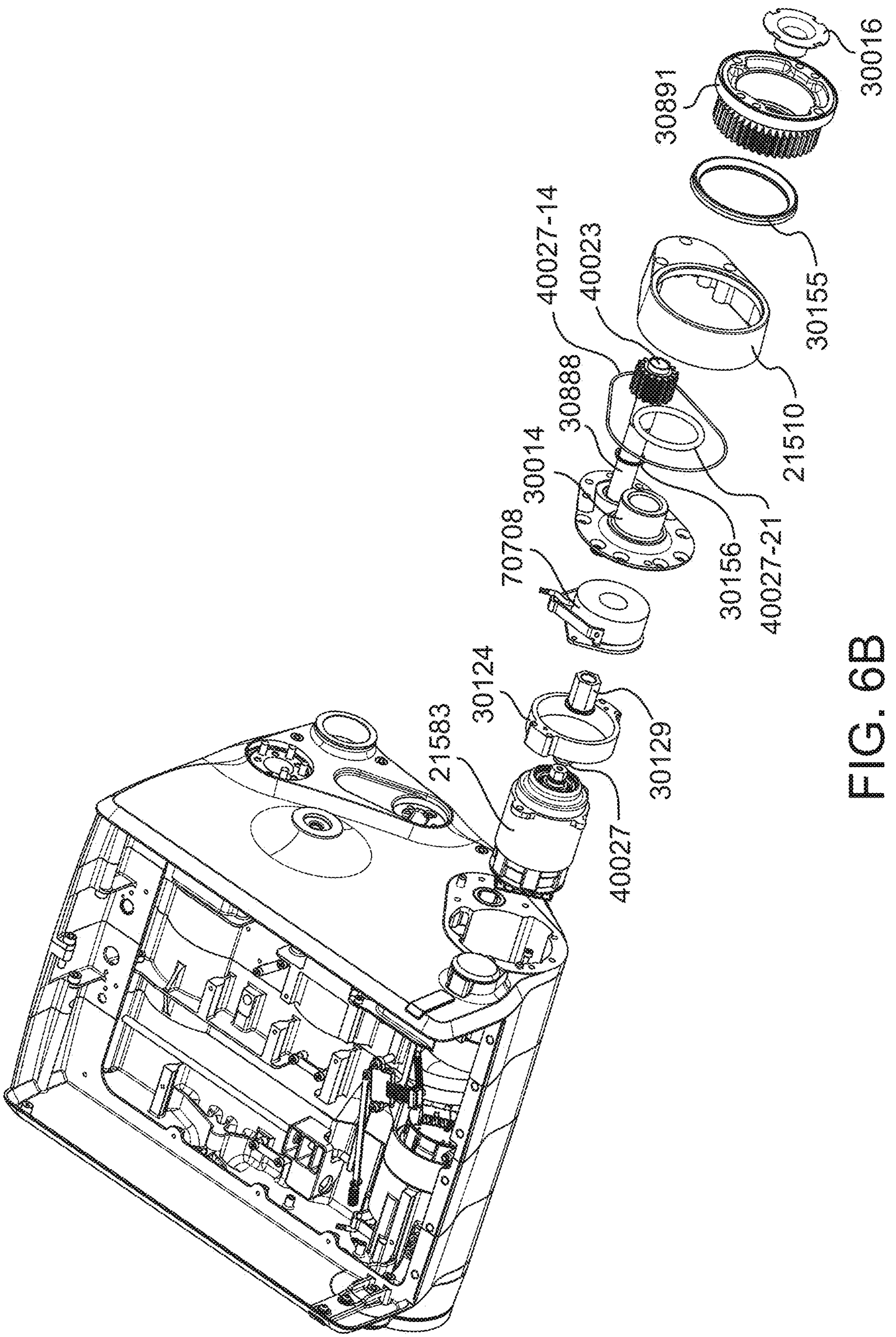
FIG. 6B is a perspective diagram of the cluster motor assembly of the present teachings.

Referring now primarily to FIGS. 6A and 6B, cluster assembly can include cluster housing 30010/30011 (FIG. 6K), cluster interface pin 30160 (FIG. 6A), and o-ring 40027-6 (FIG. 6A) that can environmentally isolate the interior of central gearbox 21514 at the cluster connection. Each cluster assembly can include a two-stage gear train replicated on both left and right sides of central gearbox 21514 to drive each cluster assembly simultaneously. Each cluster assembly can independently operate the set of two wheels 21203 (FIG. 6A) on wheel cluster 21100 (FIG. 6A), thereby providing forward, reverse and rotary motion of the MD, upon command. The cluster assembly can provide the structural support for wheel clusters 21100 (FIG. 6A) and the power transmission for the wheels 21203 (FIG. 6A). The cluster assembly can include, but is not limited to including, ring gear nut 30016 (FIG. 6B), ring gear 21591 (6J), ring gear seal 30155 (FIG. 6B), cluster interface cover 21510 (FIG. 6C), first configuration cluster plate interface 30014 (FIG. 6I), cluster interface gasket 40027-14 (FIG. 6B), cluster rotate stage four pinion shaft 30888 (FIG. 31A4), brake with manual release 70708 (FIG. 3I), brushless DC servomotor 2-inch stack 21583 (FIG. 3D), and motor adapter 30124 (FIG. 6B). Second configuration cluster interface plate 30014A (FIG. 6H) can alternatively provide the functionality of first configuration cluster interface plate 30014 (FIG. 6I). The cluster interface assembly can drive cluster wheel drive assembly 21100 (FIG. 6A) under the control of powerbase processors on powerbase controller board 50001 (FIG. 15B). The cluster interface assembly can provide the mechanical power to rotate wheel drive assemblies 21100 (FIG. 6A) together, allowing for functions dependent on cluster assembly rotation, for example, but not limited to, stair and curb climbing, uneven terrain, seat lean adjustments, and balance mode. Cluster motor 21583 (FIG. 6B) can supply input torque to the cluster interface assembly. The cluster interface assembly can provide a reduction to deliver the torque required to lift the user seated upon the MD when climbing stairs or lifting up to balance mode 100-3 (FIG. 22B). Power from cluster motor 21583 (FIG. 6B) can be transmitted to the output shaft to provide the low speed, high torque performance required for stair and obstacle navigation. Cluster o-ring 40027-14 (FIG. 6B) can form a three-way seal between the cluster plate 30014 (FIG. 6A), cluster interface housing cap 30014 (FIG. 6B), and central housing 21514 (FIG. 6A).

Continuing to refer to FIG. 6B, cluster drive train damper 40027-21 can damp oscillations when it is necessary to hold the cluster drive train steady. For example, when the cluster gear train is holding the cluster in a vertical position in balance mode, the cluster drive train may be difficult to hold steady with motor commands because of the backlash in the drive train. The motor commands can generate more correction than is needed and can require corrections in a direction that can lead to oscillation. The oscillation can be damped with added friction in the cluster drive train. An elastomeric material can be clamped between the cluster output bearing and cluster interface plate 30014 that can cause friction. In some configurations, a less efficient bearing with significant drag like a bronze or plastic bushing can be used.

Figure 6N:
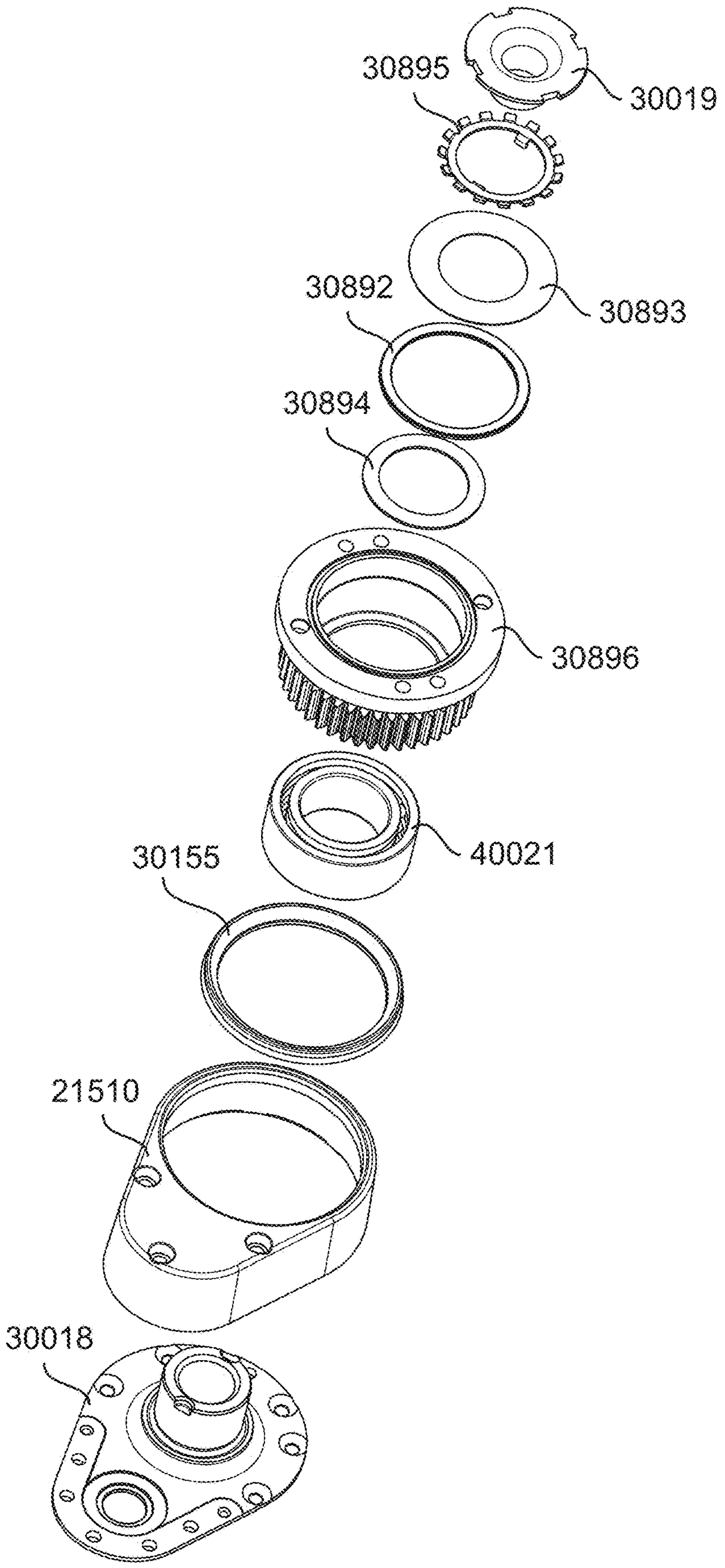
FIG. 6N is an exploded perspective diagram of the second configuration of the cluster motor assembly of the present teachings.

Referring now to FIG. 6N, in some configurations, damper ring 40027-21 can be replaced with wear ring 30892 which can be affixed to rotating ring gear 30891. In some configurations, wear ring 30892 can include polyoxymethylene such as, for example, but not limited to, DELRIN®. Wear ring 30892 can be pressed against a stationary metal surface such as, for example, but not limited to, spring 30893. Spring 30893 can be constrained to provide a consistent axial force against wear ring 30892. The amount of axial force applied can be proportional to the amount of damping desired, and can be controlled by the stiffness of spring 30893 and the amount of deflection caused by the installation of spring 30893. In some configurations, the deflection can be controlled by shim 30894, in addition to the thickness of wear ring 30892. The flange of ring gear nut 30019 can control the position of spring 30893 as spring 30893 is compressed between ring gear nut 30019 and shim 30894. Different amounts of damping can be accommodated by changing the stiffness of spring 30893 or the amount of deflection. In some configurations, the shape of wear ring 30892 can include an angled surface to allow the shape the deflected spring 30893 to contact wear ring 30892 with an even pressure over a larger surface area. The thickness of spring 30893 and the deflection distance can control the amount of friction, and either can be adjusted. In some configurations, the thickness of spring 30893 can be around 0.02 inches. In some configurations, the difference between the thickness of wear ring 30892 and the thickness of shim 30894 can set the amount of deflection distance.

Figure 6C:
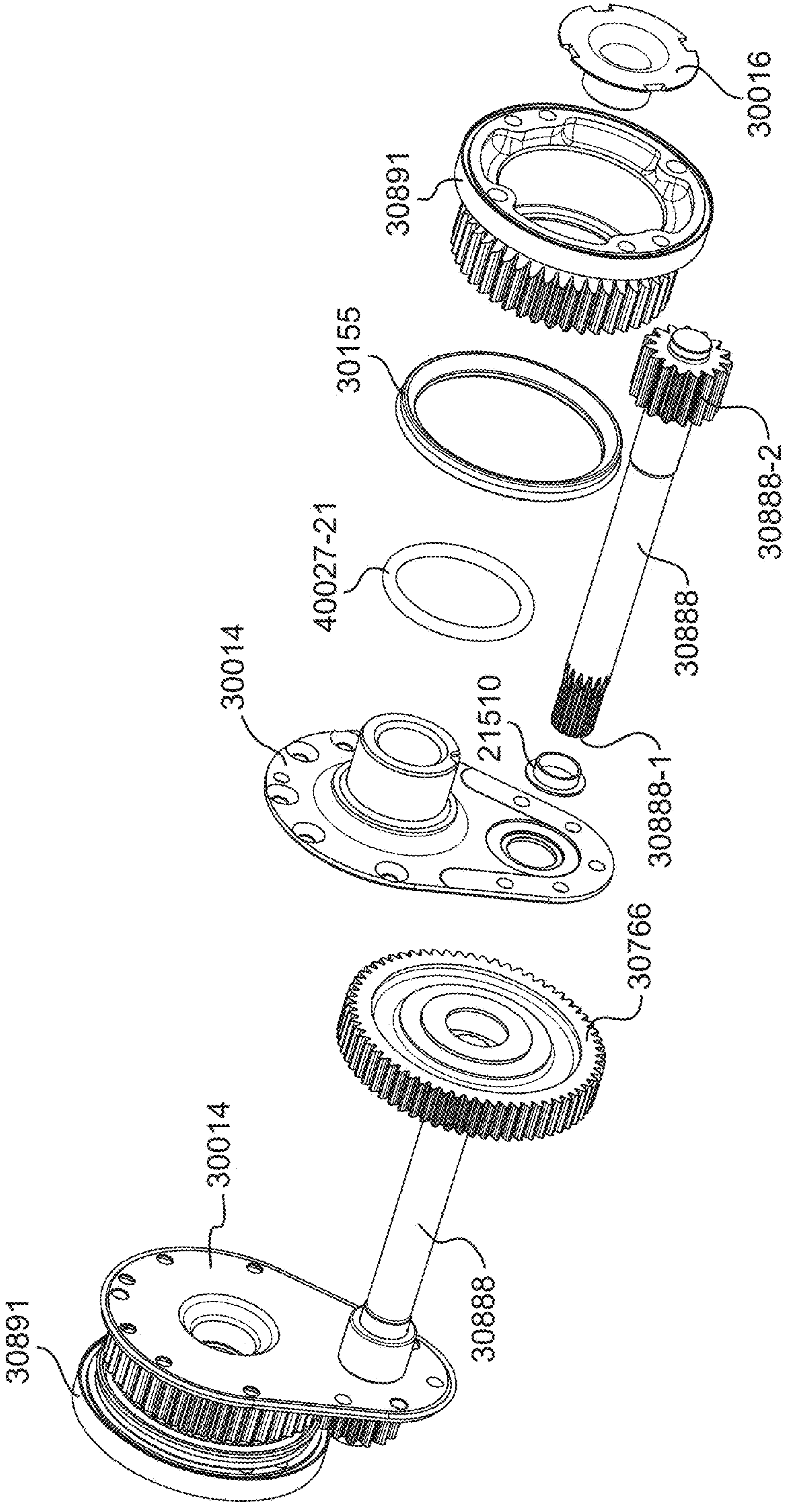
FIG. 6C is a perspective diagram of the cluster motor assembly with splines of the present teachings.
Figure 6D:
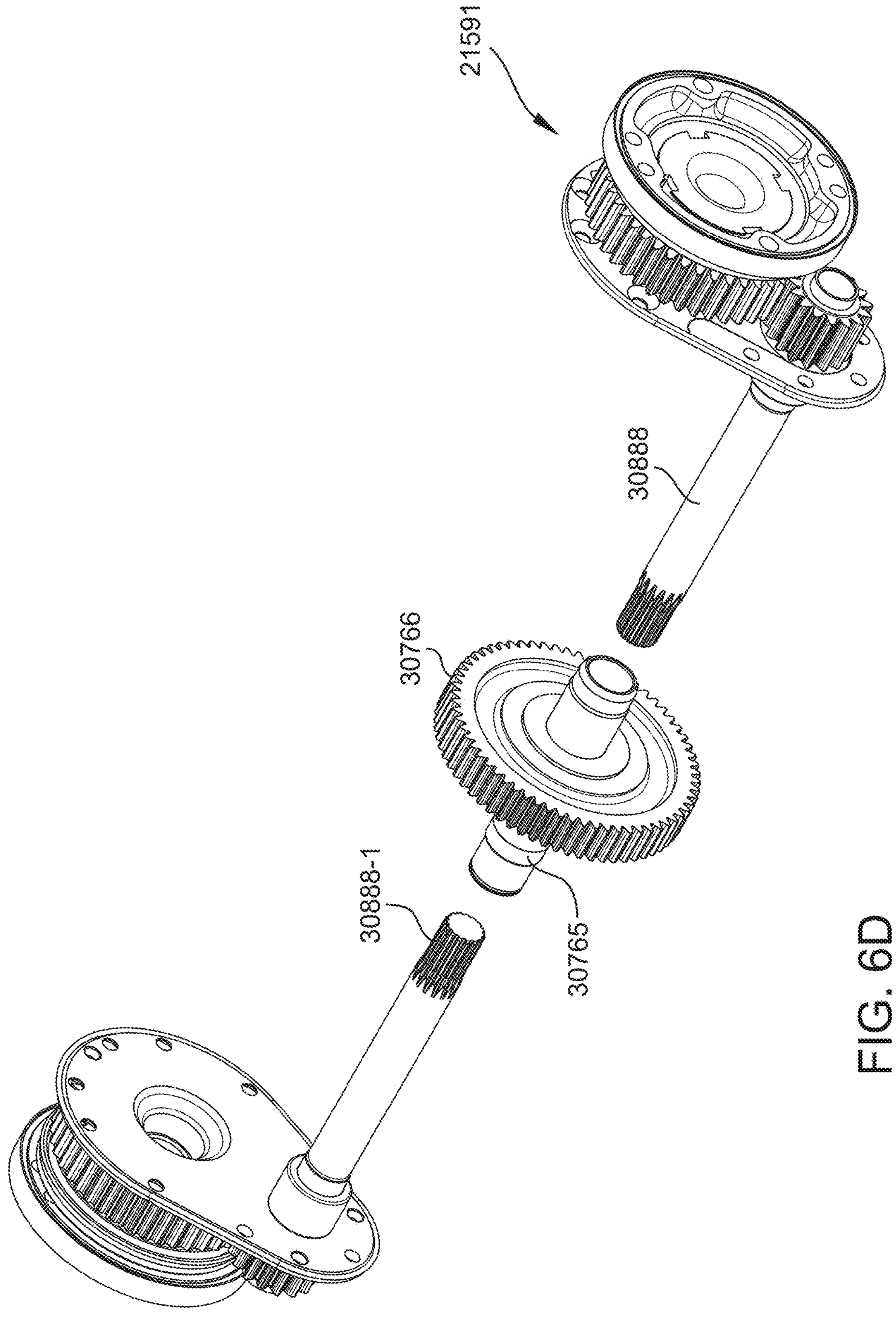
FIG. 6D is a perspective diagram of the gear-pinion cluster rotate stage 3 cross shaft and pinion shaft cluster rotate stage 4 of the present teachings.
Figure 6E:
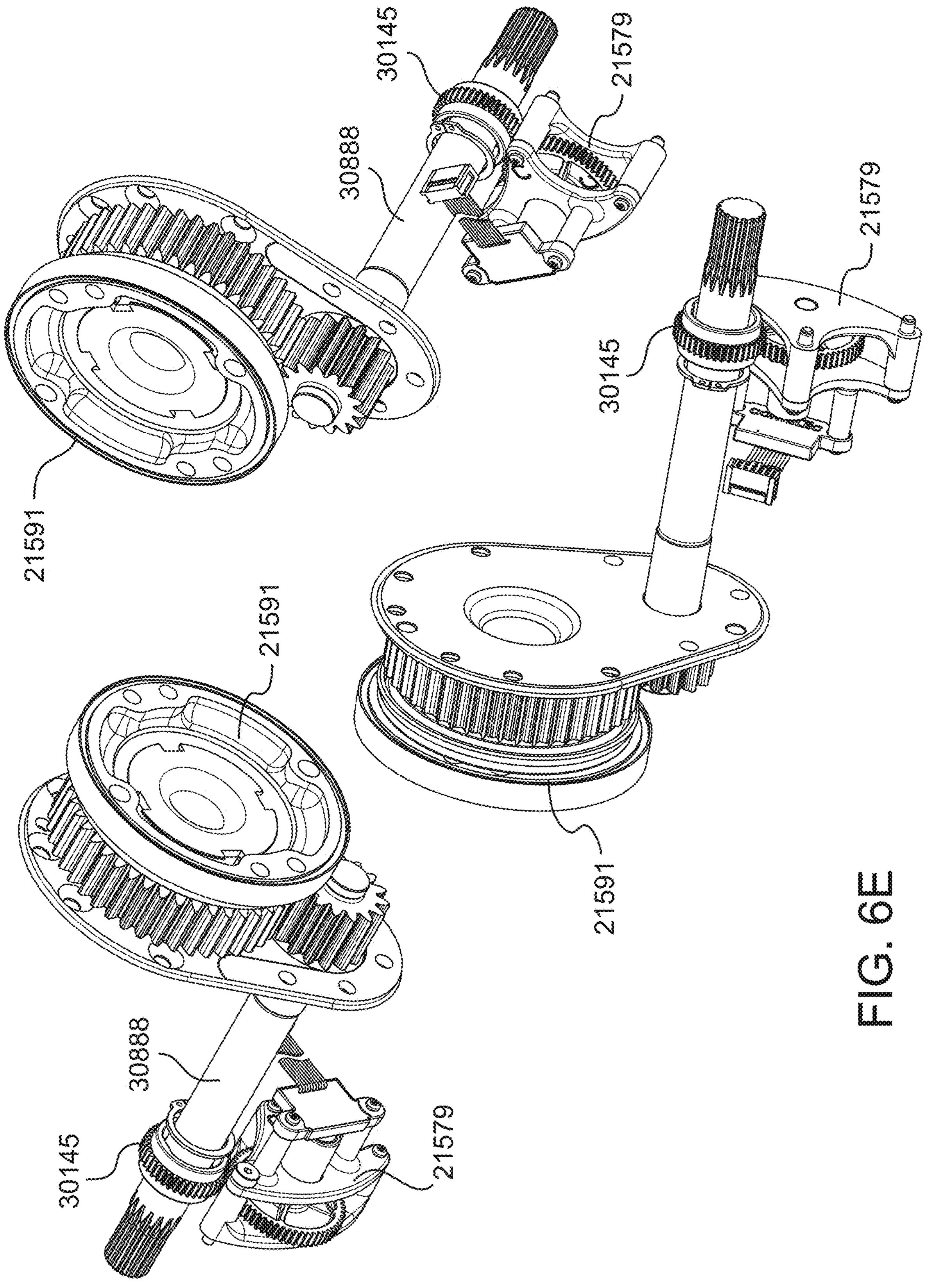
FIG. 6E is a perspective diagram of views of the pinion shaft cluster rotate stage 4 and cluster position sensor tooth cluster cross shaft gear of the present teachings.

Referring primarily to FIG. 6C, cluster cross shaft 30765 (FIG. 6D) can operably couple with ring gear 30891 that can rotate cluster housing 21100 (FIG. 6A). Each of cluster housings 21100 (FIG. 6A) can include two wheels 21203 (FIG. 6A) that are positioned symmetrically about the center of rotation of cluster housing 21100 (FIG. 6A). In some configurations, the MD can function substantially the same regardless of which of wheels 21203 (FIG. 6A) on cluster housings 21100 (FIG. 6A) are nearest castor wheels 21001 (FIG. 4). Cluster position sensor 21579 (FIG. 30) can include, based on the symmetry, coupling with cluster cross shaft 30765 (FIG. 6C) with a gear ratio that can cause cluster position sensor 21579 (FIG. 30) to rotate one full rotation for each half rotation of cluster housing 21100 (FIG. 6A), which doubles the resolution of cluster position sensor 21579 (FIG. 30). Cluster housing 21100 (FIG. 6A) is symmetric so that, for each half revolution, the cluster will function just as if a full rotation has occurred.

Figure 6F:
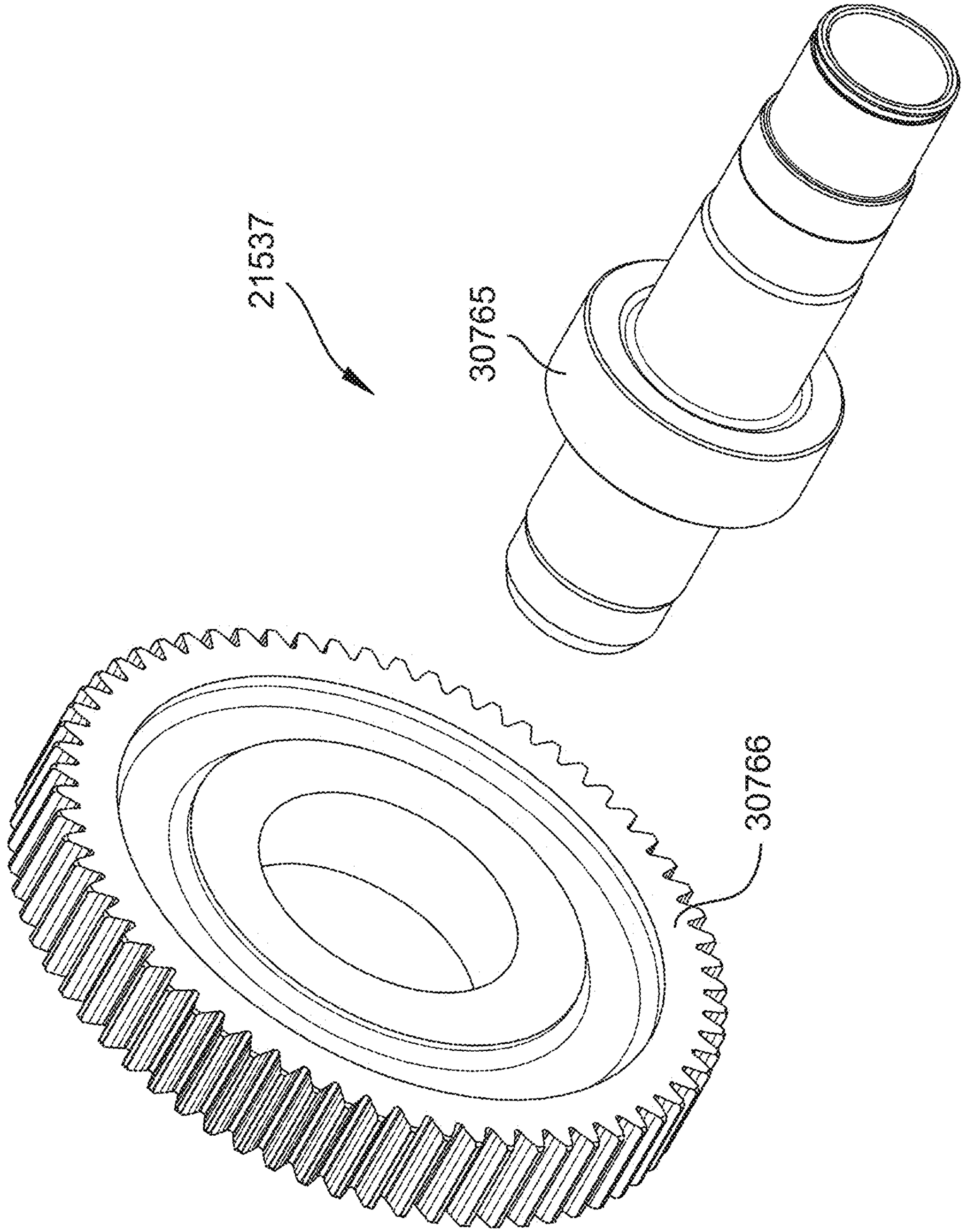
FIG. 6F is a perspective diagram of the gear-pinion cluster rotate stage 3 cross shaft of the present teachings.
Figure 6G:
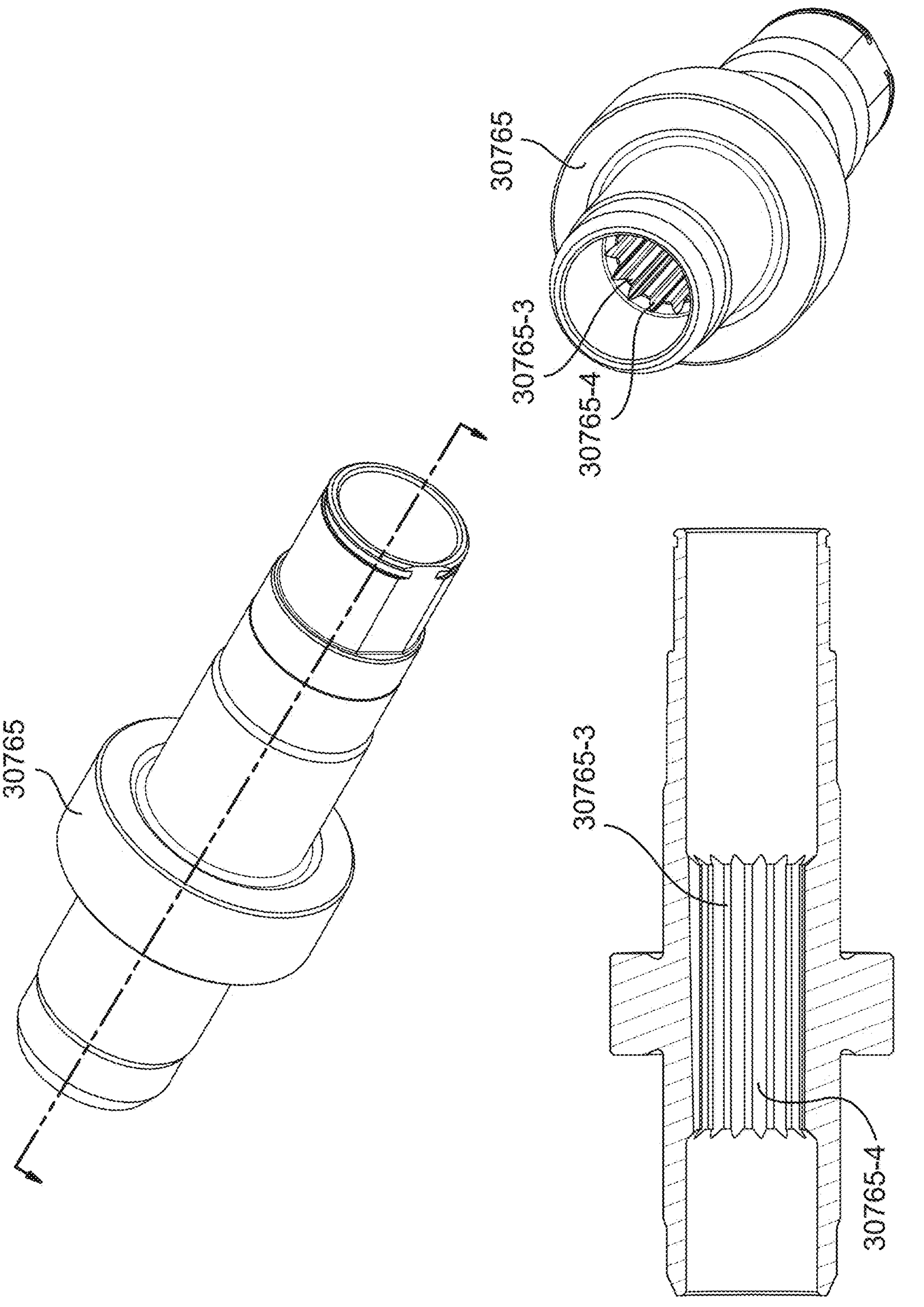
FIG. 6G is a cross section perspective diagram of the cross shaft cluster rotate of the present teachings.
Figure 6H:
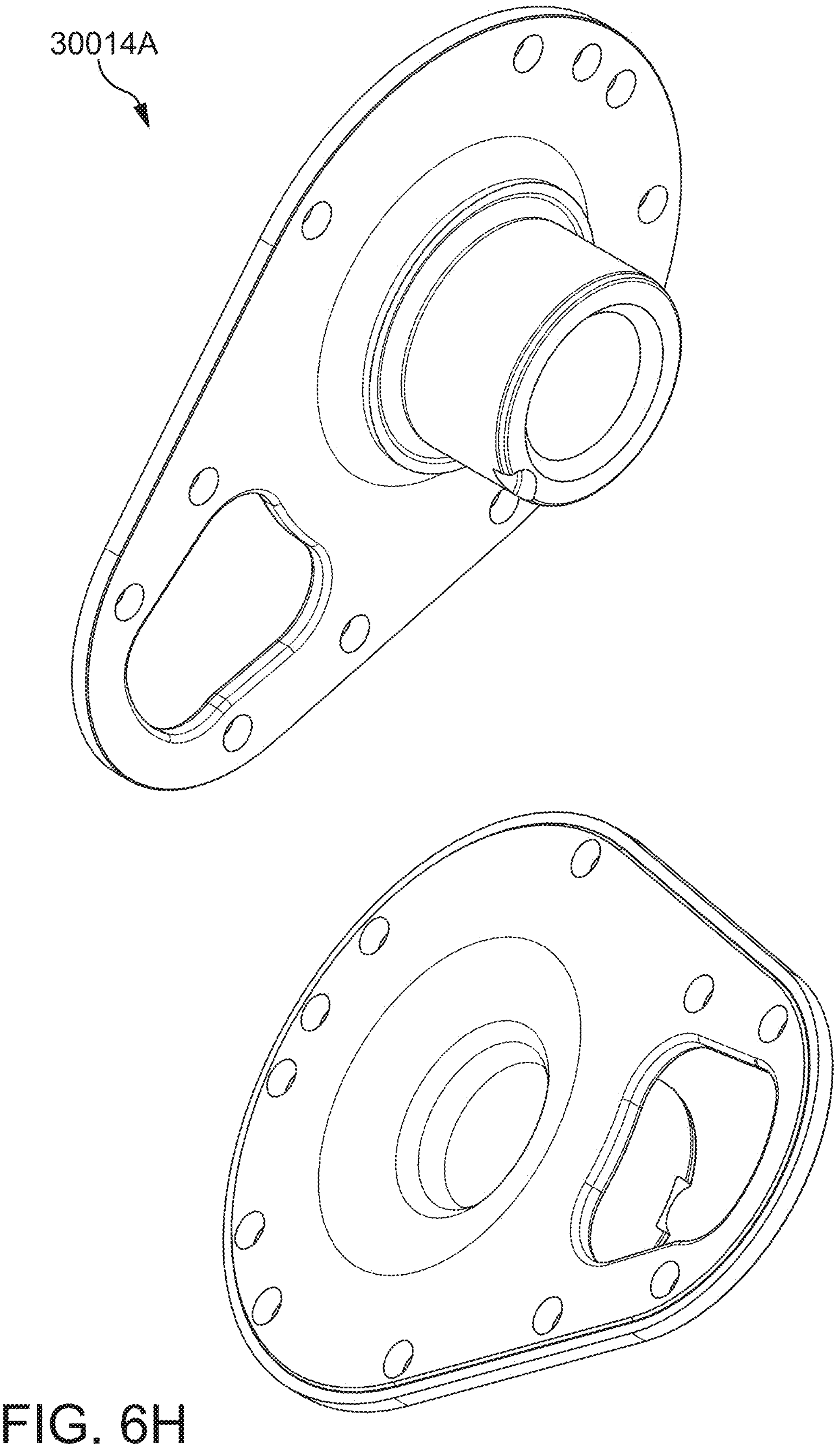
FIG. 6H is a perspective diagram of the cluster plate interface of the present teachings.
Figure 6I:
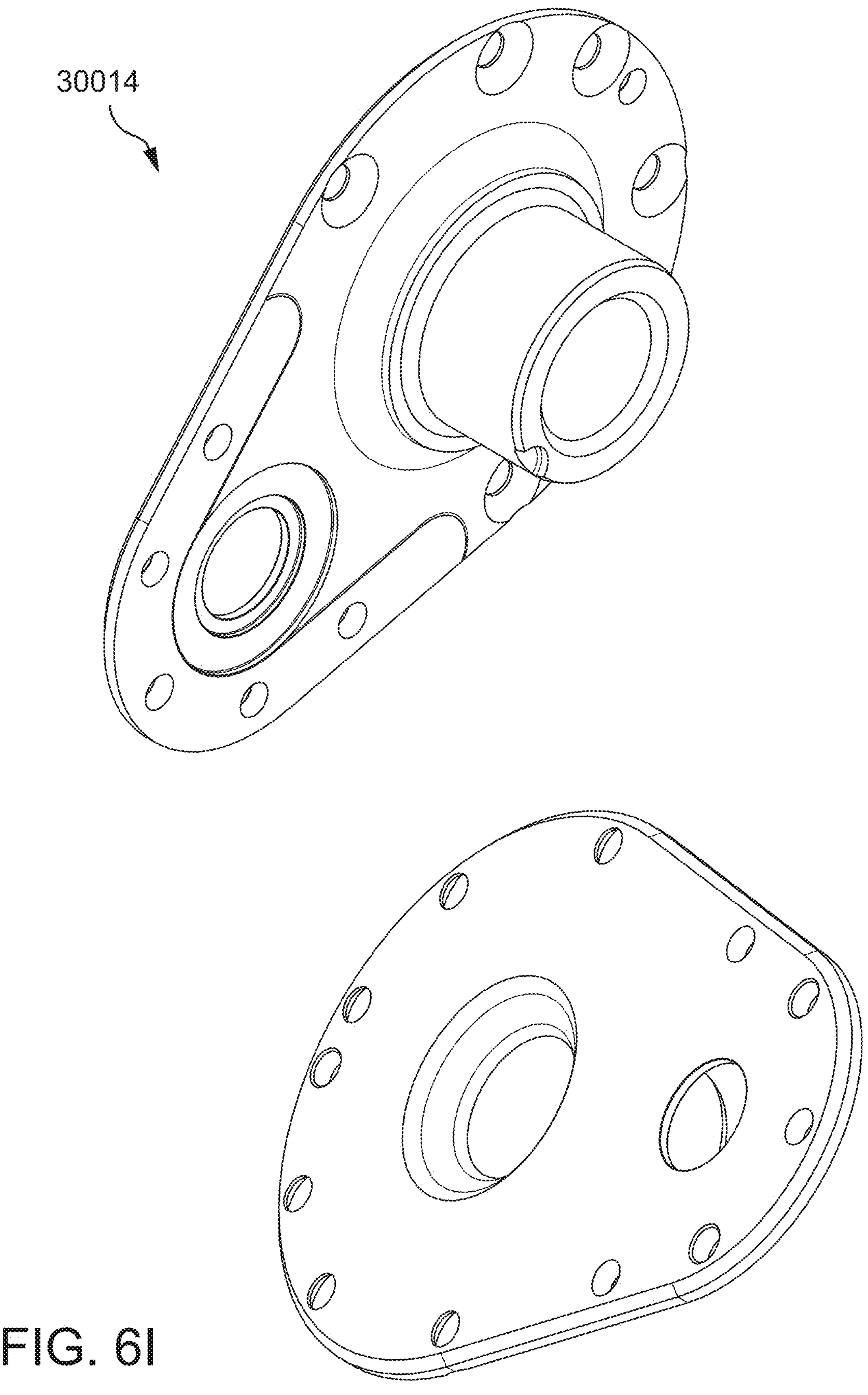
FIG. 6I is a perspective diagram of the second configuration cluster plate interface of the present teachings.
Figure 6J:
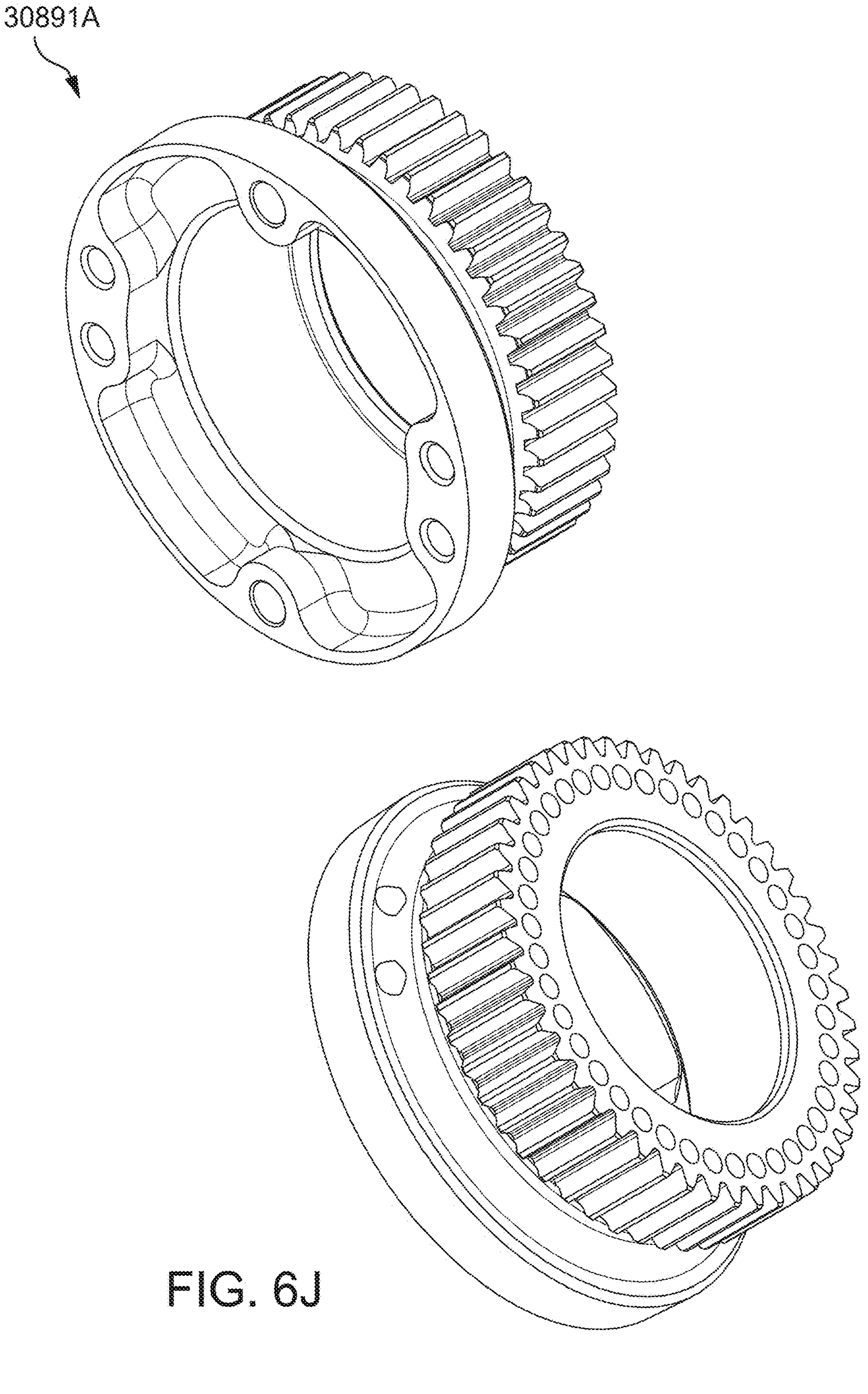
FIG. 6J is a perspective diagram of the ring gear of the present teachings.

Referring now primarily to FIGS. 6C and 6D, cluster cross shaft 30765 (FIG. 6F), part of the cluster gear train, can operably couple centrally-located third stage gear cluster rotate 30766 (FIG. 6F) to fourth stages 30888 (FIG. 6D) of the gear train that are mounted on the left and right side of central housings 21514 (FIG. 6A) under cluster interface caps 30014 (FIG. 6C). Cluster cross shaft 30765 (FIG. 6F) can include hollow shaft 30765-4 (FIG. 6G) that can include female spline 30765-3 (FIG. 6G). Fourth stages 30888 (FIG. 6D) can include male splines 30888-1 (FIG. 6C) on one end and pinion gears 30888-2 (FIG. 6C) that are aligned with the teeth of male splines 30888-1 on the other end. In this configuration, the teeth of pinion gears 30888-2 (FIG. 6C) on fourth stages 30888 (FIG. 6D) are aligned when they are assembled. In some configurations, the splines and gears can include fifteen teeth, but other numbers of teeth can be accommodated in the present teachings. The gear alignment can enable left and right cluster housings to be assembled onto the central housings so that wheels are aligned. This critical alignment enables the MD to rest on all four wheels when driving with the four main drive wheels.

Figure 6K:
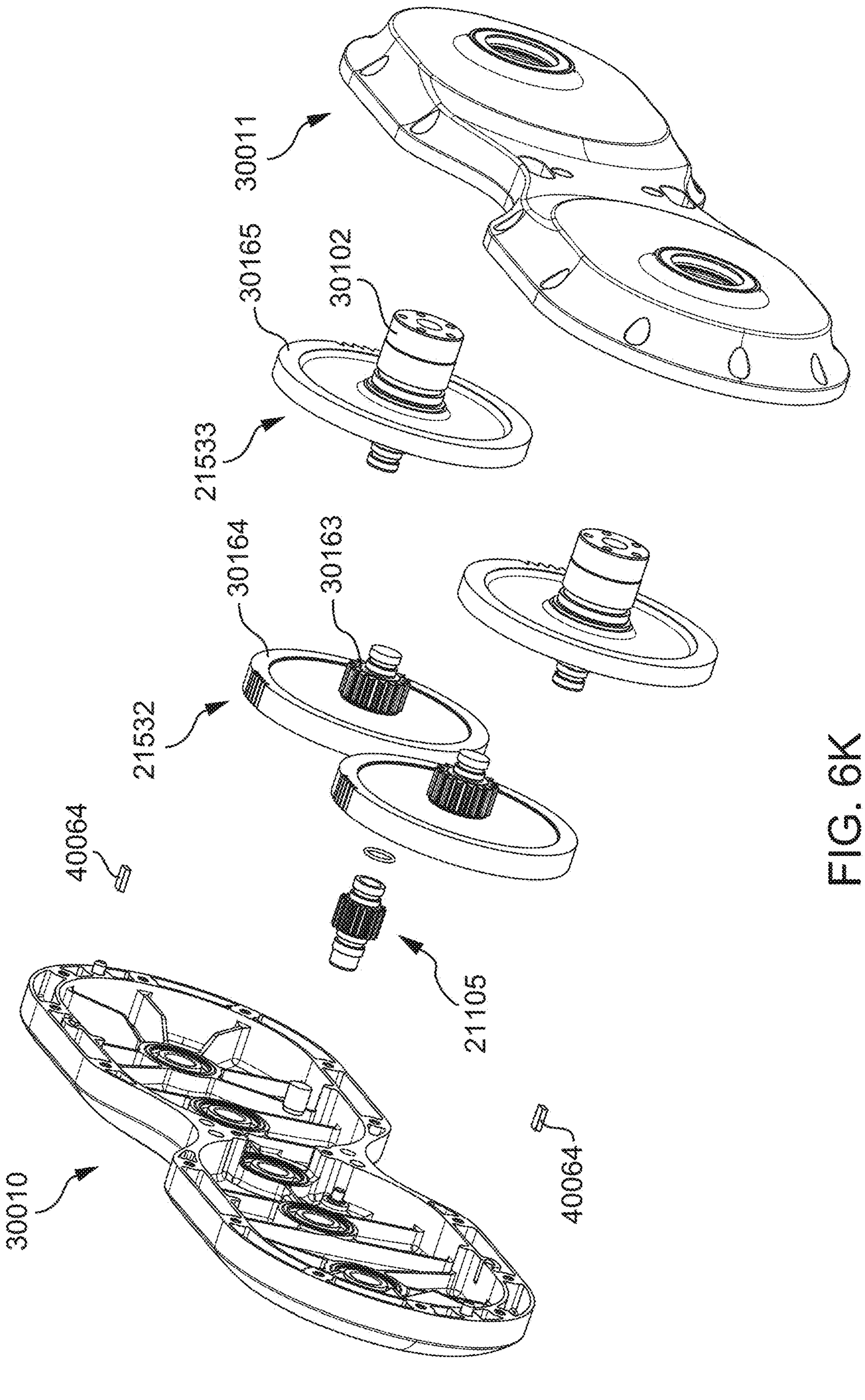
FIG. 6K is a perspective diagram of the cluster housings and gears of the present teachings.
Figure 6L:
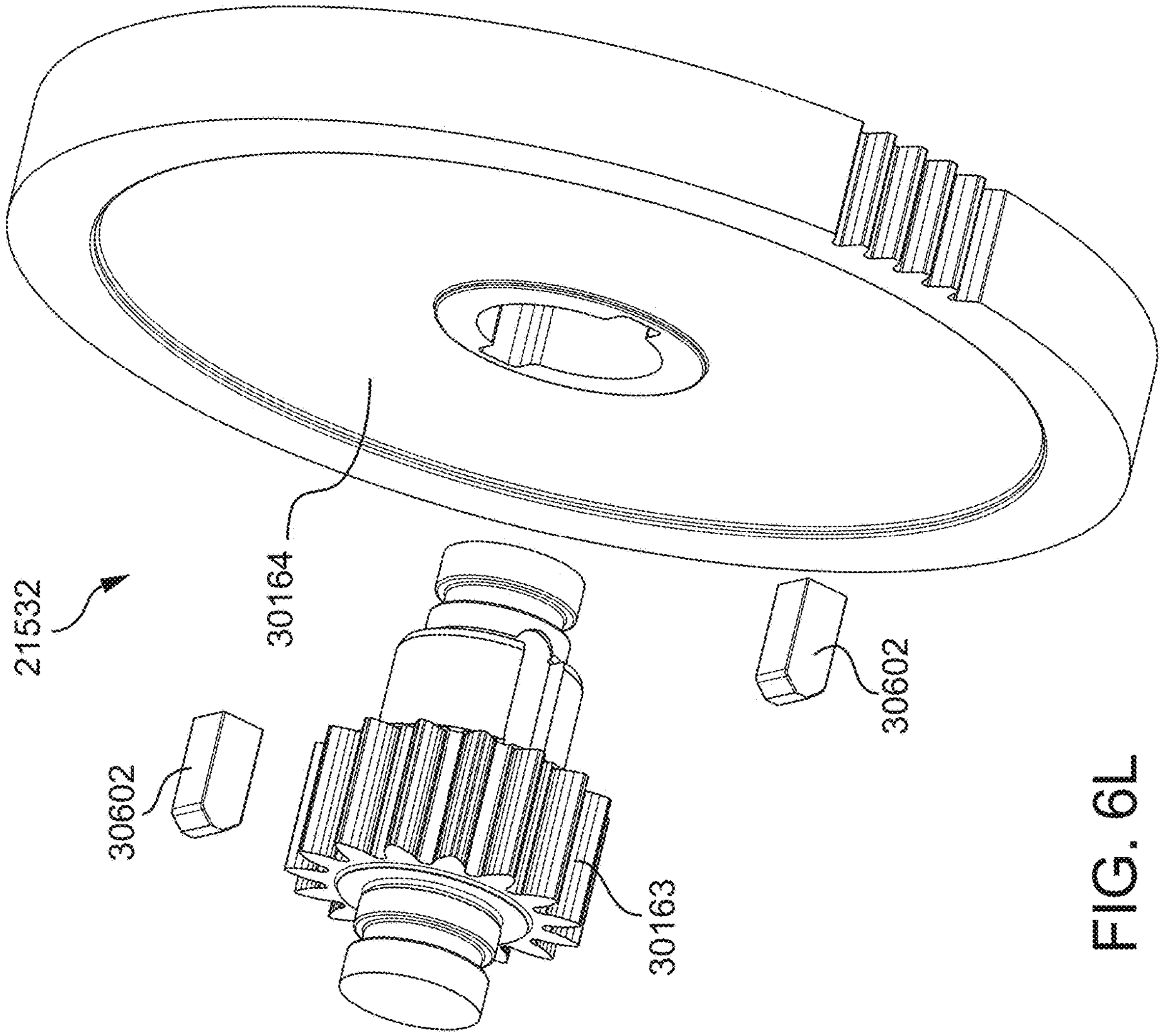
FIG. 6L is a perspective diagram of the wheel drive intermediate stage of the present teachings.

Referring now to FIG. 6K, cluster wheel drive 21100 (FIG. 6A) can include, but is not limited to including, outer cluster housing 30011, input pinion plug assembly 21105, wheel drive output gear 30165, wheel drive output shaft 30102, wheel drive intermediate shaft and pinion spur 30163, wheel drive intermediate gear 30164, and inner cluster housing 30010. At least one magnet 40064, captured between housings 30010/30011 at magnet housings 40064-1, can be positioned to be exposed to oil within cluster housing 21100A, and can attract and remove ferrous metal particulate from the oil, reducing gear, bearing, and seal wear caused by particulate in the oil. The teeth of input pinion plug 21105 can engage with wheel drive intermediate stage spur 30163, and wheel drive intermediate stage spur 30163 can engage with the wheel drive output gear 30165. When drive assembly 21532 (FIG. 6L) rotates, output stage spur 21533 rotates, the output stage spur shaft rotates, and wheel 21203 (FIG. 6A) can rotate. Wheel drive intermediate stage spur 30163 (FIG. 6L) can achieve and maintain correct positioning by coupling with gear key 30602 (FIG. 6L) that fits within the shaft cavity of wheel drive intermediate gear 30164 (FIG. 6L).

Figure 6M:
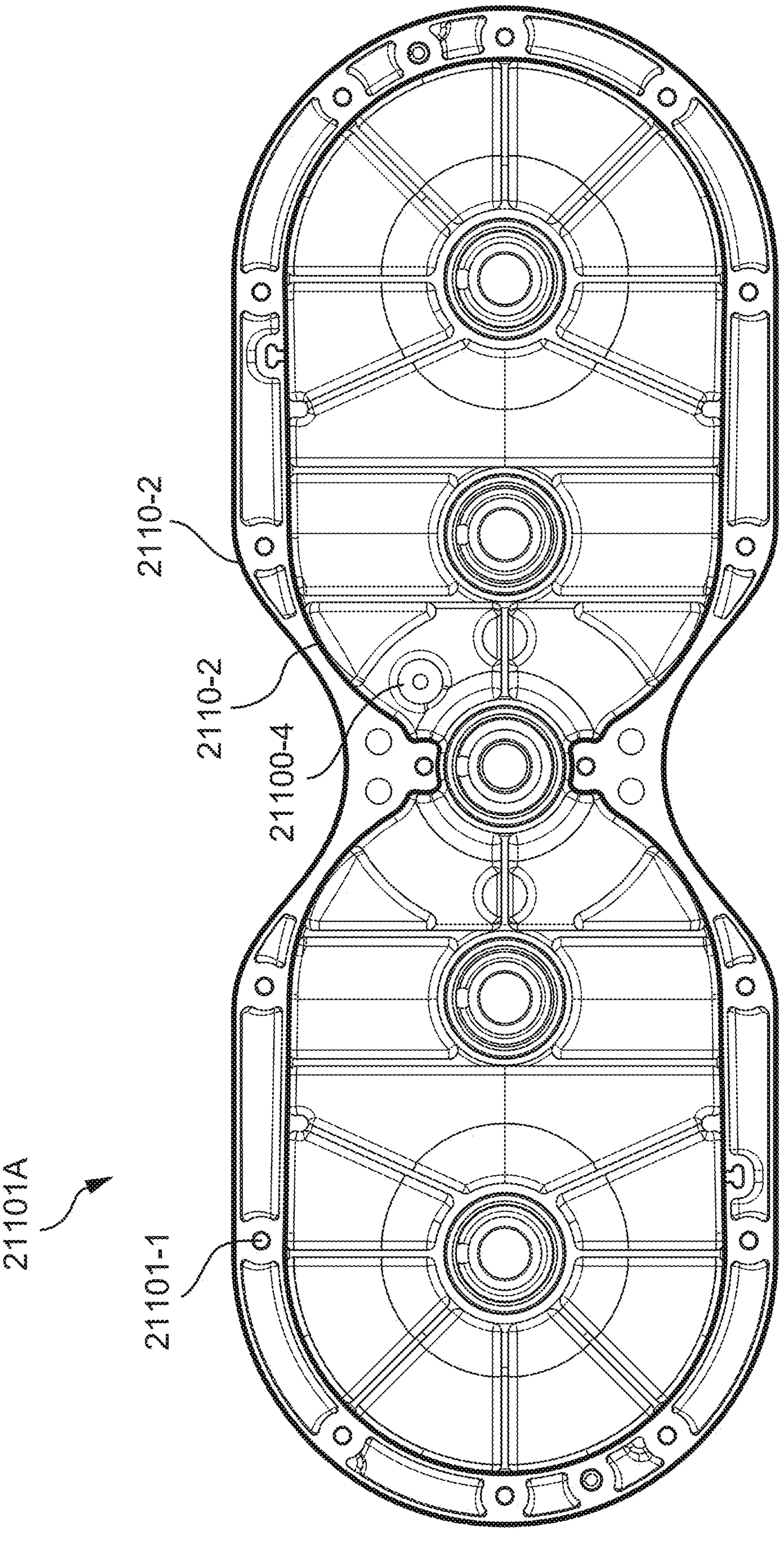
FIG. 6M is a plan view of the cluster housing of the present teachings including a sealing bead.

Referring now to FIG. 6M, clam shell housings 21101A can include seams 21100-1 around the perimeter to retain oil within housings 21101A, and prevent environmental contamination to housings 21101A. Bonding material 21101-2, for example, but not limited to, an elastomeric bonding material, can be applied to mating surfaces of housings 21100A. Lips and/or o-ring seals can surround each shaft that passes into and/or through housings 21101A. Cluster housing 21100A can include oil port 21101-4 for adding oil.

Figure 7A:
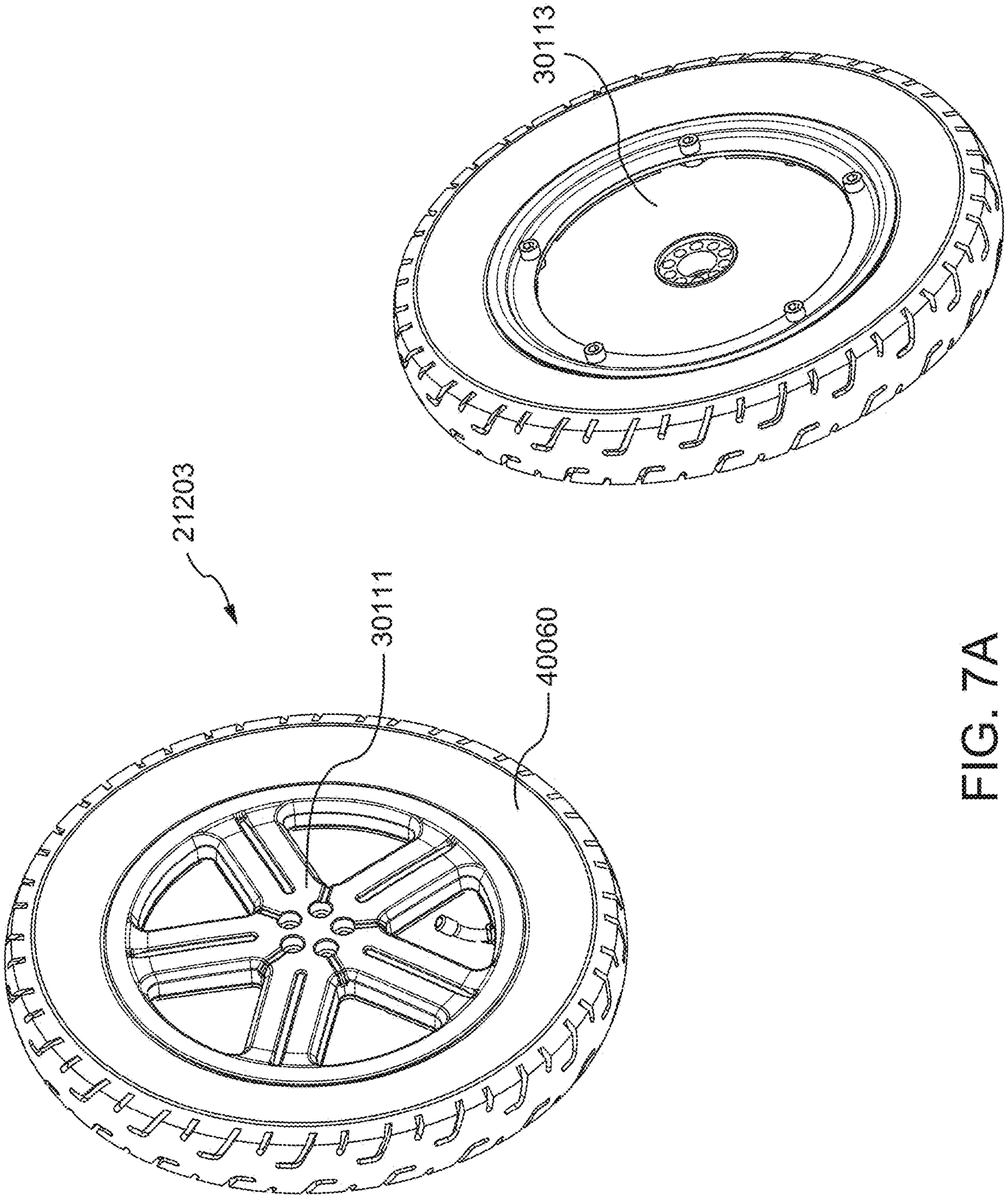
FIG. 7A is a perspective diagram of the tire of the present teachings.

Referring now primarily to FIG. 7A, the main drive wheels can be large enough to allow the MD to climb over obstacles, but small enough to fit securely on the tread of a stair. The compliance of the tires can reduce vibrations transmitted to the user and loads transmitted to the MD. The main drive wheels can remain fixed to the MD unless intentional action is taken by the user or a technician. The tires can be designed to minimize electrostatic build-up during surface traversal/contact. Split rim wheel pneumatic tire assembly 21203 can be mounted onto cluster assembly 21100 (FIG. 6A) of the MD to afford wheeled movement to the MD.

Figure 7B:
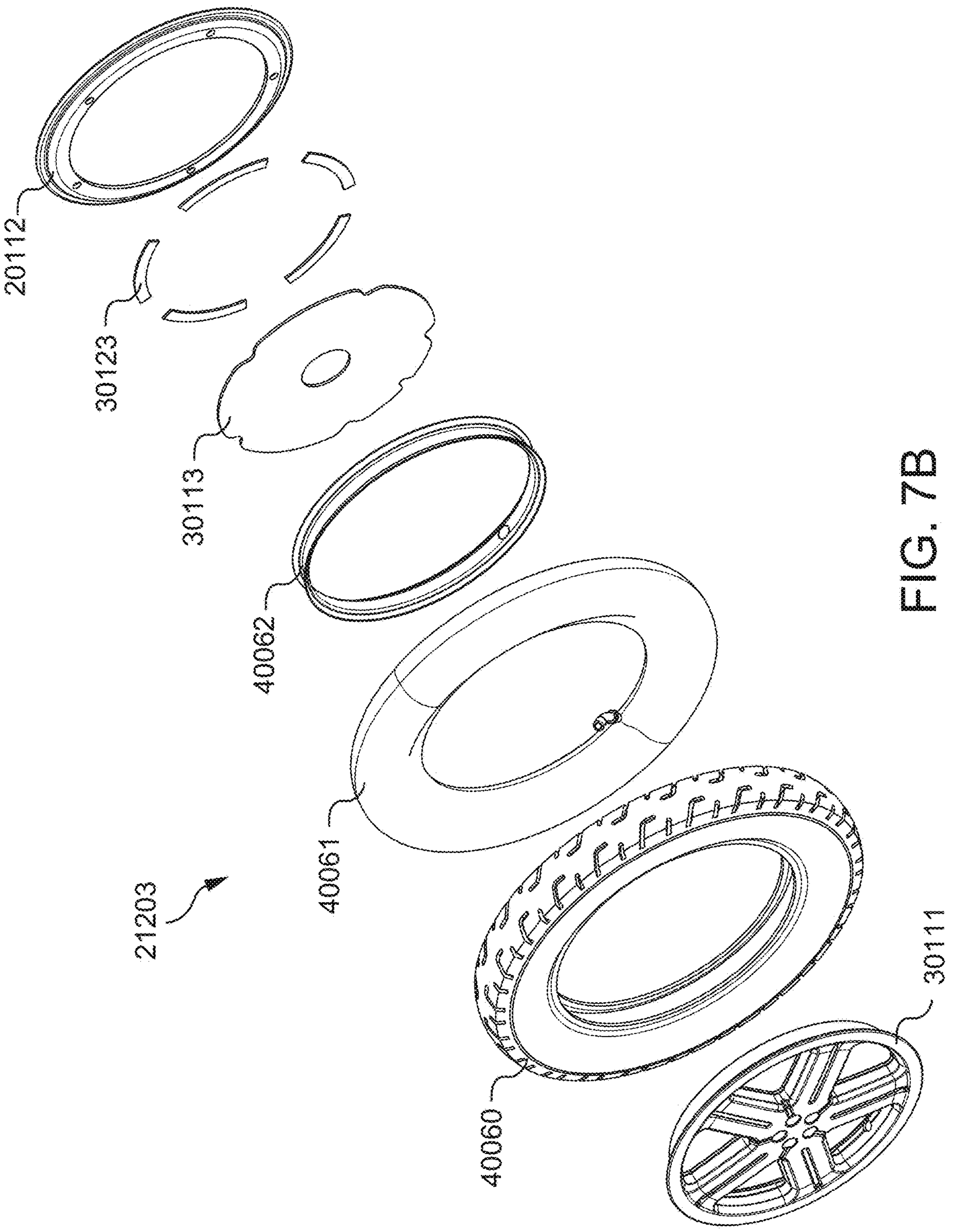
FIG. 7B is a perspective diagram of the tire assembly of the present teachings.
Figure 7C:
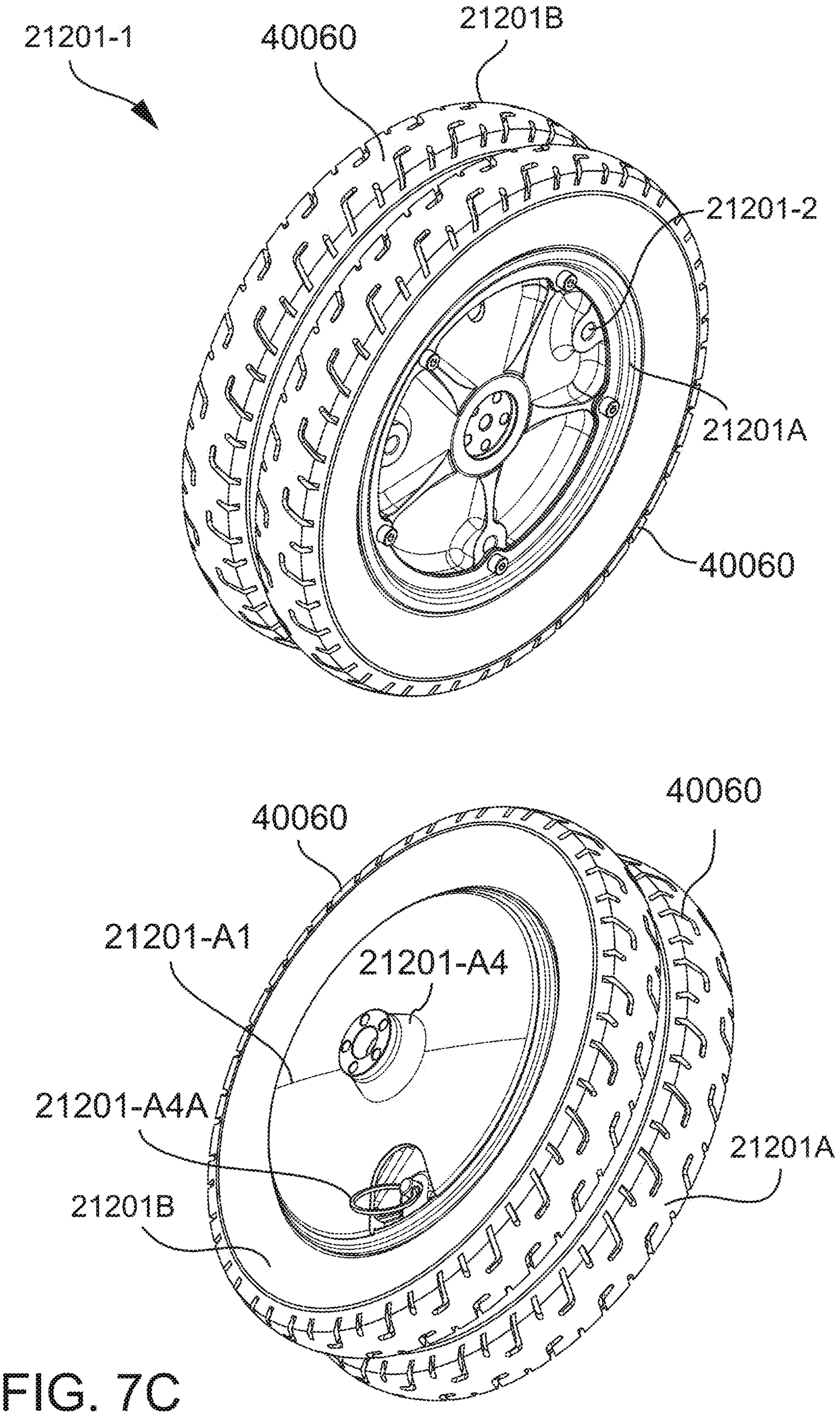
FIG. 7C is a perspective diagram of the dual tire assembly of the present teachings.
Figure 7D:
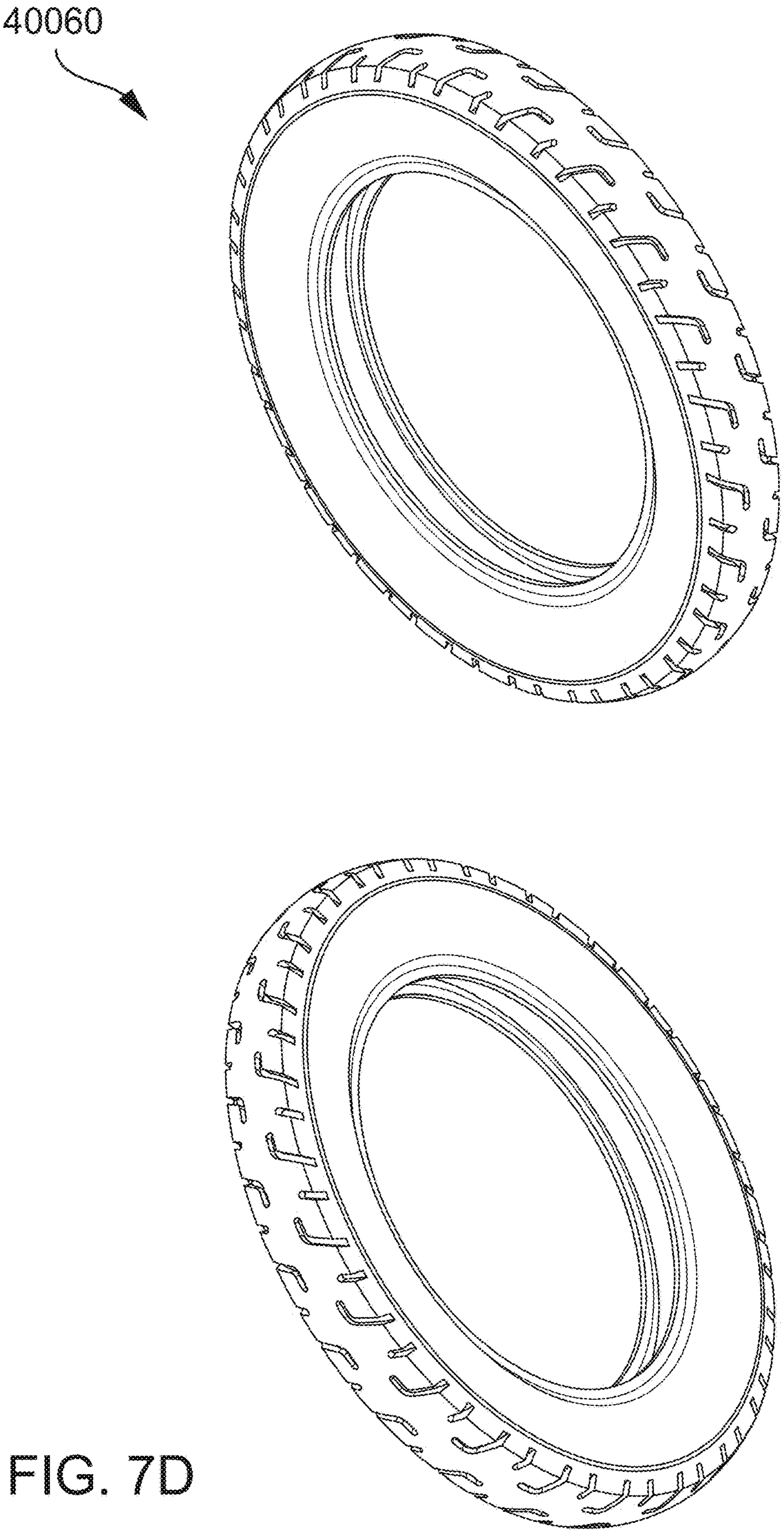
FIG. 7D is a perspective diagram of the tire of the present teachings.
Figure 7E:
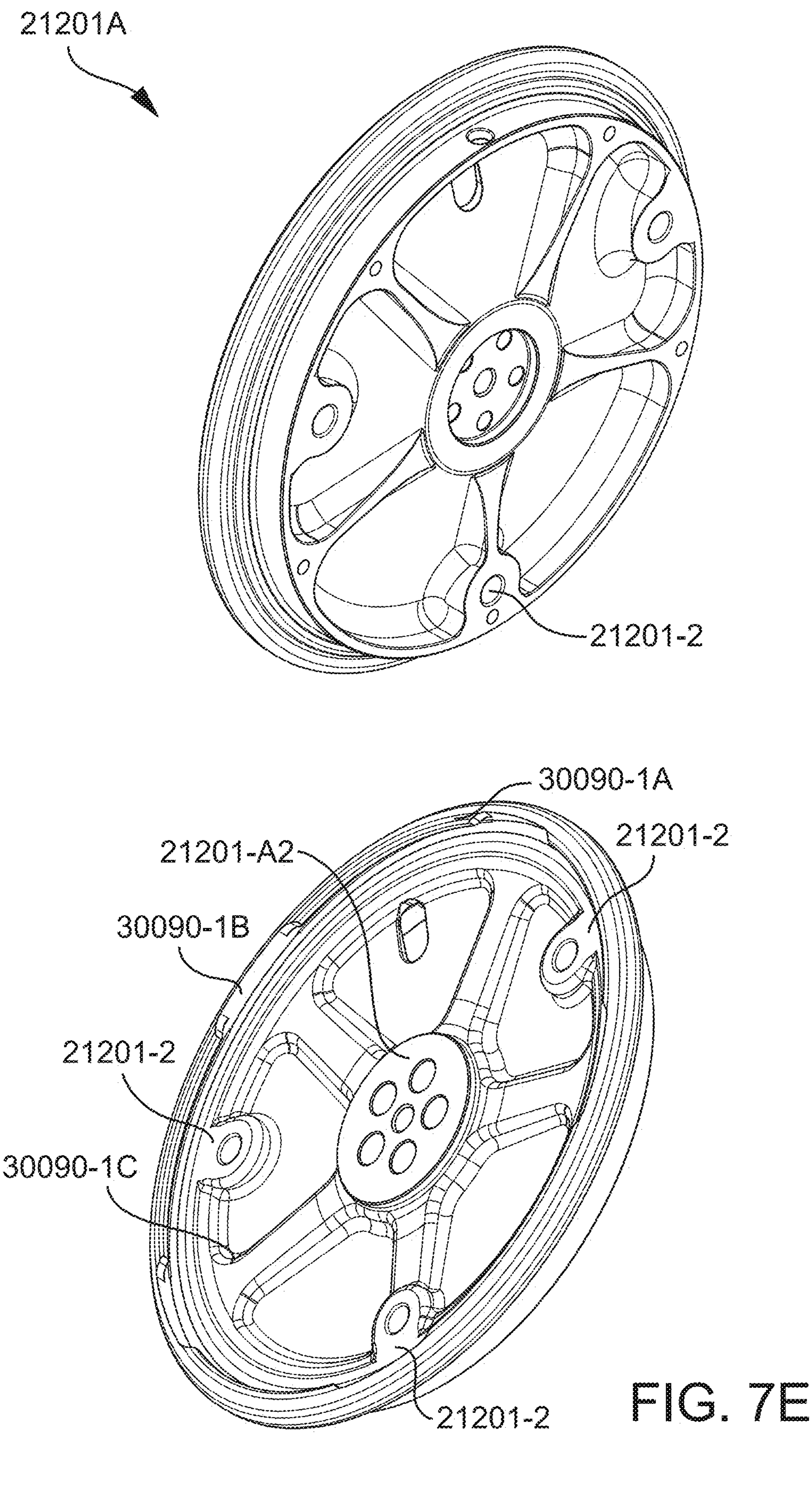
FIG. 7E is a perspective diagram of the wheel of the present teachings.
Figure 7F:
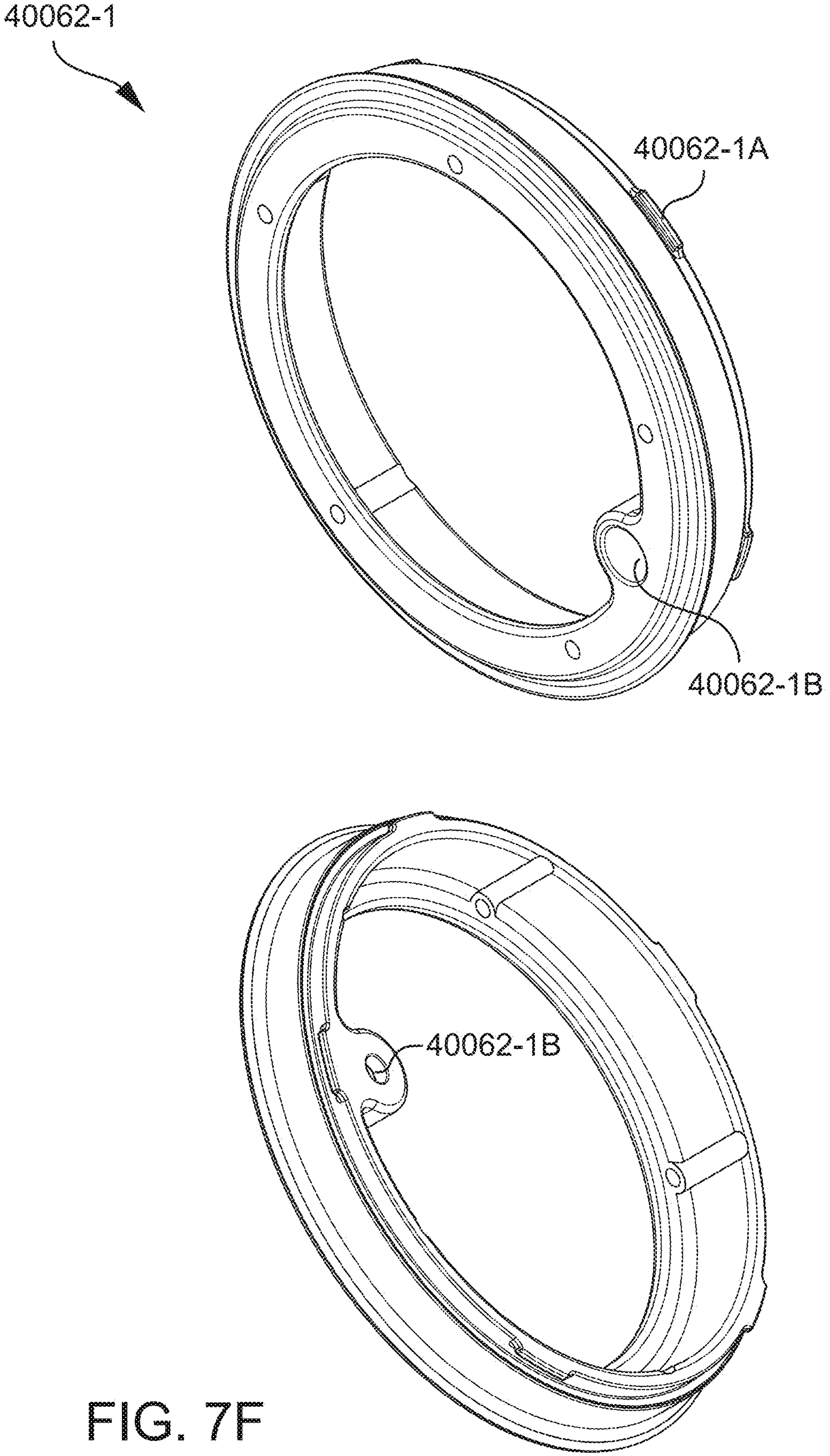
FIG. 7F is a perspective diagram of the attachment base of the present teachings.
Figure 7G:
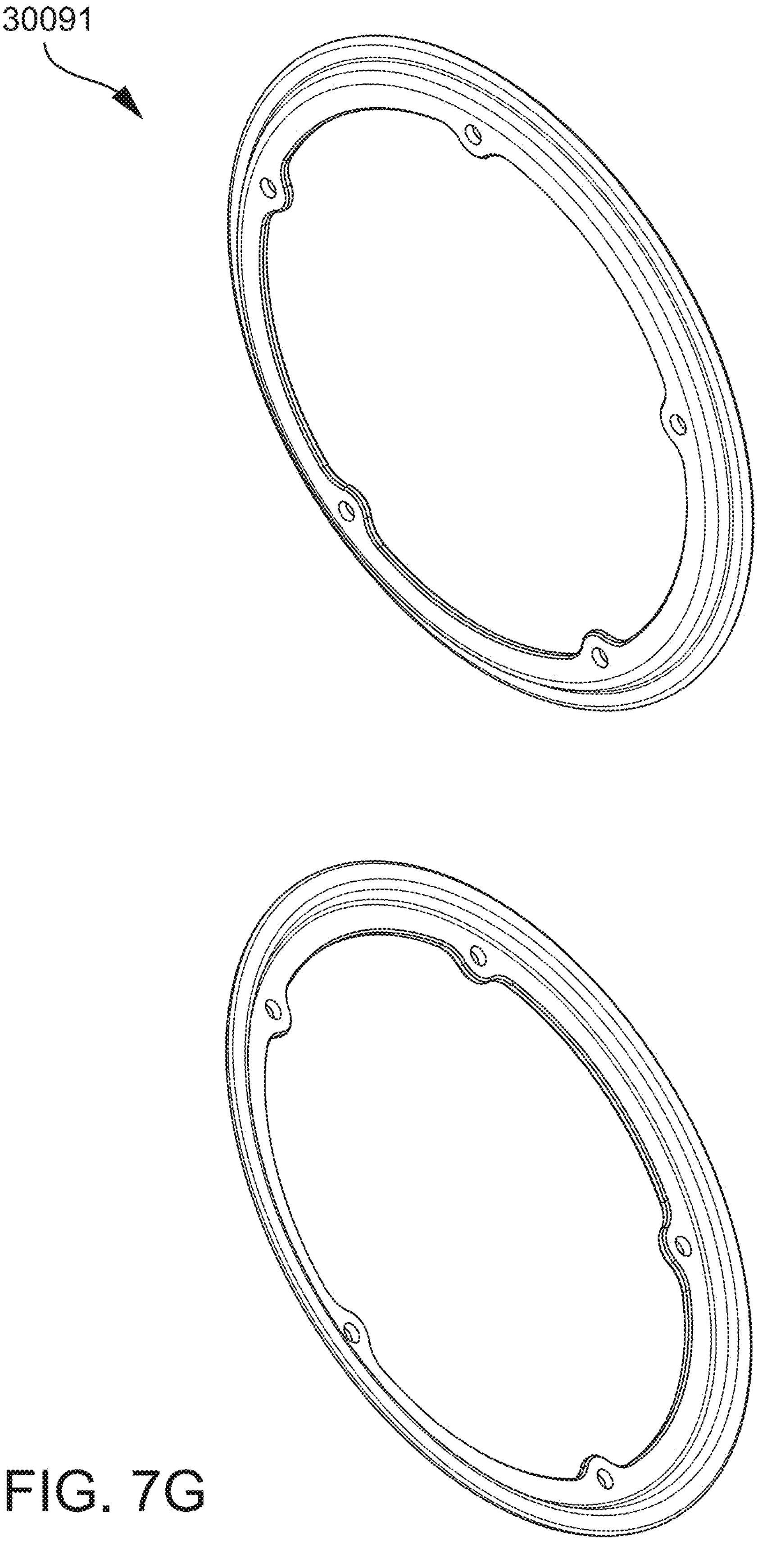
FIG. 7G is a perspective diagram of the inner split rim of the present teachings.
Figure 7H:
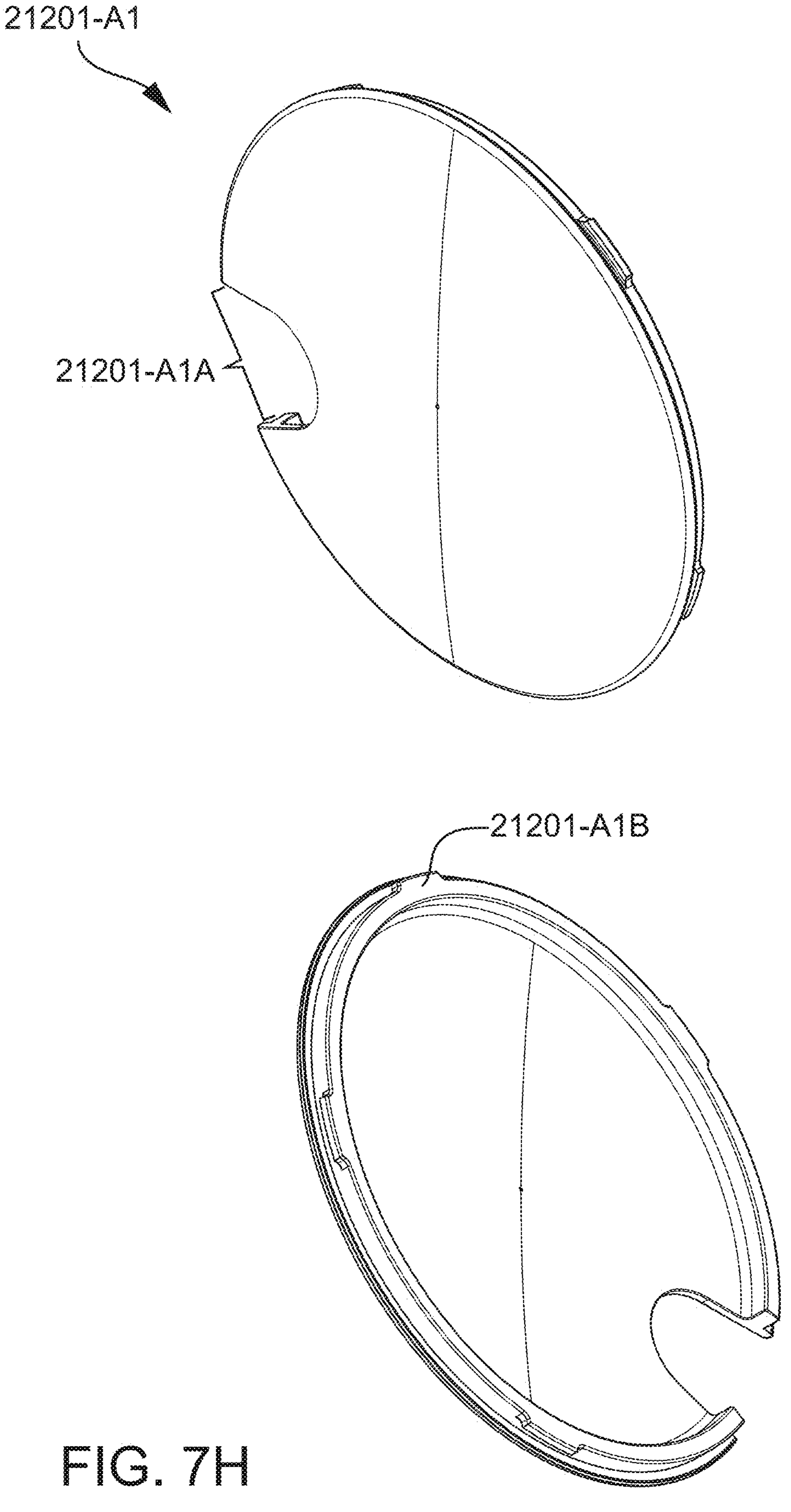
FIG. 7H is a perspective diagram of the hubcap of the present teachings.
Figure 7I:
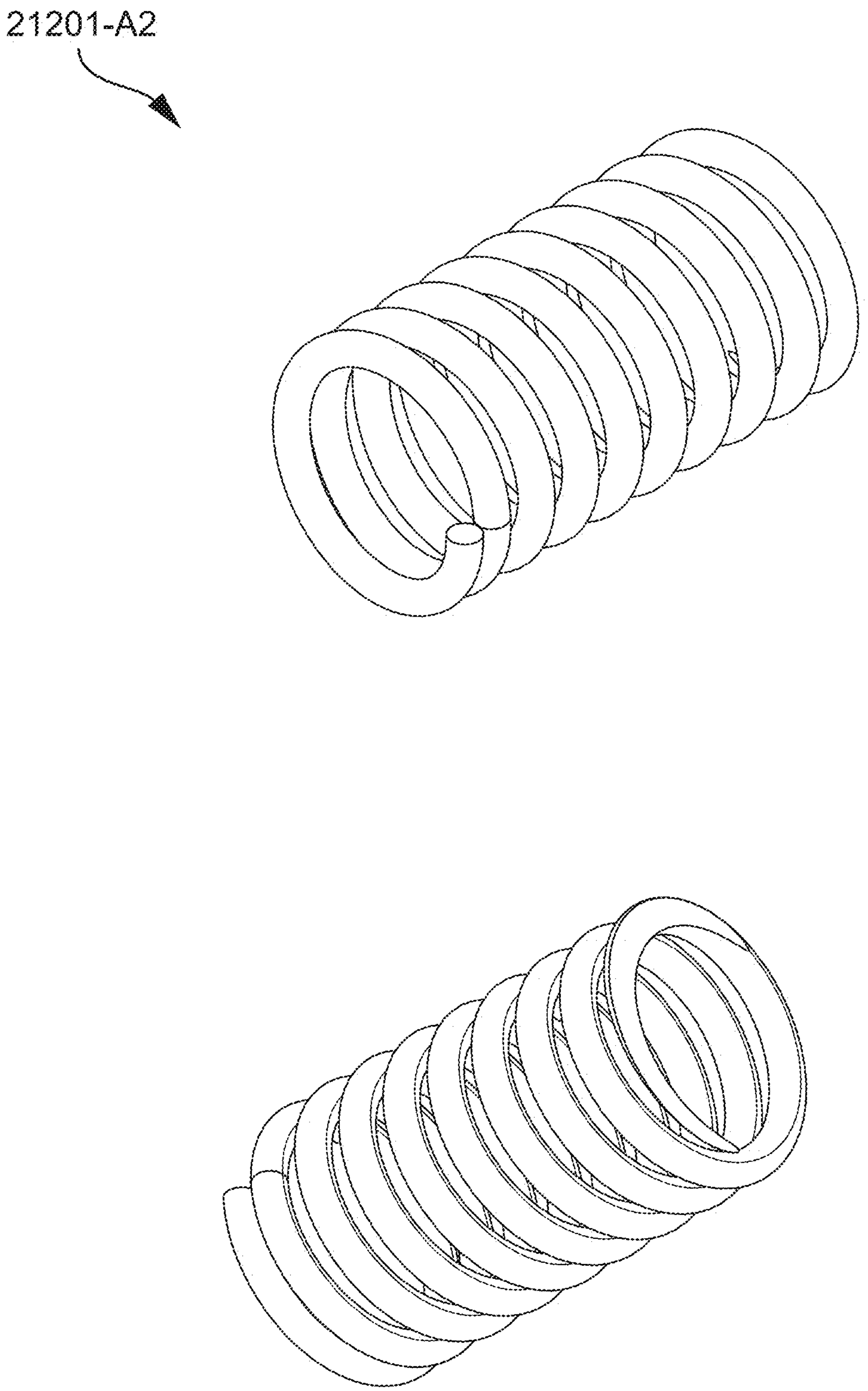
FIG. 7I is a perspective diagram of the locking pin spring of the present teachings.

Referring now to FIG. s, split rim wheel tire assembly 21203 can include, but is not limited to including, outer split rim 30111, tire 40060 (FIG. 7D), inner tube 40061, rim strip 40062, shield disk 30113, shield disk spacer 30123, and inner split rim 30091 (FIG. 7G). Shield disk spacer can inhibit shield disk from rattling. Pneumatic tire can house inner tube 40061 which can surround rim strip 40062, which can inhibit pinching of inner tube 40061. Shield disk 30113 can be captured between the inner and outer rim of split rim assembly 21203. Shield disk 30113 can be preloaded in a pre-selected shape, for example, to enable securing positioning. Shield disk 30113 can guard against foreign object protrusion through wheel tire assembly 21203. Shield disk 30113 can provide a smooth surface that can discourage foreign object jamming and wheel damage. Shield disk 30113 can provide customization opportunities, for example, custom colors and designs can be selected and provided on shield disk 30113. In some configurations, tire assembly 21203 can accommodate solid tires such as, for example, but not limited to, foam-filled tires. Tire selection can be based on the features that a user desires such as durability, smooth ride, and low failure rate.

Figure 7J:
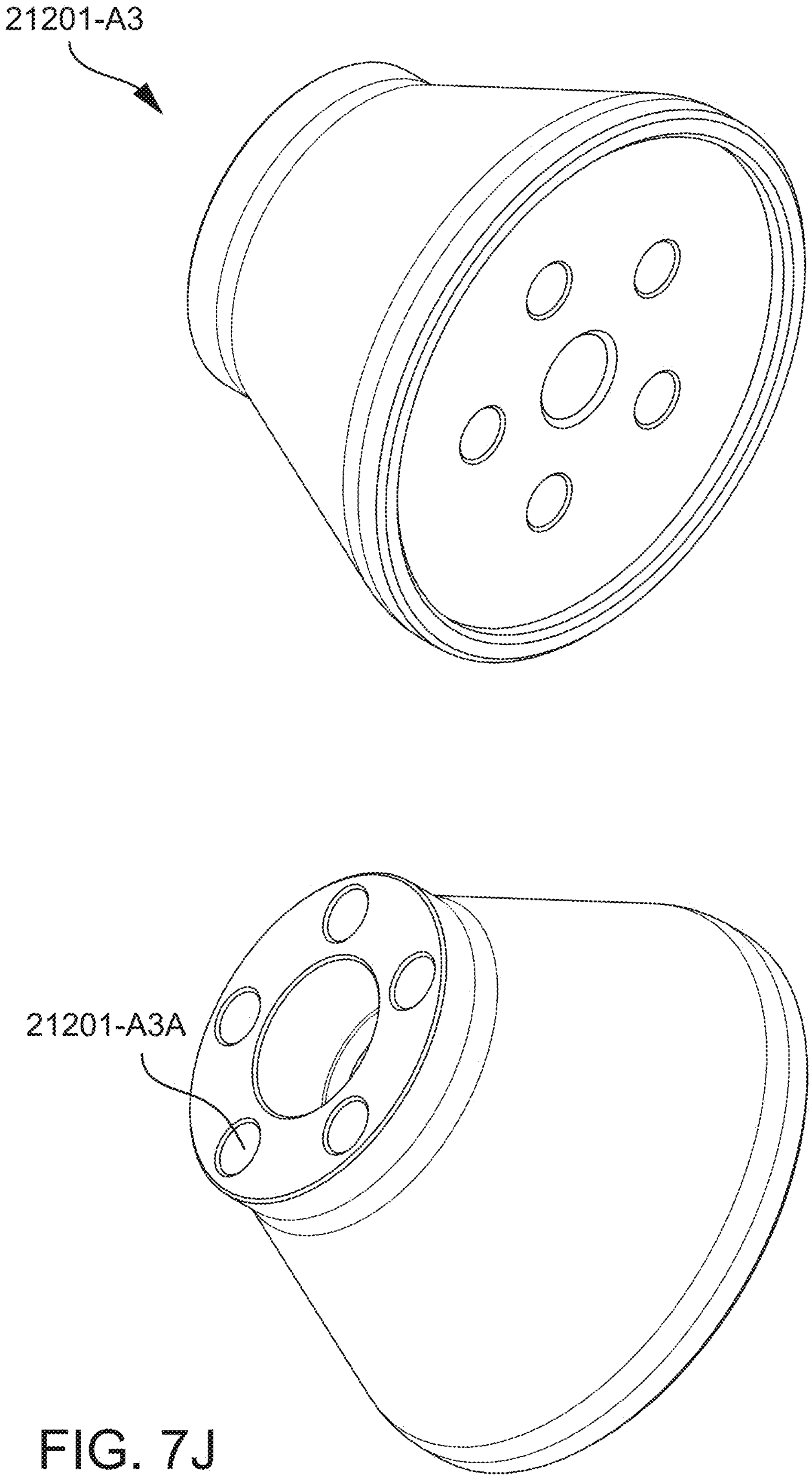
FIG. 7J is a perspective diagram of the fastener housing of the present teachings.
Figure 7K:
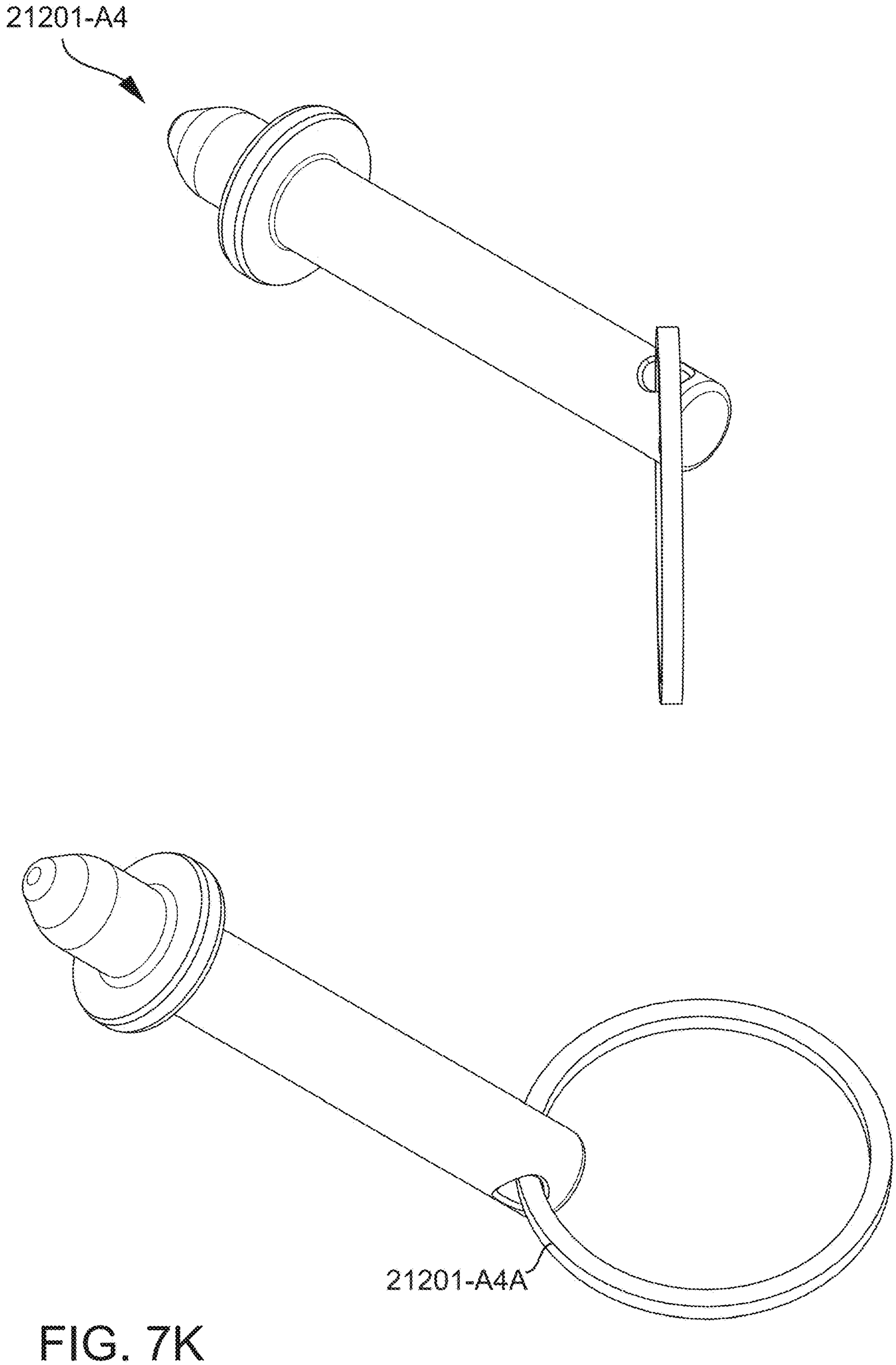
FIG. 7K is a perspective diagram of the locking pin of the present teachings.
Figure 7L:
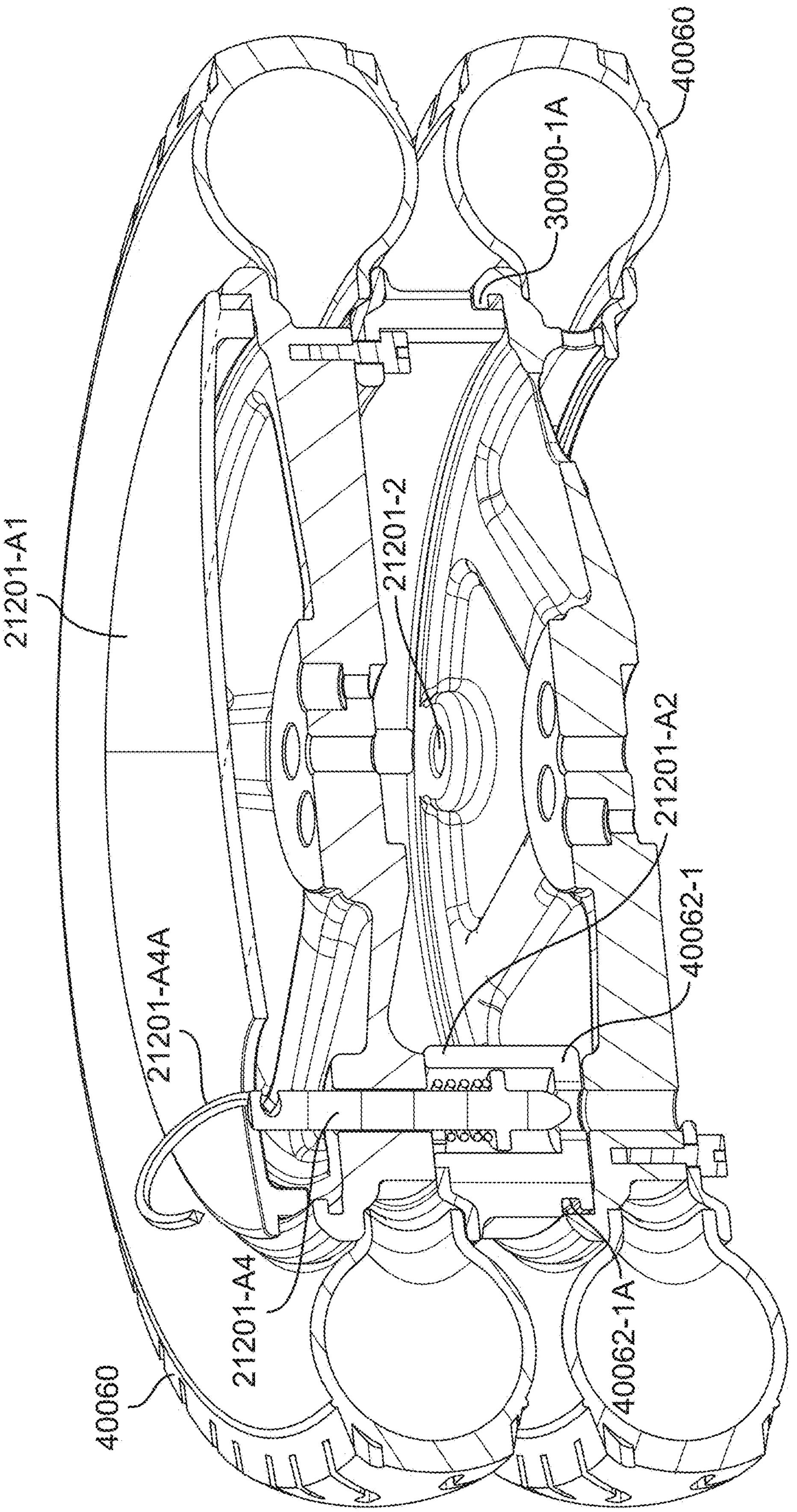
FIG. 7L is a perspective cross section diagram of the dual tire assembly with locking pin partially inserted.
Figure 7M:
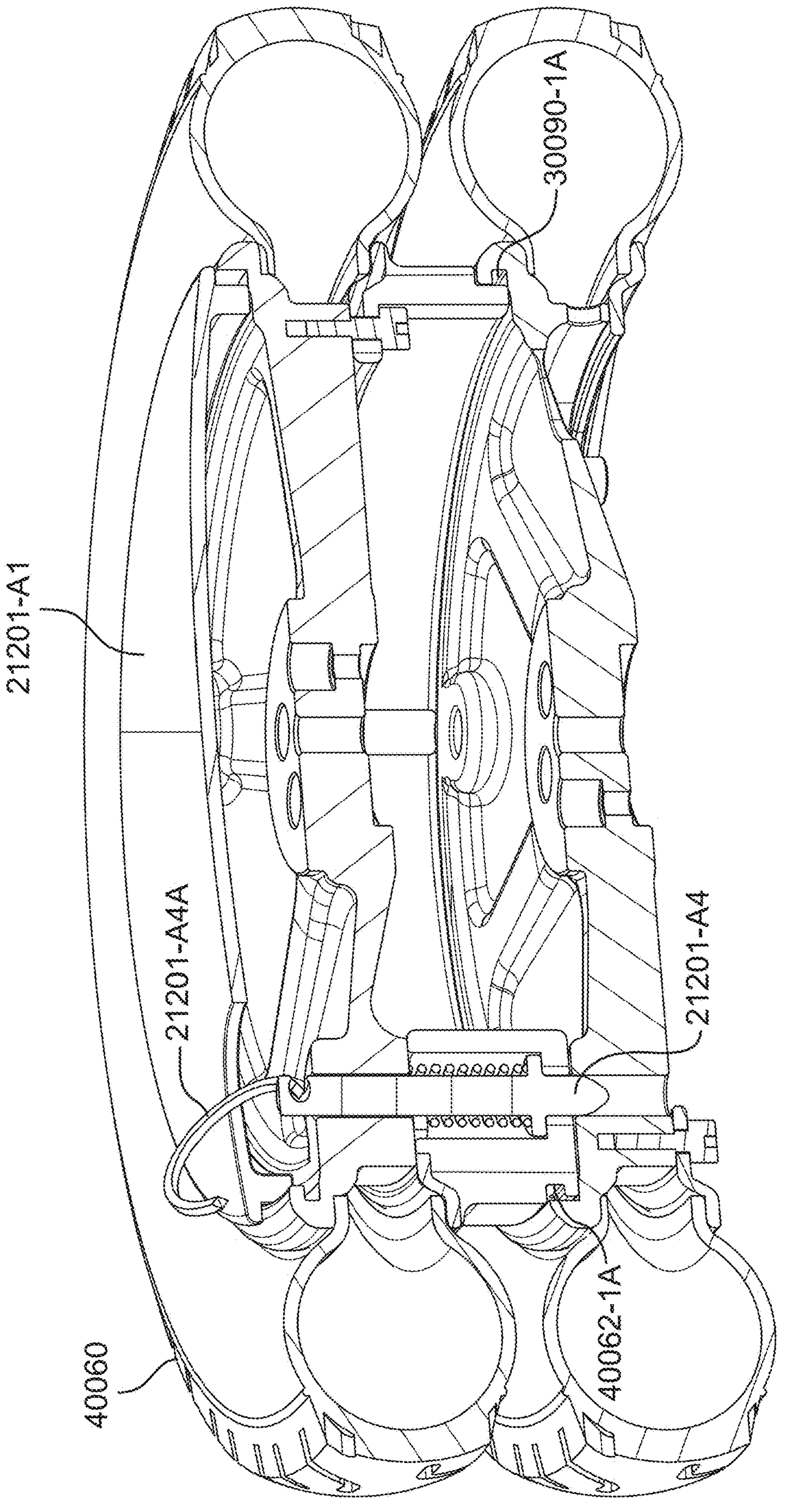
FIG. 7M is a perspective cross section diagram of the dual tire assembly with locking pin fully inserted.
Figure 7N:
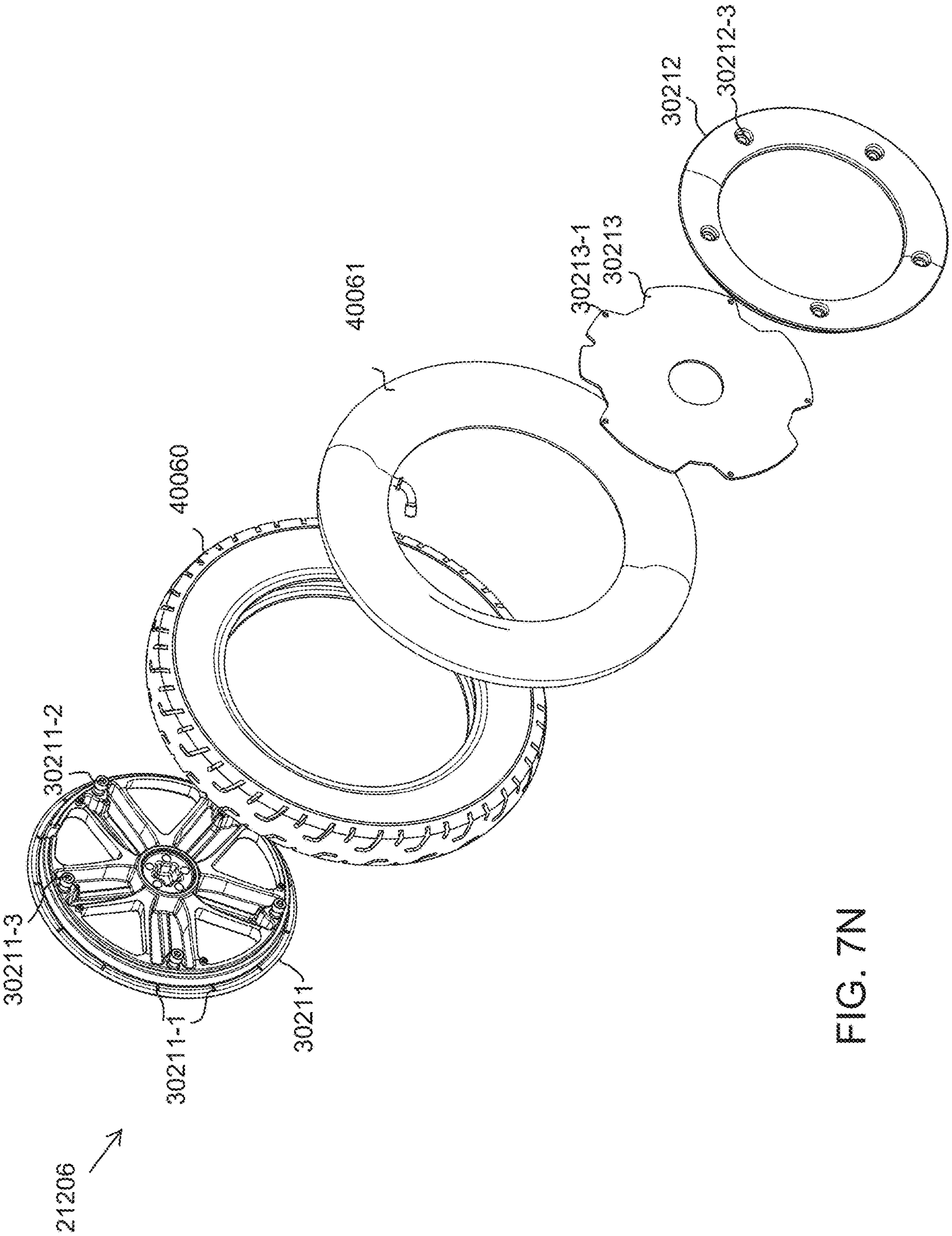
FIGS. 7N and 7O are exploded perspective diagrams of the second configuration of the tire assembly of the present teachings.
Figure 7O:
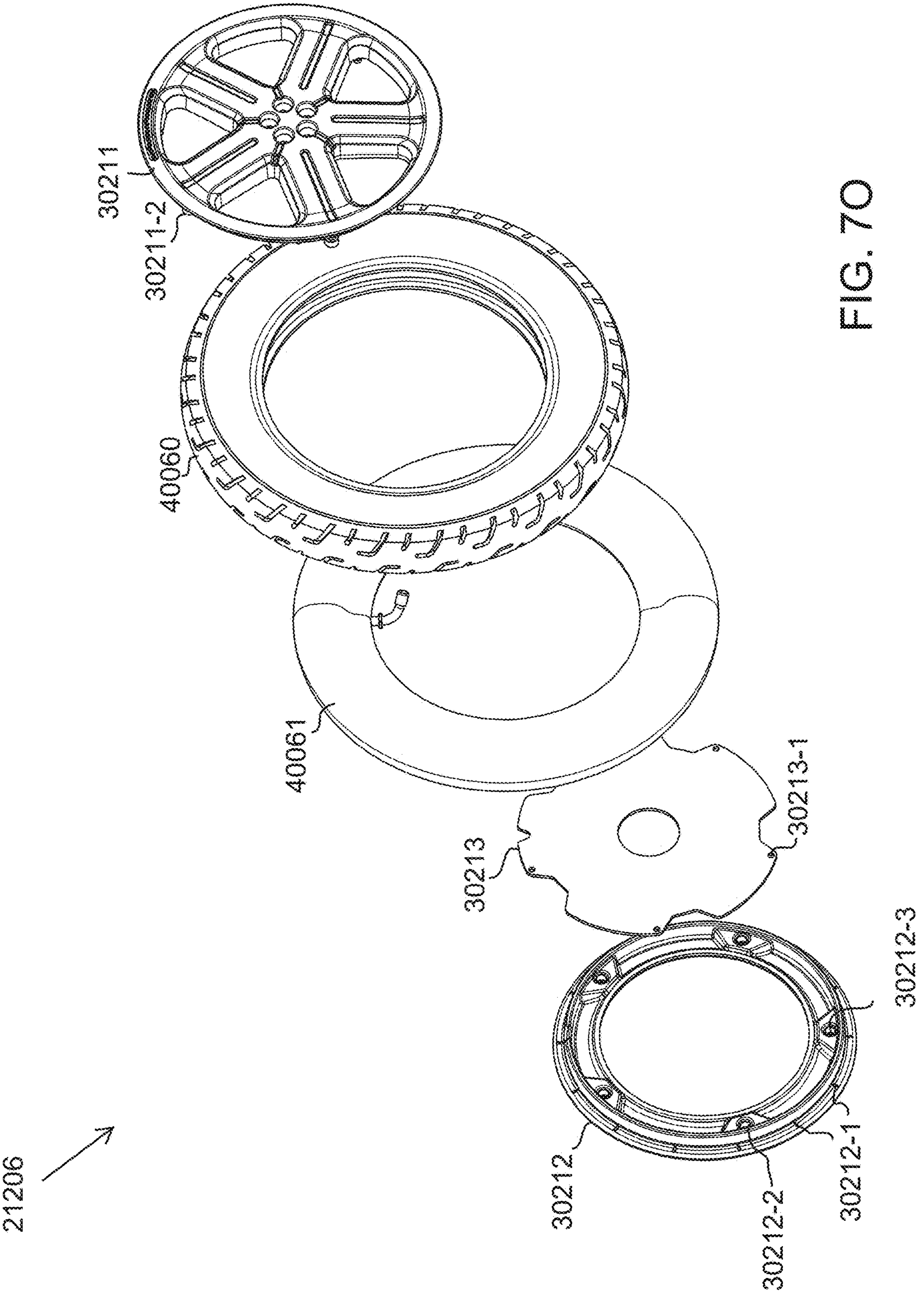

Referring now to FIGS. 7N and 7O, second configuration split rim wheel tire assembly 21206 can include second configuration outer split rim 30211, tire 40060, inner tube 40061, second configuration shield disk 30213, and second configuration inner split rim 30212. Second configuration outer split rim 30211 and second configuration inner split rim 30212 can include retaining protrusions 30211-1 (FIG. 7O) and 30212-1 (FIG. 7N), respectively, that can enable secure retention of tire 40060. Retaining protrusions 30211-1 (FIG. 7O) and 30212-1 (FIG. 17N) can be spaced in any pattern, and can be any size. Second configuration outer split rim 30211 can include alignment protrusions 30211-2 (FIG. 7N) that can emerge from lug fittings and can rest within divots 30212-2 (FIG. 7O). Second configuration shield disk 30213 can include lug recesses 30213-1 (FIG. 7O). Lug fasteners 30212-4 (not shown) can securely unite second configuration outer split rim 30211, second configuration shield disk 30213, and second configuration inner split rim 30212 through lug recesses 30213-1 (FIG. 7O), 30211-3 (FIG. 7N), and 30212-3 (FIG. 7O).

Referring now to FIGS. 7C through 7M, main drive wheels 21203 (FIG. 7B) can be configured to accommodate traveling over varying types of terrain including, but not limited to, sand-like surfaces. In some configurations, each of drive wheels 21203 (FIG. 7B) such as first outer split rim 21201A (FIG. 7C), can accommodate detachable second drive wheel 21201B (FIG. 7C). Second drive wheel 21201B (FIG. 7C) can be installed by the user seated in the MD or by an assistant. Second drive wheel 21201B (FIG. 7C) can be attached to first drive wheel 21201A (FIG. 7C) by depressing second drive wheel 21201B (FIG. 7C) onto first drive wheel 21201A (FIG. 7C), rotating second drive wheel 21201B (FIG. 7C), and inserting locking pin 21201-A4 (FIG. 7K) until it becomes engaged. The attachment steps can be performed by the user seated in the MD as the user expects to encounter challenging terrain. The attachment steps can also be performed while not seated in the MD. First drive wheel 21201A (FIG. 7C) can include attachment base 40062-1 (FIG. 7F) that can provide a means for interlocking first drive wheel 21201A (FIG. 7C) with second drive wheel 21201B (FIG. 7C). Attachment base 40062-1 (FIG. 7F) can include locking pin receiver 40062-1B (FIG. 7F) and a retaining lip 30090-1A (FIG. 7E) for twist-lock wheel attachment of second drive wheel 21201B (FIG. 7C). Second drive wheel 21201B (FIG. 7C) can include locking pin 21201-A4 (FIG. 7K) that can operably mate with locking pin receiver 40062-1B (FIG. 7F) of second drive wheel 21201B (FIG. 7C). Locking pin 21201-A4 (FIG. 7K) can include spring 21201-A2 (FIG. 7I) that can enable access to locking pin 21201-A4 (FIG. 7K) after locking pin 21201-A4 (FIG. 7K) has been disengaged, and can enable secure locking of locking pin 21201-A4 (FIG. 7K) when locking pin 21201-A4 (FIG. 7K) is engaged. Attachment base 40062-1 (FIG. 7F) can include retaining tangs 40062-1A (FIG. 7F) for twist-lock wheel attachment. Retaining tangs 40062-1A (FIG. 7F) can operably couple with retaining lip 30090-1B (FIG. 7E) of first drive wheel 21201A (FIG. 7C). In some configurations, second drive wheel 21201B (FIG. 7C) can accommodate hubcap 21201-A1 (FIG. 7H) that can provide access opening 21201-A1A (FIG. 7H) for locking pin removing ring 21201-A4A (FIG. 7K). In some configurations, first drive wheel 21201A (FIG. 7C) and second drive wheel 21201B (FIG. 7C) can be different or the same sizes and/or can have different or the same treads on tires 40060.

Continuing to refer to FIGS. 7C through 7M, in some configurations, the attachment means between first drive wheel 21201A (FIG. 7C) and second drive wheel 21201B (FIG. 7C) can include a castellated push-in and rotate to lock means (not shown) having a plurality of radially extending tabs and a mounting structure having a plurality of retaining members. In some configurations, the attachment means can include an undercut or male lip (not shown). In some configurations, the attachment means can include features (not shown) on spokes 30090-1C (FIG. 7E). In some configurations, the attachment means can include fastener housing 21201-A3 (FIG. 7J) that can mount between hubs 21201-A2 (FIG. 7E) of second drive wheel 21201B (FIG. 7C) and first drive wheel 21201A (FIG. 7C). Fasteners such as, for example, but not limited to, screws or bolts can operably engage first drive wheel 21201A (FIG. 7C) with second drive wheel 21201B (FIG. 7C) through the cavities in fastener housing 21201-A3 (FIG. 7J).

Figure 8:
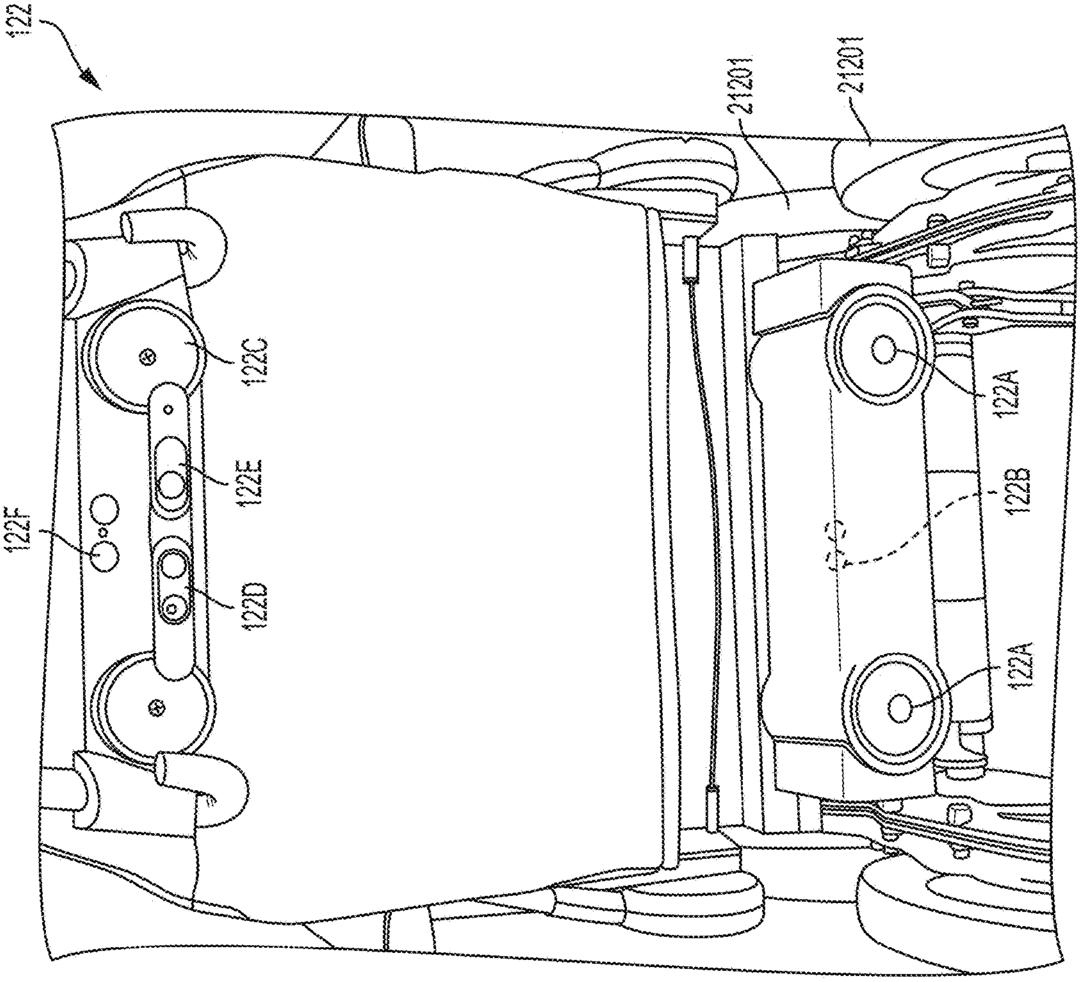
FIG. 8 is a pictorial representation of a configuration of the positioning of sensors of the mobility device of the present teachings.

Referring now primarily to FIG. 8, the MD can be fitted with any number of sensors 147 (FIG. 16B) in any configuration. In some configurations, some of sensors 147 (FIG. 16B) can be mounted on MD rear 122 to accomplish specific goals, for example, backup safety. Stereo color cameras/illumination 122A, ultrasonic beam range finder 122B, time-of-flight cameras 122D/122E, and single point LIDAR sensors 122F can be mounted, for example, but not limited to, to cooperatively sense obstacles behind the MD. The MD can receive messages that can include information from the cameras and sensors, and can enable the MD to react to what might be happening out of the view of the user. The MD can include reflectors 122C that can be optionally fitted with further sensors. Stereo color cameras/illumination 122A can be used as taillights. Other types of cameras and sensors can be mounted on the MD. Information from the cameras and sensors can be used to enable a smooth transition to balance mode 100-3 (FIG. 3A) by providing information to the MD to enable the location of obstacles that might impede the transition to balance mode (described herein).

Figure 9A:
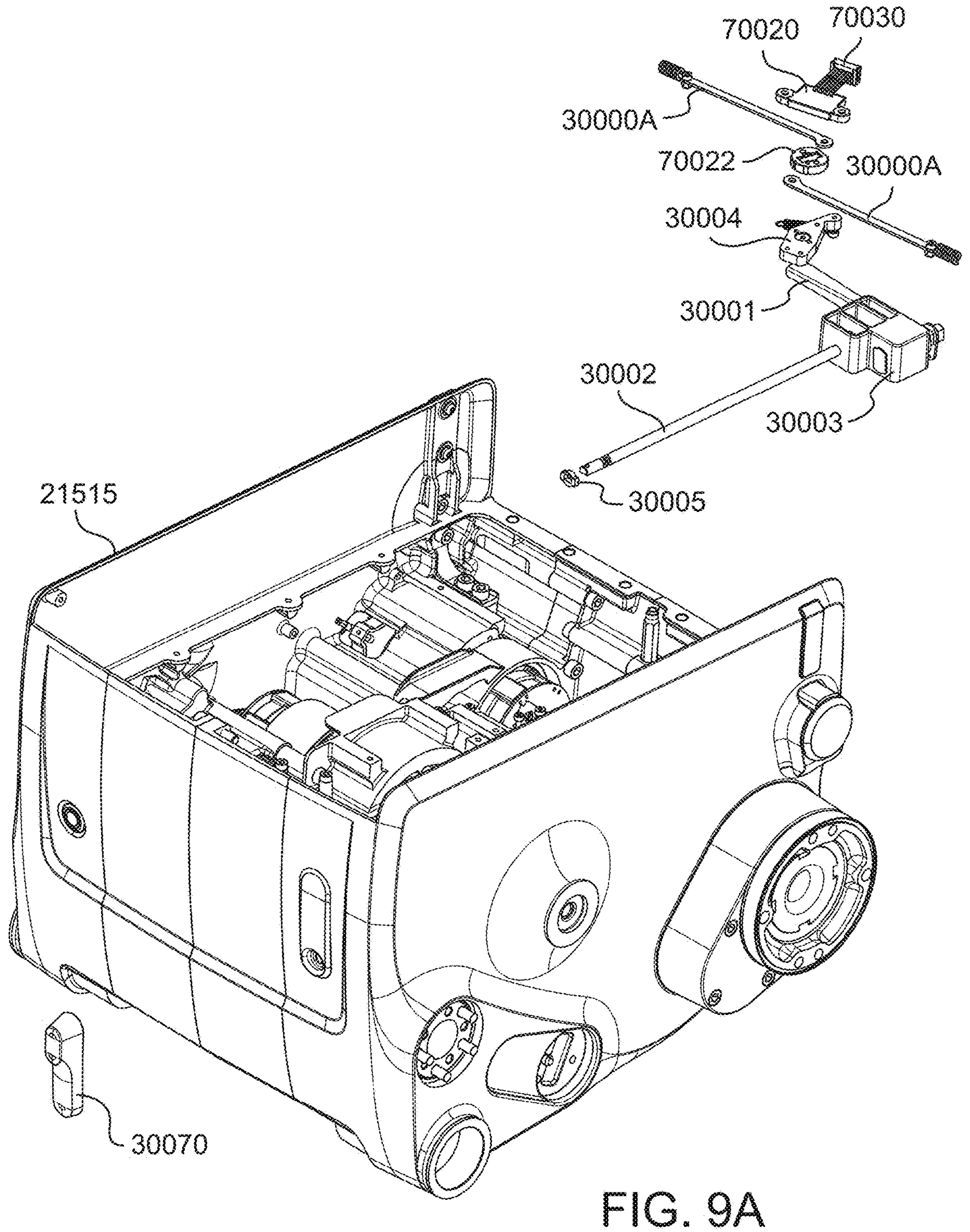
FIG. 9A is a perspective diagram of an exploded view of the manual brake assembly of the present teachings.

Referring now primarily to FIG. 9A, the service brake can be used to hold the MD in place by applying brake force to the wheel drive motor couplings, stopping the wheel from turning. The brakes can function as holding brakes whenever the device is not moving. The brakes can hold when the MD is powered on or off. A manual brake release lever can be provided so that the MD may be pushed manually with a reasonable amount of effort when power is off. In some configurations, the lever can be located at the front of the powerbase and can be accessible by either the user or an attendant. In some configurations, the manual release lever can be sensed by limit switches that can indicate the position of the manual release lever. Central gearbox 21514 can include brake release components including, but not limited to, manual brake release bracket 30003 (FIG. 9E), manual brake release shaft arm 30001 (FIG. 9H), manual brake release spring arm 30000 (FIG. 9G), Hall sensor 70020 (FIG. 9A), surface mount magnet 70022, manual brake release cam 30004 (FIG. 9F), and manual brake release shaft 30002 (FIG. 9D). Brake release lever handle 30070 (FIG. 9I) can activate manual brake release through manual brake release shaft 30002 (FIG. 9D). Manual brake release shaft 30002 (FIG. 9D) can be held in position by manual brake release bracket 30003 (FIG. 9E). Manual brake release shaft 30002 (FIG. 9D) can include tapered end 30002-2A (FIG. 9D) that can engage manual brake release shaft arm 30001 (FIG. 9H), which can be operably connected to manual brake release cam 30004 (FIG. 9F). Manual brake release cam 30004 (FIG. 9H) can be operably connected to two manual brake release spring arms 30000 (FIG. 9G). Spring arms 30000 can operably connect to brake release lever 592A (FIG. 3I). Hall sensor 70020 (FIG. 9A) can be operably coupled with PBC board 50001 (FIG. 9I).

Figure 9B:
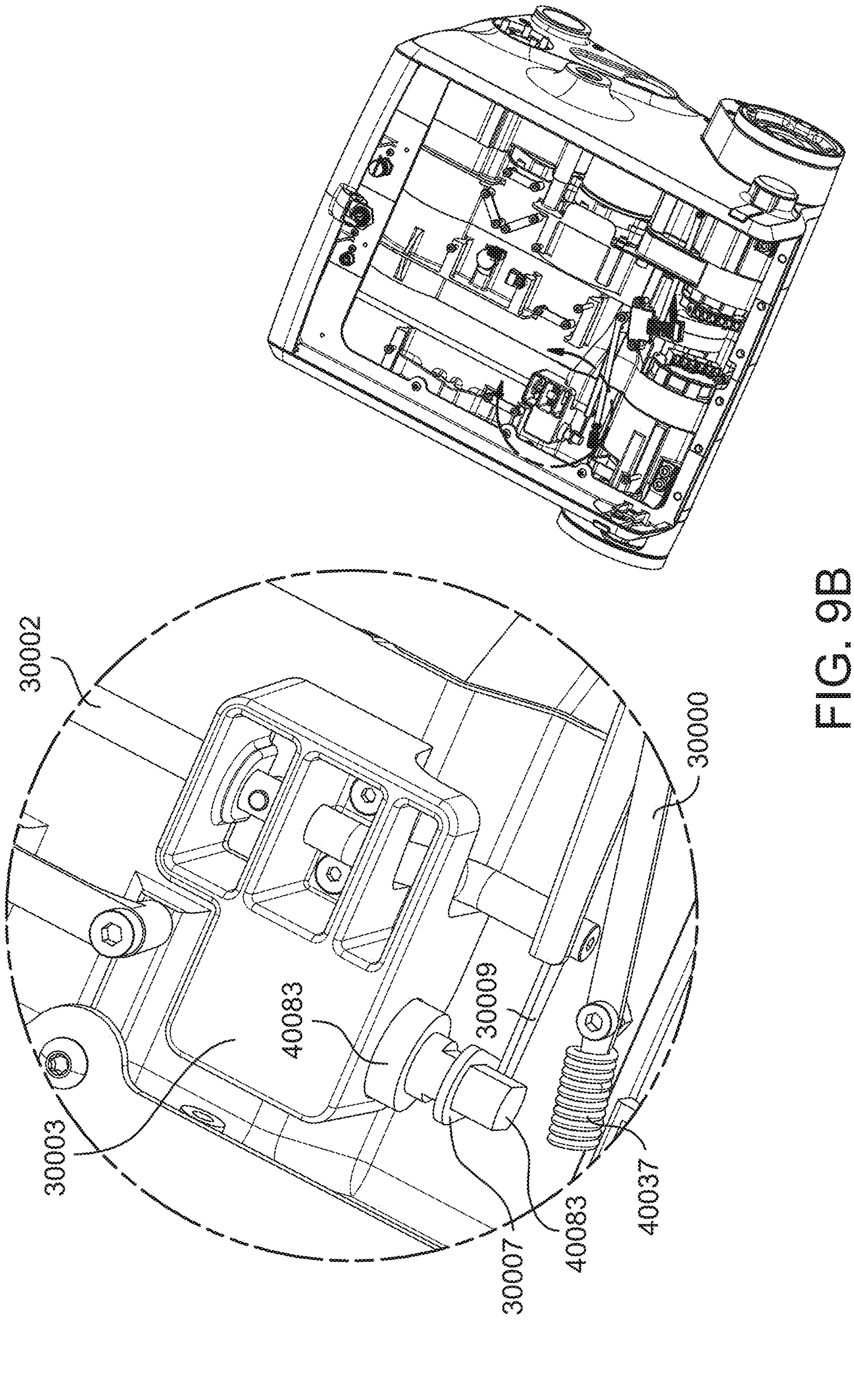
FIG. 9B is a perspective diagram of the damper of the manual brake assembly of the present teachings.
Figure 9C:
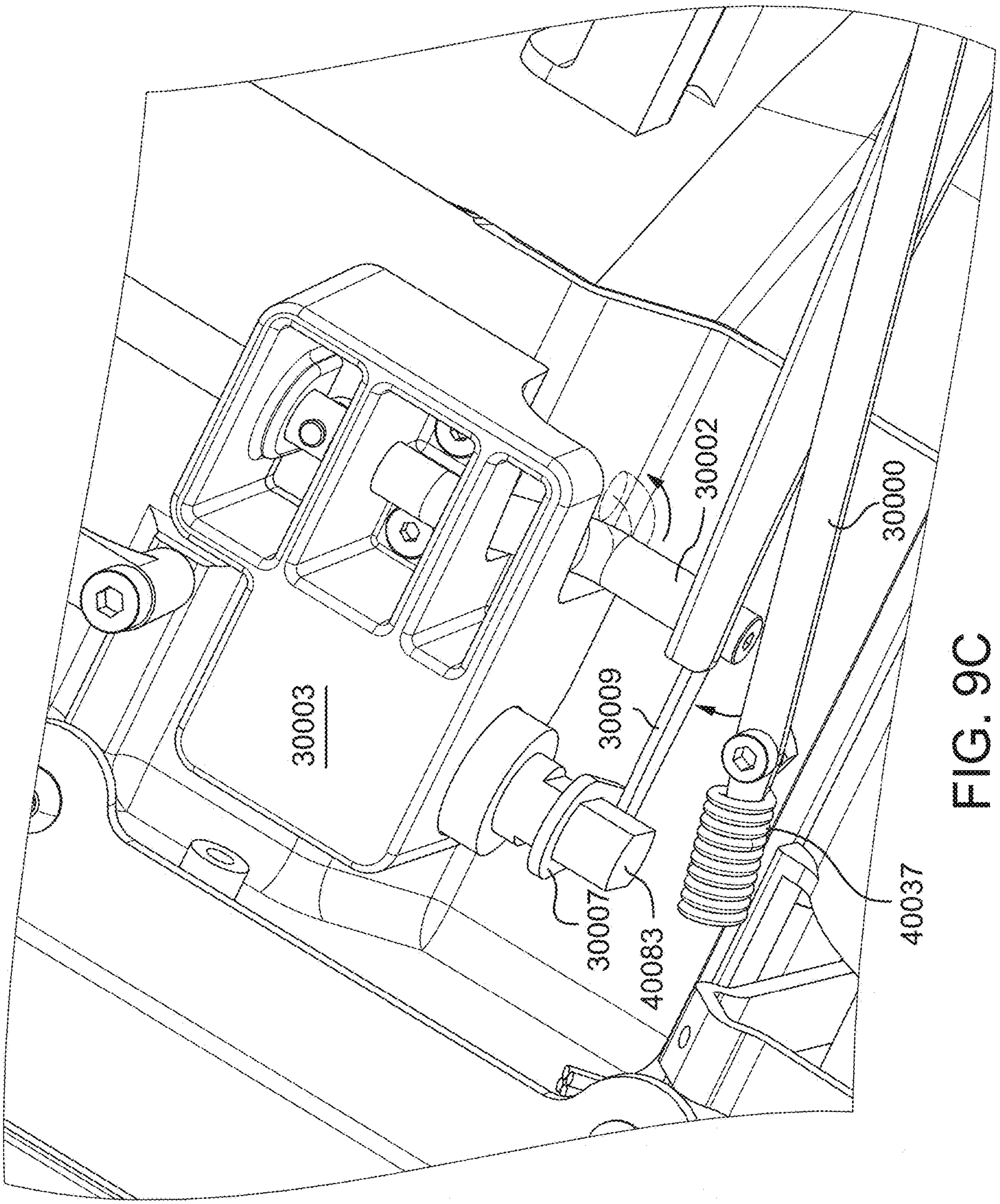
FIG. 9C is a perspective diagram of the damper in motion of the manual brake assembly of the present teachings.
Figure 9D:
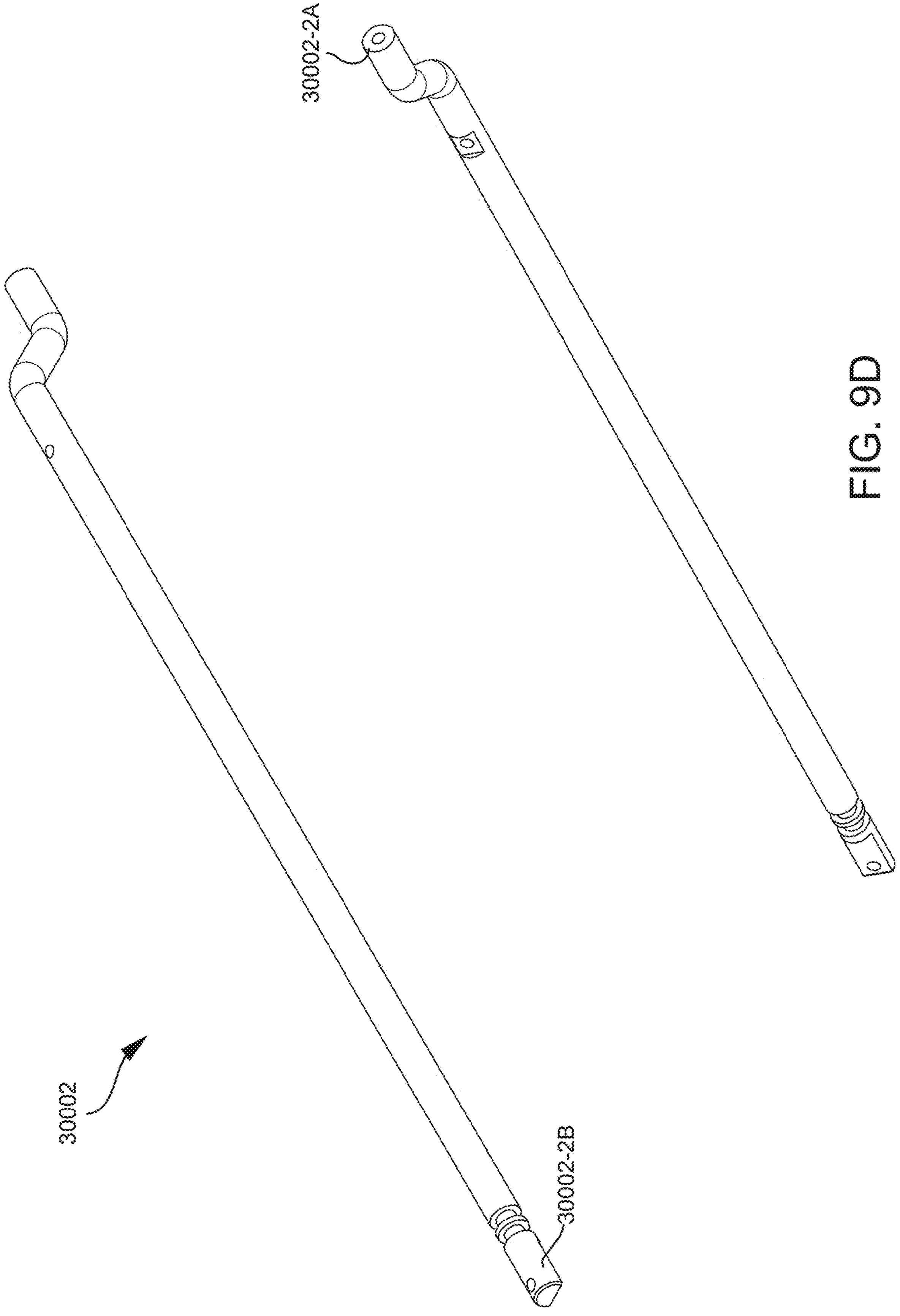
FIG. 9D is a perspective diagram of the manual brake release shaft of the present teachings.
Figure 9E:
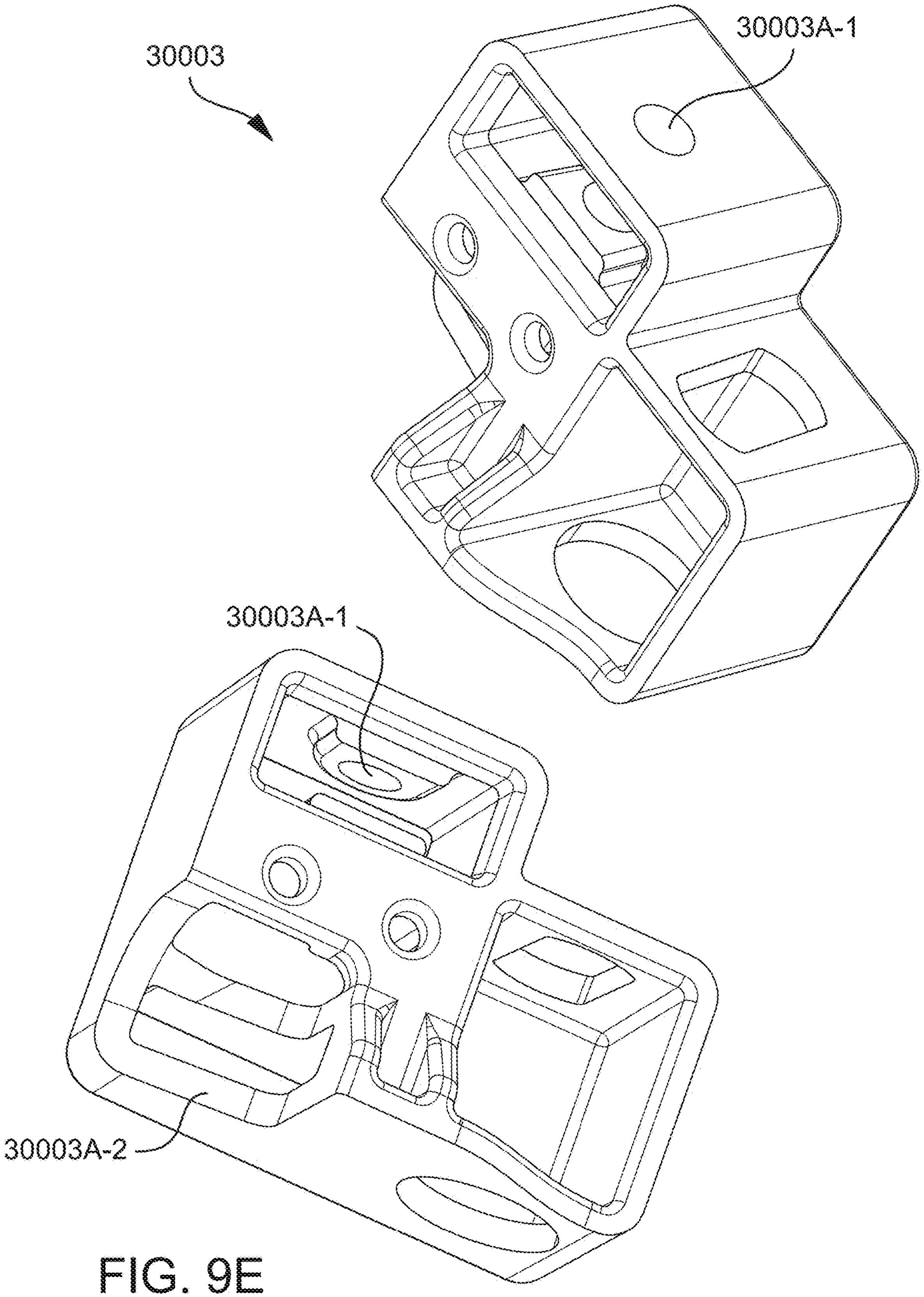
FIG. 9E is a perspective diagram of the manual brake release bracket of the present teachings.
Figure 9F:
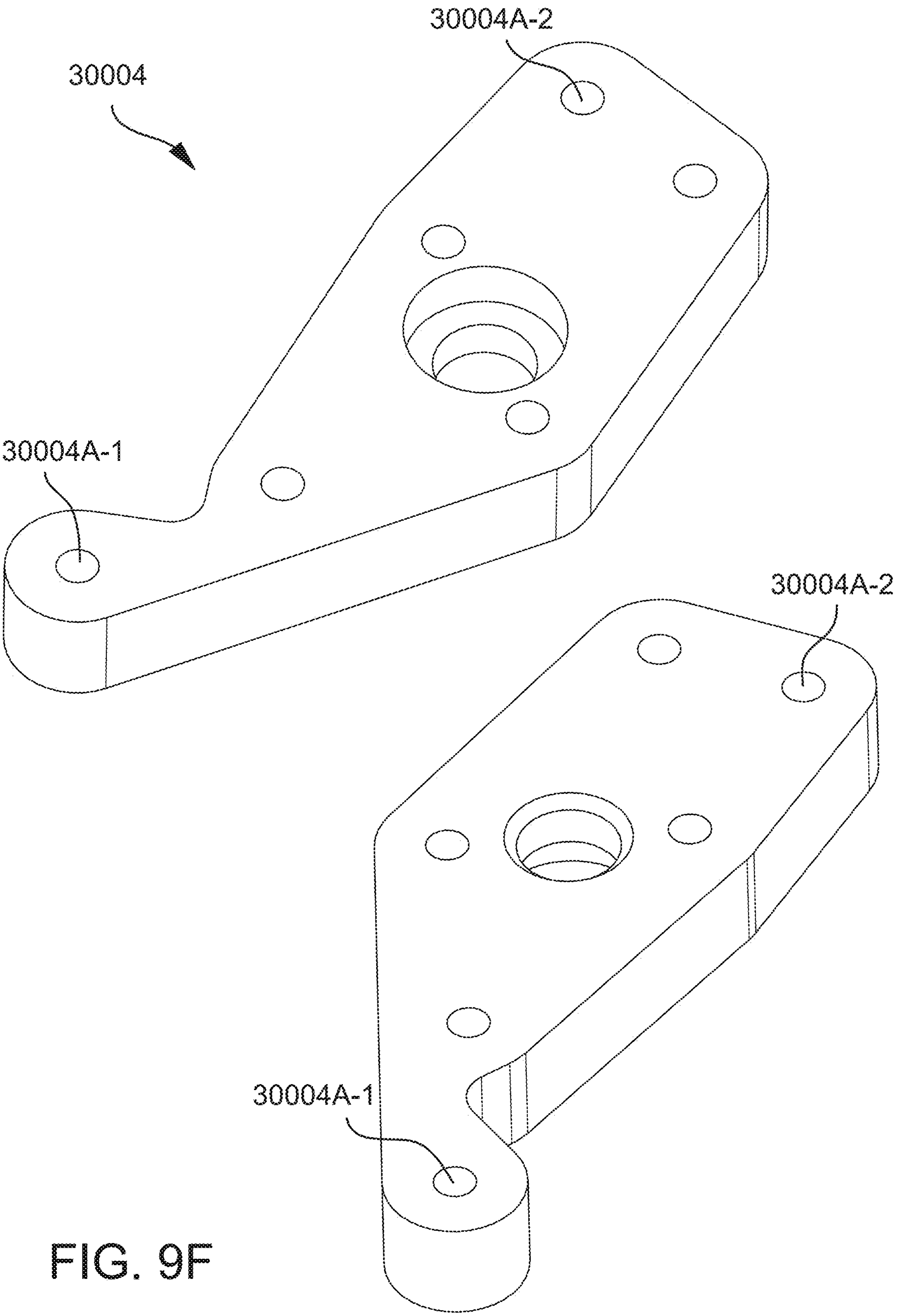
FIG. 9F is a perspective diagram of the manual brake release pivot interface of the present teachings.
Figure 9G:
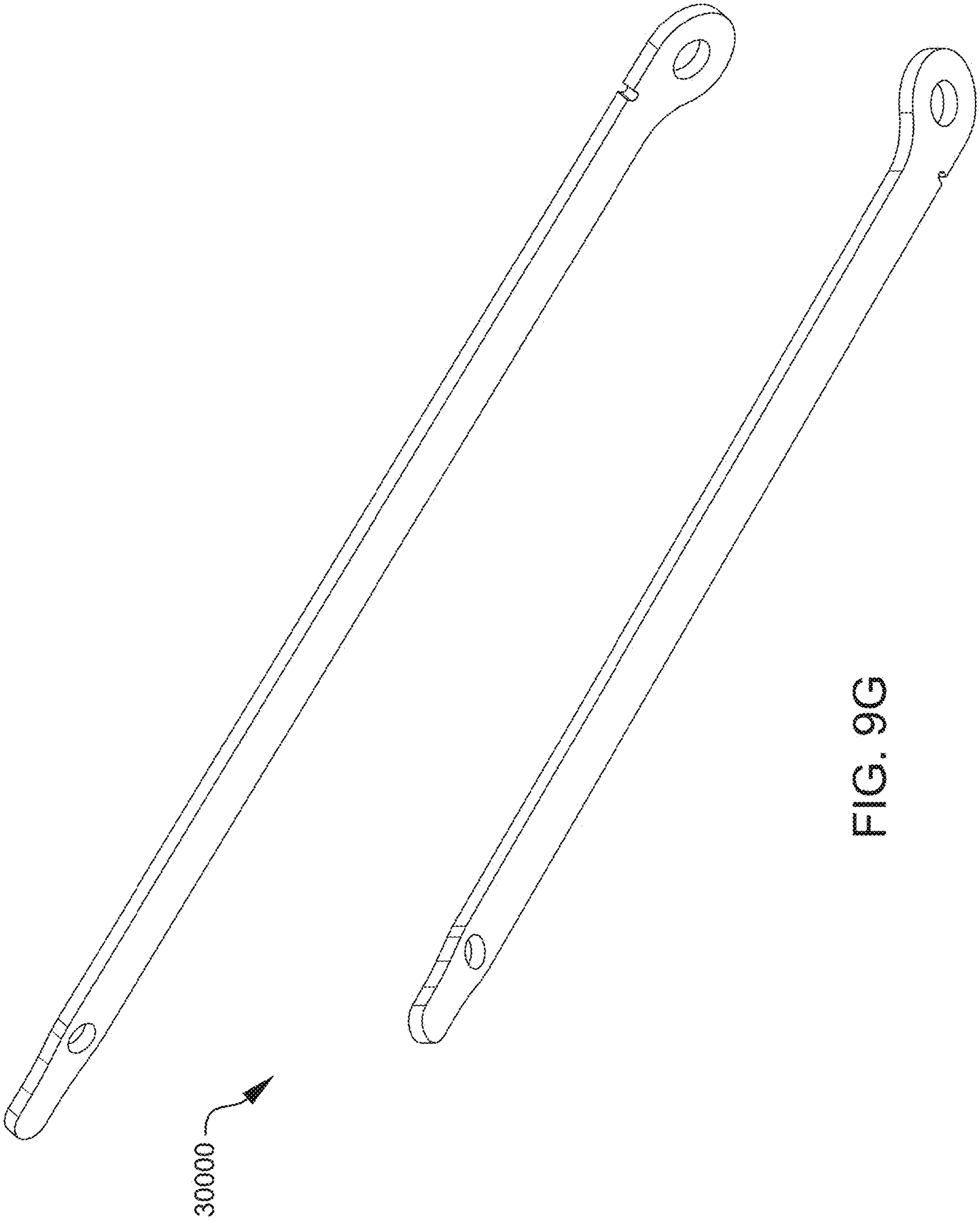
FIG. 9G is a perspective diagram of the manual brake release spring arm of the present teachings.
Figure 9H:
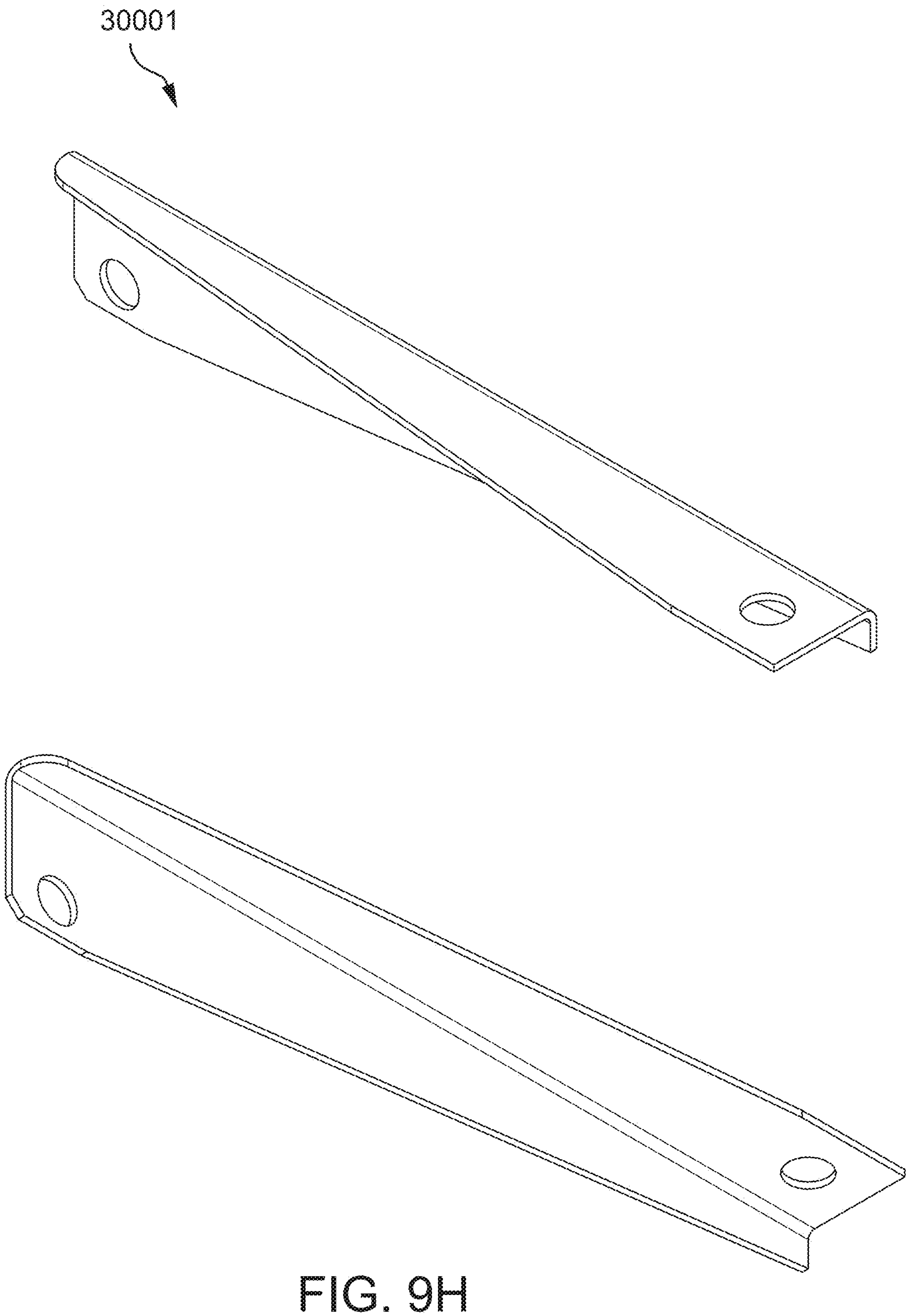
FIG. 9H is a perspective diagram of the manual brake release shaft arm of the present teachings.
Figure 9I:
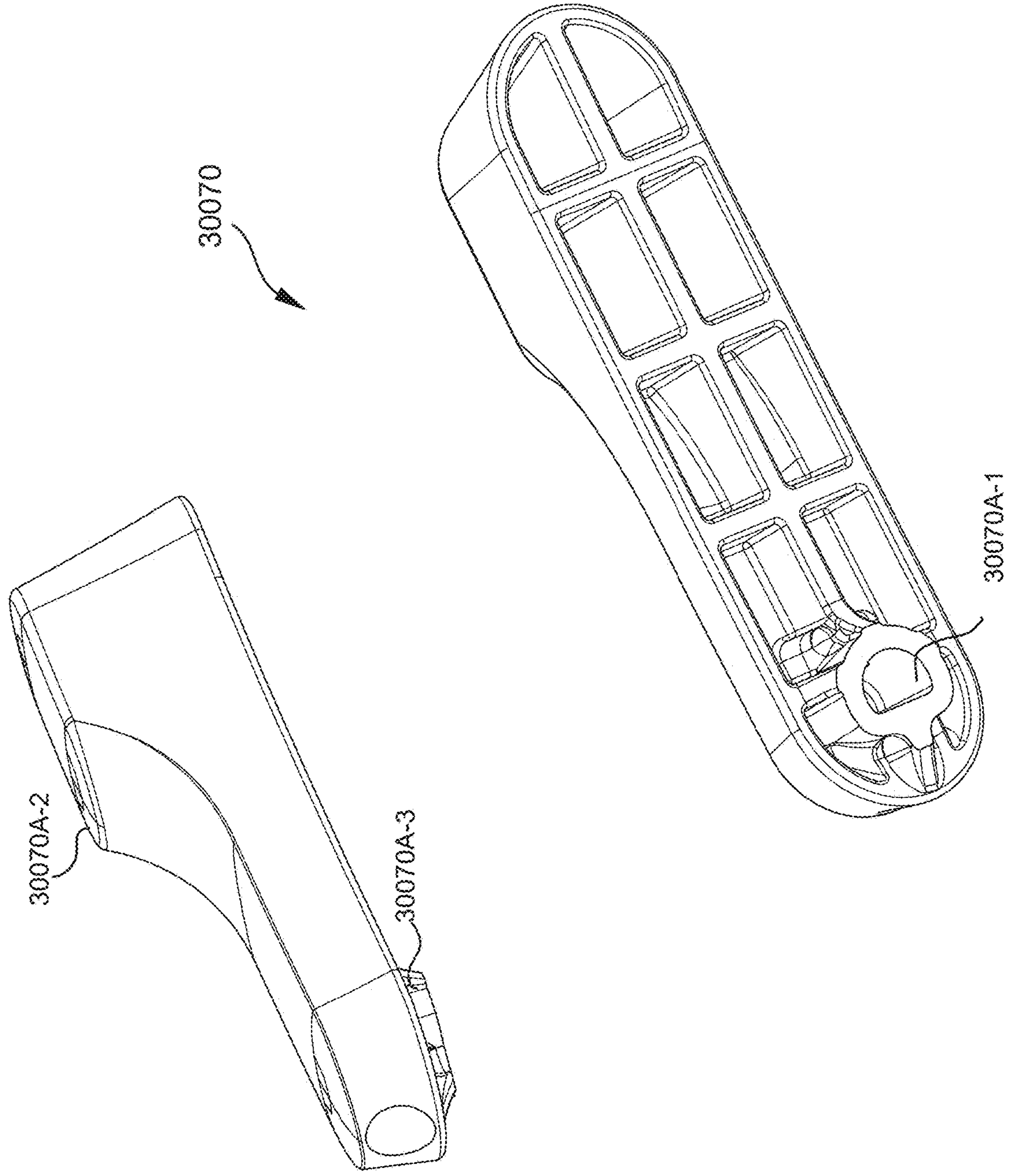
FIG. 9I is a perspective diagram of the brake release lever of the present teachings.
Figure 9J:
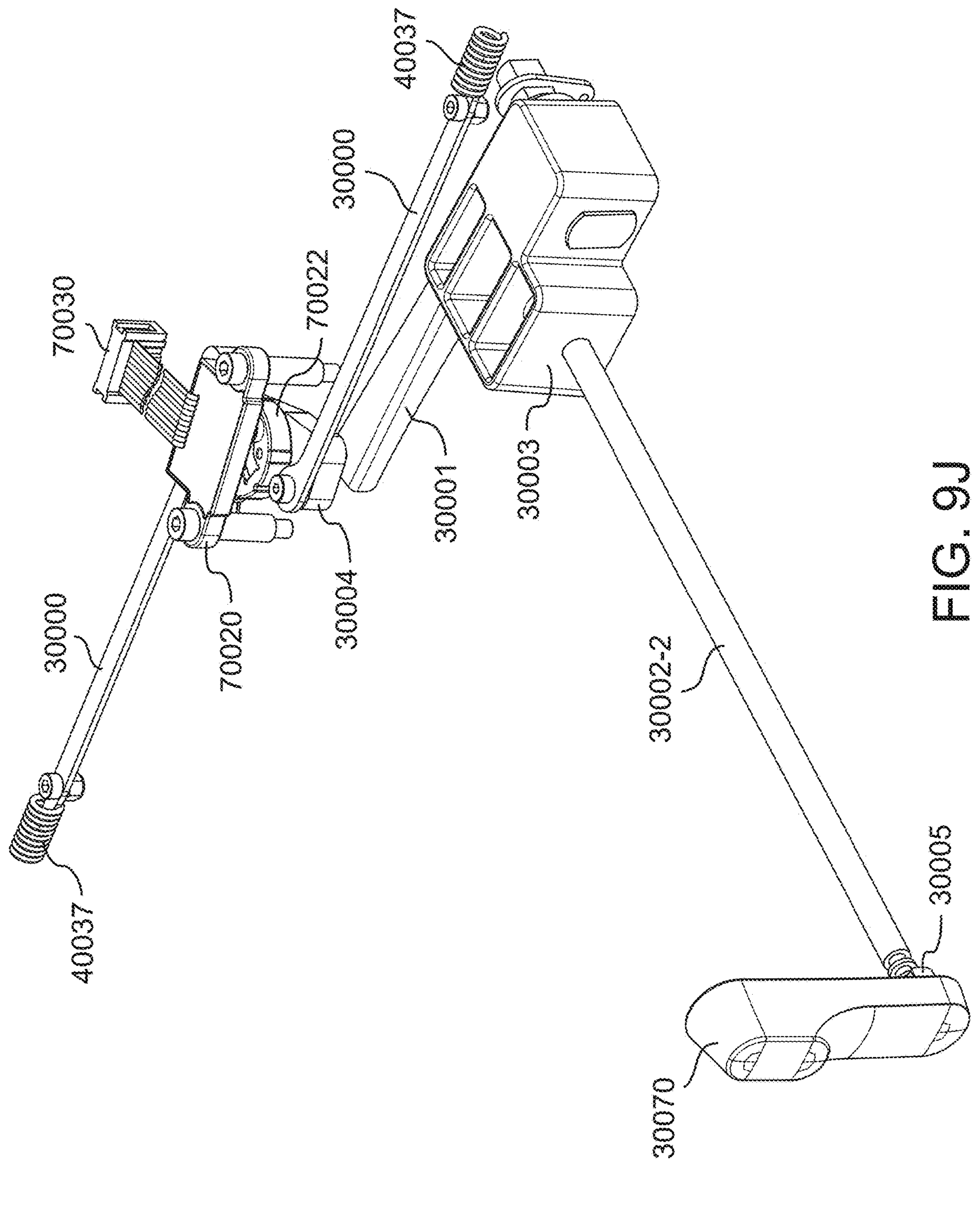
FIG. 9J is a perspective diagram of the manual brake release assembly of the present teachings.
Figure 9K:
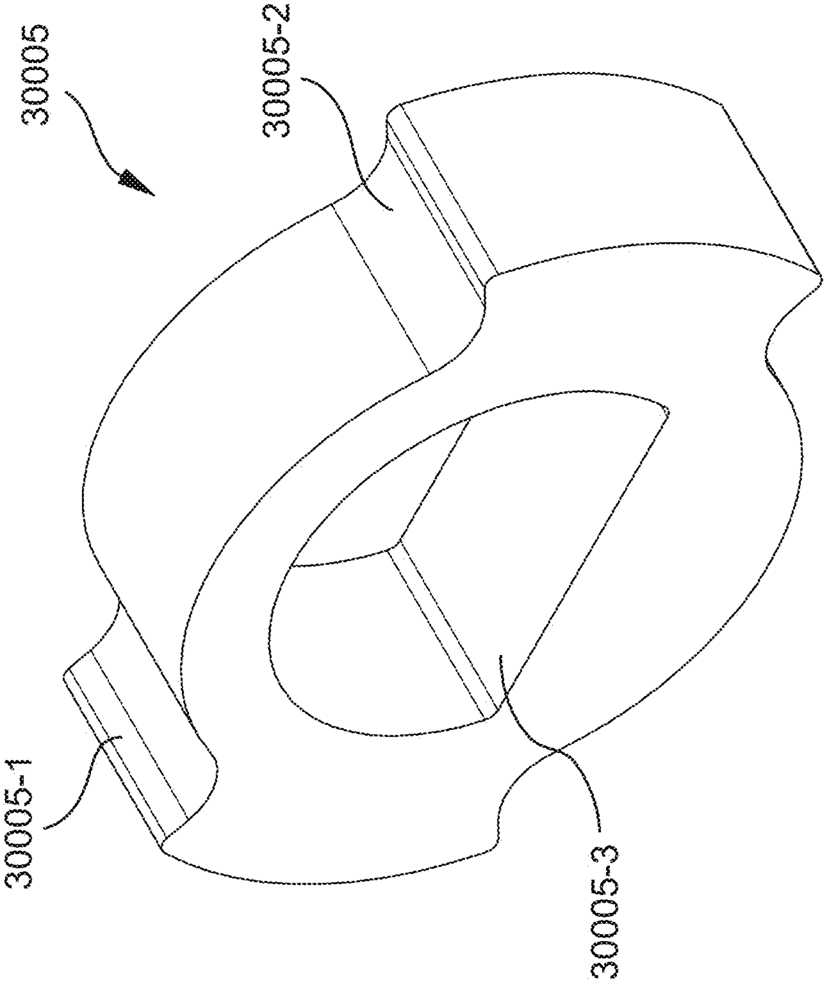
FIG. 9O is a perspective diagram of the second configuration of the manual brake assembly of the present teachings.
FIG. 9P is a magnified view of the diagram of FIG. 9M.
Figure 9L:
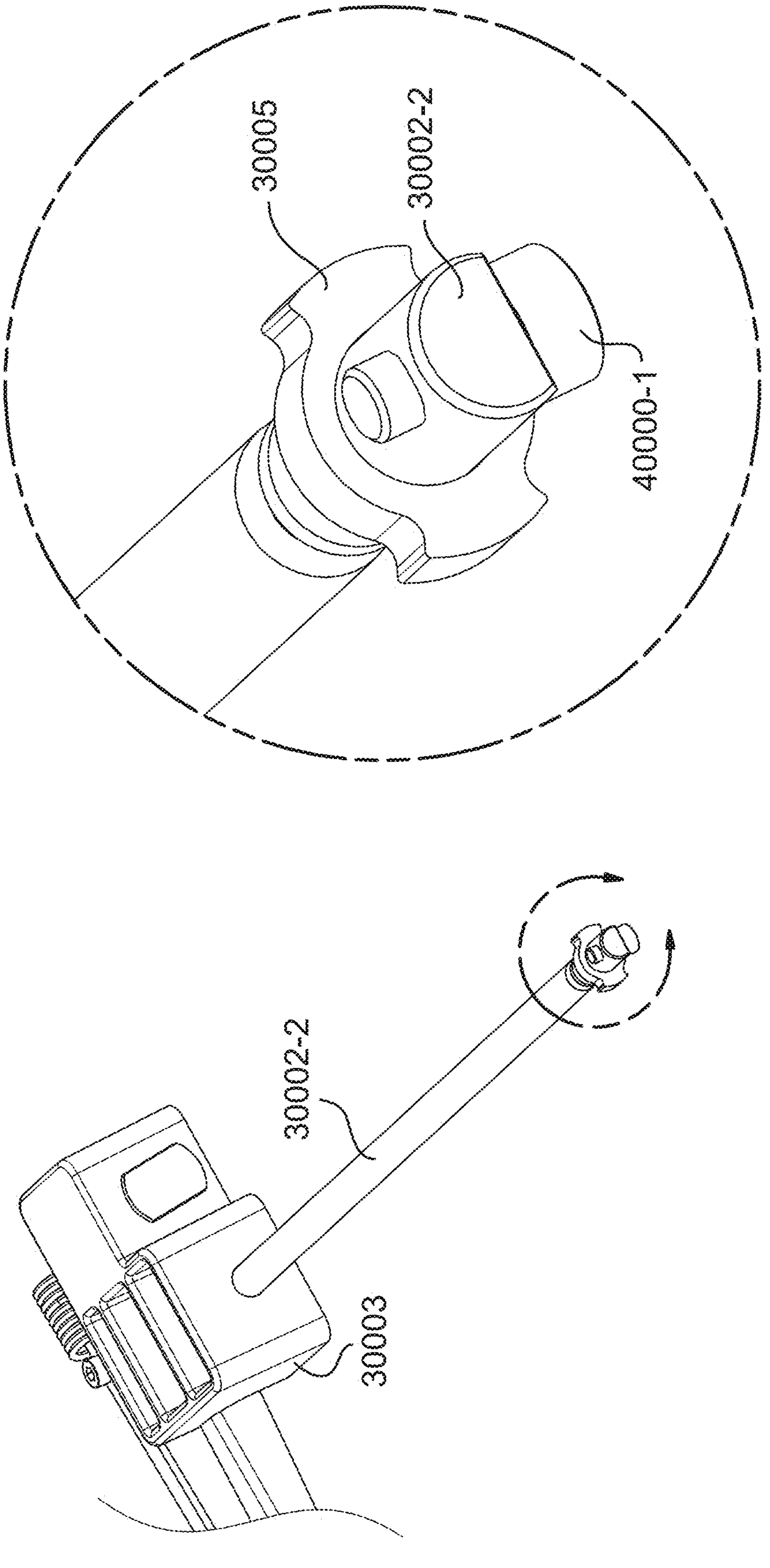
Figure 9M:
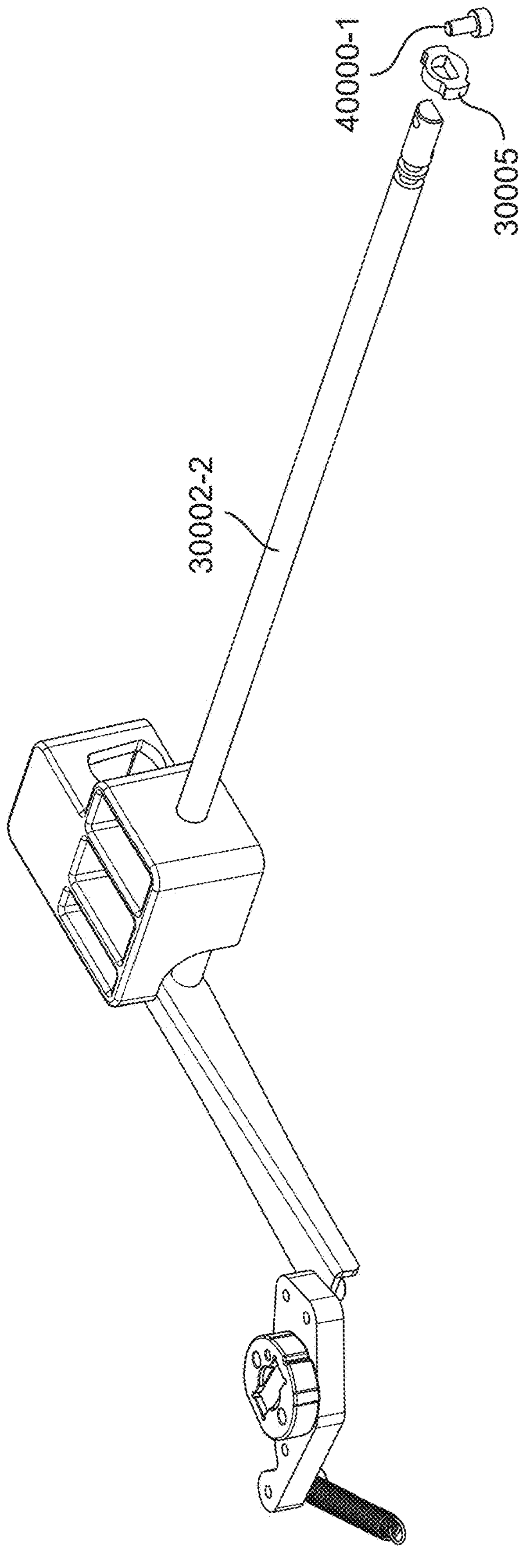
Figure 9N:
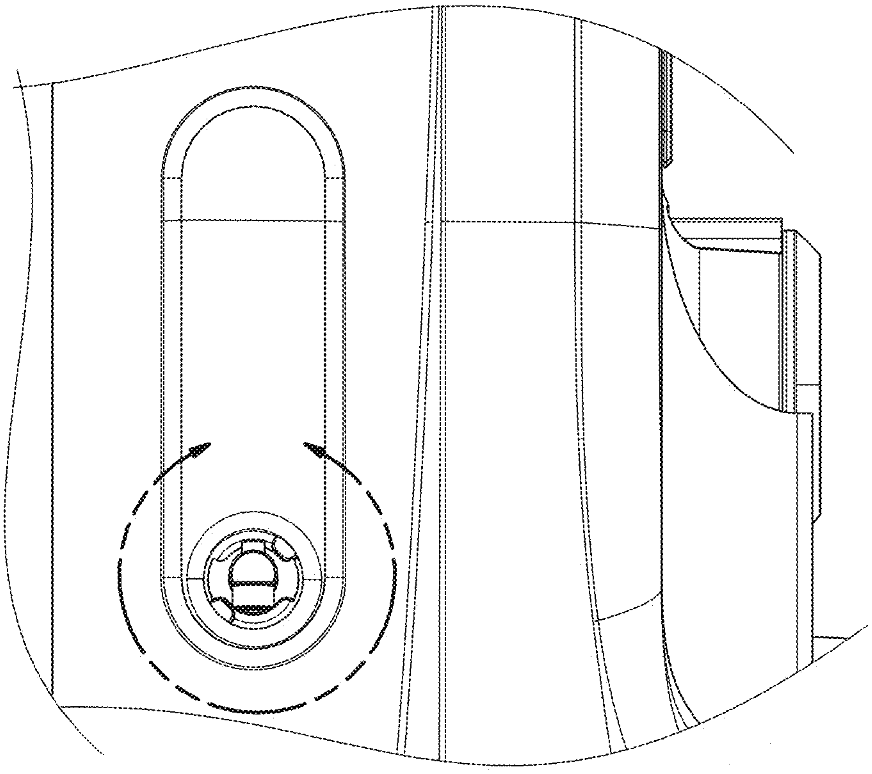
Figure 9N:
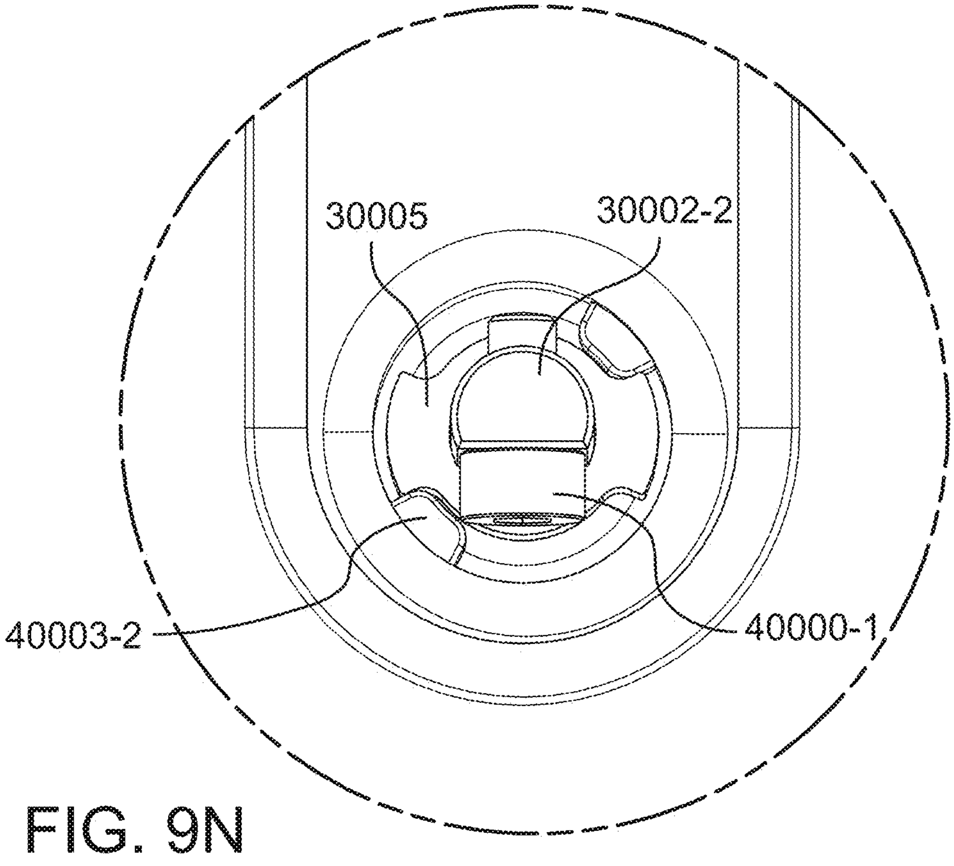
Figure 9O:
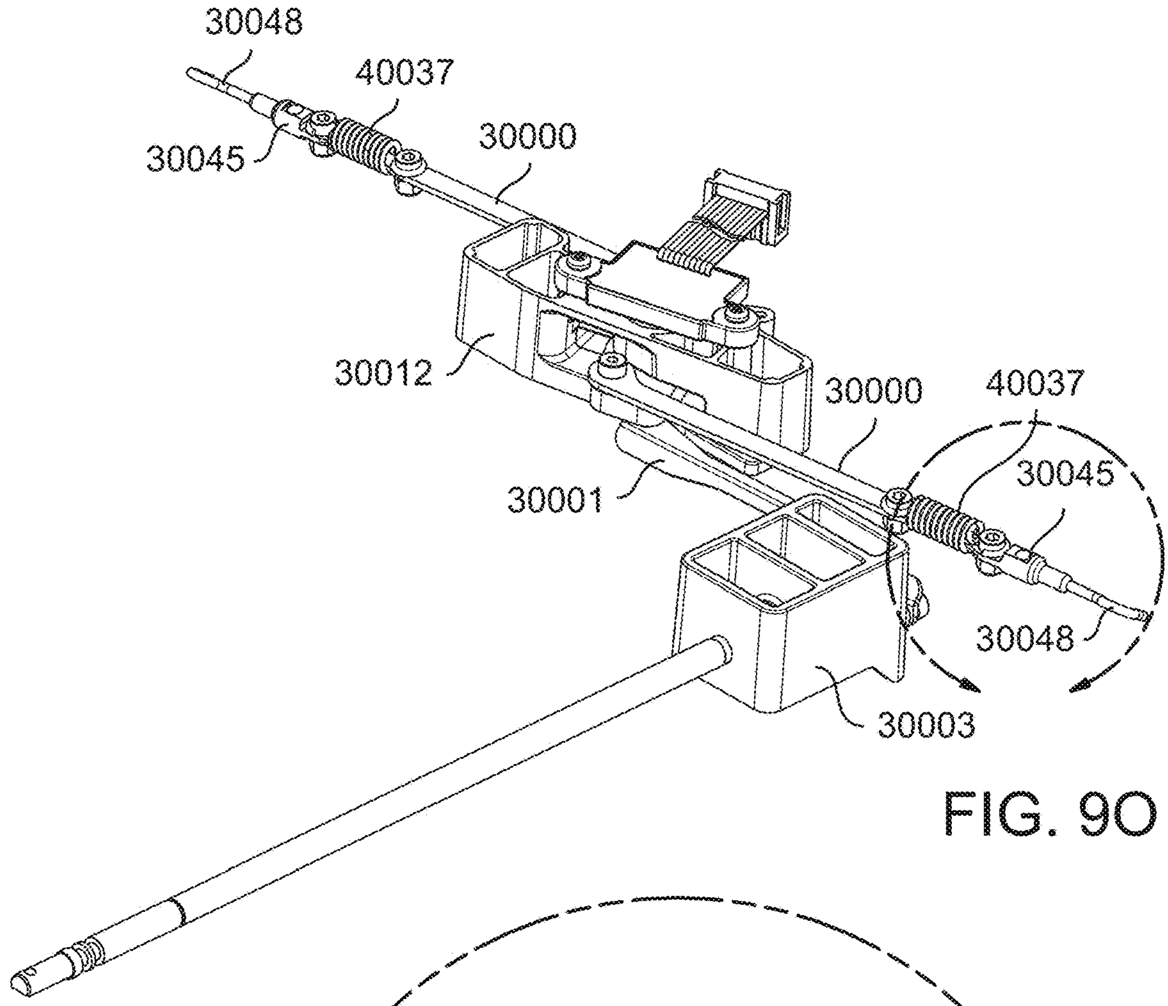
Figure 9P:
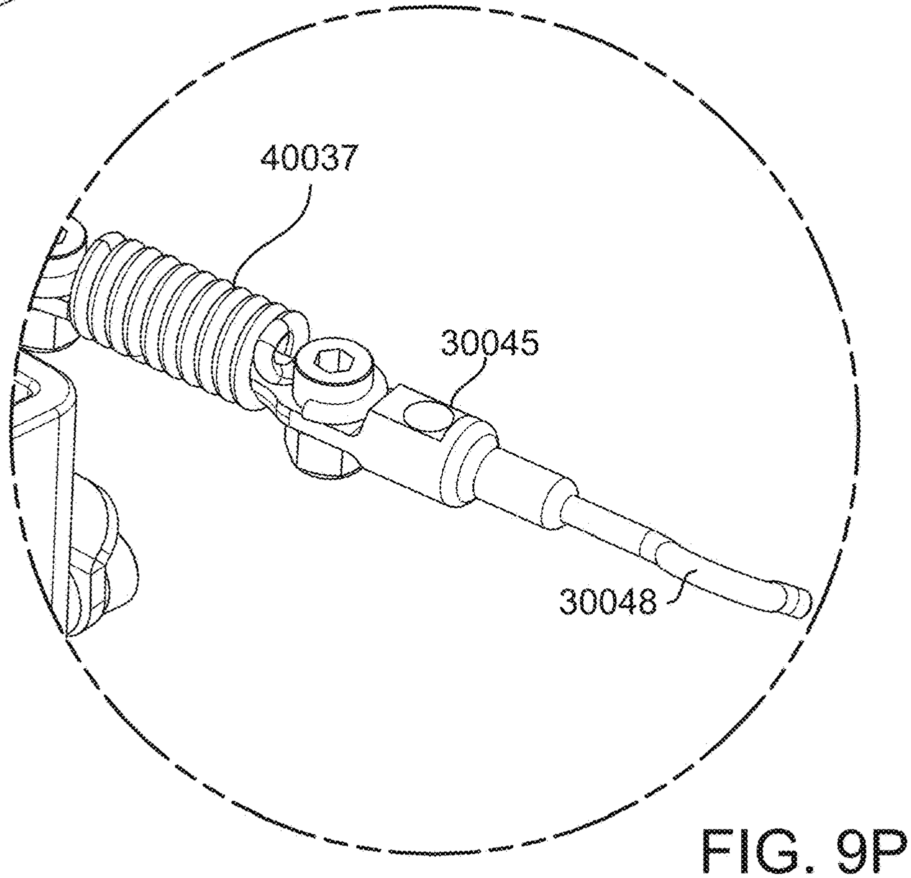

Referring now to FIGS. 9M and 9N, the manual brake release can include hook 30048 and hook interface 30045 operably coupled with spring 40037. Hook 30048 attaches through the hole in the brake lever of brake with manual release 70708 (FIG. 3I). The shape of hook 30048 can enable installation into the hole, and can inhibit hook 30048 from sliding out of the hole. The coupling between hook 30048 and hook interface 30045 can be threaded which can enable adjustment of the tension of spring 40037.

Referring now to FIGS. 9B and 9C, brake release lever handle 30070 (FIG. 9I) has a return force, for example, a spring-loaded force, pulling on it when it is in engaged position. Rotational damper 40083 can enable snap back avoidance for lever 30070 (FIG. 9I). Rotational damper 40083 can be operably coupled with brake shaft 30002 (FIG. 9D) through connecting collar 30007 and damper actuator arm 30009. Rotational damper 40083 can allow relatively unrestricted movement when lever 30070 (FIG. 9I) is turned clockwise from a vertical position where the brakes are engaged to the horizontal position where the brakes are released. When lever 30070 (FIG. 9I) is turned counter-clockwise to reengage the brakes, rotational damper 40083 can provide resistance to the rotation of brake shaft 30002 (FIG. 9D), slowing the speed at which lever 30070 (FIG. 9I) returns to the vertical position, thus substantially preventing lever 30070 (FIG. 9I) from snapping back into the vertical position. Rotational damper 40083 can be operably coupled with brake assembly stop housing 30003 (FIG. 9E). Damper actuator arm 30009 (FIG. 9B) can be operably coupled with brake shaft 30002 (FIG. 9D).

Referring now to FIG. 9I, manual brake release lever 30070 can include material that can be damaged before other manual brake release parts are damaged when excessive force is applied. If manual brake release lever 30070 is damaged, manual brake release lever 30070 can be replaced without opening of the central housing.

Referring now primarily to FIGS. 9J-9N, the manual release brake assembly can include manual brake release bracket 30003 (FIG. 9E), manual brake release shaft arm 30001 (FIG. 9H), manual brake release spring arm 30000 (FIG. 9G), Hall sensor 70020 (FIG. 9J), surface mount magnet 70022, manual brake release pivot interface 30004 (FIG. 9F), and manual brake release shaft 30002 (FIG. 9D). Brake release lever handle 30070 (FIG. 9I) can activate the manual brake release through manual brake release shaft 30002 (FIG. 9D). Manual brake release shaft 30002 (FIG. 9D) can be held in position by manual brake release bracket 30003 (FIG. 9E). Manual brake release shaft 30002 (FIG. 9D) can include tapered end 30002-2A (FIG. 9D) that can engage manual brake release shaft arm 30001 (FIG. 9H), which can be operably connected to manual brake release pivot interface 30004 (FIG. 9F). Manual brake release pivot interface 30004 (FIG. 9F) can be operably coupled with two manual brake release spring arms 30000 (FIG. 15) at fastening cavities 30004A-1 (FIG. 9F) and 30004A-2 (FIG. 9F). Spring arms 30000 (FIG. 9G) can operably couple with brake release lever 592A (FIG. 3I).

Continuing to refer primarily to FIGS. 9J-9N, the service brake can include, but is not limited to including, travel stop 30005 (FIG. 9K) that can limit the motion of lever 30070 to a clockwise direction as viewed from the front of the MD from a vertical position to a horizontal position. Travel stop 30005 (FIG. 9K) can prevent lever 30070 (FIG. 9J) from rotating in a counterclockwise direction and can assist an operator in releasing and engaging the brakes. Travel stop 30005 (FIG. 9K) can be constructed of metal and can operably couple with second brake release shaft 30002 (FIG. 9D). Travel stop 30005 (FIG. 9K) can interface with features of central housing 21515 (FIG. 9A) that can limit the rotation of shaft 30002-2 (FIG. 9L). Hall sensor 70020 can sense if the manual brake release is engaged or disengaged. Hall sensor 70020 can operably couple with both A-side and B-side electronics using cables/connector 70030 which can be mechanically isolated from the A-side and B-side electronics. Travel stop 30005 (FIG. 9M) can operably couple with shaft 30002-2 (FIG. 9L) through fastener 40000-1 (FIG. 9M). Travel stop 30005 can encounter protrusion 40003-2 which can enable limitation of the rotation of shaft 30002-2 (FIG. 9L).

Figure 11B:
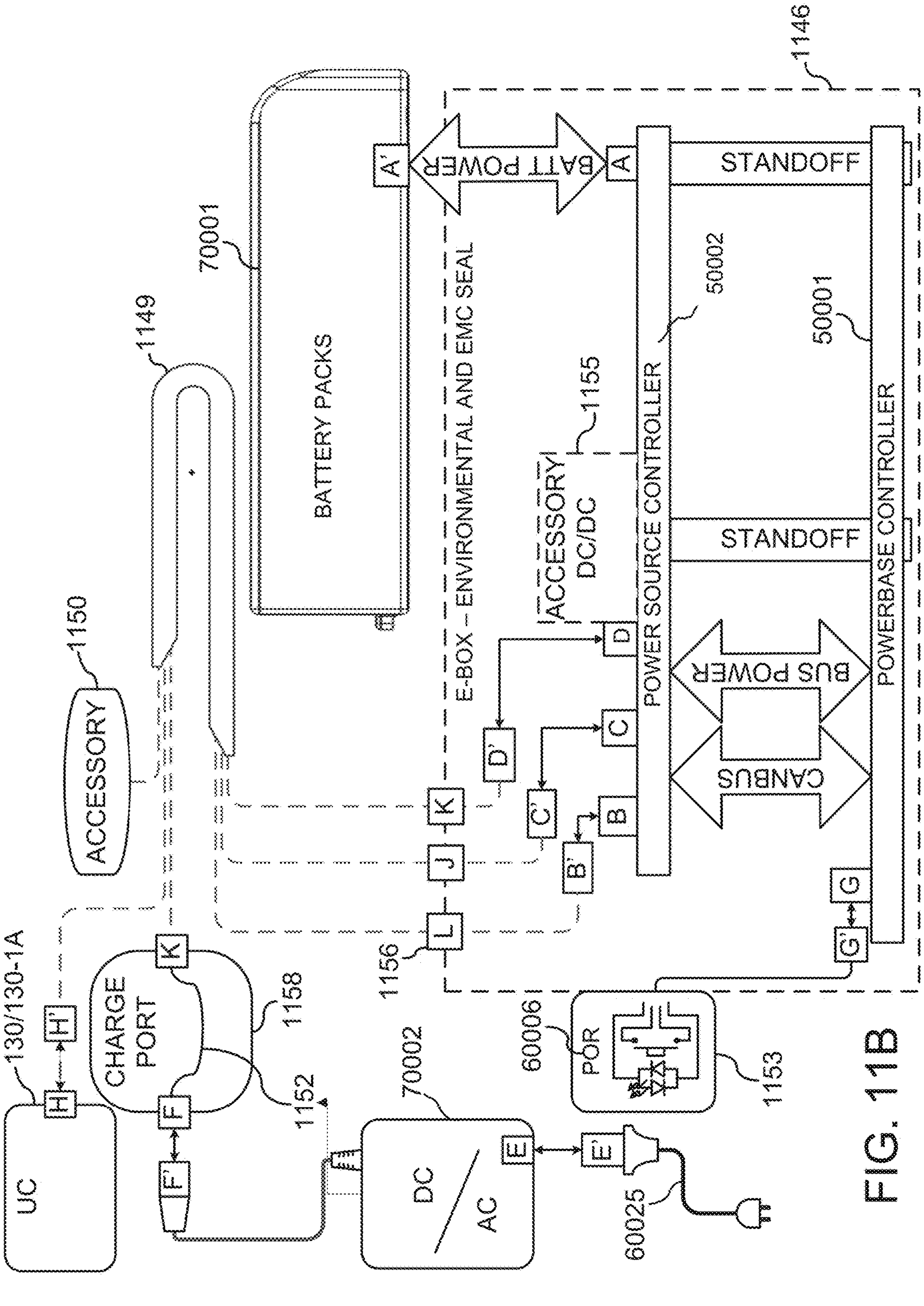
Figure 11C:
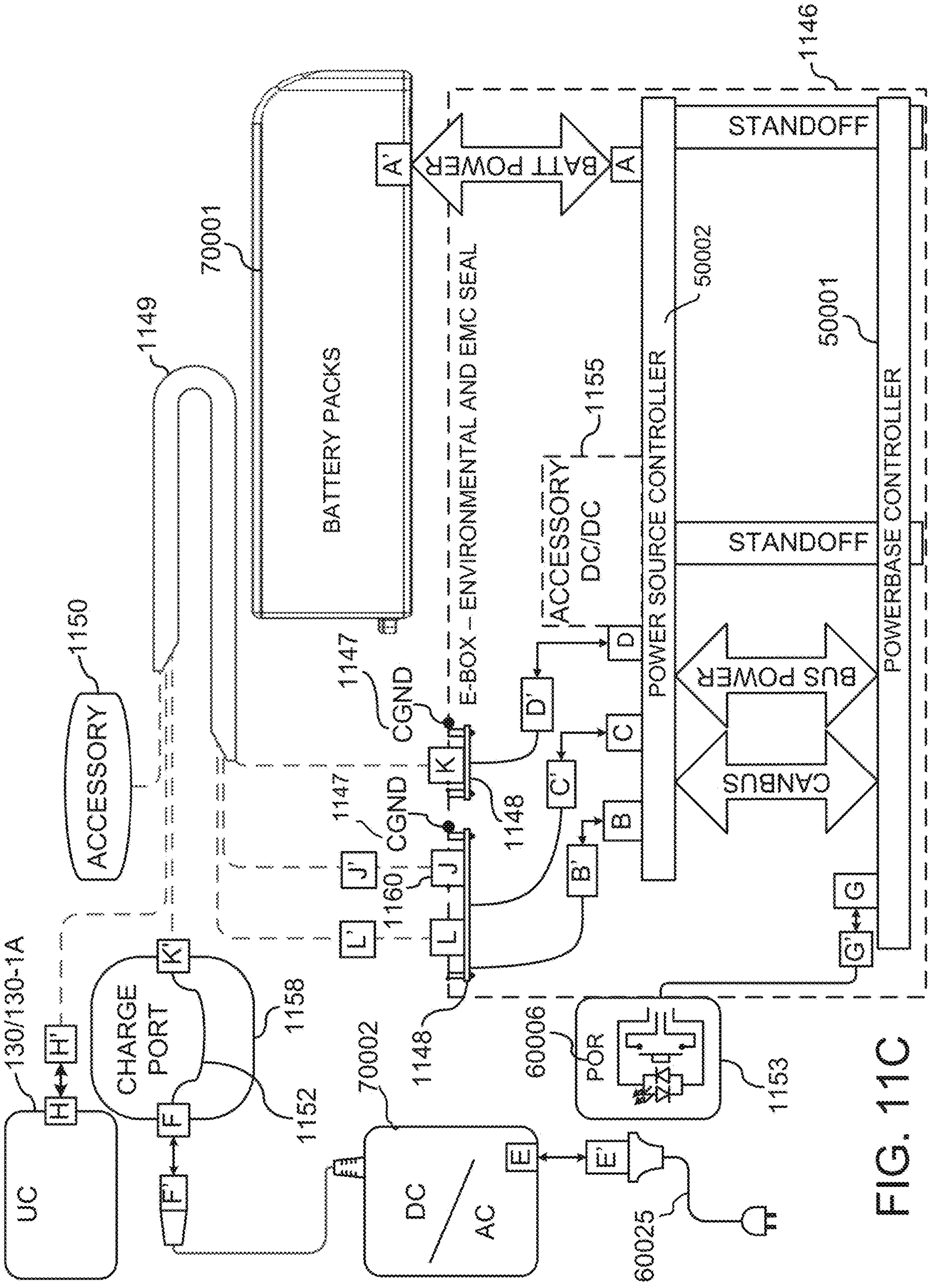
Figure 11D:
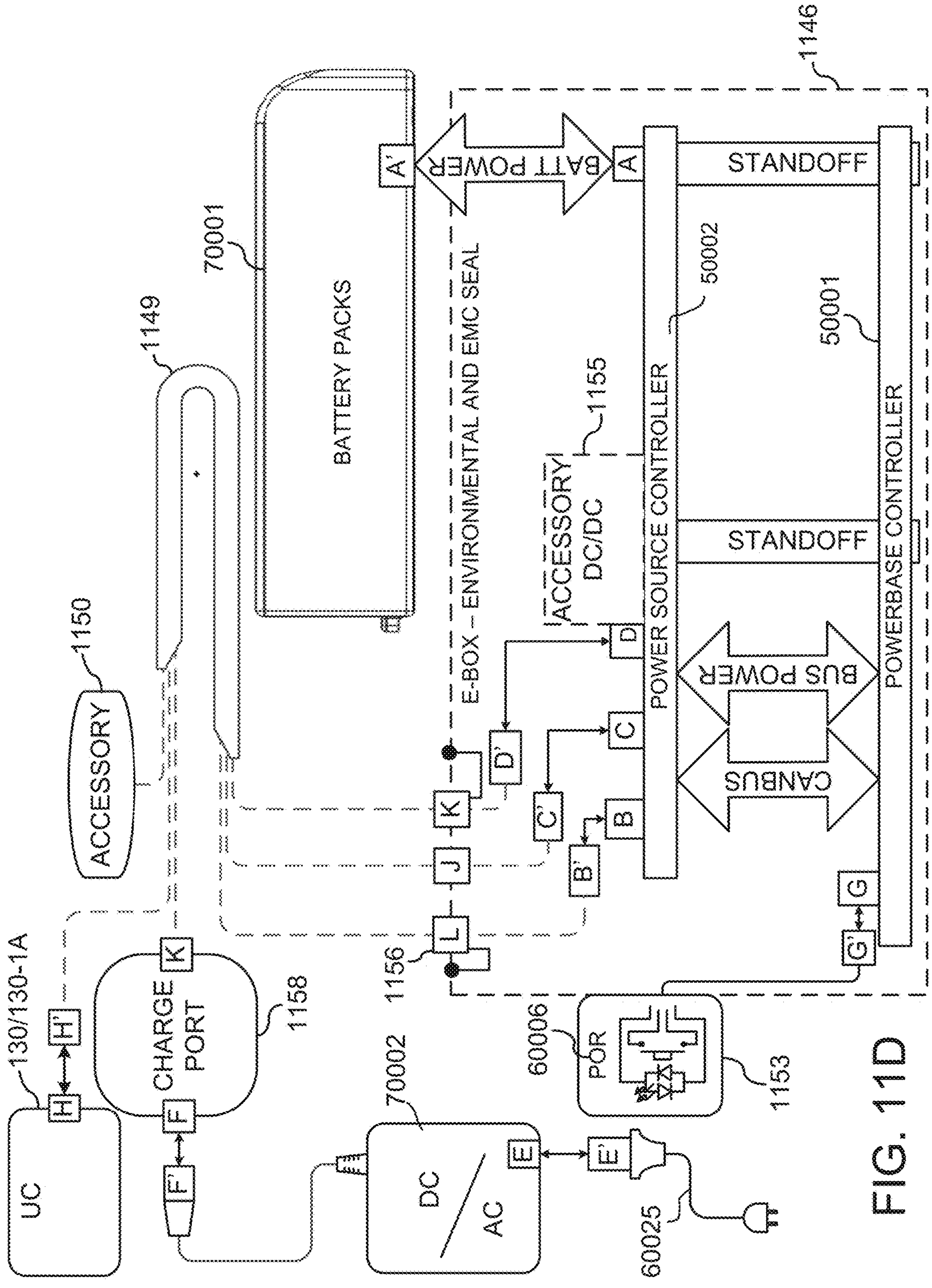
Figure 11E:
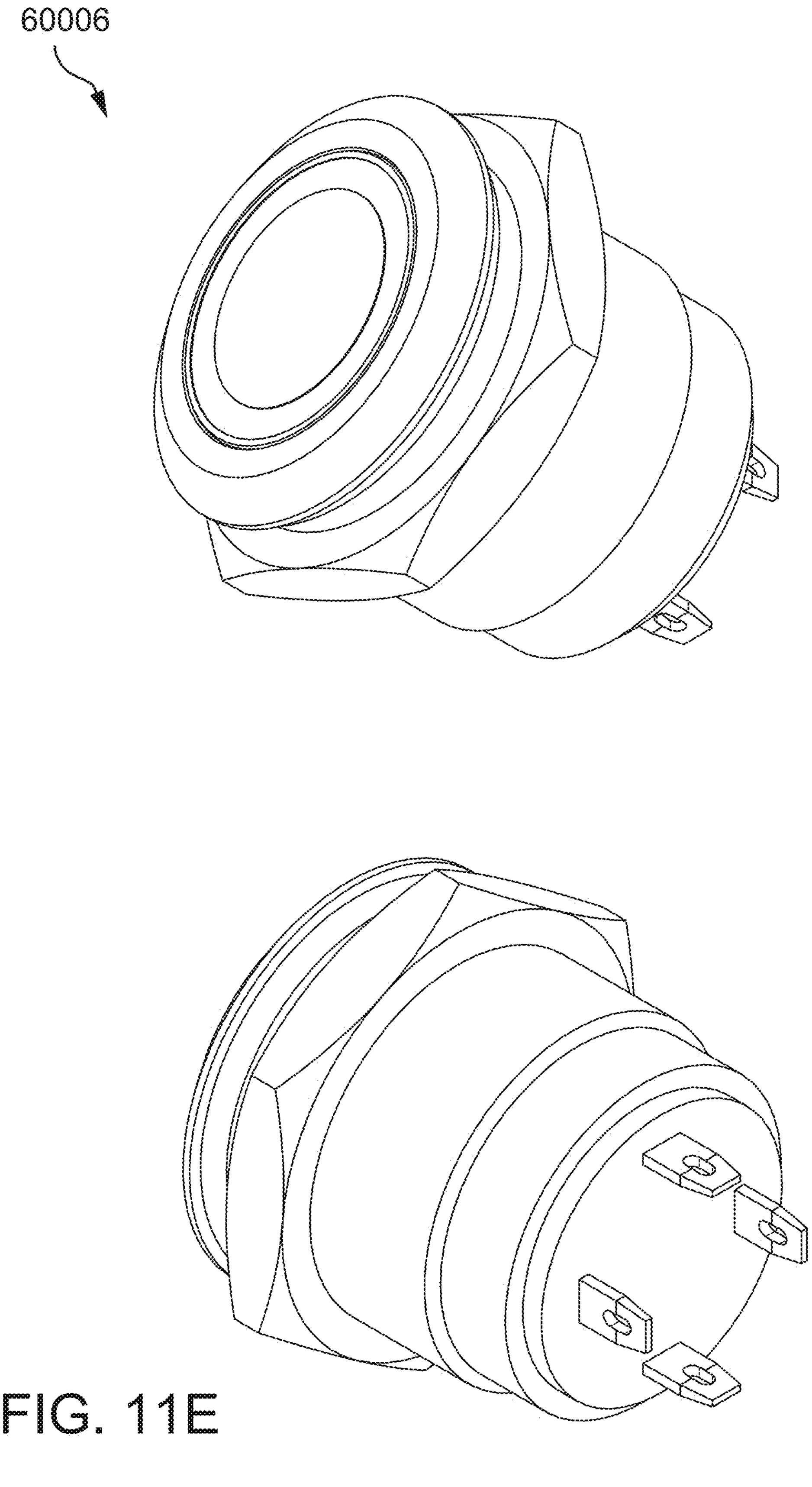

Referring now to FIGS. 10A-10E and 11B, harnesses can be mounted to straddle the inside and outside of the sealed part of central gearbox 21514 at the cable ports, and can be surrounded by sealing features such as, for example, but not limited to, o-rings or gaskets. UC port harness 60007 (FIG. 10C) can channel wires emerging from UC electromagnetic interference (EMI) filter 50007 (FIG. 10A) that can connect to PSC board 50002 (FIG. 11B). UC port harness 60007 (FIG. 10C) can include a connector, to which cable 60016 (FIG. 10A) can mate, and thereby connect UC EMI filter 50007 to UC 130 (FIG. 12A). Charge input port harness 60008 (FIG. 10D) can channel wires emerging from charge input filter 50008 (FIG. 10A) that can connect PSC board 50002 (FIG. 9I) to a charging means, for example, but not limited to, charging power supply 70002 (FIGS. 11A-11D) via charger port 1158 (FIGS. 10A, 11A-11D). Accessory port harness 60009 (FIG. 10E) can channel wires emerging from auxiliary connector filter 50009 that can connect accessory wires to PSC board 50002. The cable exit locations can be protected from impact and environmental contamination by being positioned between the front wall of the MD and batteries 70001 (FIG. 1E). Articulating cable carrier 1149 (FIGS. 11A-11D) can protect the cables and can route the cables from the central housings to the seat, protecting the cables from becoming entangled in the lifting and/or stabilizer arms.

Referring now to FIGS. 11A-11D, various wiring configurations can connect PBC board 50001, PSC board 50002, and battery packs 70001 (FIG. 1E) with UC 130, charge port 1158, and optional accessories 1150A. Emergency power off request switch 60006 can interface with e-box 1146 through panel mount 1153. Optional accessory DC/DC module 1155 can include, for example, but not limited to, a module that can plug in to PSC board 50002. In some configurations, DC/DC supply 1155 for optional accessories can be integrated into PSC board 50002 to eliminate a need for opening e-box 1146 outside of a controlled environment. In some configurations, charge port 1158 can include a solder termination of cables to a port. If transmission means 1151 includes cables, the cables can be confined by use of cable carrier 1149 such as, for example, but not limited to, IGUS® energy chain Z06-10-018 or Z06-20-028. In some configurations, e-box 1146, that can include, but is not limited to including, PBC board 50001 and PSC board 50002, can be connected to UC 130, optional accessories 1150A, and charge port 1158 through junctions 1157 (FIG. 11A) and transmission means 1151. In some configurations, strain relief means 1156 (FIG. 11C) can provide the interface between e-box 1146 and UC 130, charge port 1158, and optional accessories 1150A. In some configurations, a cable shield can be brought out to a forked connector and terminated to metal e-box 1146 with, for example, a screw (see FIG. 11D). In some configurations, one or more printed circuit boards 1148 (FIG. 11C) can operably couple with strain relief means 1156 L, J, and K (FIG. 11C), which can be mounted to e-box 1146. Strain relief means 1156 L, J, and K (FIG. 11C) can double as environmental seals and can provide channels through which electrical signals or power can pass. Strain relief means 1156 L, J, and K (FIG. 11C) can include, for example, grommets or glands, or could be overmolded and inseparable from the cables. One or more printed circuit boards 1148 (FIG. 11C) can (1) provide a place to connect internal harnesses between printed circuit boards 1148 (FIG. 11C) and PSC board 50002, and (2) provide a place for electromagnetic compatibility (EMC) filtration and electrostatic discharge (ESD) protection. EMC filtration and ESD protection can be enabled by connecting printed circuit boards 1148 (FIG. 11C) to metal e-box 1146, forming chassis ground 1147.

Continuing to refer to FIGS. 11A-11D, charger port 1158 is the location where the AC/DC power supply 70002 can be connected to the MD. The AC/DC power supply can be connected to mains power via line cord 60025. Line cord 60025 can be changed to accommodate various wall outlet styles. Charger port 1158 can be separate from UC 130 (FIG. 12A), enabling charger port 1158 to be positioned in a location that is most assessable to each end user. End users have different levels of mobility and may need charger port 1158 to be positioned in a personally-accessible location. The connector that plugs into charger port 1158 can be made without a latch to enable accessibility for users with limited hand function. Charger port 1158 can include a universal serial bus (USB) port for charging external items, such as cellphones or tablets, with the power from the MD. Charger port 1158 can be configured with male pins that operably couple with female pins on the AC/DC power supply. In some configurations, it may not be possible to operate the MD when charger port 1158 in engaged, regardless of whether the AC/DC power supply is connected to mains power.

Referring now to FIGS. 12A and 12B, user controller (UC) 130 can include, but is not limited to including, a control device (for example, but not limited to, joystick 70007), mode selection controls, seat height and tilt/lean controls, a display panel, speed selection control, a power on and off switch, an audible alert and mute capability, and a horn button. In some configurations, using the horn button while driving is allowed. UC 130 can include a means to prevent unauthorized use of the MD. UC 130 can be mounted anywhere on the MD. In some configurations, UC 130 can be mounted on a left or right arm rest. The display panel of UC 130 can include a backlight. In some configurations, UC 130 can include joystick 70007 (FIG. 12A), upper housing 30151, lower housing 30152, toggle housing 30157, undercap 30158, and button platform 50020 (FIG. 12A) that can enable selection of options through, for example, button depression. Touch screens, toggle devices, joystick, thumbwheels, and other user input devices can be accommodated by UC 130.

Referring now to FIGS. 12C and 12D, second configuration UC 130-1 can include toggle platform 70036 (FIG. 12C) that can include, for example, but not limited to, toggle lever 70036-2 and toggle switch 70036-1 that can enable selection of options. In some configurations, toggle lever 70036-2 can enable 4-way toggling (up, down, left, and right), and toggle switch 70036-1 can enable 2-way toggling. Other option selection means can replace buttons and toggles, as needed to accommodate a particular disability. UC 130 (FIG. 12A) and second configuration UC 130-1 can include cable 60026 and cable connector 60026-1. Cable connector 60026-2 can operably couple with UC PCB 50004 (FIG. 14A) to provide data and power to each configuration of the UC. Connector 60026-1 can operably couple UC 130 (FIG. 12A) with the powerbase through cable 60016 (FIG. 10A) that mates to a circuit board.

Referring now to FIGS. 12E and 12F, third configuration UC 130-1A can include thumbwheel knob 30173. Thumbwheel knob 30173 can be assembled into a blind hole, thus eliminating the need for an environmental seal at the mounting point of the thumbwheel assembly, and can eliminate a potential place for water, dust, and/or other contaminants to enter the UC housing. Further, the thumbwheel mechanism can be cleaned and serviced, and parts can be replaced without accessing the rest of the UC housing. The angle of the shaft of thumbwheel knob 30173 can be measured by a non-contact, Hall-effect sensor. The Hall-effect sensor, being a non-contact sensor, can have an essentially infinite lifetime. In some configurations, the sensor could directly output a digital signal that could, for example, be communicated to UC main processor 24004-2 (FIG. 14C), for example, via 12C. In some configurations, the sensor can be dual redundant. The sensor can provide a voltage that corresponds to the rotational position of thumbwheel knob 30173. In some configurations, the signal can be processed by an analog-to-digital converter (ADC) that outputs a value in counts; for example, a 12-bit ADC provides an output value between 0-4095 counts.

Continuing to refer to FIGS. 12E and 12F, thumbwheel knob 30173 can be used to, for example, but not limited to, adjust a maximum speed of the MD. In some configurations, thumbwheel knob 30173 can make a complete revolution with no stops. By omitting stops, the mapping of the position, the change of position, the rotational velocity, and the function of thumbwheel knob 30173 can be interpreted in a variety of different ways, depending on the configuration of the system. In some configurations, the user can dial thumbwheel knob 30173 "up" to request a higher maximum speed, and "down" to request a lower maximum speed. Change in the position of thumbwheel knob 30173, and not the absolute position at any one given frame, can be correspondent to change in the requested maximum speed. Change in requested maximum speed can be used to configure characteristics of the MD. Continually dialing thumbwheel knob 30173 "up" or "down" after reaching the maximum or minimum values respectively can cause the speed value to discontinue changing. Further dialing in the same direction after reaching the maximum or minimum can be ignored. Dialing thumbwheel knob 30173 in the reverse direction while at the maximum or minimum can be detected and can cause the gain value to change immediately, i.e. no "unwind" of ignored movement of thumbwheel knob 30173 may be necessary. Because the current absolute position of thumbwheel knob 30173 at a given frame is not the sole determinant in the gain value, changes to the position of thumbwheel knob 30173 during times when the user is unable to adjust the incremental speed can be ignored without adversely effecting subsequent calculations. Examples of such times when the user may not be able to adjust the incremental speed include, but are not limited to, mode changes and power cycling.

Continuing to refer to FIGS. 12E and 12F, in some configurations, the MD can support multiple drive speed settings, for example, two drive settings. Drive speed settings can accommodate situations in which the MD might be placed, for example, but not limited to, indoors or outdoors. For example, drive setting one and drive setting two can include different maximum speed values that may limit how fast the user can go regardless of how the joystick is maneuvered. In some configurations, when drive setting one is selected, the default maximum speed, which can be modified, can be 3 mph. In some configurations, when drive setting two is selected, the default maximum speed, which can be modified, is 6 mph. In some configurations, there can be limits on the default maximum speed. Thumbwheel knob 30173 (FIG. 12E) can allow further adjustment of the speed limits for the drive settings of the MD within the minimum and maximum speed ranges for each respective drive setting. The new maximum speed can be used to qualify the full range of possible motion applied by the joystick. In some configurations, the MD can be configured to ignore joystick movement entirely. In some configurations, if drive setting two is selected, the incremental setting can fall just above the maximum speed for drive setting one up to the maximum speed for drive setting two.

Continuing to refer to FIGS. 12E and 12F, the sensitivity of thumbwheel knob 30173 can be configurable. Depending on the sensitivity adjustment, uniform rotation of thumbwheel knob 30173 can adjust the speed gains from a relatively small amount to a relatively large amount. For example, a user with finger strength, sensitivity, and dexterity sufficient to roll and/or twist thumbwheel knob 30173 in small increments can achieve fine control of thumbwheel knob 30173 and its underlying functionality. Conversely, a user with compromised dexterity might adjust thumbwheel knob 30173 by bumping it with a knuckle or the edge of the hand. Thus, in some configurations, a relatively higher sensitivity setting can enable varying the speed gain from minimum to maximum across, for example, 180° of travel. In some configurations, a relatively lower sensitivity setting, for example, more than one rotation of thumbwheel knob 30173, can be required to traverse the same gain range. In some configurations, the sensitivity factor can be controlled by maintaining a virtual thumbwheel position, such that, for example, zero counts is equivalent to the lowest possible requested max speed, such as 8%, and a maximum counts value is equivalent to the highest possible requested max speed, such as 100%. In some configurations, the max number of counts can be configurable. In such a configuration, the degree of sensitivity may be adjusted by scaling the maximum counts value in relation to the virtual thumbwheel position. In some configurations, the default maximum counts can correspond to the number of counts for one full rotation of thumbwheel knob 30173, 4096 counts, such that one full rotation of the wheel will set the requested maximum speed for the current drive setting from 0-100 %. In some configurations, the maximum counts value can be configurable such that larger values require more rotation of the wheel to set the requested maximum speed for the current drive setting from 0-100 %. In some configurations, thumbwheel knob 30173 can rotate between hard stops of less than a complete revolution. In some configurations, the change in wheel position can indicate a change in maximum speed.

Continuing to refer to FIGS. 12E and 12F, in some configurations, the gain value can revert to a default value after a power cycle. In some configurations, the gain value can be determined by a setting saved during power down, even if thumbwheel knob 30173 moves after power down. When the MD is powered on, the virtual wheel position for the current drive setting before the preceding power off can be recalled, and the new maximum speed, when thumbwheel knob 30173 is rotated, can be based on the recalled virtual thumbwheel position. The incremental setting for each drive setting can be stored, for example, in non-volatile memory so that if the incremental setting for drive setting one is set to 75%, and the incremental setting for drive setting two is 40%, when the user returns to drive setting one, the incremental setting will be 75%.

Referring now to FIG. 12G, third configuration upper housing 30151A can include, but is not limited to including, LCD display 70040, button keypad 70035, joystick 70007, antenna 50025, spacer 30181, joystick backer ring 30154, and display coverglass 30153. In some configurations, buttons 70035 can include undermounted snapdomes (not shown) that can enable the user to sense when buttons 70035 have been depressed. Antenna 50025 can be mounted within third configuration upper housing 30151A, and can enable, for example, wireless communications between third configuration UC 130-1A (FIG. 12F). Spacer 30181 can separate LCD display 70040 from other electronics within third configuration UC 130-1A (FIG. 12F). LCD display 70040 can be protected from environmental hazards by display coverglass 30153. Joystick 70007 can include connector 70007-1 (FIG. 12H) that can provide power to joystick 70007, and can enable signal transmission from joystick 70007. In some configurations, the direction of movement of joystick 70007 can be measured by more than one independent means to enable redundancy.

Referring now to FIGS. 121-12K, UC 130 can include circuit board 50004 that can be housed and protected by upper housing 30151 and lower housing 30152. UC 130 can include display coverglass 30153 that can provide visual access to screens that can present options to the user. A display can be connected to UC PCB 50004 by flexible connector 50004-2 (FIG. 14A). Optional EMC shield 50004-3 can guard against incoming and/or outgoing emissions of electromagnetic interference to/from UC PCB 50004. Button assembly 50020-A and toggle switches 70036 can be optionally included. Buttons and/or toggles can be mounted on toggle housing 30157 which can be operably connected with lower housing 30152 and upper housing 30151 through undercap 30158. UC 130 can be mounted onto the MD in a variety of ways and locations through mounting cleat 30106. Throughout UC 130 are environment isolation features such as, for example, but not limited to, o-rings such as toggle housing ring 130A, grommets such as cable grommet 40028 (FIG. 12K), and adhesives to isolate the components such as, for example, circuit board 50004, from water, dirt, and other possible contaminants. In some configurations, joystick 70007 and speaker 60023 can be a commercially-available items. Joystick 70007, such as, for example, but not limited to, APEM HF series, can include a boot that can be accommodated by, for example, the pressure mount of boot mount cavity 30151-3 and joystick backer ring 30154.

Referring now to FIG. 12L, upper housing 30151 can include ribs 30151-5 that can support circuit board 50004. Upper housing 30151 can include mounting spacers 30151-4, space for secure mounting of joystick 70007 (FIG. 12A). Upper housing 30151 can include, but is not limited to including, display cavity 30151-2 that can provide a location for visual access means for display screens of UC 130. Upper housing 30151 can also include button cavities, for example, but not limited to, power button cavity 30151-6 and menu button cavity 30151-7. Upper housing 30151 can include formed perimeter 30151-1 that can provide a consistent look and feel with other aspects of the MD. Upper housing 30151 can be constructed of, for example, but not limited to, polycarbonate, a polycarbonate Acrylonitrile Butadiene Styrene blend, or other materials that can meet strength and weight requirements associated with the UC. Joystick 70007 (FIG. 12A) can be installed in boot mount cavity 30151-3 using, for example, gaskets, backer ring 30154 (FIG. 12Q), fastening means such as, for example, but not limited to, screws and fastener holes 30151-X, that can be used to attach joystick 70007 and backer ring 30154 (FIG. 12Q) to upper housing 30151. Installing the joystick boot can isolate UC PCB 50004 (FIG. 14A) and other sensitive components from the environment. Upper housing 30151 can include molding references 30151-X2 that can enable orientation of joystick 70007 during assembly. In some configurations, cable reference 30151-X2 can indicate where joystick cable connector 70007-1 (FIG. 12H) can be positioned.

Referring now to FIG. 12M, lower housing 30152 can join upper housing 30151 (FIG. 12L) at perimeter geometry 30152-2. The combination of lower housing 30152 and upper housing 30151 (FIG. 12L) can house UC PCB 50004 (FIG. 14A), speaker 60023 (FIG. 12K), display coverglass 30153 (FIG. 12P), and joystick backer ring 30154 (FIG. 12Q), among other parts. Environmental isolation features at the joint can include, for example, but are not limited to, gaskets, o-rings, and adhesives. Lower housing 30152 can include audio access holes 30152-1 that can be located adjacent to speaker mount location 30152-6. A commercially-available speaker can be mounted in speaker mount location 30152-6 and can be securely attached to lower housing 30152 using an attachment means such as, for example, but not limited to, an adhesive, screws, and hook-and-eye fasteners. Lower housing 30152 can include at least one post 30152-7 upon which can rest UC PCB 50004 (FIG. 121). Lower housing 30152 can include connector reliefs 30152-3 that can provide space within lower housing 30152 to accommodate, for example, but not limited to, joystick connector 50004-8 (FIG. 14A) and power and communications connector 50004-7 (FIG. 14A). Lower housing 30152 can be attached to the MD through fastening means such as, for example, screws, bolts, hook-and-eye fasteners, and adhesives. When screws are used, lower housing 30152 can include fastener receptors 30152-5 that can receive fasteners that can attach toggle housing 30157 (FIG. 12R) to lower housing 30152. Lower housing 30152 can also include pass-through guides 30152-4 that can position fasteners, for example, but not limited to, sealing fasteners, that can securely connect lower housing 30152 with undercap 30158 (FIG. 12K). Sealing fasteners can provide environmental isolation. In some configurations, lower housing 30152 can be constructed of, for example, but not limited to, die cast aluminum that can provide strength to the structure.

Referring now to FIG. 12N, third configuration lower housing 30152A can include thumbwheel geometry 30152-A1 that can accommodate thumbwheel 30173. Lower housing 30152 can optionally include ribbing (not shown) molded into inner back 30152-9. The ribbing can increase the strength and resistance to damage of UC 130, and can also provide resting positions for UC PCB 50004 (FIG. 121). Lower housing 30152A can also provide raised posts 30173-XYZ that can provide chassis ground contact points for UC PCB 50004, which can be grounded to the powerbase. Chassis ground contact 30173-2 for cable shield 60031 (FIG. 12V) can tie the metal from lower housing 30152A to the metal of the powerbase.

Referring now to FIG. 12O, third configuration lower housing 30152A can include thumbwheel enabling hardware such as, for example, but not limited to, a position sensor that can include a magnetic rotary position sensor such as, for example, the AMS AS5600 position sensor, that can sense the direction of the magnetic field created by magnet 40064 that rotates when thumbwheel knob 30173 rotates. The magnetic sensor can be mounted upon a flex circuit assembly that can provide power to and receive information from the magnetic sensor. In some configurations, to enable resistance to mechanical shock and vibration, the space around the thumbwheel position sensor chip can be filled. In some configurations, enabling hardware, including, but not limited to, bushing 40023, magnet 40064, magnet shaft 30171, o-ring 40027, retaining nut 30172, and screw 40003, can operably couple thumbwheel knob 30173 with second configuration lower housing 30152A, and can enable the movement of magnet 40064 to be reliably sensed by the magnetic sensor. Lower housing 30152A can include a cylindrical pocket in a wall of lower housing 30152A where bushing 40023 is positioned. Bushing 40023 can provide radial and axial bearing surfaces for shaft 30171. Shaft 30171 can include a flange onto which o-ring 40027 is placed. Shaft 30171 is captured by retaining, threaded, nut 30172 that includes a thru-hole sized to fit shaft 30171, and smaller than flange/o-ring 40027. When assembled, o-ring 40027 is compressed which can eliminate axial play, and can create viscous drag when shaft 30171 is turned. Thumbwheel knob 30173 is assembled to shaft 30171 with a fastening means such as, for example, but not limited to, a low-head fastener, a simple friction fit, and/or knurling. Shaft 30171 can include magnet 40064. The magnetization direction creates a vector normal to the axis of shaft 30171 which can be measured by a Hall-effect sensor. A measurement of the magnetization vector can be provided by the sensor to UC 130 (FIG. 12A). UC 130 (FIG. 12A) can compute, based on the magnetization vector direction, a relative change in maximum speed. In some configurations, at least some parts of the enabling hardware, for example, but not limited to, o-ring 40027, can be lubricated with, for example, but not limited to, silicone grease, to provide a smooth user experience. In some configurations, detents can be added to the thumbwheel assembly to provide clicks as thumbwheel knob 30173 is manipulated. Screw 40003 can pass through thumbwheel 30173 and can operably couple with magnet shaft 30171. The geometries of the enabling hardware can interlock to retain thumbwheel 30173 in second configuration lower housing 30152A, and can provide environmental isolation to the interior of UC 130 because there is no need in the shown configuration for a shaft to pierce second configuration lower housing 30152A. The geometry of the thumbwheel assembly enables in-field service and/or replacement without separating upper housing 30151 (FIG. 12E) from lower housing 30152A. In particular, thumbwheel knob 30173 can be replaced if damaged by impacts, or worn out from use. In some configurations, thumbwheel knob 30173 can be operably coupled with shaft 30171 by click-on or press-in fastening means.

Referring now to FIG. 12P, display coverglass 30153 can include clear aperture 30153-1 that can expose menu and options displays for the user. The dimensions of clear aperture 30153-1 can be, for example, but not limited to, different from the display active area. Display coverglass 30153 can include frame 30153-4 that can be masked black with a pressure sensitive adhesive layer. In some configurations, display coverglass 30153 can be masked with black paint, and double-sticky tape can be applied on top of the black masking. Clear, unmasked area 30153-3 can admit ambient light. UC 130 can vary the brightness of the display based on the ambient light. Display coverglass 30153 can include button cavities 30153-5 and 30153-6 that can provide locations for button keypad 70035. Display coverglass 30153 can include outward face 30153-2 that can, in some configurations, include coatings that can, for example, reduce glaring reflections and/or improve scratch resistance. In some configurations, a space can exist between the material of coverglass 30153 and frame 30153-4. The space can include decorative elements such as, for example, but not limited to, product logos, and can be indelibly printed and/or etched.

Referring now to FIG. 12Q, joystick backer ring 30154 can include, but is not limited to including, receptor 30154-3 to house a joystick boot and body, and holes/slots 30154-2 to fasten backer ring 30154 to upper housing 30151 (FIG. 12L). Holes/slots 30154-2 can be sized to accommodate multiple sizes of joysticks 70007 (FIG. 12A). Holes 30154-1, for example, can accommodate connections among each component of UC 130 (FIG. 12A). In some configurations, backer ring 30154 can include a pattern of notches 30154-X2 oriented circumferentially with respect to holes 30154-1 and slots 30154-2. Notches 30154-X2 can interface with ribs 30151-4 (FIG. 12M) in upper housing 30151 (FIG. 12M), and can ensure the correct rotational position of the hole and slot patterns in backer ring 30154 during assembly of UC 130 (FIG. 12A).

Referring now to FIG. 12R, toggle housing 30157 can include pocket 30157-2 that can house a toggle module, for example, but not limited to, button platform 50020-A (FIG. 12BB). Toggle housing 30157 can include connector cavity 30157-3 to accommodate a flexible cable emanating from the toggle device. Toggle housing 30157 can include through holes 30157-4 to accommodate fastening means that can connect components of UC 130 (FIG. 12A) together. Toggle housing 30157 can include lower housing connector cavities 30157-5 that can provide opening for fastening means to engage. Toggle housing 30157 can include sealing geometry 30157-6 that can enable mating/sealing between toggle housing 30157 can include and undercap 30158, that can be secured by undercap fastening means cavity 30157-8. Toggle housing 30157 can include toggle module fastener cavities 30157-7 to enable attachment of the toggle module to toggle housing 30157. Toggle housing 30157 can include forked guide 30157-1 to provide a guide for power/communications cable 60031 (FIG. 12X). O-ring 130B can enable sealing and environmental isolation between toggle housing 30157 and lower housing 30152A (FIG. 12N).

Referring now to FIGS. 12S and 12T, toggle housing second configuration 30157B can enable mounting of toggle platform 70036 (FIG. 12T). Toggle housing second configuration 30157B can include toggle lever support geometry 30157A-1 (FIG. 12S) and toggle switch support geometry 3015 7N (FIG. 12S) that can provide supporting structure for toggle lever 70036-2 (FIG. 12T) and toggle switch 70036-1 (FIG. 12T), respectively. Toggle housing second configuration 30157A can include connector cavity 30157A-3 to accommodate connections between toggle platform 70036 (FIG. 12T) and electronic components of UC 130 (FIG. 12A). Toggle housing 30157B can include pocket 30157-2 that can house a toggle module, for example, but not limited to, button platform 50020-A (FIG. 12BB). Toggle housing 30157B can include connector cavity 30157A-3 to accommodate a flexible cable emanating from the toggle device. Toggle housing 30157B can include through holes 30157A-4 to accommodate fastening means that can connect components of UC 130 (FIG. 12A) together. Toggle housing 30157B can include lower housing connector cavities 30157A-5 that can provide openings for fastening means to engage. Toggle housing 30157B can include sealing geometry 30157A-6 that can enable mating/sealing between toggle housing 30157B and undercap 30158 (FIG. 12U), that can be secured by undercap fastening means cavity 30157A-8. Toggle housing 30157B can include toggle module fastener cavities 30157A-7 to enable attachment of the toggle module to toggle housing 30157B. Toggle housing 30157B can include forked guide 30157A-1 to provide a guide for power/communications cable 60031 (FIG. 12X). An o-ring (not shown) can enable sealing and environmental isolation between toggle housing 30157B and lowering housing 30152A (FIG. 12N). Toggle lever 70036-2 (FIG. 12T) and toggle switch 70036-1 (FIG. 12T) can be positioned and sized to accommodate users having various hand geometries. In particular, toggle lever 70036-2 (FIG. 12T) can be spaced from toggle switch 70036-1 (FIG. 12T) by about 25-50 mm. Toggle lever 70036-2 (FIG. 12T) can have rounded edges, its top can be slightly convex and substantially horizontal, and it can measure 10-14 mm across its top, and can be about 19-23 mm in height. Toggle switch 70036-1 (FIG. 12T) can be about 26-30 mm long, 10-14 mm wide, and 13-17 mm high. Toggle lever 70036-2 (FIG. 12T) and toggle switch 70036-1 (FIG. 12T) can be positioned at an angle of between 15° and 45° with respect to joystick 70007 (FIG. 12K).

Referring now to FIG. 12U, undercap 30158 can include through fastening holes 30158-1 that can accommodate fastening means to operably couple the components of UC 130 (FIG. 12A). Undercap 30158 can include grommet cavity 30158-2 that can house grommet 40028 that can environmentally seal the cable entry point. Undercap 30158 can include mounting cleat face 30158-5 that can provide connection points for mounting cleat 30106 (FIG. 12Z). Undercap 30158 can include fastening accommodation 30158-4 that can enable fastening of undercap 30158 to toggle housing 30157. Undercap 30158 can include relief cuts 30158-3 for toggle module fasteners. Undercap 30158 can accommodate gasket 130A that can environmentally seal undercap 30158 to toggle housing 30157.

Referring now to FIGS. 12V-12X, second configuration undercap 30158-1 can include, but is not limited to including, EMI suppression ferrite 70041, and ferrite retainer 30174. Ferrite retainer 30174 can operably couple with second configuration undercap 30158-1 through mounting features 30158-3 (FIG. 12X) and posts 30158-2 (FIG. 12X). Retainer 30174 can be affixed to undercap 30158 by heat-staking posts 30158-2 (FIG. 12X). In some configurations, ferrite retainer 30174 can be affixed to undercap 30158 by means of threaded fasteners, adhesives, and/or snap features. In some configurations, when cable 60031 is threaded through ferrite retainer 30174, EMI suppression ferrite 70041 can protect UC 130 from EMI emissions emanating from cable 60031, which can house power and CANbus connections for UC 130. Shield 60031-4 can emerge from cable 60031 and can connect to a feature of housing 30152 at connector 60031-3. Metal barrel 60031-1 can enable the shield to continue to the powerbase.

Referring now to FIG. 12Y. UC mounting device 16074 can enable UC 130 (FIG. 12A) to be mounted securely to the MD by means of any device that can accommodate stem 16160A, stem split mate 16164, and a conventional seat mounted upon the MD through operable coupling with seat brackets 24001 (FIG. 1A). Tightening orifice 162-672 can provide a means to secure mounting device 16074 to the MD. Mounting device 16074 can include ribs 16177 that can be raised away from mounting body 16160 to accommodate UC mounting feature 30158 (FIG. 12B). UC 130 (FIG. 12A) can operably couple with mounting device 16074 by sliding mounting cleat 30106 (FIG. 12Z) between ribs 16177 and mounting body 16160. Release lever 16161 can operate in conjunction with spring-loaded release knob 16162 to enable secure fastening and easy release of UC 130 to/from mounting device 16074.

Referring now to FIG. 1200, standard connections can be used to connect a UC to the wheelchair. In some configurations, commercially-available armrests and user controller connections can provide the interface between the UC and the mobility device. The design of the UC of the present teachings can comply with accepted commercial standards in order to allow flexible use of various mobility device features. A UC that includes property-positioned threaded mounting holes, and an option for toggles, can be mounted atop a mobility device armrest with an associated armrest bracket. The joystick and the optional toggles can be cabled separately or as one. The UC mount can be, for example, but not limited to, articulated, fixed, or swingaway. In some configurations, the orientation of the joystick can be maintained by use of an articulated mount. In some configurations, the fixed mount can be adjustable with tools. In some configurations, the armrest can be pivoted out of the way to move the UC. A UC mount can be selected based at least on ease of installation and removal of the UC from the mount, cost, ease of orientation adjustment of the UC, interchangeability between toggled and toggle-less varieties, inherent strength, ease of use, and toggle mounting and cabling.

Continuing to refer to FIG. 1200, characteristics of the UC mounting mechanisms of the present teachings can include, but are not limited to including, tool-less attachment of the UC, one-handed operation, and ambidextrous structure of the UC. In some configurations, the mechanical connection between the UC and the mounting mechanism can be distinct from the electrical connection. In some configurations, the mechanical and electrical connections can be one and the same.

Continuing to refer to FIG. 12 Y-1, UC 130-2 of the present teachings can include cleat 130-2D that can engage with receiver bracket 130-2A at cleat overhang 130-2G. Receiver bracket 130-2A can provide an interface to a mounting platform such as, for example, but not limited to, an armrest or a platform adjunct such as, for example, but not limited to, a telescoping tube, and cable run. Receiver bracket 130-2A can provide at least one termination point 130-2C for power and communications cabling to the powerbase, where termination point 130-2C can operably couple with UC contacts 130-2B. Receiver bracket 130-2A can include release lever 130-2G and latch 130-2E that can operably couple with latch recess 130-2F. Receiver bracket 130-2A can be advantageously located for the convenience of the user of the MD.

Referring now to FIG. 12 PP, UC 130-3 can include receiver bracket 130-3A that can provide power charging interface mechanism 130-3B for the powered components of the MD, charge cable presence detection 130-3C, and can include charge power protection 130-3D, for example, but not limited to, fusing.

Referring now to FIGS. 12OO and 12 PP, when UC 130-2/3 is not installed, receiver bracket 130-2A13A can include accessible contacts 130-2C (FIG. 12OO), and receiver bracket 130-2A/3A can include a mechanism (not shown) for enabling/disabling power to the contacts. The mechanism can include, but is not limited to including, (a) a mechanical switch (not shown) that can be depressed when UC 130-2/3 is installed, (b) a non-contact switch (not shown) such as, for example, but not limited to, an optical sensor or digital Hall effect sensor that can detect the presence of a UC 130-2/3 in receiver bracket 130-2A/3A, (c) a magnetic reed switch (not shown) that can be activated by the presence of a magnet in UC 130-2/3, (d) communications capability (not shown) in receiver bracket 130-2A/3A that can manage enabling/disabling power to the contacts when appropriate communications messages have been exchanged between UC 130-2/3 and receiver bracket 130-2A/3A, and/or (e) an additional electrical contact (not shown) that can provide a circuit closure indication that UC 130-2/3 is present in receiver bracket 130-2A/3A. UC 130-2/3 and receiver bracket 130-2A/3A can include environmental sealing and electrostatic protection.

Referring now to FIG. 12Z, mounting cleat 30106 can enable mounting of UC 130 (FIG. 12A) onto the MD, for example, on an armrest, for example, by mounting device 16074 (FIG. 12Y). Mounting cleat 30106 can include engagement lip 30106-3 that can include a geometry that can enable sliding and locking engagement of mounting cleat 30106 with a receiver, for example, by depressing a latch button until UC 130 (FIG. 12A) is correctly positioned. At that position, the latch button could protrude into button cavity 30106-1, thereby locking UC 130 (FIG. 12A) into place. Edges 30106-4 of mounting cleat 30106 can fit within the receiver. Mounting cleat 30106 can include fastening cavities for fastening mounting cleat 30106 to mounting cleat face 30158-5 (FIG. 14A).

Referring now to FIG. 12AA, grommet 40028-1 can provide an environmental seal surrounding cable 60031 (FIG. 12X). Grommet 40028-1 can rest in grommet cavity 30158-2 (FIG. 12U), neck 40028-1B being captured by the geometry of grommet cavity 30158-2 (FIG. 12U). Cable 60031 (FIG. 12X) can traverse grommet 40028-1 from cable entry 40028-1A to cable exit 40028-1C. In some configurations, cable grommet 40028-1 can provide strain relief to cable 60031 (FIG. 12X). The strain relief can prevent damage if cable 60026 is bent or pulled. In some configurations, cable grommet 40028-1 can be an overmolded feature integral to cable 60031 (FIG. 12X).

Referring now to FIGS. 12BB and 12CC, button assembly 50020-A can enable button option entry at UC 130 (FIG. 12A). Button assembly 50020-A can include buttons 50020-A1, for example, but not limited to, momentary push buttons that can be mounted on button circuit board 50020-A9. Buttons 50020-A1 can operably couple with button circuit board 50020-A9 that can include cable connector 50020-A2 that can accommodate, for example, but not limited to, a flexible cable. Button assembly 50020-A can include spacer plate 50020-S(FIG. 12CC) that can provide cavities 50020-S1 (FIG. 12CC) for buttons 50020-A1. A coverlay (not shown) providing graphics and environmental sealing can cover buttons 50020-A1.

Referring now to FIGS. 12DD and 12EE, toggle platform 70036 can include toggle lever 70036-2 (FIG. 12T) and toggle switch 70036-1 (FIG. 12T), and toggle mount means 70036-3 to mount toggle platform 70036 onto toggle housing second configuration 30157A. Toggle mount means 70036-3 can be adjacent to toggle lever support geometry 30157A-2 (FIG. 12U). In some configurations, a low-profile toggle module 70036A (FIG. 12GG) including D-pad 70036A-2 (FIG. 12EE) in place of toggle lever 70036-2 (FIG. 12DD) and rocker switch 70036A-1 (FIG. 12EE) in place of toggle switch 70036-1 (FIG. 12DD) can be included. In some configurations, toggle lever 70036-2 (FIG. 12DD) can be replaced by two 2-way toggles (not shown), which could be similar to the controls for powered seating tilt and recline. The resulting module can include three 2-way toggles.

Referring now to FIGS. 12FF and 12QQ through 12SS, UC 22004 can include the features of UC 130-1A (FIG. 12E), but can include toggle cable 60031-B for toggles 70036, making toggles 70036 optional, and UC cable 60031-A for UC 22004. Toggle cap 22152-A can include fastener recesses 22152-B that can enable mounting plate cuts 22158-C in toggles mount bracket 22158-A to accommodate the fore/aft position of UC 22004 with respect to toggles 70036 to be modified, tooled or toollessly. Toggle mounting bracket 22158-A can couple toggles 70036 with UC 22004 by interface tab 22158-G (FIG. 12QQ). Commercially-available mounting bracket 22158-B can accommodate the mounting of both UC 22004 and toggles 70036 if present, through UC mounting recess 22158-D and toggles mounting recess 22158-F, respectively. Commercially-available mounting bracket 22158-B can accommodate attachment to an armrest (not shown) or any other part of the MD through mounting recesses 22158-E.

Referring now to FIG. 12SS, in some configurations, UC 22004 can include electrical/data coupling 60031-E between toggles 70036 and the joystick/display portion of UC 22004. Toggle interface 30158-A can receive/transmit data through electrical/data coupling 60031-E and provide the data for processing to toggles 70036. The joystick/display portion of UC 22004 can receive/transmit data through electrical/data coupling 60031-E and provide the data for processing to the joystick/display portion of the UC. In some configurations, toggles 70036 can receive/transmit data and be powered through cable 60031-B, while the joystick/display portion of UC 22004 can receive/transmit data and be powered through cable 60031-A. Junction box 60031-C can combine the signal from cables 60031-A and 60031-B to provide them to cable 60031-D.

Referring now to FIGS. 12GG and 12TT, in some configurations, toggles 70036 can be manufactured with integral UC connection 22157. Integral UC connection 22157 can include bracket mounting recesses 22157-A and can accommodate data/power cable 60031. In some configurations, UC 22004-1 can be toollessly connected to armrest mounting bracket 22158-A by, for example, wingnuts 22158-H, and can be toollessly connected to an armrest by, for example, but not limited to thumb screw 22158-1 and knob screw 22158-J.

Referring now to FIGS. 12HH, 12UU, and 12VV UC cap 482 can integrally or removably couple with cap back clamp 491. Cap back clamp 491 can trap toggles mount bracket 488, holding toggles 70036 in place with respect to UC 22004, and can provide cable recess 491B. Cable 60031-A can travel through cable recesses 491-C and 491-B before exiting from UC 22004. Cap back clamp 491 can be situated in mounting ring back clamp recess 491-A, and can be tightened into place by mounting clamp 490. Mounting clamp 490 can be tightened by compressing mount handle back clamp 492, which can provide a stable compression based on side posts 493. Uncompressed mount handle back clamp 492 can result in exemplary gap 495 (FIG. 12VV), and compressed mount handle back clamp 492 can result in exemplary gap 494 (FIG. 12VV).

Referring now to FIGS. 12II, 12WW, and 12XX, UC 22004-1 can be toollessly screw-mounted onto mounting bracket 653 through cap stud 655. Cap stud 655 can be integrated with UC connection 22157, or can be fastened to UC connection 22157. Clocking plate 654 can be positioned between cap stud 655 and mounting bracket 653. Cap stud 655 can include external threads 655-A (FIG. 12WW), and can pass through cavities 654-A (FIG. 12WW), 653-C (FIG. 12WW), and 656-A (FIG. 12WW) when cap stud threads 655-A (FIG. 12WW) are coupled with threaded nut threads 656-B (FIG. 12WW), tightening threaded nut 656 (FIG. 12WW) with cap stud 655. Fasteners 657 can be loosely screwed into threaded recesses 654-B, through adjustment channels 653-A (FIG. 12WW). UC 22004-1 can be rotated as loosened fasteners 657 (FIG. 12WW) move freely in channels 653-A (FIG. 12WW) until a desired orientation is achieved. Then fasteners 657 (FIG. 12WW) can be tightened. Tab 653-B can be used to connect UC 22004-1 to an armrest.

Referring now to FIGS. 12JJ and 12YY, UC connection 22157 can provide an interface between UC 22004-1 and clamp post 824, which can be removably or fixed mounted to UC connection 22157. Clamp-on shaft collar 819 can be attached to mounting bracket 815 using recesses 815-B and tooled or toolless fasteners. To achieve mounting of UC 22004-1, clamp post 824 can be inserted into cavities 819-E and 815-A, and clamp-on shaft collar can be tightened at tightening points 819-A (FIG. 12YY) and 819-B (FIG. 12YY) after UC 22004-1 is rotated to a desired orientation.

Referring now to FIGS. 12KK and 12ZZ through 12EEE, cap latch 849 can provide an interface between UC 22004-1 and UC mount ring latch 840. Cap latch 849 can include bayonet 849-B that can enter recess 840-F. As cap latch 849 is twisted, bayonet 849-B can depress retractable spring 843 until retractable spring 843 becomes entrapped in recess 849-A, while simultaneously experiencing resistance from bumper 1011. Bumper 1011 can rest in bumper holder 1010, and bumper holder 1010 can be held in place by protrusion 1010-A (FIG. 12BBB) which can rest in cavity 840-G (FIG. 12BBB). Retractable spring 843 can be released from recess 849-A by engaging handle 843-A (FIG. 12AAA) and pulling handle 843-A (FIG. 12AAA) away from spring stop 840-A.

Spring stop 840-A can include recess 840-D (FIG. 12ZZ) into which retractable spring 843 can be positioned. Pulling handle 843-A (FIG. 12AAA) away from spring stop 840-A can result in compressing spring 843 while removing entrapped rod 843-C from recess 849-A, allowing bayonet 849-B to move. Threads 843-B can enable spring plunger 843 to be engaged in recess 840-D. In some configurations, spring stop 840-A can be replaced by flange 829-A (FIG. 12CCC) that can include a recess that can accommodate retractable spring 843. UC mount ring latch 840 can include ribs 840-B that can increase the strength of UC mount ring latch 840, which can be used to attach UC 22004-1 to an armrest.

Referring now to FIGS. 12LL and 12FFF through 12JJJ. UC 22004-1 (FIG. 12 LL) can operably couple with cap latch 1018 (FIG. 12LL) to secure UC 22004-1 (FIG. 12LL) to the mounting mechanism of the present teachings that can interface with an armrest. Fasteners 1018-B (FIG. 12LL) can loosely engage with UC 22004-1 (FIG. 12LL) through cap latch cavities 1018-A (FIG. 12LL), UC 22004-1 (FIG. 12LL) can be rotated to a desired orientation, and fasteners 1018-B (FIG. 12LL) can be tightened. Mount plate latch 1019 (FIG. 12GGG) can operably couple with cap latch 1018 (FIG. 12LL). Mount plate latch 1019 (FIG. 12GGG) can include a geometry that can complement the geometry of UC top plate 1013 (FIG. 12FFF) so that mount plate latch 1019 (FIG. 12GGG) can fit into top plate cavity 1013-A (FIG. 12HHH). Mount plate latch 1019 (FIG. 12GGG), coupled with UC 22004-1 through cap latch 1018 (FIG. 12LL), can be inserted into top plate cavity 1013-A (FIG. 12 HHH) and rotated to secure. As mount plate latch 1019 is rotated, wings 1019-A (FIG. 12GGG) can encounter ramp features 1016-A (FIG. 12GGG) and buttons 1016-B (FIG. 12GGG) with which recesses 1019-B (FIG. 12GGG) can align and surround. Pressure to maintain the position of UC 22004-1 (FIG. 12LL) can be achieved by compression spring 1015 (FIG. 12FFF), or any other type of spring, pressing upon the base of 1016. Ramp shoes 1016-C (FIG. 12FFF) can couple with base recesses 1014-A (FIG. 12FFF) to maintain alignment of 1016 and 1014. To release this pressure to allow UC 22004-1 (FIG. 12LL) to be removed, handle 1017 (FIG. 12JJJ), operably coupled with base 1014 (FIG. 12LL), can be pulled away from base 1014 (FIG. 12LL), drawing the buttons 1016-B away from the recesses 1019-B, thus releasing the connection between button 1016-B (FIG. 12GGG) and recess 1019-B (FIG. 12GGG) and allowing mount plate latch 1019 (FIG. 12JJJ) to rotate and release UC 22004-1 (FIG. 12LL).

Referring now to FIGS. 12MM and 12KKK through 12MMM, UC 22004-1 (FIG. 12MM) can operably couple, either fixedly or removably, with undercap 1191 (FIG. 12KKK) at toggle interface 22157 (FIG. 12MM). Cleat 1349 (FIG. 12KKK) can operably couple with undercap 1191 (FIG. 12KKK) by fasteners mounted in channels 1349-B (FIG. 12KKK) and recesses 1191-A (FIG. 12KKK). Before fasteners are tightened, channels 1349-B (FIG. 12 LLL) can enable orientation adjustment of UC 22004-1 (FIG. 12MM). Separately, top plate 1189 (FIG. 12MMM) and lock plate 1353 (FIG. 12MMM) can be coupled by fasteners in aligned recesses 1353-B (FIG. 12MMM) and 1189-A (FIG. 12MMM). The combination of UC 22004-1 (FIG. 12MM), undercap 1191 (FIG. 12KKK), and cleat 1349 (FIG. 12KKK) can be aligned and inserted into top plate cavity 1189-A (FIG. 12KKK) and then rotated to align button 1349-A (FIG. 12MMM) with recess 1353-A (FIG. 12MMM). During rotation, button 1349-A (FIG. 12MMM) can travel towards recess 1353-A (FIG. 12MMM) by riding over ramps 1353-C (FIG. 12MMM). When button 1349-A (FIG. 12MMM) aligns with recess 1353-A (FIG. 12MMM), button 1349-A (FIG. 12MMM) can engage with recess 1353-A (FIG. 12MMM). Pressure to maintain position is achieved by lock plate 1353 applying pressure to button 1349-A (FIG. 12LLL). This securely attaches UC 22004-1 (FIG. 12MM) to top plate 1189 (FIG. 12MMM), and top plate 1189 can be used to mount UC 22004-1 (FIG. 12MM) on an armrest. To disengage UC 22004-1 (FIG. 12MM) from the connection to top plate 1189 (FIG. 12MMM), lock plate 1353 (FIG. 12MMM) can be depressed at lock plate end 1353-D (FIG. 12MMM), button 1349-A (FIG. 12MMM) can become free of recess 1353-A (FIG. 12MMM), and UC 22004-1 (FIG. 12MM) can be rotated to release cleat 1349 (FIG. 12KKK) from top plate 1189 (FIG. 12KKK).

Referring now to FIGS. 12NN, and 12NNN through 12QQQ, UC 22008 (FIG. 12NNN) can include a toggleless controller, and UC 22009 (FIG. 12NN) can include toggle module 22057 (FIG. 12NN), that can be included with UC core 22007-1, or can be replaced by cap 30256 (FIG. 12NNN), making toggle module 22057 (FIG. 12NN) a field-replaceable unit. Cap 30256 (FIG. 12NNN) or toggle module 22057 (FIG. 12NN) or other modules can be attached and removed, making it possible to replace toggle module 22057 (FIG. 12NN) when it is worn out and/or damaged. Toggle module 22057 (FIG. 12NN) can include an inline electrical connection interface where toggle module 22057 (FIG. 12NN) mates with UC core 22007-1. One side of inline electrical connection 50039-1 (FIG. 12000) can include flex cable 50039 (FIG. 12000), which can be mounted in lower housing 30252 (FIG. 12000) and can be connected to UC board 50004 (FIG. 12PPP) during assembly. The other side of electrical connection 50039-1 (FIG. 12000) can include a commercially-available male pin header integrated into toggles flex tail 70048-1 (FIG. 12QQQ). In some configurations. UC core 22007-1 (FIG. 12NN) can be provided as an assembled item, and can be tested as a complete unit.

Referring now to FIG. 12RRR, cable 60037 can incorporate right angle overmold 60036 where cable 60037 passes through lower housing 30252. Overmold 60036 can provide strain relief, retention in the housing, and can form an environmental seal. Overmold 60036 can incorporate flange 60036-1 that can protect cable 60037 from being pulled through. UC 20008/20009 (FIGS. 12NN/12NNN) can include ferrite 70041 to reduce EMI within UC 20008/20009 (FIGS. 12NN/12NNN). Lower housing 30252 can include grounding location 30252-12. The cable shield can extend to ring terminal 70042 which can be surrounded by star washers 40015 and connected to grounding location 30252-12?

Referring now to FIGS. 12SSS and 12TTT, upper housing 30251 (FIG. 12SSS) can include bend-resistant wall 30251-1 (FIG. 12SSS), including a wall extension that can extend behind the thumbwheel mechanism and sensor. UC 20008/20009 (FIGS. 12NN/12NNN) can include molded gasket 30261 (FIG. 12TTT) made of, for example, but not limited to, silicone. Molded gasket 30261 (FIG. 12TTT) can fit into groove 30251-3 (FIG. 12SSS) in upper housing 30251 (FIG. 12SSS). The geometry of the joint between upper housing 30251 (FIG. 12SSS) and lower housing 30252 (FIG. 12TTT) can present convoluted path 22008-1 (Section A-A. FIG. 12TTT-1) that can shield gasket 30261 (FIG. 12TTT) from environmental hazards such as, for example, but not limited to, water spray. Lower housing 30252 (FIG. 12TTT) can include fastening means and compression stops 30252-1 (FIG. 12000) that can enable overtightening protection between upper housing 30251

(FIG. 12SSS) and lower housing 30252 (FIG. 12TTT). Speaker wires 70032-1 (FIG. 12TTT) can interface with pogo target strip 50036-2. For example, speaker wires 70032-1 (FIG. 12TTT) can be soldered to pogo target strip 50036-2. Speaker wires 70032-1 (FIG. 12TTT) can be secured in place in lower housing 30252 (FIG. 12TTT) using, for example, polyimide tape or liquid adhesives. Right angle bracket 30192 (FIG. 12TTT) can engage locating features on lower housing 30252 (FIG. 12TTT) to position and secure flex circuit 50036 (FIG. 12TTT). In some configurations, speaker 70032 (FIG. 12TTT) can be rated for a 2 W output, and lower housing 30252 (FIG. 12TTT) can include, for example, but not limited to, hole pattern 30252-11 (FIG. 12RRR) for speaker 70032 (FIG. 12TTT) that can enable user-friendly speaker output.

Referring now to FIG. 12VVV, UC board 50004 can include pogo pins 50004-A (FIG. 12PPP) that can enable speaker and thumbwheel signal transfer between UC board 50004-1 (FIG. 12PPP) and flex circuit 50046 (FIG. 12TTT). Blind connections can be made as upper housing 30251 (FIG. 12SSS) and lower housing 30252 (FIG. 12TTT) are paired. Coupling with pogo pins 50004-A (FIG. 12PPP) are pogo targets 50036-1 (FIG. 12VV) that can be integral with thumbwheel flex circuit 50036 (FIG. 12TTT). UC 20008/20009 (FIGS. 12NN/12NNN) can include mounting holes 30252-10 (FIG. 12VVV) that can accommodate commonly-used mounting patterns, for example, but not limited to, R-net style.

Referring now to FIG. 12WWW, UC 20008/20009 (FIGS. 12NN/12NNN) can include integrated display 22053 that can include LCD 70040, masked coverglass 30253, antenna 50025, and electrical insulation means 40032 such as, for example, but not limited to, electrically insulating tape, such as, for example, but not limited to, KAPTON tape, to insulate UC board 50004 from the metal in liquid crystal display (LCD) 70040.

Referring now primarily to FIG. 13A, UC holder 133A can house manual and visual interfaces such as, for example, a joystick, a display, and associated electronics. In some configurations, UC assist holder 145A can be attached to visual/manual interface holder 145C toollessly. UC assist holder 145A can include electronics that can interface with processors 100 (FIG. 16B) and that can process data from sensors 122A (FIG. 8). 122B (FIG. 8), 122C (FIG. 8), 122D (FIG. 8), 122E (FIG. 8), and 122F (FIG. 8). Any of these sensors can include, but are not limited to including, an OPT8241 time-of-flight sensor from TEXAS INSTRUMENTS®, or any device that can provide a three-dimensional location of the data sensed by the sensors. UC assist holder 145A can be located anywhere on the MD and may not be limited to being mounted on visual/manual interface holder 145C.

Referring now primarily to FIG. 13B, manual/visual interface holder 145C can include, but is not limited to including, visual interface viewing window 137A and manual interface mounting cavity 133B available on first side 133E of manual/visual interface holder 145C. Connector 133C can be provided on second side 133D of manual/visual interface holder 145C to connect manual/visual interface holder 145C to UC assist holder 145A (FIG. 13C). Any of viewing window 137A, manual interface mounting cavity 133B, and connector 133C can be located on any part of manual/visual interface holder 145C, or can be absent altogether. Manual/visual interface holder 145C, visual interface viewing window 137A (FIG. 13B), manual interface mounting cavity 133B, and connector 133C can be any size. Manual/visual interface holder 145C can be constructed of any material suitable for mounting visual interface viewing window 137A, manual interface mounting cavity 133B, and connector 133C. Angle 145M can be associated with various orientations of UC holder 133A and thus can be various values. UC holder 133A can have a fixed orientation or can be hinged.

Referring now primarily to FIG. 13C, UC assist holder 145A can include, but is not limited to including, filter cavity 136G and lens cavity 136F providing visibility to, for example, but not limited to, a time-of-flight sensor optical filter and lens such as, for example, but not limited to, OPT8241 3D time-of-flight sensor by TEXAS INSTRUMENTS. UC assist holder 145A can be any shape and size and can be constructed of any material, depending on the mounting position on the MD and the sensors, processors, and power supply, for example, provided within UC assist holder 145A. Rounded edges on cavities 136G and 136F as well as holder 145A can be replaced by any shape of edge.

Referring now to FIG. 13D, UC 130-1A can optionally include a binding mechanism to attach UC 130-1A to a mounting platform. Two tabs can extend fore and aft from the based of UC 130-1A, as toe and heel tabs. The toe tab can be inserted into forward "binding" 16135 where it can be prevented from lifting out. Spring-loaded fingers to the left and right sides of forward binding 16135 can press against the cylindrical base of UC 130-1A. The heel tab can then be levered down onto the rear "binding", which can include cam-over mechanism 16133 that can clamp down onto the heel tab. The rear binding can cup the cylindrical base of UC 130-1A. To release UC 130-1A, cam-over mechanism 16133 of the rear binding can be manually opened, after which UC 130-1A can be angled out. The spring-loaded fingers of forward binding 16135 can deflect when there is a lateral impact to UC 130-1A greater than a pre-selected threshold, and UC 130-1A can pop free. In some configurations, toe and heel tabs can be reversed.

Referring now to FIG. 13E, UC 130-1A can optionally include a seat belt-like mechanism to engage UC 130-1A with mounting base 16141. Mounting base 16141 can be attached to, for example, an armrest, and can include tab locks 16143 having release buttons. Mounting tabs 16145 can engage with tab locks 16143 to mount UC 130-1A on, for example, the armrest. Depressing release buttons can disengage UC 130-1A from mounting base 16141 toollessly. Mounting base 16141 can take any suitable shape and is not limited to accommodating the shape of an armrest. Tab locks 16143 can take on any shape and can perform the locking of mounting tabs 16145 in any suitable way. Mounting tabs 16145 can complement any structure that tab locks 16143 take.

Referring now to FIG. 13F, UC 130-1A can optionally include shaped mount 16153. Shaped mounting base 16151 can include any geometric structure that can complement the geometric structure of shaped mount 16153, for example, but not limited to, triangles, squares, rectangles, and ellipses. In some configurations, shaped mount 16153 and shaped mounting base 16151 can include complementary splines. In some configurations, when UC 130-1A is mounted in the desired orientation, shaped mounting base 16151 can be coupled with UC 130-1A by fastener 16155. Fastener 16155 can include any suitable attaching mechanism include one or more screws, bolts, wingnuts, and thumb screws, and can accommodate tooled or toolless installation.

Referring now to FIG. 13G, UC 130-1A can optionally include tabbed mount 16169 that can optionally include inclined edges that can cooperatively mate with base inclined edges 16163 of tabbed mounting base 16161.

Tabbed mounting base 16161 can include mount features 16171 that can complement the tab 16169 of the tabbed mount. Tabs 16169 can be any distance apart from each other as long as they align with mount features 16171. Tabbed mounting base 16161 can optionally include cable recess 16167 and a means for retaining UC 130-1A in place in tabbed mounting base 16161. The means for retaining can include any suitable tooled or toolless means including, but not limited to, at least one magnet, at least one set screw 16165, and/or thumb screws. In some configurations, pins (not shown) on the circumference of the tabbed mount can be separated by a pre-selected amount, such as, for example, but not limited to, about 180°. In some configurations, the pins can be approximately perpendicular to the barrel axis. Tabbed mounting base 16161 can include slots on its circumference that can fit the pins. The slots can include axial and/or circumferential travel that can affix the tabbed mount. In some configurations, UC 130-1A can include at least one tab 16169A at its base and substantially cylindrical body 16169B. At least one tab 16169A and cylindrical body 16169B can fit into cavity 16167A in the receiver bracket and can provide locating and clocking. C-clip 16162 can be inserted in slot 16166 and can slide first under first overhang 16166A at one end of the receiver, then over tabs 16169, then under second overhang 16168 at the other end of the receiver bracket. C-clip 16162 can prevent UC 130-1A from lifting up and out. C-clip tab 16162A at the middle of the C-clip can include a through hole for a retention feature. C-clip 16162 can be constructed of, for example, but not limited to, a metal plate, a steel wire, or molded plastic.

Referring now to FIG. 13H, UC 130-1A can optionally include flange 16189 and orientation recesses 16187. Slide-in mounting base 16181 can include entry cavity 16183 in which flange 16189 can be positioned. UC 130-1A and flange 16189 can be slid towards orientation recess 16182 as retraction tab 16185 is pulled away from slide-in mounting base 16181. Retraction tab 16185 can control the height of orientation pin 16191. When UC 130-1A arrives in orientation recess 16182, UC 130-1A can be rotated to achieve a desired orientation with respect to slide-in mounting base 16181 (and the feature such as an armrest onto which slide-in mounting base 16181 can be attached). When the desired orientation is achieved, retraction tab 16185 can be released, and orientation pin 16191 can enter one of orientation recesses 16187, thus retaining UC 130-1A in the desired orientation. Slide-in mounting base 16181 can include a channel into which flange 16189 can slide. The ridge in slide-in mounting base 16181 that forms the channel can retain flange 16189 within slide-in mounting base 16181.

Referring now to FIG. 131, UC 130-1A can optionally include flange 16209. Slide-in mounting base 16202 can include entry cavity 16201 in which flange 16209 can be positioned. UC 130-1A and flange 16189 can be slid towards orientation recess 16203. When UC 130-1A arrives in orientation recess 16203, UC 130-1A can be rotated to achieve a desired orientation with respect to slide-in mounting base 16202 (and the feature such as an armrest onto which slide-in mounting base 16202 can be attached). When the desired orientation is achieved, retention cam 16207 can be rotated with handle 16205, thus retaining UC 130-1A in the desired orientation. Slide-in mounting base 16202 can include a channel into which flange 16209 can slide. The ridge in slide-in mounting base 16202 that forms the channel can retain flange 16209 within slide-in mounting base 16202.

Referring now to FIG. 13J, UC 130-1A can optionally include flange 16221 and faceted side 16223. Slide-in mounting base 16202 can include entry cavity 16201 in which flange 16209 can be positioned. UC 130-1A and flange 16189 can be slid towards orientation recess 16203. When UC 130-1A arrives in orientation recess 16203, UC 130-1A can be rotated to achieve a desired orientation with respect to slide-in mounting base 16202 (and the feature such as an armrest onto which slide-in mounting base 16202 can be attached). When the desired orientation is achieved, retention cam 16207 can be rotated with handle 16205, thus retaining UC 130-1A in the desired orientation. Slide-in mounting base 16202 can include a channel into which flange 16209 can slide. The ridge in slide-in mounting base 16202 that forms the channel can retain flange 16209 within slide-in mounting base 16202.

Referring now to FIG. 13K, UC 130-1A can optionally include a substantially cylindrical base that can enable receiving bracket 16243 having a tubing clamp design. In some configurations, one or more ribs (not shown) can be arrayed around the inside diameter of receiving bracket 16243, and UC 130-1A can include groves (not shown) to provide guidance when mounting UC 130-1A in receiving bracket 16243, providing an anti-rotation feature. In some configurations, receiving bracket 16243A can include hinge 16243B that can be easily opened and closed. The barrel of hinge 16243B can be placed on the inside of the clamp, and can engage a corresponding cutout in the base of UC 130-1A (not shown) as a clocking/anti-rotating feature. The clasp that holds the clamp shut can take any number of forms, depending on how much circumferential clamping is required. In some configurations, the clasp can include (a) thumbscrew 16243C (b) over-center latch 16243D (c) pin latch 16423E (d) cam on a lever 16243F, and/or (e) a groove (not shown) around at least part of the circumference of the cylindrical portion of UC 130-1A, at a seam where two housing elements come together. The clamp can include a tongue for additional retention.

Referring now to FIGS. 13M and 13N, in some configurations, receiving bracket 16243 can include balls 2501 mounted inside receiving bracket 16243. Balls 2501 can engage dimples 2503 (FIG. 13M). The size and location of dimples 2503 (FIG. 13M) can be such that, in locked position 2505 (FIG. 13M), a radial interference can be created. Receiving bracket 16243 can include ring 2507 (FIG. 13M) that can lock balls 2501 in place. Ring 2507 (FIG. 13M) can include configurations such as, for example, but not limited to, a first profile that either places solid 2513 behind balls 2501 in locked position 2505 or cavity 2509 in unlocked position 2511. Ring 2507A (FIG. 13N) can include configurations such as, for example, but not limited to, flexture cut 2515 (FIG. 13N) so that in unlocked position 2511, balls 2501 can be sprung radially inward. Flexture cut 2515 (FIG. 13N) can be cut from material between unlock position 2511 and lock position 2505. Between dimple 2503 and cavity 2509 can include material build-out 2514 in ring 2507. Build-out 2514 can be part of an over-center mechanism, since to move ring 2507 into and out of the locked position 2505, build-out 2514 can cover ball 2501 because of the flex in the components.

Referring now to FIG. 13L, UC 130-1A can optionally include grooved flange 16247. As grooved flange 16247 is surrounded by mounting ring 16245, UC 130-1A can be rotated to a desired orientation, and fastener 16241 can be tightened to catch in groove 16247. In some configurations, grooved flange 16247 can include multiple grooves to enable height adjustment of UC 130-1A.

Referring now to FIGS. 14A-14C, UC board 50004 can provide the electronics and connectors to control the activities of UC 130 (FIG. 12A). UC board 50004 can include circuit board 50004-9 upon which connectors and ICs can be mounted. For example, joystick connector 50004-8, power and communications connector 50004-7, toggles connector 50004-5, thumbwheel connector 50004-4, speaker connector 50004-6, and display connector 50004-2 can be included on mounting board 50004-9. In some configurations, UC board 50004 can include ambient light sensor 50004-X (FIG. 14A), the signal from which can be used to vary the display brightness and contrast for viewing in indoor and outdoor environments. EMC shield 50004-3 can provide EMC protection to UC board 50004. Connections 50004-1 to wireless antenna 50025 (FIG. 12H) can include, for example, but not limited to, spring contacts. Button snap domes 50004-10, for example, can accommodate button depression activation. In some configurations, button snap domes 50004-10 can each be associated with back-lighting from, for example, but not limited to, light-emitting diode (LED)s. Toggle switches and toggle levers can be accommodated similarly. UC board 50004 can process data transmitted to and from the user, PBC board 50001 (FIGS. 15A and 15B), PSC board 50002 (FIG. 15G), and a wireless antenna. UC board 50004 can perform filtering of incoming data, and can enable the transitions and workflow described in FIGS. 23A-23KK. UC board 50004 can include, but is not limited to including, a wireless transceiver that can include a processor and transceiver that can support wireless communications using, for example, but not limited to, the BLUETOOTH® low energy protocol. The wireless transceiver can include, for example, but not limited to, a Nordic Semiconductor nRF51422 chip.

Referring now to FIG. 14D, processing on the change in thumbwheel position can include method 72000 that can determine how to adjust the speed of the MD based on the movement of thumbwheel knob 30173 (FIG. 12E). Method 72000 can include, but is not limited to including, sampling 72001 the ADC and, if 72003, the user has changed from one drive setting to another, saving 72005 the virtual wheel position for the currently-selected drive setting, recovering 72007 the previous virtual thumbwheel position for the new drive setting, and recording 72015 the last ADC reading. When the user changes drive settings, a current virtual thumbwheel position for the currently selected drive can be stored for the purpose of, for example, recalling it at a later time. For instance, if the user changes from drive setting one, at a virtual thumbwheel position of 2000 counts, to drive setting two, the previous virtual thumbwheel position for drive setting one can become 2000 counts. In this example, the new virtual thumbwheel position can be whatever the setting was for drive setting two the last time the MD was in drive setting two. If 72003, the user has not changed from one drive setting to another, and if 72009 a change in the ADC is not detected, method 72000 can include recording 72015 the last ADC reading. If 72009 a change in the ADC is detected, method 72000 can include computing an ADC delta in counts, filtering 72011 the ADC delta, integrating 72013 the ADC delta into the virtual thumbwheel position, and recording 72015 the last ADC reading. Method 7200 can include calculating 72017 the speed percent based on the virtual thumbwheel position and max counts, and providing 72019 the speed percent for further processing.

Referring to FIG. 14E, filtering method 72011 for filtering the analog signal can include computing the ADC delta as, for example, the difference between the current ADC reading and the last ADC reading. If 72023 the ADC delta exceeds a wrap threshold, filtering method 72011 can include setting 72025 the ADC delta to zero and adding 72031 the ADC delta to an historic buffer. When thumbwheel knob 30173 (FIG. 12O) is rotated 360°, the count values can wrap from, for example, 4095 to 0 counts. Because of this, the ADC delta on a wrap can be a very large or a very small number. The wrap threshold can specify the number of ADC delta counts that can be considered a wrap-around value. A weighted average can be computed on a pre-selected data set of some specified size, such as, for example, the computed deltas from the previous ten frames of ADC data. The historic buffer can hold this pre-selected number of frames of data. If 72023 the ADC delta does not exceed the wrap threshold, and if 72029 the ADC delta exceeds a maximum frame delta, filtering method 72011 can include setting 72027 the ADC delta equal to the maximum frame delta and adding 72031 the ADC delta to the historic buffer. The maximum frame delta can specify the largest non-wrapping ADC delta that can be permitted. ADC deltas above this value that are below the wrap threshold can be capped at this value. Filtering method 72011 can include calculating 72031 a weighted average of the data stored in the historic buffer, and setting the ADC delta equal to the weighted average. If 72035 the ADC delta does not exceed, or is equal to, a deadband, filtering method 72011 can include setting 72037 the ADC delta to zero, flagging the ADC delta as noise, and integrating 72013 the ADC delta into the virtual thumbwheel position. The deadband can be a threshold used to filter out potential noise signals that are unlikely to constitute actual movement of thumbwheel knob 30173. If 72035 the ADC delta exceeds the deadband, and if 72037 the last sample was noise, filtering method 72011 can include setting 72041 the ADC delta to zero and integrating 72013 the ADC delta into the virtual thumbwheel position. If 72035 the ADC delta exceeds the deadband, and if 72037 the last sample was not noise, filtering method 72011 can include integrating 72013 the ADC delta into the virtual thumbwheel position.

Referring now to FIG. 14F, system 72500 for processing on the change in thumbwheel position can determine how to adjust the speed of the MD based on the movement of thumbwheel knob 30173 (FIG. 12E). System 72500 can include, but is not limited to including, sampler 72501, drive setting processor 72503, filter 72600, recorder 72507, and transmitter 72511. Sampler 72501 can include, but is not limited to including, sampling the ADC and, if, the user has changed from one drive setting to another, saving the virtual wheel position for the currently-selected drive setting, recovering the previous virtual thumbwheel position for the new drive setting, and recording the last ADC reading. When the user changes drive settings, the current virtual thumbwheel position for the currently selected drive setting can be stored for the purpose of, for example, recalling it at a later time. Recorder 72507 can include, but is not limited to including, if, the user has not changed from one drive setting to another, and if a change in the ADC is not detected, recording the last ADC reading. Filter 72600 can, if a change in the ADC is detected, filter the analog signal to determine a filtered ADC delta. Absolute position processor 72509 can include, but is not limited to including, integrating the filtered ADC delta into the virtual thumbwheel position. Recorder 72507 can include recording the last ADC reading. Speed percent processor 72505 can include, but is not limited to including, calculating the speed percent based on the virtual thumbwheel position and max counts. Transmitter 72511 can include, but is not limited to including, making the speed percent available for further processing.

Continuing to refer to FIG. 14F, filter 72600 for filtering the analog signal can include, but is not limited to including, ADC delta processor 72601, threshold processor 72603, weighted average processor 72605, deadband processor 72611, and historical buffer processor 72607. ADC delta processor 72601 can include, but is not limited to including, computing the ADC delta as, for example, the difference between the current ADC reading and the last ADC reading. If the ADC delta exceeds a wrap threshold, threshold processor 72603 can include, but is not limited to including, can include setting the ADC delta to zero and historical buffer processor 72607 can include adding the ADC delta to historic buffer 72609. Weighted average processor 72605 can include, but is not limited to including, computing a weighted average on a pre-selected data set of some specified size, such as, for example, the computed deltas from the previous ten frames of ADC data. Historic buffer 72609 can hold this pre-selected number of frames of data. If the ADC delta does not exceed the wrap threshold, and if the ADC delta exceeds a maximum frame delta, historical buffer processor 72607 can include setting the ADC delta equal to a maximum frame delta and adding the ADC delta to historic buffer 72609. Weighted average processor 72605 can include, but is not limited to including, calculating 72031 a weighted average of the data stored in historic buffer 72609, and setting the ADC delta equal to the weighted average. Deadband processor 72611 can include, but is not limited to including, if the ADC delta does not exceed, or is equal to, the deadband, setting the ADC delta to zero, flagging the ADC delta as noise, and integrating the ADC delta into the virtual thumbwheel position. The deadband can be a threshold used to filter out potential noise signals that are unlikely to constitute actual movement of thumbwheel knob 30173. Deadband processor 72611 can include, if the ADC delta exceeds the deadband, and if the last sample was noise, setting the ADC delta to zero and integrating the ADC delta into the virtual thumbwheel position. If the ADC delta exceeds the deadband, and if the last sample was not noise, deadband processor 72611 can include integrating the ADC delta into the virtual thumbwheel position.

Referring now to FIGS. 15A and 15B, central gearbox 21514 can include PSC board 50002 and PBC stack. The electronics of PSC board 50002 can manage power and provide power to PBC board 50001, and PBC board 50001 in turn provides power to the motors of the MD. PBC board 50001 can include redundant computers and electronics whose responsibilities can include processing inertial sensor data and computing the motor commands used to control the MD. Electronics for PBC board 50001 can interface with at least one inertial measurement unit (IMU) 50003 (FIG. 15B) and UC 130 (FIG. 12A). PBC board 50001 can include redundant processors that can be physically separated from each other and can have isolation barriers on their interconnections to increase the robustness of the redundant architecture. Active redundancy can enable conflict resolution during a fault condition through voting on actuator commands and other vital data. In some configurations, sensors, powerbase processors and power buses can be physically replicated in the MD. Sensor inputs, processor outputs, and motor commands from this redundant architecture can be cross-monitored and compared to determine if all the signals are within an acceptable tolerance. During normal operation all signals "agree" (are within an acceptable tolerance) and the full functionality of the MD is available to the user. If any one set of these signals is not within a range of the other three, the MD can ignore data from the non-matching set and can continue to operate using data from the remaining sensor/processor strings. Upon loss of redundancy, a fault condition can be identified and the user can be alerted, for example, via visual and audible signals. For redundancy, each of the PBC and the PSC can include an "A" side and a "B" side. The PBC "A" side can be divided into "A1" and "A2" quadrants that can be powered by the PSC "A" side. The PBC "B" side can be divided into "B1" and "B2" quadrants that can be powered by the PSC "B" side. The IMU can include, for example, four inertial sensors that can each map directly to one of the PBC quadrants.

Continuing to refer to FIGS. 15A and 15B, load sharing redundancy can be used for the power amplifiers, high voltage power buses and primary actuators in order to size the motors and batteries for normal, no-fault conditions and yet allow higher stress short duration operation during a system fault. Load sharing redundancy can allow for a lighter weight, higher performance fault tolerant system than other redundancy approaches. The MD can include multiple separate battery packs 70001 (FIG. 1E). Multiple battery packs 70001 (FIG. 1E) dedicated to each PBC side can provide redundancy so that battery failure conditions can be mitigated. The redundant load sharing components can be kept separate throughout the system to minimize the chance of a failure on one side causing a cascading failure on the other side. The power delivery components (battery packs 70001 (FIG. 1E), wiring, motor drive circuitry, and motors) can be sized to deliver sufficient power to keep the user safe while meeting the system performance requirements.

Continuing to refer to FIGS. 15A and 15B, the MD electronics and motors generate heat that can be dissipated to prevent overheating of the MD. In some configurations, components of PBC board 50001 can operate over a −25° C. to +80° C. temperature range. Heat spreader 30050 can include heat spreader plate 30050 and at least one standoff 30052 (FIG. 15B) that can penetrate holes in powerbase controller board 50001 and support inertial measure unit (IMU) assembly 50003 (FIG. 15D). Heat spreader plate 30050 can, for example, be operably connected to the central housings and the circuit boards of the MD through a thin electrically-isolating material that can provide a thermal conduction path for the heat from the electronics to the central housing. In some configurations, metal-to-metal contact between heat spreader 30050 and the mounting features on housings 30020-30023 can dissipate heat. Along with standoff grommets 30187 (FIG. 15C), standoffs 30052 (FIG. 15B) can isolate the IMU assembly from vibrations of powerbase controller board 50001 and heat spreader 30050. The vibrations can result from vibrations throughout the powerbase. The heat management system of the present teachings can include bars 30114 (FIG. 15B) mounted on heat spreader 30050 but not touching PBC board 50001, copper areas on PBC board 50001, and thermal gap pads providing heat conductivity between PBC board 50001 and heat spreader 30050.

Referring now to FIG. 15B, IMU mounting onto heat spreader 30050 can include soft-durometer grommets 30187 (FIG. 15C) that can dampen vibrations, and flex cable 50028-9B (FIG. 15C) that can provide electrical connection to PBC board 50001. IMU sensors can be isolated from vibrations generated by the seat, cluster, and wheel drive trains of the MD by mechanically isolating the IMU PCB 50003 (FIG. 15E) that sensors 608 (FIG. 15E) are mounted to. The IMU assembly can be mounted on at least one elastomeric grommet 30187 (FIG. 15C) that can attach to at least one post 30052 fastened to heat spreader plate 30050.

At least one grommet 30187 (FIG. 15C) can include a low hardness and damping ability that can limit the transmission of vibration from the MD to the IMU. Flex circuit cable 50028-9B can be compliant and may not transmit significant vibration to the IMU assembly.

Continuing to refer to FIG. 15B, flux shield 30008 can protect the electronics on PBC board 50001 from the magnetic signal from manual brake release position sensor 70020 (FIG. 9J). Flux shield 30008 can include ferrous metal, and can operably couple with heat spreader assembly 30050 between manual brake release position sensor 70020 (FIG. 9J) and PBC board 50001. The ferrous metal can intercept and redirect the magnetic flux of manual brake release position sensor 70020 (FIG. 9J) to substantially prevent interference with the electronics of PBC board 50001. To possibly increase the overall reliability of the MD, cables can utilize connectors that have a latching mechanism.

Referring now to FIGS. 15C-15D, IMU assembly 50003 can include, but is not limited to including, main board 50003B (FIG. 15D) that can include inertial sensors 608 (FIG. 15D) and memory 610 (FIG. 15D). IMU assembly 50003 can include at least one grommet 30187 (FIG. 15C) that can buffer vibrations and maintain stability of inertial sensors 608, and rigid-flex circuit 50028-9B that can connect IMU assembly 50003 to PBC board 50001 (FIG. 15B) in a way that reduces vibration transmission. Rigid-flex circuit 50028-9B can include stiffener 50028-24 that can facilitate a sturdy connection. Rigid-flex circuit 50028-9B can include a bend that can divide rigid-flex circuit cable 50028-9B into two portions that can provide a sensor interface and a connector interface. At least one grommet 30187 (FIG. 15C) can extend through main board 50003 (FIG. 15B) at cavities 608A (FIG. 15D), and through similar cavities in optional IMU shield 70015 (FIG. 15C) and PBC board 50001 (FIG. 15B), and can operably couple with stand-offs 30052 (FIG. 15B). Other geometries of rigid-flex circuit cable 50028-9B (FIG. 15C) are possible, as are other connector patterns and grommet placement.

Continuing to refer to FIGS. 15C-15D, at least one inertial sensor 608 can include, for example, but not limited to, ST Microelectronics LSM330DLC IMU. IMU assembly 50003 can include IMU PCB 50003B that can accommodate stand-offs 30052 (FIG. 15B) to enable elevating and shock-mounting IMU PCB 50003B above PBC board 50001. IMU assembly 50003 can include features to enable mounting IMU shield 70015 (FIG. 15C) onto IMU PCB 500036. Optional IMU shield 70015 can protect inertial sensors 608 (FIG. 15D) from possible interference, including, but not limited to EM interference, from PBC board 50001 (FIG. 15B) and/or PSC board 50002 (FIG. 15G). IMU PCB 50003B can include connectors that can receive/transmit signals from/to inertial sensors 608 to/from PBC board 50001 (FIG. 15B). Inertial sensors 608 (FIG. 15D) can be mounted to IMU PCB 50003B, that can allow IMU assembly 50003 to be calibrated separately from the rest of the MD. IMU PCB 50003B can provide mounting for memory 610 (FIG. 15D) that can hold, for example, calibration data. Non-volatile memory 610 (FIG. 15D) can include, for example, but not limited to, Microchip 25AA320AT-I/MNY. Storage of the calibration data can enable IMU assemblies 50003 from multiple systems to be calibrated in a single batch and installed without any additional calibration. As sensor technology changes, inertial sensor 608 (FIG. 15D) can be updated with the latest available sensors in relative electronics design isolation because IMU assembly 50003 can be relatively isolated from PBC board 50001. Inertial sensors 608 can be positioned angularly with respect to each other. The angular positioning can improve the accuracy of data received from inertial sensors 608. Inertial information, such as pitch angle or yaw rate, that may lie entirely upon one sense axis of one inertial sensor 608 can be spread across two sense axes of an angled inertial sensor. In some configurations, two inertial sensors 608 can be positioned angled 45° from two other inertial sensors 608. In some configurations, the angled inertial sensors 608 can alternate in placement with non-angled inertial sensors 608.

Referring now to FIGS. 15E and 15F, second configuration IMU assembly 50003A can include at least one inertial sensor 608. Second configuration IMU assembly 50003A can include second configuration IMU PCB 50003A-1 that can accommodate stand-offs 30052 (FIG. 15B) to enable elevating and shock-mounting second configuration IMU PCB 50003A-1 above PBC board 50001. Second configuration IMU assembly 50003A can include features to enable mounting IMU shield 70015 onto second configuration IMU PCB 50003A. Optional IMU shield 70015 can protect inertial sensors 608 from possible interference, including, but not limited to EM interference, from PBC board 50001 and/or PSC board 50002 (FIG. 15G). Second configuration IMU PCB 50003A can include connectors 609B (FIG. 15F) that can receive/transmit signals from/to inertial sensors 608 to/from PBC board 50001 (FIG. 15B). Inertial sensors 608 (FIG. 15E) can be mounted to second configuration IMU PCB 50003A. Second configuration IMU PCB 50003A can provide mounting for memory 610 (FIG. 15E) that can hold, for example, calibration data.

Referring now primarily to FIGS. 15G and 15H, PSC board 50002 can include connectors 277 (FIG. 15G) that can enable batteries 70001 (FIG. 1E) to supply power to PSC board 50002. Connectors 277 can include, for example, contacts, and circuit board mounting means, for example, but not limited to, MOLEX@MLX 44068-0059. PSC board 50002 can include at least one microcontroller 401, and can include at least one bumper 30054/30054A to buffer the interface between PSC board 50002 and e-box lid 21524 (FIG. 1G), and at least one spacer 30053 to maintain the spacing between PSC board 50002 and PBC board 50001 (FIG. 15B). In some configurations, spacer 30053, which can include, for example, metal, can be operably coupled with PSC board 50002. In some configurations, spacer 30053 can be used as an electrical connection to the chassis of the MD for EMC purposes. Spacer 30053 can provide durability and robustness to the MD. PSC board 50002 can include charge input connector 1181, UC connector 1179, auxiliary connector 1175A, at least one power interconnect to PBC connector 1173, and CANbus-to-PBC connector 1179A, connected as shown in FIGS. 151 and 15J. PSC board 50002 can include at least one power switch 401C, at least one battery charge circuit 1171/1173A, and at least one coin cell battery 1175ABC to power at least one real-time clock 1178A (FIG. 15J). PSC board 50002 is not limited to the parts listed herein, but can include any integrated circuits and other parts that could enable operation of the MD.

Referring now to FIGS. 151-15J, PSC board 50002 can communicate with batteries 70001 (FIG. 1E) connected to battery connectors 70001A (FIG. 151) that can provide power to UC 130 (FIG. 12A) and auxiliary devices through for example, but not limited to, 15-V regulator 1175, UC connector 1179. 24-V regulator 1175XYZ, and auxiliary connector 1175A. PSC board 50002 can communicate with battery management system 50015 (FIG. 1E) from which can be determined, for example, but not limited to, battery capacity and temperature. PSC board 50002 can monitor the line voltages from battery packs 70001 (FIG. 1E), and can monitor whether, for example, charger power supply cord 70002 (FIGS. 11A-11D) is plugged in. Batteries 70001 (FIG. 1E) can provide power to at least one microcontroller 401 (FIG. 15J) through, for example, but not limited to, regulator 1176 (FIG. 15J) such as, for example, but not limited to, a 3.3 V regulator, regulator 1176A (FIG. 15J) such as, for example, but not limited to, a 3 V regulator, and regulator 1177 (FIG. 15J), for example, but not limited to, a 5 V regulator. PSC board 50002 provides power to the PBC board 50001 through board-to-board connectors 1173/1173A (FIG. 15J) such as, for example, but not limited to, SAMTEC@PES-02. At least one microcontroller 401 (FIG. 15J), for example, but not limited to, Renesas RX64M, can control the opening and closing of power switch 401C (FIG. 15J) between batteries 70001 (FIG. 151) and board-to-board connectors 1173/1173A (FIG. 15J) to PBC board 50001. At least one microcontroller 401 (FIG. 15J) can include memory 1178 (FIG. 15J), for example, but not limited to, ferroelectric non-volatile memory, that can hold data after being powered off. PSC board 50002 can include a real-time clock that can be used, for example, to time stamp usage data and event logs. The real-time clock can be powered by batteries 70001 (FIG. 151) or, alternatively, by backup battery lithium coin cell 1175ABC (FIG. 15J). Communications between at least one microcontroller 401 (FIG. 15J) and batteries 70001 (FIG. 151) can be enabled by an 12C bus and 12C accelerator 1174 (FIG. 15J). Communications between at least one microcontroller 401 (FIG. 15J) and UC 130 (FIG. 12A) can be enabled by CANbus protocol through UC connector 1179 (FIGS. 151/15G). Communications between at least one microcontroller 401 (FIG. 15G) and PBC board 50001 (FIG. 15B) can be enabled by CANbus protocol through connector 1179A. Sensors 410B (FIG. 15J) can be positioned throughout PSC board 50002 to determine the actual level of the voltage coming from batteries 70001 (FIG. 1E), versus the level of voltage reported by batteries 70001 (FIG. 1E) and sensed by sensors 410A (FIG. 151). At least one sensor 410A (FIG. 151) can sense high acceleration events such as, for example, but not limited to, hard impacts, vehicle crashes, and mishandling in shipment. The high acceleration events can be logged, for example, and can be used as part of service and warranty claims, and can provide usage statistics that can, for example, provide data for quality improvement efforts. In some configurations, at least one sensor 410A (FIG. 151) can reside on PSC board 50002, and can communicate to a corresponding PSC processor 401 (FIG. 15J) via a serial peripheral interface (SPI) bus, for example.

Continuing to refer to FIGS. 151-15J, power can flow from each battery pack 70001 (FIG. 151) through PSC board 50002, through PBC board 50001 (FIG. 15B), and out to the motors. Battery packs 70001 (FIG. 151) may discharge at different rates for example, because of internal impedance differences. Because they are ganged together electrically, the A-side batteries have approximately the same voltage, and the B-side batteries have approximately the same voltage, but there could be differences between the voltage in the A-side batteries and the voltage in the B-side batteries. Bus voltage can be monitored, and if necessary, the voltage of batteries 70001 on each side can be equalized by sending a slightly larger command to the motor on the side that has a higher voltage and a smaller command to the other side. Current limiting devices can be used throughout the power distribution to prevent an over-current condition on one subsystem from affecting the power delivery to another subsystem. Anomalies caused by marginal power supply operation can be mitigated by 1) supply monitoring for critical analog circuits and 2) power supply supervisory features for digital circuits.

Figure 18B:
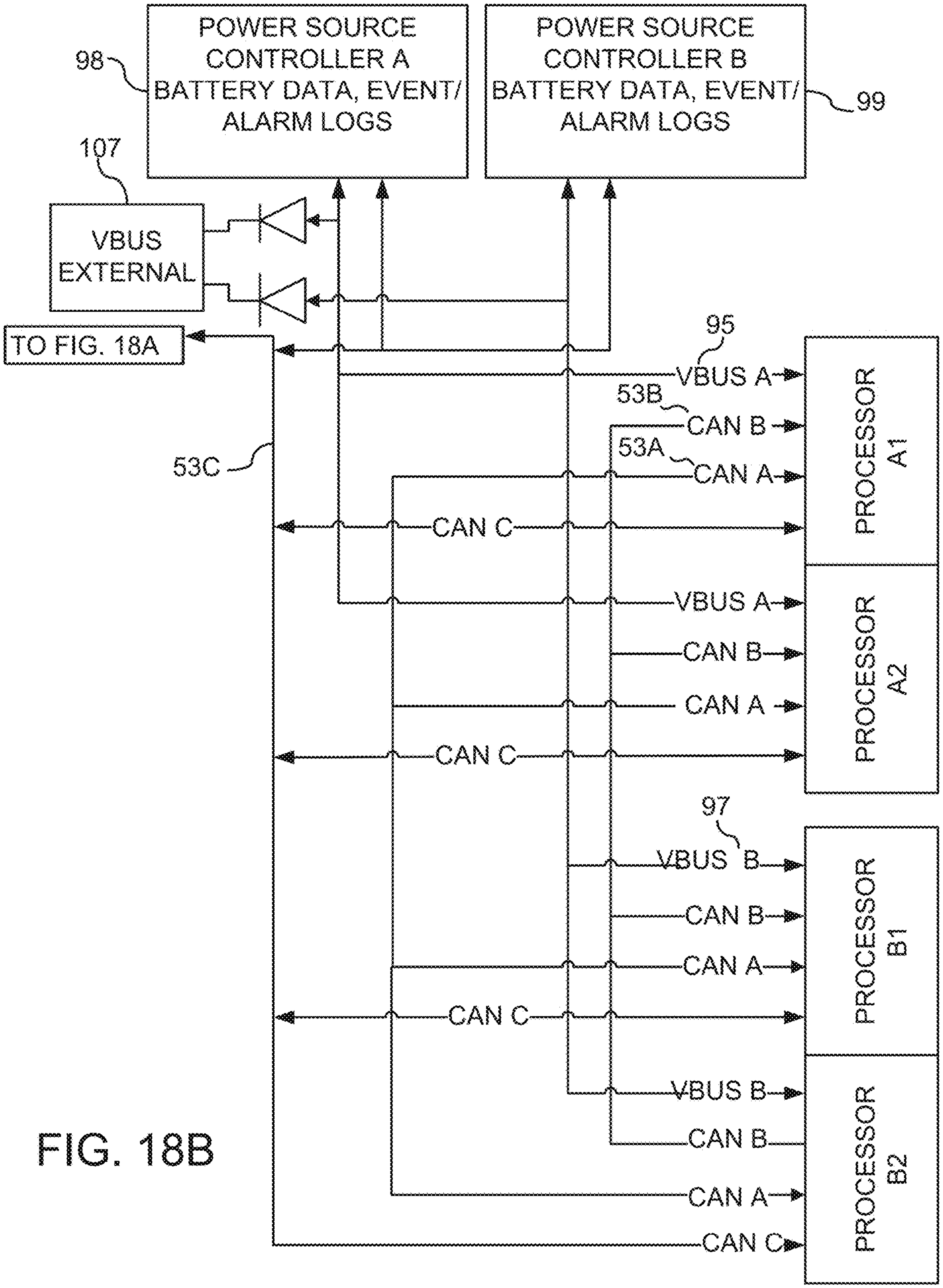

Referring now to FIG. 15J, hosts AB 401 communicate via, for example, CANbus to UC 130 (FIG. 12A) and processors A1/A2/B1/B2 (FIG. 18B). UC 130 (FIG. 12A) sends message to host AB 401 to wake up when UC 130 (FIG. 12A) powers on. Hosts A/B 401 communicate via 12C to three individual battery gauge boards, querying, for example, but not limited to, status, voltage, and current. Hosts A/B 401 detect when batteries 70001 (FIG. 1E) are present, and sense analog voltage levels of three pre-switch individual batteries and one post-switch high voltage bus. Hosts AB 401 enable main power to the PBC 50001 (FIG. 15B) and enables/controls charging of batteries 70001 (FIG. 1E) which can occur in the range of approximately 0-45° C. Hosts A/B 401 set a charge rate that can be one of pre-charge, fast, and slow. Pre-charge rate, for example, 0.4 A, can be used when the voltage of battery 70001 (FIG. 1D) is <3.0 V/cell, for example, when topping off the charge and when battery 70001 (FIG. 1E) is present with no voltage, for example, the battery output is off. Fast rate, for example, 0.9 A, can be used when four of batteries 70001 (FIG. 1D) are detected. Slow rate, for example, 0.7 A, can be used when six of batteries 70001 (FIG. 1D) are detected. Float charging can be used when batteries 70001 (FIG. 1E) are left on the MD for long periods of time, for example, months, and the MD is turned off. Hosts A/B 401 can communicate via SPI bus to memory, for example, a 1 Mbit ferroelectric rapid access memory (FRAM). Hosts AB 401 can store event/alarm logs and user configuration data.

Referring now to FIG. 15K, PSC 50002 (FIGS. 151-J) can operate in various states and can transition from state to state based on various stimuli. No power state 51001 can be entered when batteries 70001 (FIG. 1E) are not installed or are fully depleted. When 51003 batteries 70001 (FIG. 1E) are installed and/or the charger is plugged in, and when 51005 a reset signal resulting from power being applied to the MD is received, if 51007 the charger is plugged in, PSC 50002 (FIGS. 151-J) can enter charging state 51015. If 51007 the charger isn't plugged in, PSC 50002 (FIGS. 151-J) can enter sleep state 51009. If 51011 from sleep state 51009, an interrupt is received when the charger is plugged in, PSC 50002 (FIGS. 151-J) can enter charging state 51015. From charging state 51015, if 51013 the charge is disconnected, PSC 50002 (FIGS. 151-J) can enter sleep state 51009. If 51021, from sleep state 51009, PSC 50002 (FIGS. 151-J) receives 51021 wake-up information from UC 130 (FIG. 12A), PSC 50002 (FIGS. 151-J) can enter on state 51019. If 51017, from charging state 51015, UC 130 (FIG. 12A) sends 51017 power on information, PSC 50002 (FIGS. 151-J) can enter on state 51019. If 51025, from on state 51019, UC 130 (FIG. 12A) sends 51025 power off information, and if the charger is plugged in, PSC 50002 (FIGS. 151-J) can inform 51016 UC 130 (FIG. 12A) that PSC 50002 (FIGS. 151-J) is going into charging state PSC 50002 (FIGS. 151-J), and PSC 50002 (FIGS. 151-J) can enter charging state 51015. If 51025, from on state 51019, UC 130 (FIG. 12A) sends 51025 power off information, and if the charger is not plugged in, PSC 50002 (FIGS. 151-J) can turn off 51029 the main power FETs and check that the switched bus voltage is off. If 51031 the main power is off, PSC 50002 (FIGS. 151-J) can enter sleep state 51009. If 51031 the main power is not off, PSC 50002 (FIGS. 151-J) can inform 51027 UC 130 (FIG. 12A) that there is a problem powering off, and PSC 50002 (FIGS. 151-J) can enter on state 51019.

Continuing to refer to FIGS. 151-15J, estimating the power capability of batteries 70001 (FIG. 1E) in real time can provide an indication about whether or not to switch from one mode to another. Measuring the current using bus current sensors 1171C (FIG. 15J) coming from batteries 70001 (FIG. 1E) can provide an estimate of the power capability. The current measurement along with the measurement of voltage provided by voltage sensors 410B (FIG. 15J) can be used by processors 401 to indicate whether batteries 70001 (FIG. 1E) can support a mode change. Hot swap control 1171A (FIG. 151), such as, for example, but not limited to, LTC 4380 current surge stopper from Linear Technologies, can protect loads from overvoltage/overcurrent when, for example, batteries 70001 (FIG. 1E) are added to the system. During live insertion of batteries 70001 (FIG. 1E), hot swap controls 1171A (FIG. 151) can power PSC 50002 slowly and thus prevent, for example, sparking.

Referring now to FIG. 16A, the MD can include, but is not limited to including, powerbase 21514A, communications means 53, power means 54, UC 130, and remote control device 140. Powerbase 21514A can communicate with UC 130 using communications means 53 using a protocol such as, for example, but not limited to, the CANbus protocol. User controller 130 can communicate with remote control device 140 through, for example, but not limited to, wireless technology 18 such as, for example, BLUETOOTH® technology. In some configurations, powerbase 21514A can include redundancy as discussed herein. In some configurations, communications means 53 and power means 54 can operate inside powerbase 21514A and can be redundant therein. In some configurations, communications means 53 can provide communications from powerbase 21514A to components external to powerbase 21514A.

Referring now primarily to FIG. 16B, in some configurations, MD control system 200A can include, but is not limited to including, at least one powerbase processor 100 and at least one power source controller 11 that can bi-directionally communicate over serial bus 143 using system serial bus messaging system 130F. System serial bus messaging 130F can enable bi-directional communications among external applications 140 and I/O interface 130G, and UC 130. The MD can access peripherals, processors, and controllers through interface modules that can include, but are not limited to including, input/output (I/O) interface 130G and external communications interface 130D. In some configurations, I/O interface 130G can transmit/receive messages to/from, for example but not limited to, at least one of audio interface 150A, electronic interface 149A, manual interface 153A, and visual interface 151A. Audio interface 150A can provide information to audio devices such as, for example, speakers that can project, for example, alerts when the MD requires attention. Electronic interface 149A can transmit/receive messages to/from, for example, but not limited to, external sensors 147. External sensors 147 can include, but are not limited to including, time-of-flight cameras and other sensors. Manual interface 153A can transmit/receive messages to/from, for example, but not limited to, joystick 70007 (FIG. 12A) and/or switches 70036-1/2 (FIG. 12V) and buttons 70035 (FIG. 12H), and/or information lighting such as LED lights, and/or UC 130 (FIG. 12A) having, for example, a touch screen. UC 130 and processors 100 can transmit/receive information to/from I/O interface 130G, external communications 130D, and each other.

Continuing to refer primarily to FIG. 16B, system serial bus interface 130F can enable communications among UC 130, processors 100 (also shown, for example, as processor A1 43A (FIG. 18C), processor A2 43B (FIG. 18C), processor B1 43C (FIG. 18D), and processor B2 43D (FIG. 18D)), and power source controllers 11 (also shown, for example, as power source controller A 98 (FIG. 18B) and power source controller B 99 (FIG. 18B)). Messages described herein can be exchanged among UC 130 and processors 100 using, for example, but not limited to, system serial bus 143. External communications interface 130D can enable communications among, for example, UC 130 and external applications 140 using wireless communications 144 such as, for example, but not limited to, BLUETOOTH® technology. UC 130 and processors 100 can transmit/receive messages to/from external sensors 147 that can be used to enable automatic and/or semi-automatic control of the MD.

Referring now primarily to FIG. 17A, powerbase controller 50001 (FIG. 15B) can include powerbase processor 100 that can process incoming motor data 775 and sensor data 767 upon which wheel commands 769, cluster commands 771, and seat commands 773 can be at least in part based. To perform the data processing, powerbase processor 100 can include, but is not limited to including, CANbus controller 311 managing communications, motor drive control processor 305 preparing motor commands, timer interrupt service request processor 301 managing timing, voting/commit processor 329 managing the redundant data, main loop processor 321 managing various data inputs and outputs, and controller processing task 325 receiving and processing incoming data. Controller processing task 325 can include, but is not limited to including, IMU filter 753 managing IMU data preparation, speed-limiting processor 755 managing speed-related features, weight processor 757 managing weight-related features, adaptive speed control processor 759 managing obstacle avoidance, traction control processor 762 managing challenging terrain, and active stabilization processor 763 managing stability features. Inertial sensor pack 1070/23/29/35 can provide IMU data 767 to IMU filter 753 which can provide data that can result in wheel commands 769 to right wheel motor drive 19/31 and left wheel motor drive 21/33. IMU filter 753 can include, but is not limited to including, body rate to gravity rate and projected rate processor 1102 (FIG. 19A), body rate and gravity to Euler angles and rates processor 1103 (FIG. 19A), and gravity rate error and projected yaw rate error to body rates processor 1103 (FIG. 19A). Seat motor 45/47 can provide motor data 775 to weight processor 757. Voting processor 329 can include, but is not limited to including, initial vote processor 873, secondary vote processor 871, and tertiary vote processor 875.

Figure 18C:
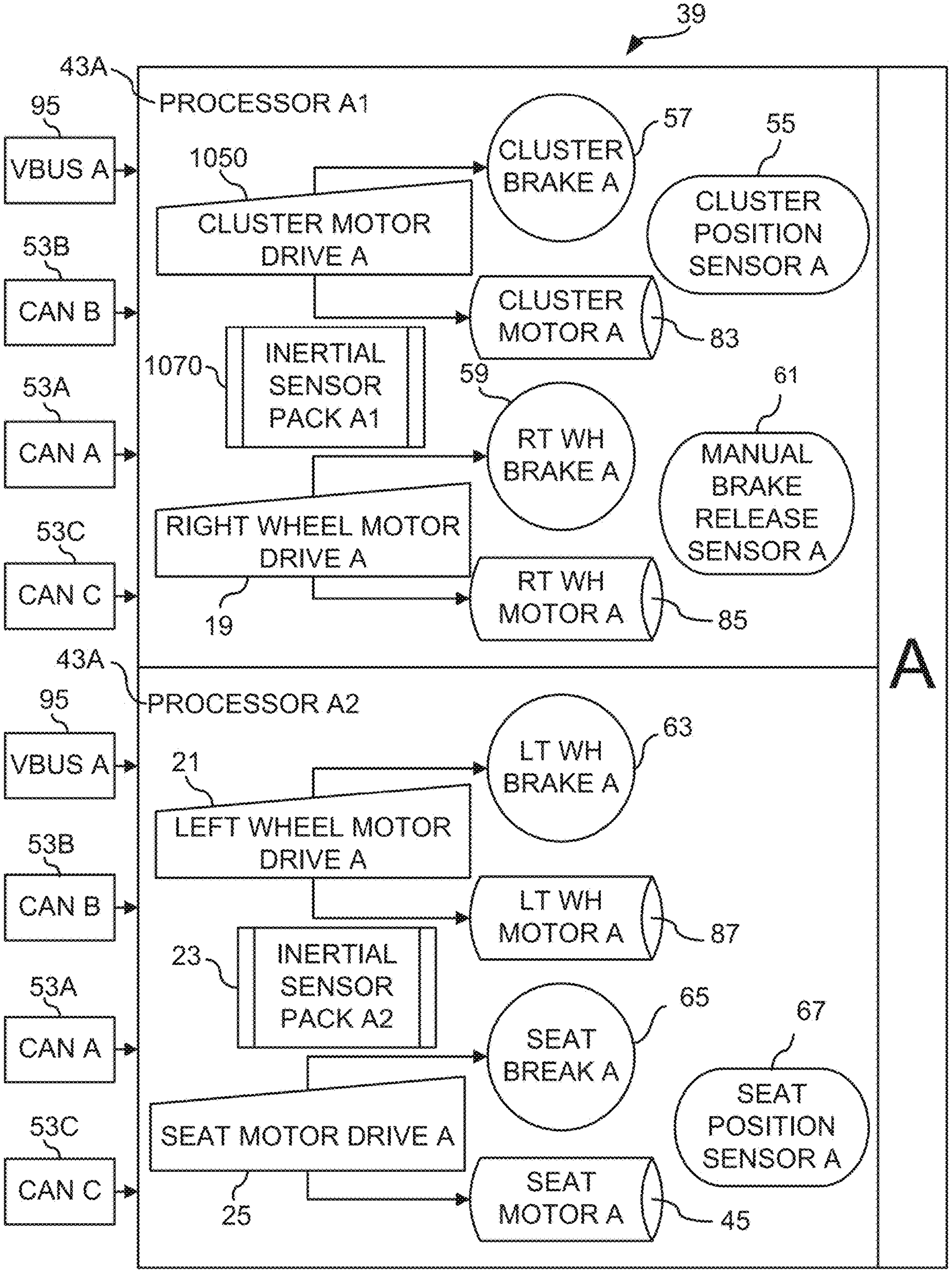
Figure 18D:
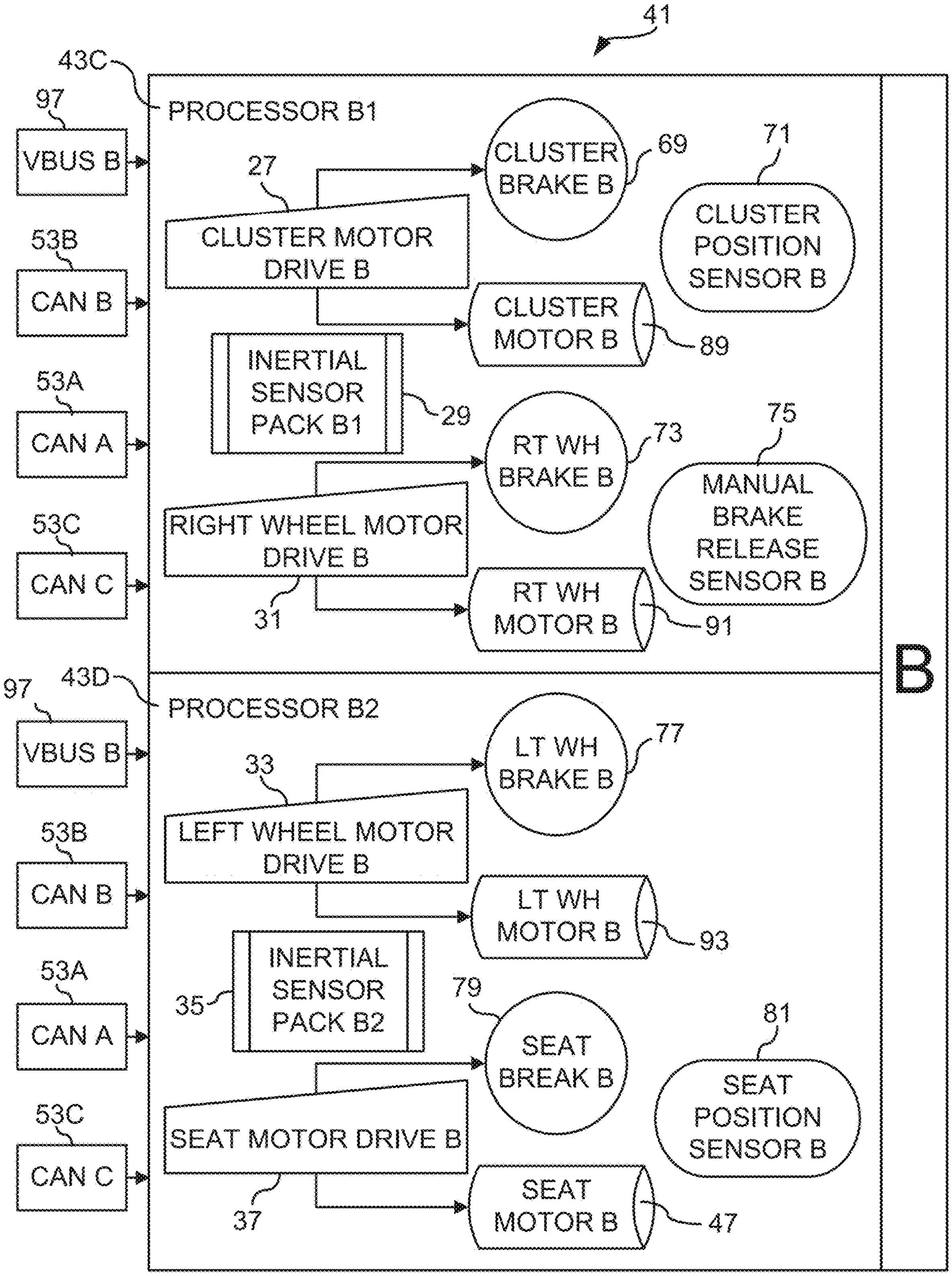

Referring now primarily to FIGS. 17B and 17C, in some configurations, powerbase processors 100 can share, through, for example, CANbus 53A/B (FIG. 18B), as controlled by CANbus controller task 311 (FIG. 17B), accelerometer and gyro data from inertial sensor packs 1070/23/29/35 (FIG. 17A). Powerbase serial buses 53A/B (FIG. 18B) can communicatively couple processors A1/A2/B1/B2 43A-43D (FIG. 18C/18D) with other components of the MD. CANbus controller 311 (FIG. 17B) can receive interrupts when CANbus messages arrive, and can maintain current frame buffer 307 (FIG. 17B) and previous frame buffer 309 (FIG. 17B). When accelerometer and gyro data (sensor data 767 (FIG. 17A)) have arrived from processors A1/A2/B1/B2 43A-43D (FIG. 18C/18D), CANbus controller 311 (FIG. 17B) can send a start commits processing message 319 (FIG. 17B) to voting/commit processor 329 (FIG. 17C). Voting/commit processor 329 (FIG. 17C) can send a commit message 331 (FIG. 17C) that can include the results of the voting process, for example, but not limited to, the voting processes of, for example, method 150 (FIGS. 21B/21C), applied to motor data 775 (FIG. 17A) and IMU data 767 (FIG. 17A), and can send start controller processing message 333 (FIG. 17C) to controller processing task 325 (FIG. 17C). Controller processing task 325 (FIG. 17C) can compute estimates based at least on, for example, received IMU data 767 (FIG. 17A) and motor data 775 (FIG. 17A), and can manage traction (traction control processor 762 (FIG. 17A)), speed (speed processor 755 (FIG. 17A), adaptive speed control processor 759 (FIG. 17A)), and stabilization (active stabilization processor 763 (FIG. 17A)) of the MD based at least on the estimates, and can send motor-related messages 335. If CANbus controller 311 (FIG. 17B) has not received messages from processors A1/A2/B1/B2 43A-D (FIG. 18C/18D) within a timeout period, such as, for example, but not limited to, 5 ms, timer interrupt service request processor 301 (FIG. 17B) can start commit backup timer 317 (FIG. 17B) that can, when the timer expires, start commits processing by sending a starts commits processing message 319 (FIG. 17B) to commits processing task 329 (FIG. 17C). Timer interrupt service request processor 301 (FIG. 17B) can also send start main loop message 315 (FIG. 17B) to main loop processor 321 (FIG. 17B) and update motors message 303 (FIG. 17B) to motor drive control 305 (FIG. 17B) when a timer has elapsed, for example, every 5 ms, and main loop processor 321 (FIG. 17B) can capture sensor data and data from user controller 130 (FIG. 16A). Main loop processor 321 (FIG. 17B) can send a synchronization message 313 (FIG. 17B) over CANbus 53A/B (FIG. 18B), if main loop processor 321 (FIG. 17B) is executing on a master of processors A1/A2/B1/B2 43A-D (FIG. 18C/18D). Main loop processor 321 (FIG. 17B) can track timed activities across powerbase processor 21514A (FIG. 16A), can start other processes, and can enable communications through powerbase output packet 323 (FIG. 17B).

Referring now primarily to FIGS. 18A-18D, PBC board 50001 (FIG. 15G) can include, but is not limited to including, at least one processor 43A-43D (FIGS. 18C/18D), at least one motor drive processor 1050, 19, 21, 25, 27, 31, 33, 37 (FIGS. 18C/18D), and at least one power source controller (PSC) processor 11A/B (FIG. 18B). PBC board 50001 (FIG. 15G) can be operably coupled with, for example, but not limited to UC 130 (FIG. 18A) through, for example, but not limited to, electronic communications means 53C and a protocol such as, for example, a CANbus protocol, and PBC board 50001 (FIG. 15G) can be operably coupled with at least one IMU and inertial system processor 1070, 23, 29, 35 (FIGS. 18C/18D). UC 130 (FIG. 18A) can be optionally operatively coupled with electronic devices such as, for example, but not limited to, computers such as tablets and personal computers, telephones, and lighting systems. UC 130 (FIG. 18A) can include, but is not limited to including, at least one joystick and at least one display. UC 130 (FIG. 18A) can include push buttons and toggles. UC 130 (FIG. 18A) can optionally be communicatively coupled with peripheral control module 1144 (FIG. 18A), sensor aid modules 1141 (FIG. 18A), and autonomous control modules 1142/1143 (FIG. 18A). Communications can be enabled by, for example, but not limited to, a CANbus protocol and an Ethernet protocol 271 (FIG. 18A).

Continuing to refer primarily to FIGS. 18A-18D, processors 39/41 (FIGS. 18C/18D) can control the commands to wheel motor processors 85/87/91/93 (FIGS. 18C/18D), cluster motor processors 1050/27 (FIGS. 18C/18D) and seat motor processors 45/47 (FIGS. 18C/18D). Processors 39/41 (FIGS. 18C/18D) can receive joystick, seat height and frame lean commands from UC 130 (FIG. 12A). Software that can enable UC 130 (FIG. 12A) can perform user interface processing including display processing, and can communicate with the external product interface. Software that can enable PSC 11A/B (FIG. 18B) can retrieve information from batteries 70001 (FIG. 1E) over a bus such as, for example, but not limited to, an 12C bus or an SMBus, and can send that information on CANbus 53A/53B (FIG. 18B) for UC 130 (FIG. 12A) to interpret. Boot code software executing on processors 39/41 (FIGS. 18C/18D) can initialize the system and can provide the ability to update application software. External applications can execute on a processor such as, for example, but not limited to, a personal computer, cell phone, and mainframe computer. External applications can communicate with the MD to support, for example, configuration and development. For example, a product interface is an external application that can be used by, for example, service, manufacturing, and clinicians, to configure and service the MD. An engineering interface is an external application that can be used by, for example, manufacturing, to communicate with UC 130 (FIG. 12A), processors 39/41 (FIGS. 18C/18D), and PSCs 11A/B (FIG. 18B) when commissioning the MD. A software installer is an external application that can be used by, for example, manufacturing and service, to install software onto UC 130 (FIG. 12A), processors 39/41 (FIGS. 18C/18D), and PSCs 11A/B (FIG. 18B).

Continuing to refer primarily to FIGS. 18C-18D, in some configurations, each at least one processor 43A-43D (FIGS. 18C/18D) can include, but is not limited to including, at least one cluster motor drive processor 1050, 27 (FIGS. 18C/18D), at least one right wheel motor drive processor 19, 31 (FIG. 18C), at least one left wheel motor drive processor 21, 33 (FIGS. 18C/18D), at least one seat motor drive processor 25, 37 (FIGS. 18C/18D), and at least one inertial sensor pack processor 1070, 23, 29, 35 (FIGS. 18C/18D). At least one processor 43A-43D can further include at least one cluster brake processor 57/69 (FIGS. 18C/18D), at least one cluster motor processor 83/89 (FIGS. 18C/18D), at least one right wheel brake processor 59/73 (FIGS. 18C/18D), at least one left wheel brake processor 63/77 (FIGS. 18C/18D), at least one right wheel motor processor 85/91 (FIGS. 18C/18D), at least one left wheel motor processor 87/93 (FIGS. 18C/18D), at least one seat motor processor 45/47 (FIGS. 18C/180), at least one seat brake processor 65/79 (FIGS. 18C/18D), at least one cluster position sensor processor 55/71 (FIGS. 18C/18D), and at least one manual brake release processor 61/75 (FIGS. 18C/18D). Processors 43A-43D can be used to drive cluster assembly 21100 (FIG. 6A) of wheels forming a ground-contacting module. The ground-contacting module can be mounted on cluster assembly 21100 (FIG. 6A), and each wheel of the ground-contacting module can be driven by a wheel motor drive commanded by right wheel motor drive processor A 19 (FIG. 18C), or redundant right wheel motor drive processor B 31 (FIG. 18D). Cluster assembly 21100 (FIG. 6A) can rotate about a cluster axis, the rotation being governed by, for example, cluster motor drive processor A 1050 (FIG. 18C), or redundant cluster motor drive processor B 27 (FIG. 18D). At least one of the sensor processors such as, for example, but not limited to, at least one cluster position sensor processor 55/71 (FIGS. 18C/18D), at least one manual brake release sensor processor 61/75 (FIGS. 18C/18D), at least one motor current sensor processors (not shown), and at least one inertial sensor pack processor 17, 23, 29, 35 (FIGS. 18C/18D) can process data transmitted from sensors residing on the MD. Processors 43A-43D (FIGS. 18C/18D) can be operably coupled to UC 130 (FIG. 18A) for receiving user input. Communications 53A-53C (FIG. 18B) among UC 130 (FIG. 18A), PSCs 11A/11B (FIG. 18B), and processors 43A-43D (FIGS. 18C/18D) can be according to any protocol including, but not limited to, a CANbus protocol. At least one Vbus 95/97 (FIG. 18B) can operably couple at least one PSC 11A/B (FIG. 18B) to processors 43A-43D (FIGS. 18C/18D) and components external to PBC board 50001 (FIG. 15G) through external Vbus 107 (FIG. 18B). In some configurations, processor A1 43A (FIG. 18C) can be the master of CANbus A 53A (FIG. 18B). Slaves on CANbus A 53A (FIG. 18B) can be processor A2 43B (FIG. 18C), processor B1 43C (FIG. 18D), and processor B2 43D (FIG. 18D). In some configurations, processor B1 43C (FIG. 18D) can be the master of CANbus B 53B (FIG. 18B). Slaves on CANbus B 53B (FIG. 18B) can be processor B2 43C (FIG. 18D), processor A1 43A (FIG. 18C), and processor A2 43B (FIG. 18C). In some configurations, UC 130 (FIG. 18A) can be the master of CANbus C 53C (FIG. 18B). Slaves on CANbus C 53C (FIG. 18B) can be PSCs 11A/B (FIG. 18B), and processors A1/A2/B1/B2 43A/B/C/D (FIGS. 18C/18D). The master node (any of processors 43A-43D (FIGS. 18C/18D) or UC 130 (FIG. 18A)) can send data to or request data from the slaves.

Referring primarily to FIGS. 18C/18D, in some configurations, powerbase controller board 50001 (FIG. 15G) can include redundant processor sets A/B 39/41 that can control cluster 21100 (FIG. 6A) and rotating drive wheels 21201 (FIG. 7B). Right/left wheel motor drive processors A/B 19/21, 31/33 can drive right/left wheel motors A/B 85/87/91/93 that drive wheels 21201 (FIG. 7B) on the right and left sides of the MD. Wheels 21201 (FIG. 7B) can be coupled to drive together. Turning can be accomplished by driving left wheel motor processors A/B 87/93 and right wheel motor processors A/B 85/91 at different rates. Cluster motor drive processor A/B 1050/27 can drive cluster motor processors A/B 83/89 that can rotate the wheel base in the fore/aft direction which can allow the MD to remain level while front wheels 21201 (FIG. 6A) are higher or lower than rear wheels 21201 (FIG. 6A). Cluster motor processors A/B 83/89 can keep the MD level when climbing up and down curbs, and can rotate the wheel base repeatedly to climb up and down stairs. Seat motor drive processor A/B 25/37 can drive seat motor processors A/B 45/47 that can raise and lower a seat (not shown).

Continuing to further refer to FIGS. 18C/18D, cluster position sensor processors A/B 55/71 can receive data from cluster position sensor that can indicate the position of cluster 21100 (FIG. 3). The data from the cluster position sensors and seat position sensors can be communicated among processors 43A-43D and can be used by processor set A/B 39/41 to determine information to be sent to, for example, right wheel motor drive processor A/B 19/31, cluster motor drive processor A/B 15/27, and seat motor drive processor A/B 25/37. The independent control of clusters 21100 (FIG. 3) and drive wheels 21201 (FIG. 7B) can allow the MD to operate in several modes, thereby allowing the user or processors 43A-43D to switch between modes, for example, in response to the local terrain.

Continuing to still further refer to FIGS. 18C/18D, inertial sensor pack processors 1070, 23, 29, 35 can receive data that can indicate, for example, but not limited to, the orientation of the MD. Each inertial sensor pack processor 1070, 23, 29, 35, can process data from, for example, but not limited to, accelerometers and gyroscopes. In some configurations, each inertial sensor pack processor 1070, 23, 29, 35 can process information from four sets of three-axis accelerometers and three-axis gyros. The accelerometer and gyro data can be fused, and a gravity vector can be produced that can be used to compute the orientation and inertial rotation rates of the MD. The fused data can be shared across processors 43A-43D and can be subjected to threshold criteria. The threshold criteria can be used to improve the accuracy of device orientation and inertial rotation rates. For example, fused data from certain of processors 43A-43D that exceed certain thresholds can be discarded. The fused data from each of processors 43A-43D that are within pre-selected limits can be, for example, but not limited to, averaged or processed in any other form. Inertial sensor pack processors 1070, 23, 29, 35 can process data from sensors such as, for example, ST®microelectronics LSM330DLC, or any sensor supplying a 3D digital accelerometer and a 3D digital gyroscope, or further, any sensor that can measure gravity and body rates. Sensor data can be subject to processing, for example, but not limited to, fiftering to improve control of the MD. Cluster position sensor processors A/B 55/71, seat position sensor processors A/B 67/81, and manual brake release sensor processors A/B 61/75 can process, but are not limited to processing, Hall sensor data. Processors 39/41 can manage the storage of information specific to a user.

Referring now primarily to FIG. 19A, at least one inertial sensor pack processor 17, 23, 29, 35 (FIGS. 18C/18D) can process sensor information from IMU 608 (FIG. 15D) through to IMU filter 9753. A state estimator can estimate dynamic states of the MD relative to an inertial coordinate system from the sensor information measured in a body coordinate system, that is, relative to the coordinate system associated with the MD. The estimation process can include relating the acceleration and rate measurements as taken by IMU board 50003 (FIG. 15B) on the axis system in which they are mounted (body coordinate systems) to the inertial coordinate system, to generate dynamic state estimates. The dynamic states relating the body coordinate frame to the inertial coordinate frame can be described with Euler angles and rates, which are computed from an estimate of the earth's gravitational field vector. The gyroscopes can supply rate measurements relative to their mounting reference frame. Pitch Euler angle 9147 and roll Euler angle 9149 can be estimated as follows.

Mapping rates from the body coordinate frame of reference to the inertial coordinate frame of reference can include evaluating the kinematic equation of the rotation of a vector.

$$\dot{G} = \hat{G}_f \times \Omega_f$$

where $\dot{G}$ is the gravity rate vector, $\hat{G}_f$ is the filtered gravity vector, and $\Omega_f$ is the body rate vector.

Integrated overtime, G provides a gravity vector estimate. The projected gravity rate estimate is as follows.

$$\dot{\gamma} = \hat{G}_f \cdot \Omega_f$$

Where, $\dot{\gamma}$ is the projected gravity rate.

Mapping inertial rates back to the body coordinate frame in order to integrate error to compensate for gyro bias can be accomplished as follows:

$$\dot{G}_e = \hat{G}_f \times \Omega_e$$

where $\dot{G}_e$ is the gravity rate error and $\Omega_e$ is the body rate error, which is equivalent to:

$$\begin{bmatrix} 0 & -G_{f_z} & G_{f_y} \\ G_{f_z} & 0 & -G_{f_x} \\ -G_{f_y} & G_{f_x} & 0 \end{bmatrix} \begin{bmatrix} \omega_{e_x} \\ \omega_{e_y} \\ \omega_{e_z} \end{bmatrix} = \begin{bmatrix} \dot{G}_{e_x} \\ \dot{G}_{e_y} \\ \dot{G}_{e_z} \end{bmatrix}$$

where $G_{f_{x\text{-}y\text{-}z}}$ are components of filtered gravity vector 9125, $\omega_{e_{x\text{-}y\text{-}z}}$ are components of filtered body rate error 9157, and $\dot{G}_{e_{x\text{-}y\text{-}z}}$ are components of filtered gravity rate error 9129. The projected gravity rate can be computed as follows.

$$\dot{\gamma}_e = \widehat{G_f} \cdot \Omega_e$$

or $$\dot{\gamma}_e = G_{f_x}\omega_{e,x} + G_{f_y}\omega_{e,y} + G_{f_z}\omega_{e,z}$$

Coupled with the matrix above, this yields a matrix that can be viewed in the Ax=b format:

$$\begin{bmatrix} 0 & -G_{f_z} & G_{f_y} \\ G_{f_z} & 0 & -G_{f_x} \\ -G_{f_y} & G_{f_x} & 0 \\ G_{f_x} & G_{f_y} & G_{f_z} \end{bmatrix} \begin{bmatrix} \omega_{e_x} \\ \omega_{e_y} \\ \omega_{e_z} \end{bmatrix} = \begin{bmatrix} \dot{G}_{e_x} \\ \dot{G}_{e_y} \\ \dot{G}_{e_z} \\ \dot{\gamma}_e \end{bmatrix}$$

To solve for body rate error 9157, the pseudo-inverse for the 'A' matrix can be computed as follows:

$$(A^T A)^{-1} A^T A x = (A^T A)^{-1} A^T b$$

The transpose 'A' matrix multiplied with the 'A' matrix yields the following matrix:

$$\begin{bmatrix} G_{f_x}{}^2 + G_{f_y}{}^2 + G_{f_z}{}^2 & 0 & 0 \\ 0 & G_{f_x}{}^2 + G_{f_y}{}^2 + G_{f_z}{}^2 & 0 \\ 0 & 0 & G_{f_x}{}^2 + G_{f_y}{}^2 + G_{f_z}{}^2 \end{bmatrix}$$

Since filtered gravity vector 9125 is a unit vector, the above matrix simplifies to a 3×3 identity matrix, whose inverse is a 3×3 identity matrix. Therefore, the pseudo-inverse solution to the Ax=b problem reduces to $$A^T A x = A^T b = \begin{bmatrix} \omega_{e_x} \\ \omega_{e_y} \\ \omega_{e_z} \end{bmatrix} = \begin{bmatrix} 0 & G_{f_z} & -G_{f_y} & G_{f_x} \\ -G_{f_z} & 0 & G_{f_x} & G_{f_y} \\ G_{f_y} & -G_{f_x} & 0 & G_{f_z} \end{bmatrix} \begin{bmatrix} \dot{G}_{e_x} \\ \dot{G}_{e_y} \\ \dot{G}_{e_z} \\ \dot{\gamma}_e \end{bmatrix} =$$

$$\begin{bmatrix} G_{f_z}\dot{G}_{e_y} - G_{f_y}\dot{G}_{e_z} + G_{f_x}\dot{\Psi}_e \\ -G_{f_z}\dot{G}_{e_x} - G_{f_x}\dot{G}_{e_z} + G_{f_y}\dot{\Psi}_e \\ G_{f_y}\dot{G}_{e_x} - G_{f_x}\dot{G}_{e_y} + G_{f_z}\dot{\Psi}_e \end{bmatrix}$$

where $\dot{\psi}_e$ is the difference between the projected gravity rate 9119 and the wheel speed derived from data received from the right/left wheel motors. The resulting matrix can be written as the following identity:

$$\omega_e = G_e \times \widehat{G_f} + \widehat{G_f} \cdot \dot{\gamma}_e$$

Filtered gravity vector 9125 can be translated into Euler pitch 9147 and Euler roll 9149: Euler angles:

$$\theta(\text{pitch}) = -a\sin(G_{fy})$$

$$\varphi(\text{roll}) = -a\tan(G_{fx}/G_{fz})$$

Filtered body rates can be translated into Euler pitch rate 9153 and Euler roll rate 9155:

$$\text{Pitch rate: } \dot{\theta} = \omega_{fx}\cos\varphi + \omega_{fz}\sin\varphi$$

$$\text{Roll rate: } \dot{\varphi} = \omega_{fx}\tan\theta\sin\varphi + \omega_{fy} - \omega_{fz}\tan\theta\cos\varphi$$

$$\text{Yaw rate: } \dot{\psi} = \omega_{fx}\frac{-\sin\varphi}{\cos\theta} + \omega_{fz}\frac{\cos\varphi}{\cos\theta}$$

Continuing to refer to FIG. 19A, IMU filter 9753 can filter gravity vector 9125 which can represent the inertial z-axis. IMU filter 9753 can provide a two-dimensional inertial reference in three-dimensional space. Measured body rates 9113 (measured, for example, from gyros that can be part of the inertial sensor packs, filtered gravity vector 9127 computed based on accelerometer data, and differential wheel speed 9139 (that can be computed from data received from the right/left wheel motor drives of left and right wheels 21201 (FIG. 1A) can be inputs to IMU filter 9753. IMU filter 9753 can compute pitch 9147, roll 9149, yaw rate 9151, pitch rate 9153, and roll rate 9155, for example, to be used to compute wheel commands 769 (FIG. 21A). Filtered output (G) and measured input ($G_{meas}$) are compared to produce an error, along with the comparison of gravity projected rate and differential wheel speed. There errors are fed back to the rate measurements to compensate for rate sensor bias. Filtered gravity vector 9125 and filtered body rates 9115 can be used to compute pitch 9147, roll 9149, yaw rate 9151, pitch rate 9153, and roll rate 9155.

Referring now to FIG. 19B, method 9250 for processing data using IMU filter 9753 (FIG. 19A) can include, but is not limited to including, subtracting 9251 gyro bias from gyro readings to remove the offset. Method 9250 can further include computing 9255 gravity rate vector 9143 (FIG. 19A) and projected gravity rate estimate 9119 (FIG. 19A) based at least on filtered body rates 9115 (FIG. 19A) and filtered gravity vector 9125 (FIG. 19A). Method 9250 can still further include subtracting 9257 the product of gain K1 and gravity vector error from gravity rate vector 9117 (FIG. 19A) and integrating 9259 filtered gravity rate 9143 (FIG. 19A) over time to produce filtered gravity vector 9125 (FIG. 19A). Gravity vector error 9129 (FIG. 19A) can be based at least on filtered gravity vector 9125 (FIG. 19A) and measured gravity vector 9127 (FIG. 19A). Method 9250 can further include computing 9261 pitch rate 9153 (FIG. 19A), roll rate 9155 (FIG. 19A), yaw rate 9151 (FIG. 19A), pitch, and roll based on filtered gravity rate vector 9125 (FIG. 19A) and filtered body rates 9115 (FIG. 19A). Gyro bias 9141 (FIG. 19A) can be computed by subtracting differential wheel speed 9139 (FIG. 19A) between wheels 21201 (FIG.

1A) from projected gravity rate estimate 9119 (FIG. 19A) to produce projected rate error 9137 (FIG. 19A). Further, the cross product of gravity vector error 9129 (FIG. 19A) and filtered gravity vector 9125 (FIG. 19A) can be computed and added to the dot product of filtered gravity vector 9125 (FIG. 19A) and projected gravity rate estimate error 9137 (FIG. 19A) to produce body rate error 9157 (FIG. 19A). Method 9250 can include computing gyro bias 9141 (FIG. 19A) based on applying gain K2 9133 (FIG. 19A) to the integration 9135 (FIG. 19A) over time of body rate error 9157 (FIG. 19A) to produce the gyro bias that is subtracted in step 9251. Equations describing method 9250 follow.

$$\dot{G}_m = \hat{G}_f \times \omega$$

where $\dot{G}_m$ is the measured gravity rate vector, $\hat{G}_f$ is the filtered gravity vector, and $\omega$ is the filtered body rate vector.

$$\dot{\gamma} = \hat{G}_f \cdot \omega$$

where $\dot{\gamma}$ is the projected rate.

$$\dot{\gamma}_e = \dot{\gamma} - V_{diff}$$

where $\dot{\gamma}_e$ is the projected rate error and $V_{diff}$ is the differential wheel speed.

$$\dot{G} = \dot{G}_m - K1 * G_{error}$$

where $\dot{G}$ is the filtered gravity rate, $\dot{G}_m$ is the measured gravity rate vector, K1 is a gain, and $G_{error}$ is the gravity error vector.

$$G_{error} = \hat{G}_f - G_m$$

where $G_m$ is the measured gravity vector from the accelerometer readings.

$$\dot{\omega}_e = \dot{G}_e \times \hat{G}_f + \hat{G}_f * \dot{\gamma}_e$$

where $\dot{\omega}_e$ is the body rate error vector and $\dot{G}_e$ is the gravity rate error vector.

$$\omega_e = K2 \; * \; \dot{\omega}_e / s$$

where $\omega_e$ is the integrated body rate error vector and K2 9133 (FIG. 19A) is a gain.

$$\omega_f = \omega_m - \omega_e$$

where $\omega_m$ is the measured body rate vector $$\hat{G}_f = \dot{G}/s$$

Referring to FIG. 20, field weakening can increase motor speed of mobility device 21513-1 (FIG. 1). Field weakening can cause motor 70707 (FIG. 6) to temporarily run faster at times when needed, for example, when unexpected circumstances arise. The electrical system equations of motion for a motor in a rotating reference frame are:

$$V_{dLN} = -\omega_e L_{LN} I_q + I_d R_{LN} \tag{1}$$

$$V_{qLN} = K_{eLN} w_m + I_q R_{LN} + \omega_e L_{LN} I_d \tag{2}$$

where $V_{dLN}$ is direct voltage line to neutral
$\omega_e$ is the electrical speed
$L_{LN}$ is the winding inductance line to neutral
$I_q$ is the quadrature current
$I_d$ is the direct current
$R_{LN}$ is the line to neutral resistance
$V_{qLN}$ is the quadrature voltage line to neutral
$K_{eLN}$ is the back electromagnetic field (EMF) line to neutral
$w_m$ is the mechanical speed Under normal field-oriented control of a brushless motor drive, where $I_d$ is regulated to zero, $$V_{dLN} = -\omega_e L_{LN} I_q \tag{3}$$

$$V_{qLN} = K_{eLN} w_m + I_q R_{LN} \tag{4}$$

To implement field weakening in a field-oriented control scheme, the term $\omega_e L_{LN} I_q$ may be increased by giving the direct current controller a non-zero current command, yielding a higher motor velocity and a diminished torque capability.

Continuing to refer to FIG. 20, field weakening in the rotating frame of reference can be implemented as follows. In a conventional drive without field weakening, the maximum command voltage is $V_{bus}/\sqrt{3}$, where $V_{bus}$ is bus voltage. As the quadrature command voltage increases, the motor drive voltage controller increases the duty cycle to match the commanded input until the duty cycle reaches its maximum and the back EMF voltage equals the command voltage. When direct current is regulated to zero, under normal motor control conditions without field weakening, $$V_{command} = V_{qLN} = K_{eLN} w_m + I_q R_{LN} \tag{5}$$

where $V_{command}$ is the commanded voltage from the powerbase.

Under field weakening conditions, the last term in equation (2) is non-zero yielding $$V_{command} = V_{qLN} - \omega_e L_{LN} I_d = K_{eLN} w_m + I_q R_{LN} \tag{6}$$

When the quadrature voltage saturates at the bus, the direct axis current can be commanded to a non-zero value to increase the motor speed to emulate a higher voltage command to the motor as seen by the powerbase wheel speed controller. By isolating the direct current component of equation (6), a direct current command may be computed:

$$I_d = -\frac{V_{command} - V_{qLN}}{\omega_e L_{LN}} \tag{7}$$

The velocity controllers can effectively command higher velocities to the motors, and the motors can behave as if they are receiving larger voltages.

Continuing to refer to FIG. 20, in some configurations, the addition of ~25 amps of direct current can nearly double the maximum speed of certain motors, allowing for relatively short bursts of relatively high speed when unexpected stabilization is required, for example. Current and voltage command limits can be computed as follows:

$$\text{Voltage Limit} = \text{PWM\_\%\_Limit} \times V_{bus}/\sqrt{3} = \sqrt{V_{qLN}^2 + V_{dLN}^2} \tag{8}$$

$$\text{Current Limit} = \text{Maximum Allowable Current (or FET temperature limit)} = \sqrt{I_{qLN}^2 + I_{dLN}^2} \tag{9}$$

The direct current controller can have priority when regulating the direct current, leaving the leftover to the quadrature controller and reporting the subsequent limits to processors A/B 39/41 (FIGS. 18C/18D).

Continuing to refer to FIG. 20, method 10160 for computing command voltage limits and current limits can include, but is not limited to including, computing 10161 the overall current limit $I_{lim}$ based on FET temperature, and computing the voltage limit $V_{lim}$ based on the measured bus voltage. ($V_{bus}/\sqrt{3}$). Method 10160 can include setting 10163 the quad voltage controller current limit based on the overall current limit and the commanded direct current from a previous measurement. Method 10160 can further include computing 10165 the direct current command, restricting the overall current limit $I_{lim}$, and computing the commanded direct voltage $V_{dLNCommanded}$. Method 10160 can include setting 10167 the quad voltage controller current limit based on the overall voltage limit and the commanded direct voltage from the direct current controller.

Continuing to refer to FIG. 20, in a conventional motor drive, voltage saturation is reported when the voltage command from the current controller saturates at the bus voltage limit $V_{bus}/\sqrt{3}$. When field weakening is used, the motor drive injects direct current to increase motor speed when the quadrature voltage saturates. The direct current controller only computes a direct current command when the commanded voltage has surpassed the capability of the bus to command quadrature voltage. Otherwise, direct currents are regulated to zero to maintain efficiency. Therefore, voltage saturation can be reported when the direct current controller attempts to regulate the direct current command to a maximum value, not when the quadrature voltage saturates at the bus voltage limit like a conventional drive. In a conventional motor drive, current saturation is reported when the current command from the voltage controller saturates at the maximum current, for example, but not limited to, 35 amps, unless otherwise limited by heat. However, the voltage controller's current command saturates when the maximum quadrature voltage command reaches the bus limit. If this remained the same for field weakening, the voltage controller would report a current saturation regardless of the actual quadrature current. Therefore, if the quadrature voltage controller is issuing a maximum current command and the quadrature current controller has not run out of voltage headroom, then maximum current has been reached. If the quadrature current controller has run out of voltage headroom, then the quadrature current controller is not capable of generating maximum current, and the current limit has not been reached.

Referring now to FIG. 20A, a method for field weakening can include, but is not limited to including, (1) measuring system parameters—phase currents, phase voltage and Hall sensors—and calculating motor position and speed from the Hall sensor measurements, and (2) converting the phase current and phase voltage to current in a stationary frame. The phase current and phase voltage can be converted to a stationary frame using a Clark transform tied to the stator.

$$\begin{bmatrix} I_x \\ I_y \end{bmatrix} = \begin{bmatrix} \frac{2}{3} & -\frac{1}{3} & -\frac{1}{3} \\ 0 & \frac{\sqrt{3}}{3} & -\frac{\sqrt{3}}{3} \end{bmatrix} \begin{bmatrix} I_A \\ I_B \\ I_C \end{bmatrix}$$

where $I_x/I_y$ is the stationary frame current, and $I_A/I_B/I_C$ is the phase current. The Method can include (3) converting the stationary phase current and phase voltage to a synchronous rotary frame tied to the rotor using a Park transform.

$$\begin{bmatrix} I_d \\ I_q \end{bmatrix} = \begin{bmatrix} \sin\theta_e & -\cos\theta_e \\ \cos\theta_e & \sin\theta_e \end{bmatrix} \begin{bmatrix} I_x \\ I_y \end{bmatrix}$$

where $I_d$ is the direct current and $I_q$ is the quadrature current. The method can include (4) calculating the minimum and maximum $I_d$ and $I_q$ commands from the measured motor parameters. The constraints for this calculation can include (a) that the following relationships hold for the motor parameters in quadrature space:

$$V_q = K_e^* w_e + R^* I_q + w_e^* L^* I_d$$

$$V_d = -w_e^* L^* I_q + R^* I_d$$

and (b) that the following limits are maintained:

i. the vector sum of $V_d$ and $V_q$ do not exceed the bus voltage $$V_{d\_cmd}^2 + V_{q\_cmd}^2 \le V_{bus}^2$$

ii. the vector sum of $I_d$ and $I_q$ do not exceed the current limit $$I_d^2 + I_q^2 < I_{max}^2$$

From $I_q^2 + I_d^2 \le I_{driveMax}^2$, step (4) can include determining where the measured $I_q$ line 3005 intersects bus voltage limit circle 3001 and drive current limit circle 3003 defining the allowed limits for bus voltage and drive current to determine the allowed $I_d$, and determining where the measured $I_d$ line 3007 intersects bus voltage limit circle 3001 and drive current limit circle 3003 defining allowed limits for bus voltage and drive current to determine the allowed $I_q$. The locus of allowed limits can be found in the intersection 3009 of circles 3001 and 3003. The method can include (5) calculating the desired $I_d$ from the calculated voltage, and limiting the desired $I_d$ according to the limits in step (1). To calculate the desired $I_d$, for a device with a DC motor with a very large bus voltage $$V = K_e \cdot \omega_e + I \cdot R$$

$$\omega_{e,max} = \frac{V_{bus}}{K_e}$$

The device runs out of torque at maximum speed, I→0. Thus $$V_{q,max} = \sqrt{V_{bus}^2 - V_d^2}$$

$$\text{If } V < V_{q,max},$$

$$V_{q,cmd} = V$$

$$I_{d,cmd} = 0$$

$$\text{If } V > V_{q,max},\ V_{q,cmd} = V_{q,max}$$

To determine the desired $I_d$, with $I_q$=0 and $w_{e,max}$ =$V_{cmd}$/$K_e$, (from DC motor equivalent)

$$V_d = R \cdot I_{d\_des}$$

$$V_q = K_e \cdot \omega_{e,max} + \omega_{e,max} \cdot L \cdot I_{d\_des}$$

Solving for $I_d$, $$\sqrt{V_{bus}^2 - (R \cdot I_{d\_des})^2} = \omega_{e,max}(K_e + L \cdot I_{d\_des})$$

$$V_{bus}^2 - R^2 I_{d\_des}^2 = \omega_{e,max}^2 (K_e^2 + 2K_e \cdot L \cdot I_{d\_des} + L^2 \cdot I_{d\_des}^2)$$

$$(R^2 + \omega_{e,max}^2 \cdot L^2) I_{d\_des}^2 + 2\omega_{e,max}^2 \cdot K_e \cdot L \cdot I_{d\_des} - V_{bus}^2 = 0$$

$$A_{weMax} I_{d\_des}^2 + 2C_{weMax} I_{d\_des} - V_{bus}^2 = 0$$

$$I_{d\_des}^2 + 2\frac{C_{weMax}}{A_{weMax}} I_{d\_des} - \frac{V_{bus}^2}{A_{weMax}} = 0$$

$$I_{d\_des} = -\frac{C_{weMax}}{A_{weMax}} - \frac{1}{2}\text{sqrt}\left(\left(\frac{C_{weMax}}{A_{weMax}}\right)^2 + 4\left(\frac{V_{bus}^2}{A_{weMax}}\right)\right)$$

The method can include (6) closing the loop on the commanded motor voltage by closing the loop on measured quadrature voltage, calculating the desired quadrature current, and limiting the desired quadrature current according to step (5). The method can include (7) closing the loop on the commanded direct current by closing the loop on measured direct current, calculating the desired direct voltage, limiting the desired direct voltage to the bus voltage command, and feeding forward the effect of wheel speed and measured quadrature current: $I_{d\_FFcmd}$ =-$w_e$*L*$I_q$ The method can include (8) closing the loop on the commanded quadrature current by closing the loop on measured quadrature current, calculating the desired quadrature voltage, limiting the desired quadrature voltage to the bus voltage command, and feeding forward the effect of wheel speed on measured direct current.

$$I_{q\_FFcmd} = K_e{}^* w_e + w_e{}^* L^* I_d$$

The method can include (9) adjusting the measured motor angle for the time t required to perform the motor command calculations stated herein.

Measured Angle=Measured angle+Δ*t**measured motor speed*

The method can include (10) converting the direct and quadrature command voltage to the stationary frame using an inverse Park transform.

$$\begin{bmatrix} V_x \\ V_y \end{bmatrix} = \begin{bmatrix} \sin\theta_e & \cos\theta_e \\ -\cos\theta_e & \sin\theta_e \end{bmatrix} \begin{bmatrix} V_d \\ V_q \end{bmatrix}$$

The method can include (11) converting stationary frame voltage commands to phase voltage commands using an inverse Clark transform.

$$\begin{bmatrix} V_A \\ V_B \\ V_C \end{bmatrix} = \begin{bmatrix} 1 & 0 \\ -\frac{1}{2} & \frac{\sqrt{3}}{2} \\ -\frac{1}{2} & -\frac{\sqrt{3}}{2} \end{bmatrix} \begin{bmatrix} V_x \\ V_y \end{bmatrix}$$

where $V_q$: Quadrature Voltage $V_d$: Direct Voltage $V$: Motor Voltage = $\sqrt{(V_d{}^2 + V_q{}^2)}$ $V_{bus}$: $V_{supply}/\sqrt{3}$: Bus line to neutral voltage $I_q$: Quadrature Current $I_d$: Direct Current $I$: Motor Current = $\sqrt{(I_d{}^2 + I_q{}^2)}$ $L$: Line to Neutral Inductance (Henry)

$R$: Line to Neutral Resistance (Ohm)

$K_e$: Line to Neutral Motor Constants (Volt/(radians/second))

$w_e$: Electrical speed in (radians/second)

$V_{cmd}$: User commanded voltage

The method can include (6) closing the loop on the commanded motor voltage by closing the loop on measured quadrature voltage, calculating the desired quadrature current, and limiting the desired quadrature current according to step (5). The method can include (7) closing the loop on the commanded direct current by closing the loop on measured direct current, calculating the desired direct voltage, limiting the desired direct voltage to the bus voltage command, and feeding forward the effect of wheel speed and measured quadrature current: $I_{d\_FFCmd}$ =−$w_e$*L*$I_q$ The method can include (8) closing the loop on the commanded quadrature current by closing the loop on measured quadrature current, calculating the desired quadrature voltage, limiting the desired quadrature voltage to the bus voltage command, and feeding forward the effect of wheel speed on measured direct current.

$$I_{q\_FFcmd} = K_e{}^*w_e + w_e{}^*L^*I_d$$

The method can include (9) adjusting the measured motor angle for the time t required to perform the motor command calculations stated herein.

Measured Angle=Measured angle+$\Delta t$*measured motor speed

The method can include (10) converting the direct and quadrature command voltage to the stationary frame using an inverse Park transform.

$$\begin{bmatrix} V_x \\ V_y \end{bmatrix} = \begin{bmatrix} \sin\theta_e & \cos\theta_e \\ -\cos\theta_e & \sin\theta_e \end{bmatrix} \begin{bmatrix} V_d \\ V_q \end{bmatrix}$$

The method can include (11) converting stationary frame voltage commands to pha: voltage commands using an inverse Clark transform.

$$\begin{bmatrix} V_A \\ V_B \\ V_C \end{bmatrix} = \begin{bmatrix} 1 & 0 \\ -\frac{1}{2} & \frac{\sqrt{3}}{2} \\ -\frac{1}{2} & -\frac{\sqrt{3}}{2} \end{bmatrix} \begin{bmatrix} V_x \\ V_y \end{bmatrix}$$

where $V_q$: Quadrature Voltage $V_d$: Direct Voltage $V$: Motor Voltage $= \sqrt{(V_d{}^2 + V_q{}^2)}$ $V_{bus}$: $V_{supply}/\sqrt{3}$: Bus line to neutral voltage $I_q$: Quadrature Current $I_d$: Direct Current $I$: Motor Current $= \sqrt{(I_d{}^2 + I_q{}^2)}$ $L$: Line to Neutral Inductance (Henry)

$R$: Line to Neutral Resistance ($\Omega$)

$K_e$: Line to Neutral Motor Constants (Volt/(radians/second))

$w_e$: Electrical speed in (radians/second)

$V_{cmd}$: User commanded voltage

Referring now primarily to FIG. 21A, to enable failsafe operation, the MD can include, but is not limited to including, redundant subsystems by which failures can be detected, for example, by comparison of data associated with each subsystem to data associated with the remaining subsystems. Failure detection in redundant subsystems can create fail-operative functionality, wherein the MD can continue to operate on the basis of the information provided by the remaining non-failing subsystems, if one subsystem is found to be defective, until the MD can be brought to a safe mode without endangering the user. If a failed subsystem is detected, the remaining subsystems can be required to agree to within prescribed limits in order for operation to continue, and operation can be terminated in case of disagreement between the remaining subsystems. Voting processor 329 can include, but is not limited to including, at least one way to determine which value to use from redundant subsystems, and in some configurations, voting processor 329 can manage different types of data in different ways, for example, but not limited to, calculated command data and inertial measurement unit data.

Continuing to refer primarily to FIG. 21A, voting processor 329 can include, but is not limited to including, initial vote processor 873, secondary vote processor 871, and tertiary vote processor 875. Initial vote processor 873 can include, but is not limited to including, computer instructions to average sensor data 767 or command data 767A, from each processor A1/A2/B1/B2 43A-43D (FIG. 18C/18D) (referred to herein as processor values). Initial vote processor 873 can further include computer instructions to compute the absolute value difference between each processor value and the average, and discard the highest absolute value difference leaving three remaining processor values. Secondary vote processor 871 can include, but is not limited to including, computer instructions to compute differences between the remaining processor values and each other, to compare the differences to a preselected threshold, to compare the processor values that have the highest difference between them to the remaining value, to vote out the processor value with the highest difference from the remaining value, to compare the voted out values to the remaining values, to vote out any difference above the pre-selected threshold, if any, and to select a remaining processor values or an average of the processor values, depending, for example, on the type of data the processor values represent. Tertiary vote processor 875 can include, but is not limited to including, computer instructions to, if there are no differences greater than the pre-selected threshold, compare the discarded value to the remaining values, vote out the discarded value if there are any differences greater than the pre-selected threshold, and select one of the remaining processor values or an average of the remaining processor values depending, for example, on the type of data the processor values represent. Tertiary vote processor 875 can also include computer instructions to, if there are no differences greater than the pre-selected threshold, select a remaining processor value or an average of the remaining processor values. It can be possible that the discarded value is not voted out and all processor values remain to be selected from or averaged. Tertiary vote processor 875 can still further include computer instructions to, if a processor value is voted out a pre-selected number of times, raise an alarm, and, if the voting scheme fails to find a processor value that satisfies the selection criteria, increment the frame counter. Tertiary vote processor 875 can also include computer instructions to, if the frame counter has not exceeded a pre-selected number of frames, discard the frame containing the processor values in which the voting scheme failed to find a processor value that satisfies the selection criteria, and to select the last frame with at least one processor value that could be used. Tertiary vote processor 875 can also include computer instructions, if the frame counter is greater than a pre-selected number of frames, to move the MD to a failsafe mode.

Referring now to FIGS. 21B and 21C, method 150 for resolving which value to use from redundant processors, referred to herein as "voting", can include, but is not limited to including, initializing 149 a counter, averaging 151 values, for example, but not limited to, sensor or command values, from each processor 43A-43D (FIG. 21A) (referred to herein as processor values), computing 153 the absolute value difference between each processor value and the average, and discarding the highest difference. Method 150 can further include computing 155 differences between the remaining processor values and each other. If 157 there are any differences greater than a preselected threshold, method 150 can include comparing 167 the values that have the highest difference between them to the remaining value, voting out 169 the value with the highest difference from the remaining value, comparing 171 the voted out values to the remaining values, and voting out 173 any difference above the pre-selected threshold and selecting one of the remaining processor values or an average of the processor values. For example, if processor values from processors A1 43A (FIG. 21A), B1 43C (FIG. 21A), and B2 43D (FIG. 21A) remain, the processor value (or an average of the processor values) from any of the remaining processors can be chosen. If 157 there are no differences greater than the pre-selected threshold, method 150 can compare 159 the voted out value to the remaining values. If 161 there are any differences greater than the pre-selected threshold, method 150 can include voting out 163 the value voted out in the compare 159 step, and selecting one of the remaining processor values or an average of the remaining processor values. If 161 there are no differences greater than the pre-selected threshold, method 150 can include selecting 165 one of the remaining processor values or an average of the remaining processor values. If 185 a processor value is voted out a pre-selected number of times, method 150 can include raising 187 an alarm. If 175 the voting scheme fails to find a processor value that satisfies the selection criteria, method 150 can include incrementing 177 the counter. If 179 the counter has not exceeded a pre-selected number, method 150 can include discarding the frame having no remaining processor values and selecting 181 a previous frame having at least one processor value that meets the selection criteria. If 179 the frame counter is greater than the pre-selected number, method 150 can include moving 183 the MD to a failsafe mode.

Referring now primarily to FIG. 21D, example1 519 of voting can include first computations 521 in which processor values for processors A1-B2 43A-43D (FIG. 21A) can be averaged and can be compared to the computed average. The processor having the largest difference from the average, in example1 519, processor A1 43A (FIG. 21A), can be discarded. Processor values from processor B2 43D (FIG. 21A) could have instead been discarded. Second computations 523 can include comparisons between the processor values of the remaining three processors A2/B1/B2 43B-43D (FIG. 21A). Comparisons can betaken between the discarded processor value of processor A1 43A (FIG. 21A) and the processor values of the three remaining processors A2/B1/B2 43B-43D (FIG. 21A). In example1 519, none of the differences exceeds the exemplary threshold of fifteen. The voting result from example1 519 is that any of the processor values from processors A1/A2/B1/B2 43A-43D (FIG. 21A) can be selected.

Referring now primarily to FIG. 21E, example2 501 of voting can include first computations 507 in which processor values for processors A1-B2 43A-43D (FIG. 21A) can be averaged and can be compared to the computed average. The processor having the largest difference from the average, in example2 501, processor A1 43A (FIG. 21A), is discarded. Second computations 509 can include comparisons between processor values of the remaining three processors A2/B1/B2 43B-43D (FIG. 21A). In example2 501, none of the differences exceeds the exemplary threshold of fifteen. Comparisons can be taken between the processor value of discarded processor A1 43A (FIG. 21A) and the processor values of the three of remaining processors A2/B1/B2 43B-43D (FIG. 21A). In example2 501, one of the differences, the difference between the processor values of processor A1 43A (FIG. 21A) and processor B2 43D (FIG. 21A), exceeds the exemplary threshold of fifteen. Since one difference exceeds the exemplary threshold, the processor value from discarded processor A1 43A (FIG. 21A) can be voted out. The voting result from example2 501 is that any of processor values from processors A2/B1/B2 43A-43D (FIG. 21A) can be selected because processor A1 43A (FIG. 21A) was voted out.

Referring now primarily to FIG. 21F, example3 503 of voting can include first computations 511 in which processor values for processors A1-B2 43A-43D (FIG. 21A) can be averaged and can be compared to the computed average. The processor having the largest difference from the average, in example3 503, processor A1 43A (FIG. 21A), is discarded. Second computations 513 can include comparisons between processor values of the remaining three processors A2/B1/B2 43B-43D (FIG. 21A). In example3 511, none of the differences exceeds the exemplary threshold of fifteen. Comparisons can be taken between the processor value of discarded processor A1 43A (FIG. 21A) and the processor values of the three remaining processors A2/B1/B2 43B-43D (FIG. 21A). In example3 511, two of the differences, the differences between processor A1 43A (FIG. 21A) and processors B1/B2 43C/43D (FIG. 21A), exceed the exemplary threshold of fifteen. Since at least one difference exceeds the exemplary threshold, the processor value from discarded processor A1 43A (FIG. 21A) can be voted out.

Referring now primarily to FIG. 21G, example4 505 of voting can include first computations 515 in which processor values for processors A1-B2 43A-43D (FIG. 21A) can be averaged and can be compared to the computed average. The processor having the largest difference from the average, in example4 515 processor B2 43D (FIG. 21A), is discarded. Second computations 517 can include comparisons between processor values of the remaining three processors A1/A2/B1 43A-43C (FIG. 21A). In example4 505, the difference between processor values of processors A1/B1 43A/C (FIG. 21A) exceeds the exemplary threshold of fifteen. Comparisons can be taken between the processor values of processors A1/B1 43A/C (FIG. 21A) with remaining processor A2 43B (FIG. 21A). In example4 505, the difference between the processor values of processors A1/A2 43A/B (FIG. 21A) equals the threshold value of fifteen, therefore, between the two processors, A1/B1 43A/C (FIG. 21A), processorAl 43A (FIG. 21A) can be discarded. Comparisons can be taken between the processor values of discarded processors A1/B2 43A/43D (FIG. 21A) and the processor values of the two remaining processors A2/B1 43B-43C (FIG. 21A). In example4 505, one of the differences, the difference between the processor values of processor A1 43A (FIG. 21A) and processor A2 43B (FIG. 21A), does not exceed the exemplary threshold of fifteen. Therefore, the processor value from processors A1 and B2 43A/D (FIG. 21A) can be voted out. The voting result from example4 505 is that the processor value from either processor A2 43B (FIG. 21A) or B1 43C (FIG. 21A) can be selected and A2 43B (FIG. 21A) is selected in example4 505.

Referring now to FIGS. 21I and 21J, when communications have been lost among processors within the MD, the voting result can be affected. Alternate method 53000 for resolving which value to use from redundant processors can take into account a loss of communications among processors. Alternate method 53000 can include reading the inertial estimates from all the processors, selecting the controller pitch and roll values from the IMU voting, determining which processor(s) to discard, voting for valid processor values, processing the voting results, and averaging the valid processor values. Alternate method 53000 can include reading 53001 sensor data from the processor that is local to the sensor and executing method 53000. If 53003 the sensor data are not valid, method 53000 can include marking all sensor data as voted out and storing 53005 the data in a data structure. Valid sensor data include data that are within a pre-selected range and data that have arrived from a sensor that has not been permanently voted out. If 53003 the sensor data are valid, method 53000 can include storing 53005 the data in a data structure. Method 53000 can include reading sensor data from processors that are remote to the processor executing method 53000, and adding 53004 data from the remote processors to the data structure under certain pre-selected conditions. The pre-selected conditions can include, but are not limited to including, adding data (1) when communications with the remote processors are in tact, (2) if the data are declared valid by the respective remote processors, and (3) if the sensor has not been previously permanently voted out. Method 53000 can include creating 53011 a list of processors having valid sensor data, and, for each sensor value or natural combination of sensor values from the list of processors having valid sensor data, determining 53013 the average value of the sensor values. Method 53000 can include ordering 53015 the list of processors with the highest ranking processor being the processor having the sensor values closest to the average value. If 53017 there are more than three valid data sets, method 53000 can include performing 53019 a three-way vote on the sensor values of the first three processors on the ordered list, updating the data structure with voted out indications for voted out data, updating the data structure with voted out indications if the fourth processor's sensor data is voted out after comparison with the remaining processors' sensor data. If 53021 there are three valid data sets, method 53000 can include performing 53023 a three-way vote on the sensor values of the three processors, and updating the data structure with voted out indications if data are voted out. If 53025 there are two valid data sets, method 53000 can include performing 53027 a two-way vote, and if the two processors disagree, updating the data structure with voted out indications for both processors' data. Method 53000 can include incrementing 53029 a counter for each sensor when the data structure has been updated with voted out indications. If 53031 the counter exceeds a pre-selected threshold, method 53000 can include permanently voting out 53033 the sensor, and discontinuing 53035 use of the voted out sensor. If 53037 at least two processors' data are not permanently voted out, method 53000 can include averaging 53039 the two processors' data, and adding 53041 the average to the inertial vector. If 53037 at least two processors' data are not available, method 53000 can include declaring 53043 a mismatch in which no sensor data is valid, and entering 53045 failsafe mode.

Referring now to FIG. 22A, the MD can operate several modes. In standard mode 100-1, the MD can operate on two drive wheels and two caster wheels. Standard mode 100-1 can provide turning performance and mobility on relatively firm, level surfaces (e.g., indoor environments, sidewalks, pavement). Seat tilt can be adjusted to provide pressure relief, tilting the seat pan and back together. From standard mode 100-1, users can transition to 4-Wheel 100-2, docking 100-5, stair 100-4, and remote 100-6 modes, and, through other modes, into balance mode 100-3. Standard mode 100-1 can be used where the surfaces are smooth and ease of turning is important, for example, but not limited to, positioning a chair at a desk, maneuvering for user transfers to and from other supports, and driving around offices or homes. Entry into standard 100-1, remote 100-6, and docking mode 100-5 can be based upon in which operating mode the MD is currently, and upon cluster/wheel velocities. In enhanced mode, or 4-Wheel mode 100-2, the MD can operate on four drive wheels, can be actively stabilized through onboard sensors, and can elevate the main chassis, casters, and seating. 4-Wheel mode 100-2 can provide the user with mobility in a variety of environments, enabling users to travel up steep inclines and over soft, uneven terrain. In 4-Wheel mode 100-2, all four drive wheels can be deployed and the caster wheels can be retracted by rotating the MD. Driving four wheels and equalizing weight distribution on the wheels can enable the MD to drive up and down steep slopes and through many types of gravel, sand, snow, and mud. Cluster rotation can allow operation on uneven terrain, maintaining the center of gravity of the device over the wheels. The drive wheels can drive up and over curbs. This functionality can provide users with mobility in a wide variety of outdoor environments. The seat height can be adjusted by the user to provide necessary clearance over obstacles and along slopes. Users can be trained to operate in 4-Wheel mode directly up or down slopes of up to 10°, and stability can be tested to 12° to demonstrate margin. The MD can operate on outdoor surfaces that are firm and stable but wet.

Continuing to refer to FIG. 22A, frost heaves and other natural phenomena can degrade outdoor surfaces, creating cracks and loose material. In 4-Wheel mode 100-2, the MD can operate on these degraded surfaces under pre-selected conditions. 4-Wheel mode 100-2 can be available for selection by users from standard 100-1, balance 100-3, and stair 100-4 modes, for example. Users may transition from 4-Wheel mode 100-2 to each of these other modes. In the event of loss of stability in balance mode 100-3 due to a loss of traction or driving into obstacles, the MD can attempt to execute an automatic transition to 4-Wheel mode 100-2. Sensor data and user commands can be processed in a closed loop control system, and the MD can react to changes in pitch caused by changes in terrain, external impacts, and other factors.

Referring now to FIG. 22E, 4-Wheel mode 100-2, as described in detail in U.S. Pat. No. 6,571,892, entitled Control System and Method, issued on Jun. 3, 2003 ('89 s), incorporated herein by reference in its entirety, can provide support for traversal of uneven terrain by the MD. 4-Wheel mode 100-2 can use both wheel and cluster motors to maintain stability. Traversing obstacles can be a dynamic activity, with the user and the MD possibly pitching fore and aft as the wheels follow the terrain and the cluster motor compensates for the changing slope of the terrain. 4-Wheel mode 100-2 can protect the user if necessary, and can coordinate the wheel and cluster motors to keep the MD underneath the user. 4-Wheel mode 100-2 can give the user the ability to traverse uneven terrain such as ramps, gravel, and curbs. 4-Wheel mode 100-2 can be used to catch automatic transitions from balance mode 100-3 if the two-wheel controller fails (due to a loss of traction, a collision, etc.), and normal transitions from stair mode 100-4 onto a top landing. In 4-Wheel mode 100-2, the wheel and cluster servos can dynamically stabilize the MD when the MD encounters difficult terrain, when center of gravity 704 is outside the wheelbase or only one set of wheels in on the ground, and situations between those extremes. The cluster servo can react to pitch errors 74003 and rate errors. Pitch error 74003 is the amount by which center of gravity 704 is offset from vertical axis 74005 passing though cluster 716. Center of gravity 704 represents the center of gravity of the MD, the user, and any payload which the user may be carrying. In some configurations, in 4-Wheel mode 100-2, center of gravity 704 can be located over center point 718 of cluster 716. In some configurations, vertical axis 74005 can pass through center point 718 of cluster 716. In some configurations, vertical axis 74005 can pass through any portion of cluster 716 disposed between transverse axes passing through the center of either wheel 714 or wheel 712 (e.g., the footprint). If the axis passes through a portion of cluster 716 that does not pass through center point 718, the distance, where the vertical axis passes through the cluster 716, from center point 718 of cluster 716 can be factored into calculations requiring the parameters described herein. When controlling the MD based upon linear displacement, the pitch error in 4-Wheel mode 100-2 can be based upon radius L 74001 and frame pitch θ 74003. The pitch error is calculated by differencing the desired and measured pitch. $\tilde{\theta}=L\sin\theta_{des}-L\sin\theta$. The desired pitch is centered around the pitch that would put center of gravity 704 directly over center point 718 or through a portion of cluster 716 that does not pass through center point 718 when the distance from center point 718 is factored in. Further computations based on the pitch error can complete the control loop for 4-Wheel mode 100-2 as described in '892 . In some configurations, to accommodate heavier and lighter users, control of the MD can be based at least on the length of the line between seat 704-1 and the head of the user, and the cosine of the angle between the position of the user and vertical.

Continuing to refer to FIG. 22A, in balance mode 100-3, the MD can operate on two drive wheels at elevated seat height and can be actively stabilized through onboard sensors. Balance mode 100-3 can provide mobility at an elevated seat height. In balance mode 100-3, the MD can mimic human balance, i.e. the MD can operate on two wheels. Additional height comes in part from rotating the clusters to put a single pair of wheels directly under the user. The seat height may be adjusted by the user as well. Balance mode 100-3 can be requested from several modes, and balance mode 100-3 can be entered if the wheel and cluster motors are substantially at rest and the MD is level. Calibration mode can be used to determine a user's center of gravity for a specific MD. In calibration mode the user can achieve balance at specified calibration points while the controller averages the pitch of the MD. The averaged value can be stored, along with seat height and cluster position, for use in calculating the user center of gravity (CG) fit parameters. The CG fit parameters can be used to determine the MD/user's center of gravity. In stair mode 100-4, the MD can use wheel clusters to climb stairs and can be actively stabilized. The MD can climb stairs by rotating the cluster while the machine is balanced—at least partially—by the user or an attendant. The user can control the motion of the cluster by offsetting the MD from the balance point. If the MD is pitched forward, the cluster can rotate in the downward climbing direction (stairs can be climbed with the user facing away from the stairs). Conversely, if the MD is pitched backwards, the cluster can rotate in the upward climbing direction. The user can balance the MD by applying moderate forces to the handrail, or alternately an assistant can balance the MD using an attendant handle on the MD. Stair mode 100-4 can enable users to ascend and descend stairs. If the MD begins to lose stability in stair mode 100-4, the MD can be made to fall on its back instead of falling forward to provide a safety feature for the user.

Continuing to refer to FIG. 22A, in remote mode 100-6, the MD can operate on four drive wheels, unoccupied. Remote mode 100-6 can provide the user with a way to operate the device when not seated in it. This mode can be useful for maneuvering the device for transfers, parking the device after a transfer (e.g., after transferring to bed the user can move the device out of the way), and other purposes. Remote mode 100-6 can be used in any environment where standard mode 100-1 may be used, as well as on steep ramps. In remote mode 100-6, the MD can be operated with the four drive wheels on the ground and the frame lean reclined such that the casters can be raised. Joystick 70007 (FIG. 12A) can be inactive unless the frame lean is at a rear detent. The rear detent can be selected to provide ample caster clearance for climbing forward up relatively steep inclines such as, for example, a 20° incline. UC 130 (FIG. 12A) can be in remote communications, for example, through a wireless interface, with a device that can control the MD in remote mode 100-6. In some configurations, the speed of the MD can be limited when a UC is managed remotely. In optional docking mode 100-5, the MD can operate on four drive wheels and two caster wheels, therefore lowering the main chassis. Docking mode 100-5 can allow the user to maneuver the MD for engagement with a docking base. Docking mode 100-5 can operate in a configuration that can lower the docking attachments to engage the MD with a vehicle docking base. Docking mode 100-5 can be used within a motor vehicle that is configured with a docking base, for example. Utility mode can be used to access various device features to configure the MD, or diagnose issues with the MD. Utility mode can be activated when the device is stationary, and in standard mode 100-1.

Continuing to refer to FIG. 22A, the MD can enter standard mode 100-1 when caster wheels 21001 (FIG. 7) are deployed, when on four drive wheels 21201 (FIG. 1A) with the frame lean reclined, or when the seat is being adjusted during a transition. In standard mode 100-1, the MD can use inertial data to set lean limits, seat height limits, speeds and accelerations to improve the stability of the MD. If inertial data are unavailable, speeds, accelerations, seat height and lean limits can take on default values that can be, but are not limited to being, conservative estimates. In standard mode 100-1, active control may not be needed to maintain the MD in an upright position. The MD can continue to be in standard mode 100-1 after failure of one of the redundant systems. In some configurations, entry into standard mode 100-1 can be dependent upon the current mode of the MD. In some configurations, entry into standard mode 100-1 can depend at least upon cluster and wheel velocities. When the MD is in remote mode 100-6, entry into standard mode 100-1 can be based upon the movement of the MD, and the position of caster wheels 21001 (FIG. 7). In some configurations, entry into standard mode 100-1 can be based on the movement of the MD. In some configurations, entry into standard mode 100-1 can activate a seat controller and can set the MD in a submode based on the current mode of the MD. Lean and seat limits of the MD, joystick status, and cluster velocity can be based on the submode. While in standard mode 100-1, the MD can receive and filter desired fore/aft and yaw velocities, calculate cluster velocity, wheel and yaw positions, and velocity errors, and can limit velocities if required. While in standard mode 100-1, the MD can apply wheel and cluster brakes to, for example, conserve power when the MD is not moving, can monitor wheel speed, and can disable joystick 70007 (FIG. 12A). In some configurations, if data originating at IMU 50003 (FIG. 15C) are inaccurate, the MD can automatically adjust back lean limits and accelerations. In some configurations, when the joystick command is the reverse of the current velocity, braking can be adjusted to minimize any abrupt change from a reverse command to a forward command that might occur and that might cause problems in stability on inclines.

Continuing to refer to FIG. 22A, in some configurations, there can be multiple machine statuses—e.g., but not limited to, driving, reclining, and transitioning—in standard mode 100-1. In driving status, caster wheels 21001 (FIG. 7) can touch the ground and forward drive wheels 21203 (FIG. 1A) can be held off the ground. In reclining status, caster wheels 21001 (FIG. 7) can be raised off the ground, the cluster can be moved by the user, and the joystick can be disabled. In transitioning status, the MD can be transitioning to 4-Wheel mode 100-2. In some configurations, transitioning can include phases such as leaning the frame back and raising/lowering the seat to access/exit 4-Wheel mode 100-2. In some configurations, a reclining angle limit for reclining status can be based on a forward lean limit that can be set to a cluster angle that can correspond to a seat pan angle of, for example, but not limited to, approximately 6° reclined from horizontal. In some configurations, the back frame lean limit for standard mode 100-1 can be based on parameters related to the center of gravity and the cluster angle. Rearward static stability can be based on the center of gravity with respect to rear drive wheel 21201 (FIG. 1A). In some configurations, a rear lean limit can be set to, for example, 13° less than rearward static stability to provide a stability margin, and there can be an absolute limit on the rear lean limit. In some configurations, additional rearward frame lean may not be allowed if the center of gravity location is outside of the wheel drive wheel base, the incline is excessive for operation in standard mode 100-1, or for other reasons.

Continuing to refer to FIG. 22A, in some configurations, joystick 70007 (FIG. 12A) can be disabled in standard mode 100-1 if caster wheels 21001 (FIG. 7) have moved off the ground due to, for example, but not limited to, a frame lean or seat height adjustment. In some configurations, joystick 70007 (FIG. 12A) can be disabled whenever the wheel motors are hot and the desired wheel velocity is in the same direction as the wheel command or the desired yaw velocity is in the same direction as the yaw command, but enabled otherwise. Desired velocity commands can be obtained from UC 130 (FIG. 12A). Desired velocity commands can be shaped to provide acceptable accelerations and braking rates for fore/aft velocity control in standard mode 100-1. Filters can be used to shape the commands to acceptable trajectories. The corner frequency of the filters can vary depending upon whether the MD is accelerating or braking. The corner frequency of the yaw filter can be reduced when the MD is traveling slowly. In some configurations, the corner frequency can be scaled when the wheel velocity is less than, for example, but not limited to, a pre-selected value such as, for example, but not limited to, 1.5 m/s. In some configurations, a filter coefficient can be scaled linearly as the wheel velocity decreases, and the decrease can be limited to a pre-selected value for example, but not limited to, 25 % of the original value. In some configurations and under certain conditions, if the MD is accelerating on level ground, the filter corner frequency can be set to a pre-selected value such as, for example, but not limited to, 0.29 Hz. Under other conditions, for example, if the MD is on a slope of, for example, up to a pre-selected value such as, for example, but not limited to, 5°, acceleration can be reduced as a linear function of pitch, a maximum corner frequency can be set to a pre-selected value such as, for example, but not limited to, 0.29 Hz, and a minimal corner frequency can be set to a pre-selected value such as, for example, but not limited to, 0.15 Hz. In some configurations, if the MD is on a slope of, for example, greater than a pre-selected value such as, for example, but not limited to, 5°, and other conditions are met, a minimal corner frequency of a pre-selected value such as, for example, but not limited to, 0.15 Hz can be used to reduce accelerations. The rearward speed can be limited to a pre-selected value such as, for example, but not limited to, 0.35 m/s if the MD is on an incline greater than a pre-selected value, for example, but not limited to, 5° and other conditions are met. In some configurations, and in some modes and/or when the MD is braking, the filter corner frequency can be set to a constant.

Referring now primarily to FIG. 22B, in some configurations, the MD can support at least one operating mode that can include, but is not limited to including, standard mode 100-1, enhanced mode 100-2, balance mode 100-3, stair mode 100-4, docking mode 100-5, and remote mode 100-6. Service modes can include, but are not limited to including, recovery mode 100-7, failsafe mode 100-9 (FIG. 22C), update mode 100-10 (FIG. 22C), self-test mode 100-13 (FIG. 22C), calibrate mode 100-8, power on mode 100-12 (FIG. 22C), and power off mode 100-11 (FIG. 22C). Mode descriptions and screen flows that accompany the modes are described herein. With respect to recovery mode 100-7, if a power off occurs when the MD is not in one of a pre-selected set of modes, such as for example, but not limited to, standard mode 100-1, docking mode 100-5, or remote mode 100-6, the MD can enter recovery mode 100-7 to safely reposition the MD into the driving position of standard mode 100-1, for example. During recovery mode 100-7, powerbase controller 100 (FIG. 22D) can select certain components to activate such as, for example, seat motor drive A/B 25/37 (FIG. 18C/18D) and cluster motor drive A/B 1050/27 (FIG. 18C/18D). Functionality can be limited to, for example, controlling the position of the seat and cluster 21100 (FIG. 6A). In calibrate mode 100-8, powerbase controller 100 (FIG. 22D) can receive data related to the center of gravity of the MD from, for example, user controller 130 (FIG. 12A) and use those data to update the center of gravity data. Mode information can be supplied to active controller 64A which can supply the mode information to a mode controller.

Referring now primarily to FIGS. 22C and 22D, powerbase controller 100 (FIG. 22D) can transition the MD into failsafe mode 100-9 when powerbase controller 100 (FIG. 22D) determines that the MD can no longer effectively operate. In failsafe mode 100-9 (FIG. 22C), powerbase controller 100 (FIG. 22D) can haft at least some active operations to protect against potentially erroneous or uncontrolled motion. Powerbase controller 100 (FIG. 22D) can transition from standard mode 100-1 (FIG. 22B) to update mode 100-10 (FIG. 22C) to, for example, but not limited to, enable communications with applications that can be executing external to the MD. Powerbase controller 100 (FIG. 22D) can transition to self-test mode 100-13 (FIG. 22C) when the MD is first powered. In self-test mode 100-13 (FIG. 22C), electronics in powerbase controller 100 (FIG. 22D) can perform self diagnostics and can synchronize with one another. In some configurations, powerbase controller 100 (FIG. 22D) can perform system self-tests to check the integrity of systems that are not readily testable during normal operation, for example, memory integrity verification tests and disable circuitry tests. While in self-test mode 100-13 (FIG. 22C), operational functions can be disabled. The mode controller can determine a requested mode and can set the mode into which the MD can transition. In some configurations, powerbase controller 100 (FIG. 22D) can calibrate the center of gravity of the MD. Powerbase controller 100 (FIG. 22D) can control task creation, for example, through controller task 325, and can control user notifications through, for example user notify task 165.

Referring now to FIGS. 23A-23K, a first configuration of the process by which the user interfaces with the MD can include a workflow that can be user-friendly specifically for disabled users. When the power button on UC 130 (FIG. 12A) is selected, UC 130 (FIG. 12A) can display startup screen 1000 (FIG. 23A), for example, but not limited to, a splash screen. If 10001 (FIG. 23A) the MD is in recovery mode, and if 10001A (FIG. 23F) the recovery happens under certain circumstances, UC 130 (FIG. 12A) can display specific graphic user interface (GUI) information for the particular kind of recovery. If 10001 (FIG. 23A) the MD is not in recovery mode, UC 130 (FIG. 12A) can display home screen 1020 (FIG. 24A) that can include, for example, various icons, a notification banner that can display notification icons, current time, current mode, current speed, and battery status. If the user selects changing the seat height, and if 10001C (FIG. 23B) the user can change the seat height in the current mode, UC 130 (FIG. 12A) can send 10005A (FIG. 23B) a seat height change command to processors A/B 39/41 (FIGS. 18C/18D). If 10001C (FIG. 23B) the user cannot change the seat height in the current mode, UC 130 (FIG. 12A) can ignore 10005B (FIG. 23B) the seat height change request. The user can also choose to lean/tilt the seat. If 10001D (FIG. 23B) the user can lean the seat in the current mode, UC 130 (FIG. 12A) can display 10005D (FIG. 23B) a seat lean icon. If 10001D (FIG. 23B) the user cannot lean the seat in the current mode, UC 130 (FIG. 12A) can ignore 10005C (FIG. 23B) the seat lean request. The user can move a UC input device, for example, joystick 70007 (FIG. 12A). If 10001E (FIG. 23C) the movement is a double tap forward or backward, or a quick push and hold, UC 130 (FIG. 12A) can display transition screen 1040 (FIG. 241). In some configurations, the user is moving from/to balance mode 100-3 (FIG. 22B) to/from standard mode 100-1 (FIG. 22B) and UC 130 (FIG. 12A) can display icons associated with balance mode 100-3 (FIG. 22B) and standard mode 100-1 (FIG. 22B), for example. If 10001E (FIG. 23C) the movement is not a double tap forward or backward, and if 10001F (FIG. 23C) the movement is a single hold motion forward or backward, UC 130 (FIG. 12A) can display transition screen 1040 (FIG. 241). If 10001F (FIG. 23C) the movement is not a single hold motion forward or backward, UC 130 (FIG. 12A) can display home screen 1020 (FIG. 24A). The user can depress the power button while home screen 1020 (FIG. 24A) is displayed. If 10006 (FIG. 23A) UC 130 (FIG. 12A) is in standard mode 100-1 (FIG. 22B) or docking mode 100-5 (FIG. 22A), UC 130 (FIG. 12A) can transition to off state 10006B (FIG. 23A). If 10006 (FIG. 23A) UC 130 (FIG. 12A) is any mode, and if the power button is pushed quickly, UC 130 (FIG. 12A) can change 10006A (FIG. 23A) the current speed to zero, or emergency/quick stop, on home screen 1020 (FIG. 24A).

Continuing to refer to FIGS. 23A-23K, if the menu button is depressed from the home driving screen, UC 130 (FIG. 12A) can display main menu screen 1010 (FIG. 24C). If the menu button is depressed from a screen other than the home driving screen except the transition screen, the user can be brought to the home driving screen. Using main menu screen 1010 (FIG. 24C), the user can, for example, but not limited to, select a mode, adjust the seat, adjust the speed, and configure the device. Configuring the device can include, but is not limited to including, adjusting brightness, silencing non-critical cautions and alerts, clearing the service wrench, and forced power off. If the user chooses to change the mode (FIG. 23D), UC 130 (FIG. 12A) can display selection screen 1050 (FIG. 24E) where the user can select among, for example, but not limited to, standard, 4-wheel, balance, stair, docking, and remote. If the user confirms 10007A (FIG. 23E) a new mode selection, UC 130 (FIG. 12A) can display transition screen 1040 (FIG. 241), transition the MD to the selected mode, and display home screen 1020 (FIG. 24A). If the user confirms a mode that the MD is already in, home screen 1020 (FIG. 24A) is displayed. If the user chooses to adjust the seat (FIG. 23D), UC 130 (FIG. 12A) can display selection screen 1050 (FIG. 24E) where the user can select among, for example, but not limited to, various seat adjustments including, but not limited to, seat height adjustment and seat lean/tilt, and the display home screen 1020 (FIG. 24A) can be displayed. If the user chooses to adjust the speed (FIG. 23D), UC 130 (FIG. 12A) can display selection screen 1050 (FIG. 24E) where the user can select among, for example, but not limited to, various speed options such as, for example, but not limited to, speed 0 (joystick off), speed 1 (indoor), or speed 2 (outdoor). If the user confirms 10010 (FIG. 23D) the selected speed option (FIG. 23D), UC 130 (FIG. 12A) can inform processors A/B 39/41 (FIGS. 18C/18D) of the selected speed option, and can display home screen 1020 (FIG. 24A). If the clinician chooses to adjust the settings (FIG. 23D, FIG. 29-7), UC 130 (FIG. 12A) can display selection screen 1050 (FIG. 24E) where the user and/or clinician can select among, for example, but not limited to, clearing a service wrench, viewing the service code, logging a service call, setting the brightness/contrast of UC 130 (FIG. 12A), silencing non-critical cautions and alerts, entering a service update (clinicians and service/technicians), and forcing a power off. In some configurations, UC 130 (FIG. 12A) can display settings selection screen 1050 (FIG. 24E) under pre-selected conditions, for example, but not limited to, when UC 130 (FIG. 12A) detects that a clinician is attempting to adjust the settings. If the clinician chooses to perform a CG fit (FIG. 23G), UC 130 (FIG. 12A) can display CG fit selection screen 1050 (FIG. 24E). If the clinician chooses 10005G to continue with the CG fit, UC 130 (FIG. 12A) can display transition screen 1040 (FIG. 241) having, for example, a calibration icon, or a CG fit screen 1070 (FIGS. 24M/24N). UC 130 (FIG. 12A) can display 10009-1 (FIG. 23H) a seat height icon that can guide the user in the first step necessary to perform a CG fit. When the user completes the step, the MD can perform 10009-2 (FIG. 23H) CG fit-related calibrations. If 10009-3 (FIG. 23H) the calibrations are successful, UC 130 (FIG. 12A) can display 10009-4 (FIG. 23H) seat lean and/or seat height icons that can guide the user in the second through sixth steps (FIGS. 23H-23J) necessary to perform a CG fit. If 10009-3 (FIG. 23H) the calibrations are not successful, UC 130 (FIG. 12A) can transition 10009-6 (FIG. 23H) the MD to standard mode 100-1 (FIG. 22B), and can identify 10009-7 (FIG. 23H) a caution before returning to CG fit selection screen 1070 (FIGS. 24M/24N) to begin CG fit again. In some configurations, a backward joystick movement at transition screen 1040 (FIG. 241) can exit all transitions. When the user successfully completes all six steps. UC 130 (FIG. 12A) can instruct processors A/B 39/41 (FIGS. 18C/18D) to transition 10012-2 (FIG. 23J) the MD to standard mode 100-1 (FIG. 22B), can display 10012-1

(FIG. 23J) a status of the CG fit, and can display menu screen 1010 (FIG. 24C) and select home screen 1020 (FIG. 24A) depending on user input. If the user selects (FIG. 23G) to view a service code and/or to adjust the brightness/contrast of UC 130 (FIG. 12A), UC 130 (FIG. 12A) can display appropriate selection screens 1050 (FIG. 24E), can accept user input based on the displayed screen, and can display (FIG. 23D) menu screen 1010 (FIG. 24C) depending on user input. If the user selects (FIG. 29-11) forced power off of the MD, UC 130 (FIG. 12A) can display 10013-1 (FIG. 23K) a settings screen (FIG. 23G) that can invite power off user sequence 10013-2 (FIG. 23K) to be performed through a forward joystick hold.

Continuing to refer to FIGS. 23A-23K, left/right joystick movement on menu screen 1010 (FIG. 24C) on a particular icon can open selection screen 1050 (FIG. 24E). For example, left/right joystick movement on a mode icon can open a mode selection screen. Left/right joystick movement in mode selection, seat adjustment, speed selection, and settings can cycle the options to the user. The icons can loop around, for example, for the mode selection screen, movement of the joystick could cause icons for 4-Wheel, standard, balance, stair, docking, remote modes to appear, then to cycle back to the 4-Wheel icon. Up/down joystick movement on menu screen 1010 (FIG. 27), indicated by, for example, but not limited to, an arrow of a first pre-selected color, can change the selected icon. Up/down joystick movement on any other screen indicated by, for example, but not limited to, an arrow of a second pre-selected color, can be used as a confirmation of selection. Upon entering menu screen 1010 (FIG. 24C), an icon can be highlighted, for example, the mode icon can be highlighted. In some configurations, while driving the MD, if the user accidently hits the menu button, menu screen 1010 (FIG. 24C) may be disabled unless joystick 70007 (FIG. 12A) is in a neutral position. If the transition screen 1040 (FIG. 241) is displayed, the user can, for example, use the joystick or the toggle (if available) to complete the transition. The menu button may be disabled while transition screen 1040 (FIG. 241) is displayed. Transition screen 1040 (FIG. 241) can remain displayed until the transition has ended or there was an issue with the transition. If there is an issue with the transition, UC 130 (FIG. 12A) can provide an indication to the user that the transition was not completed properly. During a caution state, the user can drive unless the level of caution prevents the user from driving, for example, when battery 70001 (FIG. 1E) is depleted. If the user can drive, the display can include the mode and speed. If the user cannot drive, the speed icon can be replaced with a prompt that indicates what the user needs to do to be able to drive again. When the user has tilted the seat in standard mode 100-1 (FIG. 22B), UC 130 (FIG. 12A) can display, for example, a seat adjustment icon. The caution sound can continue until the user takes some action such as, for example, pressing a button. The alarm icon may remain illuminated until the alarm condition has been resolved. If the user is transitioning to standard mode 100-1 (FIG. 22B) from balance mode 100-3 (FIG. 22B), UC 130 (FIG. 12A) can indicate that the MD is transitioning to standard mode 100-1 (FIG. 22B). However, if the MD is on uneven terrain, the MD may automatically stop and proceed to 4-Wheel mode 100-2 (FIG. 22B), and UC 130 (FIG. 12A) may inform the user. In some configurations, if the load on the MD is below a pre-selected threshold, a selection of balance mode 100-3 (FIG. 22B) can be rejected. A default mode selection screen 1050 (FIG. 24E) can include 4-Wheel mode 100-2 (FIG. 22B), standard mode 100-1 (FIG. 22B), and balance mode 100-3 (FIG. 22B) options, one of which can be highlighted and positioned in, for example, a center circle, for example, standard mode 100-1 (FIG. 22B). Moving the joystick right or left can move another mode into center circle and can highlight that mode. If the user is in a mode that can prevent the user from transitioning to other modes, UC 130 (FIG. 12A) can notify the user, for example, but not limited to, by graying out the modes that cannot be accessed.

Referring now to FIGS. 23L-23X, a second configuration workflow can include screens that can enable the user and/or clinician to control the MD. When the power button is depressed by the user or clinician when the MD is in an off state, and the MD is not in recovery mode, the user can be presented with home screen 1020 (FIGS. 23L, 24A). When a screen other than home screen 1020 (FIG. 23L) is displayed, and the power button is depressed for 3 +seconds, if in standard, remote, or docking mode, the MD can shut down. In any other mode, the user can remain on the current screen, and the MD can experience an emergency stop. If there is a short depression of the power button, the speed of the MD can be modified. From home screen 1020 (FIG. 23L), the user can view the MD status and can select options based upon the MD status. Options can include, but are not limited to including, seat height and lean adjustments, and proceeding to main menu screen 1010 (FIGS. 23O, 24C). Main menu screen 1010 (FIG. 23O) can provide options such as, for example, but not limited to, mode selection (FIG. 23P), seat adjustment (FIG. 23O), speed control (FIG. 23O), and settings control (FIG. 23R). If the MD is in recovery mode when the power button is depressed (see FIG. 23V), options for recovery can include, but are not limited to including, standard recovery. Each type of recovery provides a different workflow, and possibly different instructions to the user, for example, UC 130 can instruct the user to transition from 4-wheel mode 100-2 (FIG. 22B) to standard mode 100-1 (FIG. 22B).

Continuing to refer to FIGS. 23L-23X, in some configurations, transition screen 1040 (FIGS. 23N, 241) can be displayed to guide the user through a transition from a current mode to a selected mode of the MD. In some configurations, standard mode 100-1 (FIG. 22B) can be shown automatically as the selected option when the user opens mode selection screen 1060 (FIG. 23P). In some configurations, the MD can display information about the availability of driving within drive speed area 1020-2 (FIG. 24A) on home screen 1020 (FIG. 23L). In some configurations, when main menu screen 1010 (FIG. 23O) is selected during a transition (FIG. 23Q), setting selection can be automatically shown as the selected option. In some configurations, when settings selections screen 1110 (FIG. 23R) is displayed, icons can be shown with options such as, for example, but not limited to, the CG fit, MD service, brightness/contrast edit, connect to wireless, and forced power off. The user can scroll to select the desired setting, and can scroll to confirm the selection. In some configurations, if CG fit is selected (see FIG. 23R), CG fit screens (FIGS. 24M and 24N) can be displayed when the clinician connects to UC 130. In some configurations, when wireless screen 1120 (FIG. 23R) is selected, a connected icon or a status icon can be displayed. If the clinician selects the back (menu) button, and the wireless screen is exited, the wireless connection can also be terminated. During the CG fit workflow (see FIGS. 23S-23U), UC 130 can display which way to move the joystick. The menu button can be used to move into the CG fit workflow, and out of the CG fit workflow to drive the MD. If the service screen (see FIG. 23X) is selected, there could be a service code displayed. In some configurations, a grayed service icon with 'X' can be displayed if there is no service code. An 8-digit code can be displayed if no wrench clearing is necessary. If wrench clearing is necessary, after the user enters commands given by service (for example, but not limited to, N, S, E/R, W/L), numbers 1-4 can be displayed that can correspond to the movement of the joystick. After the user has entered 6 digits, the green up arrow can be displayed for the user to then hold forward on the joystick. If the user is in a position where a forced power off is necessary (see FIG. 23VV), for example if the user is stuck in the midst of a transition, and the user holds the menu button for a pre-selected amount of time, for example, 6 +seconds, home screen 1020 (FIG. 23L) can be displayed having icons that are relevant to the condition of the MD. If the user passes through pre-selected steps and confirms power off, the MD can power down.

Referring now to FIGS. 23Y-23WW, third and fourth configuration workflows can include screens that can enable the user and/or clinician to control the MD. When the power button is depressed by the user or clinician when the MD is in an off state, and the MD is not in recovery mode, the user can be presented with home screen 1020 (FIGS. 23Y, 24A). If the power button is depressed from home screen 1020 (FIGS. 23Y, 24A), and if 10005 the user is in certain modes, for example, but not limited to, standard, docking, or remote mode, the user can be presented with a power off screen. If the power button is depressed and held for a pre-selected amount of time, for example, but not limited to, approximately two seconds, the MD can be transitioned to an off state. If the power button is not held for the pre-selected time, the user can be presented again with the power off screen. In some configurations, no confirmation is needed for the shutdown. In a mode other than one of the certain pre-selected modes, if 10006 the power button has experienced a short depression for the first time, the speed of the MD can be modified, for example, emergency stop 10006B can be instituted and home screen 1020 (FIGS. 23Y, 24A) can once again be presented to the user. If 10006 the power button has not experienced a short depression for the first time, the MD can revert to the previous value of the speed before the power button was depressed and home screen 1020 (FIGS. 23Y, 24A) can be presented to the user. From home screen 1020 (FIGS. 23Y, 24A), the user can view the MD status and can select options based upon the MD status. Options can include, but are not limited to including, seat height and lean adjustments, audio activation such as, for example, but not limited to, a horn, settings, and proceeding to main menu screen 1010 (FIGS. 23BB, 24C). Main menu screen 1010 (FIG. 23O) can provide options such as, for example, but not limited to, mode selection (FIG. 23CC), seat adjustment (FIG. 23BB), speed control FIG. 23BB), and settings control (FIG. 23EE). If the MD is in recovery mode when the power button is depressed (see FIG. 2311), options for recovery can include, but are not limited to including, standard recovery. Each type of recovery can provide a different workflow, and possibly different instructions to the user, for example, UC 130 can instruct the user to transition from 4-wheel mode 100-12 (FIG. 22B) to standard mode 100-1 (FIG. 22B). The user can be instructed in how to move from one mode to another before a transition occurs.

Continuing to refer to FIGS. 23Y-23WW, in some configurations, transition screen 1040 (FIGS. 23DD, 241) can be displayed to guide the user through a transition from a current mode to a selected mode of the MD. In some configurations, standard mode 100-1 (FIG. 22B) can be shown automatically as the selected option when the user opens mode selection screen 1060 (FIG. 23CC). In some configurations, if driving is not allowed during a transition (FIG. 23Q), the MD can display information about the availability of driving within drive speed area 1020-2 (FIG. 24A) on home screen 1020 (FIG. 23L). In some configurations, when main menu screen 1010 (FIG. 23DD) is selected during a transition (FIG. 23DD), mode selection can be automatically shown as the selected option. In some configurations, when settings selections screen 1110 (FIG. 23EE) is displayed, icons can be shown with options such as, for example, but not limited to, the CG fit, MD service, brightness/contrast edit, connect to wireless, and forced power off. The user can scroll to select the desired setting, and can scroll to confirm the selection. In some configurations, if CG fit is selected (see FIG. 23EE), CG fit screens (see FIGS. 23FF-23HH) can be displayed when the clinician sets up a connection between a wireless display and UC 130. In some configurations, the user cannot see the display. In some configurations, when connection to wireless screen 1120 (FIG. 23EE) is selected, a connected wireless icon or a status icon can be displayed. If the clinician selects the back (menu) button, and the wireless screen is exited, the wireless connection can also be terminated. During the CG fit workflow (see FIGS. 23FF-23HH), when UC 130 displays which way to move the joystick, in some configurations, if the user moves the joystick, the user can be sent to a step in the CG workflow depending on the orientation of the joystick. The menu button can be used to move into the CG fit workflow, and out of the CG fit workflow to drive the MD. If the service screen (see FIG. 23KK) is selected, there could be a service code displayed. In some configurations, a service icon with 'X' can be displayed if there is no service code and there are no existing conditions. If there are existing conditions, a service icon with "X" can be displayed with a code. If the user is in a position where a forced power off is necessary (see FIG. 23JJ), and if the user holds the menu button for a pre-selected amount of time, for example, 6 +seconds, settings (see FIG. 23EE) can be presented to the user. If the user passes through pre-selected steps and confirms power off, the MD can power down.

Continuing to refer to FIGS. 23Y-23WW, in some configurations, the user and/or clinician may, while driving, use the horn (see FIG. 23Y) and force an emergency stop by depressing the power button (see FIG. 23Y). In some configurations, depressing the menu button while driving will not cause a display of the menu button, which can be displayed with the joystick is in a neutral position. In some configurations, the horn can be enabled while the user is driving. In some configurations, depressing the power button while the MD is moving can initiate an emergency stop. In some configurations, when transitioning from one mode to another, the user can control the MD with either joystick 70007 (FIG. 12A) and/or toggle 70036-2 (FIG. 12D). In some configurations, toggle 70036-2 (FIG. 12D) can be disabled when transitioning using the menu screen. In some configurations, the joystick can be disabled with transition using the shortcut method (see FIG. 23UU). In some configurations, when transitioning from standard mode 100-1 (FIG. 22B) to balance mode 100-3 (FIG. 22B) and the terrain is uneven, the MD can stop and end the transition in 4-wheel mode 100-2 (FIG. 22B). In some configurations, if UC 130 (FIG. 12A) becomes disconnected from the MD during a transition, when UC 130 (FIG. 12A) is reconnected, the transition status can be recalled. In some configurations, if UC 130 (FIG. 12A) becomes disconnected from the MD during a transition, when UC 130 (FIG. 12A) is reconnected, and the MD has completed its startup sequence, the MD can move to recovery mode.

Continuing to refer to FIGS. 23Y-23WW, in some configurations, if the Menu button is depressed and held for a pre-selected amount of time while the transition screen is displayed, the settings screen can be displayed. In some configurations, the user can select FPO to end the transition and shut down the MD, or the user can depress the menu button to return to the transition screen. In some configurations, if the user selects mode selection from the menu, the default screen can include 4-wheel, standard, and balance (modes) with standard highlighted in the middle, for example. In some configurations, moving the joystick right or left can change which mode is highlighted, and moving the joystick up/down when the MD is currently in the selected mode can automatically display home/driving screen 1020. In some configurations, depressing the menu button from home/driving screen 1020 can open the main menu screen. In some configurations, depressing the menu button from another screen (not home/driving screen 1020) can open home/driving screen 1020.

Continuing to refer to FIGS. 23Y-23WW, in some configurations, during an alarm state, the MD can be driven, and the alarm sound can continue until the user has pressed the horn button. Left/right movement of joystick 70007 (FIG. 12A) on some screens can open a selection, while on other screens, the movement can cycle options to the user. Up/down movement of joystick 70007 (FIG. 12A) can change the selected icon on some screens, while on other screens, the movement can be used as a confirmation of the selection. In some configurations, an alarm notification can remain displayed until the alarm conditions has been resolved and/or cleared. In some configurations, the MD can retain information about the desired speed of the MD across power cycles. In some configurations, displayed screens can include an indication about which options are not enabled based on the current mode selection. In some configurations, when the MD is in standard mode and the seat is tilted, an indication of the tilt can be displayed, for example, on home/driving screen 1020.

Continuing to refer to FIGS. 23Y-23WW, in some configurations, if the joystick is in a non-neutral position, and if the power button is depressed, the MD can be stopped. In some configurations, when any screen is displayed except the transition screen and the power button is depressed, home/driving screen 1020 can be displayed and the MD can be stopped. In some configurations, when any screen is displayed except home/driving screen 1020, and the power button is depressed for a pre-selected amount of time, and the MD is in one of a set of pre-selected modes, the MD can be shut down without confirmation. When the MD is not in one of the pre-selected modes, and the power button is depressed, the MD can be stopped. In some configurations, if and emergency stop has been initiated, further depressing of the power button can bring the MD from a stopped state back to the speed the MD was traveling at when the emergency stop was initiated, or a pre-selected default speed if the MD were stopped. In some configurations, if the MD is not responding, the menu button can be depressed for a pre-selected amount of time to open the setting screen, upon which FPO can be highlighted. In some configurations, depressing the power button for pre-selected amounts of time can override certain features such as, for example, but not limited to, the parking brake during pre-selected activities.

Continuing to refer to FIGS. 23Y-23WW, in some configurations, left/right joystick movement on the menu screen can open the selection. In some configurations, left/right joystick under pre-selected conditions can cycle options to the user. In some configurations, up/down joystick movement on the menu screen can change the selected icon in the menu. In some configurations, up Joystick movement can be used as a confirmation of selection. When the menu screen is displayed, a pre-selected default icon can be highlighted. In some configurations, the joystick can drive the MD when home/driving screen 1020 is displayed, and the joystick can be used for navigation when other pre-selected screens are displayed.

Referring now to FIGS. 23LL-23WW, a fourth configuration workflow can include screens that can enable the user and/or clinician to control the MD. The workflow can be divided into subflows that can include, but are not limited to including, normal workflow 1070 (FIG. 23LL), power button workflow 1072 (FIG. 23MM), stair mode workflow1074 (FIG. 23NN), forced power off workflow 1076 (FIG. 2300), CG fit workflow 1078 (FIGS. 23XX, 23YY), recovery mode workflow 1080 (FIG. 23QQ), wireless workflow 1082 (FIG. 23RR), brightness workflow 1084 (FIG. 23SS), alarm mute workflow 1086 (FIG. 23TT), shortcut toggle workflow 1088 (FIG. 23UU), and battery charging workflow 1090 (FIG. 23VV). Normal workflow 1070 (FIG. 23LL) can include the display of startup screen 1000 and, if the MD is not in recovery mode, home/driving screen 1020 can be displayed. Otherwise, the display can transition to recovery mode workflow 1080 (FIG. 23QQ). If the menu button is depressed when home/driving screen 1020 is displayed, main menu screen 1010 can be displayed, and manipulation of the joystick to select an option can cause any of setting screen 1043, speed selection screen 1041, seat adjustment selection screen 1042, or mode selection screen 1060 to display. If the menu button is depressed, home/driving screen 1020 can be displayed. If settings screen 1043 is displayed, any of alarm mute workflow 1086 (FIG. 23TT), brightness workflow 1084 (FI. 23SS), CG fit workflow 1078 (FIGS. 23PP, 23XX), forced power off (FPO) workflow 1076 (FIG. 2300), and wireless workflow 1082 (FIG. 23RR) can be entered. If settings screen 1043 is displayed and the menu button is depressed, home/driving screen 1020 can be displayed. If speed selection screen 1041 is displayed, the user can either select a speed with the joystick or return to home/driving screen 1020 by depressing the menu button. If seat adjustment selection screen is depressed, the user can adjust the seat and return to home/driving screen 1020 by depressing the menu button. If mode selection screen 1060 is displayed, the user can choose a mode and confirm it through joystick manipulation, or return to home/driving screen 1020 by depressing the menu button. If the user chooses stair mode, the MD can enter stair mode workflow 1074 (FIG. 23NN). If the user does not choose stair mode, transition screen 1040 can be displayed, and when the transition is complete, home/driving screen 1020 can be displayed. If the user is in a position where a forced power off is necessary (see FIG. 23VV), for example if the user is stuck in the midst of a transition, and the user holds the menu button for a pre-selected amount of time, for example, 6 +seconds, home screen 1020 (FIG. 23L) can be displayed having icons that are relevant to the condition of the MD. If the user passes through pre-selected steps and confirms power off, the MD can power down.

Referring now to FIG. 23LL, in some configurations, from the startup screen, if the MD has just experienced forced power off, recovery mode workflow 1080 (FIG. 230Q) can be executed. If not, and if device security is enabled, a power on password workflow can be executed. If device security is not enabled, home screen 1020 can be displayed. The power on password workflow can include receiving either a depression of the menu button or a joystick signal. If the menu button is depressed before a password page has been displayed, in some configurations, the menu can include an abbreviated number of possible selections, for example, but not limited to, forced power off, brightness, service, alert mute, and/or wireless access. If the joystick is activated before the menu button is depressed, a password entry screen can be displayed, and the user can enter a password. When the entry is complete, either the password is recognized in which case normal workflow 1070 can be executed, or the password is not recognized in which case the user is provided an indication such as, for example, but not limited to, a red X. The user can push the toggle forward to go back to the password entry screen if desired. In some configurations, settings screen 1043 can include options such as, for example, but not limited to, service screen workflow, create/enable/disable password workflow, and hill charge workflow.

Continuing to refer to FIG. 23LL, from settings screen 1043, if the user selects the service screen workflow (not shown), an 8-digit code can be displayed if wrench clearing is necessary. If no wrench clearing is necessary, but there are existing conditions, a screen can be displayed with the code of the existing condition. The user can indicate by joystick movement to proceed to the next screen which can include spaces to enter a code. After the user enters commands given by service (for example, but not limited to, N, S, E/R, W/L), numbers 1-4 can be displayed that can correspond to the movement of the joystick. After the user has entered 6 digits, the green up arrow can be displayed to direct the user to hold forward on the joystick. The code will be checked. If the code is correct, and if there are existing conditions that could not be cleared, a screen can be displayed that can indicate the code of the condition that could not be cleared, and the wrench can be cleared. If there are no existing conditions that could not be cleared, the wrench can be cleared. If the code is not correct, and if this represents the third failed attempt, a new code can be generated and the user can try again. If the code is incorrect, but this is not the third entry attempt, the user gets another one or two chances to enter the correct code.

Continuing to refer to FIG. 23LL, from settings screen 1043, if the user selects the create password workflow (not shown), a screen can be display in which the user can enter a new password. A pre-selected type of joystick entry, such as, for example, but not limited to, a long hold forward on the joystick, can indicate that the new password entry is complete. The user can be prompted for a confirmation entry of the password, and the user can provide a pre-selected type of joystick entry to signal that the confirmation password is complete. If the new password and the confirmation are different, a display indicating a problem, such as, for example, but not limited to, a display including a red X, can be provided. The user can toggle forward to retry creating a new password. If the new password and the confirmation are the same, a screen can be displayed that can indicate by, for example, but not limited to, a pre-selected icon on the screen, that a password has been created.

Continuing to refer to FIG. 23LL, from settings screen 1043, if the user selects the enable/disable password workflow (not shown), a pre-selected joystick movement can turn off password protection, while another pre-selected joystick movement can turn on password protection, prompting the screen in which the user can enter a password. A pre-selected joystick movement can indicate that the user has completed entering the password. If the entry is correct, a screen indicating that the password has been accepted can appear. If the entry is incorrect, the user can be informed by an icon such as, for example, a red X, and can be allowed to retry password entry.

Continuing to still further refer to FIG. 23LL, from settings screen 1043, if the user selects the hill charge workflow (not shown), a hill charge screen can be displayed. The user can elect to turn hill charge on or off, depending on pre-selected joystick movements. Further joystick movements can save the hill charge setting and return to home screen 1020.

Referring now to FIG. 23MM, in some configurations, if the power button is depressed, home/driving screen 1020 (FIG. 23LL) can be displayed unless the power button is depressed while transition screen 1040 is displayed. If the MD is in standard mode 100-1 (FIG. 22A), docking mode 100-5 (FIG. 22A), or remote mode 100-6 (FIG. 22A) and the user depresses the power button for a pre-selected amount of time, the MD can power down. If the user does not depress the power button for a pre-selected amount of time, an emergency stop can be enabled in which the speed is set to 0 . If the MD is not in standard mode 100-1 (FIG. 22A), docking mode 100-5 (FIG. 22A), or remote mode 100-6 (FIG. 22A) and the user depresses the power button, an emergency stop can be enabled. The user can depress the power button again to enable the MD to return to the speed it was traveling before the power button was depressed and to return to home/driving screen 1020 (FIG. 23LL). In some configurations, when the power button is depressed, and the MD is not on, and there is sufficient battery power, startup as described in reference to the description of FIG. 23LL and elsewhere can occur. If there is not sufficient battery power, the power on request can be ignored by the system. If the MD is already powered on, and if the user is performing a transition from one mode to another or a CG fit operation, the power on request can be ignored by the system. If the user is not transitioning or not performing a CG fit operation, and if the MD is not stopped, and if the user depresses the power button for a pre-selected amount of time, and if the user is in standard, docking, or remote mode, the MD can be automatically powered down. If the MD is not moving, the MD can be automatically set in motion up to the speed at which it was traveling before the power button was depressed, and home screen 1020 (FIG. 23LL) can be displayed. If the user does not depress the power button for a pre-selected amount of time, or if the user is not in standard, docking, or remote mode, the MD can automatically be stopped.

Referring now to FIG. 23NN, if the user selects stair mode, stair mode workflow 1074 can be entered. If solo mode is selected, transition screen 1040 can be displayed followed by grab handrail confirmation screen 1092. If the user confirms that the handrail is to be used, home/driving screen 1020 (FIG. 23LL) can be displayed. If the menu button is depressed, no further input is accepted. If the user declines to use the handrail, the MD can automatically transition to 4-wheel mode 100-2 (FIG. 22A) and home/driving screen 1020 (FIG. 23LL) can be displayed. If assisted mode is selected, stair attendant confirmation screen 1094 can be displayed. If the user declines to use a stair attendant, mode selection screen 1060 can be displayed. If the user depresses the menu button, no input is accepted. If the user confirms the use of a stair attendant, transition screen 1040 can be displayed until the transition is complete, and home/driving screen 1020 (FIG. 23LL) can be displayed.

Referring now to FIG. 2300, if the user depresses and holds the menu button for a pre-selected amount of time, for example, but not limited to, 6 +seconds, forced power off workflow 1076 can be entered and settings screen 1043 can be displayed. If the joystick is manipulated, forced power off confirmation screen 1096 can be displayed, and if the menu button is depressed, home/driving screen 1020 (FIG. 23LL) can be displayed. If forced power off is confirmed, the MD is powered down. If forced power off is not confirmed, the user can be given another chance to accomplish forced power off after a pre-selected amount of time. The user can depress the menu button to display home/driving screen 1020 (FIG. 23LL). If the user does not hold the menu button for the pre-selected amount of time, home/driving screen 1020 can be displayed and main menu screen 1010 can be displayed if the menu button is depressed. The user can enable forced power off by opening setting screen 1043 and manipulating the joystick to enable display of forced power off confirmation screen 1096 as described herein.

Referring now to FIGS. 23XX and 23YY, if CG fit is selected from settings screen 1043 (FIG. 23LL), CG fit workflow 1078 can be entered. Depending on how CG fit is entered, a CG fit icon can either appear on settings screen 1043 (FIG. 23LL) or not. If the CG fit icon appears, joystick manipulation can enable a transition from standard mode 100-1 (FIG. 22A) to balance mode 100-3 (FIG. 22A). If the joystick is moved backwards, CF fit workflow 1078 can be exited. Otherwise, steps in the CG fit process can be displayed. The sub-steps for each step can include, but are not limited to including, displaying an indication that the MD is in a CG fit step, receiving a selection of a hom/ack button depression, calibrating the MD, and checking for success of the step. When all steps have executed, the MD can transition to standard mode 100-1 (FIG. 22A) and settings screen 1043 (FIG. 23LL) can be displayed with an indication that the calibration has completed. If the MD power cycles, the CG fit calibration can be removed from the MD. If all the steps did not complete successfully, the MD can transition to standard mode 100-1 (FIG. 22A), a CG fit fail icon can be displayed, and a visual and/or audible alert can be generated. Either the process can be repeated, or the menu button can be depressed, and home/driving screen 1020 (FIG. 23LL) can be displayed.

Referring now to FIG. 23QQ, following power on and the display of startup screen 1000, if the MD is in recovery mode, recovery mode workflow 1080 can executed. In particular, prompts can appear in a status area of the display to indicate how the user can return to standard mode 100-1 (FIG. 22A). In some configurations, the user can be instructed to depress the menu button. Left/right joystick input can enable mode selection screen. Further left/right joystick movement can prompt the user for stair/standard recovery, and joystick forward movement can indicate that recovery mode has been selected. In some configurations, when joystick input is complete, a password may be required. When the transition to standard mode 100-1 (FIG. 23LL) is complete, or if the MD is not in recovery mode at startup, home/driving screen 1020 (FIG. 23LL) can be displayed. In some configurations, joystick movement on home/driving screen 1020 (FIG. 23LL) can move the seat while in recovery mode.

Referring now to FIG. 23RR, when wireless connectivity is selected, wireless workflow 1082 can be executed. In particular, service update screen 1083 can be displayed, and the user can enter a passcode or provide another form of authentication. The user can be a clinician, and wireless connectivity can be used to remotely control the MD. If the user authenticates, service update screen 1083 can be displayed with an indication that the user is allowed to connect wirelessly. The user can be given up to a pre-selected number of times to authenticate.

Referring now to FIG. 23SS, when brightness adjustment is selected from settings screen 1043 (FIG. 23LL), brightness workflow 1084 can be executed. Brightness screen 1085 can be displayed, and joystick manipulation can change the brightness of the display. If the menu button is depressed, brightness settings can be saved and home/driving screen 1020 (FIG. 23LL) can be displayed.

Referring now to FIG. 23TT, when alarm mute is selected from settings screen 1043 (FIG. 23LL), alarm mute workflow 1086 can be executed. In some configurations, alarm mute screen 1087 can be displayed, and joystick manipulation can enable or disable volume. Further joystick manipulation can save the volume settings and return to home/driving screen 1020 (FIG. 23LL), while depressing the menu button can return to home/driving screen 1020 (FIG. 23LL) without saving volume settings. In some configurations, the user can depress the menu button and can manipulate the joystick to achieve an alarm screen. Further joystick manipulation can select an alarm mute option. In some configurations, non-critical alert/caution tones can be muted.

Referring now to FIG. 23UU, when shortcuts are taken from home/driving screen 1020, shortcut toggle workflow 1088 can be executed. Possible shortcuts can include, but are not limited to including, seat height shortcut, seat lean shortcut, and shortcut toggle. Because the seat height and seat lean can only be changed in certain modes, any attempts to change the seat height and/or the seat lean, including through the seat height and seat lean shortcuts, can be ignored. If the MD is in a mode in which the seat height and/or the seat lean can be changed, the seat height shortcut and/or the seat lean shortcut can be used to change the seat height and/or the seat lean. During the seat height change, the user can continue to drive. After the seat height and/or the seat lean are changed, home/driving screen 1020 (FIG. 23LL) can be displayed. In some configurations, to use the shortcut toggle, the joystick can be manipulated in a pre-selected way, for example, but not limited to, a short tap and hold. When this happens, transition screen 1040 can be displayed, and the mode of the MD can change, for example, the MD can transition from standard mode 100-1 (FIG. 22A) to balance mode 100-3 (FIG. 23LL) and vice versa. Otherwise, home/driving screen 1020 (FIG. 23LL) can be displayed. If the joystick is manipulated in a different pre-selected way, for example, a single hold or a forwards/backwards toggle, transition screen 1040 can be displayed.

Referring now to FIG. 23VV, to charge the batteries of the MD, battery charging workflow 1090 can be executed. If the MD is powered down, and if the A/C adapter is connected to the MD, a battery charging icon can be displayed until the battery is charged or until there is a battery fault. If the battery is charged, the full battery icon can be displayed. If there is a battery fault, a battery fault icon can be displayed. When the user disconnects the A/C adapter from the MD, the MD can power down. If the MD is not powered down and the A/C adapter is not connected to the MD, an indication that the battery is not charging can be displayed on home/driving screen 1020 (FIG. 23LL). If the MD is not powered down and the A/C adapter is connected to the MD, an indication of the current status, such as, for example, but not limited to, an audible alert, can be sounded until, for example, the alert is muted.

Figure 23Z:
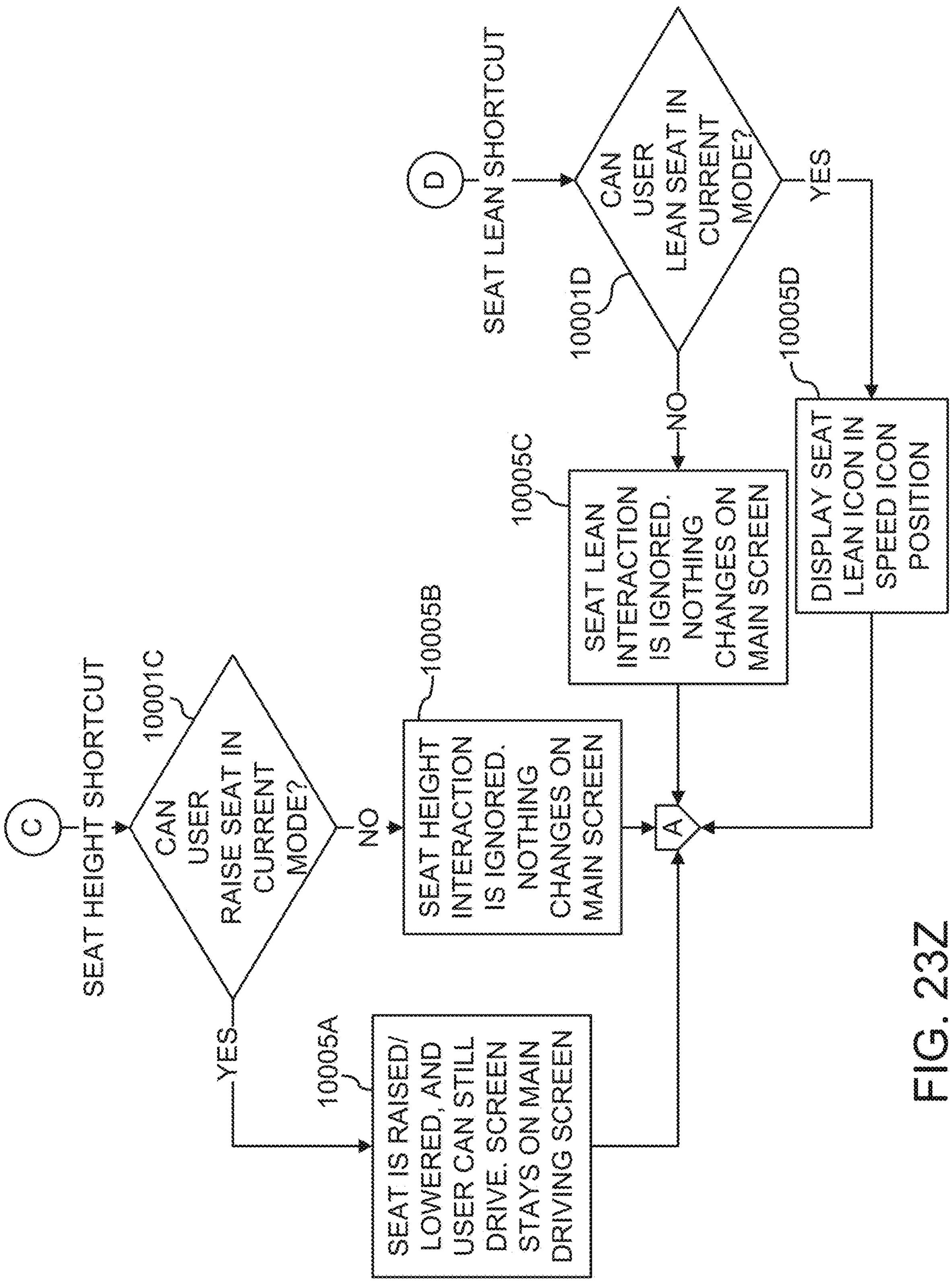
Figure 23A:
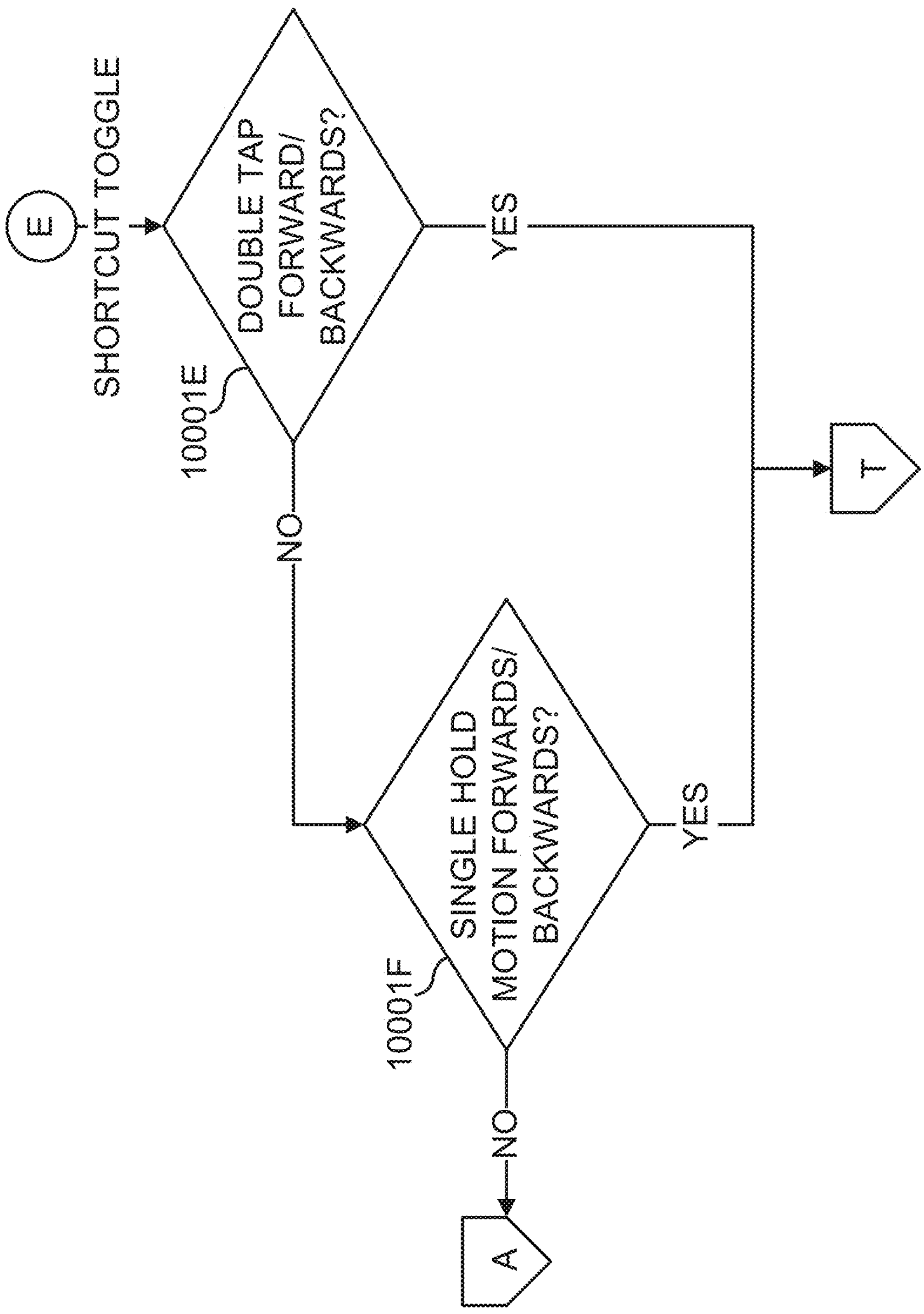
Figure 23B:
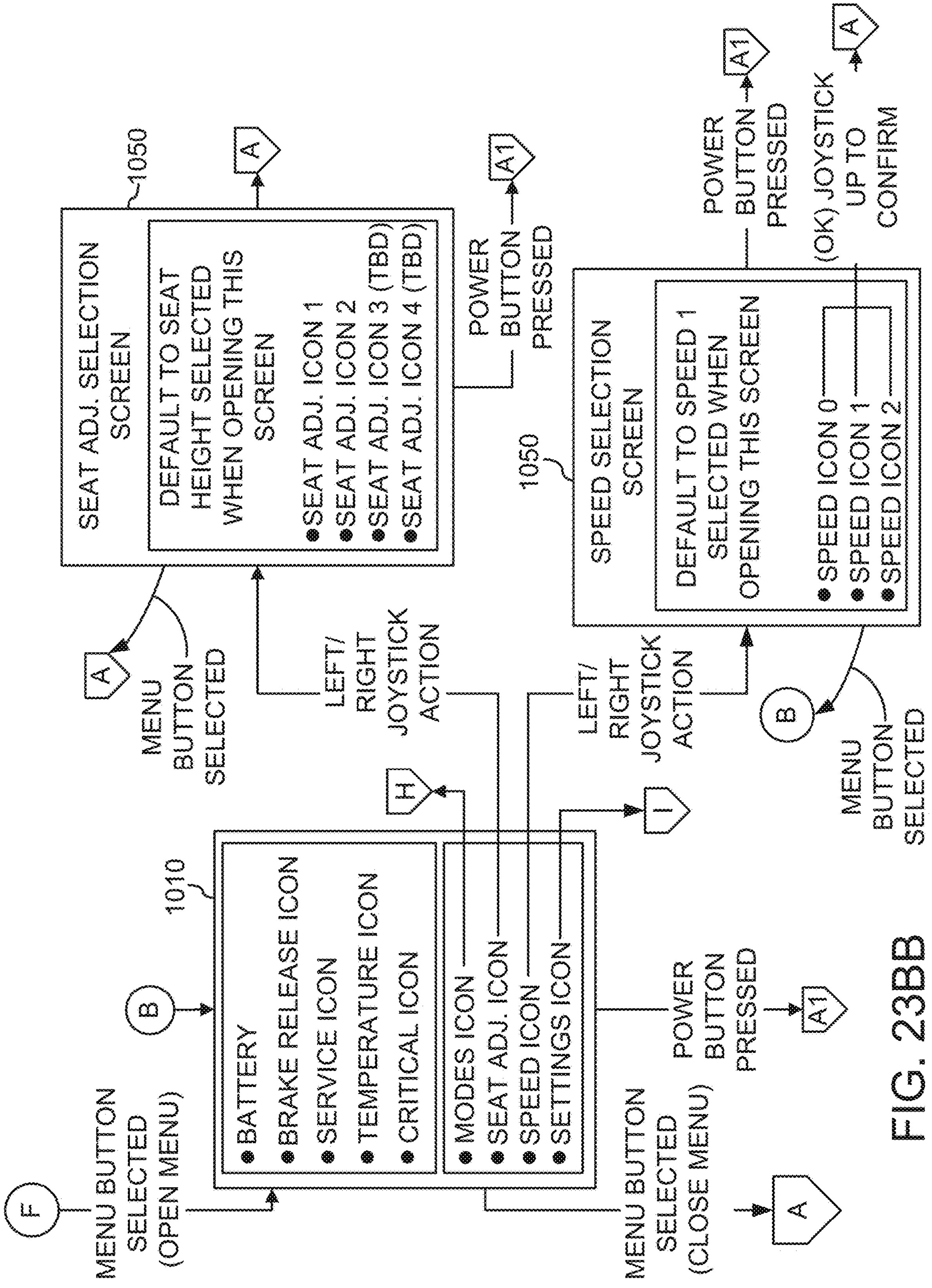
Figure 23C:
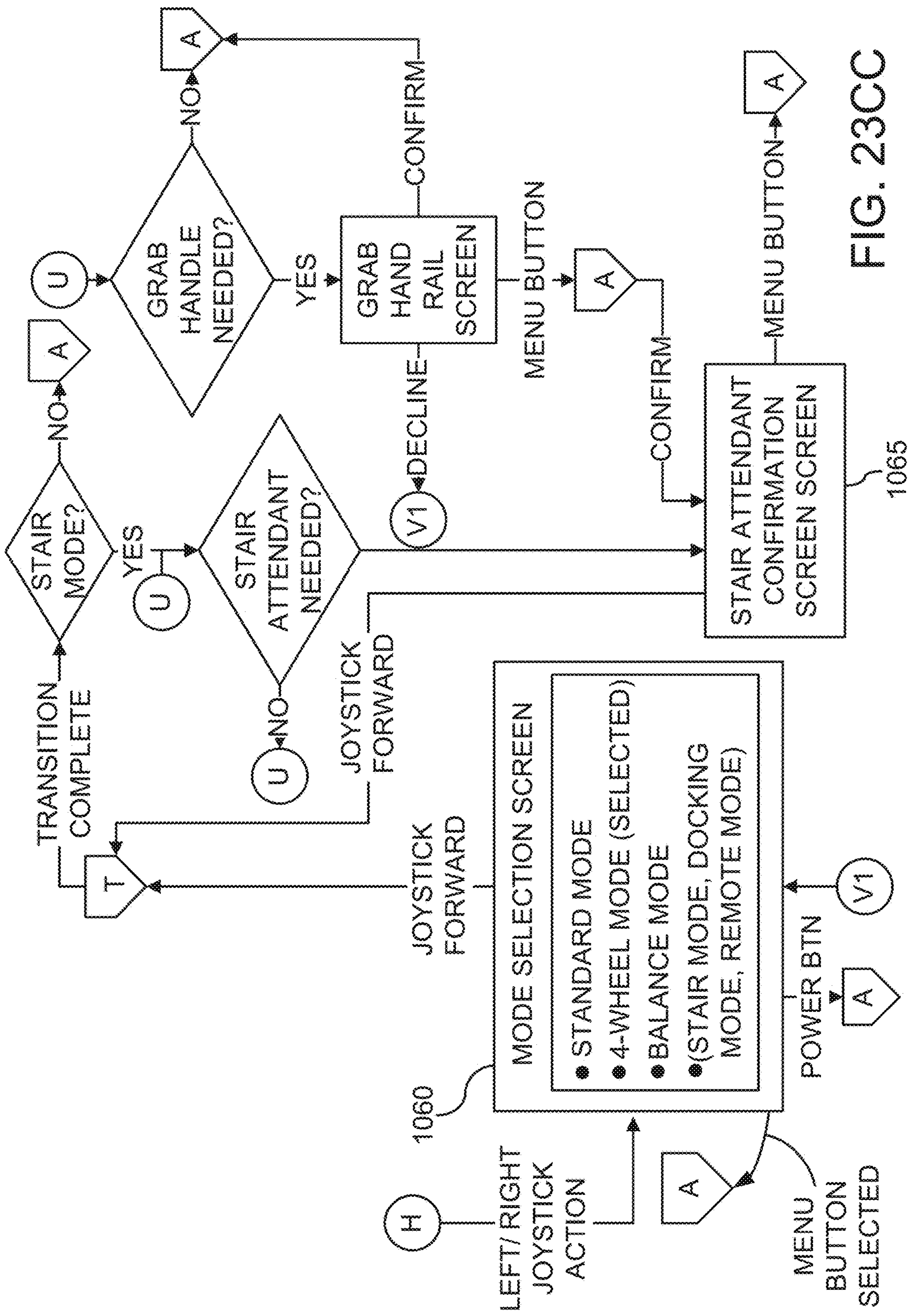
Figure 23D:
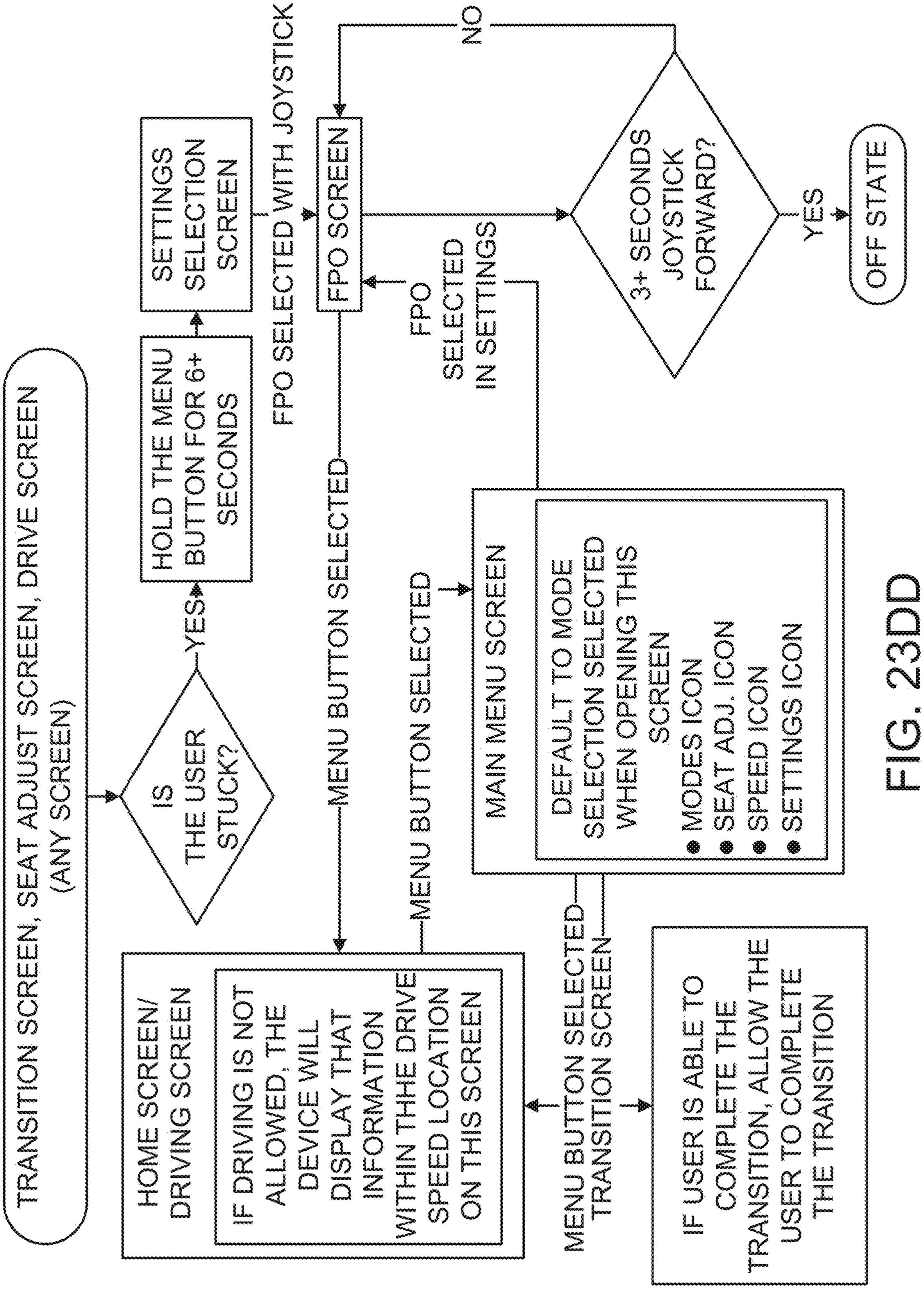
Figure 23E:
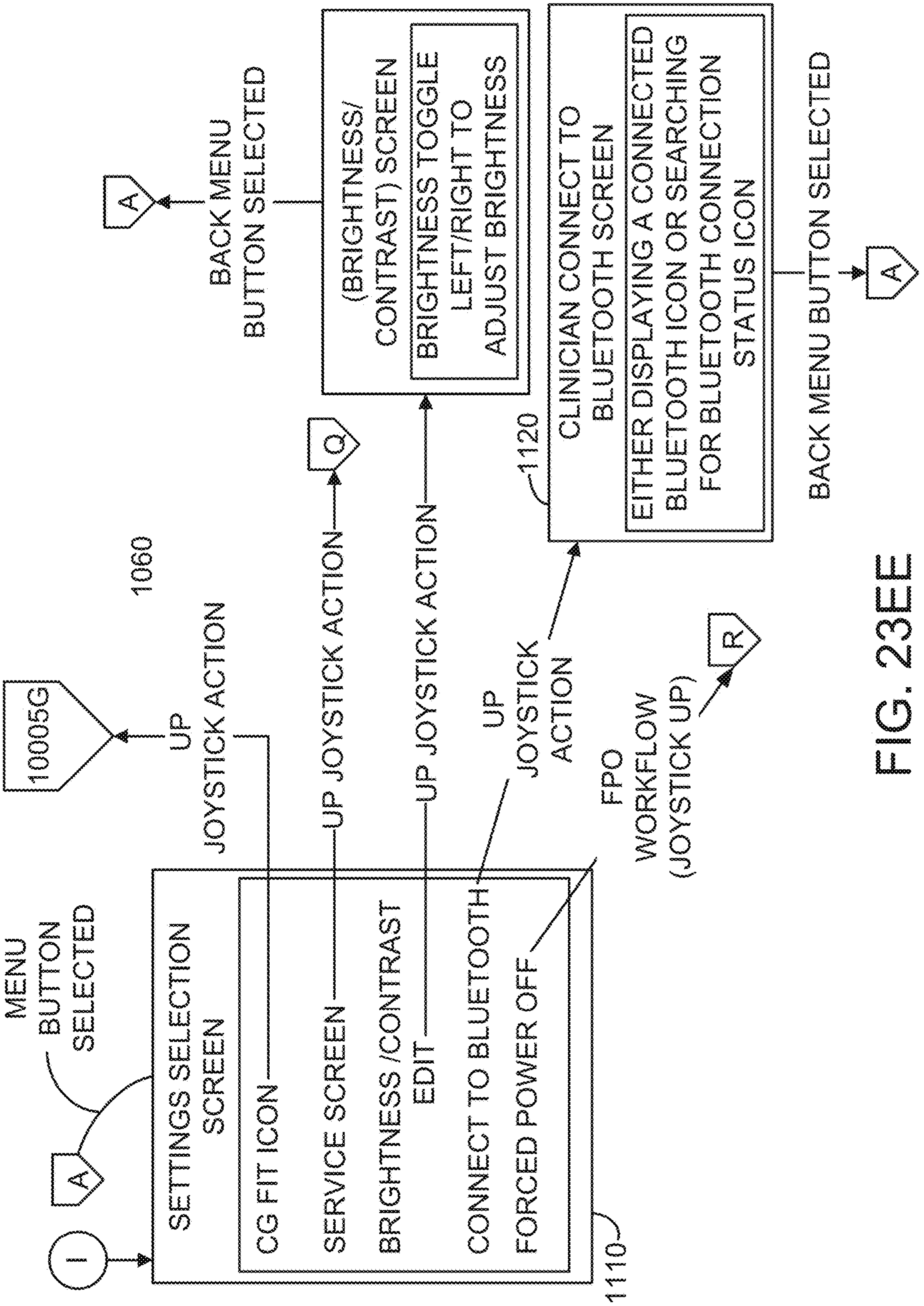
Figure 23F:
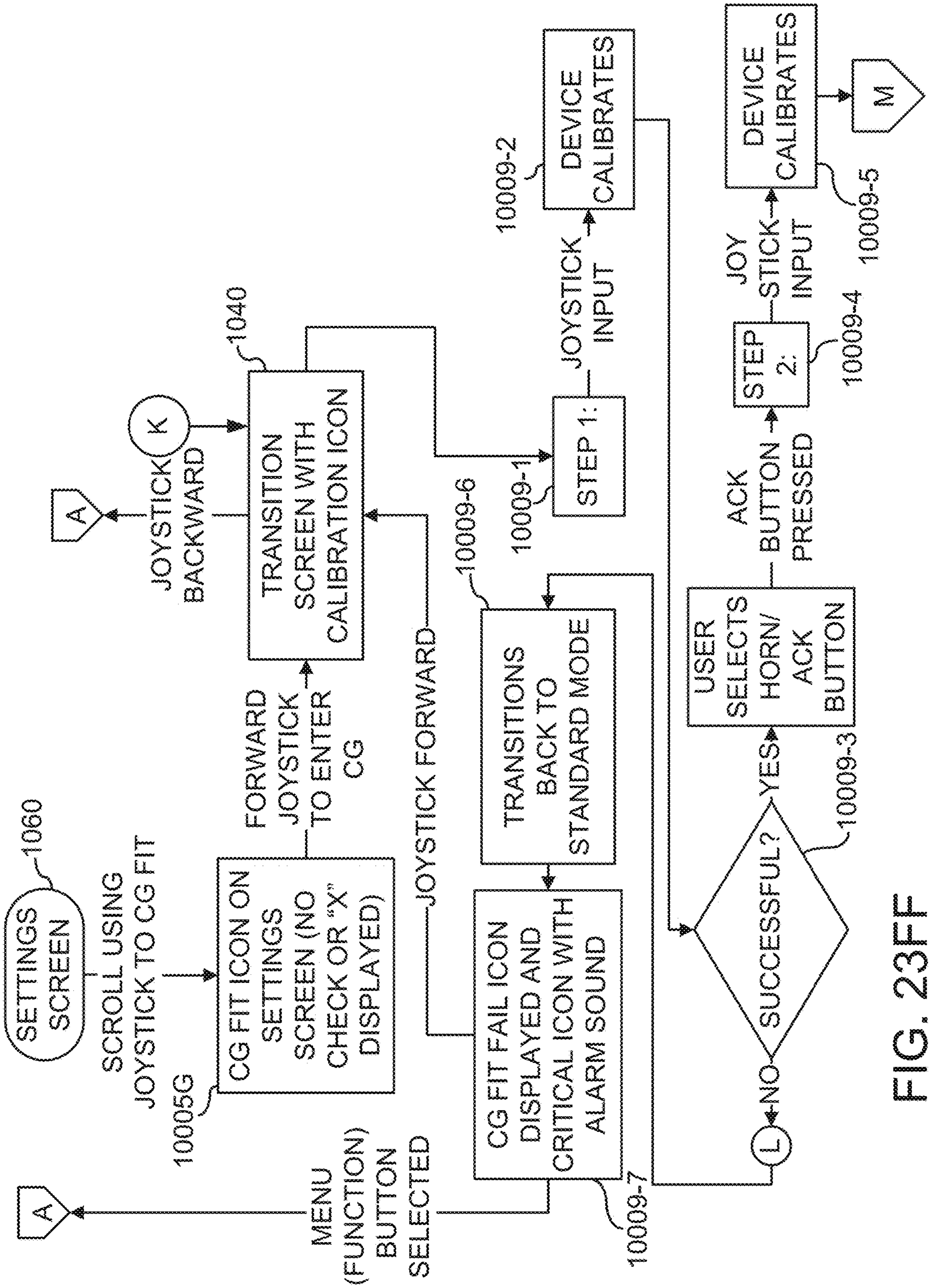
Figure 23G:
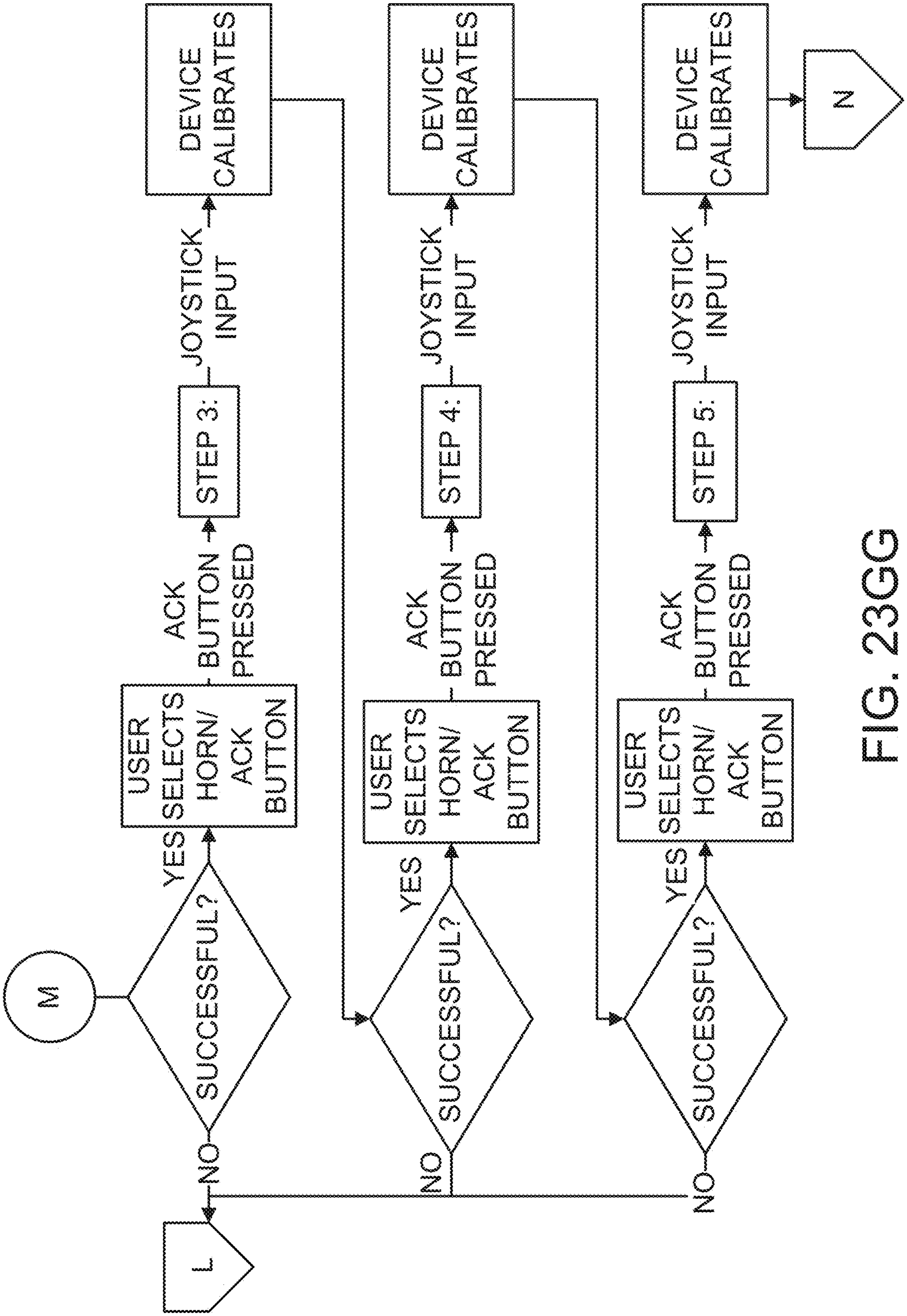
Figure 23H:
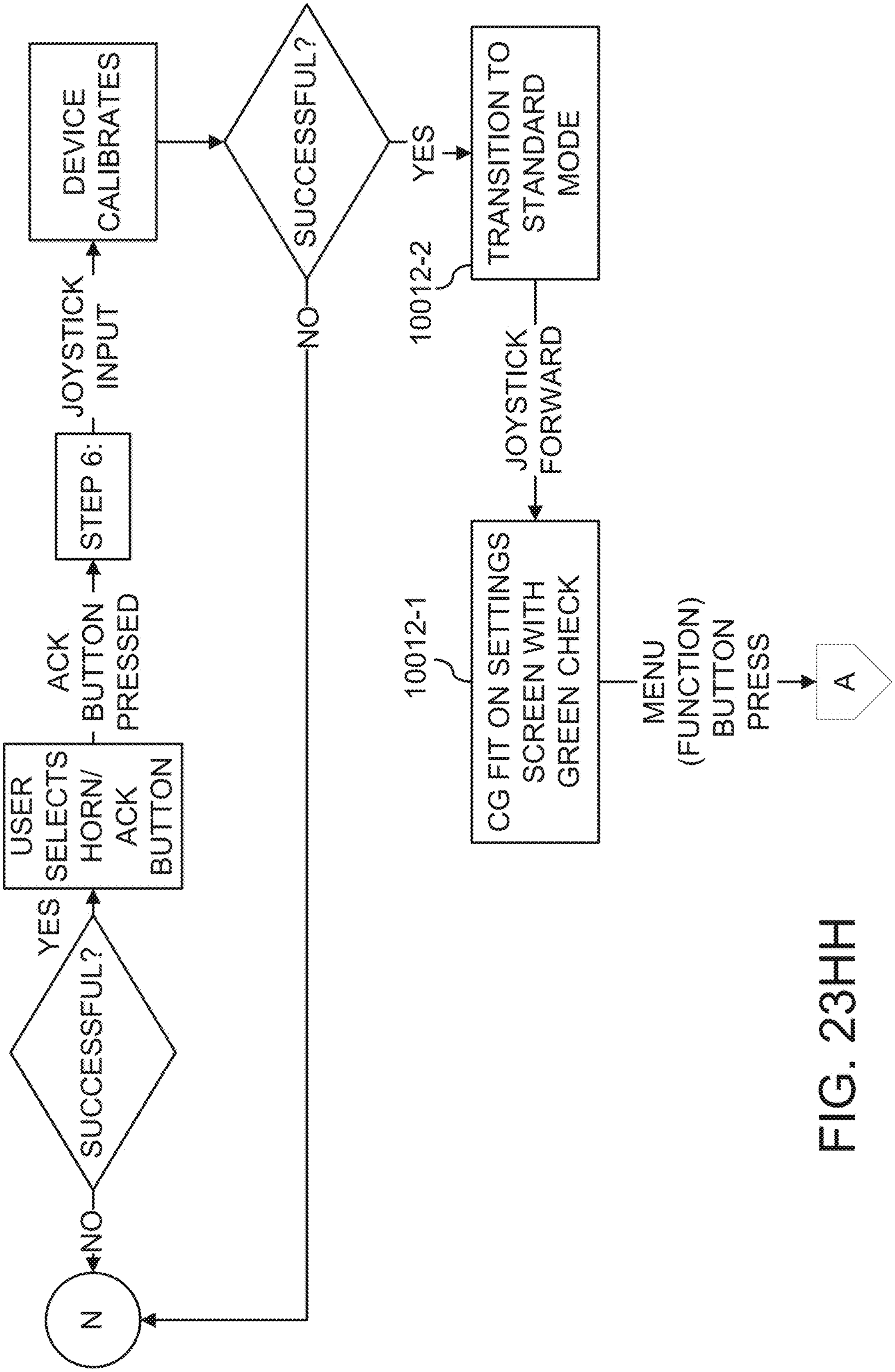
Figure 23J:
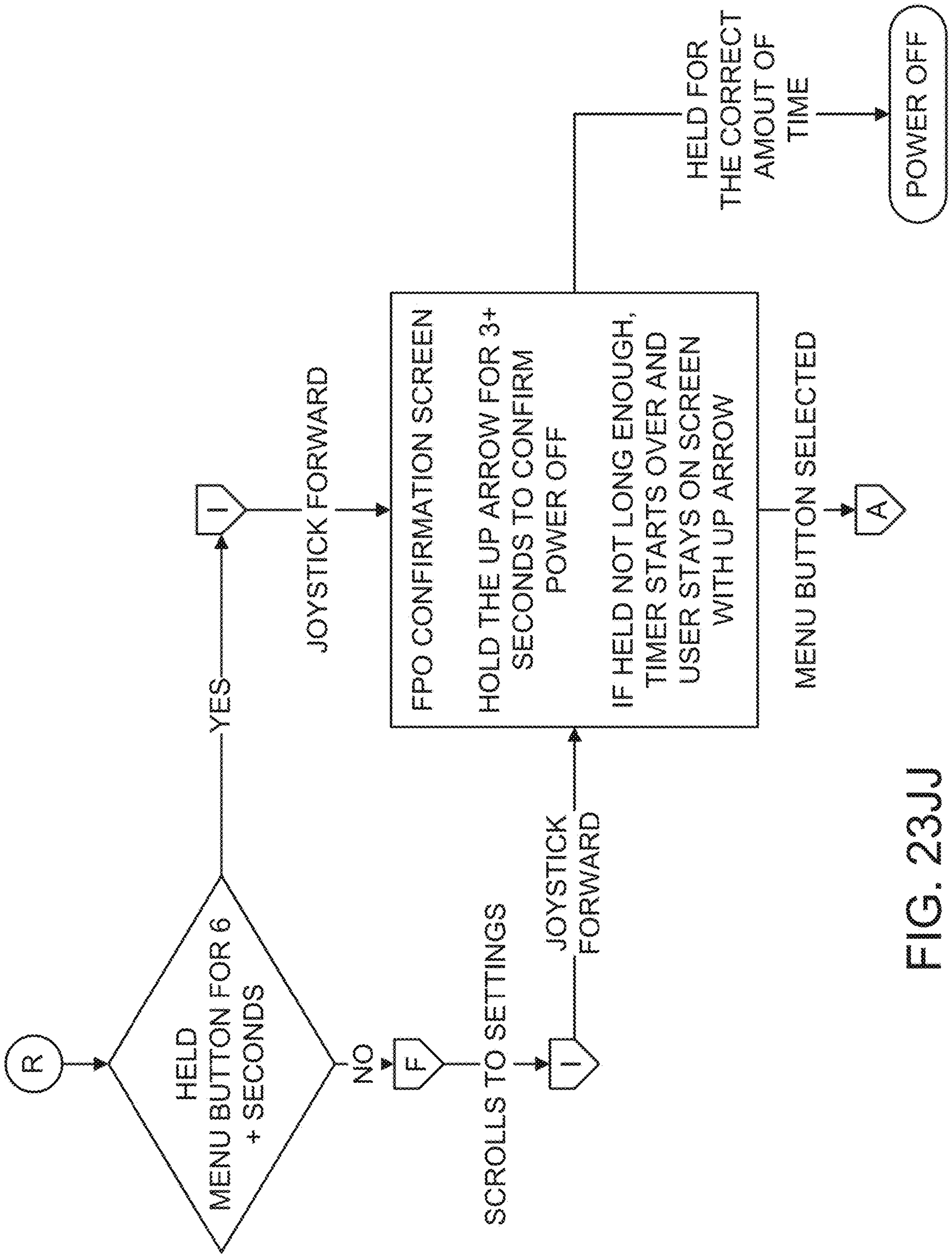
Figure 23K:
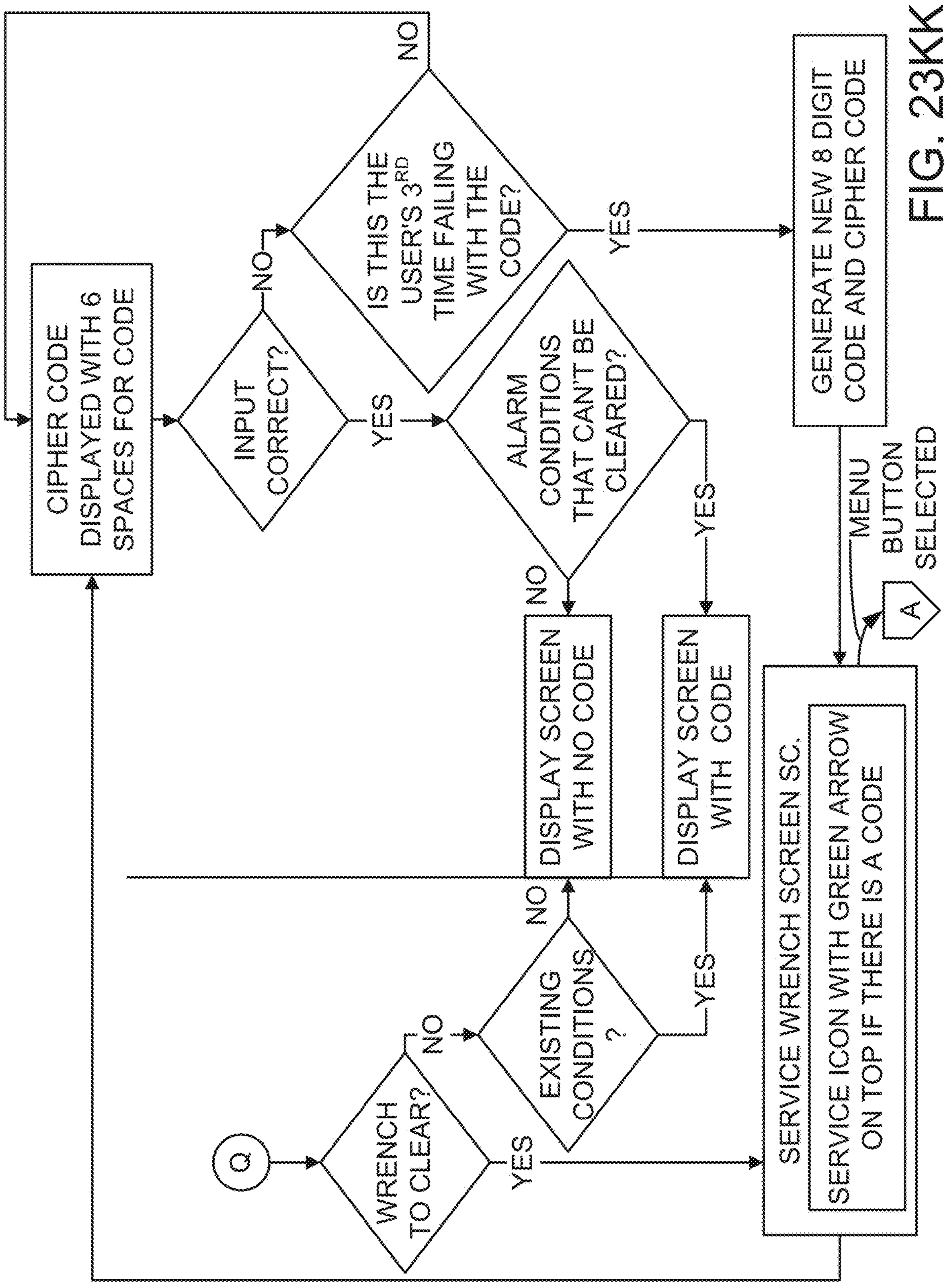
Figure 23L:
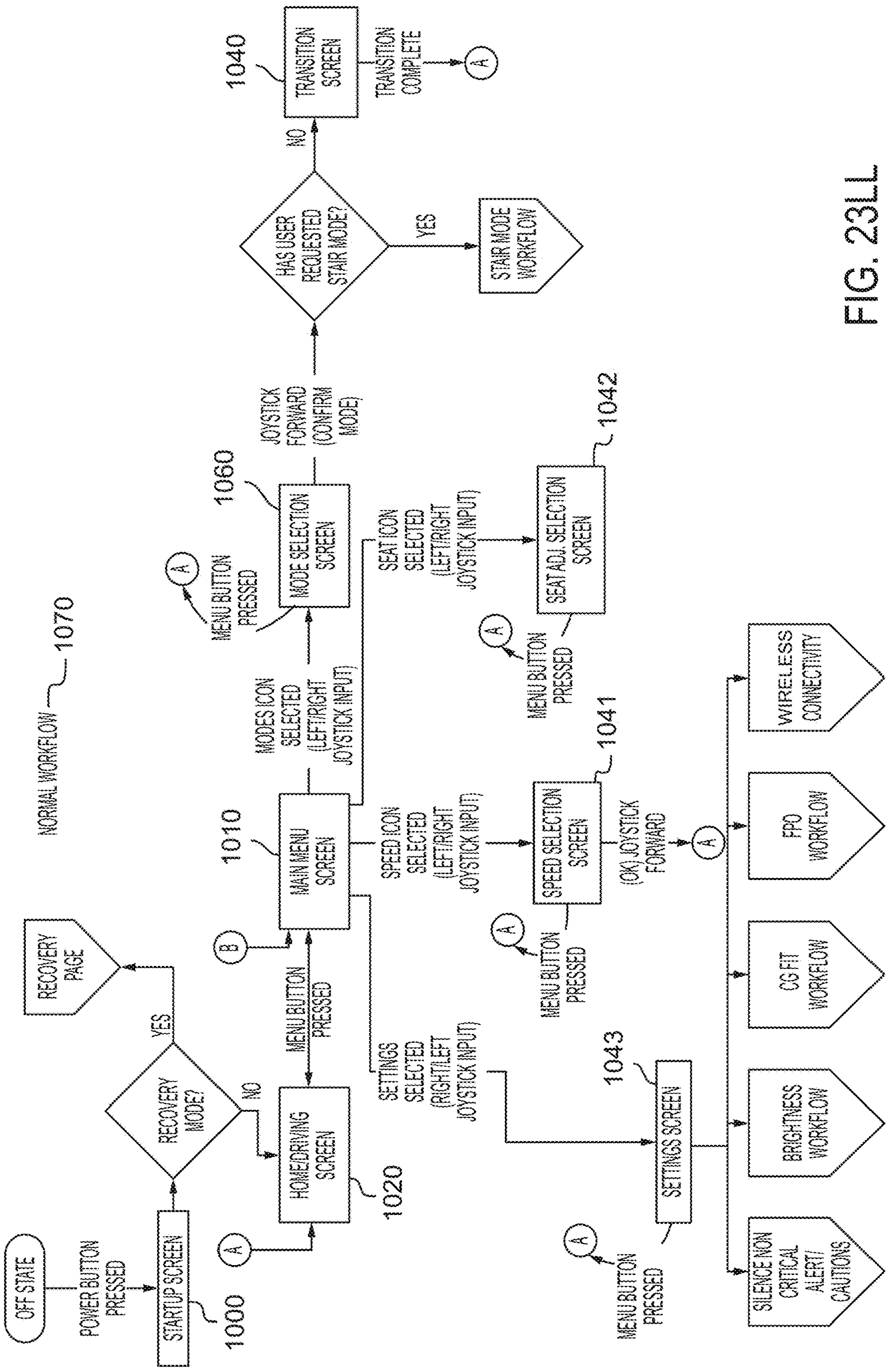
Figure 23M:
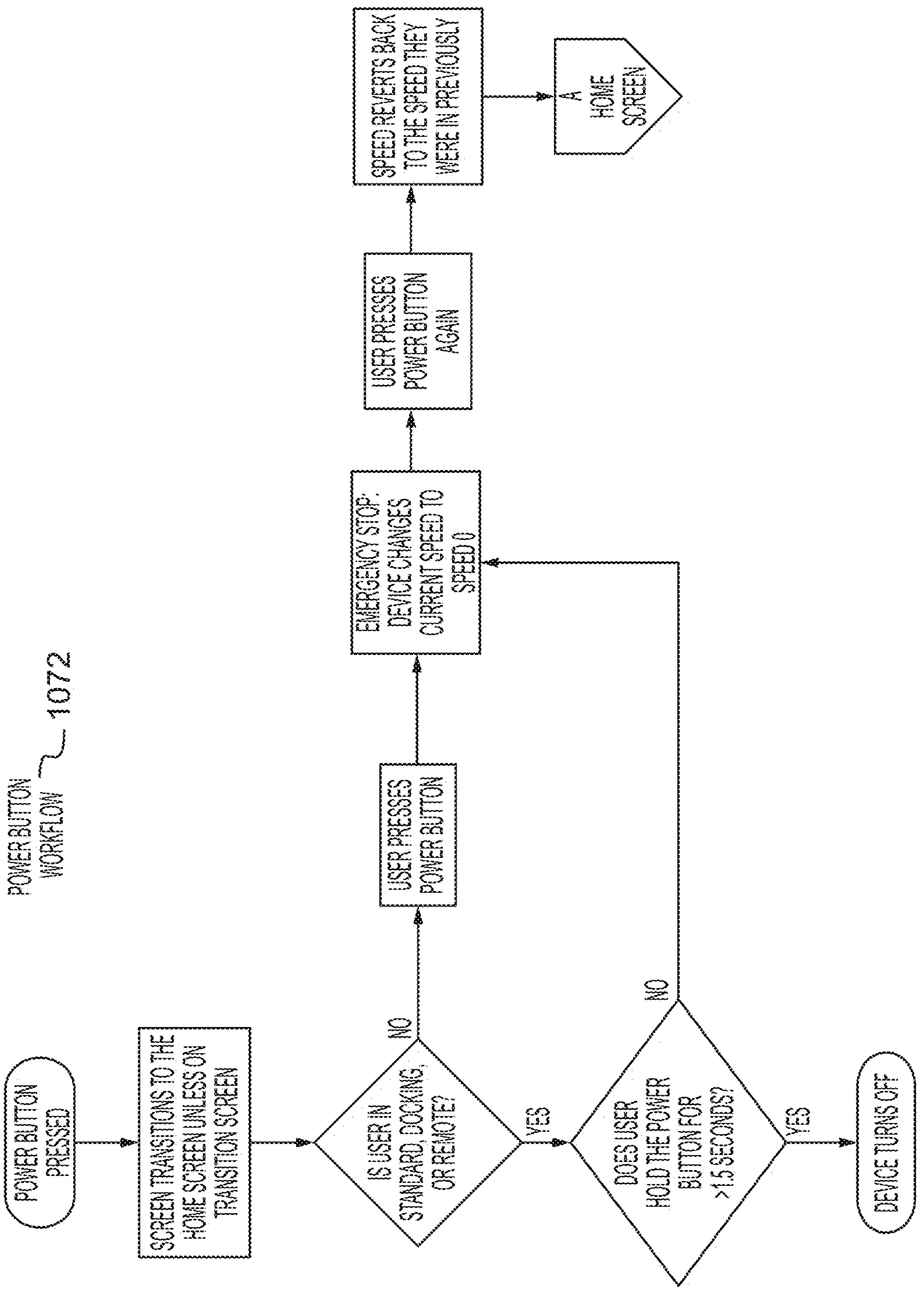
Figure 23N:
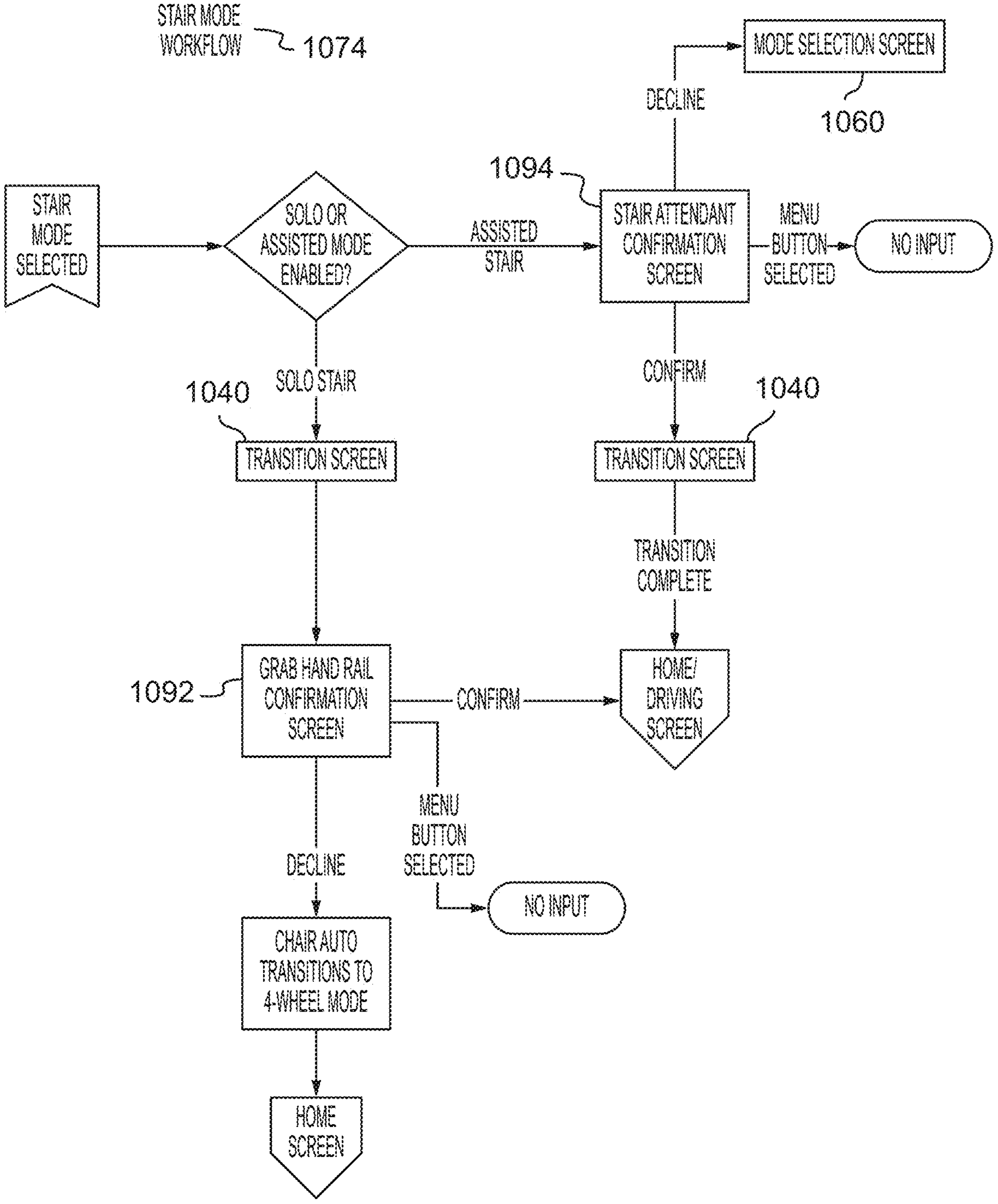
Figure 23O:
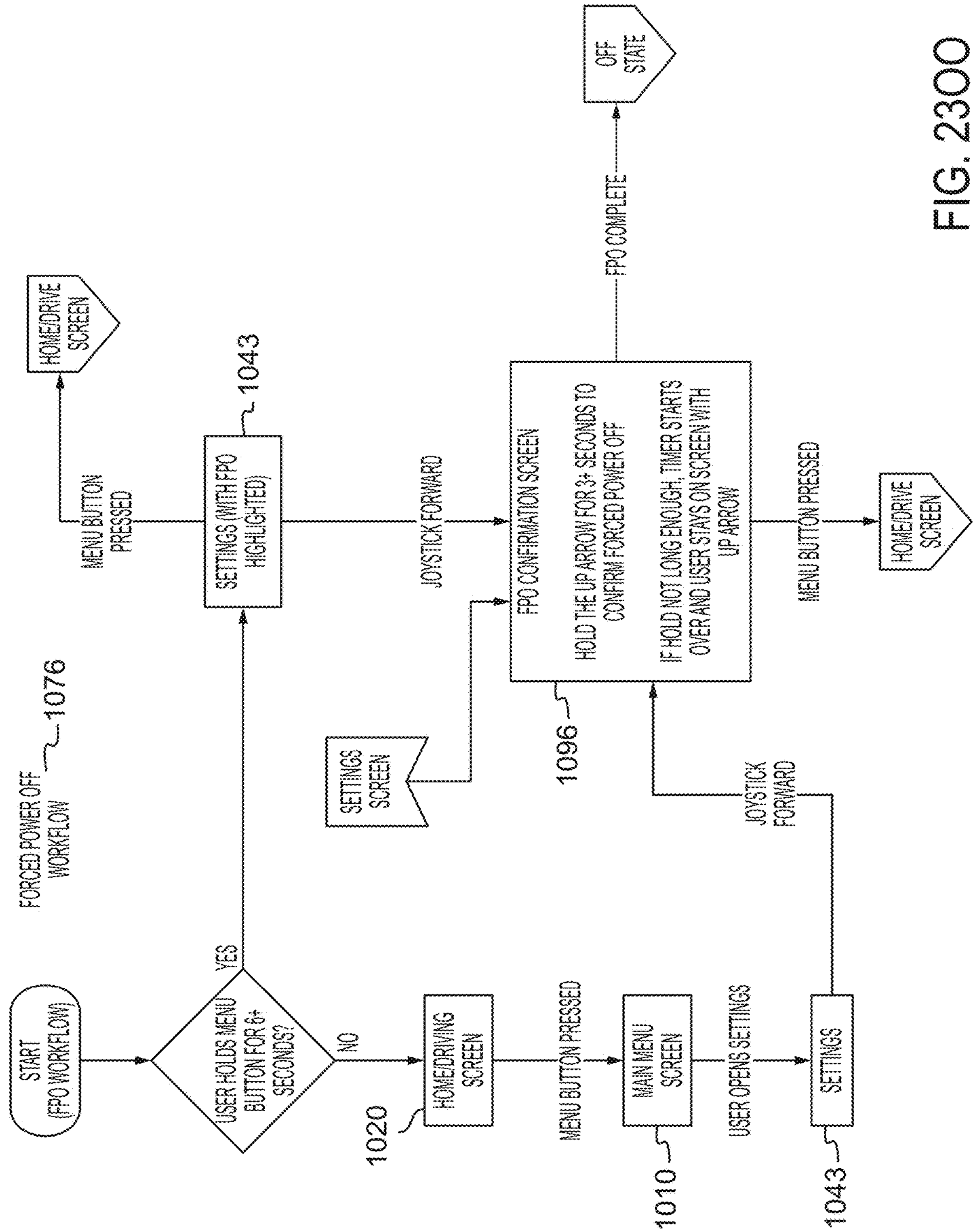
Figure 23X:
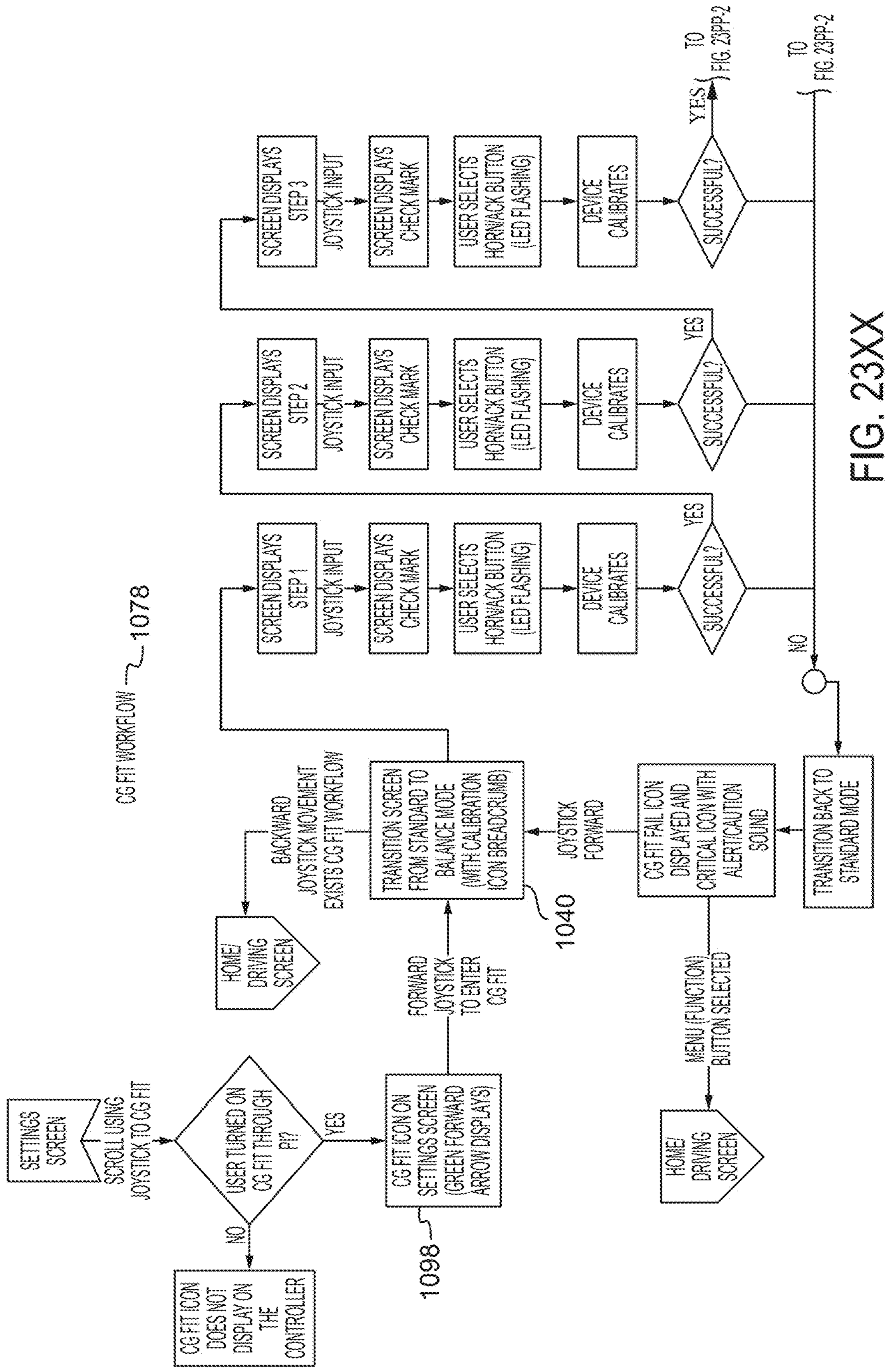
Figure 23Y:
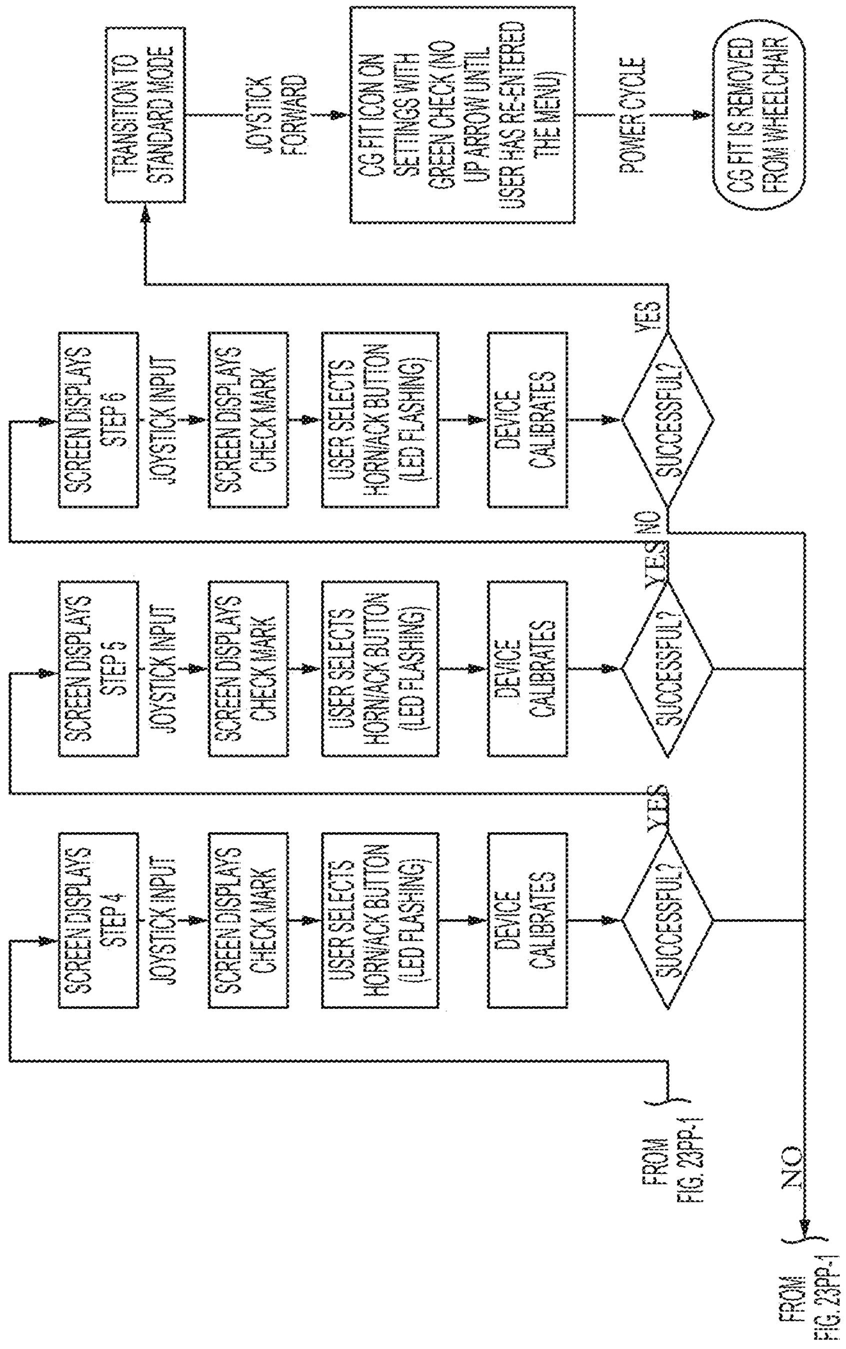
Figure 23Q:
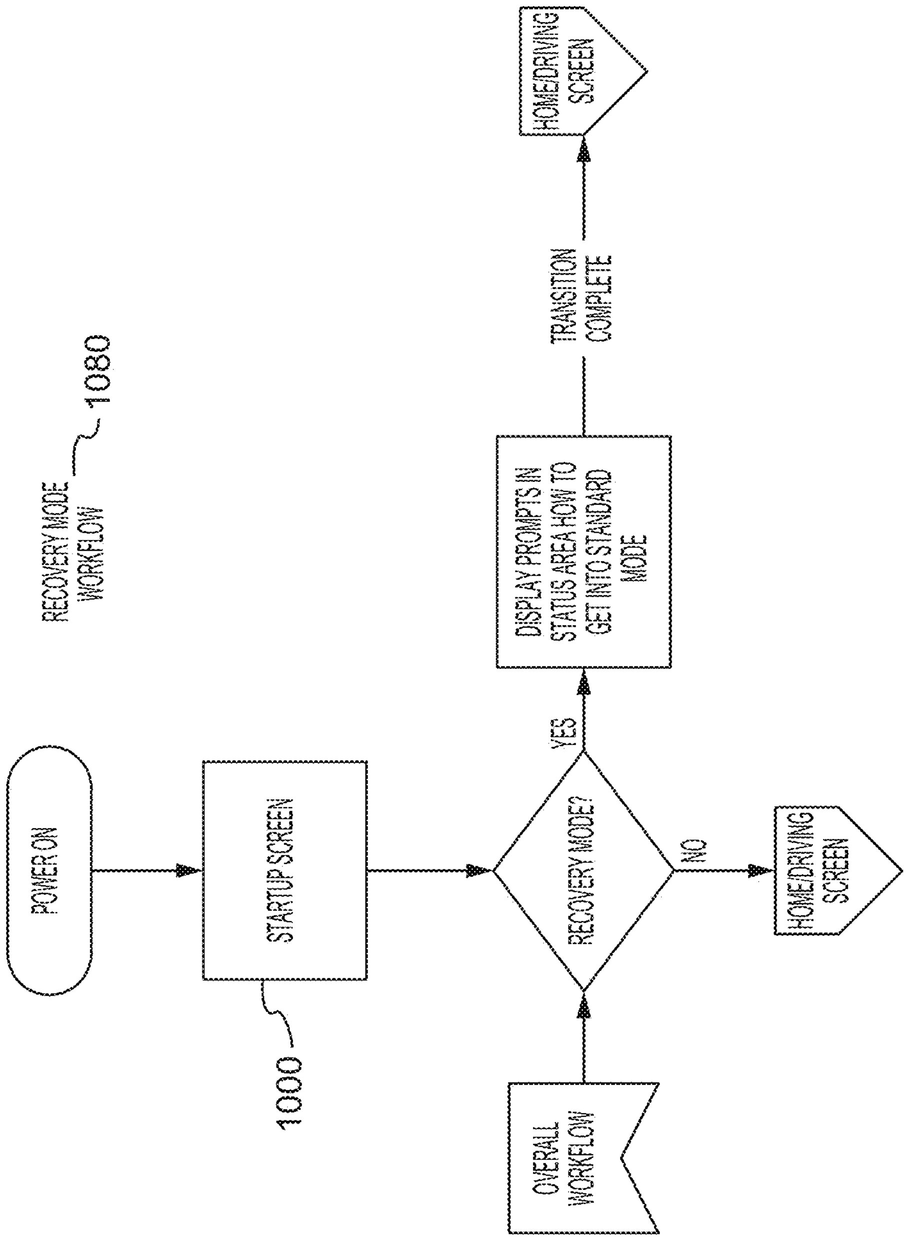
Figure 23R:
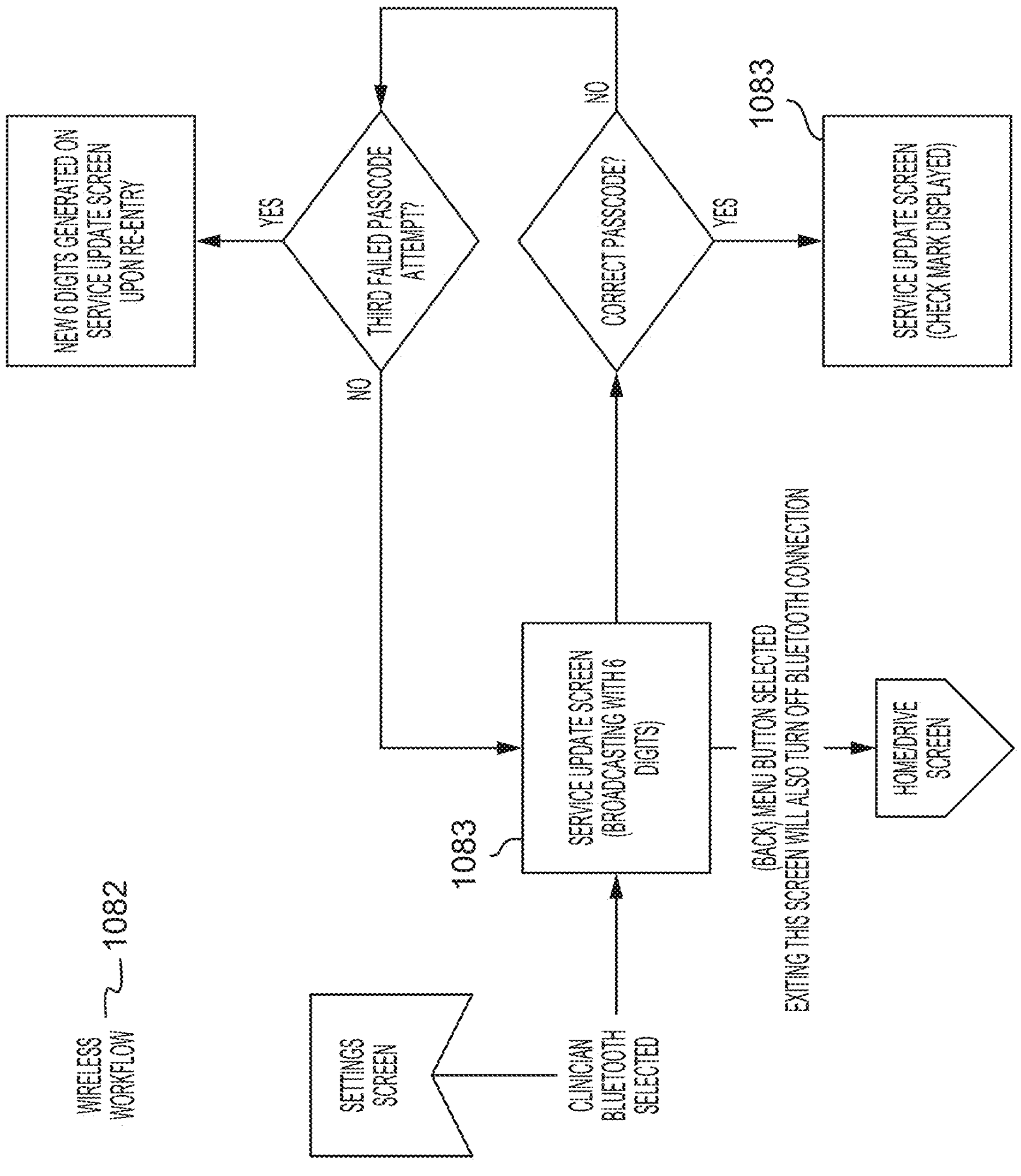
Figure 23S:
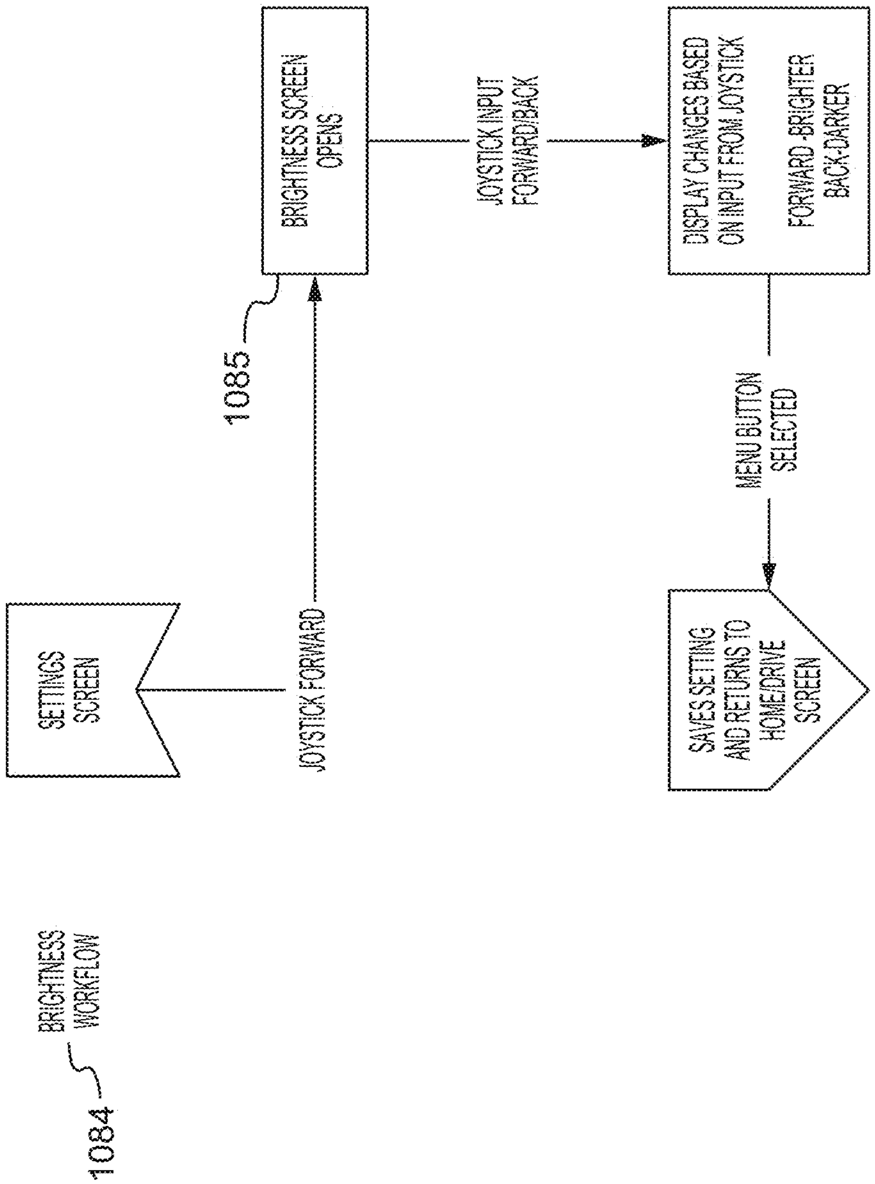
Figure 23T:
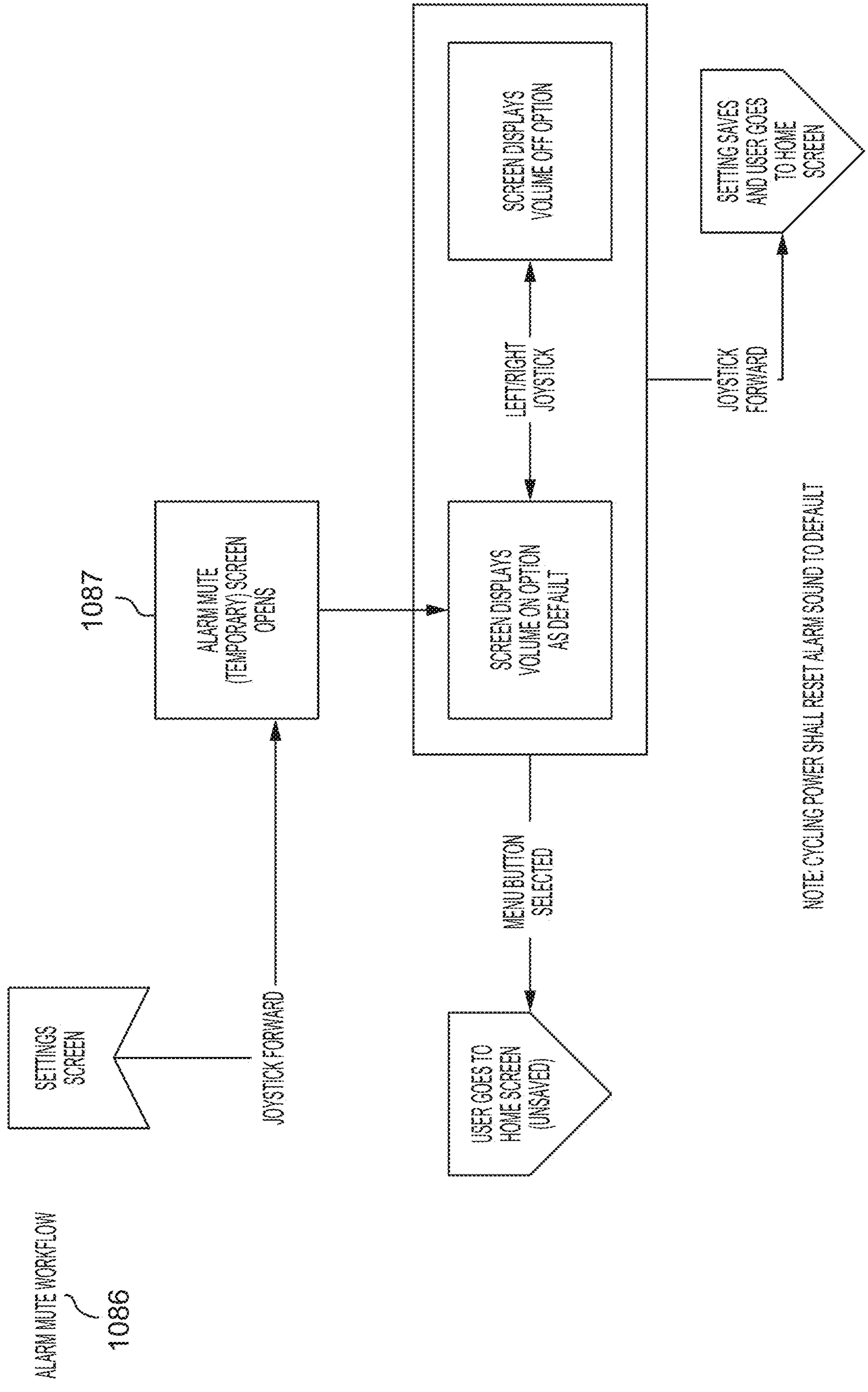
Figure 23U:
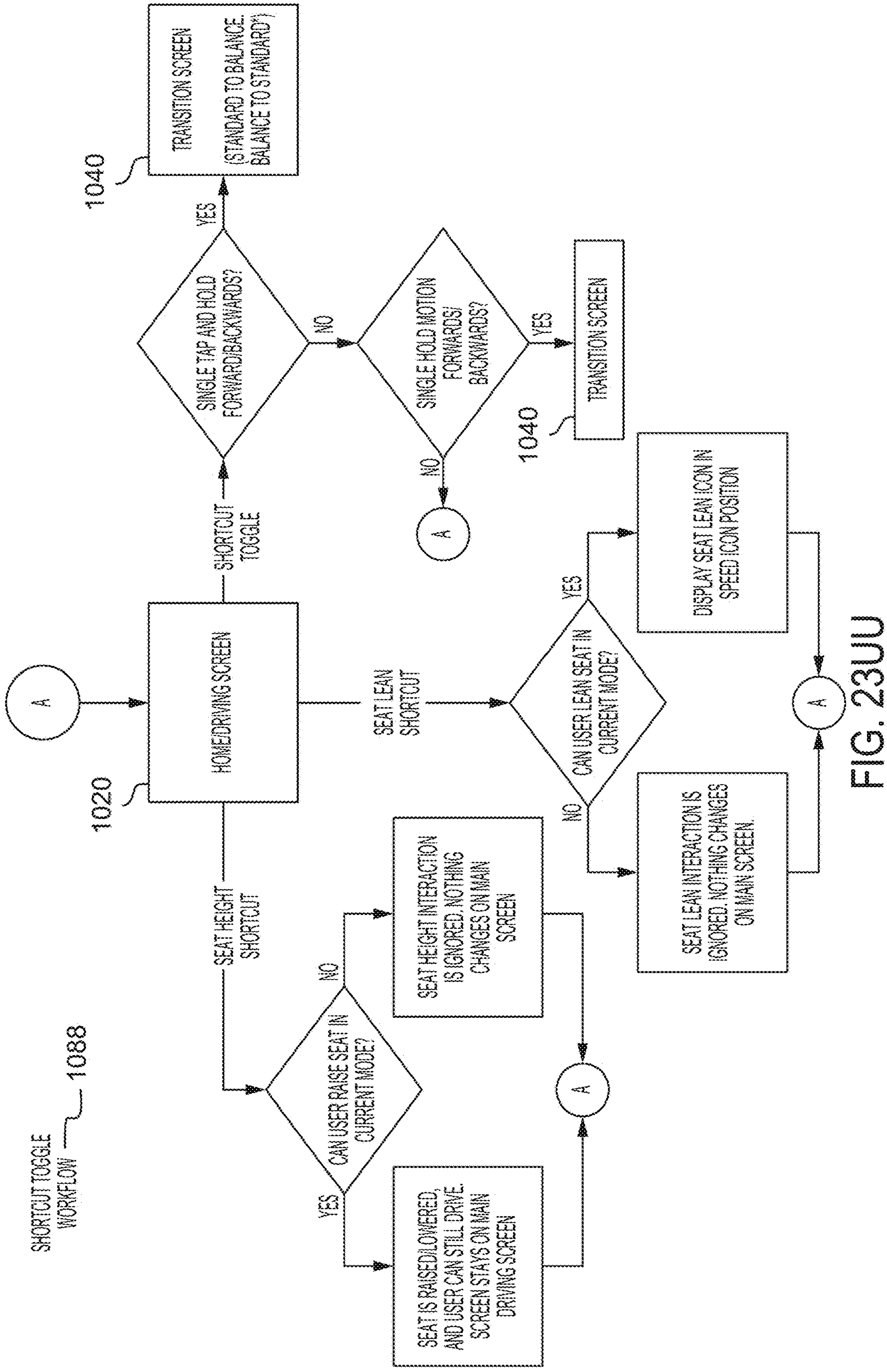
Figure 23V:
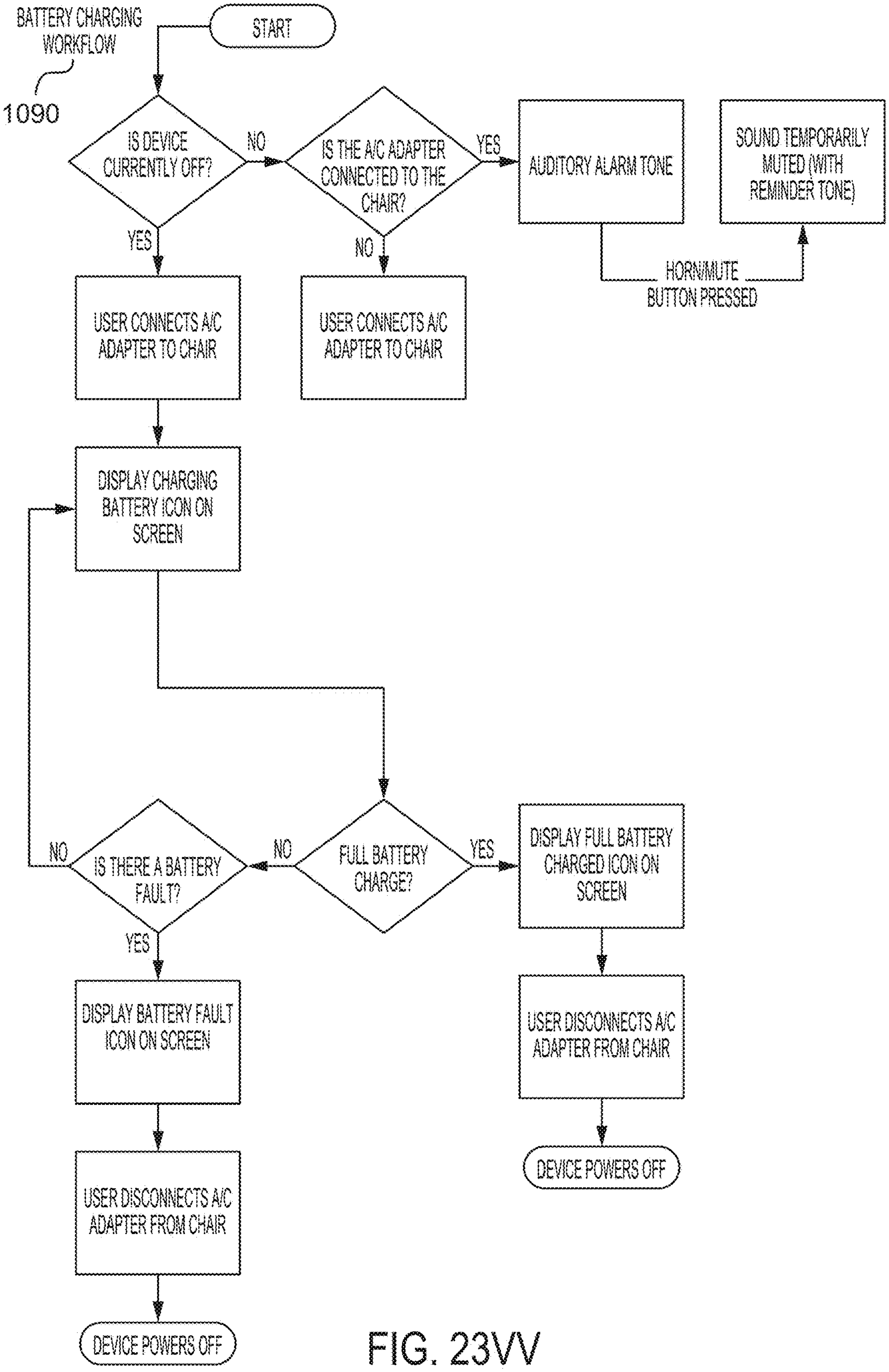
Figure 23Z:
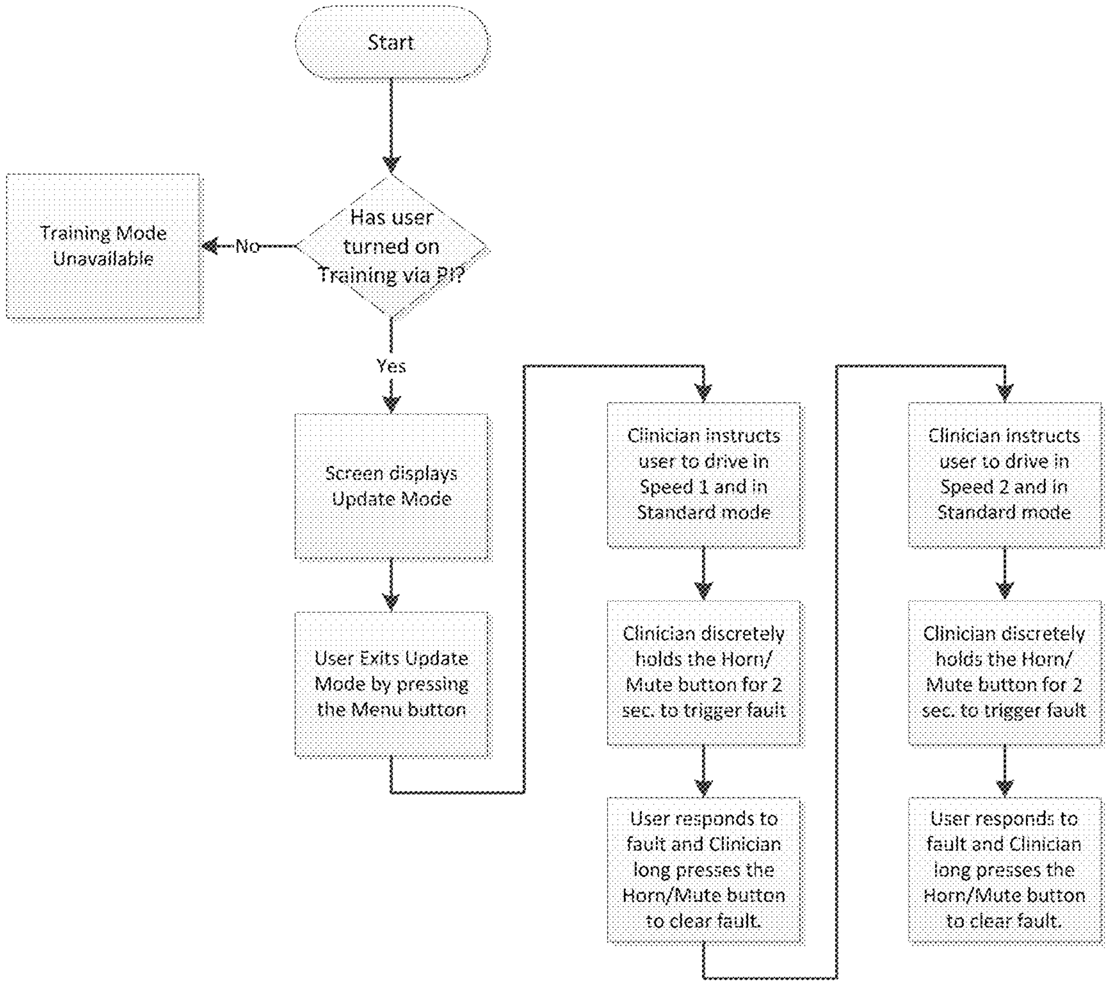

Referring now to FIGS. 23ZZ through 23BBB, when a user enables training mode, a series of manual steps that can be followed by automatic reactions can enable a user to practice various situations that the user of the MD can encounter. For example, the user can operate the MD at a speed or in a speed-limited situation and also in a desired mode. In some configurations, a clinician can trigger a fault, training the user to respond to the fault. The clinician can follow up by clearing the fault to prepare the MD for further training and/or use. In some configurations, the desired mode can include standard mode, 4-wheel mode, balance mode, and remote mode. In some configurations, the clinician can trigger/clear a fault by holding the horn/mute button for pre-selected time periods. In some configurations, power-cycling the MD can take the MD out of training mode.

Referring now to FIGS. 24A and 24B, UC home screen 1020/1020A can include, but is not limited to including, base banner 10 20A that can include, but is not limited to including, time, and indication of the status of the parking brake, an alert status, a service required status, and a temperature status. UC home screen 1020/1020A can include first screen area 1020-2 that can present, for example, but not limited to, the speed of the MD, and can also provide a shortcut for seat adjustment. A prompt can inform the user that the seat is in a position that prevents driving. Second screen area 1020-3 can display, for example, but not limited to, the current mode of the MD, for example, but not limited to, in iconic form. UC home screen 1020A (FIG. 24B) can include battery status strip 1020-4 that can provide, for example, but not limited to, battery status that can be, for example, visually highlighted in, for example, red, yellow, and green colors.

Referring now to FIGS. 24C and 24D. UC main menu screen 1010/1010A can include, but is not limited to including, base banner 10 20A and, optionally, battery status strip 1020-4 (FIG. 24D) as described herein. UC main menu screen 1010/1010A can accommodate selection of modes, seat adjustment, speed, and setting. A selection can be indicated by the presence of a highlighted icon, for example, within selected area 1010-2, which can be surrounded by further selection option arrows 1010-1. Each of selection area 1010-3 can include, but is not limited to including, an icon indicative of a possible selection option.

Referring now to FIGS. 24E-24H, UC selection screen 1050/1050A/1050B/1050C can include, but is not limited to including, base banner 10 20A and, optionally, battery status strip 1020-4 (FIG. 24F) as described herein. UC selection screen 1050/1050A/1050B/1050C can accommodate an indication of mode selected in mode selected area 1050-1. Optionally, selected mode can also be displayed in selected transition area 1050-3 that can be surrounded by unselected, but possible modes in unselected areas 1050-2 and 1050-4. UC selection screen can include breadcrumb 1050B-1 (FIG. 24G) that can provide a navigational path of the modes navigated.

Referring now to FIGS. 241 and 24J, UC transition screen 1040/1040A can include, but is not limited to including, base banner 10 20A and, optionally, battery status strip 1020-4 (FIG. 24D) as described herein. UC transition screen 1040/1040A can include target mode area 1040-1 in which an icon, for example, indicating the mode to which the transition is occurring, can be displayed. UC transition screen 1040/1040A can include transition direction area 1040-2 and transition status area 1040-3 that can indicate the status and direction of the transition from one mode to another.

Referring now to FIG. 24K, UC power off screen 1060A can include, but is not limited to including, base banner 10 20A, power off first screen area 1060A-1, power off second screen area 1060A-2, and optional battery status area 1020-4. When a user indicates a desire to power down the MD under normal conditions, for example, but not limited to, when the user depresses and holds the power button on UC 130, power off first screen area 1060A-1 can indicate the speed at which the MD is traveling, and power off second screen area 1060A-2 can indicate power off progress. In some configurations, power off progress can be indicated by the progressive changing of color of the area inside the shape in power off second screen area 1060A-2. Base banner 10 20A and optional battery status area 1020-4 are described elsewhere herein.

Referring now to FIG. 24L, UC forced power off screen 1060B can include, but is not limited to including, base banner 10 20A, forced power off first screen area 1060B-1, power off second screen area 1060A-2, and optional battery status area 1020-4. When a user indicates a desire to power down the MD under other than normal conditions, for example, but not limited to, if the MD is experiencing mechanical problems, the forced power off screen 1060A can display the progress of the power down sequence. In particular, forced power off first screen area 1060B-1 can indicate that a forced power off sequence is in progress, and power off first screen area 1060A-1 can indicate forced power off progress. In some configurations, forced power off progress can be indicated by the progressive changing of color of the area inside the shape in power off second screen area 1060A-2. In some configurations, the user can begin the forced power off sequence by navigating to a menu and selecting forced power off.

Referring now to FIGS. 24M and 24N, CG fit screen 1070 can include, but is not limited to including, base banner 10 20A, CG fit breadcrumb 1070-1, menu button indicator 1070-2, and optional battery status area 1020-4. When a user indicates a desire to perform a CG fit, the CG fit screen 1070 can display prompts for actions that can be needed to perform CG fit. In particular, CG fit breadcrumb 1070-1 can indicate that a CG fit is in progress in which prompts can be displayed that can indicate the joystick action required to move from one step in the CG fit process to the next. Steps can include raising, lowering, and tilting the MD when input is received by the MD such as laid out in FIGS. 23FF-23HH, for example. Menu button 1070-2 can be depressed when it is desired to drive the MD while a CG fit is in progress. In some configurations, completion, either successful or unsuccessful, of the CG fit process can indicate that exit of the CG fit process is possible.

Referring now to FIG. 25A, speed processor 755 can accommodate a continuously adjustable scaled factor to control the MD. A user and/or clinician can set at least one parameter bound 765 that can be adjusted according to the driving needs of the user and/or clinician. Wheel commands 769 can be calculated as a function of joystick input 629 and profile constants 768 that can include, but are not limited to including, $k_s$ 601/607 (FIG. 25E), $k_a$ 603/609 (FIG. 25E), $k_d$ 605/611 (FIG. 25E), and $k_m$ 625 (FIG. 25E), where $k_s$ 601/607 (FIG. 25E) is a maximum speed range, $k_a$ 603/609 (FIG. 25E) is an acceleration range, $k_d$ 605/611 (FIG. 25E) is a deadband range, $k_m$ 625 (FIG. 25E) is a merge range, and $k_w$ is a conversion from wheel counts to speed. Ranges of profile constants $k_s$, $k_a$, $k_d$, and $k_m$ 625 (FIG. 25E) can vary, ranges provided herein are exemplary. Parameter bounds 765 and profile constants 768 can be supplied by, for example, but not limited to, the user, can be pre-set, and can be determined in any other way. Speed processor 755 can access parameter bounds 765 and profile constants 768. Exemplary ranges for profile constants 768 can include:

$$k_s = \text{Max Speed value, can scale from, for example, but not limited to, } 1-4 \text{ m/s}$$

$$k_a = \text{Acceleration value, can scale from, for example, but not limited to, } 0.5-1.5$$

$$k_d = \textit{Deadband} \text{ value, can scale from, for example, but not limited to, } 0-5.5$$

$$k_m = \text{Merge value, can scale from, for example, but not limited to, } 0-1$$

$$k_{s,m} = k_{s,1}(1-k_m) + k_m k_{s,2}$$

$$k_{a,m} = k_{a,1}(1-k_m) + k_m k_{a,2}$$

$$k_{d,m} = k_{d,1}(1-k_m) + k_m k_{d,2}$$

where $k_{x,1}$ is the minimum of the range of gain $k_x$, and $k_{x,2}$ is maximum of the range of gain $k_x$, where x=s or a or m. Exemplary parameter bounds 765 can include:

$$J_{max} = \text{Max Joystick } \textit{Cmd}$$

$$C_1 = \text{First Order } \textit{Coeff} = k_{d,m}$$

$$C_3 = \text{Third Order } \textit{Coeff} = k_{s,m}$$

where $k_{d,m}$ is the gain $k_d$ of the merger of profile A 613 (FIG. 25E) and profile B 615 (FIG. 25E), and where $k_{s,m}$ is the gain $k_s$ of the merger of profile A 613 (FIG. 25E) and profile B 615 (FIG. 25E).

$$k_w = \text{wheel counts per m/s}$$

$$V_{max} = \text{Max Command} = C_1 J_{max} + C_3 J_{max}{}^3$$

$$k_p = \text{Proportional Gain} = \frac{k_w C_s}{V_{max}}$$

Exemplary computations for wheel command 769 can include:

$$J_i = \text{Joystick } \textit{Cmd}$$

$$W_i = k_{p,m}\left(k_{d,m} J_i + C_3 J_i{}^3\right), \text{ wheel } \frac{\text{velocity}}{\text{yaw}} \text{ command}$$

where $W_i$ 769 is the velocity or yaw command that is sent to right/left wheel motor drive 19/31, 21/33.

Continuing to refer primarily to FIG. 25A, adjusting $C_3$ can adjust the shape of the curve of the profile and therefore the user experience when user commands, for example, but not limited to, joystick commands 629, are converted to wheel commands 769. In particular, adjusting C can adjust the size of deadband 605/611 (FIG. 25E) and the maxima and minima on either side of deadband 605-611 (FIG. 25E). Speed processor 755 can include, but is not limited to including, joystick processor 756 including computer instructions to receive joystick commands 629, and profile constants processor 754 including computer instructions to access profile constants 768 and merge value 625 (FIG. 25E), and to scale profile constants 768 based at least on merge value 625 (FIG. 25E), for example, but not limited to, as shown in equations set out herein. Speed processor 755 can also include bounds processor 760 including computer instructions to compute a maximum velocity based at least on profile constants 768 and a maximum joystick command, and to compute a proportional gain based at least on profile constants 768 and the maximum velocity, as shown, for example, but not limited to, in equations set out herein. Speed processor 755 can also include wheel command processor 761 including computer instructions to compute wheel command 769 based at least on profile constants 768 and joystick commands 629, as shown, for example, but not limited to, in equations set out herein, and provide wheel commands 769 to wheel motor drives 19/31/21/33.

Referring now primarily to FIG. 25B, method 550 for accommodating a continuously adjustable scale factor can include, but is not limited to including, receiving 551 joystick commands 629 (FIG. 25A), accessing 553 profile constants 768 (FIG. 25A) and a merge value (shown exemplarily as merge value 625 (FIG. 25E) which portrays the merger of profile A 613 (FIG. 25E) and profile B 615 (FIG. 25E)), scaling 555 profile constants 768 (FIG. 25A) based at least on the merge value, computing 557 a maximum velocity based at least on profile constants 768 (FIG. 25A) and a maximum joystick command (shown exemplarily as the maximum of speed 601 (FIG. 25E), acceleration 603 (FIG. 25E), and deadband 605 (FIG. 25E)), computing 559 a proportional gain based at least on profile constants 768 (FIG. 25A) and the maximum velocity, computing 561 wheel command 769 (FIG. 25A) based at least on profile constants 768 (FIG. 25A) and joystick commands 629 (FIG. 25A), and providing 563 wheel commands 769 (FIG. 25A) to wheel motor drives 19/31/21/33 (FIG. 25A). In some configurations, powerbase controller 100 can modify joystick command 629 provided by user controller 130 before joystick commands 629 are provided to joystick processor 756. In some configurations, user controller 130 could be receiving joystick commands 629 from a joystick, whereas in some configurations, user controller 130 can include the joystick.

Referring now primarily to FIG. 25C, joystick 130 (FIG. 12A) can be configured to have different transfer functions to be used under different conditions according to, for example, the abilities of the user. Speed template (transfer function) 700 shows an exemplary relationship between physical displacement 702 of joystick 70007 (FIG. 12A) and output 703 of UC 130 (FIG. 12A) after transfer function processing with a particular transfer function. Forward and reverse travel of joystick 70007 (FIG. 12A) can be interpreted as forward longitudinal requests and reverse longitudinal requests, respectively, as viewed from a user in the seat of the MD, and can be equivalent to commanded velocity. Left and right travel of joystick 70007 (FIG. 12A) can be interpreted as left turn requests and right turn requests, respectively, as viewed from a user in the seat, and can be equivalent to a commanded turn rate. Joystick output 703 can be modified during certain conditions such as, for example, but not limited to, battery voltage conditions, height of the seat, mode, failed conditions of joystick 70007 (FIG. 12A), and when speed modification is requested by powerbase controller 100 (FIG. 25A). Joystick output 703 can be ignored and joystick 70007 (FIG. 12A) can be considered as centered, for example, but not limited to, when a mode change occurs, while in update mode, when the battery charger is connected, when in stair mode, when joystick 70007 (FIG. 12A) is disabled, or under certain other conditions.

Continuing to refer primarily to FIG. 25C, the MD can be configured to suit a particular user. In some configurations, the MD can be tailored to user abilities, for example, by setting speed templates and mode restrictions. In some configurations, the MD can receive commands from external applications 140 (FIG. 16B) executing on devices such as, for example, but not limited to, a cell phone, a computer tablet, and a personal computer. The commands can provide, for example, default and/or dynamically-determinable settings for configuration parameters. In some configurations, a user and/or an attendant can configure the MD.

Referring now primarily to FIG. 25D, in some configurations, speed settings can control the system response to joystick movement. In some configurations, a speed setting such as speed 0 can be used to disable a response to joystick movement, a speed setting such as speed 1 can be used to set a maximum speed that may be appropriate for indoor travel, and a speed setting such as speed 2 can be used to set a maximum speed that may be appropriate for outdoor and/or hallway travel. The MD can be configured with any number of speed settings, and the relationship between joystick movement and motor commands can include non-linear functions. For example, a parabolic relationship could provide finer control at low speeds. In some configurations, a thumbwheel assembly as in FIG. 12P can be used to apply a gain on top of the described speed settings. In some configurations, the gain can vary from 0 to 1 , and a gain of 1 can be used when no speed variations are desired over configured speeds. When the thumbwheel assembly is used to change the gain by dialing thumbwheel knob 30173 (FIG. 12N) "down", the maximum speed and every speed along the configured speed trajectory can be reduced proportionally to the amount of the dialing "down". Any maxima for speeds 1 and 2, for example, can be configured, and minima can be configured as well. In some configurations, speed 2 can include a minimum speed that is greater than the maximum speed of speed 1 (see FIG. 25N), the speed 2 minimum speed and the speed 1 maximum speed can overlap (see FIG. 25L), and the speed 2 minimum can approximately equal the speed 1 maximum (see FIG. 25M). In some configurations, the speed 1 and speed 2 minima and maxima can be adjusted so that speed 1 and speed 2 don't overlap, and thus skipping from speed 1 to speed 2 or vice versa can be disabled. In some configurations, when the current speed setting is already at its maximum, for instance, further dialing "up" of the thumbwheel 30173 (FIG. 12N) can be ignored and can result in no change in speed. However, any dialing "down" of the thumbwheel can immediately cause the speed gain to decrease proportionally to the "downward" movement of the thumbwheel. Similarly, when the current speed setting is at its minimum, dialing the thumbwheel "down" can result in no change, but dialing "up" can immediately cause an increase in speed gain.

Continuing to refer to FIG. 25D, in some configurations, manipulation of thumbwheel knob 30173 (FIG. 12N) can be interpreted as a desired for a speed setting change. In some configurations, continuing to dial the thumbwheel "up" when the gain is already saturated at that speed's maximum can indicate a request to increase the speed setting. Similarly, continuing to dial down when the gain is at its minimum can indicate a request for a lower speed setting. In some configurations, dialing thumbwheel knob 30173 (FIG. 12N), pausing any thumbwheel assembly manipulation, and resuming dialing of thumbwheel knob 30173 (FIG. 12N) can indicate a request for a change in speed settings. In some configurations, multiple manipulations surrounding one or more pauses can indicate a request for a change in speed settings. In some configurations, the rate of manipulation of thumbwheel knob 30173 (FIG. 12N) can indicate, rather than a change in the gain itself, instead a request to change the speed setting.

Referring now primarily to FIG. 25E, a user and/or clinician can use a graphical user interface display that could be, for example, but not limited to, included in user controller 130 (FIG. 12A), to enable configuration of drive options in the form of joystick command shaping that can allow the user and/or clinician to configure the MD for driving preferences. Templates can be provided for the user/clinician to set or pre-set profile constants 768 (FIG. 25A) that can place the MD in at least one situation, for example, but not limited to, sport situation, comfort situation, or economy situation. In economy mode, for example, speed and acceleration can be limited to reduce power consumption. In sport situation, the user could be allowed to drive aggressively by, for example, but not limited to, achieving maximum speeds. Comfort situation can represent an average between economy and sport situations. Other situations can be possible. Profile constants $k_s$ 601/607, $k_a$ 603/609, $k_d$ 605/611, and $k_m$ 625 can be adjusted through, for example, but not limited to, variable display items, and wheel command velocity $W_i$ can be computed and graphed based at least on adjusted $k_s$ 601/607, $k_a$ 603/609, $k_d$ 605/611, and $k_m$ 625. For example, profiles A/B 613/615 can result from adjusting speed and deadpan ranges such that $k_s$ 601 and $k_s$ 607 differ, and $k_d$ 605 and $k_d$ 611 are similar. Wheel command velocity $W_i$ can be computed and graphed for a range of joystick command counts 629 for both the minimum values (profile A 613) of $k_s$ 601/607, $k_a$ 603/609, $k_d$ 605/611, and $k_m$ 625 and the maximum values (profile B 615) of $k_s$ 601/607, $k_a$ 603/609, $k_d$605/611, and $k_m$ 625. Profile A 613 and profile B 615 can be averaged for an easier comparison with other configurations of profile constants $k_s$ 601/607, $k_a$ 603/609, $k_d$ 605/611, and $k_m$ 625. For example, first joystick control graph 600 indicates that an average wheel command 617 of 1.5 m/s at 100 joystick command counts results from a first configuration of $k_s$ 601/607, $k_a$ 603/609, $k_d$ 605/611, and $k_m$ 625.

Referring now to FIG. 25F, when $k_s$ 601 and $k_s$ 607 are similar, and $k_d$ 605 and $k_d$611 differ, wheel command velocity $W_i$ can be computed and graphed for a range of joystick command counts 629 for both the minimum values (profile A 623) of $k_s$ 601/607, $k_a$ 603/609, $k_d$ 605/611, and $k_m$ 625 and the maximum values (profile B 621) of $k_s$ 601/607, $k_a$ 603/609, $k_d$605/611, and k, 625. Profile A 623 and profile B 621 can be averaged and compared to other configurations of profile constants $k_s$ 601/607, $k_a$ 603/609, $k_d$ 605/611, and $k_m$ 625. For example, second joystick control graph 700A indicates that an average wheel command 617 of 1.75 m/s at 100 joystick command counts results from a second configuration of profile constants $k_s$ 601/607, $k_a$ 603/609, $k_d$ 605/611, and $k_m$ 625. Changes to $k_a$ 603 and $k_a$ 609 can scale filter constants under certain circumstances. Further, joystick command 629 can be filtered by a joystick filter to enable speed-sensitive steering by managing accelerations. For example, a relatively low corner frequency CF of the joystick filter can result in a relatively high damped response between joystick commands 629 and activity of the MD. For example, the corner frequency CF can be an adjustable function of speed which could result in, for example, but not limited to, a relatively high relationship between joystick commands 629 and wheel command velocity $W_i$ 769 when the MD is traveling at a relatively high speed, and a relatively lower relationship between joystick commands 629 and wheel command velocity $W_i$ 769 when the MD is traveling at a relatively low speed. For example, wheel command velocity $W_i$ 769 can be compared to a full speed threshold T and the corner frequency CF can be set according to the result of the comparison. In some configurations, if wheel command velocity $W_i$ 769 is less than a value based at least on the threshold T, the corner frequency CF can be set to a first value, or if wheel command velocity $W_i$ 769 is less than the threshold T, the corner frequency CF can be set to another value, for example (W*CF)/T. Deceleration rate and acceleration rate can be managed separately and can be independent of one another. For example, deceleration rate may not be allowed to be as aggressive as acceleration rate. The deceleration rate can, for example, depend on the acceleration rate or can dynamically vary in some other way, or can be a fixed value. The user can, for example, control the deceleration rate.

Referring now to FIG. 25G, adaptive speed control processor 759 for adaptive speed control of the MD can include, but is not limited to including, terrain/obstacle data receiver 1107 including computer instructions to receive terrain and obstacle data in the vicinity of the MD. By using terrain and obstacle detection sensors for example, but not limited to, light detection and ranging (LIDAR), remote sensing technology can measure distance by illuminating a target with a laser and analyzing the reflected light, stereo cameras, and radar. Adaptive speed control processor 759 can also include mapping processor 1109 including computer instructions to map obstacles and approaching terrain in real time based at least on the terrain and obstacle data. Adaptive speed control processor 759 can further include virtual valley processor 1111 including computer instructions to compute virtual valleys based at least on the mapped data. Virtual valley processor 1111 can delineate a sub-area referred to herein as a virtual valley in the vicinity of the MD. The virtual valley can include at least one low point, gradual and/or dramatic elevation increases from the at least one low point, and at least one rim surrounding the at least one low point in which the gradual and/or dramatic elevation increases terminate at the rim. In the virtual valley, a relatively high wheel command 769 can be required to turn out of the virtual valley, possibly pre-disposing the MD to stay in the low point of the virtual valley. Adaptive speed control processor 759 can further include collision possible processor 1113 including computer instructions to compute collision possible areas based at least on the mapped data. Collision possible areas can be sub-areas in which, when in the vicinity of the MD, adaptive speed control processor 759 can make it difficult to steer the MD into the obstacle. Collision possible areas can, for example, prevent the MD from running into objects. The position of the MD can be measured from, for example, any part or parts of the MD, for example, the center, the periphery, or anywhere in between. Adaptive speed control processor 759 can further include slow-down processor 1115 including computer instructions to compute slow-down areas based at least on the mapped data and the speed of the MD. Adaptive speed control processor 759 can slow the MD in the slow-down areas. Adaptive speed control processor 759 can further make it difficult to turn into slow-down areas relative to turning into non-slow-down areas. Adaptive speed control processor 759 can recognize any number of types of slow-down areas, each having a set of characteristics. For example, adaptive speed control processor 759 can adjust the processing of fore-aft commands to the MD in some types of slow-down areas differently than in others. In some configurations, the size of the different types of slow-down areas can change as the speed of the MD changes. Adaptive speed control processor 759 can still further include preferences processor 1117 including computer instructions to receive user preferences with respect to the slow-down areas. Adaptive speed control processor 759 can include wheel command processor 761 including computer instructions to compute wheel commands 769 based at least on, for example, but not limited to, the virtual valleys, the collision possible areas, the slow-down areas, and the user preferences, and provide wheel commands 769 to wheel motor drives 19/31/21/33. When adaptive speed control processor 759 detects that the MD has entered, for example, a collision possible area, adaptive speed control processor 759 can, for example, move the MD away from the collision possible area. Adaptive speed control processor 759 can move the MD in a direction to the direction opposite the collision possible area, a direction parallel to the collision possible area, or a direction that moves the MD into a collision free area.

Referring now primarily to FIG. 25H, method 1150 for adaptive speed control of the MD can include, but is not limited to including, receiving 1151 terrain and obstacle detection data, mapping 1153 terrain and obstacles, if any, in real time based at least on the terrain and obstacle detection data, optionally computing 1155 virtual valleys, if any, based at least on the mapped data, computing 1157 collision possible areas, if any, based at least on the mapped data, computing 1159 slow-down areas if any based at least on the mapped data and the speed of the MD, receiving 1161 user preferences, if any, with respect to the slow-down areas and desired direction and speed of motion, computing 1163 wheel commands 769 (FIG. 25G) based at least on the collision possible areas, the slow-down areas, and the user preferences and optionally the virtual valleys, and providing 1165 wheel commands 769 (FIG. 25G) to wheel motor drives 19/31/21/33 (FIG. 25G). Collision possible areas can include discreet obstacles that can include a buffer that can follow the contour of the discreet obstacle, or can follow a type of outline, for example, but not limited to, a polygon, enclosing the discreet obstacle. Collision possible areas can also include a number of discreet obstacles viewed as a single discreet obstacle. The transition area between one sub-area and another can be, for example, abrupt or gradual. The shape of a virtual valley can be dynamic based at least upon the position of the MD in the virtual valley.

Referring now to FIG. 25I, gradient map 1120A can be used to indicate to the user at, for example, but not limited to, user controller 130 (FIG. 12A), either periodically or dynamically updated, the sub-areas in the vicinity of the MD. For example, collision possible areas 1121 can be places in which adaptive speed control processor 759 can make it automatically impossible to steer into and the MD can be automatically prevented from running into objects and can be, for example, but not limited to, steered to a different direction of travel. In some configurations, the position of the MD can be measured from the center of the MD and, in some configurations, the edge of the MD can be substantially near to the physical objects in the vicinity of the MD. In some configurations, first slow-down areas 1125 can be places in which adaptive speed control processor 759 can automatically slow down the MD slightly and can make turning into first slow-down areas 1125 more difficult than turning into no-barriers sub-areas 1127. In some configurations, second slow-down areas 1123 can be places in which adaptive speed control processor 759 can automatically slow down fore-aft commands to the MD more than in first slow-down sub-areas 1125, and adaptive speed control processor 759 can automatically make turning into second slow-down sub-areas 1123 harder than turning into first slow-down sub-areas 1125.

Referring now to FIG. 25J, path map 1130 can indicate path 1133 that the MD can follow when adaptive speed control processor 759 (FIG. 25G) recognizes special sub-areas in the vicinity of the MD. As user controller 130 (FIG. 16A) receives forward velocity commands, the MD, under the control of adaptive speed control processor 759 (FIG. 25G), can veer according to path 1133 towards no barriers sub-area 1127 and, for example, turn to a less collision-likely direction of travel.

Referring now to FIG. 25K, adaptive speed control processor 759 can recognize objects that are moving (referred to herein as dynamic objects). Terrain/obstacle data receiver 1107 can receive from sensors 1105 terrain/obstacle detection data 1101 that is characteristic of non-stationary (dynamic) object 1134. Preferences processor 1117 can, for example, receive joystick commands 629 that indicate that straight path 1132 is the user-selected direction of travel, but when dynamic object 1134 is ahead of the MD and straight path 1132 would intersect with dynamic object 1134, dynamic object processor 1119 (FIG. 25G) can designate a set of sub-areas around dynamic object 1134 starting with first slow down area 1125, then transitioning to second slow-down sub-area 1123, and finally transitioning to collision possible sub-area 1121. When sensors 1105 recognize the sub-areas in the vicinity of dynamic object 1134, slow-down processor 1115 can slow the MD when entering first slow-down sub-area 1125 and dynamic object processor 1119 can match the pace of dynamic object 1134 in second slow-down sub-area 1123. If preferences processor 1117 receives an aggressive forward command in first slow-down sub-areas 1125 and/or second slow-down sub-area 1123, or an oblique command, dynamic object processor 1119 can adjust path 1132 to veer as, for example, in path 1131, to follow the safest closest path past dynamic object 1134. Forward velocity commands, in the absence of adaptive speed control processor 759 (FIG. 25G), could have the MD follow path 1132 directly through first slow-down sub-area 1125, second slow-down sub-area 1123, and collision possible subarea 1121.

Referring now primarily to FIG. 26A, traction control processor 762 can adjust the torque applied to wheels 21201 (FIG. 6A) to minimize slipping. In particular, adjusting the torque can prevent wheels 21201 (FIG. 6A) from excessive slipping. When the linear acceleration measured by inertial sensor packs 1070/23/29/35 and linear acceleration measured from the wheel velocity disagree by a pre-selected threshold, cluster 21100 (FIG. 6A) can drop such that wheels 21201 (FIG. 6A) and caster assemblies 21000 (FIG. 7) are on the ground. Having wheels 21201 (FIG. 6A) and caster assemblies 21000 (FIG. 7) on the ground at once can lengthen the wheelbase of the MD and can increase the friction coefficient between the MD and the ground. Linear acceleration processor 1351 can include computer instructions to compute the acceleration of the MD based at least on the speed of wheels 21201 (FIG. 6A). IMU acceleration processor 1252 can include computer instructions to compute the IMU acceleration based at least on sensor data 767 from inertial sensor pack 1070/23/29135. Traction loss processor 1254 can compute the difference between the MD acceleration and the IMU acceleration, and compare the difference to a pre-selected threshold. If the threshold is exceeded, wheel/cluster command processor 761 can send cluster commands 771 (FIG. 17A) to cluster 21100 (FIG. 6A) to drop such that wheels 21201 (FIG. 6A) and caster assembly 21000 (FIG. 7) are on the ground. Wheel/cluster command processor 761 can adjust the torque to wheel motor drives 19/21/31/33 by dynamically adjusting drive current limits if traction loss is detected. In some configurations, wheel/cluster command processor 761 can compute torque values for wheels 21201 (FIG. 6A) that can be independent of each other and based at least on the speed of the MD and the speed of wheels 21201 (FIG. 6A). In some configurations, traction loss processor 1254 can include computer instructions to dynamically adjust the center of gravity of the MD, for example, but not limited to, backwards and forwards to manage traction for the MD.

Continuing to still further refer to FIG. 26A, in standard mode 100-1 (FIG. 22B), cluster 21100 (FIG. 6A) can be rotated to affect traction so that wheels 21201 (FIG. 6A) can come in contact with the ground when aggressive and/or quick braking is requested. Aggressive braking can occur when the MD is traveling forward and receives a reverse command from, for example, user controller 130 (FIG. 12A), that exceeds a pre-selected threshold. In enhanced mode 100-2 (FIG. 22B), traction control processor 762 can accomplish traction control by (1) detecting the loss of traction by taking the difference between a gyro measured device yaw and differential wheel speed of predicted device yaw, and (2) reducing the torque to wheel motors drives A/B 19/21/31/33 by dynamically reducing the drive current limits when loss of traction is detected.

Referring now primarily to FIG. 26B, method 1250 for controlling traction of the MD can include, but is not limited to including, computing 1253 the linear acceleration of the MD, and receiving 1255 the IMU measured acceleration of the MD. If 1257 the difference between an expected linear acceleration and a measured linear acceleration of the MD is greater than or equal to a preselected threshold, adjusting 1259 the torque to cluster/wheel motor drives 19/21/31/33 (FIG. 2C/D). If 1257 the difference between an expected linear acceleration and a measured linear acceleration of the MD is less than a preselected threshold, method 1250 can continue testing for loss of traction (step 1253).

Referring now to FIG. 27A, tipping of the MD can be controlled to actively stabilize the MD and to protect against, for example, a rearward fall. In some configurations, standard mode 100-1 (FIG. 22A) may not be actively stabilized. If caster wheels 21001 are against an obstacle such that forward motion does not occur, a continuous forward command can build up. Excess command in this scenario could lead to a rearward fall. In some configurations, an overall command limit can be placed on the wheel command to prevent excessive wheel command from building up when the wheels are unable to move. In some configurations, anti-tipping can be enabled when the rearward pitch of the MD falls in a range such as, for example, but not limited to, between about 5° and 30°. Tipping control can be disabled when caster wheels 21001 are raised during frame lean adjustments, or when the MD is transitioning to 4-Wheel mode 100-2, or under certain conditions in IMU 50003 (FIG. 15C).

Continuing to refer to FIG. 27A, when the MD is tipped backwards on rear wheels 21201, the MD can drive rear wheels 21201 backwards to attempt recovery from a potential rearwards fall. Tipping control can be implemented through the interaction of anti-tip and wheel controllers, with motor control authority of the two controllers governed by ramp functions that depend on rearward pitch angle. Wheel speed proportional and integral errors and pitch proportional and derivative errors can be multiplied by the ramp functions to change the behavior of the MD on a rearward pitch angle. Pitch error can be computed relative to a nominal pitch of, for example, but not limited to, −6.0°. Pitch rate can be filtered to smooth erroneous measurements, and can be filtered, for example, but not limited to, with a 0.7 Hz filter. A deadband can be applied to the pitch rate values. Controller gains can be applied as variable functions when multiplied by ramp functions that vary between 0 and 1 over the range of the pitched back error. The ramp functions can be used continuously in standard mode 100-1.

Continuing to refer to FIG. 27A, the wheel controller can compute commands based on desired wheel velocity from the joystick input while simultaneously responding to rearward pitch values in order to prevent the chair from falling over backwards. A PI loop can be used to compute a command based on the wheel velocity error. The dynamic state of the MD, as characterized by the value of the pitched back error, can be used to determine which of the terms is used to compute the wheel fore/aft command. Ramp functions can be based on the pitch of the MD. The ramp functions are sliding gains that operate on pitch, pitch rate, and wheel errors. The ramp functions can allow the wheel controller and the anti-tipping controller to interact to maintain stability and controllability of the MD. Tipping control can be disabled if, for example, but not limited to, inertial sensors on the MD have not been initialized or if the inertial estimator has faulted, and if the MD has tipped over.

Referring now primarily to FIG. 27B, in standard mode wheel control, method 8750 can include determining if 8267 stabilization is possible based on, for example, whether the MD has already tipped over, or if there has been an inertial estimator fault, or if the MD is transitioning. If 8267 stabilization is not possible, various actions can be taken depending on whether or not stabilization is not possible. If 8267 stabilization is possible, method 8750 can include computing 8255 a stabilization metric based on, for example, but not limited to, the distance the MD has moved since active stabilization has been engaged and the measured pitch angle. Method 8750 can include computing 8257 a stabilization factor based on, for example, but not limited to, the measured pitch angle, filtered to allow only rearward angles and subjected to a proportional gain. The stabilization factor can be based on the measured pitch rate around which has been placed a hysteresis band and to which a derivative gain has been applied. Ramp functions can be applied to the stabilization factor. Method 8750 can include computing 8259 wheel command inputs based on the derivative over time of the desired fore-aft velocity, the desired fore-aft velocity, the measured fore-aft velocity, the desired yaw velocity, and the measured yaw velocity. The derivative of the velocity can be used to compute a feed forward component. The desired and measured fore-aft velocities can be inputs to a PI controller, and ramp functions can be applied to the result. The desired and measured yaw velocities can be inputs to a proportional controller. If 8261 the metric indicates that stabilization is needed, method 8750 can include computing right/left wheel voltage commands based on the wheel command inputs and the stabilization factor. If 8261 the metric indicates that stabilization is not needed, method 8750 can include computing right/left wheel voltage commands based on the wheel command inputs.

Referring now primarily to FIG. 27C, the controls to implement method 8750 (FIG. 27B) are shown. Filter 8843 can be applied to measured pitch angle 8841 to allow pitch rates in the rearward tip direction, and hysteresis band 8849 can be placed around measured pitch rate 8847. The derivative of desired fore-aft velocity 8853 is used as a feed forward term in the wheel controller. Desired fore-aft velocity 8853 and measured fore-aft velocity 8855 can be fed to first proportional-integral (PI) controller 8857, and ramp functions 8859 can be applied to the output of first PI controller 8857. Desired yaw velocity 8861 and measured yaw velocity 8863 can be fed to proportional controller 8865. If active stabilization is engaged, the measured pitch angle 8841, filtered and with proportional gain 8845 applied, is combined with measured pitch rate 8847, modified and with derivative gain 8851 applied. Ramp functions 8867 can be applied to the combination. Right wheel voltage command 768A and left wheel voltage command 768B can be based upon the combination result, and the results of PI controller 8857 and proportional controller 8865.

Continuing to refer to FIG. 27C, the CG fit of the MD can estimate a maximum allowed acceleration that can help prevent backwards falls based at least on pitch angle θ 705 (FIG. 27A) and a center of gravity determination for the MD. Active stabilization processor 763 can include a closed loop controller that can maintain the stability of the MD by automatically decelerating forward motion and accelerating backward motion when the MD begins tipping backwards. Dynamic metric 845, that can be based at least on, for example, but not limited to, measured pitch angle, and can control whether to include the pitch rate feedback in wheel voltage commands 768, thereby metering the application of active stabilization. Optionally, the anti-tip controller can base its calculations at least in part on the CG location. If the anti-tip controller drives the MD backwards beyond a preselected distance, the MD can enter fail-safe mode.

Referring now to FIG. 27D, active stabilization processor 763 can include, but is not limited to including, center of gravity estimator 1301 including computer instructions to estimate the center of gravity based at least on the mode, and inertial estimator 1303 to estimate the pitch angle required to maintain balance based at least on the center of gravity estimate. In some configurations, the location of center of gravity 181 (FIG. 27A) can be used to set the frame lean limits. In some configurations, an estimate of the location of center of gravity 181 (FIG. 27A) can be used to, for example, but not limited to, actively stabilize mobility device 120 (FIG. 27A) and regulate transitions between modes. The location of center of gravity 181 (FIG. 27A) can vary with each user and seat setup combination, and is a function of the height of seat 105 (FIG. 27A) and the position of cluster 21100 (FIG. 3). An estimate of center of gravity 181 (FIG. 27A) over a range of seat heights and cluster positions that can occur during normal operation of mobility device 120 (FIG. 27A) can be calculated. Calibration parameters can be calculated that can be used to determine various reference pitch angles that can relate the location of center of gravity 181 (FIG. 27A) to the balance point of the system. The calibration parameters can allow the reference angles to be calculated every control cycle as the seat height and the cluster position change. The estimation process can include balancing mobility device 120 (FIG. 27A) and its load at various angles of cluster 21100 (FIG. 3) and various heights of seat 105 (FIG. 27A), and collecting data at each location including the pitch angle of mobility device 120 (FIG. 27A) with respect to gravity. These data can be used to error check the result of the estimation process. Powerbase controller 100 can compute reference variables based at least on the location of center of gravity 181 (FIG. 27A), for example, but not limited to, (1) the angle of mobility device 120 (FIG. 27A) that places center of gravity 181 (FIG. 27A) over the axis of cluster 21100 (FIG. 3), a function of the height of seat 105 (FIG. 27A), used in enhanced mode 100-2 (FIG. 22A), and stair mode 100-4 (FIG. 22A); (2) the angle of the powerbase that can place center of gravity 181 (FIG. 27A) over one set of wheels 21201 (FIG. 27A), a function of the height of seat 105 (FIG.

27A) and the position of cluster 21100 (FIG. 3), used in balance mode 100-3 (FIG. 22A); and (3) the distance from a pivot point of cluster 21100 (FIG. 3) to an estimated center of gravity, a function of the height of seat 105 (FIG. 27A), used in standard mode 100-1 (FIG. 22A) and stair mode 100-4 (FIG. 22A). These values can allow the controllers to maintain active balance.

Referring now to FIG. 27E, method 11350 for computing center of gravity fit (CG fit) can include, but is not limited to including, (1) entering 11351 the balancing mode, (2) measuring 11353 data including a pitch angle required to maintain the balancing the balance at a pre-selected position of the at least one wheel cluster and a pre-selected position of the seat, (3) moving 11355 the mobility device/user pair to a plurality of pre-selected points and collecting calibration data at each of the plurality of pre-selected points, (4) repeating 11357 steps (2) and (3) at each of the plurality of pre-selected points, (5) verifying 11359 that the measured data fall within pre-selected limits, and (6) generating 11361 a set of calibration coefficients to establishing the center of gravity at any usable cluster and seat position during machine operation based on the verified measured data. Method 11350 can optionally include storing the coefficients into, for example, but not limited to, non-volatile memory for use during operation of mobility device 120 (FIG. 27A). A method for entering a vehicle while seated in the MD can include, but is not limited to including, receiving an indication that the MD is encountering a ramp between the ground and the vehicle, directing the clusters of wheels to maintain contact with the ground, changing the orientation of the cluster of wheels according to the indication to maintain the device center of gravity between the wheels, and dynamically adjusting the distance between the seat and the clusters of wheels to prevent contact between the seat and wheels while keeping the seat as low as possible. The MD and the user can clear the doorjam of the vehicle if the seat remains as low and as close to the clusters of wheels as possible, and if the MD is actively stabilized while the MD traverses the ramp into and out of the vehicle. A method for moving a balancing mobility device on relatively steep terrain can include, but is not limited to including, receiving an indication that the mobility device is upon the steep terrain, directing the clusters of wheels to maintain contact with the ground, and dynamically adjusting the distance between the seat and the clusters of wheels based at least on the indication and active stabilization of the mobility device. The method can optionally include setting a travel speed of the mobility device based on the indication.

Referring now primarily to FIG. 28A, controller gains, for certain loads on the MD, can be a function of the weight of the load, and stability of the MD is a function of at least the controller gains. Controller gains can include, but are not limited to including, gains applied during enhanced mode 100-2 (FIG. 22B) to stabilize the MD when, for example, the load is light, or when transitioning into balance mode 100-3 (FIG. 22B). Powerbase controller 100 can include at least one default value for the center of gravity for the MD. The weight of the load on the MD can determine which default value for the center of gravity is used. The weight of the load, and/or the change of weight of the load, and the chosen default value of the center of gravity can be used to adjust controller gains. Controller gains can include a range of discreet values or analog values. For example, if the load falls out of the seat, the MD can experience relatively large accelerations resulting from a relatively small input torque. In some configurations, the change in load weight on the seat can change the controller gain based at least on the load weight. Weight processor 757 can adjust the stability of the MD based at least on the change in load weight. Weight processor 757 can determine the weight of the load based at least on, for example, but not limited to, motor current of seat motor 45/47 (FIG. 18C/18D). Weight processor 757 can potentially detect unstable situations by, for example, but not limited to, processing collected pitch rate data using a rolling discrete fast Fourier transform, recognizing values of the resulting pitch rate frequency that could represent instability-generating changes, filtering the pitch rate frequencies based at least on the recognized values, squaring the filtered pitch rate frequencies, and analyzing the squared pitch rate frequencies based at least on known profiles of potential instability. Weight processor 757 for stabilizing the MD can include, but is not limited to including, weight estimation processor 956 including computer instructions to estimate the weight of a load on the MD, controller gains processor 947 including computer instructions to compute controller gains based at least on the weight, and wheel command processor 761 applying the controller gains to control the MD.

Referring now primarily to FIG. 28B, method 800 for stabilizing the MD can include, but is not limited to including, estimating 851 the weight and/or change in weight of a load on the MD, choosing 853 a default value or values for the center of gravity of the MD, computing 855 controller gains based at least on the weight and/or change in weight and the center of gravity values, and applying 857 the controller gains to control the MD.

Referring now primarily to FIG. 28C, weight-current processor can measure the weight of the load on the MD. Weight-current processor 758 can include, but is not limited to including, position and function receiver 1551, motor current processor 1552, and torque-weight processor 1553. Position and function receiver 1551 can receive sensor data 767 and mode information 776 to determine possible actions that can be taken with respect to the load. Motor current processor 1552 can process measured electrical current to seat motor drive 25/37 (FIG. 18C/18D) when, for example, but not limited to, the MD is transitioning to enhanced mode 100-2 (FIG. 22B). Since the motor current is proportional to torque, torque-weight processor 1553 can use the current readings to provide an estimate of the torque required to lift the load in the seat. In some configurations, for an exemplary motor, MD geometry, and height of the seat, the weight of the load on the seat can be computed as follows, where SC=seat correction, SH=seat height, and MC=motor current:

SC=a*SH+b, where a and b are constants determined by the geometry of the MD.

$$MC\text{ (corrected)} = MC\text{ (measured)} + SC$$

If MC (corrected) >T then weight=c*MC (corrected) *MC (corrected)+d*MC (corrected)—e, where c, d, and e are constants relating the motor current to the user, seat, and UC weight. The total system weight is the sum of the user/seat/UC weight and the weight of the powerbase and the wheels.

Continuing to refer primarily to FIG. 28C, when the seat reaches a stable position and when the seat brake is engaged, there is no current going through the motor windings. When the seat brake is released, the current that is required to hold the position of the seat can be measured. In some configurations, the weight of the load can be estimated by computing a continuous estimate of the weight based at least on continuous monitoring of the current signal from seat motor processors 45/47 (FIG. 18C/18D). Predicting abrupt changes in weight can be based at least on, for example, but not limited to, accelerometer data, current data from other than seat motor processors 45/47 (FIG. 18C/18D), the current required to slew cluster 21100 (FIG. 6A), and wheel acceleration. The specific predictor can be based at least on whether the MD is stationary or moving.

Referring now primarily to FIG. 28D, method 900 for computing the weight on the MD can include, but is not limited to including, receiving 951 the position of a load on the MD, receiving 953 the setting of the MD to standard mode 100-1 (FIG. 22B), measuring 955 the motor current required to move the MD to enhanced mode 100-2 (FIG. 22B) at least once, computing 957 a torque based at least on the motor current, computing 959 a weight of the load based at least on the torque, and adjusting 961 controller gains based at least on the weight to stabilize the MD.

Referring now to FIG. 29A, the MD can provide enhanced functionality 145 to a user, for example, but not limited to, assisting a user in avoiding obstacles, traversing doors, traversing stairs, traveling on elevators, and parking/transporting the MD. In general, The MD can receive user input (for example UI data 633) and/or input from the MD through, for example, but not limited to, messages from user interface devices and sensors 147. The MD can further receive sensor input through, for example, but not limited to sensor processing systems 661. UI data 633 and output from sensor processing systems 661, for example, can inform command processor 601A to invoke the mode that has been automatically or manually selected. Command processor 601A can pass UI data 633 and output from sensor processing systems 661 to a processor that can enable the invoked mode. The processor can generate movement commands 630 at least based on previous movement commands 630, UI data 633, and output from sensor processing systems 661.

Continuing to refer to FIG. 29A, the MD can include, but is not limited to including, command processor 601A, movement processor 603A, simultaneous location and mapping (SLAM) processor 609A, point cloud library (PCL) processor 611A, geometry processor 613A, and obstacle processor 607A. Command processor 601A can receive user interface (UI) data 633 from the message bus. UI data 633 can include, but is not limited to including, signals from, for example, joystick 70007 (FIG. 12A) providing an indication of a desired movement direction and speed of the MD. UI data 633 can also include selections such as an alternate mode into which the MD could be transitioned. In some configurations, in addition to the modes described with respect to FIG. 22B, the MD can process mode selections such as, but not limited to, door mode 605A, rest room mode 605B, enhanced stair mode 605C, elevator mode 605D, mobile park mode 605E, and static storage/charging mode 605F. Any of these modes can include a move-to-position mode, or the user can direct the MD to move to a certain position. Message bus 54 can receive control information in the form of UI data 633 for the MD, and can receive a result of the processing done by the MD in the form of commands such as movement commands 630 that can include, but are not limited to including, speed and direction. Movement commands 630 can be provided, by message bus 54, to The MD which can transmit this information to wheel motor drives 19/21/31/33 (FIGS. 18C/18D) and cluster motor drives 1050/27 (FIGS. 18C/18D). Movement commands 630 can be determined by movement processor 603A based on information provided by the mode-specific processors. Mode-specific processors can determine mode-dependent data 657, among other things, based on information provided through sensor-handling processors 661.

Continuing to refer primarily to FIG. 29A, sensor-handling processors 661 can include, but are not limited to including, MD geometry processor 613A. PCL processor 611A, SLAM processor 609A, and obstacle processor 607A. Movement processor 603A can provide movement commands 630 to the sensor-handling processors 661 to provide information necessary to determine future movements of the MD. Sensors 147 can provide environmental information 651 that can include, for example, but not limited to, obstacles 623 and geometric information about the MD. In some configurations, sensors 147 can include at least one time-of-flight sensor that can be mounted anywhere on the MD. There can be multiple of sensors 147 mounted on the MD. PCL processor 611A can gather and process environmental information 651, and can produce PCL data 655. The PCL, a group of code libraries for processing 2D/3D image data, can, for example, assist in processing environmental information 651. Other processing techniques can be used.

Continuing to refer primarily to FIG. 29A, MD geometry processor 613A can receive MD geometry information 649 from sensors 147, can perform any processing necessary to prepare MD geometry information 649 for use by the mode-dependent processors, and can provide the processed of MD geometry information 649 to the mode-dependent processors. The geometry of the MD can be used for, but is not limited to being used for, automatically determining whether or not the MD can fit in and/or through a space such as, for example, a stairway and a door. SLAM processor 609A can determine navigation information 653 based on, for example, but not limited to, UI data 633, environmental information 651 and movement commands 630. The MD can travel in a path at least in part set out by navigation information 653. Obstacle processor 607A can locate obstacles 623 and distances 621 to obstacles 623. Obstacles 623 can include, but are not limited to including, doors, stairs, automobiles, and miscellaneous features in the vicinity of the path of the MD.

Referring now to FIGS. 29B and 29C, method 650 for processing at least one obstacle 623 (FIG. 29D) while navigating the MD can include, but is not limited to including, receiving at least one movement command, and receiving and segmenting 1151 (FIG. 29B) PCL data 655 (FIG. 29D), identifying 1153 (FIG. 29B) at least one plane within the segmented PCL data 655 (FIG. 29D), and identifying 1155 (FIG. 29B) at least one obstacle 623 (FIG. 29D) within the at least one plane. Method 650 can further include determining 1157 (FIG. 29B) at least one situation identifier 624 (FIG. 29D) based at least on the at least one obstacle, UI data 633 (FIG. 29D), and movement commands 630 (FIG. 29D), and determining 1159 (FIG. 29B) distance 621 (FIG. 29D) between the MD and at least one obstacle 623 (FIG. 29D) based at least on at least one situation identifier 624 (FIG. 29D). Method 650 can also include accessing 1161 (FIG. 29B) at least one allowed command related to distance 621 (FIG. 29D), at least one obstacle 623 (FIG. 29D), and at least one situation identifier 624 (FIG. 29D). Method 650 can still further include accessing 1163 (FIG. 29B) at least one automatic response to the at least one allowed command, mapping 1167 (FIG. 29C) at least one movement command 630 (FIG. 29D) with one of the at least one allowed commands, and providing 1169 (FIG. 29C) at least one movement command 630 (FIG. 29D) and the at least one automatic response associated with the mapped allowed command to the mode-dependent processors.

Continuing to refer to FIGS. 29B and 29C, at least one obstacle 623 (FIG. 29D) can optionally include at least one stationary object and/or at least one moving object. Distance 621 (FIG. 29D) can optionally include a fixed amount and/or a dynamically-varying amount. At least one movement command 630 (FIG. 29D) can optionally include a follow command, at least one pass-the-at-least-one-obstacle command, a travel beside-the-at-least-one-obstacle command, and a do-not-follow-the-at-least-one obstacle command. Method 650 can optionally include storing obstacle data 623 (FIG. 29D), and allowing access to stored obstacle data, for example, stored in cloud storage 607G (FIG. 29D) and/or local storage 607H (FIG. 29D), by systems external to the MD. PCL data 655 (FIG. 29D) can optionally include sensor data 147 (FIG. 29A). Method 650 can optionally include collecting sensor data 147 (FIG. 29A) from at least one time-of-flight sensor mounted on the MD, analyzing sensor data 147 (FIG. 29A) using a point cloud library (PCL), tracking the at least one moving object using simultaneous location and mapping (SLAM) with detection and tracking of moving objects (DATMO) based on the location of the MD, identifying the at least one plane within obstacle data 623 (FIG. 29D) using, for example, but not limited to, random sample consensus and a PCL library, and providing the at least one automatic response associated with the mapped allowed command to the mode-dependent processors. Method 650 can also optionally include receiving a resume command, and providing, following the resume command, at least one movement command 630 (FIG. 29D) and the at least one automatic response associated with the mapped allowed command to the mode-dependent processors. The at least one automatic response can optionally include a speed control command.

Referring now to FIG. 29D, obstacle processor 607A for processing at least one obstacle 623 while navigating the MD can include, but is not limited to including, nav/PCL data processor 607F receiving and segmenting PCL data 655 from PCL processor 611A, identifying at least one plane within the segmented PCL data 655, and identifying at least one obstacle 623 within the at least one plane. Obstacle processor 607A can further include distance processor 607E determining at least one situation identifier 624 based at least on UI data 633, at least one movement command 630, and at least one obstacle 623. Distance processor 607E can determine distance 621 between the MD and at least one obstacle 623 based at least on at least one situation identifier 624. Moving object processor 607D and/or stationary object processor 607C can access at least one allowed command related to distance 621, at least one obstacle 623, and at least one situation identifier 624. Moving object processor 607D and/or stationary object processor 607C can access at least one automatic response, from automatic response list 627, associated with the at least one allowed command. Moving object processor 607D and/or stationary object processor 607C can access at least one movement command 630 including, for example, speed/signal command and direction command/signal, and map at least one movement command 630 with one of the at least one allowed commands. Moving object processor 607D and/or stationary object processor 607C can provide at least one movement command 630 and the at least one automatic response associated with the mapped allowed command to the mode-dependent processors.

Continuing to refer to FIG. 29D, stationary object processor 607C can optionally perform any special processing necessary when encountering at least one stationary object, and moving object processor 607D can optionally perform any special processing necessary when encountering at least one moving object. Distance processor 607E can optionally process distance 621 that can be a fixed and/or a dynamically-varying amount. At least one movement command 630 can optionally include a follow command, a pass command, a travel-beside command, a move-to-position command, and a do-not-follow command. Nav/PCL processor 607F can optionally store obstacles 623, for example, but not limited to, in local storage 607H and/or on storage cloud 607G, and can allow access to the stored obstacles 623 by systems external to the MD such as, for example, but not limited to, external applications 140 (FIG. 16B). PCL processor 611A can optionally collect sensor data 147 (FIG. 29A) from at least one time-of-flight camera mounted on the MD, and can analyze sensor data 147 (FIG. 29A) using a point cloud library (PCL) to yield PCL data 655. Moving object processor 607D can optionally track the at least one moving object using navigation information 653 collected by simultaneous location and mapping (SLAM) processor 609A based on the location of the MD, identify the at least one plane using, for example, but not limited to, random sample consensus and a PCL library, and can provide at least one movement command 630 based on the at least one automatic response associated with the mapped allowed command to the mode-dependent processors. Obstacle processor 607A can optionally receive a resume command, and provide, following the resume command, at least one movement command 630 based on the at least one automatic response associated with the mapped allowed command to the mode-dependent processors. The at least one automatic response can optionally include a speed control command. For example, if joystick 70007 (FIG. 12A) indicates a direction that could position the MD in a collision course with obstacle 623, such as, for example, a wall, the at least one automatic response can include speed control to protect the MD from a collision. The at least one automatic response could be overridden by a contrary user command, for example, joystick 70007 (FIG. 12A) could be released and movement of the MD could be halted. Joystick 70007 (FIG. 12A) could then be re-engaged to restart movement of the MD towards obstacle 623.

Referring now primarily to FIGS. 29E-29H, environmental information 651 (FIG. 29A) can be received from sensors 147 (FIG. 29A). The MD can process environmental information 651 (FIG. 29A). In some configurations, PCL processor 611A (FIG. 29A) can process environmental information 651 (FIG. 29A) using, for example, and depending upon sensor 147 (FIG. 29A), point cloud library (PCL) functions. As the MD moves along travel path 2001B (FIG. 29H) around potential obstacles 2001A, sensors 147 (FIG. 29A) can detect a cloud of points from, for example, and depending upon sensor 147 (FIG. 29A), box 2005 (FIGS. 29G-29H) that can include data that could take the shape of frustum 2003A (FIGS. 29F-29H). A sample consensus method, for example, but not limited to, the random sample consensus method, from, for example, but not limited to, the PCL, can be used to find a plane among the cloud of points. The MD can create a projected cloud and can determine point cloud inliers, and from these, determine a centroid of the projected cloud. Central reference point 148 can be used to determine the location of environmental features with respect to the MD. For example, whether the MD is moving towards or away from an obstacle, or where a door hinge is with respect to the MD can be determined based on the location of central reference point 148. Sensors 147 (FIG. 29A) can include, for example, time-of-flight sensor 147A.

Referring now primarily to FIG. 291, method 750 for enabling the MD to navigate stairs can include, but is not limited to including, receiving 1251 at least one stair command, and receiving 1253 environmental information 651 (FIG. 29A) from sensors 147 (FIG. 29A) mounted on the MD through obstacle processor 607A (FIG. 29A). Method 750 can further include locating 1255, based on environmental information 651 (FIG. 29A), at least one of staircases 643 (FIG. 29J) within environmental information 651 (FIG. 29A), and receiving 1257 selection of selected staircase 643A (FIG. 29J) from the at least one of staircases 643 (FIG. 29J). Method 750 can still further include measuring 1259 at least one characteristic 645 (FIG. 29J) of selected staircase 643A (FIG. 29J), and locating 1261, based on environmental information 651 (FIG. 29J), obstacles 623 (FIG. 29J), if any, on selected staircase 643A (FIG. 29J). Method 750 can also include locating 1263, based on environmental information 651 (FIG. 29J), a last stair of selected staircase 643A (FIG. 29J), and providing 1265 movement commands 630 (FIG. 29J) to move the MD on selected staircase 643A (FIG. 29J) based on the measured at least one characteristic 645 (FIG. 29J), the last stair, and obstacles 623 (FIG. 29J), if any. If 1267 the last stair has not been reached, method 750 can continue providing movement commands 630 (FIG. 29J) to move the MD. Method 750 can optionally include locating at least one of staircases 643 (FIG. 29J) based on GPS data, and building and saving a map of selected staircase 643A (FIG. 29J) using, for example, but not limited to, SLAM. Method 750 can also optionally include accessing geometry 649 (FIG. 29J) of the MD, comparing geometry 649 (FIG. 29J) to at least one of characteristics 645 (FIG. 29J) of selected staircase 643A (FIG. 29J), and modifying the step of navigating based on the step of comparing. At least one of characteristics 645 (FIG. 29J) can optionally include the height of at least one riser of selected staircase 643A (FIG. 29J), the surface texture of the at least one riser, and the surface temperature of the at least one riser. Method 750 can optionally include generating an alert if the surface temperature falls outside of a threshold range and the surface texture falls outside of a traction set. The threshold range can optionally include temperatures below 33° F. The traction set can optionally include a carpet texture. Method 750 can further include determining, based on environmental information 651 (FIG. 29J), the topography of an area surrounding selected staircase 643A (FIG. 29J), and generating an alert if the topography is not flat. Method 750 can still further optionally include accessing a set of extreme circumstances.

Referring now primarily to FIG. 29J, automated navigation of stairs can be enabled by stair processor 605C for enabling the MD to navigate stairs. Sensors 147 (FIG. 29A) on the MD can determine if any environmental information 651 (FIG. 29A) includes at least one staircase 643. In conjunction with any automatic determination of a location of at least one staircase 643, UI data 633 can include the selection of stair mode 100-4 (FIG. 22B) which can invoke an automatic, semi-automatic, or semi-manual stair-climbing process. Either automatic location of at least one staircase 643 or reception of UI data 633 can invoke stair processor 605C for enhanced stair navigation functions. Stair processor 605C can receive data from obstacle processor 607A such as, for example, at least one obstacle 623, distance 621 to at least one obstacle 623, situation 624, navigation information 653, and geometry information 649 for the MD. Navigation information can include, but is not limited to including, a possible path for the MD to traverse. At least one obstacle 623 can include, among other obstacles, at least one staircase 643. Stair processor 605C can locate at least one staircase 643, and can either automatically or otherwise determine selected staircase 643A based on, for example, but not limited to, navigation information 653 and/or UI data 633 and/or MD geometry information 649. Characteristics 645 of selected staircase 643A, such as, for example, riser information, can be used to determine a first stair and distance to next stair 640. Stair processor 605C can determine movement commands 630 of the MD based on, for example, but not limited to, characteristics 645, distance 621, and navigation information 647. Movement processor 603A can move the MD based on movement commands 630, and distance to next stair 640, and can transfer control to sensor processing 661 after a stair from selected staircase 643A has been traversed. Sensor processing 661 can either proceed with navigating selected staircase 643A or can continue following the path set out by navigation information 653, depending upon whether the MD has completed traversing selected staircase 643A. While the MD is traversing selected staircase 643A, obstacle processor 607A can detect obstacles 623 on selected staircase 643A and stair processor 605C can provide movement commands 630 to avoid obstacles 623. Locations of obstacles 623 can be stored for future use locally to the MD and/or external to the MD.

Continuing to refer primarily to FIG. 29J, stair processor 605C can include, but is not limited to including, staircase processor 641B receiving at least one stair command included in UI data 633, and staircase locator 641A receiving environmental information 651 (FIG. 29A) from sensors 147 (FIG. 29A) mounted on the MD through obstacle processor 607A (FIG. 29A). Staircase locator 641A can further locate, based on environmental information 651 (FIG. 29A), at least one of staircases 643 within environmental information 651 (FIG. 29A), and can receive the choice of selected staircase 643A from at least one of staircases 643. Selected staircase 643A can be stored in storage 643B for possible future use. Stair characteristics processor 641C can measure at least one of characteristics 645 of selected staircase 643A, and can locate, based on environmental information 651, at least one obstacle 623, if any, on selected staircase 643A. Stair movement processor 641D can locate, based on environmental information 651, a last stair of selected staircase 643A, and provide to movement processor 603A movement commands 630 for the MD to move on selected staircase 643A based on the measured at least one of characteristics 645, the last stair, and at least one obstacle 623, if any. Staircase locator 641A can optionally locate at least one of staircases 643 based on global positioning system (GPS) data, and can build and save a map of selected staircase 643A using SLAM. The map can be saved for use locally to the MD, and/or for use by other devices. Staircase processor 641B can optionally access geometry 649 of the MD, compare geometry 649 to at least one of characteristics 645 of selected staircase 643A, and can modify the navigation of the MD based on the comparison. Staircase processor 641B can optionally generate an alert if the surface temperature of the risers of selected staircase 643A falls outside of a threshold range and the surface texture of selected staircase 643A falls outside of a traction set. Stair movement processor 641D can optionally determine, based on environmental information 651 (FIG. 29A), the topography of an area surrounding selected staircase 643A, and can generate an alert if the topography is not flat. Stair movement processor 641D can optionally access a set of extreme circumstances.

Referring now primarily to FIGS. 29K-29L, method 850 for negotiating door 675 (FIG. 29M) while maneuvering the MD, where door 675 (FIG. 29M) can include a door swing, a hinge location, and a doorway, can include, but is not limited to including, receiving and segmenting 1351 (FIG. 29K) environmental information 651 (FIG. 29A) from sensors 147 (FIG. 29A) mounted on the MD. Environmental information 651 (FIG. 29A) can include geometry of the MD. Method 850 can include identifying 1353 (FIG. 29K) at least one plane within the segmented sensor data, and identifying 1355 (FIG. 29K) door 675 (FIG. 29M) within the at least one plane. Method 850 can further include measuring 1357 (FIG. 29K) door 675 (FIG. 29M) to provide door measurements. Method 850 can also include determining 1361 (FIG. 29K) the door swing. Method 850 can further include providing 1363 (FIG. 29L) at least one movement command 630 (FIG. 29M) to move the MD for access to a handle of door 675 (FIG. 29M), and providing 1365 (FIG. 29L) at least one movement command 630 (FIG. 29M) to move the MD away from door 675 (FIG. 29M), as door 675 (FIG. 29M) opens, by a distance based on the door measurements. If door 675 (FIG. 29M) swings in, method 850 can include providing at least one movement command to move the MD against door 675 (FIG. 29M), thus positioning door 675 (FIG. 29M) for movement of the MD through the doorway. Method 850 can also include providing 1367 (FIG. 29L) at least one movement command 630 (FIG. 29M) to move the MD forward through the doorway, the MD maintaining door 675 (FIG. 29M) in an open position, if the door swing is towards the MD.

Referring now to FIG. 29M, sensor processing 661 can determine, through information from sensors 147 (FIG. 29A), the hinge side of door 675, and the direction, angle, and distance of door. Movement processor 603A can generate commands to the MD such as start/stop turning left, start/stop turning right, start/stop moving forward, start/stop moving backwards, and can facilitate door mode 605A by stopping the MD, cancelling the goal that the MD can be aiming to complete, and centering joystick 70007 (FIG. 12A). Door processor 671B can determine whether door 675 is, for example, push to open, pull to open, or a slider. Door processor 671B can determine the width of door 675 by determining the current position and orientation of the MD, and determining the x/y/z location of the door pivot point. If door processor 671B determines that the number of valid points in the image of door 675 derived from obstacles 623 and/or PCL data 655 (FIG. 29A) is greater than a threshold, door processor 671B can determine the distance from the MD to door 675. Door processor 671B can determine if door 675 is moving based on successive samples of PCL data 655 (FIG. 29A) from sensor processor 661. In some configurations, door processor 671B can assume that a side of the MD is even with the handle side of door 675, and can use that assumption, along with the position of the door pivot point, to determine the width of door 675.

Continuing to refer primarily to FIG. 29M, if the movement of door 675 is towards the MD, door movement processor 671D can generate and provide movement commands 630 to movement processor 603A to move the MD backward by a pre-determined or dynamically-determined percentage of the amount door 675 is moving. Movement processor 603A can provide movement commands 630 to the MD, and the MC can accept GUI data 633A and provide GUI data 633A to movement processor 603A. If door 675 is moving away from the MD, door movement processor 671D can generate movement commands 630 to direct the MD to move forward by a pre-determined or dynamically-determined percentage of the amount that door 675 moves. The amount the MD moves either forward or backward can be based on the width of door 675. Door processor 671B can locate the side of door 675 that provides the open/close function for door 675 based on the location of the door pivot point. Door processor 671B can determine the distance to the plane in front of sensors 147 (FIG. 16B). Door movement processor 671D can generate movement commands 630 to direct the MD to move through door 675. Door movement processor 671D can wait a pre-selected amount of time for the move of the MD to complete, and door movement processor 671D can generate movement commands 630 to adjust the location of the MD based on the position of door 675. Door processor 671B can determine the door angle and the door pivot point. Door processor 671B can determine if door 675 is stationary, can determine if door 675 is moving, and can determine the direction door 675 is moving. When door mode 605A is complete, door movement processor 671D can generate movement commands 630 that can direct the MD to discontinue movement.

Continuing to still further refer primarily to FIG. 29M, door mode 605A for negotiating door 675 while maneuvering the MD, where door 675 can include a door swing, a hinge location, and a doorway, can include, but is not limited to including, sensor processing 661 receiving and segmenting environmental information 651 from sensors 147 (FIG. 29A) mounted on the MD, where environmental information 651 can include geometry 649 of the MD. Door mode 605A can also include door locator 671A identifying at least one plane within the segmented sensor data, and identifying door 675 within the at least one plane. Door processor 671B can include measuring door 675 to provide door measurements 645A. Door movement processor 671D can provide at least one movement command 630 to move the MD away from door 675 if door measurements 645A are smaller than geometry 649 of the MD. Door processor 671B can also include determining the door swing, and door movement processor 671D can provide at least one movement command 630 to move the MD forward through the doorway. The MD can open door 675 and maintain door 675 in an open position if the door swing is away from the MD. Door movement processor 671D can provide at least one movement command 630 to move the MD for access to a handle of door 675, and can provide at least one movement command 630 to move the MD away from door 675, as door 675 opens, by a distance based on door measurements 645A. Door movement processor 671D can provide at least one movement command 630 to move the MD forward through the doorway. The MD can maintain door 675 in an open position if the door swing is towards the MD.

Referring now to FIG. 29N, the MD can automatically negotiate using rest room facilities. The MD can automatically locate a door to a rest room, and to a rest room stall, if there are multiple doors, can automatically generate movement commands 630 (FIG. 29O) to move the MD through the door(s), and can automatically position the MD relative to rest room fixtures. After use of the rest room fixtures is complete, the MD can automatically locate the door(s) and automatically generate movement commands 630 (FIG. 29O) to move the MD through the door(s) to exit the rest room stall and/or rest room. Method 950 for negotiating, in the MD, a rest room stall in a rest room, where the rest room stall can have door 675 (FIG. 29O), and door 675 (FIG. 29O) can have a door threshold and a door swing, can include, but is not limited to including, providing 1451 at least one movement command 630 (FIG. 29O) to cause the MD to traverse the door threshold entering the rest room.

Method 950 can also include providing 1453 at least one movement command 630 (FIG. 29O) to position the MD for accessing an egress handle of the door, and providing 1455 at least one movement command 630 (FIG. 29O) to move the MD away from door 675 (FIG. 29O), as door 675 (FIG. 29O) closes, if the door swing is towards the MD. Method 950 can also include providing 1457 at least one movement command 630 (FIG. 29O) to move the MD (FIG. 100) toward door 675 (FIG. 29O), as door 675 (FIG. 29O) closes, if the door swing is away from the MD, and providing 1459 at least one movement command 630 (FIG. 29O) to position the MD alongside a first rest room fixture. Method 950 can include providing 1461 at least one movement command 630 (FIG. 29O) to stop the MD, and can include providing 1463 at least one movement command 630 (FIG. 29O) to position the MD near a second rest room fixture. Method 950 can include providing 1465 at least one movement command 630 (FIG. 29O) to traverse the door threshold to exit the rest room stall.

Continuing to refer primarily to FIG. 29N, automatically traversing the doorthreshold can optionally include, but is not limited to including, receiving and segmenting 1351 (FIG. 29K) environmental information 651 (FIG. 29A) from sensors 147 (FIG. 29A) mounted on the MD. Environmental information 651 (FIG. 1O) can include geometry of the MD. Automatically traversing the door threshold can also optionally include identifying 1353 (FIG. 29K) at least one plane within the segmented sensor data, and identifying 1355 (FIG. 29K) door 675 (FIG. 29M) within the at least one plane. Automatically traversing the door threshold can further optionally include measuring 1357 (FIG. 29K) door 675 (FIG. 29M) to provide door measurements, and providing 1359 (FIG. 29K) at least one movement command 630 (FIG. 29O) to move the MD away from door 675 (FIG. 29M) if the door measurements are smaller than geometry 649 (FIG. 29M) of the MD. Automatically traversing the door threshold can also optionally include determining 1361 (FIG. 29K) the door swing, and providing 1363 (FIG. 29K) at least one movement command 630 (FIG. 29O) to move the MD forward through the doorway, the MD opening door 675 (FIG. 29M) and maintaining door 675 (FIG. 1A) in an open position, if the door swing is away from the MD. Automatically traversing the door threshold can further optionally include providing 1365 (FIG. 29L) at least one movement command 630 (FIG. 29O) to move the MD for access to a handle of the door, and providing 1367 (FIG. 29L) at least one movement command 630 (FIG. 29O) to move the MD away from door 675 (FIG. 29M), as door 675 (FIG. 29M) opens, by a distance based on the door measurements. Automatically traversing the door threshold can also optionally include providing 1369 (FIG. 29L) at least one movement command 630 (FIG. 29O) to move the MD forward through the doorway, the MD maintaining door 675 (FIG. 29M) in an open position, if the door swing is towards the MD. Method 950 can optionally include automatically locating the rest room, and automatically driving the MD to the rest room. SLAM techniques can optionally be used to locate a destination, for example, a rest room. The MD can optionally access a database of frequently-visited locations, can receive a selection one of the frequently-visited locations, and can provide at least one movement command 630 (FIG. 29O) to move the MD to the selected location which can include, for example, but not limited to, a rest room.

Referring now to FIG. 29O, rest room mode 605B for negotiating, in the MD, a rest room stall in a rest room, where the rest room stall can have a door, and the door can have a door threshold and a door swing, can include, but is not limited to including, door mode 605A providing at least one movement command 630 to cause the MD to traverse the door threshold entering the rest room. The rest room can also include fixtures such as for example, but not limited to, toilets, sinks, and changing tables. Entry/exit processor 681C can provide at least one movement command 630 to position the MD for accessing an egress handle of the door, and can providing at least one movement command 630 to move the MD away from the door, as the door closes, if the door swing is towards the MD. Entry/exit processor 681C can provide at least one movement command 630 to move the MD toward door 675, as door 675 closes, if the swing of door 675 is away from the MD. Fixture processor 681B can provide at least one movement command 630 to position the MD alongside a first rest room fixture, and can provide at least one movement command to stop the MD. Fixture processor 681B can also provide at least one movement command 630 to position the MD near a second rest room fixture. Entry/exit processor 681C can provide at least one movement command 630 to traverse the door threshold to exit the rest room stall.

Referring now to FIGS. 29P and 29Q, method 1051 for automatically storing the MD in a vehicle, such as, for example, but not limited to, an accessible van, can assist a user in independent use of the vehicle. When the user exits the MD and enters the vehicle, possibly as the vehicle's driver, the MD can remain parked outside of the vehicle. If the MD is to accompany the user in the vehicle for later use, mobile park mode 605E (FIG. 29R) can provide movement commands 630 (FIG. 29R) to the MD to cause the MD to store itself either automatically or upon command, and to be recalled to the door of the vehicle as well. The MD can be commanded to store itself through commands received from external applications 140 (FIG. 16B), for example. In some configurations, a computer-driven device such as a cell phone, laptop, and/or tablet can be used to execute external application 140 (FIG. 16B) and generate information that could ultimately control the MD. In some configurations, the MD can automatically proceed to mobile park mode 605E after the user exits the MD when the MD has been placed in park mode by, for example, the user. Movement commands 630 (FIG. 29R) can include commands to locate the door of the vehicle at which the MD will enter to be stored, and to direct the MD to the door. Mobile park mode 605E (FIG. 29R) can determine error conditions such as, for example, but not limited to, if the door is too small for the MD to enter and can alert the user of the error condition through, for example, but not limited to, an audio alert through audio interface 150A (FIG. 16B) and/or a message to external application 140 (FIG. 16B). If the door is wide enough for the MD to enter, mobile park mode 605E (FIG. 29R) can provide vehicle control commands to command the vehicle to open the door. Mobile park mode 605E (FIG. 29R) can determine when the vehicle door is open and whether or not there is space for the MD to be stored. Mobile park mode 605E (FIG. 29R) can invoke obstacle processing 607A (FIG. 29M) to assist in determining the status of the vehicle door and if there is room in the vehicle to store the MD. If mobile park mode 605E (FIG. 29R) determines that there is enough room for the MD, mobile park mode 605E (FIG. 29R) can provide movement commands 630 (FIG. 29R) to move the MD into the storage space in the vehicle. Mobile park mode 605E (FIG. 29R) can provide vehicle control commands to command the vehicle to lock the MD into place, and to close the vehicle door. When the MD is again needed, external application 140 (FIG. 16B), for example, can be used to invoke mobile park mode 605E. Mobile park mode 605E (FIG. 29R) can recall the status of the MD and can begin processing by providing vehicle control commands to command the vehicle to unlock the MD and open the door of the vehicle. Mobile park mode 605E (FIG. 29R) can once again locate the door of the vehicle, or can access the location of the door from, for example, local storage 607H (FIG. 29M) and/or cloud storage 607G (FIG. 29M). Mobile park mode 605E (FIG. 29R) can provide movement commands 630 (FIG. 29R) to move the MD through the vehicle door and to the passenger door to which it had been summoned by, for example, external application 140 (FIG. 16B). In some configurations, the vehicle can be tagged in places such as, for example, the entry door for storage of the MD. Mobile park mode 605E can recognize the tags, such as, for example, but not limited to, fiducials, bar codes, and/or QR CODES@tags, and can execute the method described herein as a result of recognizing the tags. Other tags can be included, such as tags within the storage compartment to indicate the proper storage location and tags on vehicle passenger doors. The tags can be radio frequency identification (RFID) enabled, for example, and the MD can include an RFID reader.

Continuing to refer primarily to FIGS. 29P and 29Q, method 1051 for automatically storing the MD in a vehicle can include, but is not limited to including, providing 1551 at least one movement command 630 (FIG. 29R) to locate the door of the vehicle at which the MD will enter to be stored in a storage space in the vehicle, and providing 1553 at least one movement command 630 (FIG. 29R) to direct the MD to the door. If 1555 the vehicle door is wide enough for the MD to enter, method 1051 can include providing 1557 at least one vehicle control command to command the vehicle to open the door. If 1559 the door is open and if 1561 there is room in the vehicle to store the MD, method 1051 can include providing 1563 at least one movement command 630 (FIG. 29R) to move the MD into the storage space in the vehicle. Method 1051 can include providing 1565 at least one vehicle control command to command the vehicle to lock the MD into place, and to close the door of the vehicle. If 1555 the vehicle door is not wide enough, or if 1559 the vehicle door is not open, or if 1561 there is no space for the MD, method 1051 can include alerting 1567 the user, and providing 1569 at least one movement command 630 (FIG. 29R) to return the MD to the user.

Continuing to refer primarily to FIGS. 29P and 29Q, the at least one movement command 630 (FIG. 29R) to store the MD can be received from external application 140 (FIG. 16B) and/or automatically generated. Method 1051 can optionally include alerting the user of error conditions through, for example, but not limited to, an audio alert through audio interface 150A (FIG. 16B) and/or a message to external application 140 (FIG. 16B). Method 1051 can optionally invoke obstacle processing 607A (FIG. 29M) to assist in locating the door of the vehicle, to determine if there is enough room in the vehicle to store the MD, and to locate any locking mechanism in the vehicle. When the MD is again needed, that is, when the user has arrived at a destination in the vehicle, external application 140 (FIG. 1A), for example, can be used to invoke the MD. Method 1051 can include recalling the status of the MD and can include providing vehicle control commands to command the vehicle to unlock the MD and open the door of the vehicle. Method 1051 can include locating the door of the vehicle, or can include accessing the location of the vehicle door from, for example, local storage 607H (FIG. 29M) and/or cloud storage 607G (FIG. 29M). Method 1051 can include providing movement commands 630 (FIG. 29R) to move the MD through the vehicle door and to the passenger door to which it had been summoned by, for example, but not limited to, external application 140 (FIG. 16B).

Referring now to FIG. 29R, mobile park mode 605E can include, but is not limited to including, vehicle door processor 691D that can provide at least one movement command 630 to locate door 675 of the vehicle at which the MD will enter to be stored in a storage space in the vehicle. Vehicle door processor 691D can also provide at least one movement command 630 to direct the MD to door 675. If door 675 is wide enough for the MD to enter, vehicle command processor 691C can provide at least one vehicle control command to command the vehicle to open door 675. If door 675 is open and if there is room in the vehicle to store the MD, space processor 691B can provide at least one movement command 630 to move the MD into the storage space in the vehicle. Vehicle command processor 691C can provide at least one vehicle control command to command the vehicle to lock the MD into place, and to close door 675 of the vehicle. If door 675 is not wide enough, or if door 675 is not open, or if there is no space for the MD, error processor 691E can alert the user, and can provide at least one movement command 630 to return the MD to the user.

Continuing to refer to FIG. 29R, vehicle door processor 691D can optionally recall the status of the MD, and vehicle command processor 691C can provide vehicle control commands to command the vehicle to unlock the MD and open door 675 of the vehicle. Vehicle door processor 691D can once again locate door 675 of the vehicle, or can access the location of door 675 from, for example, local storage 607H (FIG. 29M) and/or cloud storage 607G (FIG. 29M), and/or door database 673B. Vehicle door processor 691D can provide movement commands 630 to move the MD through door 675 and to the passenger door to which it had been summoned by, for example, external application 140 (FIG. 16B).

Referring now primarily to FIG. 29S, method 1150 for storing/recharging the MD can assist the user in storing and possibly recharging the MD. For example, the MD could be recharged when the user sleeps. After the user exits the MD, commands can be initiated at, for example, external application 140 (FIG. 168), to move perhaps riderless the MD to a storage/docking area. In some configurations, a mode selection by the user while the user occupies the MD can initiate automatic storage/docking functions after the user has exited the MD. When the MD is again needed, commands can be initiated by external application 140 (FIG. 16B) to recall the MD to the user. Method 1150 can include, but is not limited to including, locating 1651 at least one storage/charging area, and providing 1655 at least one movement command 630 (FIG. 29T) to move the MD from a first location to the storage/charging area. Method 1150 can include locating 1657 a charging dock in the storage/charging area and providing 1663 at least one movement command 630 (FIG. 29T) to couple the MD with the charging dock. Method 1150 can optionally include providing at least one movement command 630 (FIG. 29T) to move the MD to the first location when the MD receives an invocation command. If 1653 there is no storage/charging area, or if 1659 there is no charging dock, or if 1666 the MD cannot couple with the charging dock, method 1150 can optionally include providing 1665 at least one alert to the user, and providing 1667 at least one movement command 630 (FIG. 29T) to move the MD to the first location.

Referring now to FIG. 29T, static storage/charging mode 605F can include, but is not limited to including, storage/charging area processor 702A that can locate at least one storage/charging area, and can provide at least one movement command 630 to move the MD from a first location to storage/charging area. Coupling processor 702D can locate a charging dock in storage/charging area, and can provide at least one movement command 630 to couple the MD with the charging dock. Return processor 702B can optionally provide at least one movement command 630 to move the MD to the first location when the MD receives an invocation command. If there is no storage/charging area, or if there is no charging dock, or if the MD cannot couple with the charging dock, error processor 702E can optionally provide at least one alert to the user, and can providing at least one movement command 630 to move the MD to the first location.

Referring now to FIG. 29U, method 1250 for negotiating an elevator while maneuvering the MD can assist a user in getting on and off elevator 685 (FIG. 29V) in the MD. Sensor processing 661 can be used to locate elevator 685 (FIG. 29V), for example, or elevator location 685A (FIG. 29V) can be determined from local storage 607H (FIG. 29M) and/or storage cloud 607G (FIG. 29M). When elevator 685 (FIG. 29V) is located, and when the user selects the desired elevator direction, and when elevator 685 (FIG. 29V) arrives and the door opens, elevator mode 605D (FIG. 29V) can provide movement commands 630 (FIG. 29V) to move the MD into elevator 685 (FIG. 29V). The geometry of elevator 685 (FIG. 29V) can be determined and movement commands 630 (FIG. 29V) can be provided to move the MD into a location that makes it possible for the user to select a desired activity from the elevator selection panel. The location of the MD can also be appropriate for exiting elevator 685 (FIG. 29V). When the elevator door opens, movement commands 630 (FIG. 29V) can be provided to move the MD to fully exit elevator 685 (FIG. 29V). Method 1250 can include, but is not limited to including, locating elevator 685 (FIG. 29V), where elevator 685 (FIG. 29V) has an elevator door and an elevator threshold associated with the elevator door. Method 1250 can include providing at least one movement command 630 (FIG. 29V) to move the MD through the elevator door beyond the elevator threshold. Method 1250 can also include determining the geometry of elevator 685 (FIG. 29V), and providing at least one movement command 630 (FIG. 29V) to move the MD into a floor selection/exit location relative to the elevator threshold. Method 1250 can also include providing at least one movement command 630 (FIG. 29V) to move the MD across and beyond the elevator threshold to exit elevator 685 (FIG. 29V).

Referring now primarily to FIG. 29V, elevator mode 605D can include, but is not limited to including, elevator locator 711A that can locate elevator 685 having an elevator door and an elevator threshold associated with the elevator door. Elevator locator 711A can save obstacles 623, elevators 685, and elevator locations 685A in elevator database 683B, for example. Elevator database 683B can be located locally or remotely from MD 120 . Entry/exit processor 711B can provide at least one movement command 630 to move the MD through the elevator door beyond the elevator threshold to either enter or exit elevator 685. Elevator geometry processor 711D can determine the geometry of elevator 685. Entry/exit processor 711B can provide at least one movement command 630 to move the MD into a floor selection/exit location relative to the elevator threshold.

Referring now primarily to FIG. 30A, system serial bus (SSB) 143 (FIG. 16B) can provide communications through use of, for example, a CANbus protocol. Devices connected to SSB 143 (FIG. 16B) can be programmed to respond/listen to specific messages received, processed, and transmitted by SSB messaging 130F (FIG. 16B). Messages can include packets, which can include, but are not limited to including, data and a CANbus device identification that can identify the source of the packet. Devices receiving CANbus packets can ignore invalid CANbus packets. When an invalid CANbus packet is received, the received device can take alternative measures, depending on, for example, the current mode of the MD, the previous CANbus messages, and the receiving device. The alternate measures can, for example, maintain stability of the MD. The bus master of SSB 143 (FIG. 16B) can transmit master sync packet 901 to establish a bus alive sequence on a frame basis and synchronize the time base. (Powerbase processor) PBP A1 43A (FIG. 18C), for example, can be designated the master of SSB 143 (FIG. 16B), and PBP B1 43C (FIG. 18D), for example, can be designated as the secondary master of SSB 143 (FIG. 16B) if PBP A1 43A (FIG. 18C) is no longer transmitting on the bus. The master of SSB 143 (FIG. 16B) can transmit master sync packet 901 at a periodic rate, for example, but not limited to, every 20 ms+/−1%. Devices communicating using SSB 143 (FIG. 16B) can synchronize the transmitting of messages to the beginning of master sync packet 901. PSC packets 905 can include data originated by PSC 11 (FIG. 16B), and PBP packets 907 can include data originated by PBP 100 (FIG. 16B).

Referring now primarily to FIG. 30B, user control packets 903 can include header, message ID, and data for messages traveling primarily to and from external applications 140 (FIG. 16B) wirelessly, for example, but not limited to, using a BLUETOOTH® protocol. User control packets 903 (FIG. 30A) can include, for example, packet format 701. Packet format 701 can include, but is not limited to including, status 701A, error device identification 701B, mode requested 701C, control out 701D, commanded velocity 701E, commanded turn rate 701F, seat control 701G, and system data 701H. Status 701A can include, but is not limited to including, possibilities such as, for example, self test in progress, device okay, non-fatal device failure (data OK), and fatal device failure in which receiving devices can ignore the data in the packet If UC 130, for example, receives a device failure status, UC 130 can post an error to, for example, a graphical user interface (GUI) on UC 130 (FIG. 12A). Error device ID 701B can include the logical ID of the device for which received communications has been determined to be erroneous. Error device ID 701B can be set to zero when no errors are received.

Referring now primarily to FIG. 30C, mode requested code 701C (FIG. 30B) can be defined such that a single bit error may not indicate another valid mode. For example, mode codes can include, but are not limited to including, self-test, standard, enhanced or 4-wheel, stair, balance, docking, remote, calibration, update, power off, power on, fail safe, recovery, flasher, door, mobile storage, static storage/charging, rest room, elevator, and enhanced stair, the meanings of which are discussed herein. Mode requested code 701C can indicate if the mode being requested should be processed to (1) either maintain the current mode or execute an allowed mode change or (2) enable situation-dependent processing. In some configurations, special situations can require automatic control of the MD. For example, the MD can transition from stair mode 100-4 (FIG. 22B) automatically to enhanced mode 100-2 (FIG. 22B) when the MD has reached a top landing of a staircase. In some configurations, the MD can, for example, but not limited to, modify the response of the MD to commands from joystick 70007 (FIG. 12A), for example, by setting the MD to a particular mode. In some configurations, the MD can automatically be set to a slow driving mode when the MD is transitioned out of stair mode 100-4 (FIG. 22B). In some configurations, when the MD transitions from stair mode 100-4 (FIG. 22B) automatically to enhanced mode 100-2 (FIG. 22B), joystick 70007 (FIG. 12A) can be disabled. When a mode is selected through, for example, but not limited to, user entry, mode availability can be determined based at least in part on current operating conditions.

Continuing to refer primarily to FIG. 30C, in some configurations, if a transition is not allowed to a user-selected mode from the current mode, the user can be alerted. Certain modes and mode transitions can require user notification and possibly user assistance. For example, adjustments to the seat can be needed when positioning the MD for a determination of the center of gravity of the MD along with the load on the MD. The user can be prompted to perform specific operations based on the current mode and/or the mode to which the transition can occur. In some configurations, the MD can be configured for, for example, but not limited to, fast, medium, medium dampened, or slow speed templates. The speed of the MD can be modified by using, for example, speed template 700 (FIG. 25A) relating output 703 (FIG. 25A) (and wheel commands) to joystick displacement 702 (FIG. 25A).

Referring now to FIG. 30D, control out 701D (FIG. 30B) can include, but is not limited to including, indications such as, for example, but not limited to, OK to power down 801A, drive selection 801B, emergency power off request 801C, calibration state 801D, mode restriction 801E, user training 801F, and joystick centered 801G. In some configurations, OK to power down 801A can be defined to be zero if power down is not currently allowed, and drive selection 801B can be defined to specify motor drive 1 (bit 6=0 ) or motor drive 2 (bit 6 =1). In some configurations, emergency power off request 801C can be defined to indicate if an emergency power off request is normal (bit 5=0 ), or an emergency power off request sequence is in process (bit 5=1), and calibration state 801D can be defined to indicate a request for user calibration (bit 4=1). In some configurations, mode restriction 801E can be defined to indicate whether or not there are restrictions for entering a particular mode. If the mode can be entered without restriction, bit 3 can be zero. If there are restrictions to entering a mode, for example, but not limited to, balance-critical modes can require certain restrictions to maintain the safety of the passenger of the MD, bit 3 can be one. User training 801F can be defined to indicate if user training is possible (bit 2=1), or not (bit 2=0 ), and joystick centered 801G can be defined to indicate if joystick 70007 (FIG. 12A) is centered (bits 0-1=2), or not (bits 0–1=1).

Referring again primarily to FIG. 30B, commanded velocity 701E can include, for example, a value representing forward or reverse speed. Forward velocity can include a positive value and reverse velocity can be a negative value, for example. Commanded turn rate 701F can include a value representing a left or right commanded turn rate. A left turn can include a positive value and a right turn can include a negative value. The value can represent the differential velocity between the left and right of wheels 21201 (FIG. 1A) equivalently scaled to commanded velocity 701E.

Referring again primarily to FIG. 30D, joystick 70007 (FIG. 12A) can include multiple redundant hardware inputs. Signals such as, for example, commanded velocity 701E (FIG. 30B), commanded turn rate 701F (FIG. 30B), and joystick-centered 801G can be received and processed. Commanded velocity 701E (FIG. 30B) and commanded turn rate 701F (FIG. 30B) can be determined from a first of the multiple hardware inputs, and joystick-centered 801G can be determined from a second of the hardware inputs. Values of joystick-centered 801G can indicate when a non-zero of commanded velocity 701E (FIG. 30B) and a non-zero of commanded turn rate 701F (FIG. 30B) are valid. Fault conditions for joystick 70007 (FIG. 12A) in, for example, the X and Y directions can be detected. For example, each axis of joystick 70007 (FIG. 12A) can be associated with dual sensors. Each sensor pair input (X (commanded velocity 701E (FIG. 30B)) and Y (command turn rate 701F (FIG. 30B)) can be associated with an independent A/D converter, each with a voltage reference channel check input. In some configurations, commanded velocity 701E (FIG. 30B) and commanded turn rate 701F (FIG. 30B) can be held to zero by the secondary input to avoid mismatch. If joystick-centered 801G is within a minimum deadband, or joystick 70007 (FIG. 12A) is faulted, joystick 70007 (FIG. 12A) can be indicated as centered. A deadband can indicate the amount of displacement of joystick 70007 (FIG. 12A) that can occur before a non-zero output from joystick 70007 (FIG. 12A) can appear. The deadband range can set the zero reference region to include an electrical center position that can be, for example, but not limited to, 45 % to 55% of the defined signal range.

Referring now primarily to FIG. 30E, seat control 701G (FIG. 30B) can convey seat adjustment commands. Frame lean command 921 can include values such as, for example, invalid, lean forward, lean rearward, and idle. Seat height command 923 can include values such as, for example, invalid, lower seat down, raise seat up, and idle.

Referring now to FIG. 31A, remote control of the MD can be enabled by secure communications between control device 5107 and controlled device 5111, a configuration of which can include the MD (also referred to as mobility device 5111A (FIG. 31D). Control device 5107 can include, but is not limited to including, a cell phone, a personal computer, and a tablet-based device, and is also referred to herein as an external device, a configuration of which can include external application 5107A (FIG. 31D). In some configurations, UC 130 (FIG. 12A) can include support for wireless communications to/from mobility device 5111A (FIG. 31D). Mobility device 5111A (FIG. 31D) and external application 5107A (FIG. 31D) can accommodate virtual joystick software that can, for example, override the commands generated by joystick 70007 (FIG. 121). Control device 5107 can include voice recognition that can be used to control controlled device 5111. Control device 5107 and controlled device 5111 can communicate using a first protocol, a second protocol, and, for example, a wireless protocol such as, for example, but not limited to, the BLUETOOTH® Low Energy (BLE) protocol. Control device 5107 can execute external applications that can enable wireless control of controlled device 5111. Communications between control device 5107 and controlled device 5111 can include, but are not limited to including, securely pairing local and remote radios associated with control device 5107 and controlled device 5111, encrypting traffic across the local and remote radios, filtering pre-selected devices from the list of advertising peripheral radios, and whitelisting pre-selected paired radios for streamlining the scan/pair/connect sequence. Control device 5107 can enable user selection of one of a group of advertising devices, and can enable communications with network storage 5113. Data from controlled device 5111, such as, for example, but not limited to, event logs, can be requested by control device 5107 and uploaded to network storage 5113. In some configurations, control device 5107 can listen for the notification of new data and can determine if the new data are to be uploaded to network storage 5115. Any data that are to be uploaded can be queued for transmission to network storage 5113. In some configurations, if control device 5107 is connected to a WiFi network, control device can attempt to upload any data that is not currently residing in network storage 5113. In some configurations, if control device 5107 is connected to a cell network, or network storage 5113 is not reachable, control device 5107 can queue the data and attempt to send it when the network status changes. In some configurations, the data can be deleted from control device 5107 and controlled device 5111 when network storage 5113 confirms that the data have been received and/or stored successfully. In some configurations, data can include event log data and raw data generated by controlled device 5111. Controlled device interface 5103 can include, but is not limited to including, data structures that can represent the state of controlled device interface 5115. In some configurations, data can be maintained for a pre-selected amount of time. In some configurations, after the pre-selected amount of time, the data can be deleted if, for example, there is insufficient space on control device 5107. In some configurations, the data can be purged in priority order with low priority events purged before medium priority events. Medium priority data can be purged before high priority data. In some configurations, engineering events can be low priority and removed first, device events can be medium priority and removed if low events and/or other low priority data have already been removed, and therapy events can be high priority and removed if space is needed. Control device 5107 can provide view controllers that can support device registration and device association of network storage 5113. Control device 5107 can provide the ability to determine if a device is registered and associated with network storage 5113.

Continuing to refer primarily to FIG. 31A, external application 5107A (FIG. 31D) can simulate operation of controlled device interface 5103, and can enable a workflow that can assist the user in setting up and changing information about controlled device interface 5103. External application 5107A (FIG. 31D) can provide user selection of controlled device interface 5103 that can advertise an available wireless connection. External application 5107A (FIG. 31D) can include initial setup of controlled device interface 5103 that can include accessing and sending configuration parameters to controlled device interface 5103 including date and time, alert/alarm notification settings, and configuration options. Initial setup can include configuring a communications interface to communicate with network storage 5113. External application 5107A (FIG. 31D) can provide visibility into events happening on controlled device 5111 including providing the ability to retrieve event data from controlled device interface 5103 and providing a view of data that are relevant to therapeutic decisions. External application 5107A (FIG. 31D) can retain data destined for network storage 5113 until wireless communications link 5136 is available.

Referring now to FIG. 31B, the first protocol can support communications between control device 5107 (FIG. 31A) that can be physically remote from control device interface 5115 (FIG. 31A). In some configurations, the first protocol can include the RIS protocol in which each message can include header 5511, payload 5517, and data check 5519. Messaging systems executing on control device 5107 (FIG. 31A) and control device interface 5115 (FIG. 31A) can parse header 5511 and verify data check section 5519. Header 5511 can include, but is not limited to including, length of payload 5501, command 5503, sub-command 5515, and sequence number 5505. Sequence number 5505 can be incremented for each new message sent. Data check section 5519 can include, but is not limited to including, a CRC of header 5511 and payload 5517. The first protocol can include, but is not limited to including, messages that can vary in length. Messages can include header 5511, payload 5517, and CRC 5519. Control device interface 5115 (FIG. 31A) can require that certain messages be available in the first protocol to support remote control of controlled device 5111 (FIG. 31A). The first protocol can transparently tunnel messages formatted in a second protocol and encapsulated within messages formatted according to the first protocol for transmission and reception over, for example, wireless link 5136 (FIG. 31A). Devices that communicate using the second protocol can be compatible with any updates that might happen in the wireless protocol and/or first protocol and can require no changes to operate seamlessly. Various types of medical devices can be controlled by using a generic shell protocol such as the RIS protocol that can surround the medical device-specific protocol and/or message set such as the service component architecture (SCA) protocol.

Continuing to refer primarily to FIG. 31B, communications device drivers can provide driver bytes 5513 before message header 5511 that can be used by, for example, a serial peripheral interface (SPI) and remote communications drivers. Messages can be identified by the combination of command 5503 and sub-command 5515. Each command 5503 and sub-command 5515 pair specifies the specific format and intent of the message. Sub-command 5515 can include a response bit that can indicate that the message is a response to command 5503. When a packet is received which passes the CRC validation, a response will be sent. All response messages will have the response bit of sub-command 5515 set. In some configurations, sequence number 5505 of the response message must match sequence number 5505 of the original message. If the message is not a valid command, or the command cannot currently be processed by the system, the response will be a negative acknowledgement with a code to indicate the reason the message is considered invalid or inoperable. Messages that fail CRC validation or unexpected message responses can be dropped and treated the same as any message lost during transport. The application code performing the send on the source node can be responsible for generating a timeout, performing retries and ultimately self-generating a dropped message negative acknowledgement response in the case of dropped messages. Control device interface 5111 (FIG. 1) and controlled device interface 5103 can detect and react to communications issues such as, for example, but not limited to, CRC inconsistencies, timeouts, and therapy number inconsistencies. Sub-command 5515 can include a response bit that can indicate that the message is a response to command 5503.

Continuing to refer to FIG. 31B, in some configurations, a maximum message length can be imposed that may not include driver bytes 5513. If controlled device 5111 (FIG. 31A) is a medical device, messages can include therapy commands that can include therapy number 5613 (FIG. 32A) in payload 5517. In some configurations, a next therapy number can be provided in either a status message or a response. Therapy commands can be rejected if controlled device 5111 (FIG. 31A) has not been configured for therapy. Therapy commands can be rejected by controlled device 5111 (FIG. 31A) if therapy number 5613 (FIG. 32A) is not valid.

Continuing to still further refer to FIG. 31B, first protocol CRC 5519 can be computed over header 5511 and payload 5517. When a message is received that has passed CRC validation, a response message can be sent. In some configurations, if the message does not include a valid command 5503, or command 5503 cannot currently be processed by the system, the response can include a negative acknowledgement that can have a code that can indicate the reason the message is considered invalid or inoperable. Messages that fail CRC validation or unexpected message responses can be dropped and treated the same as any message lost during transport. Controlled device interface 5103 (FIG. 31A) and control device interface 5115 (FIG. 31A) can both perform source node functions because they can each be the originator of and/or conduit for source messages. Whichever of controlled device interface 5103 (FIG. 31A) or control device interface 5115 (FIG. 31A) sends the message can generate a timeout if necessary, perform message send retries, if necessary, and self-generate a dropped message negative acknowledgement response if a dropped message is detected.

Referring now to FIG. 31C, controlled device interface 5103 (FIG. 1) and control device interface 5115 (FIG. 1) can manage the extraction from first protocol messages of messages formatted according to the second protocol and insertion of messages formatted according to the second protocol as payload 5517 (FIG. 4A) of messages formatted according to the first protocol. Communications message management can include identifying first protocol messages and extracting tunneled second protocol messages as needed. First protocol messages that include second protocol messages can be processed separately from other messages. First protocol messages can be prepared and queued for transmission separately depending on whether second protocol messages are included. Messages formatted according to the second protocol can include control byte 5521, message ID 5523, data 5525, and CRC 5527 computed over control byte 5521, message ID 5523, and data 5525. Control byte 5521 can be used for message addressing and can include a message sequence number that can be generated by controlled device interface 5103 (FIG. 31A) and can be echoed back by control device interface 5115 (FIG. 31A). The sequence number can be used by controlled device interface 5103 (FIG. 31A) to match a received response message to a sent request message. In some configurations, sequence numbers can begin at 0 h, can be incremented after a message is sent, and roll to 0 h after Fh. Control byte 5521 can indicate the identification from where a response to the message can be expected. Control byte 5521 can include a processor ID that can identify the processor for which the message is intended.

Continuing to refer to FIG. 31C, message ID 5523 can provide a command and/or an indication of the identity of message data 5525. In some configurations, message ID 5523 can take on the exemplary values in Table I. In some configurations, the sender of the message having message ID 5523 can expect an exemplary response as shown in Table I.

TABLE I

| ID | Message | Expected Response | Payload |
|---|---|---|---|
| 00h | No Message | | |
| 01h | Initialize | 02h | Protocol version # and application ID |
| 02h | Confirm Initialize | N/A | Initialization results and version numbers |
| 03h | Status | N/A | Status code and previous message ID |
| 04h | Resend Last Message | All Msgs | |
| 05h | Communication Complete | 03h | |
| 06h | Get Application CRC | 07h | |
| 07h | Send Application CRC | N/A | CRC value |
| 10h-2Ah | Controlled device-specific messages | | |
| 2Bh | Set Event Log Status | 2Ch | |
| 2Ch | Send Current Event Log Status | N/A | # event log entries |
| 2Dh | Get Event Segment | 33h | Event index, segment # |
| 2Eh | Clear Events | 03h | |
| 2Fh | Set Alarm Log Status | 30h | |
| 30h | Send Current Alarm Log Status | N/A | # of alarm log entries |
| 31h | Get Alarm Segment | 33h | Alarm index, segment # |
| 32h | Clear Alarms | 03h | |
| 33h | Send Log Segment | N/A | Alarm segment |
| 34h-41h | Controlled device-specific messages | | |
| 42h | Get Real Time Clock | 44h | Clock type ID |
| 44h | Send Real Time Clock-Integer | 03h | Real time clock integer value and clock type ID |
| 45h | Get Serial Number | 46h | Of controlled device |
| 46h | Send Serial Number | 46h | Serial number of controlled device |
| 47h | Get Service Flag | 48h | |
| 48h | Send Service Flag | 48h | Equipment service flag to indicate issues with controlled device |
| 49h-FFh | Controlled device-specific messages | | |

Continuing to refer to FIG. 31C, second protocol messages that can be exchanged can include, but are not limited to including, an initialization message that can be sent from control device 5107 (FIG. 31A) to controlled device 5111 (FIG. 31A), and an initialization response message that can be sent from controlled device 5111 (FIG. 31A) to control device 5107 (FIG. 31A). The initialization message can include, but is not limited to including, a protocol map, an application ID, a communication timeout value, and padding. Second protocol messages can include a device control command that can be sent from control device 5107 (FIG. 31A) to controlled device 5111 (FIG. 31A), and that can include the device control information. Second protocol messages can include commands used to interface with a wireless protocol such as, for example, the BLUETOOTH® protocol, that can enable communications between control device 5107 (FIG. 31A) and controlled device 5111 (FIG. 31A). The commands can kick off actions such as, for example, scanning for peripherals, discontinuing the scan, retrieving names of peripherals, connecting a peripheral such as, for example, controlled device 5111 (FIG. 31A) operating as a peripheral with control device 5107 (FIG. 31A), and canceling the peripheral connection. The commands can interrogate peripherals, for example, by discovering services and characteristics of the peripherals, reading and setting values of the characteristics. Responses to the commands can include, but are not limited to including, status updates with respect to peripherals, connections, services, and characteristics.

Referring now primarily to FIGS. 31B and 31C, first protocol commands can include disabling wireless communications in which control device interface 5115 (FIG. 31A) can continue operating without control device 5107 (FIG. 31A), and in which control device 5107 (FIG. 31A) can reactivate if an alarm is received from control device interface 5115 (FIG. 31A). Second protocol commands can include commands such as, for example, but not limited to, echo, set/get system events, erase logs, get data, force alarm, set log record on control device 5111 (FIG. 31A), force reset of control device 5111 (FIG. 31A), startup test for control device 5111 (FIG. 31A), integration test commands, and radio service commands. Second protocol commands can include commands such as, for example, but not limited to, setting an identification of control device 5111 (FIG. 31A), setting of calibration and measurement options, executing of manufacturing tests, and providing a list of events.

Referring now to FIG. 31D, wireless communications system 100P can enable control of controlled device 5111 (FIG. 31A), for example, but not limited to, mobility device 5111A, through, for example, but not limited to, external application (EA) 5107A executing on control device 5107 (FIG. 31A) (a cell phone, a PC, or a tablet, for example). In some configurations, a user interface means associated with mobility device 5111A can include support for wireless communications to/from mobility device 5111A. Mobility device 5111A and external application 5107A can accommodate a user interface executing as part of external application 5107A that can, for example, override the commands generated by the user interface means associated with mobility device 5111A. For example, a virtual joystick executing as a part of external application 5107A can override the commands of the physical joystick associated with a wheelchair. Mobility device 5111A and external application 5107A can decode and use the messages moving between them. Wireless communications system 100P can include, but is not limited to including, protocol conversion processes 5317, input queues 5311/5335, output queues 5309/5333, state machines 5305E and 5305M, and wireless processors 5325/5330. Protocol conversion processes 5317 can feed SCA output queues 53190/53360 and RIS output queues 53340/53030 with messages generated by external application 5107A and mobility device 5111A. Protocol conversion processes 5317 can receive messages from SCA input queues 53191/53361 and RIS input queues 53341/53031 that have received messages input queues 5311/5335. Input queues 5311/5355 can feed SCA input queues 53191/53361 and RIS input queues 53341/53031 with messages received from external application BLE chip 5325 and medical device BLE chip 5330 (through serial 1/O processor 5339). Output queues 5309/5333 can feed external application BLE chip 5325 and medical device BLE chip 5330 (through serial I/O processor 5339). Medical device state machine 5305M can manage the process of communicating wirelessly from the perspective of medical device 5111A. External application state machine 5305E can manage the process of communicating wirelessly from the perspective of external application 5107A. In particular, both medical device state machine 5305M and external application state machine 5305E can manage the entry and exit of states from which messages can be generated and sent and/or received according pre-selected protocols. The messages can, for example, direct mobility device 5111A and/or external application 5107A to respond to a status of dradio 5349. External application wireless processor 5325 can execute on control device 5107 (FIG. 31A) and can communicate with external application 5107A. Medical device wireless processor 5330 can execute on mobility device 5111A and can communicate with components of mobility device 5111A.

Continuing to refer to FIG. 31D, both external application wireless processor 5325 and medical device wireless processor 5330 can include a processor, for example, but not limited to, advanced RISC machine (ARM) processor 5329, that can execute wireless control code, termed herein, for convenience, dradio 5349. In some configurations, the processor can include, but is not limited to including, state machines that can manage the radio and can add functionality to a wireless communications transport layer. In some configurations, the processor can control a BLUETOOTH® soft device such as, for example, but not limited to, a Nordic Semiconductor S1×0 SoftDevice. Dradio 5349 executing on control device 5107 (FIG. 31A) can include at least one external application radio state machine 5305E, and dradio 5349 executing on mobility device 5111A can include at least one medical device radio state machine 5305M. At least one radio state machine can manage the states of/O to soft device 5347. Soft device 5347 can include a wireless protocol processor such as, for example, but not limited to, a processor that communicates using the BLE protocol.

Continuing to refer to FIG. 31D, the BLE protocol covers the four lowest layers and associated protocols defined by the BLUETOOTH® specification (Specification of the BLUETOOTH® System, Dec. 2, 2014 , https://www.bluetooth.org/en-us/specification/adopted-specifications). BLE devices operate in the unlicensed 2.4 GHz Industrial Scientific Medical band. Radio frequency (RF) channels are defined in the 2.4 GHz industrial, scientific, and medical (ISM) band, and the RF channels are allocated into two BLE physical channels: advertising and data. The advertising physical channel uses three RF channels for discovering devices, initiating a connection and broadcasting data. The data physical channel uses up to 37 RF channels for communication between connected devices. The BLE includes a link layer that uses one physical channel at a time. The link layer has one packet format used for both advertising channel packets and data channel packets. All packets can include a cyclic redundancy check (CRC). Data whitening is used to avoid long sequences of zeros or ones, e.g. 0000000 b or 1111111 b, in the data bit stream and is performed after the CRC in the transmitter. De-whitening is performed before the CRC in the receiver. A linear feedback shift register (LFSR) can be used to generate a de-whitening value. Each byte in the input string is exclusively OR'd with the de-whitening value, and the result is saved in a counted output string. The link layer may perform device filtering based on the device address of the peer device. Link layer device filtering is used by the link layer to minimize the number of devices to which it responds. The set of devices that the link layer uses for device filtering is called the white list.

Continuing to refer to FIG. 31D, to comply with the BLE protocol, standby, advertising, scanning, initiating, and connection states must be available. Advertising state includes transmitting advertising packets and listening for responses. Scanning state includes listening for packets from advertising devices. Initiating state includes listening for advertising from specific devices and initiating connections. A connection is considered to be established when a data channel packet has been received from the peer device. When two devices are in a connection, one device acts as a master, the other as a slave. If the connection state is entered from the initiating state, the device entering the connection state becomes the master. If the connection state is entered from advertising state, the device entering the connection state becomes the slave. The master controls the timing of a connection event. A connection event is a point of synchronization between the master and the slave. The link layer can enable the encryption of packets after entering the connection state.

Continuing to refer to FIG. 31D, both external application radio state machine 5305E and medical device radio state machine 5305M can manage the states of radios 5331, and can provide information about radios 5331 to external application 5107A and mobility device 5111A. Dradio 5349 can include general-purpose functionality and customized services to support mobility device 5111A, for example. Mobility device 5111A can be customized for users of varying abilities and physical characteristics, and a training mode can be configured for new users. Mobility device 5111A can be remotely controlled for stowage, and parametric and performance data can be downloaded to mobility device 5111A. When mobility device 5111A enters a wireless-enabled mode, external application 5107A can send commands to mobility device 5111A and can receive the corresponding responses. External application 5107A and mobility device 5111A can create, for example, but not limited to, first protocol messages 5135A (FIG. 31A) formatted according to a first protocol such as, for example, but not limited to, the remote interface specification (RIS) protocol (see FIG. 4A), to communicate information to processors of mobility device 5111A, and vice versa. External application 5107A and mobility device 5111A can create, for example, but not limited to, messages formatted according to a second protocol such as, for example, but not limited to, the SCA protocol (see FIG. 4B), to communicate control commands and data to processors of mobility device 5111A. The second protocol can be extensible to accommodate various types of controlled devices 5111 (FIG. 1) and various functions available through external application 5107A. For example, a radio-control application executing on an IPOD® device can exchange messages with mobility device 5111A by using, for example, but not limited to, messages following the RIS protocol (see FIG. 4A), and can send virtual device commands to mobility device 5111A by using, for example, but not limited to, messages following the SCA protocol (see FIG. 31B).

Continuing to refer to FIG. 31D, at the user's command, dradios 5349 can, through state machines 5305E/M and soft device 5347, cooperate to scan for peripheral radios, choose one that is advertising its readiness to communicate, and initiate a wireless session with the desired peripheral radio, for example, but not limited to, the peripheral radio of mobility device 5111A. If BLUETOOTH® communications are used, radio 5331 and soft device 5347 can provide BLUETOOTH® central radio functionality required to set up and maintain communications between mobility device 5111A and control device 5107 (FIG. 31A). In some configurations, external applications 5107A executing on ANDROIDS devices and iOS devices can use a wireless mechanism internal to ANDROIDS devices or iOS devices to communicate with mobility device 5111A. External application state machine 5305E can set up, control, and monitor wireless chip 5325 in a particular mode, such as, for example, central radio mode.

Continuing to refer to FIG. 31D, dradio 5349 can manage radio 5331 through functionality such as, for example, but not limited to, sending messages and responses to command and interrogate radio 5331, sending data over wireless link 5136, securely pairing remote radios 5331, encrypting radio traffic, filtering pre-selected devices from the list of advertising peripheral radios, and whitelisting the last-paired remote radios 5331, which can assist with the scan/pair/connect sequence. With respect to mobility device 5111A, state machine 5305M can manage radio 5331, serial I/O processor 5339 can provide low-level, thread-safe serial 1/O support, and RIS-SCA process 5317 can extract/embed SCA messages from/in RIS protocol payloads. In some configurations, RIS-only messages that are transmitted/received by radio 5331 can be discarded by external application wireless state machine 5305E or controlled device interface 5103 (FIG. 31A). Encapsulated SCA messages, for example, but not limited to, commands and status requests, can be placed upon SCA output queue 5319O for transfer to output queue 5309. To support various types of controlled devices 5111 (FIG. 1). RIS messages specific to a particular type of controlled devices 5111 (FIG. 31A) can augment a basic set of RIS messages. For incoming data packets, SCA messages can be extracted from incoming RIS messages, and the messages can be dispatched to thread-safe, circular queues for consumption by external application 5107A or mobility device 5111A. Outgoing messages can be queued separately depending on whether they are RIS or SCA messages. RIS messages that originate with external application 5107A can be placed on RIS output Q 53030 and moved to output queue 5309 when a queue slot is available. RIS-SCA process 5317 can retrieve SCA messages from RIS messages and vice versa to maintain transparency to SCA-aware software in system 100P.

Continuing to refer to FIG. 31D, in some configurations, the encapsulation of messages formatted in the second protocol within messages formatted in the first protocol can enable flexible communications between mobility device 5111A and external application 5107A. External application 5107A can receive information from, for example, a user, and the information can be translated into second protocol messages that can then be encapsulated in first protocol messages and transmitted to mobility device 5111A. Wireless state machines 5305E/M can include software constructs that can manage the states of wireless processors 5325/5330. State machines 5305E/M can maintain the synchronization of peripheral and central radio states of mobility device 5111A and external application 5107A.

Referring now primarily to FIG. 31E, external application state machine 5305E (FIG. 31D) can recognize states such as, for example, but not limited to idle state 3001 in which radio 5331 experiences no activity, and start-up state 3003 in which radio 5331 is started up. In start-up state 3003, external application state machine 5305E (FIG. 31D) is set up to listen for a status message from radio 5331 (FIG. 31D) that tells external application state machine 5305E (FIG. 31D) that radio 5331 (FIG. 31D) is ready to begin. In check state 3005, external application state machine 5305E (FIG. 31D) can await the ready-to-begin status message. Other states can include send state 3007 in which external application state machine 5305E (FIG. 31D) can request information about dradio 5349 (FIG. 31D), for example, but not limited to, its software version number, can send a start radio command to dradio 5349 (FIG. 31D), can send a command to dradio 5349 (FIG. 31D) to open up pairing with mobility device 5111A (FIG. 31D), and can inform dradio 5349 (FIG. 31D) about which of possible mobility devices 5111A (FIG. 31D) the user has selected. Wait for acknowledgement state 3009 can set external application state machine 5305E (FIG. 31D) in a state awaiting a response from the last sent message, for example, but not limited to, acknowledgements concerning radio version number, radio start, pairing, start scan, and parse data. With respect to the parse data acknowledgement, wait for acknowledgement state 3009 can inform dradio 5349 (FIG. 31D) that a response was received and loops back to the previous state until a pairing is selected or until scanning is stopped. Other responses that can be awaited can include responses to connect messages and connect status messages in which the state is awaiting the successful connection of mobility device 5111A (FIG. 31D) with the device's external application 5107A (FIG. 31D). Wait to scan state 3011 awaits a command to begin the pairing process and listens for responses from available mobility devices 5111A (FIG. 31D). Start scan state 3013 sends a command to dradio 5349 (FIG. 31D) to start scanning for available mobility devices 5111A (FIG. 31D) and sets up a state machine to enable the connection in which external application state machine 5305E (FIG. 31D) enters connected state 3015. If wireless link 5136 (FIG. 31D) is lost, or if message responses time out, or at an external request, external application state machine 5305E (FIG. 31D) can enter start reset state 3017 from which radio reset state 3019 can be entered in which a reset command is sent to dradio 5349 (FIG. 31D), followed by a wait for a response to the reset command. Stop state 3021 can set up external application state machine 5305E (FIG. 31D) to clean up and return to idle state 3001.

Referring now to FIG. 31F, mobility device state machine 5305M (FIG. 31D) can include states such as, for example, but not limited to, idle state 3101 in which there is no radio activity, start-up state 3103 in which radio 5331 (FIG. 31D) is enabled, advertise go-ahead state 3105 in which mobility device 5111A (FIG. 32) receives the go-ahead to advertise the availability of mobility device 5111A (FIG. 31D) for radio communication, and advertise state 3107 in which mobility device 5111A (FIG. 31D) identifying information is made available to listening radios such as, for example, radio 5331 (FIG. 31D) associated with external application 5107A (FIG. 31D). States can further include waiting for connect request state 3109, accepting a connect request state, connected state 3111 in which mobility device 5111A (FIG. 31D) can communicate with the desired central radio, and waiting state 3113 in which mobility device 5111A (FIG. 31D) awaits the end of a wireless session, whether by user action, or loss of radio signal. States can further include reset request state 3117 from which radio 5331 (FIG. 31D) can be placed in reset state 3119, and auto-reconnect state 3115 in which radio 5331 (FIG. 31D) can attempt to automatically reconnect to the wireless session, depending on how the wireless session ended.

Referring now to FIG. 31G, external application 5107A (FIG. 31D) can provide the interface between user interface 5107B executing on an external device and a wireless communications means. In some configurations, the wireless communications means can be based upon the BLUETOOTH® Low Energy protocol, and can include configuring communications between mobility device 5111A and external application 5107A, initiating the sending of messages between mobility device 5111A and external application 5107A, breaking up of large messages, and enabling virtual joystick commands that are initiated by a user of the external device and are transmitted to mobility device 5111A. Messages that can be exchanged can include, but are not limited to including, scan for devices, stop scan, and retrieve devices, where devices can include mobility device 5111A. Mobility device 5111A and external application 5107A can communicate with wireless processors 5325/5330 that can manage the transmission and reception of messages from between external application 5107A and mobility device 5111A. External application 5107A can generate create message 2001 using, for example, but not limited to, an applications program interface that can communicate with external application wireless processor 5325, which can receive create message 2001, and use the information from create message 2001 to build and send advertising information 2003 to mobility device wireless processor 5330. Advertising information 2003 can include, but is not limited to including, company identification, project identification, and customer identification. Mobility device wireless processor 5330 can use advertising information 2003 to build and send advertising data 2005A through external application wireless processor 5325 to external application 5107A, which can build and send device information to user interface 5107B to display on the external device. External application 5107A can send connect request 2007 to external application wireless processor 5325, which can build and send a connect request to mobility device wireless processor 5330. Mobility device wireless processor 5330 can respond to the connect request through external application wireless processor 5325 to external application 5107A, which can react to the response by sending service request 2009 to external application wireless processor 5325, which can respond by sending services 2011 to external application 5107A. Connect request 2007 can include commands to connect mobility device 5111A and/or cancel the connection to mobility device 5111A. The response to connect request 2007 can include success or failure notifications. External application 5107A can receive services 2011 and notify external device user interface 5107B that the device is connected. As communications start-up is in progress, a central manager within external application wireless processor 5325 can update the state of external application wireless processor 5325 and send the updated state information to external application 5107A. A disconnect request and response could be exchanged while communications are in progress, and external application wireless processor 5325 can provide the disconnect request to external application 5107A. As communications start-up is in progress, external application 5107A can query mobility device 5111A by sending messages such as, for example, but not limited to, discovering the services and characteristics of mobility device 5111A, and requesting reading and writing values from/to mobility device 5111A. The query can be answered by a response that can provide data and status of mobility device 5111A.

Referring now to FIG. 31H, following communications start-up, external application 5107A can initiate communications with mobility device 5107A by commanding external application wireless processor 5325 to send initialization message 2013, send device control enable message 2027, and send heartbeat message 2025 to mobility device wireless processor 5330. Mobility device wireless processor 5330 can receive joystick enable message 2027 and notify mobility device 5111A that the device control of external application 5107A is enabled. External application wireless processor 5325 can request, through mobility device wireless processor 5330, a status of mobility device 5111A. Mobility device 5111A can receive the status request, access the status, and send status message 2119 through mobility device wireless processor 5330 and external application wireless processor 5325 to external application 5107A, which can provide the status to external device user interface 5107B. External application wireless processor 5325 can request, through mobility device wireless processor 5330, a log from mobility device 5111A. Mobility device 5111A can receive the log request, access the log, and send log message 2121 through mobility device wireless processor 5330 and external application wireless processor 5325 to external application 5107A, which can provide the log to an external storage device.

Referring to FIG. 32A, there can be several ways that the security of controlled device 5111 (FIG. 31A) can be compromised. External communications and internal controls can be explicitly or accidently exploited causing minor to catastrophic results. Identifying specific ways that the exploitation, referred to herein as threats, can occur and be mitigated can be done by analyzing points where attacks can occur in communications and controls of controlled device 5111 (FIG. 31A). The sum of the points can be referred to as the attack surface. The objective of making controlled device 5111 (FIG. 31A) more secure can be achieved by reducing the size of the attack surface as much as possible, for example, by reducing the number of points. Remaining points can be mitigated. The resulting risk to controlled device 5111 (FIG. 31A) can be quantified by assigning severity scores to the points where attacks can occur. This can be done by, for example, but not limited to, assessment tools such as Common Vulnerability Scoring System (CVSS). With respect to threat analysis, external communications can be put at risk through, for example, but not limited to, malicious modification threats 5603 of message traffic, eavesdropping and replay threats 5601, and co-opting control threats 5621 of control device interface 5115 (FIG. 31A). Internal control compromises can include, but are not limited to including, malicious and/or erroneous applications 5617 that can cause intended and/or unintended results that can compromise security of controlled device 5111 (FIG. 31A). In-flight modification 5603 of message traffic can be detected by standard procedures that can be available in commercial wireless products 5607 such as, for example, but not limited to, products that adhere to the BLE standard in which a secure link can be established using Elliptic Curve Diffie-Hellman key exchange and AES-128 encryption. CRC protection 5605 can also be used to detect in-flight threats.

Continuing to refer to FIG. 32A, with respect to man-in-the-middle (MitM) threats 5601, when wireless devices are first paired, an attacker can place itself "in the middle" of the connection. Two valid but separate wireless encrypted connections can be established with a bad actor placing itself in the middle and reading or modifying unencrypted clear text that can be available between the two encrypted connections. MitM attacks 5601 can include an attackers monitoring messages, and altering and/or injecting messages into a communication channel. One example is active eavesdropping, in which the attacker makes independent connections with the victims and relays messages between them to make them believe they are talking directly to each other over a private connection, when in fact the entire conversation is controlled by the attacker. The attacker can intercept messages passing between the two victims and inject new ones. The victim(s) can also be subject to a replay attack in which the MitM records traffic and inserts new messages containing the same text, and then continually plays the messages back. Standard security features of commercial wireless protocols 5607, such as, for example, authentication, confidentiality, and authorization, can thwart some types of MitM attacks 5601. Authentication can include verifying the identity of communicating devices based on their device addresses. Confidentiality can include protecting information from eavesdropping by ensuring that only authorized devices can access and view transmitted data. Authorization can include insuring that a device is authorized to use a service. MitM threats 5601 can be thwarted by using a passkey entry pairing method, an out of band pairing method, or a numeric comparison method.

Continuing to refer to FIG. 32A, personal identification number (PIN) protection 5609 from MitM threats 5601 can include the exchange of a code, for example a six-digit code, between control device interface 5115 (FIG. 31A) and control device 5107 (FIG. 31A) using a short-term key. The six-digit code can be exchanged one bit at a time, and both sides must agree on the bit setting before another bit can be exchanged. At pairing time, control device 5107 (FIG. 31A) can request entry of a six-digit code that can be physically located on control device interface 5115 (FIG. 31A), and control device interface 5115 (FIG. 31A) can respond with the same six-digit code. MitM threats 5601 have no access to the six-digit code physically located on control device interface 5115 (FIG. 31A) and can therefore not assume control of control device interface 5115 (FIG. 31A) from control device 5107 (FIG. 31A). The pairing mechanism is the process in which control device 5107 (FIG. 31A) and control device interface 5115 (FIG. 31A) exchange identity information that paves the way for setting up encryption keys for future data exchange.

Continuing to refer to FIG. 32A, anyone who buys a complete system can know the controlled device PIN and can stage MitM attacks 5601. The MitM can operate the system and figure out the first protocol. Or the MitM could grab the message traffic between control device 5107 (FIG. 31A) and control device interface 5115 (FIG. 31A) and learn first protocol. Or the MitM could examine internal electrical busses of control device interface 5115 (FIG. 31A) to capture the first protocol traffic and figure out the first protocol. Clear text obfuscation 5611 can thwart these types of threats. Clear text obfuscation 5611 can include randomizing clear text so that even if the same message is sent repeatedly, the eavesdropped version varies randomly. Either of control device 5107 (FIG. 31A) or control device interface 5115 (FIG. 31A) can obfuscate the clear text in the message before transmitting the message, and either of control device interface 5115 (FIG. 31A) or control device 5107 (FIG. 31A) can deobfuscate the clear text. Once obfuscated, the messages appear to be random lengths and appear to contain random data and the clear text cannot be seen outside of the control device interface 5115 (FIG. 31A) or control device 5107 (FIG. 31A). The obfuscation algorithm on control device 5107 (FIG. 31A) can be kept secret through a security feature such as, for example, Licel's DexProtector tool. The obfuscation algorithm can be kept secret on control device interface 5115 (FIG. 31A) by setting the radio processor in control device interface 5115 (FIG. 31A) to disallow readback of the code and access to debugging features. In some configurations, the obfuscation algorithm can be "stateless" in that transmitted messages can be recovered independently of any previous message traffic, obviating the need to maintain any shared state between the sender and the receiver. In some configurations, even for clear text that is a series of messages of the same length, the length of the obfuscated messages can vary randomly. In some configurations, a first number of bytes of every message can be random. In some configurations, the algorithm can execute without read only memory (ROM) for data tables and with a relatively small amount of rapid access memory (RAM), code, and compute cycles.

Continuing to refer to FIG. 32A, in some configurations, trust boundary 5619 can be maintained between control device 5107 (FIG. 31A) and network storage 5113 (FIG. 31A). Trust boundaries 5619 are the places where the location of data associated with a system can create potential opportunities for trust violations, for example, if the data are outside the control of control device 5107 (FIG. 31A) and/or controlled device 5111 (FIG. 31A), or where the data leave the external application infrastructure. Trust can be maintained through the exchange of keys and encryption of messages between, for example, control device 5107 (FIG. 31A) and network storage 5113 (FIG. 31A). Trust boundary 5619 can exist between control device 5107 (FIG. 31A) and controlled device 5115 (FIG. 31A). Trust can be maintained across this interface through the use of BLE secure communications and PIN bonding with controlled device 5111 (FIG. 31A). In some configurations, trust boundaries 5619 can occur within control device 5107 (FIG. 31A), between, for example, external application 5107A (FIG. 31D) and system services. Trust can be established by the use of a key and sandboxing on control device 5107 (FIG. 31A) to keep data safe from other applications. In some configurations, databases can be protected by file encryption, protecting the data files with file system encryption tied to the application keys. Trust can be maintained through the exchange of keys and encryption of messages between control device 5107 and network storage 5113.

Referring now to FIG. 32B, method 5150 for obfuscating plain text can include, but is not limited to including, generating 5151 a random byte and using the random byte as a random key, transforming 5153 the random key into a count of random bytes in a known range, generating 5155 the number of random bytes that equals the count, and transforming 5157 several of the random bytes into a linear feedback shift register (LFSR) seed value. Method 5150 can include whitening 5159 an input counted string using the LFSR seed value.

Referring now to FIG. 32C, method 5160 for deobfuscating the clear text can include, but is not limited to including, transforming 5161 the random key into the count of random bytes in the known range, transforming 5163 several of the random bytes into the LFSR Seed value, dewhitening 5165 the original counted string byte count value, dewhitening 5167 the counted string using the byte count value.

Referring again to FIG. 32A, the MitM can record a message between control device 5107 (FIG. 31A) and control device interface 5115 (FIG. 31A) and can replay it incessantly. If control device 5111 (FIG. 31A) is a medical device, a random therapy message number transmitted by controlled device can thwart replay attacks because control device 5107 (FIG. 31A) must reiterate the random therapy message number with a next command message. If control device 5107 (FIG. 31A) does not include the random therapy message number, controlled device can reject the message, thereby preventing replaying the same message repeatedly.

Referring now to FIG. 32D, since anybody who has a wireless device that can communicate according to the wireless protocol used between control device 5107 (FIG. 31A) and control device interface 5115 (FIG. 31A) can hack in between control device interface 5115 (FIG. 31A) and control device 5107 (FIG. 31A), challenge/response process 5615 can be used to thwart malicious actors. For example, if a third party application becomes readily available, for example, for sale on mobile devices in application stores, control device interface 5115 (FIG. 31A) or control device 5107 (FIG. 31A), either acting as sender, can present a challenge to control device 5107 (FIG. 31A) or control device interface 5115 (FIG. 31A), either acting as receiver, and the receiver must present the correct response. The method, from the point of view of the sender, for thwarting security threats by challenge/response can include, but is not limited to including, picking 7701 a large random number, sending 7703 the large random number to a receiver, and transforming 7705/7709, by the sender and the receiver, the large random number in the same secret way. The method can include hashing or encrypting 7707/7711, by the sender and the receiver, the transformed number in a cryptographically-secure way, receiving 7713, from the receiver, the hashed or encrypted number, and checking 7715 that the number hashed or encrypted by the sender and the number hashed or encrypted by the receiver are equal. The challenge/response process can rely on both sender and receiver using the same secret transform algorithm. At no time does the transformed number travel over the radio in an unencrypted fashion, protecting the secret transform. To keep the algorithm secret, a controller can use commercially-available tools such as, for example, but not limited to, Licel's DEXProtector, that can provide, for example, string, class, and resource encryption, integrity control, and hiding of application programming interfaces.

Referring now to FIG. 33, event handing, including handling of error and fault conditions, can include dynamic, flexible, and integrated event management among UC 130, PSCs 98/99, and processors 39/41. Event handling can include, but is not limited to including, event receiver 2101, event lookup processor 2103, and event dispatch processor 2105. Event receiver 2101 can receive event 2117 from any parts of the MD including, but not limited to, UC 130, PSC 98/99, and PB 39/41. Event lookup processor 2103 can receive event 2117 from event receiver 2101, and can transform event 2117 to event index 2119. Event lookup process 2103 can use means such as, for example, but not limited to, table lookup and hashing algorithms to create a means to locate event information. Event lookup process 2103 can provide event index 2119 to event dispatch processor 2105. Event dispatch processor 2105 can determine, based at least in part on event index 2119, event entry 2121. Event entry 2121 can include information that can be relevant to responding to event 2117. Events can be processed by UC 130, PSC 98/99, and PB 39/41, each of which can include, but is not limited to including, status level processor 2107, filter processor 2109, action processor 2111, and indications processor 2115. Status level processor 2107 can extract a status level, for example, but not limited to, a fault category, from event entry 2121, and can provide indications based on the status level. In some configurations, status levels, for example, a range of values, can accommodate conditions ranging from transient to severe, and can provide indications ranging from possible audible tones to flashing lights and automatic power down. UC 130 can audibly and visually notify the user when, for example, but not limited to, a potential failure condition is detected, and can allow the user to disable alerts, such as, for example, audible alerts. UC 130 can request user confirmation for events such as, for example, but not limited to, powering off, and powering off can be disabled at certain times, for example, but not limited to, in 4-Wheel mode 100-2 (FIG. 22A), balance mode 100-3 (FIG. 22A), and stair mode 100-4 (FIG. 22A).

Continuing to refer to FIG. 33, filter processor 2109 can extract from event entry 2121 an indication of when the event 2117 is to be handled. In some configurations, event 2117 can be handled immediately, or can be handled after an elapsed number of times event 2117 has been reported. In some configurations, the reports can be non-consecutive. In some configurations, events 2117 can be reported at a first rate and can be processed at a second rate. In some configurations, event 2117 can be handled when reported, instead of deferring the handling for batch processing, when event 2117 is detected at pre-selected times or for pre-selected types of errors. Each of UC 130, PSC 98/99, and PB 39/41 can include a particular event count threshold. In some configurations, event handling can be latched if a pre-selected number of events 2117 has occurred. In some configurations, the latching can be maintained until a power cycle.

Continuing to still further refer to FIG. 33, action processor 2111 can extract from event entry 2121 an indication of what action is associated with event 2117. In some configurations, actions can include commanding the MD to discontinue motion and placing data in an event log and/or alarm log. In some configurations, event and/or alarm log data from PB 39/41, UC 130, and PSC 98/99 can be managed by PSC 98/99. In some configurations, an external application can retrieve event and/or alarm log data from PSC 98 and PSC 99 and synchronize the data. The data can include a list of alarms and reports that can be associated with particular events and status identifications such as, for example, but not limited to, controller failure and position sensor fault. Controller failures can be associated with an explicit reason for failure that can be logged. In some configurations, event 2117 can be escalated, where escalation can include reporting events 2117 that can be associated with the reported event. In some configurations, event entry 2121 can specify an accumulator to be incremented when event 2117 is detected. In some configurations, the accumulators in all of PB 39/41, UC 130, and PSC 98/99 can be managed by PSC 98/99 and accessed by an external application. In some configurations, event entry 2121 can include a specification of a service-required indication associated with event 2117, which can also be managed by PSC 98/99 and retrieved by an external application as described herein. In some configurations, event entry 2121 can include a black box trigger name to be used when event 2117 is detected. Restriction processor 2113 can extract from event entry 2121 information about immediate and downstream effects of event 2117. In some configurations, immediate effects can include user notifications, for example, audible and visible notifications can be made available when the battery needs to be charged, when the temperature of the MD exceeds a pre-selected threshold, and when the MD needs service. Immediate effects can also include notifying the user of the severity of event 2117. In some configurations, downstream effects can include restricting operational modes based on events 2117. In some configurations, entry can be restricted into enhanced, balance, stair, and remote modes. In some configurations, downstream effects can include effects on the operation of the MD, for example limiting speed, disabling motion, transitioning into certain modes automatically, restricting MD lean, restricting power off, and blocking external application communication. In some configurations, a return to 4-wheel mode can be automatic under certain pre-selected conditions such as, for example, but not limited to, the transition to balancing on two wheels has failed, the pitch of the MD has exceeded the safe operating limit for balance mode, and/or the wheels have lost traction in balance mode.

Continuing to refer to FIG. 33, indications processor 2115 can extract from event entry 2121 any indications that should be raised as a result of event 2117. In some configurations, indications can be raised when there is a loss of communications between components of the MD, for example, between PSC 98/99 and UC 130, and between PB 39 and PB 41, and when battery voltage is below a pre-selected threshold. In some configurations, event entry 2121 can provide communications between processes, for example, status flags can provide the status of seat, cluster, yaw, pitch, and IMU indicators.

Referring now to FIG. 34A, seat assembly 40000 can be removably positioned upon a wheelchair base, for example, by use of the connecting features located on seatpan mounting bracket 30001. To provide comfort and security to the user, seat assembly 40000 can include first configuration footrest 40017, seat cushion 30002, backrest cushion 30017, and armrest cushions 30046. First configuration footrest 40017 can be mounted to height-adjustable first configuration bottom post 40021 and first configuration top post 40019. Seatpan mounting bracket 30001 can include tie down 30069 that can be used to secure the wheelchair and seat to, for example, an automobile seat belt. Seatpan mounting bracket 30001 can be coupled with rear tube holder bracket 30011 that can be coupled with first configuration top back frame bracket 40011. First configuration top back frame bracket 40011 can couple the seat back with attendant handle 50001.

In some configurations, running cables from the UC to the powerbase can include inserting fasteners such as, for example, but not limited to, button head cap screws (BHCS) through the seatpan, and threading the screws into an anchor link of cable chain 1149 (FIGS. 11A-11D) and a plate that can include threaded holes. In some configurations, running cables from the UC to the powerbase can include an intermediate plate to couple an anchor plate of cable chain 1149 (FIGS. 11A-11D) with the seatpan. The intermediate plate can rest between the seatpan and the anchor plate. The intermediate plate can accept BHCSs through the seatpan to fasten the seatpan to the intermediate plate. The intermediate plate can accept fasteners such as, for example, but not limited to, flat head cap screws (FHCS), to fasten the anchor plate to the intermediate plan, and thus to the seatpan. In some configurations, an anchor link of cable chain 1149 (FIGS. 11A-11D) can include mounting holes outside of the central channel of cable chain 1149 (FIGS. 11A-11D). Fasteners can thread through the seatpan directly into the anchor link.

Referring now to FIG. 34B, seatpan mounting bracket 30001 can be coupled with rear tube holder bracket 30011 by fold hinge bracket 30010. The folding of backrest shell 30019 onto seat cushion 30002 can be enabled by applying pressure to fold handle 30014 engaging springs on guide pins. In some configurations, the angle of backrest shell 30019, and therefore backrest cushion 30017 (FIG. 34A), can be adjusted by rotating backrest angle adjust knob 40049. In some configurations, the angle of backrest shell 30019 can be fixed and backrest angle adjust knob 40049 can be omitted. Adjustment of the height of armrest structures 30043, and therefore armrest cushions 30046, can be enabled by a combination of vertical back frame canes 30013 (FIG. 2A) (one for each armrest structure 30043) and armrest mount brackets 30040 (one for each armrest structure 30043).

Referring now to FIGS. 34C-341, second configuration seat assembly 40000-1 can include, but is not limited to including, user controller attachment bracket 30226 that can securely attach user controller 22006 to armrest bracket 30043. User controller 22006 can include any desired shape, size, and functionality, and can be commercially available or custom-built. A joystick and/or toggles can be included. User controller 22006 can be operably coupled with a power base (not shown) by any desired means, including, but not limited to, by cable 22128, that can be routed so as not to interfere with the movement of seat assembly 40000-1. User controller attachment bracket 30226 can be operably coupled with either of armrest brackets 30043 or elsewhere as desired. Second configuration seat assembly 40000-1 can include footrest 30064 that can rotate towards second configuration lower footrest post 30062 when not in use. Second configuration lower footrest post 30062 can be positionally adjusted with respect to seat bracket 30001 to raise or lower second configuration footrest 30064. Second configuration lower footrest post 30062 can be attached, by any suitable means such as, for example, but not limited to, screws, bolts, hook-and-eye, and magnets, to second configuration upper footrest post 30061 according to the desired position of footrest 30064. Armrest structure 30043 (FIGS. 34H and 341) can be rotated towards the backrest for user convenience and for streamlined transporting of the seat.

Referring now primarily to FIGS. 35A-35E, the seat, backrest, and arms of second configuration seat assembly 40000-1 can by operably coupled by second configuration top back frame bracket, rear tube holder bracket 30011, and second configuration armrest mount bracket 30040. Second configuration armrest mount bracket 30040 can surround vertical back frame cane 30013 that can include a first end and a second end. The first end of vertical back frame cane 30013 can engage rear tube holder bracket 30011, and the second end of vertical back frame cane 30013 can engage second configuration top back frame bracket 30012. Vertical back frame cane 30013 can be secured between top back frame bracket 30012 and rear tube holder bracket 30011 by bolt 40000-10. Bushings 40014-3 can surround second configuration armrest mount bracket 30040 as it slides up and down along vertical back frame cane 30013. Second configuration armrest mount bracket 30040 can enable both adjustment of the height of the armrest and the rotation of the armrest towards the backrest. Height adjustment of armrest structure 30043 can be accomplished by a push button action of armrest height adjustment button 30045 by the user. Armrest narrow flanged bushing 40014-2, armrest wide flanged bushing 40014-1, and armrest nut with hole 30044 can operably couple armrest structure 30043 with armrest mount bracket 30040 and armrest height adjustment button 30045 through, for example, but not limited to, a threaded coupling. Armrest mount bracket 30040 can operably couple armrest structure 30043 with vertical back frame cane 30013 that can operably couple armrest structure 30043 with rear tube holder bracket 30011 and second configuration top back frame bracket 30012. Within armrest mount bracket 30040 are components that can enable height adjustment of armrest structure 30043. The components can include, but are not limited to including, button transition rod 40011-1 that can operably couple armrest height adjustment button 30045 with button slide 30042. Button transition rod 40011-1 can achieve aligned coupling with button slide 30042 through its placement in button slide cavity 40061-3 (FIG. 401). Button slide 30042 can control the release of the current position of armrest structure 30043 by positionally interacting with male lock pin 30041-1. Male lock pin 30041-1 and female lock pin 30041-2 can cooperatively engage with vertical back frame cane 30013 to establish the height of the armrest. Button slide 30042 can respond to a depression of button 30045 by disengaging male/female lock pins 30041-1/2 from vertical back frame cane 30013 to allow second configuration armrest mount bracket 30040 to slide along vertical back frame cane 30013. When armrest height adjust button 30045 is depressed, button slide 30042 is depressed, moving button slide lock position 40061-1 (FIG. 401) and releasing the lock on armrest structure 30043 enabled by the contact between button slide lock position 40061-1 (FIG. 401) and male lock pin 30041-1. As button slide 30042 is depressed, button slide open position 40061-3 (FIG. 401) can become aligned with male lock pin 30041-1, and can enable male lock pin 30041-1 and female lock pin 30041-1 to retreat from back frame cane cavity 40025-2 (FIG. 40J), releasing the lock on the position of armrest structure 30043 and allowing armrest mount bracket 30040 to slide in channel 40025-1 (FIG. 40J). Armrest mount bracket 30040 can be provide a low-friction sliding surface between vertical back frame cane 30013 and armrest mount bracket 30040. Spring arm mechanism 40017 can enable the return of button 30045 to engaged position with respect to button slide 30042, male lock pin 30041-1, and female lock pin 30041-1. In some configurations, adjustment screw 40025-3 (FIG. 40K) can be used to bolt armrest structure 30043 to vertical back frame cane 30013.

Referring now to FIGS. 35F-35G, second configuration armrest 30048 can be operably coupled with armrest mount bracket 30040 (FIG. 35A) in the same way as has been described herein. Second configuration armrest 30048 can include second configuration armrest structure 30043-1, armrest shell 30047, and second configuration armrest cushion 30046-1. Second configuration armrest structure 30043-1 can include curvature 30043-1C that can enable positional accommodation during use of second configuration armrest 30048. Second configuration armrest structure 30043-1 can include a support structure that can taper with respect to curvature 30043-1C, relatively smaller support structure 30043-1D being associated with armrest shell interface 30043-1E, and relatively larger support structure 30043-1G being associated with area 30043-1K between armrest shell interface 30043-1E and armrest mount bracket interface 30043-1J. The support structure can provide stable resistance to pressure placed upon armrest shell interface 30043-1E. The support structure can be continuous or discontinuous, and can be constructed of the same or different material from armrest shell interface 30043-1E. Second configuration armrest structure 30043-1 can include rotation stops 30043-1H that can maintain the rotation of second configuration armrest 30048 within a preselected number of degrees. Armrest shell 30047 can be situated between second configuration armrest structure 30043-1 and second configuration armrest cushion 30046-1. Armrest shell 30047 can include structure interface 30047-1 that can be operably coupled to second configuration armrest structure 30043-1 and second configuration armrest cushion 30046-1, and can include cushion interface 30047-2 that can be operably coupled to second configuration armrest cushion 30046-1. Armrest shell 30047 can decouple the geometry of second configuration armrest structure 30043-1 from the geometry of second configuration armrest cushion 30046-1 by providing a mounting platform for second configuration armrest cushion 30046-1. Thus the geometry of second configuration armrest structure 30043-1 can remain fixed while the geometry of second configuration armrest cushion 30046-1 can vary based on user preference and need. Armrest cushion 30046-1 can include, for example, relatively narrower edge 30043-1B that can cooperatively, with relatively wider edge 30043-1A, accommodate arm comfort while maintaining space for the torso in the seat assembly. Armrest cushion 30046-1 can thus be contoured to accommodate the arm's geometry, and can be attached to armrest shell 30047 by any suitable fastening means such as, for example, but not limited to, glue, magnets, screws, bolts, and hook-and-eye fasteners. Armrest shell 30047 can be attached to second configuration armrest structure 30043-1 by any suitable means as well.

Referring now to FIGS. 36A, 36B, and 37A, seatpan bracket 30001 can operably couple footrest 30064 with rear tube holder bracket 30011. Seatpan bracket 30001 can include mounting points for at least one vehicle tie down 30069, fold hinge bracket 30010, and footrest mount bracket 30060 (FIG. 36B). Fold hinge bracket 30010 can enable secure mounting of rear tube holder bracket 30011 that can enable folding of the backrest towards seatpan bracket 30001 when fold handle 30014 is shifted. Seatpan bracket 30001 can include seatpan alignment cavities 30001-2 (FIG. 37A) and 30001-1 (FIG. 37A) that can matingly align seatpan bracket 30001 with seat shell 30000 (FIG. 371). Seatpan wings 30001-3 (FIG. 37A) can enable operable coupling of seatpan bracket 30001 with a seat mounting device (not shown) such as, for example, but not limited to, a powerbase for a motorized wheelchair.

Referring now to FIGS. 37B-37F, the backrest can be locked in place, and also can be released and folded towards the seat cushion. When the backrest is folded forward, the armrests can be rotated towards the backrest to enable compact storage. The junction between armrest structure 30043 (FIG. 37B) and second configuration armrest mount bracket 30040 (FIG. 37B) can enable smooth rotation of armrest structure 30043 (FIG. 37B). Fold hinge bracket 30010 can include bottom hinge knuckles 30010A (FIG. 37C) mounted to hinge leaf 30010B (FIG. 37C). Rear tube holder bracket 30011 can include top hinge knuckles 30011A (FIG. 37C) that can operably couple with bottom hinge knuckles 30010A (FIG. 37C) and surround hinge pin 30020 (FIG. 37C). When fold handle 30014 (FIG. 37C) is lifted, at least one spring pin 40010, engaged within spring pin cylinder 40017 (FIG. 37C), can release at least one retention hook 30015, protruding from retention hook cavity 30015B (FIG. 37C), and can enable at least one retention hook 30015 to disengage from at least one retention hook rest 30015A (FIG. 37C). At least one retention hook 30015 can engage with cavity 30011B (FIG. 37C). It is then possible to rotate rear tube holder bracket 30011, operably coupled with the backrest, towards seat bracket 30001. The backrest can be lifted back into an operational position, rotating rear tube holder bracket 30011 away from seat bracket 30001. At a pre-selected point in the rotation, at least one retention hook 30015 (FIG. 37C) can engage with at least one retention hook rest 30015A (FIG. 37C), locking the backrest in place.

Referring now to FIG. 37G, rear tube holder bracket 30011 can be shaped to accommodate a seat cushion, in particular, rear tube holder bracket 30011 can include a curvature angle 30011E that can be varied, during manufacture, depending upon the shape of the seat cushion. Rear tube holder bracket 30011 can include fastening cavity 30011D that can accommodate bolt 40000-10 (FIG. 35A), and cane cavity 30011C that can accommodate vertical back frame cane 30013 (FIG. 35A).

Referring now to FIG. 37H-37M, seat shell 30000 can be mounted atop seat bracket 30001 (FIG. 37A). Seat shell 30000 can provide an interface between seat cushion 30002 (FIG. 37K) and seatpan mounting bracket 30001 (FIG. 37A). Seat shell 30000 can be contoured to retain seat cushion 30002 (FIG. 37K) while, at the same time, providing edges, such as chamfered or beveled edges, that can enable comfortable seating. For example, seat shell 30000 can include at least one seat shell side rest 40079-1 (FIG. 371) that can retard lateral motion of seat cushion 30002 (FIG. 37K). Seat shell 30000 can include seat shell bottom 40079-2 (FIG. 371) that can include seat alignment first feature 40079-10 (FIG. 37J) and seat alignment feature second feature 40079-11 (FIG. 37J) described herein. Seat shell 30000 can include at least one seat magnet 40079-3 (FIG. 371) that can enable operable coupling between seat shell 30000 and seat cushion 30002 (FIG. 37K). Seat shell 30000 can be constructed of multiple parts or can be a single piece. In some configurations, seat shell 30000 can include seat shell front right 40079-6 (FIG. 37J), seat shell front left 40079-7 (FIG. 37J), seat shell rear right 40079-8 (FIG. 37J), and seat shell rear left 40079-9 (FIG. 37J) that can be joined together by, for example, at least one seat shell bolt 40079-4 (FIG. 37J) and/or at least one seat shell pin 40079-5 (FIG. 37J). When the parts of seat shell 30000 are joined, at least one seat shell rib 40079-12 (FIG. 371) can be formed.

Referring now to FIG. 37N, seat cushion 30002 can rest upon seat shell 30000 (FIG. 371), and can be operably coupled with seat shell 30000 (FIG. 371) through the coupling of fastening means such as, for example, but not limited to, at least one seat magnet 40079-3 (FIG. 371) with at least one seat cushion magnet 40013-1 on seat cushion shell interface 40013-3. Seat shell ribs 40079-12 (FIG. 37J) can be accommodated by seat cushion troughs 40013-2. Seat cushion 30002 can include user seat surface 40013-4 that can, in some configurations, include padding for comfort. Seat cushion 30002 can include any type and amount of padding and any type of upholstery.

Referring now to FIG. 38, optional attendant handle 50001 can be retracted to reduce its height, and can be set to a specific height to accommodate the attendant. In particular, handle grasp 50001-2 can be depressed. The depression can reduce the length of handle post top 50001-1 by sliding it into handle post bottom 50001-3. Handle interface 50001-6 can include pivot bolt cavity 50001-4 that can rest upon backrest pivot shaft 40011-5 (FIG. 36B), the combination of which can enable snap placement of attendant handle 50001 with respect to backrest shell 30019. Attendant handle 50001 can include knob shaft accommodation 50001-5 that can provide space for threaded knob shaft 40011-1 (FIG. 36A). Attendant handle 50001 can enable an attendant to assist a user in, for example, but not limited to, climbing stairs.

Referring now to FIGS. 39A-39F, backrest shell 30019 can include knob interface bracket 40023-1 (FIG. 39B) that can accommodate angle adjustment knob 40049 (FIG. 39C), if it is present, through an operable coupling enabled by connecting screw cavity 40023-2 (FIG. 39B). Backrest shell 30019 can include multiple parts or can be manufactured as a single piece. In some configurations, backrest shell 30019 can include mirrored image backrest shell right 40023-4 (FIG. 39B) and backrest shell left 40023-5 (FIG. 39B) that can be joined at backrest shell ribs 40023-6 (FIG. 39B). Backrest shell right 40023-4 (FIG. 39B) and backrest shell left 40023-5 (FIG. 39B) can include at least one backrest magnet 40023-3 (FIG. 39B) that can accommodate attachment of backrest cushion 30017 (FIG. 39F). Attachment means to couple backrest shell 30019 with backrest cushion 30017 (FIG. 39F) can include, but are not limited to including, backrest magnets 40023-3 (FIG. 39B) that can be attached to backrest shell 30019 by any kind of fasteners including, but not limited to screws, bolts, hook-and-eye fasteners, and glue. Backrest shell 30019 can include at least one backrest spacer 40023-7 (FIG. 39B) that can provide for positioning of additional cushioning. At least one backrest spacer 40023-7 (FIG. 39B) can include recess 30019C (FIG. 39C) that can accommodate means to attach various pieces of backrest shell 30019 together.

Referring now to FIGS. 39G-391, first configuration top back frame bracket 40011 (FIG. 39G) can provide recesses for mounting backrest angle adjust knob 40049 (FIG. 6H), if present. Angle adjust knob 40049 (FIG. 39H) can be operably coupled with threaded knob shaft 40011-1 (FIG. 39H) that can include a cavity to accommodate bracket knob connecting screw 40011-8 (FIG. 39G). Backrest angle adjust knob 40049 (FIG. 39H) can cause the angle of backrest shell 30019 (FIG. 39E) (and therefore backrest cushion 30017 (FIG. 39F)) to change during travel along threaded knob shaft 40011-1 (FIG. 39H) by threaded footrest insert 40011-2 (FIG. 39H) and retaining ring 40011-4 (FIG. 39H). Retaining ring 40011-4 (FIG. 39H) can include, but is not limited to including, an axially or radially assembled ring, an inverted ring, a beveled ring, and a spiral ring. Bracket knob connecting screw 40011-8 (FIG. 39G) can operably couple backrest shell 30019 (FIG. 39B) with backrest angle adjust knob 40049 (FIG. 39H) through knob interface bracket 40023-1 (FIG. 39B) to enable positional adjustment of backrest shell 30019 (FIG. 39B) by rotating backrest angle adjust knob 40049. Backrest angle adjust knob 40049 (FIG. 39H) can be operably coupled with connecting pin 40011-10 (FIG. 39G). When backrest angle adjust knob 40049 (FIG. 39H) is rotated, pressure is placed upon connecting pin 40011-10 (FIG. 39G) which can cause rotation of backrest shell 30019 (FIG. 39B). First configuration top back frame bracket 40011 (FIG. 39G) can provide recesses for backrest pivot shaft 40011-5 (FIG. 39C) that can be held in place by, for example, but not limited to, pivot shaft bolts 40011-7 (FIG. 39H) and recessed bolthead washers 40011-6 (FIG. 39H).

Referring now primarily to FIG. 39F, backrest cushion structure 30017 can include contoured backrest cushion 40003-2 on a first side of backrest cushion structure 30017. Contoured backrest cushion 40003-2 can be sized and padded to interface with a specific user. Backrest cushion structure 30017 can include backrest shell interface 40003-3 that can interface with backrest shell 30019. Backrest shell interface 40003-3 can include recessed features that can include at least one backrest cushion magnet 40003-1 that can operably couple with at least one backrest shell magnet 40023-3 (FIG. 35B) to enable removable coupling between backrest shell 30019 (FIG. 39B) and backrest cushion structure 30017. The recessed features can accommodate backrest spacers 40023-7 (FIG. 35B).

Referring now to FIGS. 39J-39L, second configuration top back frame bracket 30012 can include backrest rotation pin 30018 that can be held in place by rotation pin bolt 40002 (FIG. 39K) and rotation pin bushing 30085 (FIG. 39K). Second configuration top back frame bracket 30012 can include at least one spacer 40020 that can maintain the distance between backrest shell 30019 (FIG. 39F) and top back frame bracket 30012. Top back frame bracket 30012 can include curvature angle 30012D (FIG. 39J) that can be varied, during manufacture, according to the shape of the backrest. Any shape of the backrest can be accommodated by modifying curvature angle 30012D (FIG. 39J) of top back frame bracket 30012. Top back frame bracket 30012 can operably couple with vertical back frame cane 30013 (FIG. 35A) at cane cavity 30012C (FIG. 39J). Second configuration top back frame bracket 30012 can operably couple with backrest shell 30019 by means of backrest rotation pin 30018 that can simultaneously pass through backrest pin cavities 30019A/30019B (FIG. 39L) and top bracket pin cavities 30012A (FIG. 39L).

Referring now to FIG. 40A, first configuration armrest mount bracket 40053 can include contoured rests 40053-4 that can surround and admit female lock pin 30041-2 (FIG. 35A). Adjustment screw cavity 40053-5 can accommodate adjustment screw 40025-3 (FIG. 40J). At least one armrest wing 40053-3 can enable alignment of first configuration armrest mount bracket 40053 with armrest structure 30043 (FIG. 34A). Recesses 40053-1 can operably couple armrest nut with hole 30044.

Referring now to FIGS. 40B-40D, armrest structure 30043 (FIG. 40B) can operably couple with first configuration armrest mount bracket 40053 (FIG. 40B), that can slide along vertical back frame cane 30013 (FIG. 40B). Armrest structure 30043 (FIG. 40C) can also operably couple with second configuration armrest mount bracket 30040 (FIG. 40C).

Referring now to FIGS. 40E-40L, second configuration armrest mount bracket 30040 (FIGS. 40F, 40G) can include rectangular alignment tabs 30040-4 that can surround and admit female lock pin 30041-2 (FIG. 35A) at recess 30040-5 (FIG. 40H) and can rest in cane cavity 40025-1 (FIG. 40J-40L). Alignment tabs 30040-4 can maintain the position of vertical back frame cane 30013 (FIG. 40D) within second configuration armrest mount bracket 30040. At least one armrest wing 30040-2 can enable alignment of second configuration armrest mount bracket 30040 with armrest structure 30043 (FIG. 34A). Adjustment screw cavity 30040-3 can accommodate adjustment screw 40025-3 (FIG. 40K). Vertical back frame cane 30013 (FIG. 35A) can rest in holder 30041-1 (FIG. 40L) within mount bracket cavity 30040-1 (FIG. 40H). Positional maintenance pins 30041-2 (FIG. 40K) can rest in pin cavities 40025-4 (FIG. 40J) to maintain the position of second configuration vertical back frame cane 30013 (FIG. 40D) between second configuration top back frame bracket 30012 (FIG. 35A) and rear tube holder bracket 30011 (FIG. 35A).

Referring now to FIGS. 41A and 41B, second configuration footrest 30064, second configuration lower footrest post 30062, and second configuration upper footrest post 30061 can combine to provide a footrest structure for seat assembly 40000-1. The height of footrest 30064 can be adjusted by raising and lowering second configuration lower footrest post 30062. The height can be secured by engaging a fastening means such as, for example, but not limited to, at least one screw 40054 coupling fastening cavities of second configuration upper footrest post 30061 and second configuration lower footrest post 30062. The angle of footrest 30064 can be adjusted by turning screw 30064D (FIG. 41B) either counterclockwise or clockwise, depending on the desired angle with respect to second configuration lower footrest post 30061.

Referring now to FIG. 41C, in some configurations, the orientation of first configuration upper footrest post 40019 and first configuration lower footrest post 40021 can be adjusted forwards and backwards relative to the direction of motion and seat cushion 30002. In some configurations, the position of first configuration footrest 40017 can be adjusted forwards and backwards to accommodate the comfort needs of the user. First configuration lower footrest post 40021 can telescope into first configuration upper footrest post 40019 to enable adjustment of the length of the footrest structure. In some configurations, the relative positions of first configuration lower footrest post 40021 and first configuration upper footrest post 40019 can be maintained by fastening means such as, for example, but not limited to, screws, bolts, hook-and-eye fasteners, and glue.

Referring now to FIGS. 41D-41E, footrest mount bracket 40029 can operably couple the footrest structure with seat pan mounting bracket 30001 (FIG. 37A). Upper footrest spacer 40043 (FIG. 41E), legrest flanged bushing 40037 (FIG. 41E), recessed bolthead washer 40039 (FIG. 41E), legrest swing bolt 40226 (FIG. 41E), and footrest o-ring 40045 (FIG. 41E) can, in combination, enable limited forward-backward movement of upper footrest post 40019. The forward position of the footrest structure can be maintained by spring plunger 40027. Lower footrest spacer 40033 (FIG. 41E), footrest swing bolt 40237 (FIG. 41E), footrest washer 40031 (FIG. 41E), and footrest nut 40238 (FIG. 41E) can, in combination, enable folding of first configuration footrest 40017 towards lower footrest post 40021. First configuration footrest 40017 can accommodate both feet, and can be constructed as a single item or in parts. The foot-facing surface of first configuration footrest 40017 can include non-slip features 40017-1 and rear stop 40017-2.

Referring now to FIGS. 41F-41I, second configuration footrest 30064 can be operably coupled with second configuration lower footrest post 30062, which can cooperatively engage with second configuration upper footrest post 30061 to raise and lower footrest 30064. Second configuration upper footrest post 30061 can be operably coupled with seat bracket 30001 (FIG. 34A), by means of footrest bracket 30060, and can include limited backward rotation in response to pressure exerted upon footrest 30064. Bumper 30063, constructed of a compliant material, can buffer the effect of the pressure. Joints in the seat assembly can be reinforced by a combination of recessed bushing 30085 (FIG. 41H), for example, and bolt 40002 (FIG. 41H). Bolt 40002 (FIG. 41H) can be inserted into the recess of recessed bushing 30085 (FIG. 41H) and engaged therein. Any subsequent stress on the joint can be met by both the strength of bolt 40002 (FIG. 41H) itself in addition to the strength of recessed bushing 30085 (FIG. 41H). Further, the head of bolt 40002 (FIG. 41H) can reside within the recess of recessed bushing 30085 (FIG. 41H), maintaining a flush appearance. Other joints in the seat assembly can be constructed in a similar manner.

Referring now to FIGS. 42A-42C, a seating assembly 110 can offer a plurality of automated or user-operable features to facilitate expedient performance of routine tasks by user of seating assembly 110, specifically when seating assembly 110 is provided on a wheelchair or any other mobility device. Seating assembly 110 can be further constructed to suit pre-determined requirements of individuals with physical constraints. These physical constraints can range from injuries or issues related to the lower body organs, spinal cord issues or neurological issues damaging communication of brain with other parts of the body. It should be noted that the use of the seating assembly 110 cannot be limited to individuals with above discussed apprehensions only and can be used by any individual irrespective of any physical constraints. Further, seating assembly 110 can be used by individuals of varying ages and body types. Most features of the seating assembly 110 can be adjustable and/or can be removably attached based on user preferences.

Continuing to refer to FIGS. 42A-42C, seating assembly 110 can be employed with a mobility device such that seating assembly 110 can engage a user controller 120 that can operate features of a mobility device/wheelchair and seating assembly 110. User controller (UC) 120 can also comprise structural features such as but not limited to, mounts, coupling junctions, etc., to engage with seating assembly 110 and subsequently with a mobility device (not shown). Structural features as discussed above and others, (not shown) can enable mounting of UC 120 with seating assembly 110 and/or with another component of mobility device/wheelchair. Positioning of UC 120, with respect to seat assembly 110, can be governed by degree of comfort with which user of seating assembly 110 can reach and operate UC 120. In some configurations, UC 120 can be mounted to seating assembly 110 through user control mount 125.

Continuing to refer to FIGS. 42A-42C, UC mount 125 can be constructed to have substantially ambidextrous parts, enabling cost-effective manufacture of UC mount 125. UC mount 125 can be manufactured based on user preference. Armrests 133A and 133B (FIG. 45A) can be engaged with the remainder of seating assembly 110 through corresponding armrest supports 135A and 135B. Each armrest support 135A, 135B can comprise a first region that can attach respective armrest 135A and 135B to a frame (not shown) of seating assembly 110 and a second region configured to receive at least one arm cushion thereupon. Arm cushion 131A can be committed to armrest 133A and arm cushion 131B can be dedicated to armrest 133B (FIG. 12A).

Referring to FIGS. 42B and 42C, second regions of arm supports 135A and 135B can further comprise corresponding base surfaces 137A (FIG. 42B) that can face away from arm cushions 131A and 131B. These base surfaces 137A (FIG. 42C) can provide receiving platforms to engage UC mount 125, the UC tilt mechanism. A coupling assembly 140 (FIG. 43A) can moveably attach UC mount 125 with the armrest base surfaces 137A. In some configurations, a plurality of coupling assemblies 140 (FIG. 43A) can be used to engage UC mount 125 with at least one of armrests 133A and/or 133B. Coupling assemblies 140 (FIG. 43A) can operate jointly or discretely from one another for achieving engagement. Moveably coupling UC mount 125 with armrest base surface 137A can allow UC 120 to be placed in more than one position, alternating towards vertical position 155A and towards horizontal position 155B. Each of the optional positions can allow the user to conveniently operate UC 120 and consequently operate the mobility device/wheelchair that can be operably coupled with seating assembly 110. Provision of optional positions for UC 120 can allow user to align with respect to a piece of furniture without being obstructed by a rigid position of UC 120. For example, the user of a mobility device such as a wheelchair with seating assembly 110 can sit against a table or desk maintaining or adjusting the distance between the wheelchair and the table without any obstruction from or damage to UC 120.

Referring now to FIGS. 42B-42C, locking apparatus 143 on UC mount 125 can allow UC 120 to be held in first position 150 (FIG. 42B) when a locking mechanism is deployed. In unlocked condition, UC mount 125 can be transitioned and held into second position 153 (FIG. 42C). Seat assembly 110 can include first position 150 (FIG. 42B) in which user control mount 125 is locked, and second position 153 (FIG. 42C) in which user control mount 125 is unlocked. In unlocked condition, the user of seating assembly 110 can adjust UC 120 into a preferred position by shifting UC mount 125 away from armrest 133A. Second position 153 (FIG. 42C) can be variable. In first position 150 (FIG. 42B) or when user mount 125 is operably coupled with armrest support 135A, UC mount 125 can be generally parallel to armrest 133A. While in second position 153 (FIG. 42C), UC mount 125 can form an angle with respect to armrest 133A, causing displacement of UC 120.

Referring now to FIG. 43A, coupling assembly 140 can operate in conjunction with locking mechanism 143 to engage UC mount 125 (FIG. 42B) with armrest 133A, and can enable UC mount 125 (FIG. 42B) to reversibly displace from first position 150 (FIG. 42B) to a second position 153 (FIG. 42C). Locking mechanism 143 can optionally comprise receptacle 147 (FIG. 43B) and lever 145. Receptacle

147 (FIG. 43B) can engage with base surface 137A of armrest 133A, and can jointly operate with lever 145 to engage shaft 121 (FIG. 42C) of UC mount 125 with base surface 137A. In a locked position. UC mount shaft 121 (FIG. 42C) can be operably coupled with base surface 137A such that a coupling segment of lever 145 can link with a complementing coupling part in receptacle 147 (FIG. 43B) and trap shaft 121 (FIG. 42C) there between. Receptacle 147 (FIG. 43B) can comprise primary receptacle 147A (FIG. 43B) and secondary receptacle 147B (FIG. 43B). Primary receptacle 147A (FIG. 43B), which can roughly match the cylindrical shape of telescoping tube 121A, can serve as a trench to receive, and provide lateral restraint for, shaft 121 (FIG. 42C) of UC mount 125 when it is in first position/locked position 150 (FIG. 42B). Lever 145 can be operably engaged with shaft 121 (FIG. 42C) and can comprise bar segment 144 (FIG. 42B) that can serve as a coupling segment, and can be trapped into secondary receptacle 147B (FIG. 43B) when UC mount 125 is in a locked position. The user can trap or release bar segment 144 (FIG. 42B) from secondary receptacle 147B (FIG. 43B) by operating lever 145 (FIG. 43B) that can include a paddle configured to be operated by a user. While in first position 150 (FIG. 42B) or locked position, lever 145 can be angled with respect to shaft 121 (FIG. 42C) of mount 125, such that bar segment 144 (FIG. 42B) is confined in secondary receptacle 147B (FIG. 43B). In second position 153 (FIG. 42C), lever 145 can form a renewed angle with respect to shaft 121 (FIG. 42C), releasing bar segment 144 (FIG. 42B) from secondary receptacle 147B (FIG. 42C). The coupling can allow a user to unlock and displace UC 120 (FIG. 42B) at a desirable angle with respect to armrest 133A (FIG. 43A). In some configurations, shaft 121 (FIG. 42C) can include a telescopic conduit such that a user can alter the length of shaft 121 (FIG. 42C) as per the length of the user's arm. In some configurations, telescoping conduit can be secured without tools, for example, but not limited to, securing with wing nuts and/or thumb screws. In some configurations, shaft 121 (FIG. 42C) can include a multi-part component. In some configurations, shaft 121 (FIG. 42C) can include a single, continuous elongation. In some configurations, shaft 121 can include a filler such as, for example, a textured tape.

Referring now specifically to FIGS. 43A and 43B, coupling assembly 140 can engage at least one end of UC mount 125 with armrest 133A. A pivoting assembly 160 and bracket 161 can form coupling assembly 140 such that bracket 161 can enable engagement between base 137A and pivoting assembly 160. Bracket 161 can be rigidly fastened with base surface 137A and pivoting assembly 160 engages therewith such that rotary portion (not shown) can pivot away and towards base surface 137A. Bracket 161 can further comprise cylindrical protrusion that can serve as roller 162 (FIG. 44D) around which pivoting assembly 160 can be operatively housed. Pivoting assembly 160 can engage with bracket 161 by receiving roller 162 (FIG. 44D) into a roller space 163. Coupling and frictional interaction between roller 162 (FIG. 44D) and remaining components of pivoting assembly 160 have been discussed in greater detail in later part of this specification. Bracket 161 can be affixed to base 137A through fastening agents such as, but not limited to, screws, bolts, pins, etc., fastening components such as those enlisted above and others. Similar fastening agents can be employed for receptacle 147 (FIG. 43B) and lever 145 of locking mechanism 143. A user control bed 123 can be a part of UC mount 125 such that bed 123 can permanently couple with shaft 121. User control 125 can be held on the UC bed 123 through fastening components such as, but not limited to, screws and bolts affixed therewith. A base (not shown) of the user control 120 and/or UC bed 123 can provide a plurality of fastening junctions that can allow a user to orient UC 120 as required. Displacement of UC mount shaft 121 can cause subsequent displacement of UC bed 123 and hence UC 120.

Figure 44A:
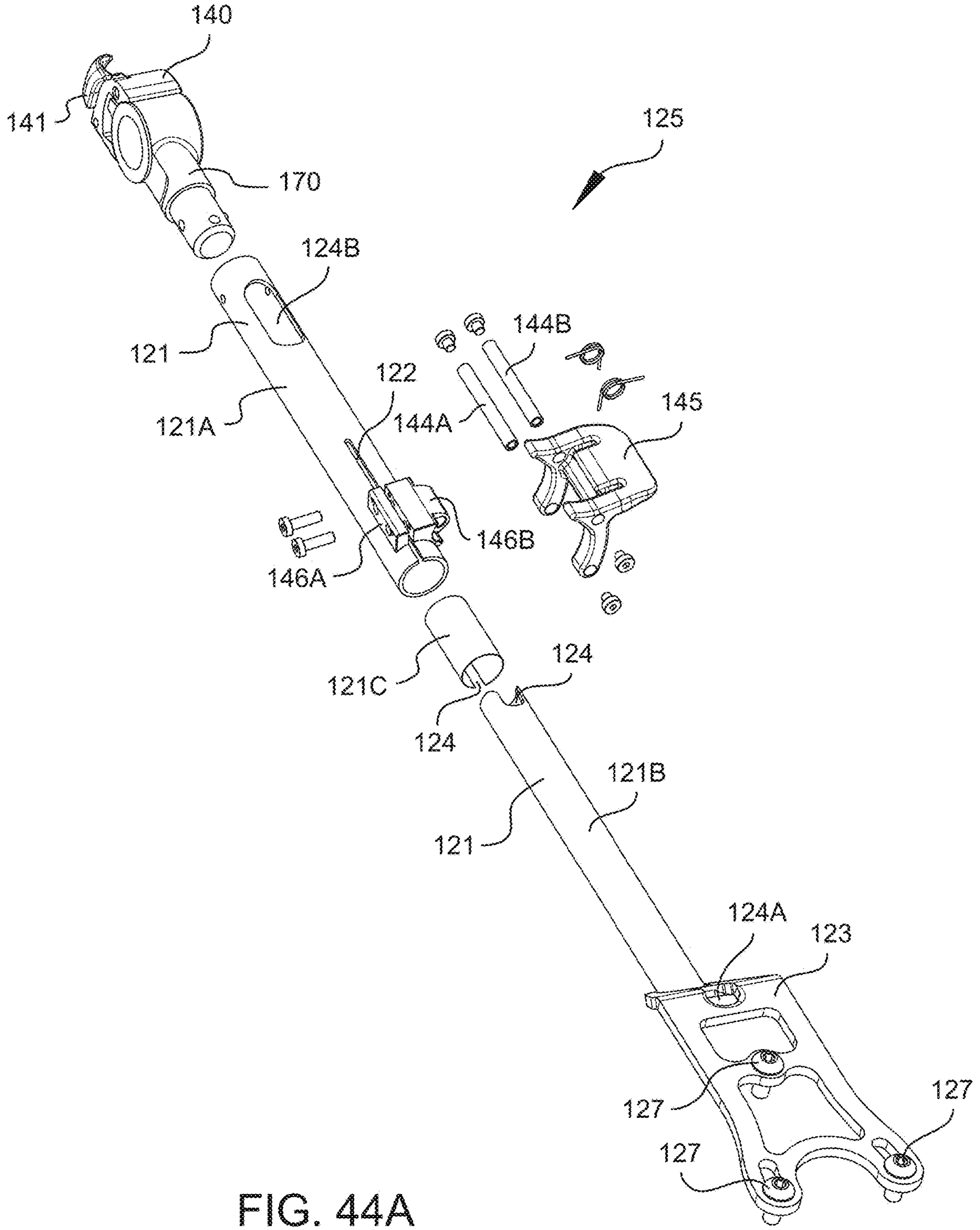

Referring now to FIG. 44A, UC mount 125 can comprise a shaft 121 operably coupled with UC bed 123 on the distal end of shaft 121, and pivoting assembly 140 on the proximal end of shaft 121. Fasteners 127 can operably couple UC 120 (FIG. 42A) with UC mount bed 123. Any kind and shape of user controller with fastening points the approximate locates of fasteners 127 can be attached to UC mount bed 123. Shaft 121 can include a multi-part component. Shaft 121 of can include first tube 121A and a second tube 121B. Second tube 121B can at least partially nest inside first tube 121A and can cooperatively, with first tube 121A, provide a telescopic elongation to adjust the combined length of shaft 121. In some configurations, first tube 121A can possess a diameter larger than the diameter of second tube 121B to achieve nesting and telescopic length adjustment. Shaft segments 121A and 121B can provide a roll degree of freedom therewith, providing additional positioning options to user. Shaft segment 121A can comprise a longitudinal incision 122 to receive shaft segment 121B of varying diameters. Incision 122 can further allow first shaft segment 121A to acceptably deform when a second shaft segment 121B is received therein. In some configurations, shaft 121 can include rigid or incompressible spacer 121C to ensure compact fitting between first shaft segment 121A and second shaft segment 121B. In some configurations, shaft 121 can include no spacer or can be a single-piece, continuous device. When UC mount 125 is in position 150 (FIG. 42B), bumpers (not shown) formed by a cavity within receptacle 147, extending into the cylindrical cutout of second lever segment 147A can press against first shaft segment 121A, creating a compression that can inhibit possible unwanted mechanical movement.

Continuing to refer to FIG. 44A, shaft 121 and shaft segments 121A, 121B, and 121C can jointly define track 124 in shaft 121. Track 124 can house cables or power and data cords (not shown) between UC 120 (FIG. 45A) and a mobility device. First aperture 124A, disposed on a distal end of shaft 121 can serve an entry gate for receiving cables or cords from UC 120 (FIG. 45A) that can be attached to UC mount bed 123. Cables and cords can extend along track 124 and can exit from a second aperture 124B, that can be disposed on proximal end of shaft 121. Apertures 124A and 124B can further facilitate swapping of cable unions, as required. Exiting cables and cords can be engaged with hanger 141 that can be optionally integrated with coupling assembly 140. The layout for receiving cables can enable cable management related to the mobility device.

Continuing to refer to FIG. 44A, incision 122 on first shaft segment 121 can be pinched by constricting blocks 146A and 146B. Blocks 146A and 146B can be optionally disposed on either sides of incision 122 and can be constricted together through fastening features such as, but not limited to screws, pins, and bolts. In some configurations, blocks 146A, 146B can be welded onto shaft segment 121A as a single block. Shaft segment 121A can be slitted to provide incision 122 and uniformly divided blocks 146A and 146B on either sides of incision 122. At least one of divided blocks 146A and/or 146B can further comprise an attachment means to engage lever 145 therewith. Divided blocks 146A. 146B and lever 145 can together, at least partly, form locking mechanism 143 (FIG. 45A). Lever 145 can serve as user operated portion of locking mechanism 143 (FIG. 45A) and receptacle 147 (FIG. 42C) can jointly achieve locking and releasing of shaft 121.

Continuing to refer to FIG. 44A, lever 145 can comprise two segments. First lever segment 144A can jointly operate with receptacle 147 (FIG. 42C) to trap and release shaft 121. In some configurations, first lever segment 144A can include a bar that can be held in primary receptacle 147B (FIG. 42C). Second lever segment 147B (FIG. 42C) can serve to attach lever 145 with at least one of divided blocks 146A and/or 146B to primarily engage lever 145 with shaft 121. In some configurations, the engagement can optionally include a hinge connection to allow desirable operation of lever 145. In some configurations, swiveling motion of lever 145 can be achieved by force application from a user operation on lever 145, and can engage or release first lever segment 144A with primary receptacle 147B (FIG. 42C), causing shaft 121 to be engaged or disengaged from secondary receptacle 147A (FIG. 42C) of receptacle 147 (FIG. 42C). The swivel motion can be spring-loaded.

Figure 44B:
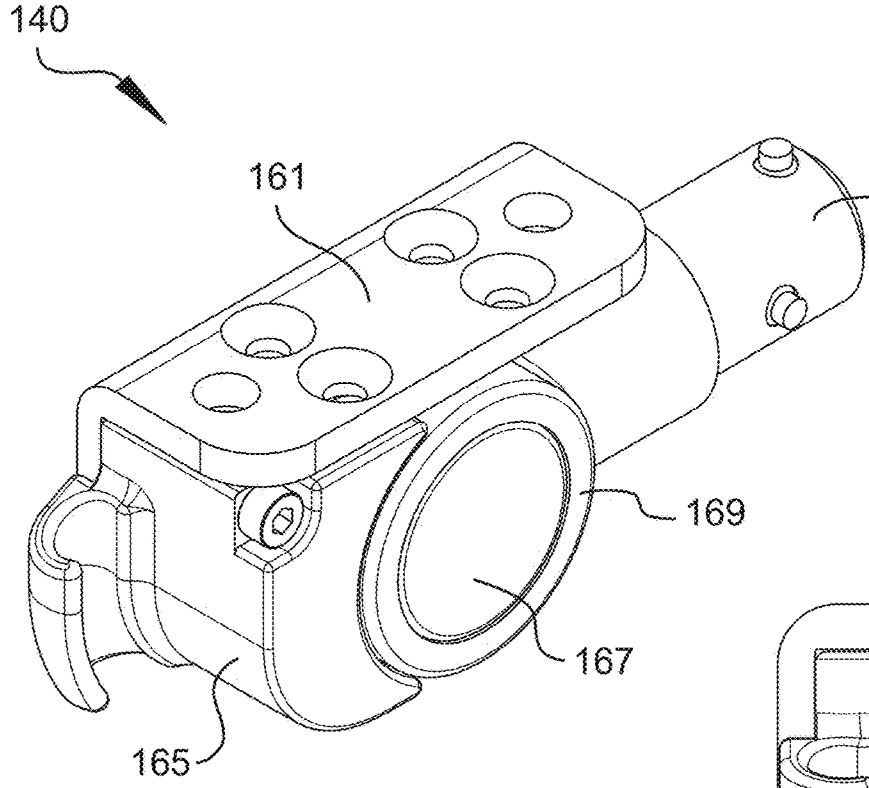
Figure 44B:
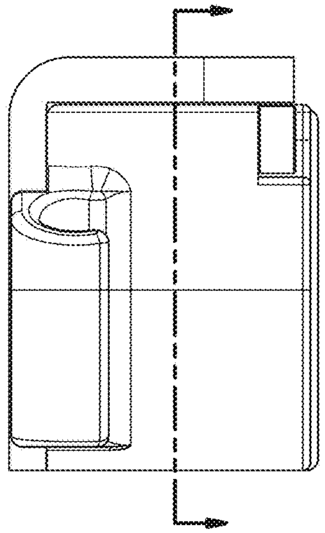
Figure 44C:
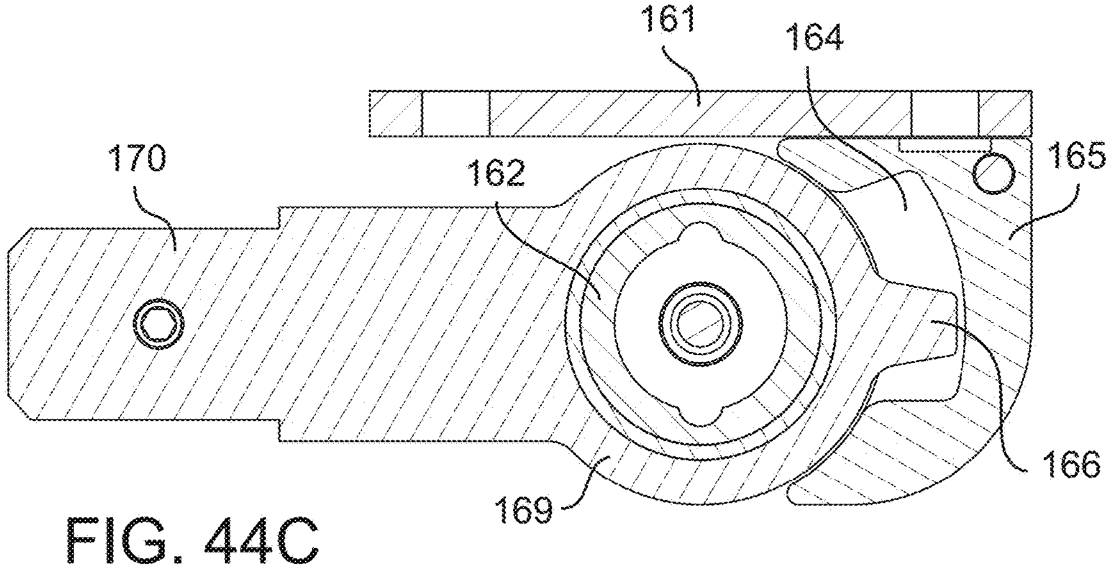
Figure 44D:
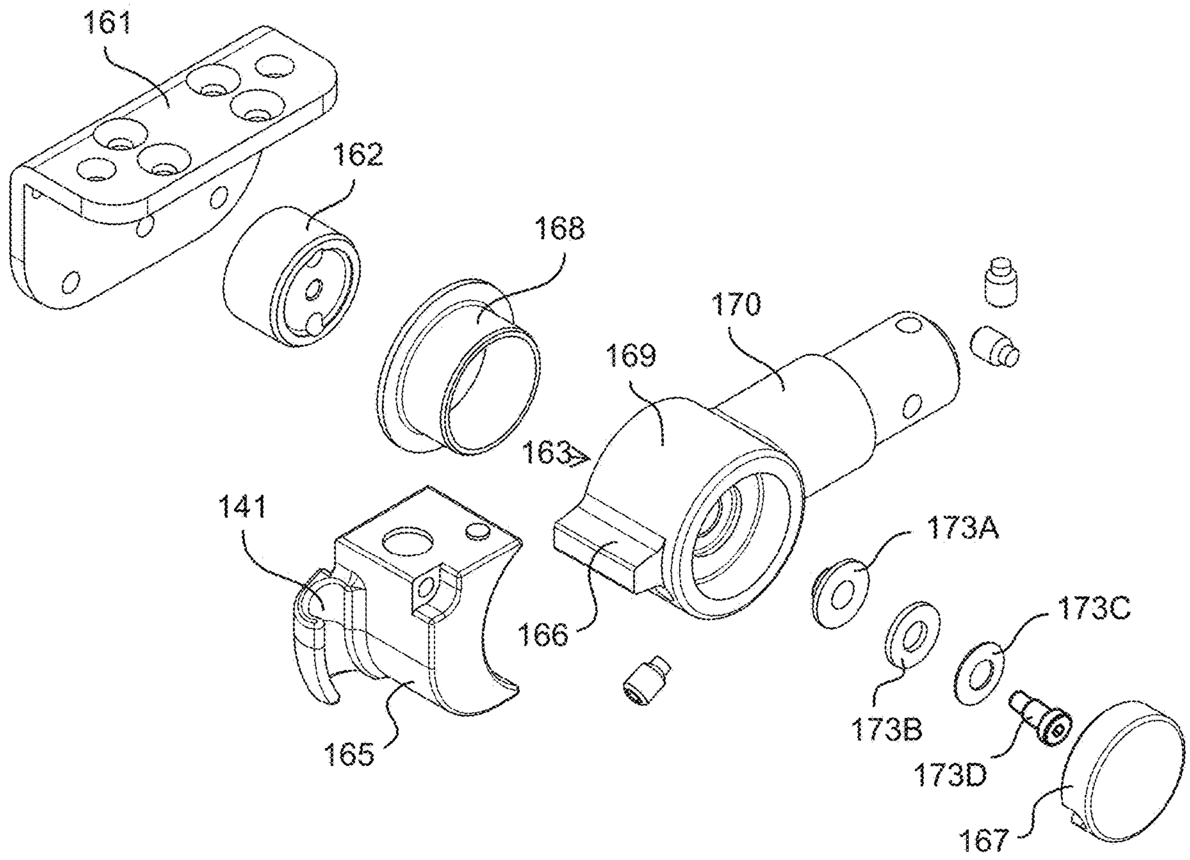

Referring now to FIGS. 44B-44D, pivoting assembly 140 (FIG. 44B) can be optionally positioned at the proximal end of shaft 121, allowing operable engagement between UC mount 120 (FIG. 42A) and base 137A (FIG. 42C) belonging to one of armrests 133A or 133B (FIG. 45A). Bracket 161 can rigidly engage with armrest base 137A (FIG. 42C) and can further couple with a housing 165 therewith. Bracket 161 can be integrated with roller 162 (FIG. 44D) such that roller 162 (FIG. 44D) can receive other components of rotary structure 169. In some configurations, bracket 161 and roller 162 (FIG. 44D) can be a single, continuous component. Rotary structure 169 can receive roller 162 (FIG. 44D) in a roller space 163 (FIG. 44D). At least one bearing and/or bushing such as but not limited to, flanged bushing 168 (FIG. 44D) can be employed to provide a thrust bearing between bracket 161 and rotary structure 169. In some configurations, flanged bushing 168 (FIG. 44D) can be replaced by or supplemented with any other component/s that can enable avoidance of contact between similar materials of bracket 161 and rotary structure 169. Flanged bushing 168 (FIG. 44D) can serve as a radial bearing in rotary structure 169 (FIG. 44D) for roller 162 (FIG. 44D). The radial compression between the surfaces of roller space 163 (FIG. 44D), flanged bushing 168 (FIG. 44D) and roller 162 (FIG. 44D) can largely govern required friction to allow pivoting motion of pivoting assembly 160 (FIG. 43A).

Referring to FIG. 44D, in company with receiving roller 162, rotary structure 169 can also operably engage with housing 165. Rotary structure 169 can be composed of a cylindrical portion disposed in between a radial projection 166 and an elongated portion 170. Projection 166 can partially oscillate in pocket 164 (FIG. 44C) of housing 165 such that its oscillation can transition into a pivoting motion of rotary structure 169 and consequently pivot elongation 170. At least a part of the periphery of housing 165 can serve as hard-stops for regulating oscillatory motion of projection 166. In some configurations, hard stop elements can be provided in housing 165 and, in some configurations, hard stop elements can be distinct from the body of housing 165. In some configurations, housing 165 can limit travel to 30°. In some configurations, housing 165 can be manufactured by machining or printing. In some configurations, pocket 164 (FIG. 44C) of housing 165 can comprise one or more shim structures that can be removably retained therein. As a result, a variable hard stop can be provided for oscillatory motion of projection 166. Altering the motion of projection 166 can impact the angular adjustment of UC mount 120 (FIG. 42A) with respect to shaft 121 (FIG. 44A). Shaft 121 (FIG. 44A) can couple with pivoting assembly 140 (FIG. 44B) by at least partially retaining elongation 170 in track 124 of hollow shaft 121 (FIG. 44A).

Continuing to refer to FIG. 44D, a plurality of washers or like components such as but not limited to, compression springs, can be employed in rotary structure 169 to provide axial pre-load between rotary structure 169 and bracket 161 through flanged bushing 168. The pre-load can create additional friction. In some configurations, bushing 173A, flat washer 173B and Belleville washer 173C, held together by, for example, shoulder bolt 173D can achieve the pre-load. The number and type of washers and/or bushings can be varied based on the extent of pre-load desired. End cap 167 can be affixed to rotary structure 169 to enclose rotary components. Materials and dimensions of the sub-components of rotary structure 169 can be determined based on a desired friction there between such that UC mount 125 (FIG. 44A) can be pivoted with a desired force application and can halt at a desirable second position 153 (FIG. 42C). Additional fastening elements can be employed to ensure a uniform pivoting of most sub-components of rotary structure 169. In some configurations, rotary structure 169 can be a solid piece, without roller pocket 163 and/or roller 162.

Referring now to FIG. 45A, third configuration seating assembly 110 can comprise headrest 113 that can be disposed on backrest 130. Headrest 113 can be engaged with backrest 130 through discrete attachments 114 that can be completely dedicated to this coupling. Attachment 114 can allow user to alter position of headrest 113 with respect to backrest 130. As a result, users of varying heights can adjust headrest 113 as per personal convenience. In some configurations, rails 109 (FIG. 42A) can serve as pairing means for accepting headrest 113 with backrest 130. In some configurations, headrest 113 can be rigidly fastened to rails 109 (FIG. 42A) or can be adjustably fastened to rails 109 (FIG. 42A). In case of an adjustable attachment between headrest 113 and rails 109 (FIG. 42A), a user can alter the position of headrest 113 with respect to backrest 130 and the desired height of attendant handle 115. A plurality of attachment mechanisms can be employed for adjustably engaging headrest 113 with rails 109 (FIG. 42A). At least one attachment mechanism can cause headrest 113 to slide along length of rails 109 (FIG. 42A). Headrest 113 can further be composed of cushion 113A and base 113B. Attachments 114 and/or rails 109 (FIG. 42A) can be partially or completely captured between cushion 113A and base 113B to ensure the attachments and/or rails 109 (FIG. 42A) do not interfere when a user's head rests on headrest 113. In some configurations, headrest 113 can be removably attached with attachment 114 and/or rails 109 (FIG. 42A). As a result, user can enjoy an option of using seating assembly 110 without headrest 113, when desired.

Referring now to FIGS. 45B-45C, attendant handle 115 can be housed in backrest 130. Handle 115 can serve as an auxiliary feature to maneuver seating assembly 110 (FIG. 45A) by an individual other than user of seat assembly 110 (FIG. 45A). Handle 115 is also referred to as an attendant handle since it can be used by an attendant assisting a user of seat assembly 110 (FIG. 45A) during occasions that demand additional and/or external support to supplement movement capability of a wheelchair or mobility device containing seating assembly 110 (FIG. 45A). In some configurations, an attendant can use handle 115 when a user of seat assembly 110 (FIG. 45A) is climbing stairs in a wheelchair or any mobility device that can contain seat assembly 110 (FIG. 45A). In some configurations, when a user is operating a wheelchair or mobility device over a terrain that offers a higher friction against wheels of the wheelchair or mobility device, handle 115 can be used. Attendant handle, such as, but not limited to, attendant handle 115 can serve as a convenient gripping and force bearing component to maneuver a wheelchair or mobility device on which seat assembly 110 (FIG. 45A) may be affixed.

Figure 46A:
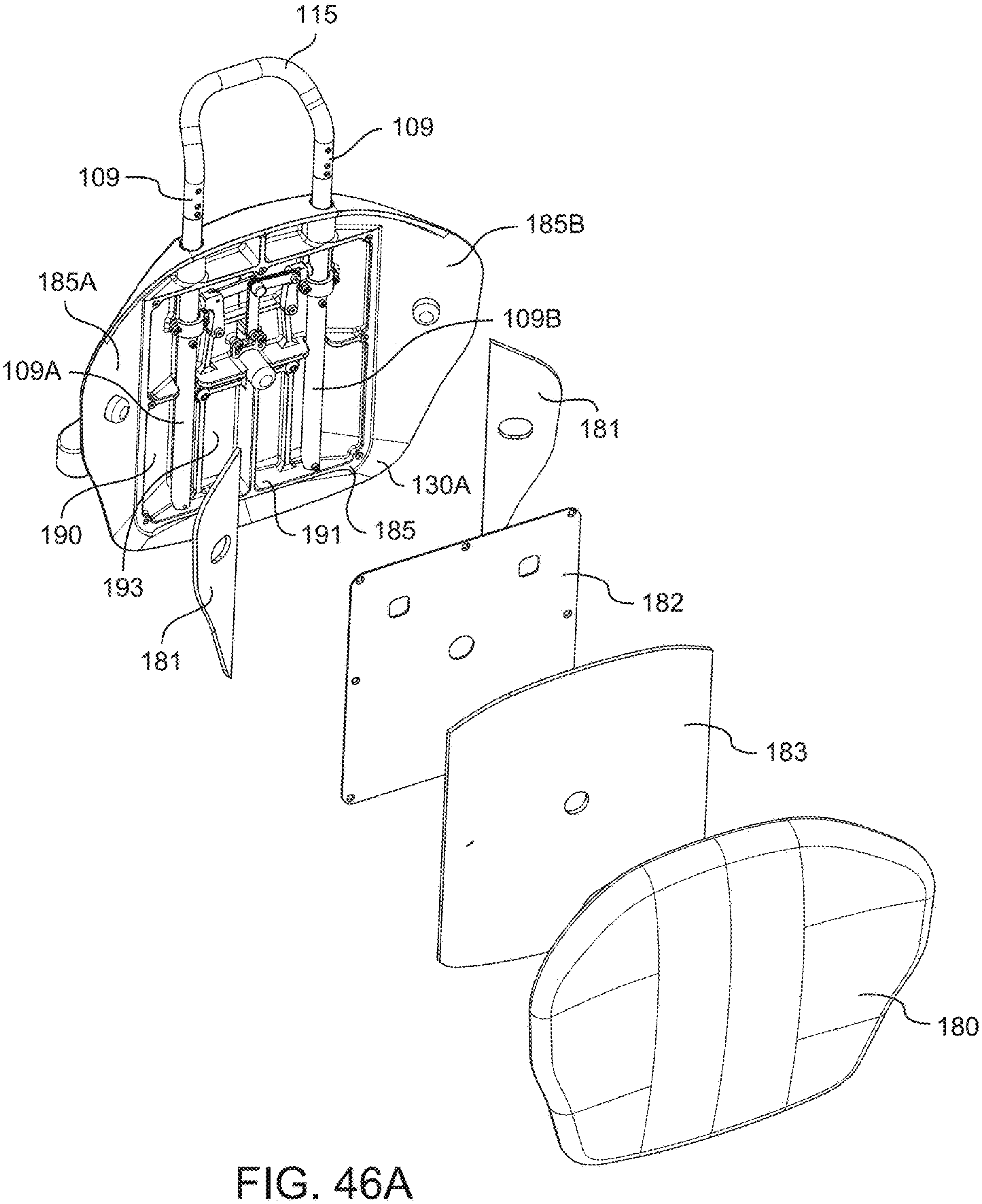

Continuing to refer to FIGS. 45B-45C, handle rails 109 can moveably engage attendant handle 115 with backrest 130. Handle 115 can travel away from and towards backrest 130 through handle rails 109. The travelling motion of handle rails 109 can occur along the length of rail slots or pathways 109A and 109B that can nest in backrest 130. An attendant can adjust the length of attendant handle 115, as per preference and/or required by any circumstances. Backrest 130 can further comprise a front surface 130A (FIG. 46A) and an opposing back surface 130B. Front surface 130A (FIG. 46A) can provide a mounting surface for cushion surface 180 that can cover or partially cover front surface 130A (FIG. 46A). A plurality of engagement methods can be employed to attach cushion surface 180 to front surface 130A (FIG. 46A). In some configurations, cushion surface 180 can be coupled with front surface 130A (FIG. 46A) through a fastener such as, but not limited to, a screw or a bolt. In some configurations, cushion surface 180 can be coupled with front surface 130A (FIG. 46A) through VELCRO® strips provided on the opposing side of cushion surface 180 that can mate with corresponding VELCRO® strips disposed on front surface 130A (FIG. 46A). The engagement methods can allow a user of seat assembly 110 (FIG. 45A) to conveniently switch cushion surface 180 as per preference.

Referring to FIG. 45C, back surface 130B of backrest 130 can comprise latch 200 to operate attendant handle 115. Latch 200 can further comprise flange 205 that can participate in operating and locking the mechanism, optionally disposed in the interior of front surface 130A (FIG. 46A) of backrest 130 (FIG. 45A). Raised supports 202, in conjunction with frame portion 210, can retain latch 200 against back surface 130B of backrest 130. Raised supports 202 can be integral with back surface 130B and can provide a first pair of apertures 212A (FIG. 46D). In some configurations, raised supports 202 can be molded with back surface 130B during manufacture. In some configurations, raised supports 202 can be welded to backrest 130 (FIG. 45A). Raised supports 202, latch 200 and frame 210 can provide coupling features that can further mutually align to engage latch 200 there between.

Referring now to FIG. 46A, front surface 130A can include a plurality of cover layers that can enclose an attendant handle operating assembly 190. Casing 191 can be integrated with or attached to backrest 130 (FIG. 45A), and can house attendant handle operating assembly 190. In some configurations, backrest 130 (FIG. 45A) can be molded with casing 191 and a plurality of subframes 193 can be provided therein. The plurality of subframes 193 can receive corresponding components that can make up attendant handle operating assembly 190. Securing layers 181, 182 and 183 can be positioned between attendant handle operating assembly casing 191 and cushion surface 180. Layers 181, 182, 183 can ensure a reliable covering of attendant handle operating mechanism 190 such that mechanism 190 can function without external intervention that can obstruct operating of assembly 190. A combination of cover layers 181, 182 and 183 can further serve as an upholstery or padding to receive cushion surface 180. A plurality of combinations can be used to cover operating assembly 190 and a plurality of permutations and combinations of these layers can serve as upholstery for cushioning surface. The combinations can include, but are not limited to, a varying number of cover layers, varying material/s for cover layer and similar alternations. Additionally, cover layers 181, 182, 183 can be fastened using a number of fasteners such as, but not limited to, screws, bolts, and pins. Cover layers can be positioned such that fasteners or engaging agents do not interfere with handle operating assembly 190. In some configurations, casing 191 can be embossed into inner face 185, allowing components of assembly 190 to be nested therein. Platforms or surfaces 185A and 185B can receive cover layers 181 can assist in further partially providing upholstery for layers 182 and 183 and cushion surface 180. A desirable spaced enclosure can be formed through casing 191 and cover layers 181, 182, 183, that can retain operating assembly 190, and can allow unobstructed functioning of components of operating assembly 190.

Continuing to refer to FIG. 46A, covering layers 181, 182 and 183 of present teachings can be a single-part or a multi-part component. A first or immediate covering layer 181 that can face operating assembly 190, can optionally be a two or more-piece component such that each component piece engages with an area of inner face 185 of backrest 130 (FIG. 45A). In some configurations, the engagement can occur at an area other than the area occupied by attendant handle operating assembly 190. In some configurations, inner surface 185 can be divided into two regions. First region 185A can be occupied by attendant handle operating mechanism assembly 190, and second region 185B can partially or completely accept cover layers 181, 182 and 183 to engage with surface 185. Region 185A can be centrally located on surface 185, and region 185B can be positioned peripherally and can engage layers 182 and 183 therewith. Each piece of first layer 181 can mate to entirely cover casing 191. Covering layers such as, but not limited to, cover layers 181 and 183, can affix thereupon to provide a secure cover for casing 191. A plurality of fastening agents such as, but not limited to, screws, bolts, and pins, can be used to combine covering layers 181, 182 and 183.

Figure 46B:
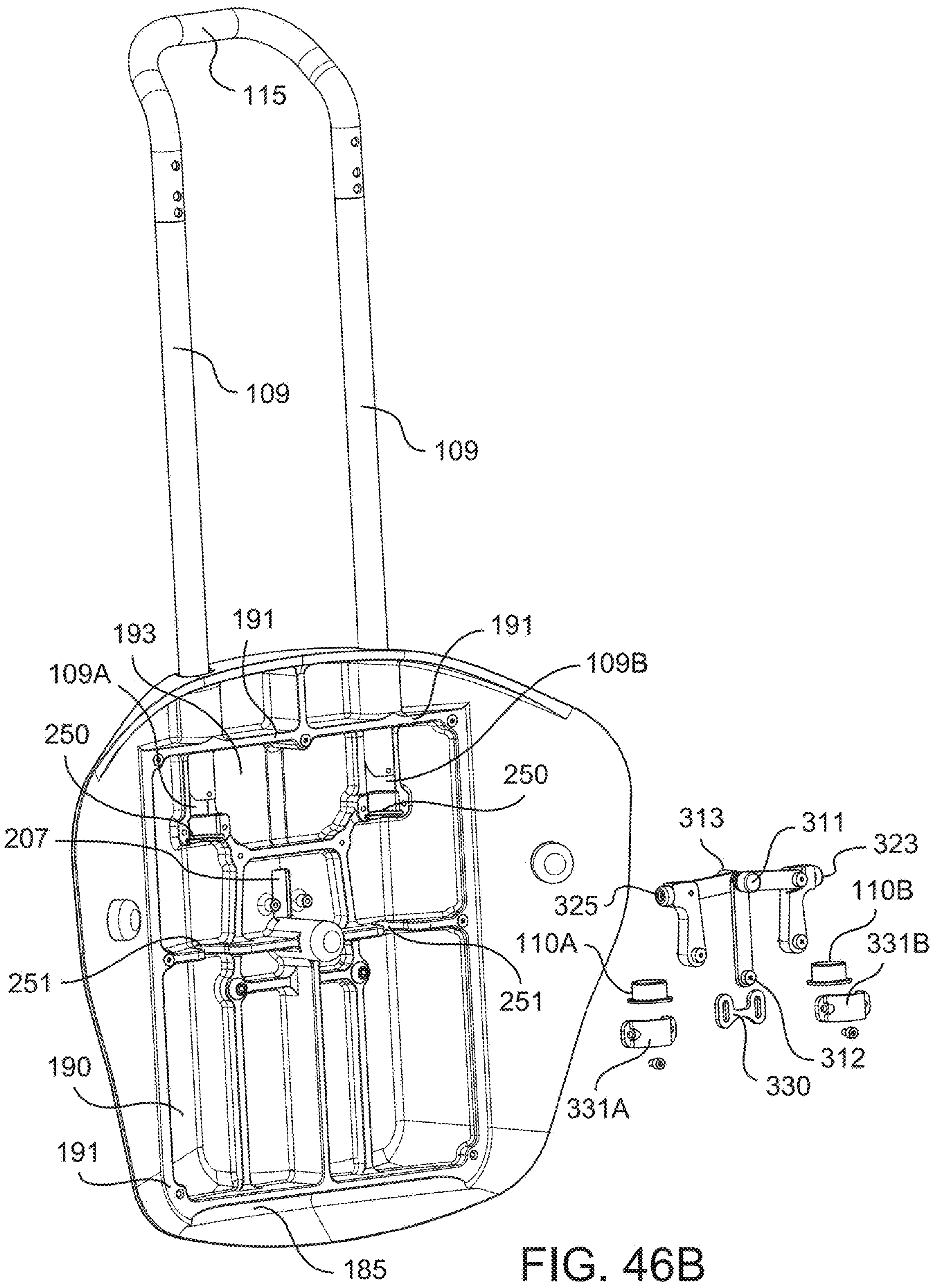

Referring now to FIG. 46B, inner face 185 of backrest 130 can comprise an optionally embossed or pressed case 191 that can house attendant handle operating mechanism 190. A plurality of subframes 193 can be provided in case 191. The plurality of subframes 193 can serve as receptacles for moving parts that can jointly retain, lock, release and allow rails 109 along substantially vertical pathways or slots 109A and 109B. Subframes 193 can also serve as receptacles and/or fastening junctions for moving components housed therein. One purpose of these moving components can be to trap and release rails 109 by operation of latch 200 (FIG. 45B). Attendant handle operating assembly 190 can comprise at least one focal point 311 that can serve as an engagement junction for most moving components of assembly 190. Adjustable joint 312 can optionally engage a second engagement point of moving components of assembly 190 such that adjustable joint 312 can be restricted to travel at variable hard stop 330. In some configurations, operating assembly 190 can comprise a plurality of beams or bars that can mate at focal point 311.

Continuing to refer to FIG. 46B, case 191 can comprise pathways 109A and 109B for rails 109 of attendant handle 115. Rails 109 can be inserted through a plurality of aligned apertures in backrest 130 (FIG. 45A) to receive and retain rails 109. Subframes 193 can further define edges 250 and 251 along each pathway 109A and 109B. Edges 250 and 251 can be sized and shaped to at least partially rim received rails 109. Edges 250 and 251 can serve at alignment junctions to ensure that rails 109 do not derail pathways 109A and 109B. Attachment features in the form of cuffs 110A and 110B can be held by edges 250 and/or 251. Cuffs 110A and 110B can be retained in edges 250 and/or 251 and can subsequently receive rails 109 therein. In some configurations, cuffs 110A and 110B can serve as bushings to provide a smooth sliding surface for rails 109. Traps 331A and 331B can retain cuffs 110A and 110B to enable positioning of rails 109. Edges 250 and 251 can be dimensioned to receive rails 109 along with retaining members 110A, 110B and traps 331A, 331B and any other retaining members, such as, but not limited to, bushings and washers. Following alignment in pathways 109A and 109B, the disposition of moving components of operating assembly 190 can enable capturing and releasing rails 109 in pathways 109A and 109B.

Figure 46C:
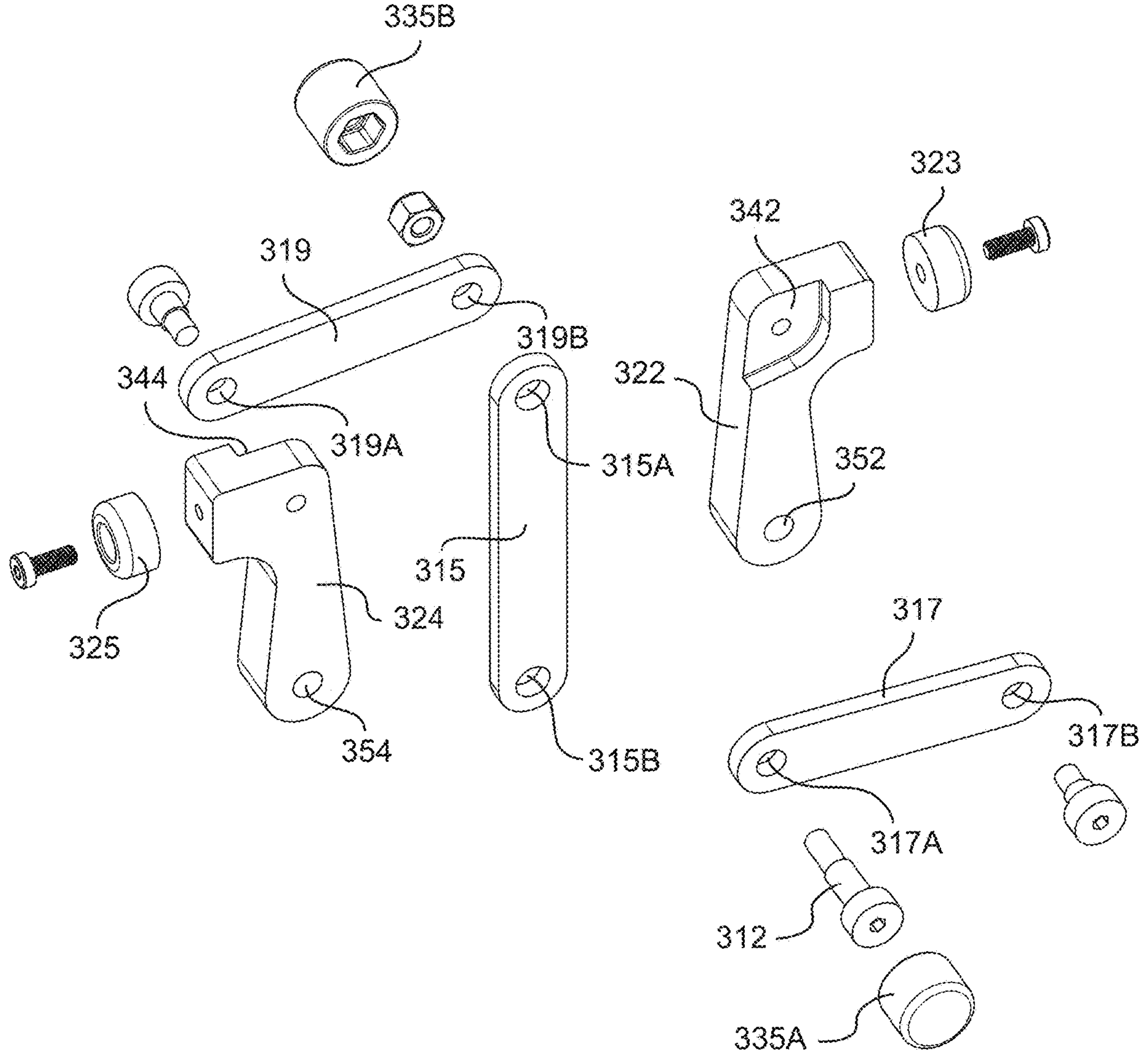
Figure 46D:
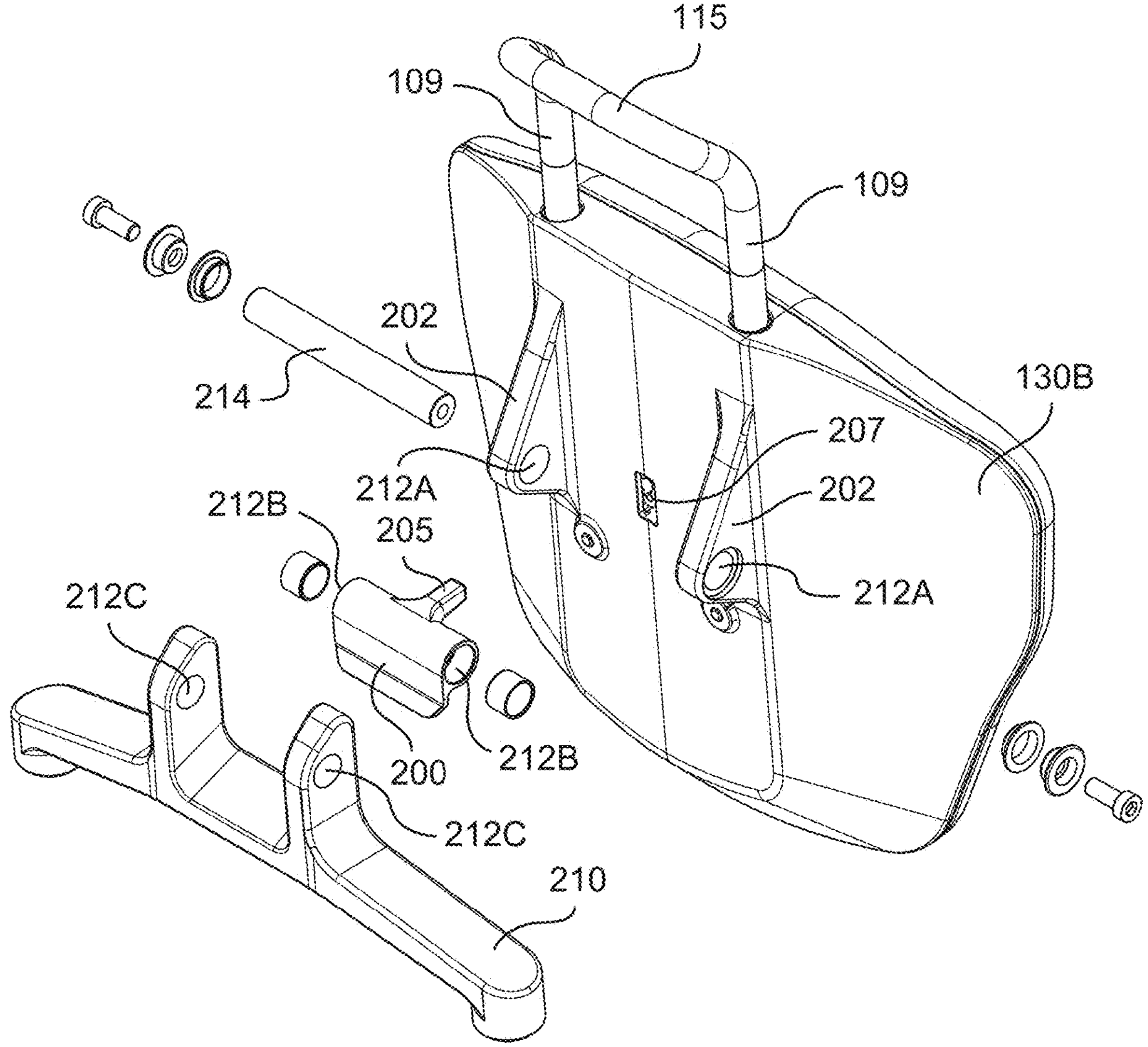

Referring now to FIG. 46C, stoppers 322, 324 can commit to each of rails 109 (FIG. 46B). Stoppers 322, 324 can couple with displaceable components of operating assembly 190 (FIG. 46B) such that operation of these components can cause stoppers 322, 324 to halt and maintain rails 109 at a desirable junction in corresponding pathways 109A and 109B (FIG. 46B). In some configurations, bumpers 323, 325 can couple with stoppers 322, 324 and can compress against rails 109 to halt and maintain rails 109 in their halted position. It should be noted that bumpers 323, 325 (FIG. 46C) can be sized in varying geometries such that chosen geometry can suffice to engage with stopper 322 on one end, and compress against rails 109 (FIG. 46B) on another. A plurality of similar or dissimilar sized bumpers 323, 325 can be employed with stoppers 322 and 324. For achieving a locked position, displacing components of operating assembly 190 (FIG. 46B) can thrust stoppers 322 towards rails 109 (FIG. 46B) and for releasing or in an unlocked position, stoppers 322, 324 can be retracted away from rails 109 (FIG. 46B). In some configurations, a compression spring (not shown) can be held between stoppers 322 and 324 such that on being retracted from rails 109 (FIG. 46B), stoppers 322 and 324 can be maintained at a known distance there between. Variable hard stop 330 (FIG. 466) can be disposed at a junction in case 191 (FIG. 46B) such that displaceable components of assembly 190 (FIG. 46B) can be refrained from travelling beyond hard stop 330 (FIG. 46B). Geometry of hard stop 330 (FIG. 46B) can be constructed to allow variable positioning of hard stop 330 (FIG. 46B).

Continuing to refer primarily to FIG. 46C, displaceable components of operating assembly 190 (FIG. 46B) can comprise central beam 315 with at least two engagement points 315A and 315B. One of engagement points 315A or 315B can engage at focal point 311 (FIG. 46B) and another of engagement points can be affixed at flexible point 312. A plurality of side beams such as but not limited to a first set of side beams 317 and a second set of side beams 319 can engage with central beam 315. Each set of side beam/s 317 and 319 can comprise at least two sets of corresponding engagement points each, 317A, 317B, 319A, and 319B. At least one of engagement points belonging to each side beam 317 and 319 can couple with first engagement point 315A of central beam 315 and can optionally unite at focal point 311. First set of side beams 317 can extend substantially perpendicular to central beam 315 and can further engage with at least one of stoppers 322 through engagement point 317B, for example. Second set of side beams 319 can engage with central beam 315 at focal point 311 and can extend generally perpendicular to central beam 315. The engagement can be achieved through engagement point 319B or engagement point 319A, for example, and can couple second set of side beam/s 319 with second stopper 322.

Continuing to refer primarily to FIG. 46C, at least one stopper 322, 324 can commit to one of rails 109A (FIG. 46B) and/or 109B (FIG. 46B). First set of side beams 317 can engage with first stopper 322 through second engagement point 317B of first set of side beams 317. Second stopper 324 can engage with second set of side beams 319 through engagement points 319A. Each stopper 322, 324 can further comprise coupling surfaces 342 and 344, respectively. Coupling surfaces 342 and 344 can receive and retain engagement points 317B and 319A, respectively. Fastening of side beams 317, 319 with respective stoppers 322, 324 can be achieved through fastening agents such as, but not limited to, screws, bolts, and pins. Stoppers 322 and 324 can engage with casing and/or enclosure 191 (FIG. 46B) through fasteners at coupling junctions 352 and 354 of stoppers 322 and 324. Fastening of stoppers 322 and 324 with casing or enclosure 191 (FIG. 46B) can enable stoppers 322 and 324 to retain a desired degree of movement for when handle operating assembly 190 (FIG. 46B) transitions from a locked position to an unlocked position and vice versa. In some configurations, stopper 322 and/or 324 can retain a freedom of pivoting around coupling junctions 352 and 354.

Referring primarily to FIG. 46D, pre-determined disposition of moving components of operating assembly 190 (FIG. 46B) can contribute in achieving locking and unlocking of rails 109 (FIG. 46B) through operating assembly 190 (FIG. 46B). Bridging orifice 207 can allow flange 205 to pass there through and receive a fastening agent such as, but not limited to, shoulder screw 312 (FIG. 46C) which can further couple with engagement points of central beam 315 (FIG. 46C) and side beams 317, 319. Shoulder screw 312 (FIG. 46C) can engage with flange 205 across bridging orifice 207 and can receive second set of side beam 319 (FIG. 46C), central beam 315 (FIG. 46C) and first set of side beam 317 (FIG. 46C) such that raising and lowering of focal pin 313 (FIG. 46B) can subsequently raise and lower engagement assembly of side beams 317, 319 (FIG. 46C) and central beam 315. Above discussed engagement can further trap central beam 315 (FIG. 46B) between first set of side beam/s 317 and second set of side beam/s 319 (FIG. 46B).

Continuing to refer to FIG. 46D, back surface 130B of backrest 130 (FIG. 45A) can retain latch 200. Attachment of latch 200 can be achieved by engaging bar 214 through first set of apertures 212A that can exist on raised features 202 on backrest 130 (FIG. 45A), second set of apertures or latch apertures 212B, and third set of apertures 212C. The engagement can enable latch 200 to retain a rotary motion around bar 214. User-generated rotation of latch 200 can generate a linear force allowing flange 205 to travel along the length of bridging orifice 207, and can enable linear motion of flexible pin 313 (FIG. 46B) that can enable a user to actuate assembly 190 (FIG. 46B).

Figure 47A:
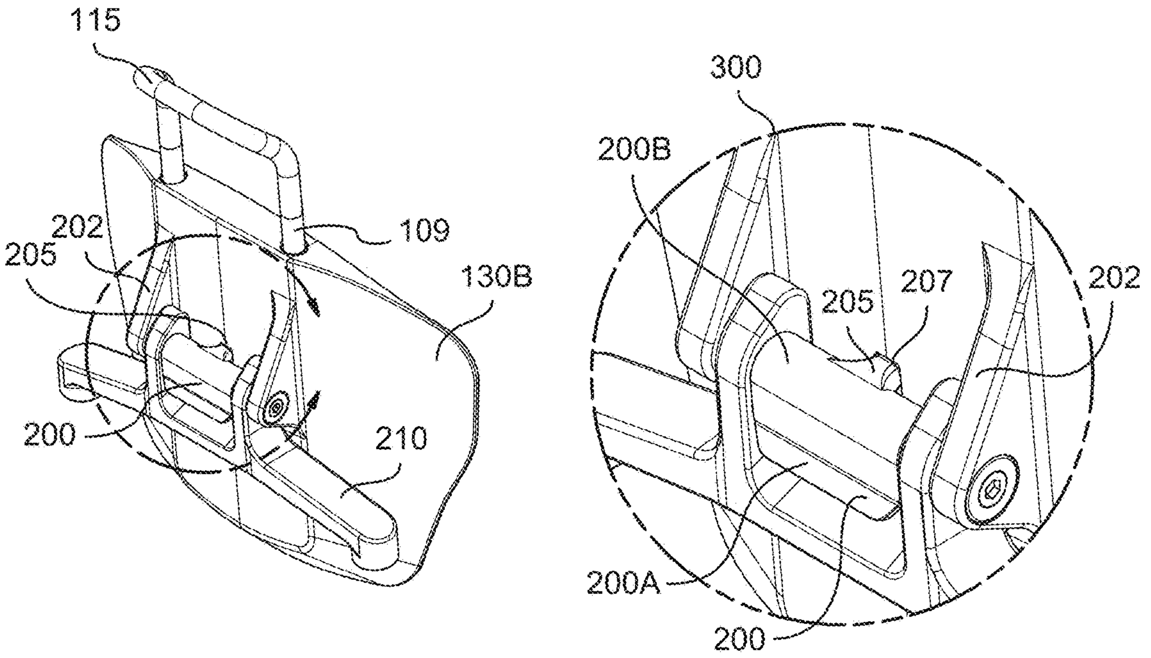
Figure 47B:
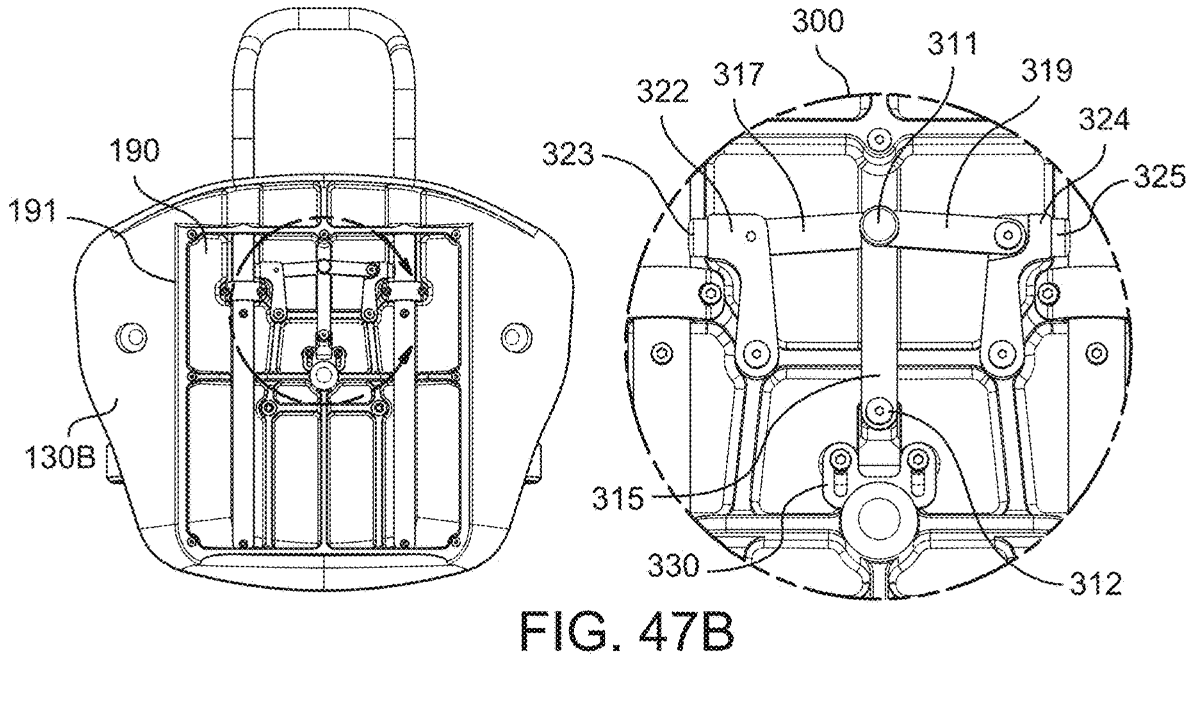
Figure 47C:
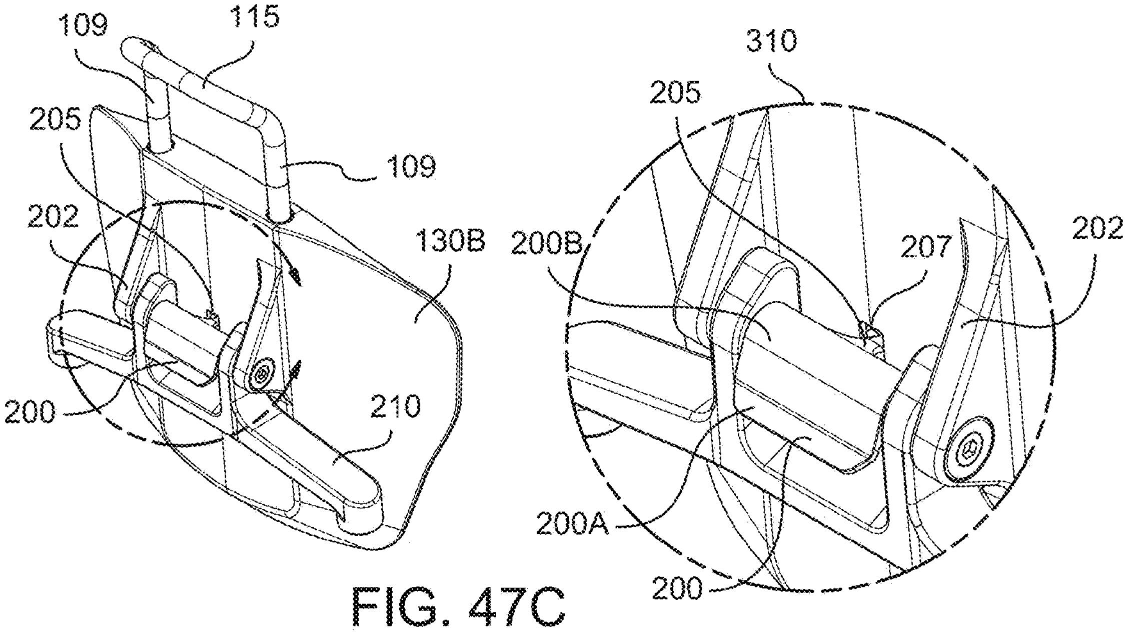
Figure 47D:
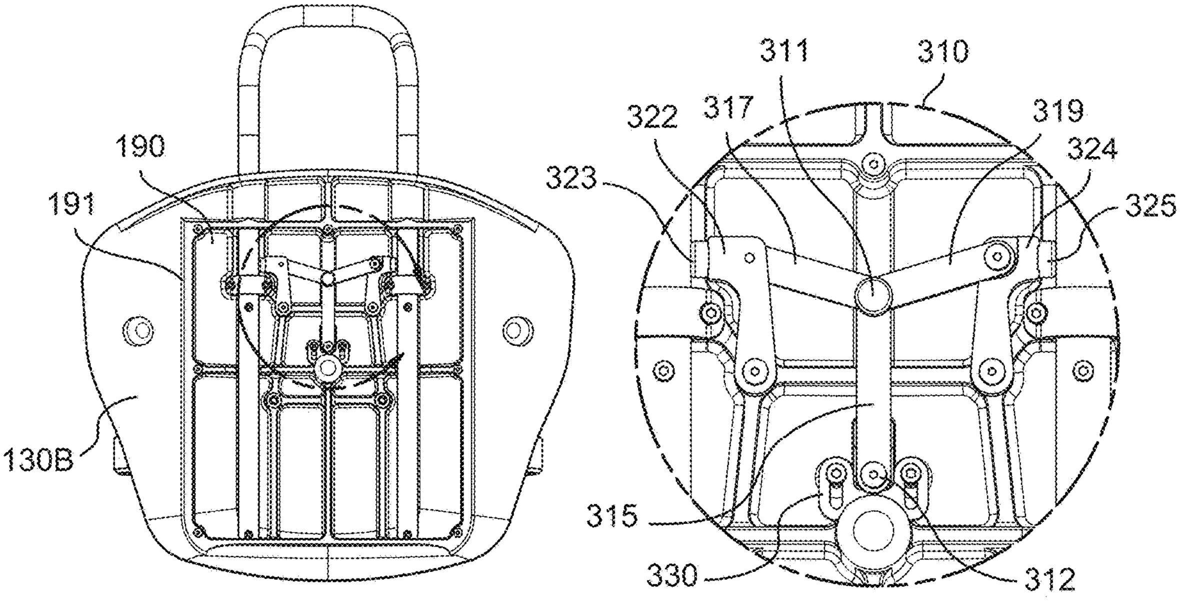

Referring now to FIG. 47A, latch 200 can be held in a locked positon 300 or unlocked position 310 (FIG. 47C). In locked position 300, latch 200 can enable attendant handle operating mechanism 190 (FIG. 47B) to trap attendant handle 115 such that an application of force for adjusting the length of handle 115 cannot displace attendant handle 115 (FIG. 47A) from the position in which it is stationed. In unlocked position 310 (FIG. 47C), attendant handle operating assembly 190 (FIG. 47B) can allow attendant handle 115 to be adjusted in terms of its protruding height by applying a desired force on handle 115. Latch 200 in a locked position (FIGS. 47A and 14B) can be compared with latch 200 in an unlocked position (FIGS. 47C and 47D). Flange 205 can serve as an interface or force transfer agent between latch 200 and handle operating assembly 190 (FIG. 47B).

Continuing to refer to FIG. 47A, a plurality of geometries and designs can be given to latch 200. In some configurations, latch 200 can include a gripping or pushing surface that the user can contact for operating latch 200. In some configurations, latch 200 can include handle portion 200A and rotatable portion 200B. In locked position, handle portion 200A can be pushed away form backrest surface 130B (FIG. 47B) causing a partial rotation of rotatable portion 200B. Flange 205 can extend from rotatable portion 200B such that rotational displacement of latch 200 can displace flange 205 through bridging orifice 207. Displacement of flange 205 towards frame portion 210, as seen on back surface 130B of backrest 130 (FIG. 46B), can enable displacement of adjustable joint 312 such that engaged central beam 315 (FIG. 47B) can also be displaced away from frame portion 210 and can further cause focal point 311 (FIG. 47B) to shift.

Referring now to FIG. 47B, shifting of focal point 311, in locking positon 300 (FIG. 47A) can cause side beams 317, 319 to extend substantially perpendicular to central beam 315. Side beams 317, 319 can exert a thrust on stoppers 322 and 324, causing them to displace towards rails 109 (FIG. 47A) of handle 115 (FIG. 47A). Bumpers 323, 325 can compress against corresponding rails 109 (FIG. 47A) and cease rails 109 (FIG. 47A) from travelling along pathways 109A, 109B (FIG. 45B).

Referring now to FIGS. 47C and 47D, to enable rails 109 (FIG. 47C) to adjustably travel along respective pathways 109A, 109B (FIG. 45B), handle operating mechanism 190 (FIG. 47D) can release rails 109 (FIG. 47C) by rotatably displacing latch 200 (FIG. 47C) into an unlocked position. In the unlocked position, handle portion 200A (FIG. 47C) of latch 200 (FIG. 47C) can appear to be lifted away from back surface 130B (FIG. 47D). As a result, flange 205 can be displaced toward frame portion 210 (FIG. 47C) along the length of bridging orifice 207 (FIG. 47C), and can result in displacement of adjustable joint 312 (FIG. 47D). Variable hard stop 330 (FIG. 47D) can be positioned in casing 191 (FIG. 47D) of inner face 185A (FIG. 46A) of backrest 130 (FIG. 45A), can serve as a hard stop for flexible point 312 (FIG. 47D), and can restrict rotation of latch 200 (FIG. 47C). Central beam 315 (FIG. 47D) can operably couple adjustable joint 312 (FIG. 47D) with focal point 311 (FIG. 47D), and can enable displacement of focal point 311 (FIG. 47D) towards frame portion 210 (FIG. 47C). Shifting of focal point 311 (FIG. 47D) can cause side beams 317, 319 (FIG. 47D) to displace from their substantially perpendicular position with respect to central beam 315 (FIG. 47D). Displaced side beams 317, 319 (FIG. 47D) can retract stoppers 324, 322 (FIG. 47D) from pathways 109A, 109B (FIG. 45B). The retraction can result in loosening contact between stopper bumpers 323, 325 (FIG. 47D) and respective rails 109 (FIG. 47C). As a result, rails 109 (FIG. 47C) can freely travel along length of travel ways 109A, 109B (FIG. 45B). A user can choose an appropriate length of handle 115 (FIG. 47C) extending of out backrest 130 (FIG. 45A) and can retain the chosen length when transitioning into locked position 300 (FIG. 47B) by operating latch 200 (FIG. 47C).

Configurations of the present teachings are directed to computer systems for accomplishing the methods discussed in the description herein, and to computer readable media containing programs for accomplishing these methods. The raw data and results can be stored for future retrieval and processing, printed, displayed, transferred to another computer, and/or transferred elsewhere. Communications links can be wired or wireless, for example, using cellular communication systems, military communications systems, and satellite communications systems. Parts of the system can operate on a computer having a variable number of CPUs. Other alternative computer platforms can be used.

The present configuration is also directed to software for accomplishing the methods discussed herein, and computer readable media storing software for accomplishing these methods. The various modules described herein can be accomplished on the same CPU, or can be accomplished on a different computer. In compliance with the statute, the present configuration has been described in language more or less specific as to structural and methodical features. It is to be understood, however, that the present configuration is not limited to the specific features shown and described, since the means herein disclosed comprise preferred forms of putting the present configuration into effect.

Methods can be, in whole or in part, implemented electronically. Signals representing actions taken by elements of the system and other disclosed configurations can travel over at least one live communications network. Control and data information can be electronically executed and stored on at least one computer-readable medium. The system can be implemented to execute on at least one computer node in at least one live communications network. Common forms of at least one computer-readable medium can include, for example, but not be limited to, a floppy disk, a flexible disk, a hard disk, magnetic tape, or any other magnetic medium, a compact disk read only memory or any other optical medium, punched cards, paper tape, or any other physical medium with patterns of holes, a random access memory, a programmable read only memory, and erasable programmable read only memory (EPROM), a Flash EPROM, or any other memory chip or cartridge, or any other medium from which a computer can read. Further, the at least one computer readable medium can contain graphs in any form, subject to appropriate licenses where necessary, including, but not limited to, Graphic Interchange Format (GIF), Joint Photographic Experts Group (JPEG), Portable Network Graphics (PNG), Scalable Vector Graphics (SVG), and Tagged Image File Format (TIFF).

While the present teachings have been described above in terms of specific configurations, it is to be understood that they are not limited to these disclosed configurations. Many modifications and other configurations will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

We claim:

1. System for controlling a mobility device comprising a processor configured for:

- a workflow process configured for filtering user commands based on a status of said mobility device and defining filtered commands; and
- a mobility device command process configured for issuing commands based on the filtered commands;
- wherein said mobility device is configured for responding to the commands that are configured for controlling moving said mobility device.

2. System of claim 1 wherein the mobility device command process is configured for issuing commands to the mobility device based on sensor data.

3. System of claim 2 wherein the sensor data relate to obstacles in a path of said mobility device.

4. System of claim 1 further comprising a user interface subsystem comprising:

a user input device configured for receiving user commands;

a user command processor configured for processing the user commands;

a user output device configured for transmitting information from said user command processor to said mobility device command process.

5. System of claim 4 further comprising a data exchange port configured for exchanging data between the user interface subsystem and said mobility device command process.

6. System of claim 4 further comprising a power supply port configured for powering said user interface subsystem.

7. System of claim 4 wherein said user input device comprises a thumbwheel configured for providing movement data throughout a full rotation of the thumbwheel and thumbwheel position, wherein:

said user interface subsystem is configured for retaining the thumbwheel position across a power cycle; and the thumbwheel position is associated with a user interface subsystem characteristic.

8. System of claim 1 wherein said workflow process is configured for:

responding to a subflow process;

providing a command from a set of allowed commands to said mobility device; and being selected based on the user commands.

9. System of claim 1 wherein said workflow process comprises one or more of:

a normal workflow comprising: a speed selection, a settings selection, a seat adjustment selection, a mode selection, and combinations thereof;

a power button workflow configured for being responsive to subflow process based on a status of a power button and comprising: an emergency stop, a revert to a previous button status, and combinations thereof;

a stair mode workflow comprising a solo mode stair climbing, an assisted mode stair climbing, and combinations thereof;

a forced power off workflow comprising insuring a power off selection and powering the mobility device off;

a center of gravity fit workflow comprising calibrating the mobility device for a user;

a recovery mode workflow comprising providing recovery information to the user; and a wireless workflow comprising requesting a password from the user.

10. System of claim 1 wherein said mobility device command process is configured for managing changes in operating modes of said mobility device based on a power capability.

* * * * *